(12) United States Patent
Taveras et al.

(10) Patent No.: US 12,037,354 B2
(45) Date of Patent: Jul. 16, 2024

(54) CYCLIC PANTETHEINE DERIVATIVES AND USES THEREOF

(71) Applicant: VectivBio Comet AG, Basel (CH)

(72) Inventors: Arthur George Taveras, Boston, MA (US); Enej Kuscer, Wassenaar (NL); Angelina Roberta Sekirnik, Leiden (NL); Dharini Shah, Boston, MA (US); Mercedes Valls Seron, Leiden (NL)

(73) Assignee: VectivBio Comet AG, Basel (CH)

( * ) Notice: Subject to any disclaimer, the term of this patent is extended or adjusted under 35 U.S.C. 154(b) by 0 days.

(21) Appl. No.: 17/298,658

(22) PCT Filed: Dec. 2, 2019

(86) PCT No.: PCT/US2019/063986
§ 371 (c)(1),
(2) Date: May 31, 2021

(87) PCT Pub. No.: WO2020/113213
PCT Pub. Date: Jun. 4, 2020

(65) Prior Publication Data
US 2023/0072313 A1    Mar. 9, 2023

Related U.S. Application Data

(60) Provisional application No. 62/941,644, filed on Nov. 27, 2019, provisional application No. 62/941,643, filed on Nov. 27, 2019, provisional application No. 62/795,490, filed on Jan. 22, 2019, provisional application No. 62/794,503, filed on Jan. 18, 2019, provisional application No. 62/774,759, filed on Dec. 3, 2018, provisional application No. 62/773,952, filed on Nov. 30, 2018.

(51) Int. Cl.
| | |
|---|---|
| C07F 9/6574 | (2006.01) |
| C07C 327/22 | (2006.01) |
| C07C 327/32 | (2006.01) |
| C07C 327/34 | (2006.01) |
| C07D 207/28 | (2006.01) |
| C07D 307/33 | (2006.01) |
| C07D 319/06 | (2006.01) |
| C07D 491/113 | (2006.01) |
| C07D 493/10 | (2006.01) |
| C07F 7/08 | (2006.01) |
| C07F 9/09 | (2006.01) |
| C07F 9/12 | (2006.01) |
| C07F 9/6571 | (2006.01) |

(52) U.S. Cl.
CPC ........ *C07F 9/65742* (2013.01); *C07C 327/22* (2013.01); *C07C 327/32* (2013.01); *C07C 327/34* (2013.01); *C07D 207/28* (2013.01); *C07D 307/33* (2013.01); *C07D 319/06* (2013.01); *C07D 491/113* (2013.01); *C07D 493/10* (2013.01); *C07F 7/081* (2013.01); *C07F 9/091* (2013.01); *C07F 9/12* (2013.01); *C07F 9/657154* (2013.01)

(58) Field of Classification Search
CPC ........... C07F 9/65742; C07F 9/657154; C07D 319/06; C07D 491/113; C07D 493/10
USPC ......................................................... 558/73
See application file for complete search history.

(56) References Cited

U.S. PATENT DOCUMENTS

| | | |
|---|---|---|
| 5,053,426 A | 10/1991 | Bloom et al. |
| 2020/0048249 A1 | 2/2020 | Jones et al. |

(Continued)

FOREIGN PATENT DOCUMENTS

| | | |
|---|---|---|
| WO | WO-9511673 A1 | 5/1995 |
| WO | WO-9511893 A1 | 5/1995 |

(Continued)

OTHER PUBLICATIONS

Baddiley, J. et al. "Coenzyme A. VII. Pantetheine -2' and -2',4'-phosphates and a new method for the synthesis of cyclic phosphates", Journal of the Chemical Society, Issue 0, 1953, p. 903-906.

(Continued)

*Primary Examiner* — Kristin A Vajda
(74) *Attorney, Agent, or Firm* — COOLEY LLP

(57) ABSTRACT

The present disclosure relates to compounds of Formula (P) or (II'-0): (Formulae (I'), (II'-0)), and pharmaceutically acceptable salts or solvates thereof. The present disclosure also relates to pharmaceutical compositions comprising the compounds and therapeutic and diagnostic uses of the compounds and pharmaceutical compositions.

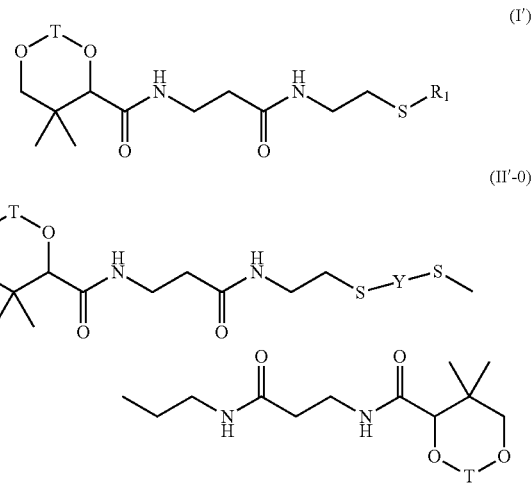

18 Claims, 2 Drawing Sheets
Specification includes a Sequence Listing.

(56) References Cited

U.S. PATENT DOCUMENTS

| | | |
|---|---|---|
| 2020/0172508 A1 | 6/2020 | Fleck et al. |
| 2020/0231570 A1 | 7/2020 | Pham et al. |
| 2020/0291041 A1 | 9/2020 | Serrano-Wu et al. |
| 2022/0017501 A1 | 1/2022 | Burns et al. |
| 2022/0183295 A1 | 6/2022 | Burns et al. |
| 2022/0220117 A1 | 7/2022 | Larsen et al. |

FOREIGN PATENT DOCUMENTS

| | | |
|---|---|---|
| WO | WO-2018022529 A1 | 2/2018 |
| WO | WO-2020110056 A1 | 6/2020 |
| WO | WO-2020154420 A2 | 7/2020 |

OTHER PUBLICATIONS

Hwang et al. "Enzymatic and Cellular Study of a Serotonin N-acetyltransferase Phosphopantetheine-based Prodrug", Bioorganic & Medicinal Chemistry, vol. 15, No. 5, 2007, pp. 2147-2155.

Nakamura et al. "Growth responses of Bifidobacterium bifidum to S-Sulfonic Acid-Type Pantetheine Related Compounds",, Japanese Journal of Microbiology, vol. 16, No. 3, 1972, pp. 239-242.

RN: 20903-52-0; Database CA [Online] Chemical Abstracts Service, Nov. 16, 1984, 1 page.

RN: 38564-94-2; Database CA [Online] Chemical Abstracts Service, Nov. 16, 1984, 2 pages.

Agarwal, V., et al., "Chemoenzymatic Synthesis of Acyl Coenzyme A Substrates Enables in Situ Labeling of Small Molecules and Proteins," Organic Letters, Sep. 2015, vol. 17 (18), pp. 4452-4455.

CYCLIC PANTETHEINE DERIVATIVES AND USES THEREOF

RELATED APPLICATIONS

This application claims the benefit of, and priority to, U.S. Provisional Patent Application Nos. 62/941,644, filed on Nov. 27, 2019; 62/941,643, filed on Nov. 27, 2019; 62/795,490, filed on Jan. 22, 2019; 62/794,503, filed on Jan. 18, 2019; 62/774,759, filed on Dec. 3, 2018; and 62/773,952, filed on Nov. 30, 2018, the entire contents of each of which are incorporated by reference in their entireties.

BACKGROUND

Coenzyme A (CoA) and acyl-CoA derivatives are involved in very diverse functions of cell metabolism, energy and regulation. CoA is derived from pantothenate, which is a required vitamin (B5) in mammals. Pantothenate can be obtained from the diet and from intestinal bacteria. CoA synthesis from pantothenate occurs in a five-step enzymatic reaction, the first of which is catalyzed by pantothenate kinase (PANK), followed by 4'-phosphopantothenoylcysteine synthetase (PPCS), 4'-phospho-N-pantothenoylcysteine decarboxylase (PPCDC), 4'-phosphopantetheine adenylyltransferase (PPAT) and dephospho-CoA kinase (DPCK).

The main function of CoA is to deliver different acyl groups to participate in various metabolic and regulatory processes. CoA is acylated by forming a high energy thioester bond between an acyl group and the free sulfhydryl substituent of CoA. Among the different acyl-CoA derivatives, Acetyl-Coenzyme A (acetyl-CoA) plays a particularly important role. CoA is acetylated to acetyl CoA during the process of carbohydrate, fatty acid and amino acid catabolism. One primary function of acetyl-CoA is to deliver an acetyl group to the citric acid cycle (also known as the Krebs cycle) for energy production. Acetyl-CoA is also an important intermediate in other biological pathways, including, but not limited to fatty acid and amino acid metabolism, steroid synthesis, acetylcholine synthesis, melatonin synthesis and acetylation pathways (e.g. lysine acetylation, post-translational acetylation). Acetyl-CoA concentrations also influence the activity or specificity of various enzymes, including, but not limited to pyruvate dehydrogenase kinase and pyruvate carboxylase, either in an allosteric manner or by altering substrate availability. Acetyl-CoA also controls key cellular processes, including energy metabolism, mitosis, and autophagy, both directly and via the epigenetic regulation of gene expression by influencing the acetylation profile of several proteins, including, but not limited to histones.

Acetyl-CoA is synthesized in vivo in several ways, including extramitochondrially and intramitochondrially. Intramitochondrially, when glucose levels are high, acetyl-CoA is produced as an end-product of glycolysis through a pyruvate dehydrogenase reaction, in which pyruvate undergoes oxidative decarboxylation to form acetyl-CoA. Other conversions between pyruvate and acetyl-CoA occur, including the disproportionation of pyruvate into acetyl-CoA and formic acid by pyruvate formate lyase. At lower glucose levels, acetyl-CoA is produced by β-oxidation of fatty acids. Fatty acids are first converted to an acyl-CoA, which is further degraded in a four-step cycle of dehydrogenation, hydration, oxidation and thiolysis to form acetyl-CoA. These four steps are performed by acyl-CoA dehydrogenase, enoyl-CoA hydratase, 3-hydroxyacyl-CoA dehydrogenase and thiolase respectively. Additionally, degradation of amino acids such as leucine, isoleucine, lysine, tryptophan, phenylalanine and tyrosine can also produce acetyl-CoA. For example, branched chain amino acids are converted to α-ketoacids by transamination in the cytosol, then transferred to mitochondria via a carnitine shuttle transport, and finally processed inside the mitochondrial matrix by an α-ketoacid dehydrogenase complex where an α-ketoacil-CoA undergoes a multi-step dehydrogenation, carboxylation and hydration to produce acetyl-CoA. Acetyl-CoA can also be synthesized intramitochondrially by acetyl-CoA synthetase, which is an enzyme that uses acetate and ATP to acetylate CoA. In addition, there are organ-specific pathways for mitochondrial acetyl-CoA generation. For instance, neurons can employ the ketone bodies D-b-hydroxybutyrate and acetoacetate to generate acetyl-CoA (Cahill, 2006) and hepatocytes can produce acetyl-CoA from ethanol as a carbon source through conversion via acetaldehyde and acetate.

Extramitochondrially, Acetyl-CoA can be produced by ATP citrate lyase, which converts citrate made by the tricarboxylic acid cycle into acetyl-CoA and oxaloacetate. Secondly, acetyl-CoA can also be produced in the cytosol from acetate in an ATP-dependent reaction catalyzed by acyl-CoA synthetase.

Decreased levels of acetyl-CoA can be caused by the inhibition, loss of, or decrease in activity of the various metabolic enzymes and pathways of acetyl-CoA biosynthesis. Diseases such as organic acidemias of deficient branched chain amino acid catabolism or fatty acid oxidation disorders, such as short chain acyl-CoA dehydrogenase deficiency (SCADD), medium chain acyl-CoA dehydrogenase deficiency (MCADD), long chain acyl-CoA dehydrogenase deficiency (LCADD) and very long chain acyl-CoA dehydrogenase deficiency (VLCADD) can lead to a decrease in acetyl-CoA levels and the accumulation of other CoA species including acyl-CoA species. These diseases can lead to symptoms such as hypoglycemia, liver dysfunction, lethargy, seizures, coma and even death. Thus, there is a need in the art for compositions and methods for the treatment of CoA deficiency, acetyl-CoA deficiency, and other acyl-CoA deficiencies.

In addition to acetyl, CoA may accept many other acyl-species, such as, but not limited to, propionyl, butyryl, 2-hydroxyisobutyryl, crotonyl, malonyl, succinyl and glutaryl, with such acylated acyl-CoA species also playing an important role in cellular metabolism and regulation including as carriers of energy through their high-energy thioester bond, as donors of carbon units in anabolic processes or as donors of acyl groups in cellular regulation through protein modification, such as, but not limited to, histone lysine modifications.

SUMMARY

In some aspects, the present disclosure provides, inter alia, a compound of Formula (I') or (II'-0):

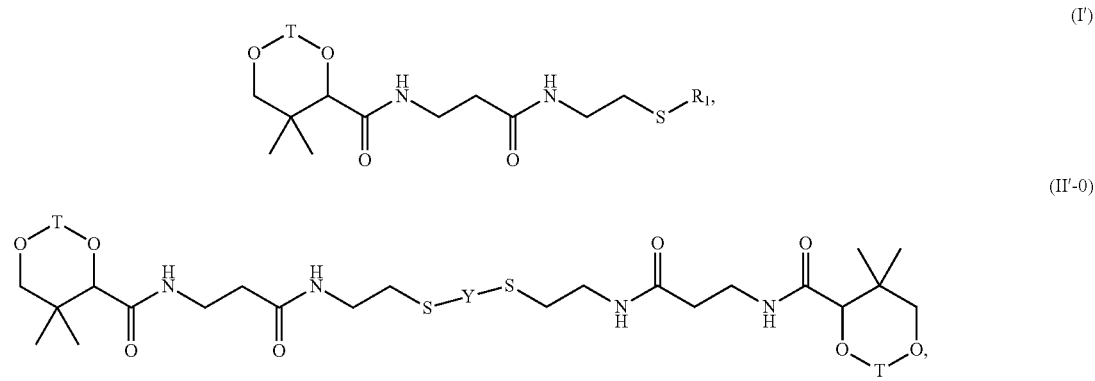

or a pharmaceutically acceptable salt or solvate thereof, wherein:
each T is independently

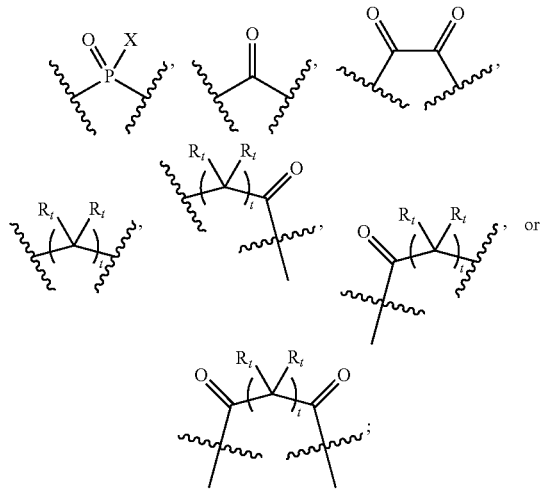

each $R_t$ is independently $R_1$, $R_{1a}$, $R_{1b}$ or $R_{1c}$; or
two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$;
t is an integer ranging from 0 to 5;
$R_1$ is H, $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_n$—$R_{1a}$, —C(=O)CH$_2$—[C(=O)CH$_2$]$_p$—[CH$_2$]$_q$—$R_{1a}$, —C(=O)CH($R_{1a}$)—[C(=O)CH($R_{1a}$)]$_p$—[CH$_2$]$_q$—$R_{1a}$, —C(=O)CH$_2$—[CH(O$R_{1c}$)—CH$_2$]$_p$—[CH$_2$]$_q$—$R_{1a}$, —C(=O)CH$_2$—[C(=O)CH$_2$]$_p$—[CH(O$R_{1c}$)—CH$_2$]$_r$—[CH$_2$]$_q$—$R_{1a}$, —C(=O)CH$_2$—[CH(O$R_{1c}$)—CH$_2$]$_r$—[C(=O)CH$_2$]$_p$—[CH$_2$]$_q$—$R_{1a}$, —C(=O)O$R_{1c}$, —C(=O)N($R_{1c}$)$_2$, —C(=O)—CH=CH—C(=O)O$R_{1c}$, —C(=O)—[CH$_2$]$_q$—C(=O)O$R_{1c}$, —C(=O)CH$_2$—[C(=O)CH$_2$]$_p$—[CH$_2$]$_q$—C(=O)O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$, —S$R_{1d}$,

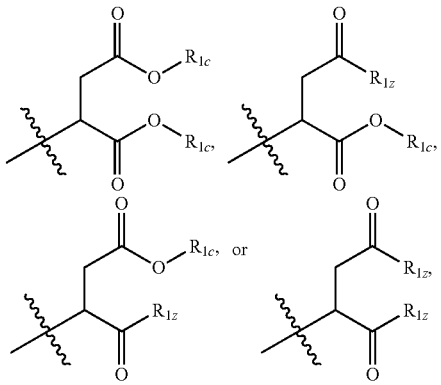

wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties;
each $R_{1a}$ is independently H, oxo, halogen, $C_1$-$C_{20}$ alkyl, $C_2$-$C_{20}$ alkenyl, —O$R_{1c}$, —C(=O)O$R_{1c}$, —C(=O)N($R_{1c}$)$_2$, —N($R_{1c}$)$_2$, —N($R_{1c}$)C(=O)$R_{1b}$, —N($R_{1c}$)C(=O)$R_{1z}$, —N($R_{1c}$)C(=O)O$R_{1c}$, —OC(=O)$R_{1b}$, —OC(=O)$R_{1z}$, —OC(=O)O$R_{1c}$, —OSi($R_{1g}$)$_3$, —SC(=O)$R_{1b}$, —SC(=O)$R_{1z}$, —SC(=O)O$R_{1c}$, —SC(=O)N($R_{1c}$)$_2$, —C(=O)$R_{1b}$, —C(=O)$R_{1z}$, —S$R_{1d}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;
each $R_{1b}$ is independently H, $C_1$-$C_{20}$ alkyl, $C_2$-$C_{20}$ alkenyl, $C_2$-$C_{20}$ alkynyl, —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=CH—C(=O)O$R_{1c}$, —C(=O)O$R_{1c}$, —C(=O)N($R_{1c}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1e}$;

each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$; or two $R_{1c}$ together with the one or more intervening atoms to which they are connected, form $C_3$-$C_{12}$ cycloalkyl or $C_3$-$C_{12}$ heterocycloalkyl, wherein the $C_3$-$C_{12}$ cycloalkyl or $C_3$-$C_{12}$ heterocycloalkyl is optionally substituted with one or more $R_{1e}$;

each $R_{1d}$ is independently H, $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1e}$ is independently H, halogen, $C_1$-$C_{20}$ alkyl, $C_2$-$C_{20}$ alkenyl, $C_2$-$C_{20}$ alkynyl, —$OR_{1g}$, —C(=O)$OR_{1g}$, —C(=O)N($R_{1g}$)$_2$, —N($R_{1g}$)$_2$, —N($R_{1g}$)C(=O)$R_{1f}$, —N($R_{1g}$)C(=O)$R_{1z}$, —N($R_{1g}$)C(=O)$OR_{1g}$, —OC(=O)$R_{1f}$, —OC(=O)$R_{1z}$, —OC(=O)$OR_{1g}$, —OSi($R_{1g}$)$_3$, —$SR_{1g}$, —$N^+(R_{1g})_3$, —SC(=O)$R_{1f}$, —SC(=O)$R_{1z}$, —SC(=O)$OR_{1g}$, —SC(=O)N($R_{1g}$)$_2$, —C(=O)$R_{1f}$, —C(=O)$R_{1z}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1f}$ is independently H, $C_1$-$C_{20}$ alkyl, $C_2$-$C_{20}$ alkenyl, $C_2$-$C_{20}$ alkynyl, —OSi($R_{1g}$)$_3$, —CH$_2$C(=O)$OR_{1g}$, —CH=CH—C(=O)$OR_{1g}$, —C(=O)$OR_{1g}$, —C(=O)N($R_{1g}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1g}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{2}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1z}$;

each $R_{1z}$ is independently

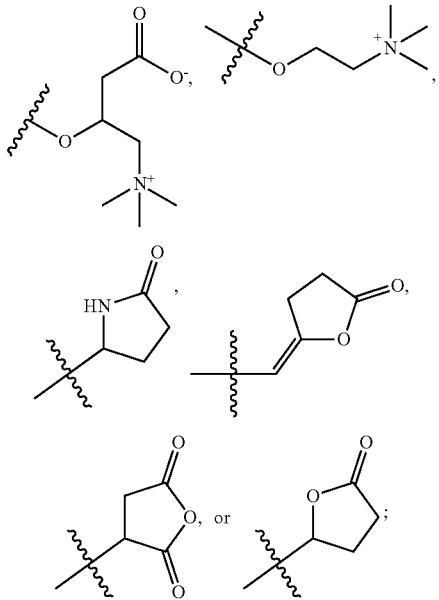

each n is independently an integer ranging from 0 to 20;
each p is independently an integer ranging from 0 to 20;
each q is independently an integer ranging from 0 to 20;
each r is independently an integer ranging from 0 to 20;
each X is independently —$OR_{1c}$, —$SR_{1c}$, —N($R_{1c}$)$_2$,

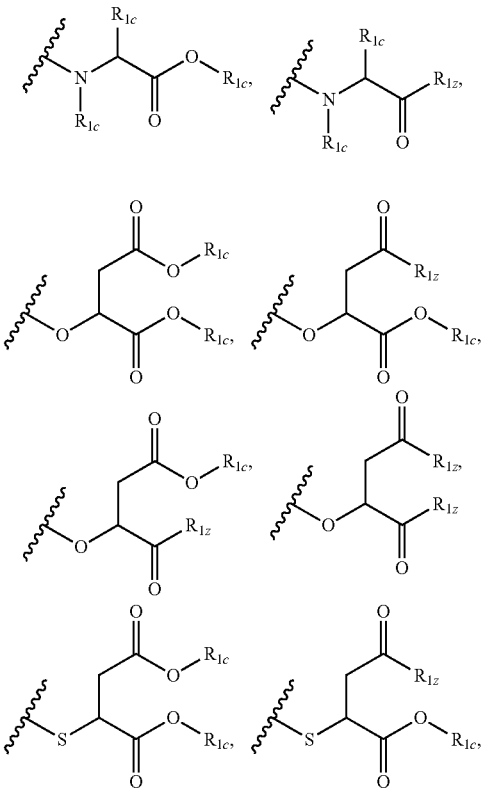

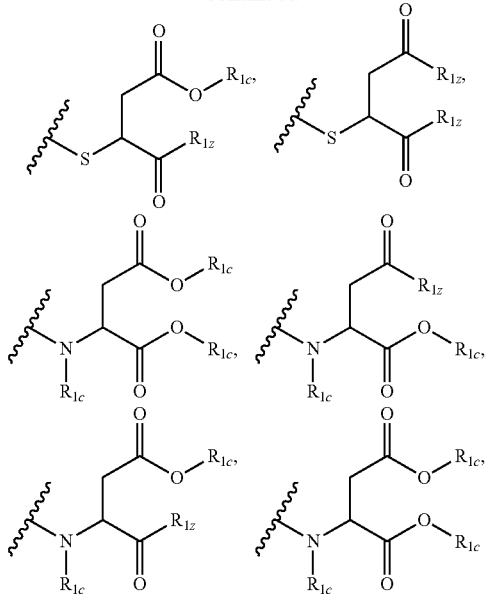

or $R_{1z}$; and

Y is a bond or $C_1$-$C_{20}$ alkyl optionally substituted with one or more $R_{1d}$.

In some aspects, the present disclosure provides, inter alia, a compound of Formula (I') or (II'):

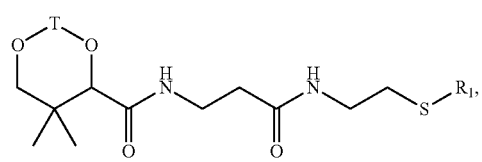
(I')

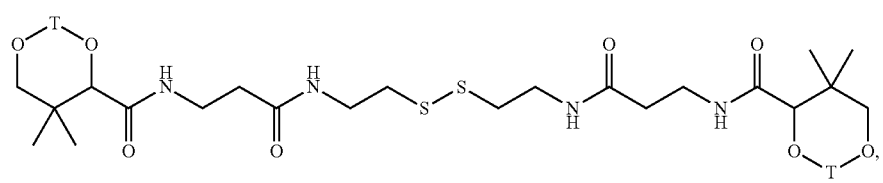
(II')

or a pharmaceutically acceptable salt or solvate thereof, wherein:

each T is independently

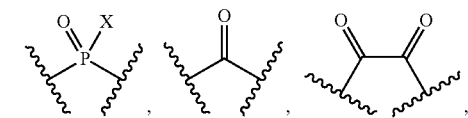

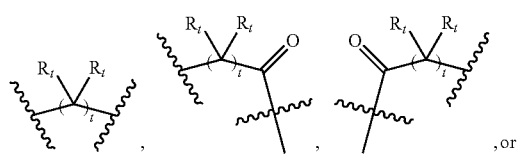

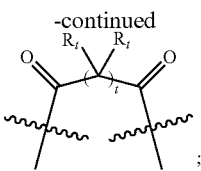

each $R_t$ is independently $R_1$, $R_{1a}$, or $R_{1b}$; or two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$;

t is an integer ranging from 0 to 5;

$R_1$ is H, $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_n$—$R_{1a}$, C(=O)CH$_2$—[C(=O)CH$_2$]$_p$—[CH$_2$]$_q$—$R_{1a}$, —C(=O)CH($R_{1a}$)—[C(=O)CH($R_{1a}$)]$_p$—[CH$_2$]$_q$—$R_{1a}$, —C(=O)CH$_2$—[CH(OR$_{1c}$)—CH$_2$]$_p$—[CH$_2$]$_q$—$R_{1a}$, —C(=O)CH$_2$—[C(=O)CH$_2$]$_p$—[CH(OR$_{1c}$)—CH$_2$]$_r$—[CH$_2$]$_q$—$R_{1a}$, —C(=O)CH$_2$[—CH(OR$_{1c}$)—CH$_2$]$_r$—[C(=O)CH$_2$]$_p$—[CH$_2$]$_q$—$R_{1a}$, —C(=O)OR$_{1c}$, —C(=O)N(R$_{1c}$)$_2$, —C(=O)—CH=CH—C(=O)OR$_{1c}$, —C(=O)—[CH$_2$]$_q$—C(=O)OR$_{1c}$, —C(=O)—CH$_2$CH$_2$—C(=O)OR$_{1c}$, —C(=O)CH$_2$—[C(=O)CH$_2$]$_p$—[CH$_2$]$_q$— C(=O)OR$_{1c}$, —C(=O)—[CH$_2$]$_q$—C(=O)R$_{1z}$, —C(=O)—CH$_2$CH$_2$—C(=O)R$_{1z}$, —C(=O)CH$_2$—[C(=O)CH$_2$]$_p$—[CH$_2$]$_q$— C(=O)R$_{1z}$, —SR$_{1d}$,

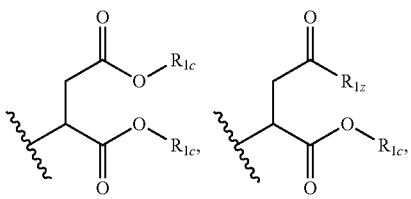

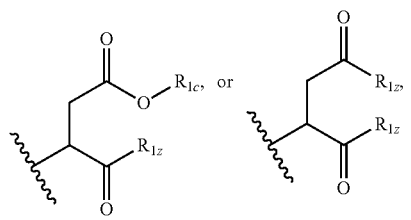

wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties;

each $R_{1a}$ is independently H, oxo, halogen, $C_1$-$C_{20}$ alkyl, $C_2$-$C_{20}$ alkenyl, —$OR_{1c}$, —$C(=O)R_{1c}$, —$C(=O)N(R_{1c})_2$, —$N(R_{1c})_2$, —$N(R_{1c})C(=O)R_{1b}$, —$N(R_{1c})C(=O)R_{1z}$, —$N(R_{1c})C(=O)OR_{1c}$, —$OC(=O)R_{1b}$, —$OC(=O)R_{1z}$, —$OC(=O)OR_{1c}$, —$SC(=O)R_{1b}$, —$SC(=O)R_{1z}$, —$SC(=O)OR_{1c}$, —$SC(=O)N(R_{1c})_2$, —$C(=O)R_{1b}$, —$C(=O)R_{1z}$, —$SR_{1d}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;

each $R_{1b}$ is independently H, $C_1$-$C_{20}$ alkyl, $C_2$-$C_{20}$ alkenyl, $C_2$-$C_{20}$ alkynyl, —$(CH_2)_q$—$C(=O)OR_{1c}$, —$CH_2$—$C(=O)$—$(CH_2)_q$—$C(=O)OR_{1c}$, —$CH_2$—$[C(=O)CH_2]_p$—$[CH_2]_q$—$C(=O)OR_{1c}$, —$CH=CH$—$C(=O)OR_{1c}$, —$C(=O)OR_{1c}$, —$C(=O)N(R_{1c})_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;

each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1d}$ is independently H, $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1e}$ is independently H, halogen, $C_1$-$C_{20}$ alkyl, $C_2$-$C_{20}$ alkenyl, $C_2$-$C_{20}$ alkynyl, —$OR_{1g}$, —$C(=O)OR_{1g}$, —$C(=O)N(R_{1g})_2$, —$N(R_{1g})_2$, —$N(R_{1g})C(=O)R_{1f}$, —$N(R_{1g})C(=O)R_{1z}$, —$N(R_{1g})C(=O)OR_{1g}$, —$OC(=O)R_{1f}$, —$OC(=O)R_{1z}$, —$OC(=O)OR_{1g}$, —$SR_{1g}$, —$N^+(R_{1g})_3$, —$SC(=O)R_{1f}$, —$SC(=O)R_{1z}$, —$SC(=O)OR_{1g}$, —$SC(=O)N(R_{1g})_2$, —$C(=O)R_{1f}$, —$C(=O)R_{1z}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1f}$ is independently H, $C_1$-$C_{20}$ alkyl, $C_2$-$C_{20}$ alkenyl, $C_2$-$C_{20}$ alkynyl, —$CH_2C(=O)OR_{1g}$, —$CH=CH$—$C(=O)OR_{1g}$, —$C(=O)OR_{1g}$, —$C(=O)N(R_{1g})_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1g}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1z}$;

each $R_{1z}$ is independently

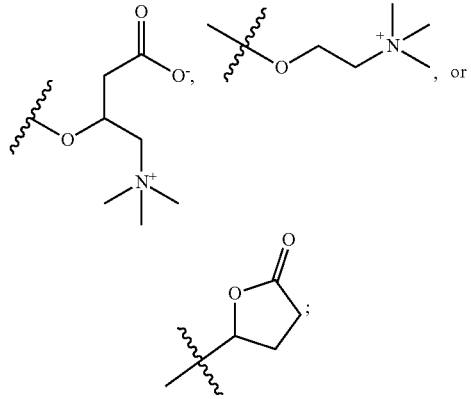

each n is independently an integer ranging from 0 to 20;
each p is independently an integer ranging from 0 to 20;
each q is independently an integer ranging from 0 to 20;
each r is independently an integer ranging from 0 to 20; and each X is independently —$OR_{1c}$, —$SR_{1c}$, —$N(R_{1c})_2$,

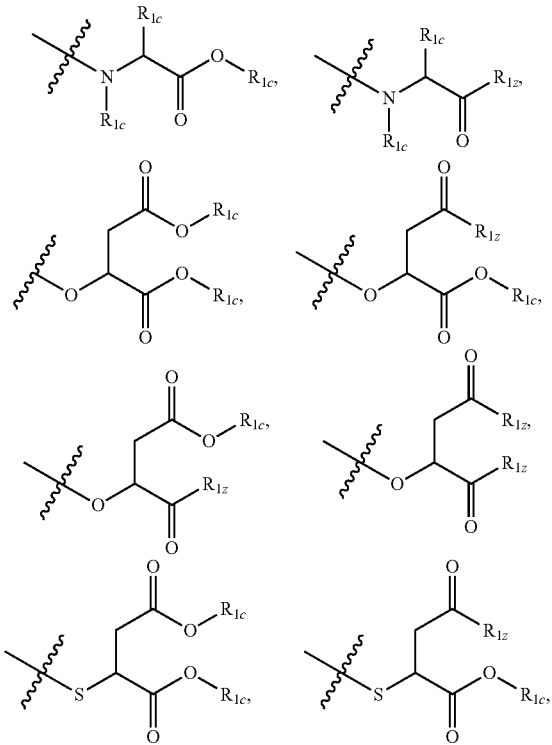

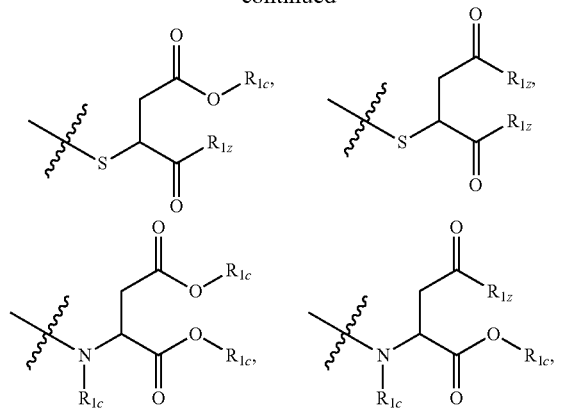
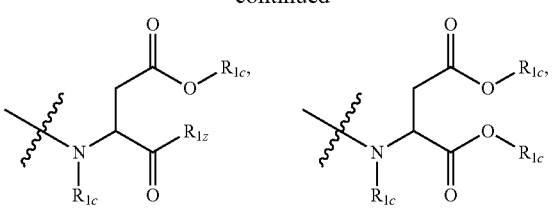
In some aspects, the present disclosure provides, inter alia, a compound of Formula (I), (II), (III), (IV), (V), or (VI):
(I)
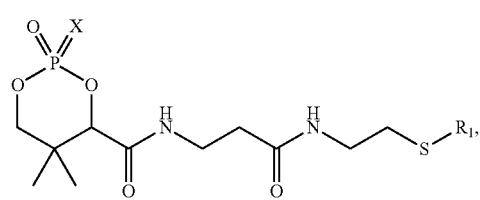
(II)
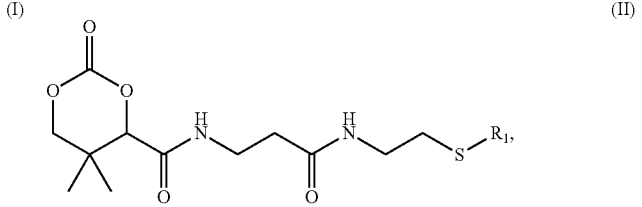
(III)
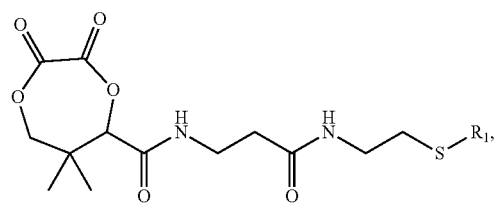
(IV)
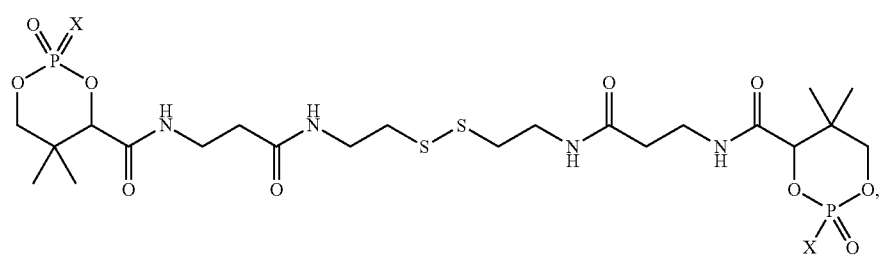
(V)
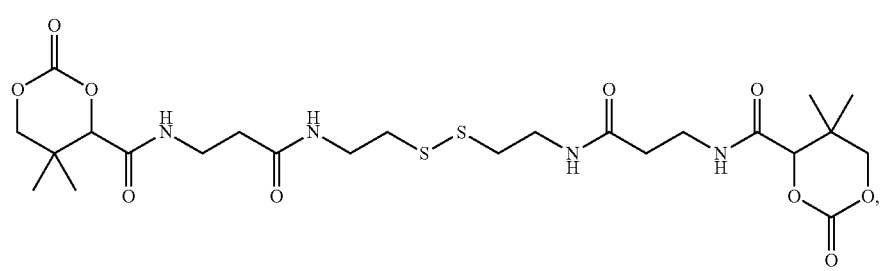

-continued (VI)

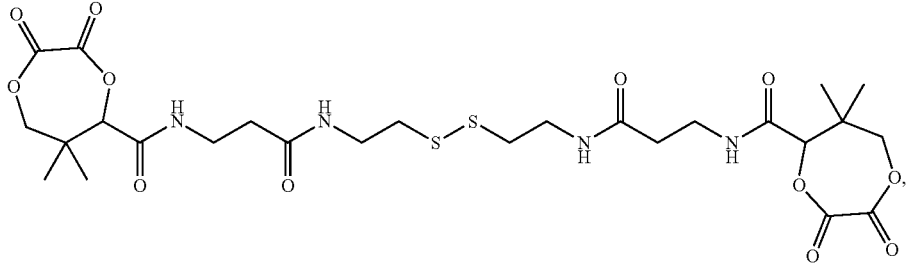

or a pharmaceutically acceptable salt or solvate thereof, wherein:

$R_1$ is H, $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_n$—$R_{1a}$, —C(=O)CH$_2$—[C(=O)CH$_2$]$_p$—[CH$_2$]$_q$—$R_{1a}$, —C(=O)CH$_2$—[CH(O$R_{1c}$)—CH$_2$]$_p$—[CH$_2$]$_q$—$R_{1a}$, —C(=O)CH$_2$—[C(=O)CH$_2$]$_p$—[CH(O$R_{1c}$)—CH$_2$]$_r$—[CH$_2$]$_q$—$R_{1a}$, —C(=O)CH$_2$—[CH(O$R_{1c}$)—CH$_2$]$_r$—[C(=O)CH$_2$]$_p$—[CH$_2$]$_q$—$R_{1a}$, —C(=O)O$R_{1c}$, —C(=O)N($R_{1c}$)$_2$, —C(=O)—CH=CH—C(=O)O$R_{1c}$, —C(=O)—[CH$_2$]$_q$—C(=O)O$R_{1c}$, —C(=O)—CH$_2$CH$_2$—C(=O)O$R_{1c}$, —C(=O)CH$_2$—[C(=O)CH$_2$]$_p$—[CH$_2$]$_q$—C(=O)O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$, —S$R_{1d}$,

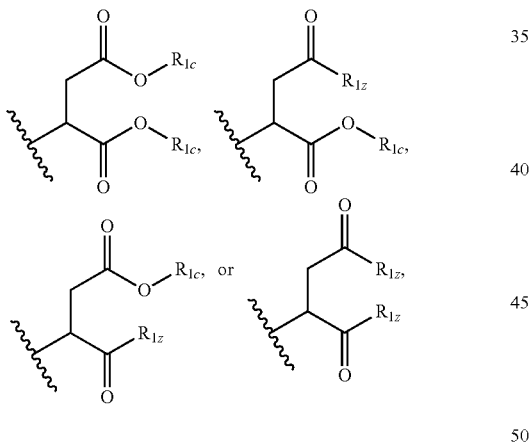

wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties;

each $R_{1a}$ is independently H, oxo, halogen, $C_1$-$C_{20}$ alkyl, $C_2$-$C_{20}$ alkenyl, —O$R_{1c}$, —C(=O)O$R_{1c}$, —C(=O)N($R_{1c}$)$_2$, —N($R_{1c}$)$_2$, —N($R_{1c}$)C(=O)$R_{1b}$, —N($R_{1c}$)C(=O)$R_{1z}$, —N($R_{1c}$)C(=O)O$R_{1c}$, —OC(=O)$R_{1b}$, —OC(=O)$R_{1z}$, —OC(=O)O$R_{1c}$, —SC(=O)$R_{1b}$, —SC(=O)$R_{1z}$, —SC(=O)O$R_{1c}$, —SC(=O)N($R_{1c}$)$_2$, —C(=O)$R_{1b}$, —C(=O)$R_{1z}$, —S$R_{1d}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1e}$;

each $R_{1b}$ is independently H, $C_1$-$C_{20}$ alkyl, $C_2$-$C_{20}$ alkenyl, $C_2$-$C_{20}$ alkynyl, —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH—H—C(=O)O$R_{1c}$, —C(=O)O$R_{1c}$, —C(=O)N($R_{1c}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;

each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1d}$ is independently H, $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1e}$ is independently H, halogen, $C_1$-$C_{20}$ alkyl, $C_2$-$C_{20}$ alkenyl, $C_2$-$C_{20}$ alkynyl, —O$R_{1g}$, —C(=O)O$R_{1g}$, —C(=O)N($R_{1g}$)$_2$, —N($R_{1g}$)$_2$, —N($R_{1g}$)C(=O)$R_{1f}$, —N($R_{1g}$)C(=O)$R_{1z}$, —N($R_{1g}$)C(=O)O$R_{1g}$, —OC(=O)$R_{1f}$, —OC(=O)$R_{1z}$, —OC(=O)O$R_{1g}$, —S$R_{1g}$, —N$^+$($R_{1g}$)$_3$, —SC(=O)$R_{1f}$, —SC(=O)$R_{1z}$, —SC(=O)O$R_{1g}$, —SC(=O)N($R_{1g}$)$_2$, —C(=O)$R_{1f}$, —C(=O)$R_{1z}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1f}$ is independently H, $C_1$-$C_{20}$ alkyl, $C_2$-$C_{20}$ alkenyl, $C_2$-$C_{20}$ alkynyl, —CH$_2$C(=O)O$R_{1g}$, —CH=CH—C(=O)O$R_{1g}$, —C(=O)O$R_{1g}$, —C(=O)N($R_{1g}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1g}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1z}$;

each $R_{1z}$ is independently

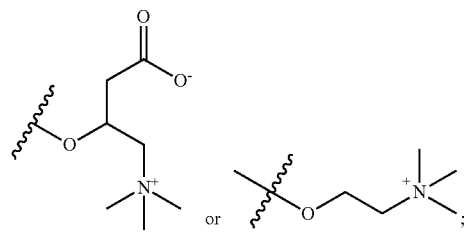

each n is independently an integer ranging from 0 to 20;
each p is independently an integer ranging from 0 to 20;
each q is independently an integer ranging from 0 to 20;
each r is independently an integer ranging from 0 to 20; and
each X is independently —$OR_{1c}$, —$SR_{1c}$, —$N(R_{1c})_2$,

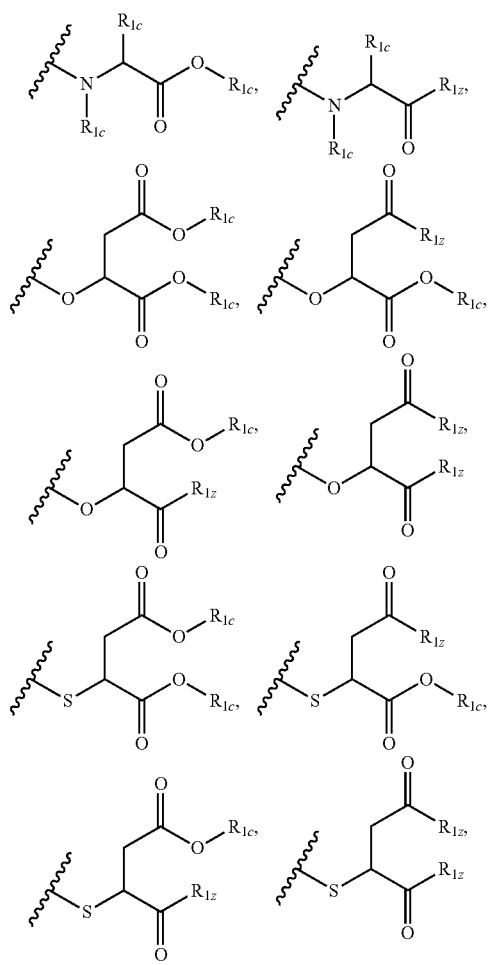

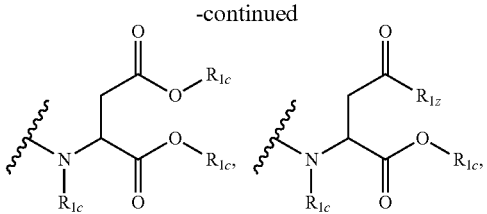

In some aspects, the present disclosure provides a method of treating or preventing a disease in a subject, comprising administering to the subject a therapeutically effective amount of at least one compound of the present disclosure.

In some aspects, the present disclosure provides at least one compound of the present disclosure for use in treating or preventing a disease in a subject, wherein the at least one compound of the present disclosure is for administration to the subject in at least one therapeutically effective amount.

In some aspects, the present disclosure provides use of at least one compound of the present disclosure for the manufacture of a medicament for treating or preventing a disease in a subject, wherein the at least one compound of the present disclosure is for administration to the subject in at least one therapeutically effective amount.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Compounds of the Present Disclosure

Figure 1:
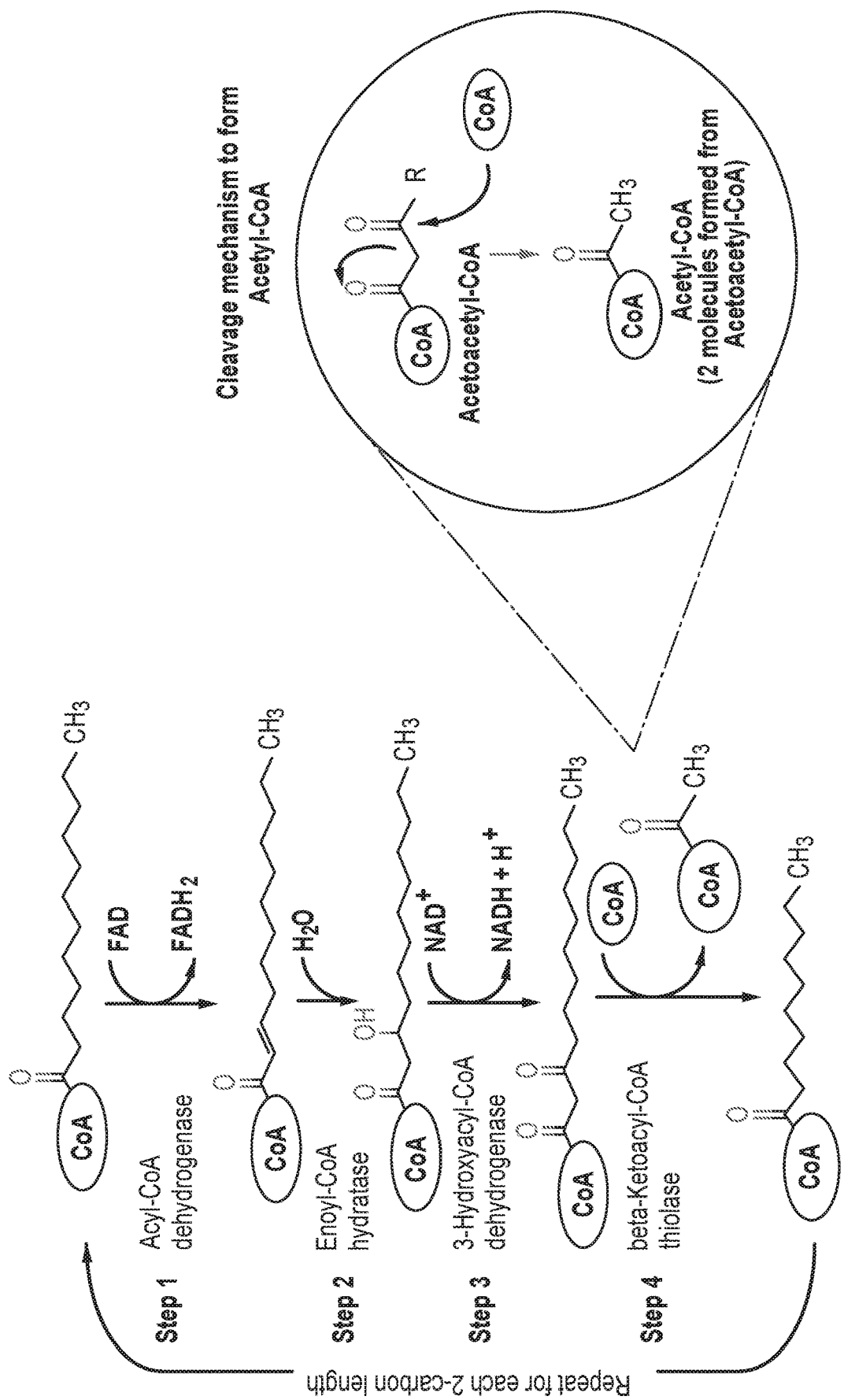
FIG. 1 is a schematic overview of fatty acid oxidation and the synthesis of acetyl-CoA.
Figure 2:
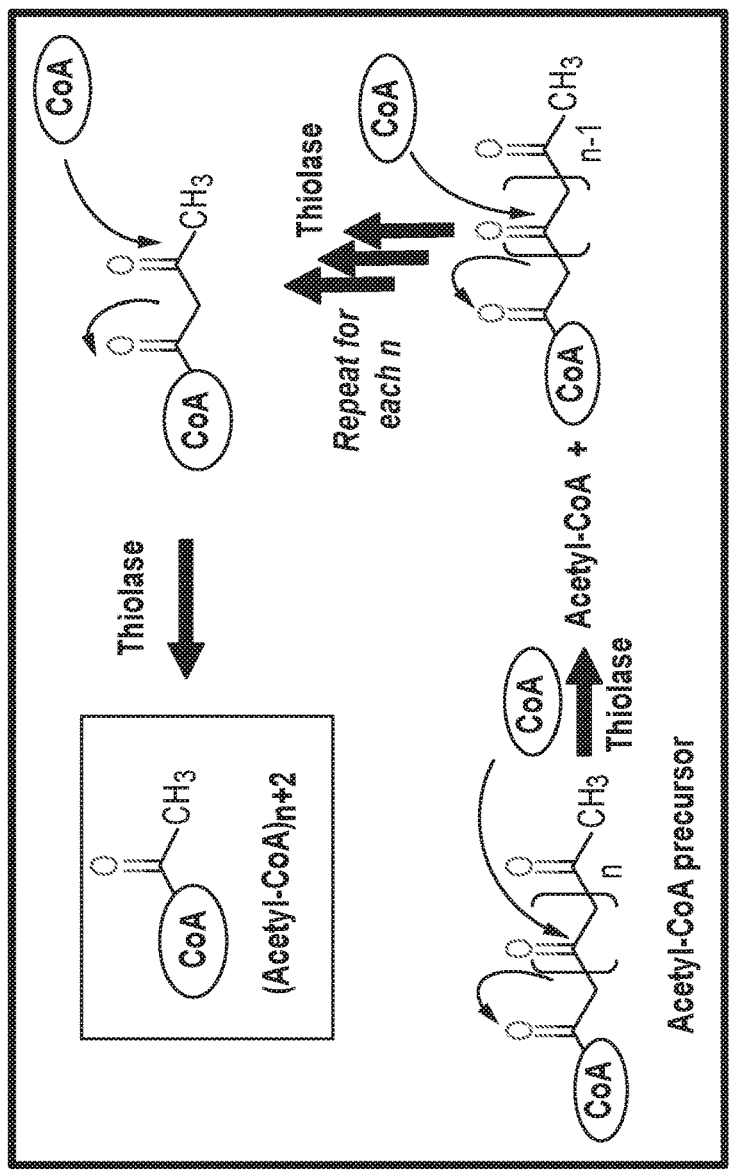
FIG. 2 is a schematic overview of a compound of the present disclosure being converted into more than two equivalents of acetyl-CoA.

In some aspects, the present disclosure provides, inter alia, a compound of Formula (I') or (II'-0):

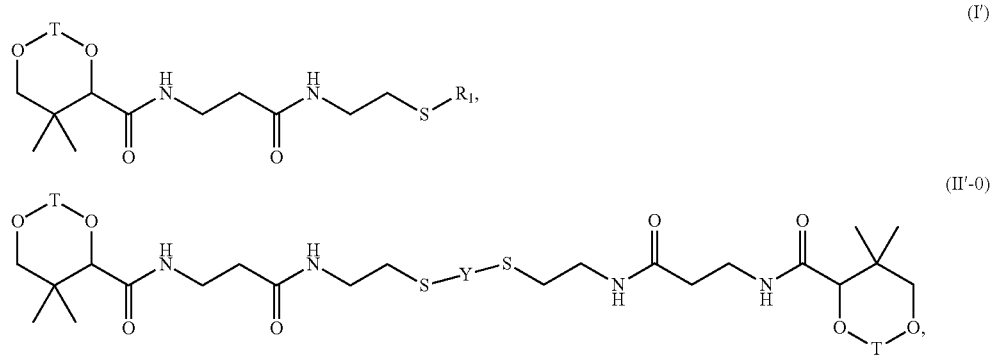

or a pharmaceutically acceptable salt or solvate thereof, wherein:
each T is independently

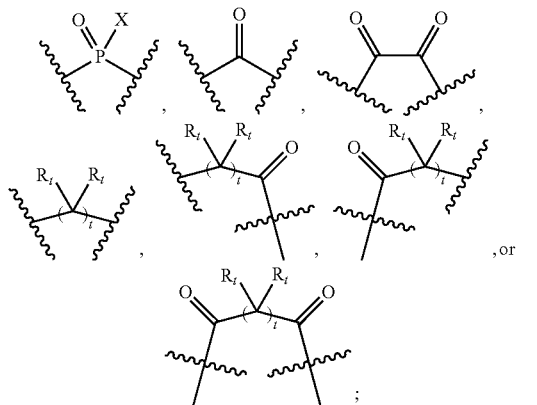
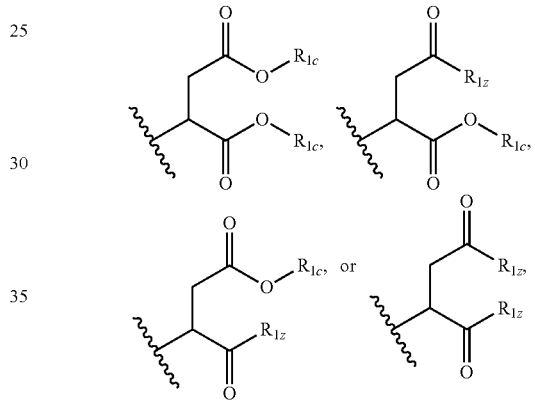

each $R_t$ is independently $R_1$, $R_{1a}$, $R_{1b}$ or $R_{1c}$; or two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$;
t is an integer ranging from 0 to 5;
$R_1$ is H, $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_n$—$R_{1a}$, —C(=O)CH$_2$—[C(=O)CH$_2$]$_p$—[CH$_2$]$_q$—$R_{1a}$, —C(=O)CH($R_{1a}$)—[C(=O)CH($R_{1a}$)]$_p$—[CH$_2$]$_q$—$R_{1a}$, —C(=O)CH$_2$—[CH(O$R_{1c}$)—CH$_2$]$_p$—[CH$_2$]$_q$—$R_{1a}$, —C(=O)CH$_2$—[C(=O)CH$_2$]$_p$—[CH(O$R_{1c}$)—CH$_2$]$_r$[CH$_2$]$_q$—$R_{1a}$, —C(=O)CH$_2$—[CH(O$R_{1c}$)—CH$_2$]$_r$—[C(=O)CH$_2$]$_p$—[CH$_2$]$_q$—$R_{1a}$, —C(=O)O$R_{1c}$, —C(=O)N($R_{1c}$)$_2$, —C(=O)—CH=CH—C(=O)O$R_{1c}$, —C(=O)—[CH$_2$]$_q$—C(=O)O$R_{1c}$, —C(=O)—CH$_2$CH$_2$—C(=O)O$R_{1c}$, —C(=O)CH$_2$—[C(=O)CH$_2$]$_p$—[CH$_2$]$_q$—C(=O))O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$, —S$R_{1d}$, wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties;

each $R_{1a}$ is independently H, oxo, halogen, $C_1$-$C_{20}$ alkyl, $C_2$-$C_{20}$ alkenyl, —O$R_{1c}$, —C(=O)O$R_{1c}$, —C(=O)N($R_{1c}$)$_2$, —N($R_{1c}$)$_2$, —N($R_{1c}$)C(=O)$R_{1b}$, —N($R_{1c}$)C(=O)$R_{1z}$, —N($R_{1c}$)C(=O)O$R_{1c}$, —OC(=O)$R_{1b}$, —OC(=O)$R_{1z}$, —OC(=O)O$R_{1c}$, —OSi($R_{1g}$)$_3$, —SC(=O)$_{1b}$, —SC(=O)$R_{1z}$, —SC(=O)O$R_{1c}$, —SC(=O)N($R_{1c}$)$_2$, —C(=O)$R_{1b}$, —C(=O)$R_{1z}$, —S$R_{1d}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;

each $R_{1b}$ is independently H, $C_1$-$C_{20}$ alkyl, $C_2$-$C_{20}$ alkenyl, $C_2$-$C_{20}$ alkynyl, —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=CH—C(=O)O$R_{1c}$, —C(=O)O$R_{1c}$, —C(=O)N($R_{1c}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;

each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-

$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$; or two $R_{1c}$ together with the one or more intervening atoms to which they are connected, form $C_3$-$C_{12}$ cycloalkyl or $C_3$-$C_{12}$ heterocycloalkyl, wherein the $C_3$-$C_{12}$ cycloalkyl or $C_3$-$C_{12}$ heterocycloalkyl is optionally substituted with one or more $R_{1c}$;

each $R_{1d}$ is independently H, $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1e}$ is independently H, halogen, $C_1$-$C_{20}$ alkyl, $C_2$-$C_{20}$ alkenyl, $C_2$-$C_{20}$ alkynyl, —$OR_{1g}$, —C(=O)$OR_{1g}$, —C(=O)N($R_{1g}$)$_2$, —N($R_{1g}$)$_2$, —N($R_{1g}$)C(=O)$R_{1f}$, —N($R_{1g}$)C(=O)$R_{1z}$, —N($R_{1g}$)C(=O)$OR_{1g}$, —OC(=O)$R_{1f}$, —OC(=O)$R_{1z}$, —OC(=O)$OR_{1g}$, —OSi($R_{1g}$)$_3$, —$SR_{1g}$, —$N^+(R_{1g})_3$, —SC(=O)$R_{1f}$, —SC(=O)$R_{1z}$, —SC(=O)$OR_{1g}$, —SC(=O)N($R_{1g}$)$_2$, —C(=O)$R_{1f}$, —C(=O)$R_{1z}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1f}$ is independently H, $C_1$-$C_{20}$ alkyl, $C_2$-$C_{20}$ alkenyl, $C_2$-$C_{20}$ alkynyl, —OSi($R_{1g}$)$_3$, —$CH_2$C(=O)$OR_{1g}$, —CH=CH—C(=O)$OR_{1g}$, —C(=O)$OR_{1g}$, —C(=O)N($R_{1g}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1g}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1z}$;

each $R_{1z}$ is independently

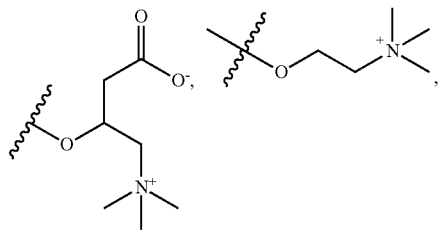

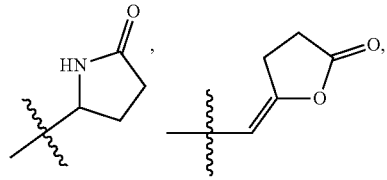

-continued

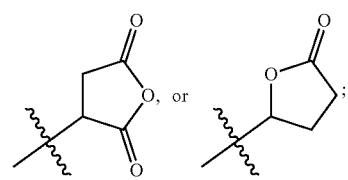

each n is independently an integer ranging from 0 to 20;

each p is independently an integer ranging from 0 to 20;

each q is independently an integer ranging from 0 to 20;

each r is independently an integer ranging from 0 to 20;

each X is independently —$OR_{1c}$, —N($R_{1c}$)$_2$,

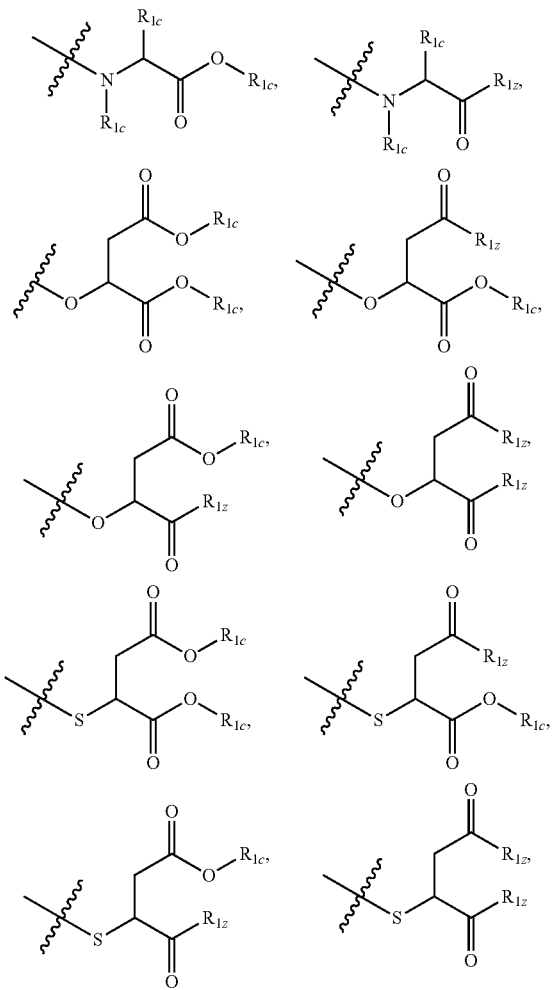

-continued

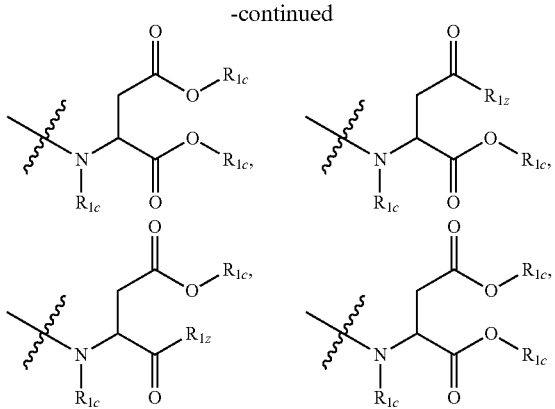

or $R_{1z}$; and

Y is a bond or $C_1$-$C_{20}$ alkyl optionally substituted with one or more $R_{1e}$.

In some aspects, the present disclosure provides a compound of Formula (I') or (II'):

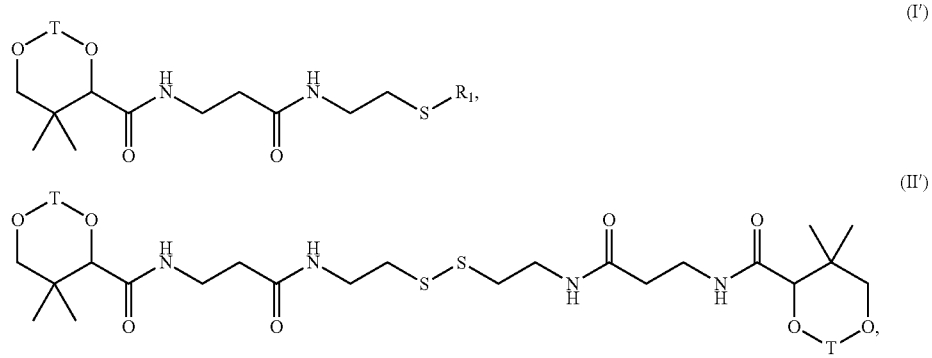

or a pharmaceutically acceptable salt or solvate thereof, wherein:

each T is independently

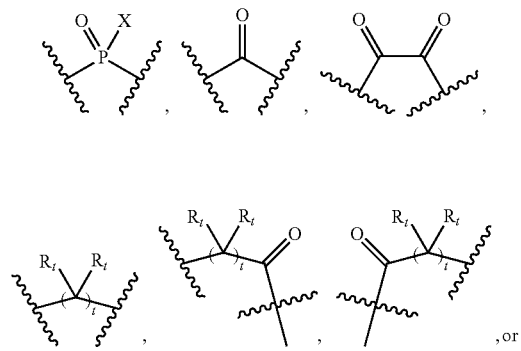

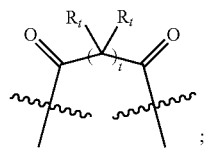

;

each $R_t$ is independently $R_1$, $R_{1a}$, or $R_{1b}$; or two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$;

t is an integer ranging from 0 to 5;

$R_1$ is H, $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_n$—$R_{1a}$, —C(=O)CH$_2$—[C(=O)CH$_2$]$_p$—[CH$_2$]$_q$—$R_{1a}$, —C(=O)CH($R_{1a}$)—[C(=O)CH($R_{1a}$)]$_p$—[CH$_2$]$_q$—$R_{1a}$, —C(=O)CH$_2$—[CH(O$R_{1c}$)—CH$_2$]$_p$—[CH$_2$]$_q$—$R_{1a}$, —C(=O)CH$_2$—[C(=O)CH$_2$]$_p$—[CH(O$R_{1c}$)—CH$_2$]$_r$[CH$_2$]$_q$—$R_{1a}$, —C(=O)CH$_2$—[CH(O$R_{1c}$)—CH$_2$]$_r$—[C(=O)CH$_2$]$_p$—[CH$_2$]$_q$—$R_{1a}$, —C(=O)O$R_{1c}$, —C(=O)N($R_{1c}$)$_2$, —C(=O)—CH=CH—C(=O)O$R_{1c}$, —C(=O)—[CH$_2$]$_q$—C(=O)O$R_{1c}$, —C(=O)—CH$_2$CH$_2$—C(=O)O$R_{1c}$, —C(=O)CH$_2$—[C(=O)CH$_2$]$_p$—[CH$_2$]$_q$—C(=O)O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$, —S$R_{1d}$,

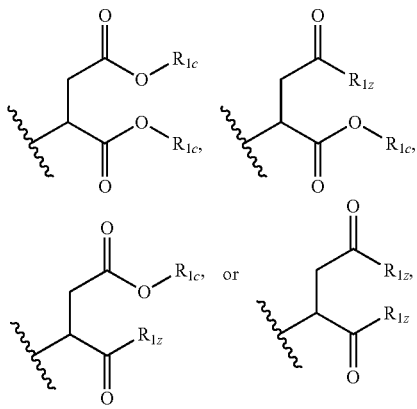

wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties;

each $R_{1a}$ is independently H, oxo, halogen, $C_1$-$C_{20}$ alkyl, $C_2$-$C_{20}$ alkenyl, —O$R_{1c}$, —C(=O)O$R_{1c}$, —C(=O)N($R_{1c}$)$_2$, —N($R_{1c}$)$_2$, —N($R_{1c}$)C(=O)$R_{1b}$, —N($R_{1c}$)C(=O)$R_{1z}$, —N($R_{1c}$)C(=O)O$R_{1c}$, —OC(=O)$R_{1b}$, —OC(=O)$R_{1z}$, —OC(=O)O$R_{1c}$, —SC(=O)$R_{1b}$, —SC(=O)R$_{1z}$, —SC(=O)OR$_{1c}$, —SC(=O)N(R$_{1c}$)$_2$, —C(=O)R$_{1b}$, —C(=O)R$_{1z}$, —SR$_{1d}$, or R$_{1g}$, wherein the C$_1$-C$_{20}$ alkyl, C$_2$-C$_{20}$ alkenyl, or C$_2$-C$_{20}$ alkynyl is optionally substituted with one or more R$_{1d}$;

each R$_{1b}$ is independently H, C$_1$-C$_{20}$ alkyl, C$_2$-C$_{20}$ alkenyl, C$_2$-C$_{20}$ alkynyl, —(CH$_2$)$_q$—C(=O)OR$_{1c}$, —CH$_2$—C(=O)—(CH$_2$)$_q$—C(=O)OR$_{1c}$, —CH$_2$—[C(=O)CH$_2$]$_p$—[CH$_2$]$_q$—C(=O)OR$_{1c}$, —CH=CH—C(=O)OR$_{1c}$, —C(=O)OR$_{1c}$, —C(=O)N(R$_{1c}$)$_2$, or R$_{1z}$, wherein the C$_1$-C$_{20}$ alkyl, C$_2$-C$_{20}$ alkenyl, or C$_2$-C$_{20}$ alkynyl is optionally substituted with one or more R$_{1c}$;

each R$_{1c}$ is independently H, C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl), wherein the C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) is optionally substituted with one or more R$_{1e}$;

each R$_{1d}$ is independently H, C$_1$-C$_{20}$ alkyl, C$_2$-C$_{20}$ alkenyl, C$_2$-C$_{20}$ alkynyl, C$_3$-C$_{10}$ cycloalkyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl), wherein the C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) is optionally substituted with one or more R$_{1e}$;

each R$_{1e}$ is independently H, halogen, C$_1$-C$_{20}$ alkyl, C$_2$-C$_{20}$ alkenyl, C$_2$-C$_{20}$ alkynyl, —OR$_{1g}$, —C(=O)OR$_{1g}$, —C(=O)N(R$_{1g}$)$_2$, —N(R$_{1g}$)$_2$, —N(R$_{1g}$)C(=O)R$_{1f}$, —N(R$_{1g}$)C(=O)R$_{1z}$, —N(R$_{1g}$)C(=O)OR$_{1g}$, —OC(=O)R$_{1f}$, —OC(=O)R$_{1z}$, —OC(=O)OR$_{1g}$, —SR$_{1g}$, —N$^+$(R$_{1g}$)$_3$, —SC(=O)R$_{1f}$, —SC(=O)R$_{1z}$, —SC(=O)OR$_{1g}$, —SC(=O)N(R$_{1g}$)$_2$, —C(=O)R$_{1c}$, —C(=O)R$_{1z}$, or R$_{1z}$, wherein the C$_1$-C$_{20}$ alkyl, C$_2$-C$_{20}$ alkenyl, or C$_2$-C$_{20}$ alkynyl is optionally substituted with one or more R$_{1z}$;

each R$_{1f}$ is independently H, C$_1$-C$_{20}$ alkyl, C$_2$-C$_{20}$ alkenyl, C$_2$-C$_{20}$ alkynyl, —CH$_2$C(=O)OR$_{1g}$, —CH=CH—C(=O)OR$_{1g}$, —C(=O)OR$_{1g}$, —C(=O)N(R$_{1g}$)$_2$, or R$_{1z}$, wherein the C$_1$-C$_{20}$ alkyl, C$_2$-C$_{20}$ alkenyl, or C$_2$-C$_{20}$ alkynyl is optionally substituted with one or more R$_{1z}$;

each R$_{1g}$ is independently H, C$_1$-C$_{20}$alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl), wherein the C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) is optionally substituted with one or more R$_{1z}$;

each R$_{1z}$ is independently

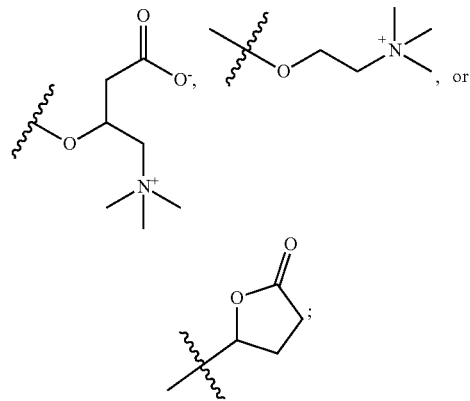

each n is independently an integer ranging from 0 to 20;
each p is independently an integer ranging from 0 to 20;
each q is independently an integer ranging from 0 to 20;
each r is independently an integer ranging from 0 to 20; and
each X is independently —OR$_{1c}$, —SR$_{1c}$, —N(R$_{1c}$)$_2$,

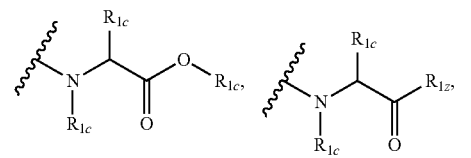

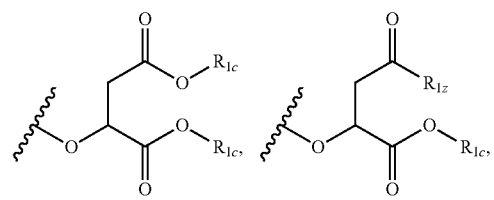

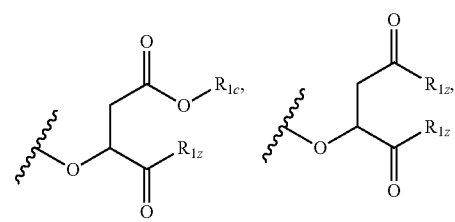

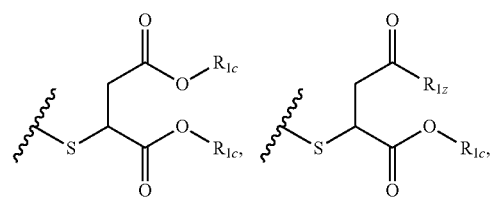

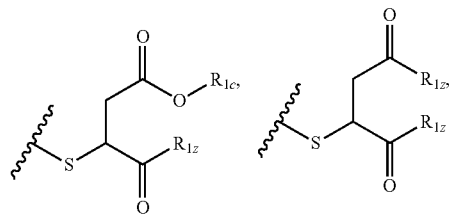

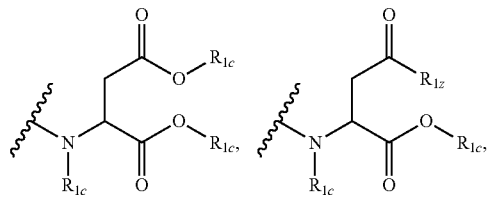 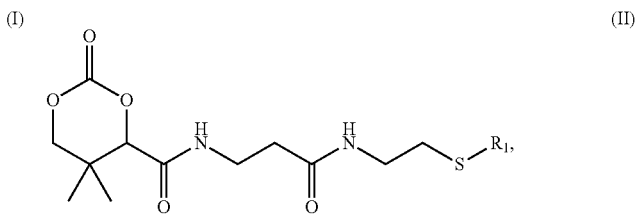

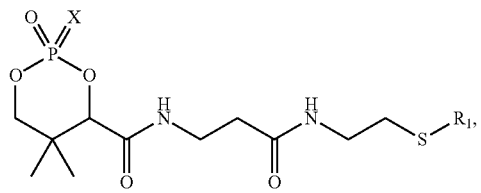

or $R_{1z}$.

It is understood that, for a compound of Formula (I') or (II'), T, $R_t$, t, $R_1$, $R_{1a}$, $R_{1b}$, $R_{1g}$, $R_{1d}$, $R_{1e}$, $R_{1f}$, $R_{1g}$, $R_{1z}$, X, n, p, q, and r can each be, where applicable, selected from the groups described herein, and any group described herein for any of T, $R_t$, t, $R_1$, $R_{1a}$, $R_{1b}$, $R_{1c}$, $R_{1d}$, $R_{1e}$, $R_{1f}$, $R_{1g}$, $R_{1z}$, X, n, p, q, and r can be combined, where applicable, with any group described herein for one or more of the remainder of T, $R_t$, t, $R_1$, $R_{1a}$, $R_{1b}$, $R_{1c}$, $R_{1d}$, $R_{1e}$, $R_{1f}$, $R_{1g}$, $R_{1z}$, X, n, p, q, and r.

In some aspects, the present disclosure provides a compound of Formula (I), (II), (IV), (V), or (VI):

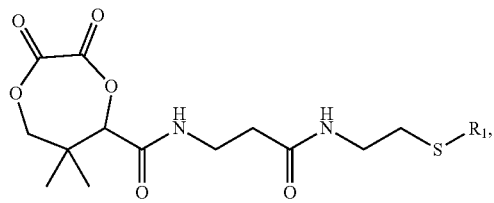

(III)

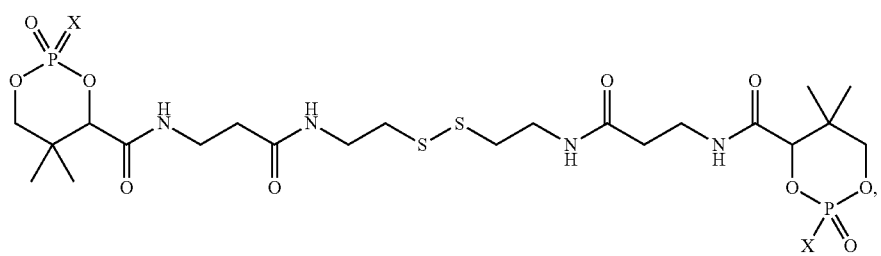

(IV)

(V)

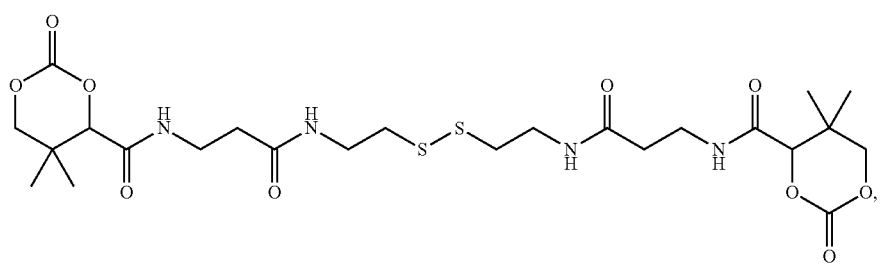

(VI)

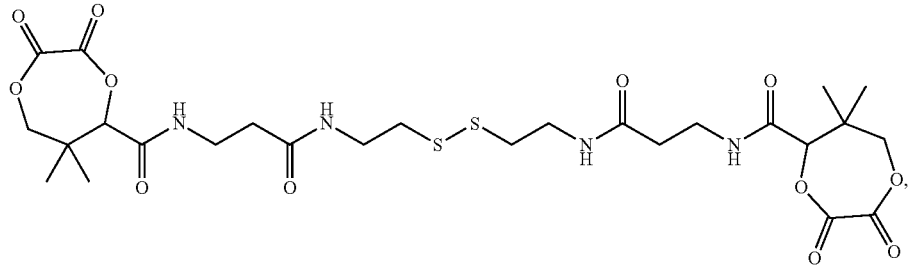

or a pharmaceutically acceptable salt or solvate thereof, wherein:

$R_1$ is H, $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_n$—$R_{1a}$, C(=O)CH$_2$—[C(=O)CH$_2$]$_p$—[CH$_2$]$_q$—$R_{1a}$, —C(=O)CH$_2$—[CH(OR$_{1c}$)—CH$_2$]$_p$—[CH$_2$]$_q$—$R_{1a}$, —C(=O)CH$_2$—[C(=O)CH$_2$]$_p$—[CH(OR$_{1c}$)—CH$_2$]$_r$—[CH$_2$]$_q$—$R_{1a}$, —C(=O)CH$_2$—[CH(OR$_{1c}$)—CH$_2$]$_r$—[C(=O)CH$_2$]$_p$—[CH$_2$]$_q$—$R_{1a}$, —C(=O)OR$_{1c}$, —C(=O)N(R$_{1c}$)$_2$, —C(=O)—CH=CH—C(=O)OR$_{1c}$, —C(=O)—[CH$_2$]$_q$—C(=O)OR$_{1c}$, —C(=O)—CH$_2$CH$_2$—C(=O)OR$_{1c}$, —C(=O)CH$_2$—[C(=O)CH$_2$]$_p$—[CH$_2$]$_q$—C(=O)OR$_{1c}$, —C(=O)—[CH$_2$]$_q$—C(=O)R$_{1z}$, —C(=O)—CH$_2$CH$_2$—C(=O)R$_{1z}$, C(=O)CH$_2$—[C(=O)CH$_2$]$_p$—[CH$_2$]$_q$—C(=O)R$_{1z}$, —SR$_{1d}$,

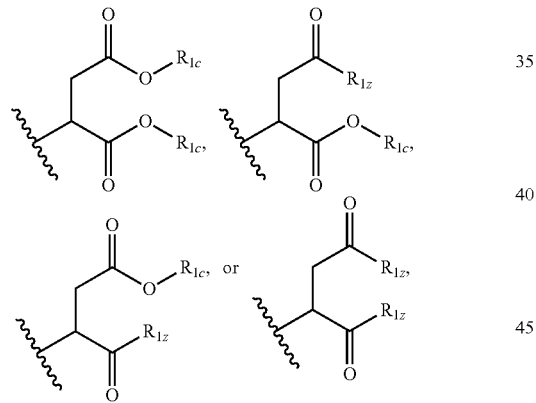

wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties;

each $R_{1a}$ is independently H, oxo, halogen, $C_1$-$C_{20}$ alkyl, $C_2$-$C_{20}$ alkenyl, —OR$_{1c}$, —C(=O)OR$_{1c}$, —C(=O)N(R$_{1c}$)$_2$, —N(R$_{1c}$)$_2$, —N(R$_{1c}$)C(=O)R$_{1b}$, —N(R$_{1c}$)C(=O)R$_{1z}$, —N(R$_{1c}$)C(=O)OR$_{1c}$, —OC(=O)R$_{1b}$, —OC(=O)R$_{1z}$, —OC(=O)OR$_{1c}$, —SC(=O)R$_{1b}$, —SC(=O)R$_{1z}$, —SC(=O)OR$_{1c}$, —SC(=O)N(R$_{1c}$)$_2$, —C(=O)R$_{1b}$, —C(=O)R$_{1z}$, —SR$_{1d}$, or R$_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;

each $R_{1b}$ is independently H, $C_1$-$C_{20}$ alkyl, $C_2$-$C_{20}$ alkenyl, $C_2$-$C_{20}$ alkynyl, —(CH$_2$)$_q$—C(=O)OR$_{1c}$, —CH$_2$—C(=O)—(CH$_2$)$_q$—C(=O)OR$_{1c}$, —CH$_2$—[C(=O)CH$_2$]$_p$—[CH$_2$]$_q$—C(=O)OR$_{1c}$, —CH=CH—C(=O)OR$_{1c}$, —C(=O)OR$_{1c}$, —C(=O)N(R$_{1c}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1c}$;

each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1d}$ is independently H, $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1c}$;

each $R_{1e}$ is independently H, halogen, $C_1$-$C_{20}$ alkyl, $C_2$-$C_{20}$ alkenyl, $C_2$-$C_{20}$ alkynyl, —OR$_{1g}$, —C(=O)OR$_{1g}$, —C(=O)N(R$_{1g}$)$_2$, —N(R$_{1g}$)$_2$, —N(R$_{1g}$)C(=O)R$_{1f}$, —N(R$_{1g}$)C(=O)R$_{1z}$, —N(R$_{1g}$)C(=O)OR$_{1g}$, —OC(=O)R$_{1f}$, —OC(=O)R$_{1z}$, —OC(=O)OR$_{1g}$, —SR$_{1g}$, —N$^+$(R$_{1g}$)$_3$, —SC(=O)R$_{1f}$, —SC(=O)R$_{1z}$, —SC(=O)OR$_{1g}$, —SC(=O)N(R$_{1g}$)$_2$, —C(=O)R$_{1f}$, —C(=O)R$_{1z}$, or R$_{1g}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1f}$ is independently H, $C_1$-$C_{20}$ alkyl, $C_2$-$C_{20}$ alkenyl, $C_2$-$C_{20}$ alkynyl, —CH$_2$C(=O)OR$_{1g}$, —CH=CH—C(=O)OR$_{1g}$, —C(=O)OR$_{1g}$, —C(=O)N(R$_{1g}$)$_2$, or R$_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1g}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1z}$;

each $R_{1z}$ is independently

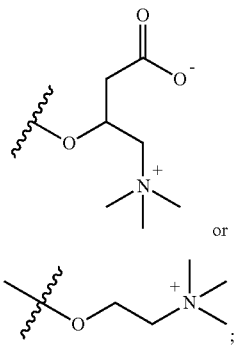

or

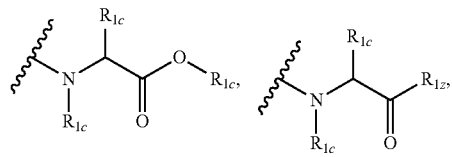

;

each n is independently an integer ranging from 0 to 20;
each p is independently an integer ranging from 0 to 20;
each q is independently an integer ranging from 0 to 20;
each r is independently an integer ranging from 0 to 20; and
each X is independently —$OR_{1c}$, —$SR_{1c}$, —$N(R_{1c})_2$,

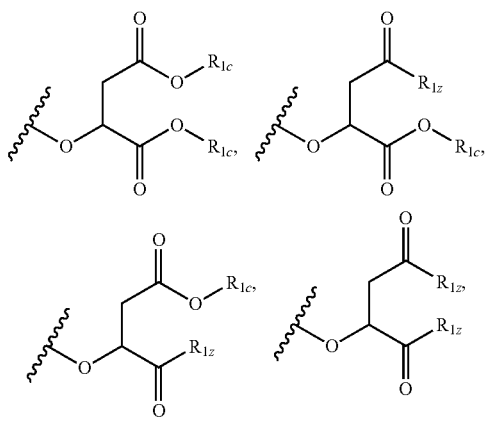

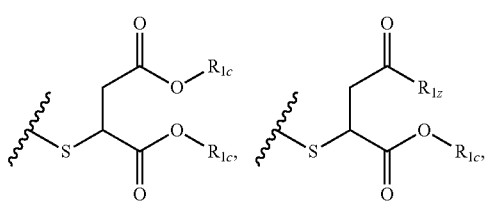

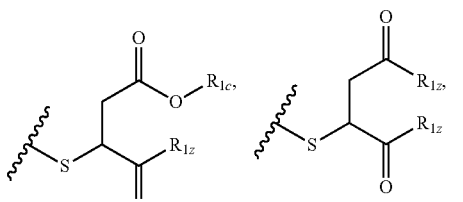

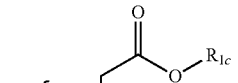
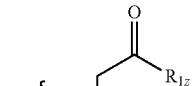

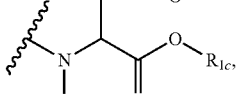
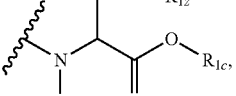

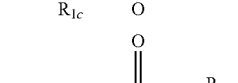
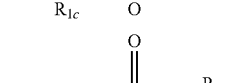

or $R_{1z}$.

It is understood that, for a compound of Formula (T), (II), (III), (IV), (V), or (VI), $R_1$, $R_{1a}$, $R_{1b}$, $R_{1c}$, $R_{1d}$, $R_{1e}$, $R_{1f}$, $R_{1g}$, $R_{1z}$, X, n, p, q, and r can each be, where applicable, selected from the groups described herein, and any group described herein for any of $R_1$, $R_{1a}$, $R_{1b}$, $R_{1c}$, $R_{1d}$, $R_{1e}$, $R_{1f}$, $R_{1g}$, $R_{1z}$, X, n, p, q, and r can be combined, where applicable, with any group described herein for one or more of the remainder of $R_1$, $R_{1a}$, $R_{1b}$, $R_{1c}$, $R_{1d}$, $R_{1e}$, $R_{1f}$, $R_{1g}$, $R_{1z}$, X, n, p, q, and r.

Variable T

In some embodiments, T is

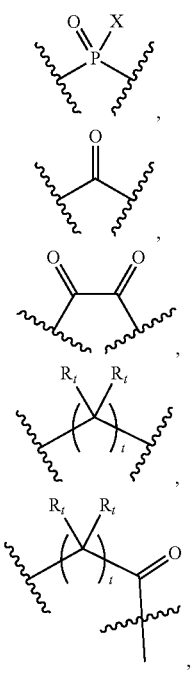

-continued
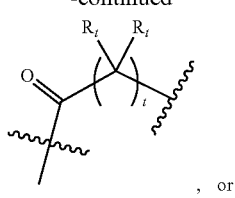
, or
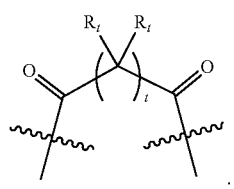
In some embodiments, T is
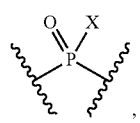
,
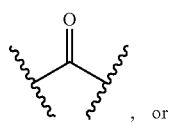
, or
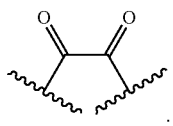 [SMILES: *C(=O)C(*)=O]
In some embodiments, T is
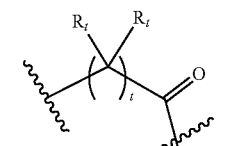
,
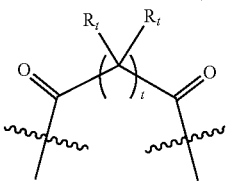
, or
In some embodiments, T is
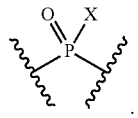
.
In some embodiments, T is
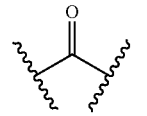
or
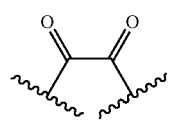
.
In some embodiments, T is
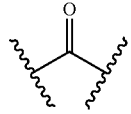
.
In some embodiments, T is
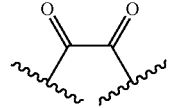
.
In some embodiments, T is
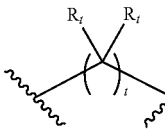
.
In some embodiments, T is
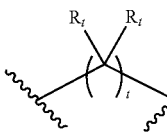
,
and t is an integer ranging from 1 to 5.

In some embodiments, T is

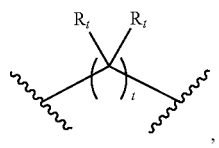, and each $R_t$ is independently $R_1$, $R_{1a}$, or $R_{1b}$.

In some embodiments, T is

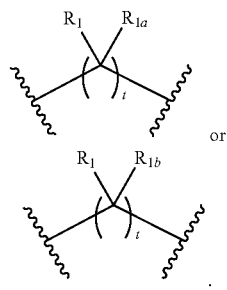

or

In some embodiments, T is

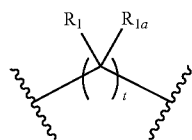

In some embodiments, T is

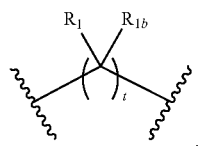

In some embodiments, T is

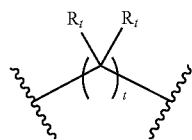, and two $R_t$, together with the one or more intervening atoms they are attached to, form a $C_3$-$C_{12}$ cycloalkyl or $C_3$-$C_{12}$ heterocycloalkyl.

In some embodiments, T is

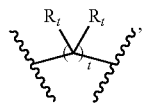, and two $R_t$, together with the one or more intervening atoms they are attached to, form a $C_3$-$C_{12}$ cycloalkyl.

In some embodiments, T is

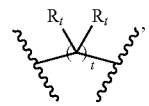, and two $R_t$, together with the one or more intervening atoms they are attached to, form a $C_3$-$C_{12}$ heterocycloalkyl.

In some embodiments, T is

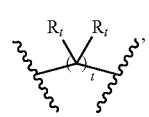, and two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

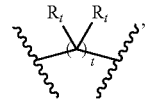, and two $R_t$, together with the one or more intervening atoms they are attached to, form a $C_3$-$C_{12}$ cycloalkyl optionally substituted with one or more $R_{1a}$.

In some embodiments, T is

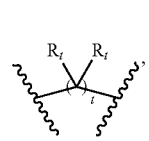, and two $R_t$, together with the one or more intervening atoms they are attached to, form a $C_3$-$C_{12}$ heterocycloalkyl optionally substituted with one or more $R_{1a}$.

In some embodiments, T is

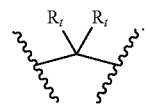.

In some embodiments, T is

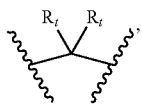

and each $R_t$ is independently $R_1$, $R_{1a}$, or $R_{1b}$.

In some embodiments, T is

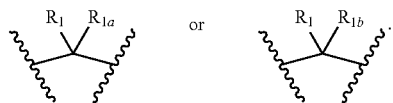

In some embodiments, T is

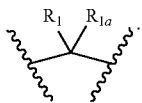

In some embodiments, T is

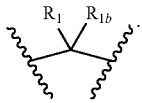

In some embodiments, T is

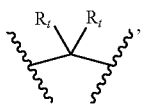

and two $R_t$, together with the carbon atom they are attached to, form a $C_3$-$C_{12}$ cycloalkyl or $C_3$-$C_{12}$ heterocycloalkyl.

In some embodiments, T is

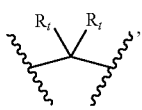

and two $R_t$, together with the carbon atom they are attached to, form a $C_3$-$C_{12}$ cycloalkyl.

In some embodiments, T is

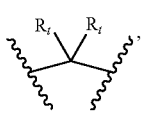

and two $R_t$, together with the carbon atom they are attached to, form a $C_3$-$C_{12}$ heterocycloalkyl.

In some embodiments, T is

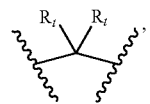

and two $R_t$, together with the carbon atom they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

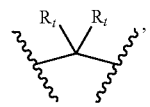

and two $R_t$, together with the carbon atom they are attached to, form a $C_3$-$C_{12}$ heterocycloalkyl optionally substituted with one or more $R_{1a}$.

In some embodiments, T is

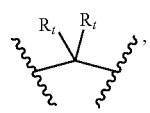

and two $R_t$, together with the carbon atom they are attached to, form a $C_3$-$C_{12}$ cycloalkyl optionally substituted with one or more $R_{1a}$.

In some embodiments, T is

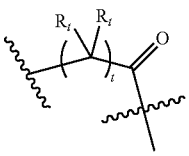

In some embodiments, T is

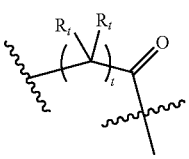

and t is an integer ranging from 1 to 5.

In some embodiments, T is

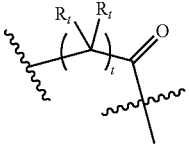

and each $R_t$ is independently $R_1$, $R_{1a}$, or $R_{1b}$.

In some embodiments, T is

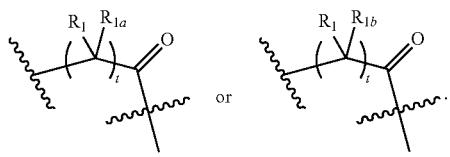

or

In some embodiments, T is

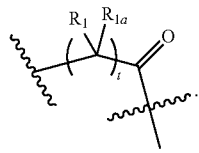

In some embodiments, T is

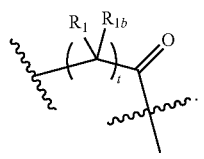

In some embodiments, T is

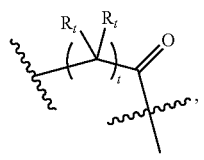

and two $R_t$, together with the one or more intervening atoms they are attached to, form a $C_3$-$C_{12}$ cycloalkyl or $C_3$-$C_{12}$ heterocycloalkyl.

In some embodiments, T is

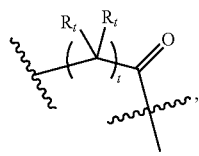

and two $R_t$, together with the one or more intervening atoms they are attached to, form a $C_3$-$C_{12}$ cycloalkyl.

In some embodiments, T is

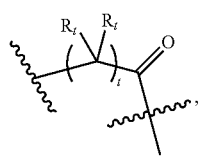

and two $R_t$, together with the one or more intervening atoms they are attached to, form a $C_3$-$C_{12}$ heterocycloalkyl.

In some embodiments, T is

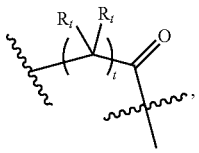

and two $R_1$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

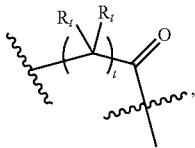

and two $R_t$, together with the one or more intervening atoms they are attached to, form a $C_3$-$C_{12}$ cycloalkyl optionally substituted with one or more $R_{1a}$.

In some embodiments, T is

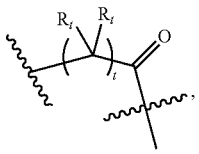

and two $R_t$, together with the one or more intervening atoms they are attached to, form a $C_3$-$C_{12}$ heterocycloalkyl optionally substituted with one or more $R_{1a}$.

In some embodiments, T is

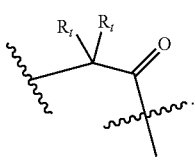

In some embodiments, T is

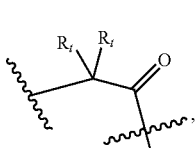

and each $R_1$ is independently $R_1$, $R_{1a}$, or $R_{1b}$.

In some embodiments, T is

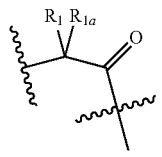 or 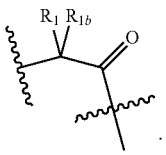.

In some embodiments, T is

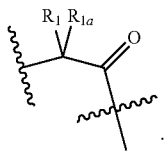.

In some embodiments, T is

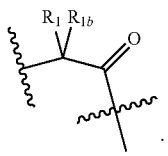.

In some embodiments, T is

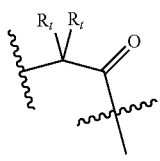, and two $R_t$, together with the carbon atom they are attached to, form a $C_3$-$C_{12}$ cycloalkyl or $C_3$-$C_{12}$ heterocycloalkyl.

In some embodiments, T is

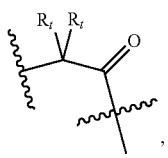, and two $R_t$, together with the carbon atom they are attached to, form a $C_3$-$C_{12}$ cycloalkyl.

In some embodiments, T is

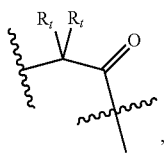, and two $R_t$, together with the carbon atom they are attached to, form a $C_3$-$C_{12}$ heterocycloalkyl.

In some embodiments, T is

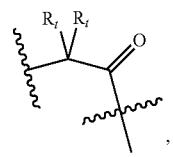, and two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

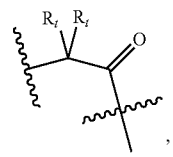, and two $R_t$, together with the one or more intervening atoms they are attached to, form a $C_3$-$C_{12}$ cycloalkyl optionally substituted with one or more $R_{1a}$.

In some embodiments, T is

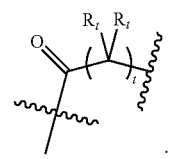, and two $R_t$, together with the one or more intervening atoms they are attached to, form a $C_3$-$C_{12}$ heterocycloalkyl optionally substituted with one or more $R_{1a}$.

In some embodiments, T is

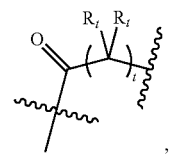, and t is an integer ranging from 1 to 5.

In some embodiments, T is

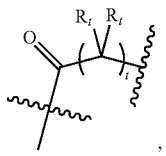

, and each $R_t$ is independently $R_1$, $R_{1a}$, or $R_{1b}$.

In some embodiments, T is

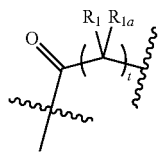 or 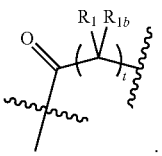 .

In some embodiments, T is

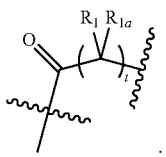 .

In some embodiments, T is

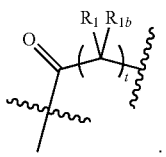 .

In some embodiments, T is

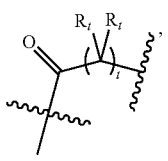 , and two $R_t$, together with the one or more intervening atoms they are attached to, form a $C_3$-$C_{12}$ cycloalkyl or $C_3$-$C_{12}$ heterocycloalkyl.

In some embodiments, T is

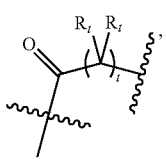 , and two $R_t$, together with the one or more intervening atoms they are attached to, form a $C_3$-$C_{12}$ cycloalkyl.

In some embodiments, T is

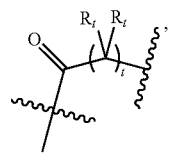 , and two $R_t$, together with the one or more intervening atoms they are attached to, form a $C_3$-$C_{12}$ heterocycloalkyl.

In some embodiments, T is

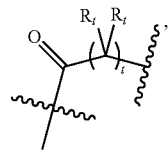 , and two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

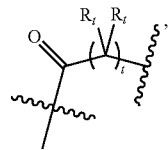 , and two $R_t$, together with the one or more intervening atoms they are attached to, form a $C_3$-$C_{12}$ cycloalkyl optionally substituted with one or more $R_{1a}$.

In some embodiments, T is

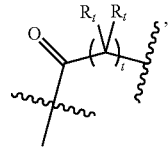 , and two $R_t$, together with the one or more intervening atoms they are attached to, form a $C_3$-$C_{12}$ heterocycloalkyl optionally substituted with one or more $R_{1a}$.

In some embodiments, T is

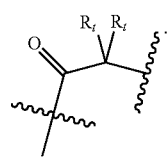 .

In some embodiments, T is

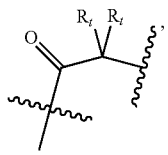

and each $R_t$ is independently $R_1$, $R_{1a}$, or $R_{1b}$.

In some embodiments, T is

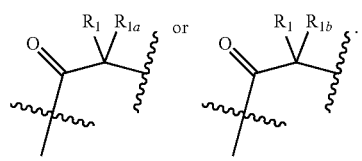

In some embodiments, T is

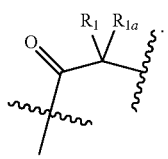

In some embodiments, T is

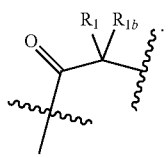

and two $R_t$, together with the carbon atom they are attached to, form a $C_3$-$C_{12}$ cycloalkyl or $C_3$-$C_{12}$ heterocycloalkyl.

In some embodiments, T is

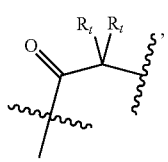

and two $R_t$, together with the carbon atom they are attached to, form a $C_3$-$C_{12}$ cycloalkyl.

In some embodiments, T is

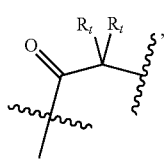

and two $R_t$, together with the carbon atom they are attached to, form a $C_3$-$C_{12}$ cycloalkyl.

In some embodiments, T is

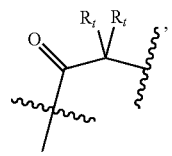

and two $R_t$, together with the carbon atom they are attached to, form a $C_3$-$C_{12}$ heterocycloalkyl.

In some embodiments, T is

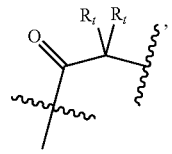

and two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

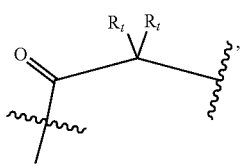

and two $R_t$, together with the one or more intervening atoms they are attached to, form a $C_3$-$C_{12}$ cycloalkyl optionally substituted with one or more $R_{1a}$.

In some embodiments, T is

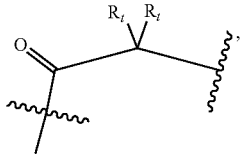

and two $R_t$, together with the one or more intervening atoms they are attached to, form a $C_3$-$C_{12}$ heterocycloalkyl optionally substituted with one or more $R_{1a}$.

In some embodiments, T is

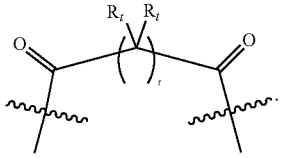

In some embodiments, T is

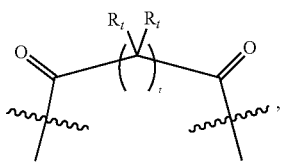

and t is an integer ranging from 1 to 5.

In some embodiments, T is

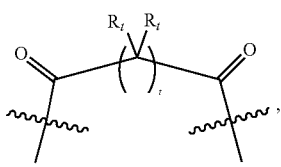

and each $R_t$ is independently $R_1$, $R_{1a}$, or $R_{1b}$.

In some embodiments, T is

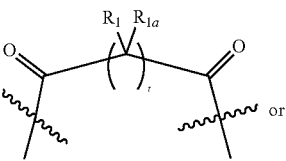

or

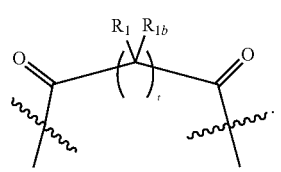

In some embodiments, T is

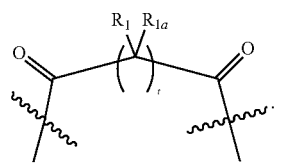

In some embodiments, T is

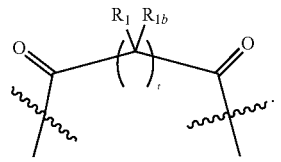

In some embodiments, T is

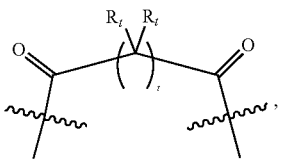

and two $R_t$, together with the one or more intervening atoms they are attached to, form a $C_3$-$C_{12}$ cycloalkyl or $C_3$-$C_{12}$ heterocycloalkyl.

In some embodiments, T is

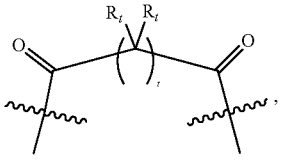

and two $R_t$, together with the one or more intervening atoms they are attached to, form a $C_3$-$C_{12}$ cycloalkyl.

In some embodiments, T is

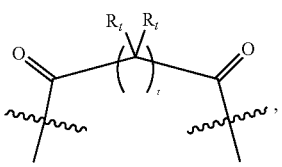

and two $R_t$, together with the one or more intervening atoms they are attached to, form a $C_3$-$C_{12}$ heterocycloalkyl.

In some embodiments, T is

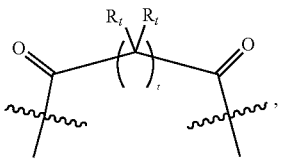

and two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

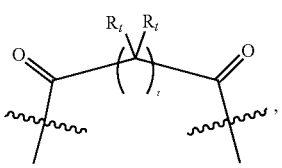

and two $R_t$, together with the one or more intervening atoms they are attached to, form a $C_3$-$C_{12}$ cycloalkyl optionally substituted with one or more $R_{1a}$ In some embodiments, T is

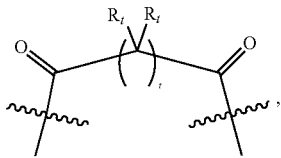

and two $R_t$, together with the one or more intervening atoms they are attached to, form a $C_3$-$C_{12}$ heterocycloalkyl optionally substituted with one or more $R_{1a}$.

In some embodiments, T is

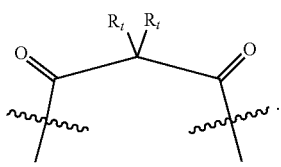

In some embodiments, T is

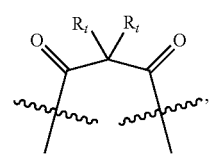

and each $R_t$ is independently $R_1$, $R_{1a}$, or $R_{1b}$.

In some embodiments, T is

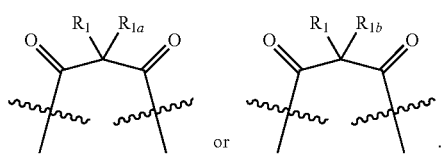

In some embodiments, T is

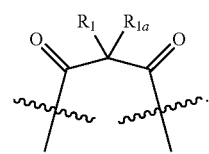

In some embodiments, T is

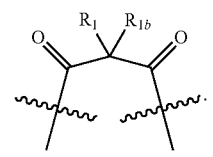

In some embodiments, T is

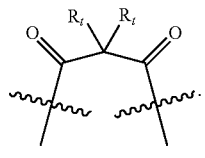

and two $R_t$, together with the carbon atom they are attached to, form a $C_3$-$C_{12}$ cycloalkyl or $C_3$-$C_{12}$ heterocycloalkyl.

In some embodiments, T is

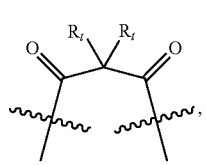

and two $R_t$, together with the carbon atom they are attached to, form a $C_3$-$C_{12}$ cycloalkyl.

In some embodiments, T is

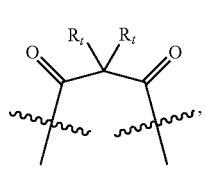

and two $R_t$, together with the carbon atom they are attached to, form a $C_3$-$C_{12}$ heterocycloalkyl.

In some embodiments, T is

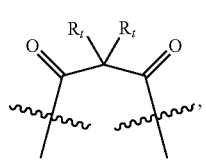

and two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more $R_{1a}$.

In some embodiments, T is

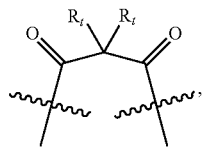

and two $R_t$, together with the one or more intervening atoms they are attached to, form a $C_3$-$C_{12}$ cycloalkyl optionally substituted with one or more $R_{1a}$.

In some embodiments, T is

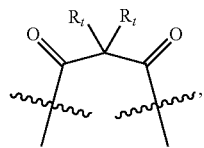

and two $R_t$, together with the one or more intervening atoms they are attached to, form a $C_3$-$C_{12}$ heterocycloalkyl optionally substituted with one or more $R_{1a}$.

In some embodiments, each T is independently

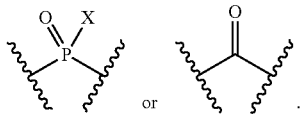

In some embodiments, each T is independently

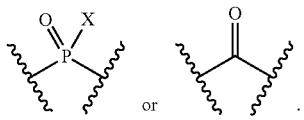

In some embodiments, each T is independently

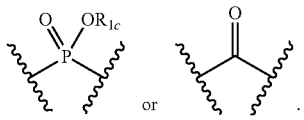

In some embodiments, each T is independently

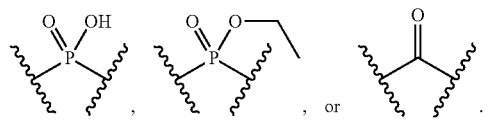

In some embodiments, each T is independently

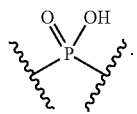 [SMILES: *P(*)(=O)O]

In some embodiments, each T is independently

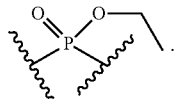 [SMILES: *P(*)(=O)OCC]

In some embodiments, each T is independently

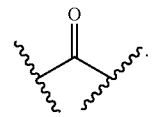 [SMILES: *C(*)=O]

Variable $R_t$

In some embodiments, at least one $R_t$ is $R_1$ or $R_{1a}$.
In some embodiments, at least one $R_t$ is $R_1$ or $R_{1b}$.
In some embodiments, at least one $R_t$ is $R_{1a}$ or $R_{1b}$.
In some embodiments, at least one $R_t$ is $R_1$.
In some embodiments, at least one $R_t$ is $R_{1a}$.
In some embodiments, at least one $R_t$ is $R_{1b}$.
In some embodiments, at least one $R_t$ is $R_1$, and at least one $R_t$ is $R_{1a}$.
In some embodiments, at least one $R_t$ is $R_1$, and at least one $R_t$ is $R_{1b}$.
In some embodiments, at least one $R_t$ is $R_{1a}$, and at least one $R_t$ is $R_{1b}$.
In some embodiments two $R_t$, together with the one or more intervening atoms they are attached to, form $C_3$-$C_{12}$ cycloalkyl or $C_3$-$C_{12}$ heterocycloalkyl.
In some embodiments two $R_t$, together with the one or more intervening atoms they are attached to, form $C_3$-$C_{12}$ cycloalkyl.
In some embodiments two $R_t$, together with the one or more intervening atoms they are attached to, form $C_3$-$C_{12}$ heterocycloalkyl.

Variable t

In some embodiments, t is an integer ranging from 0 to 5.
In some embodiments, t is 0.
In some embodiments, t is an integer ranging from 1 to 5.
In some embodiments, t is 1.
In some embodiments, t is 2.
In some embodiments, t is 3.
In some embodiments, t is 4.
In some embodiments, t is 5.

Variable $R_1$

In some embodiments, $R_1$ is H.
In some embodiments, $R_1$ is $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_n$—$R_{1a}$, —C(=O)CH$_2$—[C(=O)CH$_2$]$_p$—[CH$_2$]$_q$—$R_{1a}$, —C(=O)CH$_2$—[CH(OR$_{1c}$)—CH$_2$]$_p$—[CH$_2$]$_q$—$R_{1a}$, —C(=O)CH$_2$—[C(=O)CH$_2$]$_p$—[CH(OR$_{1c}$)—CH$_2$]$_r$[CH$_2$]$_q$—$R_{1a}$, —C(=O)CH$_2$—[CH(OR$_{1c}$)—CH$_2$]$_r$—[C(=O)CH$_2$]$_p$—[CH$_2$]$_q$—$R_{1a}$, —C(=O)OR$_{1c}$, —C(=O)N(R$_{1c}$)$_2$, —C(=O)—CH=CH—C(=O)OR$_{1c}$, —C(=O)—[CH$_2$]$_q$—C(=O)OR$_{1c}$, —C(=O)—CH$_2$CH$_2$—C(=O)OR$_{1c}$, —C(=O)CH$_2$—[C(=O)CH$_2$]$_p$—[CH$_2$]$_q$—C(=O)OR$_{1c}$, —C(=O)—[CH$_2$]$_q$—C(=O)R$_{1z}$, —C(=O)—CH$_2$CH$_2$—C(=O)R$_{1z}$, —C(=O)CH$_2$—[C(=O)CH$_2$]$_p$—[CH$_2$]$_q$—C(=O)R$_{1z}$, —SR$_{1d}$,

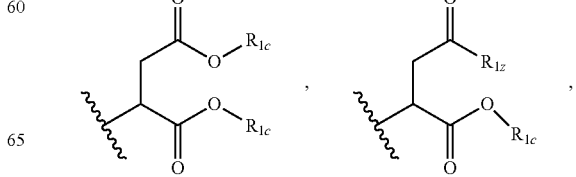

-continued wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties.

In some embodiments, $R_1$ is $C_1$-$C_{20}$ alkyl, $C_2$-$C_{20}$ alkenyl, $C_2$-$C_{20}$ alkynyl, —C(=O)$R_{1b}$, —C(=O)$R_{1z}$, —C(=O)—(CH=CH)$_u$—$R_{1a}$, —C(=O)CH$_2$—[C(=O)CH$_2$]$_p$—[CH$_2$]$_q$—$R_{1a}$, —C(=O)CH($R_{1a}$)—[C(=O)CH($R_{1a}$)]$_p$—[CH$_2$]q-$R_{1a}$, —C(=O)CH$_2$—[CH(O$R_{1c}$)—CH$_2$]$_p$—[CH$_2$]$_q$—$R_{1a}$, —C(=O)CH$_2$—[C(=O)CH$_2$]$_p$—[CH(O$R_{1c}$)—CH$_2$]$_r$[CH$_2$]$_q$—$R_{1a}$, —C(=O)CH$_2$—[CH(O$R_{1c}$)—CH$_2$]$_r$—[C(=O)CH$_2$]$_p$—[CH$_2$]$_q$—$R_{1a}$, —C(=O)O$R_{1c}$, —C(=O)N($R_{1c}$)$_2$, —C(=O)—CH=CH—C(=O)O$R_{1c}$, —C(=O)—[CH$_2$]$_q$—C(=O)O$R_{1c}$, —C(=O)—CH$_2$CH$_2$—C(=O)O$R_{1c}$, —C(=O)CH$_2$—[C(=O)CH$_2$]$_p$—[CH$_2$]$_q$—C(=O)O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$, —S$R_{1d}$, wherein the $C_1$-$C_{20}$ alkyl, $C_2$-$C_{20}$ alkenyl or $C_2$-$C_{20}$ alkynyl is optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties.

In some embodiments, $R_1$ is $C_1$-$C_{20}$ alkyl, $C_2$-$C_{20}$ alkenyl, or $C_2$-$C_{20}$ alkynyl optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties.

In some embodiments, $R_1$ is $C_1$-$C_{20}$ alkyl, $C_2$-$C_{20}$ alkenyl, or $C_2$-$C_{20}$ alkynyl substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are optionally replaced by one or more carbonyl moieties.

In some embodiments, $R_1$ is $C_1$-$C_{20}$ alkyl, $C_2$-$C_{20}$ alkenyl, or $C_2$-$C_{20}$ alkynyl optionally substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are replaced by one or more carbonyl moieties.

In some embodiments, $R_1$ is $C_1$-$C_{20}$ alkyl, $C_2$-$C_{20}$ alkenyl, or $C_2$-$C_{20}$ alkynyl substituted with one or more $R_{1a}$, and wherein one or more methylene moieties in the $C_1$-$C_{20}$ alkyl, $C_2$-$C_{20}$ alkenyl, or $C_2$-$C_{20}$ alkynyl are replaced by one or more carbonyl moieties.

In some embodiments, $R_1$ is $C_1$-$C_{20}$ alkyl (e.g., methyl, ethyl, propyl, butyl, pentyl, hexyl, or heptyl).

In some embodiments, $R_1$ is $C_1$-$C_{20}$ alkyl (e.g., methyl, ethyl, propyl, butyl, pentyl, hexyl, or heptyl) optionally substituted with one or more $R_{1a}$, and wherein one or more methylene moieties in the $C_1$-$C_{20}$ alkyl are optionally replaced by one or more carbonyl moieties.

In some embodiments, $R_1$ is $C_1$-$C_{20}$ alkyl (e.g., methyl, ethyl, propyl, butyl, pentyl, hexyl, or heptyl) substituted with one or more $R_{1a}$, and wherein one or more methylene moieties in the $C_1$-$C_{20}$ alkyl are optionally replaced by one or more carbonyl moieties.

In some embodiments, $R_1$ is $C_1$-$C_{20}$ alkyl (e.g., methyl, ethyl, propyl, butyl, pentyl, hexyl, or heptyl) optionally substituted with one or more $R_{1a}$, and wherein one or more methylene moieties in the $C_1$-$C_{20}$ alkyl are replaced by one or more carbonyl moieties.

In some embodiments, $R_1$ is $C_1$-$C_{20}$ alkyl (e.g., methyl, ethyl, propyl, butyl, pentyl, hexyl, or heptyl) substituted with one or more $R_{1a}$, and wherein one or more methylene moieties in the $C_1$-$C_{20}$ alkyl is by carbonyl moieties.

In some embodiments, $R_1$ is $C_2$-$C_{20}$ alkenyl (e.g., ethenyl, propenyl, butenyl, pentenyl, or hexenyl).

In some embodiments, $R_1$ is $C_2$-$C_{20}$ alkenyl (e.g., ethenyl, propenyl, butenyl, pentenyl, or hexenyl) optionally substituted with one or more $R_{1a}$, and wherein one or more methylene moieties in the $C_2$-$C_{20}$ alkenyl are optionally replaced by one or more carbonyl moieties.

In some embodiments, $R_1$ is $C_2$-$C_{20}$ alkenyl (e.g., ethenyl, propenyl, butenyl, pentenyl, or hexenyl) substituted with one or more $R_{1a}$, and wherein one or more methylene moieties in the $C_2$-$C_{20}$ alkenyl are optionally replaced by one or more carbonyl moieties.

In some embodiments, $R_1$ is $C_2$-$C_{20}$ alkenyl (e.g., ethenyl, propenyl, butenyl, pentenyl, or hexenyl) optionally substituted with one or more $R_{1a}$, and wherein one or more methylene moieties in the $C_2$-$C_{20}$ alkenyl are replaced by one or more carbonyl moieties.

In some embodiments, $R_1$ is $C_2$-$C_{20}$ alkenyl (e.g., ethenyl, propenyl, butenyl, pentenyl, or hexenyl) substituted with one or more $R_{1a}$, and wherein one or more methylene moieties in the $C_2$-$C_{20}$ alkenyl are replaced by one or more carbonyl moieties.

In some embodiments, $R_1$ is $C_2$-$C_{20}$ alkynyl (e.g., ethynyl, propynyl, butynyl, pentynyl, or hexynyl).

In some embodiments, $R_1$ is $C_2$-$C_{20}$ alkynyl (e.g., ethynyl, propynyl, butynyl, pentynyl, or hexynyl) optionally substituted with one or more $R_{1a}$, and wherein one or more methylene moieties in the $C_2$-$C_{20}$ alkenyl are optionally replaced by one or more carbonyl moieties.

In some embodiments, $R_1$ is $C_2$-$C_{20}$ alkynyl (e.g., ethynyl, propynyl, butynyl, pentynyl, or hexynyl) substituted with one or more $R_{1a}$, and wherein one or more methylene moieties in the $C_2$-$C_{20}$ alkenyl are optionally replaced by one or more carbonyl moieties.

In some embodiments, $R_1$ is $C_2$-$C_{20}$ alkynyl (e.g., ethynyl, propynyl, butynyl, pentynyl, or hexynyl) optionally substituted with one or more $R_{1a}$, and wherein one or more methylene moieties in the $C_2$-$C_{20}$ alkenyl are replaced by one or more carbonyl moieties.

In some embodiments, $R_1$ is $C_2$-$C_{20}$ alkynyl (e.g., ethynyl, propynyl, butynyl, pentynyl, or hexynyl) substituted with one or more $R_{1a}$, and wherein one or more methylene moieties in the $C_2$-$C_{20}$ alkenyl are replaced by one or more carbonyl moieties.

It is understood that, when two or more methylene moieties are replaced by carbonyl moieties, the resulting two or more carbonyl moieties may each independently be adjacent to the other one or more resulting carbonyl moieties, or being separated from the other one or more resulting carbonyl moieties by one or more alkylene moieties, alkene moieties, or alkyne moieties. In some embodiments, at least two resulting carbonyl moieties are adjacent to each other. In some embodiments, at least two resulting carbonyl moieties are separated by an alkylene moiety, alkene moiety, or alkyne moiety. In some embodiments, at least two resulting carbonyl moieties are separated by an alkylene moiety. In some embodiments, at least two resulting carbonyl moieties are separated by a methylene moiety.

In some embodiments, $R_1$ is —C(=O)$R_{1b}$, —C(=O)$R_{1z}$, —C(=O)—(CH=CH)$_n$—$R_{1a}$, —C(=O)CH$_2$—[C(=O)CH$_2$]$_p$—[CH$_2$]$_q$—$R_{1a}$, —C(=O)CH$_2$—[CH(O$R_{1c}$)—CH$_2$]$_p$—[CH$_2$]$_q$—$R_{1a}$, —C(=O)CH$_2$—[C(=O)CH$_2$]$_p$—[CH(O$R_{1c}$)—CH$_2$]$_r$[CH$_2$]$_q$—$R_{1a}$, —C(=O)CH$_2$—[CH(O$R_{1c}$)—CH$_2$]$_r$[C(=O)CH$_2$]$_p$—[CH$_2$]$_q$—$R_{1a}$, —C(=O)O$R_{1c}$, —C(=O)N($R_{1c}$)$_2$, —C(=O)—CH=CH—C(=O)O$R_{1c}$, —C(=O)—[CH$_2$]$_q$—C(=O)O$R_{1c}$, —C(=O)—CH$_2$CH$_2$—C(=O)O$R_{1c}$, —C(=O)CH$_2$—[C(=O)CH$_2$]$_p$—[CH$_2$]$_q$—C(=O)O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$, —S$R_{1d}$,

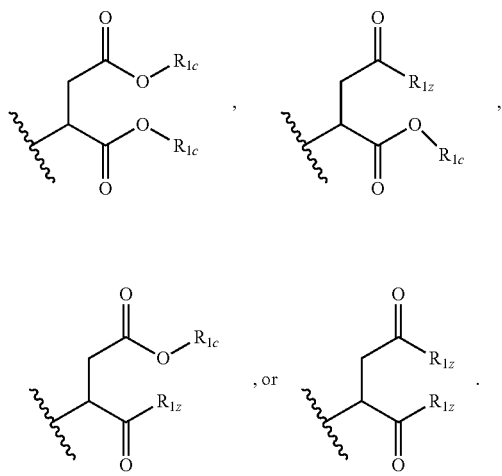

In some embodiments, $R_1$ is —C(=O)$R_{1b}$, —C(=O)$R_{1z}$, —C(=O)—(CH=CH)$_n$—$R_{1a}$, C(=O)CH$_2$—[C(=O)CH$_2$]$_p$—[CH$_2$]$_q$—$R_{1a}$, C(=O)CH($R_{1a}$)—[C(=O)CH($R_{1a}$)]$_p$—[CH$_2$]$_q$—$R_{1a}$, —C(=O)CH$_2$—[CH(O$R_{1c}$)—CH$_2$]$_p$—[CH$_2$]$_q$—$R_{1a}$, —C(=O)CH$_2$—[C(=O)CH$_2$]$_p$—[CH(O$R_{1c}$)—CH$_2$]$_r$[CH$_2$]$_q$—$R_{1a}$, —C(=O)CH$_2$—[CH(O$R_{1c}$)—CH$_2$]$_r$[C(=O)CH$_2$]$_p$—[CH$_2$]$_q$—$R_{1a}$, —C(=O)O$R_{1c}$, —C(=O)N($R_{1c}$)$_2$, —C(=O)—CH=CH—C(=O)O$R_{1c}$, —C(=O)—[CH$_2$]$_q$—C(=O)O$R_{1c}$, —C(=O)—CH$_2$CH$_2$—C(=O)O$R_{1c}$, C(=O)CH$_2$—[C(=O)CH$_2$]$_p$—[CH$_2$]$_q$—C(=O)O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$, —S$R_{1a}$,

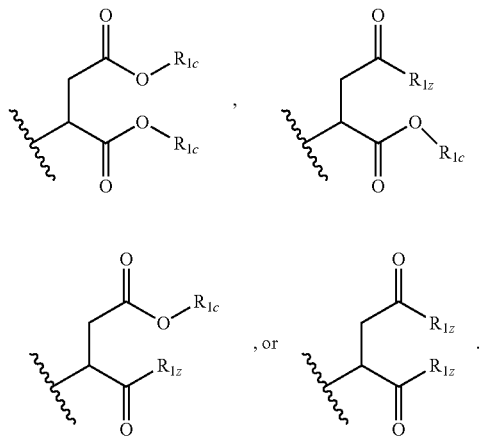

In some embodiments, $R_1$ is —C(=O)$R_{1b}$.

In some embodiments, $R_1$ is —C(=O)$R_{1b}$, wherein $R_{1b}$ is H, $C_1$-$C_{20}$ alkyl, $C_2$-$C_{20}$ alkenyl, $C_2$-$C_{20}$ alkynyl, —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=H—C(=O)O$R_{1c}$, —C(=O)O$R_{1c}$, —C(=O)N($R_{1c}$)$_2$, or $R_{1z}$, wherein the $C_1$-$C_{20}$ alkyl, or $C_2$-$C_{20}$ alkenyl or $C_2$-$C_{20}$ alkynyl is optionally substituted with one or more $R_{1e}$.

In some embodiments, $R_1$ is —C(=O)H.

In some embodiments, $R_1$ is —C(=O)$R_{1b}$, wherein $R_{1b}$ is $C_1$-$C_{20}$ alkyl, $C_2$-$C_{20}$ alkenyl, $C_2$-$C_{20}$ alkynyl, —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=H—C(=O)O$R_{1c}$, —C(=O)O$R_{1c}$, —C(=O)N($R_{1c}$)$_2$, or $R_{1z}$, wherein the $C_1$-$C_{20}$ alkyl, or $C_2$-$C_{20}$ alkenyl or $C_2$-$C_{20}$ alkynyl is optionally substituted with one or more $R_{1e}$.

In some embodiments, $R_1$ is —C(=O)$R_{1b}$, wherein $R_{1b}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, $R_1$ is —C(=O)$R_{1b}$, wherein $R_{1b}$ is —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=CH—C(=O)O$R_{1c}$, —C(=O)O$R_{1c}$, or —C(=O)N($R_{1c}$)$_2$.

In some embodiments, $R_1$ is —C(=O)—(CH$_2$)$_q$—C(=O)O$R_{1c}$.

In some embodiments, $R_1$ is —C(=O)—CH$_2$CH$_2$—C(=O)O$R_{1c}$.

In some embodiments, $R_1$ is —C(=O)—CH$_2$—C(=O)—(CH$_2$)$_q$—C(=O)O$R_{1c}$.

In some embodiments, $R_1$ is —C(=O)—CH$_2$—C(=O)—CH$_2$CH$_2$—C(=O)O$R_{1c}$.

In some embodiments, $R_1$ is —C(=O)—CH=CH—C(=O)O$R_{1c}$.

In some embodiments, $R_1$ is —C(=O)$R_{1z}$.

In some embodiments, $R_1$ is

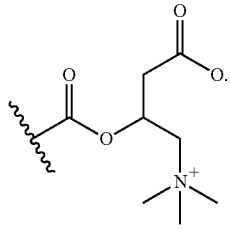

In some embodiments, $R_1$ is

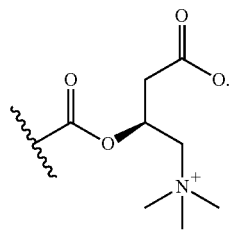

In some embodiments, $R_1$ is

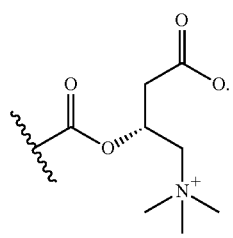

In some embodiments, $R_1$ is

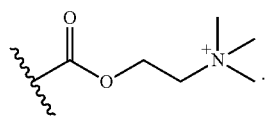

In some embodiments, $R_1$ is $-C(=O)-(CH=CH)_n-R_{1a}$, $-C(=O)CH_2-[C(=O)CH_2]_p-[CH_2]_q-R_{1a}$, $-C(=O)CH_2-[CH(OR_{1c})-CH_2]_p-[CH_2]_q-R_{1a}$, $-C(=O)CH_2-[C(=O)CH_2]_p-[CH(OR_{1c})-CH_2]_r-[CH_2]_q-R_{1a}$, or $-C(=O)CH_2-[CH(OR_{1c})-CH_2]_r-[C(=O)CH_2]_p-[CH_2]_q-R_{1a}$.

In some embodiments, $R_1$ is $-C(=O)-(CH=CH)_n-C(=O)OR_{1c}$, $-C(=O)CH_2-[C(=O)CH_2]_p-[CH_2]_q-C(=O)OR_{1c}$, $-C(=O)CH_2-[CH(OR_{1c})-CH_2]_p-[CH_2]_q-C(=O)OR_{1c}$, $-C(=O)CH_2-[C(=O)CH_2]_p-[CH(OR_{1c})-CH_2]_r-[CH_2]_q-C(=O)OR_{1c}$, or $-C(=O)CH_2-[CH(OR_{1c})-CH_2]_r-[C(=O)CH_2]_p-[CH_2]_q-C(=O)OR_{1c}$.

In some embodiments, $R_1$ is $-C(=O)-(CH=CH)_n-R_{1a}$. In some embodiments, $R_1$ is $-C(=O)-R_{1a}$. In some embodiments, $R_1$ is $-C(=O)-CH=CH-R_{1a}$.

In some embodiments, $R_1$ is $-C(=O)-(CH=CH)_n-C(=O)OR_{1c}$. In some embodiments, $R_1$ is $-C(=O)-CH=CH-C(=O)OR_{1c}$.

In some embodiments, $R_1$ is $-C(=O)-(CH=CH)_n-C(=O)R_{1z}$. In some embodiments, $R_1$ is $-C(=O)-Rh$. In some embodiments, $R_1$ is $-C(=O)-CH=CH-C(=O)R_{1z}$.

In some embodiments, $R_1$ is

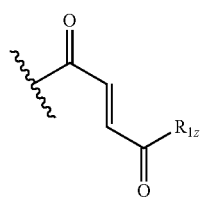

In some embodiments, $R_1$ is

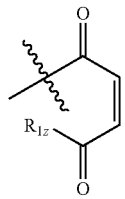

In some embodiments, $R_1$ is $-C(=O)CH_2-[C(=O)CH_2]_p-[CH_2]_q-R_{1a}$.

In some embodiments, $R_1$ is $-C(=O)CH(R_{1a})-[C(=O)CH(R_{1a})]_p-[CH_2]_q-R_{1a}$.

In some embodiments, $R_1$ is $-C(=O)CH_2-[C(=O)CH(R_{1a})]_p-[CH_2]_q-R_{1a}$.

In some embodiments, $R_1$ is $-C(=O)CH(R_{1a})-[C(=O)CH_2]_p-[CH_2]_q-R_{1a}$.

In some embodiments, $R_1$ is $-C(=O)CH_2-[C(=O)CH_2]_p-R_{1a}$.

In some embodiments, $R_1$ is $-C(=O)CH(R_{1a})-[C(=O)CH(R_{1a})]_p-R_{1a}$.

In some embodiments, $R_1$ is $-C(=O)CH_2-[C(=O)CH_2]_p-C(=O)OR_{1c}$.

In some embodiments, $R_1$ is $-C(=O)CH(R_{1a})-[C(=O)CH(R_{1a})]_p-[CH_2]_q-C(=O)OR_{1c}$.

In some embodiments, $R_1$ is $-C(=O)CH_2-[C(=O)CH_2]_p-C(=O)OR_{1c}$.

In some embodiments, $R_1$ is $-C(=O)CH(R_{1a})-[C(=O)CH(R_{1a})]_p-C(=O)OR_{1c}$.

In some embodiments, $R_1$ is

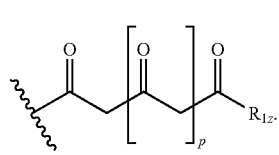

In some embodiments, $R_1$ is not

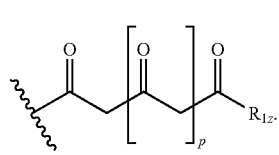

In some embodiments, $R_1$ is

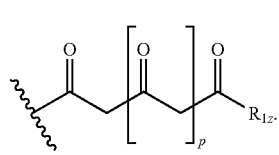

In some embodiments, $R_1$ is

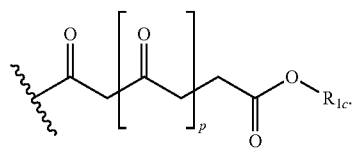

In some embodiments, $R_1$ is

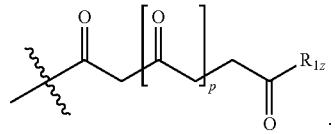

In some embodiments, $R_1$ is

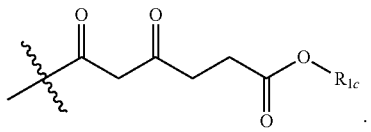

In some embodiments, $R_1$ is

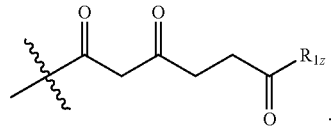

In some embodiments, $R_1$ is

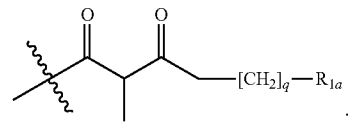

In some embodiments, $R_1$ is

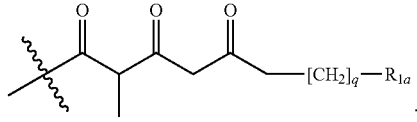

In some embodiments, $R_1$ is

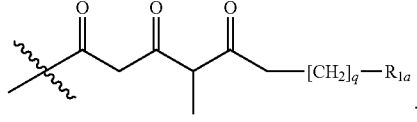

In some embodiments, $R_1$ is

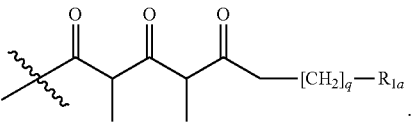

In some embodiments, $R_1$ is

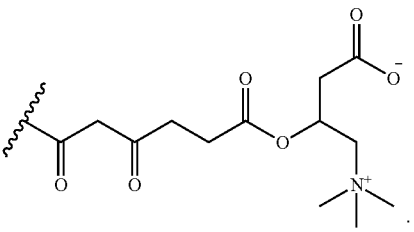 [SMILES: *C(=O)CC(=O)CCC(=O)OC(CC(=O)[O-])C[N+](C)(C)C]

In some embodiments, $R_1$ is

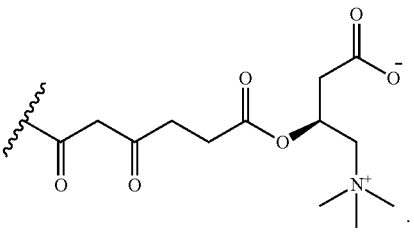 [SMILES: *C(=O)CC(=O)CCC(=O)O[C@@H](CC(=O)[O-])C[N+](C)(C)C]

In some embodiments, $R_1$ is

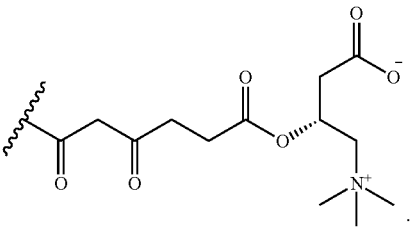 [SMILES: *C(=O)CC(=O)CCC(=O)O[C@H](CC(=O)[O-])C[N+](C)(C)C]

In some embodiments, $R_1$ is

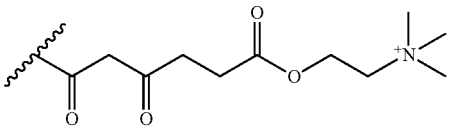 [SMILES: *C(=O)CC(=O)CCC(=O)OCC[N+](C)(C)C]

In some embodiments, $R_1$ is —C(=O)CH$_2$—[CH$_2$]$_q$—R$_{1a}$.

In some embodiments, $R_1$ is —C(=O)CH$_2$—[CH$_2$]$_q$—C(=O)OR$_{1c}$.

In some embodiments, $R_1$ is —C(=O)—[CH$_2$]$_q$—C(=O)R$_{1a}$.

In some embodiments, $R_1$ is —C(=O)—CH$_2$—C(=O)R$_{1a}$.

In some embodiments, $R_1$ is —C(=O)—CH$_2$—C(=O)—OR$_{1c}$.

In some embodiments, $R_1$ is —C(=O)—CH$_2$—C(=O)—C(=O)OR$_{1c}$.

In some embodiments, $R_1$ is —C(=O)—CH$_2$—C(=O)—C(=O)N(R$_{1c}$)$_2$.

In some embodiments, $R_1$ is —C(=O)—CH$_2$—C(=O)—N(R$_{1c}$)$_2$.

In some embodiments, $R_1$ is —C(=O)—CH$_2$—C(=O)—NH(R$_{1c}$).

In some embodiments, $R_1$ is —C(=O)—CH$_2$—C(=O)—N(R$_{1c}$)C(=O)R$_{1b}$.

In some embodiments, $R_1$ is —C(=O)—CH$_2$—C(=O)—N(R$_{1c}$)C(=O)R$_{1z}$.

In some embodiments, $R_1$ is —C(=O)—CH$_2$—C(=O)—N(R$_{1c}$)C(=O)OR$_{1c}$.

In some embodiments, $R_1$ is —C(=O)—CH$_2$—C(=O)—OC(=O)R$_{1b}$.

In some embodiments, $R_1$ is —C(=O)—CH$_2$—C(=O)—OC(=O)R$_{1z}$.

In some embodiments, $R_1$ is —C(=O)—CH$_2$—C(=O)—OC(=O)OR$_{1c}$.

In some embodiments, $R_1$ is —C(=O)—CH$_2$—C(=O)—SC(=O)R$_{1b}$.

In some embodiments, $R_1$ is —C(=O)—CH$_2$—C(=O)—SC(=O)R$_{1z}$.

In some embodiments, $R_1$ is —C(=O)—CH$_2$—C(=O)—SC(=O)OR$_{1c}$.

In some embodiments, $R_1$ is —C(=O)—CH$_2$—C(=O)—SC(=O)N(R$_{1c}$)$_2$.

In some embodiments, $R_1$ is —C(=O)—CH$_2$—C(=O)—C(=O)R$_{1b}$.

In some embodiments, $R_1$ is —C(=O)—CH$_2$—C(=O)—C(=O)R$_{1z}$.

In some embodiments, $R_1$ is —C(=O)—CH$_2$—C(=O)—SR$_{1d}$.

In some embodiments, $R_1$ is —C(=O)—CH$_2$—C(=O)R$_{1z}$.

In some embodiments, $R_1$ is

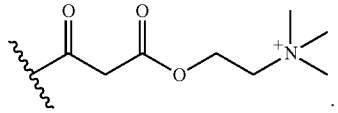

In some embodiments, $R_1$ is

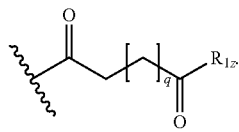

In some embodiments, $R_1$ is

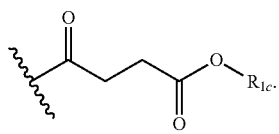

In some embodiments, $R_1$ is

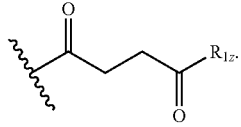

In some embodiments, $R_1$ is

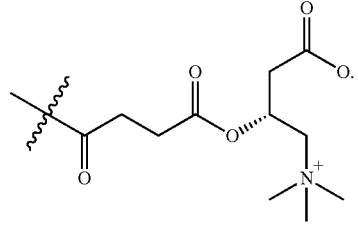

In some embodiments, $R_1$ is

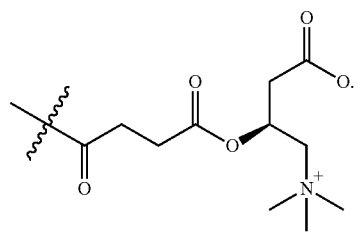

In some embodiments, $R_1$ is

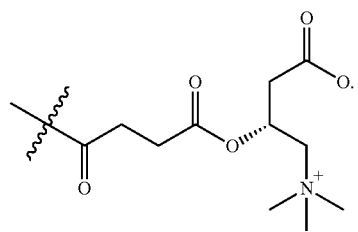

In some embodiments, $R_1$ is

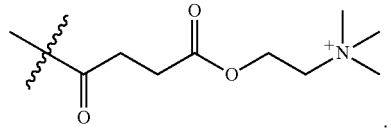

In some embodiments, $R_1$ is —C(=O)CH$_2$—[C(=O)CH$_2$]$_p$—[CH$_2$]$_q$—R$_{1z}$. In some embodiments, $R_1$ is —C(=O)CH$_2$—[C(=O)CH$_2$]$_p$—R$_{1z}$. In some embodiments, $R_1$ is —C(=O)CH$_2$—[CH$_2$]$_q$—R$_{1z}$.

In some embodiments, $R_1$ is —C(=O)CH$_2$—[CH(OR$_{1c}$)—CH$_2$]$_p$—[CH$_2$]$_q$—R$_{1a}$. In some embodiments, $R_1$ is —C(=O)CH$_2$—[CH(OR$_{1c}$)—CH$_2$]$_p$—R$_{1a}$. In some embodiments, $R_1$ is —C(=O)CH$_2$—[CH$_2$]$_q$—R$_{1a}$.

In some embodiments, $R_1$ is —C(=O)CH$_2$—[CH(OR$_{1c}$)—CH$_2$]$_p$—[CH$_2$]$_q$—C(=O)OR$_{1c}$. In some embodiments, $R_1$ is —C(=O)CH$_2$—[CH(OR$_{1c}$)—CH$_2$]$_p$—C(=O)OR$_{1c}$. In some embodiments, $R_1$ is —C(=O)CH$_2$—[CH$_2$]$_q$—C(=O)OR$_{1c}$.

In some embodiments, $R_1$ is —C(=O)CH$_2$—[CH(OR$_{1c}$)—CH$_2$]$_p$—[CH$_2$]$_q$—C(=O)R$_{1z}$. In some embodiments, $R_1$ is —C(=O)CH$_2$—[CH(OR$_{1c}$)—CH$_2$]$_p$—C(=O)R$_{1z}$. In some embodiments, $R_1$ is —C(=O)CH$_2$—[CH$_2$]$_q$—C(=O)R$_{1z}$.

In some embodiments, $R_1$ is —C(=O)CH$_2$—[C(=O)CH$_2$]$_p$—[CH(OR$_{1c}$)—CH$_2$]$_r$—[CH$_2$]$_q$—R$_{1a}$. In some embodiments, $R_1$ is —C(=O)CH$_2$—[CH(OR$_{1c}$)—CH$_2$]$_r$—[CH$_2$]$_q$—R$_{1a}$. In some embodiments, $R_1$ is —C(=O)CH$_2$—[C(=O)CH$_2$]$_p$—[CH$_2$]$_q$—R$_{1a}$. In some embodiments, $R_1$ is —C(=O)CH$_2$—[C(=O)CH$_2$]$_p$—[CH(OR$_{1c}$)—CH$_2$]$_r$—R$_{1a}$. In some embodiments, $R_1$ is —C(=O)CH$_2$—[CH$_2$]$_q$—R$_{1a}$. In some embodiments, $R_1$ is —C(=O)CH$_2$—[CH(OR$_{1c}$)—CH$_2$]$_r$—R$_{1a}$. In some embodiments, $R_1$ is —C(=O)CH$_2$—[C(=O)CH$_2$]$_p$—R$_{1a}$.

In some embodiments, $R_1$ is —C(=O)CH$_2$—[CH(OR$_{1c}$)—CH$_2$]$_r$[C(=O)CH$_2$]$_p$—[CH$_2$]$_q$—R$_{1a}$. In some embodiments, $R_1$ is —C(=O)CH$_2$—[C(=O)CH$_2$]$_p$—[CH$_2$]$_q$—R$_{1a}$. In some embodiments, $R_1$ is —C(=O)CH$_2$—[CH(OR$_{1c}$)—CH$_2$]$_r$[CH$_2$]$_q$—R$_{1a}$. In some embodiments, $R_1$ is —C(=O)CH$_2$—[CH(OR$_{1c}$)—CH$_2$]$_r$—[C(=O)CH$_2$]$_p$—R$_{1a}$. In some embodiments, $R_1$ is —C(=O)CH$_2$[CH$_2$]$_q$—R$_{1a}$. In some embodiments, $R_1$ is —C(=O)CH$_2$—[C(=O)CH$_2$]$_p$—R$_{1a}$. In some embodiments, $R_1$ is —C(=O)CH$_2$—[CH(OR$_{1c}$)—CH$_2$]$_r$—R$_{1a}$.

In some embodiments, $R_1$ is —C(=O)CH$_2$—[C(=O)CH$_2$]$_p$—[CH(OR$_{1c}$)—CH$_2$]$_r$[CH$_2$]$_q$—C(=O)OR$_{1c}$. In some embodiments, $R_1$ is —C(=O)CH$_2$—[CH(OR$_{1c}$)—CH$_2$]$_r$[CH$_2$]$_q$—C(=O)OR$_{1c}$. In some embodiments, $R_1$ is —C(=O)CH$_2$—[C(=O)CH$_2$]$_p$—[CH$_2$]$_q$—C(=O)OR$_{1c}$. In some embodiments, $R_1$ is —C(=O)CH$_2$—[C(=O)CH$_2$]$_p$—[CH(OR$_{1c}$)—CH$_2$]$_r$—C(=O)OR$_{1c}$. In some embodiments, $R_1$ is C(=O)CH$_2$—[CH$_2$]$_q$—C(=O)OR$_{1c}$. In some embodiments, $R_1$ is —C(=O)CH$_2$—[CH(OR$_{1c}$)—CH$_2$]$_r$—C(=O)OR$_{1c}$. In some embodiments, $R_1$ is —C(=O)CH$_2$—[C(=O)CH$_2$]$_p$—C(=O)OR$_{1c}$.

In some embodiments, $R_1$ is —C(=O)CH$_2$—[CH(OR$_{1c}$)—CH$_2$]$_r$[C(=O)CH$_2$]$_p$—[CH$_2$]$_q$—C(=O)OR$_{1c}$. In some embodiments, $R_1$ is —C(=O)CH$_2$—[C(=O)CH$_2$]$_p$—[CH$_2$]$_q$—C(=O)OR$_{1c}$. In some embodiments, $R_1$ is —C(=O)CH$_2$—[CH(OR$_{1c}$)—CH$_2$]$_r$[CH$_2$]$_q$—C(=O)OR$_{1c}$. In some embodiments, $R_1$ is —C(=O)CH$_2$—[CH(OR$_{1c}$)—CH$_2$]$_r$[C(=O)CH$_2$]$_p$—C(=O)OR$_{1c}$. In some embodiments, $R_1$ is —C(=O)CH$_2$—[CH$_2$]$_q$—C(=O)OR$_{1c}$. In some embodiments, $R_1$ is —C(=O)CH$_2$—[C(=O)CH$_2$]$_p$—C(=O)OR$_{1c}$. In some embodiments, $R_1$ is —C(=O)CH$_2$—[CH(OR$_{1c}$)—CH$_2$]$_r$ C(=O)OR$_{1c}$.

In some embodiments, $R_1$ is —C(=O)OR$_{1c}$, —C(=O)N(R$_{1c}$)$_2$, —C(=O)—CH=CH—C(=O)OR$_{1c}$.

In some embodiments, $R_1$ is —C(=O)OR$_{1c}$.

In some embodiments, $R_1$ is —C(=O)OH.

In some embodiments, $R_1$ is —C(=O)OR$_{1c}$, wherein R$_{1c}$ is C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1e}$.

In some embodiments, $R_1$ is —C(=O)OR$_{1c}$, wherein R$_{1c}$ is C$_1$-C$_{20}$ alkyl, C$_2$-C$_{20}$ alkenyl, or C$_2$-C$_{20}$ alkynyl optionally substituted with one or more R$_{1e}$.

In some embodiments, $R_1$ is —C(=O)OR$_{1c}$, wherein R$_{1c}$ is C$_3$-C$_{12}$ cycloalkyl, C$_3$-C$_{12}$ heterocycloalkyl, C$_3$-C$_{12}$ aryl, or C$_3$-C$_{12}$ heteroaryl optionally substituted with one or more R$_{1e}$.

In some embodiments, $R_1$ is —C(=O)OR$_{1c}$, wherein R$_{1c}$ is —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1e}$.

In some embodiments, $R_1$ is —C(=O)N(R$_{1c}$)$_2$.

In some embodiments, $R_1$ is —C(=O)N(R$_{1c}$)$_2$, wherein at least one R$_{1c}$ is H.

In some embodiments, $R_1$ is —C(=O)N(R$_{1c}$)$_2$, wherein at least one R$_{1c}$ is C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1e}$.

In some embodiments, $R_1$ is —C(=O)N(R$_{1c}$)$_2$, wherein at least one R$_{1c}$ is C$_1$-C$_{20}$ alkyl, C$_2$-C$_{20}$ alkenyl, or C$_2$-C$_{20}$ alkynyl optionally substituted with one or more R$_{1e}$.

In some embodiments, $R_1$ is —C(=O)N(R$_{1c}$)$_2$, wherein at least one R$_{1c}$ is C$_3$-C$_{12}$ cycloalkyl, C$_3$-C$_{12}$ heterocycloalkyl, C$_3$-C$_{12}$ aryl, or C$_3$-C$_{12}$ heteroaryl optionally substituted with one or more R$_{1e}$.

In some embodiments, $R_1$ is —C(=O)N(R$_{1c}$)$_2$, wherein at least one R$_{1c}$ is —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1c}$.

In some embodiments, $R_1$ is —C(=O)—CH=CH—C(=O)OR$_{1c}$.

In some embodiments, $R_1$ is —C(=O)—CH=CH—C(=O)OH.

In some embodiments, $R_1$ is —C(=O)—CH=CH—C(=O)OR$_{1c}$, wherein R$_{1c}$ is C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1c}$.

In some embodiments, $R_1$ is —C(=O)—CH=CH—C(=O)OR$_{1c}$, wherein R$_{1c}$ is C$_1$-C$_{20}$ alkyl, C$_2$-C$_{20}$ alkenyl, or C$_2$-C$_{20}$ alkynyl optionally substituted with one or more R$_{1e}$.

In some embodiments, $R_1$ is —C(=O)—CH=CH—C(=O)OR$_{1c}$, wherein R$_{1c}$ is C$_3$-C$_{12}$ cycloalkyl, C$_3$-C$_{12}$ heterocycloalkyl, C$_3$-C$_{12}$ aryl, or C$_3$-C$_{12}$ heteroaryl optionally substituted with one or more R$_{1c}$.

In some embodiments, $R_1$ is —C(=O)—CH=CH—C(=O)OR$_{1c}$, wherein R$_{1c}$ is —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1e}$.

In some embodiments, $R_1$—C(=O)—[CH$_2$]$_q$—C(=O)OR$_{1c}$.

In some embodiments, $R_1$—C(=O)—CH$_2$CH$_2$—C(=O)OR$_{1c}$.

In some embodiments, $R_1$—C(=O)CH$_2$—[C(=O)CH$_2$]$_p$—[CH$_2$]$_q$—C(=O)OR$_{1c}$.

In some embodiments, $R_1$—C(=O)—[CH$_2$]$_q$—C(=O)R$_{1z}$.

In some embodiments, $R_1$—C(=O)—CH$_2$CH$_2$—C(=O)R$_{1z}$.

In some embodiments, $R_1$—C(=O)CH$_2$—[C(=O)CH$_2$]$_p$—[CH$_2$]$_q$—C(=O)R$_{1z}$.

In some embodiments, $R_1$ is —SR$_{1d}$.

In some embodiments, $R_1$ is —SH.

In some embodiments, $R_1$ is —$SR_{1d}$, wherein $R_{1d}$ is $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$ is —$SR_{1d}$, wherein $R_{1d}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, $R_1$ is —$SR_{1d}$, wherein $R_{1d}$ is $C_3$-$C_{10}$ cycloalkyl, $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, $R_1$ is —$SR_{1d}$, wherein $R_{1d}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$ is

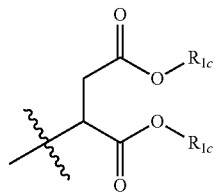

(e.g.,

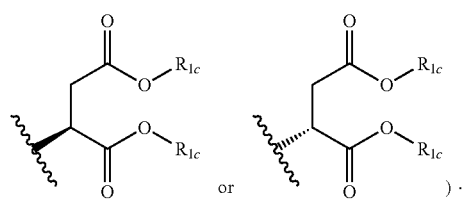

).

In some embodiments, $R_1$ is

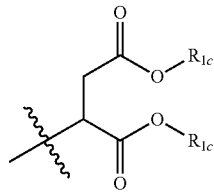

(e.g.,

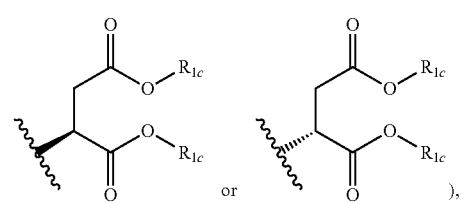

), wherein at least one $R_{1c}$ is H.

In some embodiments, $R_1$ is

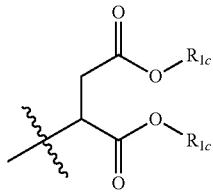

(e.g.,

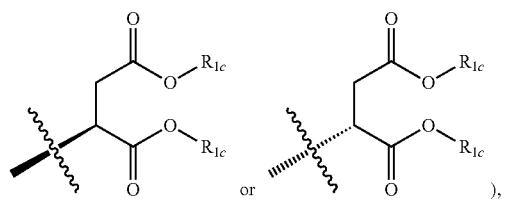

), wherein at least one $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$ is

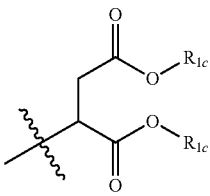

(e.g.,

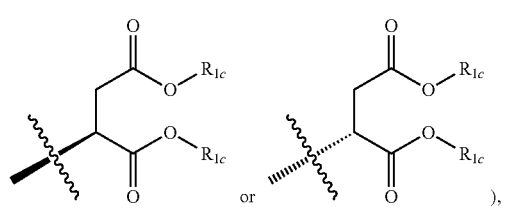

), wherein at least one $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, $R_1$

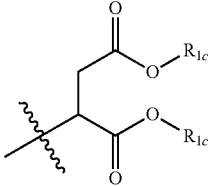

(e.g.,

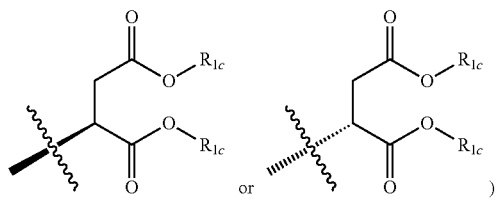

or ), wherein at least one $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, $R_1$ is

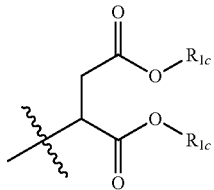

(e.g.,

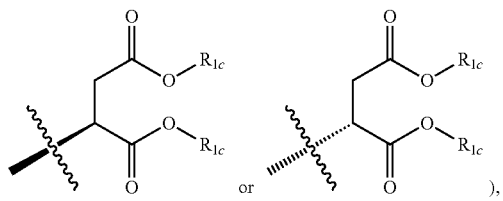

or ), wherein at least one $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$ is

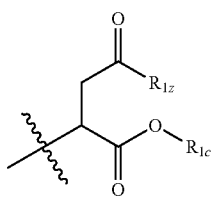

(e.g.,

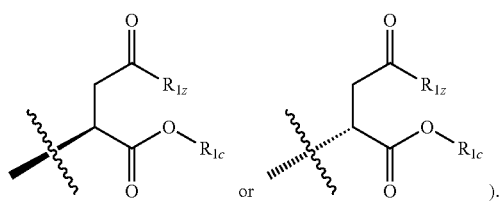

or ).

In some embodiments, $R_1$ is

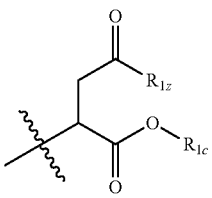

(e.g.,

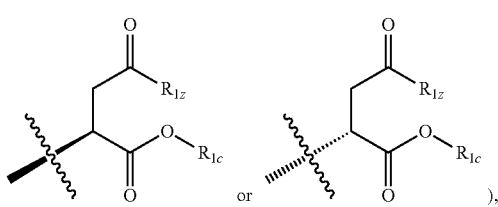

or ), wherein $R_{1c}$ is H.

In some embodiments, $R_1$ is

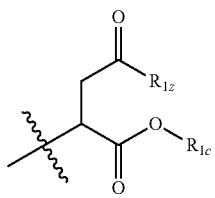

(e.g.,

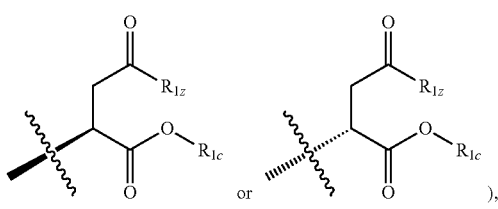

or ), wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$ is

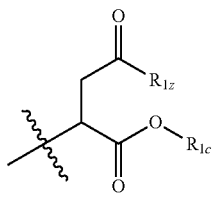

(e.g.,

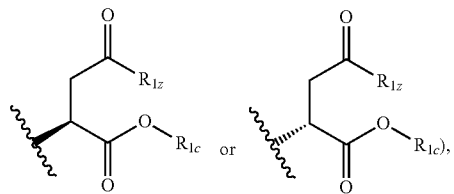

wherein $R_{1c}$ is $C_1$-$C_{20}$ alkyl, $C_2$-$C_{20}$ alkenyl, or $C_2$-$C_{20}$ alkynyl optionally substituted with one or more $R_{1c}$.

In some embodiments, $R_1$ is

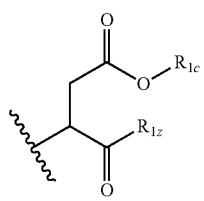

(e.g.,

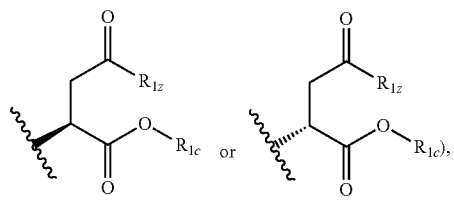

wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, $R_1$ is

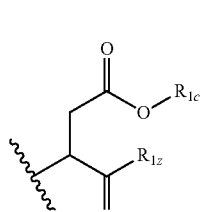

(e.g.,

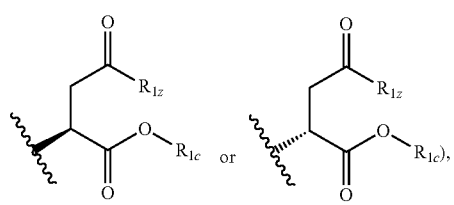

wherein $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$ is

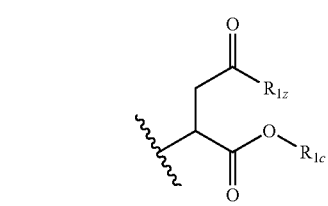

(e.g.,

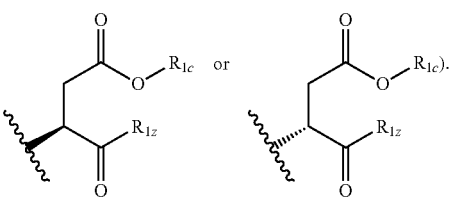

In some embodiments, $R_1$ is

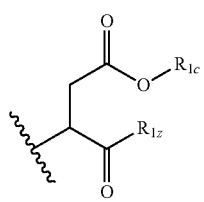

(e.g.,

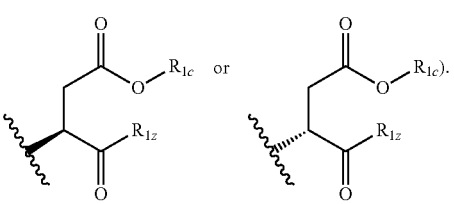

wherein $R_{1c}$ is H.

In some embodiments, $R_1$ is (e.g.,

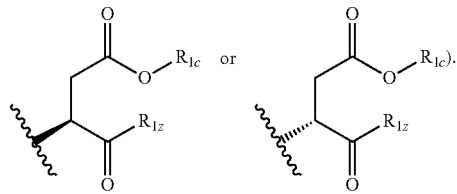

wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$ is

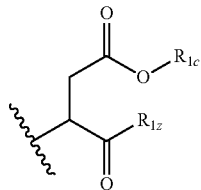

(e.g.

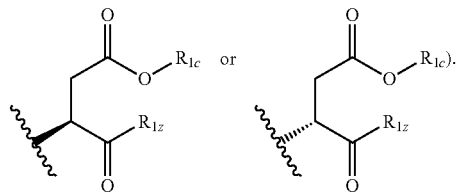

wherein $R_{1c}$ is $C_1$-$C_{20}$ alkyl, $C_2$-$C_{20}$ alkenyl, or $C_2$-$C_{20}$ alkynyl optionally substituted with one or more $R_{1c}$.

In some embodiments, $R_1$ is

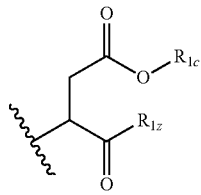

(e.g.,

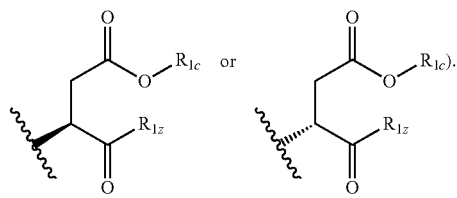

wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, $R_1$ is

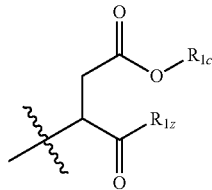

(e.g.,

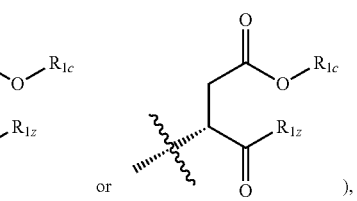

wherein $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, $R_1$

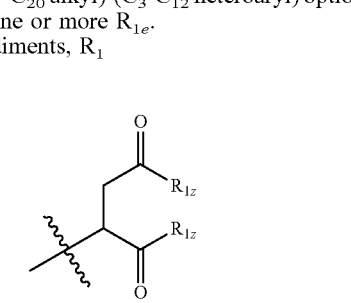

(e.g.,

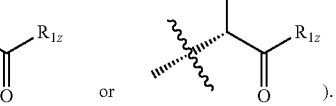

In some embodiments, $R_1$ is —C(=O)—$R_{1a}$, —C(=O)—CH$_2$—$R_{1a}$, —C(=O)—CH$_2$CH$_2$—$R_{1a}$ or —C(=O)—CH=CH—$R_{1a}$, wherein $R_{1a}$ is $C_1$-$C_{20}$ alkyl, —C(=O)$R_{1b}$, or —C(=O)O$R_{1c}$, wherein the $C_1$-$C_{20}$ alkyl is optionally substituted with one or more $R_{1e}$.

In some embodiments, $R_1$ is —C(=O)—$R_{1a}$, wherein —$R_{1a}$ is $C_1$-$C_{20}$ alkyl.

In some embodiments, $R_1$ is —C(=O)—CH$_3$.

In some embodiments, $R_1$ is —C(=O)—CH$_2$—$R_{1a}$, wherein $R_{1a}$ is $C_1$-$C_{20}$ alkyl optionally substituted with one or more $R_{1e}$, wherein $R_{1e}$ is —OH.

In some embodiments, $R_1$ is —C(=O)—CH$_2$—$R_{1a}$, wherein $R_{1a}$ is ethyl substituted one —OH.

In some embodiments, $R_1$ is —C(=O)—CH$_2$—CH(OH)—CH$_3$.

In some embodiments, $R_1$ is —C(=O)—CH$_2$—R$_{1a}$, wherein R$_{1a}$ is —C(=O)R$_{1b}$.

In some embodiments, $R_1$ is —C(=O)—CH$_2$—C(=O)—R$_{1b}$, wherein R$_{1b}$ is C$_1$-C$_{20}$ alkyl.

In some embodiments, $R_1$ is —C(=O)—CH$_2$—C(=O)—CH$_3$.

In some embodiments, $R_1$ is —C(=O)—CH$_2$CH$_2$—R$_{1a}$, wherein R$_{1a}$ is C$_1$-C$_{20}$ alkyl or —C(=O)OR$_{1c}$.

In some embodiments, $R_1$ is —C(=O)—CH$_2$CH$_2$—C(=O)OR$_{1c}$, wherein R$_{1c}$ is H or C$_1$-C$_{20}$ alkyl.

In some embodiments, $R_1$ is —C(=O)—CH$_2$CH$_2$—C(=O)OH.

In some embodiments, $R_1$ is —C(=O)—CH$_2$CH$_2$—C(=O)OCH$_3$.

In some embodiments, $R_1$ is —C(=O)—CH=CH—R$_{1a}$, wherein —R$_{1a}$ is C$_1$-C$_{20}$ alkyl or —C(=O)OR$_{1c}$.

In some embodiments, $R_1$ is —C(=O)—CH=CH—R$_{1a}$, wherein —R$_{1a}$ is C$_1$-C$_{20}$ alkyl.

In some embodiments, $R_1$ is —C(=O)—CH=CH—CH$_3$.

In some embodiments, $R_1$ is —C(=O)—CH=CH—C(=O)OR$_{1c}$, wherein R$_{1c}$ is H or C$_1$-C$_{20}$ alkyl.

In some embodiments, $R_1$ is —C(=O)—CH=CH—C(=O)OH.

In some embodiments, $R_1$ is —C(=O)—CH=CH—C(=O)OCH$_3$.

In some embodiments, $R_1$ is —C(=O)—CH$_3$, —C(=O)—CH$_2$—CH(OH)—CH$_3$, —C(=O)—CH$_2$—C(=O)—CH$_3$, —C(=O)—CH$_2$CH$_2$—C(=O)OH, —C(=O)—CH$_2$CH$_2$—C(=O)OCH$_3$, —C(=O)—CH=CH—CH$_3$, —C(=O)—CH=H—C(=O)OH, or —C(=O)—CH=CH—C(=O)OCH$_3$.

Variable R$_{1a}$

In some embodiments, at least one R$_{1a}$ is H.

In some embodiments, at least one R$_{1a}$ is halogen, C$_1$-C$_{20}$ alkyl, C$_2$-C$_{20}$ alkenyl, —OR$_{1c}$, —C(=O)OR$_{1c}$, —C(=O)N(R$_{1c}$)$_2$, —N(R$_{1c}$)$_2$, —N(R$_{1c}$)C(=O)R$_{1b}$, —N(R$_{1c}$)C(=O)R$_{1z}$, —N(R$_{1c}$)C(=O)OR$_{1c}$, —OC(=O)R$_{1b}$, —OC(=O)R$_{1z}$, —OC(=O)OR$_{1c}$, —SC(=O)R$_{1b}$, —SC(=O)R$_{1a}$, —SC(=O)OR$_{1c}$, —SC(=O)N(R$_{1c}$)$_2$, —C(=O)R$_{1b}$, —C(=O)R$_{1z}$, —SR$_{1d}$, or R$_{1z}$, wherein the C$_1$-C$_{20}$ alkyl, C$_2$-C$_{20}$ alkenyl, or C$_2$-C$_{20}$ alkynyl is optionally substituted with one or more R$_{1e}$.

In some embodiments, at least one R$_{1a}$ is halogen, C$_1$-C$_{20}$ alkyl, or C$_2$-C$_{20}$ alkenyl, wherein the C$_1$-C$_{20}$ alkyl, C$_2$-C$_{20}$ alkenyl, or C$_2$-C$_{20}$ alkynyl is optionally substituted with one or more R$_{1c}$.

In some embodiments, at least one R$_{1a}$ is halogen (e.g., F, Cl, Br, I). In some embodiments, at least one R$_{1a}$ is F or Cl. In some embodiments, at least one R$_{1a}$ is F. In some embodiments, at least one R$_{1a}$ is Cl.

In some embodiments, at least one R$_{1a}$ is C$_1$-C$_{20}$ alkyl (e.g., methyl, ethyl, propyl, butyl, pentyl, hexyl, or heptyl).

In some embodiments, at least one R$_{1a}$ is C$_1$-C$_{20}$ alkyl (e.g., methyl, ethyl, propyl, butyl, pentyl, hexyl, or heptyl) substituted with one or more R$_{1e}$.

In some embodiments, at least one R$_{1a}$ is C$_1$-C$_{20}$ alkyl (e.g., methyl, ethyl, propyl, butyl, pentyl, hexyl, or heptyl) substituted with one or more R$_{1z}$.

In some embodiments, at least one R$_{1a}$ is C$_2$-C$_{20}$ alkenyl (e.g., ethenyl, propenyl, butenyl, pentenyl, or hexenyl).

In some embodiments, at least one R$_{1a}$ is C$_2$-C$_{20}$ alkenyl (e.g., ethenyl, propenyl, butenyl, pentenyl, or hexenyl) substituted with one or more R$_{1e}$.

In some embodiments, at least one R$_{1a}$ is C$_2$-C$_{20}$ alkenyl (e.g., ethenyl, propenyl, butenyl, pentenyl, or hexenyl) substituted with one or more R$_{1z}$.

In some embodiments, at least one R$_{1a}$ is C$_2$-C$_{20}$ alkynyl (e.g., ethynyl, propynyl, butynyl, pentynyl, or hexynyl).

In some embodiments, at least one R$_{1a}$ is C$_2$-C$_{20}$ alkynyl (e.g., ethynyl, propynyl, butynyl, pentynyl, or hexynyl) substituted with one or more R$_{1e}$.

In some embodiments, at least one R$_{1a}$ is C$_2$-C$_{20}$ alkynyl (e.g., ethynyl, propynyl, butynyl, pentynyl, or hexynyl) substituted with one or more R$_{1z}$.

In some embodiments, at least one R$_{1a}$ is —OR$_{1c}$, —C(=O)OR$_{1c}$, —C(=O)N(R$_{1c}$)$_2$, —N(R$_{1c}$)$_2$, —N(R$_{1c}$)C(=O)R$_{1b}$, —N(R$_{1c}$)C(=O)R$_{1z}$, —N(R$_{1c}$)C(=O)OR$_{1c}$, —OC(=O)R$_{1b}$, —OC(=O)R$_{1z}$, —OC(=O)OR$_{1c}$, —SC(=O)R$_{1b}$, —SC(=O)R$_{1z}$, —SC(=O)OR$_{1c}$, —SC(=O)N(R$_{1c}$)$_2$, —C(=O)R$_{1b}$, —C(=O)R$_{1z}$, Or —SR$_{1d}$.

In some embodiments, at least one R$_{1a}$ is —OR$_{1c}$.

In some embodiments, at least one R$_{1a}$ is —OH.

In some embodiments, at least one R$_{1a}$ is —OR$_{1c}$, wherein R$_{1c}$ is C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl), wherein the C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) is optionally substituted with one or more R$_{1e}$.

In some embodiments, at least one R$_{1a}$ is —OR$_{1c}$, wherein R$_{1c}$ is C$_1$-C$_{20}$ alkyl, C$_2$-C$_{20}$ alkenyl, or C$_2$-C$_{20}$ alkynyl optionally substituted with one or more R$_{1e}$.

In some embodiments, at least one R$_{1a}$ is —OR$_{1c}$, wherein R$_{1c}$ is C$_3$-C$_{12}$ cycloalkyl, C$_3$-C$_{12}$ heterocycloalkyl, C$_3$-C$_{12}$ aryl, or C$_3$-C$_{12}$ heteroaryl optionally substituted with one or more R$_{1e}$.

In some embodiments, at least one R$_{1a}$ is —OR$_{1c}$, wherein R$_{1c}$ is —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1e}$.

In some embodiments, at least one R$_{1a}$ is —C(=O)OR$_{1c}$.

In some embodiments, at least one R$_{1a}$ is —C(=O)OH.

In some embodiments, at least one R$_{1a}$ is —C(=O)OR$_{1c}$, wherein R$_{1c}$ is C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl), wherein the C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) is optionally substituted with one or more R$_{1e}$.

In some embodiments, at least one R$_{1a}$ is —C(=O)OR$_{1c}$, wherein R$_{1c}$ is C$_1$-C$_{20}$ alkyl, C$_2$-C$_{20}$ alkenyl, or C$_2$-C$_{20}$ alkynyl optionally substituted with one or more R$_{1e}$.

In some embodiments, at least one R$_{1a}$ is —C(=O)OR$_{1c}$, wherein R$_{1c}$ is C$_3$-C$_{12}$ cycloalkyl, C$_3$-C$_{12}$ heterocycloalkyl, C$_3$-C$_{12}$ aryl, or C$_3$-C$_{12}$ heteroaryl optionally substituted with one or more R$_{1e}$.

In some embodiments, at least one R$_{1a}$ is —C(=O)OR$_{1c}$, wherein R$_{1c}$ is —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1e}$.

In some embodiments, at least one R$_{1a}$ is —C(=O)N(R$_{1c}$)$_2$.

In some embodiments, at least one $R_{1a}$ is —C(=O)NHR$_{1c}$.

In some embodiments, at least one $R_{1a}$ is —C(=O)NH$_2$.

In some embodiments, at least one $R_{1a}$ is —C(=O)N(R$_{1c}$)$_2$, wherein at least one $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1a}$ is —C(=O)N(R$_{1c}$)$_2$, wherein at least one $R_{1c}$ is $C_1$-$C_{20}$ alkyl, $C_2$-$C_{20}$ alkenyl, or $C_2$-$C_{20}$ alkynyl optionally substituted with one or more $R_{1c}$.

In some embodiments, at least one $R_{1a}$ is —C(=O)N(R$_{1c}$)$_2$, wherein at least one $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1a}$ is —C(=O)N(R$_{1c}$)$_2$, wherein at least one $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —N(R$_{1c}$)$_2$.

In some embodiments, at least one $R_{1a}$ is —NH$_2$.

In some embodiments, at least one $R_{1a}$ is —NHR$_{1c}$.

In some embodiments, at least one $R_{1a}$ is —(R$_{1c}$)$_2$, wherein at least one $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1c}$.

In some embodiments, at least one $R_{1a}$ is —N(R$_{1c}$)$_2$, wherein at least one $R_{1c}$ is $C_1$-$C_{20}$ alkyl, $C_2$-$C_{20}$ alkenyl, or $C_2$-$C_{20}$ alkynyl optionally substituted with one or more $R_{1c}$.

In some embodiments, at least one $R_{1a}$ is —N(R$_{1c}$)$_2$, wherein at least one $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1a}$ is —N(R$_{1c}$)$_2$, wherein at least one $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —N(R$_{1c}$)C(=O)R$_{1b}$.

In some embodiments, at least one $R_{1a}$ is —N(R$_{1c}$)C(=O)H.

In some embodiments, at least one $R_{1a}$ is —N(R$_{1c}$)C(=O)R$_{1b}$, wherein R$_{1b}$ is $C_1$-$C_{20}$ alkyl, $C_2$-$C_{20}$ alkenyl, $C_2$-$C_{20}$ alkynyl, —(CH$_2$)$_q$—C(=O)OR$_{1c}$, —CH$_2$—C(=O)—(CH$_2$)$_q$—C(=O)OR$_{1c}$, —CH$_2$—[C(=O)CH$_2$]$_p$—[CH$_2$]$_q$—C(=O)OR$_{1c}$, —CH=CH—C(=O)OR$_{1c}$, —C(=O)OR$_{1c}$, —C(=O)N(R$_{1c}$)$_2$, or R$_{1z}$, wherein the $C_1$-$C_{20}$ alkyl, or $C_2$-$C_{20}$ alkenyl or $C_2$-$C_{20}$ alkynyl is optionally substituted with one or more R$_{1c}$.

In some embodiments, at least one $R_{1a}$ is —N(R$_{1c}$)C(=O)R$_{1b}$, wherein R$_{1b}$ is $C_1$-$C_{20}$ alkyl, $C_2$-$C_{20}$ alkenyl, or $C_2$-$C_{20}$ alkynyl optionally substituted with one or more R$_{1c}$.

In some embodiments, at least one $R_{1a}$ is —N(R$_{1c}$)C(=O)R$_{1b}$, wherein R$_{1b}$ is —(CH$_2$)$_q$—C(=O)OR$_{1c}$, —CH$_2$—C(=O)—(CH$_2$)$_q$—C(=O)OR$_{1c}$, —CH$_2$—[C(=O)CH$_2$]$_p$—[CH$_2$]$_q$—C(=O)OR$_{1c}$, —CH=CH—C(=O)OR$_{1c}$, —C(=O)OR$_{1c}$, or —C(=O)N(R$_{1c}$)$_2$.

In some embodiments, at least one $R_{1a}$ is —N(R$_{1c}$)C(=O)R$_{1z}$.

In some embodiments, at least one $R_{1a}$ is

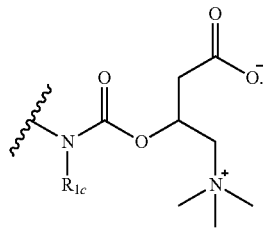

In some embodiments, at least one $R_{1a}$ is

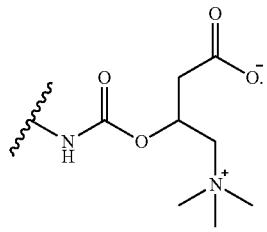

In some embodiments, at least one $R_{1a}$ is

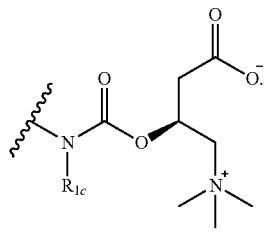

In some embodiments, at least one $R_{1a}$ is

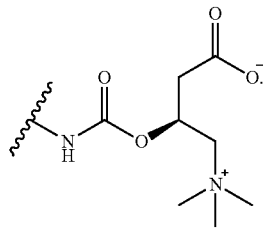

In some embodiments, at least one $R_{1a}$ is

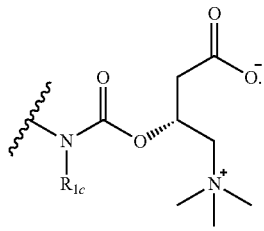

In some embodiments, at least one $R_{1a}$ is

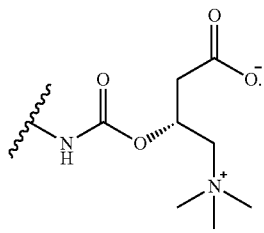

In some embodiments, at least one $R_{1a}$ is

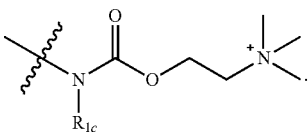

In some embodiments, at least one $R_{1a}$ is

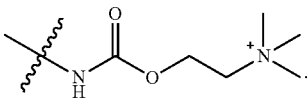 [SMILES: *NC(=O)OCC[N+](C)(C)C]

In some embodiments, at least one $R_{1a}$ is —NHC(=O)$R_{1b}$.

In some embodiments, at least one $R_{1a}$ is —N($R_{1c}$)C(=O)$R_{1b}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1a}$ is —N($R_{1c}$)C(=O)$R_{1b}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1a}$ is —N($R_{1c}$)C(=O)$R_{1b}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1a}$ is —N($R_{1c}$)C(=O)$R_{1b}$, wherein $R_{1c}$ is —($C_1$-$C_{20}$ cycloal-kyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —N($R_{1c}$)C(=O)O$R_{1c}$.

In some embodiments, at least one $R_{1a}$ is —NHC(=O)O$R_{1c}$.

In some embodiments, at least one $R_{1a}$ is —N($R_{1c}$)C(=O)OH.

In some embodiments, at least one $R_{1a}$ is —N($R_{1c}$)C(=O)O$R_{1c}$, wherein at least one $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl). —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1a}$ is —N($R_{1c}$)C(=O)O$R_{1c}$, wherein at least one $R_{1c}$ is $C_1$-$C_{20}$ alkyl, $C_2$-$C_{20}$ alkenyl, or $C_2$-$C_{20}$ alkynyl optionally substituted with one or more $R_{1c}$.

In some embodiments, at least one $R_{1a}$ is —N($R_{1c}$)C(=O)O$R_{1c}$, wherein at least one $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1a}$ is —N($R_{1c}$)C(=O)O$R_{1c}$, wherein at least one $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —OC(=O)$R_{1b}$.

In some embodiments, at least one $R_{1a}$ is —OC(=O)H.

In some embodiments, at least one $R_{1a}$ is —OC(=O)$R_{1b}$, wherein $R_{1b}$ is $C_1$-$C_{20}$ alkyl, $C_2$-$C_{20}$ alkenyl, $C_2$-$C_{20}$ alkynyl, —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=CH—C(=O)O$R_{1c}$, —C(=O)O$R_{1c}$, —C(=O)N($R_{1c}$)$_2$, or $R_{1z}$, wherein the $C_1$-$C_{20}$ alkyl, or $C_2$-$C_{20}$ alkenyl or $C_2$-$C_{20}$ alkynyl is optionally substituted with one or more $R_{1e}$.

In some embodiments, at least one $R_{1a}$ is —OC(=O)$R_{1b}$, wherein $R_{1b}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1a}$ is —OC(=O)$R_{1b}$, wherein $R_{1b}$ is —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=CH—C(=O)O$R_{1c}$, —C(=O)O$R_{1c}$, or —C(=O)N($R_{1c}$)$_2$.

In some embodiments, at least one $R_{1a}$ is —OC(=O)$R_{1z}$.

In some embodiments, at least one $R_{1a}$ is

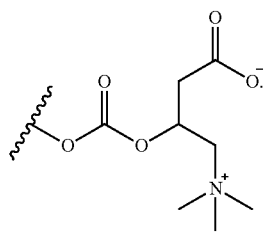

In some embodiments, at least one $R_{1a}$ is

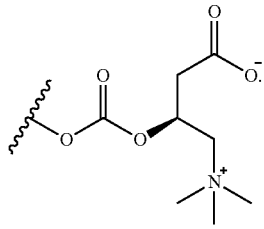

In some embodiments, at least one $R_{1a}$ is

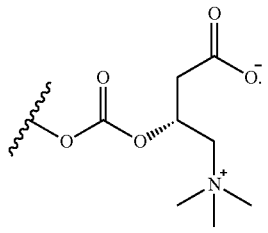

In some embodiments, at least one $R_{1a}$ is

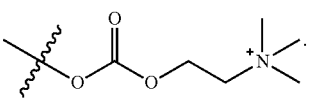 [SMILES: *OC(=O)OCC[N+](C)(C)C]

In some embodiments, at least one $R_{1a}$ is —OC(=O) $OR_{1c}$.

In some embodiments, at least one $R_{1a}$ is —OC(=O)OH.

In some embodiments, at least one $R_{1a}$ is —OC(=O) $OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1a}$ is —OC(=O) $OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1a}$ is —OC(=O) $OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1c}$.

In some embodiments, at least one $R_{1a}$ is —OC(=O) $OR_{1c}$, wherein $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —SC(=O)$R_{1b}$.

In some embodiments, at least one $R_{1a}$ is —SC(=O)H.

In some embodiments, at least one $R_{1a}$ is —SC(=O)$R_{1b}$, wherein $R_{1b}$ is $C_1$-$C_{20}$ alkyl, $C_2$-$C_{20}$ alkenyl, $C_2$-$C_{20}$ alkynyl, —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)

$OR_{1c}$, —CH=CH—C(=O)O$R_{1c}$, —C(=O)O$R_{1c}$, —C(=O)N($R_{1c}$)$_2$, or $R_{1z}$, wherein the $C_1$-$C_{20}$ alkyl, or $C_2$-$C_{2n}$ alkenyl or $C_2$-$C_{20}$ alkynyl is optionally substituted with one or more $R_{1e}$.

In some embodiments, at least one $R_{1a}$ is —SC(=O)$R_{1b}$, wherein $R_{1b}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1a}$ is —SC(=O)$R_{1b}$, wherein $R_{1b}$ is —(CH$_2$)$_q$—C(=O)O$R_{1c}$, —CH$_2$—C(=O)—(CH$_2$)$_q$—C(=O)O$R_{1c}$, —CH$_2$—[C(=O)CH$_2$]$_p$—[CH$_2$]$_q$—C(=O)O$R_{1c}$, —CH=CH—C(=O)O$R_{1c}$, —C(=O)O$R_{1c}$, or —C(=O)N($R_{1c}$)$_2$.

In some embodiments, at least one $R_{1a}$ is —SC(=O)$R_{1z}$.

In some embodiments, at least one $R_{1a}$ is

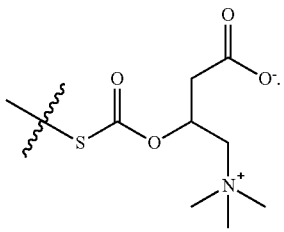

In some embodiments, at least one $R_{1a}$ is

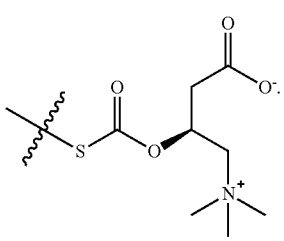

In some embodiments, at least one $R_{1a}$ is

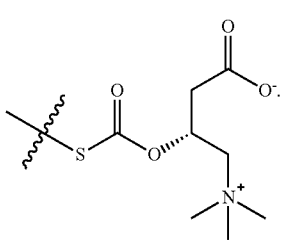

In some embodiments, at least one $R_{1a}$ is

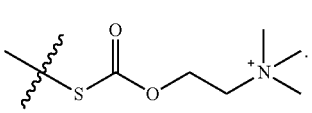 [SMILES: *SC(=O)OCC[N+](C)(C)C]

In some embodiments, at least one $R_{1a}$ is —SC(=O) $OR_{1c}$.

In some embodiments, at least one $R_{1a}$ is —SC(=O)OH.

In some embodiments, at least one $R_{1a}$ is —SC(=O) $OR_{1c}$, wherein $R_{1c}$ is $C_1$-$C_{20}$ alkyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1a}$ is —SC(=O)OR$_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1a}$ is —SC(=O)OR$_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1a}$ is —SC(=O)OR$_{1c}$, wherein $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —SC(=O)N(R$_{1c}$)$_2$.

In some embodiments, at least one $R_{1a}$ is —SC(=O)NHR$_{1c}$.

In some embodiments, at least one $R_{1a}$ is —SC(=O)NH$_2$.

In some embodiments, at least one $R_{1a}$ is —SC(=O)N(R$_{1c}$)$_2$, wherein at least one $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1a}$ is —SC(=O)N(R$_{1c}$)$_2$, wherein at least one $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1a}$ is —SC(=O)N(R$_{1c}$)$_2$, wherein at least one $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1c}$.

In some embodiments, at least one $R_{1a}$ is —SC(=O)N(R$_{1c}$)$_2$, wherein at least one $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —C(=O)R$_{1b}$.

In some embodiments, at least one $R_{1a}$ is —C(=O)H.

In some embodiments, at least one $R_{1a}$ is —C(=O)R$_{1b}$, wherein $R_{1b}$ is $C_1$-$C_{20}$ alkyl, $C_2$-$C_{20}$ alkenyl, $C_2$-$C_{20}$ alkynyl, —(CH$_2$)$_q$—C(=O)OR$_{1c}$, —CH$_2$—C(=O)—(CH$_2$)$_q$—C(=O)OR$_{1c}$, —CH$_2$—[C(=O)CH$_2$]$_p$—[CH$_2$]$_q$—C(=O)OR$_{1c}$, —CH=H—C(=O)OR$_{1c}$, —C(=O)OR$_{1c}$, —C(=O)N(R$_{1c}$)$_2$, or R$_{1z}$, wherein the $C_1$-$C_{20}$ alkyl, or $C_2$-$C_{20}$ alkenyl or $C_2$-$C_{20}$ alkynyl is optionally substituted with one or more $R_{1e}$.

In some embodiments, at least one $R_{1a}$ is —C(=O)R$_{1b}$, wherein $R_{1b}$ is $C_1$-$C_{20}$ alkyl, $C_2$-$C_{20}$ alkenyl, or $C_2$-$C_{20}$ alkynyl optionally substituted with one or more $R_{1c}$.

In some embodiments, at least one $R_{1a}$ is —C(=O)R$_{1b}$, wherein $R_{1b}$ is —(CH$_2$)$_q$—C(=O)OR$_{1c}$, —CH$_2$—C(=O)—(CH$_2$)$_q$—C(=O)OR$_{1c}$, —CH$_2$—[C(=O)CH$_2$]$_p$—[CH$_2$]$_q$—C(=O)OR$_{1c}$, —CH=CH—C(=O)OR$_{1c}$, —C(=O)OR$_{1c}$, or —C(=O)N(R$_{1c}$)$_2$.

In some embodiments, at least one $R_{1a}$ is —C(=O)CH$_2$C(=O)OR$_{1c}$.

In some embodiments, at least one $R_{1a}$ is —C(=O)—CH=H—C(=O)OR$_{1c}$.

In some embodiments, at least one $R_{1a}$ is —C(=O)R$_{1z}$.

In some embodiments, at least one $R_{1a}$ is

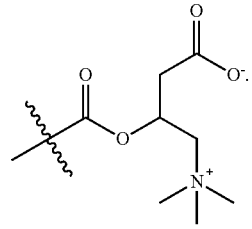

In some embodiments, at least one $R_{1a}$ is

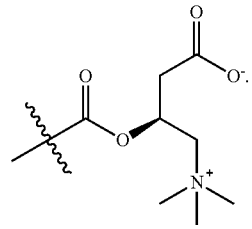

In some embodiments, at least one $R_{1a}$ is

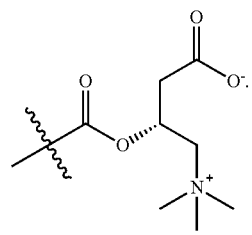

In some embodiments, at least one $R_{1a}$ is

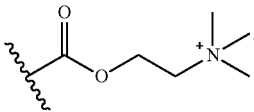

In some embodiments, at least one $R_{1a}$ is —SR$_{1d}$.

In some embodiments, at least one $R_{1a}$ is —SR$_{1d}$.

In some embodiments, at least one $R_{1a}$ is —SH.

In some embodiments, at least one $R_{1a}$ is —SR$_{1d}$, wherein $R_{1d}$ is $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is —SR$_{1d}$, wherein $R_{1d}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1a}$ is —$SR_{1d}$, wherein $R_{1d}$ is $C_3$-$C_{10}$ cycloalkyl, $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1a}$ is —$SR_{1d}$, wherein $R_{1d}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1a}$ is

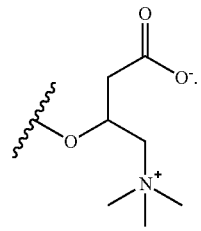

In some embodiments, at least one $R_{1a}$ is

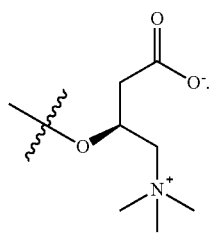

In some embodiments, at least one $R_{1a}$ is

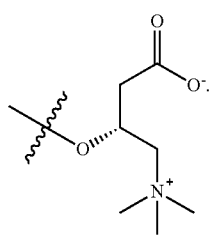

In some embodiments, at least one $R_{1a}$ is

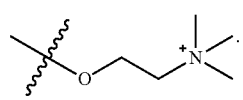 [SMILES: *OCC[N+](C)(C)C]

Variable $R_{1b}$

In some embodiments, at least one $R_{1b}$ is H.

In some embodiments, at least one $R_{1b}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is $C_1$-$C_{20}$ alkyl (e.g., methyl, ethyl, propyl, butyl, pentyl, hexyl, or heptyl).

In some embodiments, at least one $R_{1b}$ is $C_1$-$C_{20}$ alkyl (e.g., methyl, ethyl, propyl, butyl, pentyl, hexyl, or heptyl) substituted with one or more $R_{1e}$.

In some embodiments, at least one $R_{1b}$ is $C_1$-$C_{20}$ alkyl (e.g., methyl, ethyl, propyl, butyl, pentyl, hexyl, or heptyl) substituted with one or more $R_{1z}$.

In some embodiments, at least one $R_{1b}$ is $C_2$-$C_{20}$ alkenyl (e.g., ethenyl, propenyl, butenyl, pentenyl, or hexenyl).

In some embodiments, at least one $R_{1b}$ is $C_2$-$C_{20}$ alkenyl (e.g., ethenyl, propenyl, butenyl, pentenyl, or hexenyl) substituted with one or more $R_{1e}$.

In some embodiments, at least one $R_{1b}$ is $C_2$-$C_{20}$ alkenyl (e.g., ethenyl, propenyl, butenyl, pentenyl, or hexenyl) substituted with one or more $R_{1z}$.

In some embodiments, at least one $R_{1b}$ is $C_2$-$C_{20}$ alkynyl (e.g., ethynyl, propynyl, butynyl, pentynyl, or hexynyl).

In some embodiments, at least one $R_{1b}$ is $C_2$-$C_{20}$ alkynyl (e.g., ethynyl, propynyl, butynyl, pentynyl, or hexynyl) substituted with one or more $R_{1e}$.

In some embodiments, at least one $R_{1b}$ is $C_2$-$C_{20}$ alkynyl (e.g., ethynyl, propynyl, butynyl, pentynyl, or hexynyl) substituted with one or more $R_{1z}$.

In some embodiments, at least one $R_{1b}$ is —$(CH_2)_q$—$C(=O)OR_{1c}$, —$CH_2$—$C(=O)$—$(CH_2)_q$—$C(=O)OR_{1c}$, —$CH_2$—$[C(=O)CH_2]_p$—$[CH_2]_q$—$C(=O)OR_{1c}$, —$CH=CH$—$C(=O)OR_{1c}$, —$C(=O)OR_{1c}$, —$C(=O)N(R_{1c})_2$, or $R_{1z}$.

In some embodiments, at least one $R_{1b}$ is —$(CH_2)_q$—$C(=O)OR_{1c}$.

In some embodiments, at least one $R_{1b}$ is —$(CH_2)_q$—$C(=O)OH$.

In some embodiments, at least one $R_{1b}$ is —$(CH_2)_q$—$C(=O)OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1b}$ is —$(CH_2)_q$—$C(=O)OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —$(CH_2)_q$—$C(=O)OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —$(CH_2)_q$—$C(=O)OR_{1c}$, wherein $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1b}$ is —$CH_2CH_2$—$C(=O)OR_{1c}$.

In some embodiments, at least one $R_{1b}$ is —$CH_2CH_2$—$C(=O)OH$.

In some embodiments, at least one $R_{1b}$ is —$CH_2CH_2$—$C(=O)OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1b}$ is —$CH_2CH_2$—$C(=O)OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —$CH_2CH_2$—$C(=O)OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —$CH_2CH_2$—$C(=O)OR_{1c}$, wherein $R_{1c}$ is —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH_2$—$C(=O)$—$(CH_2)_q$—$C(=O)OR_{1c}$.

In some embodiments, at least one $R_{1b}$ is —$CH_2$—$C(=O)$—$(CH_2)_q$—$C(=O)OH$.

In some embodiments, at least one $R_{1b}$ is —$CH_2$—$C(=O)$—$(CH_2)_q$—$C(=O)OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH_2$—$C(=O)$—$(CH_2)_q$—$C(=O)OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —$CH_2$—$C(=O)$—$(CH_2)_q$—$C(=O)OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —$CH_2$—$C(=O)$—$(CH_2)_q$—$C(=O)OR_{1c}$, wherein $R_{1c}$ is —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH_2$—$[C(=O)CH_2]_p$—$[CH_2]_q$—$C(=O)OR_{1c}$.

In some embodiments, at least one $R_{1b}$ is —$CH_2$—$[C(=O)CH_2]_p$—$[CH_2]_q$—$C(=O)OH$.

In some embodiments, at least one $R_{1b}$ is —$CH_2$—$[C(=O)CH_2]_p$—$[CH_2]_q$—$C(=O)OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH_2$—$[C(=O)CH_2]_p$—$[CH_2]_q$—$C(=O)OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —$CH_2$—$[C(=O)CH_2]_p$—$[CH_2]_q$—$C(=O)OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —$CH_2$—$[C(=O)CH_2]_p$—$[CH_2]_q$—$C(=O)OR_{1c}$, wherein $R_{1c}$ is —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH_2$—$C(=O)$—$CH_2CH_2$—$C(=O)OR_{1c}$.

In some embodiments, at least one $R_{1b}$ is —$CH_2$—$C(=O)$—$CH_2CH_2$—$C(=O)OH$.

In some embodiments, at least one $R_{1b}$ is —$CH_2$—$C(=O)$—$CH_2CH_2$—$C(=O)OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH_2$—$C(=O)$—$CH_2CH_2$—$C(=O)OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —$CH_2$—$C(=O)$—$CH_2CH_2$—$C(=O)OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —$CH_2$—$C(=O)$—$CH_2CH_2$—$C(=O)OR_{1c}$, wherein $R_{1c}$ is —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH=CH$—$C(=O)OR_{1c}$.

In some embodiments, at least one $R_{1b}$ is —$CH$—$H$—$C(=O)OH$.

In some embodiments, at least one $R_{1b}$ is —$CH=CH$—$C(=O)OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$CH=CH$—$C(=O)OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —$CH=CH$—$C(=O)OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —$CH=CH$—$C(=O)OR_{1c}$, wherein $R_{1c}$ is —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$C(=O)OR_{1c}$.

In some embodiments, at least one $R_{1b}$ is —$C(=O)OH$.

In some embodiments, at least one $R_{1b}$ is —$C(=O)OR_{1c}$, wherein $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$C(=O)OR_{1c}$, wherein $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —$C(=O)OR_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —$C(=O)OR_{1c}$, wherein $R_{1c}$ is —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) optionally substituted with one or more $R_{1e}$.

In some embodiments, at least one $R_{1b}$ is —$C(=O)N(R_{1c})_2$.

In some embodiments, at least one $R_{1b}$ is —$C(=O)NHR_{1c}$.

In some embodiments, at least one $R_{1b}$ is —$C(=O)NH_2$.

In some embodiments, at least one $R_{1b}$ is —C(=O)N$(R_{1c})_2$, wherein at least one $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1b}$ is —C(=O)N$(R_{1c})_2$, wherein at least one $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1b}$ is —C(=O)O$R_{1c}$, wherein $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1b}$ is —C(=O)N$(R_{1c})_2$, wherein at least one $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1b}$ is $R_{1z}$.

In some embodiments, at least one $R_{1b}$ is

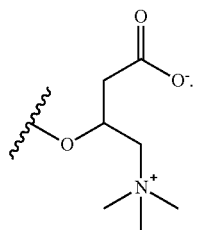

In some embodiments, at least one $R_{1b}$ is

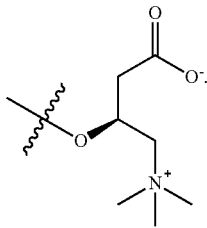

In some embodiments, at least one $R_{1b}$ is

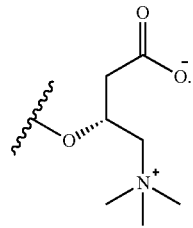

In some embodiments, at least one $R_{1b}$ is

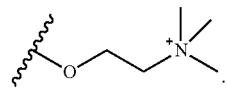 [SMILES: *OCC[N+](C)(C)C]

Variable $R_{1c}$

In some embodiments, at least one $R_{1c}$ is H.

In some embodiments, at least one $R_{1c}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1c}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1c}$ is $C_1$-$C_{20}$ alkyl (e.g., methyl, ethyl, propyl, butyl, pentyl, hexyl, or heptyl).

In some embodiments, at least one $R_{1c}$ is $C_1$-$C_{20}$ alkyl (e.g., methyl, ethyl, propyl, butyl, pentyl, hexyl, or heptyl) substituted with one or more $R_{1e}$.

In some embodiments, at least one $R_{1c}$ is $C_1$-$C_{20}$ alkyl (e.g., methyl, ethyl, propyl, butyl, pentyl, hexyl, or heptyl) substituted with one or more $R_{1z}$.

In some embodiments, at least one $R_{1c}$ is $C_2$-$C_{20}$ alkenyl (e.g., ethenyl, propenyl, butenyl, pentenyl, or hexenyl).

In some embodiments, at least one $R_{1c}$ is $C_2$-$C_{20}$ alkenyl (e.g., ethenyl, propenyl, butenyl, pentenyl, or hexenyl) substituted with one or more $R_{1e}$.

In some embodiments, at least one $R_{1c}$ is $C_2$-$C_{20}$ alkenyl (e.g., ethenyl, propenyl, butenyl, pentenyl, or hexenyl) substituted with one or more $R_{1z}$.

In some embodiments, at least one $R_{1c}$ is $C_2$-$C_{20}$ alkynyl (e.g., ethynyl, propynyl, butynyl, pentynyl, or hexynyl).

In some embodiments, at least one $R_{1c}$ is $C_2$-$C_{20}$ alkynyl (e.g., ethynyl, propynyl, butynyl, pentynyl, or hexynyl) substituted with one or more $R_{1e}$.

In some embodiments, at least one $R_{1c}$ is $C_2$-$C_{20}$ alkynyl (e.g., ethynyl, propynyl, butynyl, pentynyl, or hexynyl) substituted with one or more $R_{1z}$.

In some embodiments, at least one $R_{1c}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1c}$ is $C_3$-$C_{12}$ cycloalkyl optionally substituted with one or more $R_{1c}$. In some embodiments, at least one $R_{1c}$ is $C_3$-$C_{12}$ cycloalkyl. In some embodiments, at least one $R_{1c}$ is $C_3$-$C_{12}$ cycloalkyl substituted with one or more $R_{1e}$. In some embodiments, at least one $R_{1c}$ is $C_3$-$C_{12}$ cycloalkyl substituted with one or more $R_{1z}$.

In some embodiments, at least one $R_{1c}$ is $C_3$-$C_{12}$ heterocycloalkyl optionally substituted with one or more $R_{1c}$. In some embodiments, at least one $R_{1c}$ is $C_3$-$C_{12}$ heterocycloalkyl. In some embodiments, at least one $R_{1c}$ is $C_3$-$C_{12}$ heterocycloalkyl substituted with one or more $R_{1e}$. In some embodiments, at least one $R_{1c}$ is $C_3$-$C_{12}$ heterocycloalkyl substituted with one or more $R_{1z}$.

In some embodiments, at least one $R_{1c}$ is $C_3$-$C_{12}$ aryl optionally substituted with one or more $R_{1e}$. In some embodiments, at least one $R_{1c}$ is $C_3$-$C_{12}$ aryl. In some embodiments, at least one $R_{1c}$ is $C_3$-$C_{12}$ aryl substituted with one or more $R_{1e}$. In some embodiments, at least one $R_{1c}$ is $C_3$-$C_{12}$ aryl substituted with one or more $R_{1z}$.

In some embodiments, at least one $R_{1c}$ is $C_3$-$C_{12}$ heteroaryl optionally substituted with one or more $R_{1e}$. In some embodiments, at least one $R_{1c}$ is $C_3$-$C_{12}$ heteroaryl. In some embodiments, at least one $R_{1c}$ is $C_3$-$C_{12}$ heteroaryl substituted with one or more $R_{1e}$. In some embodiments, at least one $R_{1c}$ is $C_3$-$C_{12}$ heteroaryl substituted with one or more $R_{1z}$.

In some embodiments, at least one $R_{1c}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1c}$ is —($C_1$-$C_{20}$ alkyl)-($C_3$-$C_{12}$ cycloalkyl) optionally substituted with one or more $R_{1e}$. In some embodiments, at least one $R_{1c}$ is —($C_1$-$C_{20}$ alkyl)-($C_3$-$C_{12}$ cycloalkyl). In some embodiments, at least one $R_{1c}$ is —($C_1$-$C_{20}$ alkyl)-($C_3$-$C_{12}$ cycloalkyl) substituted with one or more $R_{1e}$. In some embodiments, at least one $R_{1c}$ is —($C_1$-$C_{20}$ alkyl)-($C_3$-$C_{12}$ cycloalkyl) substituted with one or more $R_{1z}$.

In some embodiments, at least one $R_{1c}$ is —($C_1$-$C_{20}$ alkyl)-($C_3$-$C_{12}$ heterocycloalkyl) optionally substituted with one or more $R_{1e}$. In some embodiments, at least one $R_{1c}$ is —($C_1$-$C_{20}$ alkyl)-($C_3$-$C_{12}$ heterocycloalkyl). In some embodiments, at least one $R_{1c}$ is —($C_1$-$C_{20}$ alkyl)-($C_3$-$C_{12}$ heterocycloalkyl) substituted with one or more $R_{1e}$. In some embodiments, at least one $R_{1c}$ is —($C_1$-$C_{20}$ alkyl)-($C_3$-$C_{12}$ heterocycloalkyl) substituted with one or more $R_{1z}$.

In some embodiments, at least one $R_{1c}$ is —($C_1$-$C_{20}$ alkyl)-($C_3$-$C_{12}$ aryl) optionally substituted with one or more $R_{1e}$. In some embodiments, at least one $R_{1c}$ is —($C_1$-$C_{20}$ alkyl)-($C_3$-$C_{12}$ aryl). In some embodiments, at least one $R_{1c}$ is —($C_1$-$C_{20}$ alkyl)-($C_3$-$C_{12}$ aryl) substituted with one or more $R_{1e}$. In some embodiments, at least one $R_{1c}$ is —($C_1$-$C_{20}$ alkyl)-($C_3$-$C_{12}$ aryl) substituted with one or more $R_{1z}$.

In some embodiments, at least one $R_{1c}$ is —($C_1$-$C_{20}$ alkyl)-($C_3$-$C_{12}$ heteroaryl) optionally substituted with one or more $R_{1e}$. In some embodiments, at least one $R_{1c}$ is —($C_1$-$C_{20}$ alkyl)-($C_3$-$C_{12}$ heteroaryl). In some embodiments, at least one $R_{1c}$ is —($C_1$-$C_{20}$ alkyl)-($C_3$-$C_{12}$ heteroaryl) substituted with one or more $R_{1e}$. In some embodiments, at least one $R_{1c}$ is —($C_1$-$C_{20}$ alkyl)-($C_3$-$C_{12}$ heteroaryl) substituted with one or more $R_{1z}$.

Variable $R_{1d}$

In some embodiments, at least one $R_{1d}$ is H.

In some embodiments, at least one $R_{1d}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$.

In some embodiments, at least one $R_{1d}$ is $C_1$-$C_{20}$ alkyl, $C_2$-$C_{20}$ alkenyl, or $C_2$-$C_{20}$ alkynyl optionally substituted with one or more $R_{1e}$.

In some embodiments, at least one $R_{1d}$ is $C_1$-$C_{20}$ alkyl (e.g., methyl, ethyl, propyl, butyl, pentyl, hexyl, or heptyl).

In some embodiments, at least one $R_{1d}$ is $C_1$-$C_{20}$ alkyl (e.g., methyl, ethyl, propyl, butyl, pentyl, hexyl, or heptyl) substituted with one or more $R_{1e}$.

In some embodiments, at least one $R_{1d}$ is $C_1$-$C_{20}$ alkyl (e.g., methyl, ethyl, propyl, butyl, pentyl, hexyl, or heptyl) substituted with one or more $R_{1z}$.

In some embodiments, at least one $R_{1d}$ is $C_2$-$C_{20}$ alkenyl (e.g., ethenyl, propenyl, butenyl, pentenyl, or hexenyl).

In some embodiments, at least one $R_{1d}$ is $C_2$-$C_{20}$ alkenyl (e.g., ethenyl, propenyl, butenyl, pentenyl, or hexenyl) substituted with one or more $R_{1e}$.

In some embodiments, at least one $R_{1d}$ is $C_2$-$C_{20}$ alkenyl (e.g., ethenyl, propenyl, butenyl, pentenyl, or hexenyl) substituted with one or more $R_{1z}$.

In some embodiments, at least one $R_{1d}$ is $C_2$-$C_{20}$ alkynyl (e.g., ethynyl, propynyl, butynyl, pentynyl, or hexynyl).

In some embodiments, at least one $R_{1d}$ is $C_2$-$C_{20}$ alkynyl (e.g., ethynyl, propynyl, butynyl, pentynyl, or hexynyl) substituted with one or more $R_{1e}$.

In some embodiments, at least one $R_{1d}$ is $C_2$-$C_{20}$ alkynyl (e.g., ethynyl, propynyl, butynyl, pentynyl, or hexynyl) substituted with one or more $R_{1z}$.

In some embodiments, at least one $R_{1d}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1e}$.

In some embodiments, at least one $R_{1d}$ is $C_3$-$C_{12}$ cycloalkyl optionally substituted with one or more $R_{1e}$. In some embodiments, at least one $R_{1d}$ is $C_3$-$C_{12}$ cycloalkyl. In some embodiments, at least one $R_{1d}$ is $C_3$-$C_{12}$ cycloalkyl substituted with one or more $R_{1e}$. In some embodiments, at least one $R_{1d}$ is $C_3$-$C_{12}$ cycloalkyl substituted with one or more $R_{1z}$.

In some embodiments, at least one $R_{1d}$ is $C_3$-$C_{12}$ heterocycloalkyl optionally substituted with one or more $R_{1e}$. In some embodiments, at least one $R_{1d}$ is $C_3$-$C_{12}$ heterocycloalkyl. In some embodiments, at least one $R_{1d}$ is $C_3$-$C_{12}$ heterocycloalkyl substituted with one or more $R_{1e}$. In some embodiments, at least one $R_{1d}$ is $C_3$-$C_{12}$ heterocycloalkyl substituted with one or more $R_{1z}$.

In some embodiments, at least one $R_{1d}$ is $C_3$-$C_{12}$ aryl optionally substituted with one or more $R_{1e}$. In some embodiments, at least one $R_{1d}$ is $C_3$-$C_{12}$ aryl. In some embodiments, at least one $R_{1d}$ is $C_3$-$C_{12}$ aryl substituted with one or more $R_{1e}$. In some embodiments, at least one $R_{1d}$ is $C_3$-$C_{12}$ aryl substituted with one or more $R_{1z}$.

In some embodiments, at least one $R_{1d}$ is $C_3$-$C_{12}$ heteroaryl optionally substituted with one or more $R_{1e}$. In some embodiments, at least one $R_{1d}$ is $C_3$-$C_{12}$ heteroaryl. In some embodiments, at least one $R_{1d}$ is $C_3$-$C_{12}$ heteroaryl substituted with one or more $R_{1e}$. In some embodiments, at least one $R_{1d}$ is $C_3$-$C_{12}$ heteroaryl substituted with one or more $R_{1z}$.

In some embodiments, at least one $R_{1d}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1e}$.

In some embodiments, at least one $R_{1d}$ is —($C_1$-$C_{20}$ alkyl)-($C_3$-$C_{12}$ cycloalkyl) optionally substituted with one or more $R_{1e}$. In some embodiments, at least one $R_{1d}$ is —($C_1$-$C_{20}$ alkyl)-($C_3$-$C_{12}$ cycloalkyl). In some embodiments, at least one $R_{1d}$ is —($C_1$-$C_{20}$ alkyl)-($C_3$-$C_{12}$ cycloalkyl) substituted with one or more $R_{1e}$. In some embodiments, at least one $R_{1d}$ is —($C_1$-$C_{20}$ alkyl)-($C_3$-$C_{12}$ cycloalkyl) substituted with one or more $R_{1z}$.

In some embodiments, at least one $R_{1d}$ is —($C_1$-$C_{20}$ alkyl)-($C_3$-$C_{12}$ heterocycloalkyl) optionally substituted with one or more $R_{1e}$. In some embodiments, at least one $R_{1d}$ is —($C_1$-$C_{20}$ alkyl)-($C_3$-$C_{12}$ heterocycloalkyl). In some embodiments, at least one $R_{1d}$ is —($C_1$-$C_{20}$ alkyl)-($C_3$-$C_{12}$ heterocycloalkyl) substituted with one or more $R_{1e}$. In some embodiments, at least one $R_{1d}$ is —($C_1$-$C_{20}$ alkyl)-($C_3$-$C_{12}$ heterocycloalkyl) substituted with one or more $R_{1z}$.

In some embodiments, at least one $R_{1d}$ is —($C_1$-$C_{20}$ alkyl)-($C_3$-$C_{12}$ aryl) optionally substituted with one or more $R_{1c}$. In some embodiments, at least one $R_{1d}$ is —($C_1$-$C_{20}$ alkyl)-($C_3$-$C_{12}$ aryl). In some embodiments, at least one $R_{1d}$ is —($C_1$-$C_{20}$ alkyl)-($C_3$-$C_{12}$ aryl) substituted with one or more $R_{1e}$. In some embodiments, at least one $R_{1d}$ is —($C_1$-$C_{20}$ alkyl)-($C_3$-$C_{12}$ aryl) substituted with one or more $R_{1z}$.

In some embodiments, at least one $R_{1d}$ is —($C_1$-$C_{20}$ alkyl)-($C_3$-$C_{12}$ heteroaryl) optionally substituted with one or more $R_{1e}$. In some embodiments, at least one $R_{1d}$ is —($C_1$-$C_{20}$ alkyl)-($C_3$-$C_{12}$ heteroaryl). In some embodiments, at least one $R_{1d}$ is —($C_1$-$C_{20}$ alkyl)-($C_3$-$C_{12}$ heteroaryl) substituted with one or more $R_{1e}$. In some embodiments, at least one $R_{1d}$ is —($C_1$-$C_{20}$ alkyl)-($C_3$-$C_{12}$ heteroaryl) substituted with one or more $R_{1z}$.

Variable $R_{1e}$

In some embodiments, at least one $R_{1e}$ is H.

In some embodiments, at least one $R_{1e}$ is halogen, $C_1$-$C_{20}$ alkyl, $C_2$-$C_{20}$ alkenyl, $C_2$-$C_{20}$ alkynyl, —$OR_{1g}$, —C(=O)$OR_{1g}$, —C(=O)N($R_{1g}$)$_2$, —N($R_{1g}$)$_2$, —N($R_{1g}$)C(=O)$R_{1f}$, —N($R_{1g}$)C(=O)$R_{1z}$, —N($R_{1g}$)C(=O)$OR_{1g}$, —OC(=O)$R_{1f}$, —OC(=O)$R_{1z}$, —OC(=O)$OR_{1g}$, —$SR_{1g}$, —N$^+$($R_{1g}$)$_3$, —SC(=O)$R_{1f}$, —SC(=O)$R_{1z}$, —SC(=O)$OR_{1g}$, —SC(=O)N($R_{1g}$)$_2$, —C(=O)$R_{1f}$, —C(=O)$R_{1z}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$.

In some embodiments, at least one $R_{1e}$ is halogen (e.g., F, Cl, Br, I).

In some embodiments, at least one $R_{1e}$ is F or Cl. In some embodiments, at least one $R_{1e}$ is F. In some embodiments, at least one $R_{1e}$ is Cl.

In some embodiments, at least one $R_{1e}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is $C_1$-$C_{20}$ alkyl (e.g., methyl, ethyl, propyl, butyl, pentyl, hexyl, or heptyl).

In some embodiments, at least one $R_{1e}$ is $C_1$-$C_{20}$ alkyl (e.g., methyl, ethyl, propyl, butyl, pentyl, hexyl, or heptyl) substituted with one or more $R_{1z}$.

In some embodiments, at least one $R_{1e}$ is $C_2$-$C_{20}$ alkenyl (e.g., ethenyl, propenyl, butenyl, pentenyl, or hexenyl).

In some embodiments, at least one $R_{1e}$ is $C_2$-$C_{20}$ alkenyl (e.g., ethenyl, propenyl, butenyl, pentenyl, or hexenyl) substituted with one or more $R_{1z}$.

In some embodiments, at least one $R_{1e}$ is $C_2$-$C_{20}$ alkynyl (e.g., ethynyl, propynyl, butynyl, pentynyl, or hexynyl).

In some embodiments, at least one $R_{1e}$ is $C_2$-$C_{20}$ alkynyl (e.g., ethynyl, propynyl, butynyl, pentynyl, or hexynyl) substituted with one or more $R_{1z}$.

In some embodiments, at least one $R_{1e}$ is —$OR_{1g}$, —C(=O)$OR_{1g}$, —C(=O)N($R_{1g}$)$_2$, —N($R_{1g}$)$_2$, —N($R_{1g}$)C(=O)$R_{1f}$, —N($R_{1g}$)C(=O)$R_{1z}$, —N($R_{1g}$)C(=O)$OR_{1g}$, —OC(=O)$R_{1f}$, —OC(=O)$R_{1z}$, —OC(=O)$OR_{1g}$, —$SR_{1g}$, —N$^+$($R_{1g}$)$_3$, —SC(=O)$R_{1f}$, —SC(=O)$R_{1z}$, —SC(=O)$OR_{1g}$, —SC(=O)N($R_{1g}$)$_2$, —C(=O)$R_{1f}$, —C(=O)$R_{1z}$, or $R_{1z}$.

In some embodiments, at least one $R_{1c}$ is —$OR_{1g}$, —C(=O)$OR_{1g}$, —C(=O)N($R_{1g}$)$_2$, —N($R_{1g}$)$_2$, —N($R_{1g}$)C(=O)$R_{1f}$, —N($R_{1g}$)C(=O)$R_{1z}$, —N($R_{1g}$)C(=O)$OR_{1g}$, —OC(=O)$R_{1f}$, —OC(=O)$R_{1z}$, —OC(=O)$OR_{1g}$, —$SR_{1g}$, —N$^+$($R_{1g}$)$_3$, —SC(=O)$R_{1f}$, —SC(=O)$R_{1z}$, —SC(=O)$OR_{1g}$, —SC(=O)N($R_{1g}$)$_2$, —C(=O)$R_{1f}$, or —C(=O)$R_{1z}$.

In some embodiments, at least one $R_{1e}$ is —$OR_{1g}$.

In some embodiments, at least one $R_{1e}$ is —OH.

In some embodiments, at least one $R_{1e}$ is —$OR_{1g}$, wherein $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —$OR_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —$OR_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —$OR_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —C(=O)$OR_{1g}$.

In some embodiments, at least one $R_{1e}$ is —C(=O)OH.

In some embodiments, at least one $R_{1e}$ is —C(=O)$OR_{1g}$, wherein $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1c}$ is —C(=O)$OR_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1c}$ is —C(=O)$OR_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1c}$ is —C(=O)$OR_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1c}$ is —C(=O)N($R_{1g}$)$_2$.

In some embodiments, at least one $R_{1e}$ is —C(=O)NH$R_{1g}$.

In some embodiments, at least one $R_{1e}$ is —C(=O)NH$_2$.

In some embodiments, at least one $R_{1e}$ is —C(=O)N($R_{1g}$)$_2$, wherein at least one $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —C(=O)N($R_{1g}$)$_2$, wherein at least one $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —C(=O)N($R_{1g}$)$_2$, wherein at least one $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —C(=O)N($R_{1g}$)$_2$, wherein at least one $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1c}$ is —N($R_{1g}$)$_2$.

In some embodiments, at least one $R_{1c}$ is —NH$R_{1g}$.

In some embodiments, at least one $R_{1c}$ is —NH$_2$.

In some embodiments, at least one $R_{1c}$ is —N($R_{1g}$)$_2$, wherein at least one $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1z}$.

In some embodiments, at least one R$_{1c}$ is —N(R$_{1g}$)$_2$, wherein at least one R$_{1g}$ is C$_1$-C$_{20}$ alkyl, C$_2$-C$_{20}$ alkenyl, or C$_2$-C$_{20}$ alkynyl optionally substituted with one or more R$_{1z}$.

In some embodiments, at least one R$_{1c}$ is —N(R$_{1g}$)$_2$, wherein at least one R$_{1g}$ is C$_3$-C$_{12}$ cycloalkyl, C$_3$-C$_{12}$ heterocycloalkyl, C$_3$-C$_{12}$ aryl, or C$_3$-C$_{12}$ heteroaryl optionally substituted with one or more R$_{1z}$.

In some embodiments, at least one R$_{1e}$ is —N(R$_{1g}$)$_2$, wherein at least one R$_{1g}$ is —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1g}$.

In some embodiments, at least one R$_{1e}$ is —N(R$_{1g}$)C(=O)R$_{1f}$.

In some embodiments, at least one R$_{1e}$ is —NHC(=O)R$_{1f}$.

In some embodiments, at least one R$_{1e}$ is —N(R$_{1g}$)C(=O)H.

In some embodiments, at least one R$_{1e}$ is —NHC(=O)H.

In some embodiments, at least one R$_{1e}$ is —N(R$_{1g}$)C(=O)R$_{1f}$, wherein R$_{1g}$ is C$_1$-C$_{20}$ alkyl, C$_2$-C$_{20}$ alkenyl, C$_2$-C$_{20}$ alkynyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1z}$.

In some embodiments, at least one R$_{1e}$ is —N(R$_{1g}$)C(=O)R$_{1f}$, wherein R$_{1g}$ is C$_1$-C$_{20}$ alkyl, C$_2$-C$_{20}$ alkenyl, or C$_2$-C$_{20}$ alkynyl optionally substituted with one or more R$_{1z}$.

In some embodiments, at least one R$_{1e}$ is —N(R$_{1g}$)C(=O)R$_{1f}$, wherein R$_{1g}$ is C$_3$-C$_{12}$ cycloalkyl, C$_3$-C$_{12}$ heterocycloalkyl, C$_3$-C$_{12}$ aryl, or C$_3$-C$_{12}$ heteroaryl optionally substituted with one or more R$_{1z}$.

In some embodiments, at least one R$_{1e}$ is —N(R$_{1g}$)C(=O)R$_{1f}$, wherein R$_{1g}$ is —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl) optionally substituted with one or more R$_{1z}$.

In some embodiments, at least one R$_{1e}$ is —N(R$_{1g}$)C(=O)R$_{1f}$, wherein R$_{1f}$ is C$_1$-C$_{20}$ alkyl, C$_2$-C$_{20}$ alkenyl, C$_2$-C$_{20}$ alkynyl, —CH$_2$C(=O)OR$_{1g}$, —CH=CH—C(=O)OR$_{1g}$, —C(=O)OR$_{1g}$, —C(=O)N(R$_{1g}$)$_2$, or R$_{1g}$, wherein the C$_1$-C$_{20}$ alkyl, C$_2$-C$_{20}$ alkenyl, or C$_2$-C$_{20}$ alkynyl is optionally substituted with one or more R$_{1z}$.

In some embodiments, at least one R$_{1e}$ is —N(R$_{1g}$)C(=O)R$_{1f}$, wherein R$_{1f}$ is C$_1$-C$_{20}$ alkyl, C$_2$-C$_{20}$ alkenyl, or C$_2$-C$_{20}$ alkynyl optionally substituted with one or more R$_{1z}$.

In some embodiments, at least one R$_{1e}$ is —N(R$_{1g}$)C(=O)R$_{1f}$, wherein R$_{1f}$—CH$_2$C(=O)OR$_{1g}$, —CH=CH—C(=O)OR$_{1g}$, —C(=O)OR$_{1g}$, —C(=O)N(R$_{1g}$)$_2$, or R$_{1z}$.

In some embodiments, at least one R$_{1e}$ is —N(R$_{1g}$)C(=O)R$_{1f}$, wherein R$_{1f}$—CH$_2$C(=O)OR$_{1g}$, —CH=CH—C(=O)OR$_{1g}$, —C(=O)OR$_{1g}$, or —C(=O)N(R$_{1g}$)$_2$.

In some embodiments, at least one R$_{1e}$ is —N(R$_{1g}$)C(=O)R$_{1z}$.

In some embodiments, at least one R$_{1e}$ is

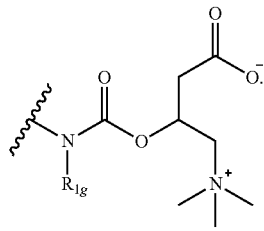

In some embodiments, at least one R$_{1e}$ is

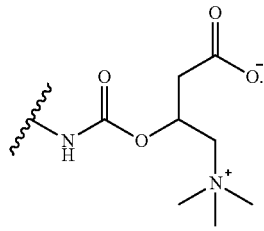

In some embodiments, at least one R$_{1e}$ is

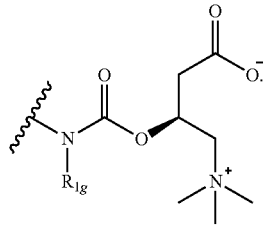

In some embodiments, at least one R$_{1e}$ is

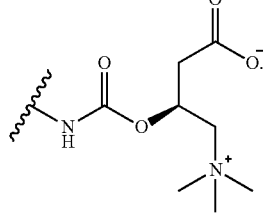

In some embodiments, at least one R$_{1e}$ is

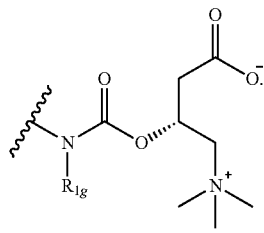

In some embodiments, at least one $R_{1e}$ is

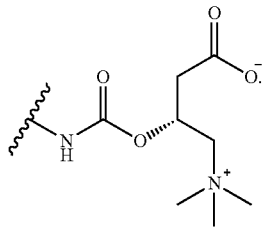

In some embodiments, at least one $R_{1e}$ is

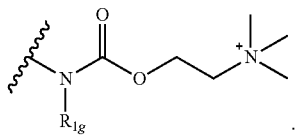

In some embodiments, at least one $R_{1e}$ is

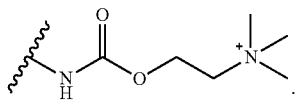 [SMILES: *NC(=O)OCC[N+](C)(C)C]

In some embodiments, at least one $R_{1e}$ is —N($R_{1g}$)C(=O)O$R_{1g}$.
In some embodiments, at least one $R_{1e}$ is —N($R_{1g}$)C(=O)OH.
In some embodiments, at least one $R_{1e}$ is —NHC(=O)O$R_{1g}$.
In some embodiments, at least one $R_{1e}$ is —NHC(=O)OH.
In some embodiments, at least one $R_{1e}$ is —N($R_{1g}$)C(=O)O$R_{1g}$, wherein at least one $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.
In some embodiments, at least one $R_{1c}$ is —N($R_{1g}$)C(=O)O$R_{1g}$, wherein at least one $R_{1g}$ is $C_1$-$C_{20}$ alkyl, $C_2$-$C_{20}$ alkenyl, or $C_2$-$C_{20}$ alkynyl optionally substituted with one or more $R_{1z}$.
In some embodiments, at least one $R_{1c}$ is —N($R_{1g}$)C(=O)O$R_{1g}$, wherein at least one $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.
In some embodiments, at least one $R_{1e}$ is —N($R_{1g}$)C(=O)O$R_{1g}$, wherein at least one $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1f}$.
In some embodiments, at least one $R_{1e}$ is —OC(=O)$R_{1f}$.
In some embodiments, at least one $R_{1e}$ is —OC(=O)H.
In some embodiments, at least one $R_{1e}$ is —OC(=O)$R_{1f}$, wherein $R_{1e}$ is $C_1$-$C_{20}$ alkyl, $C_2$-$C_{20}$ alkenyl, $C_2$-$C_{20}$ alkynyl, —CH$_2$C(=O)O$R_{1g}$, —CH=H—C(=O)O$R_{1g}$, —C(=O)O$R_{1g}$, —C(=O)N($R_{1g}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$.
In some embodiments, at least one $R_{1e}$ is —OC(=O)$R_{1f}$, wherein $R_{1e}$ is $C_1$-$C_{20}$ alkyl, $C_2$-$C_{20}$ alkenyl, or $C_2$-$C_{20}$ alkynyl optionally substituted with one or more $R_{1z}$.
In some embodiments, at least one $R_{1c}$ is —OC(=O)$R_{1f}$, wherein $R_{1f}$—CH$_2$C(=O)O$R_{1g}$, —CH=CH—C(=O)O$R_{1g}$, —C(=O)O$R_{1g}$, —C(=O)N($R_{1g}$)$_2$, or $R_{1z}$.
In some embodiments, at least one $R_{1e}$ is —OC(=O)$R_{1f}$, wherein $R_{1f}$—CH$_2$C(=O)O$R_{1g}$, —CH=CH—C(=O)O$R_{1g}$, —C(=O)O$R_{1g}$, or —C(=O)N($R_{1g}$)$_2$.
In some embodiments, at least one $R_{1e}$ is —OC(=O)$R_{1z}$.
In some embodiments, at least one $R_{1e}$ is
In some embodiments, at least one $R_{1e}$ is

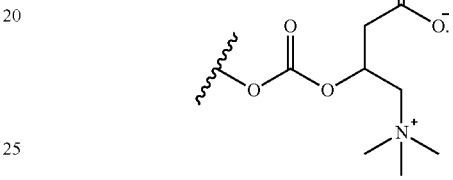

In some embodiments, at least one $R_{1e}$ is

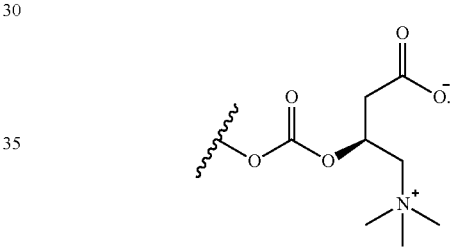

In some embodiments, at least one $R_{1e}$ is

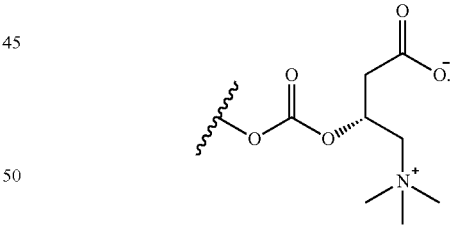

In some embodiments, at least one $R_{1e}$ is

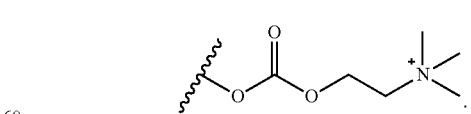

In some embodiments, at least one $R_{1e}$ is —OC(=O)O$R_{1g}$.
In some embodiments, at least one $R_{1e}$ is —OC(=O)OH.
In some embodiments, at least one $R_{1e}$ is —OC(=O)O$R_{1g}$, wherein $R_{1g}$ is $C_1$-$C_{20}$ alkyl, $C_2$-$C_{20}$ alkenyl. $C_2$-$C_{20}$ alkynyl. $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1c}$ is —OC(=O)OR$_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1c}$ is —OC(=O)OR$_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —OC(=O)OR$_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —SR$_{1g}$.

In some embodiments, at least one $R_{1e}$ is —SH.

In some embodiments, at least one $R_{1e}$ is —SR$_{1g}$, wherein $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —SR$_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —SR$_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1c}$ is —SR$_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —N$^+$(R$_{1g}$)$_3$.

In some embodiments, at least one $R_{1e}$ is —N$^+$H(R$_{1g}$)$_2$.

In some embodiments, at least one $R_{1e}$ is —N$^+$H$_2$R$_{1g}$.

In some embodiments, at least one $R_{1e}$ is —N$^+$H$_3$.

In some embodiments, at least one $R_{1e}$ is —N$^+$(R$_{1g}$)$_3$, wherein at least one $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1c}$ is —N$^+$(R$_{1g}$)$_3$, wherein at least one $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1c}$ is —N$^+$(R$_{1g}$)$_3$, wherein at least one $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —N$^+$(R$_{1g}$)$_3$, wherein at least one $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more Rip.

In some embodiments, at least one $R_{1e}$ is —SC(=O)R$_{1f}$.

In some embodiments, at least one $R_{1e}$ is —SC(=O)H.

In some embodiments, at least one $R_{1e}$ is —SC(=O)R$_{1f}$, wherein $R_{1f}$ is $C_1$-$C_{20}$ alkyl, $C_2$-$C_{20}$ alkenyl, $C_2$-$C_{20}$ alkynyl, —CH$_2$C(=O)OR$_{1g}$, —CH=CH—C(=O)OR$_{1g}$, —C(=O)OR$_{1g}$, —C(=O)N(R$_{1g}$)$_2$, or R$_{1g}$, wherein the $C_1$-$C_{20}$ alkyl, $C_2$-$C_{20}$ alkenyl, or $C_2$-$C_{20}$ alkynyl is optionally substituted with one or more $R_{1g}$.

In some embodiments, at least one $R_{1e}$ is —SC(=O)R$_{1f}$, wherein $R_{1f}$ is $C_1$-$C_{20}$ alkyl, $C_2$-$C_{20}$ alkenyl, or $C_2$-$C_{20}$ alkynyl optionally substituted with one or more $R_{1g}$.

In some embodiments, at least one $R_{1e}$ is —SC(=O)R$_{1f}$, wherein $R_{1f}$—CH$_2$C(=O)OR$_{1g}$, —CH=CH—C(=O)OR$_{1g}$, —C(=O)OR$_{1g}$, —C(=O)N(R$_{1g}$)$_2$, or R$_{1g}$.

In some embodiments, at least one $R_{1e}$ is —SC(=O)R$_{1f}$, wherein $R_{1f}$—CH$_2$C(=O)OR$_{1g}$, —CH=CH—C(=O)OR$_{1g}$, —C(=O)OR$_{1g}$, or —C(=O)N(R$_{1g}$)$_2$.

In some embodiments, at least one $R_{1e}$ is —SC(=O)R$_{1z}$.

In some embodiments, at least one $R_{1c}$ is

[chemical structure]

In some embodiments, at least one $R_{1e}$ is

[chemical structure]

In some embodiments, at least one $R_{1e}$ is

[chemical structure]

In some embodiments, at least one $R_{1e}$ is

[chemical structure]

In some embodiments, at least one $R_{1e}$ is —SC(=O)OR$_{1g}$.

In some embodiments, at least one $R_{1e}$ is —SC(=O)OH.

In some embodiments, at least one $R_{1e}$ is —SC(=O)OR$_{1g}$, wherein $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —SC(=O)$OR_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —SC(=O)$OR_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —SC(=O)$OR_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —SC(=O)N($R_{1g}$)$_2$.

In some embodiments, at least one $R_{1e}$ is —SC(=O)$NHR_{1g}$.

In some embodiments, at least one $R_{1e}$ is —SC(=O)$NH_2$.

In some embodiments, at least one $R_{1e}$ is —SC(=O)N($R_{1g}$)$_2$, wherein at least one $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —SC(=O)N($R_{1g}$)$_2$, wherein at least one $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1E}$ is —SC(=O)N($R_{1g}$)$_2$, wherein at least one $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —SC(=O)N($R_{1g}$)$_2$, wherein at least one $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —C(=O)$R_{1f}$.

In some embodiments, at least one $R_{1e}$ is —C(=O)H.

In some embodiments, at least one $R_{1e}$ is —C(=O)$R_{1f}$, wherein $R_{1f}$ is $C_1$-$C_{20}$ alkyl, $C_2$-$C_{20}$ alkenyl, $C_2$-$C_{20}$ alkynyl, —$CH_2$C(=O)$OR_{1g}$, —CH=H—C(=O)$OR_{1g}$, —C(=O)$OR_{1g}$, —C(=O)N($R_{1g}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$.

In some embodiments, at least one $R_{1e}$ is —C(=O)$R_{1f}$, wherein $R_{1f}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —C(=O)$R_{1f}$, wherein $R_{1f}$—$CH_2$C(=O)$OR_{1g}$, —CH=CH—C(=O)$OR_{1g}$, —C(=O)N($R_{1g}$)$_2$, or $R_{1z}$.

In some embodiments, at least one $R_{1e}$ is —SC(=O)$R_{1f}$, wherein $R_{1f}$—$CH_2$C(=O)$OR_{1g}$, —CH=H—C(=O)$OR_{1g}$, —C(=O)$OR_{1g}$, or —C(=O)N($R_{1g}$)$_2$.

In some embodiments, at least one $R_{1e}$ is —C(=O)$R_{1z}$.

In some embodiments, at least one $R_{1e}$ is

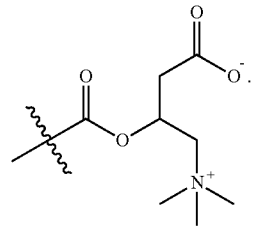

In some embodiments, at least one $R_{1e}$ is

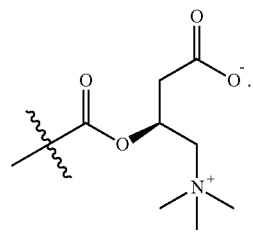

In some embodiments, at least one $R_{1e}$ is

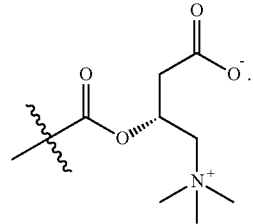

In some embodiments, at least one $R_{1e}$ is

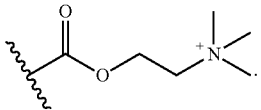

In some embodiments, at least one $R_{1e}$ is $R_{1z}$.

In some embodiments, at least one $R_{1e}$ is

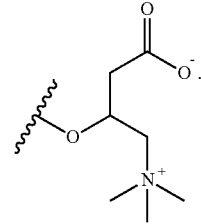

In some embodiments, at least one $R_{1e}$ is

[structure]

In some embodiments, at least one $R_{1e}$ is

[structure]

In some embodiments, at least one $R_{1e}$ is

[structure]

Variable $R_{1f}$

In some embodiments, at least one $R_{1f}$ is H.

In some embodiments, at least one $R_{1f}$ is $C_1$-$C_{20}$ alkyl, $C_2$-$C_{20}$ alkenyl, $C_2$-$C_{20}$ alkynyl, —$CH_2C(=O)OR_{1g}$, —CH=CH—C(=O)$OR_{1g}$, —C(=O)$OR_{1g}$, —C(=O)N($R_{1g}$)$_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$.

In some embodiments, at least one $R_{1f}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1f}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1f}$ is $C_1$-$C_{20}$ alkyl (e.g., methyl, ethyl, propyl, butyl, pentyl, hexyl, or heptyl).

In some embodiments, at least one $R_{1f}$ is $C_1$-$C_{20}$ alkyl (e.g., methyl, ethyl, propyl, butyl, pentyl, hexyl, or heptyl) substituted with one or more $R_{1z}$.

In some embodiments, at least one $R_{1f}$ is $C_2$-$C_{20}$ alkenyl (e.g., ethenyl, propenyl, butenyl, pentenyl, or hexenyl).

In some embodiments, at least one $R_{1f}$ is $C_2$-$C_{20}$ alkenyl (e.g., ethenyl, propenyl, butenyl, pentenyl, or hexenyl) substituted with one or more $R_{1z}$.

In some embodiments, at least one $R_{1f}$ is $C_2$-$C_{20}$ alkynyl (e.g., ethynyl, propynyl, butynyl, pentynyl, or hexynyl).

In some embodiments, at least one $R_{1f}$ is $C_2$-$C_{20}$ alkynyl (e.g., ethynyl, propynyl, butynyl, pentynyl, or hexynyl) substituted with one or more $R_{1z}$.

In some embodiments, at least one $R_{1f}$ is —$CH_2C(=O)OR_{1g}$, —CH=CH—C(=O)$OR_{1g}$, —C(=O)$OR_{1g}$, —C(=O)N($R_{1g}$)$_2$, or $R_{1c}$.

In some embodiments, at least one $R_{1f}$ is —$CH_2C(=O)OR_{1g}$, —CH=CH—C(=O)$OR_{1g}$, —C(=O)$OR_{1g}$, or —C(=O)N($R_{1g}$)$_2$.

In some embodiments, at least one $R_{1f}$ is —$CH_2C(=O)OR_{1g}$.

In some embodiments, at least one $R_{1e}$ is —$CH_2C(=O)OH$.

In some embodiments, at least one $R_{1e}$ is —$CH_2C(=O)OR_{1g}$, wherein $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —$CH_2C(=O)OR_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —$CH_2C(=O)OR_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1c}$ is —$CH_2C(=O)OR_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1f}$ is —CH=CH—C(=O)$OR_{1g}$.

In some embodiments, at least one $R_{1e}$ is —CH=CH—C(=O)OH.

In some embodiments, at least one $R_{1e}$ is —CH=CH—C(=O)$OR_{1g}$, wherein $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —CH=CH—C(=O)$OR_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —CH=CH—C(=O)$OR_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —CH=CH—C(=O)$OR_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1f}$ is —C(=O)$OR_{1g}$.

In some embodiments, at least one $R_{1e}$ is —C(=O)OH.

In some embodiments, at least one $R_{1e}$ is —C(=O)$OR_{1g}$, wherein $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1e}$ is —C(=O)$OR_{1g}$, wherein $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1e}$ is —C(=O)$OR_{1g}$, wherein $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1e}$ is —C(=O)$OR_{1g}$, wherein $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-

$C_{12}$ aryl), or —($C_1$-$C_{20}$alkyl)-($C_3$-$C_{12}$ heteroaryl) optionally substituted with one or more $R_{1g}$.

In some embodiments, at least one $R_{1f}$ is —C(=O)N($R_{1g}$)$_2$.

In some embodiments, at least one $R_{1f}$ is —C(=O)NH$R_{1g}$.

In some embodiments, at least one $R_{1f}$ is —C(=O)NH$_2$.

In some embodiments, at least one $R_{1f}$ is —C(=O)N($R_{1g}$)$_2$, wherein at least one $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1f}$ is —C(=O)N($R_{1g}$)$_2$, wherein at least one $R_{1g}$ is $C_1$-$C_{20}$ alkyl, $C_2$-$C_{20}$ alkenyl, or $C_2$-$C_{20}$ alkynyl optionally substituted with one or more $R_{1g}$.

In some embodiments, at least one $R_{1f}$ is —C(=O)N($R_{1g}$)$_2$, wherein at least one $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1f}$ is —C(=O)N($R_{1g}$)$_2$, wherein at least one $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1g}$.

In some embodiments, at least one $R_{1f}$ is $R_{1z}$.

In some embodiments, at least one $R_{1f}$ is

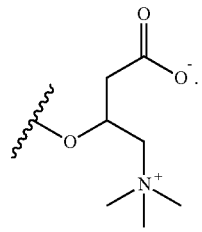

In some embodiments, at least one $R_{1f}$ is

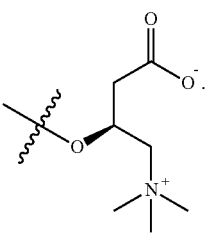

In some embodiments, at least one $R_{1f}$ is

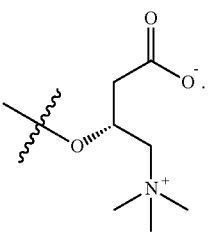

In some embodiments, at least one $R_{1f}$ is

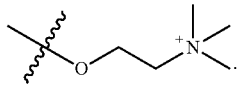

Variable $R_{1g}$

In some embodiments, at least one $R_{1g}$ is H.

In some embodiments, at least one $R_{1g}$ is $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$alkyl)-($C_3$-$C_{12}$ heteroaryl) is optionally substituted with one or more $R_{1z}$.

In some embodiments, at least one $R_{1g}$ is $C_1$-$C_{20}$ alkyl, $C_2$-$C_{20}$ alkenyl, or $C_2$-$C_{20}$ alkynyl optionally substituted with one or more $R_{1z}$.

In some embodiments, at least one $R_{1g}$ is $C_1$-$C_{20}$ alkyl (e.g., methyl, ethyl, propyl, butyl, pentyl, hexyl, or heptyl).

In some embodiments, at least one $R_{1g}$ is $C_1$-$C_{20}$ alkyl (e.g., methyl, ethyl, propyl, butyl, pentyl, hexyl, or heptyl) substituted with one or more $R_{1z}$.

In some embodiments, at least one $R_{1g}$ is $C_2$-$C_{20}$ alkenyl (e.g., ethenyl, propenyl, butenyl, pentenyl, or hexenyl).

In some embodiments, at least one $R_{1g}$ is $C_2$-$C_{20}$ alkenyl (e.g., ethenyl, propenyl, butenyl, pentenyl, or hexenyl) substituted with one or more $R_{1z}$.

In some embodiments, at least one $R_{1g}$ is $C_2$-$C_{20}$ alkynyl (e.g., ethynyl, propynyl, butynyl, pentynyl, or hexynyl).

In some embodiments, at least one $R_{1g}$ is $C_2$-$C_{20}$ alkynyl (e.g., ethynyl, propynyl, butynyl, pentynyl, or hexynyl) substituted with one or more $R_{1z}$.

In some embodiments, at least one $R_{1g}$ is $C_3$-$C_{12}$ cycloalkyl, $C_3$-$C_{12}$ heterocycloalkyl, $C_3$-$C_{12}$ aryl, or $C_3$-$C_{12}$ heteroaryl optionally substituted with one or more $R_{1z}$.

In some embodiments, at least one $R_{1g}$ is $C_3$-$C_{12}$ cycloalkyl optionally substituted with one or more $R_{1z}$. In some embodiments, at least one $R_{1g}$ is $C_3$-$C_{12}$ cycloalkyl. In some embodiments, at least one $R_{1g}$ is $C_3$-$C_{12}$ cycloalkyl substituted with one or more $R_{1z}$.

In some embodiments, at least one $R_{1g}$ is $C_3$-$C_{12}$ heterocycloalkyl optionally substituted with one or more $R_{1z}$. In some embodiments, at least one $R_{1g}$ is $C_3$-$C_{12}$ heterocycloalkyl. In some embodiments, at least one $R_{1g}$ is $C_3$-$C_{12}$ heterocycloalkyl substituted with one or more $R_{1z}$.

In some embodiments, at least one $R_{1g}$ is $C_3$-$C_{12}$ aryl optionally substituted with one or more $R_{1g}$. In some embodiments, at least one $R_{1g}$ is $C_3$-$C_{12}$ aryl. In some embodiments, at least one $R_{1g}$ is $C_3$-$C_{12}$ aryl substituted with one or more $R_{1z}$.

In some embodiments, at least one $R_{1g}$ is $C_3$-$C_{12}$ heteroaryl optionally substituted with one or more $R_{1z}$. In some embodiments, at least one $R_{1g}$ is $C_3$-$C_{12}$ heteroaryl. In some embodiments, at least one $R_{1g}$ is $C_3$-$C_{12}$ heteroaryl substituted with one or more $R_{1z}$.

In some embodiments, at least one $R_{1g}$ is —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) optionally substituted with one or more $R_{1z}$.

In some embodiments, at least one $R_{1g}$ is —($C_1$-$C_{20}$ alkyl)-($C_3$-$C_{12}$ cycloalkyl) optionally substituted with one or more $R_{1g}$. In some embodiments, at least one $R_{1g}$ is —($C_1$-$C_{20}$ alkyl)-($C_3$-$C_{12}$ cycloalkyl). In some embodiments, at least one $R_{1g}$ is —($C_1$-$C_{20}$ alkyl)-($C_3$-$C_{12}$ cycloalkyl) substituted with one or more $R_{1e}$.

In some embodiments, at least one $R_{1g}$ is —($C_1$-$C_{20}$ alkyl)-($C_3$-$C_{12}$ heterocycloalkyl) optionally substituted with one or more $R_{1z}$. In some embodiments, at least one $R_{1g}$ is —($C_1$-$C_{20}$ alkyl)-($C_3$-$C_{12}$ heterocycloalkyl). In some embodiments, at least one $R_{1g}$ is —($C_1$-$C_{20}$ alkyl)-($C_3$-$C_{12}$ heterocycloalkyl) substituted with one or more $R_{1z}$.

In some embodiments, at least one $R_{1g}$ is —($C_1$-$C_{20}$ alkyl)-($C_3$-$C_{12}$ aryl) optionally substituted with one or more $R_{1z}$. In some embodiments, at least one $R_{1g}$ is —($C_1$-$C_{20}$ alkyl)-($C_3$-$C_{12}$ aryl). In some embodiments, at least one $R_{1g}$ is —($C_1$-$C_{20}$ alkyl)-($C_3$-$C_{12}$ aryl) substituted with one or more $R_{1z}$.

In some embodiments, at least one $R_{1g}$ is —($C_1$-$C_{20}$ alkyl)-($C_3$-$C_{12}$ heteroaryl) optionally substituted with one or more $R_{1z}$. In some embodiments, at least one $R_{1g}$ is —($C_1$-$C_{20}$ alkyl)-($C_3$-$C_{12}$ heteroaryl). In some embodiments, at least one $R_{1g}$ is —($C_1$-$C_{20}$ alkyl)-($C_3$-$C_{12}$ heteroaryl) substituted with one or more $R_{1z}$.

Variable $R_{1z}$

In some embodiments, at least one $R_{1z}$ is

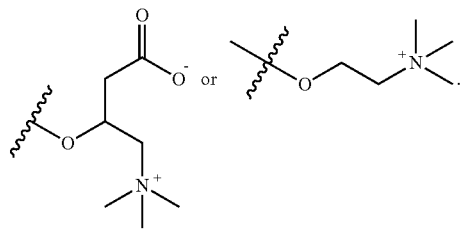

In some embodiments, at least one $R_{1z}$ is

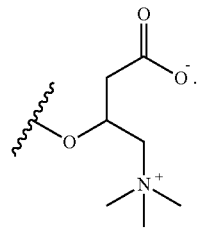

In some embodiments, at least one $R_{1z}$ is

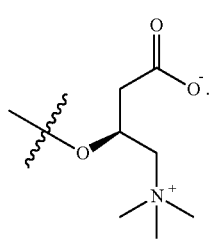

In some embodiments, at least one $R_{1z}$ is

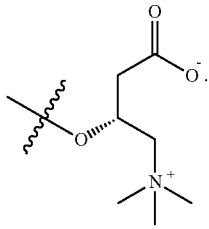

In some embodiments, at least one $R_{1z}$ is

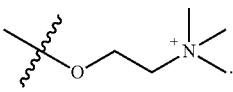

In some embodiments, all of the one or more $R_{1z}$ is

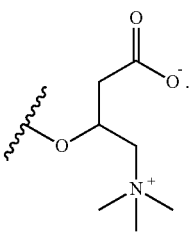

In some embodiments, all of the one or more $R_{1z}$ is

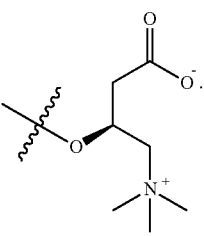

In some embodiments, all of the one or more $R_{1z}$ is

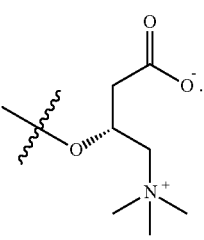

In some embodiments, all of the one or more $R_{1z}$ is

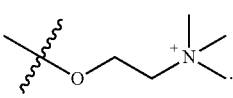

In some embodiments, at least one of the two or more $R_{1z}$ is

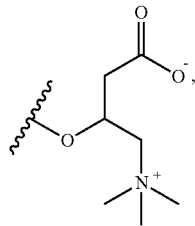

and at least one of the two or more $R_{1z}$ is

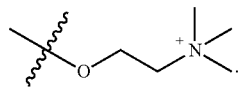

In some embodiments, at least one of the two or more $R_{1z}$ is

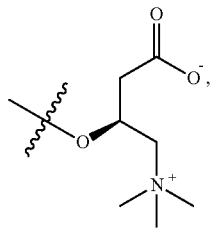

and at least one of the two or more $R_{1z}$ is

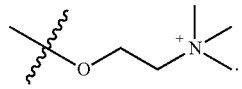

In some embodiments, at least one of the two or more $R_{1z}$ is

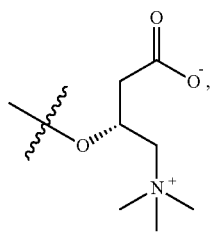

and at least one of the two or more $R_{1z}$ is

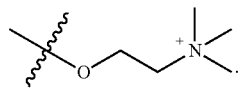

In some embodiments, at least one $R_{1z}$ is

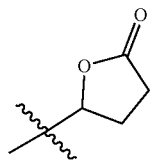

In some embodiments, at least one $R_{1z}$ is

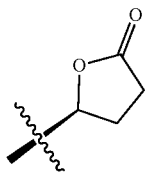

In some embodiments, at least one $R_{1z}$ is

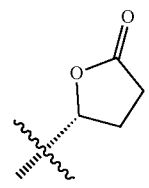

Variables n, p, q, and r

In some embodiments, n is from 0 to 20, from 0 to 15, from 0 to 10, from 0 to 6, from 0 to 4, or from 0 to 2.

In some embodiments, n is from 1 to 20, from 2 to 20, from 3 to 20, from 4 to 20, from 5 to 20, from 6 to 20, from 7 to 20, from 8 to 20, from 9 to 20, from 10 to 20, from 11 to 20, from 12 to 20, from 13 to 20, from 14 to 20, from 15 to 20, from 16 to 20, from 17 to 20, from 18 to 20, or from 19 to 20.

In some embodiments, n is 0.

In some embodiments, n is from 1 to 10 (e.g., 1, 2, 3, 4, 5, 6, 7, 8, 9, or 10). In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, n is from 11 to 20 (e.g., 11, 12, 13, 14, 15, 16, 17, 18, 19, or 20).

In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20.

In some embodiments, p is from 0 to 20, from 0 to 15, from 0 to 10, from 0 to 6, from 0 to 4, or from 0 to 2.

In some embodiments, p is from 1 to 20, from 2 to 20, from 3 to 20, from 4 to 20, from 5 to 20, from 6 to 20, from 7 to 20, from 8 to 20, from 9 to 20, from 10 to 20, from 11 to 20, from 12 to 20, from 13 to 20, from 14 to 20, from 15 to 20, from 16 to 20, from 17 to 20, from 18 to 20, or from 19 to 20.

In some embodiments, p is 0.

In some embodiments, p is from 1 to 10 (e.g., 1, 2, 3, 4, 5, 6, 7, 8, 9, or 10). In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10.

In some embodiments, p is from 11 to 20 (e.g., 11, 12, 13, 14, 15, 16, 17, 18, 19, or 20).

In some embodiments, p is 11. In some embodiments, p is 12. In some embodiments, p is 13. In some embodiments, p is 14. In some embodiments, p is 15. In some embodiments, p is 16. In some embodiments, p is 17. In some embodiments, p is 18. In some embodiments, p is 19. In some embodiments, p is 20.

In some embodiments, q is from 0 to 20, from 0 to 15, from 0 to 10, from 0 to 6, from 0 to 4, or from 0 to 2.

In some embodiments, q is from 1 to 20, from 2 to 20, from 3 to 20, from 4 to 20, from 5 to 20, from 6 to 20, from 7 to 20, from 8 to 20, from 9 to 20, from 10 to 20, from 11 to 20, from 12 to 20, from 13 to 20, from 14 to 20, from 15 to 20, from 16 to 20, from 17 to 20, from 18 to 20, or from 19 to 20.

In some embodiments, q is 0.

In some embodiments, q is from 1 to 10 (e.g., 1, 2, 3, 4, 5, 6, 7, 8, 9, or 10). In some embodiments, q is 1. In some embodiments, q is 2. In some embodiments, q is 3. In some embodiments, q is 4. In some embodiments, q is 5. In some embodiments, q is 6. In some embodiments, q is 7. In some embodiments, q is 8. In some embodiments, q is 9. In some embodiments, q is 10.

In some embodiments, r is from 11 to 20 (e.g., 11, 12, 13, 14, 15, 16, 17, 18, 19, or 20). In some embodiments, r is 11. In some embodiments, r is 12. In some embodiments, r is 13. In some embodiments, r is 14. In some embodiments, r is 15. In some embodiments, r is 16. In some embodiments, r is 17. In some embodiments, r is 18. In some embodiments, r is 19. In some embodiments, r is 20.

In some embodiments, r is from 0 to 20, from 0 to 15, from 0 to 10, from 0 to 6, from 0 to 4, or from 0 to 2.

In some embodiments, r is from 1 to 20, from 2 to 20, from 3 to 20, from 4 to 20, from 5 to 20, from 6 to 20, from 7 to 20, from 8 to 20, from 9 to 20, from 10 to 20, from 11 to 20, from 12 to 20, from 13 to 20, from 14 to 20, from 15 to 20, from 16 to 20, from 17 to 20, from 18 to 20, or from 19 to 20.

In some embodiments, r is 0.

In some embodiments, r is from 1 to 10 (e.g., 1, 2, 3, 4, 5, 6, 7, 8, 9, or 10). In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is from 11 to 20 (e.g., 11, 12, 13, 14, 15, 16, 17, 18, 19, or 20). In some embodiments, r is 11. In some embodiments, r is 12. In some embodiments, r is 13. In some embodiments, r is 14. In some embodiments, r is 15. In some embodiments, r is 16. In some embodiments, r is 17. In some embodiments, r is 18. In some embodiments, r is 19. In some embodiments, r is 20.

Variable X

In some embodiments, at least one X is $-OR_{1c}$.
In some embodiments, at least one X is $-SR_{1c}$.
In some embodiments, at least one X is $-N(R_{1c})_2$.
In some embodiments, at least one X is

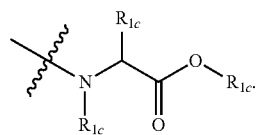

In some embodiments, at least one X is

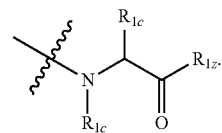

In some embodiments, at least one X is

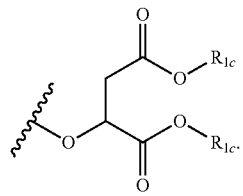

In some embodiments, at least one X is

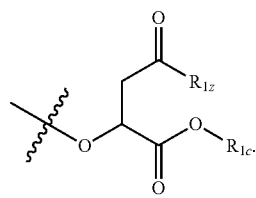

In some embodiments, at least one X

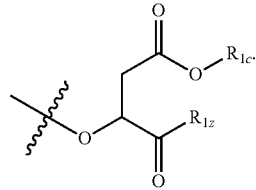

In some embodiments, at least one X is

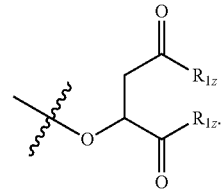

In some embodiments, at least one X is

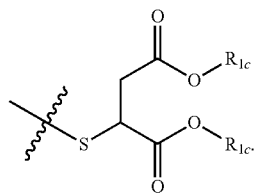

In some embodiments, at least one X is

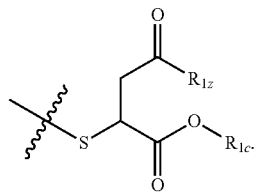

In some embodiments, at least one X is

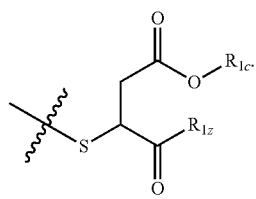

In some embodiments, at least one X is

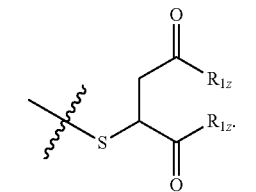

In some embodiments, at least one X is

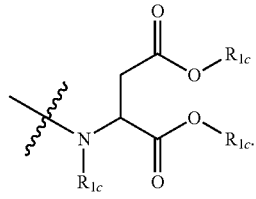

In some embodiments, at least one X is

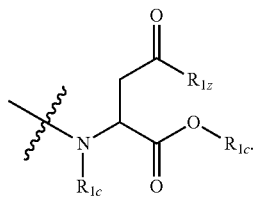

In some embodiments, at least one X is

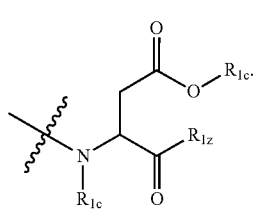

In some embodiments, at least one X is

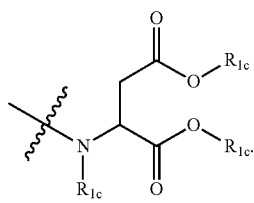

In some embodiments, at least one X is $R_{1z}$.

In some embodiments, at least one X is

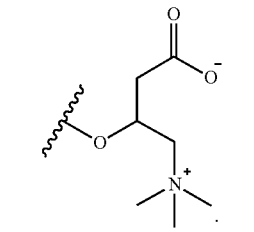 [SMILES: *OC(CC(=O)[O-])C[N+](C)(C)C]

In some embodiments, at least one X is

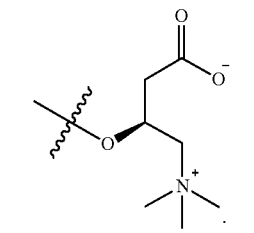 [SMILES: *O[C@@H](CC(=O)[O-])C[N+](C)(C)C]

In some embodiments, at least one X is

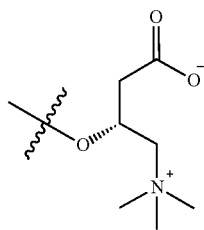 [SMILES: *O[C@H](CC(=O)[O-])C[N+](C)(C)C]

In some embodiments, at least one X is

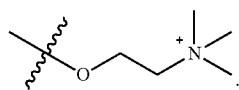 [SMILES: *OCC[N+](C)(C)C]

Exemplary Formulae and Compounds

In some embodiments, each T is independently

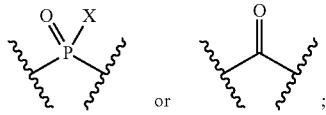

and $R_1$ is —C(=O)—$R_{1a}$, —C(=O)—$CH_2$—$R_{1a}$, —C(=O)—$CH_2CH_2$—$R_{1a}$ or —C(=O)—CH=CH—$R_{1a}$, wherein $II_{1a}$ is $C_1$-$C_{20}$ alkyl, —C(=O)$R_{1b}$, or —C(=O)O$R_{1c}$, wherein the $C_1$-$C_{20}$ alkyl is optionally substituted with one or more $R_{1e}$.

In some embodiments, each T is independently

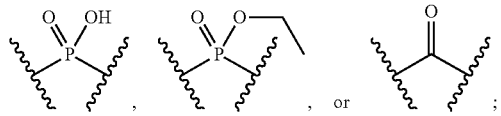

and $R_1$ is —C(=O)—$CH_s$, —C(=O)—$CH_2$—CH(OH)—$CH_3$, —C(=O)—$CH_2$—C(=O)—$CH_3$, —C(=O)—$CH_2CH_2$—C(=O)OH, —C(=O)—$CH_2$—C(=O)$OCH_3$, —C(=O)—CH—H—$CH_3$, —C(=O)—CH—H—C(=O)OH, or —C(=O)—CH—H—C(=O)$OCH_3$.

In some embodiments, the compound is of Formula (I'-1) or (I'-2):

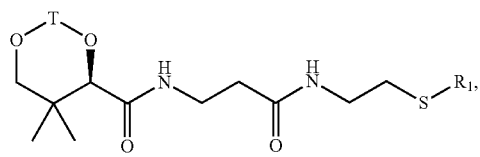

(I'-1)

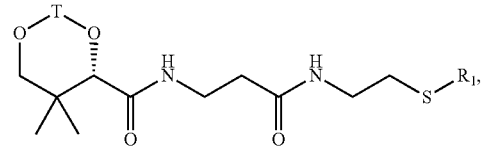

(I'-2)

or a pharmaceutically acceptable salt or solvate thereof.

In some embodiments, the compound is of Formula (I'-1) or a pharmaceutically acceptable salt or solvate thereof.

In some embodiments, the compound is of Formula (I'-2) or a pharmaceutically acceptable salt or solvate thereof.

In some embodiments, the compound is of Formula (Ia'):

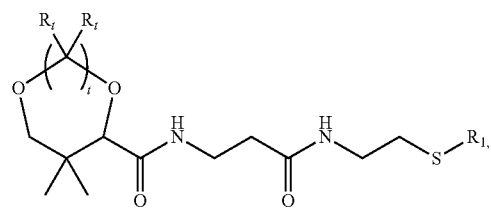

(Ia')

or a pharmaceutically acceptable salt or solvate thereof.

In some embodiments, the compound is of Formula (Ia'-1) or (Ia'-2):

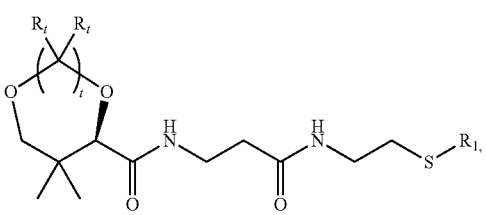

(Ia'-1)

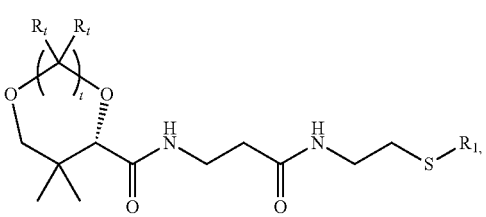

(Ia'-2)

or a pharmaceutically acceptable salt or solvate thereof.

In some embodiments, the compound is of Formula (Ia'-1) or a pharmaceutically acceptable salt or solvate thereof.

In some embodiments, the compound is of Formula (Ia'-2) or a pharmaceutically acceptable salt or solvate thereof.

In some embodiments, the compound is of Formula (Ib'):

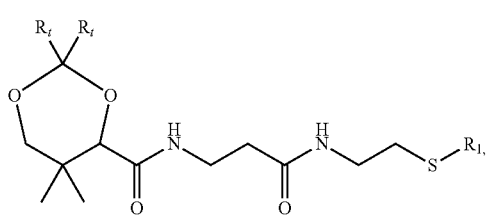
(Ib')

or a pharmaceutically acceptable salt or solvate thereof.

In some embodiments, the compound is of Formula (Ib'-1) or (Ib'-2):

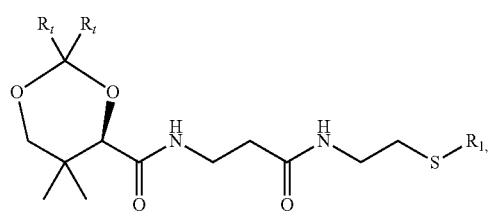
(Ib'-1)

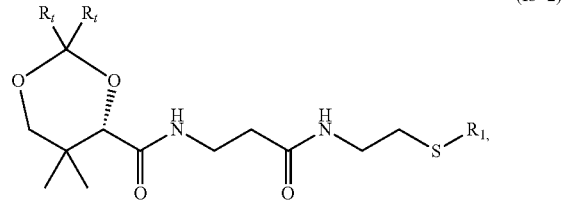
(Ib'-2)

or a pharmaceutically acceptable salt or solvate thereof.

In some embodiments, the compound is of Formula (Ib'-1) or a pharmaceutically acceptable salt or solvate thereof.

In some embodiments, the compound is of Formula (Ib'-2) or a pharmaceutically acceptable salt or solvate thereof.

In some embodiments, the compound is of Formula (II'-1) or (II'-2):

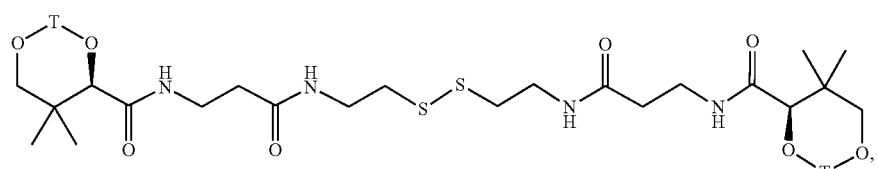
(II'-1)

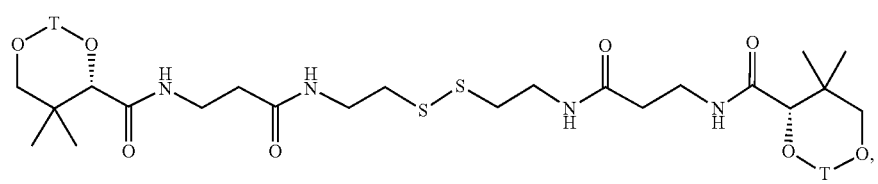
(II'-2)

or a pharmaceutically acceptable salt or solvate thereof.

In some embodiments, the compound is of Formula (II'-1) or a pharmaceutically acceptable salt or solvate thereof.

In some embodiments, the compound is of Formula (II'-2) or a pharmaceutically acceptable salt or solvate thereof.

In some embodiments, the compound is of Formula (IIa'):

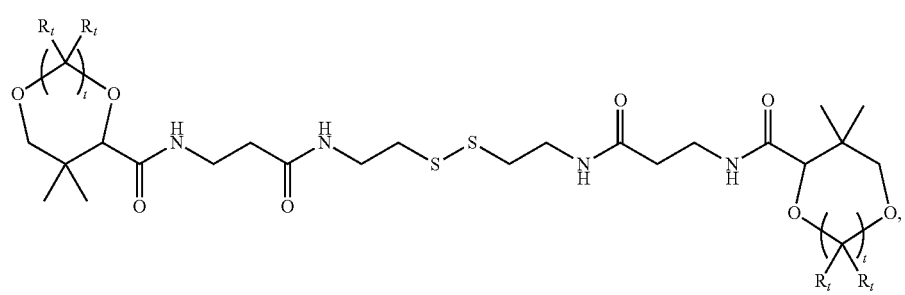
(IIa')

or a pharmaceutically acceptable salt or solvate thereof.

In some embodiments, the compound is of Formula (IIa'-1) or (IIa'-2):

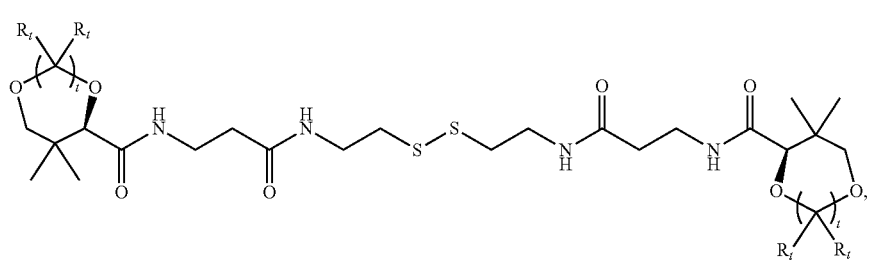

(IIa'-1)

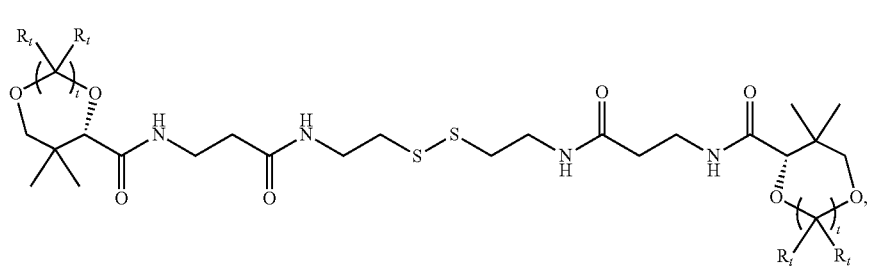

(IIa'-2)

or a pharmaceutically acceptable salt or solvate thereof.

In some embodiments, the compound is of Formula (IIa'-1) or a pharmaceutically acceptable salt or solvate thereof.

In some embodiments, the compound is of Formula (IIa'-2) or a pharmaceutically acceptable salt or solvate thereof.

In some embodiments, the compound is of Formula (IIb'):

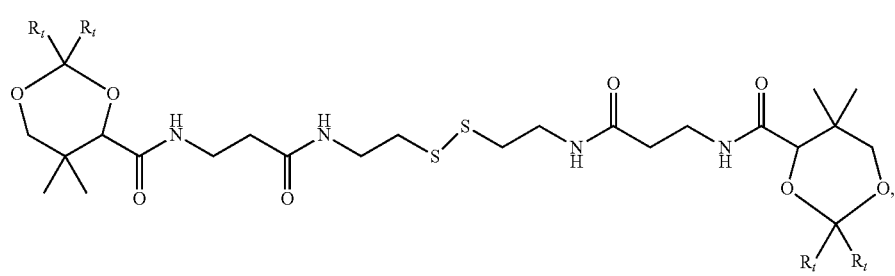

(IIb')

or a pharmaceutically acceptable salt or solvate thereof.

In some embodiments, the compound is of Formula (IIb'-1) or (IIb'-2):

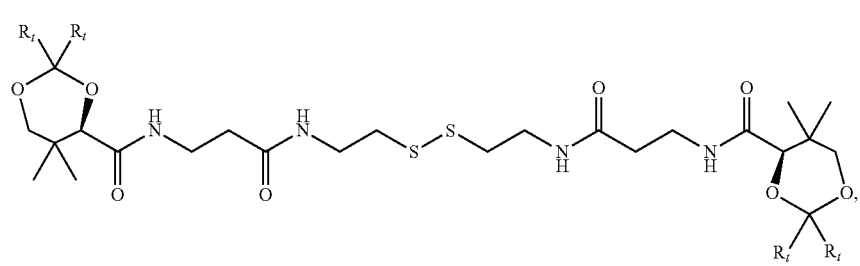

(IIb'-1)

-continued (IIb'-2)

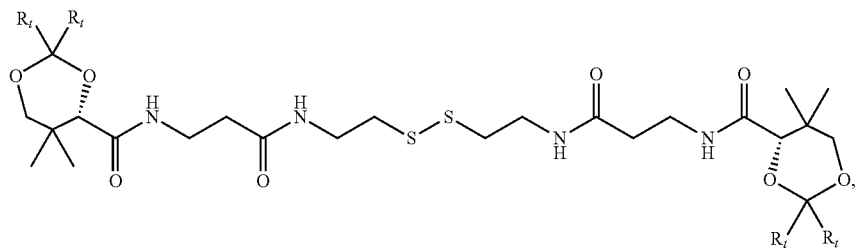

or a pharmaceutically acceptable salt or solvate thereof.

In some embodiments, the compound is of Formula (IIb'-1) or a pharmaceutically acceptable salt or solvate thereof.

In some embodiments, the compound is of Formula (IIb'-2) or a pharmaceutically acceptable salt or solvate thereof.

In some embodiments, the compound is of Formula (I-1) or (I-2):

(I-1)

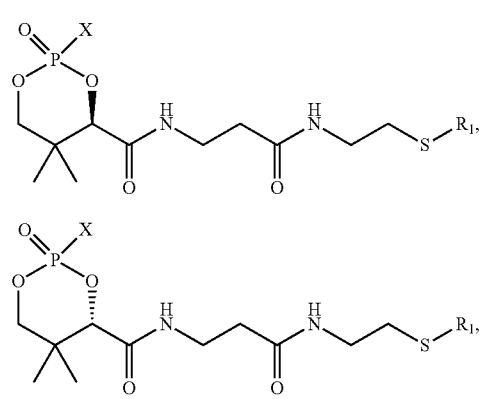

(I-2)

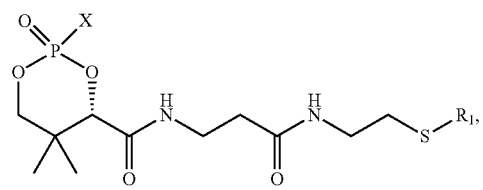

or a pharmaceutically acceptable salt or solvate thereof.

In some embodiments, the compound is of Formula (I-1) or a pharmaceutically acceptable salt or solvate thereof.

In some embodiments, the compound is of Formula (I-2) or a pharmaceutically acceptable salt or solvate thereof.

In some embodiments, the compound is of Formula (Iaa), (Iab), (Iac), or (Iad):

(Iaa)

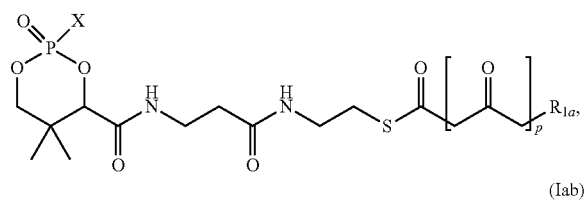

(Iab)

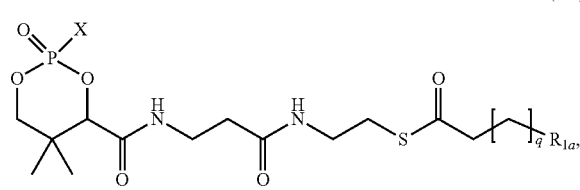

(Iac)

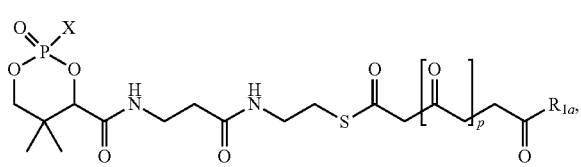

(Iad)

or a pharmaceutically acceptable salt or solvate thereof.

In some embodiments, the compound is of Formula (Iaa) or a pharmaceutically acceptable salt or solvate thereof.

In some embodiments, the compound is of Formula (Iab) or a pharmaceutically acceptable salt or solvate thereof.

In some embodiments, the compound is of Formula (Iac) or a pharmaceutically acceptable salt or solvate thereof.

In some embodiments, the compound is of Formula (Iad) or a pharmaceutically acceptable salt or solvate thereof.

In some embodiments, the compound is of Formula (Iaa-1), (Iaa-2), (Iab-1), (Iab-2), (Iac-1), (Iac-2), (Iad-1), or (Iad-2):

(Iaa-1)

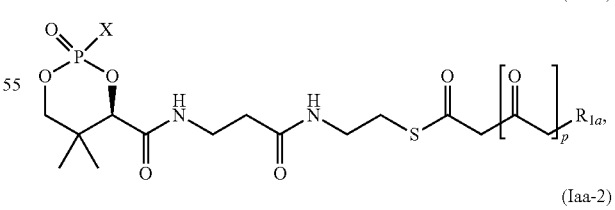

(Iaa-2)

-continued

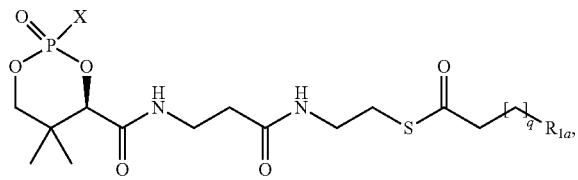
(Iab-1)

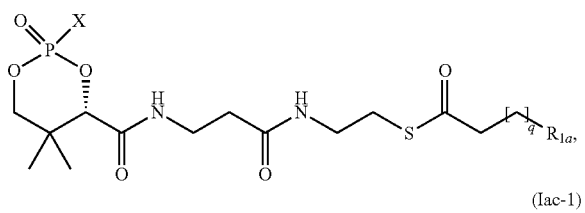
(Iab-2)

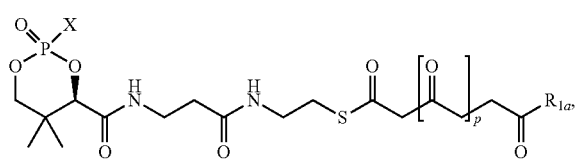
(Iac-1)

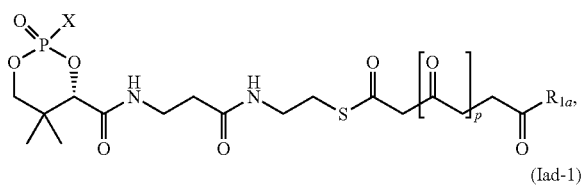
(Iac-2)

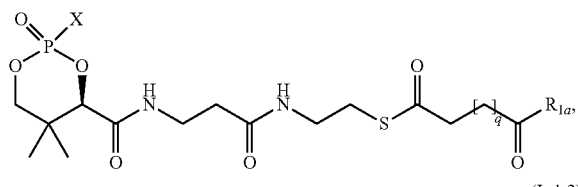
(Iad-1)

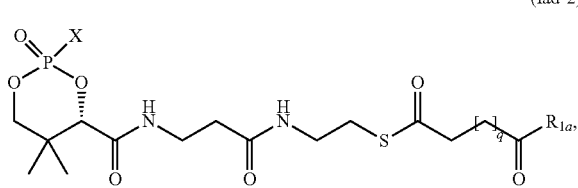
(Iad-2)

or a pharmaceutically acceptable salt or solvate thereof.

In some embodiments, the compound is of Formula (Iaa-1) or a pharmaceutically acceptable salt or solvate thereof.

In some embodiments, the compound is of Formula (Iaa-2) or a pharmaceutically acceptable salt or solvate thereof.

In some embodiments, the compound is of Formula (Iab-1) or a pharmaceutically acceptable salt or solvate thereof.

In some embodiments, the compound is of Formula (Iab-2) or a pharmaceutically acceptable salt or solvate thereof.

In some embodiments, the compound is of Formula (Iac-1) or a pharmaceutically acceptable salt or solvate thereof.

In some embodiments, the compound is of Formula (Iac-2) or a pharmaceutically acceptable salt or solvate thereof.

In some embodiments, the compound is of Formula (Iad-1) or a pharmaceutically acceptable salt or solvate thereof.

In some embodiments, the compound is of Formula (Iad-2) or a pharmaceutically acceptable salt or solvate thereof.

In some embodiments, the compound is of Formula (Iae), (Iaf), (Iag), or (Iah):

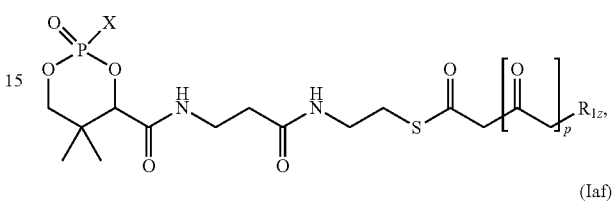
(Iae)

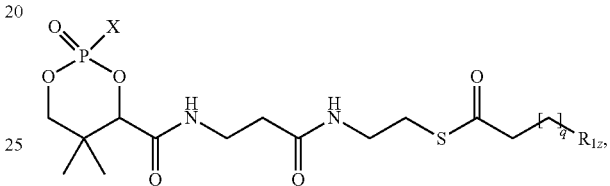
(Iaf)

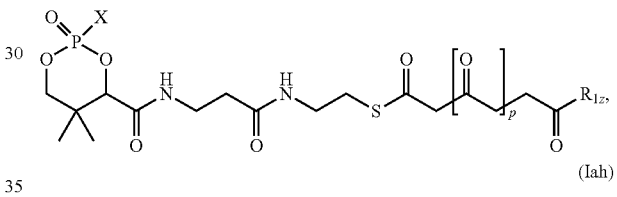
(Iag)

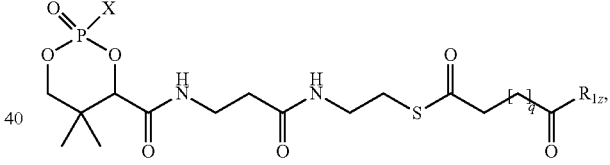
(Iah)

or a pharmaceutically acceptable salt or solvate thereof.

In some embodiments, the compound is of Formula (Iae) or a pharmaceutically acceptable salt or solvate thereof.

In some embodiments, the compound is of Formula (Iaf) or a pharmaceutically acceptable salt or solvate thereof.

In some embodiments, the compound is of Formula (Iag) or a pharmaceutically acceptable salt or solvate thereof.

In some embodiments, the compound is of Formula (Iah) or a pharmaceutically acceptable salt or solvate thereof.

In some embodiments, the compound is of Formula (Iae-1), (Iae-2), (Iaf-1), (Iaf-2), (Iag-1), (Iag-2), (Iah-1), or (Iah-2):

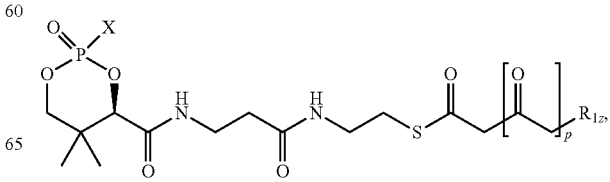
(Iae-1)

In some embodiments, the compound is of Formula (Iaf-2) or a pharmaceutically acceptable salt or solvate thereof.

In some embodiments, the compound is of Formula (Iag-1) or a pharmaceutically acceptable salt or solvate thereof.

In some embodiments, the compound is of Formula (Iag-2) or a pharmaceutically acceptable salt or solvate thereof.

In some embodiments, the compound is of Formula (Iah-1) or a pharmaceutically acceptable salt or solvate thereof.

In some embodiments, the compound is of Formula (Iah-2) or a pharmaceutically acceptable salt or solvate thereof.

In some embodiments, the compound is of Formula (Iai), (Iaj), (Iak), (Ial), (Iam), or (Ian):

or a pharmaceutically acceptable salt or solvate thereof.

In some embodiments, the compound is of Formula (Iae-1) or a pharmaceutically acceptable salt or solvate thereof.

In some embodiments, the compound is of Formula (Iae-2) or a pharmaceutically acceptable salt or solvate thereof.

In some embodiments, the compound is of Formula (Iaf-1) or a pharmaceutically acceptable salt or solvate thereof.

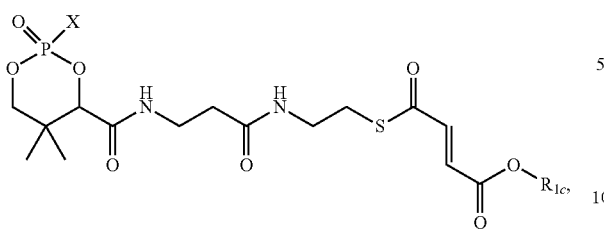
(Ian)

or a pharmaceutically acceptable salt or solvate thereof.

In some embodiments, the compound is of Formula (Iai) or a pharmaceutically acceptable salt or solvate thereof.

In some embodiments, the compound is of Formula (Iaj) or a pharmaceutically acceptable salt or solvate thereof.

In some embodiments, the compound is of Formula (Iak) or a pharmaceutically acceptable salt or solvate thereof.

In some embodiments, the compound is of Formula (Ial) or a pharmaceutically acceptable salt or solvate thereof.

In some embodiments, the compound is of Formula (Iam) or a pharmaceutically acceptable salt or solvate thereof.

In some embodiments, the compound is of Formula (Ian) or a pharmaceutically acceptable salt or solvate thereof.

In some embodiments, the compound is of Formula (Iai-1), (Iai-2), (Iaj-1), (Iaj-2), (Iak-1), (Iak-2), (Ial-1), (Ial-2), (Iam-1), (Iam-2), (Ian-1), or (Ian-2):

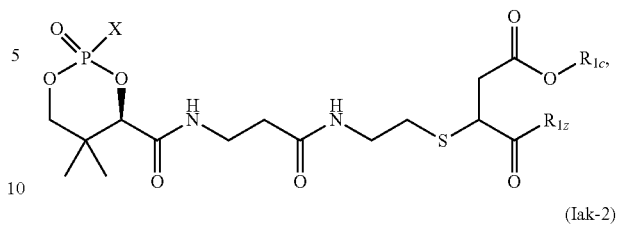
(Iak-1)

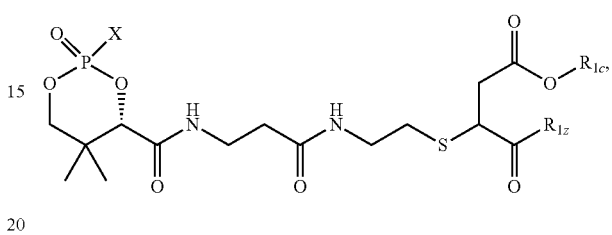
(Iak-2)

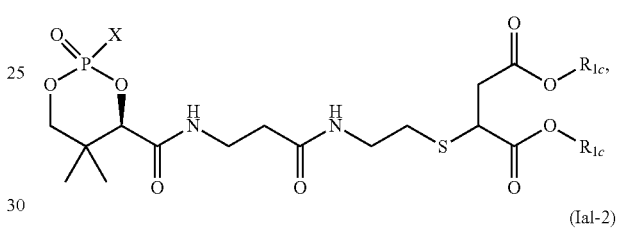
(Ial-1)

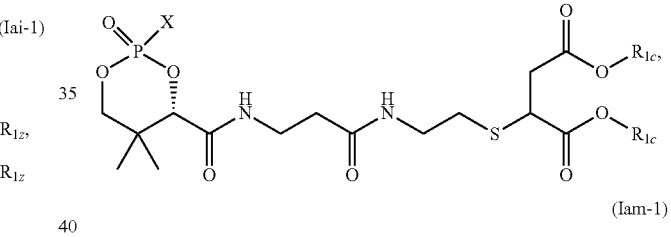
(Ial-2)

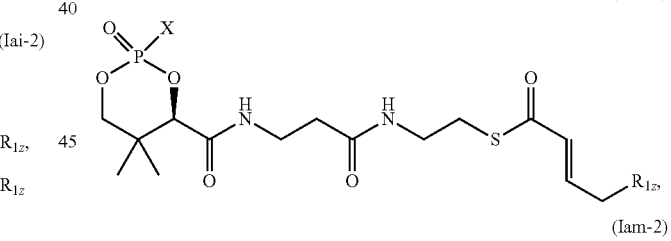
(Iam-1)

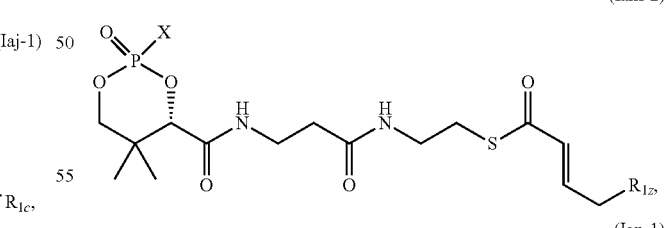
(Iam-2)

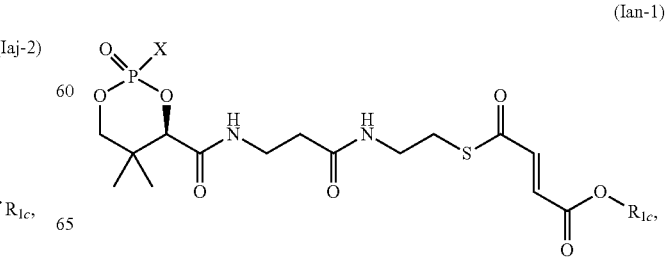
(Ian-1)

-continued (Ian-2)

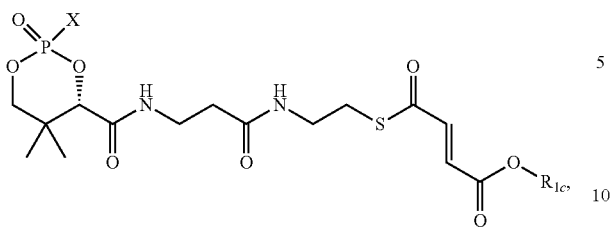

or a pharmaceutically acceptable salt or solvate thereof.

In some embodiments, the compound is of Formula (Iai-1) or a pharmaceutically acceptable salt or solvate thereof.

In some embodiments, the compound is of Formula (Iai-2) or a pharmaceutically acceptable salt or solvate thereof.

In some embodiments, the compound is of Formula (Iaj-1) or a pharmaceutically acceptable salt or solvate thereof.

In some embodiments, the compound is of Formula (Iaj-2) or a pharmaceutically acceptable salt or solvate thereof.

In some embodiments, the compound is of Formula (Iak-1) or a pharmaceutically acceptable salt or solvate thereof.

In some embodiments, the compound is of Formula (Iak-2) or a pharmaceutically acceptable salt or solvate thereof.

In some embodiments, the compound is of Formula (Ial-1) or a pharmaceutically acceptable salt or solvate thereof.

In some embodiments, the compound is of Formula (Ial-2) or a pharmaceutically acceptable salt or solvate thereof.

In some embodiments, the compound is of Formula (Iam-1) or a pharmaceutically acceptable salt or solvate thereof.

In some embodiments, the compound is of Formula (Iam-2) or a pharmaceutically acceptable salt or solvate thereof.

In some embodiments, the compound is of Formula (Ian-1) or a pharmaceutically acceptable salt or solvate thereof.

In some embodiments, the compound is of Formula (Ian-2) or a pharmaceutically acceptable salt or solvate thereof.

In some embodiments, the compound is of Formula (Iba), (Ibb), (Ibc), or (Ibd):

(Iba)

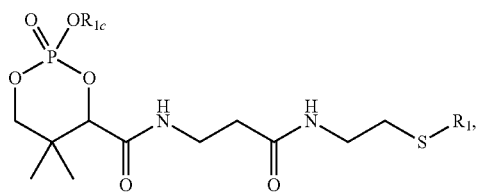

(Ibb)

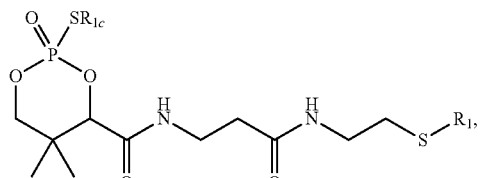

(Ibc)

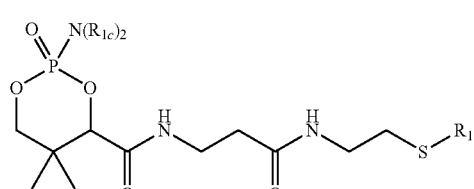

(Ibd)

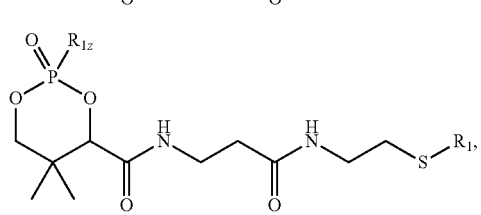

or a pharmaceutically acceptable salt or solvate thereof.

In some embodiments, the compound is of Formula (Iba) or a pharmaceutically acceptable salt or solvate thereof.

In some embodiments, the compound is of Formula (Ibb) or a pharmaceutically acceptable salt or solvate thereof.

In some embodiments, the compound is of Formula (Ibc) or a pharmaceutically acceptable salt or solvate thereof.

In some embodiments, the compound is of Formula (Ibd) or a pharmaceutically acceptable salt or solvate thereof.

In some embodiments, the compound is of Formula (Iba-1), (Iba-2), (Ibb-1), (Ibb-2), (Ibc-1), (Ibc-2), or (Ibd-1), or (Ibd-2):

(Iba-1)

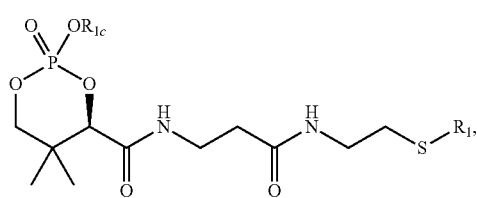

(Iba-2)

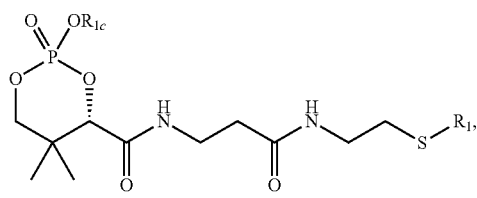

(Ibb-1)

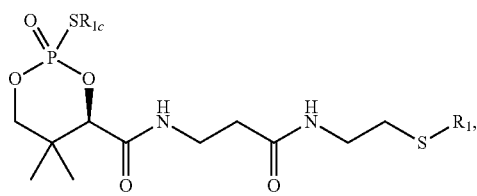

-continued

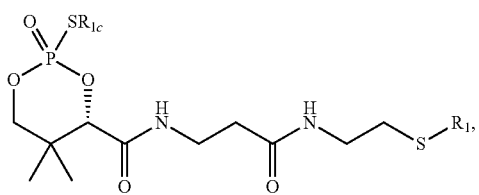
(Ibb-2)

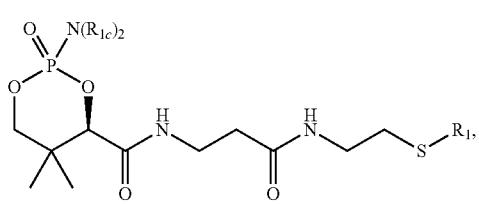
(Ibc-1)

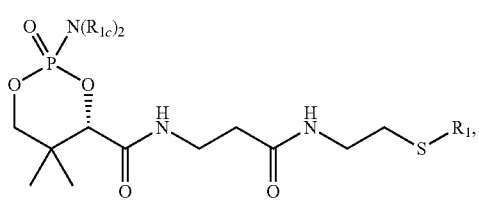
(Ibc-2)

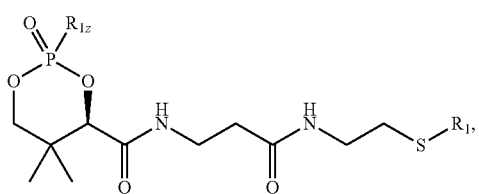
(Ibd-1)

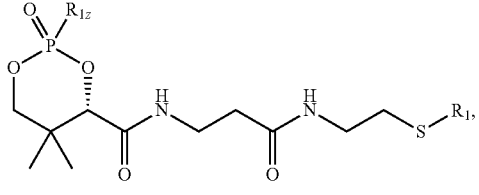
(Ibd-2)

or a pharmaceutically acceptable salt or solvate thereof.

In some embodiments, the compound is of Formula (Iba-1) or a pharmaceutically acceptable salt or solvate thereof.

In some embodiments, the compound is of Formula (Iba-2) or a pharmaceutically acceptable salt or solvate thereof.

In some embodiments, the compound is of Formula (Ibb-1) or a pharmaceutically acceptable salt or solvate thereof.

In some embodiments, the compound is of Formula (Ibb-2) or a pharmaceutically acceptable salt or solvate thereof.

In some embodiments, the compound is of Formula (Ibc-1) or a pharmaceutically acceptable salt or solvate thereof.

In some embodiments, the compound is of Formula (Ibc-2) or a pharmaceutically acceptable salt or solvate thereof.

In some embodiments, the compound is of Formula (Ibd-1) or a pharmaceutically acceptable salt or solvate thereof.

In some embodiments, the compound is of Formula (Ibd-2) or a pharmaceutically acceptable salt or solvate thereof.

In some embodiments, the compound is of Formula (Ibe), or (Ibf):

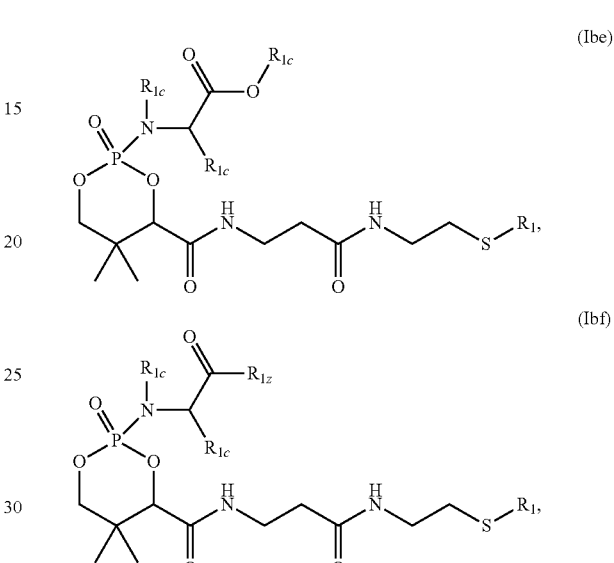

or a pharmaceutically acceptable salt or solvate thereof.

In some embodiments, the compound is of Formula (Ibe) or a pharmaceutically acceptable salt or solvate thereof.

In some embodiments, the compound is of Formula (Ibf) or a pharmaceutically acceptable salt or solvate thereof.

In some embodiments, the compound is of Formula (Ibe-1), (Ibe-2), (Ibf-1), or (Ibf-2):

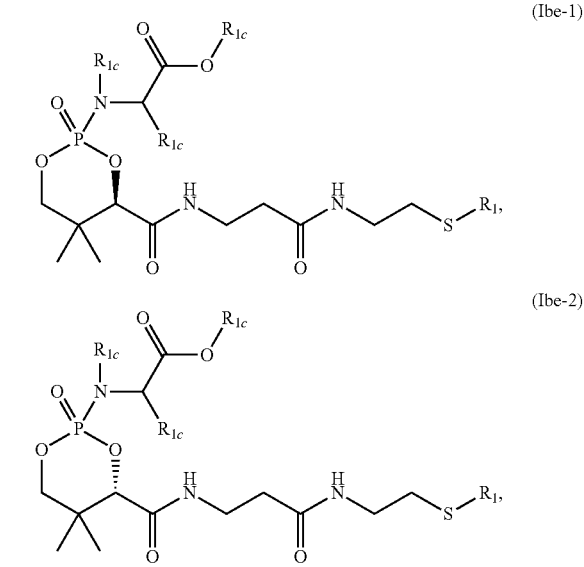

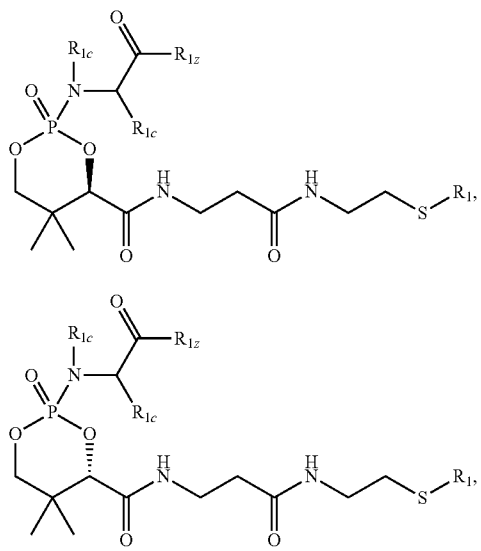

or a pharmaceutically acceptable salt or solvate thereof.

In some embodiments, the compound is of Formula (Ibe-1) or a pharmaceutically acceptable salt or solvate thereof.

In some embodiments, the compound is of Formula (Ibe-2) or a pharmaceutically acceptable salt or solvate thereof.

In some embodiments, the compound is of Formula (Ibf-1) or a pharmaceutically acceptable salt or solvate thereof.

In some embodiments, the compound is of Formula (Ibf-2) or a pharmaceutically acceptable salt or solvate thereof.

In some embodiments, the compound is of Formula (Ibg), (Ibh), (Ibi), or (Ibj):

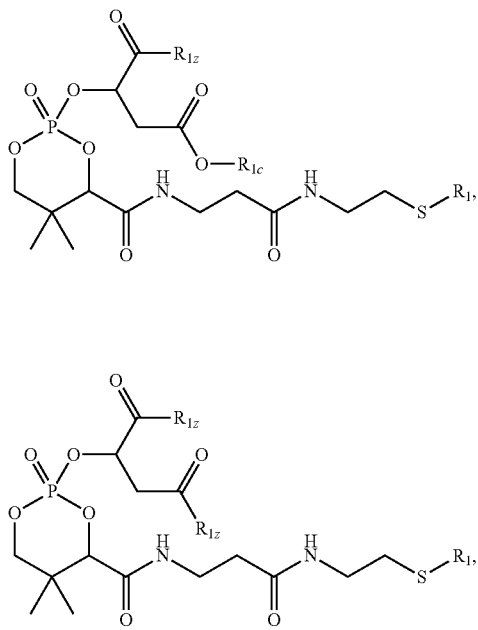

or a pharmaceutically acceptable salt or solvate thereof.

In some embodiments, the compound is of Formula (Ibg) or a pharmaceutically acceptable salt or solvate thereof.

In some embodiments, the compound is of Formula (Ibh) or a pharmaceutically acceptable salt or solvate thereof.

In some embodiments, the compound is of Formula (Ibi) or a pharmaceutically acceptable salt or solvate thereof.

In some embodiments, the compound is of Formula (Ibj) or a pharmaceutically acceptable salt or solvate thereof.

In some embodiments, the compound is of Formula (Ibg-1), (Ibg-2), (Ibh-1), (Ibh-2), (Ibi-1), (Ibi-2), (Ibj-1), or (Ibj-2):

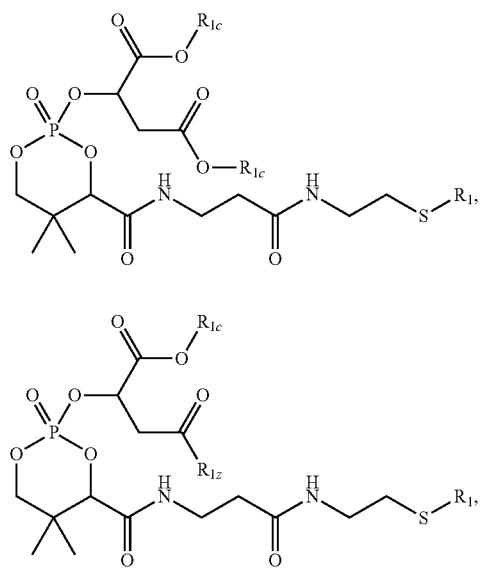

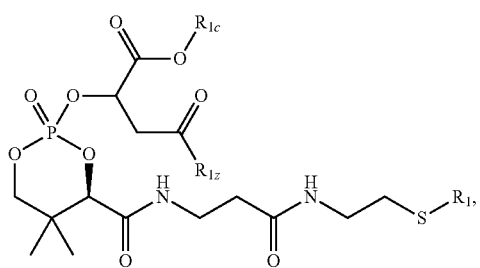

(Ibh-1)

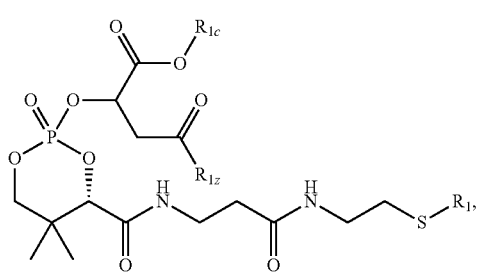

(Ibh-2)

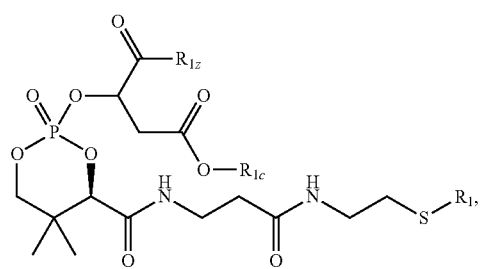

(Ibi-1)

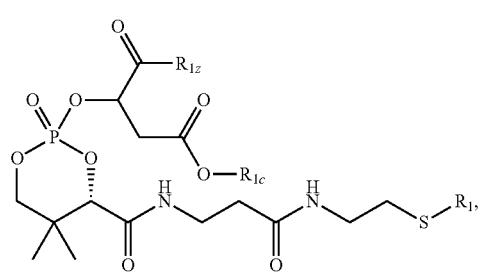

(Ibi-2)

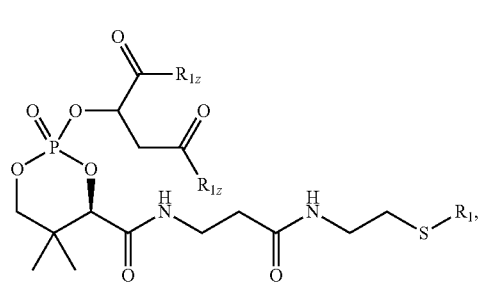

(Ibj-1)

(Ibj-2)

or a pharmaceutically acceptable salt or solvate thereof.

In some embodiments, the compound is of Formula (Ibg-1) or a pharmaceutically acceptable salt or solvate thereof.

In some embodiments, the compound is of Formula (Ibg-2) or a pharmaceutically acceptable salt or solvate thereof.

In some embodiments, the compound is of Formula (Ibh-1) or a pharmaceutically acceptable salt or solvate thereof.

In some embodiments, the compound is of Formula (Ibh-2) or a pharmaceutically acceptable salt or solvate thereof.

In some embodiments, the compound is of Formula (Ibi-1) or a pharmaceutically acceptable salt or solvate thereof.

In some embodiments, the compound is of Formula (Ibi-2) or a pharmaceutically acceptable salt or solvate thereof.

In some embodiments, the compound is of Formula (Ibj-1) or a pharmaceutically acceptable salt or solvate thereof.

In some embodiments, the compound is of Formula (Ibj-2) or a pharmaceutically acceptable salt or solvate thereof.

In some embodiments, the compound is of Formula (Ibk), (Ibl), (Ibm), or (Ibn):

(Ibk)

(Ibl)

(Ibm)

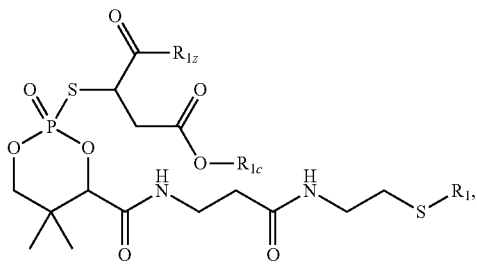

(Ibn)

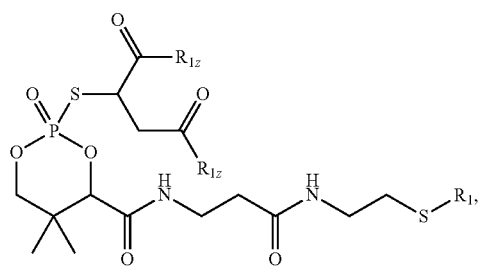

or a pharmaceutically acceptable salt or solvate thereof.

In some embodiments, the compound is of Formula (Ibk) or a pharmaceutically acceptable salt or solvate thereof.

In some embodiments, the compound is of Formula (Ibl) or a pharmaceutically acceptable salt or solvate thereof.

In some embodiments, the compound is of Formula (Ibm) or a pharmaceutically acceptable salt or solvate thereof.

In some embodiments, the compound is of Formula (Ibn) or a pharmaceutically acceptable salt or solvate thereof.

In some embodiments, the compound is of Formula (Ibk-1), (Ibk-2), (Ibl-1), (Ibl-2), (Ibm-1), (Ibm-2), (Ibn-1), or (Ibn-2):

(Ibk-1)

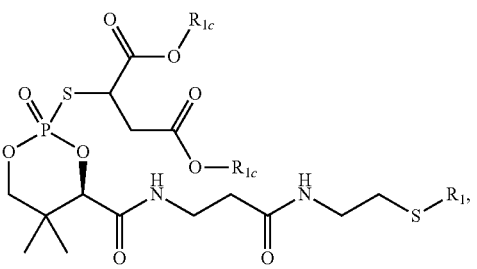

(Ibk-2)

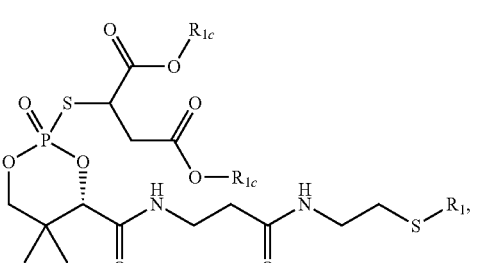

(Ibl-1)

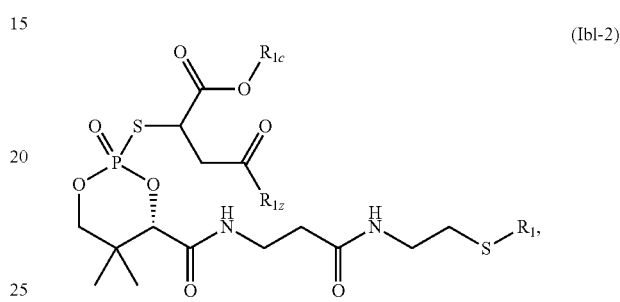

(Ibl-2)

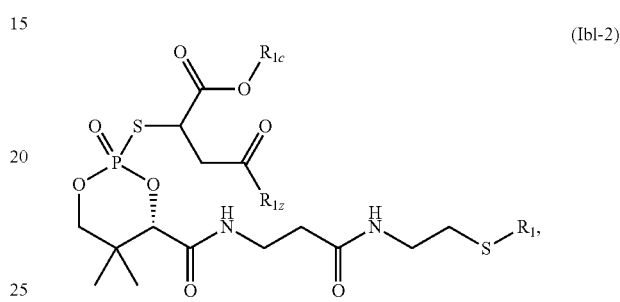

(Ibm-1)

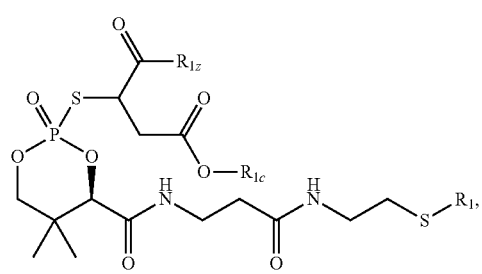

(Ibm-2)

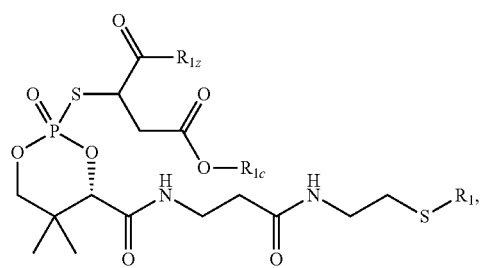

(Ibn-1)

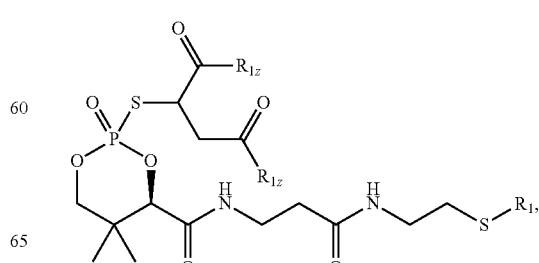

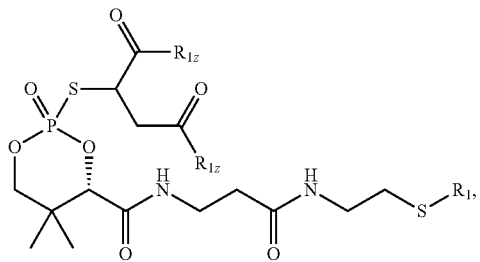

(Ibn-2)

or a pharmaceutically acceptable salt or solvate thereof.

In some embodiments, the compound is of Formula (Ibk-1) or a pharmaceutically acceptable salt or solvate thereof.

In some embodiments, the compound is of Formula (Ibk-2) or a pharmaceutically acceptable salt or solvate thereof.

In some embodiments, the compound is of Formula (Ibl-1) or a pharmaceutically acceptable salt or solvate thereof.

In some embodiments, the compound is of Formula (Ibl-2) or a pharmaceutically acceptable salt or solvate thereof.

In some embodiments, the compound is of Formula (Ibm-1) or a pharmaceutically acceptable salt or solvate thereof.

In some embodiments, the compound is of Formula (Ibm-2) or a pharmaceutically acceptable salt or solvate thereof.

In some embodiments, the compound is of Formula (Ibn-1) or a pharmaceutically acceptable salt or solvate thereof.

In some embodiments, the compound is of Formula (Ibn-2) or a pharmaceutically acceptable salt or solvate thereof.

In some embodiments, the compound is of Formula (Ibo), (Ibp), (Ibq), or (Ibr):

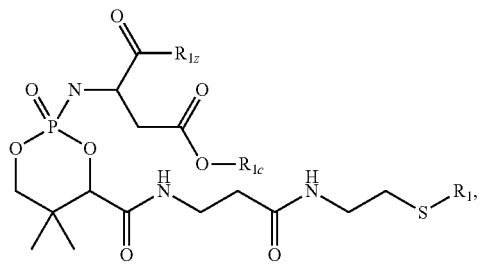

(Ibq)

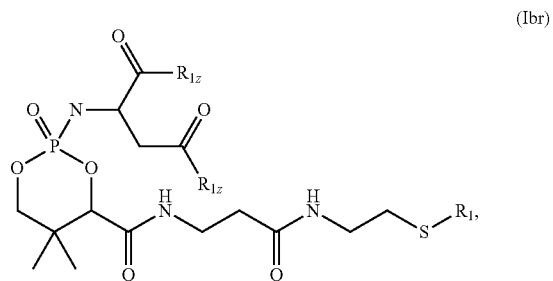

(Ibr)

or a pharmaceutically acceptable salt or solvate thereof.

In some embodiments, the compound is of Formula (Ibo) or a pharmaceutically acceptable salt or solvate thereof.

In some embodiments, the compound is of Formula (Ibp) or a pharmaceutically acceptable salt or solvate thereof.

In some embodiments, the compound is of Formula (Ibq) or a pharmaceutically acceptable salt or solvate thereof.

In some embodiments, the compound is of Formula (Ibr) or a pharmaceutically acceptable salt or solvate thereof.

In some embodiments, the compound is of Formula (Ibo-1), (Ibo-2), (Ibp-1), (Ibp-2), (Ibq-1), (Ibq-2), (Ibr-1), or (Ibr-2):

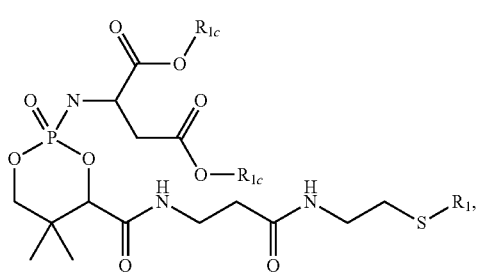

(Ibo)

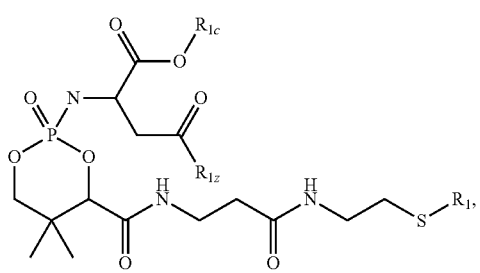

(Ibp)

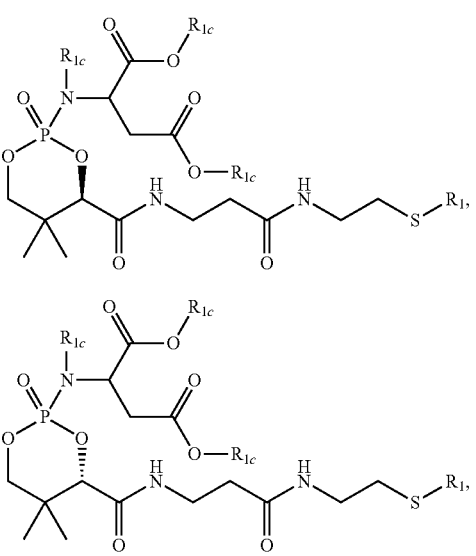

(Ibo-1)

(Ibo-2)

-continued (Ibp-1)

(Ibp-2)

(Ibq-1)

(Ibq-2)

(Ibr-1)

(Ibr-2)

or a pharmaceutically acceptable salt or solvate thereof.

In some embodiments, the compound is of Formula (Ibo-1) or a pharmaceutically acceptable salt or solvate thereof.

In some embodiments, the compound is of Formula (Ibo-2) or a pharmaceutically acceptable salt or solvate thereof.

In some embodiments, the compound is of Formula (Ibp-1) or a pharmaceutically acceptable salt or solvate thereof.

In some embodiments, the compound is of Formula (Ibp-2) or a pharmaceutically acceptable salt or solvate thereof.

In some embodiments, the compound is of Formula (Ibq-1) or a pharmaceutically acceptable salt or solvate thereof.

In some embodiments, the compound is of Formula (Ibq-2) or a pharmaceutically acceptable salt or solvate thereof.

In some embodiments, the compound is of Formula (Ibr-1) or a pharmaceutically acceptable salt or solvate thereof.

In some embodiments, the compound is of Formula (Ibr-2) or a pharmaceutically acceptable salt or solvate thereof.

In some embodiments, the compound is of Formula (II-1) or (II-2):

(II-1)

(II-2)

or a pharmaceutically acceptable salt or solvate thereof.

In some embodiments, the compound is of Formula (II-1) or a pharmaceutically acceptable salt or solvate thereof.

In some embodiments, the compound is of Formula (II-2) or a pharmaceutically acceptable salt or solvate thereof.

In some embodiments, the compound is of Formula (IIaa), (IIab), (IIac), or (IIad):

(IIaa)

(IIab)

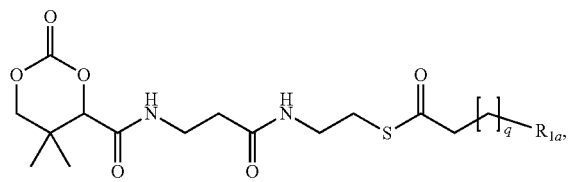

(IIac)

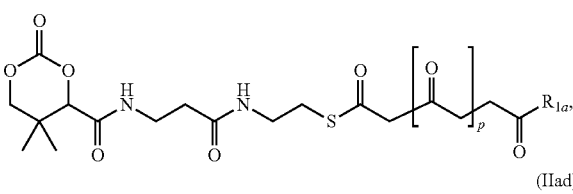

(IIad)

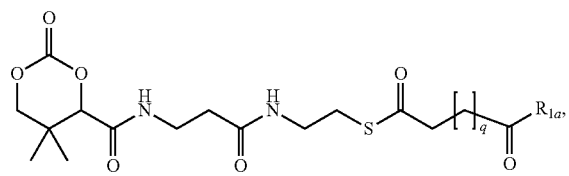

or a pharmaceutically acceptable salt or solvate thereof.

In some embodiments, the compound is of Formula (IIaa) or a pharmaceutically acceptable salt or solvate thereof.

In some embodiments, the compound is of Formula (IIab) or a pharmaceutically acceptable salt or solvate thereof.

In some embodiments, the compound is of Formula (IIac) or a pharmaceutically acceptable salt or solvate thereof.

In some embodiments, the compound is of Formula (IIad) or a pharmaceutically acceptable salt or solvate thereof.

In some embodiments, the compound is of Formula (IIaa-1), (IIaa-2), (IIab-1), (IIab-2), (IIac-1), (IIac-2), (IIad-1), or (IIad-2):

(IIaa-1)

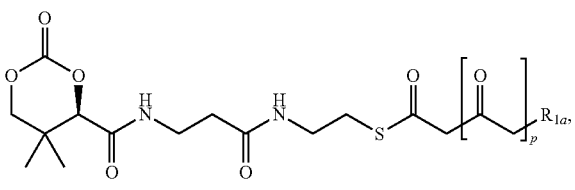

(IIaa-2)

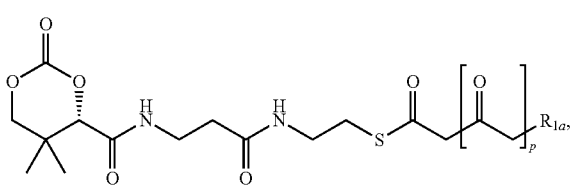

(IIab-1)

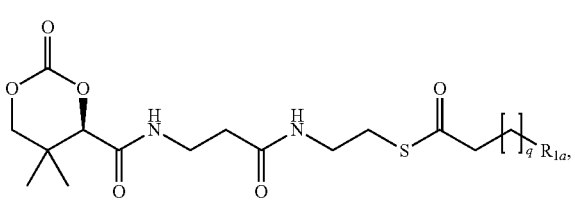

(IIab-2)

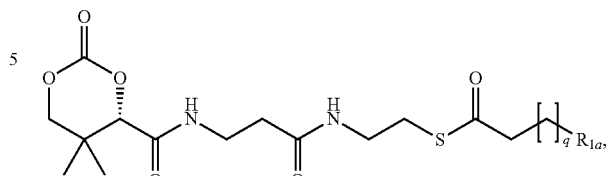

(IIac-1)

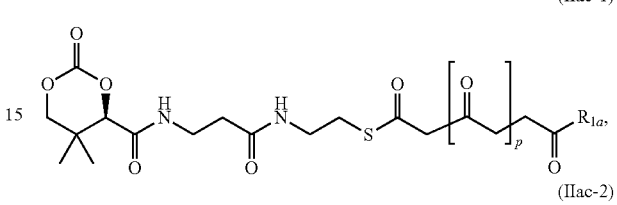

(IIac-2)

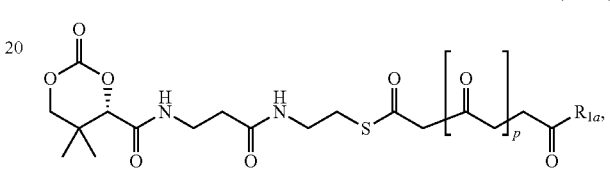

(IIad-1)

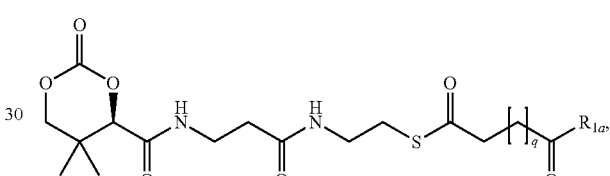

(IIad-2)

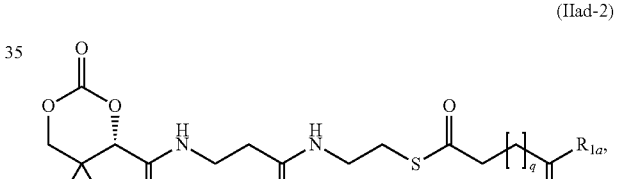

or a pharmaceutically acceptable salt or solvate thereof.

In some embodiments, the compound is of Formula (IIaa-1) or a pharmaceutically acceptable salt or solvate thereof.

In some embodiments, the compound is of Formula (IIaa-2) or a pharmaceutically acceptable salt or solvate thereof.

In some embodiments, the compound is of Formula (IIab-1) or a pharmaceutically acceptable salt or solvate thereof.

In some embodiments, the compound is of Formula (IIab-2) or a pharmaceutically acceptable salt or solvate thereof.

In some embodiments, the compound is of Formula (IIac-1) or a pharmaceutically acceptable salt or solvate thereof.

In some embodiments, the compound is of Formula (IIac-2) or a pharmaceutically acceptable salt or solvate thereof.

In some embodiments, the compound is of Formula (IIad-1) or a pharmaceutically acceptable salt or solvate thereof.

In some embodiments, the compound is of Formula (IIad-2) or a pharmaceutically acceptable salt or solvate thereof.

In some embodiments, the compound is of Formula (IIae), (IIaf), (IIag), or (IIah):

(IIae)
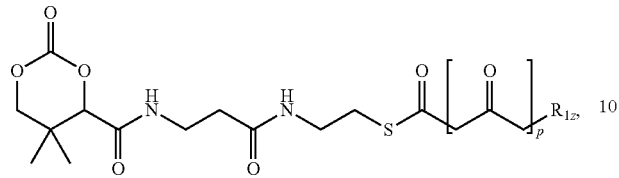

(IIaf)
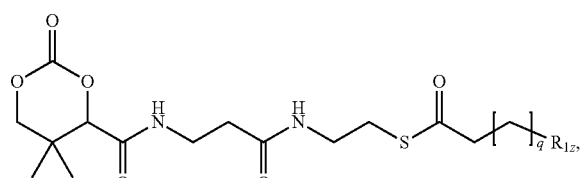

(IIag)
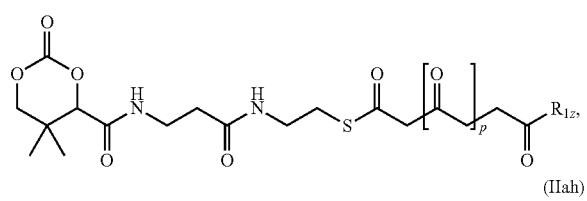

(IIah)
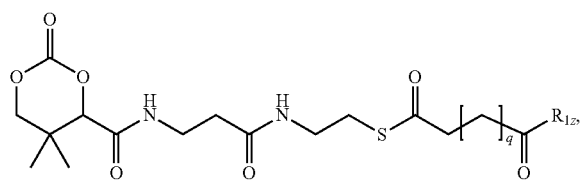

or a pharmaceutically acceptable salt or solvate thereof.

In some embodiments, the compound is of Formula (IIae) or a pharmaceutically acceptable salt or solvate thereof.

In some embodiments, the compound is of Formula (IIaf) or a pharmaceutically acceptable salt or solvate thereof.

In some embodiments, the compound is of Formula (IIag) or a pharmaceutically acceptable salt or solvate thereof.

In some embodiments, the compound is of Formula (IIah) or a pharmaceutically acceptable salt or solvate thereof.

In some embodiments, the compound is of Formula (IIae-1), (IIae-2), (IIaf-1), (IIaf-2), (IIag-1), (IIag-2), (IIah-1), or (IIah-2):

(IIae-1)
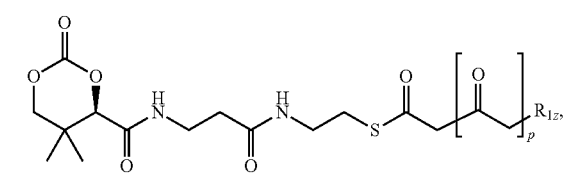

(IIae-2)
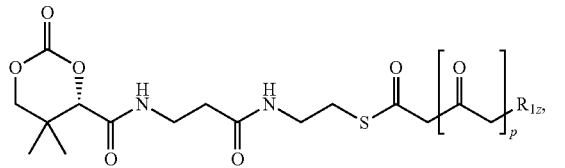

(IIaf-1)
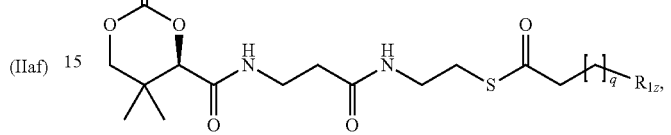

(IIaf-2)
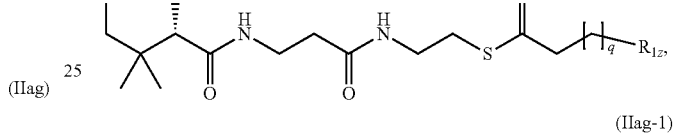

(IIag-1)
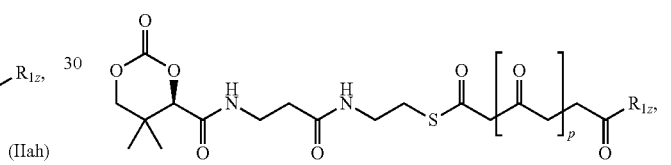

(IIag-2)
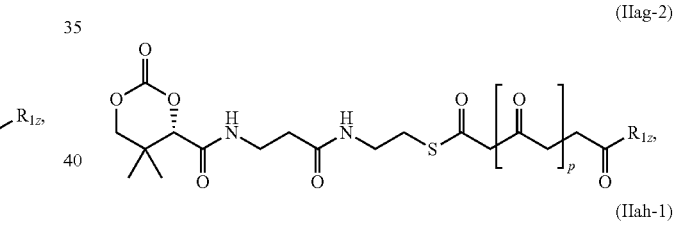

(IIah-1)
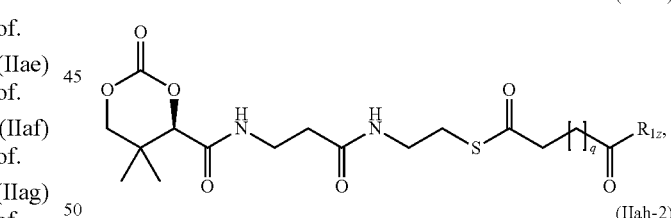

(IIah-2)
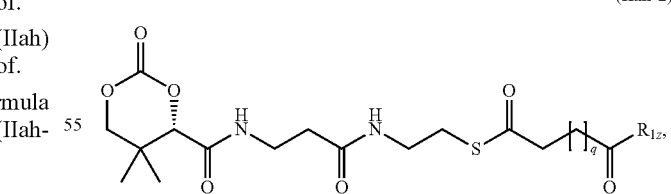

or a pharmaceutically acceptable salt or solvate thereof.

In some embodiments, the compound is of Formula (IIae-1) or a pharmaceutically acceptable salt or solvate thereof.

In some embodiments, the compound is of Formula (IIae-2) or a pharmaceutically acceptable salt or solvate thereof.

In some embodiments, the compound is of Formula (IIaf-1) or a pharmaceutically acceptable salt or solvate thereof.

In some embodiments, the compound is of Formula (IIaf-2) or a pharmaceutically acceptable salt or solvate thereof.

In some embodiments, the compound is of Formula (IIag-1) or a pharmaceutically acceptable salt or solvate thereof.

In some embodiments, the compound is of Formula (IIag-2) or a pharmaceutically acceptable salt or solvate thereof.

In some embodiments, the compound is of Formula (IIah-1) or a pharmaceutically acceptable salt or solvate thereof.

In some embodiments, the compound is of Formula (IIah-2) or a pharmaceutically acceptable salt or solvate thereof.

In some embodiments, the compound is of Formula (IIai), (IIaj), (IIak), (IIal), (IIam), or (IIan):

(IIai)
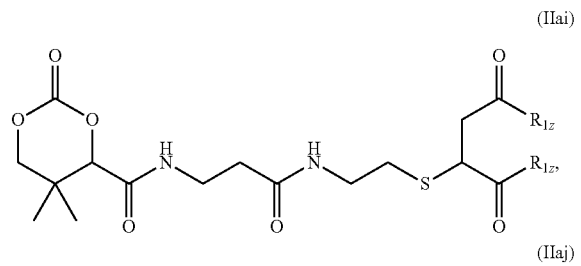

(IIaj)
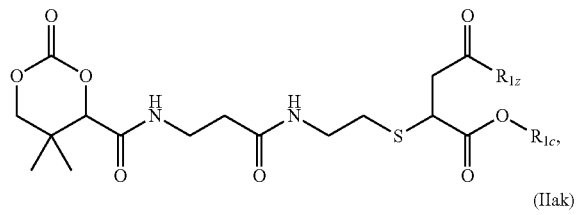

(IIak)
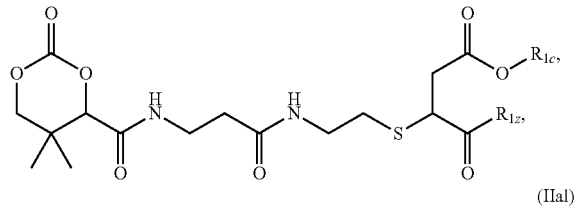

(IIal)
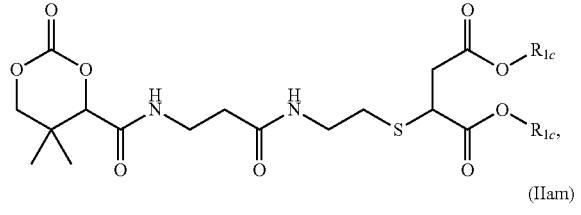

(IIam)
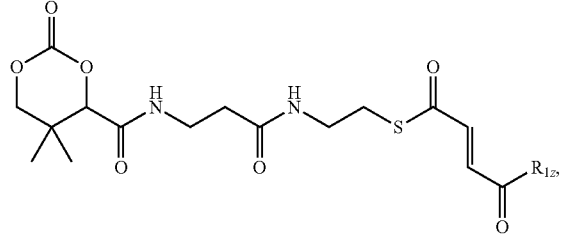

(IIan)
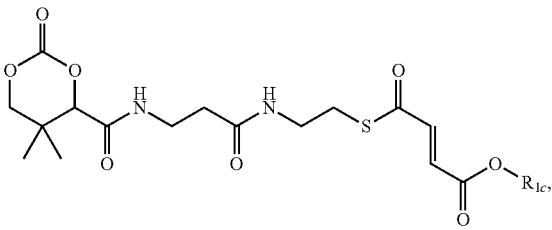

or a pharmaceutically acceptable salt or solvate thereof.

In some embodiments, the compound is of Formula (IIai) or a pharmaceutically acceptable salt or solvate thereof.

In some embodiments, the compound is of Formula (IIaj) or a pharmaceutically acceptable salt or solvate thereof.

In some embodiments, the compound is of Formula (IIak) or a pharmaceutically acceptable salt or solvate thereof.

In some embodiments, the compound is of Formula (IIal) or a pharmaceutically acceptable salt or solvate thereof.

In some embodiments, the compound is of Formula (IIam) or a pharmaceutically acceptable salt or solvate thereof.

In some embodiments, the compound is of Formula (IIan) or a pharmaceutically acceptable salt or solvate thereof.

In some embodiments, the compound is of Formula (IIai-1), (IIai-2), (IIaj-1), (IIaj-2), (IIak-1), (IIak-2), (IIal-1), (IIal-2), (IIam-1), (IIam-2), (IIan-1), or (IIan-2):

(IIai-1)
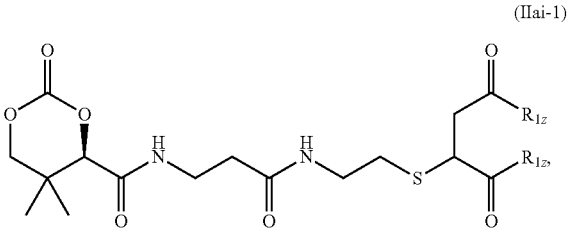

(IIai-2)
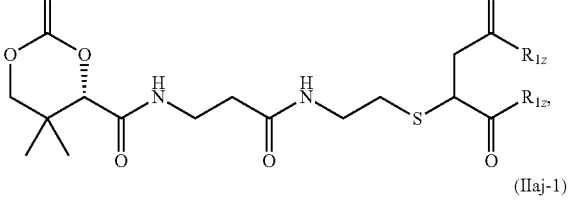

(IIaj-1)
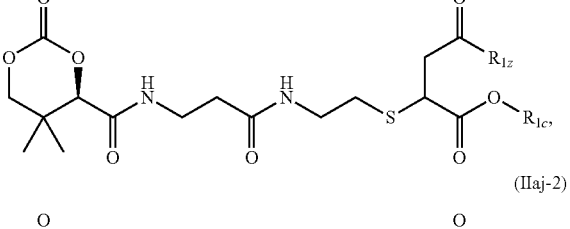

(IIaj-2)
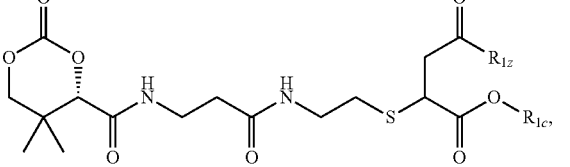

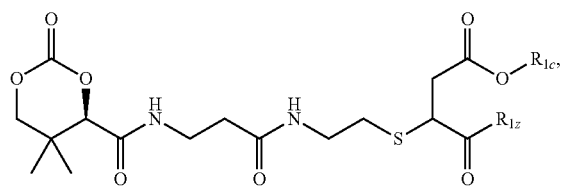
(IIak-1)

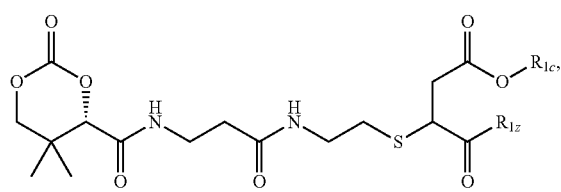
(IIak-2)

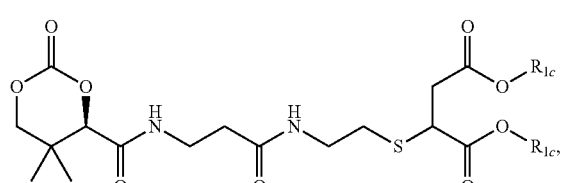
(IIal-1)

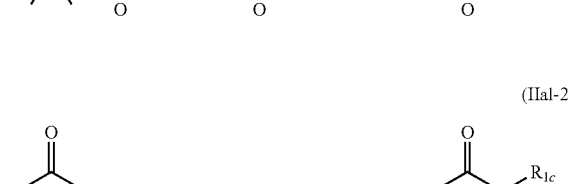
(IIal-2)

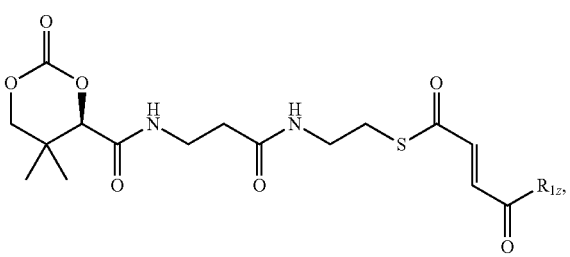
(IIam-1)

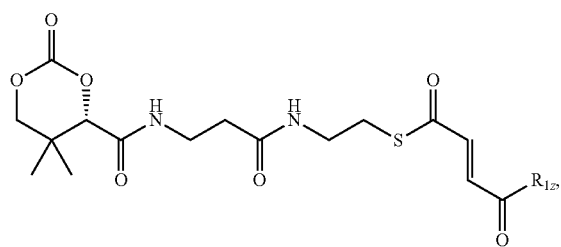
(IIam-2)

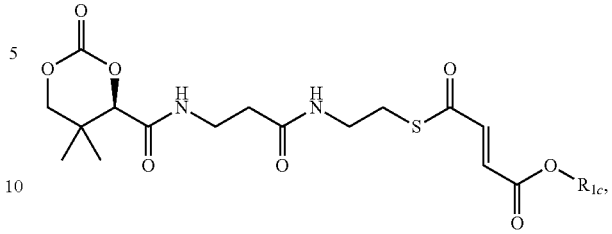
(IIan-1)

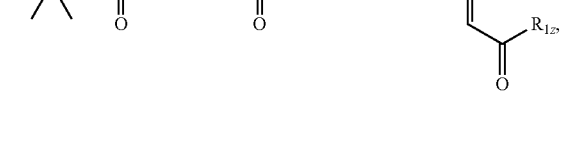
(IIan-2)

or a pharmaceutically acceptable salt or solvate thereof.

In some embodiments, the compound is of Formula (IIai-1) or a pharmaceutically acceptable salt or solvate thereof.

In some embodiments, the compound is of Formula (IIai-2) or a pharmaceutically acceptable salt or solvate thereof.

In some embodiments, the compound is of Formula (IIaj-1) or a pharmaceutically acceptable salt or solvate thereof.

In some embodiments, the compound is of Formula (IIaj-2) or a pharmaceutically acceptable salt or solvate thereof.

In some embodiments, the compound is of Formula (IIak-1) or a pharmaceutically acceptable salt or solvate thereof.

In some embodiments, the compound is of Formula (IIak-2) or a pharmaceutically acceptable salt or solvate thereof.

In some embodiments, the compound is of Formula (IIal-1) or a pharmaceutically acceptable salt or solvate thereof.

In some embodiments, the compound is of Formula (IIal-2) or a pharmaceutically acceptable salt or solvate thereof.

In some embodiments, the compound is of Formula (IIam-1) or a pharmaceutically acceptable salt or solvate thereof.

In some embodiments, the compound is of Formula (IIam-2) or a pharmaceutically acceptable salt or solvate thereof.

In some embodiments, the compound is of Formula (IIan-1) or a pharmaceutically acceptable salt or solvate thereof.

In some embodiments, the compound is of Formula (IIan-2) or a pharmaceutically acceptable salt or solvate thereof.

In some embodiments, the compound is of Formula (III-1) or (III-2):

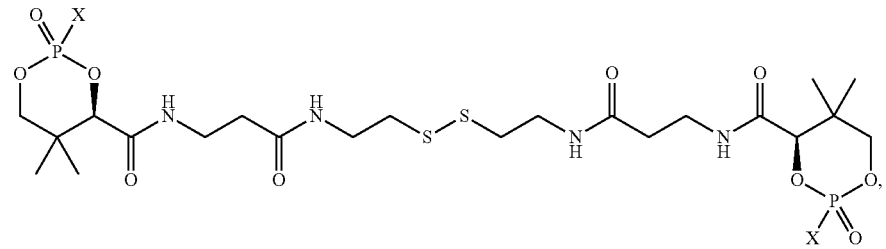

(III-1)

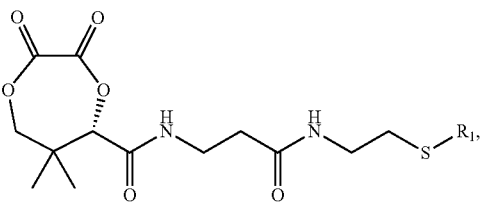

(III-2)

or a pharmaceutically acceptable salt or solvate thereof.

In some embodiments, the compound is of Formula (III-1) or a pharmaceutically acceptable salt or solvate thereof.

In some embodiments, the compound is of Formula (III-2) or a pharmaceutically acceptable salt or solvate thereof.

In some embodiments, the compound is of Formula (IV-1) or (IV-2):

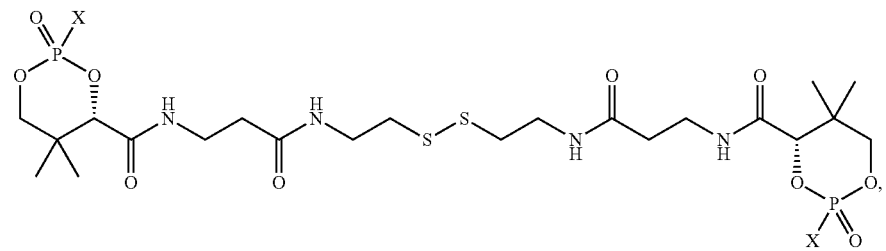

(IV-1)

(IV-2)

or a pharmaceutically acceptable salt or solvate thereof.

In some embodiments, the compound is of Formula (IV-1) or a pharmaceutically acceptable salt or solvate thereof.

In some embodiments, the compound is of Formula (IV-2) or a pharmaceutically acceptable salt or solvate thereof.

In some embodiments, the compound is of Formula (V-1) or (V-2):

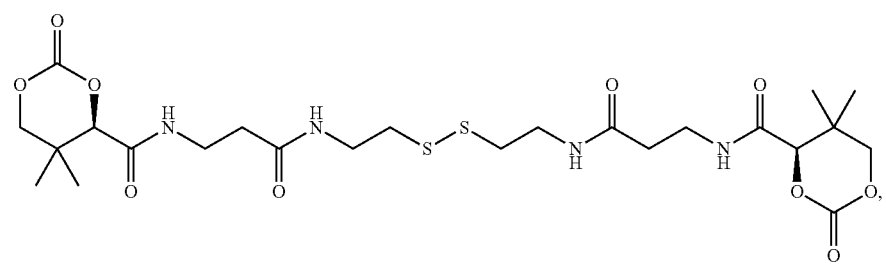

(V-1)

-continued

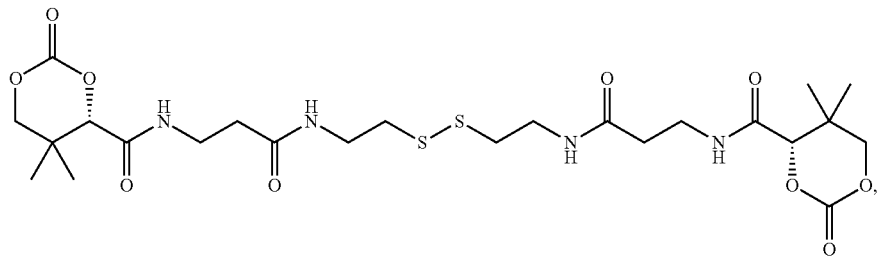

(V-2)

or a pharmaceutically acceptable salt or solvate thereof.

In some embodiments, the compound is of Formula (V-1) or a pharmaceutically acceptable salt or solvate thereof.

In some embodiments, the compound is of Formula (V-2) or a pharmaceutically acceptable salt or solvate thereof.

In some embodiments, the compound is of Formula (VI-1) or (VI-2):

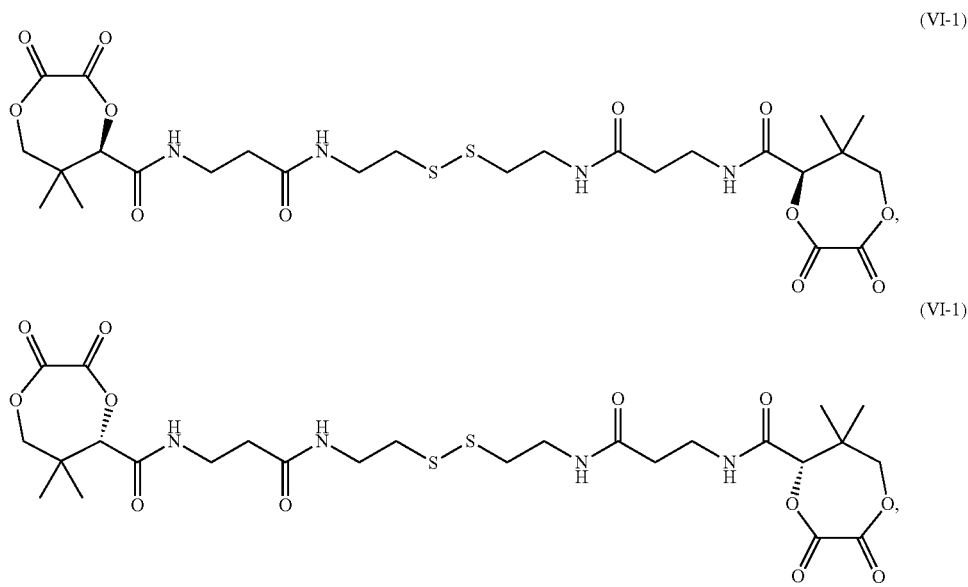

(VI-1)

(VI-1)

or a pharmaceutically acceptable salt or solvate thereof.

In some embodiments, the compound is of Formula (V-1) or a pharmaceutically acceptable salt or solvate thereof.

In some embodiments, the compound is of Formula (V-2) or a pharmaceutically acceptable salt or solvate thereof.

In some embodiments, each T is independently

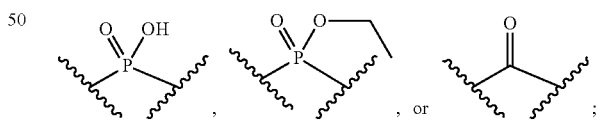

or ;

and $R_1$ is —C(=O)—$R_{1a}$, —C(=O)—CH$_2$—$R_{1a}$, —C(=O)—CH$_2$CH$_2$—$R_{1a}$ or —C(=O)—CH=CH—$R_{1a}$, wherein Ilia is $C_1$-$C_{20}$ alkyl, —C(=O)$R_{1b}$, or —C(=O) O$R_{1c}$, wherein the $C_1$-$C_{20}$ alkyl is optionally substituted with one or more $R_{1e}$.

In some embodiments, each T is independently

, or ;

and $R_1$ is —C(=O)—CH$_3$, —C(=O)—CH$_2$—CH(OH)—CH$_3$, —C(=O)—CH$_2$—C(=O)—CH$_3$, —C(=O)—CH$_2$CH$_2$—C(=O)OH, —C(=O)—CH$_2$CH$_2$—C(=O) OCH$_3$, —C(=O)—CH=CH—CH$_3$, —C(=O)—CH=CH—C(=O)OH, or —C(=O)—CH=CH—C(=O) OCH$_3$.

It is understood that, for a compound of any one of the Formulae disclosed herein, $R_1$, $R_{1a}$, $R_{1b}$, $R_{1c}$, $R_{1d}$, $R_{1e}$, $R_{1f}$, $R_{1g}$, $R_{1z}$, X, n, p, q, and r can each be, where applicable, selected from the groups described herein, and any group described herein for any of $R_1$, $R_{1a}$, $R_{1b}$, $R_{1g}$, $R_{1d}$, $R_{1e}$, $R_{1f}$, $R_{1g}$, $R_{1z}$, X, n, p, q, and r can be combined, where applicable, with any group described herein for one or more of the remainder of $R_1$, $R_{1a}$, $R_{1b}$, $R_{1c}$, $R_{1d}$, $R_{1e}$, $R_{1f}$, $R_{1g}$, $R_{1z}$, X, n, p, q, and r.

In some embodiments, the compound is selected from the compounds described in Table 1 and pharmaceutically acceptable salts thereof.

In some embodiments, the compound is selected from the compounds described in Table 1.

In some embodiments, the compound is selected from Compound Nos. 1-446 and pharmaceutically acceptable salts thereof.

In some embodiments, the compound is selected from Compound Nos. 1-446.

In some embodiments, the compound is selected from Compound Nos. 447-516 and pharmaceutically acceptable salts thereof.

In some embodiments, the compound is selected from Compound Nos. 447-516.

In some embodiments, the compound is selected from Compound Nos. 517-527 and pharmaceutically acceptable salts thereof.

In some embodiments, the compound is selected from Compound Nos. 517-527.

In some embodiments, the compound is selected from Compound Nos. 528-555 and pharmaceutically acceptable salts thereof.

In some embodiments, the compound is selected from Compound Nos. 556-581 and pharmaceutically acceptable salts thereof.

In some embodiments, the compound is selected from Compound Nos. 582-607 and pharmaceutically acceptable salts thereof.

In some embodiments, the compound is selected from Compound Nos. 608-699 and pharmaceutically acceptable salts thereof.

In some embodiments, the compound is selected from Compound Nos. 700-747 and pharmaceutically acceptable salts thereof.

In some embodiments, the compound is selected from Compound Nos. 748-794 and pharmaceutically acceptable salts thereof.

In some embodiments, the compound is selected from Compound Nos. 795-818 and pharmaceutically acceptable salts thereof.

In some embodiments, the compound is selected from Compound Nos. 819-844 and pharmaceutically acceptable salts thereof.

In some embodiments, the compound is selected from Compound Nos. 849-932 and pharmaceutically acceptable salts thereof.

In some embodiments, the compound is selected from Compound Nos. 1, 5, 21, 36, 39, 42, 61, 447, 448, and 485, and pharmaceutically acceptable salts thereof.

In some embodiments, the compound is selected from Compound Nos. 1, 5, 21, 36, 39, 42, 61, 447, 448, and 485.

TABLE 1

| Compound No. | Structure |
|---|---|
| 1 | 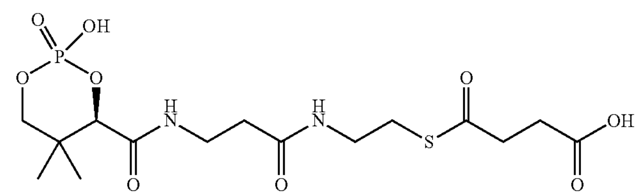 |
| 2 | 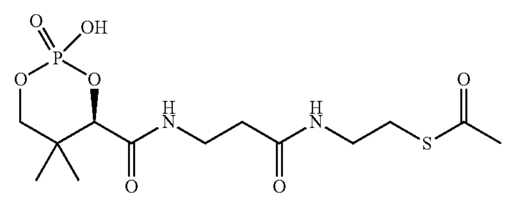 |
| 3 | 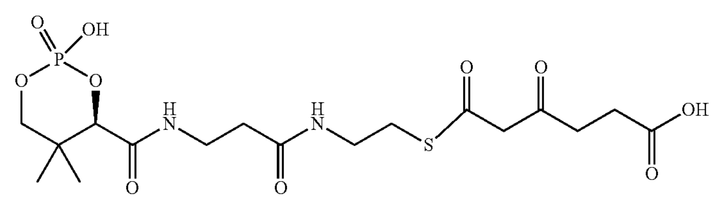 |
| 4 | 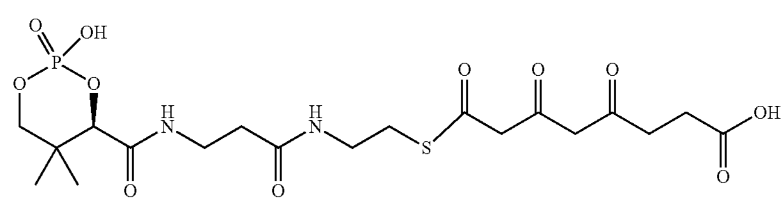 |

TABLE 1-continued

| Compound No. | Structure |
|---|---|
| 5 | 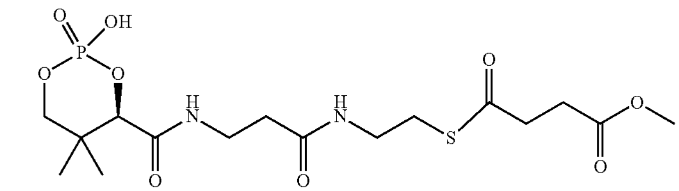 |
| 6 | 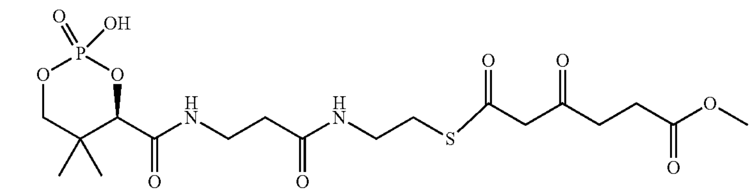 |
| 7 | 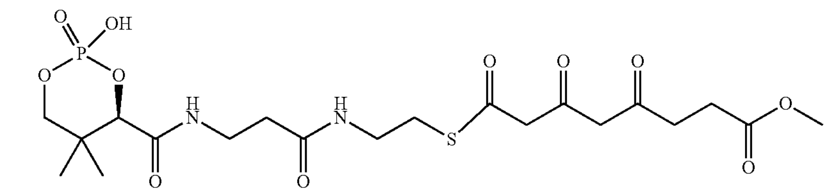 |
| 8 | 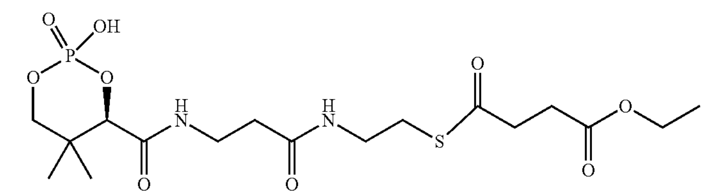 |
| 9 | 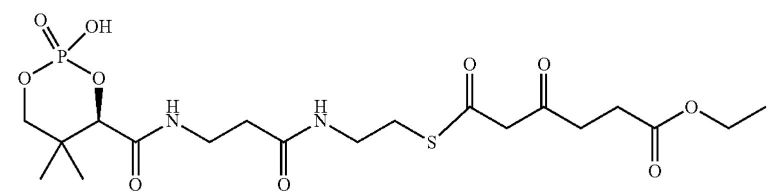 |
| 10 | 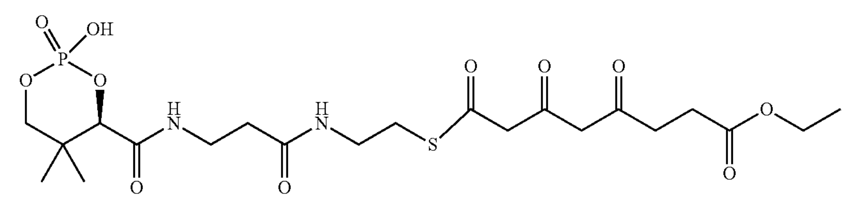 |
| 11 | 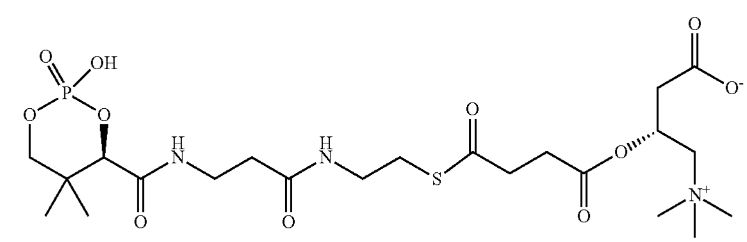 |

TABLE 1-continued

| Compound No. | Structure |
|---|---|
| 12 | 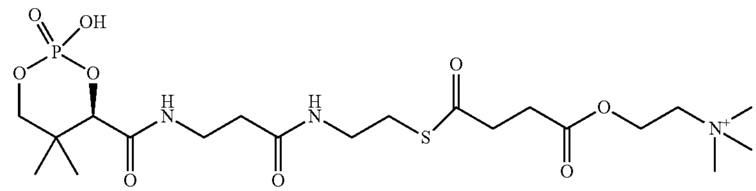 |
| 13 | 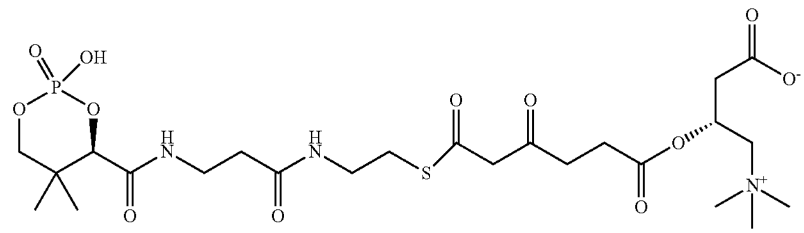 |
| 14 | 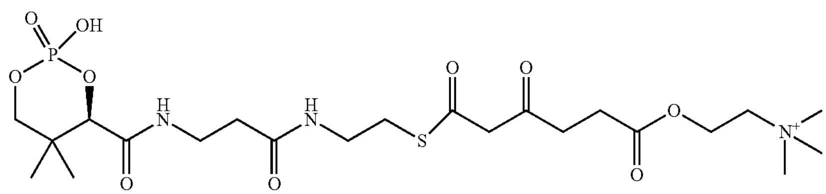 |
| 15 | 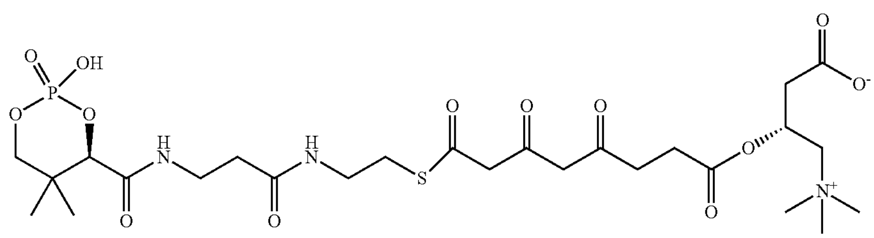 |
| 16 | 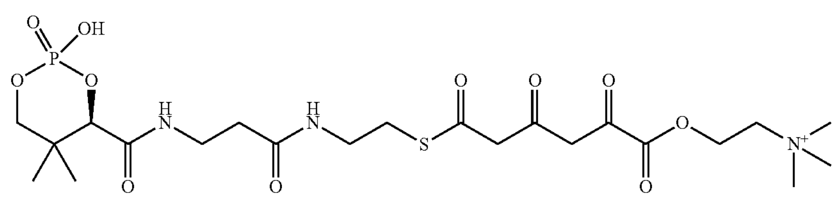 |
| 17 | 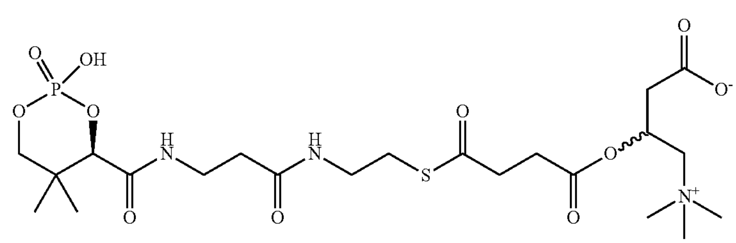 |
| 18 | 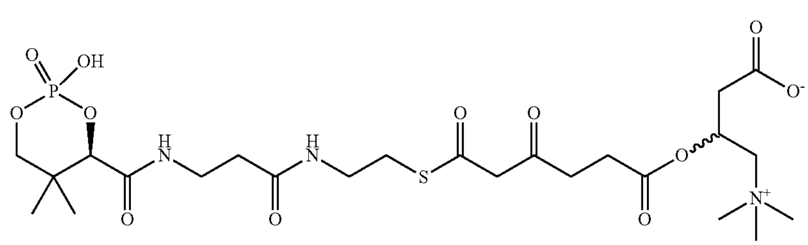 |

TABLE 1-continued

| Compound No. | Structure |
|---|---|
| 19 | 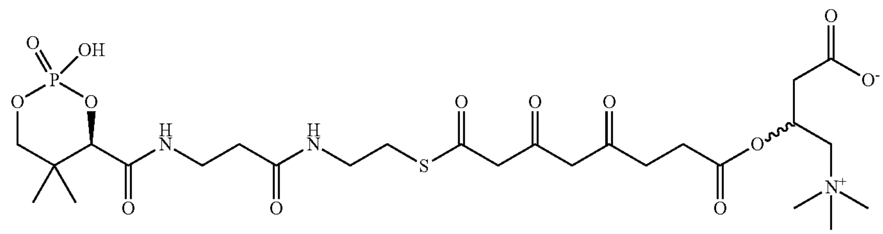 |
| 20 | 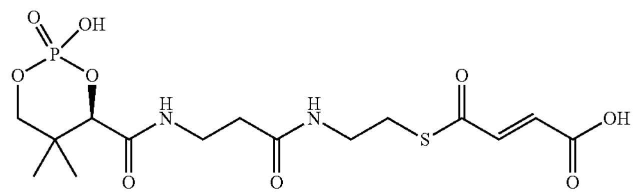 |
| 21 | 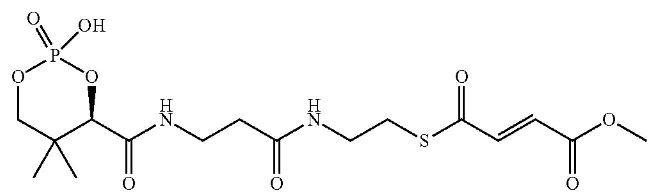 |
| 22 | 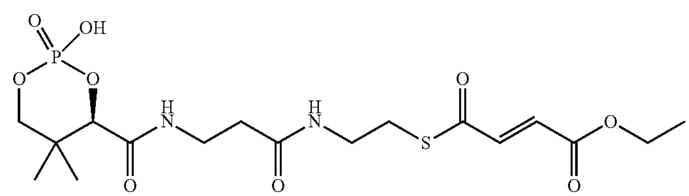 |
| 23 | 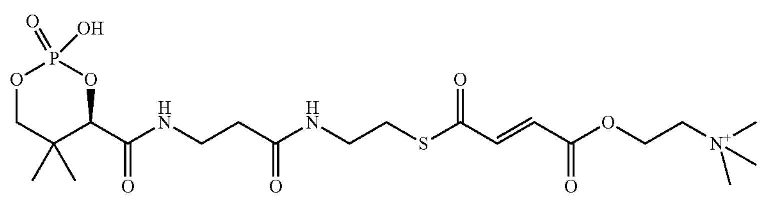 |
| 24 | 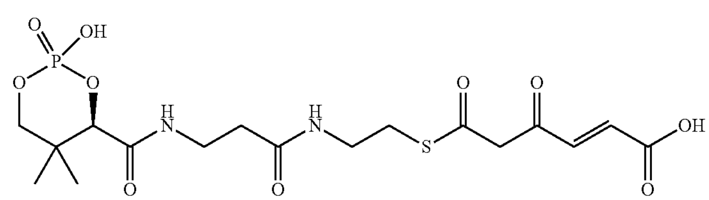 |
| 25 | 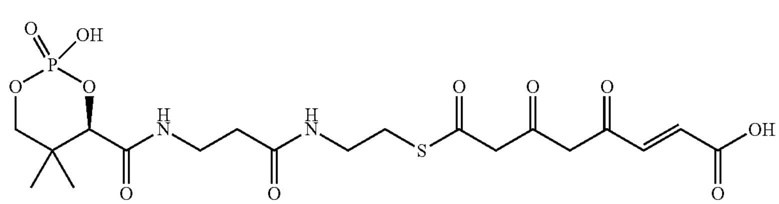 |

TABLE 1-continued
| Compound No. | Structure |
|---|---|
| 26 | 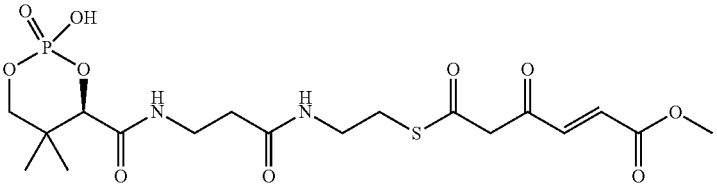 |
| 27 | 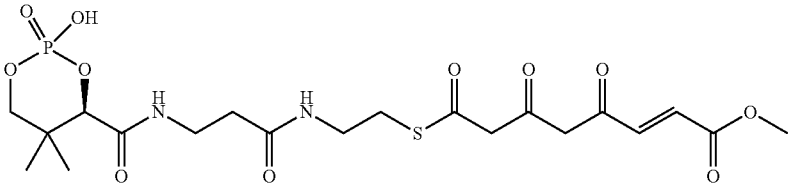 |
| 28 | 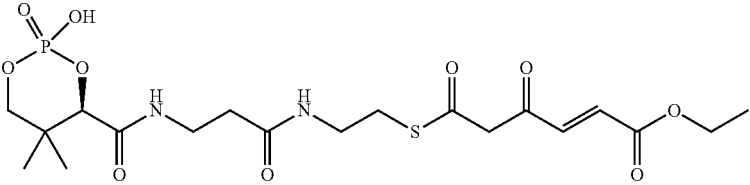 |
| 29 | 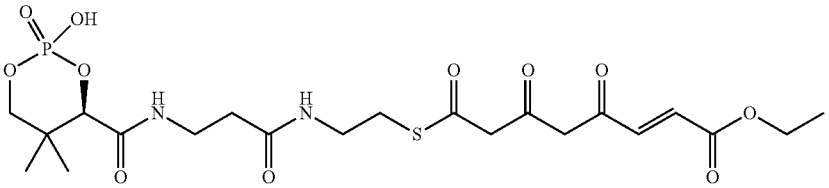 |
| 30 | 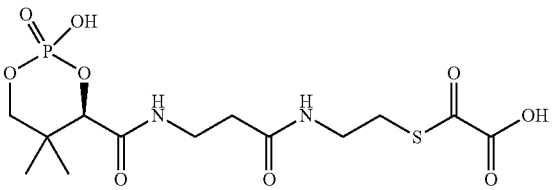 |
| 31 | 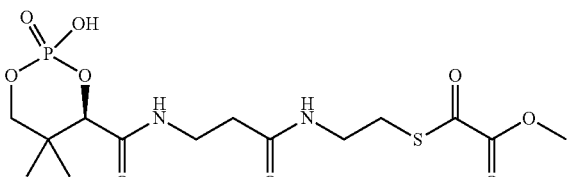 |
| 32 | 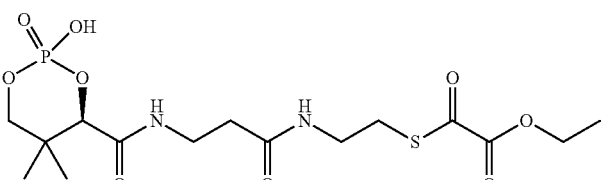 |
| 33 | 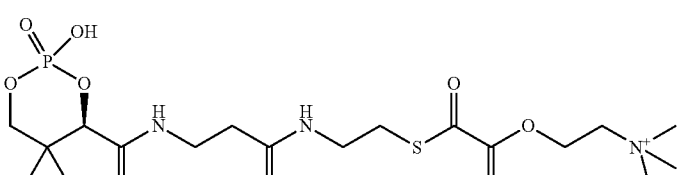 |

TABLE 1-continued
| Compound No. | Structure |
|---|---|
| 34 | 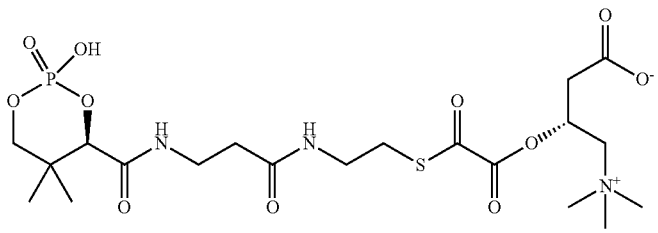 |
| 35 | 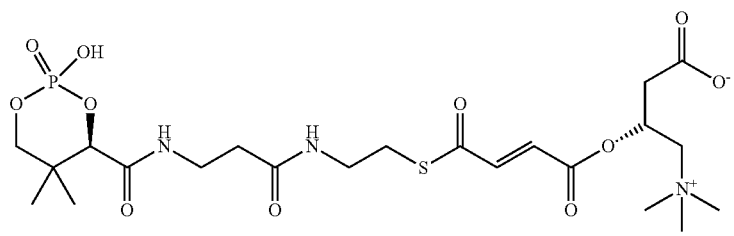 |
| 36 | 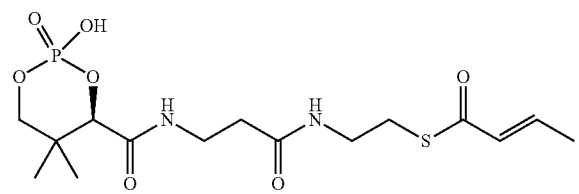 |
| 37 | 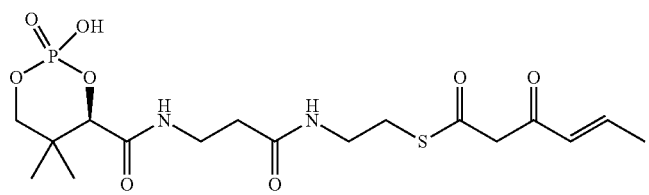 |
| 38 | 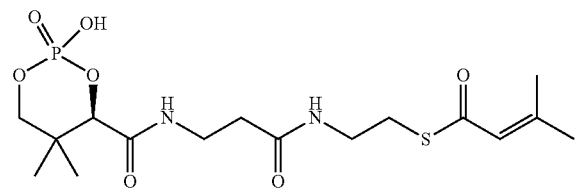 |
| 39 | 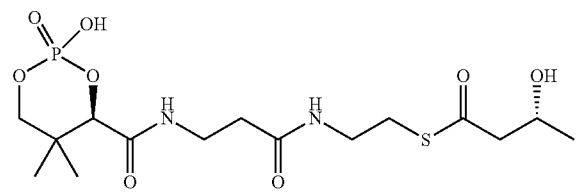 |
| 40 | 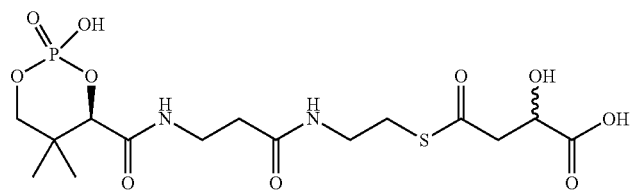 |

TABLE 1-continued

| Compound No. | Structure |
|---|---|
| 41 | *(chemical structure)* |
| 42 | *(chemical structure)* |
| 43 | *(chemical structure)* |
| 44 | *(chemical structure)* |
| 45 | *(chemical structure)* |
| 46 | *(chemical structure)* |
| 47 | *(chemical structure)* |

TABLE 1-continued

| Compound No. | Structure |
|---|---|
| 48 | 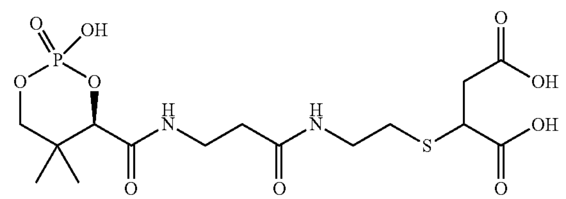 |
| 49 | 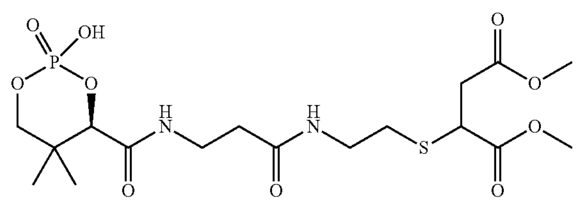 |
| 50 | 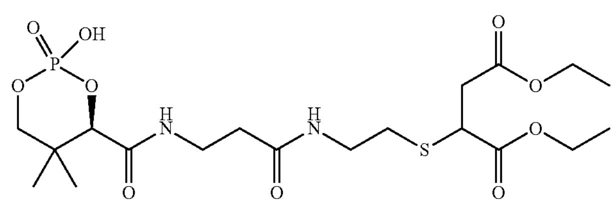 |
| 51 | 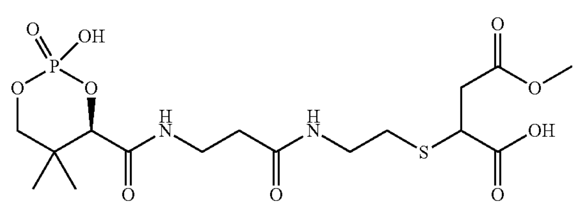 |
| 52 | 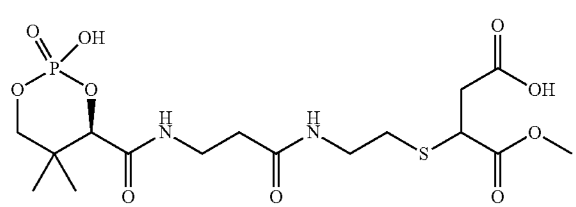 |
| 53 | 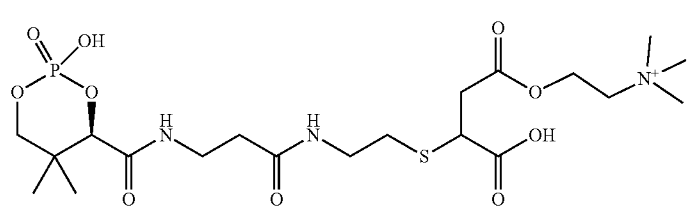 |
| 54 | 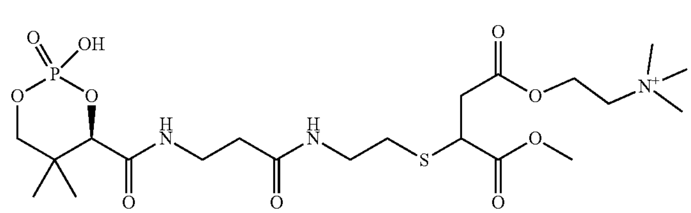 |

TABLE 1-continued
| Compound No. | Structure |
|---|---|
| 55 | 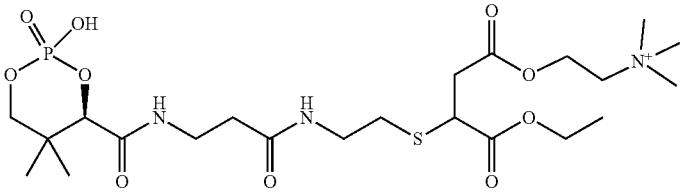 |
| 56 | 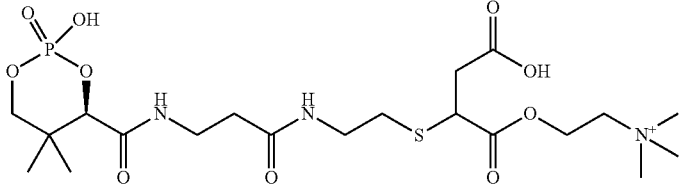 |
| 57 | 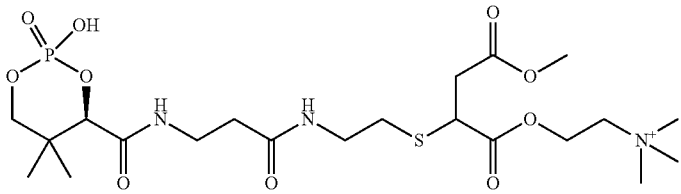 |
| 58 | 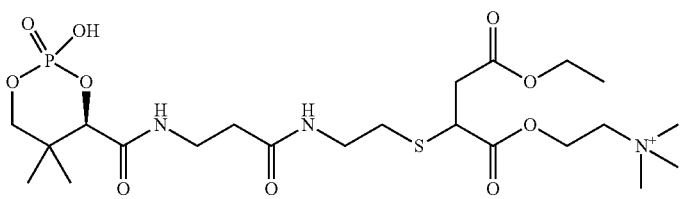 |
| 59 | 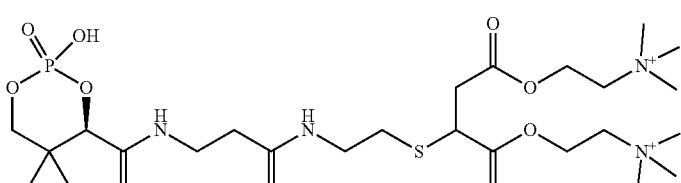 |
| 60 | 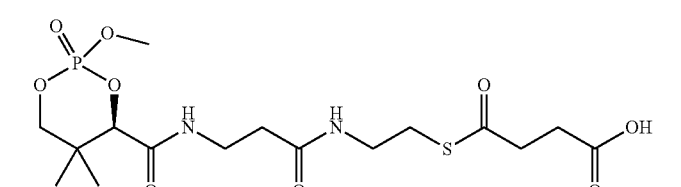 |
| 61 | 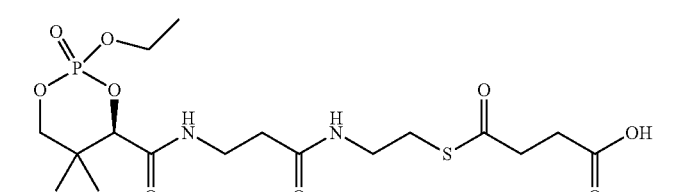 |

TABLE 1-continued
| Compound No. | Structure |
|---|---|
| 62 | 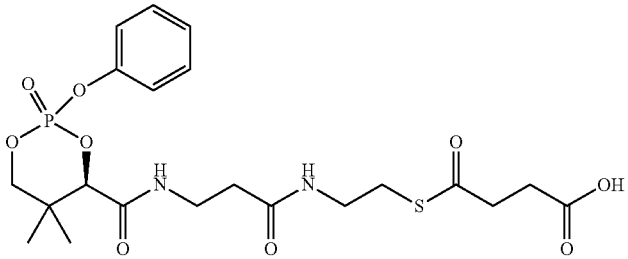 |
| 63 | 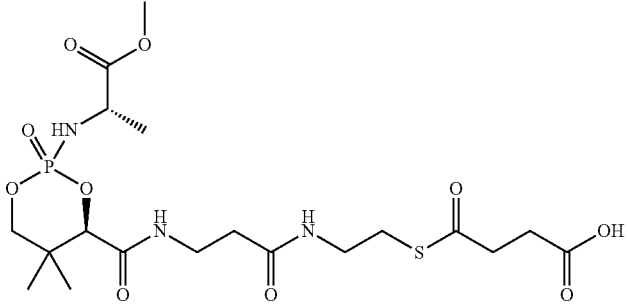 |
| 64 | 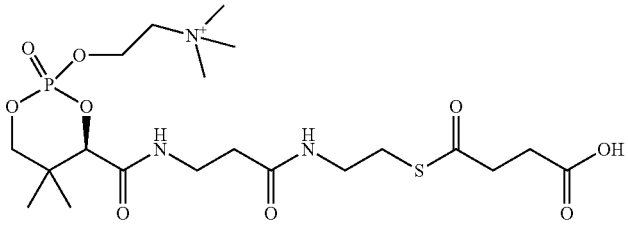 |
| 65 | 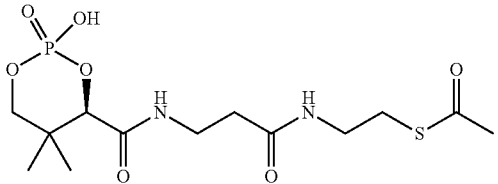 |
| 66 | 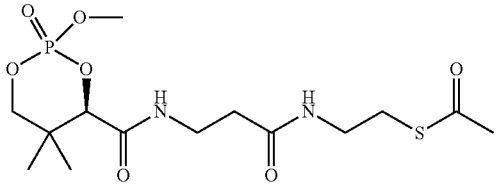 |
| 67 | 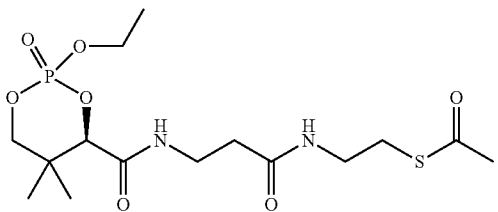 |

TABLE 1-continued

| Compound No. | Structure |
|---|---|
| 68 | 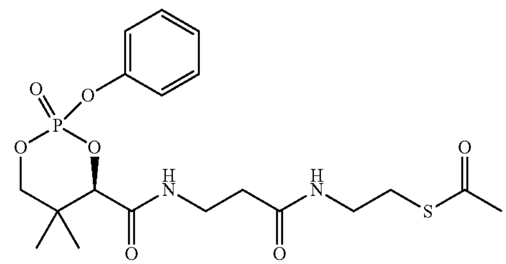 |
| 69 | 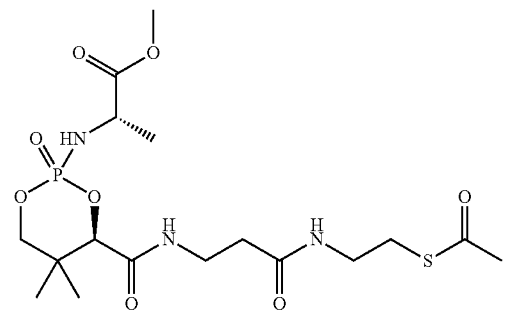 |
| 70 | 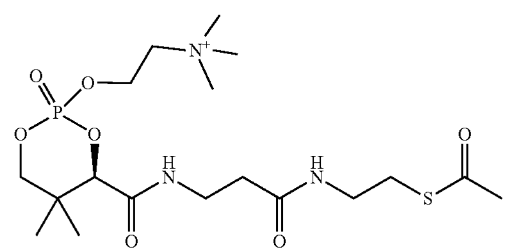 |
| 71 | 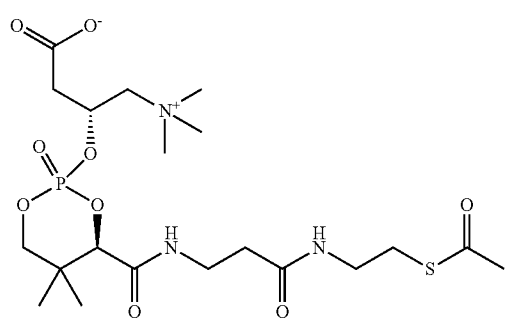 |
| 72 | 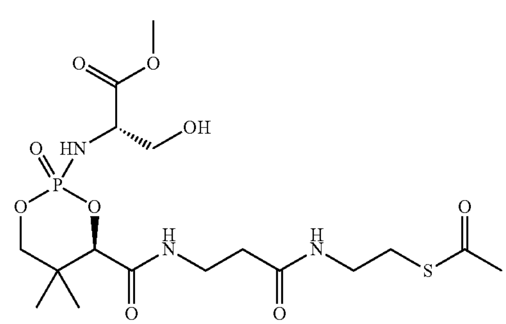 |

TABLE 1-continued

| Compound No. | Structure |
|---|---|
| 73 | (chemical structure) |
| 74 | (chemical structure) |
| 75 | (chemical structure) |
| 76 | (chemical structure) |
| 77 | (chemical structure) |
| 78 | (chemical structure) |

TABLE 1-continued
| Compound No. | Structure |
|---|---|
| 79 | 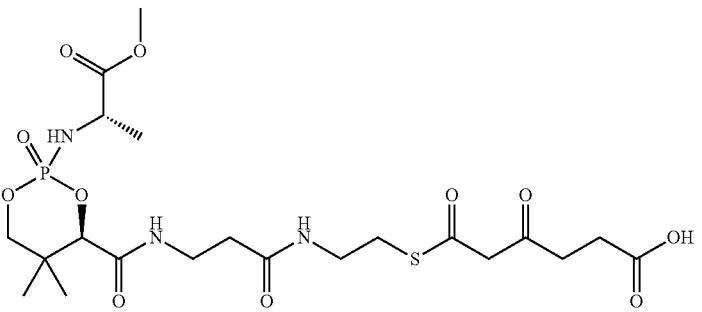 |
| 80 | 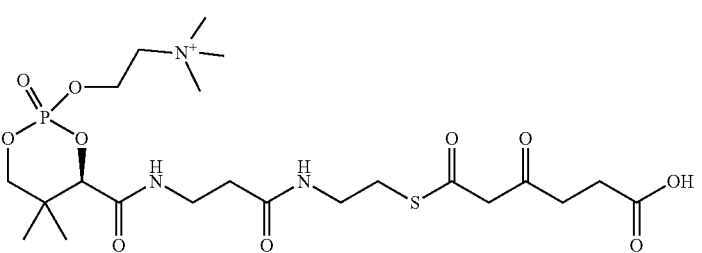 |
| 81 | 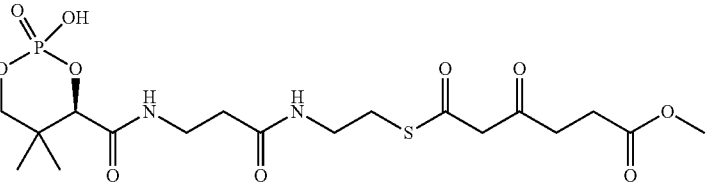 |
| 82 | 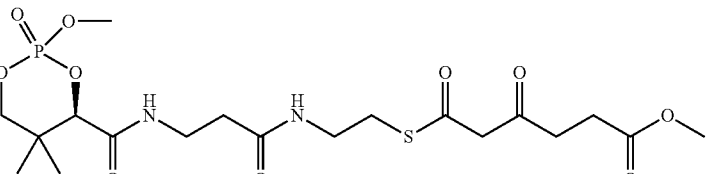 |
| 83 | 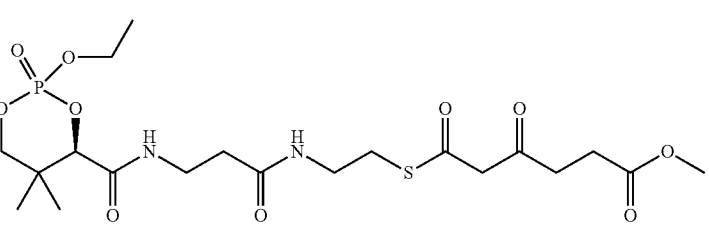 |
| 84 | 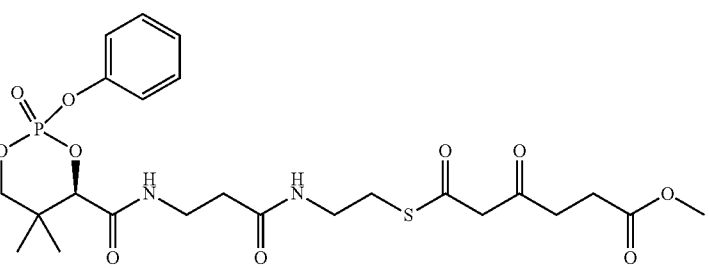 |

TABLE 1-continued

| Compound No. | Structure |
|---|---|
| 85 | (chemical structure) |
| 86 | (chemical structure) |
| 87 | (chemical structure) |
| 88 | (chemical structure) |
| 89 | (chemical structure) |
| 90 | (chemical structure) |

TABLE 1-continued
| Compound No. | Structure |
|---|---|
| 91 | 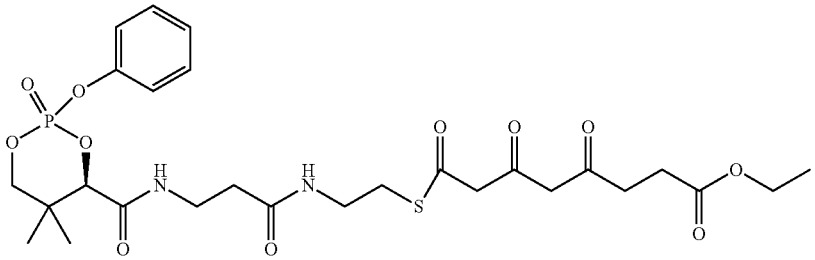 |
| 92 | 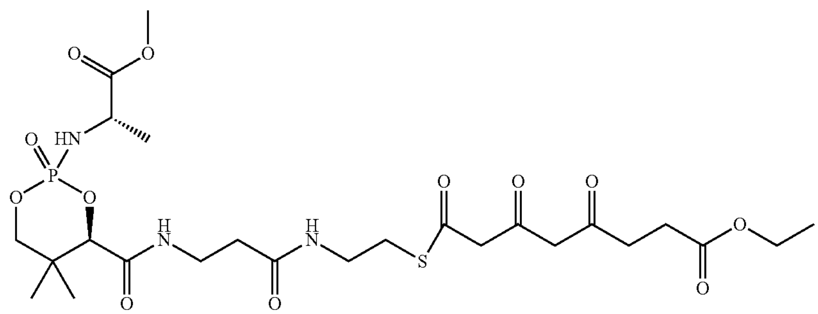 |
| 93 | 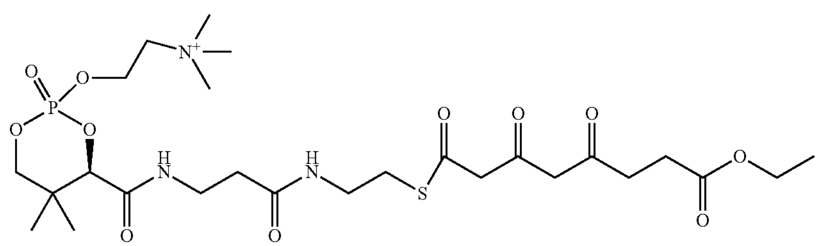 |
| 94 | 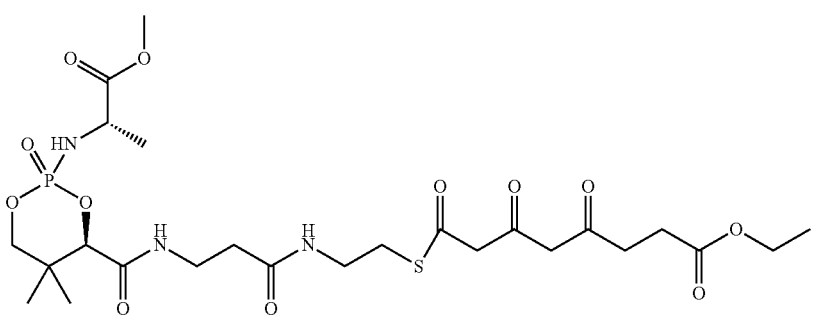 |
| 95 | 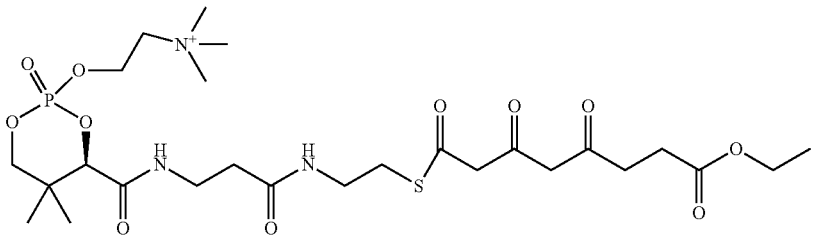 |

TABLE 1-continued
| Compound No. | Structure |
|---|---|
| 96 | 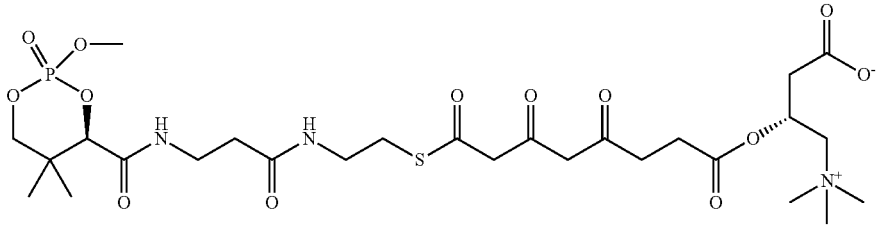 |
| 97 | 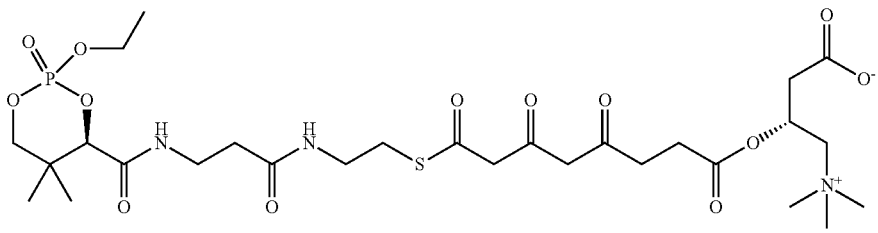 |
| 98 | 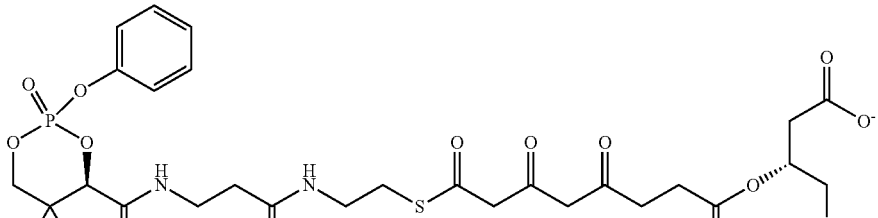 |
| 99 | 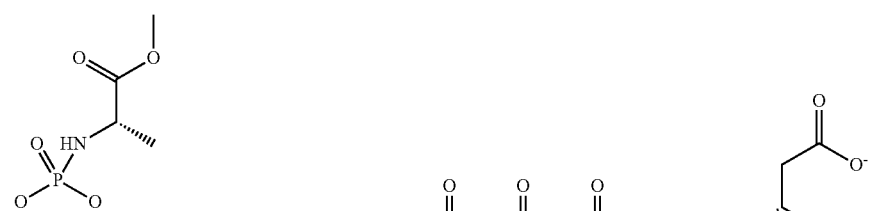 |
| 100 | 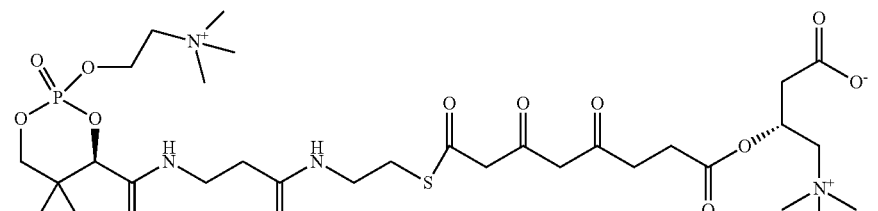 |

TABLE 1-continued
| Compound No. | Structure |
|---|---|
| 101 | 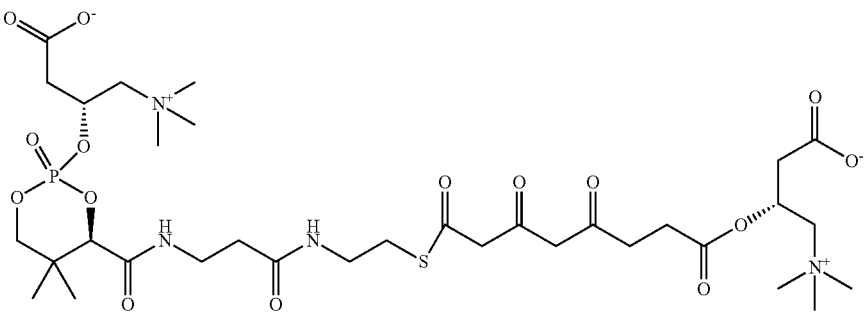 |
| 102 | 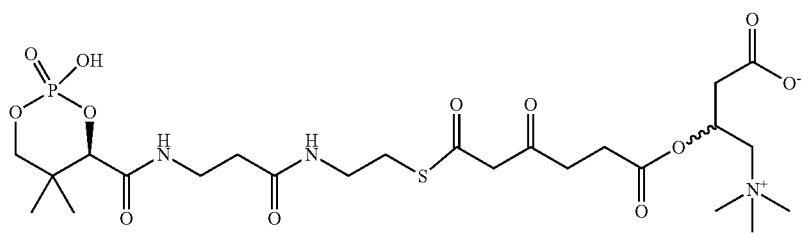 |
| 103 | 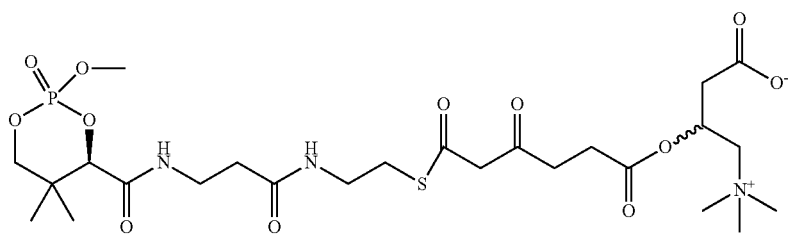 |
| 104 | 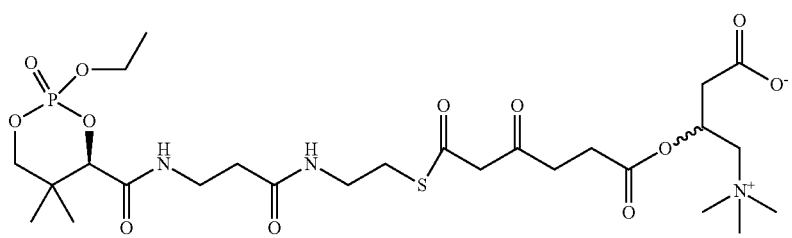 |
| 105 | 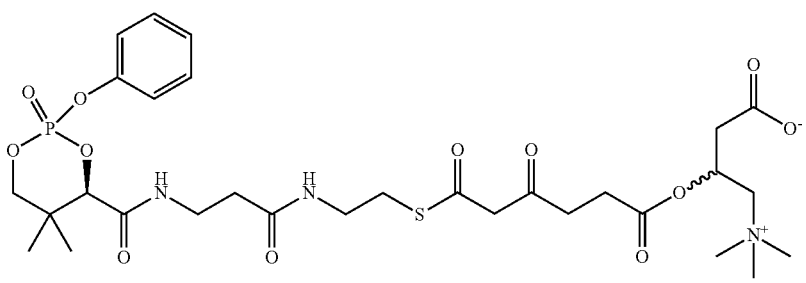 |

TABLE 1-continued
| Compound No. | Structure |
|---|---|
| 106 | 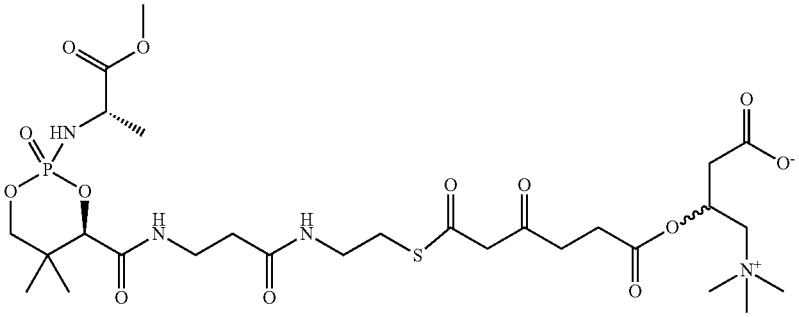 |
| 107 | 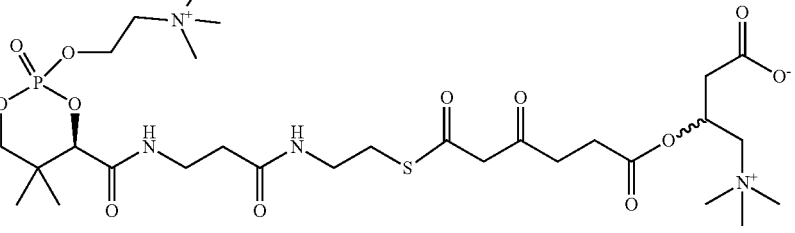 |
| 108 | 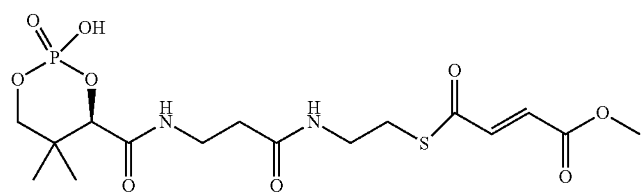 |
| 109 | 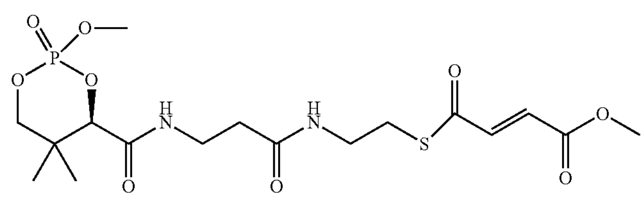 |
| 110 | 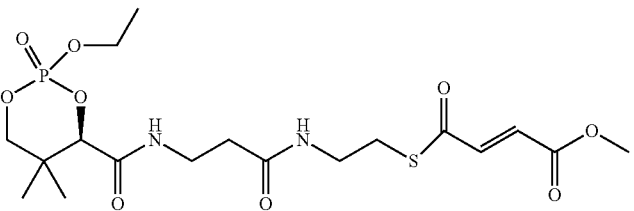 |
| 111 | 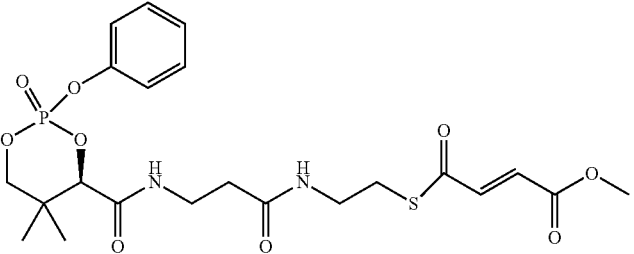 |

TABLE 1-continued

| Compound No. | Structure |
|---|---|
| 112 | 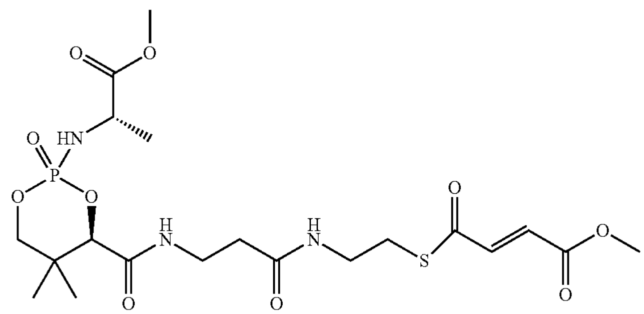 |
| 113 | 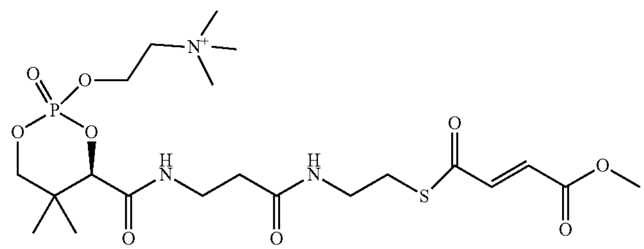 |
| 114 | 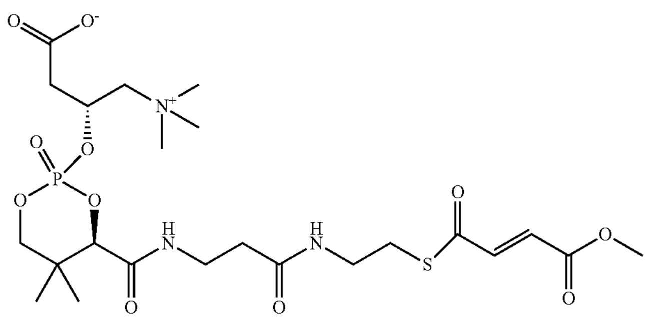 |
| 115 | 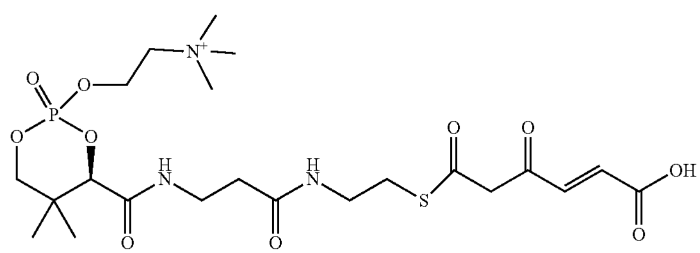 |
| 116 | 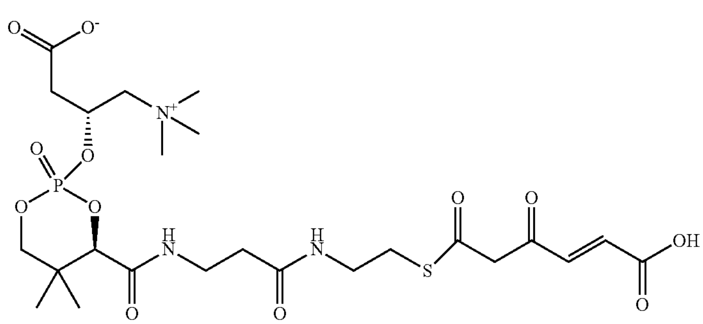 |

TABLE 1-continued

| Compound No. | Structure |
|---|---|
| 117 | 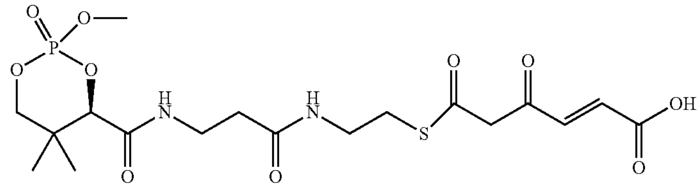 |
| 118 | 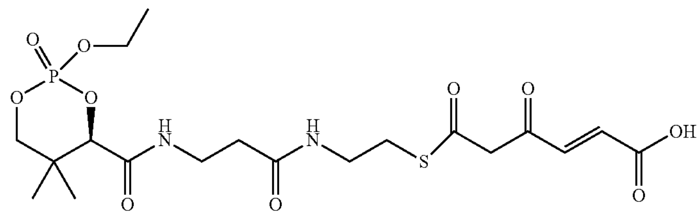 |
| 119 | 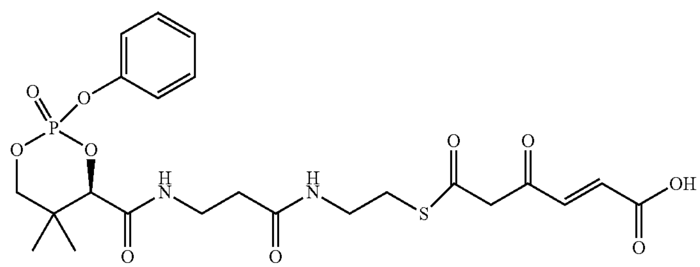 |
| 120 | 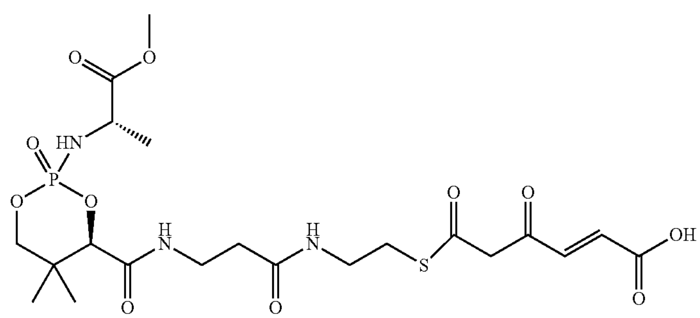 |
| 121 | 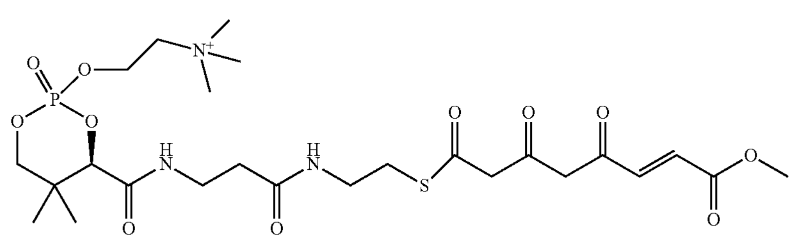 |
| 122 | 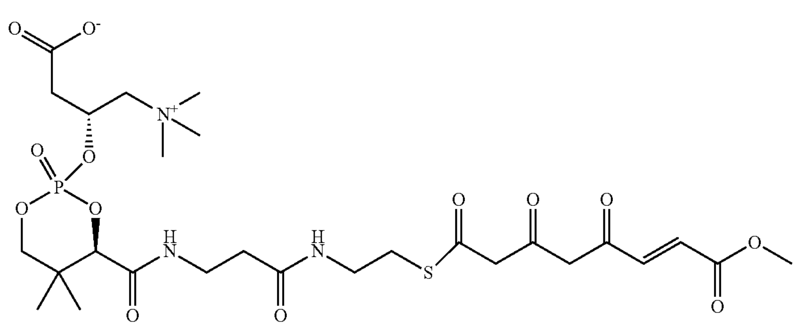 |

TABLE 1-continued

| Compound No. | Structure |
|---|---|
| 123 | 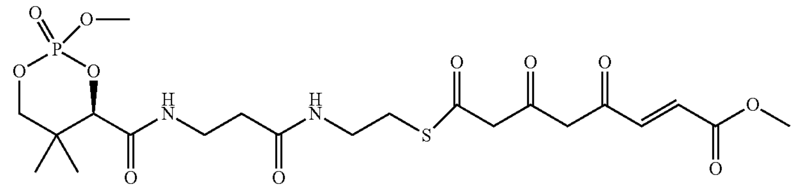 |
| 124 | 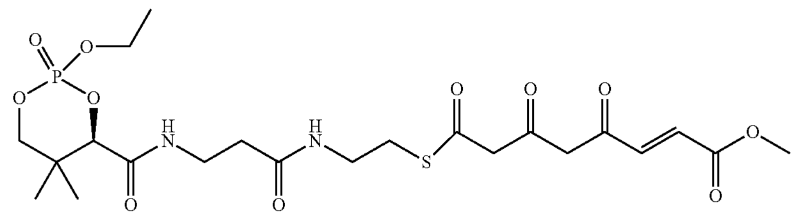 |
| 125 | 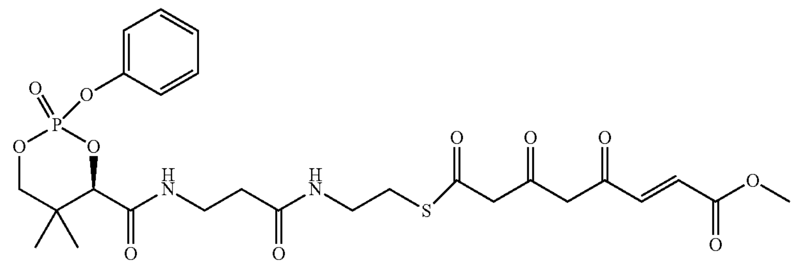 |
| 126 | 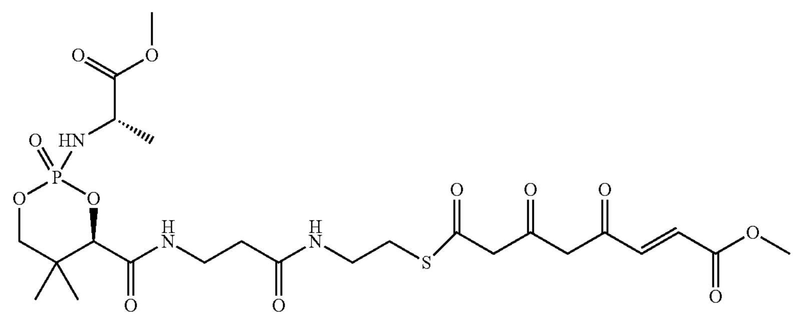 |
| 127 | 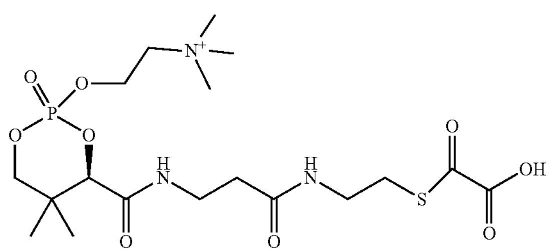 |
| 128 | 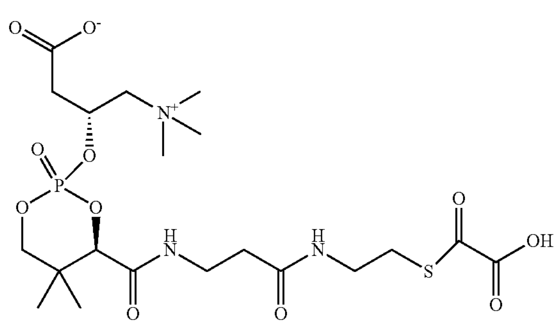 |

TABLE 1-continued

| Compound No. | Structure |
|---|---|
| 129 | (structure) |
| 130 | (structure) |
| 131 | (structure) |
| 132 | (structure) |
| 133 | (structure) |

TABLE 1-continued

| Compound No. | Structure |
|---|---|
| 134 | 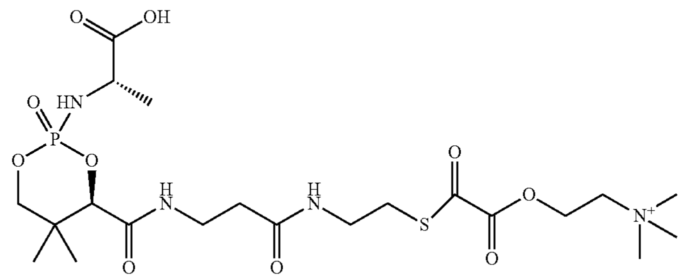 |
| 135 | 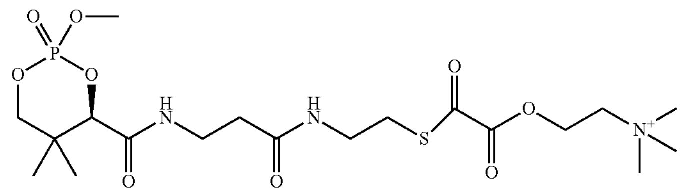 |
| 136 | 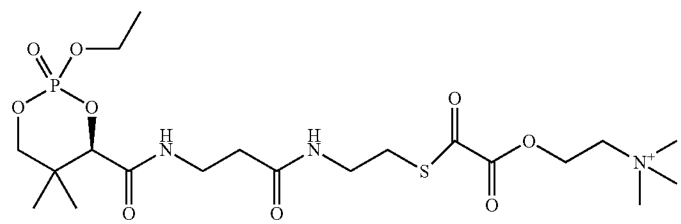 |
| 137 | 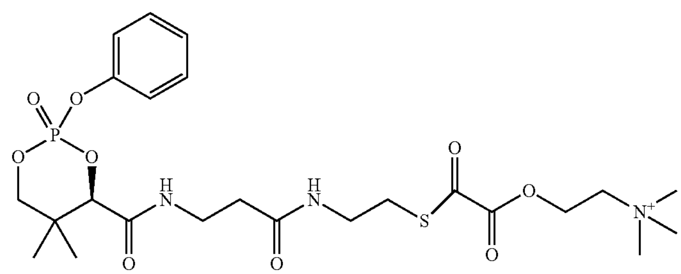 |
| 138 | 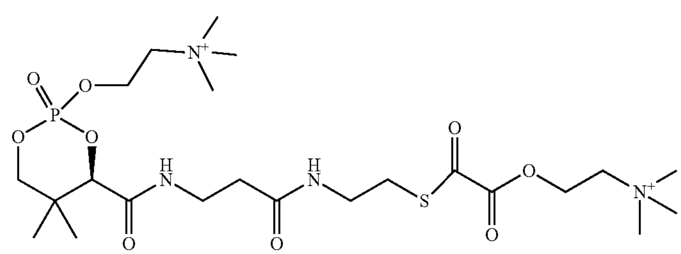 |
| 139 | 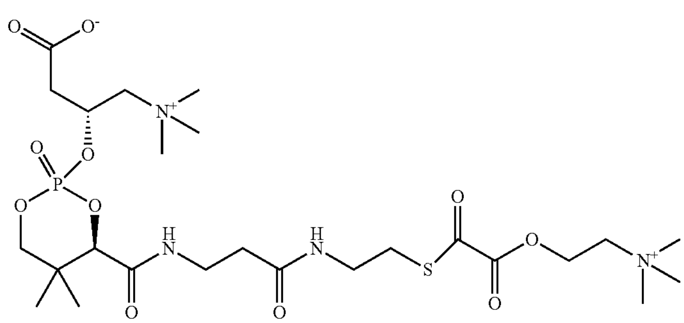 |

TABLE 1-continued

| Compound No. | Structure |
|---|---|
| 140 | 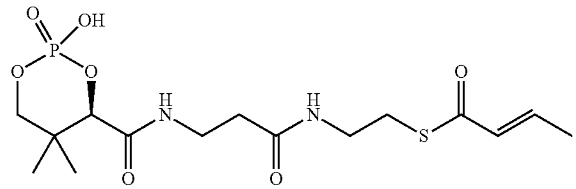 |
| 141 | 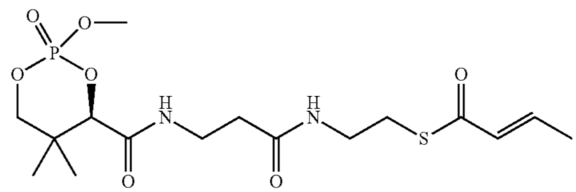 |
| 142 | 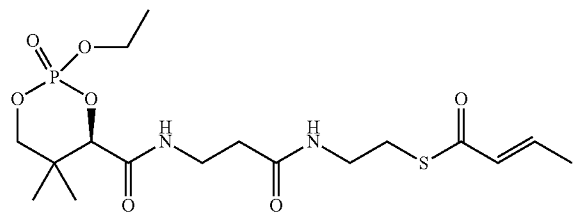 |
| 143 | 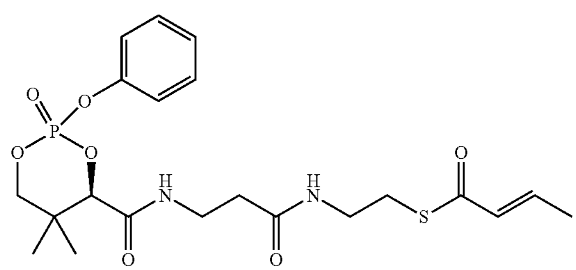 |
| 144 | 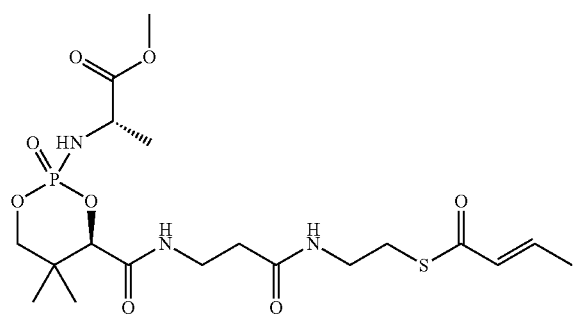 |
| 145 | 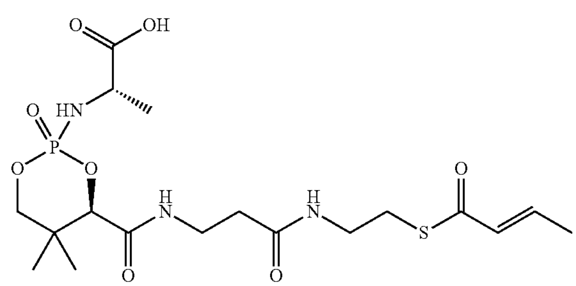 |

TABLE 1-continued
| Compound No. | Structure |
|---|---|
| 146 | 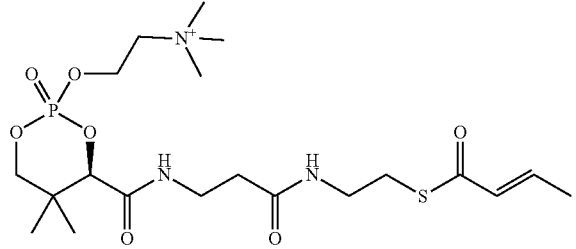 |
| 147 | 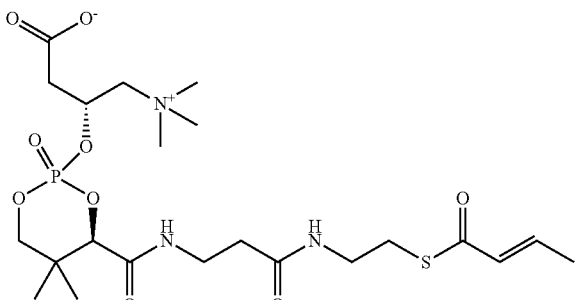 |
| 148 | 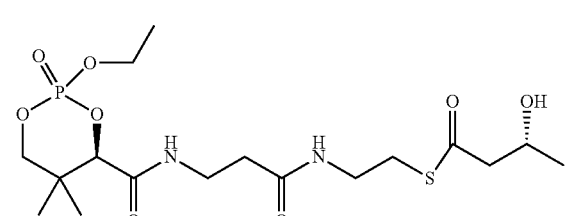 |
| 149 | 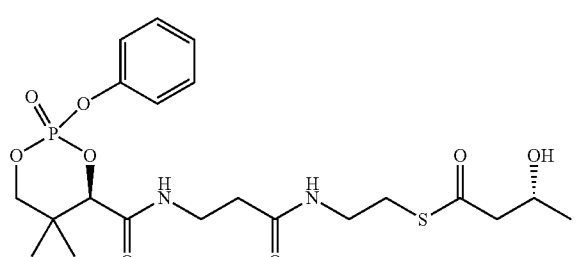 |
| 150 | 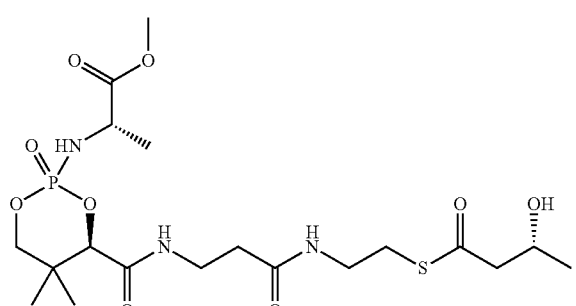 |

TABLE 1-continued
| Compound No. | Structure |
|---|---|
| 151 | 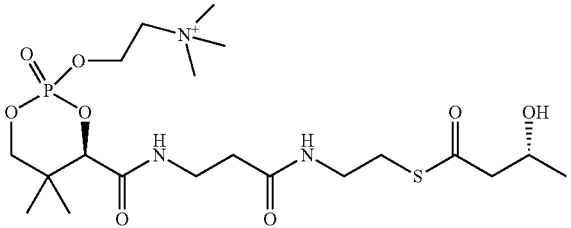 |
| 152 | 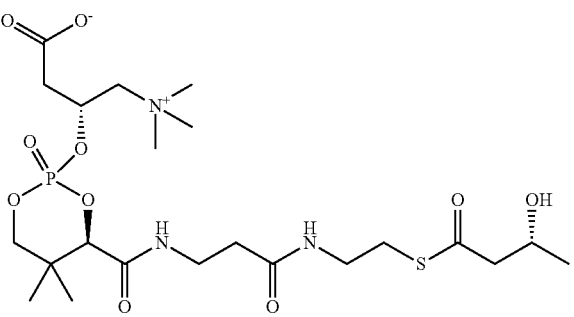 |
| 153 | 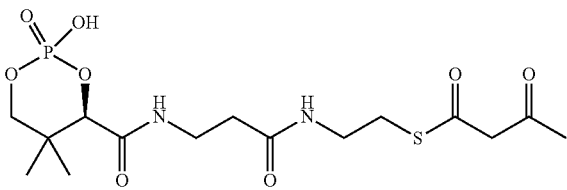 |
| 154 | 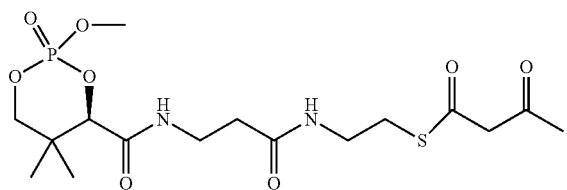 |
| 155 | 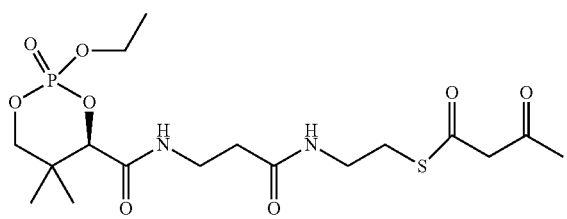 |
| 156 | 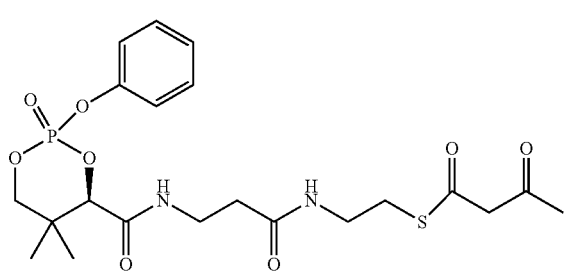 |

TABLE 1-continued
| Compound No. | Structure |
|---|---|
| 157 | 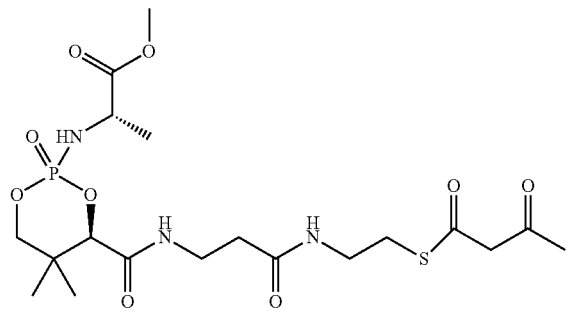 |
| 158 | 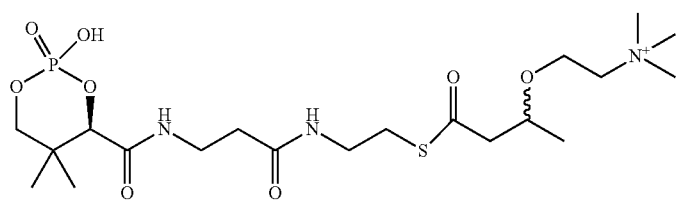 |
| 159 | 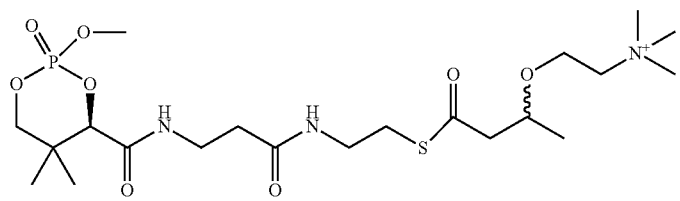 |
| 160 | 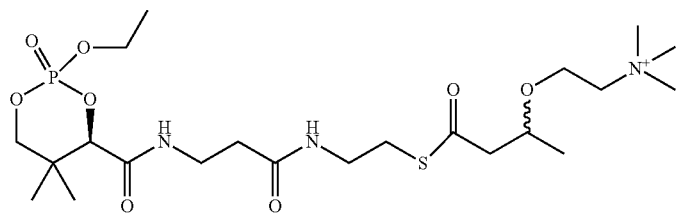 |
| 161 | 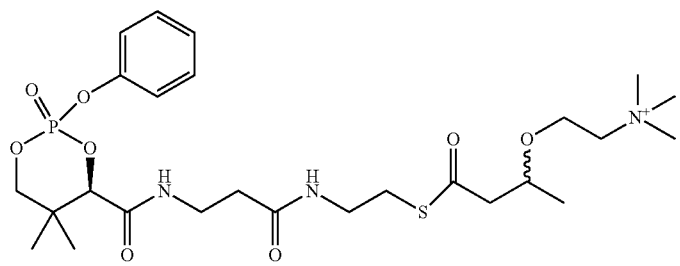 |
| 162 | 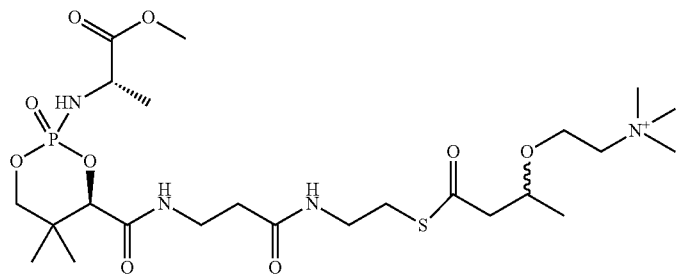 |

TABLE 1-continued
| Compound No. | Structure |
|---|---|
| 163 | 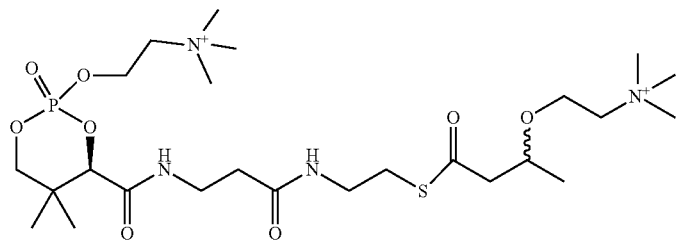 |
| 164 | 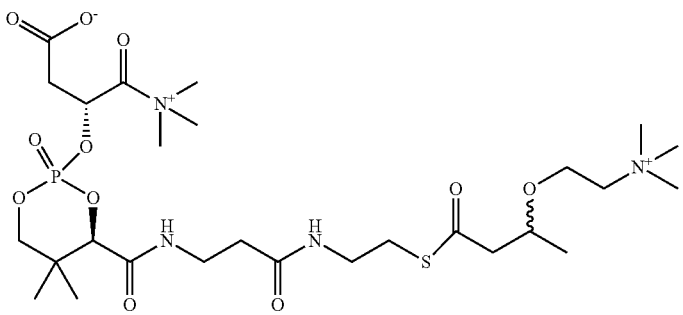 |
| 165 | 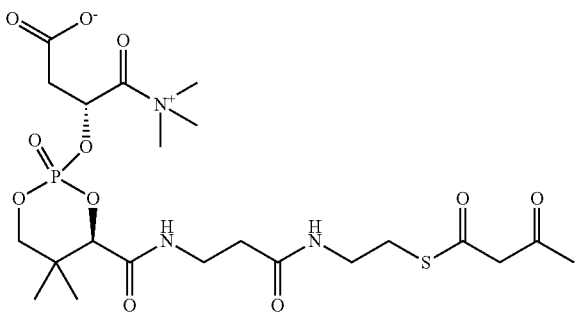 |
| 166 | 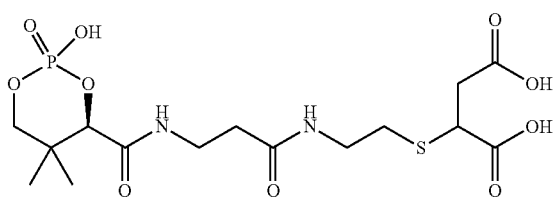 |
| 167 | 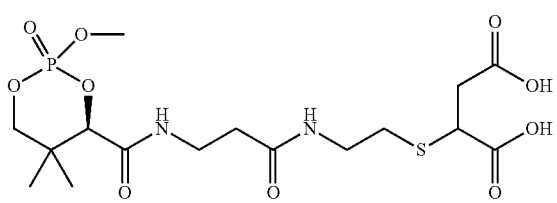 |
| 168 | 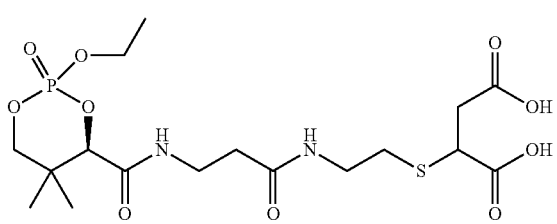 |

TABLE 1-continued
| Compound No. | Structure |
|---|---|
| 169 | 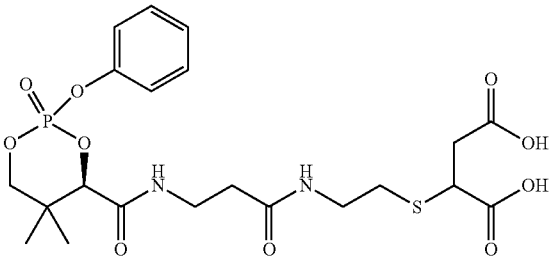 |
| 170 | 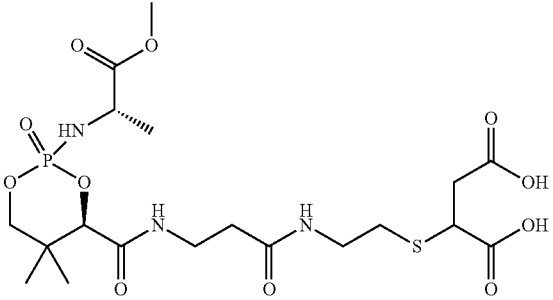 |
| 171 | 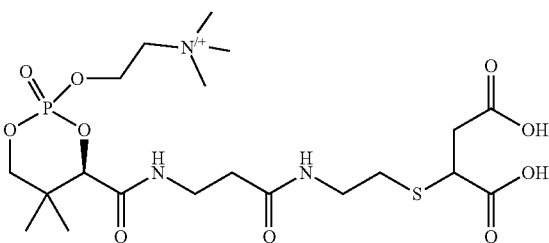 |
| 172 | 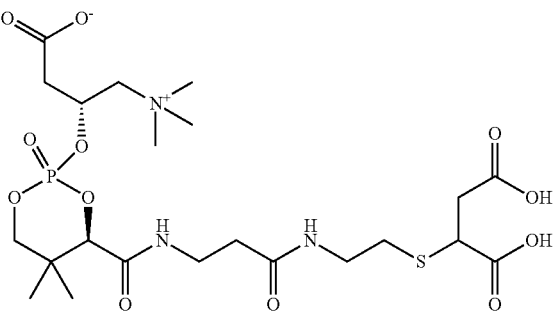 |
| 173 | 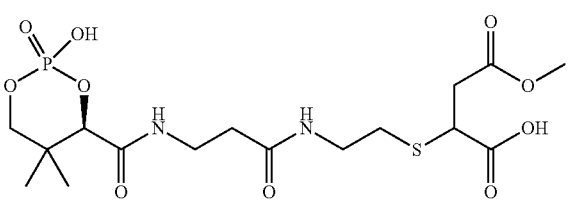 |
| 174 | 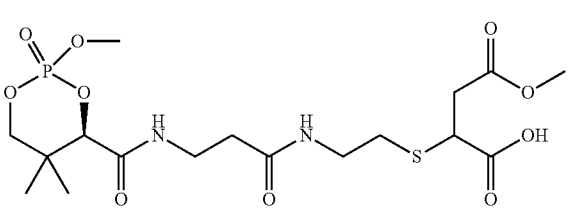 |

TABLE 1-continued

| Compound No. | Structure |
|---|---|
| 175 | 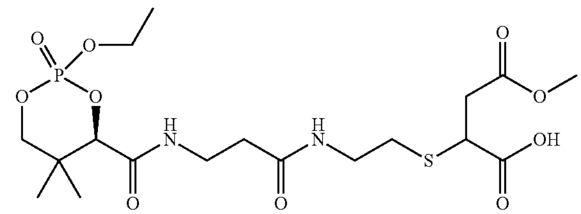 |
| 176 | 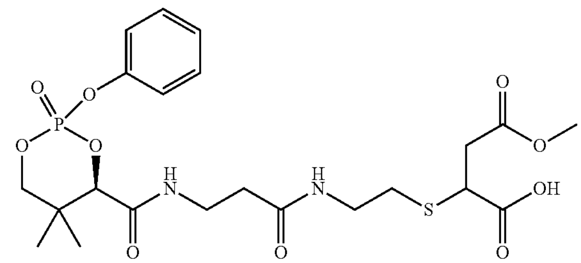 |
| 177 | 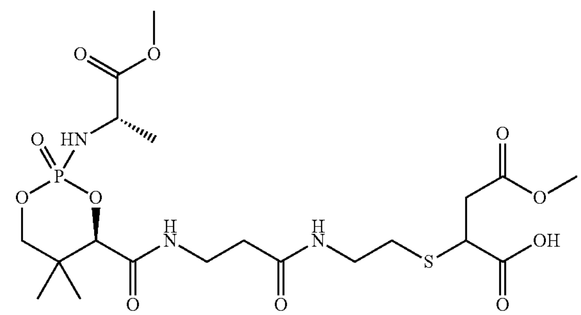 |
| 178 | 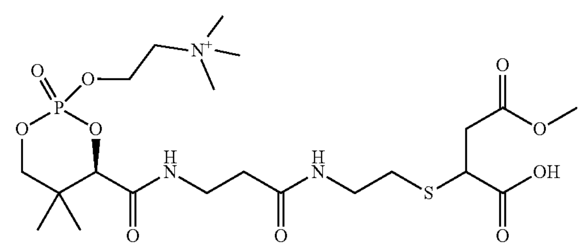 |
| 179 | 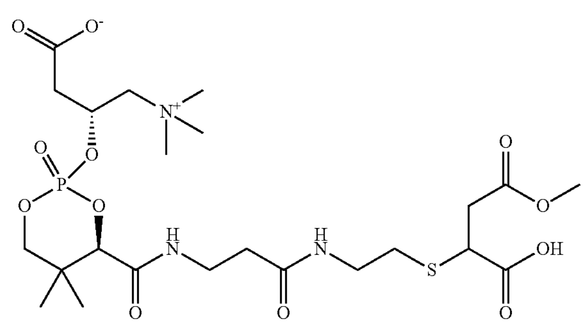 |
| 180 | 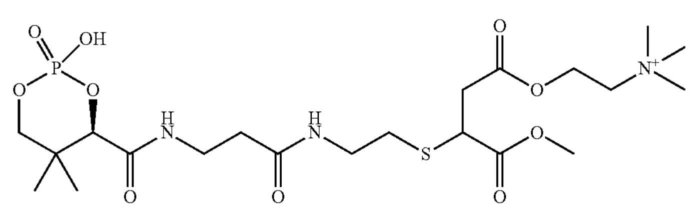 |

TABLE 1-continued
| Compound No. | Structure |
|---|---|
| 181 | 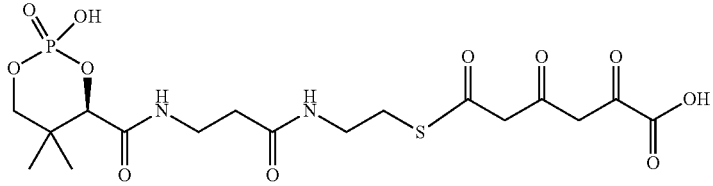 |
| 182 | 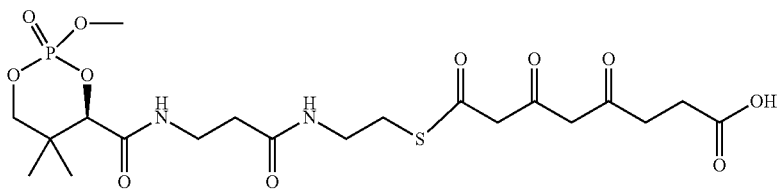 |
| 183 | 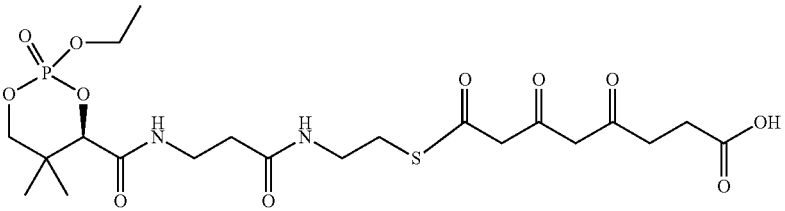 |
| 184 | 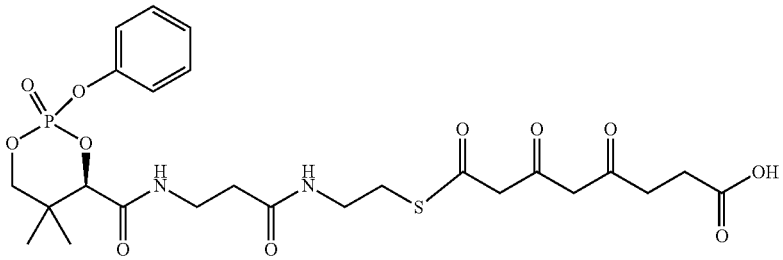 |
| 185 | 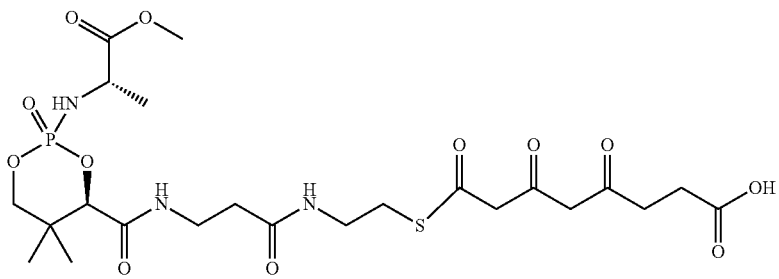 |
| 186 | 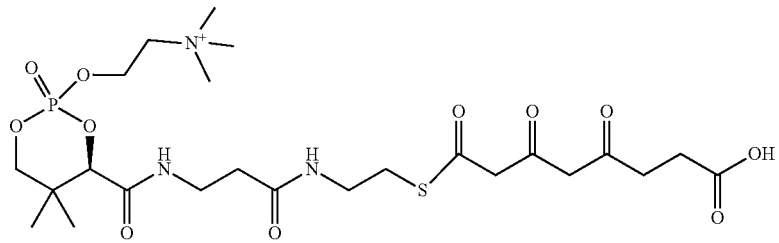 |

TABLE 1-continued

| Compound No. | Structure |
|---|---|
| 187 | 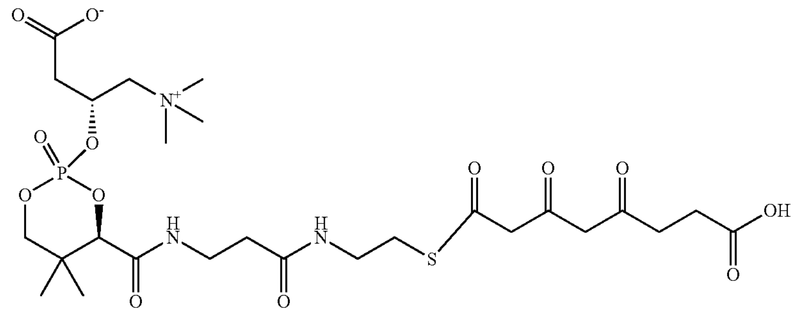 |
| 188 | 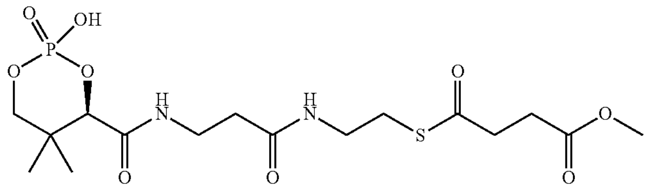 |
| 189 | 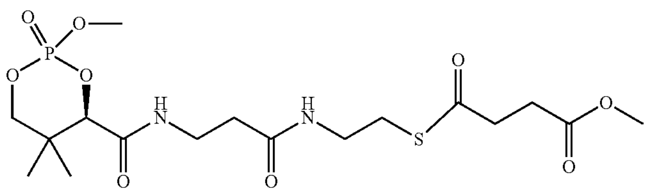 |
| 190 | 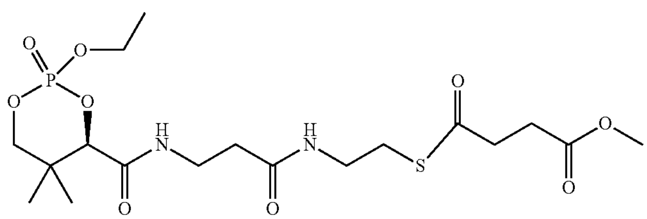 |
| 191 | 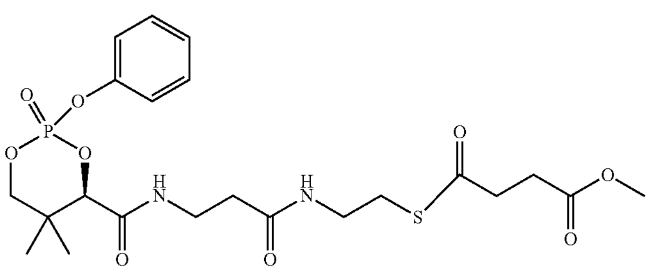 |
| 192 | 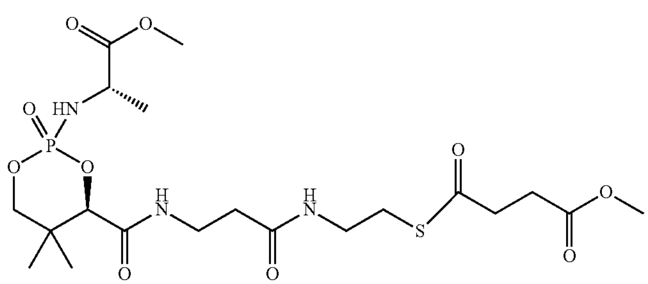 |

TABLE 1-continued

| Compound No. | Structure |
|---|---|
| 193 | 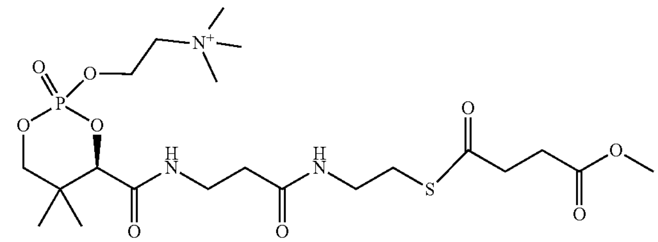 |
| 194 | 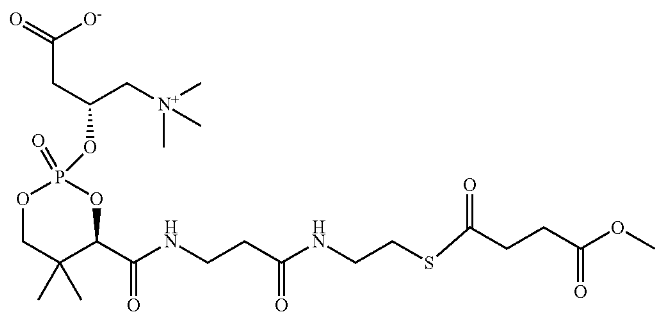 |
| 195 | 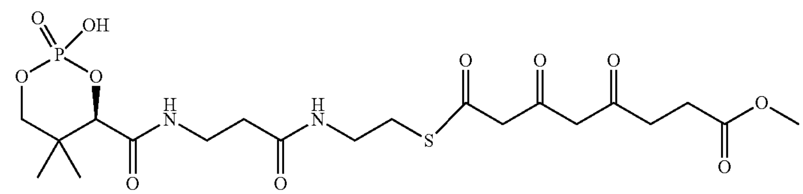 |
| 196 | 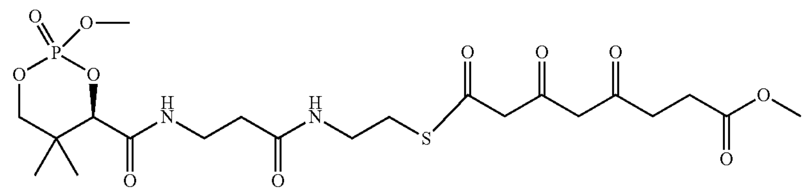 |
| 197 | 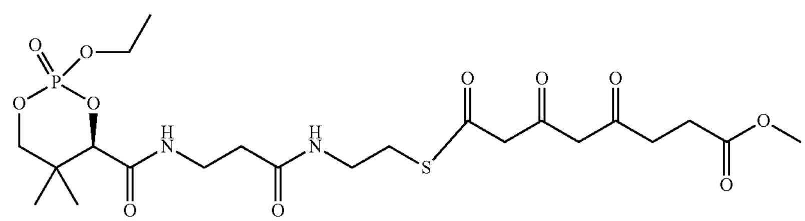 |
| 198 | 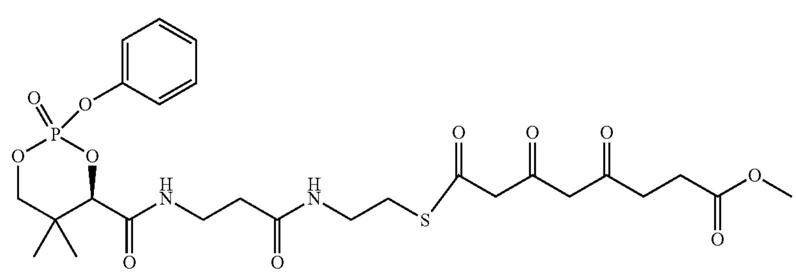 |

TABLE 1-continued
| Compound No. | Structure |
|---|---|
| 199 | 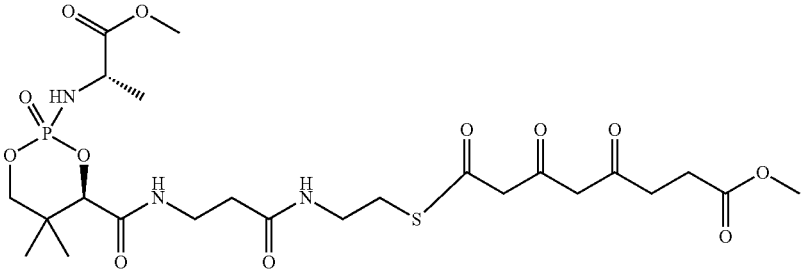 |
| 200 | 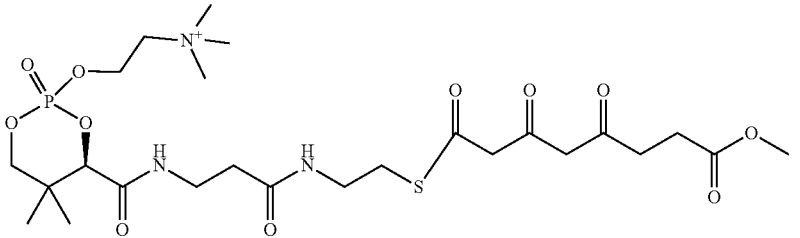 |
| 201 | 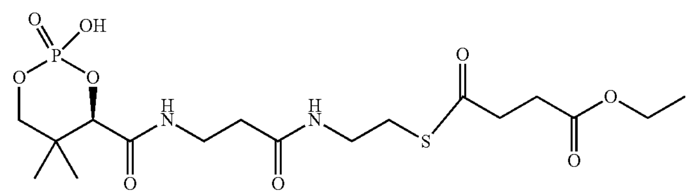 |
| 202 | 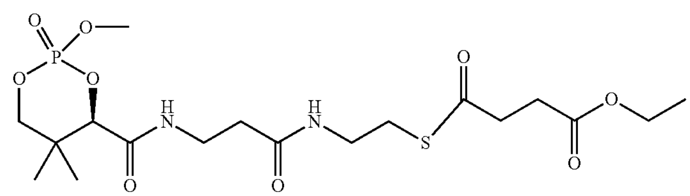 |
| 203 | 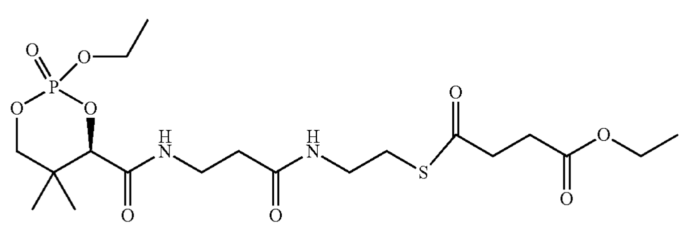 |
| 204 | 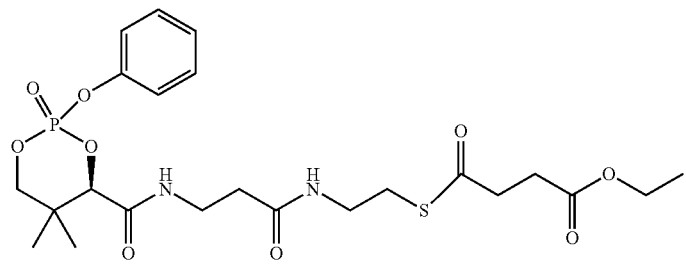 |

TABLE 1-continued

| Compound No. | Structure |
|---|---|
| 205 | (structure) |
| 206 | (structure) |
| 207 | (structure) |
| 208 | (structure) |
| 209 | (structure) |
| 210 | (structure) |

TABLE 1-continued

| Compound No. | Structure |
|---|---|
| 211 | 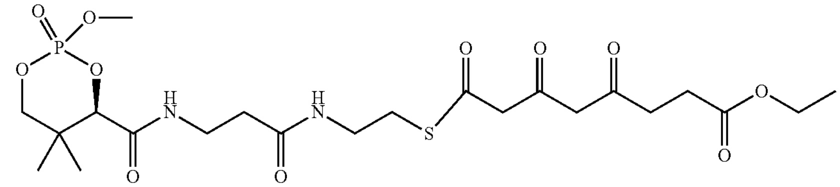 |
| 212 | 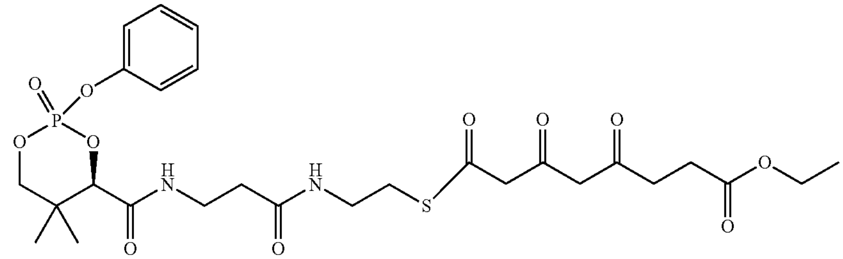 |
| 213 | 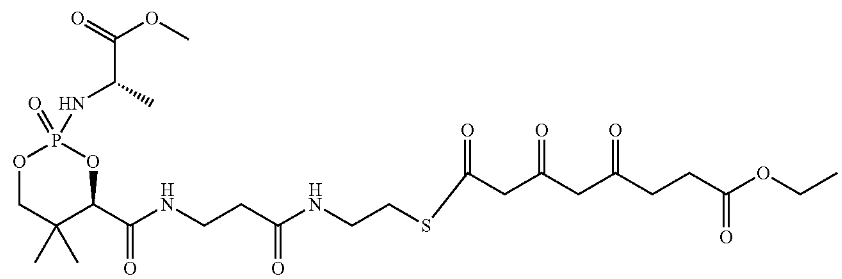 |
| 214 | 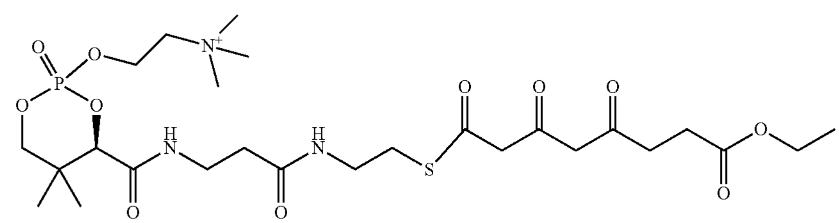 |
| 215 | 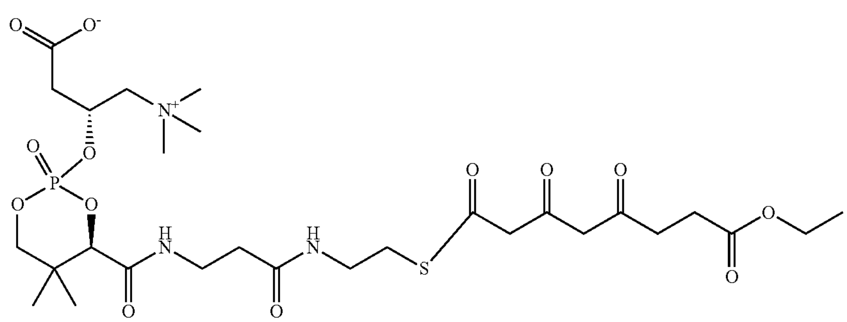 |
| 216 | 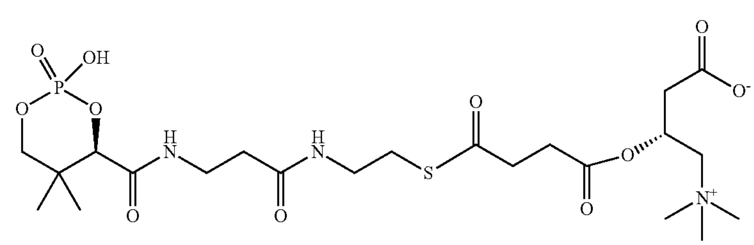 |

TABLE 1-continued
| Compound No. | Structure |
|---|---|
| 217 | 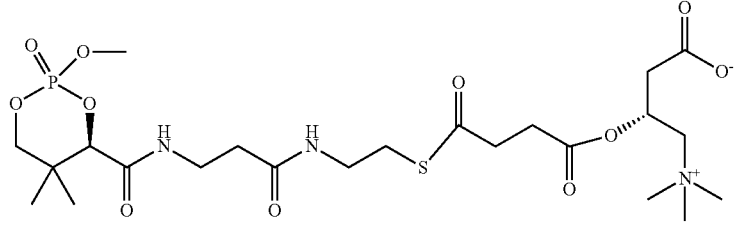 |
| 218 | 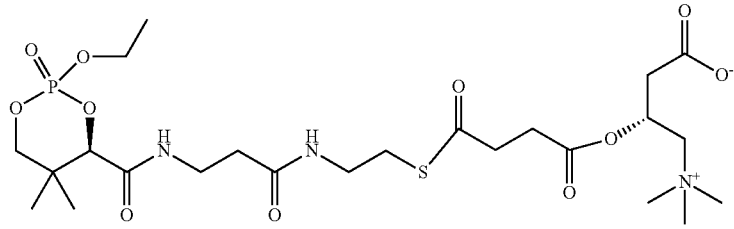 |
| 219 | 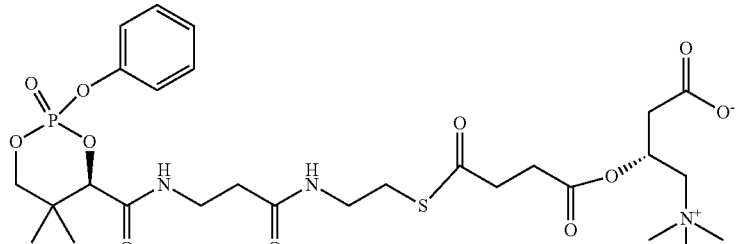 |
| 220 | 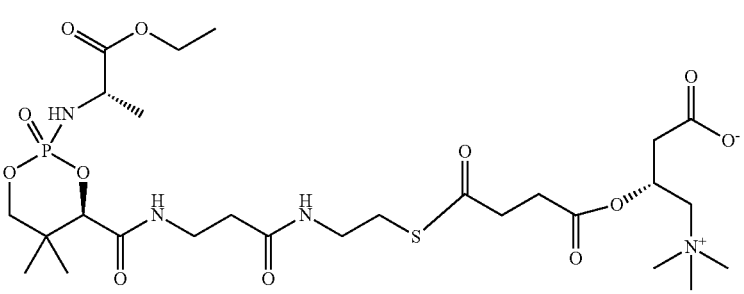 |
| 221 | 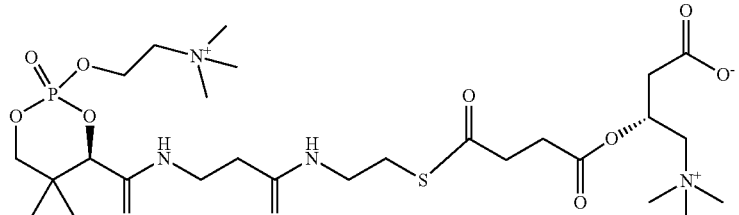 |
| 222 | 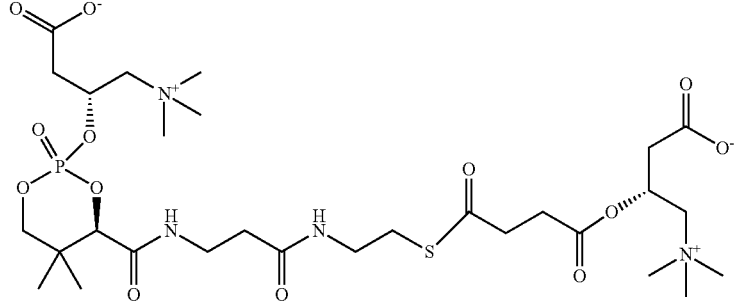 |

TABLE 1-continued
| Compound No. | Structure |
|---|---|
| 223 | 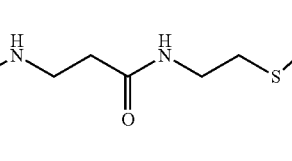 |
| 224 | 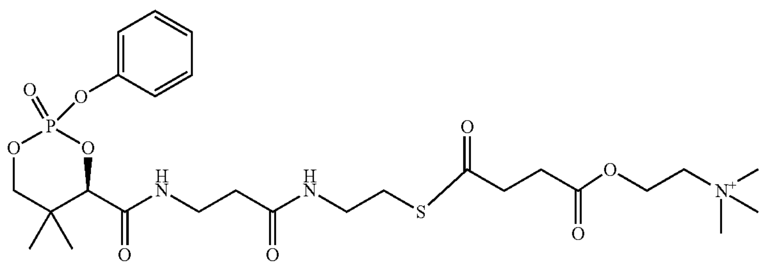 |
| 225 | 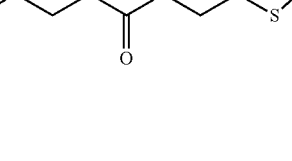 |
| 226 | 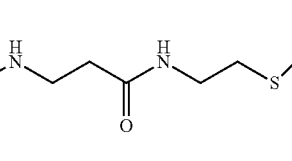 |
| 227 | 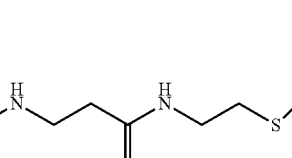 |
| 228 | 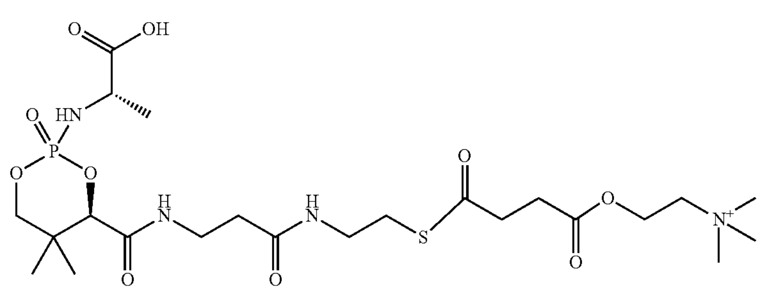 |

TABLE 1-continued

| Compound No. | Structure |
|---|---|
| 229 | 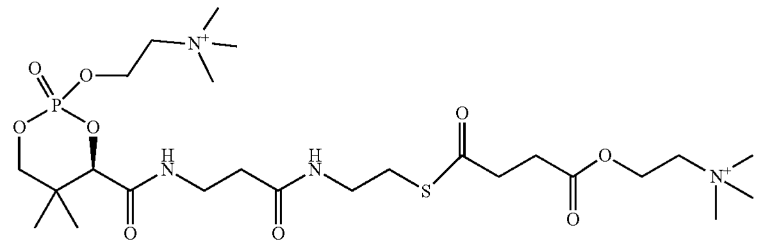 |
| 230 | 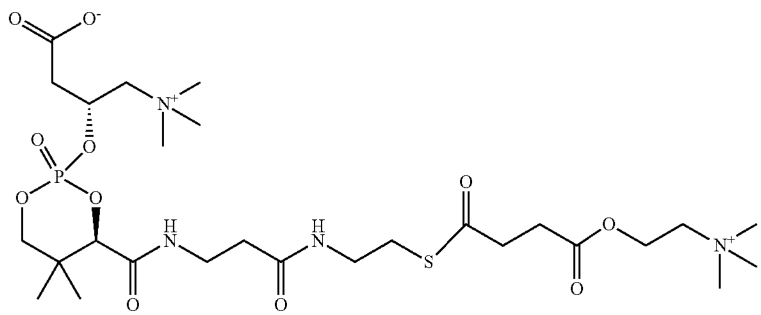 |
| 231 | 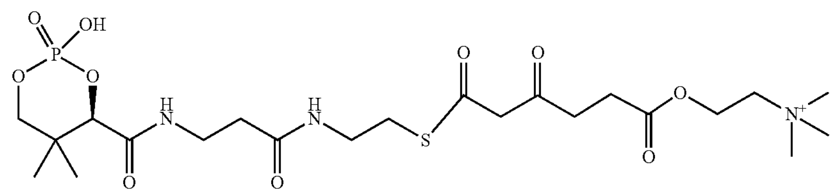 |
| 232 | 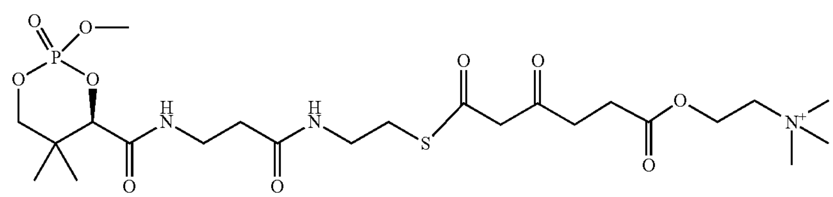 |
| 233 | 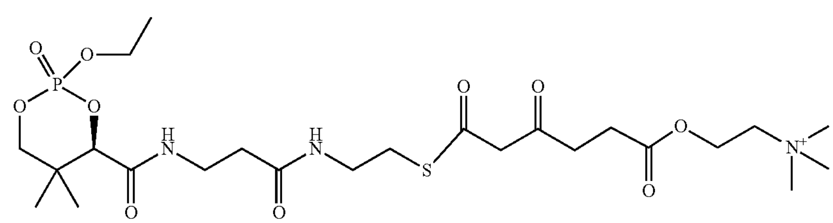 |
| 234 | 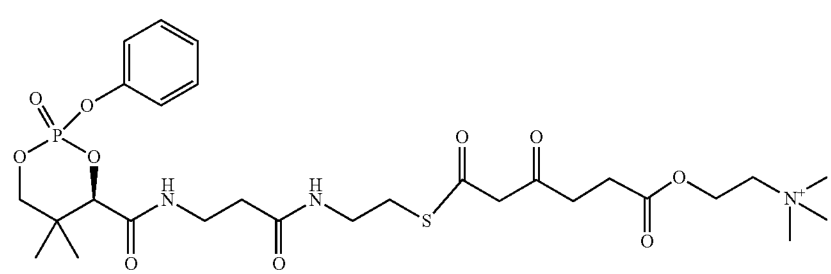 |

TABLE 1-continued
| Compound No. | Structure |
|---|---|
| 235 | 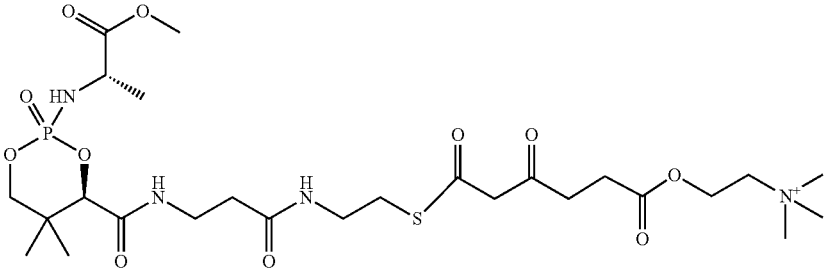 |
| 236 | 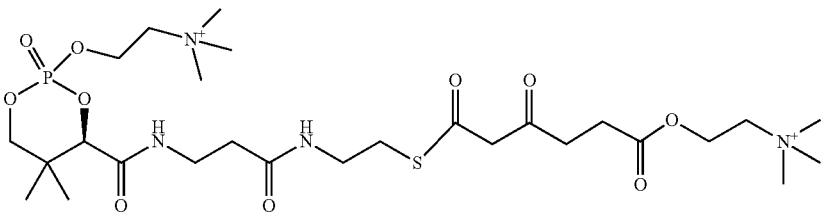 |
| 237 | 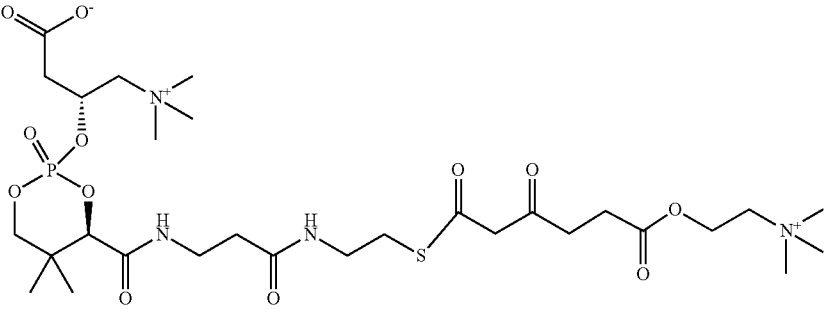 |
| 238 | 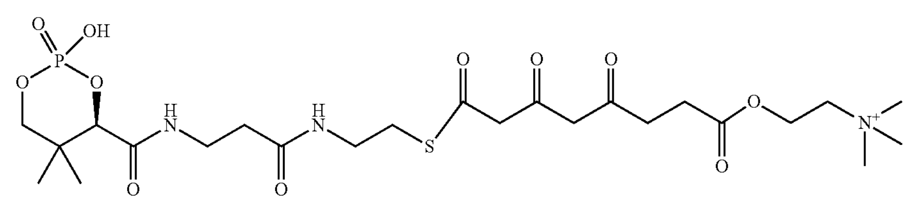 |
| 239 | 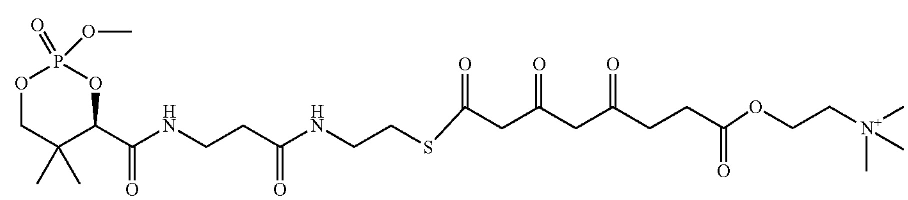 |
| 240 | 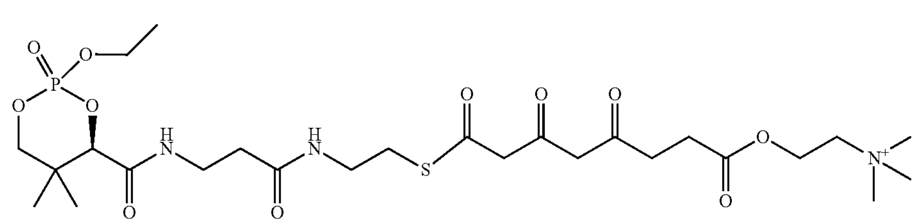 |

TABLE 1-continued
| Compound No. | Structure |
|---|---|
| 241 | 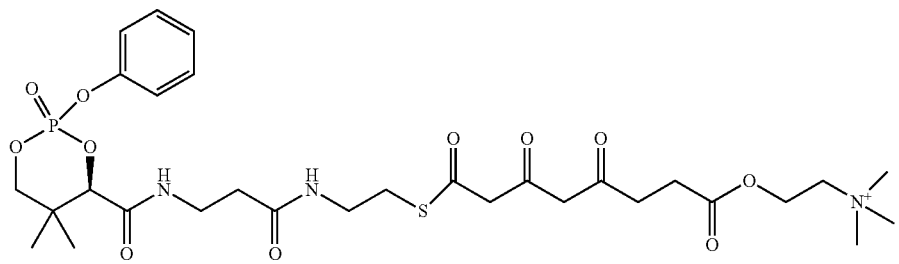 |
| 242 | 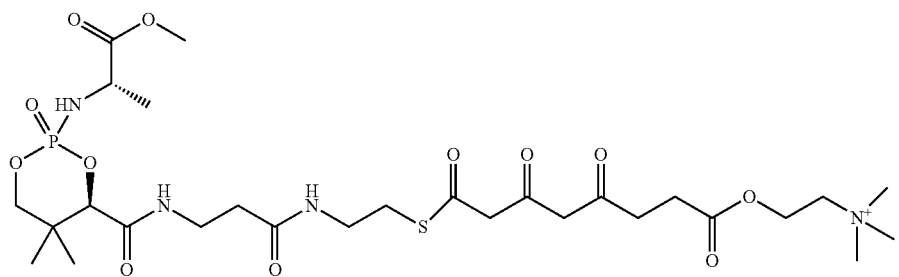 |
| 243 | 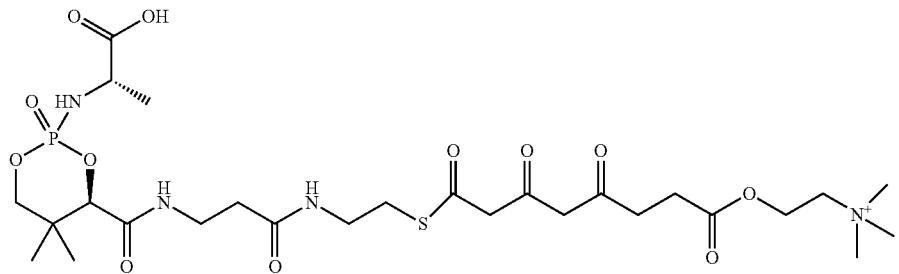 |
| 244 | 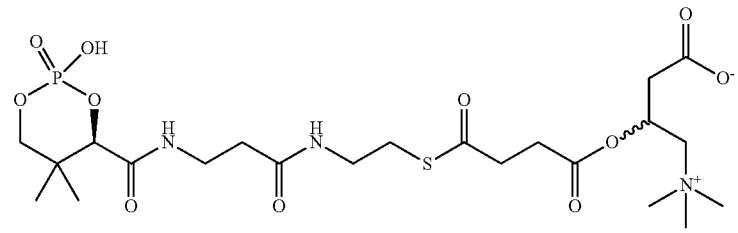 |
| 245 | 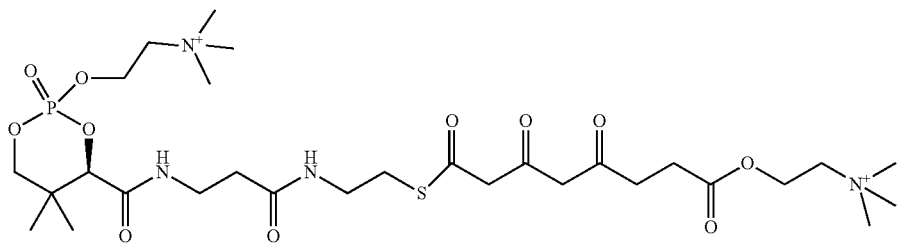 |

TABLE 1-continued

| Compound No. | Structure |
| --- | --- |
| 246 | 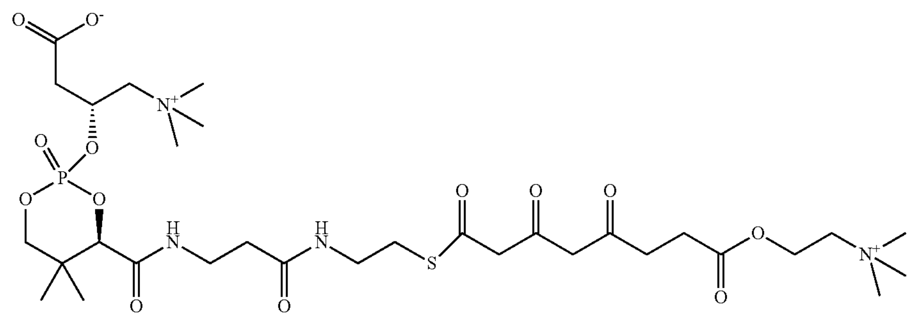 |
| 247 | 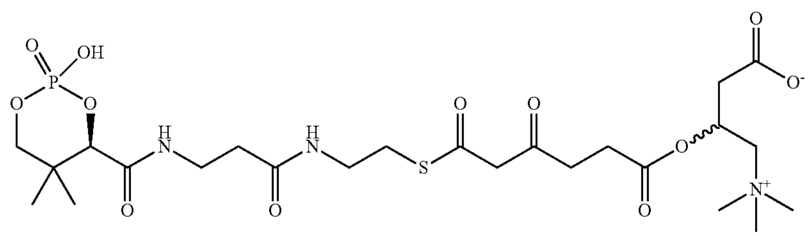 |
| 248 | 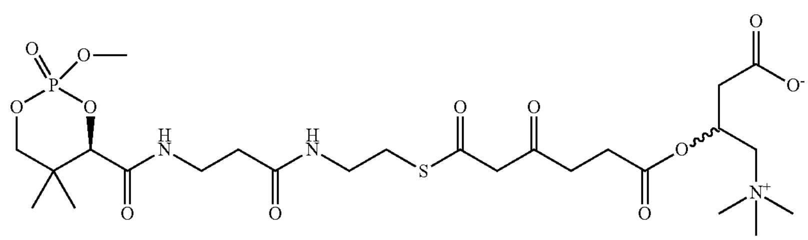 |
| 249 | 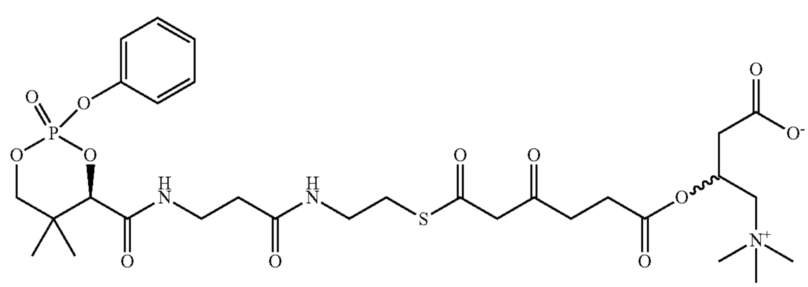 |
| 250 | 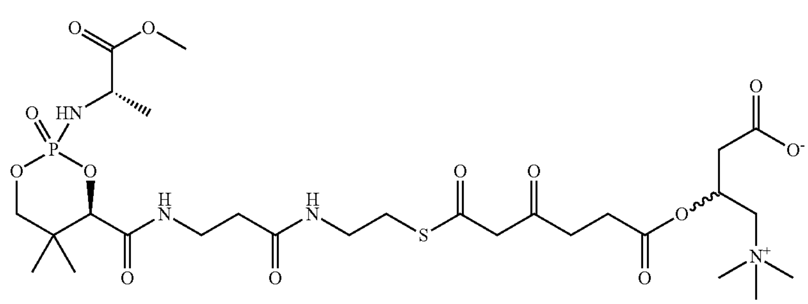 |

TABLE 1-continued

| Compound No. | Structure |
|---|---|
| 251 | (structure) |
| 252 | (structure) |
| 253 | (structure) |
| 254 | (structure) |
| 255 | (structure) |
| 256 | (structure) |

TABLE 1-continued

| Compound No. | Structure |
|---|---|
| 257 | 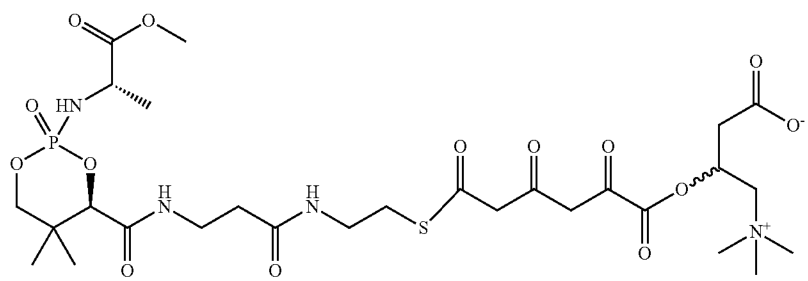 |
| 258 | 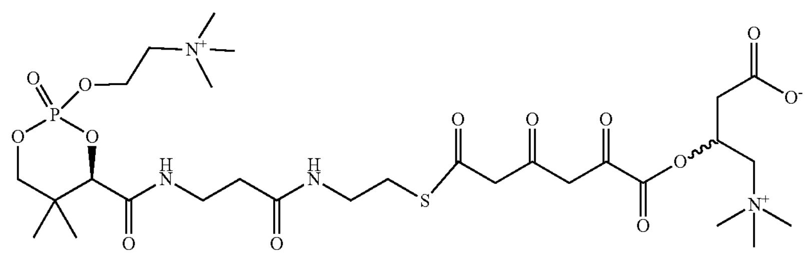 |
| 259 | 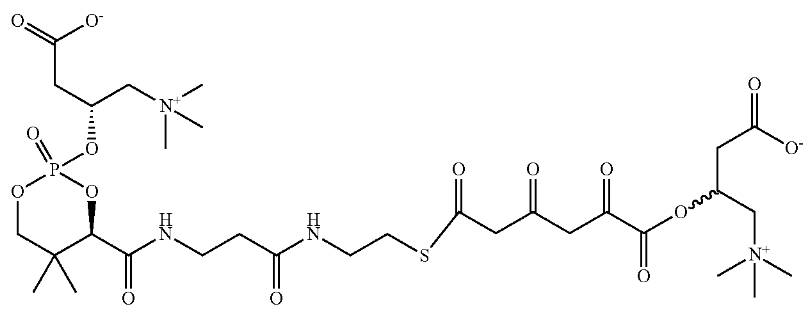 |
| 260 | 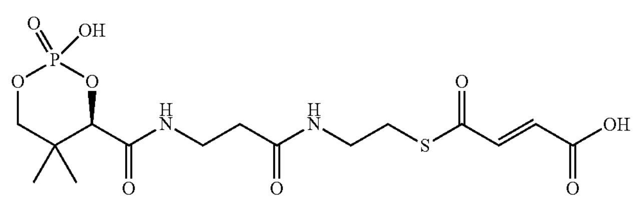 |
| 261 | 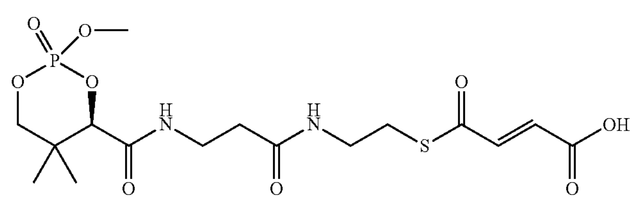 |
| 262 | 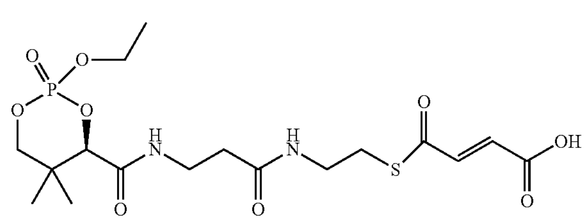 |

TABLE 1-continued
| Compound No. | Structure |
|---|---|
| 263 | 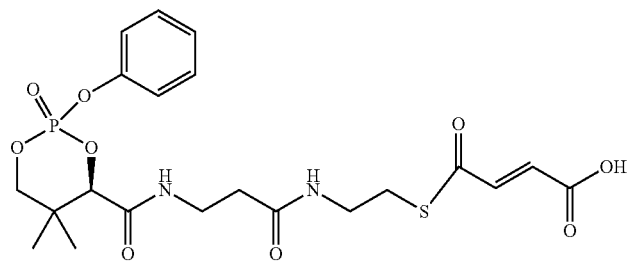 |
| 264 | 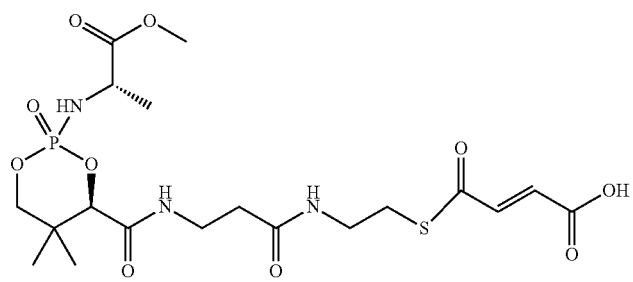 |
| 265 | 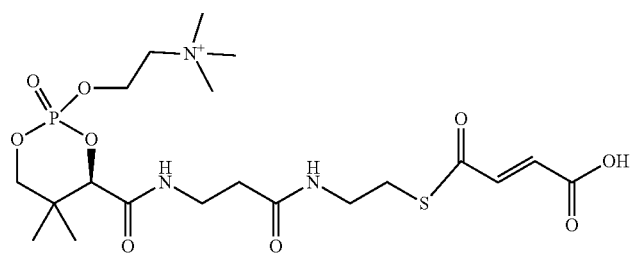 |
| 266 | 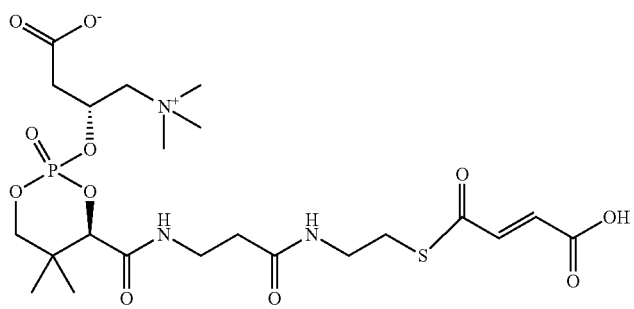 |
| 267 | 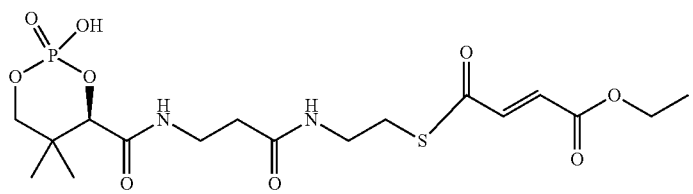 |
| 268 | 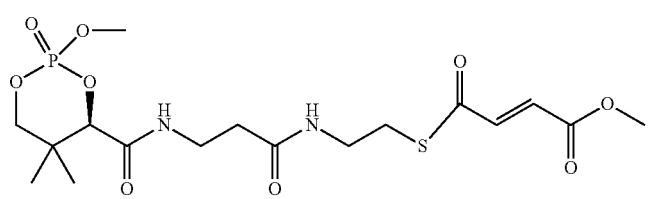 |

TABLE 1-continued

| Compound No. | Structure |
|---|---|
| 269 | 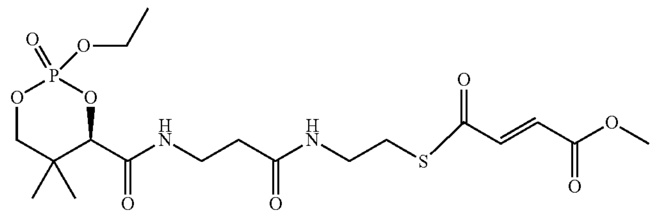 |
| 270 | 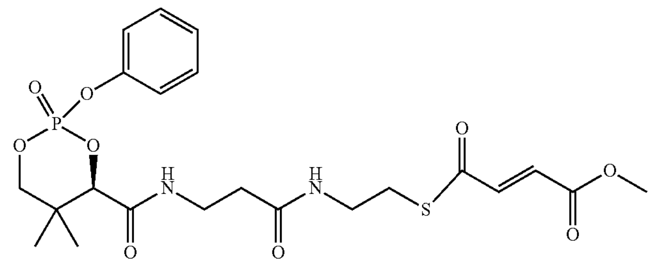 |
| 271 | 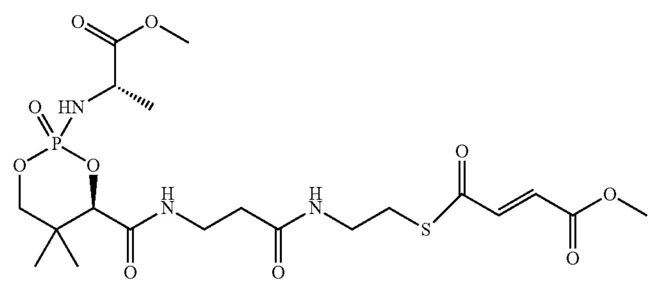 |
| 272 | 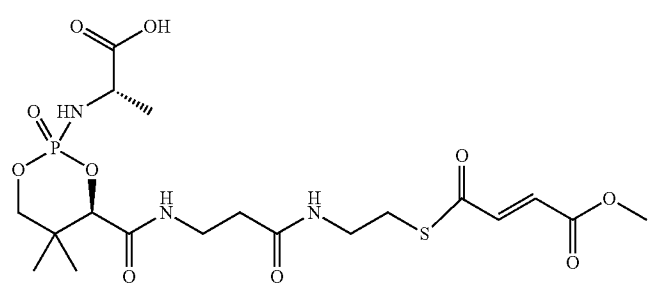 |
| 273 | 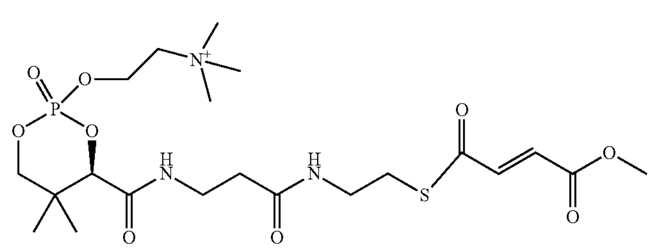 |

TABLE 1-continued
| Compound No. | Structure |
|---|---|
| 274 | 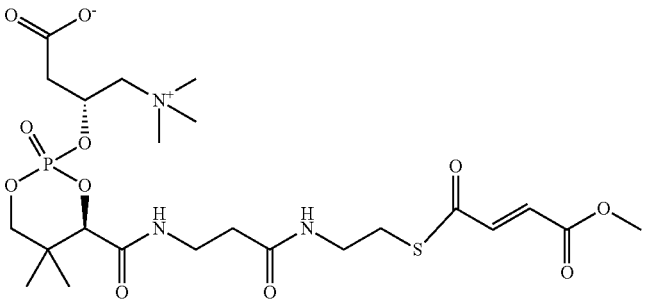 |
| 275 | 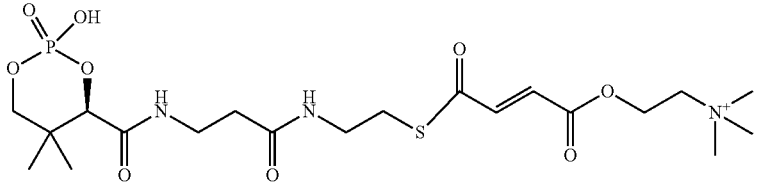 |
| 276 | 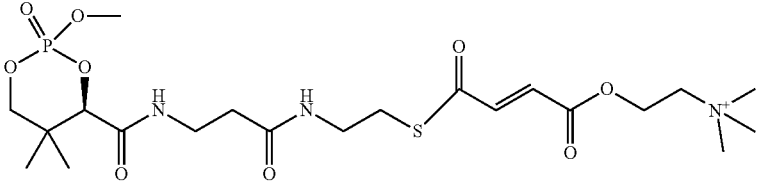 |
| 277 | 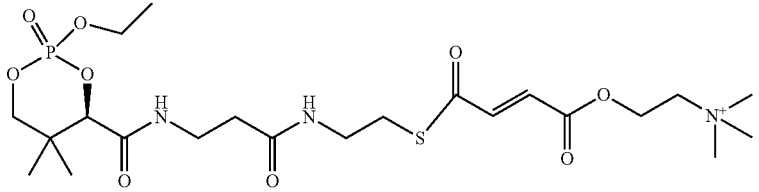 |
| 278 | 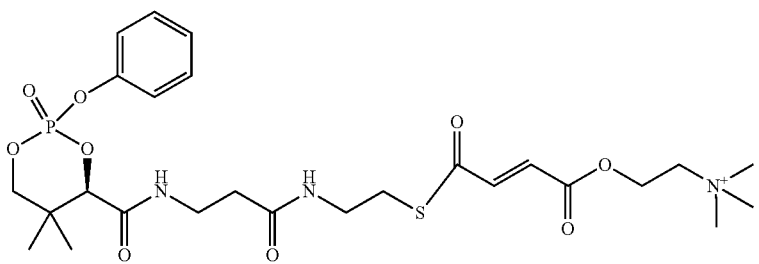 |
| 279 | 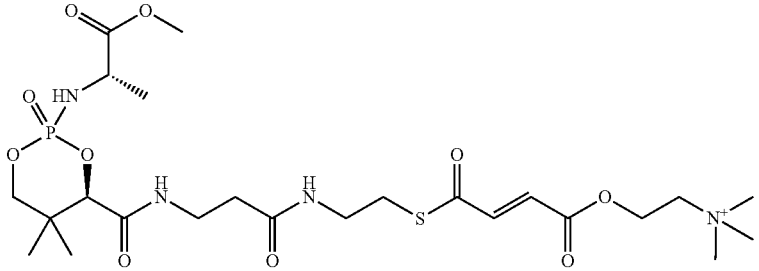 |

TABLE 1-continued

| Compound No. | Structure |
|---|---|
| 280 | 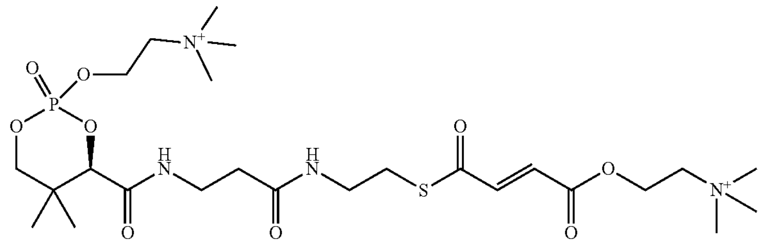 |
| 281 | 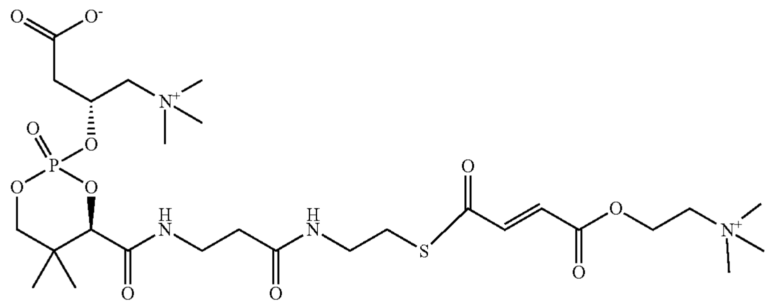 |
| 282 | 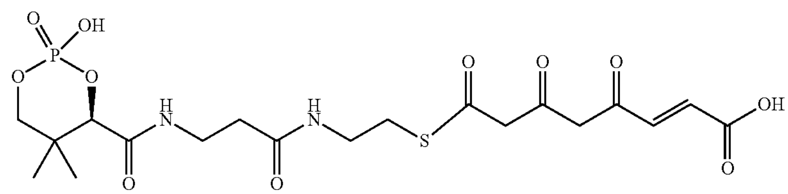 |
| 283 | 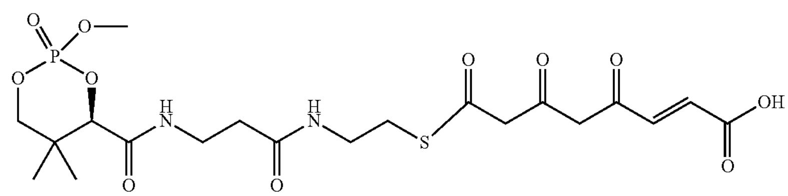 |
| 284 | 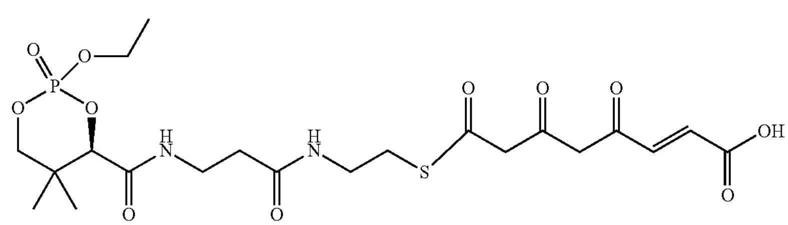 |
| 285 | 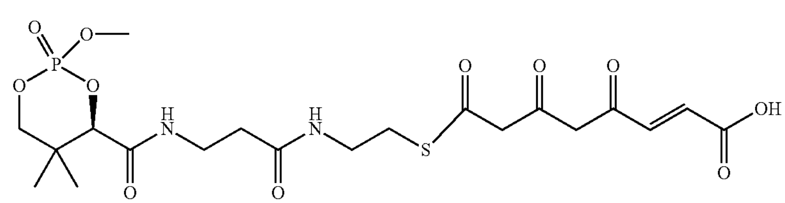 |

TABLE 1-continued
| Compound No. | Structure |
|---|---|
| 286 | 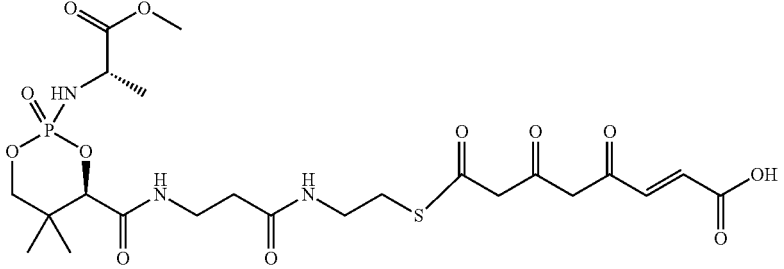 |
| 287 | 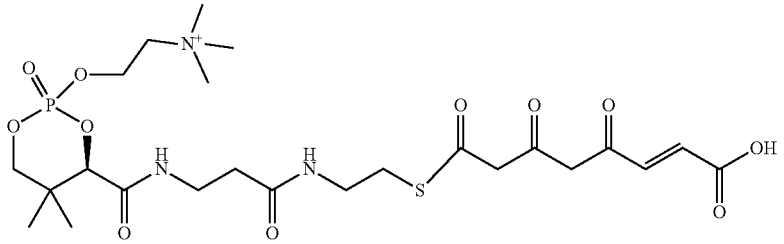 |
| 288 | 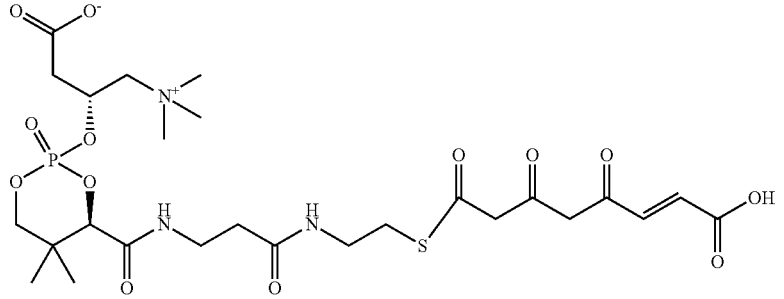 |
| 289 | 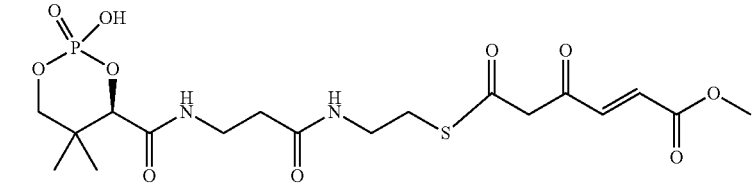 |
| 290 | 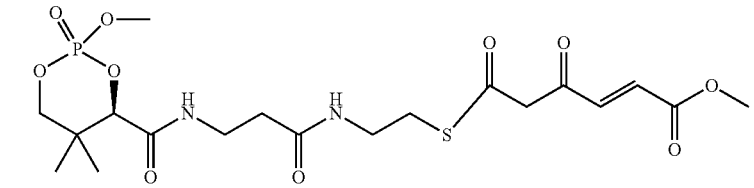 |
| 291 | 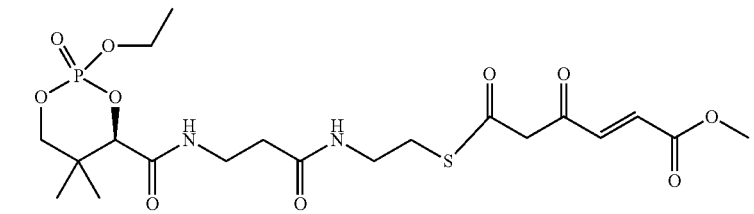 |

TABLE 1-continued
| Compound No. | Structure |
|---|---|
| 292 | 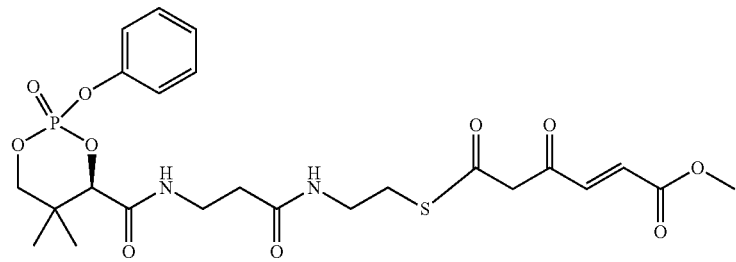 |
| 293 | 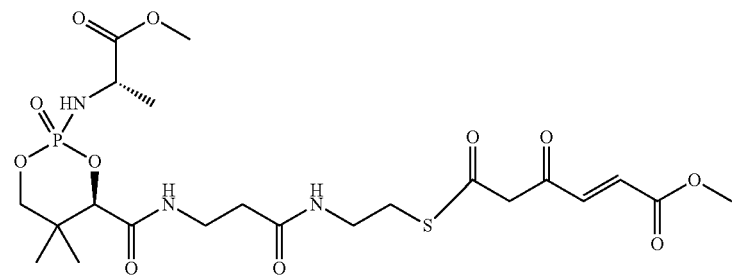 |
| 294 | 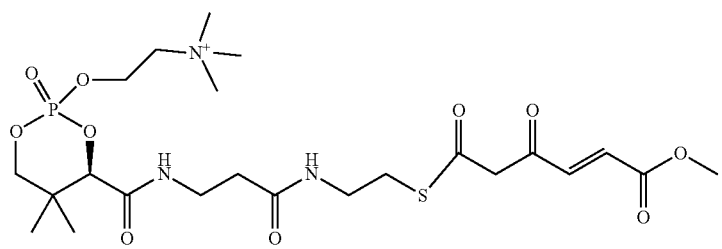 |
| 295 | 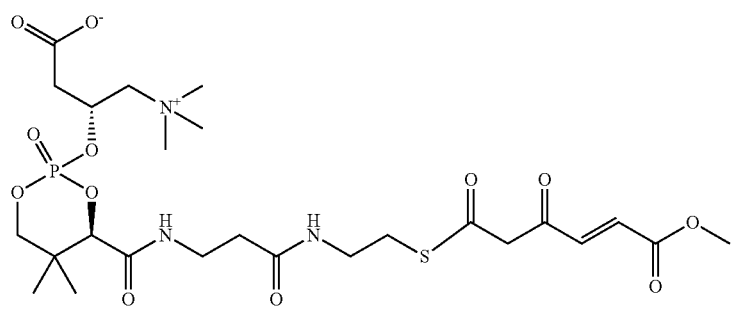 |
| 296 | 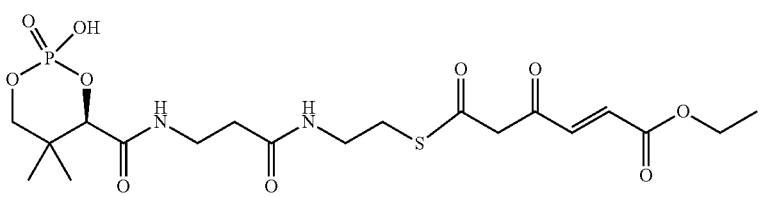 |
| 297 | 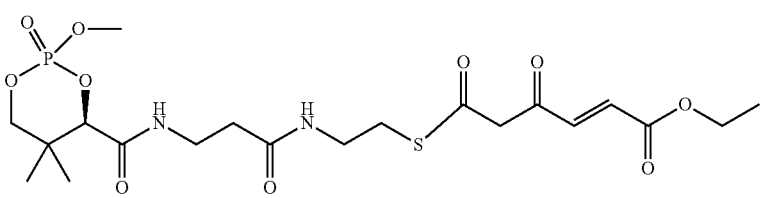 |

TABLE 1-continued
| Compound No. | Structure |
|---|---|
| 298 | 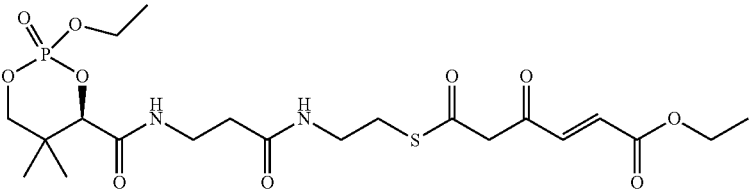 |
| 299 | 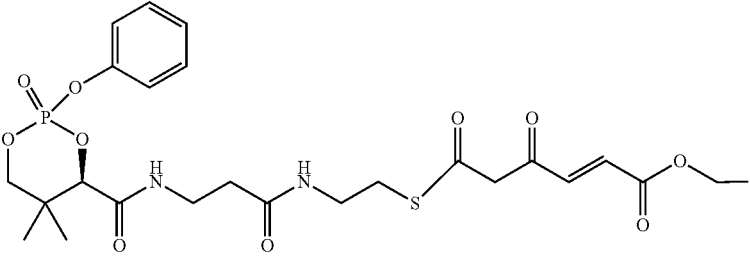 |
| 300 | 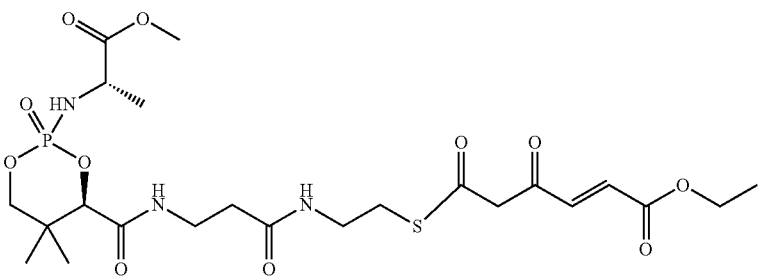 |
| 301 | 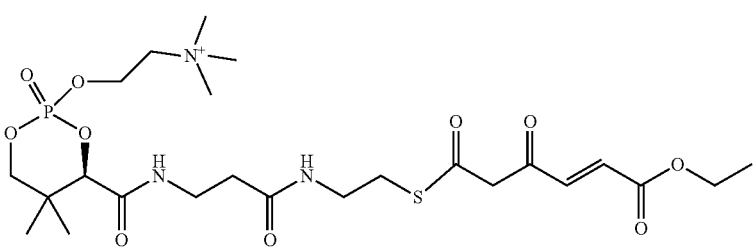 |
| 302 | 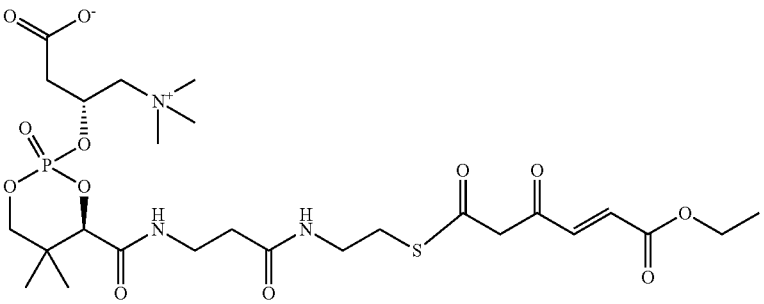 |
| 303 | 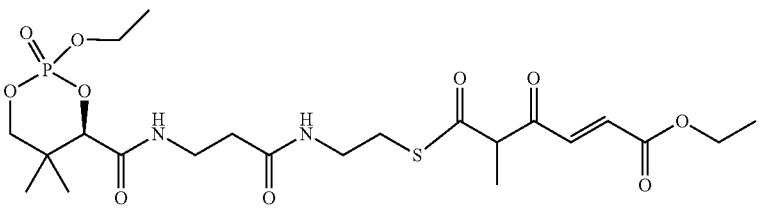 |

TABLE 1-continued

| Compound No. | Structure |
|---|---|
| 304 | 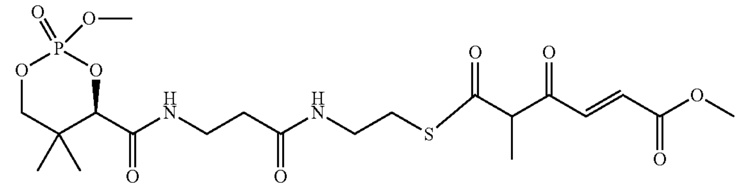 |
| 305 | 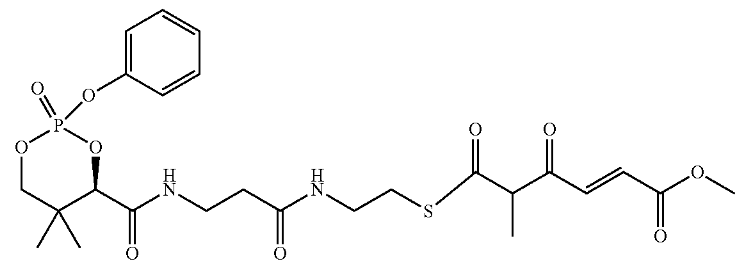 |
| 306 | 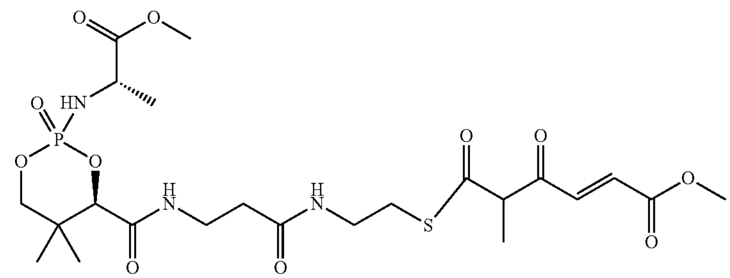 |
| 307 | |
| 308 | 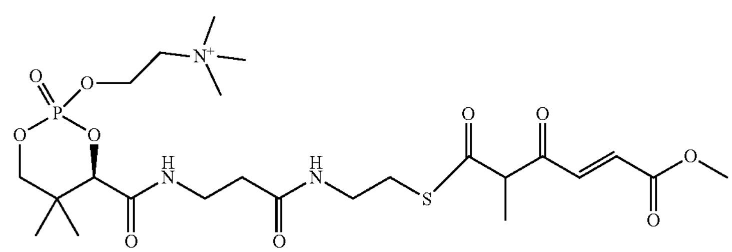 |
| 309 | 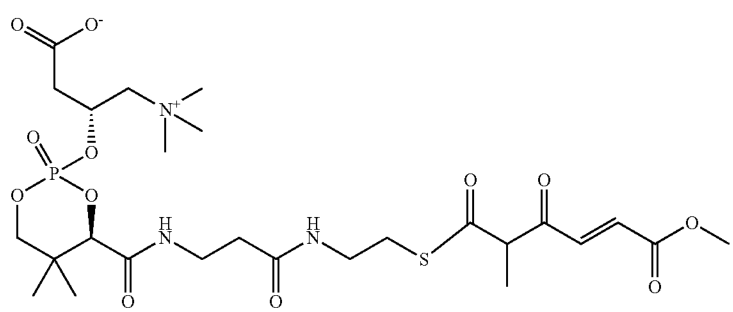 |
| 310 | 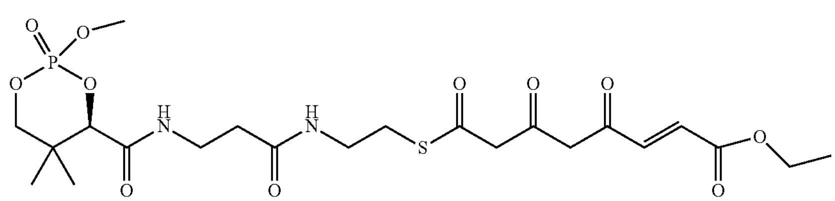 |

TABLE 1-continued

| Compound No. | Structure |
|---|---|
| 311 | 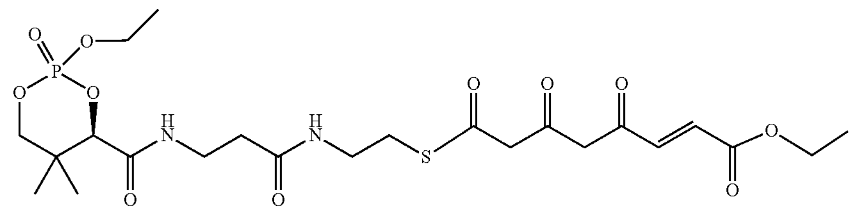 |
| 312 | 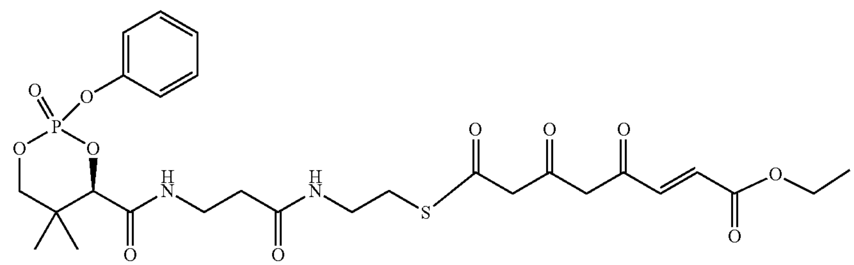 |
| 313 | 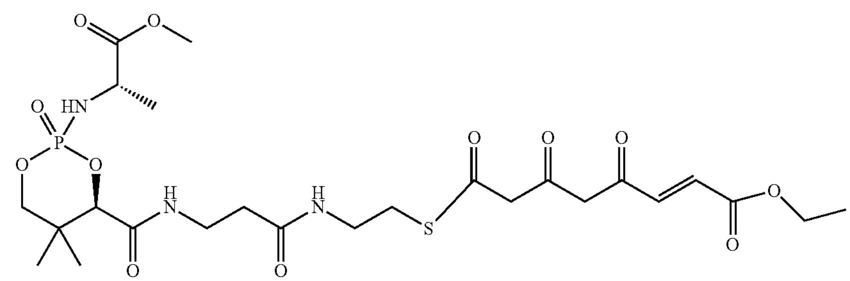 |
| 314 | 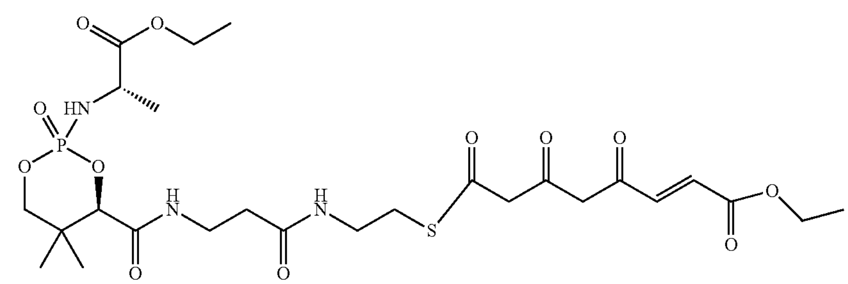 |
| 315 | 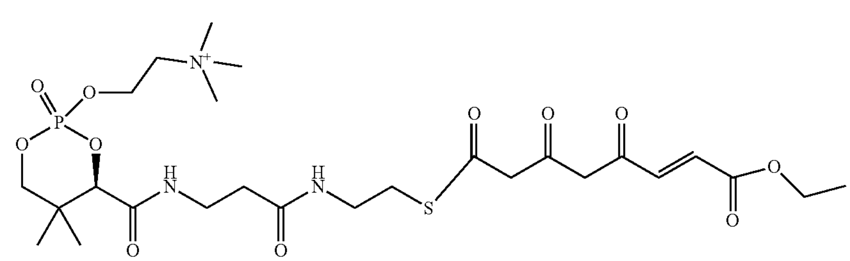 |

TABLE 1-continued

| Compound No. | Structure |
|---|---|
| 316 | 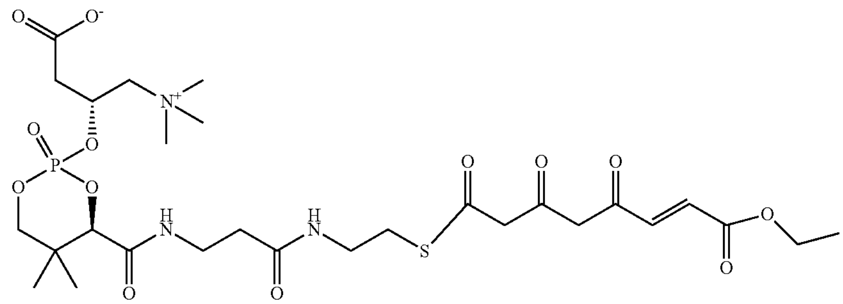 |
| 317 | 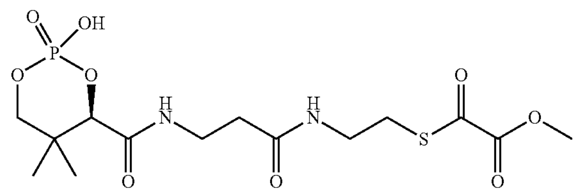 |
| 318 | 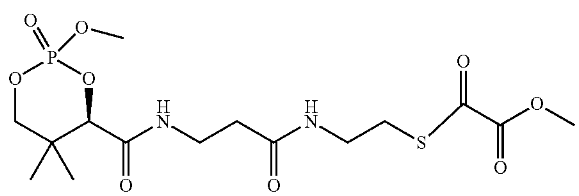 |
| 319 | 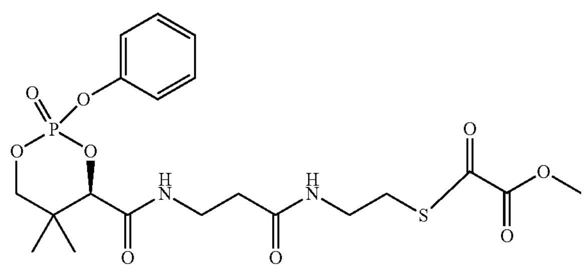 |
| 320 | 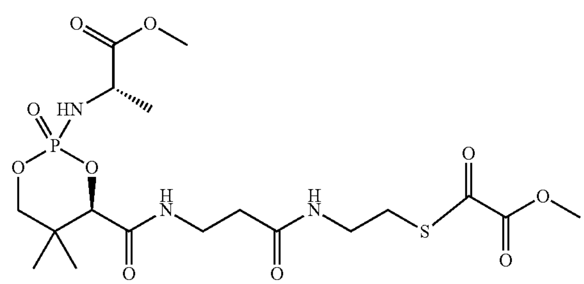 |
| 321 | 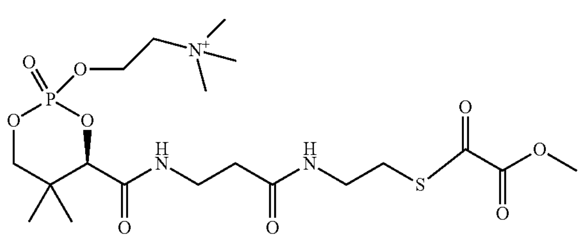 |

| Compound No. | Structure |
|---|---|
| 322 | 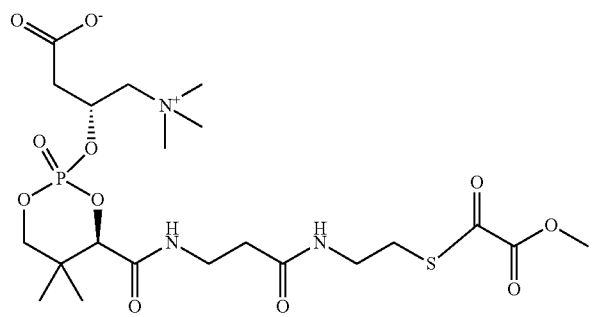 |
| 323 | 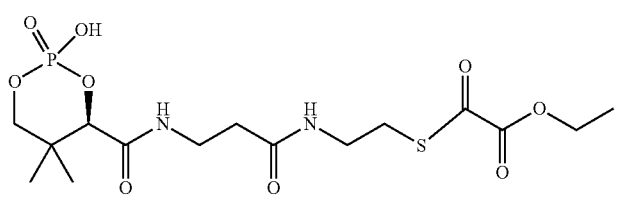 |
| 324 | 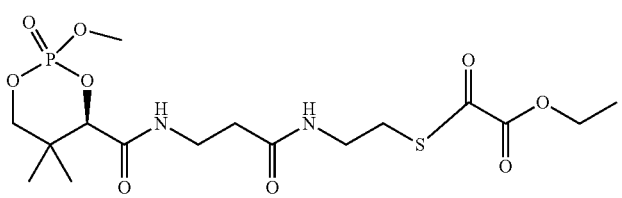 |
| 325 | 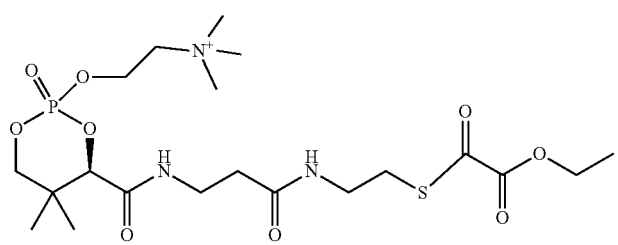 |
| 326 | 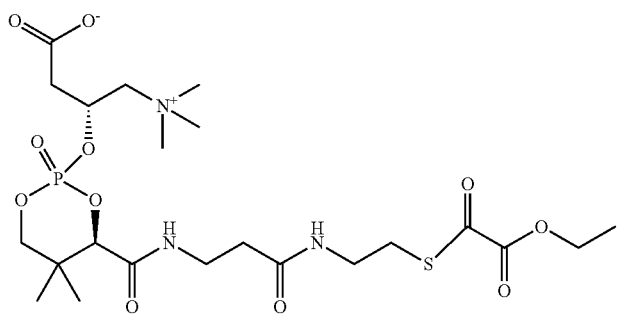 |
| 327 | 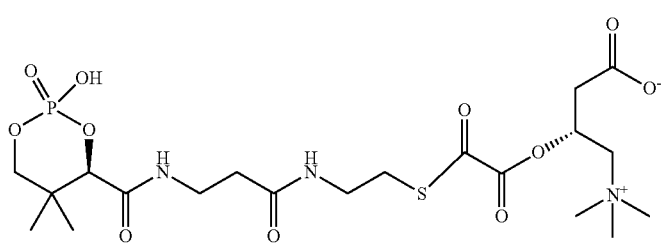 |

TABLE 1-continued

| Compound No. | Structure |
|---|---|
| 328 | 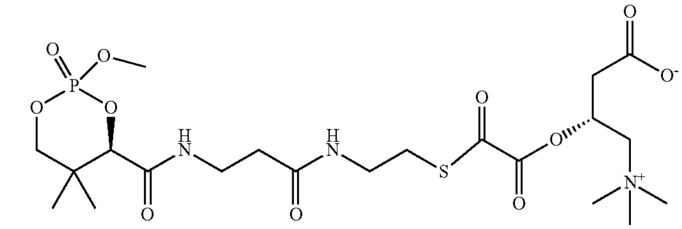 |
| 329 | 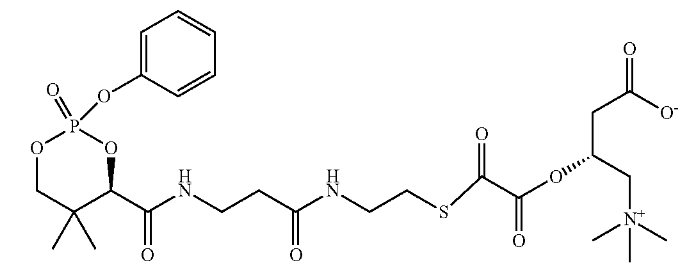 |
| 330 | 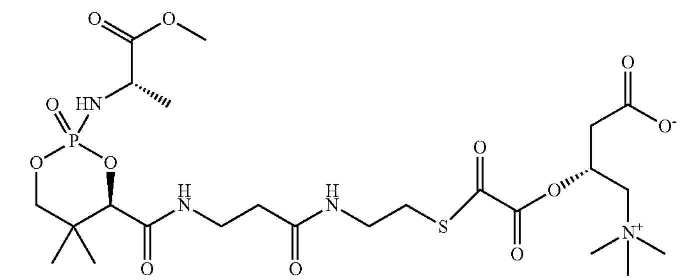 |
| 331 | 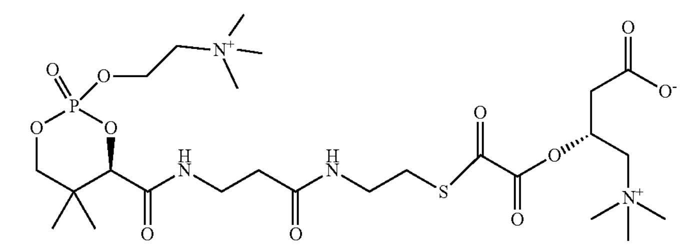 |
| 332 | 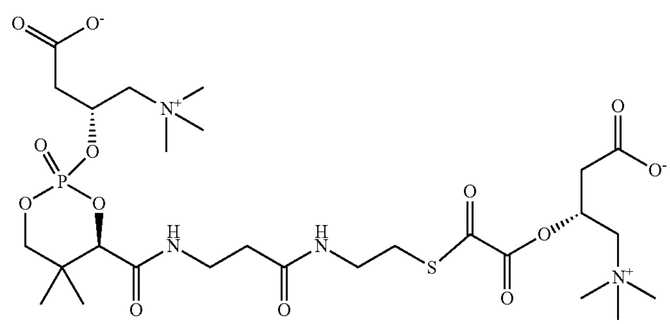 |
| 333 | 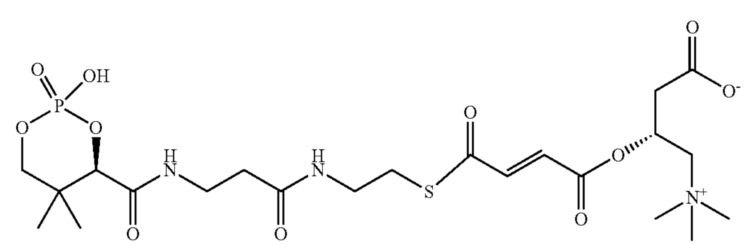 |

TABLE 1-continued

| Compound No. | Structure |
|---|---|
| 334 | 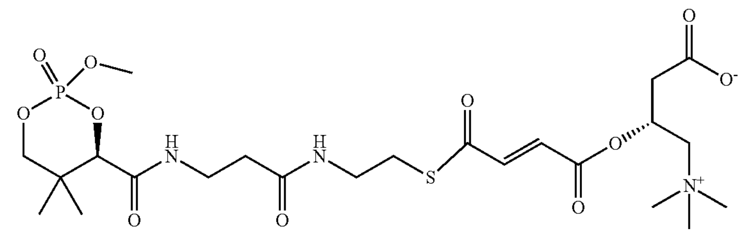 |
| 335 | 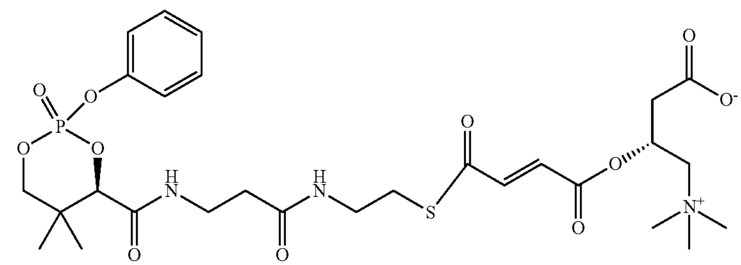 |
| 336 | 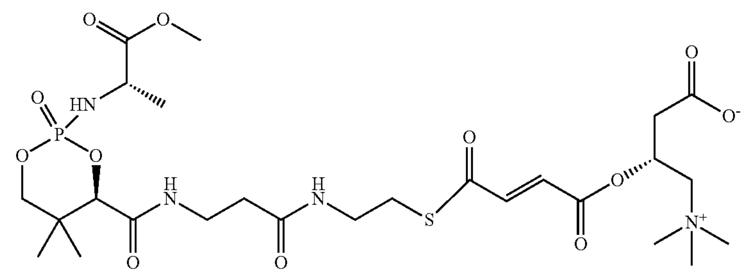 |
| 337 | 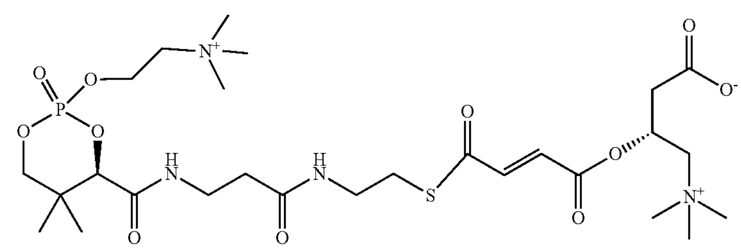 |
| 338 | 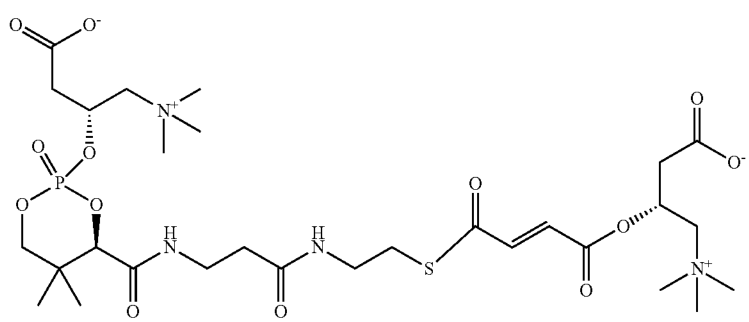 |
| 339 | 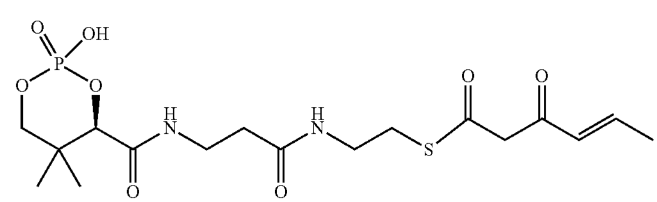 |

| Compound No. | Structure |
|---|---|
| 340 | 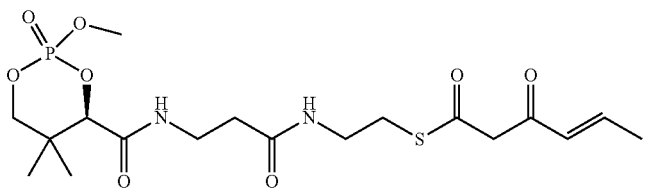 |
| 341 | 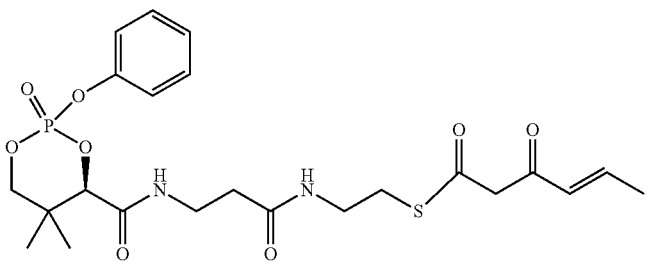 |
| 342 | 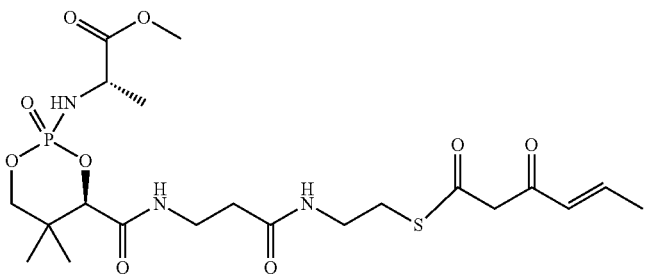 |
| 343 | 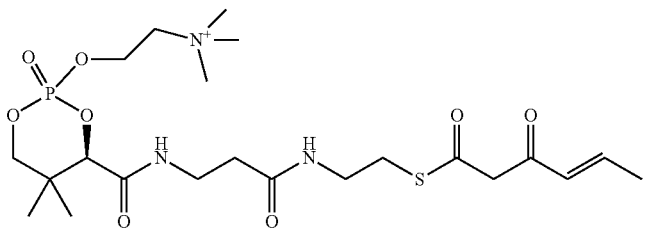 |
| 344 | 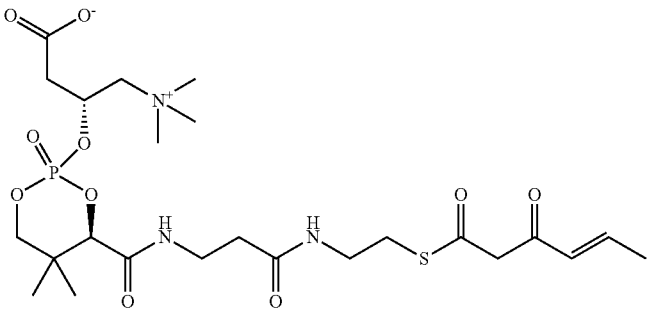 |
| 345 | 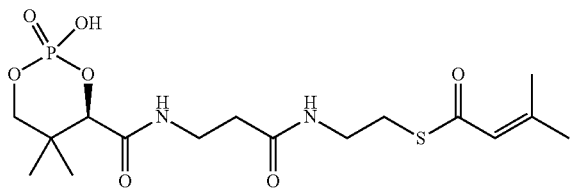 |

TABLE 1-continued
| Compound No. | Structure |
|---|---|
| 346 | 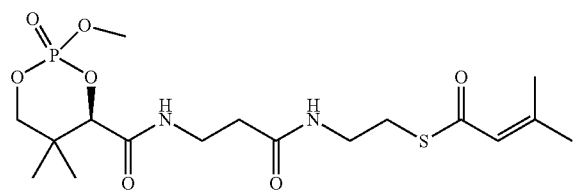 |
| 347 | 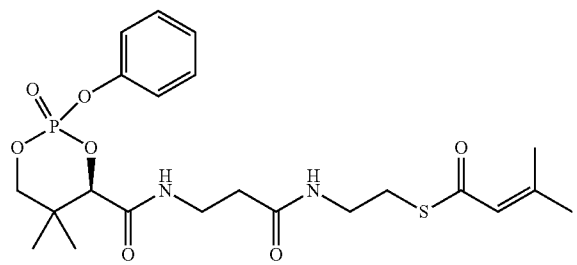 |
| 348 | 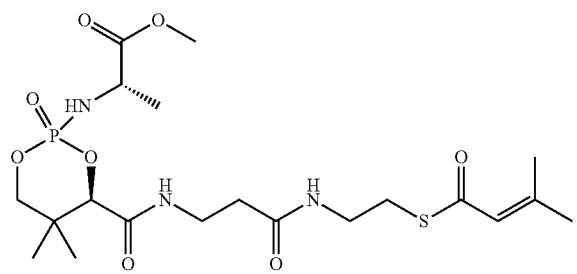 |
| 349 | 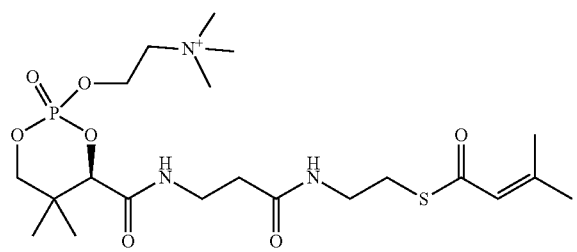 |
| 350 | 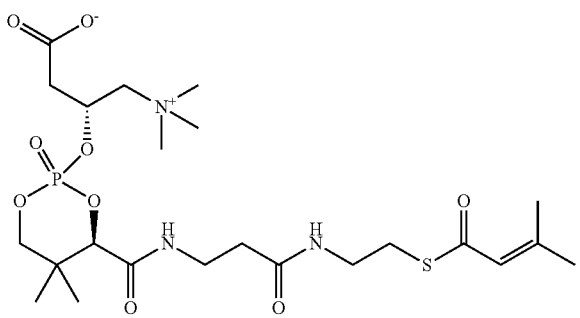 |
| 351 | 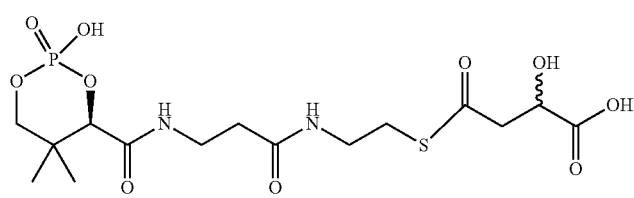 |

TABLE 1-continued

| Compound No. | Structure |
|---|---|
| 352 | 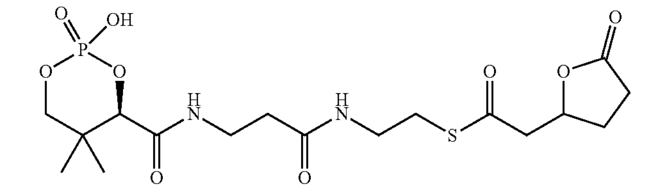 |
| 353 | 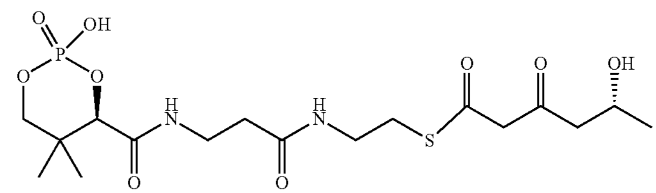 |
| 354 | 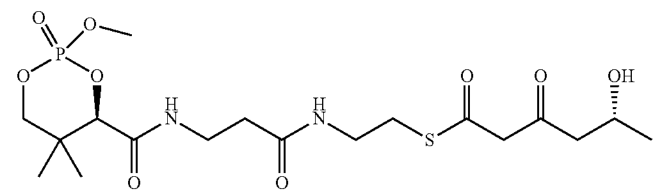 |
| 355 | 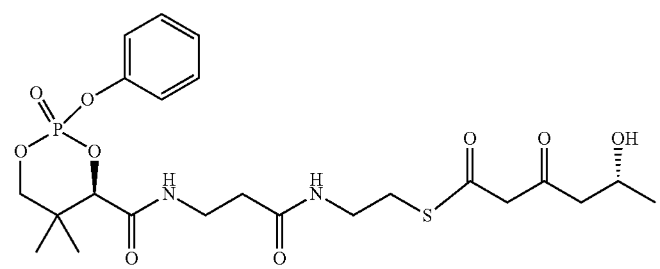 |
| 356 | 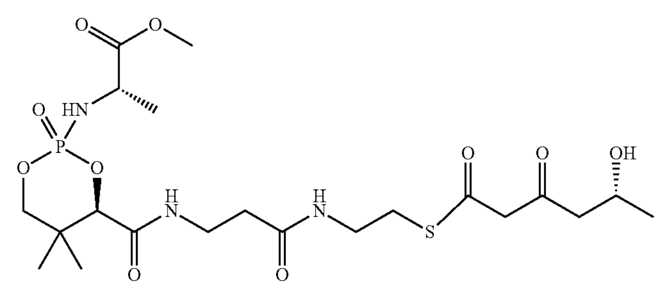 |
| 357 | 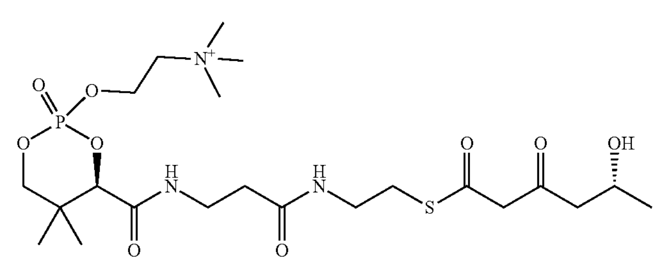 |

| Compound No. | Structure |
|---|---|
| 358 | 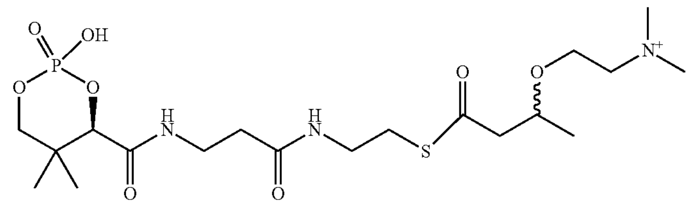 |
| 359 | 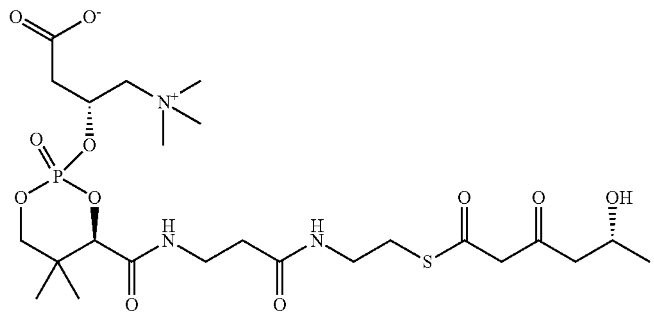 |
| 360 | 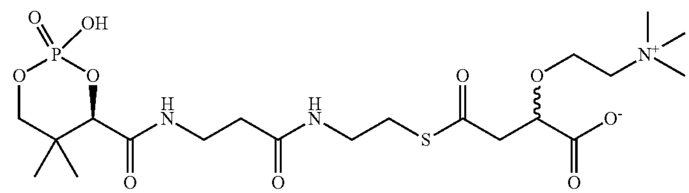 |
| 361 | 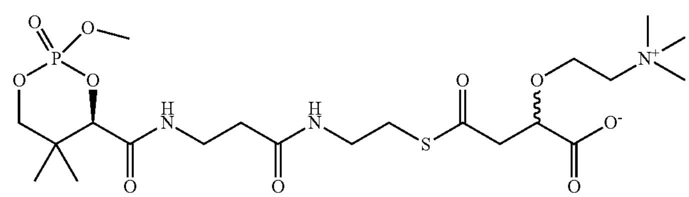 |
| 362 | 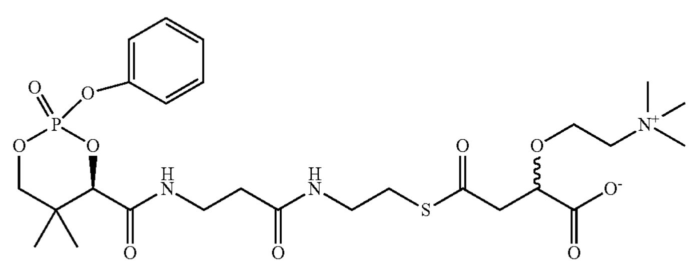 |
| 363 | 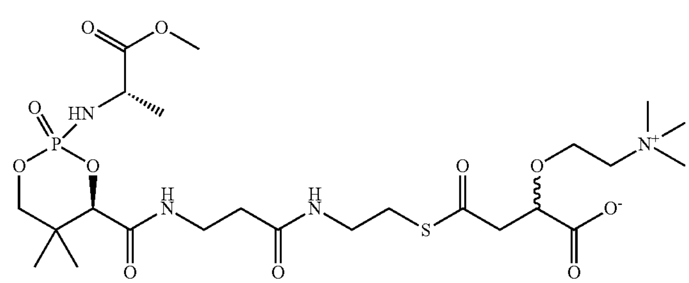 |

TABLE 1-continued

| Compound No. | Structure |
|---|---|
| 364 | (chemical structure) |
| 365 | (chemical structure) |
| 366 | (chemical structure) |
| 367 | (chemical structure) |
| 368 | (chemical structure) |
| 369 | (chemical structure) |

TABLE 1-continued
| Compound No. | Structure |
|---|---|
| 370 | 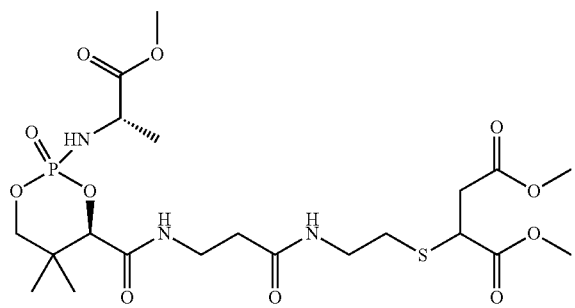 |
| 371 | 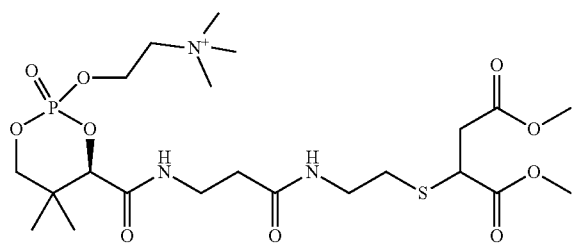 |
| 372 | 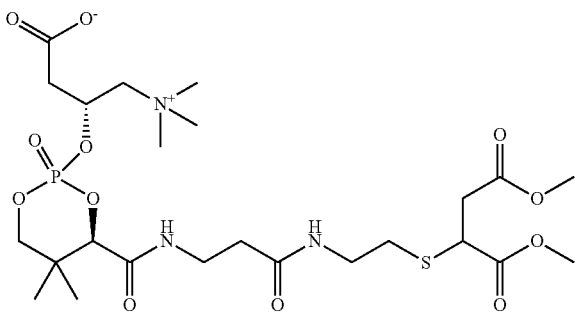 |
| 373 | 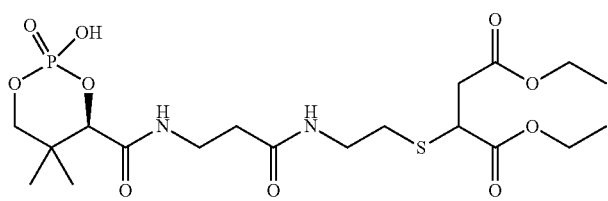 |
| 374 | 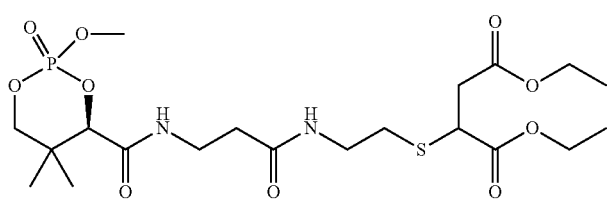 |
| 375 | 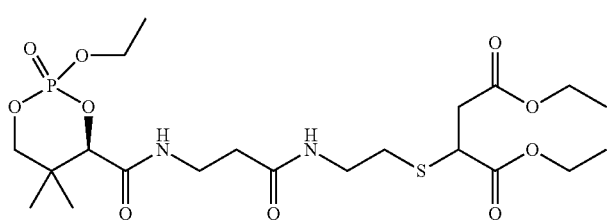 |

TABLE 1-continued
| Compound No. | Structure |
|---|---|
| 376 | 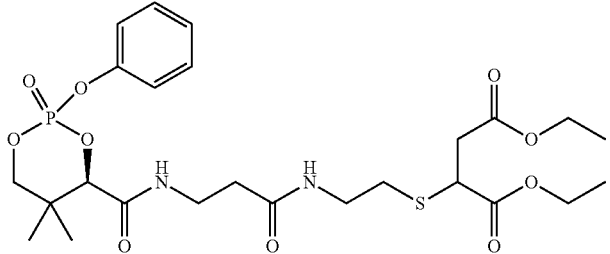 |
| 377 | 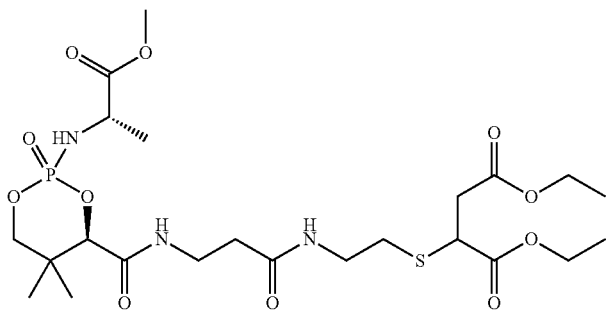 |
| 378 | 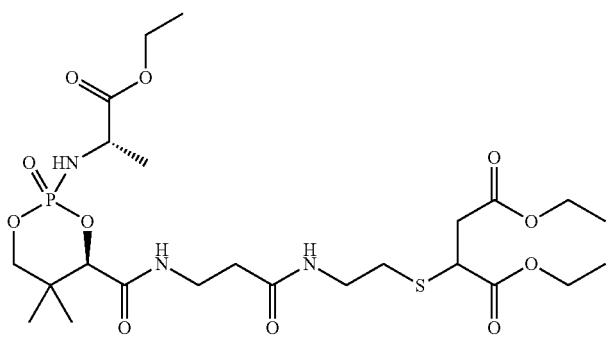 |
| 379 | 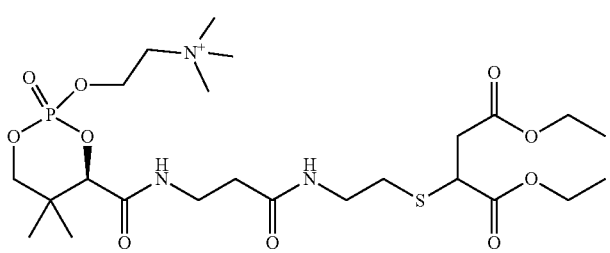 |
| 380 | 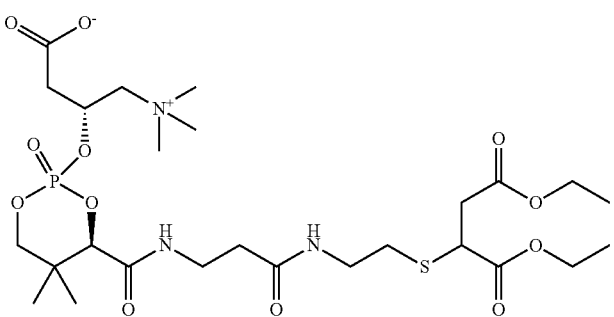 |

TABLE 1-continued

| Compound No. | Structure |
|---|---|
| 381 | 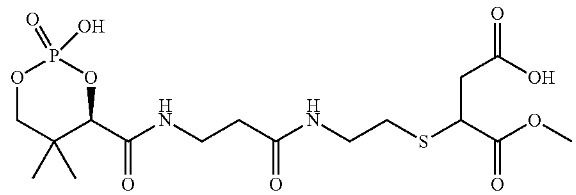 |
| 382 | 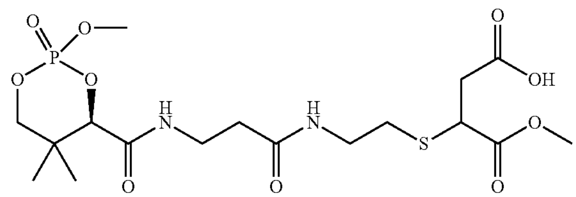 |
| 383 | 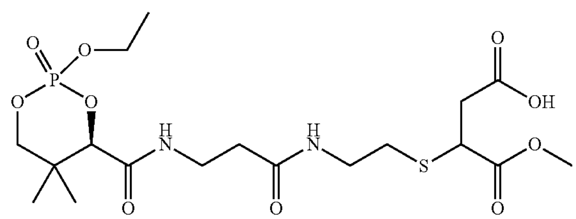 |
| 384 | 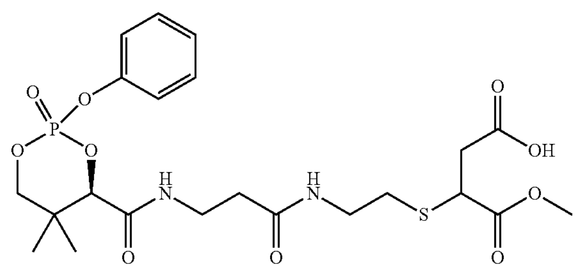 |
| 385 | 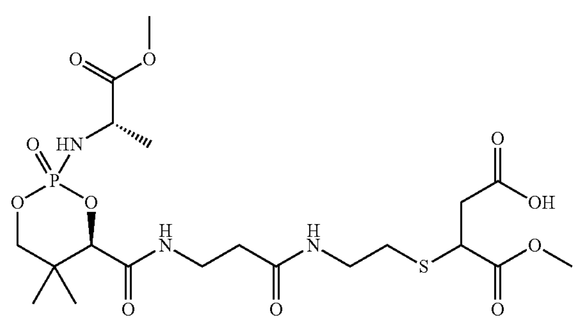 |
| 386 | 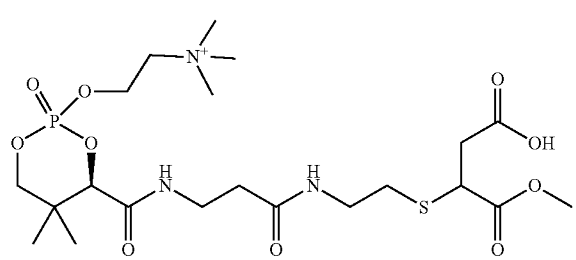 |

TABLE 1-continued
| Compound No. | Structure |
|---|---|
| 387 | 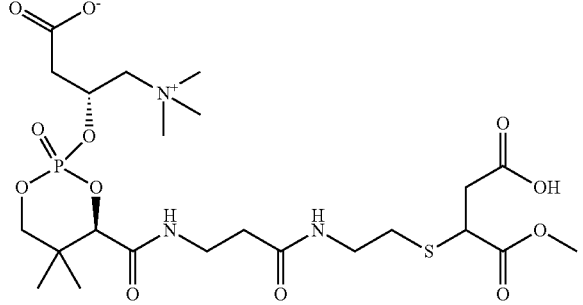 |
| 388 | 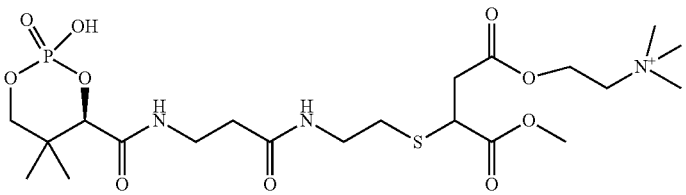 |
| 389 | 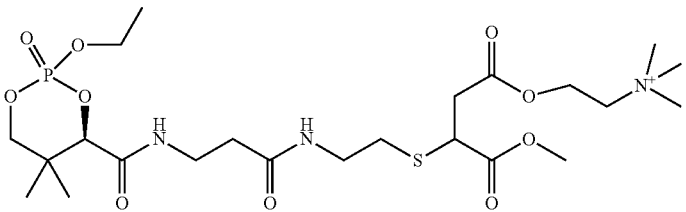 |
| 390 | 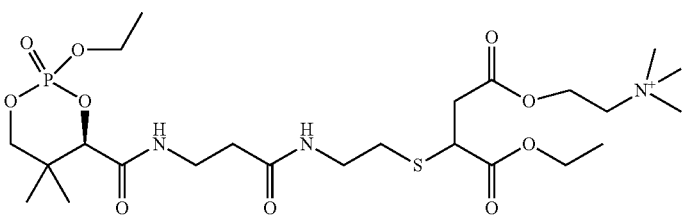 |
| 391 | 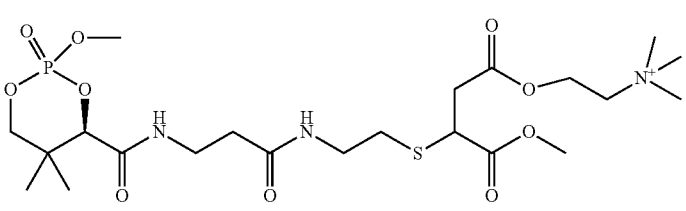 |
| 392 | 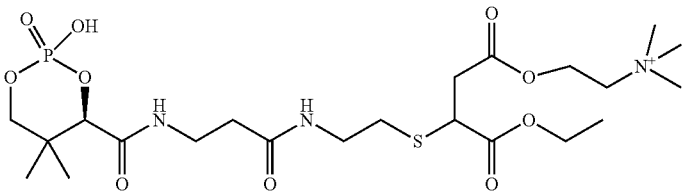 |

TABLE 1-continued

| Compound No. | Structure |
|---|---|
| 393 | 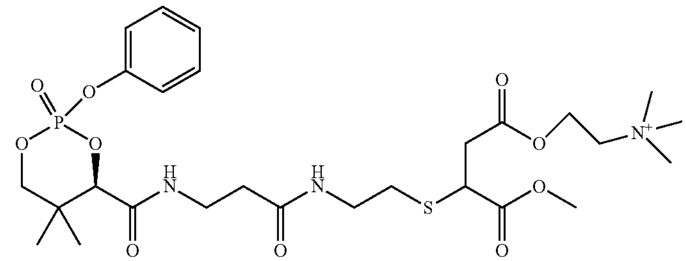 |
| 394 | 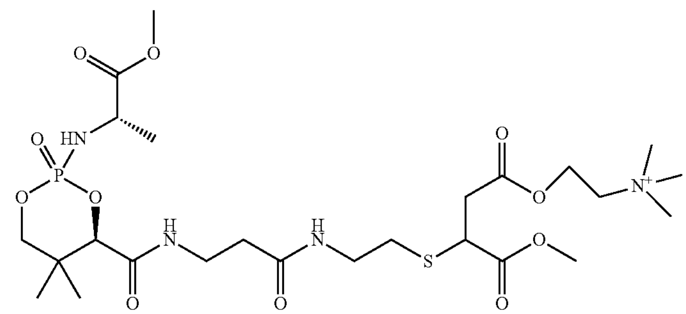 |
| 395 | 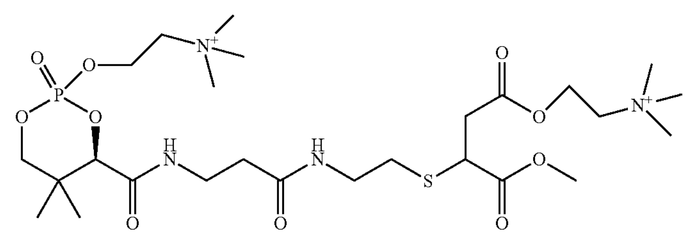 |
| 396 | 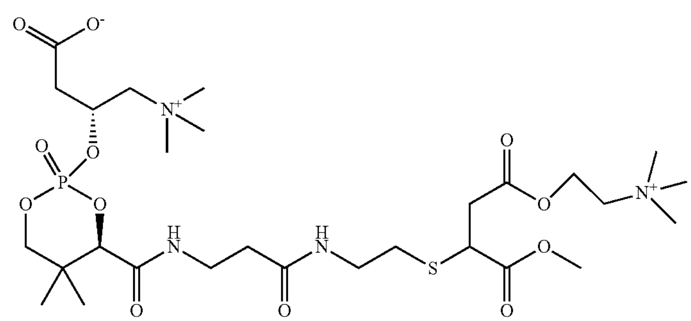 |
| 397 | 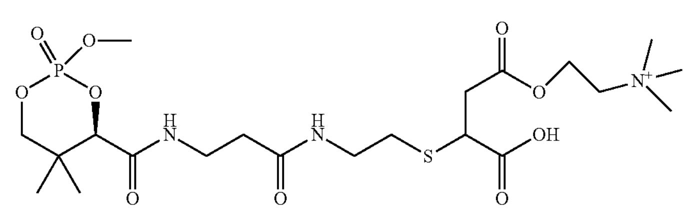 |

TABLE 1-continued

| Compound No. | Structure |
|---|---|
| 398 | 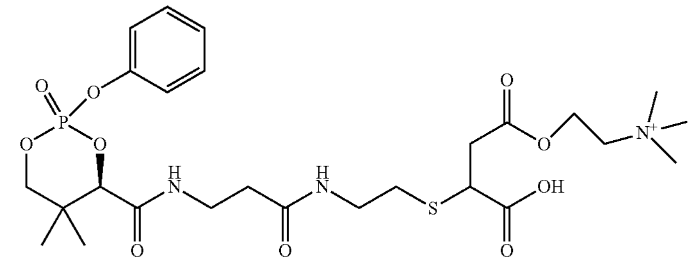 |
| 399 | 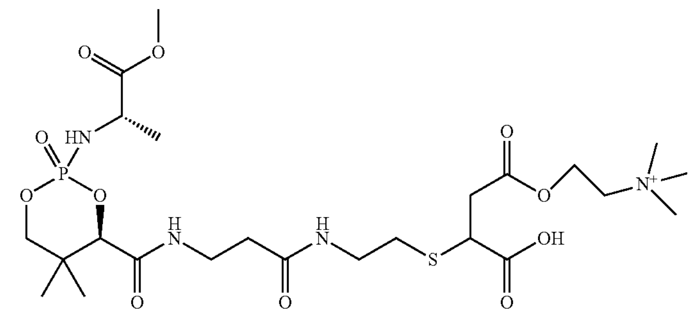 |
| 400 | 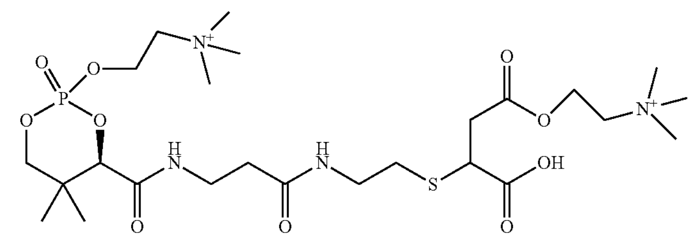 |
| 401 | 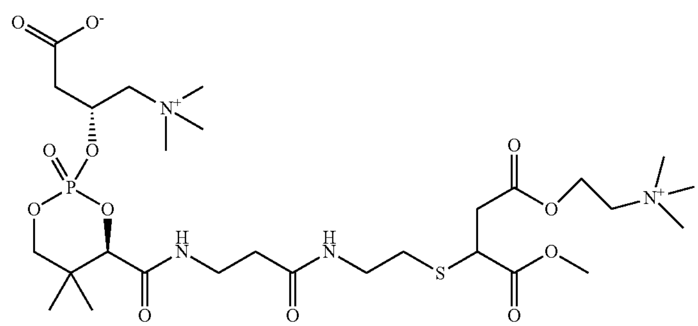 |
| 402 | 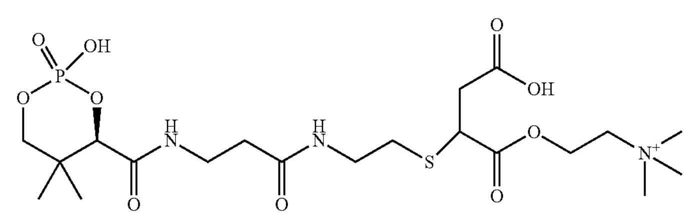 |
| 403 | 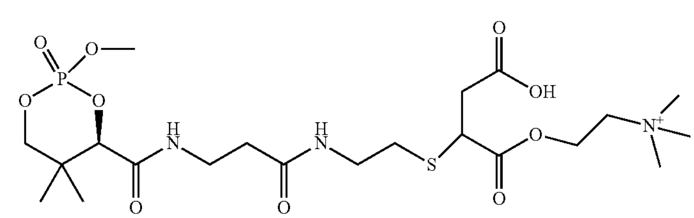 |

TABLE 1-continued
| Compound No. | Structure |
|---|---|
| 404 | 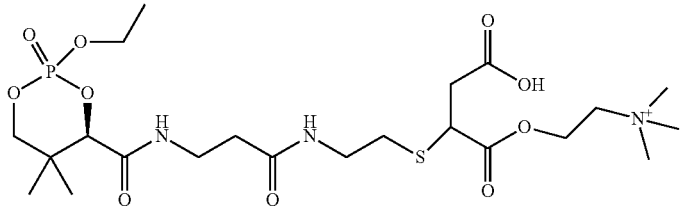 |
| 405 | 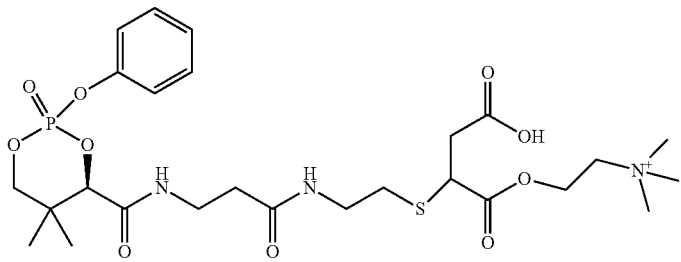 |
| 406 | 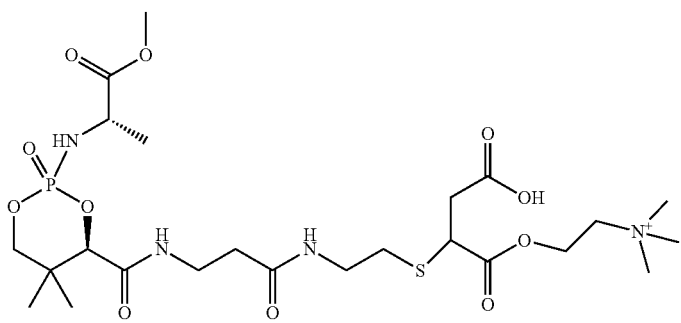 |
| 407 | 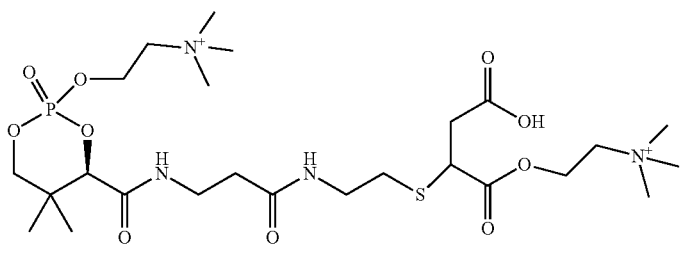 |
| 408 | 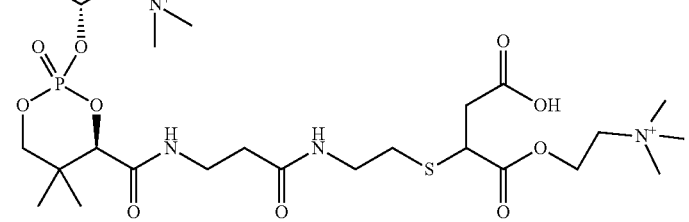 |

TABLE 1-continued

| Compound No. | Structure |
|---|---|
| 409 | 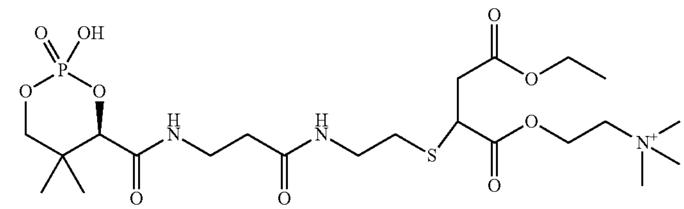 |
| 410 | 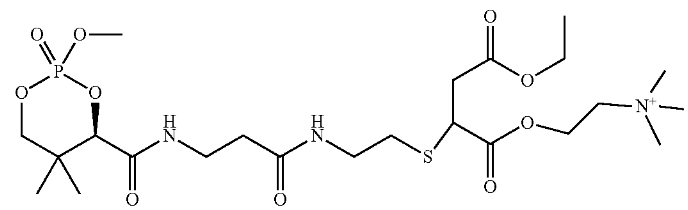 |
| 411 | 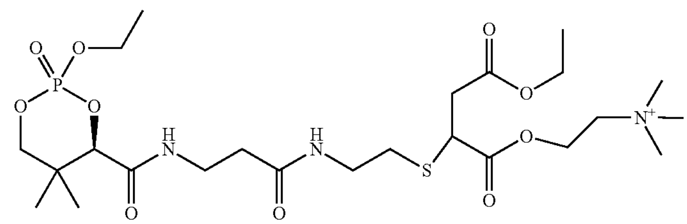 |
| 412 | 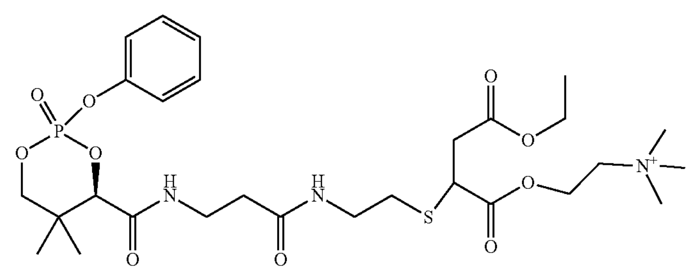 |
| 413 | 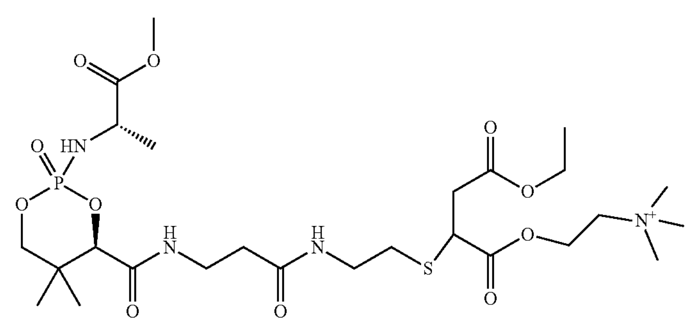 |
| 414 | 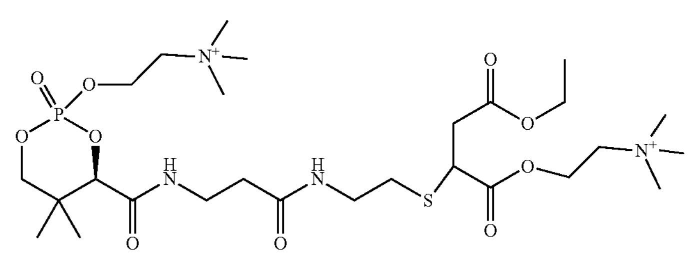 |

TABLE 1-continued

| Compound No. | Structure |
|---|---|
| 415 | (chemical structure) |
| 416 | (chemical structure) |
| 417 | (chemical structure) |
| 418 | (chemical structure) |
| 419 | (chemical structure) |
| 420 | (chemical structure) |

TABLE 1-continued

| Compound No. | Structure |
|---|---|
| 421 | 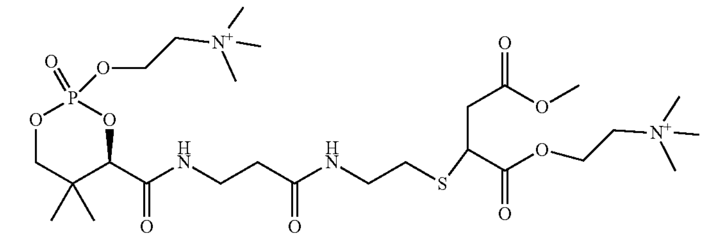 |
| 422 | 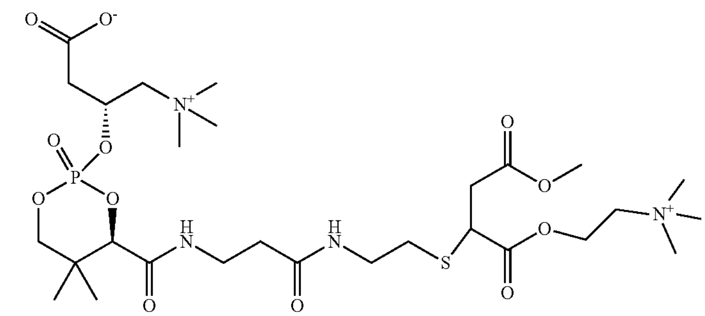 |
| 423 | 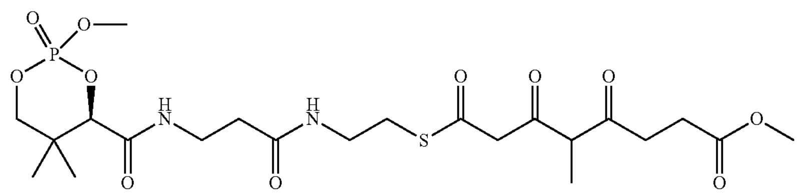 |
| 424 | 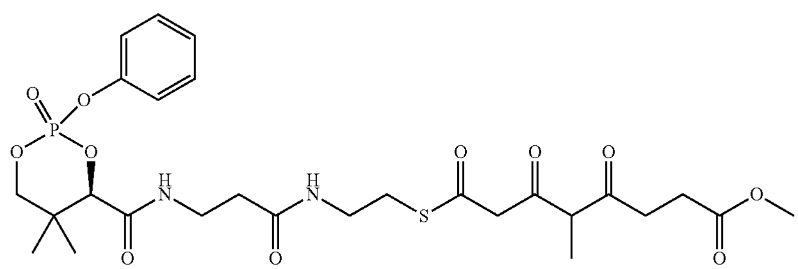 |
| 425 | 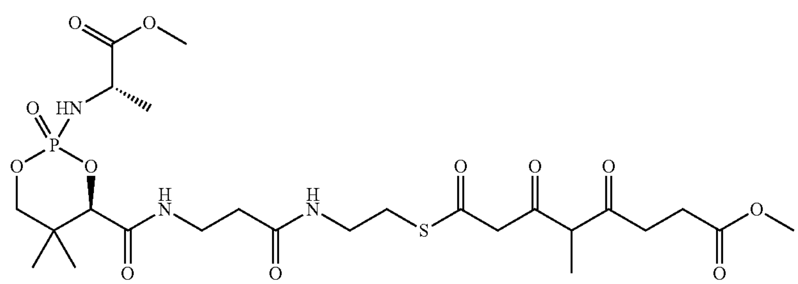 |
| 426 | 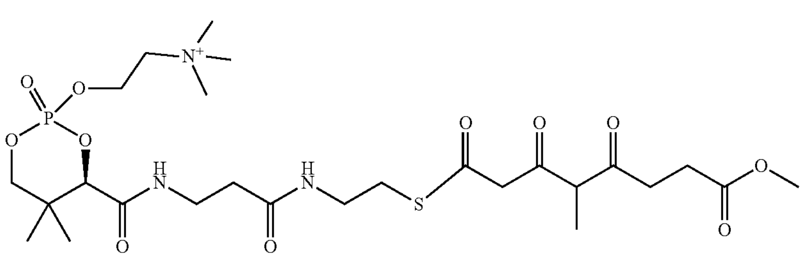 |

TABLE 1-continued

| Compound No. | Structure |
|---|---|
| 427 | 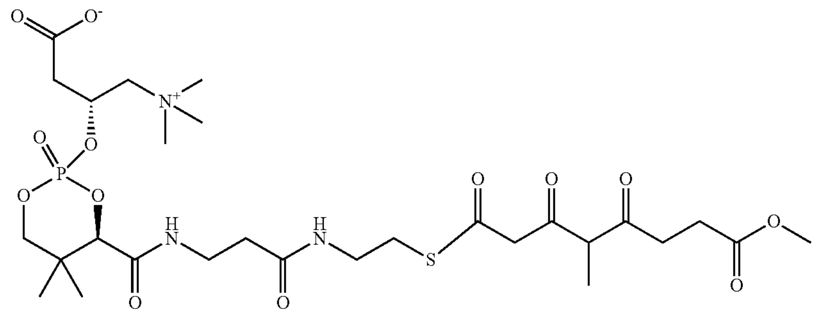 |
| 428 | 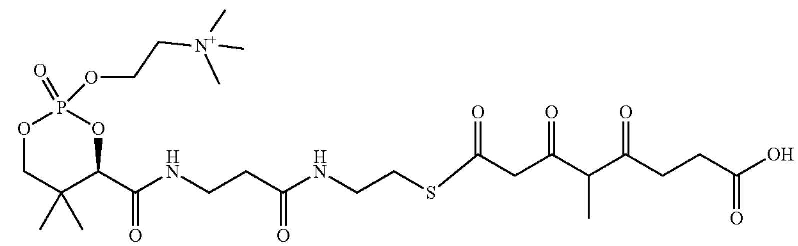 |
| 429 | 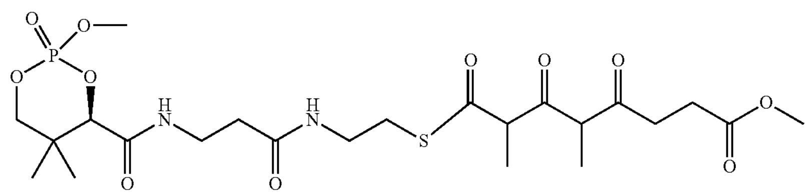 |
| 430 | 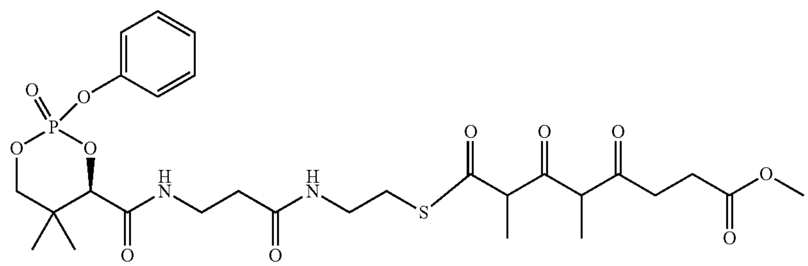 |
| 431 | 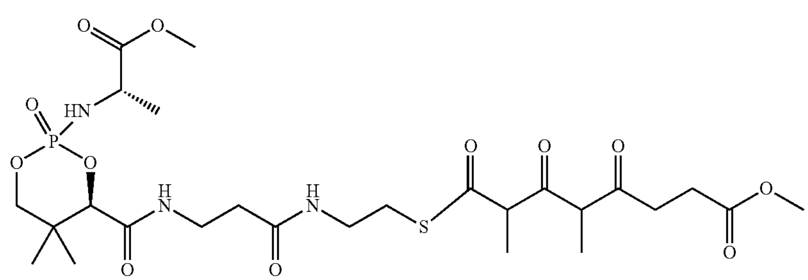 |
| 432 | 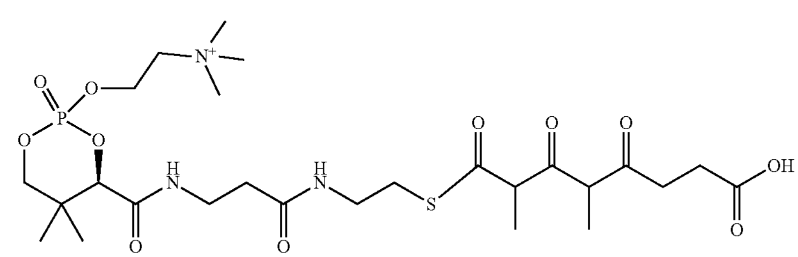 |

TABLE 1-continued
| Compound No. | Structure |
|---|---|
| 433 | 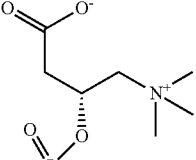 |
| 434 | 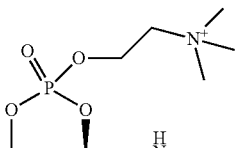 |
| 435 | 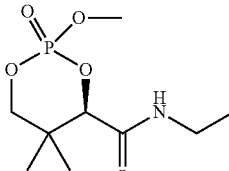 |
| 436 | 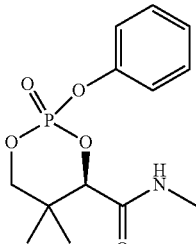 |
| 437 | 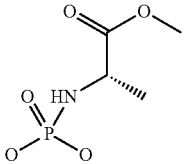 |
| 438 | 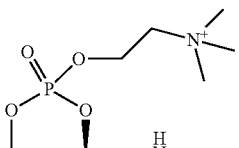 |

TABLE 1-continued

| Compound No. | Structure |
|---|---|
| 439 | 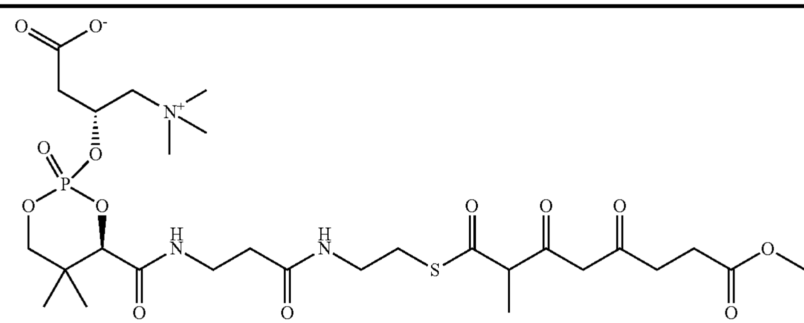 |
| 440 | 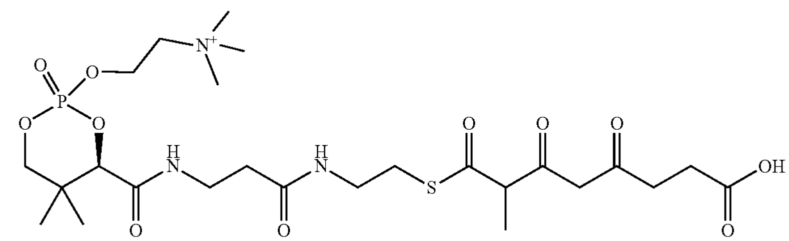 |
| 441 | 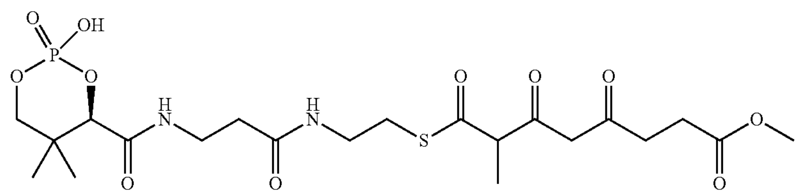 |
| 442 | 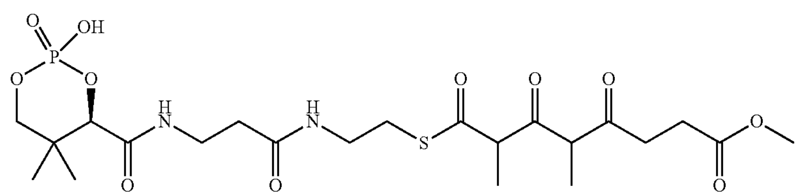 |
| 443 | 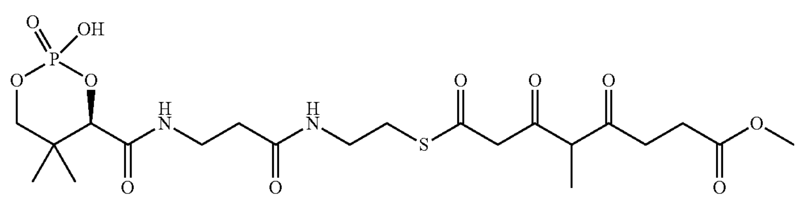 |
| 444 | 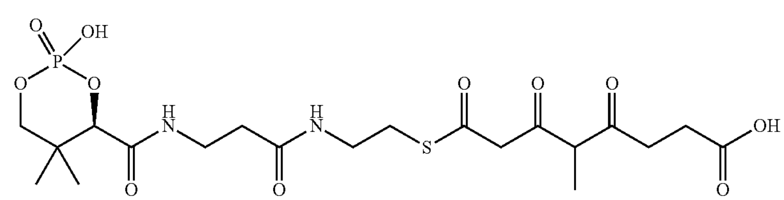 |
| 445 | 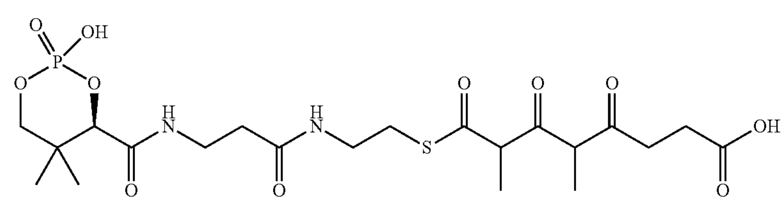 |

US 12,037,354 B2
TABLE 1-continued
| Compound No. | Structure |
|---|---|
| 446 | 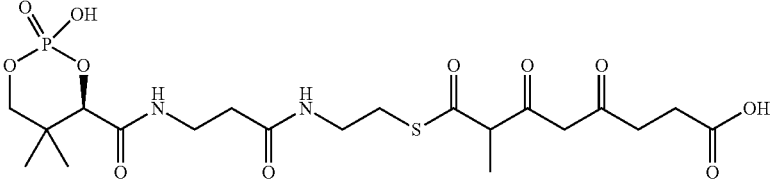 |
| 447 | 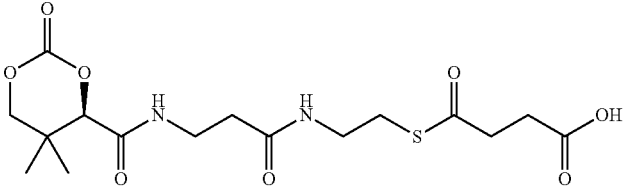 [SMILES: CC1(C)COC(=O)O[C@H]1C(=O)NCCC(=O)NCCSC(=O)CCC(=O)O] |
| 448 | 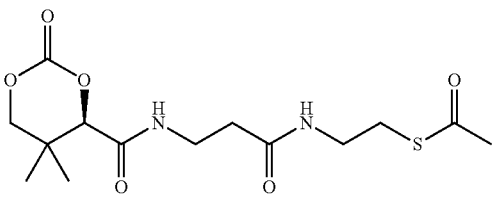 [SMILES: CC(=O)SCCNC(=O)CCNC(=O)[C@@H]1OC(=O)OCC1(C)C] |
| 449 | 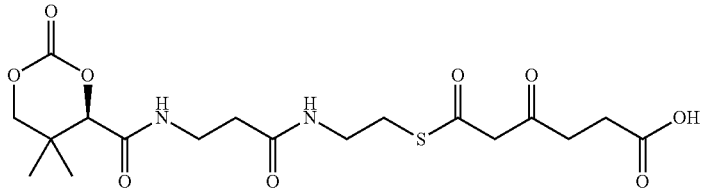 [SMILES: CC1(C)COC(=O)O[C@H]1C(=O)NCCC(=O)NCCSC(=O)CC(=O)CCC(=O)O] |
| 450 | 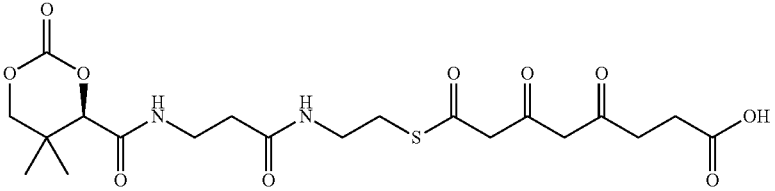 [SMILES: CC1(C)COC(=O)O[C@H]1C(=O)NCCC(=O)NCCSC(=O)CC(=O)CC(=O)CCC(=O)O] |
| 451 | 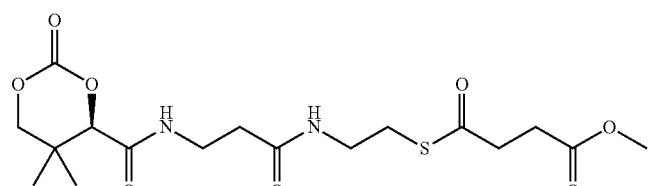 |
| 452 | 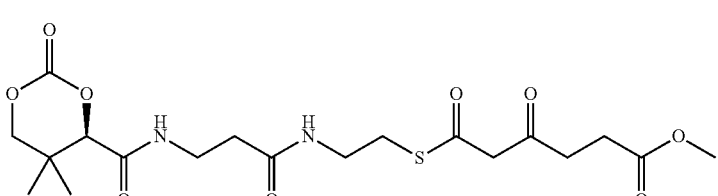 |

TABLE 1-continued
| Compound No. | Structure |
|---|---|
| 453 | 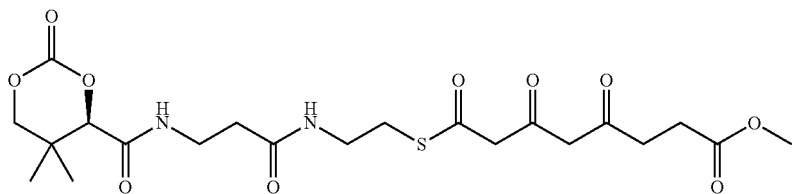 [SMILES: COC(=O)CCC(=O)CC(=O)CC(=O)SCCNC(=O)CCNC(=O)[C@@H]1OC(=O)OCC1(C)C] |
| 454 | 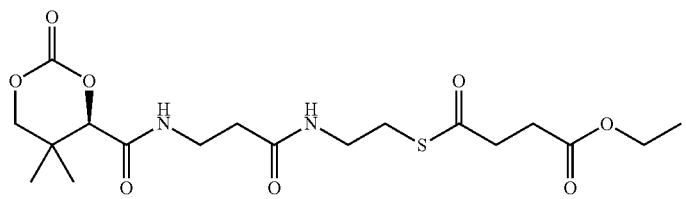 [SMILES: CCOC(=O)CCC(=O)SCCNC(=O)CCNC(=O)[C@@H]1OC(=O)OCC1(C)C] |
| 455 | 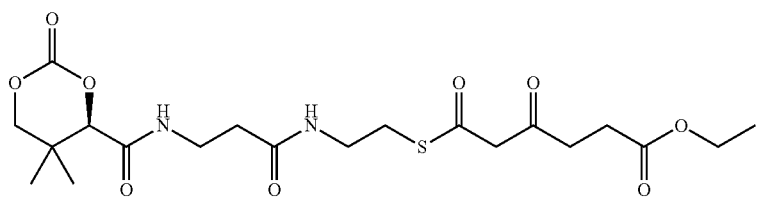 [SMILES: CCOC(=O)CCC(=O)CC(=O)SCCNC(=O)CCNC(=O)[C@@H]1OC(=O)OCC1(C)C] |
| 456 | 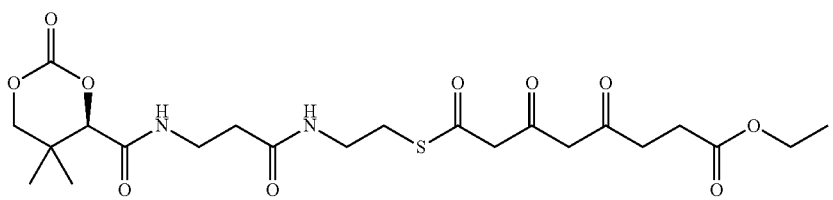 [SMILES: CCOC(=O)CCC(=O)CC(=O)CC(=O)SCCNC(=O)CCNC(=O)[C@@H]1OC(=O)OCC1(C)C] |
| 457 | 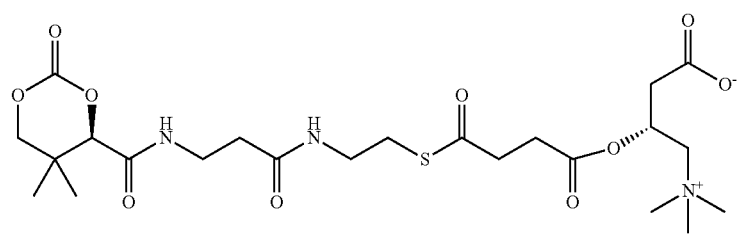 [SMILES: CC1(C)COC(=O)O[C@H]1C(=O)NCCC(=O)NCCSC(=O)CCC(=O)O[C@H](CC(=O)[O-])C[N+](C)(C)C] |
| 458 | 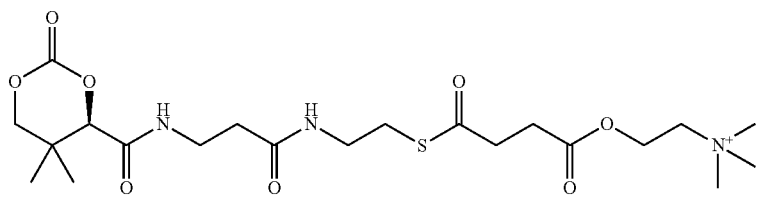 [SMILES: CC1(C)COC(=O)O[C@H]1C(=O)NCCC(=O)NCCSC(=O)CCC(=O)OCC[N+](C)(C)C] |
| 459 | 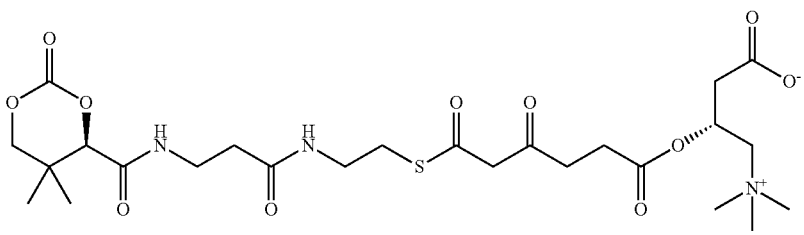 [SMILES: CC1(C)COC(=O)O[C@H]1C(=O)NCCC(=O)NCCSC(=O)CC(=O)CCC(=O)O[C@H](CC(=O)[O-])C[N+](C)(C)C] |

TABLE 1-continued

| Compound No. | Structure |
|---|---|
| 460 | 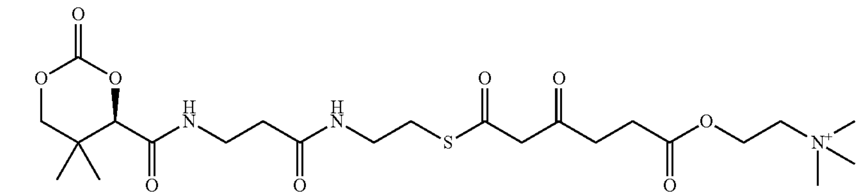 [SMILES: CC1(C)COC(=O)O[C@H]1C(=O)NCCC(=O)NCCSC(=O)CC(=O)CCC(=O)OCC[N+](C)(C)C] |
| 461 | 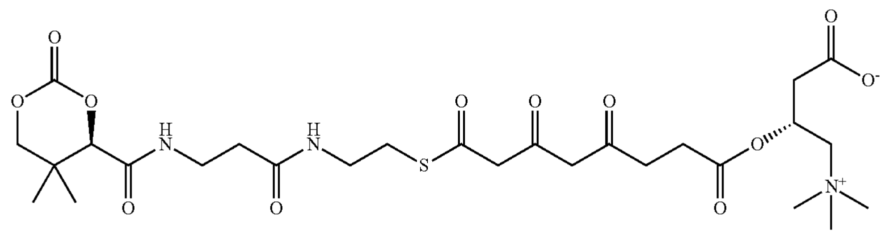 [SMILES: CC1(C)COC(=O)O[C@H]1C(=O)NCCC(=O)NCCSC(=O)CC(=O)CC(=O)CCC(=O)O[C@H](CC(=O)[O-])C[N+](C)(C)C] |
| 462 | 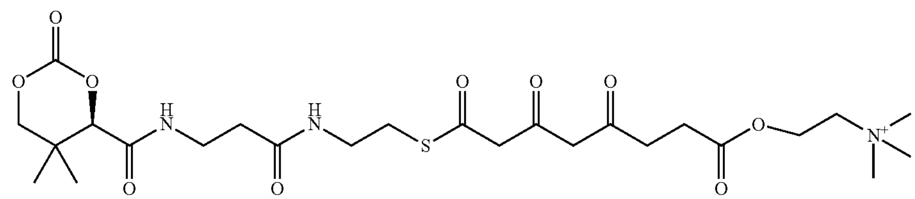 [SMILES: CC1(C)COC(=O)O[C@H]1C(=O)NCCC(=O)NCCSC(=O)CC(=O)CC(=O)CCC(=O)OCC[N+](C)(C)C] |
| 463 | 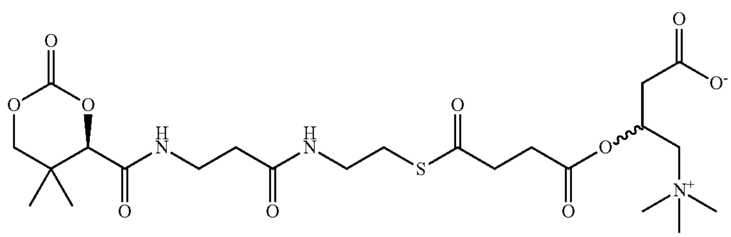 [SMILES: CC1(C)COC(=O)O[C@H]1C(=O)NCCC(=O)NCCSC(=O)CCC(=O)OC(CC(=O)[O-])C[N+](C)(C)C] |
| 464 | 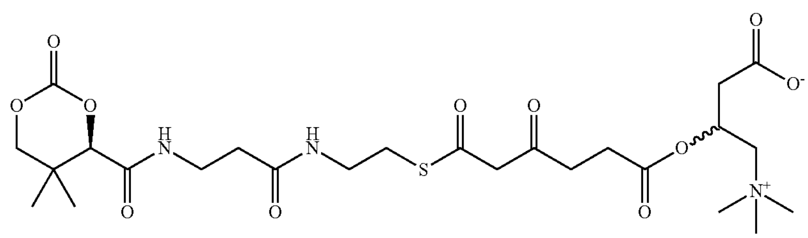 [SMILES: CC1(C)COC(=O)O[C@H]1C(=O)NCCC(=O)NCCSC(=O)CC(=O)CCC(=O)OC(CC(=O)[O-])C[N+](C)(C)C] |
| 465 | 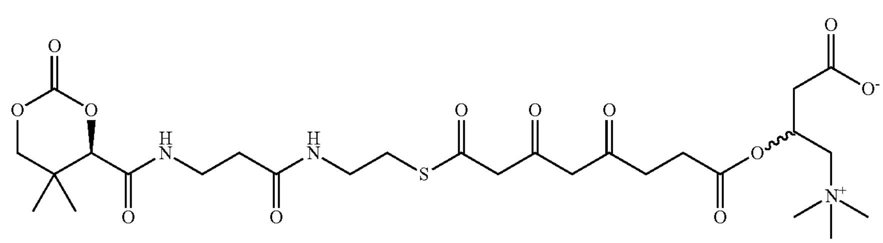 [SMILES: CC1(C)COC(=O)O[C@H]1C(=O)NCCC(=O)NCCSC(=O)CC(=O)CC(=O)CCC(=O)OC(CC(=O)[O-])C[N+](C)(C)C] |
| 466 | 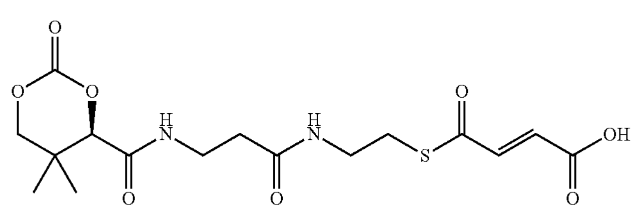 [SMILES: CC1(C)COC(=O)O[C@H]1C(=O)NCCC(=O)NCCSC(=O)/C=C/C(=O)O] |

| Compound No. | Structure |
|---|---|
| 467 | 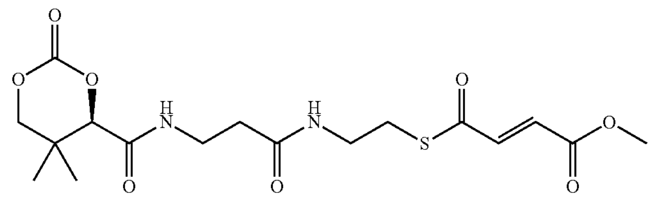 [SMILES: COC(=O)/C=C/C(=O)SCCNC(=O)CCNC(=O)[C@@H]1OC(=O)OCC1(C)C] |
| 468 | 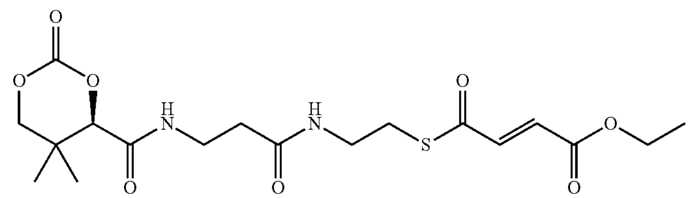 [SMILES: CCOC(=O)/C=C/C(=O)SCCNC(=O)CCNC(=O)[C@@H]1OC(=O)OCC1(C)C] |
| 469 | 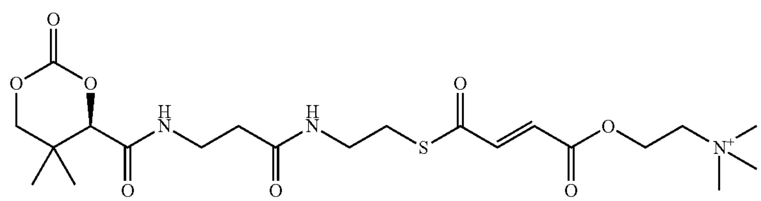 [SMILES: CC1(C)COC(=O)O[C@H]1C(=O)NCCC(=O)NCCSC(=O)/C=C/C(=O)OCC[N+](C)(C)C] |
| 470 | 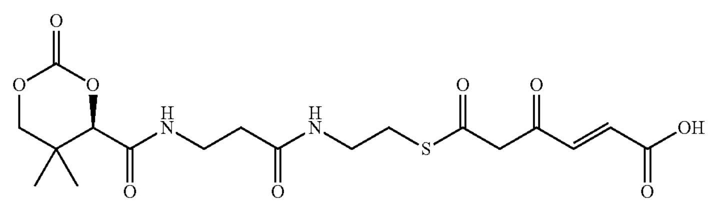 [SMILES: CC1(C)COC(=O)O[C@H]1C(=O)NCCC(=O)NCCSC(=O)CC(=O)/C=C/C(=O)O] |
| 471 | 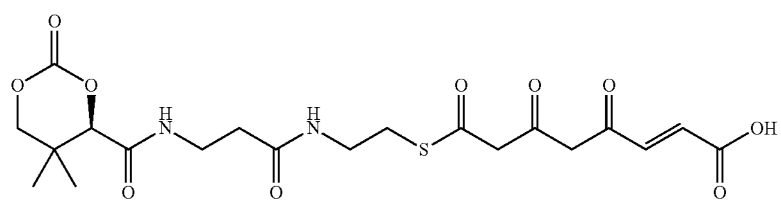 [SMILES: CC1(C)COC(=O)O[C@H]1C(=O)NCCC(=O)NCCSC(=O)CC(=O)CC(=O)/C=C/C(=O)O] |
| 472 | 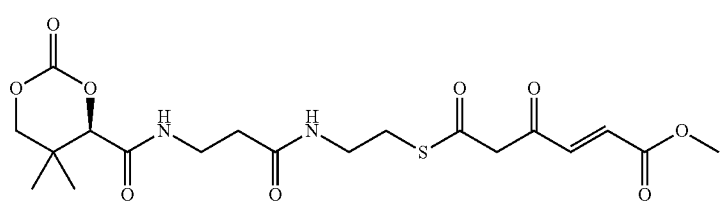 [SMILES: COC(=O)/C=C/C(=O)CC(=O)SCCNC(=O)CCNC(=O)[C@@H]1OC(=O)OCC1(C)C] |
| 473 | 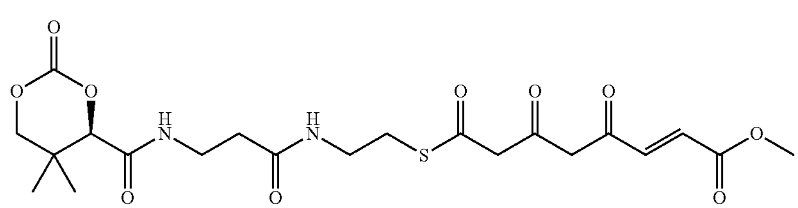 [SMILES: COC(=O)/C=C/C(=O)CC(=O)CC(=O)SCCNC(=O)CCNC(=O)[C@@H]1OC(=O)OCC1(C)C] |

TABLE 1-continued

| Compound No. | Structure |
|---|---|
| 474 | 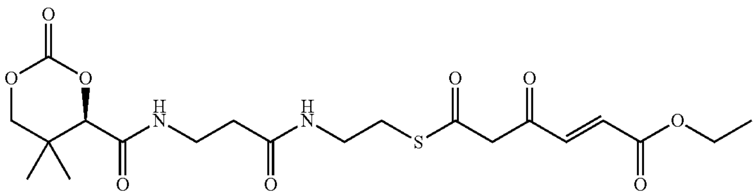 [SMILES: CCOC(=O)/C=C/C(=O)CC(=O)SCCNC(=O)CCNC(=O)[C@@H]1OC(=O)OCC1(C)C] |
| 475 | 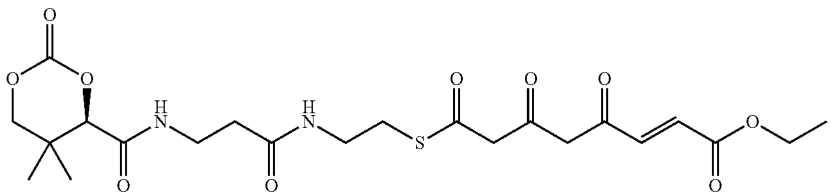 [SMILES: CCOC(=O)/C=C/C(=O)CC(=O)CC(=O)SCCNC(=O)CCNC(=O)[C@@H]1OC(=O)OCC1(C)C] |
| 476 | 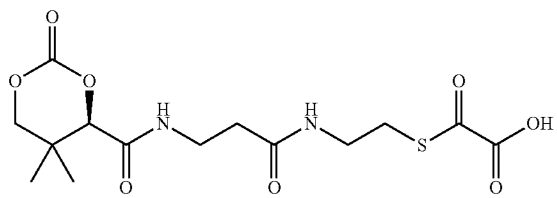 [SMILES: CC1(C)COC(=O)O[C@H]1C(=O)NCCC(=O)NCCSC(=O)C(=O)O] |
| 477 | 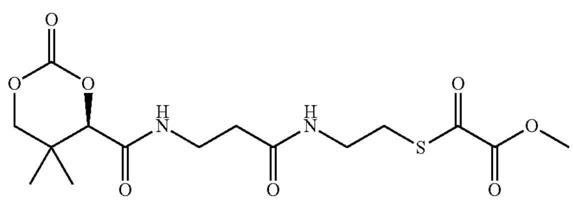 [SMILES: COC(=O)C(=O)SCCNC(=O)CCNC(=O)[C@@H]1OC(=O)OCC1(C)C] |
| 478 | 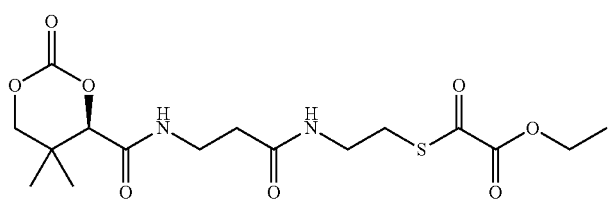 [SMILES: CCOC(=O)C(=O)SCCNC(=O)CCNC(=O)[C@@H]1OC(=O)OCC1(C)C] |
| 479 | 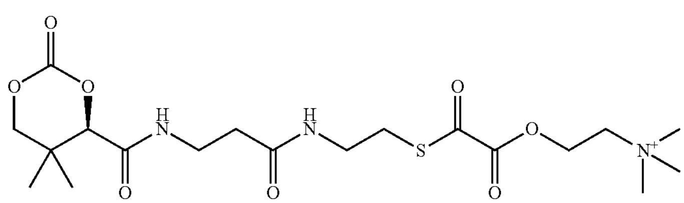 [SMILES: CC1(C)COC(=O)O[C@H]1C(=O)NCCC(=O)NCCSC(=O)C(=O)OCC[N+](C)(C)C] |
| 480 | 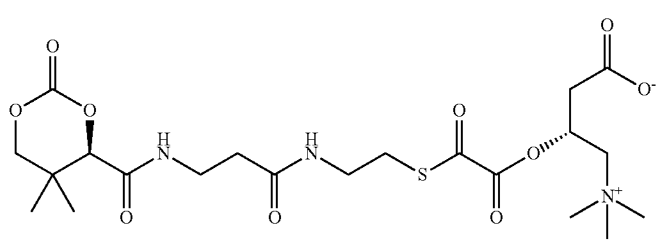 [SMILES: CC1(C)COC(=O)O[C@H]1C(=O)NCCC(=O)NCCSC(=O)C(=O)O[C@H](CC(=O)[O-])C[N+](C)(C)C] |

| Compound No. | Structure |
|---|---|
| 481 | 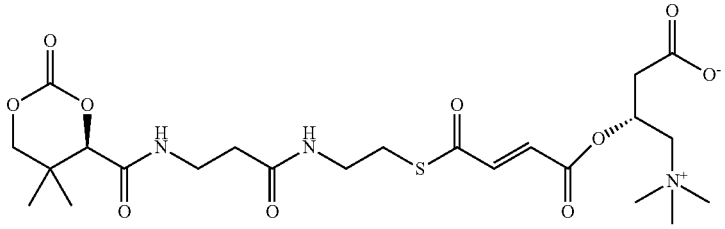 [SMILES: CC1(C)COC(=O)O[C@H]1C(=O)NCCC(=O)NCCSC(=O)/C=C/C(=O)O[C@H](CC(=O)[O-])C[N+](C)(C)C] |
| 482 | 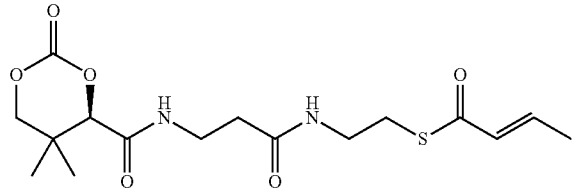 [SMILES: C/C=C/C(=O)SCCNC(=O)CCNC(=O)[C@@H]1OC(=O)OCC1(C)C] |
| 483 | 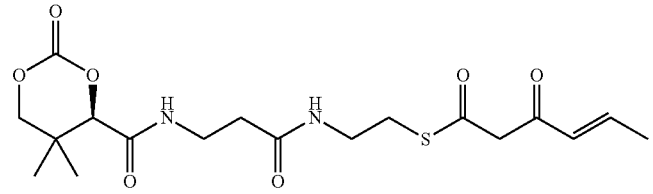 [SMILES: C/C=C/C(=O)CC(=O)SCCNC(=O)CCNC(=O)[C@@H]1OC(=O)OCC1(C)C] |
| 484 | 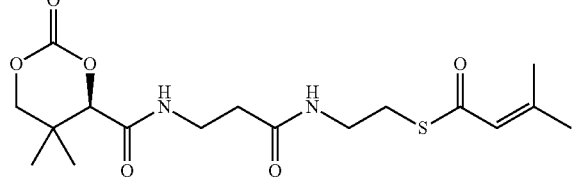 |
| 485 | 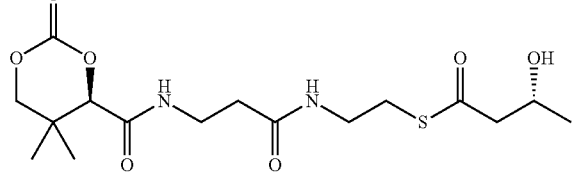 |
| 486 | 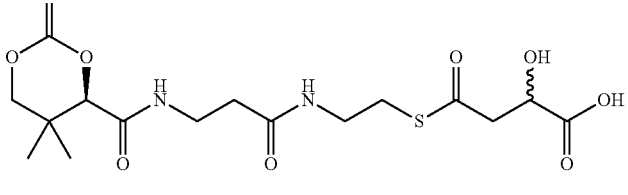 |
| 487 | 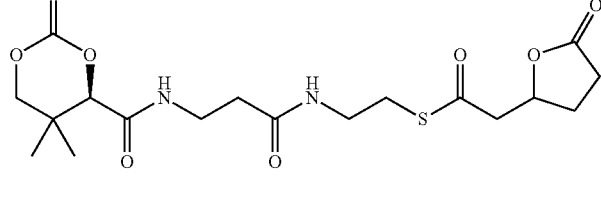 |

TABLE 1-continued
| Compound No. | Structure |
|---|---|
| 488 | 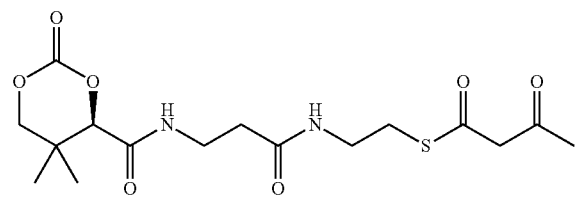 [SMILES: CC(=O)CC(=O)SCCNC(=O)CCNC(=O)[C@@H]1OC(=O)OCC1(C)C] |
| 489 | 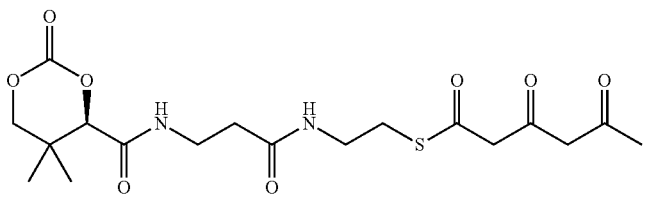 [SMILES: CC(=O)CC(=O)CC(=O)SCCNC(=O)CCNC(=O)[C@@H]1OC(=O)OCC1(C)C] |
| 490 | 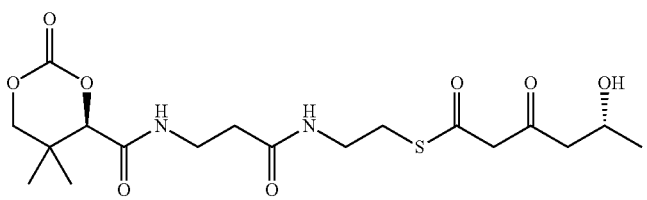 [SMILES: C[C@@H](O)CC(=O)CC(=O)SCCNC(=O)CCNC(=O)[C@@H]1OC(=O)OCC1(C)C] |
| 491 | 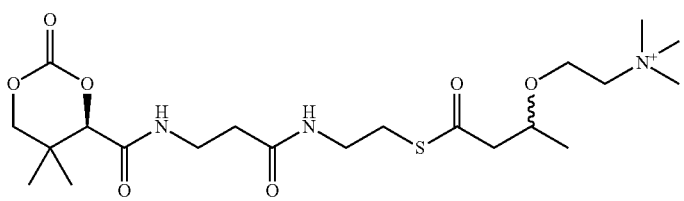 [SMILES: CC(CC(=O)SCCNC(=O)CCNC(=O)[C@@H]1OC(=O)OCC1(C)C)OCC[N+](C)(C)C] |
| 492 | 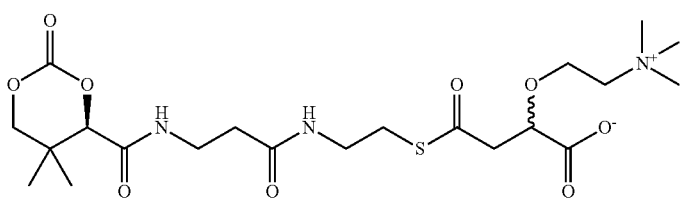 [SMILES: CC1(C)COC(=O)O[C@H]1C(=O)NCCC(=O)NCCSC(=O)CC(OCC[N+](C)(C)C)C(=O)[O-]] |
| 493 | 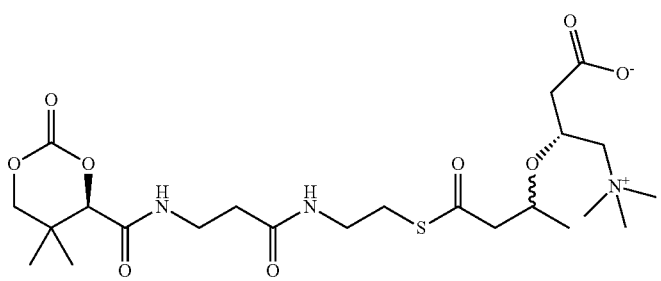 [SMILES: CC(CC(=O)SCCNC(=O)CCNC(=O)[C@@H]1OC(=O)OCC1(C)C)O[C@H](CC(=O)[O-])C[N+](C)(C)C] |
| 494 | 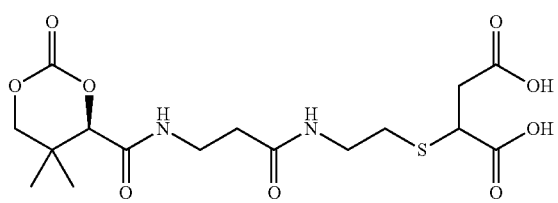 [SMILES: CC1(C)COC(=O)O[C@H]1C(=O)NCCC(=O)NCCSC(CC(=O)O)C(=O)O] |

TABLE 1-continued

| Compound No. | Structure |
|---|---|
| 495 | 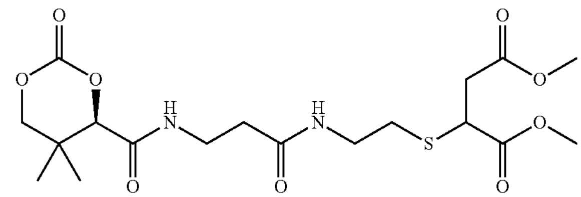 [SMILES: COC(=O)CC(SCCNC(=O)CCNC(=O)[C@@H]1OC(=O)OCC1(C)C)C(=O)OC] |
| 496 | 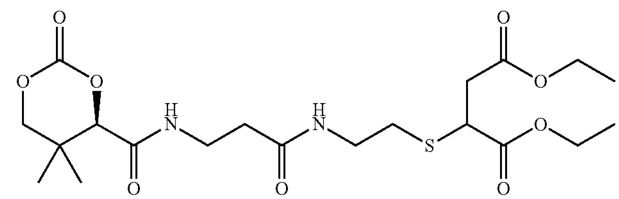 [SMILES: CCOC(=O)CC(SCCNC(=O)CCNC(=O)[C@@H]1OC(=O)OCC1(C)C)C(=O)OCC] |
| 497 | 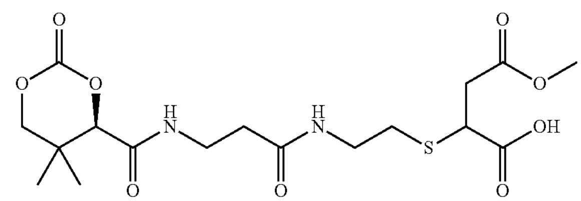 [SMILES: COC(=O)CC(SCCNC(=O)CCNC(=O)[C@@H]1OC(=O)OCC1(C)C)C(=O)O] |
| 498 | 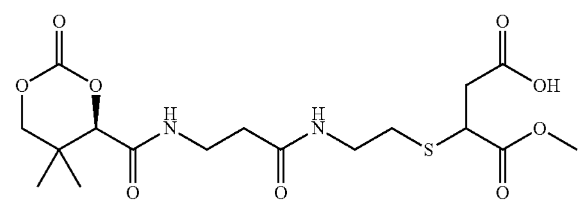 [SMILES: COC(=O)C(CC(=O)O)SCCNC(=O)CCNC(=O)[C@@H]1OC(=O)OCC1(C)C] |
| 499 | 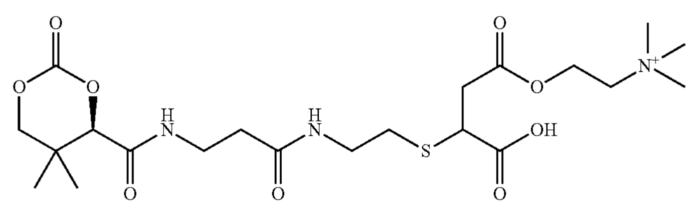 [SMILES: CC1(C)COC(=O)O[C@H]1C(=O)NCCC(=O)NCCSC(CC(=O)OCC[N+](C)(C)C)C(=O)O] |
| 500 | 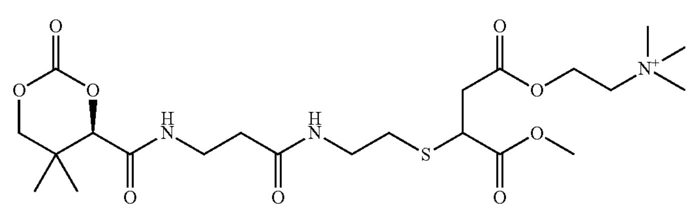 [SMILES: COC(=O)C(CC(=O)OCC[N+](C)(C)C)SCCNC(=O)CCNC(=O)[C@@H]1OC(=O)OCC1(C)C] |
| 501 | 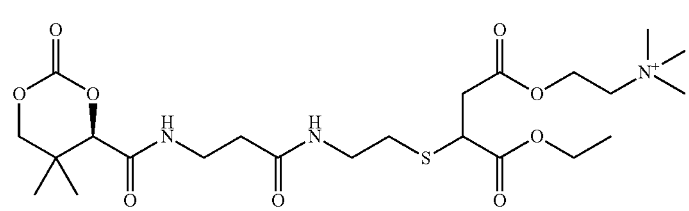 [SMILES: CCOC(=O)C(CC(=O)OCC[N+](C)(C)C)SCCNC(=O)CCNC(=O)[C@@H]1OC(=O)OCC1(C)C] |

TABLE 1-continued
| Compound No. | Structure |
|---|---|
| 502 | 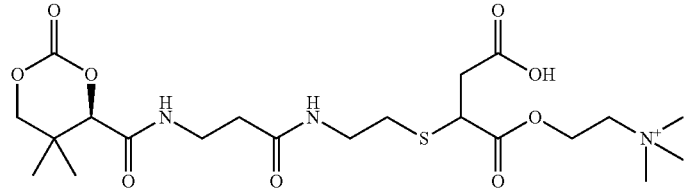 [SMILES: CC1(C)COC(=O)O[C@H]1C(=O)NCCC(=O)NCCSC(CC(=O)O)C(=O)OCC[N+](C)(C)C] |
| 503 | 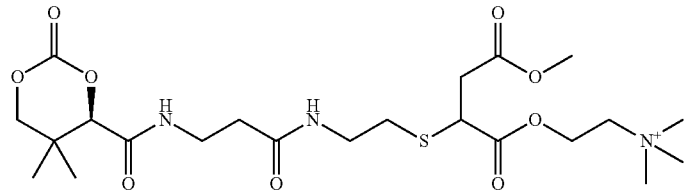 [SMILES: COC(=O)CC(SCCNC(=O)CCNC(=O)[C@@H]1OC(=O)OCC1(C)C)C(=O)OCC[N+](C)(C)C] |
| 504 | 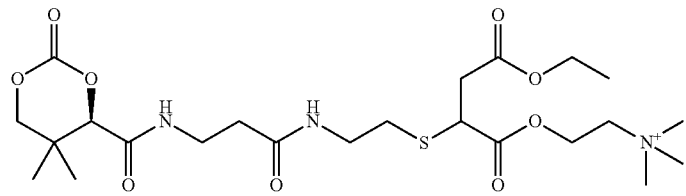 [SMILES: CCOC(=O)CC(SCCNC(=O)CCNC(=O)[C@@H]1OC(=O)OCC1(C)C)C(=O)OCC[N+](C)(C)C] |
| 505 | |
| 506 | 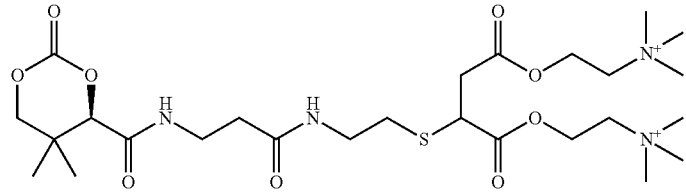 [SMILES: CC1(C)COC(=O)O[C@H]1C(=O)NCCC(=O)NCCSC(CC(=O)OCC[N+](C)(C)C)C(=O)OCC[N+](C)(C)C] |
| 507 | 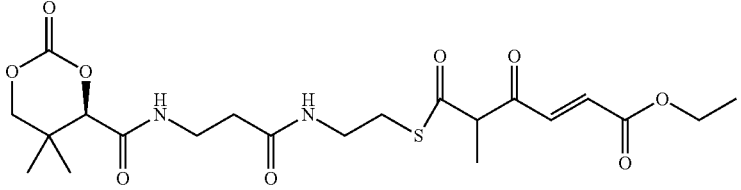 [SMILES: CCOC(=O)/C=C/C(=O)C(C)C(=O)SCCNC(=O)CCNC(=O)[C@@H]1OC(=O)OCC1(C)C] |
| 508 | 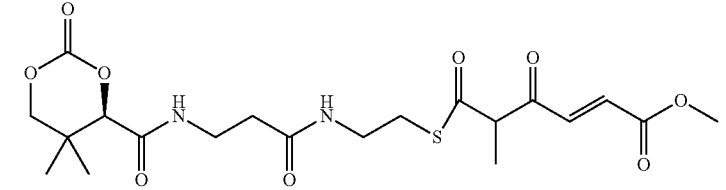 [SMILES: COC(=O)/C=C/C(=O)C(C)C(=O)SCCNC(=O)CCNC(=O)[C@@H]1OC(=O)OCC1(C)C] |
| 509 | 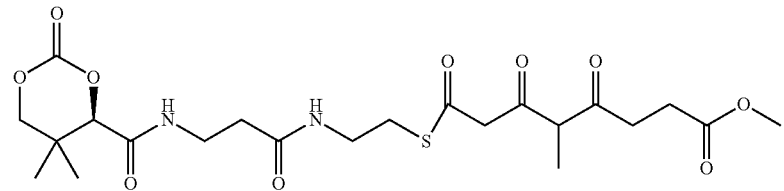 [SMILES: COC(=O)CCC(=O)C(C)C(=O)CC(=O)SCCNC(=O)CCNC(=O)[C@@H]1OC(=O)OCC1(C)C] |

TABLE 1-continued

| Compound No. | Structure |
| --- | --- |
| 510 | 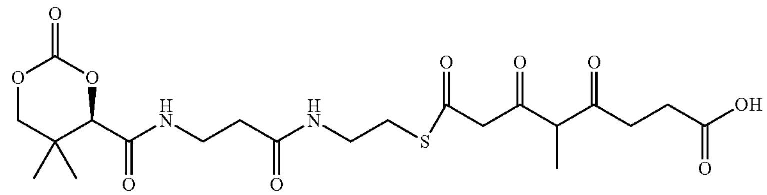 [SMILES: CC(C(=O)CCC(=O)O)C(=O)CC(=O)SCCNC(=O)CCNC(=O)[C@@H]1OC(=O)OCC1(C)C] |
| 511 | 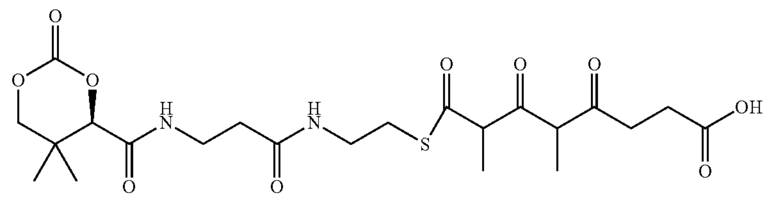 [SMILES: CC(C(=O)CCC(=O)O)C(=O)C(C)C(=O)SCCNC(=O)CCNC(=O)[C@@H]1OC(=O)OCC1(C)C] |
| 512 | 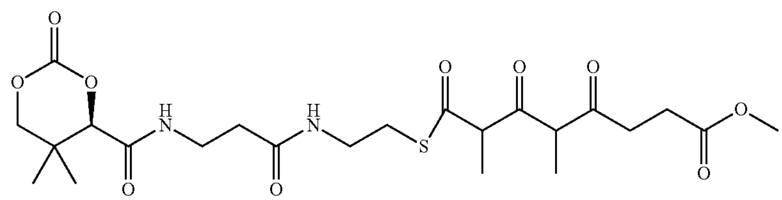 [SMILES: COC(=O)CCC(=O)C(C)C(=O)C(C)C(=O)SCCNC(=O)CCNC(=O)[C@@H]1OC(=O)OCC1(C)C] |
| 513 | 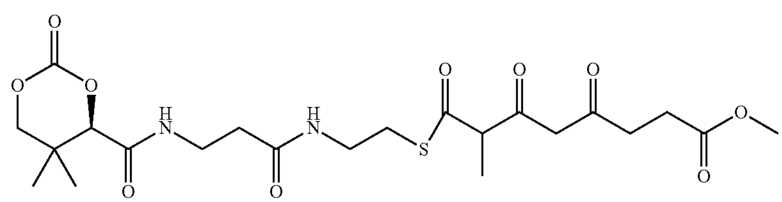 [SMILES: COC(=O)CCC(=O)CC(=O)C(C)C(=O)SCCNC(=O)CCNC(=O)[C@@H]1OC(=O)OCC1(C)C] |
| 514 | 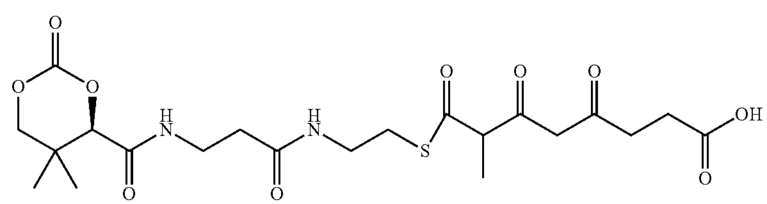 [SMILES: CC(C(=O)CC(=O)CCC(=O)O)C(=O)SCCNC(=O)CCNC(=O)[C@@H]1OC(=O)OCC1(C)C] |
| 515 | 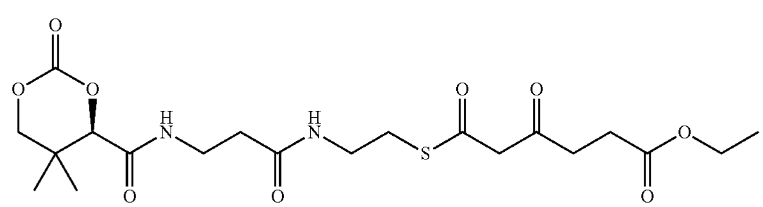 [SMILES: CCOC(=O)CCC(=O)CC(=O)SCCNC(=O)CCNC(=O)[C@@H]1OC(=O)OCC1(C)C] |
| 516 | 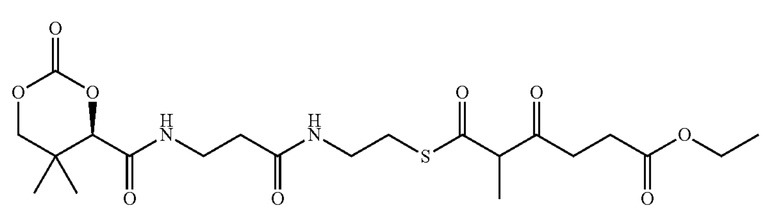 [SMILES: CCOC(=O)CCC(=O)C(C)C(=O)SCCNC(=O)CCNC(=O)[C@@H]1OC(=O)OCC1(C)C] |

TABLE 1-continued

| Compound No. | Structure |
| --- | --- |
| 517 | 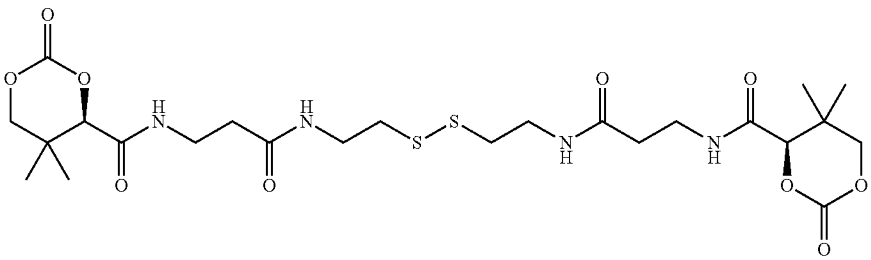 [SMILES: CC1(C)COC(=O)O[C@H]1C(=O)NCCC(=O)NCCSSCCNC(=O)CCNC(=O)[C@@H]1OC(=O)OCC1(C)C] |
| 518 | 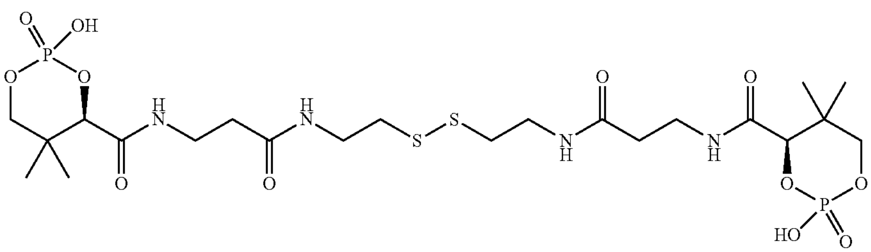 |
| 519 | 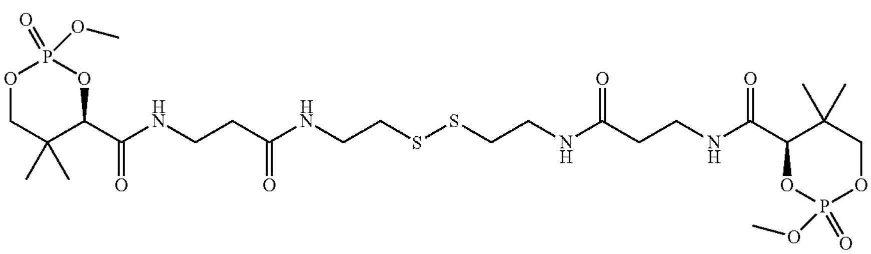 |
| 520 | 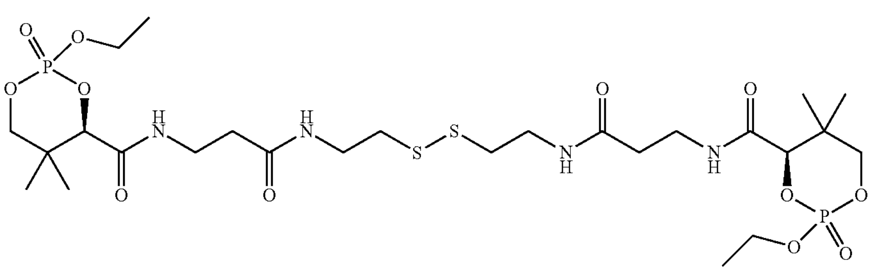 |
| 521 | 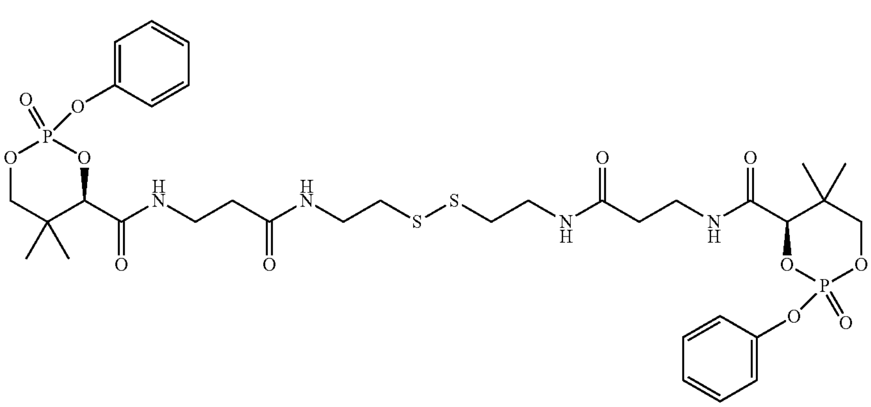 |

TABLE 1-continued
| Compound No. | Structure |
|---|---|
| 522 | 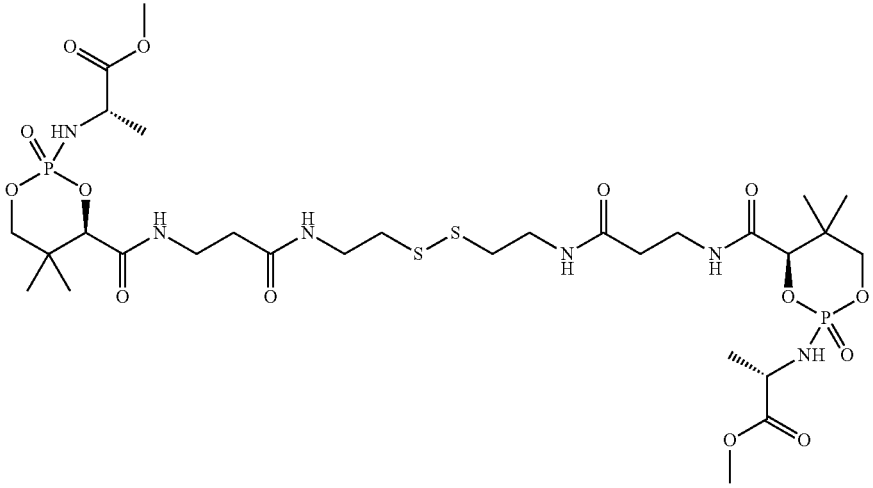 |
| 523 | 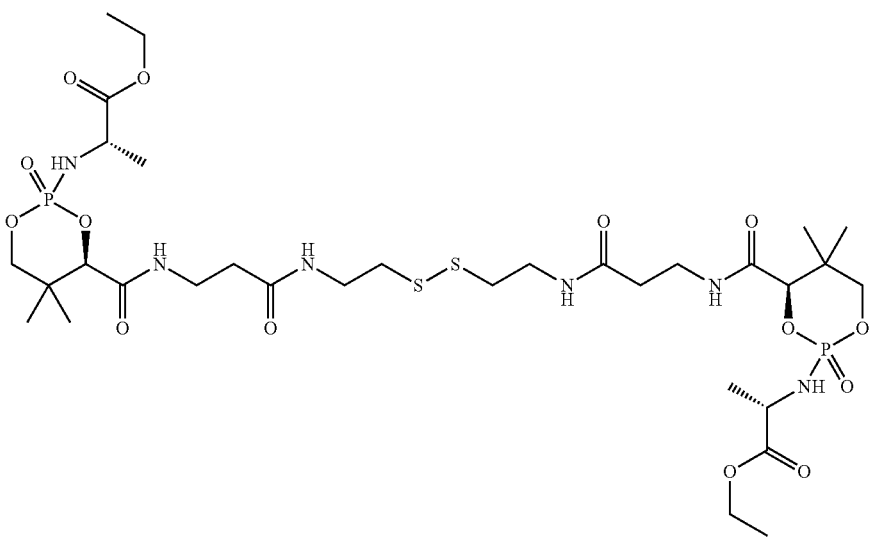 |
| 524 | 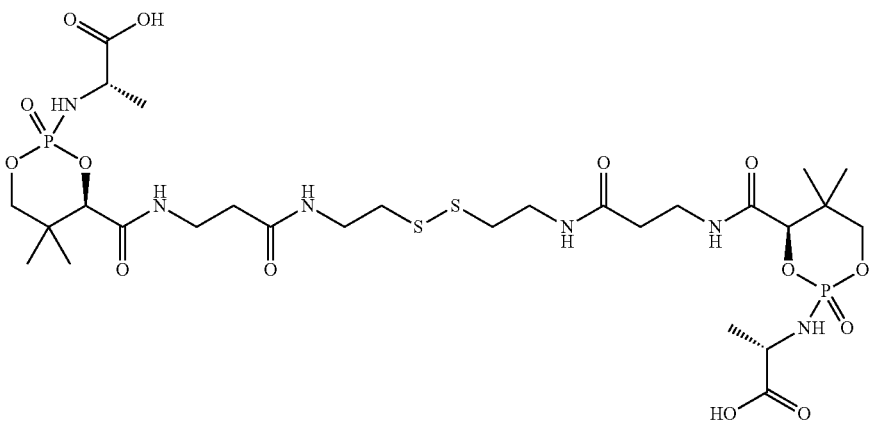 |

TABLE 1-continued

| Compound No. | Structure |
|---|---|
| 525 | 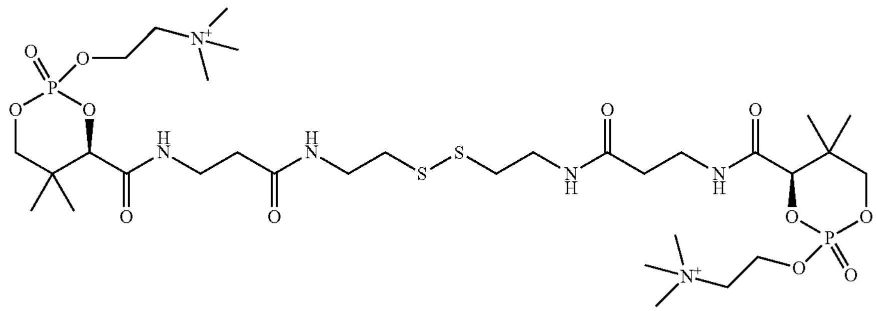 |
| 526 | 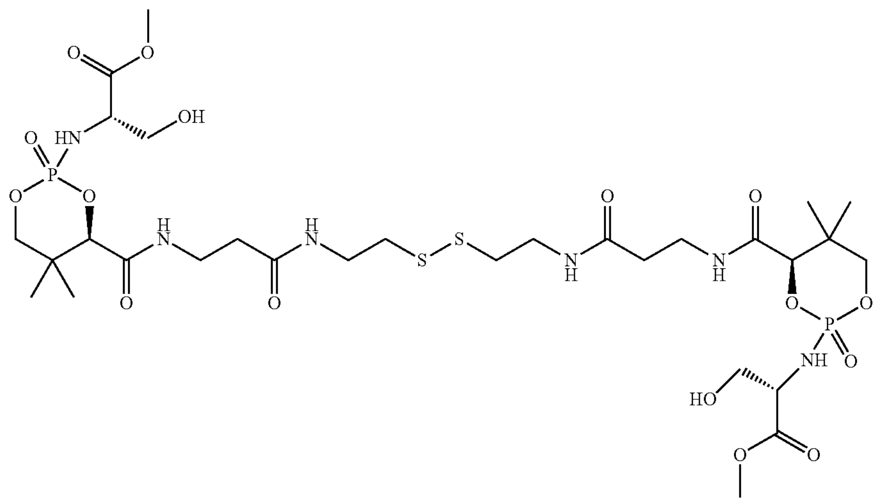 |
| 527 | 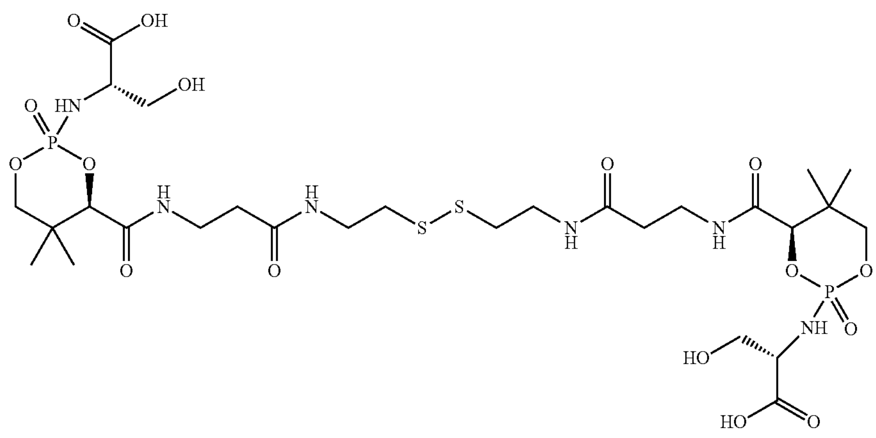 |
| 528 | 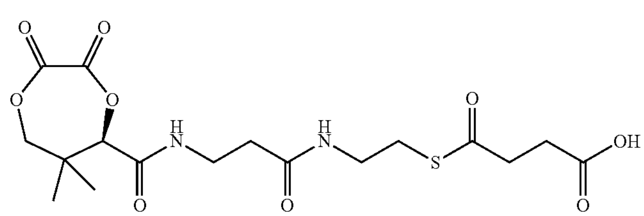 [SMILES: CC1(C)COC(=O)C(=O)O[C@H]1C(=O)NCCC(=O)NCCSC(=O)CCC(=O)O] |

TABLE 1-continued

| Compound No. | Structure |
|---|---|
| 529 | 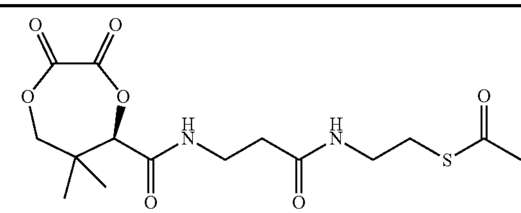 |
| 530 | 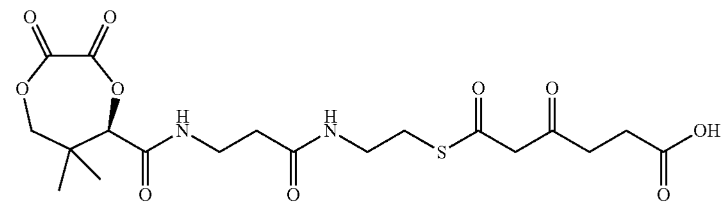 [SMILES: CC1(C)COC(=O)C(=O)O[C@H]1C(=O)NCCC(=O)NCCSC(=O)CC(=O)CCC(=O)O] |
| 531 | 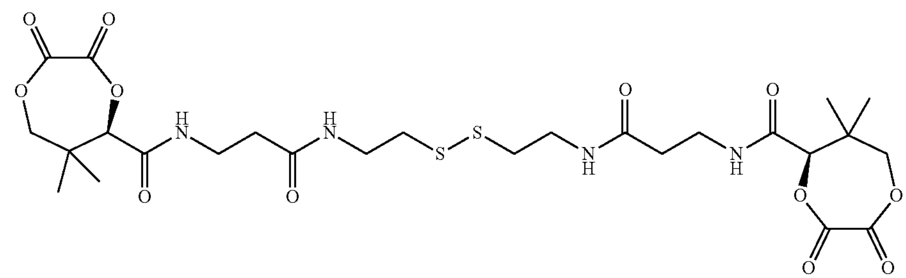 [SMILES: CC1(C)COC(=O)C(=O)O[C@H]1C(=O)NCCC(=O)NCCSSCCNC(=O)CCNC(=O)[C@@H]1OC(=O)C(=O)OCC1(C)C] |
| 532 | 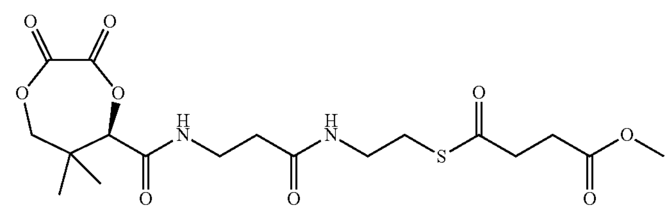 [SMILES: COC(=O)CCC(=O)SCCNC(=O)CCNC(=O)[C@@H]1OC(=O)C(=O)OCC1(C)C] |
| 533 | 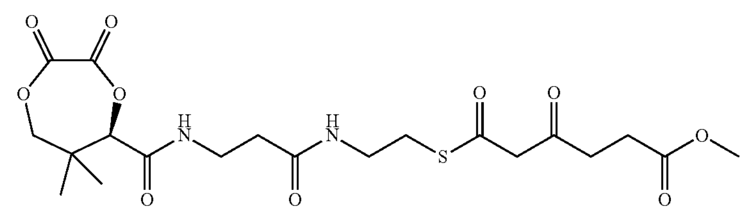 [SMILES: COC(=O)CCC(=O)CC(=O)SCCNC(=O)CCNC(=O)[C@@H]1OC(=O)C(=O)OCC1(C)C] |
| 534 | 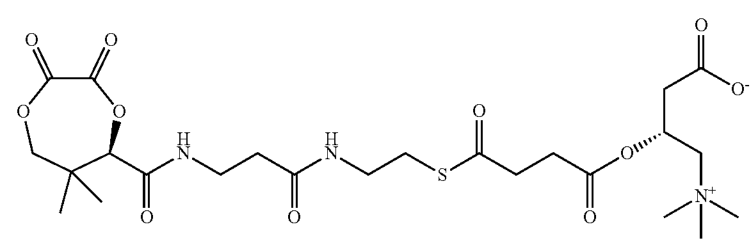 [SMILES: CC1(C)COC(=O)C(=O)O[C@H]1C(=O)NCCC(=O)NCCSC(=O)CCC(=O)O[C@H](CC(=O)[O-])C[N+](C)(C)C] |
| 535 | 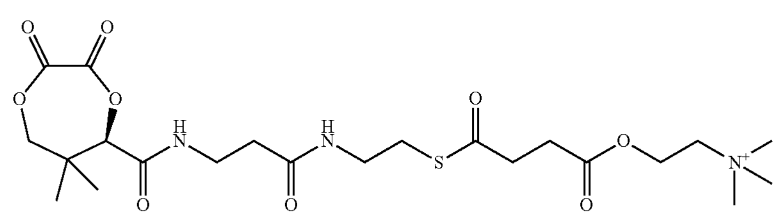 [SMILES: CC1(C)COC(=O)C(=O)O[C@H]1C(=O)NCCC(=O)NCCSC(=O)CCC(=O)OCC[N+](C)(C)C] |

TABLE 1-continued
| Compound No. | Structure |
|---|---|
| 536 | 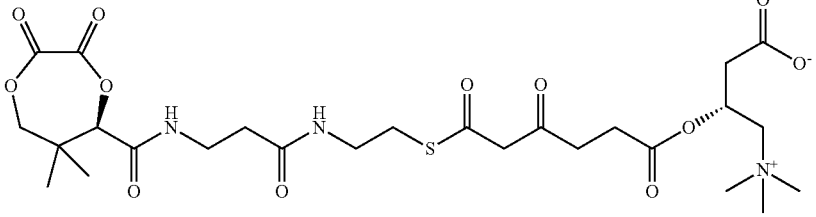 |
| 537 | 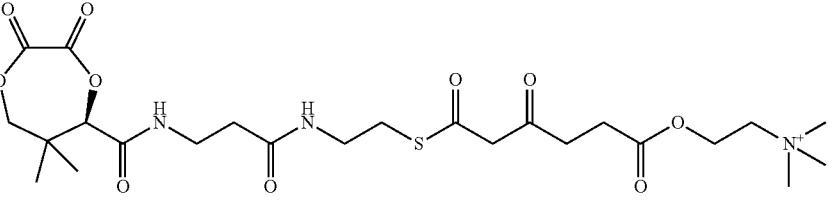 |
| 538 | 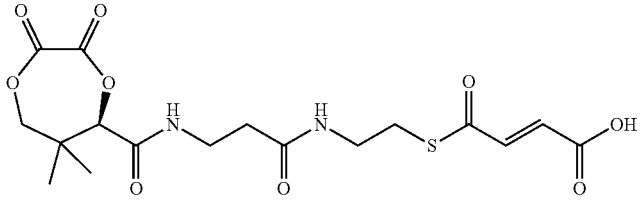 [SMILES: CC1(C)COC(=O)C(=O)O[C@H]1C(=O)NCCC(=O)NCCSC(=O)/C=C/C(=O)O] |
| 539 | 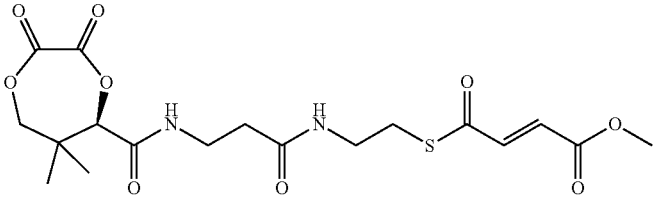 [SMILES: COC(=O)/C=C/C(=O)SCCNC(=O)CCNC(=O)[C@@H]1OC(=O)C(=O)OCC1(C)C] |
| 540 | 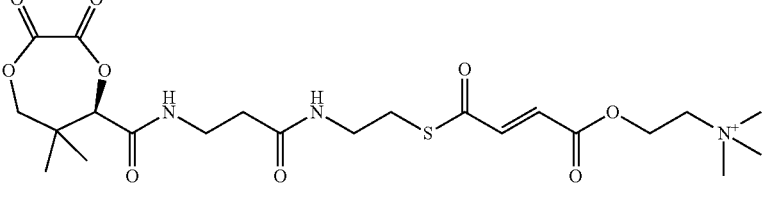 |
| 541 | 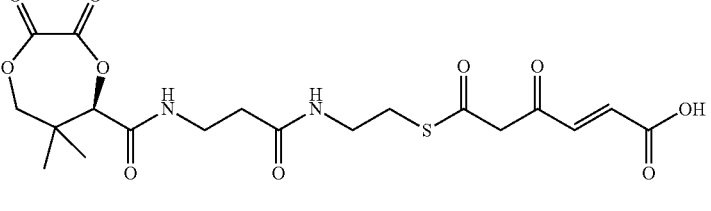 |
| 542 | 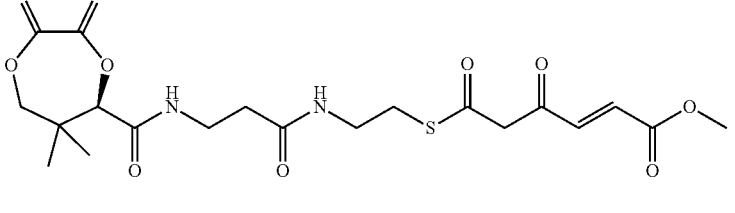 |

TABLE 1-continued

| Compound No. | Structure |
|---|---|
| 543 | (structure) |
| 544 | (structure) |
| 545 | (structure) |
| 546 | (structure) |
| 547 | (structure) |
| 548 | (structure) |
| 549 | (structure) |

TABLE 1-continued

| Compound No. | Structure |
|---|---|
| 550 | 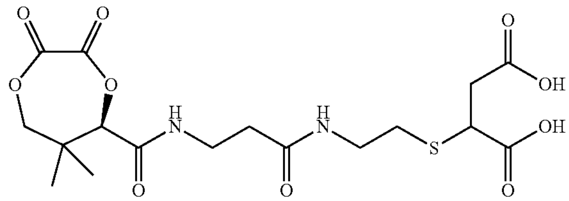 [SMILES: CC1(C)COC(=O)C(=O)O[C@H]1C(=O)NCCC(=O)NCCSC(CC(=O)O)C(=O)O] |
| 551 | 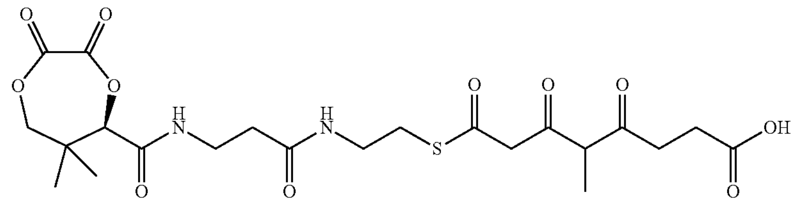 [SMILES: CC(C(=O)CCC(=O)O)C(=O)CC(=O)SCCNC(=O)CCNC(=O)[C@@H]1OC(=O)C(=O)OCC1(C)C] |
| 552 | 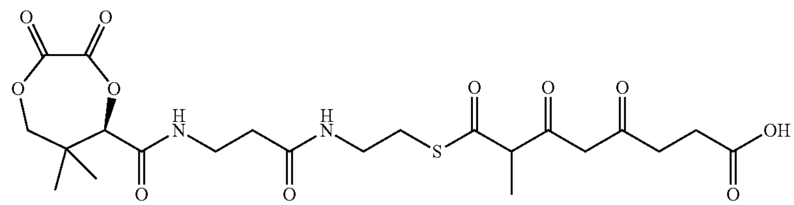 [SMILES: CC(C(=O)CC(=O)CCC(=O)O)C(=O)SCCNC(=O)CCNC(=O)[C@@H]1OC(=O)C(=O)OCC1(C)C] |
| 553 | 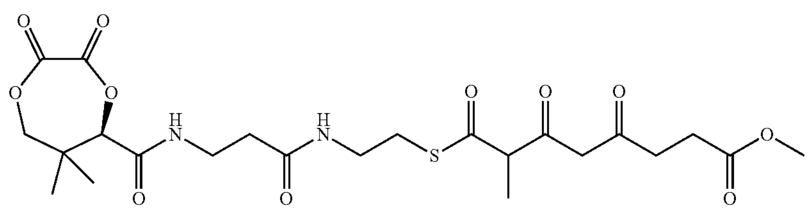 [SMILES: COC(=O)CCC(=O)CC(=O)C(C)C(=O)SCCNC(=O)CCNC(=O)[C@@H]1OC(=O)C(=O)OCC1(C)C] |
| 554 | 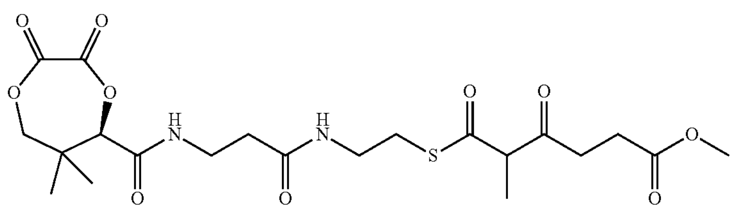 [SMILES: COC(=O)CCC(=O)C(C)C(=O)SCCNC(=O)CCNC(=O)[C@@H]1OC(=O)C(=O)OCC1(C)C] |
| 555 | 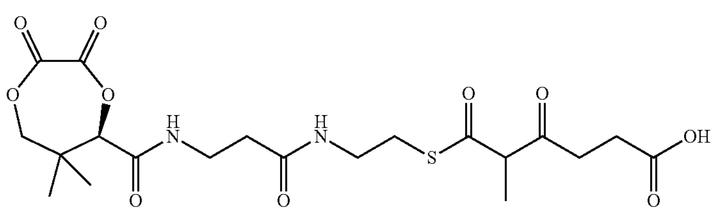 [SMILES: CC(C(=O)CCC(=O)O)C(=O)SCCNC(=O)CCNC(=O)[C@@H]1OC(=O)C(=O)OCC1(C)C] |
| 556 | 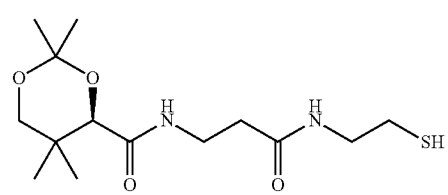 [SMILES: CC1(C)OCC(C)(C)[C@H](C(=O)NCCC(=O)NCCS)O1] |

TABLE 1-continued
| Compound No. | Structure |
|---|---|
| 557 | 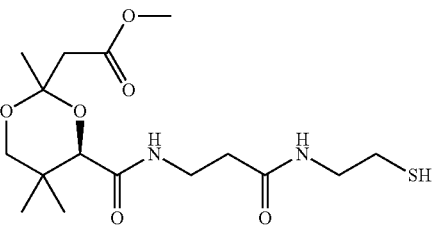 |
| 558 | 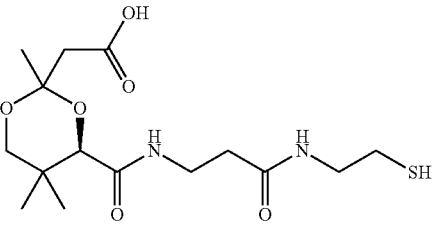 |
| 559 | 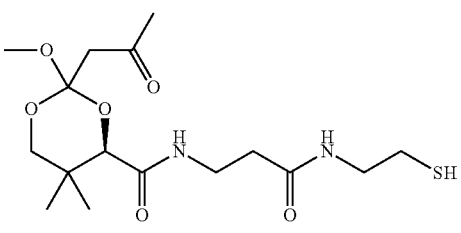 |
| 560 | 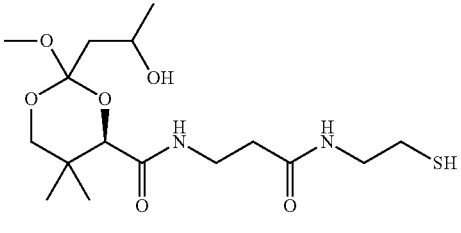 |
| 561 | 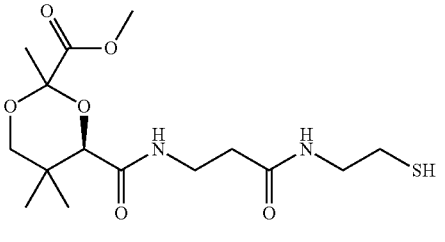 |
| 562 | 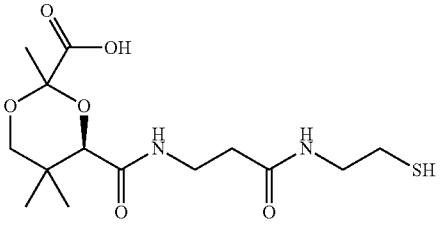 |

TABLE 1-continued

| Compound No. | Structure |
|---|---|
| 563 | 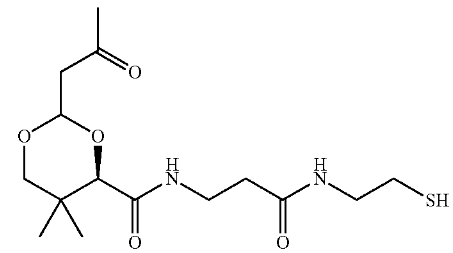 |
| 564 | 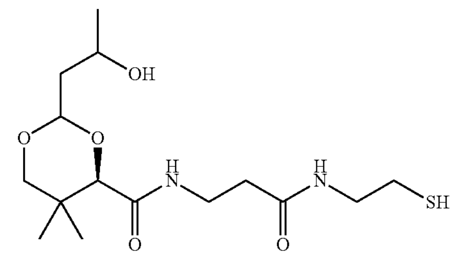 |
| 565 | 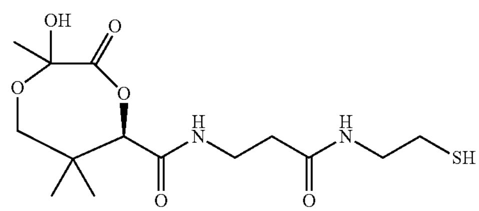 |
| 566 | 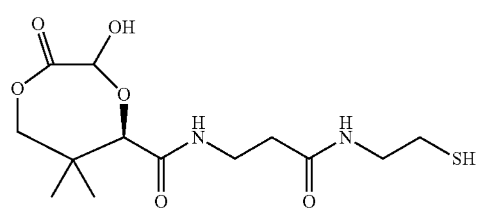 |
| 567 | 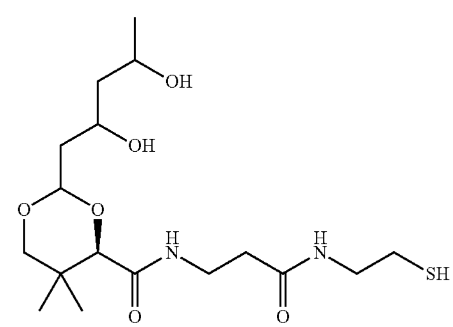 |

TABLE 1-continued

| Compound No. | Structure |
|---|---|
| 568 | *(chemical structure)* |
| 569 | *(chemical structure)* |
| 570 | *(chemical structure)* |
| 571 | *(chemical structure)* |

TABLE 1-continued
| Compound No. | Structure |
|---|---|
| 572 | 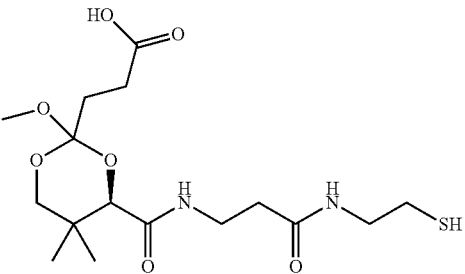 |
| 573 | 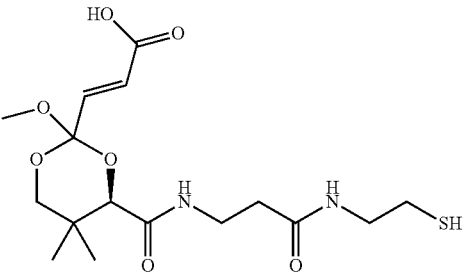 |
| 574 | 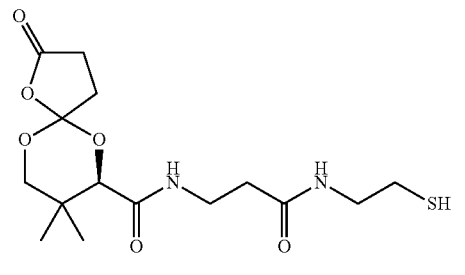 |
| 575 | 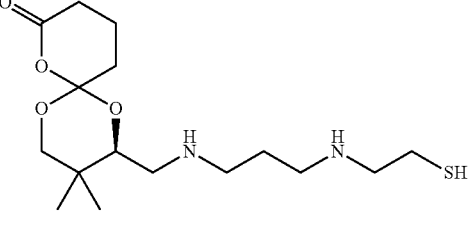 |
| 576 | 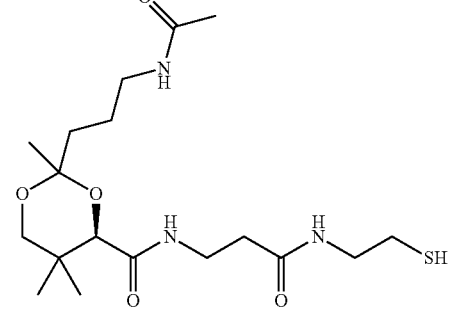 |
| 577 | 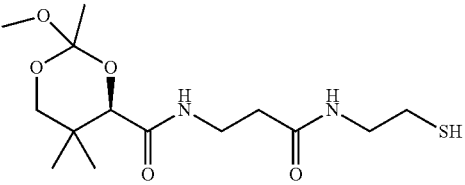 |

TABLE 1-continued
| Compound No. | Structure |
|---|---|
| 578 | 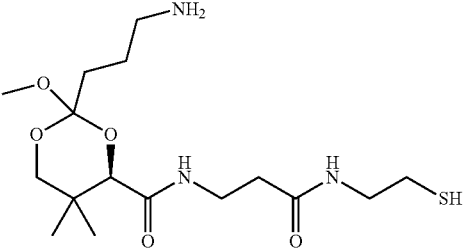 |
| 579 | 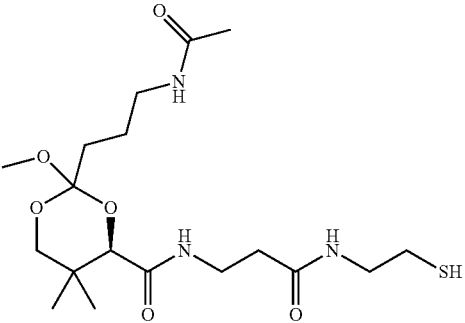 |
| 580 | 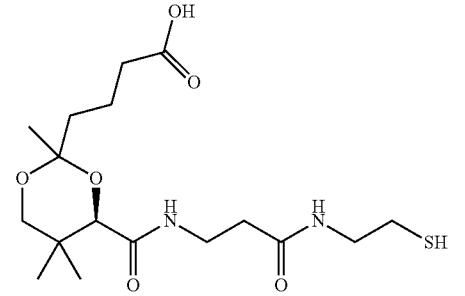 |
| 581 | 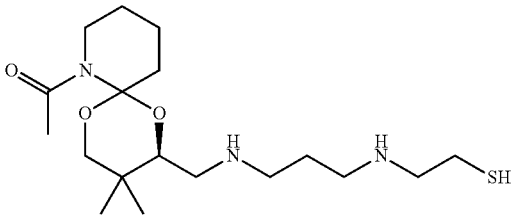 |
| 582 | 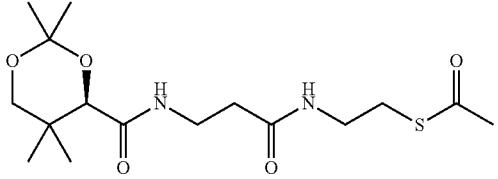 [SMILES: CC(=O)SCCNC(=O)CCNC(=O)[C@@H]1OC(C)(C)OCC1(C)C] |
| 583 | 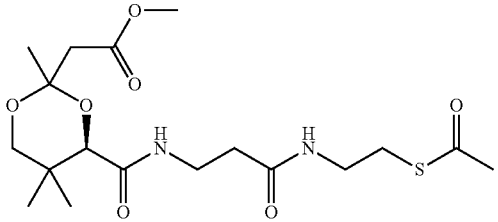 |

TABLE 1-continued
| Compound No. | Structure |
|---|---|
| 584 | 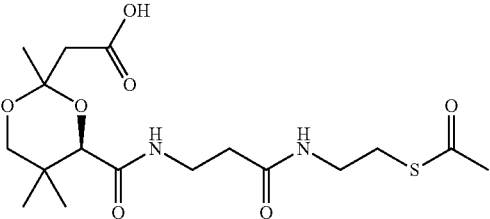 |
| 585 | 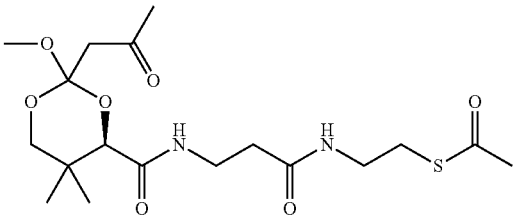 |
| 586 | 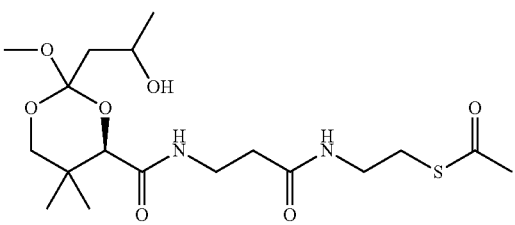 |
| 587 | 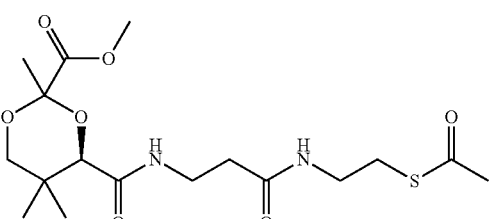 |
| 588 | 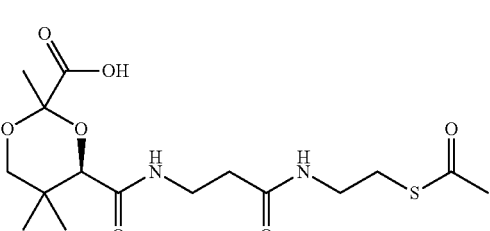 |
| 589 | 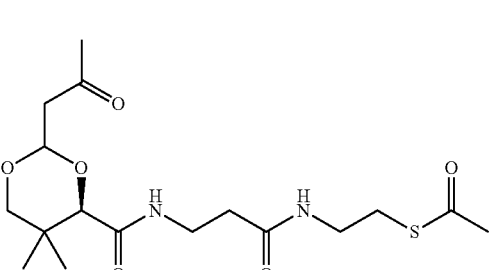 |

TABLE 1-continued
| Compound No. | Structure |
|---|---|
| 590 | 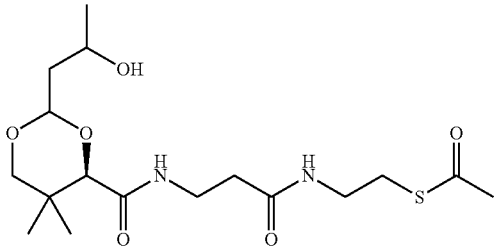 |
| 591 | 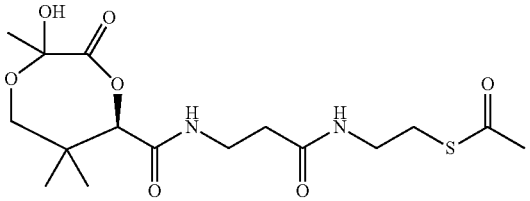 |
| 592 | 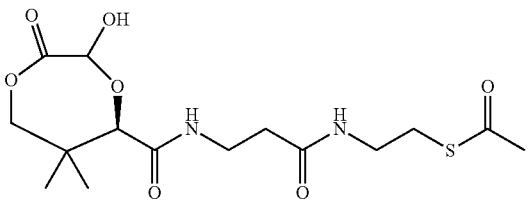 |
| 593 | 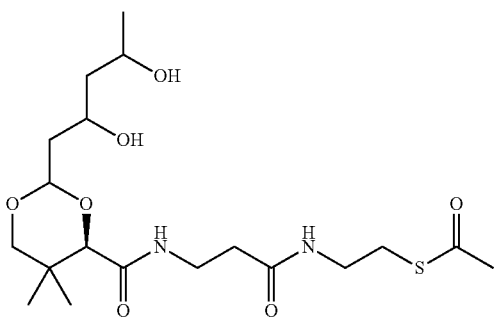 |
| 594 | 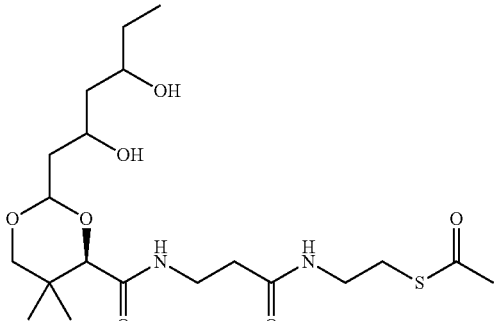 |

TABLE 1-continued

| Compound No. | Structure |
|---|---|
| 595 | 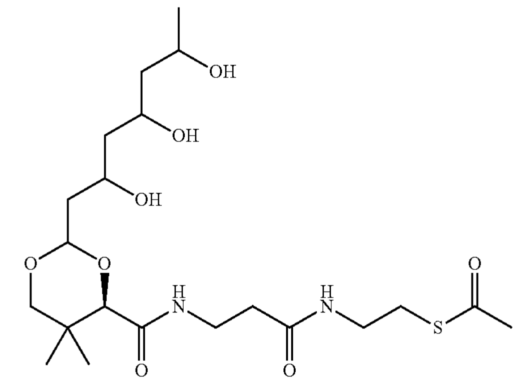 |
| 596 | 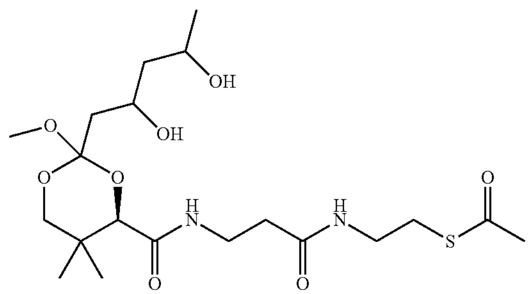 |
| 597 | 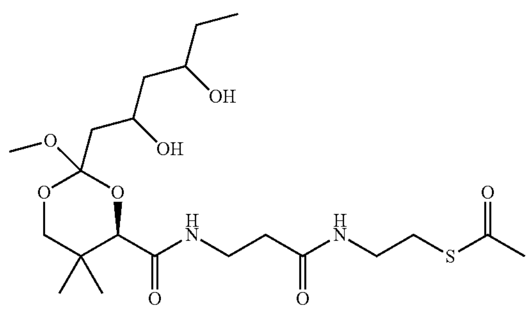 |
| 598 | 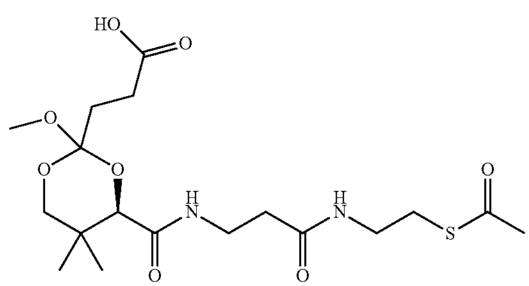 |
| 599 | 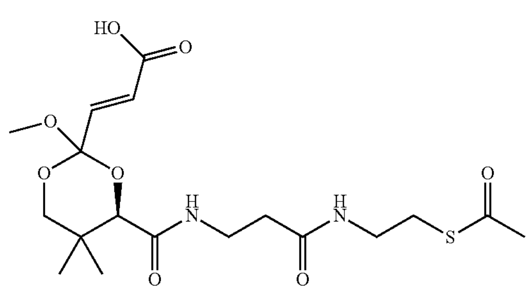 |

TABLE 1-continued
| Compound No. | Structure |
|---|---|
| 600 | 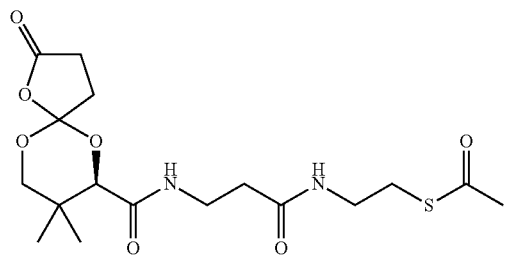 |
| 601 | 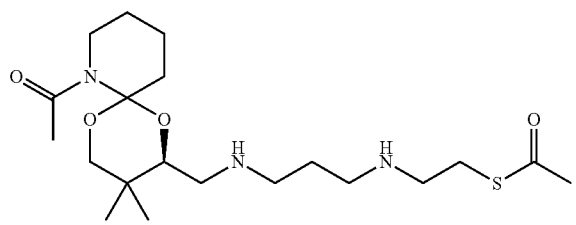 |
| 602 | 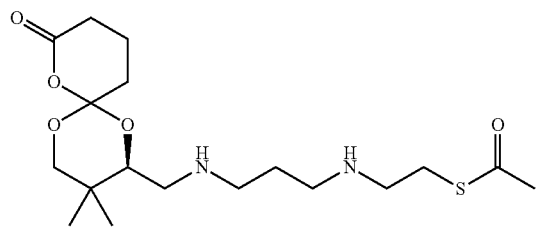 |
| 603 | 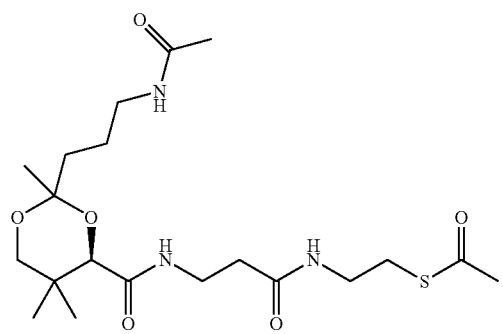 |
| 604 | 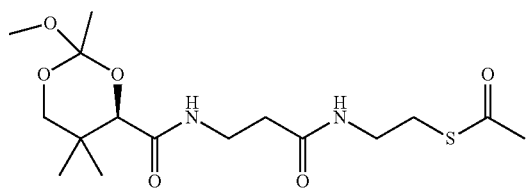 |
| 605 | 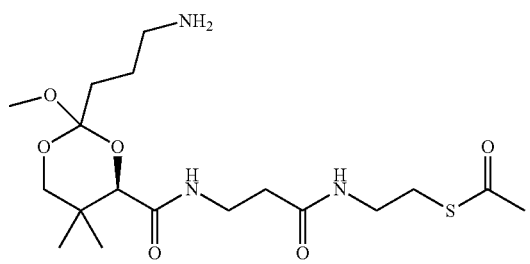 |

TABLE 1-continued

| Compound No. | Structure |
|---|---|
| 606 | 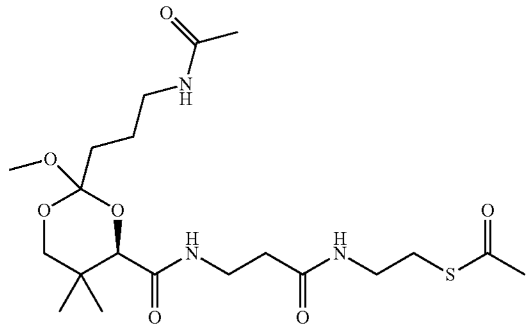 |
| 607 | 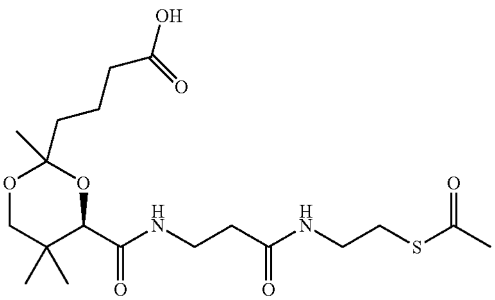 |
| 608 | 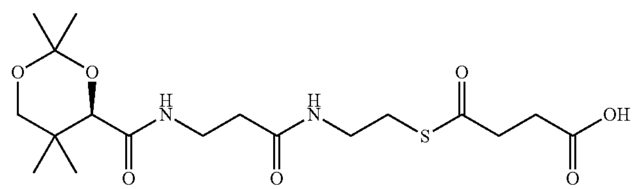 [SMILES: CC1(C)OCC(C)(C)[C@H](C(=O)NCCC(=O)NCCSC(=O)CCC(=O)O)O1] |
| 609 | 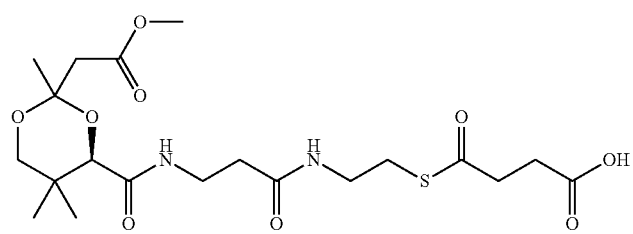 |
| 610 | 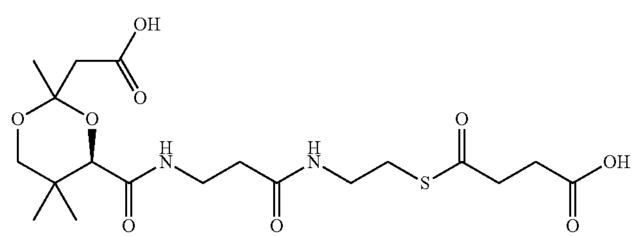 |
| 611 | 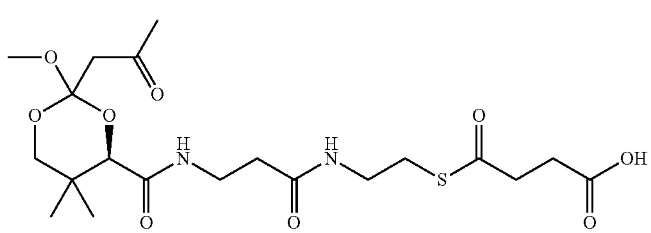 |

TABLE 1-continued
| Compound No. | Structure |
|---|---|
| 612 | 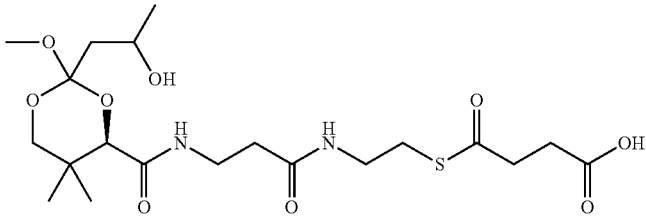 |
| 613 | 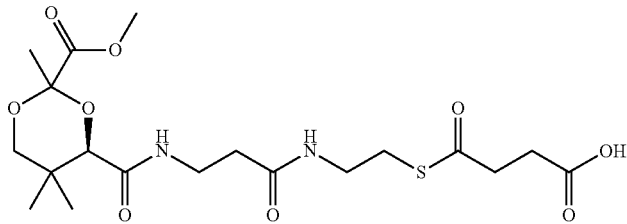 |
| 614 | 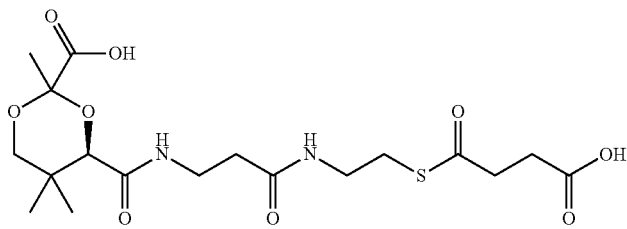 |
| 615 | 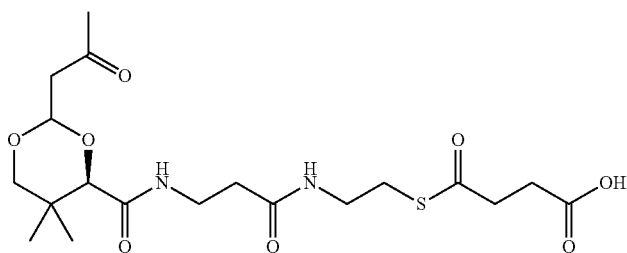 |
| 616 | 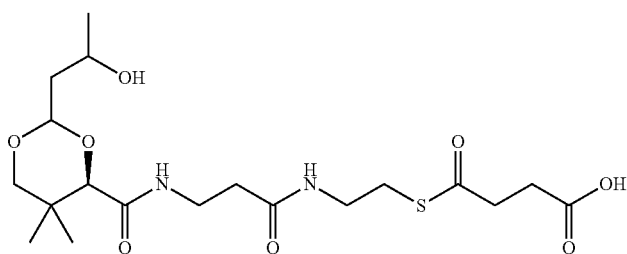 |
| 617 | 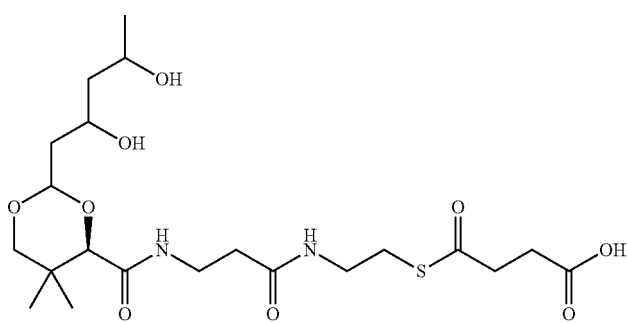 |

TABLE 1-continued

| Compound No. | Structure |
|---|---|
| 618 | 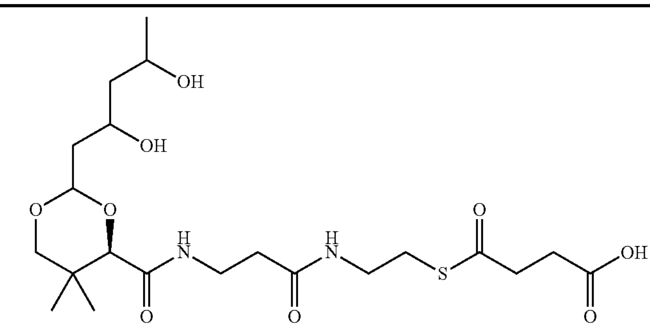 |
| 619 | 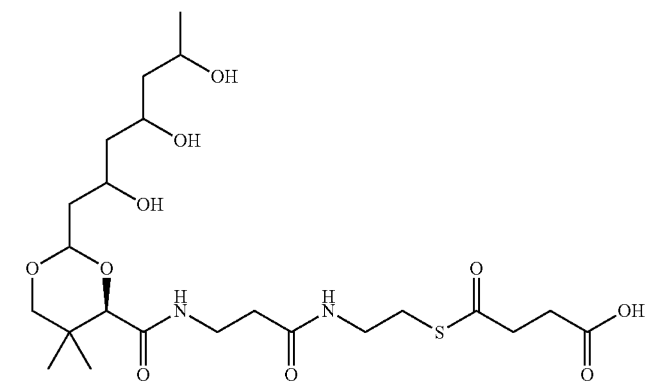 |
| 620 | 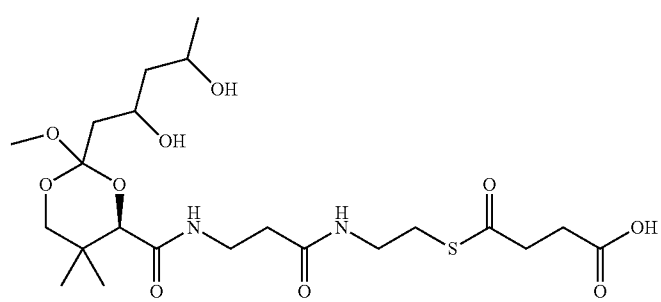 |
| 621 | 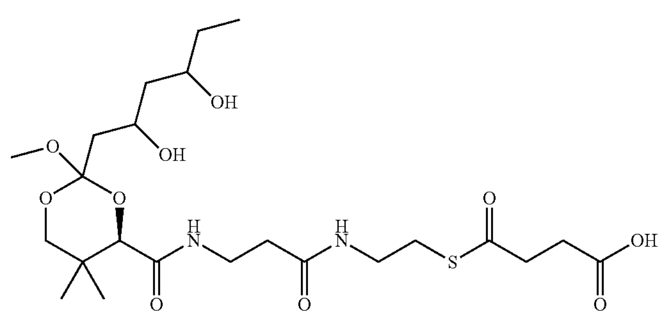 |
| 622 | 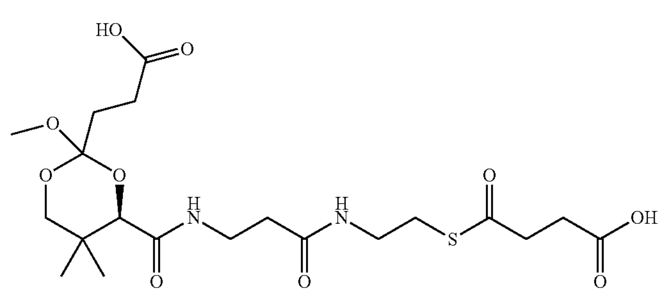 |

TABLE 1-continued
| Compound No. | Structure |
|---|---|
| 623 | 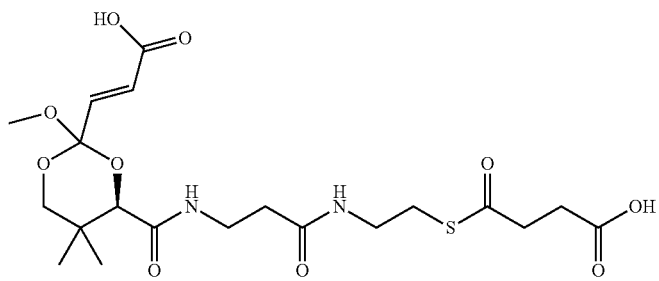 |
| 624 | 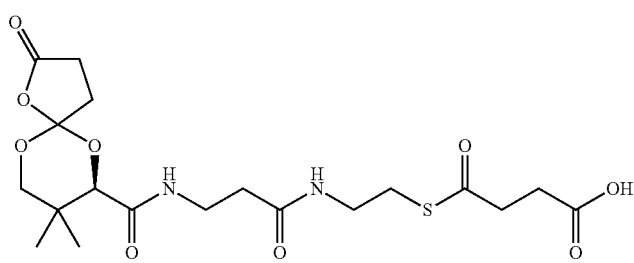 |
| 625 | 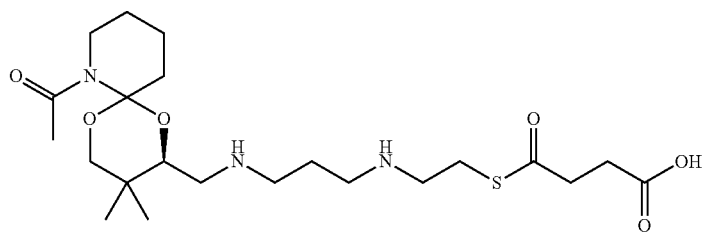 |
| 626 | 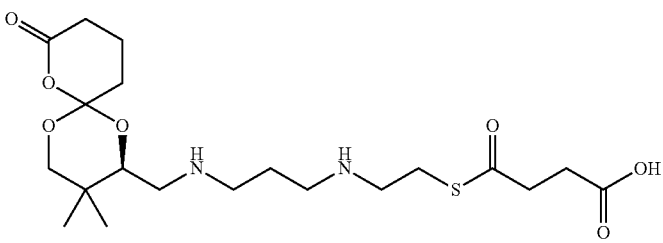 |
| 627 | 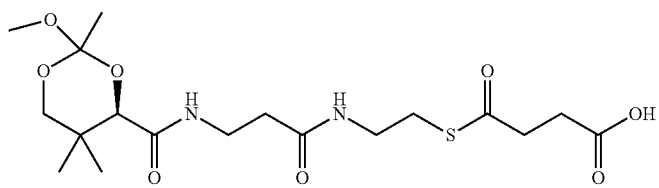 |
| 628 | 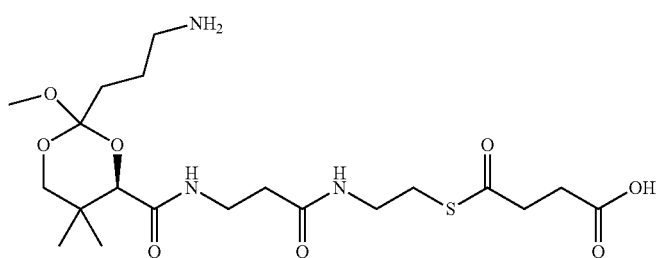 |

| Compound No. | Structure |
|---|---|
| 629 | 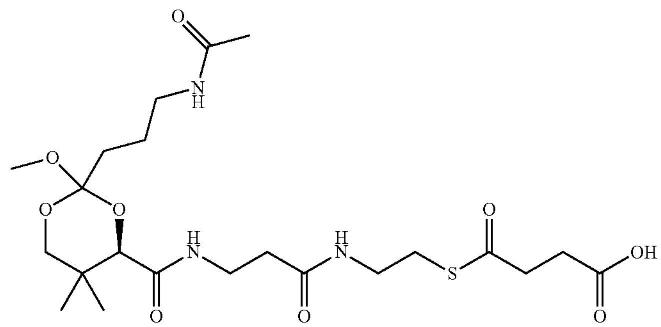 |
| 630 | 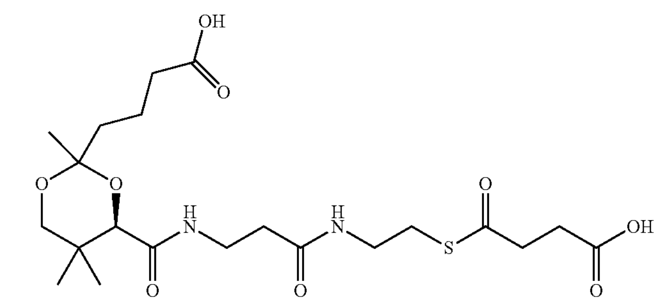 |
| 631 | 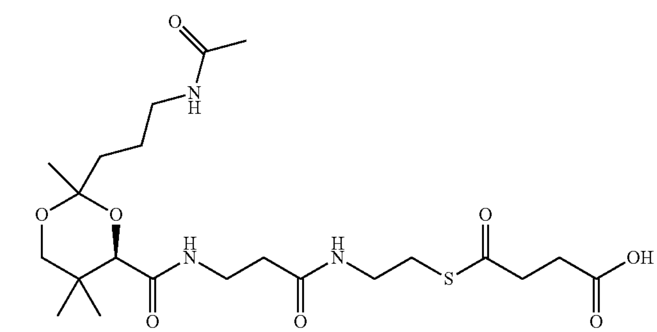 |
| 632 | 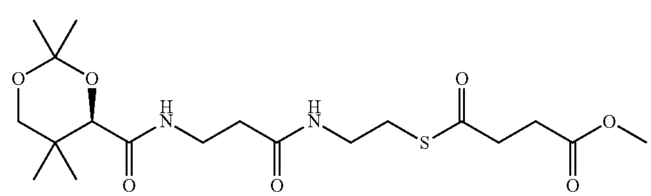 [SMILES: COC(=O)CCC(=O)SCCNC(=O)CCNC(=O)[C@@H]1OC(C)(C)OCC1(C)C] |
| 633 | 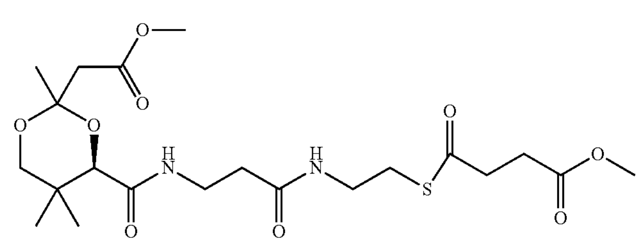 |

TABLE 1-continued
| Compound No. | Structure |
|---|---|
| 634 | 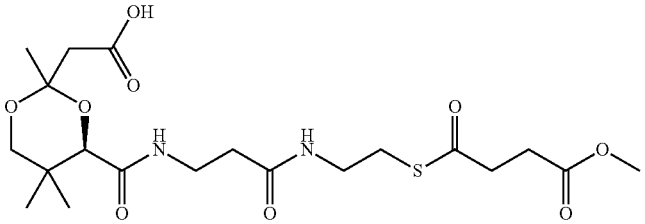 |
| 635 | 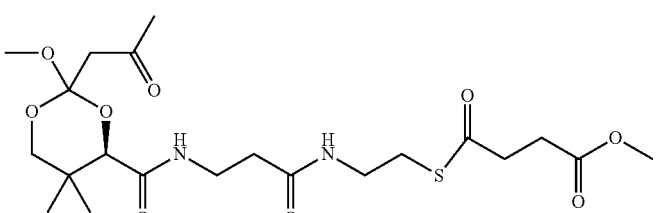 |
| 636 | 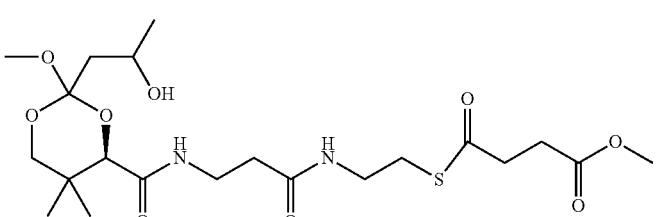 |
| 637 | 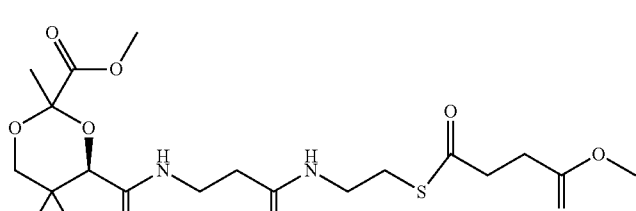 |
| 638 | 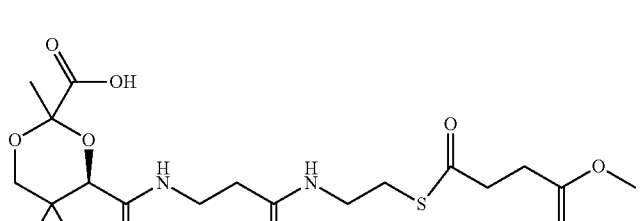 |
| 639 | 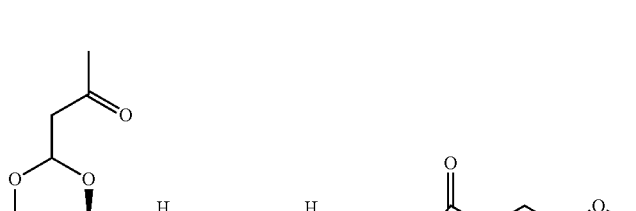 |

TABLE 1-continued

| Compound No. | Structure |
|---|---|
| 640 | 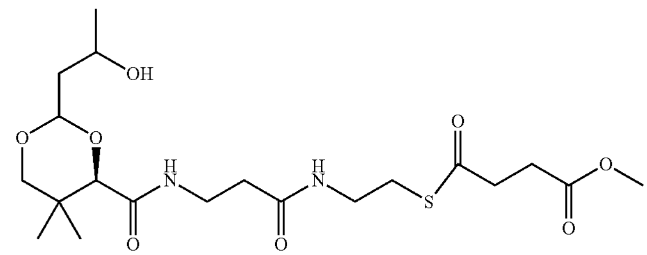 |
| 641 | 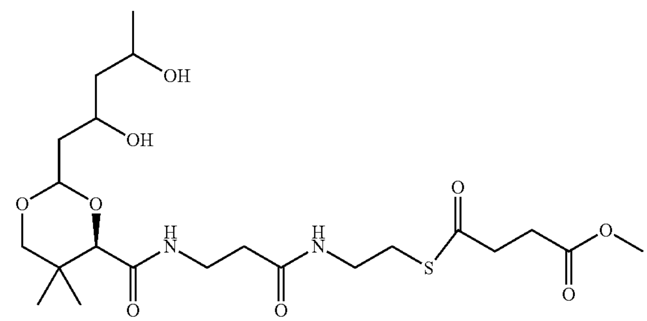 |
| 642 | 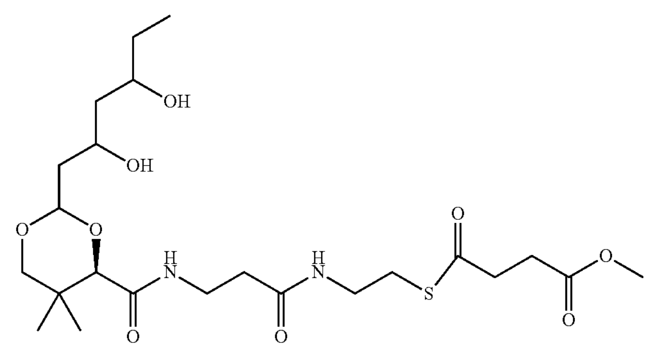 |
| 643 | 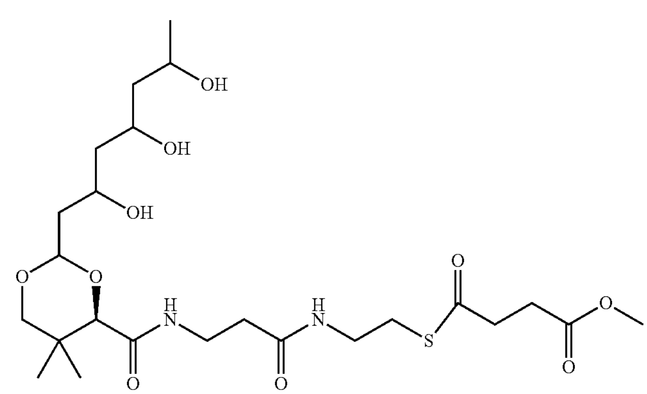 |

TABLE 1-continued

| Compound No. | Structure |
|---|---|
| 644 | 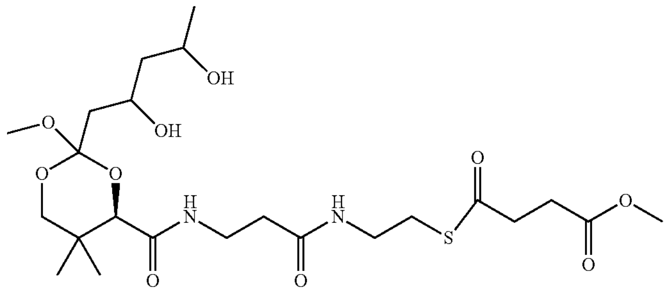 |
| 645 | 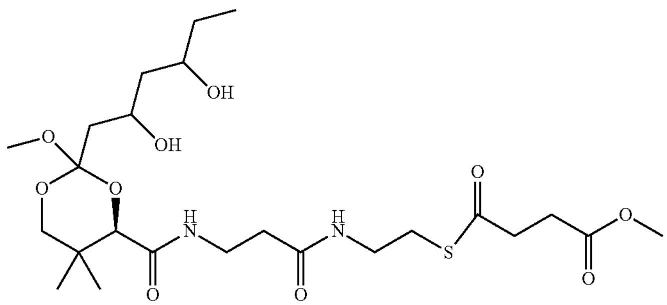 |
| 646 | 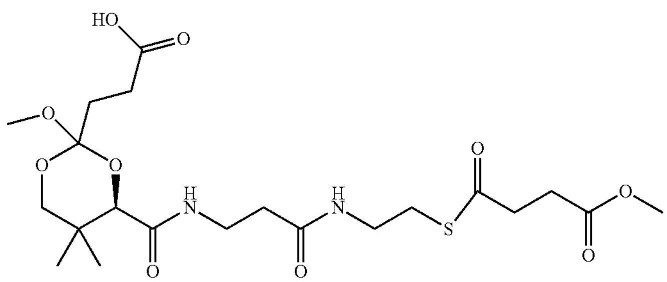 |
| 647 | 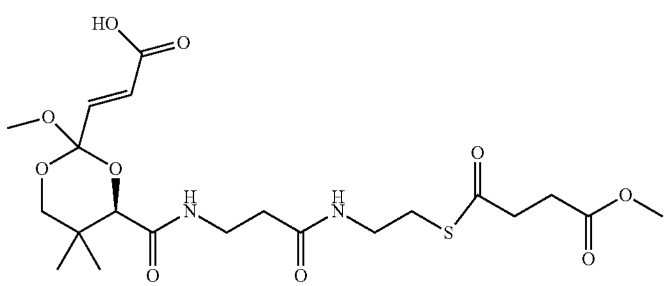 |
| 648 | 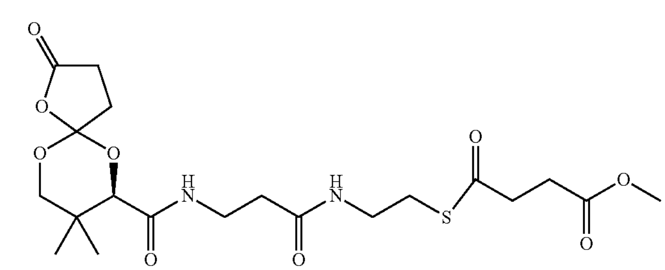 |

TABLE 1-continued

| Compound No. | Structure |
|---|---|
| 649 | 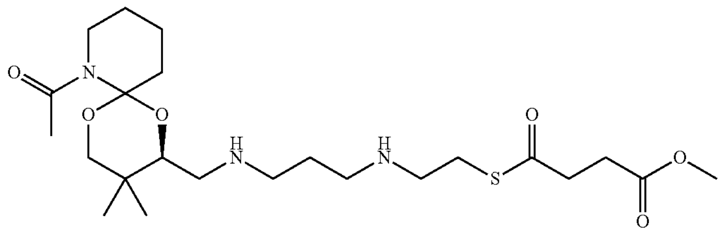 |
| 650 | 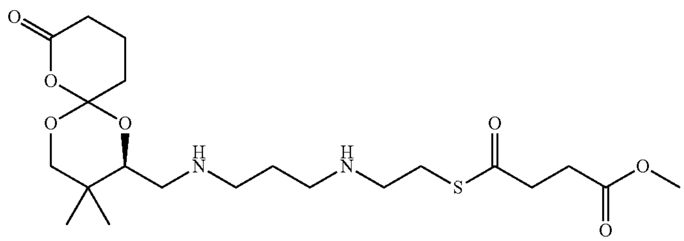 |
| 651 | 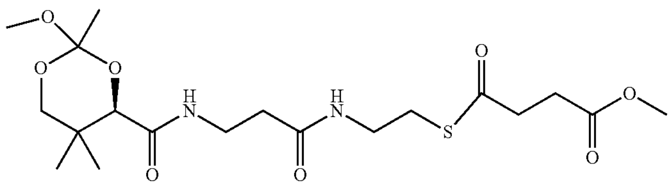 |
| 652 | 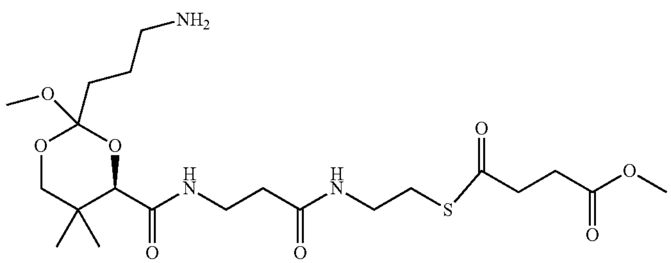 |
| 653 | 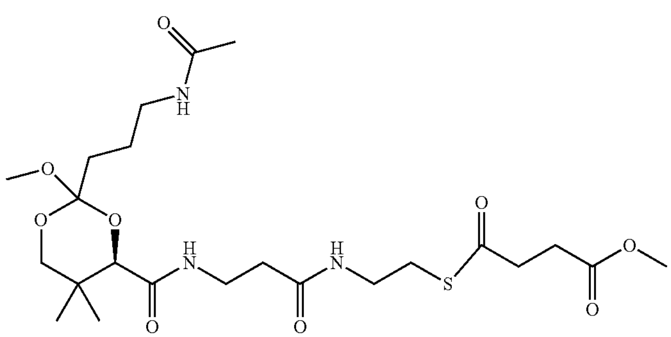 |
| 654 | 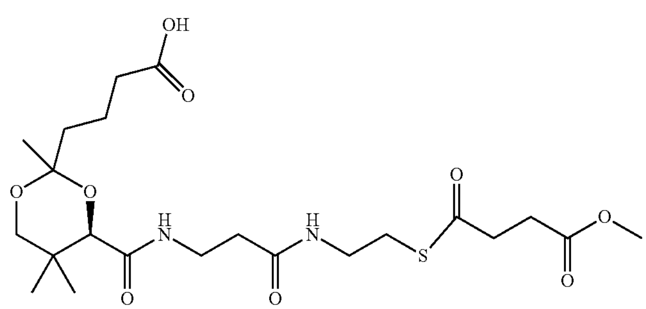 |

TABLE 1-continued
| Compound No. | Structure |
|---|---|
| 655 | 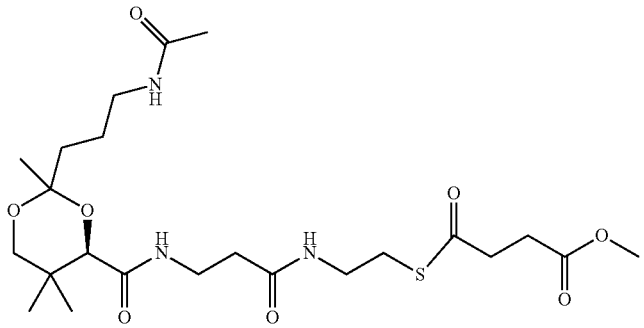 |
| 656 | 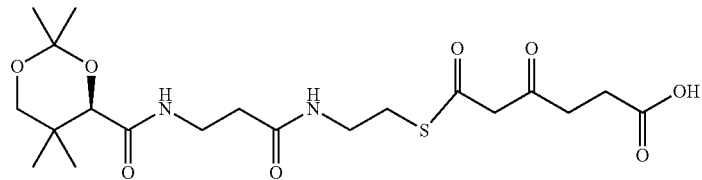 [SMILES: CC1(C)OCC(C)(C)[C@H](C(=O)NCCC(=O)NCCSC(=O)CC(=O)CCC(=O)O)O1] |
| 657 | 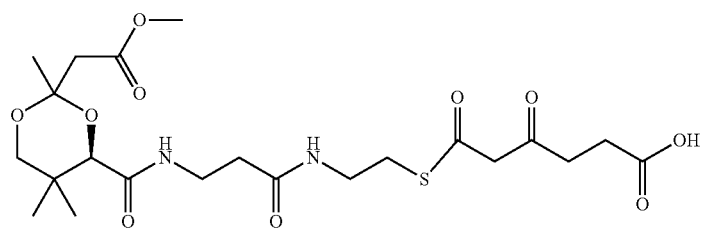 |
| 658 | 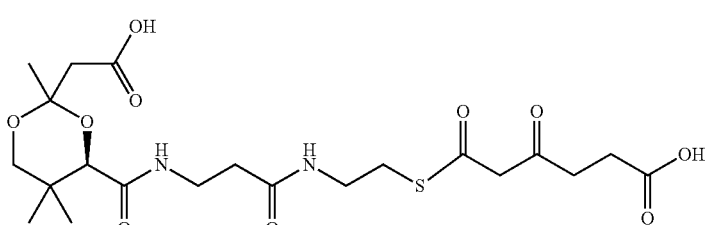 |
| 659 | 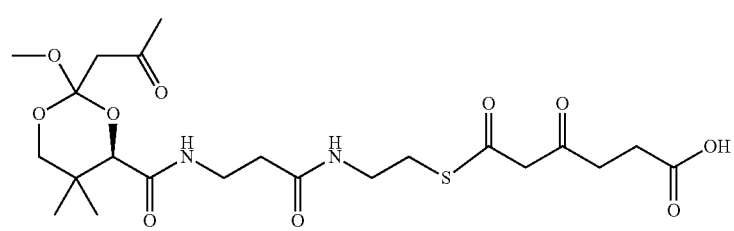 |
| 660 | 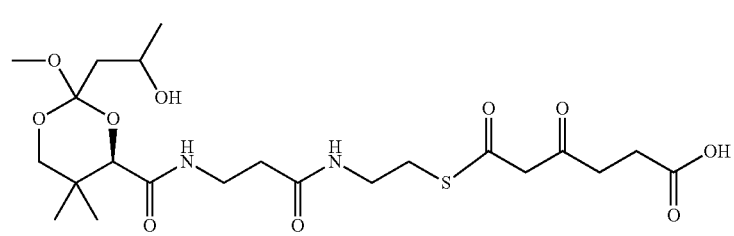 |

TABLE 1-continued
| Compound No. | Structure |
|---|---|
| 661 | 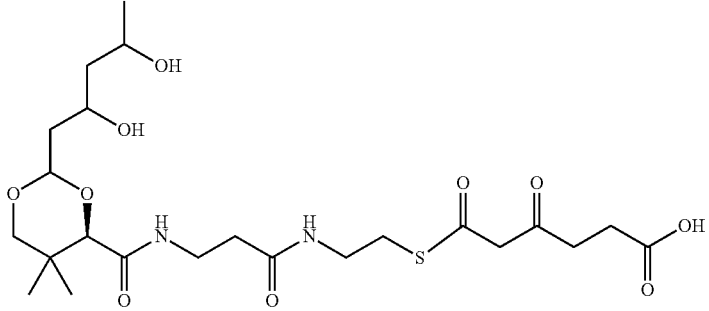 |
| 662 | 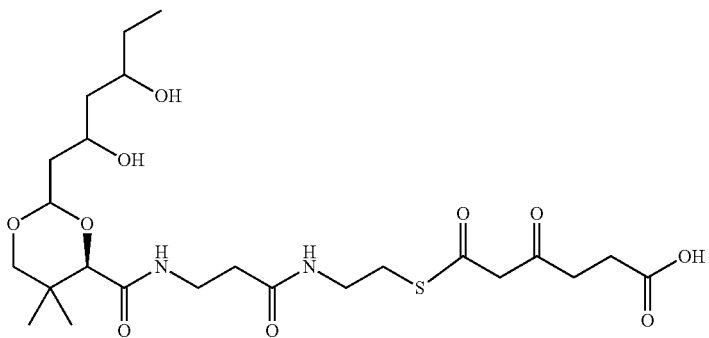 |
| 663 | 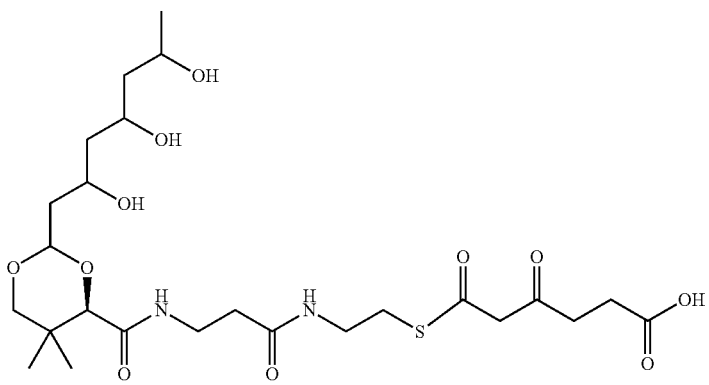 |
| 664 | 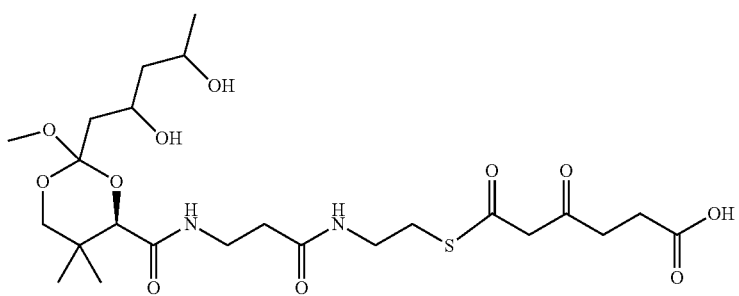 |

TABLE 1-continued

| Compound No. | Structure |
|---|---|
| 665 | 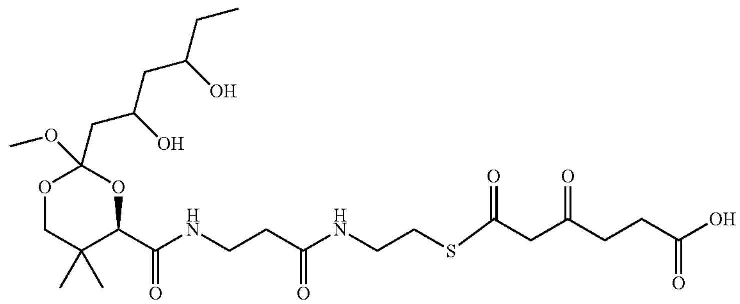 |
| 666 | 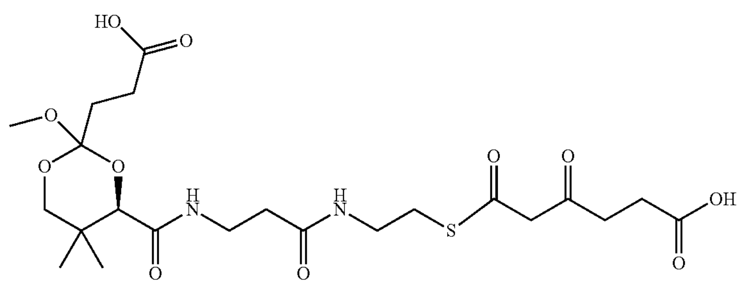 |
| 667 | 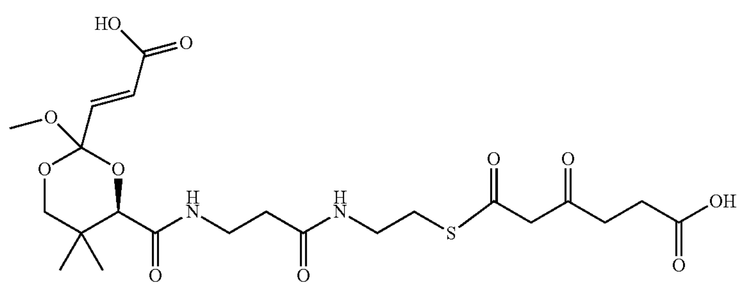 |
| 668 | 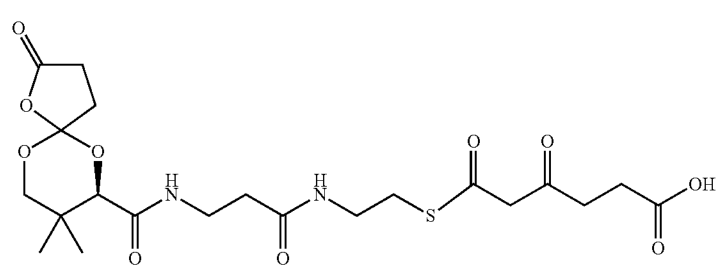 |
| 669 | 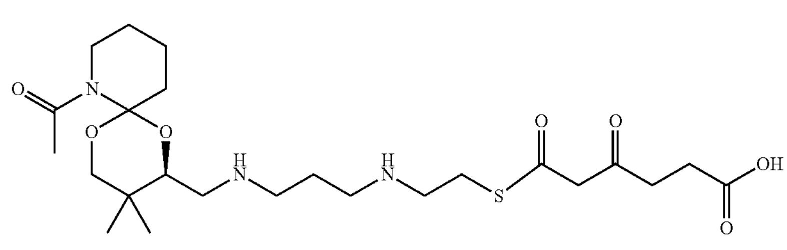 |

TABLE 1-continued

| Compound No. | Structure |
|---|---|
| 670 | 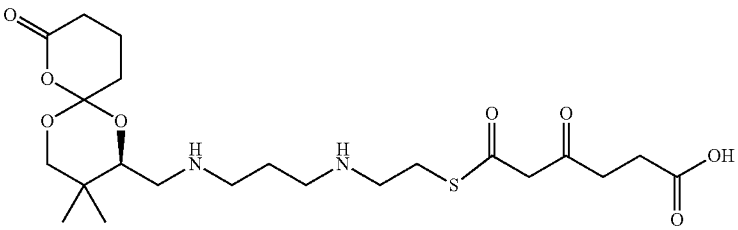 |
| 671 | 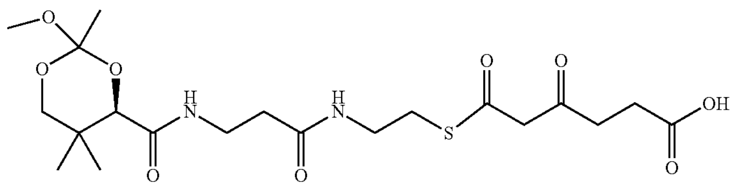 |
| 672 | 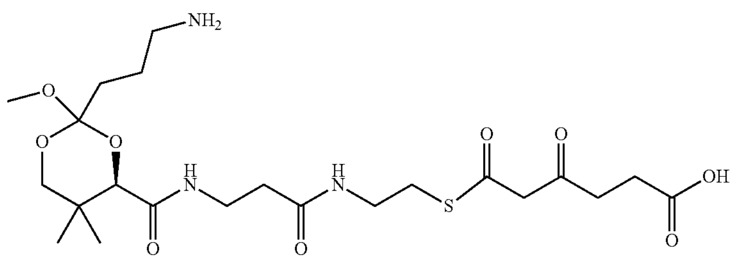 |
| 673 | 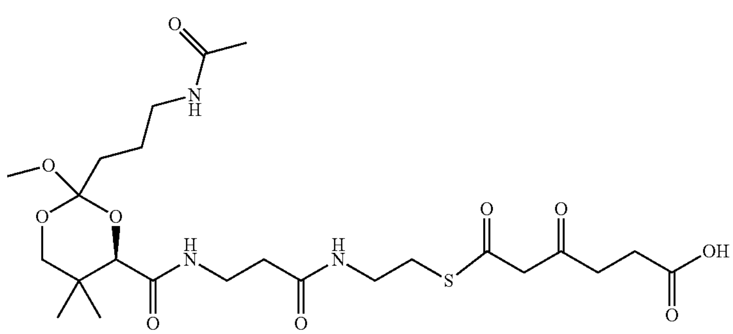 |
| 674 | 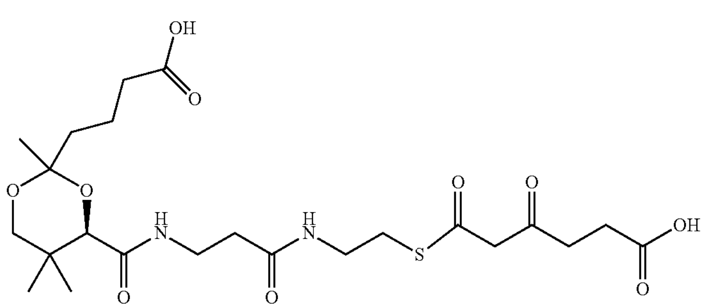 |

TABLE 1-continued

| Compound No. | Structure |
|---|---|
| 675 | 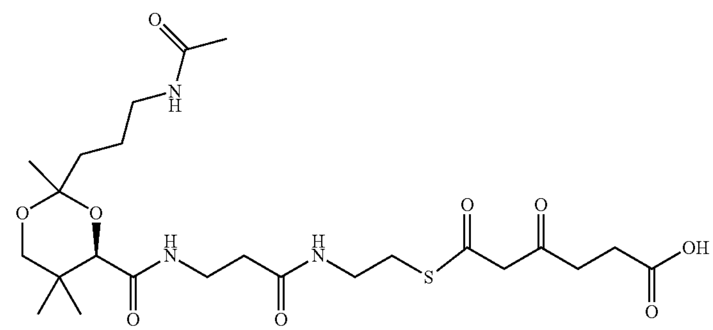 |
| 676 | 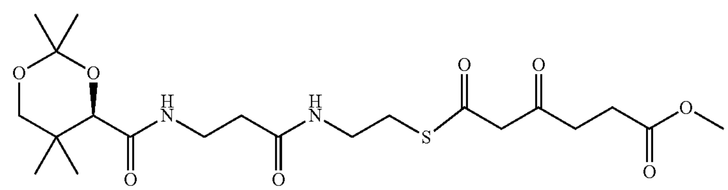 [SMILES: COC(=O)CCC(=O)CC(=O)SCCNC(=O)CCNC(=O)[C@@H]1OC(C)(C)OCC1(C)C] |
| 677 | 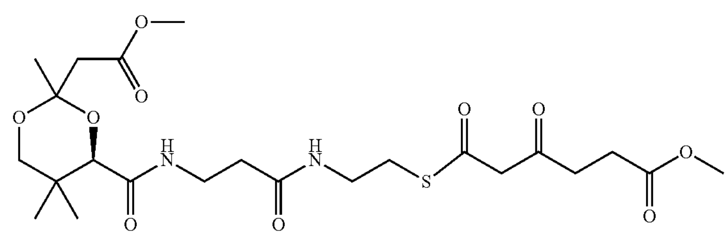 |
| 678 | 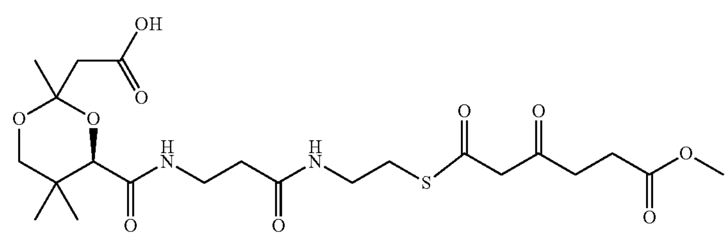 |
| 679 | 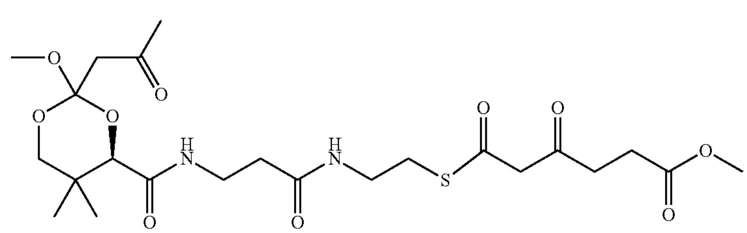 |
| 680 | 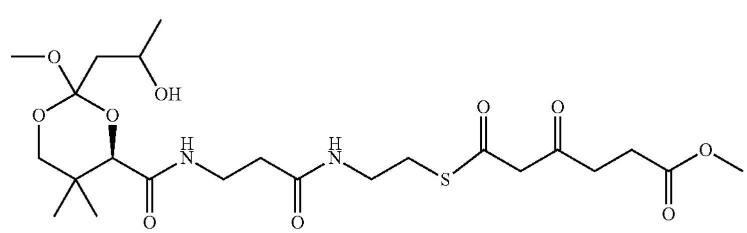 |

TABLE 1-continued
| Compound No. | Structure |
|---|---|
| 681 | 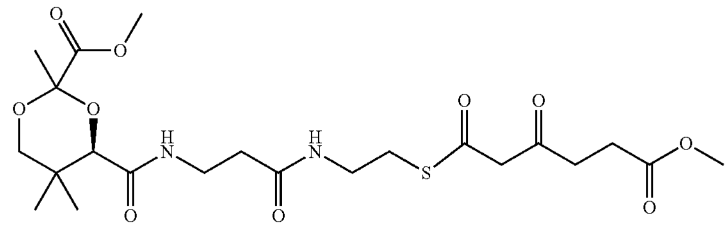 |
| 682 | 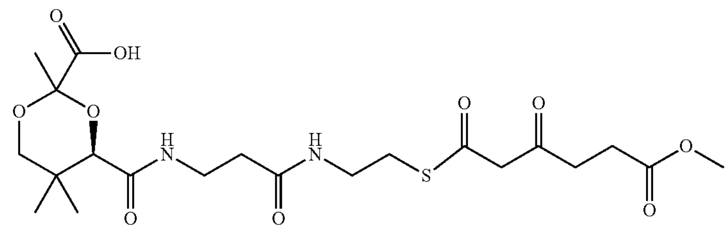 |
| 683 | 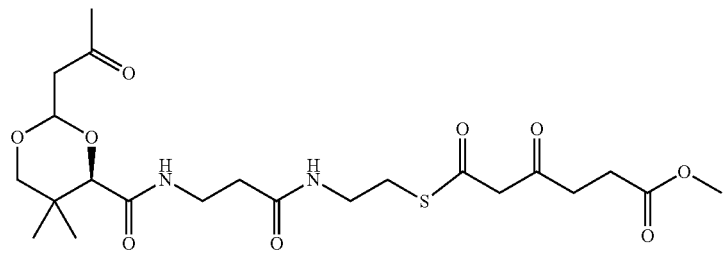 |
| 684 | 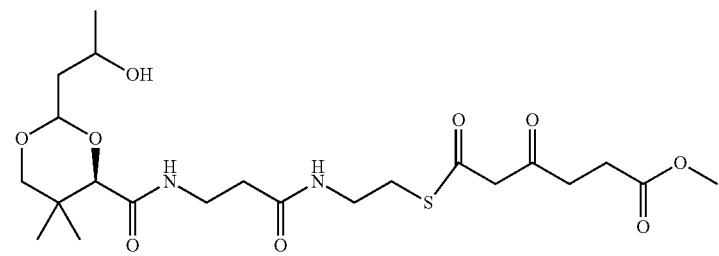 |
| 685 | 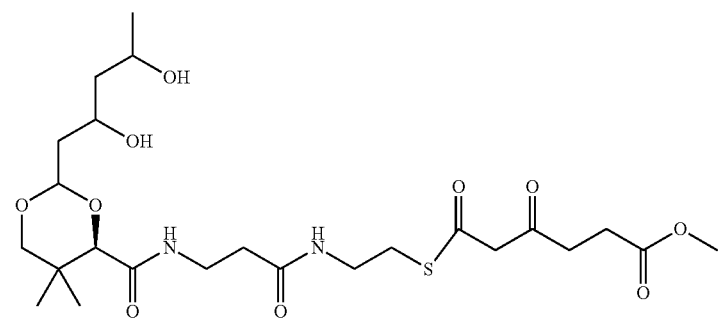 |

TABLE 1-continued

| Compound No. | Structure |
|---|---|
| 686 | 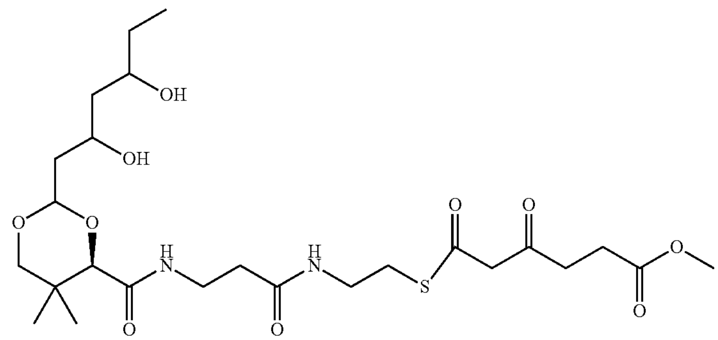 |
| 687 | 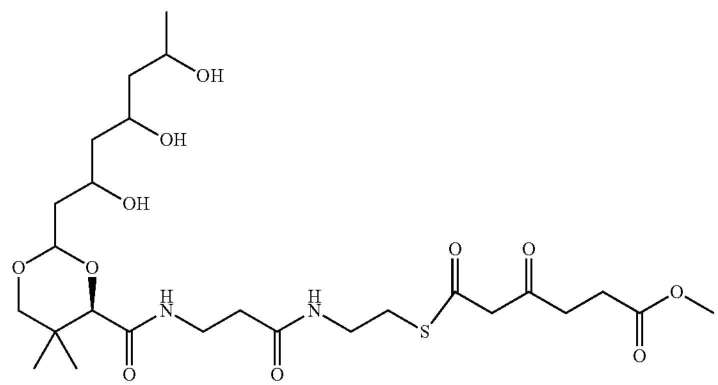 |
| 688 | 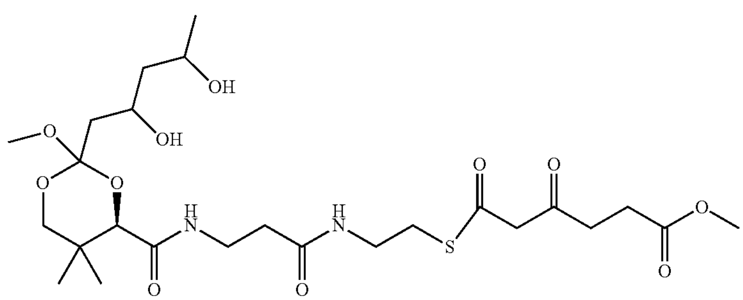 |
| 689 | 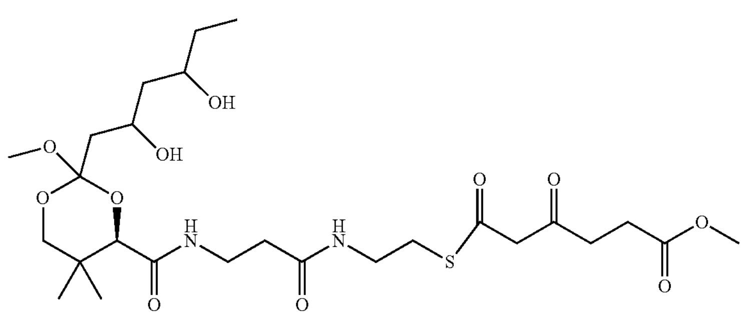 |

TABLE 1-continued
| Compound No. | Structure |
|---|---|
| 690 | 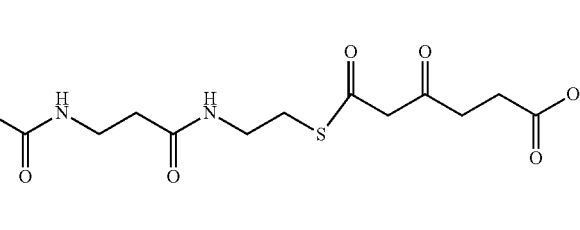 |
| 691 | 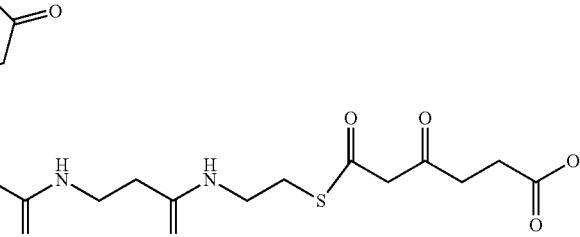 |
| 692 | 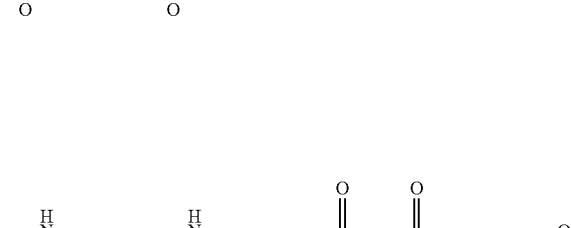 |
| 693 | 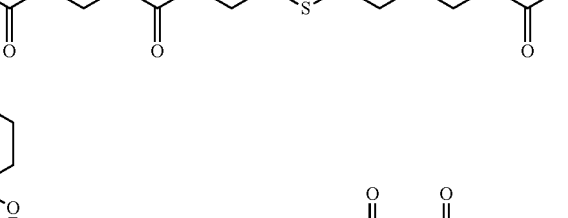 |
| 694 | 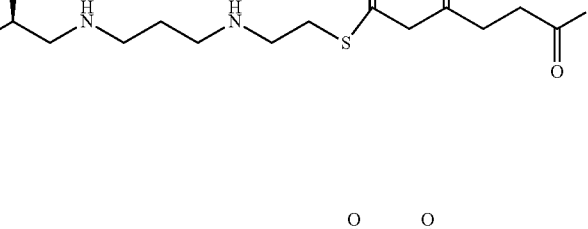 |
| 695 | 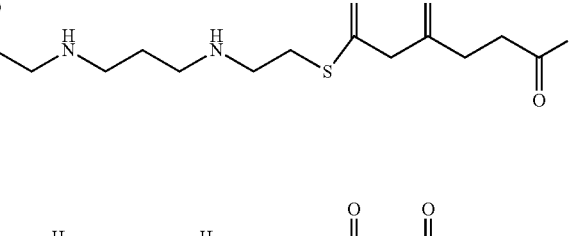 |

TABLE 1-continued

| Compound No. | Structure |
|---|---|
| 696 | 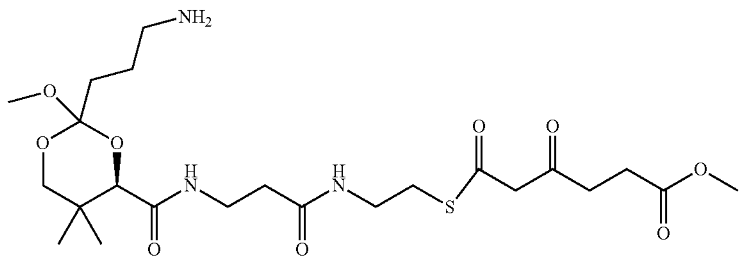 |
| 697 | 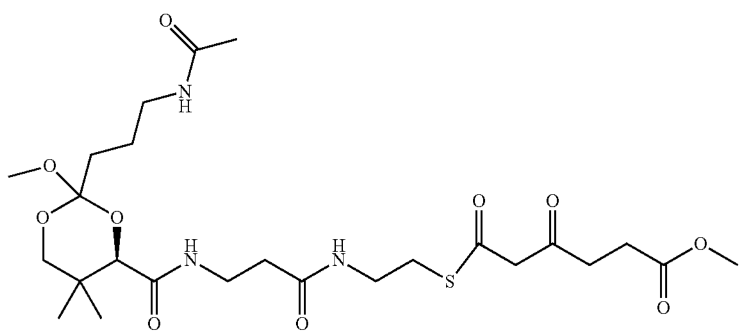 |
| 698 | 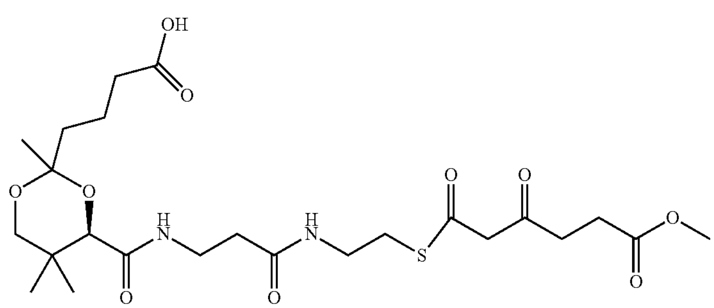 |
| 699 | 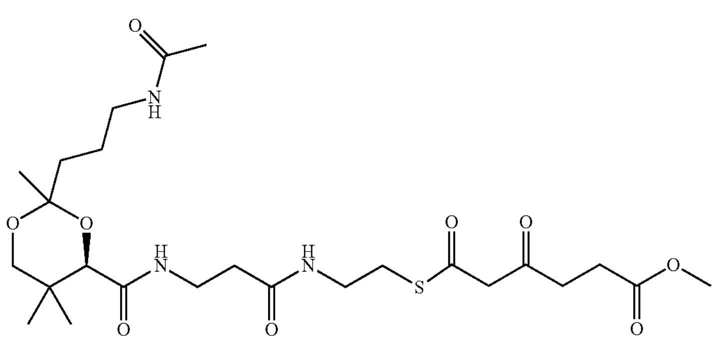 |
| 700 | 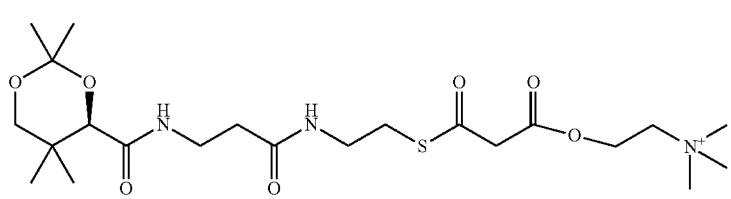 [SMILES: CC1(C)OCC(C)(C)[C@H](C(=O)NCCC(=O)NCCSC(=O)CC(=O)OCC[N+](C)(C)C)O1] |

TABLE 1-continued
| Compound No. | Structure |
|---|---|
| 701 | 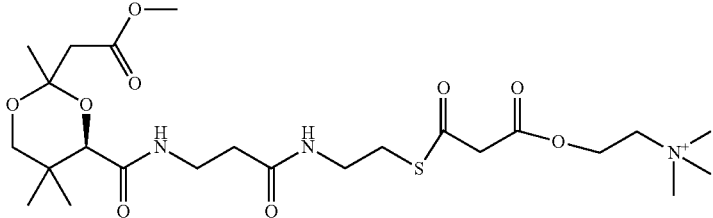 |
| 702 | 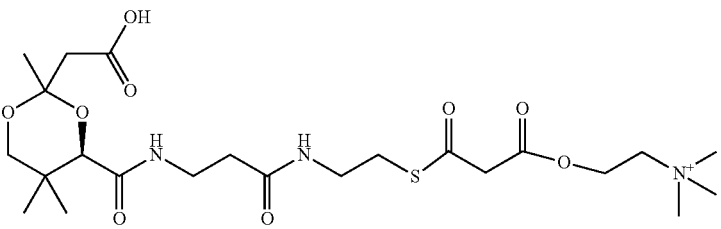 |
| 703 | 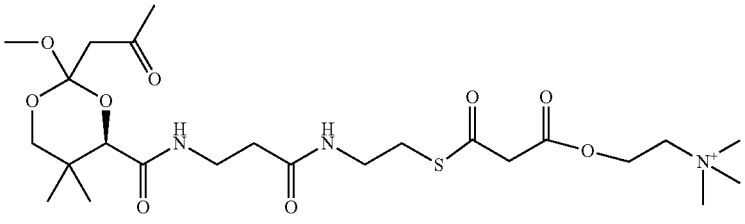 |
| 704 | 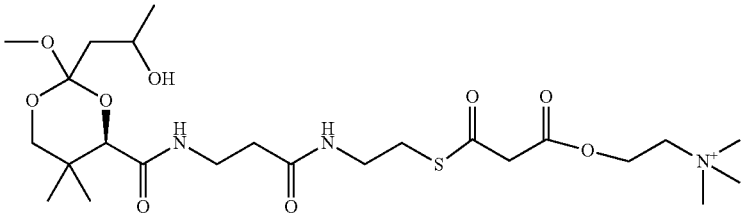 |
| 705 | 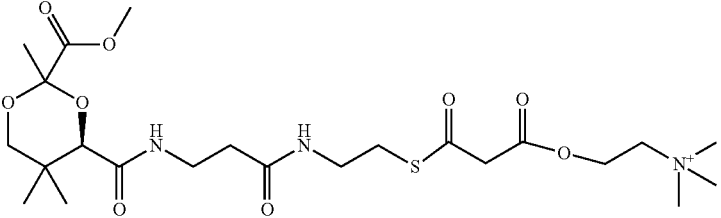 |
| 706 | 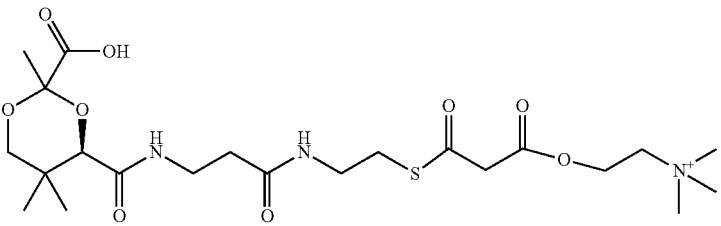 |

TABLE 1-continued
| Compound No. | Structure |
|---|---|
| 707 | 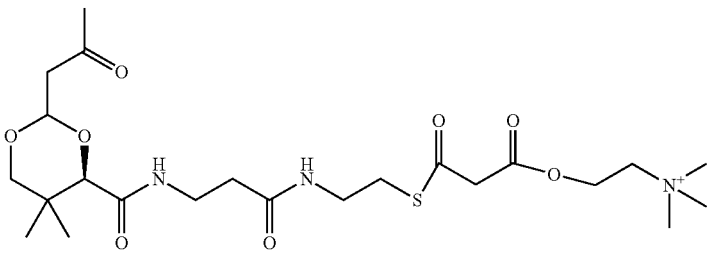 |
| 708 | 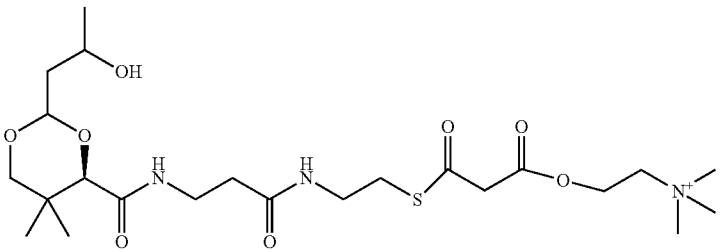 |
| 709 | 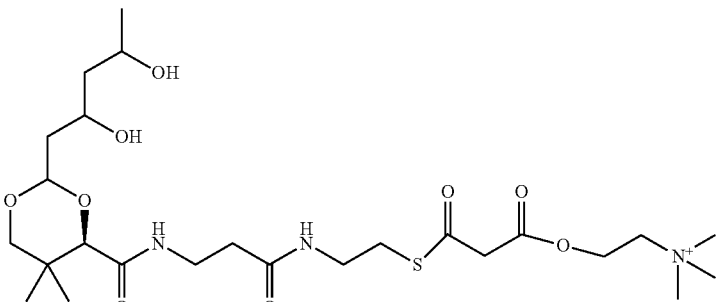 |
| 710 | 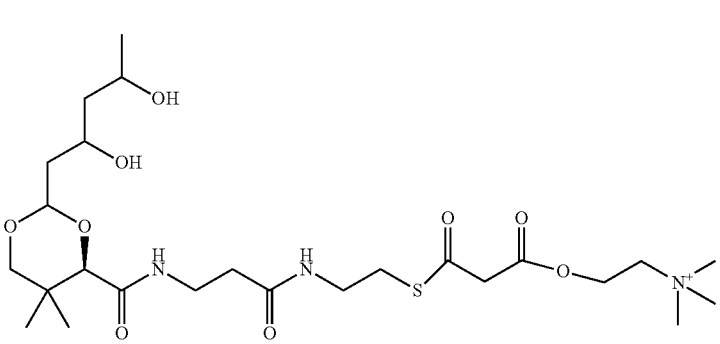 |
| 711 | 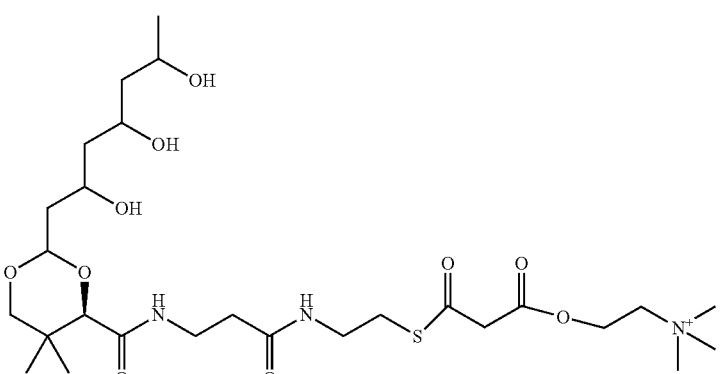 |

TABLE 1-continued

| Compound No. | Structure |
|---|---|
| 712 | 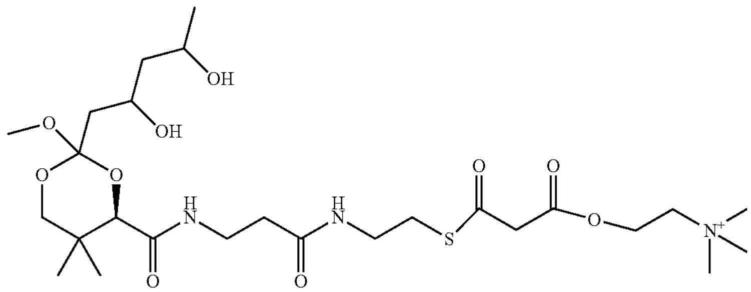 |
| 713 | 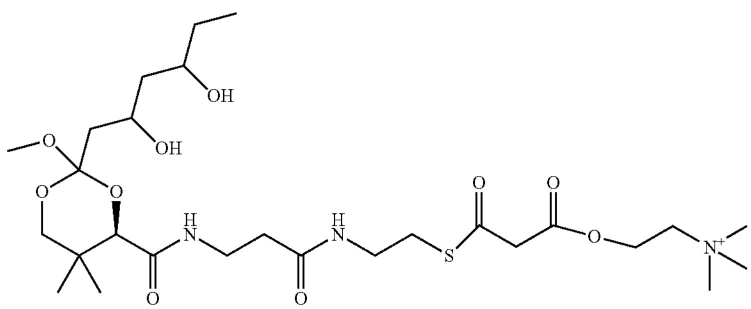 |
| 714 | 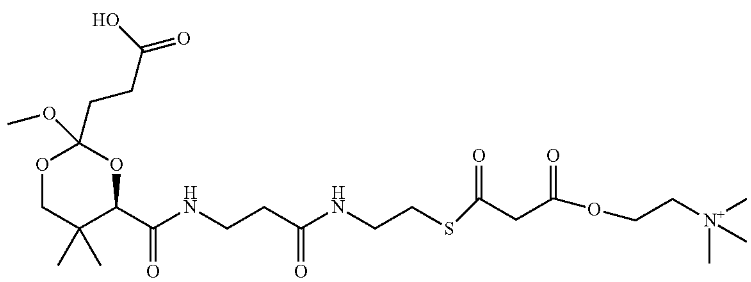 |
| 715 | 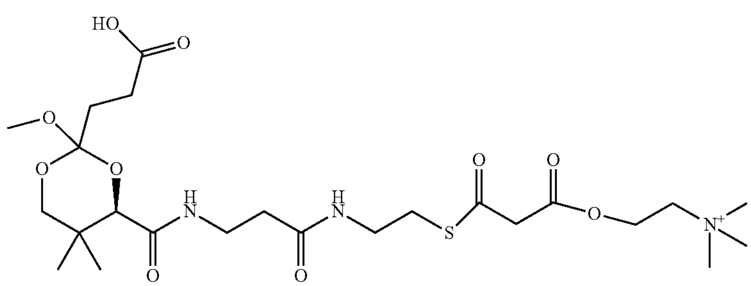 |
| 716 | 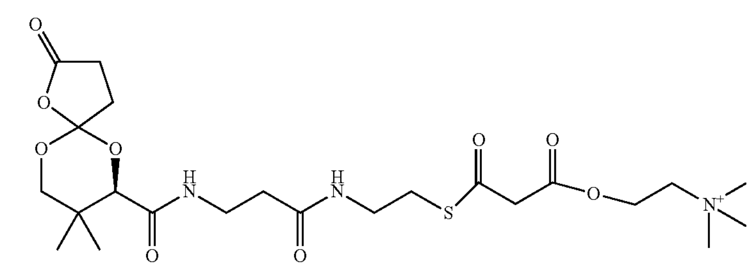 |

TABLE 1-continued

| Compound No. | Structure |
|---|---|
| 717 | 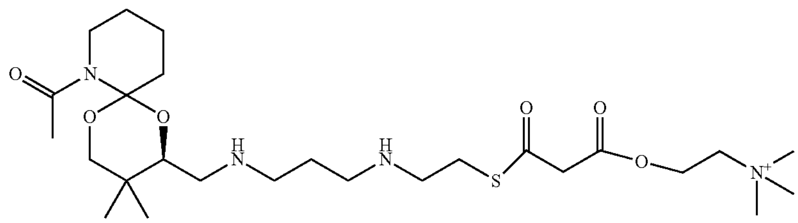 |
| 718 | 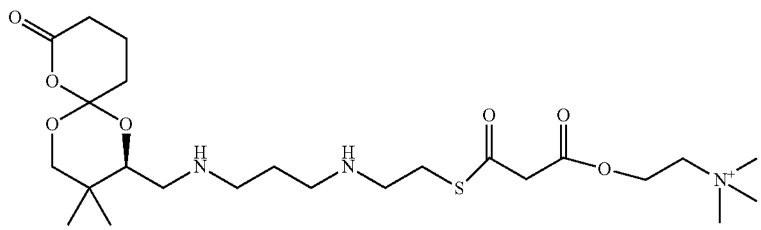 |
| 719 | 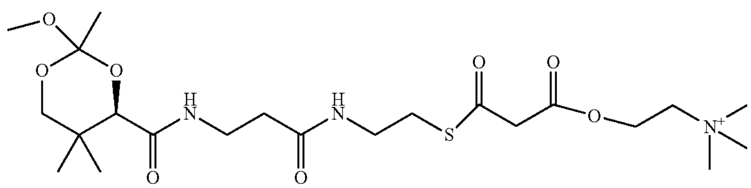 |
| 720 | 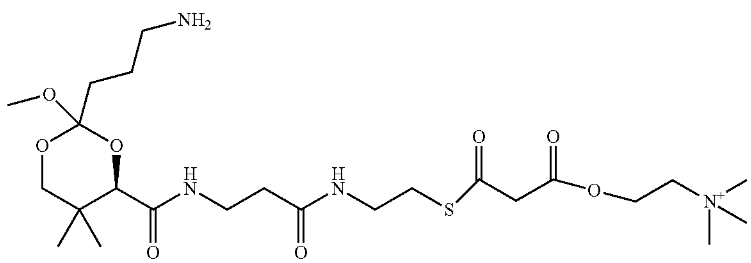 |
| 721 | 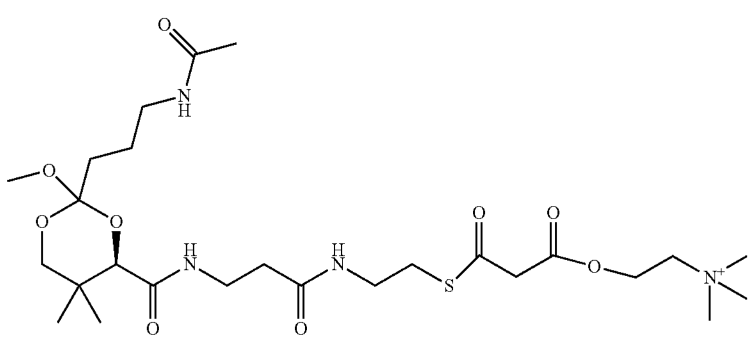 |
| 722 | 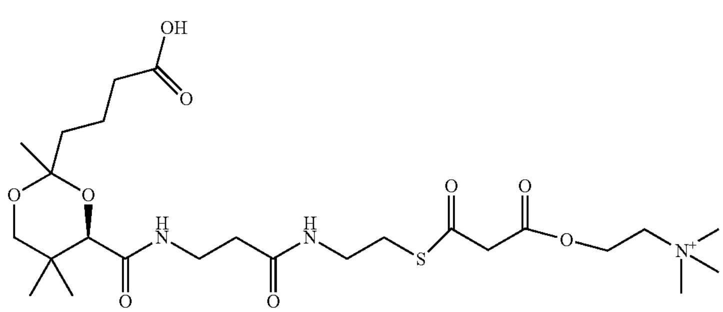 |

TABLE 1-continued
| Compound No. | Structure |
|---|---|
| 723 | 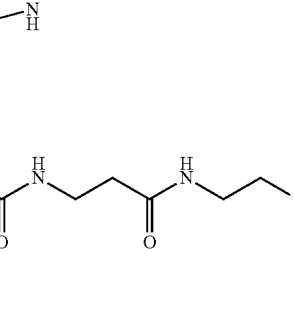 |
| 724 | 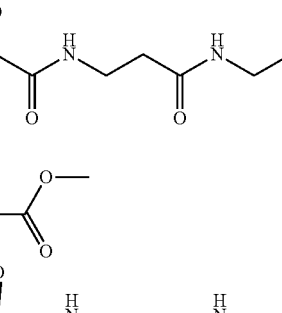 |
| 725 | 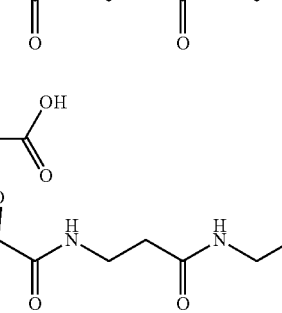 |
| 726 | 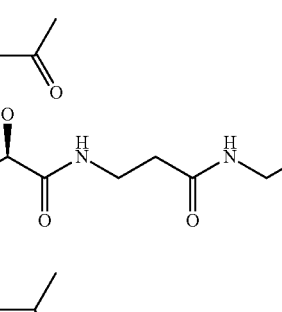 |
| 727 | 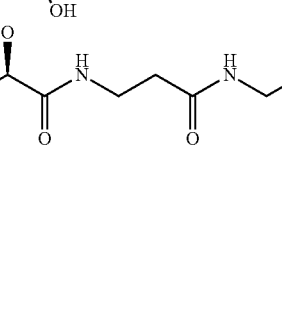 |
| 728 | 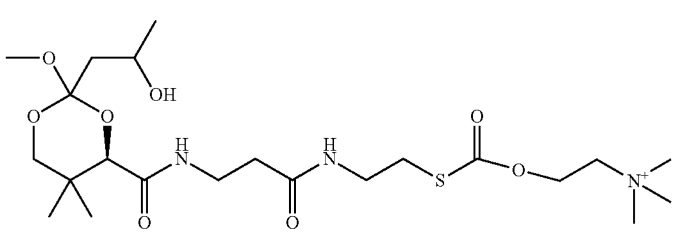 |

TABLE 1-continued

| Compound No. | Structure |
|---|---|
| 729 | 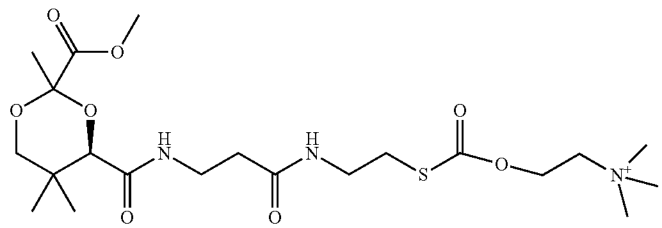 |
| 730 | 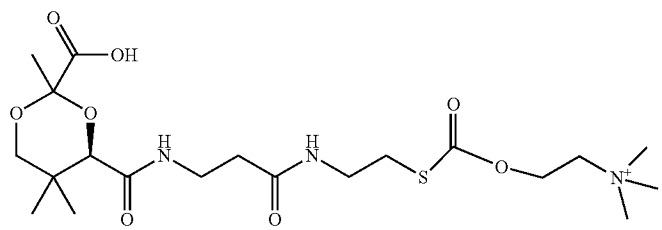 |
| 731 | 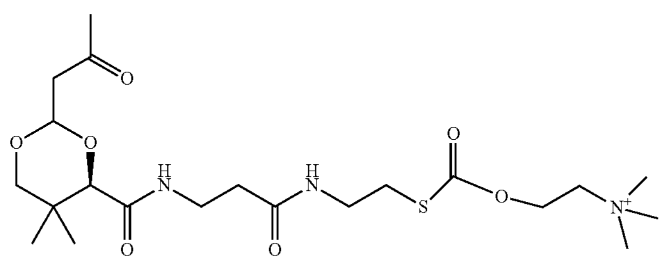 |
| 732 | 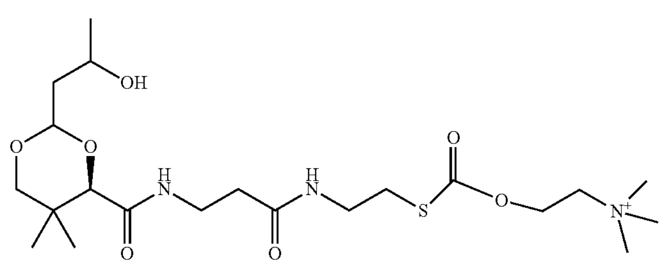 |
| 733 | 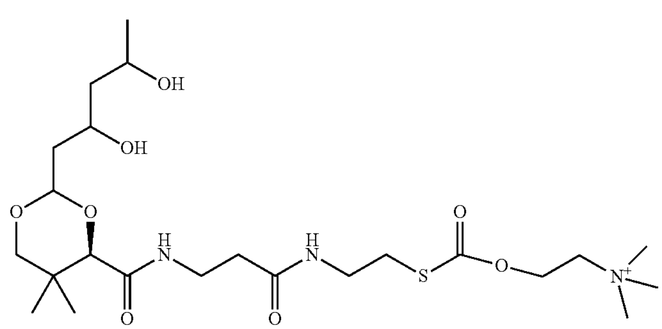 |

TABLE 1-continued

| Compound No. | Structure |
|---|---|
| 734 | 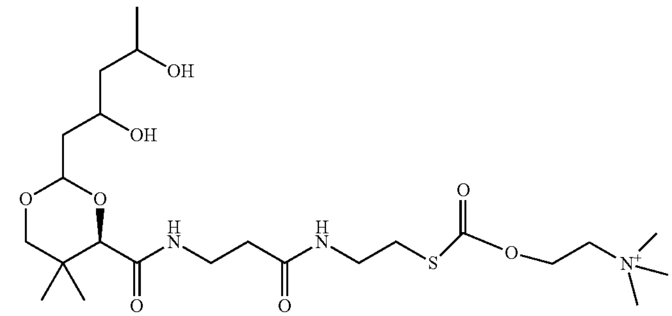 |
| 735 | 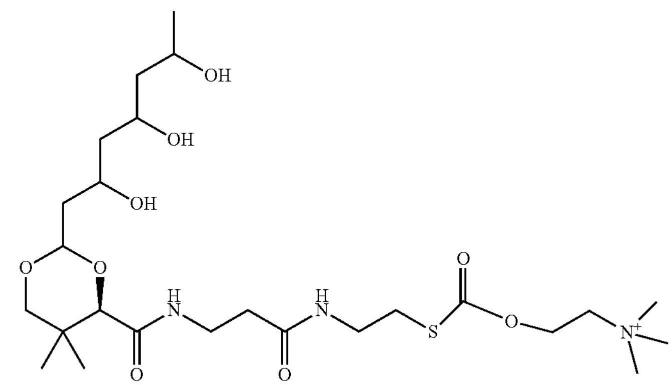 |
| 736 | 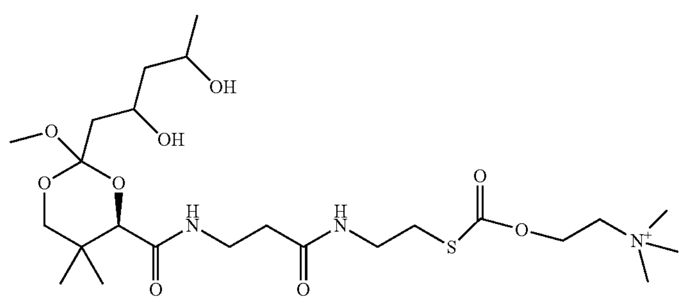 |
| 737 | 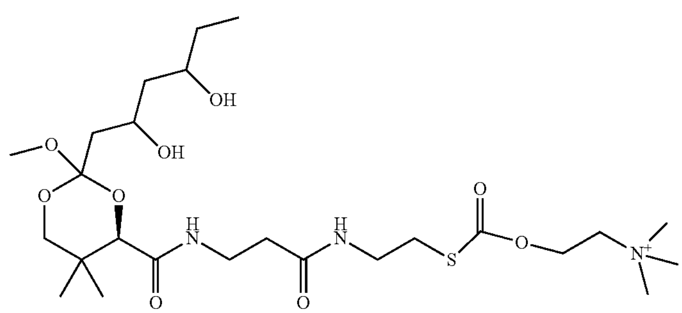 |
| 738 | 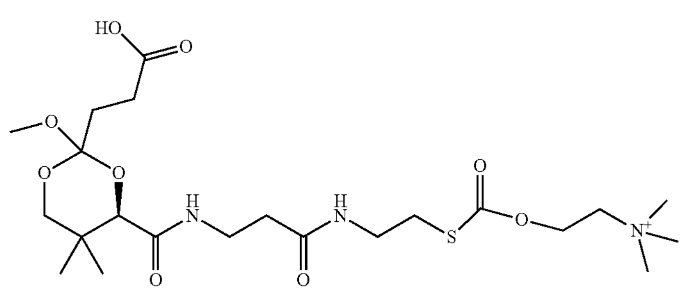 |

TABLE 1-continued
| Compound No. | Structure |
|---|---|
| 739 | 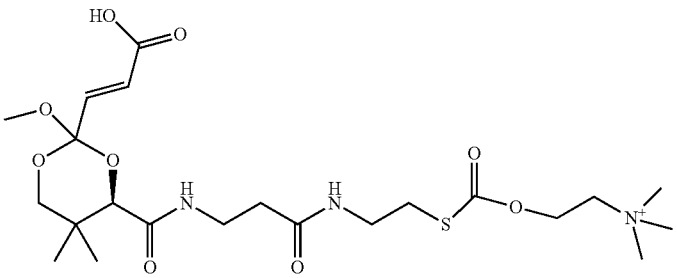 |
| 740 | 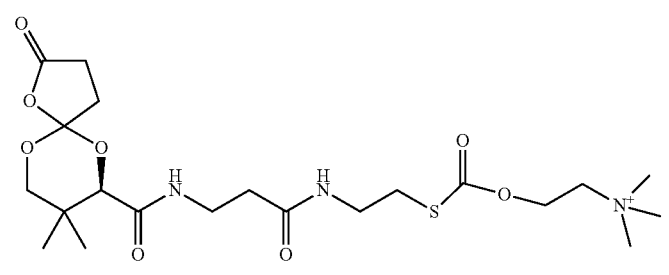 |
| 741 | 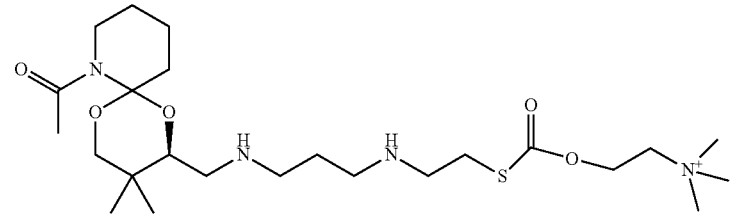 |
| 742 | 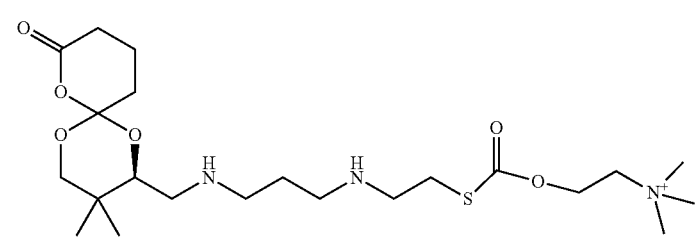 |
| 743 | 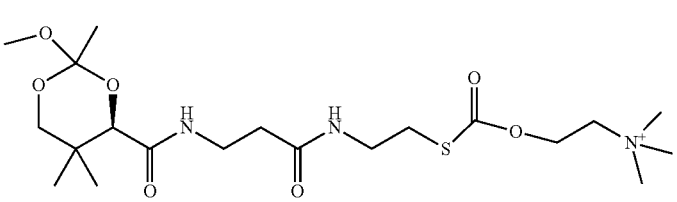 |
| 744 | 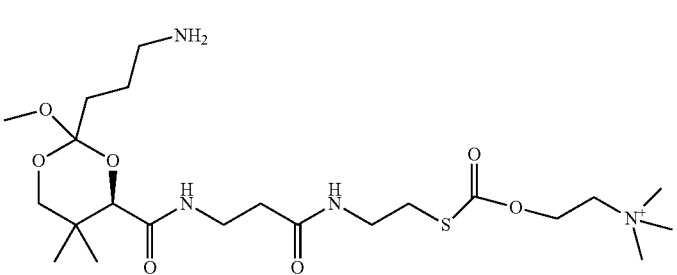 |

TABLE 1-continued
| Compound No. | Structure |
|---|---|
| 745 | 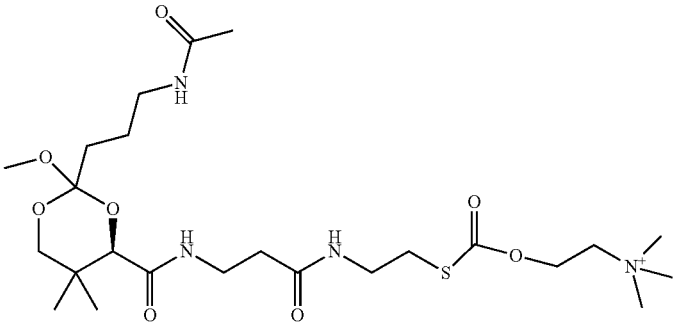 |
| 746 | 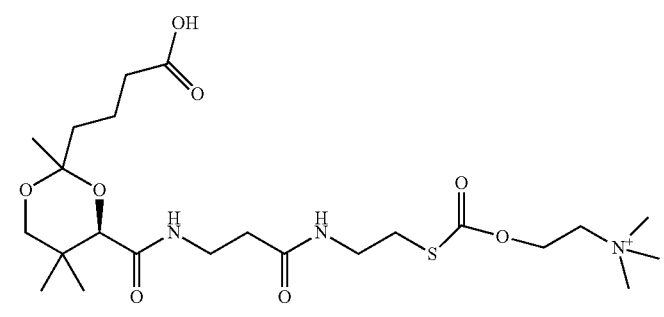 |
| 747 | 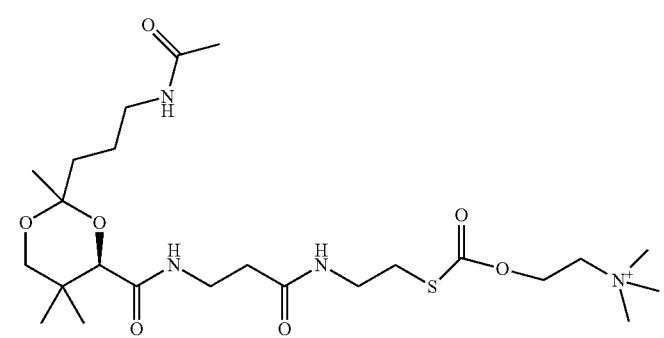 |
| 748 | 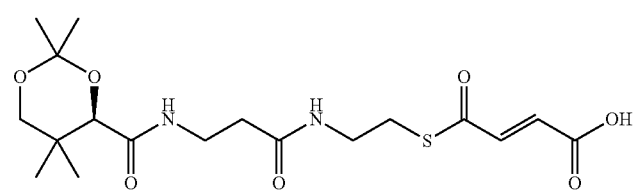 [SMILES: CC1(C)OCC(C)(C)[C@H](C(=O)NCCC(=O)NCCSC(=O)/C=C/C(=O)O)O1] |
| 749 | 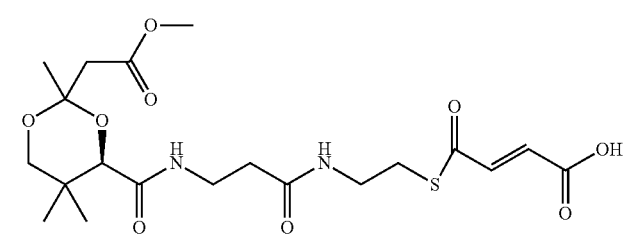 |

TABLE 1-continued

| Compound No. | Structure |
|---|---|
| 750 | 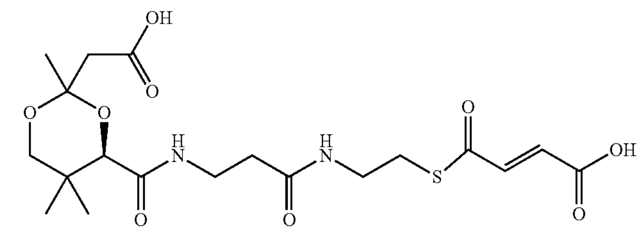 |
| 751 | 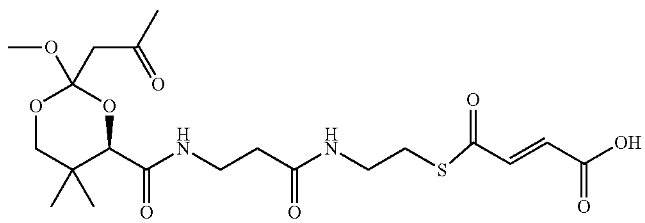 |
| 752 | 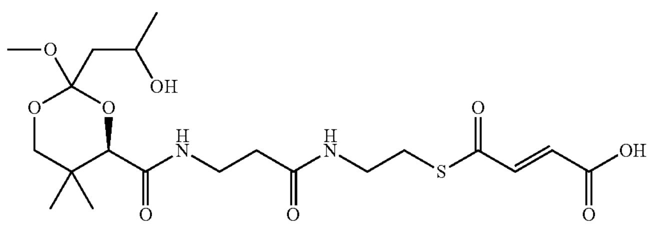 |
| 753 | 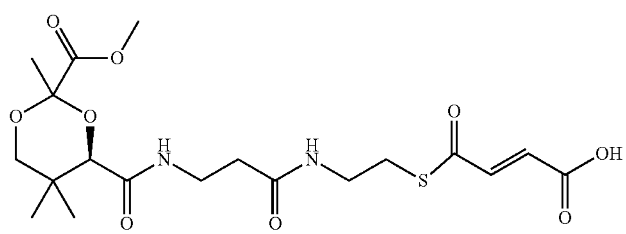 |
| 754 | 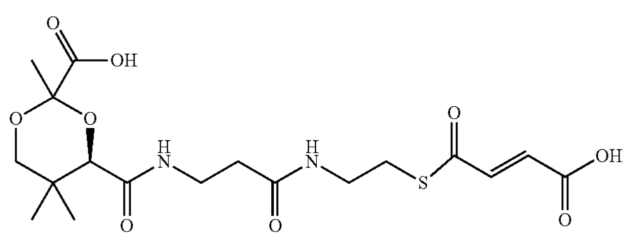 |
| 755 | 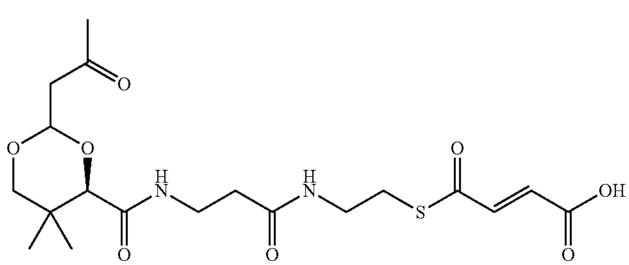 |

TABLE 1-continued
| Compound No. | Structure |
|---|---|
| 756 | 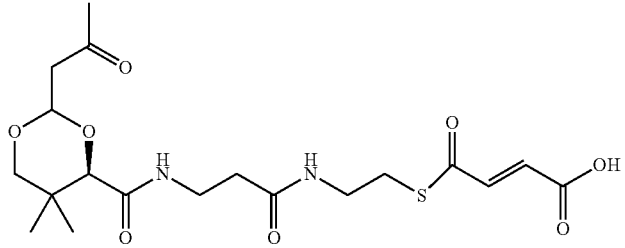 |
| 757 | 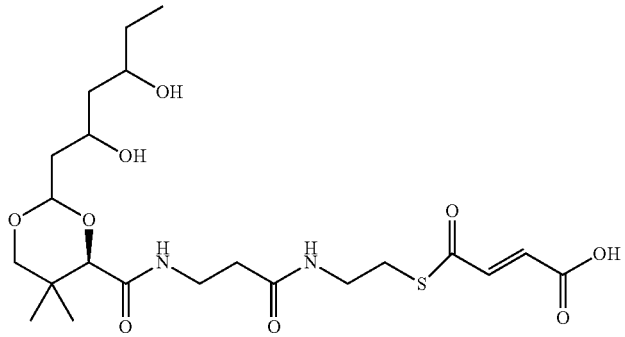 |
| 758 | 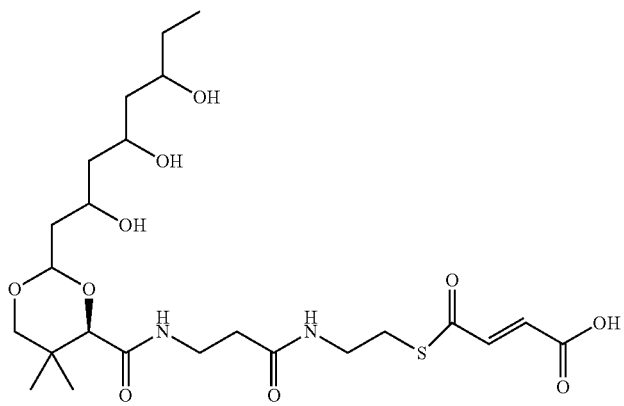 |
| 759 | 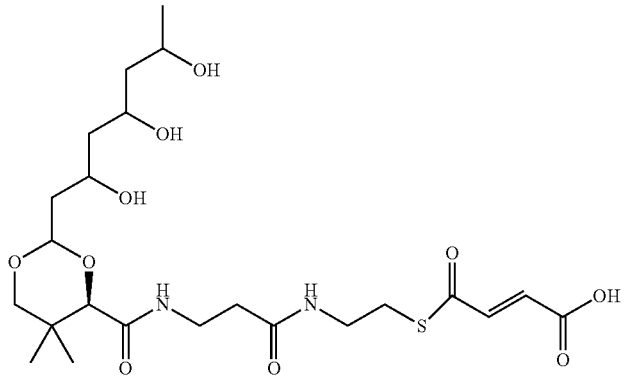 |

| Compound No. | Structure |
|---|---|
| 760 | (chemical structure) |
| 761 | (chemical structure) |
| 762 | (chemical structure) |
| 763 | (chemical structure) |
| 764 | (chemical structure) |

TABLE 1-continued
| Compound No. | Structure |
|---|---|
| 765 | 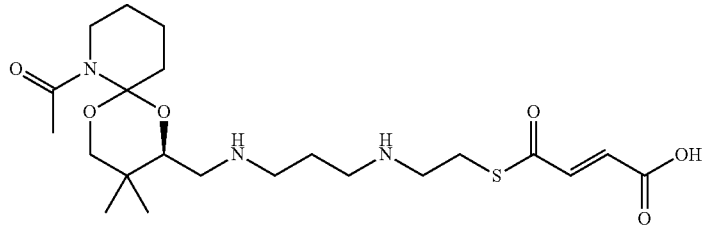 |
| 766 | 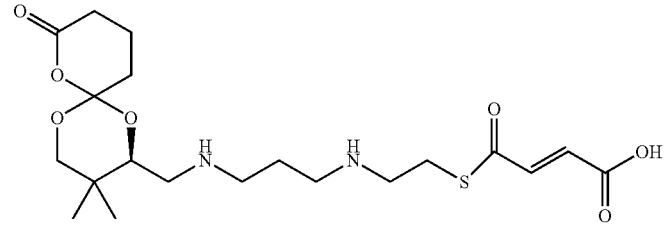 |
| 767 | 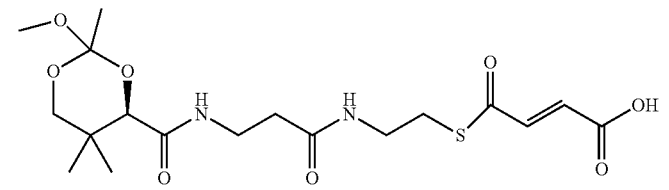 |
| 768 | 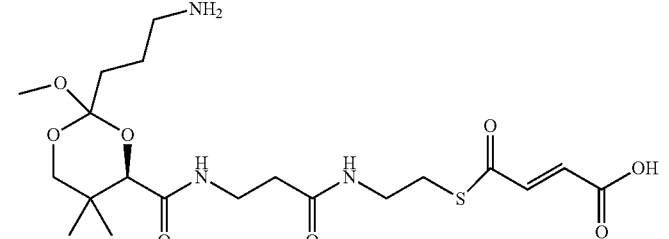 |
| 769 | 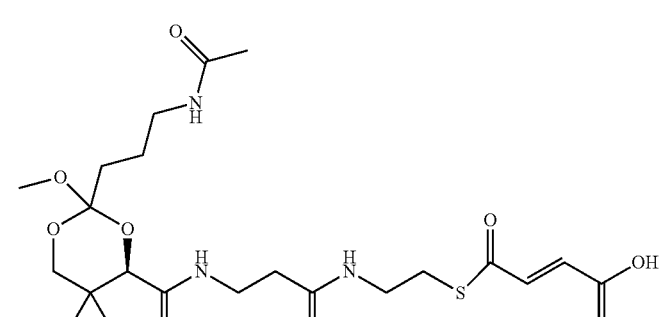 |
| 770 | 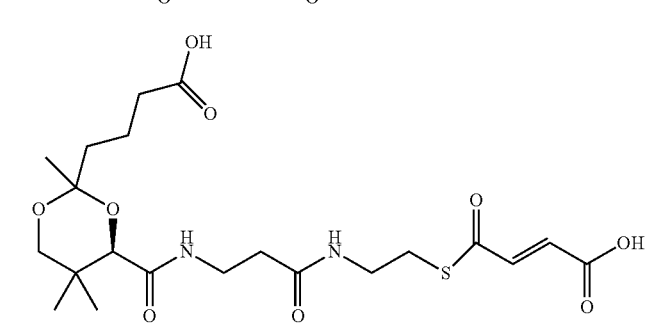 |

TABLE 1-continued

| Compound No. | Structure |
|---|---|
| 771 | 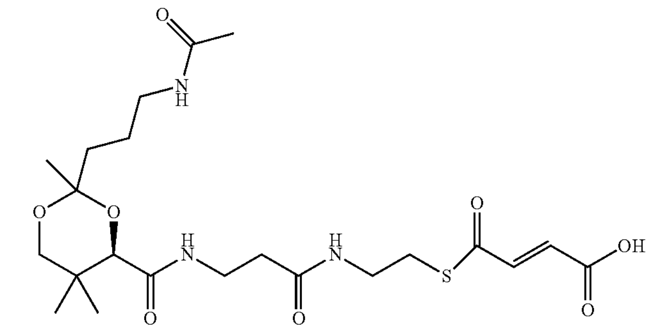 |
| 772 | 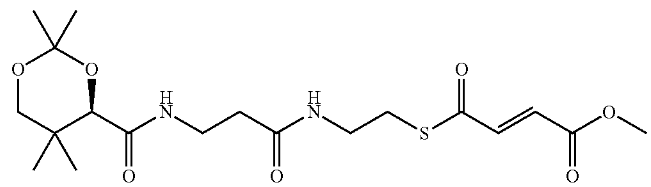 [SMILES: COC(=O)/C=C/C(=O)SCCNC(=O)CCNC(=O)[C@@H]1OC(C)(C)OCC1(C)C] |
| 773 | 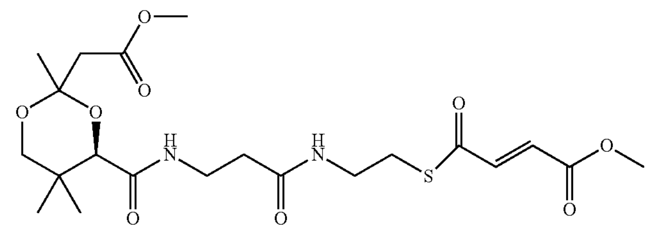 |
| 774 | 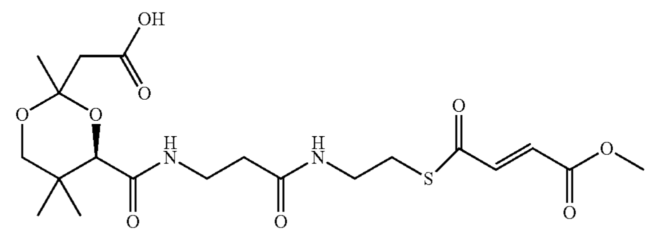 |
| 775 | 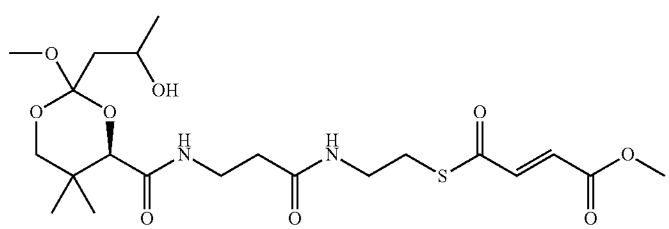 |
| 776 | 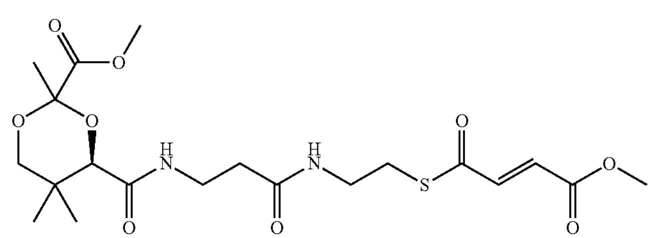 |

TABLE 1-continued
| Compound No. | Structure |
|---|---|
| 777 | 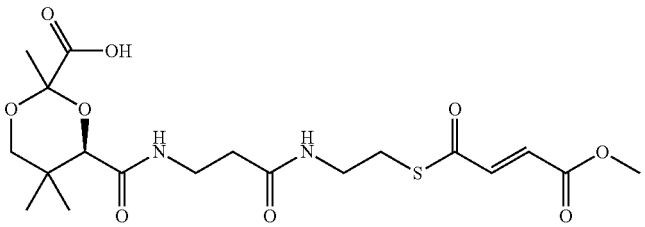 |
| 778 | 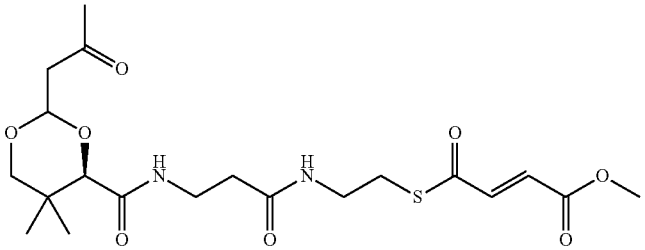 |
| 779 | 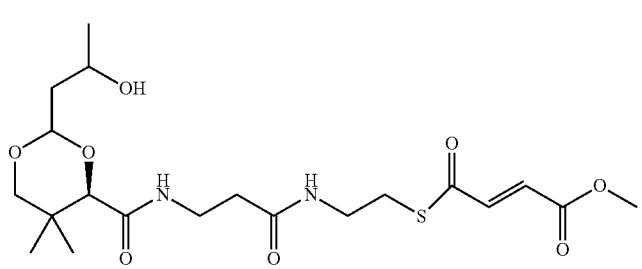 |
| 780 | 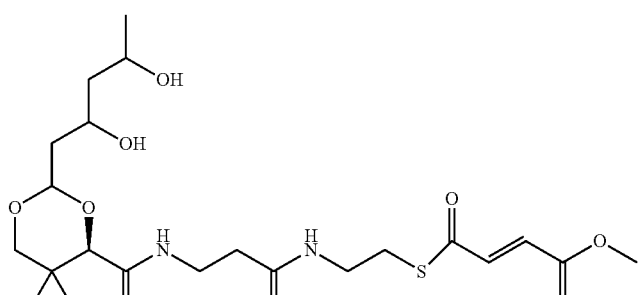 |
| 781 | 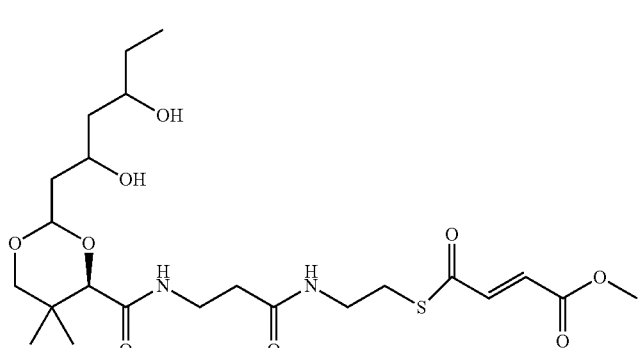 |

TABLE 1-continued

| Compound No. | Structure |
|---|---|
| 782 | 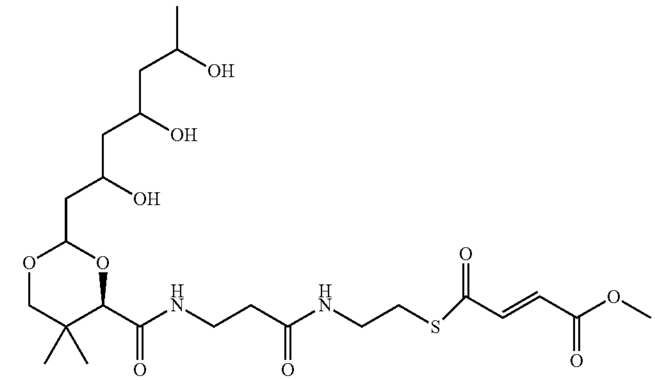 |
| 783 | 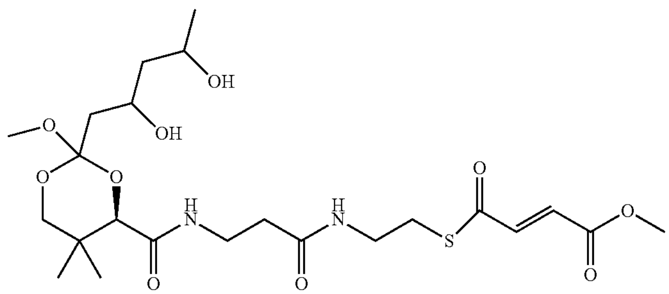 |
| 784 | 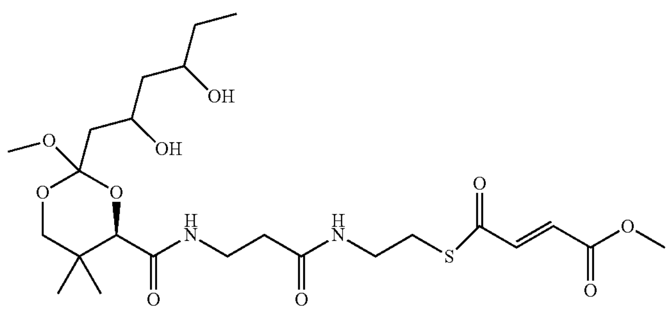 |
| 785 | 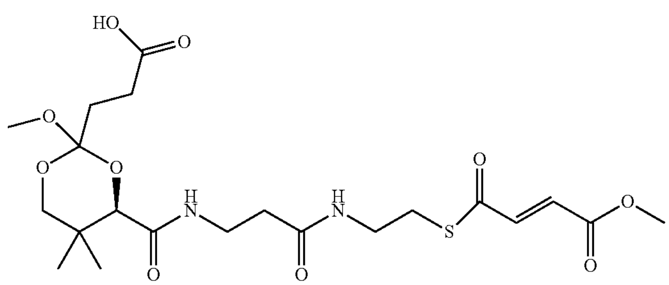 |
| 786 | 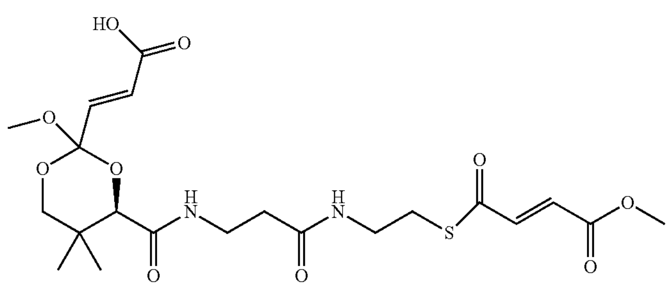 |

TABLE 1-continued

| Compound No. | Structure |
|---|---|
| 787 | 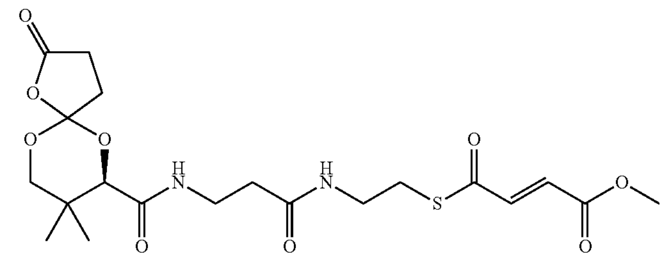 |
| 788 | 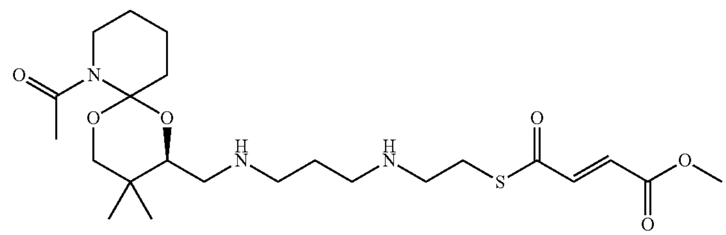 |
| 789 | 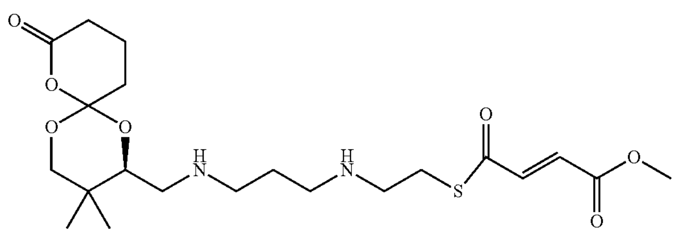 |
| 790 | 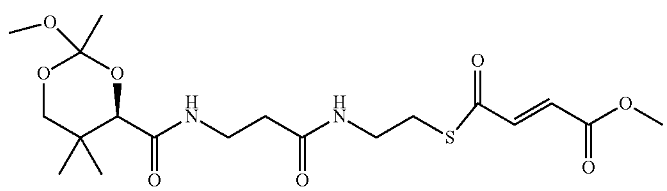 |
| 791 | 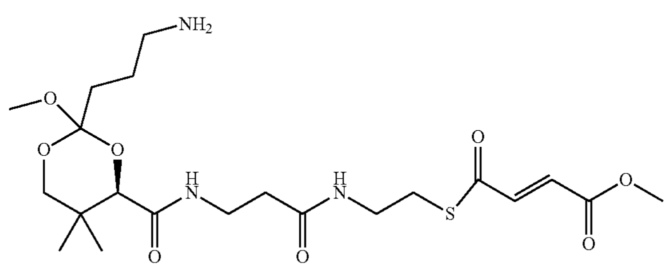 |
| 792 | 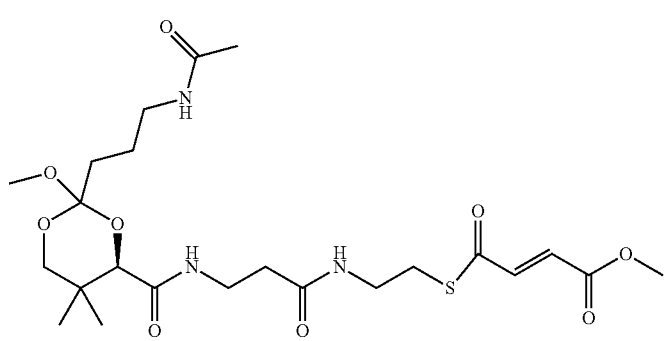 |

TABLE 1-continued

| Compound No. | Structure |
|---|---|
| 793 | 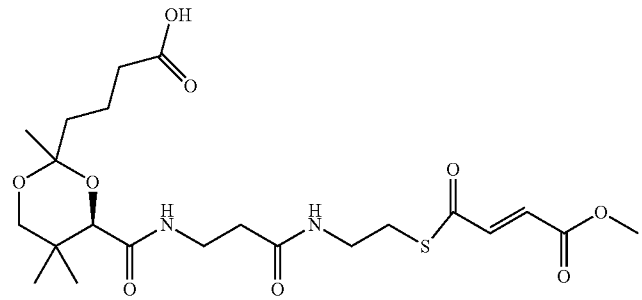 |
| 794 | 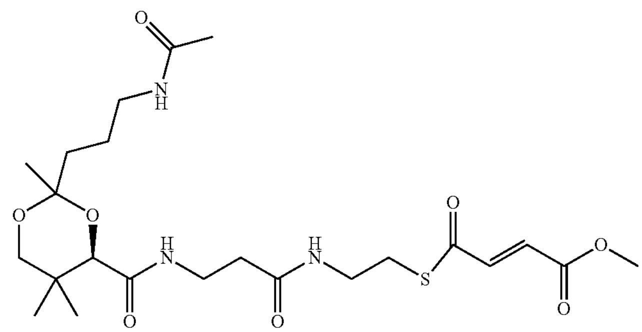 |
| 795 | 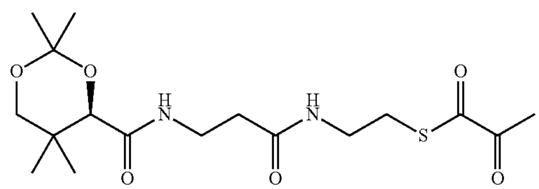 [SMILES: CC(=O)C(=O)SCCNC(=O)CCNC(=O)[C@@H]1OC(C)(C)OCC1(C)C] |
| 796 | 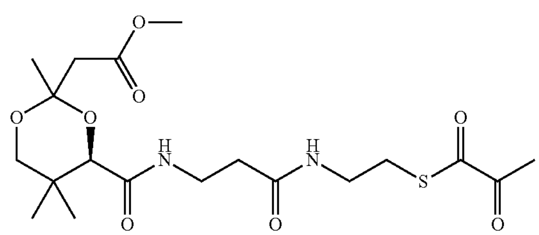 |
| 797 | 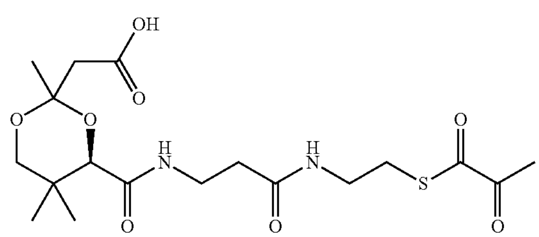 |
| 798 | 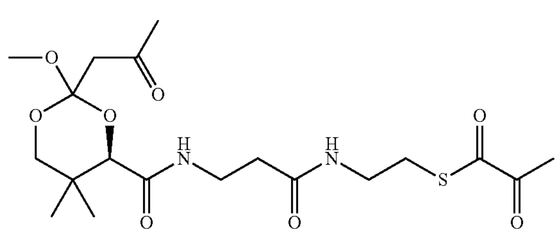 |

TABLE 1-continued

| Compound No. | Structure |
|---|---|
| 799 | 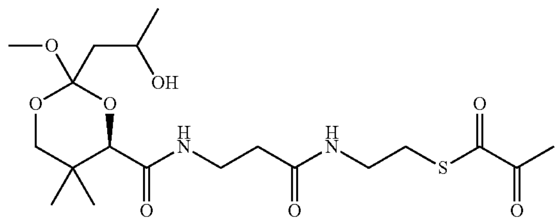 |
| 800 | 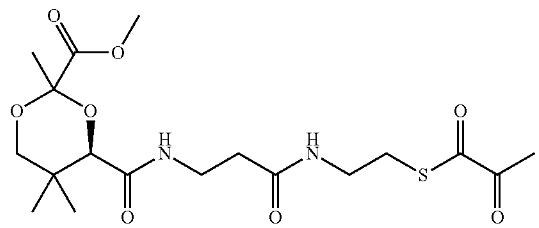 |
| 801 | 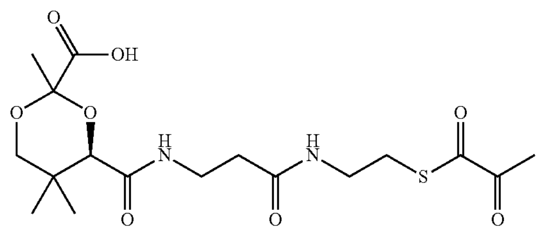 |
| 802 | 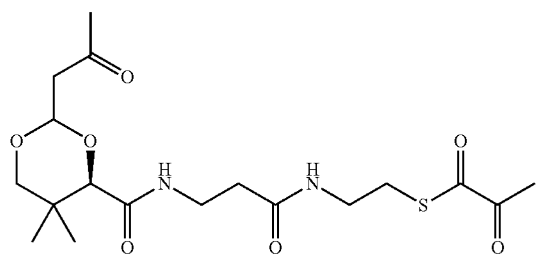 |
| 803 | 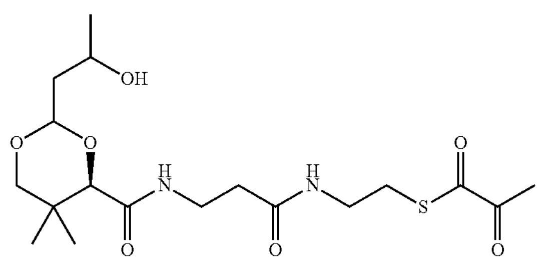 |
| 804 | 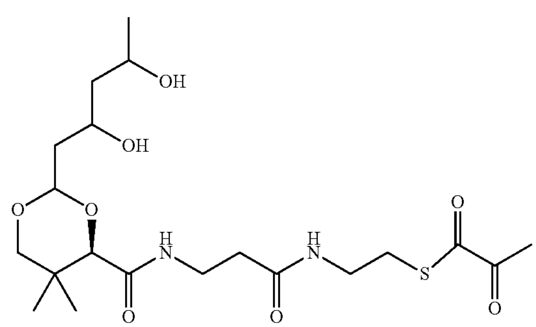 |

TABLE 1-continued

| Compound No. | Structure |
|---|---|
| 805 | 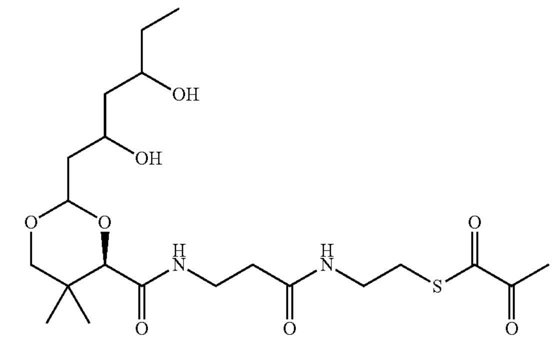 |
| 806 | 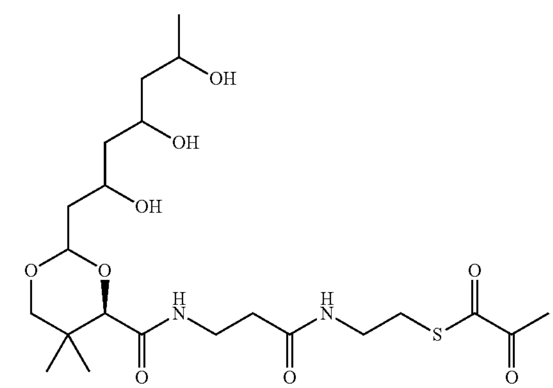 |
| 807 | 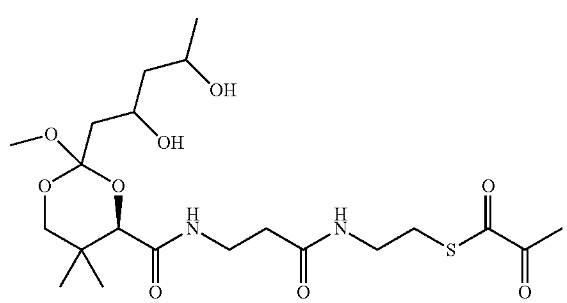 |
| 808 | 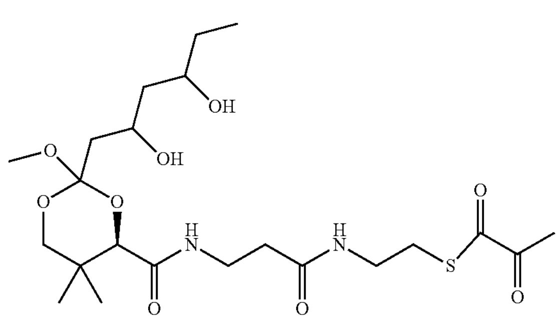 |

TABLE 1-continued
| Compound No. | Structure |
|---|---|
| 809 | 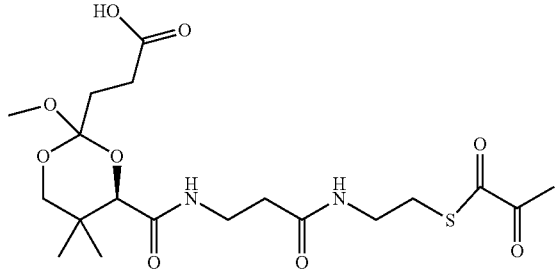 |
| 810 | 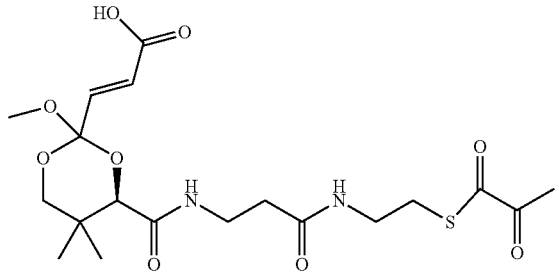 |
| 811 | 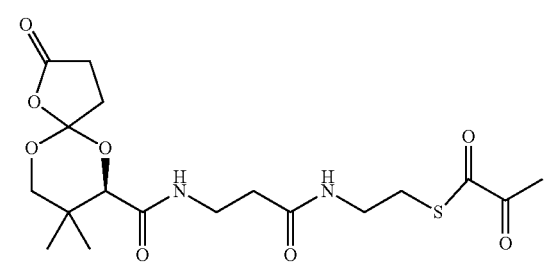 |
| 812 | 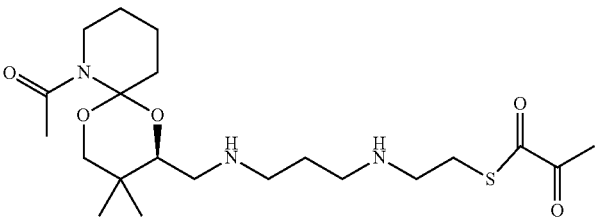 |
| 813 | 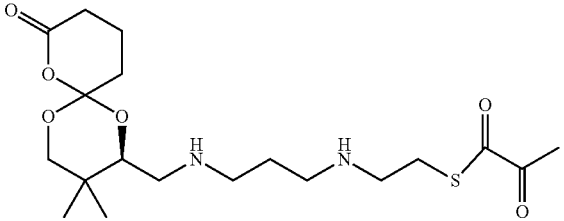 |
| 814 | 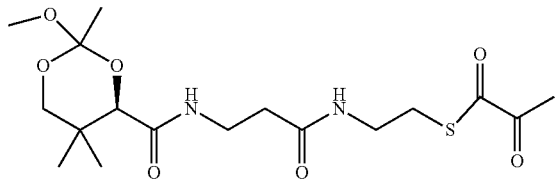 |

TABLE 1-continued
| Compound No. | Structure |
|---|---|
| 815 | 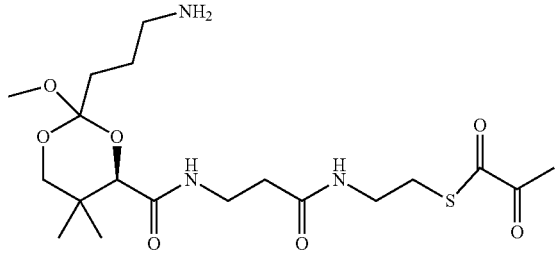 |
| 816 | 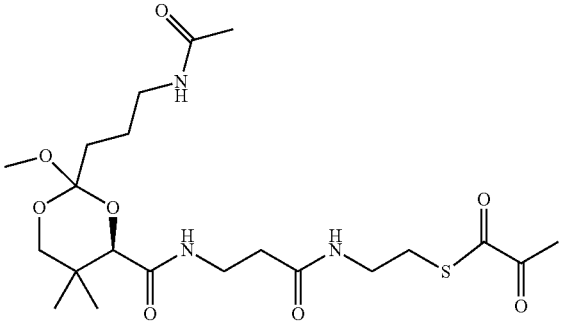 |
| 817 | 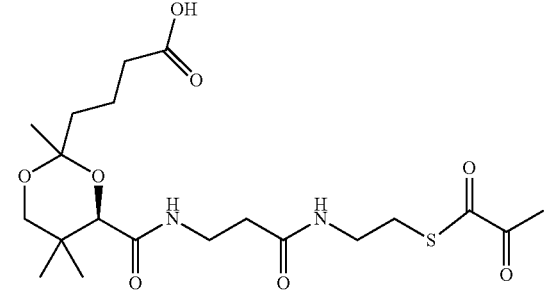 |
| 818 | 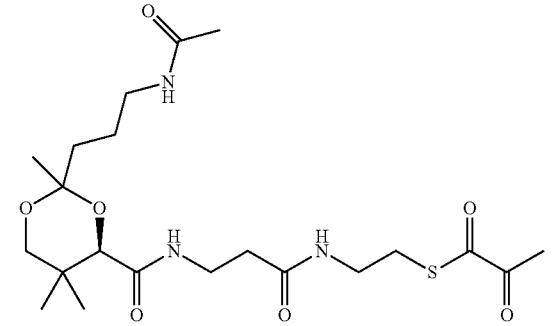 |
| 819 | 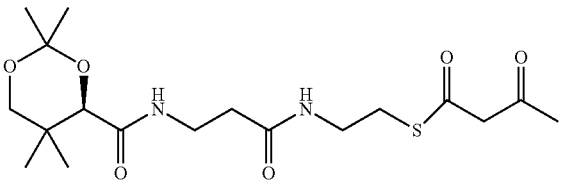 [SMILES: CC(=O)CC(=O)SCCNC(=O)CCNC(=O)[C@@H]1OC(C)(C)OCC1(C)C] |

TABLE 1-continued

| Compound No. | Structure |
|---|---|
| 820 | 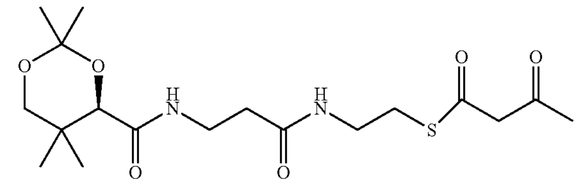 [SMILES: CC(=O)CC(=O)SCCNC(=O)CCNC(=O)[C@@H]1OC(C)(C)OCC1(C)C] |
| 821 | 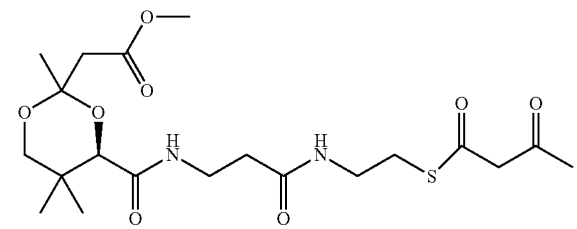 |
| 822 | 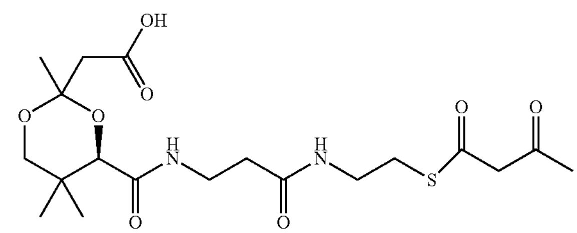 |
| 823 | 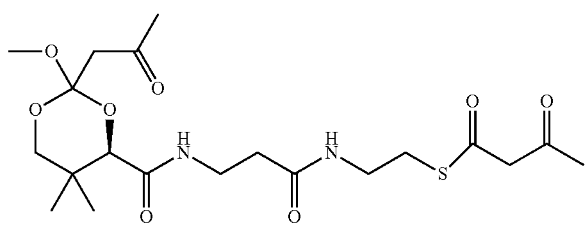 |
| 824 | 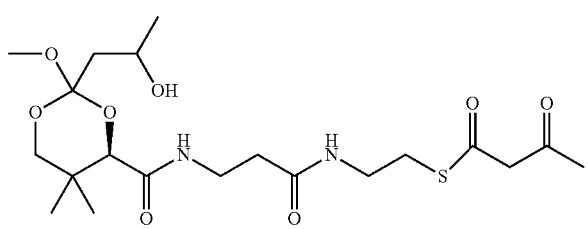 |
| 825 | 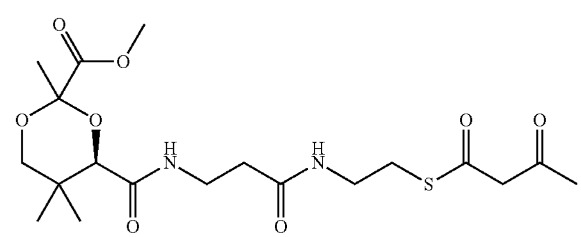 |
| 826 | 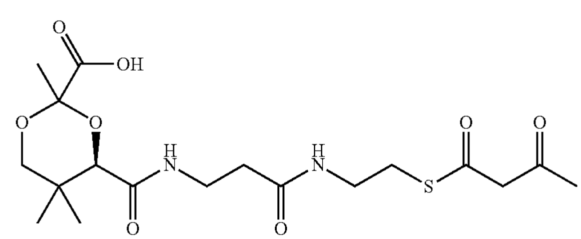 |

TABLE 1-continued

| Compound No. | Structure |
|---|---|
| 827 | 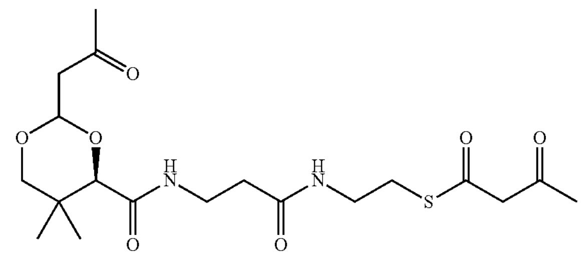 |
| 828 | 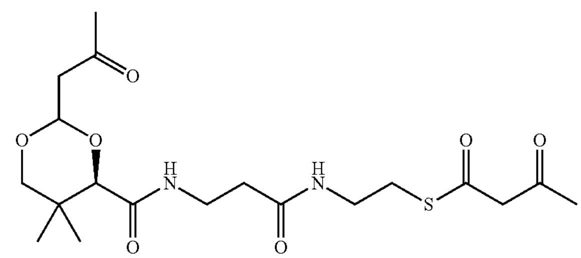 |
| 829 | 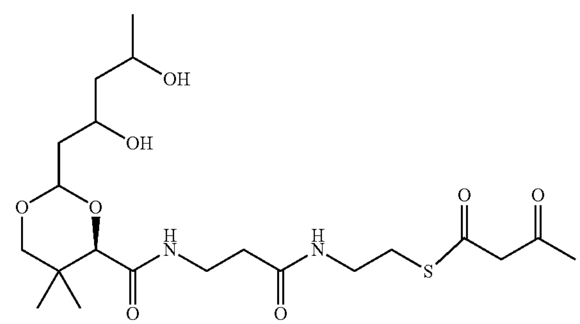 |
| 830 | 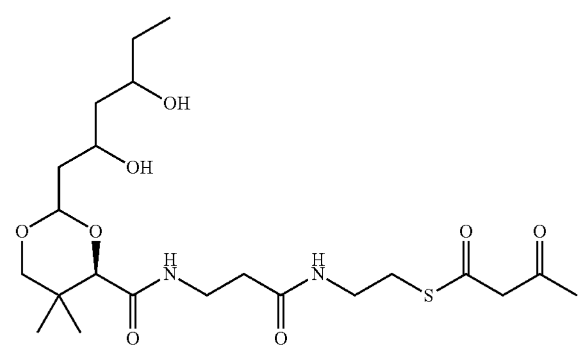 |
| 831 | 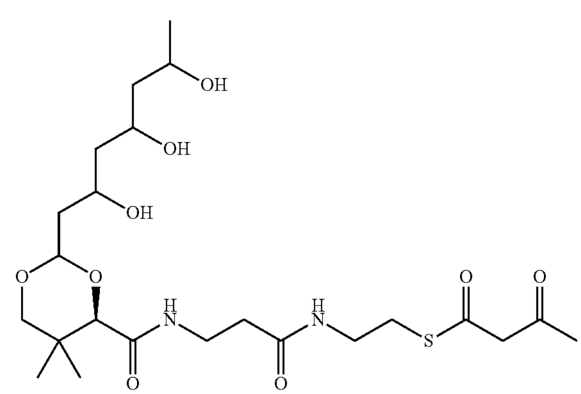 |

TABLE 1-continued
| Compound No. | Structure |
|---|---|
| 832 | 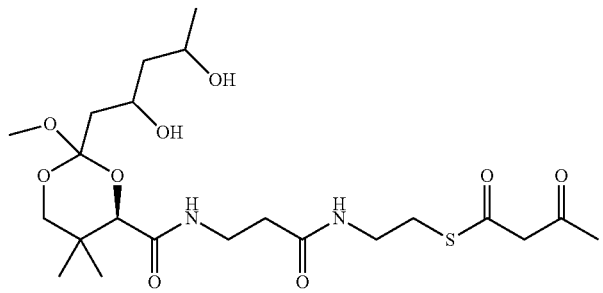 |
| 833 | 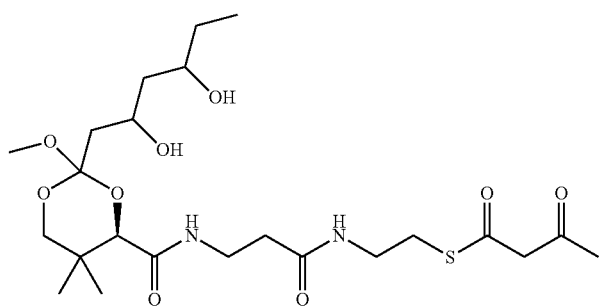 |
| 834 | 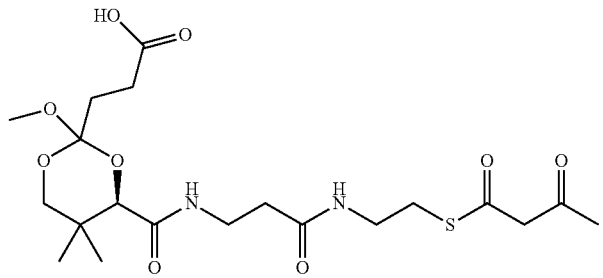 |
| 835 | 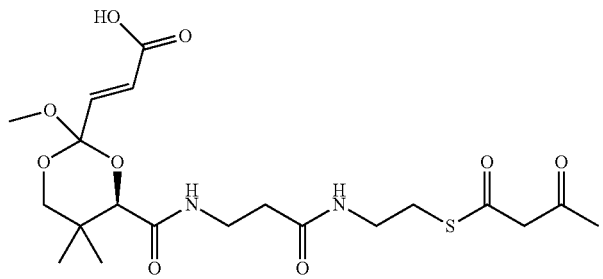 |
| 836 | 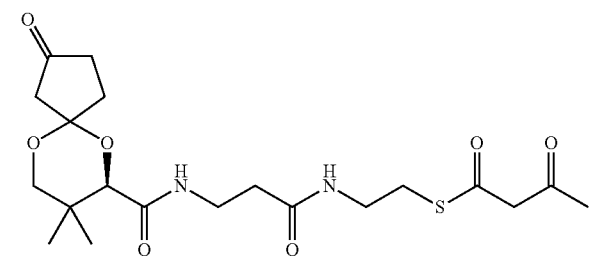 |

TABLE 1-continued

| Compound No. | Structure |
|---|---|
| 837 | 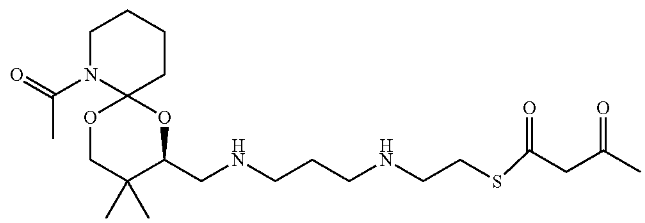 |
| 838 | 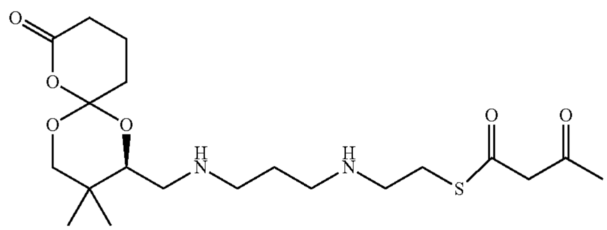 |
| 839 | 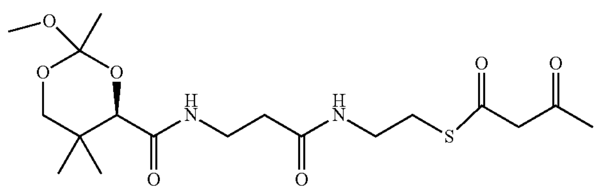 |
| 840 | 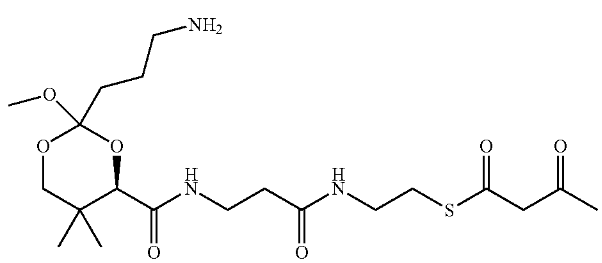 |
| 841 | 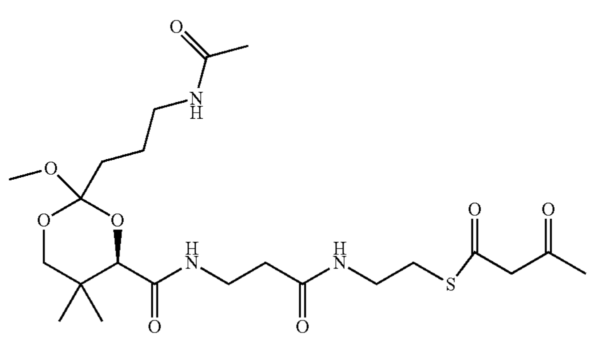 |
| 842 | 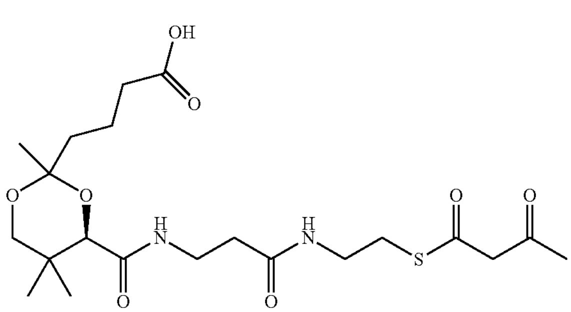 |

TABLE 1-continued
| Compound No. | Structure |
|---|---|
| 843 | 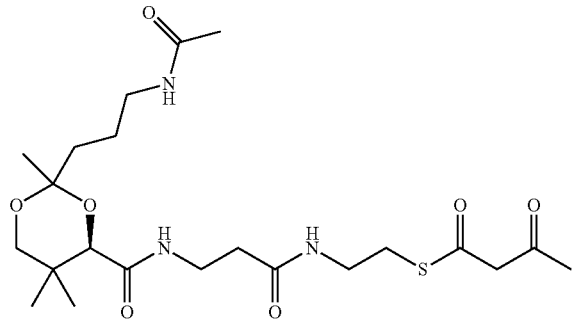 |
| 844 | 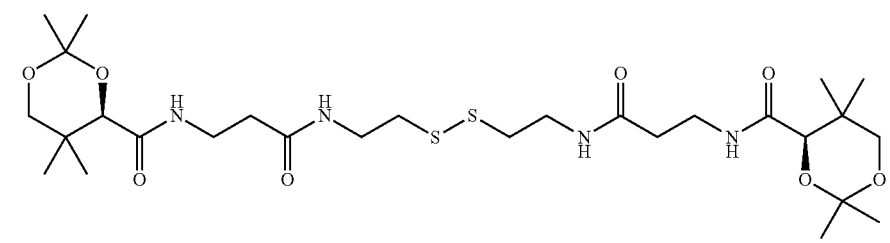 [SMILES: CC1(C)OCC(C)(C)[C@H](C(=O)NCCC(=O)NCCSSCCNC(=O)CCNC(=O)[C@@H]2OC(C)(C)OCC2(C)C)O1] |
| 849 | 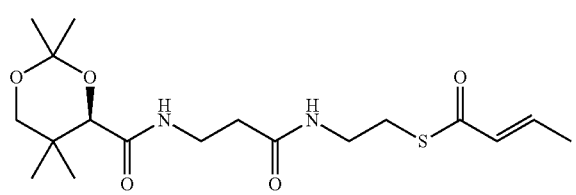 [SMILES: C/C=C/C(=O)SCCNC(=O)CCNC(=O)[C@@H]1OC(C)(C)OCC1(C)C] |
| 850 | 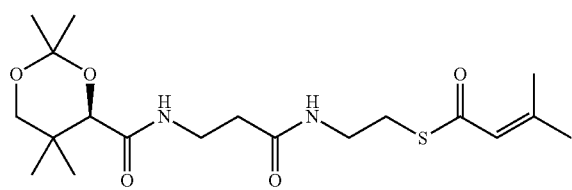 [SMILES: CC(C)=CC(=O)SCCNC(=O)CCNC(=O)[C@@H]1OC(C)(C)OCC1(C)C] |
| 851 | 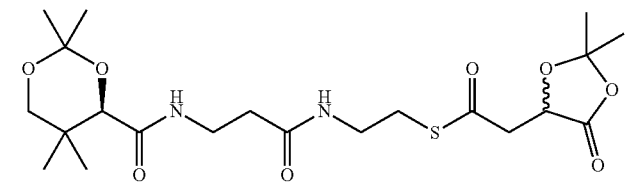 [SMILES: CC1(C)OC(=O)C(CC(=O)SCCNC(=O)CCNC(=O)[C@@H]2OC(C)(C)OCC2(C)C)O1] |
| 852 | 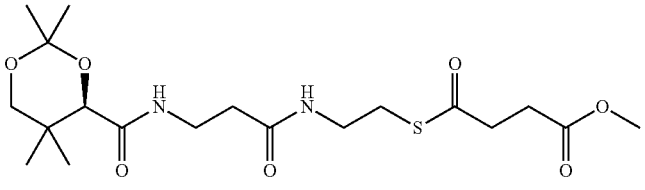 [SMILES: COC(=O)CCC(=O)SCCNC(=O)CCNC(=O)[C@@H]1OC(C)(C)OCC1(C)C] |
| 853 | 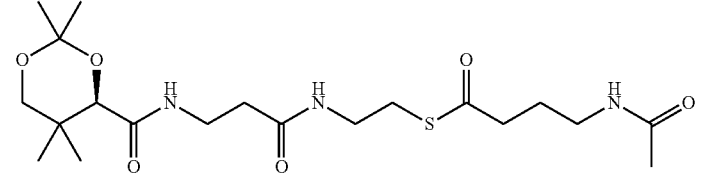 [SMILES: CC(=O)NCCCC(=O)SCCNC(=O)CCNC(=O)[C@@H]1OC(C)(C)OCC1(C)C] |

TABLE 1-continued

| Compound No. | Structure |
|---|---|
| 854 | 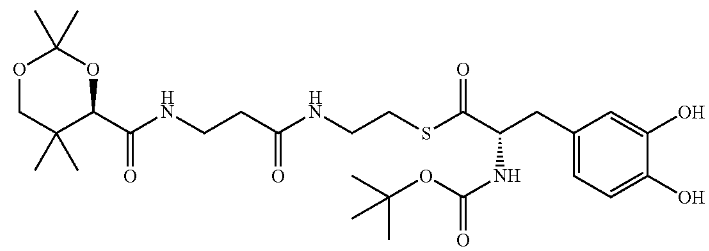 [SMILES: CC(C)(C)OC(=O)N[C@@H](Cc1ccc(O)c(O)c1)C(=O)SCCNC(=O)CCNC(=O)[C@@H]1OC(C)(C)OCC1(C)C] |
| 855 | 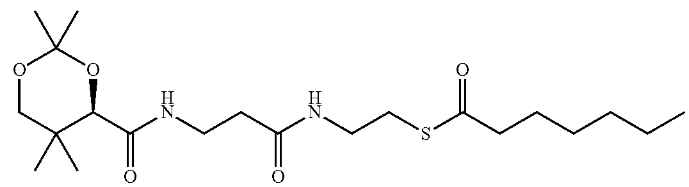 [SMILES: CCCCCCC(=O)SCCNC(=O)CCNC(=O)[C@@H]1OC(C)(C)OCC1(C)C] |
| 856 | 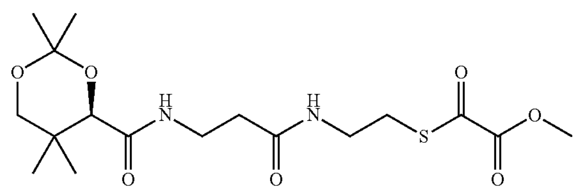 [SMILES: COC(=O)C(=O)SCCNC(=O)CCNC(=O)[C@@H]1OC(C)(C)OCC1(C)C] |
| 857 | 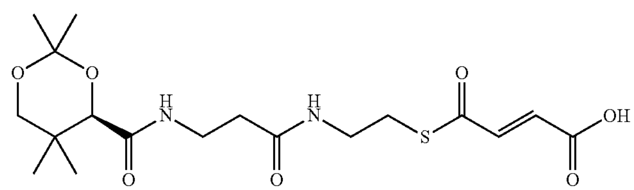 [SMILES: CC1(C)OCC(C)(C)[C@H](C(=O)NCCC(=O)NCCSC(=O)/C=C/C(=O)O)O1] |
| 858 | 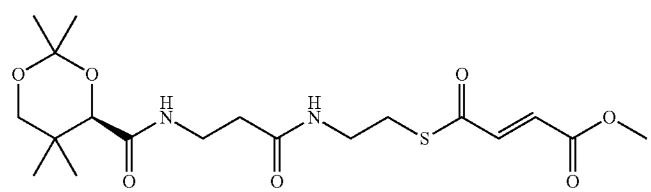 [SMILES: COC(=O)/C=C/C(=O)SCCNC(=O)CCNC(=O)[C@@H]1OC(C)(C)OCC1(C)C] |
| 859 | 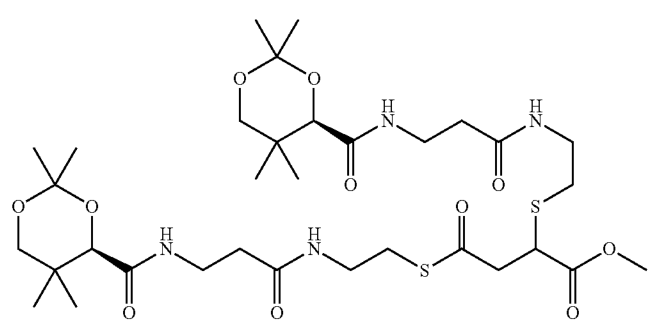 [SMILES: COC(=O)C(CC(=O)SCCNC(=O)CCNC(=O)[C@@H]1OC(C)(C)OCC1(C)C)SCCNC(=O)CCNC(=O)[C@@H]1OC(C)(C)OCC1(C)C] |
| 860 | 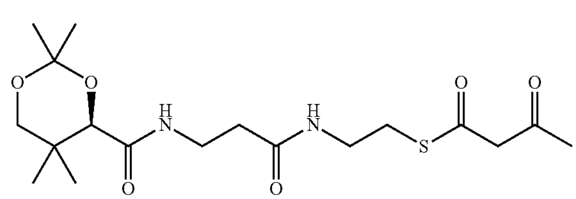 [SMILES: CC(=O)CC(=O)SCCNC(=O)CCNC(=O)[C@@H]1OC(C)(C)OCC1(C)C] |

TABLE 1-continued
| Compound No. | Structure |
|---|---|
| 861 | 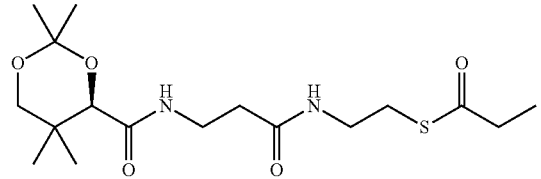 [SMILES: CCC(=O)SCCNC(=O)CCNC(=O)[C@@H]1OC(C)(C)OCC1(C)C] |
| 862 | 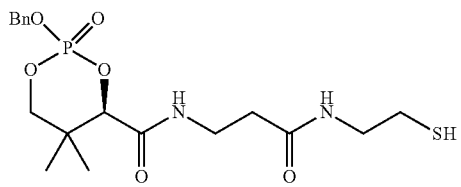 |
| 863 | 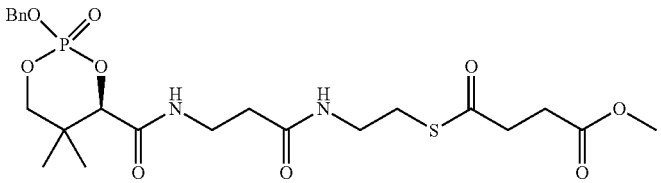 |
| 864 | 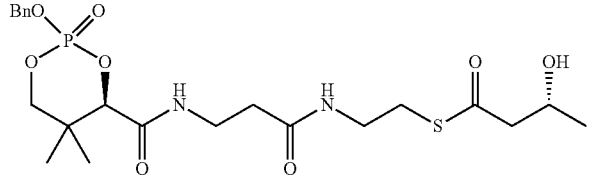 |
| 865 | 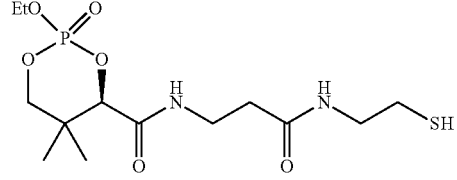 |
| 866 | 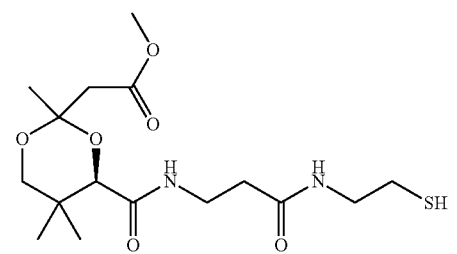 |
| 867 | 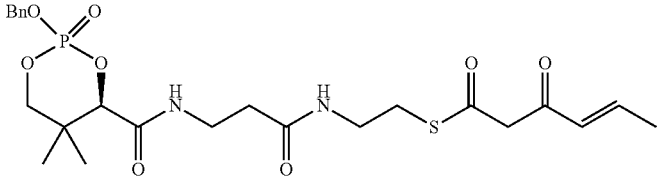 |

| Compound No. | Structure |
|---|---|
| 868 | *(chemical structure)* |
| 869 | *(chemical structure)* |
| 870 | *(chemical structure)* |
| 871 | *(chemical structure)* |
| 872 | *(chemical structure)* |

TABLE 1-continued

| Compound No. | Structure |
|---|---|
| 873 | 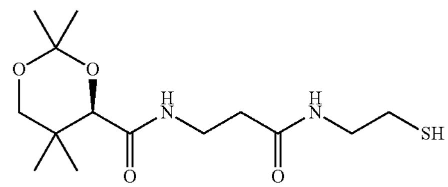 [SMILES: CC1(C)OCC(C)(C)[C@H](C(=O)NCCC(=O)NCCS)O1] |
| 874 | 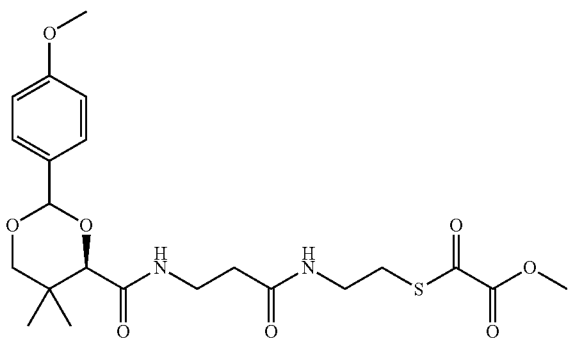 |
| 875 | 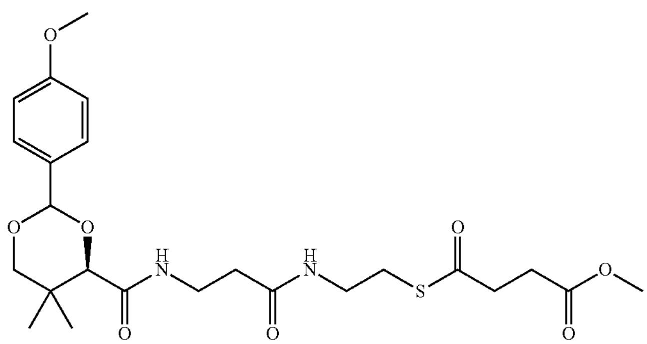 |
| 876 | 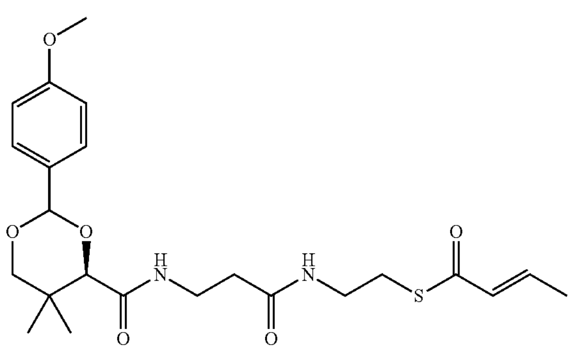 |
| 877 | 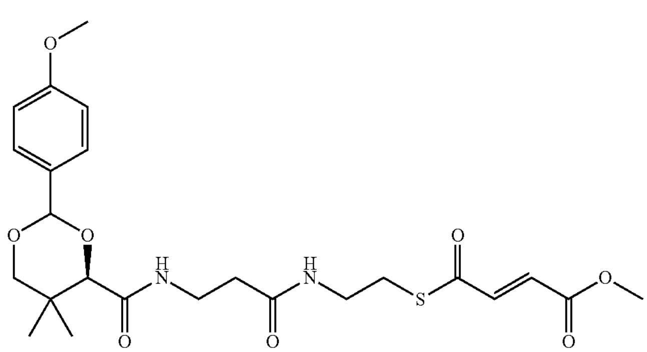 |

TABLE 1-continued

| Compound No. | Structure |
|---|---|
| 878 | 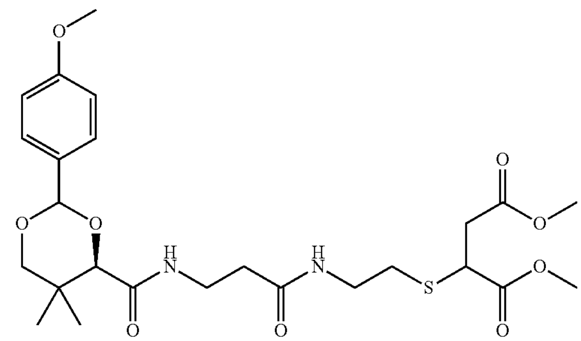 |
| 879 | 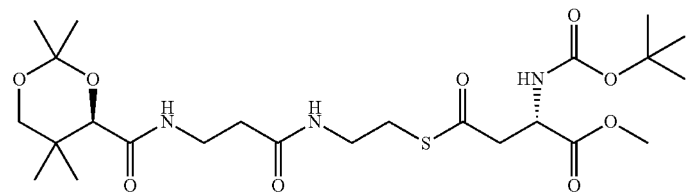 [SMILES: COC(=O)[C@H](CC(=O)SCCNC(=O)CCNC(=O)[C@@H]1OC(C)(C)OCC1(C)C)NC(=O)OC(C)(C)C] |
| 880 | 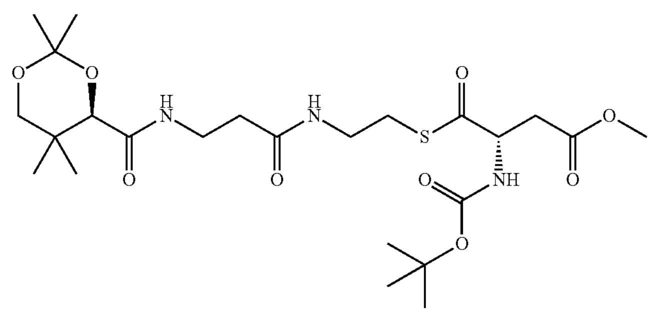 [SMILES: COC(=O)C[C@H](NC(=O)OC(C)(C)C)C(=O)SCCNC(=O)CCNC(=O)[C@@H]1OC(C)(C)OCC1(C)C] |
| 881 | 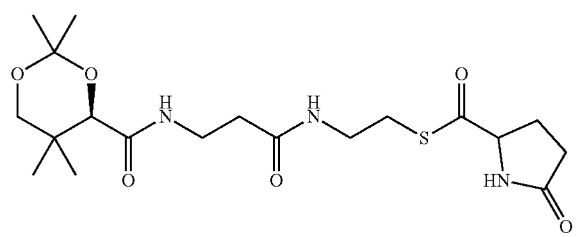 [SMILES: CC1(C)OCC(C)(C)[C@H](C(=O)NCCC(=O)NCCSC(=O)C2CCC(=O)N2)O1] |
| 882 | 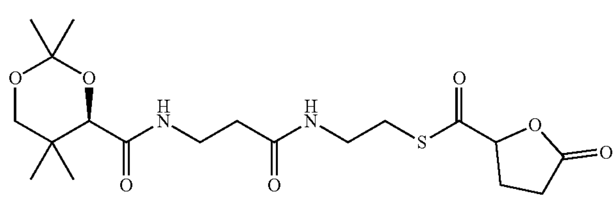 [SMILES: CC1(C)OCC(C)(C)[C@H](C(=O)NCCC(=O)NCCSC(=O)C2CCC(=O)O2)O1] |

TABLE 1-continued

| Compound No. | Structure |
|---|---|
| 883 | 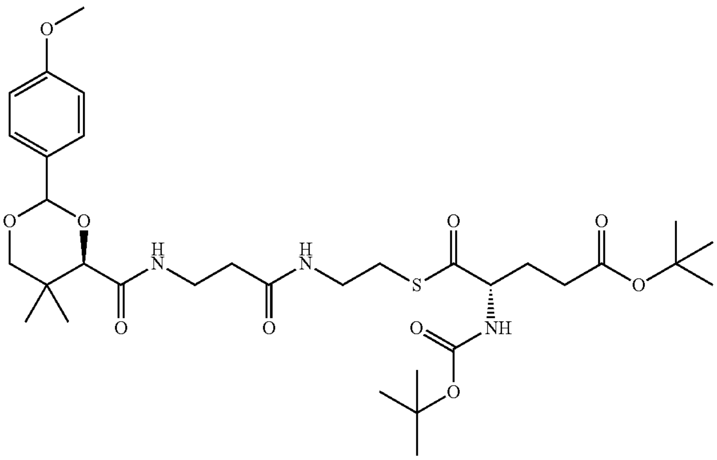 |
| 884 | 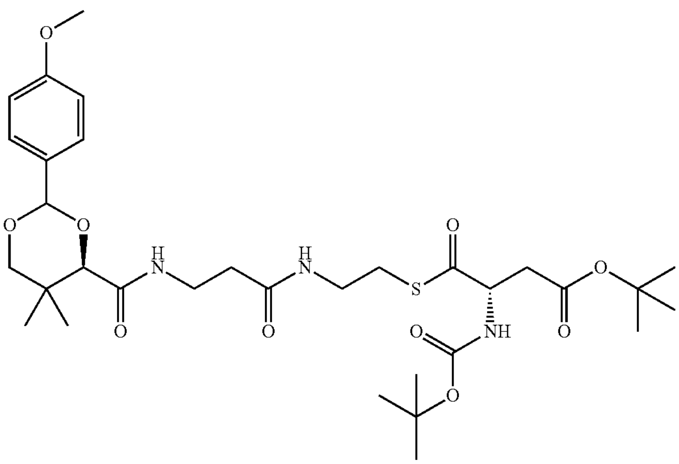 |
| 885 | 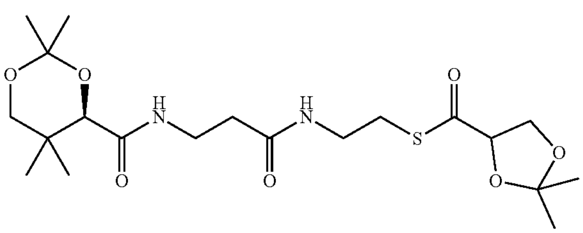 [SMILES: CC1(C)OCC(C(=O)SCCNC(=O)CCNC(=O)[C@@H]2OC(C)(C)OCC2(C)C)O1] |
| 886 | 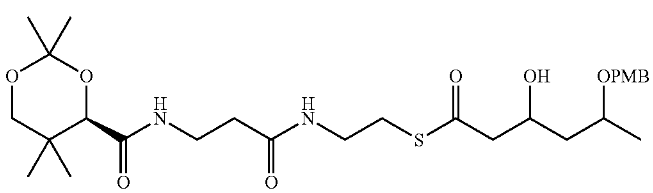 |
| 887 | 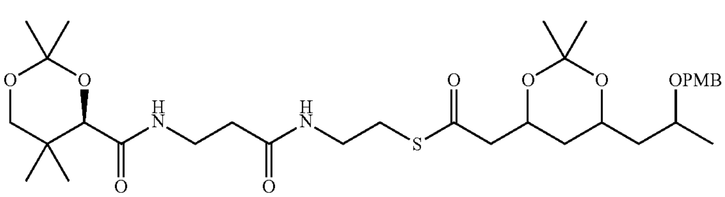 |

US 12,037,354 B2
455 456
TABLE 1-continued
| Compound No. | Structure |
|---|---|
| 888 | 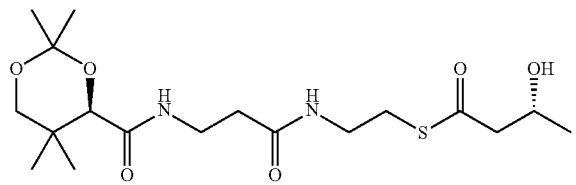 [SMILES: C[C@@H](O)CC(=O)SCCNC(=O)CCNC(=O)[C@@H]1OC(C)(C)OCC1(C)C] |
| 889 | 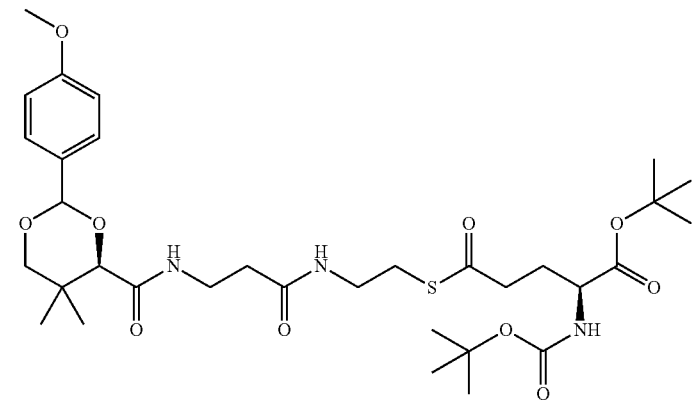 |
| 890 | 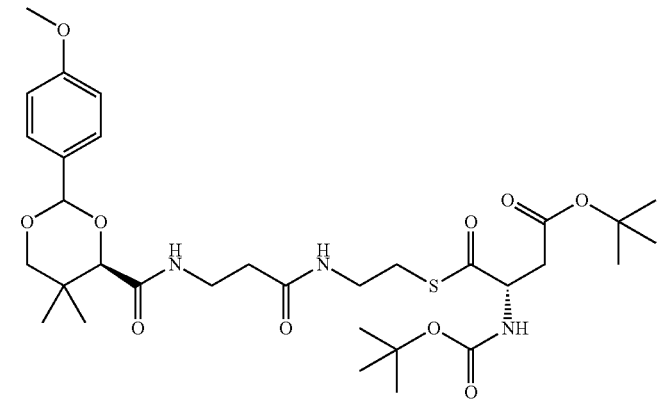 [SMILES: COc1ccc(C2OCC(C)(C)[C@H](C(=O)NCCC(=O)NCCSC(=O)[C@H](CC(=O)OC(C)(C)C)NC(=O)OC(C)(C)C)O2)cc1] |
| 891 | 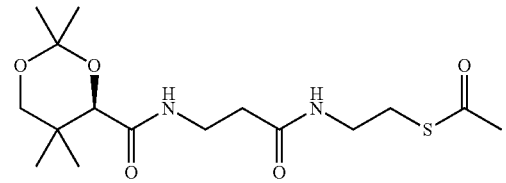 [SMILES: CC(=O)SCCNC(=O)CCNC(=O)[C@@H]1OC(C)(C)OCC1(C)C] |
| 892 | 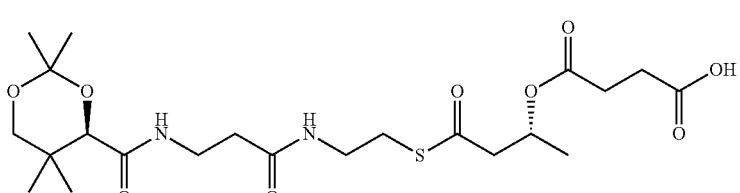 |
| 893 | 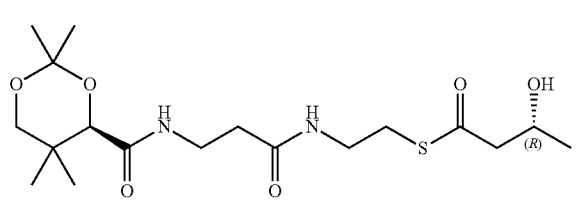 |

TABLE 1-continued

| Compound No. | Structure |
|---|---|
| 894 | 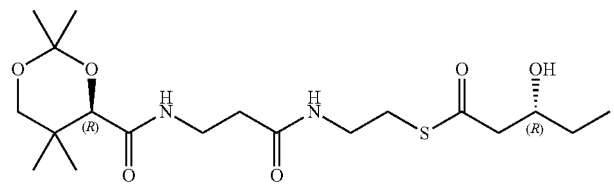 |
| 895 | 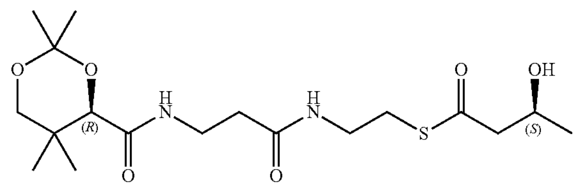 |
| 896 | 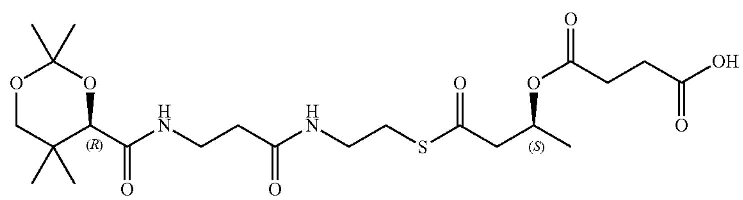 |
| 897 | 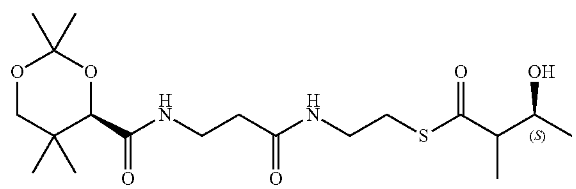 |
| 898 | 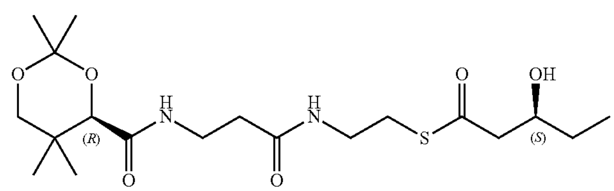 |
| 899 | 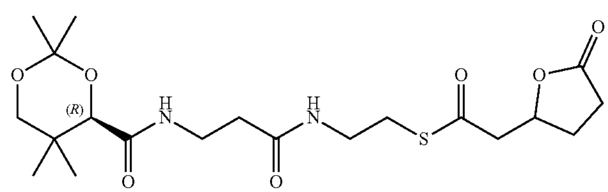 |
| 900 | 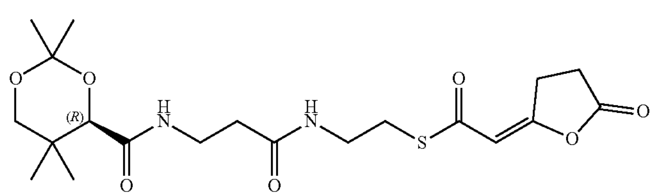 |
| 901 | 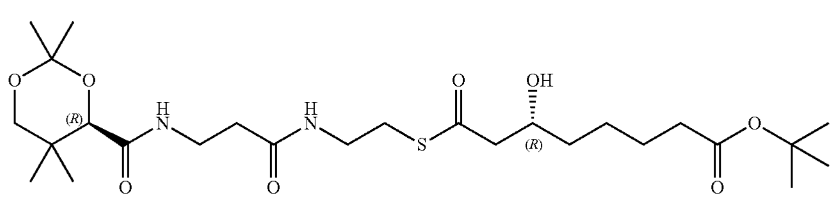 |

TABLE 1-continued

| Compound No. | Structure |
|---|---|
| 902 | 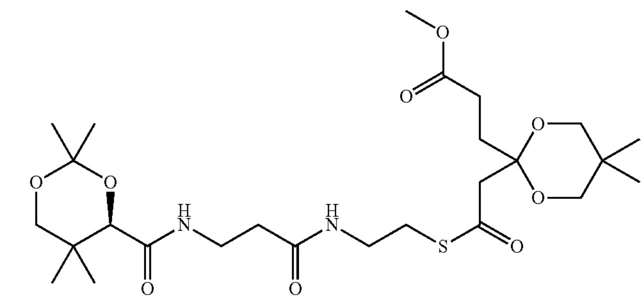 [SMILES: COC(=O)CCC1(CC(=O)SCCNC(=O)CCNC(=O)[C@@H]2OC(C)(C)OCC2(C)C)OCC(C)(C)CO1] |
| 903 | 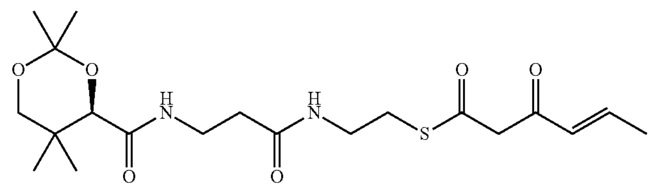 [SMILES: C/C=C/C(=O)CC(=O)SCCNC(=O)CCNC(=O)[C@@H]1OC(C)(C)OCC1(C)C] |
| 904 | 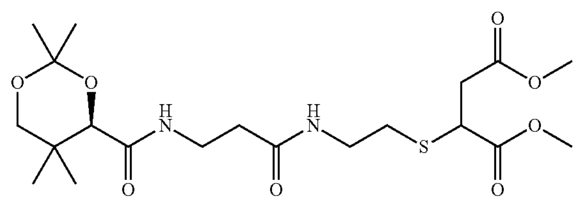 [SMILES: COC(=O)CC(SCCNC(=O)CCNC(=O)[C@@H]1OC(C)(C)OCC1(C)C)C(=O)OC] |
| 905 | 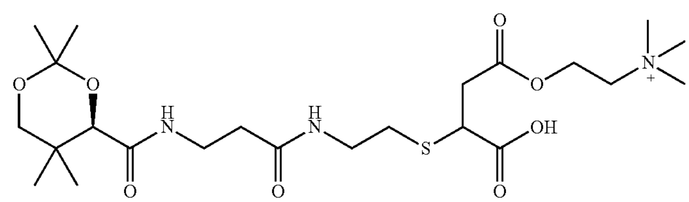 |
| 906 | 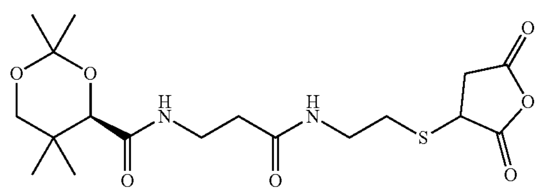 [SMILES: CC1(C)OCC(C)(C)[C@H](C(=O)NCCC(=O)NCCSC2CC(=O)OC2=O)O1] |
| 907 | 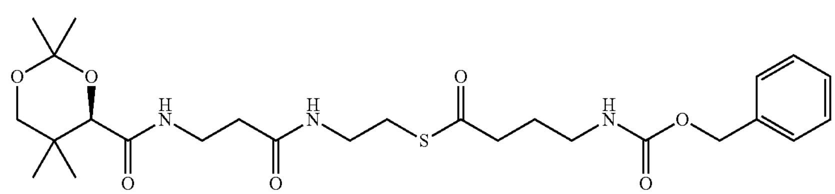 [SMILES: CC1(C)OCC(C)(C)[C@H](C(=O)NCCC(=O)NCCSC(=O)CCCNC(=O)OCc2ccccc2)O1] |
| 908 | 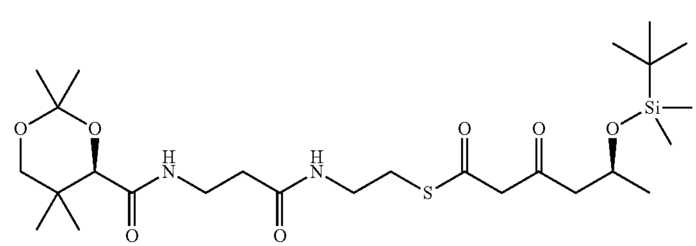 [SMILES: C[C@@H](CC(=O)CC(=O)SCCNC(=O)CCNC(=O)[C@@H]1OC(C)(C)OCC1(C)C)O[Si](C)(C)C(C)(C)C] |

TABLE 1-continued
| Compound No. | Structure |
|---|---|
| 909 | 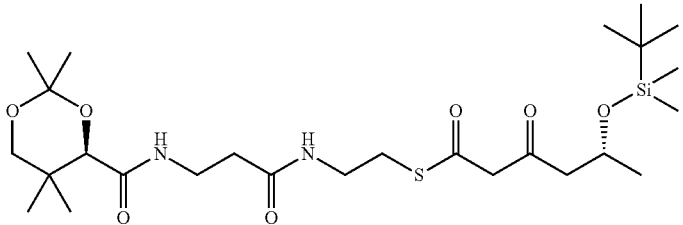 [SMILES: C[C@H](CC(=O)CC(=O)SCCNC(=O)CCNC(=O)[C@@H]1OC(C)(C)OCC1(C)C)O[Si](C)(C)C(C)(C)C] |
| 910 | 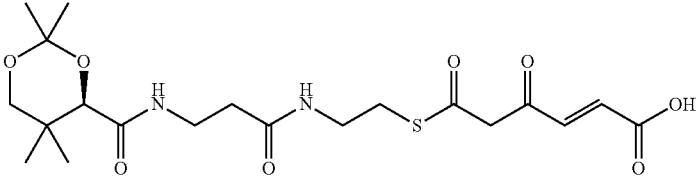 [SMILES: CC1(C)OCC(C)(C)[C@H](C(=O)NCCC(=O)NCCSC(=O)CC(=O)/C=C/C(=O)O)O1] |
| 911 | 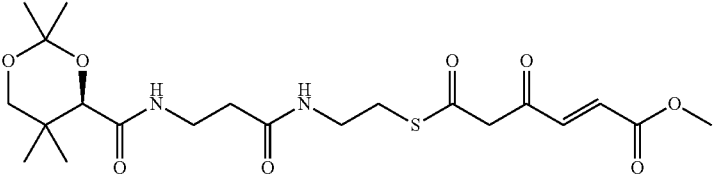 [SMILES: COC(=O)/C=C/C(=O)CC(=O)SCCNC(=O)CCNC(=O)[C@@H]1OC(C)(C)OCC1(C)C] |
| 912 | 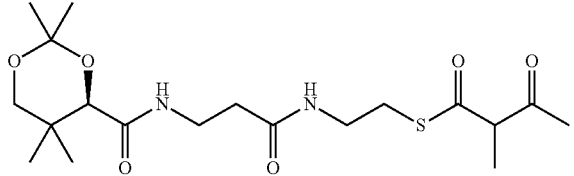 [SMILES: CC(=O)C(C)C(=O)SCCNC(=O)CCNC(=O)[C@@H]1OC(C)(C)OCC1(C)C] |
| 913 | 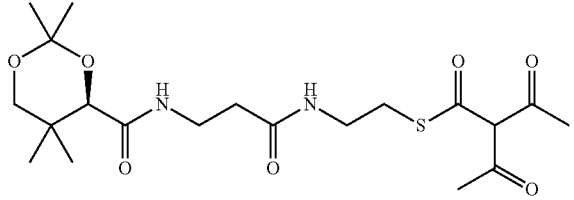 [SMILES: CC(=O)C(C(C)=O)C(=O)SCCNC(=O)CCNC(=O)[C@@H]1OC(C)(C)OCC1(C)C] |
| 914 | 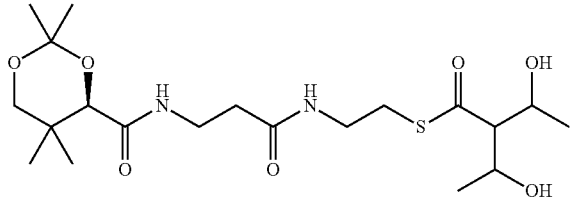 [SMILES: CC(O)C(C(=O)SCCNC(=O)CCNC(=O)[C@@H]1OC(C)(C)OCC1(C)C)C(C)O] |
| 915 | 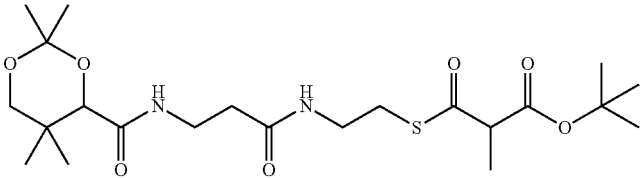 [SMILES: CC(C(=O)OC(C)(C)C)C(=O)SCCNC(=O)CCNC(=O)C1OC(C)(C)OCC1(C)C] |

TABLE 1-continued
| Compound No. | Structure |
|---|---|
| 916 | 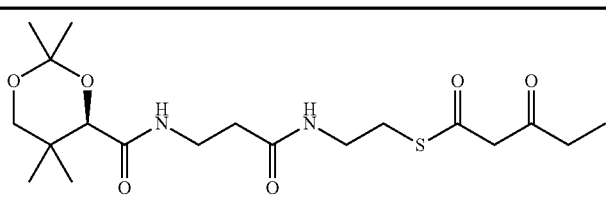 |
| 917 | 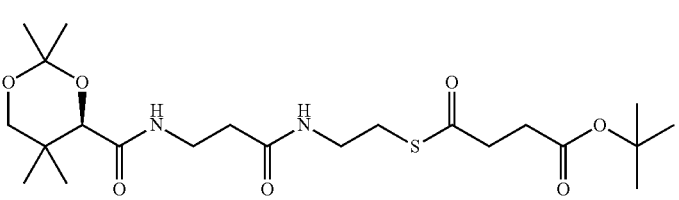 [SMILES: CC(C)(C)OC(=O)CCC(=O)SCCNC(=O)CCNC(=O)[C@@H]1OC(C)(C)OCC1(C)C] |
| 918 | 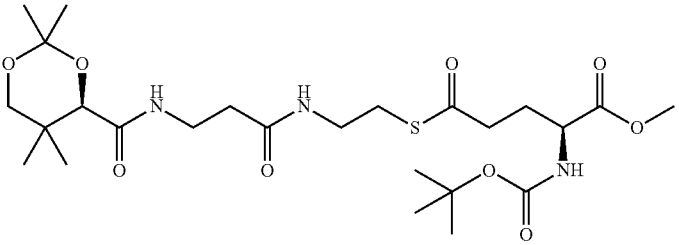 [SMILES: COC(=O)[C@H](CCC(=O)SCCNC(=O)CCNC(=O)[C@@H]1OC(C)(C)OCC1(C)C)NC(=O)OC(C)(C)C] |
| 919 | 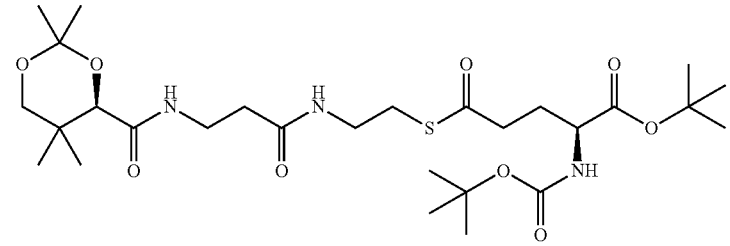 [SMILES: CC(C)(C)OC(=O)N[C@@H](CCC(=O)SCCNC(=O)CCNC(=O)[C@@H]1OC(C)(C)OCC1(C)C)C(=O)OC(C)(C)C] |
| 920 | 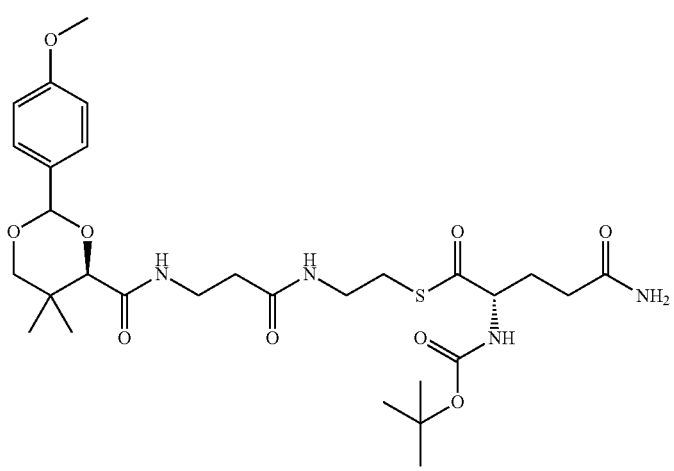 |

TABLE 1-continued

| Compound No. | Structure |
| --- | --- |
| 921 | 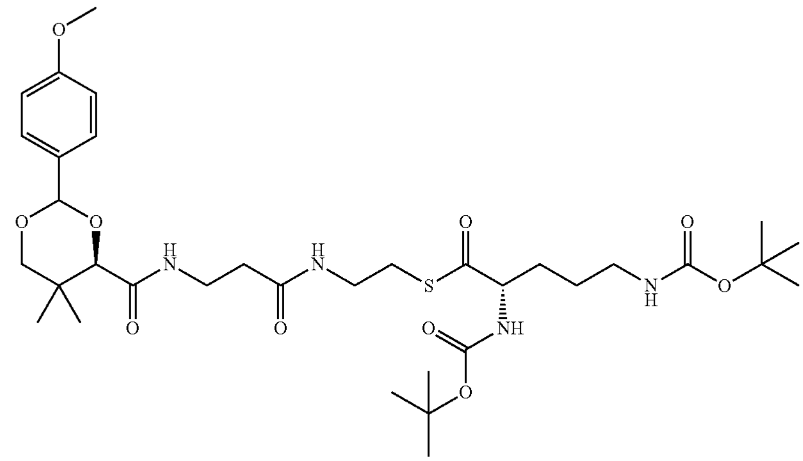 |
| 922 | 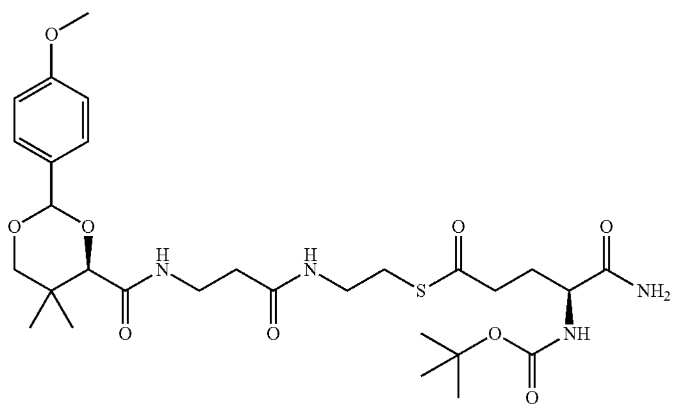 |
| 923 | 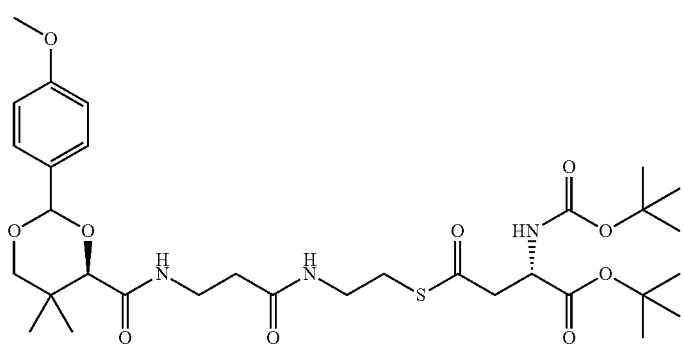 |
| 924 | 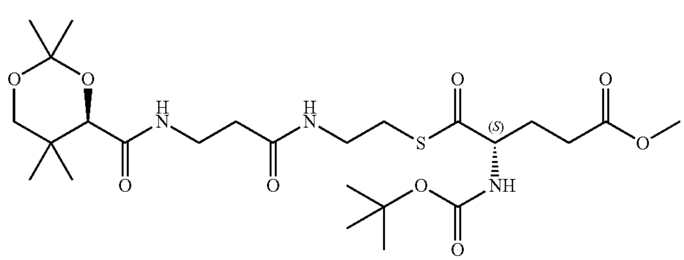 |

TABLE 1-continued
| Compound No. | Structure |
|---|---|
| 925 | 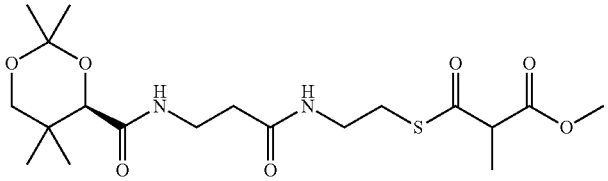 [SMILES: COC(=O)C(C)C(=O)SCCNC(=O)CCNC(=O)[C@@H]1OC(C)(C)OCC1(C)C] |
| 926 | 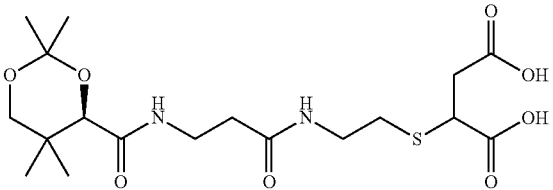 [SMILES: CC1(C)OCC(C)(C)[C@H](C(=O)NCCC(=O)NCCSC(CC(=O)O)C(=O)O)O1] |
| 927 | 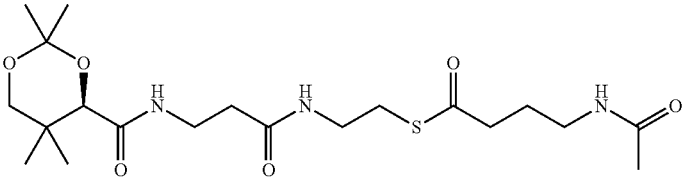 [SMILES: CC(=O)NCCCC(=O)SCCNC(=O)CCNC(=O)[C@@H]1OC(C)(C)OCC1(C)C] |
| 928 | 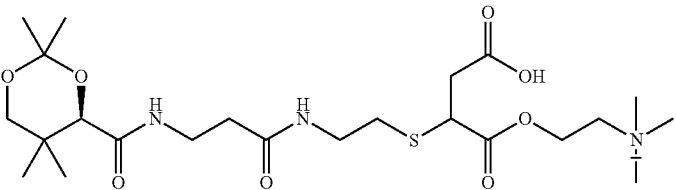 |
| 929 | 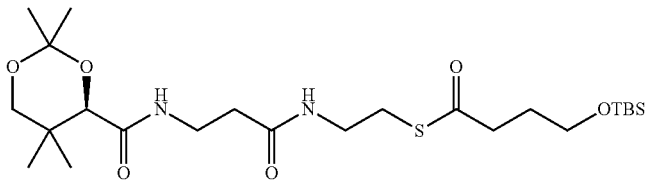 [SMILES: CC1(C)OCC(C)(C)[C@H](C(=O)NCCC(=O)NCCSC(=O)CCCO[Si](C)(C)C(C)(C)C)O1] |
| 930 | 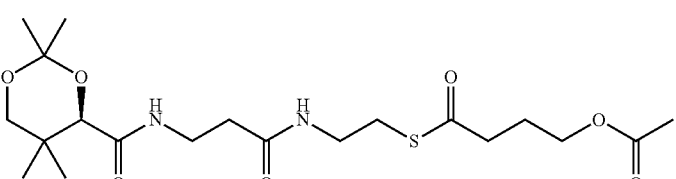 |
| 931 | 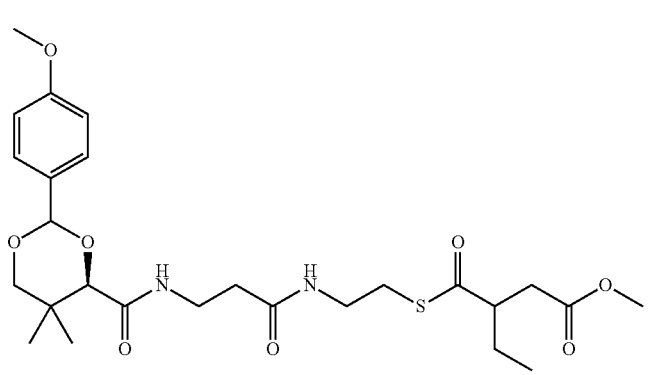 |

TABLE 1-continued
| Compound No. | Structure |
|---|---|
| 932 | 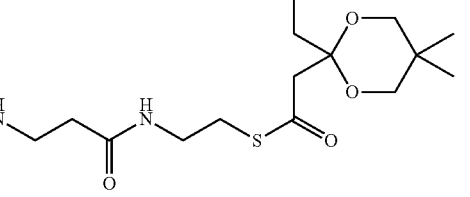 |
| 933 | 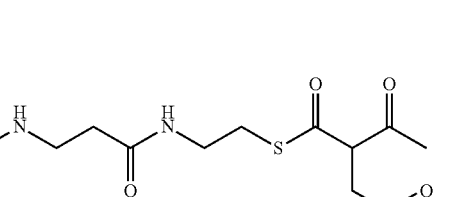 |
| 934 | 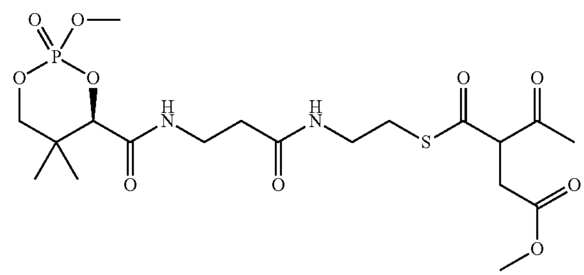 |
| 935 | 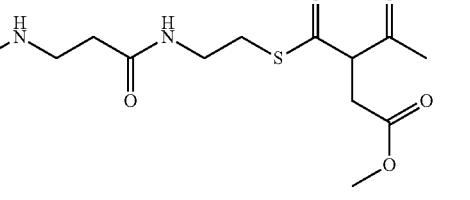 |
| 936 | 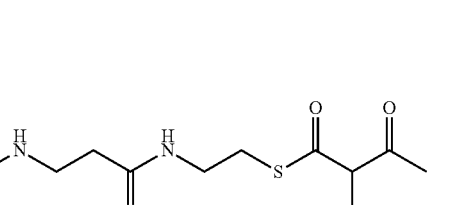 |

TABLE 1-continued

| Compound No. | Structure |
|---|---|
| 937 | 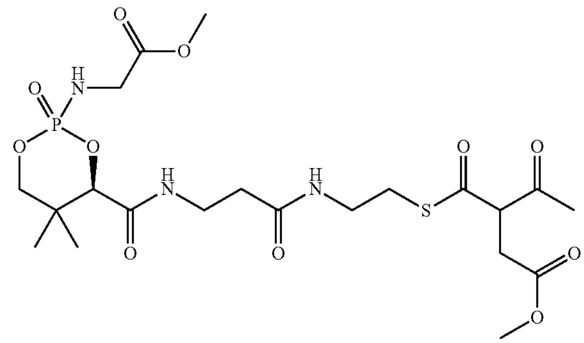 |
| 938 | 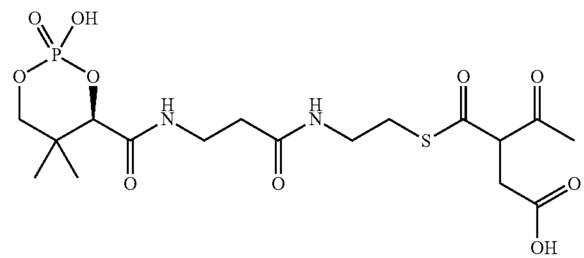 |
| 939 | 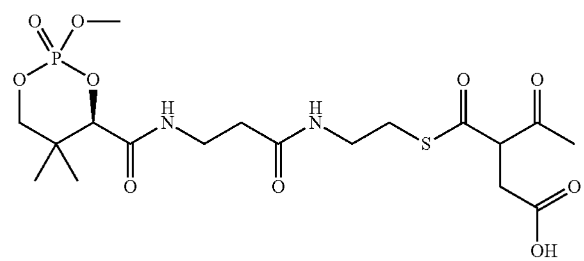 |
| 940 | 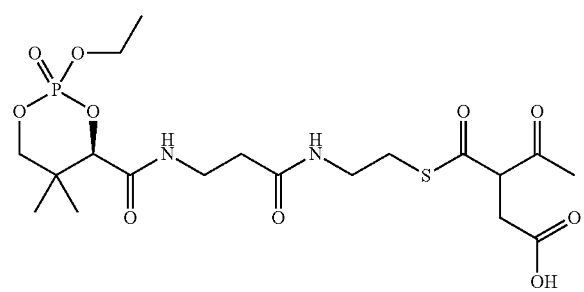 |
| 941 | 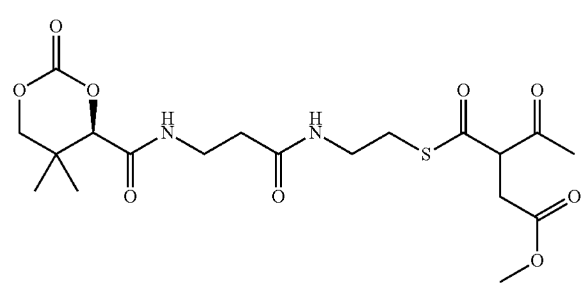 [SMILES: COC(=O)CC(C(C)=O)C(=O)SCCNC(=O)CCNC(=O)[C@@H]1OC(=O)OCC1(C)C] |

TABLE 1-continued

| Compound No. | Structure |
|---|---|
| 942 | (structure shown) |

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1 and pharmaceutically acceptable salts and solvates thereof.

In some embodiments, the compound is an isotopic derivative of any one of the compounds described in Table 1.

It is understood that the isotopic derivative can be prepared using techniques known in the art. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

In some embodiments, the compound is a deuterium labeled compound of any one of the compounds described in Table 1 and pharmaceutically acceptable salts and solvates thereof.

In some embodiments, the compound is a deuterium labeled compound of any one of the compounds described in Table 1.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (750/o deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognised techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the invention or a pharmaceutically acceptable salt or solvate thereof that contains the aforementioned deuterium atom(s) is within the scope of the disclosure. Further, substitution with heavier deuterium (i.e., $^2H$) may afford certain therapeutic advantages resulting from greater metabolic stability, e.g., increased in vivo half-life or reduced dosage requirements.

It is to be understood that a compound of the present disclosure may be depicted in a neutral form, a cationic form (e.g., carrying one or more positive charges), an anionic form (e.g., carrying one or more negative charges), or a zwitterion form (e.g., carrying one or more positive charges and one or more negative charges), all of which are intended to be included in the scope of the present disclosure. For example, when a compound of the present disclosure is depicted in a neutral form, it should be understood that such depiction also refers to the various neutral forms, cationic forms, anionic forms, and zwitterion forms of the compound.

It is to be understood that the compounds of the present disclosure and any pharmaceutically acceptable salts and solvates thereof, comprise stereoisomers, mixtures of stereoisomers, polymorphs of all isomeric forms of said compounds.

As used herein, the term "pharmaceutically acceptable salt" refers to a derivative of the compound of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc. Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3. It is to be understood that all references to pharmaceutically acceptable salts include solvent addition forms (solvates) or crystal forms (polymorphs) as defined herein, of the same salt.

As used herein, the term "solvate" refers to solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Sac.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

It is also to be understood that certain compounds of the present disclosure may exist in solvated as well as unsolvated forms such as, for example, hydrated forms. A suitable pharmaceutically acceptable solvate is, for example, a hydrate such as hemi-hydrate, a monohydrate, a di-hydrate or a tri-hydrate. It is to be understood that the disclosure encompasses all such solvated forms that possess inflammasome inhibitory activity.

It is also to be understood that certain compounds of the present disclosure may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of the present disclosure may exist in a number of different tautomeric forms and references to compounds of the formula I include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketoneenethiol, and nitro/aci-nitro.

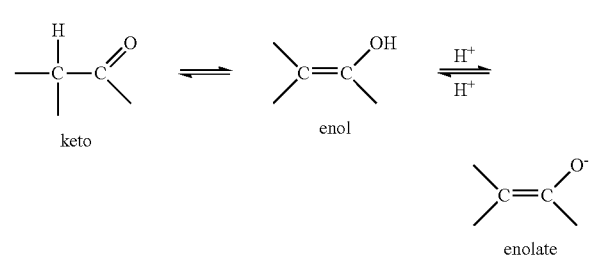

Compounds of the present disclosure containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of the present disclosure may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include in vivo cleavable ester derivatives that may be formed at a carboxy group or a hydroxy group in a compound of the present disclosure and in vivo cleavable amide derivatives that may be formed at a carboxy group or an amino group in a compound of the present disclosure.

Accordingly, the present disclosure includes those compounds of the present disclosure as defined hereinbefore when made available by organic synthesis and when made available within the human or animal body by way of cleavage of a prodrug thereof. Accordingly, the present disclosure includes those compounds of the present disclosure that are produced by organic synthetic means and also such compounds that are produced in the human or animal body by way of metabolism of a precursor compound, that is a compound of the present disclosure may be a synthetically-produced compound or a metabolically-produced compound.

A suitable pharmaceutically acceptable prodrug of a compound of the present disclosure is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of the present disclosure that possesses a carboxy group is, for example, an in vivo cleavable ester thereof. An in vivo cleavable ester of a compound of the present disclosure containing a carboxy group is, for example, a pharmaceutically acceptable ester which is cleaved in the human or animal body to produce the parent acid. Suitable pharmaceutically acceptable esters for carboxy include $C_1$-$C_6$ alkyl esters such as methyl, ethyl and tert-butyl, $C_1$-$C_6$ alkoxymethyl esters such as methoxymethyl esters, $C_1$-$C_6$ alkanoyloxymethyl esters such as pivaloyloxymethyl esters, 3-phthalidyl esters, $C_3$-$C_8$ cycloalkylcarbonyloxy-$C_1$-$C_6$ alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_1$-$C_6$ alkoxycarbonyloxy-C1-6 alkyl esters such as methoxycarbonyloxymethyl and 1-methoxycarbonyloxyethyl esters.

A suitable pharmaceutically acceptable prodrug of a compound of the present disclosure that possesses a hydroxy group is, for example, an in vivo cleavable ester or ether thereof. An in vivo cleavable ester or ether of a compound of the present disclosure containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of the present disclosure that possesses a carboxy group is, for example, an in vivo cleavable amide thereof, for example an amide formed with an amine such as ammonia, a C1-4alkylamine such as methylamine, a ($C_1$-$C_4$ alkyl)2amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of the present disclosure that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of the present disclosure may be exerted in part by one or more metabolites that are formed within the human or animal body after administration of a compound of the present disclosure. As stated hereinbefore, the in vivo effects of a compound of the present disclosure may also be exerted by way of metabolism of a precursor compound (a prodrug).

Though the present disclosure may relate to any compound or particular group of compounds defined herein by way of optional, preferred or suitable features or otherwise in terms of particular embodiments, the present disclosure may also relate to any compound or particular group of compounds that specifically excludes said optional, preferred or suitable features or particular embodiments. A feature of the disclosure concerns particular structural groups at R1, which is relevant to the scope of the claims, as defined herein. In some cases, specific groups define structures that are not relevant to the present invention and thus may be disclaimed. Such structures may be disclaimed where R1 corresponds to a phenyl directly substituted with at least 2 groups including: 1 halogen group and 1 methyl group; 2 or more halogen groups; or 2 methyl groups.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium on carbon.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

General routes for the preparation of a compound of the application are described in Schemes 1-3 herein.

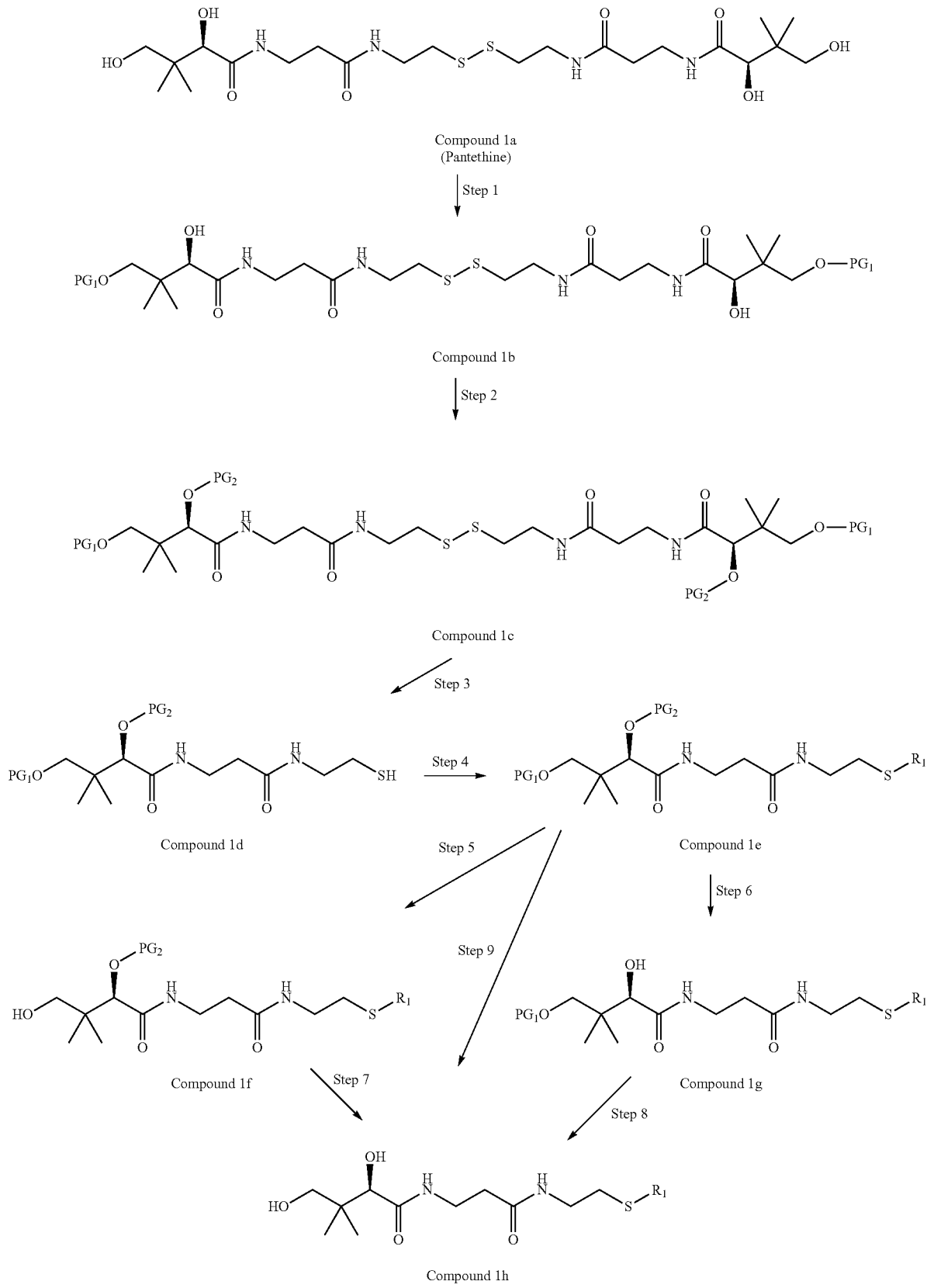
Scheme 1

Compounds of the present disclosure are generally made by sequential modification of the primary and secondary OH groups (into Compound 1b and 1c, respectively) of commercially-available pantethine (Compound 1a), followed by reduction of the disulfide Compound 1c with a suitable reducing agent, and subsequent transformation of the resulting free thiol (SH; Compound 1 d) into the desired R1-substituted pantetheine derivative (Compound 1e) with its OH groups protected as —OPG1 and —OPG2 (See Scheme 1).

Further transformation of the —OPG1 and —OPG2 groups on these $R_1$-substituted compounds (such as Compound 1e) can be effected by deprotection of the O-protecting groups (such as PG1 and/or PG2 in Compound 1 d and/or Compound 1e and/or Compound 1f), either selectively or in a one-pot reaction, to give the desired unprotected OH intermediate compound(s) (either Compound 1f and/or Compound 1g and/or Compound 1h).

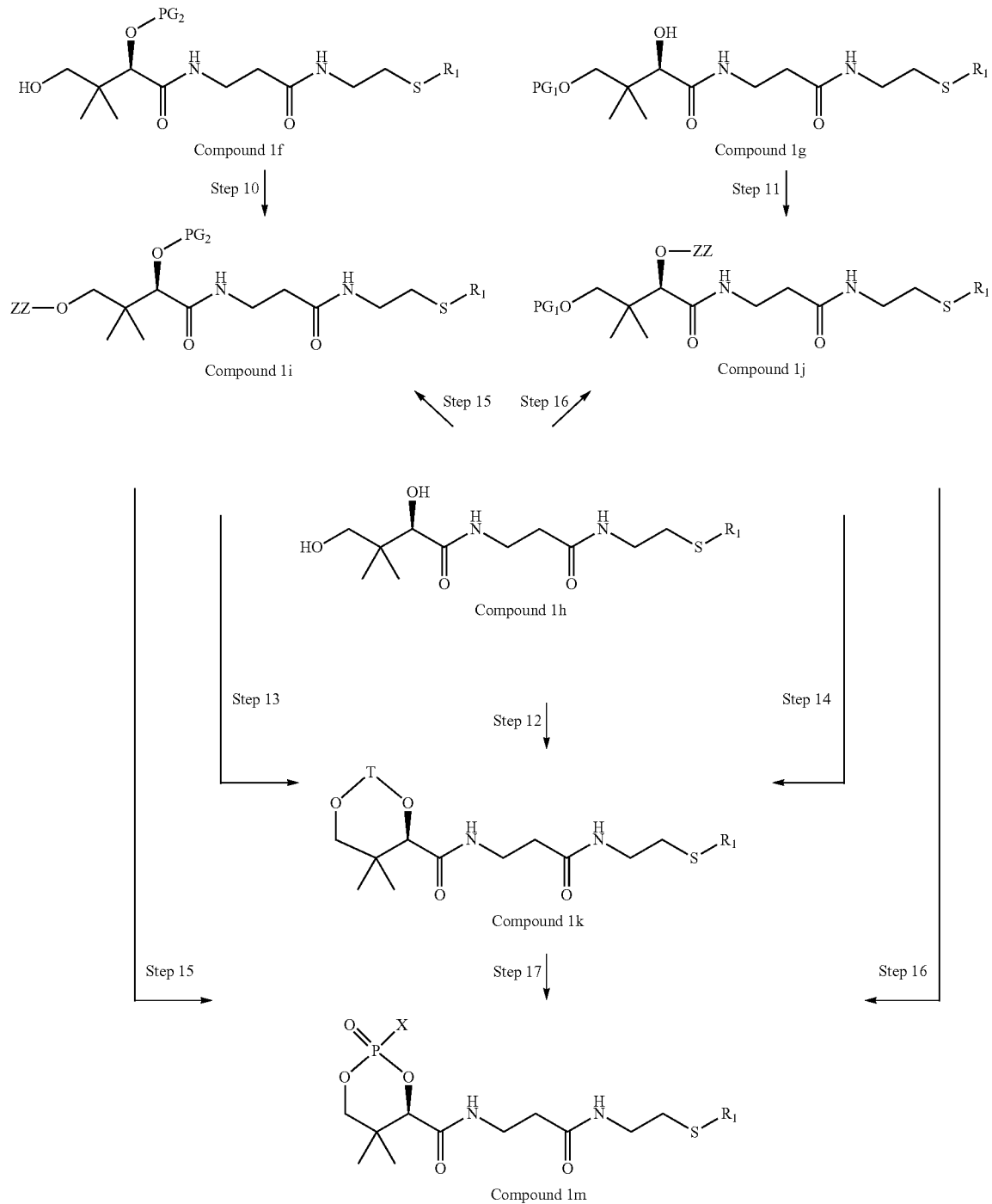

Scheme 2

These OH intermediates (either Compound 1f and/or Compound 1g and/or Compound 1h) can be further modified on the OH oxygen with a suitable oxo-reactive electrophile (such as but not limited to phosphorousoxychloride (POCl3) and/or carbonyldiimidazole and/or oxalyl chloride) in the presence of a suitable base) to provide the —OZZ-substituted intermediate compounds 1i and/or 1j. Further reaction of intermediate compounds 1 i and/or 1j by deprotection of the —OPG2 and/or —OPG3 groups, if needed, with a suitable reducing agent followed by cyclization of the resulting intermediates in the presence of a suitable base, and at room temperature, cool temperature and/or with heating) in Step 13 and/or Step 14 and/or Step 15 and/or Step 16 will provide the $R_1$-substituted cyclic Compounds 1k disclosed in this present invention (See Scheme 2) where T is the cyclic linking group (such as but not limited to —(C=O)—, —(C=O)—(C=O)— and/or —(P=O)(X)—).

Bis-OH intermediate Compound 1h can be modified on the OH oxygen atoms with a suitable oxo-reactive electrophile (such as but not limited to phosphorousoxychloride (POCl3) and/or carbonyldiimidazole and/or oxalyl chloride in the presence of a suitable base, and at room temperature, cool temperature and/or with heating) in Step 12 to provide the R1-substituted cyclic Compounds 1k disclosed in this present invention (See Scheme 2) where T is the cyclic linking group (such as but not limited to —(C=O)—, —(C=O)—(C=O)— and/or —(P=O)(X)—).

For some compounds of the present invention where the T linking moiety in Compound 1k is —(P=O)(X)—, the X group can be displaced with a suitable nucleophile in the presence of a suitable base to produce Compounds 1m of the present invention.

Alternatively, as shown in Scheme 3, reaction of the commercially-available pantethine (Compound 1a) with a suitable oxo-reactive electrophile (such as but not limited to phosphorousoxychloride (POCl3) and/or carbonyldiimidazole and/or oxalyl chloride) in the presence of a suitable base and with or without heating or cooling) would provide the bis cyclized disulfide Compound 1n where T is the cyclic linking group (such as but not limited to —(C=O)—, —(C=O)—(C=O)— and/or —(P=O)(X)—). Reduction of the disulfide Compound 1n with a suitable reducing agent, and subsequent transformation of the resulting free thiol (Compound 1k where $R_1$=H) with thio reactive R1-containing electrophiles and a suitable base would provide the desired R1-substituted Compounds 1k (Step 19). For some compounds of the present invention where the T linking moiety in Compound 1k is —(P=O)(X)—, the X group can be displaced with a suitable nucleophile in the presence of a suitable base to produce Compounds 1m of the present invention (Step 17).

Alternatively, Compound 1n, where T is the cyclic linking group selected from —(P=O)(X)— and where X is a leaving group, may be further transformed into the disulfide Compound 1p (Step 20) where T is the cyclic linking group —(P=O)(X)— and X is a substituent of the present invention. Reduction of the disulfide Compound 1p with a suitable reducing agent (Step 21), and subsequent transformation of the resulting free thiol (Compound 1m where $R_1$=H) with thio reactive R1-containing electrophiles and a suitable base would provide the desired R1-substituted compounds of this invention, Compounds 1m.

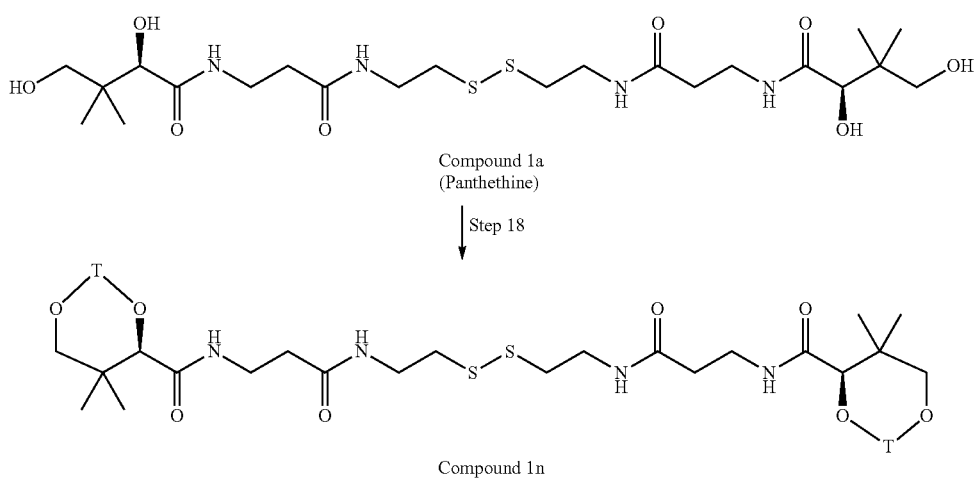

Scheme 3

-continued

Step 19 | Step 20

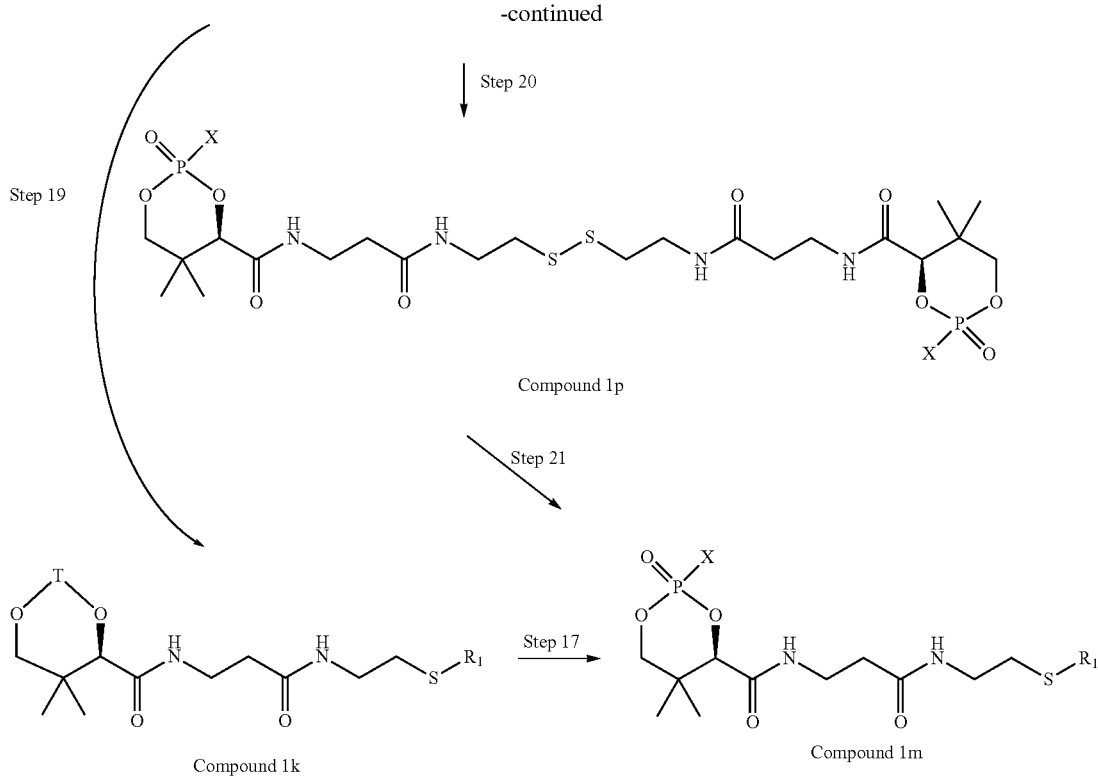

Compound 1p

Step 21

Compound 1k

Step 17

Compound 1m

Scheme 4

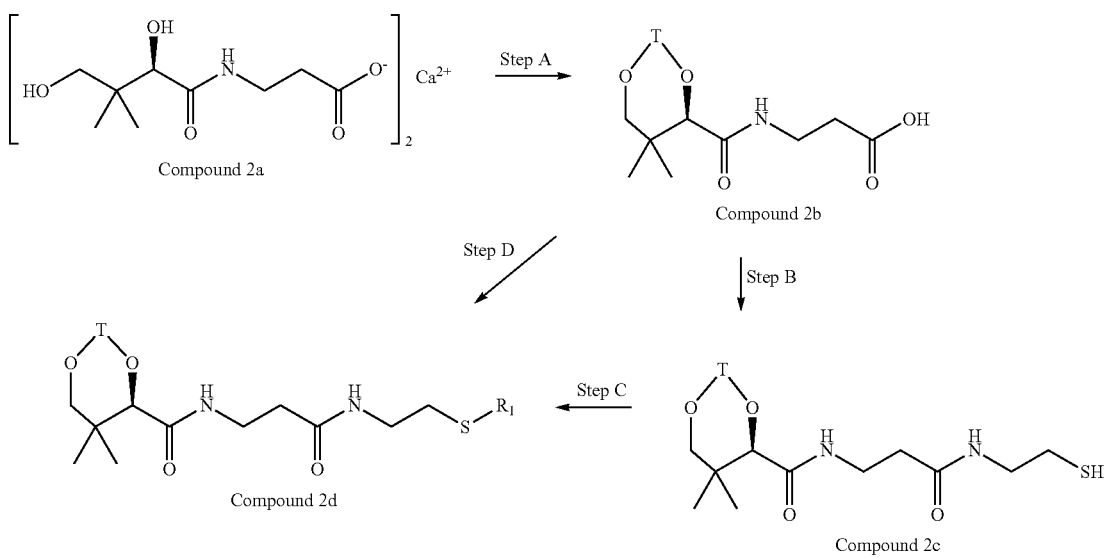

Compound 2a

Step A

Compound 2b

Step D

Step B

Compound 2d

Step C

Compound 2c

Alternatively, compounds of the present disclosure can be made by treatment of commercially available pantothenic acid calcium salt (Compound 2a) in the presence of a ketone and catalytic acid (including but not limited to pTSA, under dehydrating conditions (including but not limited to 3Angstrom molecular sieves) as shown in Step A to generate the cyclic ketal Compound 2b. This compound can be coupled with cysteamine as shown in Step B using a suitable coupling agent to provide Compounds 2c of the present invention. Compound 2c can be further modified as shown in Step C by reacting it with a thio reactive agent such as indicated above to provide Compounds 2d of the present invention. Alternatively, an S-substituted cysteamine can be coupled with Compound 2b in the presence of a suitable coupling agent, and if needed a suitable base such as but not limited to triethyl amine, to provide Compounds 2d directly. In some examples, the T moiety in Compound 2d can be further transformed to remove protecting groups on T (such as but not limited to esters and amine protecting groups) and using suitable deprotection chemistry such as but not limited to saponification and/or catalytic hydrogenation, to produce unprotected derivatives of Compound 2d, which are also compounds of the present invention.

Alternatively, commercially available pantethine may be treated similarly as in Step A above to provide the bis cyclic ketal derivative of pantethine, which can be further modified and transformed as indicated in the above Schemes and generic description.

All of these transformations may be effectively conducted by one skilled in the art using suitable methods.

It should be understood that in the description and formulae shown above, the various groups are as defined herein, except where otherwise indicated. Furthermore, for synthetic purposes, the compounds in the Schemes are mere representatives with elected substituents to illustrate the general synthetic methodology of a compound disclosed herein.

Biological Assays

Compounds and methods designed, selected and/or optimized as described above can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure and detecting the effect of the methods of the present disclosure. These in vitro or in vivo biological assays can include, but are not limited to, enzymatic activity assays, electrophoretic mobility shift assays, reporter gene assays, in vitro cell viability assays, and the assays described herein.

Pharmaceutical Compositions

In some aspects, the present disclosure provides a pharmaceutical composition comprising a compound of the present disclosure as an active ingredient.

In some embodiments, the pharmaceutical composition comprises a compound of the present disclosure, or a pharmaceutically acceptable salt or solvate thereof, and one or more pharmaceutically acceptable carriers or excipients.

In some embodiments, the pharmaceutical composition comprises a compound of any one of the Formulae disclosed herein.

In some embodiments, the pharmaceutical composition comprises a compound selected from Table 1.

It is to be understood that a pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., imprinting disorders, and the like) and the health of the patient should preferably be closely monitored during and for a reasonable period after treatment.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

It is to be understood that the pharmaceutical compositions can be included in a container, pack, or dispenser together with instructions for administration.

Methods of Use

In some aspects, the present disclosure provides methods comprising administering to a subject a therapeutically effective amount of at least one compound of the present disclosure, as described in full detail herein.

The present disclosure provides a method of activating or enhancing Coenzyme A (also referred to as CoA, free CoA or CoA-SH) synthesis in a subject comprising administering to the subject a therapeutically effective amount of at least one compound of the present disclosure. The present disclosure provides at least one compound of the present disclosure for use in activating or enhancing CoA synthesis in a subject, wherein the at least one compound of the present disclosure is for administration to the subject in at least one therapeutically effective amount. The present disclosure provides a use of at least one compound of the present disclosure for the manufacture of a medicament for activating or enhancing CoA synthesis in a subject, wherein the at least one compound of the present disclosure is for administration to the subject in at least one therapeutically effective amount.

The present disclosure provides a method of increasing Coenzyme A (also referred to as CoA, free CoA or CoA-SH) concentrations in a subject comprising administering to the subject a therapeutically effective amount of at least one compound of the present disclosure. The present disclosure provides at least one compound of the present disclosure for use in increasing CoA concentrations in a subject, wherein the at least one compound of the present disclosure is for administration to the subject in at least one therapeutically effective amount. The present disclosure provides a use of at least one compound of the present disclosure for the manufacture of a medicament for increasing CoA concentrations in a subject, wherein the at least one compound of the present disclosure is for administration to the subject in at least one therapeutically effective amount.

The present disclosure provides a method of activating or enhancing acetyl-CoA synthesis in a subject comprising administering to the subject a therapeutically effective amount of at least one compound of the present disclosure. The present disclosure provides at least one compound of the present disclosure for use in activating or enhancing acetyl-CoA synthesis in a subject, wherein the at least one compound of the present disclosure is for administration to the subject in at least one therapeutically effective amount. The present disclosure provides a use of at least one compound of the present disclosure for the manufacture of a medicament for activating or enhancing acetyl-CoA synthesis in a subject, wherein the at least one compound of the present disclosure is for administration to the subject in at least one therapeutically effective amount.

The present disclosure provides a method of increasing acetyl-CoA concentrations in a subject comprising administering to the subject a therapeutically effective amount of at least one compound of the present disclosure. The present disclosure provides at least one compound of the present disclosure for use in increasing acetyl-CoA concentrations in a subject, wherein the at least one compound of the present disclosure is for administration to the subject in at least one therapeutically effective amount. The present disclosure provides a use of at least one compound of the present disclosure for the manufacture of a medicament for increasing acetyl-CoA concentrations in a subject, wherein the at least one compound of the present disclosure is for administration to the subject in at least one therapeutically effective amount.

The present disclosure provides a method of activating or enhancing acyl-CoA synthesis in a subject, wherein the acyl group can include, but is not limited to, a formyl group, a acetyl group, a propionyl group, a butyryl group, a crotonyl group, a malonyl group, a succinyl group, a glutaryl group, a myristoyl, a palmitoyl group, comprising administering to the subject a therapeutically effective amount of at least one compound of the present disclosure. The present disclosure provides at least one compound of the present disclosure for use in activating or enhancing acyl-CoA synthesis in a subject, wherein the at least one compound of the present disclosure is for administration to the subject in at least one therapeutically effective amount. The present disclosure provides a use of at least one compound of the present disclosure for the manufacture of a medicament for activating or enhancing acyl-CoA synthesis in a subject, wherein the at least one compound of the present disclosure is for administration to the subject in at least one therapeutically effective amount.

The present disclosure provides a method increasing acyl-CoA concentrations in a subject, wherein the acyl group can include, but is not limited to, a formyl group, a acetyl group, a propionyl group, a butyryl group, a crotonyl group, a malonyl group, a succinyl group, a glutaryl group, a myristoyl, a palmitoyl group, comprising administering to the subject a therapeutically effective amount of at least one compound of the present disclosure. The present disclosure provides at least one compound of the present disclosure for use in increasing acyl-CoA concentrations in a subject, wherein the at least one compound of the present disclosure is for administration to the subject in at least one therapeutically effective amount. The present disclosure provides a use of at least one compound of the present disclosure for the manufacture of a medicament for increasing acyl-CoA concentrations in a subject, wherein the at least one compound of the present disclosure is for administration to the subject in at least one therapeutically effective amount.

The present disclosure provides a method of activating or enhancing synthesis of the at least one precursor of CoA in a subject, wherein the at least one prescursor can include, but are not limited to, pantothenate, phosphopantothenate, pantetheine, pantethine, phosphopantetheine, dephospho-CoA and any other precursor known in the art, comprising administering to the subject a therapeutically effective amount of at least one compound of the present disclosure. The present disclosure provides at least one compound of the present disclosure for use in activating or enhancing the synthesis of at least one precursor of CoA in a subject, wherein the at least one compound of the present disclosure is for administration to the subject in at least one therapeutically effective amount. The present disclosure provides a use of at least one compound of the present disclosure for the manufacture of a medicament for activating or enhancing the synthesis of at least one precursor of CoA in a subject, wherein the at least one compound of the present disclosure is for administration to the subject in at least one therapeutically effective amount.

The present disclosure provides a method increasing the concentration of at least one precursor of CoA in a subject, wherein the at least one precursor can include, but is not limited to, pantothenate, phosphopantothenate, pantetheine, phosphopantetheine, dephospho-CoA and any other precursor known in the art, comprising administering to the subject a therapeutically effective amount of at least one compound of the present disclosure. The present disclosure provides at least one compound of the present disclosure for use in increasing the concentration of at least one precursor of CoA in a subject, wherein the at least one compound of the present disclosure is for administration to the subject in at least one therapeutically effective amount. The present disclosure provides a use of at least one compound of the present disclosure for the manufacture of a medicament for increasing the concentration of at least one precursor of CoA in a subject, wherein the at least one compound of the present disclosure is for administration to the subject in at least one therapeutically effective amount.

The present disclosure provides a method of activating or enhancing synthesis of at least one precursor of acyl-CoA in a subject, wherein the at least one precursor can include, but is not limited to, acyl-pantothenate, acyl-phosphopantothenate, acyl-pantetheine, acyl-pantethine, acyl-phosphopantetheine, acyl-dephospho-CoA and any other precursors known in the art, wherein the acyl group can include, but is not limited to, a formyl group, an acetyl group, a propionyl group, a butyryl group, a crotonyl group, a malonyl group, a succinyl group, a glutaryl group, a myristoyl, a palmitoyl group, the method comprising administering to the subject a therapeutically effective amount of at least one compound of the present disclosure. The present disclosure provides at least one compound of the present disclosure for use in activating or enhancing the synthesis of at leas tone precursor of acyl-CoA in a subject, wherein the at least one compound of the present disclosure is for administration to the subject in at least one therapeutically effective amount. The present disclosure provides a use of at least one compound of the present disclosure for the manufacture of a medicament for activating or enhancing the synthesis of at least one precursor of acyl-CoA in a subject, wherein the at least one compound of the present disclosure is for administration to the subject in at least one therapeutically effective amount.

The present disclosure provides a method increasing concentrations of at least one precursor of acyl-CoA in a subject, wherein the at least one precurose can include, but is not limited to, acyl-pantothenate, acyl-phosphopantothenate, acyl-pantetheine, acyl-pantethine, acyl-phosphopantetheine, acyl-dephospho-CoA and any other precursors known in the art, wherein the acyl group can include, but is not limited to, a formyl group, an acetyl group, a propionyl group, a butyryl group, a crotonyl group, a malonyl group, a succinyl group, a glutaryl group, a myristoyl, a palmitoyl group, the method comprising administering to the subject a therapeutically effective amount of at least one compound of the present disclosure. The present disclosure provides at least one compound of the present disclosure for use in increasing the concentration of at least one precursor of acyl-CoA in a subject, wherein the at least one compound of the present disclosure is for administration to the subject in at least one therapeutically effective amount. The present disclosure provides a use of at least one compound of the present disclosure for the manufacture of a medicament for increasing the concentration of at least one precursors of acyl-CoA in a subject, wherein the at least one compound of the present disclosure is for administration to the subject in at least one therapeutically effective amount.

The present disclosure provides a method of activating or enhancing the synthesis of at least one active metabolite derived from any of the aforementioned species (free CoA, acyl-CoA, acetyl-CoA, precursors of free CoA, precursors of acyl-CoA, precursors of acetyl-CoA, etc.) in a subject, wherein the at least one active metabolite can include, but is not limited to, branched or linear organic acids, including, but not limited to, crotonic acid, propionic acid, butanoic acid, pentanoic acid, hexanoic acid, heptanoic acid; (alpha-, beta-, and gamma-) keto acids, including, but not limited to, pyruvic acid, oxaloacetic acid, alpha-ketoglutarate, acetoacetic acid, levulinic acid; hydroxy acids, including, but not limited to, lactic acid, 3-hydroxypropionic acid, 3-hydroxybutyric acid, 4-hydroxybutyric acid; saturated dicarboxylic acids, including, but not limited to, oxalic acid, malonic acid, methylmalonic acid, succinic acid, glutaric acid, adipic acid, pimelic acid, suberic acid, azelaic acid, sebacic acid; unsaturated dicarboxylic acids, including, but not limited to maleic acid, fumaric acid, glutaconic acid; quaternary ammonium cations, including, but not limited to, choline, choline phosphates, carnitines; amino acids, including, but not limited to glycine, alanine, 3,4-dihydroxyphenylalanine (DOPA), gamma-aminobutyric acid (GABA); lactams and lactones, including, but not limited to, pyrrolidinone, furanone, dihydrofuranone, or derivatives thereof, including, but not limited to, esters, ketals, hydroxylated, aminated, acetylated, or methylated species, the method comprising administering to the subject a therapeutically effective amount of at least one compound of the present disclosure. The present disclosure provides at least one compound of the present disclosure for use in activating or enhancing the synthesis of at least one of the said active metabolites in a subject, wherein the at least one compound of the present disclosure is for administration to the subject in at least one therapeutically effective amount. The present disclosure provides a use of at least one compound of the present disclosure for the manufacture of a medicament for activating or enhancing the synthesis of at least one of the said active metabolites in a subject, wherein the at least one compound of the present disclosure is for administration to the subject in at least one therapeutically effective amount.

The present disclosure provides a method increasing the concentration of at least one active metabolite derived from any of the aforementioned species (free CoA, aryl-CoA, acetyl-CoA, precursors of free CoA, precursors of acyl-CoA, precursors of acetyl-CoA, etc.) in a subject, wherein the at least one active metabolite can include, but is not limited to, branched or linear organic acids, including, but not limited to, crotonic acid, propionic acid, butanoic acid, pentanoic acid, hexanoic acid, heptanoic acid; (alpha-, beta-, and gamma-) keto acids, including, but not limited to, pyruvic acid, oxaloacetic acid, alpha-ketoglutarate, acetoacetic acid, levulinic acid; hydroxy acids, including, but not limited to, lactic acid, 3-hydroxypropionic acid, 3-hydroxybutyric acid, 4-hydroxybutyric acid; saturated dicarboxylic acids, including, but not limited to, oxalic acid, malonic acid, methylmalonic acid, succinic acid, glutaric acid, adipic acid, pimelic acid, suberic acid, azelaic acid, sebacic acid; unsaturated dicarboxylic acids, including, but not limited to maleic acid, fumaric acid, glutaconic acid; quaternary ammonium cations, including, but not limited to, choline, choline phosphates, carnitines; amino acids, including, but not limited to glycine, alanine, 3,4-dihydroxyphenylalanine (DOPA), gamma-aminobutyric acid (GABA); lactams and lactones, including, but not limited to, pyrrolidinone, furanone, dihydrofuranone, or derivatives thereof, including, but not limited to, esters, ketals, hydroxylated, aminated, acetylated, or methylated species, the method comprising administering to the subject a therapeutically effective amount of at least one compound of the present disclosure. The present disclosure provides at least one compound of the present disclosure for use in increasing the concentration of at least one of the said active metabolites in a subject, wherein the at least one compound of the present disclosure is for administration to the subject in at least one therapeutically effective amount. The present disclosure provides a use of at least one compound of the present disclosure for the manufacture of a medicament for increasing the concentration of at least one of the said active metabolites in a subject, wherein the at least one compound of the present disclosure is for administration to the subject in at least one therapeutically effective amount.

The present disclosure provides a method of treating a disease in a subject comprising administering to the subject a therapeutically effective at least one compound of the present disclosure. The present disclosure provides at least one compound of the present disclosure for use in treating a disease in a subject, wherein the at least one compound of the present disclosure is for administration to the subject in at least one therapeutically effective amount. The present disclosure provides a use of at least one compound of the present disclosure for the manufacture of a medicament for treating a disease in a subject, wherein the at least one compound of the present disclosure is for administration to the subject in at least one therapeutically effective amount.

The present disclosure provides a method of preventing a disease in a subject comprising administering to the subject a therapeutically effective amount of at least one compound of the present disclosure. The present disclosure provides at least one compound of the present disclosure for use in preventing a disease in a subject, wherein the at least one compound of the present disclosure is for administration to the subject in at least one therapeutically effective amount. The present disclosure provides a use of at least one compound of the present disclosure for the manufacture of a medicament for preventing a disease in a subject, wherein the at least one compound of the present disclosure is for administration to the subject in at least one therapeutically effective amount.

In some aspects, a disease can be a disease that is characterized by and/or associated with decreased concentrations of one or more of free CoA, acetyl-CoA, acyl-CoA, a precursor of free CoA, an active metabolite of free CoA, an active metabolite of a free CoA precursor, a precursor of acetyl-CoA, an active metabolite of acetyl-CoA, an active metabolite of an acetyl-CoA precursor, a precursor of acyl-CoA, an active metabolite of acyl-CoA, an active metabolite of an acyl-CoA precursor. Thus, the present disclosure provides a method of treating a disease characterized by and/or associated with decreased concentrations of one or more of free CoA, acetyl-CoA, acyl-CoA, a precursor of free CoA, an active metabolite of free CoA, an active metabolite of a free CoA precursor, a precursor of acetyl-CoA, an active metabolite of acetyl-CoA, an active metabolite of an acetyl-CoA precursor, a precursor of acyl-CoA, an active metabolite of acyl-CoA, an active metabolite of an acyl-CoA precursor in a subject, the method comprising administering to the subject a therapeutically effective amount of at least one compound of the present disclosure. The present disclosure provides a method of preventing a disease characterized by and/or associated with decreased concentrations of one or more of free CoA, acetyl-CoA, aryl-CoA, a precursor of free CoA, an active metabolite of free CoA, an active metabolite of a free CoA precursor, a precursor of acetyl-CoA, an active metabolite of acetyl-CoA, an active metabolite of an acetyl-CoA precursor, a precursor of acyl-CoA, an active metabolite of acyl-CoA, an active metabolite of an acyl-CoA precursor in a subject comprising administering to the subject a therapeutically effective amount of at least one compound of the present disclosure.

In some aspects, an active metabolite of free CoA, an active metabolite of acetyl-CoA, an active metabolite of acyl-CoA, an active metabolite of a free CoA precursor, an active metabolite of an acetyl-CoA precursor and/or active metabolite of an acyl-CoA precursor can include, but is not limited to, branched or linear organic acids, including, but not limited to, crotonic acid, propionic acid, butanoic acid, pentanoic acid, hexanoic acid, heptanoic acid; (alpha-, beta-, and gamma-) keto acids, including, but not limited to, pyruvic acid, oxaloacetic acid, alpha-ketoglutarate, acetoacetic acid, levulinic acid; hydroxy acids, including, but not limited to, lactic acid, 3-hydroxypropionic acid, 3-hydroxybutyric acid, 4-hydroxybutyric acid; saturated dicarboxylic acids, including, but not limited to, oxalic acid, malonic acid, methylmalonic acid, succinic acid, glutaric acid, adipic acid, pimelic acid, suberic acid, azelaic acid, sebacic acid; unsaturated dicarboxylic acids, including, but not limited to maleic acid, fumaric acid, glutaconic acid; quaternary ammonium cations, including, but not limited to, choline, choline phosphates, carnitines; amino acids, including, but not limited to glycine, alanine, 3,4-dihydroxyphenylalanine (DOPA), gamma-aminobutyric acid (GABA); lactams and lactones, including, but not limited to, pyrrolidinone, furanone, dihydrofuranone, or derivatives thereof, including, but not limited to, esters, ketals, hydroxylated, aminated, acetylated, or methylated species.

In some aspects, a disease can be a disease that is characterized by and/or associated with the loss of or decrease in activity of short chain acyl-CoA dehydrogenase (also referred to as short chain 3-hydroxyacyl-CoA dehydrogenase). A disease can be characterized by and/or associated with short chain acyl-CoA dehydrogenase deficiency. Thus, the present disclosure provides a method of treating short chain acyl-CoA dehydrogenase deficiency in a subject comprising administering to the subject a therapeutically effective amount of at least one compound of the present disclosure. The present disclosure provides a method of preventing short chain acyl-CoA dehydrogenase deficiency in a subject comprising administering to the subject a therapeutically effective amount of at least one compound of the present disclosure.

A disease can be a disease that is characterized by and/or associated with lose of or decrease in activity of short chain acyl-CoA dehydrogenase such that the short chain acyl-CoA dehydrogenase activity in the subject having the disease is no more than 90%, or no more than 80%, or no more than 70%, or no more than 60%, or no more than 50%, or no more than 40%, or no more than 30%, or no more than 20%, or no more than 10% of the short chain acyl-CoA dehydrogenase activity in a subject not having the disease.

In some aspects, a disease can be a disease that is characterized by and/or associated with a loss of or decrease in activity of medium chain acyl-CoA dehydrogenase (also referred to as medium chain 3-hydroxyacyl-CoA dehydrogenase). A disease can be characterized by and/or associated with medium chain acyl-CoA dehydrogenase deficiency. Thus, the present disclosure provides a method of treating medium chain acyl-CoA dehydrogenase deficiency in a subject comprising administering to the subject a therapeutically effective amount of at least one compound of the present disclosure. The present disclosure provides a method of preventing medium chain acyl-CoA dehydrogenase deficiency in a subject comprising administering to the subject a therapeutically effective amount of at least one compound of the present disclosure.

A disease can be a disease that is characterized by and/or associated with lose of or decrease in activity of medium chain acyl-CoA dehydrogenase such that the medium chain acyl-CoA dehydrogenase activity in the subject having the disease is no more than 90%, or no more than 80%, or no more than 70%, or no more than 60%, or no more than 50%, or no more than 40%, or no more than 30%, or no more than 20%, or no more than 10% of the medium chain acyl-CoA dehydrogenase activity in a subject not having the disease.

In some aspects, a disease can be a disease that is characterized by and/or associated with a loss of or decrease in activity of long chain acyl-CoA dehydrogenase (also referred to as long chain 3-hydroxyacyl-CoA dehydrogenase). A disease can be characterized by and/or associated with long chain acyl-CoA dehydrogenase deficiency. Thus, the present disclosure provides a method of treating long chain acyl-CoA dehydrogenase deficiency in a subject comprising administering to the subject a therapeutically effective amount of at least one compound of the present disclosure. The present disclosure provides a method of preventing long chain acyl-CoA dehydrogenase deficiency in a subject comprising administering to the subject a therapeutically effective amount of at least one compound of the present disclosure.

A disease can be a disease that is characterized by and/or associated with lose of or decrease in activity of long chain acyl-CoA dehydrogenase such that the long chain acyl-CoA dehydrogenase activity in the subject having the disease is no more than 90%, or no more than 80%, or no more than 70%, or no more than 60%, or no more than 50%, or no more than 40%, or no more than 30%, or no more than 20%, or no more than 10% of the long chain acyl-CoA dehydrogenase activity in a subject not having the disease.

In some aspects, a disease can be a disease that is characterized by and/or associated with a loss of or decrease in activity of very long chain acyl-CoA dehydrogenase (also referred to as very long chain 3-hydroxyacyl-CoA dehydrogenase). A disease can be characterized by and/or associated with very long chain acyl-CoA dehydrogenase deficiency. Thus, the present disclosure provides a method of treating very long chain acyl-CoA dehydrogenase deficiency in a subject comprising administering to the subject a therapeutically effective amount of at least one compound of the present disclosure. The present disclosure provides a method of preventing very long chain acyl-CoA dehydrogenase deficiency in a subject comprising administering to the subject a therapeutically effective amount of at least one compound of the present disclosure.

A disease can be a disease that is characterized by and/or associated with lose of or decrease in activity of very long chain acyl-CoA dehydrogenase such that the very long chain acyl-CoA dehydrogenase activity in the subject having the disease is no more than 90%, or no more than 80%, or no more than 70%, or no more than 60%, or no more than 50%, or no more than 40%, or no more than 30%, or no more than 20%, or no more than 10% of the very long chain acyl-CoA dehydrogenase activity in a subject not having the disease.

In some aspects, a disease can be a disease that is characterized and/or associated with decreased concentrations of acetyl-CoA. Thus, the present disclosure provides a method of treating a disease characterized by and/or associated with decreased concentrations of acetyl-CoA in a subject comprising administering to the subject a therapeutically effective amount of at least one compound of the present disclosure. The present disclosure provides a method of preventing a disease characterized by and/or associated with decreased concentrations of acetyl-CoA in a subject comprising administering to the subject a therapeutically effective amount of at least one compound of the present disclosure.

In some aspects, a disease can be a disease that is characterized by and/or associated with a decrease in the concentration of acetyl-CoA, such that the concentration of acetyl-CoA in the subject having the disease is no more than 90%, or no more than 80%, or no more than 70%, or no more than 60%, or no more than 50%, or no more than 40%, or no more than 30%, or no more than 20%, or no more than 10% of the concentration of acetyl-CoA in a subject not having the disease.

In some aspects, a disease can be a disease that is characterized and/or associated with decreased concentrations of free CoA. Thus, the present disclosure provides a method of treating a disease characterized by and/or associated with decreased concentrations of free CoA in a subject comprising administering to the subject a therapeutically effective amount of at least one compound of the present disclosure. The present disclosure provides a method of preventing a disease characterized by and/or associated with decreased concentrations of free CoA in a subject comprising administering to the subject a therapeutically effective amount of at least one compound of the present disclosure. As used herein, free CoA is used in its broadest sense to refer to Coenzyme A with a free thiol group (CoA-SH).

In some aspects, a disease can be a disease that is characterized by and/or associated with a decrease in the concentration of free CoA, such that the concentration of free CoA in the subject having the disease is no more than 90%, or no more than 80%, or no more than 70%, or no more than 60%, or no more than 50%, or no more than 40%, or no more than 30%, or no more than 20%, or no more than 10% of the concentration of acetyl-CoA in a subject not having the disease.

In some aspects, a disease can be a disease that is characterized and/or associated with decreased concentrations of at least one species of acyl-CoA. Thus, the present disclosure provides a method of treating a disease characterized by and/or associated with decreased concentrations of such species of acyl-CoA in a subject comprising administering to the subject a therapeutically effective amount of at least one compound of the present disclosure. The present disclosure provides a method of preventing a disease characterized by and/or associated with decreased concentrations of at least one species of acyl-CoA in a subject comprising administering to the subject a therapeutically effective amount of at least one compound of the present disclosure.

In some aspects, a disease can be a disease that is characterized by and/or associated with a decrease in the concentration of at least one species of acyl-CoA, such that the concentration of such species of acyl-CoA in the subject having the disease is no more than 90%, or no more than 80%, or no more than 70%, or no more than 60%, or no more than 50%, or no more than 40%, or no more than 30%, or no more than 20%, or no more than 10% of the concentration of such species of acyl-CoA in a subject not having the disease.

In some aspects, a disease can be a disease that is characterized by and/or associated with an increase in at least one CoA species, including, but not limited to, acyl-CoA species. A disease can be a disease that is characterized and/or associated with an increase in at least one CoA species, including but not limited to, acyl-CoA species, such that the concentration of the at least one CoA species in the subject having the disease is at least about two times, or about three times, or about four times, or about five times, or about six times, or about seven times, or about eight times, or about nine times, or about ten times, or about 20 times, or about 30 times, or about 40 times, or about 50 times, or about 60 times, or about 70 times, or about 80 times, or about 90 times, or about 100 times, or about 1000 times the concentration of the at least one CoA species in a subject not having the disease. The increase in the at least one CoA species can cause a concomitant decrease in the concentration of free CoA and/or acetyl-CoA in the subject having the disease. The increase in the at least one CoA species can be caused by impaired fatty acid metabolism, impaired amino acid metabolism, impaired glucose metabolism or any combination thereof.

A disease can be a disease characterized by and/or associated with a disrupted balance between free CoA and acetyl-CoA.

A disease can be a CoA sequestration, toxicity or redistribution (CASTOR) disease. Thus, the present disclosure provides a method of treating a CASTOR disease in a subject comprising administering to the subject a therapeutically effective amount of at least one compound of the present disclosure. The present disclosure provides a method of preventing a CASTOR disease in a subject comprising administering to the subject a therapeutically effective amount of at least one compound of the present disclosure.

In some aspects, a disease can be a disease that is characterized by and/or associated with insufficient pantothenate kinase activity. A disease can be a disease that is characterized by and/or associated with an inhibition of one or more pantothenate kinases (e.g., wild type pantothenate kinases). The inhibition of one or more pantothenate kinases can be caused by the over-accumulation of one or more CoA species, including, but not limited to, acyl-CoA species.

In some aspects, a disease can be a disease that is characterized by and/or associated with impaired or inhibited degradation of one or more acyl-CoA species. Thus, the present disclosure provides a method of treating a disease characterized by and/or associated with impaired or inhibited degradation of one or more acyl-CoA species in a subject comprising administering to the subject a therapeutically effective amount of at least one compound of the present disclosure. The present disclosure provides a method of preventing a disease characterized by and/or associated with impaired or inhibited degradation of one or more acyl-CoA species in a subject comprising administering to the subject a therapeutically effective amount of at least one compound of the present disclosure.

In some aspects, a disease can be a disease that is characterized by and/or associated with overexpressed or upregulated acyl-CoA thioesterase. In some aspects, acyl-CoA thioesterase can be ACOT4, ACOT8, ACOT12. Thus, the present disclosure provides a method of treating a disease characterized by and/or associated with overexpressed or upregulated of one or more acyl-CoA thioesterase in a subject comprising administering to the subject a therapeutically effective amount of at least one compound of the present disclosure. The present disclosure provides a method of preventing a disease characterized by and/or associated with overexpressed or upregulated of one or more acyl-CoA thioesterase in a subject comprising administering to the subject a therapeutically effective amount of at least one compound of the present disclosure.

In some aspects, a disease can be a disease that is characterized by and/or associated with accumulation of one or more fatty acids. Thus, the present disclosure provides a method of treating a disease characterized by and/or associated with accumulation of one or more fatty acids in a subject comprising administering to the subject a therapeutically effective amount of at least one compound of the present disclosure. The present disclosure provides a method of preventing a disease characterized by and/or associated with accumulation of one or more fatty acids in a subject comprising administering to the subject a therapeutically effective amount of at least one compound of the present disclosure.

In some aspects, a disease can be a disease that is characterized by and/or associated with impaired, inhibited and/or decreased degradation of one or more fatty acids. Thus, the present disclosure provides a method of treating a disease characterized by and/or associated with impaired, inhibited and/or decreased degradation of one or more fatty acids in a subject comprising administering to the subject a therapeutically effective amount of at least one compound of the present disclosure. The present disclosure provides a method of preventing a disease characterized by and/or associated with impaired, inhibited and/or decreased degradation of one or more fatty acids in a subject comprising administering to the subject a therapeutically effective amount of at least one compound of the present disclosure.

In some aspects, a disease can be a disease that is characterized by and/or associated with abnormal CoA homeostasis. A disease can be a disease that is characterized by and/or associated with abnormal acetyl-CoA homeostasis. A disease can be a disease that is characterized by and/or associated with abnormal aryl-CoA homeostasis. A disease can be a disease that is characterized by and/or associated with abnormal succinyl-CoA homeostasis.

The present disclosure provides a method of re-establishing CoA homeostasis in a subject comprising administering to the subject a therapeutically effective amount of at least one compound of the present disclosure. The present disclosure provides a method of re-stablishing acetyl-CoA homeostasis in a subject comprising administering to the subject a therapeutically effective amount of at least one compound of the present disclosure. The present disclosure provides a method of re-establishing acyl-CoA homeostasis in a subject comprising administering to the subject a therapeutically effective amount of at least one compound of the present disclosure. The present disclosure provides a method of re-establishing succinyl-CoA homeostasis in a subject comprising administering to the subject a therapeutically effective amount of at least one compound of the present disclosure.

In some aspects, a disease can be a disease that is characterized by and/or associated with abnormal energy homeostasis. A disease that is characterized by and/or associated with abnormal energy homeostasis can be a disease that is characterized by and/or associated with excessive fatty acid oxidation and synthesis. A disease that is characterized by and/or associated with abnormal energy homeostasis can be a disease that is characterized by and/or associated with deficient fatty acid oxidation and synthesis. A disease that is characterized by and/or associated with abnormal energy homeostasis can be a disease that is characterized by and/or associated with excessive glutaminolysis. A disease that is characterized by and/or associated with abnormal energy homeostasis can be a disease that is characterized by and/or associated with deficient glutaminolysis.

In some aspects, a disease can be a disease characterized by and/or associated with an abnormal energy homeostasis which is caused by abnormal CoA homeostasis. In some aspects, a disease can be a disease that is characterized and or associated with aberrant glycolysis. In some aspects, a disease can be a disease that is characterized and/or associated with elevated glycolysis. In some aspects, a disease can be a disease that is characterized and/or associated with decreased glycolysis. In some aspects, a disease can be a disease that is characterized and/or associated with aberrant lipid metabolism. In some aspects, a disease can be a disease that is characterized and/or associated with elevated lipid metabolism. In some aspects, a disease can be a disease that is characterized and/or associated with decreased lipid metabolism. In some aspects, a disease can be a disease that is characterized and/or associated with aberrant glutaminolysis. In some aspects, a disease can be a disease that is characterized and/or associated with elevated glutaminolysis. In some aspects, a disease can be a disease that is characterized and/or associated with aberrant oxidative phosphorylation. In some aspects, a disease can be a disease that is characterized and/or associated with reduced oxidative phosphorylation.

In some aspects, a disease can be a disease characterized by and/or associated with inflammation. In some aspects, a disease can be a disease characterized by and/or associated with abberant redox homeostasis. In some aspects, a disease can be a disease characterized by and/or associated with elevated oxidative stress. In some aspects, a disease can be a disease characterized by and/or associated with chronic oxidative stress. In some aspects, a disease can be a disease characterized by and/or associated with increased production of reactive oxygen species (ROS).

The present disclosure provides a method for treating a disease that is characterized by and/or associated with abnormal energy homeostasis in a subject, wherein the disease that is characterized by and/or associated with abnormal energy homeostasis can be a disease that involves at least one of aberrant glycolysis, excessive glycolysis, deficient glycolysis, aberrant fatty acid oxidation and synthesis, excessive fatty acid oxidation and synthesis, deficient fatty acid oxidation and synthesis, aberrant glutaminolysis, excessive glutaminolysis, and deficient glutaminolysis, the method comprising administering to the subject at least one compound of the present disclosure that decreases the activity of at least one metabolic pathway selected from the group consisting of glycolysis, fatty acid oxidation, fatty acid synthesis and glutaminolysis, in an amount effective to treat the disease.

The present disclosure provides a method for treating a disease that is characterized by and/or associated with inflammation in a subject, the method comprising administering to the subject at least one compound of the present disclosure that reduces inflammation in an amount effective to treat the disease. The present disclosure provides a method for treating a disease that is characterized by and/or associated with aberrant redox homeostasis in a subject, the method comprising administering to the subject at least one compound of the present disclosure that improves redox homeostasis in an amount effective to treat the disease. The present disclosure provides a method for treating a disease that is characterized by and/or associated with elevated oxidative stress in a subject, the method comprising administering to the subject at least one compound of the present disclosure that reduces the oxidative stress in an amount effective to treat the disease. The present disclosure provides a method for treating a disease that is characterized by and/or associated with increased production of reactive oxygen species (ROS) in a subject, the method comprising administering to the subject at least one compound of the present disclosure that reduces production of ROS in an amount effective to treat the disease.

In some aspects, a disease can be a disease that is characterized by and/or associated with reduced or deficient glucose uptake, deficient or downregulated glucose transporter or increased insulin resistance. In some aspects, glucose transporter can be GLUT1, GLUT2, GLUT3 and GLUT4. Thus, the present disclosure provides a method of treating a disease characterized by and/or associated with reduced or deficient glucose uptake or deficient or downregulated glucose transporter or increased insulin resistance in a subject comprising administering to the subject a therapeutically effective amount of at least one compound of the present disclosure. The present disclosure provides a method of preventing a disease characterized by and/or associated with reduced or deficient glucose uptake or deficient or downregulated glucose transporter or increased insulin resistance in a subject comprising administering to the subject a therapeutically effective amount of at least one compound of the present disclosure.

In some aspects, a disease can be a disease that is characterized by and/or associated with a decrease in fatty acid metabolism. A disease can be a disease that is characterized by and/or associated with a decrease in fatty acid metabolism such that the fatty acid metabolism activity in the subject having the disease is no more than 90%, or no more than 80%, or no more than 70%, or no more than 60%, or no more than 50%, or no more than 40%, or no more than 30%, or no more than 20%, or no more than 10% of the fatty acid metabolism activity in a subject not having the disease.

The present disclosure provides a method of preventing an inappropriate shift to fatty acid biosynthesis in a subject comprising administering to the subject a therapeutically effective amount of at least one compound of the present disclosure.

In some aspects, a disease can be a disease that is characterized by and/or associated with a decrease in amino acid metabolism. A disease can be a disease that is characterized by and/or associated with a decrease in amino acid metabolism such that the amino acid metabolism activity in the subject having the disease is no more than 90%, or no more than 80%, or no more than 70%, or no more than 60%, or no more than 50%, or no more than 40%, or no more than 30%, or no more than 20%, or no more than 10% of the amino acid metabolism activity in a subject not having the disease.

The present disclosure provides a method of increasing Acetyl-CoA biosynthesis in a subject comprising administering to the subject a therapeutically effective amount at least one compound of the present disclosure.

An increase in acetyl-CoA biosynthesis can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in acetyl-CoA biosynthesis.

The present disclosure provides a method of increasing acyl-CoA biosynthesis in a subject comprising administering to the subject a therapeutically effective amount at least one compound of the present disclosure.

An increase in acyl-CoA biosynthesis can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in acyl-CoA biosynthesis.

The present disclosure provides a method of decreasing degradation of CoA in a subject comprising administering to the subject a therapeutically effective amount of at least one compound of the present disclosure. The decreased degradation of CoA can prolong the availability and utilization of CoA.

A decrease in degradation of CoA can be about a 1%, or about a 2%, or about a 3%, or about a 4%, or about a 5%, or about a 6%, or about a 7%, or about an 8%, or about a 9%, or about a 10%, or about a 15%, or about a 20%, or about a 25%, or about a 30%, or about a 35%, or about a 40%, or about a 45%, or about a 50%, or about a 55%, or about a 60%, or about a 65%, or about a 70%, or about a 75%, or about an 80%, or about a 85%, or about a 90%, or about a 95% decrease in degradation of CoA.

The present disclosure provides a method of increasing the half-life of CoA in a subject comprising administering to the subject a therapeutically effective amount of at least one compound of the present disclosure.

An increase in the half-life of CoA can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in the half-life of CoA.

The present disclosure provides a method of prolonging the availability of CoA in a subject comprising administering to the subject a therapeutically effective amount of at least one compound of the present disclosure.

The present disclosure provides a method of prolonging the utilization of CoA in a subject comprising administering to the subject a therapeutically effective amount of at least one compound of the present disclosure.

The present disclosure provides a method of delivering an acyl moiety into the mitochondria) matrix of a mitochondrion of a subject comprising administering to the subject a therapeutically effective amount of at least one compound of the present disclosure.

The present disclosure provides a method of delivering a cargo molecule to a particular tissue, cell, or organelle in a subject comprising: providing at least one compound of the present disclosure, administering to the subject a therapeutically effective amount of the at least one compound of the present disclosure.

The present disclosure provides a method of decreasing the concentration of reactive oxygen species (ROS) in a subject comprising administering to the subject a therapeutically effective amount of at least one compound of the present disclosure.

A decrease in the concentration of ROS can be about a 1%, or about a 2%, or about a 3%, or about a 4%, or about a 5%, or about a 6%, or about a 7%, or about an 8%, or about a 9%, or about a 10%, or about a 15%, or about a 20%, or about a 25%, or about a 30%, or about a 35%, or about a 40%, or about a 45%, or about a 50%, or about a 55%, or about a 60%, or about a 65%, or about a 70%, or about a 75%, or about an 80%, or about a 85%, or about a 90%, or about a 95% decrease in the concentration of ROS.

The present disclosure provides a method of decreasing the concentration of an at least one acyl-CoA species in a subject comprising administering to the subject a therapeutically effective amount at least one compound of the present disclosure.

A decrease in the concentration of an at least one acyl-CoA species can be about a 1%, or about a 2%, or about a 3%, or about a 4%, or about a 5%, or about a 6%, or about a 7%, or about an 8%, or about a 9%, or about a 10%, or about a 15%, or about a 20%, or about a 25%, or about a 30%, or about a 35%, or about a 40%, or about a 45%, or about a 50%, or about a 55%, or about a 60%, or about a 65%, or about a 70%, or about a 75%, or about an 80%, or about a 85%, or about a 90%, or about a 95% decrease in the concentration of the at least one acyl-CoA species.

The present disclosure provides a method of increasing the fatty acid metabolism in a subject comprising administering to the subject a therapeutically effective amount of at least one compound of the present disclosure.

An increase in fatty acid metabolism can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in fatty acid metabolism.

The present disclosure provides a method of increasing the amino acid metabolism in a subject comprising administering to the subject a therapeutically effective amount of at least one compound of the present disclosure.

An increase in amino acid metabolism can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in amino acid metabolism.

The present disclosure provides a method of increasing mitochondrial respiration in a subject comprising administering to the subject a therapeutically effective amount of at least one compound of the present disclosure.

An increase in mitochondrial respiration can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase mitochondrial respiration.

As used herein, the terms "mitochondrial respiration" and "oxidative phosphorylation" are used interchangeably in their broadest sense to refer to the set of metabolic reactions and process requiring oxygen that takes place in mitochondria to convert the energy stored in macronutrients to ATP.

The present disclosure provides a method of increasing ATP concentration in a subject comprising administering to the subject therapeutically effective amount of at least one compound of the present disclosure.

An increase in ATP concentration can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase mitochondrial respiration.

Methods of Use-Mitochondrial Disease

The mitochondrion is an essential organelle responsible for cellular energy metabolism, generation of ATP and determining many key aspects of cellular function. Abnormalities in mitochondrial function and/or physiology have been reported in many unrelated pathologies including primary and secondary mitochondrial diseases, inborn errors of metabolism and other genetic diseases, neurological and muscle diseases, ageing and ageing-related degenerative disorders, cardiovascular diseases and metabolic syndrome, neuropsychiatric diseases and cancer, all with a common feature of mitochondrial dysfunction, disrupted and/or deficient energy metabolism and elevated oxidative stress (Pagano et al., 2013 Oxid Med Cel Long 2014; Camara et al., 2010 Antioxidants & Redox Signalling 13; Maldonado et at, 2019 Front Genet 10). Symptoms of mitochondrial diseases include poor growth, loss of muscle coordination, muscle weakness, visual problems, hearing problems, learning disabilities, heart disease, liver disease, kidney disease, gastrointestinal disorders, respiratory disorders, neurological problems, autonomic dysfunction and dementia. (Gorman et al., 2016 Nat Rev 2; Craven et al., 2017 Annu Rev Genom Hum Genet 18).

Impaired cell respiration and oxidative phosphorilation (oxphos) is a hallmark and one of the major contributors to pathophysiology of mitochondrial diseases. Deleterious reactive oxygen species are generated as a result of oxphos mitochondrial electron transport, requiring a rigorous activation of antioxidative defense in order to maintain homeostatic mitochondria) function. Dysregulation of antioxidant response leads to mitochondrial dysfunction and disease (Huang et al., 2019 Oxid Med Cell Longevity 2019).

In addition to impaired cell respiration and oxidative phosphorilation, a multitude of impaired mitochondria) functions contribute to mitochondrial disease. These include imbalanced mitochondrial dynamics (Janer et al., 2016 EMBO Mol Med 8), aberrant mitochondria) lipid homeostasis (Wortmann et al., 2012 Nat Genet 44), deficiencies of vitamin and cofactor metabolism (Duncan et al., 2009 Am J Hum Genet 84), and altered redox ratios and disrupted mitochondria) membrane potential (Khan et al., 2014 EMBO Mol Med 6; Titov et al., 2016 Science 352). Many aspects of mitochondrial dysfunction also contribute to the pathophysiology of cancer (Warburg et al., 1927 J Gen Physiol 8; Vyas et al., 2016 Cell 166), neurodegenerative disorders (Lin and Beal, 2006 Nature 443; Grunewald et al., 2018 Prog Neurobiol), and organismal ageing (Bratic and Larsson, 2013 J Clin Invest 123).

The mitochondrial membrane potential (ΔΨm) generated by proton pumps (Complexes I, 111 and IV) is an essential component in the process of energy storage during oxidative phosphorylation. Together with the proton gradient (ΔpH), ΔΨm forms the transmembrane potential of hydrogen ions which is harnessed to make ATP. The levels of ΔΨm and ATP in the cell are kept relatively stable and ΔΨm is often used as an indirect measurement of cell's ATP generation (Suzuki et al., 2018 Sci Reports 8). However, sustained changes in both factors may be deleterious. A long-lasting drop or rise of ΔΨmvs normal levels may induce loss of cell viability and be a cause of and/or is indicative of various pathologies (Zorova et al., 2018 Anal Biochem 552, Herst et al., 2017 Front Endocrinol 8). Among other factors, ΔΨm plays a key role in mitochondrial homeostasis through selective elimination of dysfunctional mitochondria and a reduced ΔΨm is often associated with disfunctional mitochondria and has been reported in many diseases including mitochondrial disorders such as LHON, MELAS, and Leigh syndrome (Sileikyte and Forte, 2019 Oxid Med Cell Longevity 2019), metabolic and inflammatory diseases such as Type 2 diabetes, rheumatoid arthritis and NASH (Pessayre and Fromenty, 2005 J Jepatol 42; Nomura et al., 2019 Sci Reports 9; Kim et al., 2017 Cell Death Dis 8) as well as neurodegenerative diseases such as Alzheimer's, Parkinson's, Huntington's disease, ALS, Friedreich's Ataxia and others (Huang et al., 2019 Oxid Med Cell Longevity 2019). Multiple studies have shown that drugs which improve mitochondrial function an disease pathology have a positive impact on restoring and/or increasing ΔΨm (Sileikyte and Forte, 2019 Oxid Med Cell Longevity 2019; Huang et al., 2019 Oxid Med Cell Longevity 2019).

Seahorse XF Analyzer has become the golden standard in monitoring the oxygen consumption rates (OCR) and extracellular acidification rate (ECAR), which allow for a direct measurement and quantification of mitochondria) respiration and glycolysis and has been demonstrated in numerous precnilical studies to assess the drug's impact on mitochondrial respiration and glycolysis (Yepez et al., 2018 PLoS One 13; Sakamuri et al., 2018 GeroScience 40; Leung and Chu, 2018 Methods Mol Biol 1710; Roy-Choundry and Daadi, 2019 Methods Mol Bviol 1919; Leipnitz et al., 2018 Sci Rep 8; Pokrzywinski et al., 2016 PLoS One; Reily et al., 2013 Redox Biol2013 1).

Oxidative stress resulting from impaired cell respiration and disrupted redox homeostasis is one of the halmarks of mitochondrial diseases and can occur as the result of increased ROS production, or decreased ROS protection. Multiple mitochondrial disorders with neurological deficits or neurodegeneration, including Friedrich's Ataxia (FA), Leber's hereditary optic neuropathy (LHON), Leigh Syndrome (LS), Mitochondria) encephalomyopathy, lactic acidosis, stroke-like episodes (MELAS) and Myoclonic epilepsy with ragged-red fibers (MERRF), Kearns-Sayre Syndrome (KSS) exhibit elevated exidative stress and ROS production (Pagano et al., 2014 Oxid Med Cel Longevity; Hayashi et al., 2015 Free Radic Biol Med 88).

In some aspects, a disease characterized by and/or associated with an increase of reactive oxygen species (ROS) can be a cancer-prone and/or early ageing disease, neurological and/or muscle genetic disease, primary mitochondrial DNA-related disease, secondary mitochondrial DNA-related disease, inborn errors of metabolism and other genetic diseases, CASTOR disease, inflammation and/or autoimmune disease, Cancer-prone or early ageing disease, neurological and/or muscle disease, ageing-related degenerative disorder, neurologic and neuropsychiatric disease and cancer. In some aspects, a disease characterized by and/or associated with an increase of reactive oxygen species (ROS) can be a disease selected from the group comprising Cardiovascular diseases, Metabolic syndrome, Osteoarthritis, Type 2 Diabetes mellitus, Obesity, Polycystic Ovary Syndrome (PCOS), Alzheimer's disease, Amyotrophic lateral sclerosis, Epilepsy, Myalgic encephalomyelitis/Chronic fatigue syndrome, Multiple sclerosis, Parkinson's disease, Autistic spectrum disorders, Bipolar disorder, Major depression, Obsessive-compulsive disorder, Schizophrenia, Ataxia-telangiectasia, Bloom syndrome, Cockayne syndrome, Down syndrome, Fanconi anaemia, Hutchinson-Gilford syndrome, Nijmegen breakage syndrome, Rothmund-Thomson syndrome, Werner Syndrome, Xeroderma pigmentosum, Adrenoleukodystrophy, Duchenne Muscular Dystrophy, Friedreich Ataxia, Huntington's Disease, Hyperhomocysteinaemia, Sickle Cell Disease, Thalassaemia, Leber's hereditary optic neuropathy (LHON), Leigh syndrome, subacute necrotizing encephalomyelopathy, Neuropathy, ataxia, retinitis pigmentosa, and ptosis (NARP), Mitochondria) myopathy, encephalomyopathy, lactic acidosis, stroke-like symptoms (MELAS), Myoclonic epilepsy with ragged red fibers (MERRF), Maternally inherited diabetes mellitus and deafness (MIDD), Kearns-Sayre syndrome (KSS), Chronic progressive external ophthalmoplegia (CPEO), Pearson syndrome, Alpers-Huttenlocher Syndrome and Mitochondria) neurogastrointestinal encephalomyopathy (MNGIE), Bladder cancer, Breast cancer, Cervical cancer, Colorectal cancer, Endometrial cancer, Gastric cancer, Hepatocellular carcimona growth, Lung cancer, Melanoma, Myeloid leukaemias, Oral cancer, Thyroid oncocytic carcinoma.

In some aspects, a disease can be a disease that is characterized by and/or associated with an increase of reactive oxygen species (ROS). A disease can be a disease that is characterized and/or associated with an increase of reactive oxygen species (ROS) such that the concentration of ROS in the subject having the disease is at least about two times, or about three times, or about four times, or about five times, or about six times, or about seven times, or about eight times, or about nine times, or about ten times, or about 20 times, or about 30 times, or about 40 times, or about 50 times, or about 60 times, or about 70 times, or about 80 times, or about 90 times, or about 100 times, or about 1000 times the concentration of ROS in a subject not having the disease.

Serum fibroblast growth factor 21 (FGF21) is a central metabolic regulator that regulates energy metabolism by activating the AMPK-SIRT1-PGC-1α pathway. Induction or increased expression of FGF21 leads to increased AMPK phosphorylation levels, increased cellular NAD+ levels, activation of SIRT1 and deacetylation of its downstream targets, peroxisome proliferator-activated receptor-γ coactivator-1α (PGC-1α) and histone 3 (Chau et al., 2010 PNAS 107). FGF21 was also shown to be an activator of PPARγ and Adiponectin, both central to energy homeostasis, lipid metabolism and inflammation (Goetz, 2013 Nat Rev Endocrinol 9; Hui et al., 2016 J Mol Cell Biol 8; Lin et al., 2013 Cell Metab 17)

FGF21 is a well known biomarker for mitochondrial diseases and elevated levels have been observed in inborn errors of metabolism including propionic acidemia, methylmalonic aidemia and isovaleric acidemia as well as fatty acid oxidation disorders (Molema et al., 2018 J Inh Metab Dis 41; Kirmse et al., 2017 Mol Genet Metab Rep 13, Manoli et al., 2018 JCI Insight 6), Primary mitochondrial disorders, metabolic disease, myopathies and muscular dystrophies, congenital myopathies, inflammatory myopathies, pompe disease and others (Lehtonen et al., Neurology 87) and FGF21 analogs have been successfully used in preclinical as well as clinical studies to improve metabolic health and function in mitochondrial diseases, metabolic diseases including type 2 diabetes mellitus (Staiger et al., 2017 Endocr Rev 38; Xie and Leung, 2017 Am J Physiol Endocrinol Metab 313; Zhang and Li, 2015 Front Endocrinol 6; Yang et al., 2018 Cell Death & Disease 9). Treatment with FGF21 also ameliorated neurodegeneration in rat and cellular models of Alzheimer's disease (Chen et al., 2019 Redox Biol 22). Furthermore, treatment with FGF21 increased adiponectin plasma levels and normalized insulin sensitivity in Bscl2−/− mice, a model of adipocyte dysfunction and Berardineli-Seip congenital lipodystropy (BSCL) (Dollet et al., 2016 Diabetes 65)

Improved phenotypes have been obtained in disease model mice with complex IV-deficient myopathy and mtDNA maintenance myopathy using a PPAR agonist (Yatsuga and Suomalainen, 2012 Hum Mol Genet 21; Wenz et al., 2008 Cell Metab 8) or an AMPK agonist (Viscomi et al., Cell Metab 14). PPAR agonists were also successfully demonstrated in various other metabolic and neurological diseases in terms of their rescue of mitochondrial function (Corona and Duchen, 2016 Free Eadic Biol Med 100; Mello et al., 2016 PPAR Research). Molecules boosting the levels of NAD+, which activates NAD-dependent protein deacetylase sirtuin 1 (SIRT1)-mediated mitochondrial biogenesis, as well as molecules targeting activation and/or induce expression of SIRT1 directly, have been shown to be beneficial in mouse models and human cells of mitochondrial diseases, metabolic diseases, cardiovascular disses, neurodegenerative diseases and other aging-related diseases (Cerutti et al., 2014 Cell Metab 19; Khan et al., 2014 EMBO Mol Med 6; Pirinen et al., 2014 19; Mills et al., 2016 Cell Metab 24; Rajman et al., 2018 Cell Metab 27; Kane and Sinclair, 2018 Circ Res 123; Okabe et al., 2019 J Biomed Sci 26; Bonora et al., 2019 Nat Rev Cardiol 16).

The sirtuin family of deacylase enzymes have a variety of subcellular localisations and have been found to remove a growing list of post-translational acyl modifications from target proteins. SIRT3, SIRT4, and SIRT5 are found primarily located in the mitochondria, and are involved in many of the key processes of this organelle including in regulation of energy metabolism, substrate metabolism including lipid and glutamin metabolism, redox homeostasis, cell survival pathways including proliferation and apoptosis signalling. Because of their influence on a broad range of pathways, SIRT3, SIRT4, and SIRT5 are implicated in a range of disease-states including metabolic disease such as diabetes, neurodegenerative diseases, cancer, and ageing-related disorders such as hearing-loss and cardiac dysfunction. (Osborne et al., 2016 Free Rad Biol Med 100; Kanwal, 2018 Exp Rev Clin Pharmacol 12; Lombard et al., 2011 Handb Exp Pharmacol 206; Carrico et al., 2018 Cell Metab 27).

In a well-regulated coordination between mitochondrial Sirtuins and AMPK, the mammalian target of rapamycin (mTOR), a well conserved serine/threonine kinase, functions as one of the central regulators of the mitochondrial oxygen consumption and oxidative capacity, particularly with regard to cell growth in response to nutrient status. It was demonstrated that mTOR pathway plays a significant role in determining both resting oxygen consumption and oxidative capacity. Disruption of mTOR/raptor complex lowered mitochondria) membrane potential, oxygen consumption, and ATP synthetic capacity and resulted in a dramatic alteration in the mitochondrial phosphoproteome and it was suggested that mTOR activity may play an important role in determining the relative balance between mitochondrial and non-mitochondrial sources of ATP generation (Verdin et al., 2010 Trends biochem sci 35). The mTOR signaling pathway has been implicated in a number of pathologies and has been studied at depth with great promise in a number of diseases including neurological diseases and age-related neurodegeneration, cardiometabolic disease, cancer and even aging itself (Jahrling and Laberge, 2015 Curr Top Med Chem 15; Talboom et al., 2015 NPJ Aging and Mech Disease 1; Schmeisser and Parker, 2019 Front Cell Dev Biol 7; Dat et al., 2018 Odix Med Cell Longev, Laplante and Sabatini, 2012 Cell 149; Johnson et al., 2013 Nature 493).

Alterations in mitochondrial dynamics due to mutations in proteins involved in the fusion-fission machinery represent an important pathogenic mechanism of human diseases. The most relevant proteins involved in the mitochondrial fusion process are three GTPase dynamin-like proteins: mitofusin 1 (MFN1) and 2 (MFN2), located in the outer mitochondrial membrane, and optic atrophy protein 1 (OPA1), in the inner membrane. Dynamin-related protein 1 (DRP1), a cytosolic dynamin-related GTPase, plays a central role in fission by promoting mitochondrial division through its oligomerization into multimeric spiral structures and FIST is indirectly involved in mitochondrial fission via binding DRP1. An expanding number of degenerative disorders are associated with mutations in the genes encoding MFN2 and OPAL, including Charcot-Marie-Tooth disease type 2A and autosomal dominant optic atrophy. Defective mitochondrial dynamics seem to play a significant role also in the molecular and cellular pathogenesis of more common neurodegenerative diseases, for example, Alzheimer's and Parkinson's diseases (MacVicar and Langer, 2016 J Cell Sci 129, Lee et al., J Biol Chem 292, Zheng et al., 2019 Nucleic Acids Res 47; Ranieri et al., 2013 Neurol Res Int 2013; Escobar-Henriques and Joaquim, 2019 Front Physiol 10; Schrepfer and Scorrano, 2016 Molecular cell 61).

The present disclosure provides a method of treating at least one mitochondrial disease in a subject comprising administering to the subject a therapeutically effective amount of at least one compound of the present disclosure. The present disclosure provides at least one compound of the present disclosure for use in treating at least one mitochondria) disease in a subject, wherein the at least one compound of the present disclosure is for administration to the subject in at least one therapeutically effective amount. The present disclosure provides a use of at least one compound of the present disclosure for the manufacture of a medicament for treating at least one mitochondria) disease in a subject, wherein the at least one compound of the present disclosure is for administration to the subject in at least one therapeutically effective amount.

The present disclosure provides a method of preventing at least one mitochondrial disease in a subject comprising administering to the subject a therapeutically effective amount of at least one compound of the present disclosure. The present disclosure provides at least one compound of the present disclosure for use in preventing at least one mitochondria) disease in a subject, wherein the compound is for administration to the subject in at least one therapeutically effective amount. The present disclosure provides a use of at least one compound of the present disclosure for the manufacture of a medicament for preventing at least one mitochondrial disease in a subject, wherein the compound is for administration to the subject in at least one therapeutically effective amount.

In some aspects, a disease can be a disease selected from the group comprising Age-Related Macular Degeneration (AMD) or Dry Age-Related Macular Degeneration (AMD), Alpers Disease, Autosomal Dominant Optic Atrophy (ADOA), Barth Syndrome, Becker Muscular Dystrophy (DBMD), Lethal Infantile Cardiomyopathy (LIC), Carnitine-AcylCarnitine Deficiency, Carnitine Deficiency, Creatine Deficiency Syndrome, Co-Enzyme Q10 Deficiency, Complex I Deficiency, Complex II Deficiency, Complex Ili Deficiency, Complex IV Deficiency COX Deficiency, Complex V Deficiency, Chronic progressive external ophthalmoplegia (CPEO), Carnitine palmitoyl transferase 1 (CPT 1) Deficiency, Carnitine palmitoyl transferase 2 (CPT 2) Deficiency, OCTN2 carnitine transporter deficiency, Duchenne Disease, Diabetes mellitus and deafness (DAD), Kearns-Sayre syndrome (KSS), Lactic Acidosis, Leber's Hereditary Optic Neuropathy, Leukodystrohpy (also known as Leukoencephalopathy with brainstem and spinal cord involvement and lactate elevation, commonly referred to as LBSL), Leigh Disease or Syndrome, Leber's hereditary optic neuropathy (LHON), Luft Disease, MELAS Syndrome (mitochondria) myopathy, encephalopathy, lactic acidosis, and stroke-like episodes), MEPAN (mitochondrial enoyl CoA reductase protein-associated neurodegeneration), MERRF Syndrome (myoclonic epilepsy with ragged red fibers), Mitochondrial recessive ataxia syndrome (MIRAS), Mitochondrial Cytopathy, Mitochondria) DNA Depletion Syndrome (MDDS), Mytochondrial Myopathy and Major Mytochondrial Myopathy, Mitochondrial Encephalopathy, Mitochondrial neurogastrointestinal encephalopathy (MNGIE), NARP syndrome (Neurogenic Ataxia and Retinitis Pigmentosa), Pearson Syndrome, Primary Mitochondrial Myopathy, Pyruvate Carboxylase Deficiency, Pyruvate Dehydrogenase Deficiency, POLG Mutations, Mitochondria) diseases caused by mutations in the DNA polymerase-γ (POLG), Muscular Dystrophy, Mental Retardation, Progressive external ophthalmoplegia (PEO) or Thymidine kinase 2 deficiency (TK2d), Berardineli-Seip congenital lipodystropy (BSCL).

In some aspects, a disease can be a disease selected from the group comprising acquired conditions in which mitochondrial dysfunction has been involved including, but not limited to, diseases such as diabetes, Huntington's disease, cancer, Alzheimer's disease, Parkinson's disease, ataxia, schizophrenia, as well as diseases including, but not limited to, bipolar disorder, aging and senescence, anxiety disorders, cardiovascular disease, sarcopenia and chronic fatigue syndrome, migraine headaches, strokes, traumatic brain injury, neuropathic pain, transient ischemic attack, cardiomyopathy, coronary artery disease, chronic fatigue syndrome, fibromyalgia, retinitis pigmentosa, age-related macular degeneration, diabetes, hepatitis C, primary biliary cirrhosis and cholinergic encephalopathies.

Mitochondrial encephalomyopathy, lactic acidosis, and stroke-like episodes (MELAS) and Myoclonic epilepsy with ragged-red fibers (MERRF) are two of the most common mitochondrial encephalomyopathies caused by mitochondrial point mutations m.A3243G and m.A8344G encoding mt-tRNA recognizing codons of leucine and lysine respectively. MELAS patients are presented with recurring stroke-like episodes, epilepsy, sudden headache with vomiting and convulsions, lactic acidosis of the blood and dementia and MERRF patients have progressive myoclonic and generalized tonic-clonic seizures, ataxia, deafness, dementia, and myopathy. MELAS and MERRF cells are characterized by the accumulation of ROS and patients suffer from oxidative stress, decreased GSH/GSSG ratio and elevated oxidative damage to lipids. The pathogenesis of both diseases are marked by deficiencies of complex I and/or IV leading to the ROS production and inducing the expression and activity of genes involved in antioxidant defense including superoxide dismutases and catalyse in patient muscle tissue. Antioxidant treatment has been suggested to alleviate disease progression of MELAS and MERRF (Hayashi and Cortopassi, 2015 Free Radic Biol Med 88; Nissanka and Moraes, 2017 FEBS Lett 592; Lehmann et al., 2018 J Inborn Errors of Metab Screen 6; Federico et al., 2012 J Neurol Sci; Chou et al., 2016 Sci Reports 6).

Leber's hereditary optic neuropathy (LHON) is a maternally inherited disease characterized by the bilateral central vision loss at an early age attributed to the degeneration of the retinal ganglion cells (RGCs). The disease is caused by mitochondrial point mutations, most commonly in positions G11778A/ND4, G3460A/ND1, and T14484C/ND6 reducing the functional capacity of NADH:ubiquinone oxidoreductase (complex I). Mitochondrial respiratory chain is a major source of intercellular ROS and the dysfunction of complex I in LHON enables electrons to leak producing excess ROS. It is thought that oxidative stress as a consequence of the mutation is responsible for the cellular damage resulting in apoptosis activation of RGC. The increase in oxidative stress is also exacerbated by the reduction of antioxidant defenses; glutathione peroxidases, glutathione reductase, CuZn superoxide dismutase (SOD) and MnSOD. In vitro studies showed that treatments with various antioxidants have been shown to ameliorate cell death induced by tertiary-butyl hydroperoxide (t-BH) or rotenone treatment (Hayashi and Cortopassi, 2015 Free Radic Biol Med 88; Nissanka and Moraes, 2017 FEBS Lett 592; Lehmann et al., 2018 J Inborn Errors of Metab Screen 6; Federico et at, 2012 J Neurol Sci; Sadun et al., 2015 Acta Ophthal 93; Battisti et al., J Neurol Neurosurg Psychiatry 75; Falabella et al., Oxid Med Cell Longev 2016).

Leigh syndrome is an inherited mitochondrial disease arising from one of up to 35 mutations in the nuclear or mitochondrial DNA, most commonly in SURF1 and COX assembly genes. Patients have reduced capacity to synthesize ATP resulting in multifocal spongiform degeneration affecting the central nervous system. A clinical study in 2008 by Koopman et al. identified elevation of ROS in LS patient derived fibroblast cells. The patients had mutations in the COX assembly genes resulting in reduced complex I activity and when treated with vitamin E derivative, Trolox, the concentration of ROS in patient cells were dramatically reduced. Furthermore, increase of ROS has been measured in a different LS patient fibroblast with reduction in complex V activity and decreased antioxidant defenses, SOD1 and SOD2. In a complex I deficient animal model of LS, the ndufs4 knockout mouse, there is more protein oxidative damage in the brain resulting from progressive glial activation that promotes neuronal death by both apoptotic and necrotic pathways. Similarly, in the mouse embryonic fibroblasts (MEF) cell of ndufs4fky mice, there is an increased production of superoxides and higher sensitivity to oxidative stress and treatment with antioxidant, α-tocopherol prevented synapse degeneration (Hayashi and Cortopassi, 2015 Free Radic Biol Med 88; Nissanka and Moraes, 2017 FEBS Lett 592; Lehmann et al., 2018 J Inborn Errors of Metab Screen 6; Federico et al., 2012 J Neurol Sci; Lake et al., 2015 J Neuropathol Exp Neurol 74, Wojtala et al., 2017 Mitochondrion 37).

Kearns-Sayre syndrome (KSS) is a rare mitochondrial cytopathy which belongs to a group of mitochondrial DNA (mtDNA) deletion syndromes that also includes Pearson syndrome and progressive external ophthalmoplegia (PEO). Typical features of KSS include progressive external ophthalmoplegia and pigmentary retinopathy, and frequently including heart block, cerebellar ataxia or increased cerebrospinal fluid (CSF) protein level (>100 mg/dL) and increased serum lactate levels as well as impairments in musculoskeletal, central nervous, cardiovascular, and endocrine systems (Khambatta et al., 2014 Int J Gen Med 7). Muscle biopsy reveals characteristic "ragged red fibers". Most patients with KSS have large (1.3-10 kb) mtDNA deletions, which generally include, in addition to several tRNA genes, protein genes coding for complex I, IV, and V subunits, which lead to disruption of mitochondrial function and health and dysfunctional energy metabolism including impaired oxidative phosphorylation and reduced ATP production. The ragged red fibers observed in muscle biopsy indicate a combined defect of respiratory complexes I and IV (Lopez-Gallardo et al., 2009 Mitochondrion 9; Holloman et al., 2013 BMJ Case Rep 2013; Khambatta et al., 2014 Int J Gen Med 7).

Methods of Use—Inborn Errors of Metabolism

Inborn errors of metabolism (IEM) form a large class of genetic diseases involving congenital disorders of metabolism. The majority are due to defects of single genes that code for enzymes that facilitate conversion of various substances (substrates) into others (products). In most of the disorders, problems arise due to accumulation of substances which are toxic or interfere with normal cellular metabolism and regulation, or to the effects of reduced ability to synthesize essential compounds. IEM comprise a diverse group of over 1,000 congenital disorders with current newborn screening methods more than 1 in 2,000 newborns are identified as having a metabolic disorder (Arnold 2018 Ann Trans Med 24).

Traditionally the inherited metabolic diseases were classified as disorders of carbohydrate metabolism, amino acid metabolism, organic acid metabolism, or lysosomal storage diseases, however many smaller disease categories have been suggested recently. Some of the major IEM categories are Disorders of carbohydrate metabolism (such as pyruvate dehydrogenase deficiency, glycogen storage disease, G6PD deficiency), Disorders of amino acid metabolism (such as propionic aciduria, methylmalonic aciduria, maple syrup urine disease, glutaric acidemia type 1, phenylketonuria), Urea Cycle Disorders (such as Carbamoyl phosphate synthetase I deficiency, Ornithine Transcarbamylase Deficiency), Disorders of fatty acid oxidation and mitochondrial metabolism (such as Long chain acyl-CoA dehydrogenase deficiency and Medium-chain acyl-coenzyme A dehydrogenase deficiency), Disorders of porphyrin metabolism (such as acute intermittent porphyria), Disorders of purine or pyrimidine metabolism (such as Lesch-Nyhan syndrome), Disorders of steroid metabolism (such as lipoid congenital adrenal hyperplasia, congenital adrenal hyperplasia), Disorders of mitochondrial function (such as Leigh syndrome, Kearns-Sayre syndrome, MELAS), Disorders of peroxisomal function (such as Zellweger syndrome), Lysosomal storage disorders (such as Gaucher's disease, Niemann-Pick disease) and many others (Saudubray et al. 2016 Inborn Metabolic Diseases, Springer).

Because of the enormous number of IEM diseases and wide range of systems affected the clinical manifestations of IEM are very heterogenous with most common features including failure to thrive, developmental delay, seizures, dementia, encepalopathy, deafness, blindness, abnormal skin pigmentation, liver and kidney failure, etc. However, many of the IEM diseases share some of the underlying mechanistic pathogenicities and resulting abnormal metabolic biomarkers, which often serve also as diagnostic tools. Some of the most common and often shared cellular and metabolic features of IEMs are impaired mitochondrial function and physiology, impaired or abberant energy metabolism, deficient energy production, impaired NAD+/NADH homeostasis, increased ROS production, disrupted redox homeostasis and reduced GSH/GSSG ratio, abberant Fe—S metabolism and impaired heme production, accumulation of organic acids and acyl-CoA thioesters, elevated levels of acyl-carnitines, lactic acid ammonia, dysrupted post-translational gene and protein regulation (protein and histone acylation) (Garg and Smith, ed., 2017 Biomarkers in Inborn Errors of Metabolism, Elsevier, 476p).

Fibroblast growth factor 21 (FGF21) is an important hepatokine in both intermediary and mitochondrial energy metabolism. FGF21 has been shown to stimulate fatty acid oxidation and ketogenesis, reduce insulin secretion, increase insulin sensitivity and inhibit overall growth through PPAR-gamma and beta-Klotho signaling pathways on multiple tissue types, including the brain, adipose and muscle (Goetz, 2013 Nat Rev Endocrinol 9). Additionally, FGF21 may modulate OXPHOS through AMPK and SIRT1 activation. FGF21 has recently been proposed as a clinical biomarker for primary mitochondrial disorders, in particular those that manifest as myopathy and the literature suggests FGF21 levels may be even more sensitive and specific than traditional biomarkers of mitochondrial dysfunction such as creatine kinase, lactate and pyruvate (Suomalainen et al., 2011 Lancet Neurol 10) and multiple studies suggest elevated FGF21 correlates strongly with IEMs (Kirmse et al., 2017 Mol Genet Metab Rep 13; Molema et al., 2018 J Inh Metab Dis 41).

In addition to IEMs, metabolic disorders such as obesity, hyperlipidemia, and diabetes mellitus (DM) have been observed independently associated with mild-to-moderate alanine aminotransferase (ALT) elevation 4 (Liu et al., 2014 Int J Med Sci).

Some of these biomarkers are provided herein with select exemplary IEM diseases for which the said biomakers are common, but the list is not exclusive both in terms of the biomarkers as well as IEM diseases associated with these biomarkers: hyperamonemia (common biomarker in Urea cycle disorders, Hyperornithinemia-hyperammonemia-homocitrullinuria (HHH), Dibasic amino aciduria, Lysinuric protein intolerance, Hyperinsulinism-hyperammonemia, Carnitine uptake defect, Carnitine palmitoyltransferase-1 (CPT-1) deficiency, Acylcarnitine translocase deficiency, Maple urine syrup disease, Medium chain acyl-CoA dehydrogenase (MCAD) deficiency, Branched chain amino acids organic acidurias, Certain organic acidurias such as methylmalonic, propionic, isovaleric aciduria, Severe liver disease); Abnormal liver function tests with elevated Aspartate aminotransferase (AST), Alanine aminotransferase (ALT) and Bilirubin (common biomarkers in Tyrosinemia type 1, Fatty acid oxidation defects including Carnitine uptake defect, Carnitine palmitoyltransferase-1 deficiency, Carnitine palmitoyltransferase-2 deficiency, Very long chain acyl-CoA dehydrogenase deficiency, Medium chain acyl-CoA dehydrogenase deficiency, Short chain acyl-CoA dehydrogenase deficiency, Long chain 3-hydroxyacyl-CoA dehydrogenase deficiency and Multiple acyl-CoA dehydrogenase deficiency, Carbohydrate metabolism defects such as Galactosemia, Glycogen storage disease types 1, 3, 6, 9, Glycogen synthase deficiency, Pyruvate carboxylase deficiency, Galactose-1-phosphate uridyltransferase deficiency, Hereditary fructose intolerance and Fructose-1,6-diphosphatase deficiency, Lipid metabolism/Lysosomal storage defects such as Cholesterol-7-hydroxylase deficiency, 3-Hydroxy-$\Delta$5-C27-steroid dehydrogenase deficiency, 3-Oxo-$\Delta$4-5$\beta$-reductase deficiency, 3-Hydroxy-3methylglutaryl-CoA synthase deficiency, Cholesteryl ester storage disease, Gaucher's disease, type 1 Niemann-Pick disease, types A and B, Acid lipase deficiency/Wolman's disease, Hyperammonemias, Ornithine transcarbamylase deficiency, Argininosuccinic aciduria, Arginase deficiency, Lysinuric protein intolerance, Hemochromatosis, Mitochondrial disorders, al-antitrypsin deficiency, Wilson disease, Wolman's disease, Zellweger syndrome); Elevated cholesterol (common biomarker in Lipoprotein lipase deficiency, Dysbetalipoproteinemia, Defective apoB-100, Hepatic lipase deficiency, Lecithin cholesterol acyltransferase deficiency, Sterol 27-hydroxylase deficiency); Low cholesterol (common biomarker in Mevalonic aciduria, Abetalipoproteinemia, Hypobetalipoproteinemia, Smith-Lemli-Opitz syndrome, Other cholesterol biosynthesis disorders, Barth syndrome Glucosyltransferase I deficiency, ALG6-CDG (CDG-Ic)); Elevated creatine kinase (common biomarker in Fatty acid oxidation defects such as Carnitine palmitoyltransferase-2 deficiency, Very long chain acyl-CoA dehydrogenase deficiency, Long chain 3-hydroxyacyl-CoA dehydrogenase deficiency, Multiple acyl-CoA dehydrogenase deficiency, Glycogen storage disorders type 2, 3, 5, ALG6-CDG Myoadenylate deaminase deficiency); Low creatine (common biomarker in Creatine synthetic defects); Elevated creatinine/urea (common biomarker in Lysosomal cystine transport, Hyperoxaluria type 1); Low glucose (common biomarker in Fatty acids oxidation disorders, Glycogen storage disorders, Galactosemia, Fructose-1,6-diphosphatase deficiency, Pyruvate carboxylase deficiency, Multiple acyl-CoA dehydrogenase deficiency, Hereditary fructose intolerance); Low hemoglobin (common biomarker in B12 metabolism deficiency, Folate metabolism disorders, Glucose-6-phosphate dehydrogenase deficiency, 5-Oxoprolinuria Glutathione synthesis defects, Glycolysis defects); Elevated ketones (common biomarker in Methylmalonic aciduria, Propionic aciduria, Isovaleric aciduria, Pyruvate carboxylase deficiency, Gluconeogenesis defects); Elevated lactate (common biomarker in Glycogen metabolism disorders such as Amylo-1,6-glucosidase deficiency, Glucose-6-phosphate translocase deficiency, Glycogen synthetase deficiency and Liver phosphorylase deficiency, Gluconeogenesis defects such as Glucose-6-phosphatase deficiency and Fructose 1,6 diphosphatase deficiency, Lactate/Pyruvate disorders such as Pyruvate dehydrogenase deficiency and Pyruvate carboxylase deficiency, Krebs cycle/Respiratory chain/Mitochondrial defects such as Ketoglutarate dehydrogenase defect and Fumarase defect, Respiratory chain defects such as Complex I (NADH-CoQ oxidoreductase) deficiency, Complex II (Succinate-CoQ reductase) deficiency, Complex III (CoQ cytochrome C reductase, complex III) deficiency and Complex IV (Cytochrome oxidase C) deficiency, Organic acidurias such as Methylmalonic aciduria, Propionic aciduria, Isovaleric aciduria, L-2-Hydroxyglutaric aciduria, Hyperammonemias Biotinidase deficiency, Holocarboxylase synthetase deficiency and Fatty acids oxidation defects, Acquired causes such as Hypoxia Drug intoxications-salicylate, cyanide Renal insufficiency Convulsions); Low blood pH, acidosis, precence of high levels of organic acids (common biomarker in Organic acidurias such as Methylmalonic aciduria, Propionic aciduria, Isovaleric aciduria, 3-Methylcrotonylglycinuria, 3-Methylglutaconic aciduria, 3-Hydroxy-3-methylglutaryl-CoA lyase deficiency, Biotinidase deficiency, Holocarboxylase synthetase deficiency, 3-Oxothiolase deficiency, 2-Ketoglutarate dehydrogenase complex deficiency, 3-Hydroxyisobutyric aciduria, Maple syrup urine disease and Mitochondrial disorders, Fatty acid oxidation defects such as Carnitine uptake defect, Carnitine palmitoyltransferase-1 deficiency, Very long chain acyl-CoA dehydrogenase deficiency, Medium chain acyl-CoA dehydrogenase deficiency, Short chain acyl-CoA dehydrogenase deficiency, Long chain 3-hydroxyacyl-CoA dehydrogenase deficiency and Multiple acyl-CoA dehydrogenase deficiency, Carbohydrate metabolism defects such as Glycogen storage disease types 1, 3, 6, 9, Glycogen synthase deficiency, Pyruvate carboxylase deficiency, Galactosemia Fructose-1,6-diphosphatase deficiency, Glycerol kinase deficiency); Elevated serum triflycerides (common biomarker in Glycogen storage disease type 1, Lipoprotein lipase deficiency, Dysbetalipoproteinemia, Hepatic lipase deficiency, Lecithin cholesterol acyltransferase deficiency); Elevated uric acid (common biomarker in Hypoxanthine phosphoribosyl transferase deficiency, Phosphoribosyl pyrophosphate synthetase deficiency, Glycogen storage disease type 1); Low uric acid (common biomarker in Purine nucleoside phosphorylase deficiency, Molybdenum cofactor deficiency, Xanthine oxidase deficiency) as well as many other well characterized biomakers (Garg and Smith, ed., 2017 Biomarkers in Inborn Errors of Metabolism, Elsevier, 476p; Kolker et al. 2015, J Inherit Metab Dis 38).

Methylmalonic acidemia (also known as Methylmalonic aciduria or MMA) is a genetically heterogeneous group of disorders originating from impaired metabolism of certain amino acids (isoleucine, methionine, threonine, or valine), odd-chain fatty acids or cholesterol esters. MMA is biochemically characterized by the accumulation of methylmalonic acid in all body fluids and tissues (Morath et a., 2008 J Inherit Metab Dis 2008). Two main forms can be distinguished: isolated MMA and combined MMA. The isolated form may be caused by a complete ($mut^0$) or partial ($mut^-$) deficiency of the enzyme methylmalonyl-coenzyme A mutase, a defect in the transport or synthesis of its cofactor, adenosyl-cobalamin (cblA, cblB, cblD-MMA, cblH), or by a deficiency of the enzyme methylmalonyl-CoA epimerase (Manoli et al., 1993 Gene Reviews). Combined MMA presents with homocystinuria/homocystinemia (cblC, cblD-MMA/HC, cblF, cblJ) and also with malonic acidemia/aciduria (CMAMMA type) (Sloan et al., 2018 Gene Reviews).

In addition to elevated methylmalonic acid, a major hallmark of MMA disease impairment of energy metabolism including inhibition of Complex II of the respiratory chain and arrest of the TCA cycle (Okun et al., 2002 J Biol Chem; Mirandola et al., 2009 J Inh Metab Dis 31; Wongkittichote et at, 2019 Mol Genet Metab), decreased ATP/ADP ratio and collapse of ion gradients, membrane depolarization and increase in intracellular $Ca^{2+}$ levels (Melo et al., 2011 J Bioen Biomembr 43), significantly elevated intracellular ROS generation and apoptosis markers (Richard et al., 2009 Hum Mutat 30; Fontella et al., 2000 Neuroreport 11; Richard et al., 2006 J Proteome Res 5; Richard et al., 2007 J Pathol 213), deficient energy metabolism, reduced succinyl-CoA levels, reduced GSH levels, as demonstrated in both patient tissue samples as well as in mut knock-out mice (Keyzer et al., 2009 Pediatric Res 66; Valayannopolos et al., 2009 J Inh Metab Disease 32; Chandler et al., 2009 FASEB J 23; Hayasaka et al., 1982 Tohoku J Exp Med 137; Cosson et al., 2008 Mol Biosystems 12). As with many other IEM diseases, the concentration of plasma FGF21 in MMA patients was shown to correlate strongly with disease subtype, growth indices, and markers of mitochondrial dysfunction (Manoli et al., 2018 JCI Insight 3).

Several mouse models of MMA have been published with many recapitulating well the clinical phenotype of MMA including failure to thrive, and show increased methylmalonic acid, propionylcarnitine, odd chain fatty acids, and sphingoid bases. Some models also exhibit manifestations of kidney and brain damage, including increased plasma urea, impaired diuresis, elevated biomarkers, and changes in brain weight. On a high protein diet, mutant mice display disease exacerbation, including elevated blood ammonia, and catastrophic weight loss, which, in some mouse models, is rescued by hydroxocobalamin treatment (Forny et al., 2016 J Biol Chem 291; An et al., 2017 Cell Reports 21; Peters et al., 2012 PLoS One 7; Remade et al., 2018 124). A cobalamin (Cbl) deficient mouse model was also developed which recapitulated very closely the pathology and biomarkers associated with MMA (Ghosh et al., 2016 Front Nut 3).

In a MMA patient with optic neuropathy, treatment with antioxidants resulted in improved visual acuity (Pinar-Sueiro et al., 2010 J Inh Metab Dis 33) and treatment of MMA mice with antioxidants showed a significant amelioration in the loss of glomerular filtration rate and a normalization of plasma lipocalin-2 levels (Manoli et al., 2013 PNAS 110), indicating that ROS may be a viable therapeutic target with effects not restricted only to the nervous system.

Propionic acidemia (also known as Propionic aciduria or PA) is a serious, life-threatening, inherited, metabolic disorder caused by the mutations in the PCCA or PCCB gene that encode the α and β subunits of propionyl-CoA carboxylase (PCC), respectively. PCC is a biotin-dependent mitochondrial enzyme that catalyzes the reaction of propionyl-CoA to D-methylmalonyl-CoA, the first step of the propionate oxidation pathway. Propionyl-CoA derives from the catabolism of certain amino acids including BCAAs (Ile, Val, Thr, and Met), of cholesterol, and from the beta-oxidation of odd chain fatty acids and bacteria gut production. PCC deficiency results in the accumulation and excretion of propionate, 3-hydroxypropionate, methylcitrate, and propionylglycine, which are the biochemical hallmarks for diagnosis. PA leads to a multisystemic disorder that affects the cardiovascular, gastrointestinal, renal, nervous, and immune systems (Kölker et al., 2015 J Inerit Metab Dis 38; Shchelochkov et al., 2012 GeneReviews; Pena et al., 2012 Mol Gen Metab 105).

A number of in vitro and in vivo studies of propionyl-CoA metabolites have shown inhibition of enzymes involved in energy production pathways, such as respiratory chain complex III (Sauer et al., 2008 Bioenergetics 1777) and pyruvate dehydrogenase complex (Gregersen, 1981 Biochem Med 26). Furthermore, propionyl-CoA reacts with oxaloacetate to produce methylcitrate that inhibits enzymes such as phosphofructokinase aconitase and citrate synthase (Cheema-Dhadli et al., 1975 Pediat Res 9). In addition, propionate, at concentrations similar to those found in the plasma of PA patients, strongly inhibits oxygen consumption as well as oxidation of pyruvate and alpha-ketoglutarate in rat liver mitochondria (Gregersen, 1981 Biochem Med 26; Stumpf et al., 1980 Ped Res 14). Moreover, the lack of PCC that blocks the anaplerotic biosynthesis of succinyl-CoA from propionyl-CoA may result in diminished TCA cycle activity (Brunengraber et al., 2006 J Inh Metab Dis 29). Propionic acid was shown to stimulate the production of ROS in the presence of $Ca^{2+}$ influx activators in human neutrophils (Nakao et al., 1998 Cell Biol Int 22), to increase protein carbonylation in rats (Rigo et al., 2006 Neurosc Lett) and to stimulate lipid peroxidation in rat cerebral tissues (Fontella et al., 2000 Neuroreport 11). The secondary mitochondrial dysfunction in PA is manifested as a decrease in ATP and phospho-creatine production, a decrease in the activity of respiratory chain complexes, mtDNA depletion, and abnormal mitochondrial structures present in PA patients' biopsies. This is evident particularly in high-energy-demanding organs such as the brain and heart (de Keyzer et al., 2009 Ped Res 66; Mardach et al., 2005 Mol Gen Metab 85; Schwab et al., 2006 Biochem J 398). In addition, evidence of oxidative stress and cellular damage has been shown in PA patients' fibroblasts through detection of elevated intracellular 11202 levels correlating with the activation of the JNK and p38 pathways (Gallego-Villar et al., 2013 J Inh Metab Dis 36). Urinary samples from PA patients show high levels of oxidative stress markers (Mc Guire et al., 2009 Mol Gen Metab 98). Alterations in redox homeostasis and mitochondrial function were observed in a hypomorphic mouse models of PA, including increased $O^{2-}$ production and in vivo mitochondrial 1-1202 levels, mtDNA depletion, lipid oxidative damage, and tissue-specific alterations in the activities of OXPHOS complexes and in antioxidant defenses. An increase in the DNA repair enzyme 8-guanine DNA glycosylase 1 (OGG1) induced by oxidative stress was also found in the liver of PA mice show a good correlation with the altered mitochondrial function and oxidative damage detected in PA patients' samples. The hypomorphic mice also showed standard PA biomarkers such as elevations in propionyl-carnitine, methylcitrate, glycine, alanine, lysine, ammonia, and markers associated with cardiomyopathy similar to those in patients with PA (Guenzel et al., 2013 Mol Ther 21; Gallego-Villar et al., 2016 Fre Rad Biol Med 96; Rivera-Barahona et al., 2017 Mol Gen Metab 122).

Recently, in vitro and in vivo studies in PA have also shown the positive effect of antioxidant treatment. Using patients' fibroblasts, different antioxidants significantly reduced $H_2O_2$ levels and regulated the expression of antioxidant enzymes (Gallego-Villar et al., 2014 Biochem Biophys Res Comm 452). In the hypomorphic mouse model of PA, oral treatment with antioxidants protected against lipid and DNA oxidative damage and induced the expression of antioxidant enzymes (Rivera-Barahona et al., 2017 Mol Gen Metab. 122).

Glutaric aciduria type I (GA-I) is a metabolic disorder caused by the deficiency of the mitochondrial enzyme glutaryl-CoA dehydrogenase (GCDH), responsible for the oxidative decarboxylation of glutaryl-CoA to crotonyl-CoA, in the catabolic pathways of lysine and tryptophan. The deficiency causes accumulation of glutarate and 3-hydroxyglutarate, and patients are at risk of acute striatal injury during encephalopathic crises before 4 years of age, which lead to the appearance of neurological symptoms including dystonia, dyskinesia, seizures, and coma (Strauss et al., 2003 Am J Med Gen 121). Excitotoxicity, oxidative stress, and mitochondrial dysfunction induced by accumulating metabolites have been associated with brain pathogenesis, although the exact underlying mechanisms remain unclear (Amaral et al., 2015 Brain Res 1620; Kolker et al., 2008 J Inh Metab Dis 31). GCDH-deficient knockout mice ($Gcdh^{-/-}$) show a biochemical phenotype comparable to GA-I patients but do not develop striatal degeneration.

These mice exhibit protein oxidative damage and reduction of antioxidant defences in the brain when subjected to an acute lysine overload and high concentrations of glutaric acid within neurons were correlated with mitochodrial swelling and biochemical changes (depletion of alpha-ketoglutarate and accumulation of acetyl-CoA) consistent with Krebs cycle disruption (Koeller et al., 2002 Hum Mol Gen 11; Seminotti et al., 2014 J Neurol Sci 344; Zinnanti et al., 2006 Brain 129; Zinnanti et al., 2007 J Clin Invest 117).

Branched chain alpha-ketoacid dehydrogenase (BCKDH) deficiency (also known as Maple Syrup Urine Disease or MSUD) is a disease caused by the deficiency of branched-chain α-ketoacid dehydrogenase complex (BCKDHc) activity, which is characterized by elevated levels of branched-chain amino acids (BCAAs) and their corresponding α-ketoacids (BCKAs) in body fluids and tissues, resulting in complex neurological phenotypes (Strauss et al., 2006 GeneReviews). BCKDHc is regulated by reversible phosphorylation catalyzed by a specific BCKD kinase (BCKDK) that inhibits BCKDHc function, halting the catabolic pathway of BCAAs (Harris et al., 2004 Biochem Biophys Res Comm 313) and a dephosphorylation catalyzed by the mitochondrial protein phosphatase PP2Cm (encoded by the PPM1K gene) that stimulates BCKDHc activity (Oyarzabal et al., 2013 Human Mut 34). MSUD results from mutations in the genes E1α-BCKDHA, E1β-BCKDHB, and E2-DBT (Chuang and Shi, 2001 Metabolic and Molecular Basis of Inherited Disease).

Different studies have been carried out using chemical induction of the disease by BCAAs or BCKAs in cultured cells (Sitta et al., 2014 Cell Mol Neurobiol 25) and animal models (Zinnanti et al., 20098 Brain 132; Friedrich et al., 2012 Dis Mod Mech 5; Bridi et al., 2003 Int J Dev Neurosc 21; Bridi et al., 2005 Metab Brain Dis 29). All converge in the identification of oxidative stress, brain energy deficit, and/or alterations in the brain's neurotransmission balance, mostly affecting glutamate, as important neurodegenerative determinants. Recent studies in human peripheral blood mononuclear cells have shown that BCAAs stimulate the activation of the redox-sensitive transcription factor NFκB resulting in the release of proinflammatory molecules (Zhenyukh et al., 2017 Free Rad Biol Med 104). Increases in lipid and protein oxidation are detected in plasma of MSUD patients including those patients maintained at low BCAA levels indicating the presence of sustained inflammation and activation of the immune system probably as a result of unbalanced ROS production (Barschak et al., 2008 Metab Brain Dis 23; Mescka et al., 2013 Int J Dev Neurosc 31; Mescka et al., 2015 Metab Brain Dis 30).

In some aspects, a disease can be a disease selected from the group comprising medium-chain acyl-CoA dehydrogenase deficiency, biotinidase deficiency, isovaleric acidemia, very long-chain acyl-CoA dehydrogenase deficiency, long-chain L-3-OH acyl-CoA dehydrogenase deficiency, glutaric acidemia type I, 3-hydroxy-3-methylglutaric acidemia, trifunctional protein deficiency, multiple carboxylase deficiency, methylmalonic acidemia (methylmalonyl-CoA mutase deficiency), 3-methylcrotonyl-CoA carboxylase deficiency, methylmalonic acidemia (Cbl A,B), propionic acidemia, carnitine uptake defect, beta-ketothiolase deficiency, short-chain acyl-CoA dehydrogenase deficiency, glutaric acidemia type II, medium/short-chain L-3-OH acyl-CoA dehydrogenase deficiency, medium-chain ketoacyl-CoA thiolase deficiency, carnitine palmitoyltransferase II (CPT2) deficiency, methylmalonic acidemia (Cbl C,D), methylmalonic aciduria with homocystinuria, D-2-hydroxyglutaric aciduria, L-2-hydroxyglutaric aciduria, malonic acidemia, carnitine: acylcarnitine translocase deficiency, isobutyryl-CoA dehydrogenase deficiency, 2-methyl 3-hydroxybutyric aciduria, dienoyl-CoA reductase deficiency, 3-methylglutaconic aciduria, PLA2G6-associated neurodegeneration, glycine N-acyltransferase deficiency, 2-methylbutyryl-CoA-dehydrogenase-deficiency, mitochondria) acetoacetyl-CoA thiolase deficiency, dihydrolipoamide dehydrogenase deficiency/Branched chain alpha-ketoacid dehydrogenase (BCKDH) deficiency (also called Maple Syrup Urine Disease—MSUD), 3-methylglutaconyl-CoA hydratase deficiency, 3-hydroxyisobutyrate dehydrogenase deficiency, 3-hydroxy-isobutyryl-CoA hydrolase deficiency, isobutyryl-CoA dehydrogenase deficiency, methylmalonate semialdehyde dehydrogenase deficiency, bile acid-CoA: amino acid N-acyltransferase deficiency, bile acid-CoA ligase deficiency, holocarboxylase synthetase deficiency, Succinate dehydrogenase deficiency, α-Ketoglutarate dehydrogenase deficiency, deficiency of CoA synthase enzyme complex (CoASY), multiple acyl-CoA dehydrogenase deficiency, long chain 3-ketoacyl-CoA thiolase, D-3-hydroxyacyl-CoA dehydrogenase deficiency (part of DBD), aryl-CoA dehydrogenase 9 deficiency, Systemic primary carnitine deficiency, carnitine: acylcarnitine translocase deficiency I and II, acetyl-CoA carboxylase deficiency, Malonyl-CoA decarboxylase deficiency, Mitochondrial HMG-CoA synthase deficiency, succinyl-CoA:3-ketoacid CoA transferase deficiency, phytanoyl-CoA hydroxylase deficiency/Refsum disease, D-bifunctional protein deficiency (2-enoyl-CoA-hydratase and D-3-hydroxyacyl-CoA-dehydrogenase deficiency), acyl-CoA oxidase deficiency, alpha-methylacyl-CoA racemase (AMACR) deficiency, sterol carrier protein x deficiency, 2,4-dienoyl-CoA reductase deficiency, Cytosolic acetoacetyl-CoA thiolase deficiency, Cytosolic HMG-CoA synthase deficiency, lecithin cholesterol acyltransferase deficiency, choline acetyl transferase deficiency, Congenital myasthenic syndrome, pyruvate dehydrogenase deficiency, phosphoenolpyruvate carboxykinase deficiency, pyruvate carboxylase deficiency, serine palmiotyl-CoA transferase deficiency/Hereditary sensory and autonomic neuropathy type I, ethylmalonic encephalopathy, propionyl-CoA carboxylase deficiency, succinic semialdehyde dehydrogenase deficiency, glutathione reductase deficiency, glycine encephalopathy (Non-ketotic hyperglycinemia), fumarase deficiency, Reye syndrome and isovaleryl-CoA dehydrogenase deficiency, Lesch-Nyhan syndrome, 3-Hydroxy-3-methylglutaryl-CoA lyase deficiency, 3-Hydroxy-Δ5-C27-steroid dehydrogenase deficiency, 3-Hydroxyisobutyric aciduria, 3-Oxo-A4-5β-reductase deficiency, 3-Oxothiolase deficiency, Abetalipoproteinemia, Acid lipase deficiency/Wolman's disease, acute intermittent porphyria, Amylo-1, 6-glucosidase deficiency, Arginase deficiency, Argininosuccinic aciduria, B12 metabolism deficiency, Barth syndrome, Glucosyltransferase 1 deficiency, Carnitine palmitoyltransferase-1 deficiency, Cholesteryl ester storage disease, congenital adrenal hyperplasia, Defective apoB-100, Dibasic amino aciduria, Dysbetalipoproteinemia, Folate metabolism disorders, Fructose-1,6-diphosphatase deficiency, Galactose-1-phosphate uridyltransferase deficiency, Galactosemia, Gaucher's disease, Gluconeogenesis defects, Glucose-6-phosphate dehydrogenase deficiency, Glucose-6-phosphate translocase deficiency, Glycogen storage disease type 1, Glycogen synthase deficiency, Glycolysis defects, Hemochromatosis, Hepatic lipase deficiency, Hereditary fructose intolerance, Hyperammonemias, Hyperinsulinism-hyperammonemia, Hyperoxaluria type 1, Hypobetalipoproteinemia, Cholesterol-7-hydroxylase deficiency, lipoid congenital adrenal hyperplasia, Lipoprotein lipase deficiency, Liver phosphorylase deficiency, Lysinuric protein intolerance, Methylcrotonylglycinuria, Mevalonic aciduria, Niemann-Pick disease, Niemann-Pick type C disease, Ornithine transcarbamylase deficiency, Smith-Lemli-Opitz syndrome, Sterol 27-hydroxylase deficiency, Tyrosinemia type 1, Wilson disease, Wolman's disease, Zellweger syndrome, a1-antitrypsin deficiency.

In some aspects, a disease can be any of the diseases characterized by and/or associated with inborn errors of metabolism discussed herein. Thus, the present disclosure provides a method of treating a disease characterized by and/or associated with inborn errors of metabolism in a subject comprising administering to the subject a therapeutically effective at least one compound of the present disclosure. The present disclosure provides at least one compound of the present disclosure for use in treating a disease characterized by and/or associated with inborn errors of metabolism in a subject, wherein the at least one compound of the present disclosure is for administration to the subject in at least one therapeutically effective amount. The present disclosure provides a use of at least one compound of the present disclosure for the manufacture of a medicament for treating a disease characterized by and/or associated with inborn errors of metabolism in a subject, wherein the at least one compound of the present disclosure is for administration to the subject in at least one therapeutically effective amount.

The present disclosure provides a method of increasing or decreasing at least one biomarker associated with a disease characterized by and/or associated with inborn errors of metabolism in a subject comprising administering to the subject at least one therapeutically effective amount of a compound of the present disclosure. The biomarkers associated with a disease characterized by and/or associated with inborn errors of metabolism are presented herein.

In some aspects, a disease can be an endoplasmic reticulum disease, a lysosome storage disease, and/or a disorder of the peroxisome. In some aspects, a disease can be selected from, but not limited to, Niemann-Pick type C, and Wolfram syndrome.

The urea cycle disorders (UCDs) comprise diseases with congenital defects of the enzymes or transporters of the urea cycle (a metabolic pathway required for the disposal of excess nitrogen from the cells). This cycle utilizes five enzymes, two of which, carbamoylphosphate synthetase 1 and ornithine transcarbamylase are present in the mitochondrial matrix, whereas the others (argininosuccinate synthetase, argininosuccinate lyase and arginase 1) are present in the cytoplasm (Matsumoto et al. 2019 J Human Genetics, Haberle et al. 2012 Orphanet J of Rare Diseases). High concentrations of ammonia (hyperammonemia), which is a common feature in UCDs, leads to the alterations of glutamate transport in CNS, alteration in the function of the glutamate-nitric oxide-cGMP pathway, disrupted neurotransmission, increased extracellular brain glutamate concentrations, cerebral edema and ultimately cell death (Natesan et al. 2016 Biomedicine & Pharmacology 81). Hyperammonemia alters several amino acid pathways and neurotransmitter systems, as well as cerebral energy metabolism, nitric oxide synthesis, oxidative stress, mitochondrial permeability transition and signal transduction pathways (Cagnon and Braissant, 2007 Brain Res Rec 56). Excess extracellular glutamate is known to be an excitotoxic agent that activates N-methyl-D-aspartate (NMDA) receptors, which leads to disturbed nitric oxide (NO) metabolism, $Na^+/K^+$-ATPase, ATP shortage, mitochondrial dysfunction, free radical accumulation and oxidative stress (Manfort et al. 2009 Neurochem Int, 55).

Imbalances of amino acids can also contribute to the brain damage that occurs in UCDs. Spf mice, which have a single point mutation in the Otc gene, presented with some neutral amino acids accumulation in the brain (i.e., tryptophan, tyrosine, phenylalanine, methionine, and histidine), and it was suggested that the accumulation of tryptophan may cause an abnormality in serotoninergic neurotransmission (Bachmann et al. 1984 Pedia Res, 18). In addition, ATP and creatine levels are decreased in the brain of spf mice as well as Cytochrome C oxidase expression is reduced (Ratnakumari et al. 1992 Biochem Biophys Res Commun, 184). Furthermore, Acetyl-CoA is a required cofactor in the urea cycle in order to convert glutamate to N-acetyl-glutamate (N-acetylglutamate synthase), which is used to convert ammonia into carbamoylphosphate (Carbamoylphosphate synthase 1). Ornithine transcarbamylase then catalyses the synthesis of citrulline from carbamoylphosphate, which is then combined in the cytosol of hepatocytes with aspartate (derived from glutamate and TCA cycle intermediate oxaloacetate via transamination) to generate argininosuccinate (argininosuccinate synthase 1). A disruption of acetyl-CoA and/or TCA cycle homeostasis may thus further exacerbate UCD.

A treatment of pregnant spf mice with acetyl-L-carnitine, starting from day 1 of conception, resulted in restoration of the cytochrome C oxidase activity and a significant restoration of choline esterase activity levels in some brain regions of the spf/Y offspring, suggesting that acetyl-L-carnitine may be neuroprotective in $NH4^+$-induced toxicity, possibly also through acetyl-L-carnitine's ability to act as a free radical scavenger and thus may contribute to the protection against oxidative stress (Ratnakumari et al., 1995 J Pharmacol Exp 274; Rao et al., 1997 Neurosci Lett 224, Zanelli et al., 2005 Ann NY Acad Sci 1053).

The present disclosure provides a method of treating a Urea cycle disorder (UCD) in a subject comprising administering to the subject a therapeutically effective at least one compound of the present disclosure. The present disclosure provides at least one compound of the present disclosure for use in treating a Urea cycle disorder (UCD) in a subject, wherein the at least one compound of the present disclosure is for administration to the subject in at least one therapeutically effective amount. The present disclosure provides a use of at least one compound of the present disclosure for the manufacture of a medicament for treating a Urea cycle disorder (UCD) in a subject, wherein the at least one compound of the present disclosure is for administration to the subject in at least one therapeutically effective amount.

The present disclosure provides a method for treating a disease that is a Urea cycle disorder (UCD), which may be characterized and/or associated with, but not limited to, hyperammonemia, impaired glutamate metabolism, impaired NO metabolism, impaired energy metabolism, impaired CoA homeostasis, deficient ATP and elevated oxidative stress, in a subject the method comprising administering to the subject at least one compound of the present disclosure that improves the herein mentioned conditions, in an amount effective to treat the disease.

In some aspects, a disease can be a disease that is characterized by and/or associated with impaired Urea cycle and is a Urea cycle disorder (UCD). Thus, the present disclosure provides a method of treating a disease characterized by and/or associated with impaired Urea cycle in a subject, comprising administering to the subject a therapeutically effective amount of at least one compound of the present disclosure. The present disclosure provides a method of preventing a disease characterized by and/or associated with impaired Urea cycle in a subject comprising administering to the subject a therapeutically effective amount of at least one compound of the present disclosure. In some aspects, a disease characterized by and/or associated with impaired Urea cycle can be a disease selected from the group comprising Carbamyl Phosphate Synthetase I Deficiency, N-Acetylglutamate Synthetase Deficiency, Ornithine Transcarbamylase Deficiency, Argininosuccinate Synthetase Deficiency (Citrullinemia Type I), Argininosuccinate Lyase Deficiency (Argininosuccinic Aciduria), Arginase Deficiency (Hyperargininemia), Hyperornithinemia-Hyperammonemia-Homocitrullinemia or HHH syndrome (Mitochondrial ornithine carrier deficiency), Citrullinemia Type 11, also known as Citrin Deficiency (Mitochondrial aspartatelglutamate carrier deficiency), Hyperdibasic Amino Aciduria or Lysinuric Protein Intolerance (Dibasic amino acid carrier deficiency).

In some aspects, a disease can be a disease that is characterized by and/or associated with impaired Glutamate, Glutamine and/or Gamma-Aminobutyric acid (GABA) metabolism. A disease that is characterized by and/or associated with impaired Glutamate, Glutamine and/or GABA metabolism may include a disease with excessive or deficient cellular levels of Glutamate and/or Glutamine and/or GABA. Thus, the present disclosure provides a method of treating a disease characterized by and/or associated with impaired Glutamate, Glutamine and/or GABA metabolism in a subject, comprising administering to the subject a therapeutically effective amount of at least one compound of the present disclosure. The present disclosure provides a method of preventing a disease characterized by and/or associated with impaired Glutamate, Glutamine and/or GABA metabolism in a subject comprising administering to the subject a therapeutically effective amount of at least one compound of the present disclosure.

In some aspects, a disease characterized by and/or associated with impaired Glutamate, Glutamine and/or GABA metabolism can be a disease selected from the group comprising Glutamate Formiminotransferase Deficiency, Prolonged abdominal sepsis, Congenital Systemic Glutamine Deficiency, ADHD, Thiamine deficiency and Beriberi, Glutamic acid decarboxylase (GAD) deficiency, Neurofibromatosis type 1 (NF1), Homocarnosinosis, Carnosinaemia, Glutathione synthetase deficiency, Gamma-glutamylcysteine synthetase deficiency, Cystic Fibrosis, Cycle cell anaemia, Myalgic Encephalomyelitis or Chronic Fatigue Syndrome, Amyotrophic Lateral Sclerosis (ALS), Schizophrenia, HIV Infection, Chronic inflammation, Rheumatoid arthritis In some aspects, a disease can be a disease that is characterized by a deficiency of at least one metabolic precursor, vitamin and/or mineral, including, but not limited to, vitamin B6 (pyridoxal 5'-phosphate), vitamin B12 (cobalamin), vitamin B3 (niacin), cysteamine, NAD(H), inorganic pyrophosphate and/or iron. Thus, the present disclosure provides a method of treating a disease characterized by a deficiency of at least one metabolic precursor, vitamin and/or mineral in a subject, comprising administering to the subject a therapeutically effective amount of at least one compound of the present disclosure. The present disclosure provides a method of preventing a disease characterized by a deficiency of at least one metabolic precursor, vitamin and/or mineral, including, but not limited to, B6 (pyridoxal 5'-phosphate), vitamin B12 (cobalamin), cysteamine, inorganic pyrophosphate and/or iron in a subject comprising administering to the subject a therapeutically effective amount of at least one compound of the present disclosure. In some aspects, a disease characterized by a deficiency of at least one metabolic precursor, vitamin and/or mineral, including, but not limited to, vitamin B6 (pyridoxal 5'-phosphate), vitamin B12 (cobalamin), cysteamine, inorganic pyrophosphate and/or iron can be a disease selected from the group comprising Pyridox(am)ine phosphate oxidase (PNPO) deficiency, Pyridoxal-responsive epilepsy, Secondary pyridoxal-5'-phosphate (PLP) deficiencies, Congenital pernicious anaemia, Megaloblastic anaemia 1 (Imerslund-Grasbeck syndrome), Congenital transcobalamin deficiency, hyperhomocysteinemia, microcytic anaemia, Coeliac disease, Porphyria, Pellagra, Idiopathic infantile arterial calcification, pseudoxanthoma elasticum, Hutchinson-Gilford, Progeria Syndrome, Chronic kidney disease or End-stage renal disease, Crohn disease, Leigh syndrome, Leukemia, Diabetes mellitus, Nonalcoholic fatty liver (NAFLD).

Methods of Use—Inflammation

Growing evidence suggests a close link between inflammation and many chronic health conditions including diabetes, metabolic syndrome, cardiovascular disease, cancer, rheumatoid arthritis and other autoimmune diseases, inflammatory bowel disease, fibrosis, asthma, and chronic obstructive lung disease, cancer, neurodegenerative diseases and others (Zhong and Shi, 2019 Front Immunol 10, Ruparelia et al. 2016 Nat Rev Cardiol 14; Duan et al., 2019 J Immunol Res, Chen et al. 2016 Mol Med Rep 13; Gilhus and Deuschl, 2019 Nat Rev Neurol 15; Stephenson et al., 2018 Immunology 154; Li et al., 2017 Front Pharmacol 8; Greten and Grievnikov, 2019 Immunity 5).

Pro-inflammatory response is generally associated with major metabolic reprogramming of cells, ROS production, M1 macrophage activation, activation of pro-inflammatory transcription factors (such as NF-k$\beta$) and cytokine and chemokine release and the literature strongly supports these mechanisms as potential targets for therapeutic intervention with positive results demonstrated in both preclinical as well as clinical setting (Freeman et al., 2014 J Biol Chem; Geeraerts et al., 2017 Front Immunol, Stunault et al., 2018 Mediators of Inflammation; Na et al., 2019 Nat Rev Gastroent Hepat 16; Yin et al. 2018 Front Immunol 9; Hamidzadeh et al., 2017 Ann Rev Physiol 79; Croasdell et al., 2015 PPAR Research; Villapol, 2017 Cell Mol Neurobiol 38; Honnapa et al. 2016 Int J Immunopathol Pharmacol 29; Schett and Neurath, 2018 Nature Communications 9).

Numerous studies suggested the involvement of NK cells in pathogenesis of autoimmune diseases such as juvenile rheumatoid arthritis, type I diabetes, autoimmune thyroid diseases and allergic airway inflammation—asthma. The defects of NK cells regulatory function as well as cytotoxic abilities are common in patients with autoimmune diseases with serious consequences including HLH hemophagocytic lymphocytosis (HLH) and macrophage activation syndrome (MAS). Literature suggests NK cells as a therapeutic target in drug development for treatment of these autoimmune disorders (Popko and Gorska, 2015 Cent Eur Immunol 40; Kim et al. 2018 Allergy Asthma Immunol Res 10).

M1 macrophages (classically activated macrophages) are pro-inflammatory and have a central role in host defense against infection, while M2 macrophages (alternatively activated macrophages) are associated with responses to anti-inflammatory reactions and tissue remodeling, and they represent two terminals of the full spectrum of macrophage activation. M1 macrophages are polarized by lipopolysaccharide (LPS) either alone or in association with Th1 cytokines such as IFN-$\gamma$, GM-CSF (including G-CSF and M-CSF), as well as transcription factors such as STAT1, Irf5, API and NF-κB, and produce pro-inflammatory cytokines such as interleukin-113 (IL-1β), IL-6, IL-12, IL-23, and TNF-α; M2 macrophages are polarized by Th2 cytokines such as IL-4 and IL-13 as well as transcription factors such as STATE, irf4, PPARγ, CREB and Jmjd3 histone demethylase and produce anti-inflammatory cytokines such as IL-10 and TGF-β. Transformation of different phenotypes of macrophages regulates the initiation, development, and cessation of inflammatory and immune resposnse. M1/M2 macrophage balance polarization governs the fate of an organ in inflammation or injury. When the infection or inflammation is severe enough to affect an organ, macrophages first exhibit the M1 phenotype to release TNF-α, IL-1β, IL-12, and IL-23 against the stimulus. But, if M1 phase continues, it can cause tissue damage. Therefore, M2 macrophages secrete high amounts of IL-10 and TGF-β to suppress the inflammation, contribute to tissue repair, remodeling, vasculogenesis, and retain homeostasis (Liu et al., 2014 Int J Biol Sci 10; Shapouri-Moghaddam et al., 2018 J Cel Physiol 233, Atri et al., 2018 Int J Mol Sci 19, Lawrence and Natoli, 2011 Nat rev immunol 11).

In bacterial infection when the pathogen associated molecular patterns (PAMPs) presented in bacteria are recognized by pathogen recognition receptors (such as Toll-like receptors, TLRs), macrophages are activated and produce a large amount of pro-inflammatory mediators including TNF-α, IL-1, and nitric oxide (NO), which kill the invading organisms and activate the adaptive immunity. As an example, the role of macrophage activation in clearing a bacterial infection has been demonstrated in infections with *Salmonella typhimurium, Listeria monocytogenes, Helicobacter pylori, Mycobacterium tuberculosis, Mycobacterium ulcerans* and *Mycobacterium avium* (Shaughnessy and Swanson, 2007 Front Biosci 12, Sica and Mantovani, 2012 J Clin Invest 122)

In acute viral infection M1 macrophages serve as a powerful killer of invading pathogens with the secretion of inflammatory mediators, such as TNF-α and inducible nitric oxide synthase, while M2 macrophages can suppress inflammation and promote tissue healing. Influenza virus augments the phagocytic function of human macrophages, which is a major feature of M2 phenotype, to clear the apoptotic cells and accelerate the resolution of inflammation (Hoeve et al., 2012 PLoS one 7). In severe acute respiratory syndrome (SARS)-Cov infection, M2 phenotype macrophages are critical to regulate immune response and protect host from the long term progression to fibrotic lung disease by a STAT dependent pathway (Page et al., 2012 J Virol 86). In addition, severe respiratory syncytial virus (RSV) induced bronchiolitis is closely associated with mixed M1 and M2 macrophages. IL-4-STAT6 dependent M2 macrophage polarization can attenuate inflammation and epithelial damage, and cyclooxygenase-2 inhibitor, which increases expression of lung M2 macrophages, is proposed as a treatment strategy (Shirley et al., 2010 Mucos immun 3).

Both M1 and M2 phenotype macrophages are involved in parasite infestation, depending on the subtype and duration of parasite infestation models (Jensen et al., 2011 Chem host & microbe 9; Mylonas et al., 2009 J immunol 2009; Lefevre et al., 2013 Immunity 38).

Atherosclerosis is a common type of degenerative disease of the vessel wall characterized by the accumulation of apolipoprotein B-lipoproteins in the inner lining of large and medium sized arteries. Monocytes and macrophages play essential roles in the development of atherosclerosis (Swirski and Nahrendorf, 2013 Science 339). As the apolipoprotein B-lipoproteins accumulate, the endothelial cells become dysfunction and secrete a sum of chemokines, which interact with receptors on the circulating monocytes and promote them into the vessel wall. Those monocytes then transform into macrophages and take up cholesterol to give rise to a structure called atherosclerotic plaque (Fuster et al., 2010 Cardiovasc res 86). As diseases develop, atherosclerotic plaque can grow larger, even become vulnerable and rupture, potentially resulting in a heart attack, stroke and even sudden cardiac death (Moore and Tabas, 2011 Cell 145). Prevention of monocyte recruitment by blocking chemokines or their receptors could inhibit or slow down atherogenesis in mouse model of atherosclerosis, providing strong support for the essential role of macrophages in the development of atherosclerosis (Mestas and Ley, 2008 Trends in card med 18). In patients with unstable angina and myocardial infarction, the pro-inflammatory cytokines secreted by M1 phenotype macrophages were elevated, such as IL-6, with high levels predicating a poor outcome (Kirbis et al., 2010 Wiener klin woch 122). An in vitro study indicated that M1 phenotype macrophages could also induce smooth muscle cell proliferation and release of vasoactive molecules including NO, endothelins as well as eicosanoids, and they were important consequences for lipoprotein oxidation and cytotoxicity (Tsimikas and Miller, 2011 Curr pharmaceut design 17). TGF-β, secreted by M2 phenotype macrophages, inhibited the recruitment of inflammatory cells and was associated with a significant protection against atherosclerosis (Mallat et al., 2001 Circ res 89).

M2 phenotype macrophages play a major role in asthma, where they are responsible for tissue repairing and restoration of homeostasis in the microenvironment of lung tissue. In severe forms of asthma, especially in patients resistant to glucocorticoid therapy, macrophages are shown to become an M1 phenotype, which produces a great amount of pro-inflammatory mediators, including TNF-α, IL-113, NO, exacerbates the lung injury and accelerate the airway remodeling (Kim et al., 2007 J immunol 178). For instance, NO produced by M1 phenotype leads to oxidative DNA damage and inflammation, enhances mucus production, and amplifies the lung injury in murine model of allergen-induced airway disease (Naura et al., 2010 J immunol 185).

Similar to other chronic inflammation, cancer-related inflammation is also mediated by inflammatory mediators (chemokines, cytokines, and prostaglandins) and inflammatory cells, with tumor-associated macrophages (TAM) playing a major role in constituting a microenvironment for the initiation, growth and metastasis of cancers (Qian and Pollard, 2010 Cell 141). TAM are transformed into M2-like phenotype in the development of tumors, and NF-κB signal pathway is down-regulated (Pollard, 1009 Nat rev immunol 9).

Macrophage colony-stimulating factor M-CSF is produced by a wide variety of cell types, including endothelial cells, fibroblasts, and monocyte/macrophages, where it functions as a survival factor and a chemotactic agent for monocytes. Decrease and/or inhibition of M-CSF has been shown as a promising therapeutic target in several studies for multiple clinical indications including atherosclerosis (Green and Harrington, 2000 J Hematoter Stem Cell Res 9), inflammation and rheumatoid arthritis (Saleh et al., 2018 J Immunol), ovarian cancer and cutaneous lupus (Achkova and Maher, 2016 Biochem Soc Trans 15; Toy et al., 2009 Neoplasia 11; Patel and Player, 2009 Curr Top Med Chem 9).

Granulocyte-colony stimulating factor (G-CSF or GCSF) is a glycoprotein produced by endothelium, macrophages, and a number of other immune cells that stimulates the bone marrow to produce granulocytes and stem cells and release them into the bloodstream. G-CSF also stimulates the survival, proliferation, differentiation, and function of neutrophil precursors and mature neutrophils using Janus kinase (JAK)/signal transducer and activator of transcription (STAT) and Ras/mitogen-activated protein kinase (MAPK) and phosphatidylinositol 3-kinase (PI3K)/protein kinase B (Akt) signal transduction pathway. G-CSF also acts in the CNS to induce neurogenesis, to increase the neuroplasticity and to counteract apoptosis and is significantly reduced in plasma of Alzheimer's disease patients (Laske et al. 2009 J Alzheimer Dis 17). These properties are currently under investigations for the development of treatments of neurological diseases such as cerebral ischemia and Parkinson's disease, amyotrophic lateral sclerosis (ALS) and Alzheimer's disease (Deotare et al., 2015 Bone Marrow Transpl 50; Tsai et al., 2017 Cell Transpl 13). In oncology and hematology, a recombinant form of G-CSF is used with certain cancer patients to accelerate recovery and reduce mortality from neutropenia after chemotherapy, allowing higher-intensity treatment regimens (Lyman et al., 2013 Annals Oncol 24).

IFN-γ in particular is a key player in driving cellular immunity and protective functions to heighten immune responses in infections and cancers by enhancing antigen processing and presentation, increasing leukocyte trafficking, inducing an anti-viral state, boosting the anti microbial functions and affecting cellular proliferation and apoptosis. The importance of IFN-γ is further reinforced by the fact that mice possessing disruptions in the IFN-γ gene or its receptor develop extreme susceptibility to infectious diseases and rapidly succumb to them (Kak et al., 2018 Biomolec Conc 9).

IFN-γ administration can successfully impede Ebola virus infectivity and it effectively reduced viral viability and serum titers (Rhein et al., 2015 PLoS Pathogens 11). Similarly, adjunctive immune therapy including IFN-γ as one of the pivotal components also drastically improved the outcome of invasive fungal infections or sepsis (Delsing et al., 2014 BMC Inf Diseases 14). In animal infection models, administration of IFN-γ has led to better survival rate and immune responses. For example, enhanced resistance against invasive aspergillosis and disseminated *Candida albicans* infections is elicited in IFN-γ treated mice (Segal and Walth, 2006 Am J Resp Crit Care Med 173). Similarly, IFN-γ therapy bolstered pulmonary immune responses in corticosteroid-treated rats in experimental legionellosis. Improved survival and decreased pathogenic burden in lungs was observed upon IFN-γ administration in mice infected with *Cryptococcus neoformans*. IFN-γ can prove as an effective therapeutic candidate against as many as 22 infectious agents including bacteria, fungi, protozoa and helminths. Clinically IFN-γ is an FDA approved drug for the treatment of CGD, an immune-deficiency characterized by a series of recurrent infections by pyogenic bacteria. Recombinant IFN-γ elicits potent anti-proliferative, anti-angiogenic and anti-tumorigenic effects. It is known to trigger apoptotic death in tumor cells and leads to a positive disease outcome. The earliest usage of IFN-γ as a therapeutic agent was for acute leukemia and since then it has been used on and off experimentally to induce anti-proliferative tendencies in multiple cell lines. IFN-γ was successful in limiting carcinogenesis in numerous cancerous cell lines. Growth modulatory properties of IFN-γ have also made it an interesting therapeutic option for hematologic conditions and human stem cell (HSC) transplantation. Recent findings have suggested that IFN-γ can negatively regulate the expansion of HSC pool and lead to progressive loss of such cells in bone marrows and peripheral HSCs in the context of infections (Skerrett and Martin, 1994 Am J Respir Crit Care Med 149; Casadevall, 2016 Cellular microbiol 18; Seger, 2008 Brit J Haematol 140; Badaro et al. 1990 N E J Med 322; Condos et al., 1997 The Lancet 349; Milanes-Virelles et al., 2008 BMC infectious diseases 8; Raghu et al. 2004 N E J Med 350; Windbichler et al. 2000 Brit J Cancer 82; Bosserhoff et al., 2004 J Invest Dermatol 122).

Natural Killer (NK) cells are involved in the host immune response against infections due to viral, bacterial and fungal pathogens, all of which are a significant cause of morbidity and mortality in immunocompromised patients. Since the recovery of the immune system has a major impact on the outcome of an infectious complication, there is major interest in strengthening the host immune response. NK cells are already being investigated in the clinical setting as immunotherapy approach in cancer and similar therapeutic potential is suggested by the literature in the fight against infectious diseases due to the antimicrobial and antiviral properties of NK cells and promising results have been suggested in in vivo murine model studies (Cong and Wei, 2019; Front Immunol 10; Hall et al., 2013 Infect Immun 81; Schmidt et al., 2018 Oncotarget 9; Waggoner et al., 2016 Curr Opin Virol 16; Shegarfi et al., 2009 Scand J Immunol 70; Horowitz et al., 2012 Front Immunol 2; Bancroft, 1993 Curr Opin Immunol 1993 5). NK-mediated protection against respiratory infection by bacteria, viruses such as respiratory syncytial viruses (RSV), and influenza has been elaborated in murine models (Nuriev and Johansson, 2019 F1000 Res 8; Altamirano-Lagos et al., 2019 Front Microbiol 10). NK cells have also been implicated in multiple sclerosis where low levels of NK cells has been demonstrated both in murine MS model (Xu et al., J Neruoimmunol 163) as well as in patients (Benczur et al., 19080 Clin Exp Immunol 39). Immunomodulatory role of NK cells has also been implicated in cancer, asthma, type 1 diabetes, rheumatoid arthritis, systemic lupus erythematosus (Mandal and Viswanathan, 2015 Hematol Oncol Stem Cell Ther 8; Haworth et al., 2011 Immunol 186).

Dendritic cells (DCs) have a critical role in mediating innate immune response and inducing adaptive immune response and are the most potent antigen-presenting cells (APCs), capable of activating both naive and memory immune responses. DCs have a superior capacity for acquiring and processing antigens for presentation to T cells and express high levels of costimulatory or coinhibitory molecules that determine immune activation or anergy (Steinman, 2012 Annu Rev Immunol 30; Sabado et al., 2017 Cell Res 27; Lipscomb et al., 2002 Physiol rev 82). Upon antigen acquisition DCs undergo activation and maturation respectively during which time they undergo an extensive metabolic reprogramming, including a switch towards glycolysis and away from oxidative phosphorilation, a process highly connected to succinate-induced HIF-1α activation (Kelly and O'Neill, 2015 Cell Res 25; O'Neill and Pearce, 2015 J Exp Med 213). Immunotherapeutic DCs-based strategies have successfully been demonstrated in cancer (Constantino et al., 2016 Transl Res 168)

Myeloid derived Suppressor cells (MDSC) possess strong immunosuppressive activities rather than immunostimulatory properties and are known to expand in pathological situations such as chronic infections and cancer, as a result of an altered haematopoiesis. MDSC inhibition is explored as a potential target for treatment of various cancers (Toor and Elkord, 2018 96), however their activation is also being explored for their immunosuppression potential in allogeneic hematopoietic cell transplantation and Graft-versus-host disease (GVHD) (Koehn and Blazar, 20171 Leukoc Biol 102).

The regulatory T cells (Tregs, also known as suppressor T cells), are a subpopulation of T cells that modulate the immune system, maintain tolerance to self-antigens, and prevent autoimmune disease. Tregs are immunosuppressive (downregulate induction and proliferation of effector T cells). Mouse models have suggested that modulation of Tregs can treat autoimmune disease, such as IBD, rheumatoid arthritis, psoriasis, systemic lupus erythematosus, GVHD, solid organ transplant, Type 1 diabetes, and cancer and can facilitate organ transplantation and wound healing (Miyara et al., 2011 Autoimmun Rev 10; Nosbaum et al., 2016 J Immunol 196; Curiel, 2008 Curr Op Imunol 20).

A mast cell (also known as a mastocyte or a labrocyte) is a migrant granulocyte derived from the myeloid stem cell that is a part of the immune and neuroimmune systems. Mast cells have a major role in allergy and anaphylaxis, however they are also involved in wound healing, angiogenesis, immune tolerance, defense against pathogens, and blood-brain barrier function.

Mast cell activation disorders are a spectrum of immune disorders that are unrelated to pathogenic infection and involve similar symptoms that arise from secreted mast cell intermediates (Frieri, 2015 Clin Rev Allergy Immunol 54). Allergies are mediated through IgE signaling which triggers mast cell degranulation. Many forms of cutaneous and mucosal allergy are mediated in large part by mast cells; they play a central role in asthma, eczema, itch (from various causes), and allergic rhinitis and allergic conjunctivitis (Prussin and Metcalfe, 2003 J Allergy Clin Immunol 111). In anaphylaxis, the body-wide degranulation of mast cells leads to vasodilation and, if severe, symptoms of life-threatening shock. Mast cells have also been implicated in the pathology associated with autoimmune, inflammatory disorders of the joints, including rheumatoid arthritis and bullous pemphigoid.

Mastocytosis is a rare clonal mast cell disorder involving the presence of too many mast cells (mastocytes) and CD34+ mast cell precursors. Mutations in c-Kit have been associated with mastocytosis as well as with other mast cell proliferative diseases and neoplasms, such as mastocytomas (or mast cell tumors), mast cell sarcoma and mast cell leukemia (Horny et al., 2007 Pathobiology 74; Cruse et al., 2014 Immunol Allergy Clin North Am 32, Ha et al., 2018 Arch Craniofac Surg 19). Mast cell activation syndrome (MCAS) is an idiopathic immune disorder that involves recurrent and excessive mast cell degranulation and mast cell metabolic reprogramming and which produces symptoms that are similar to other mast cell activation disorders (Phong et al., 2017 J Immunol 198).

There is an increasing evidence that platelets have a central role in the host inflammation and immune responses (Thomas and Storey, 2015 Thrombosis and Haemostasis 114; Herter et al., 2014 J Thrombosis and Haemostasis 12). Activated platelets undergo an extensive metabolic reprogramming; pyruvate dehydrogenase is phosphorilated, diverting the metabolic flux away from the TCA cycle and switching the energy metabolism to aerobic glycolysis and Glut3 transporter is overexpressed with the activation through AMPK pathway (Kulkarni et al., 2019 Haematologica 104; Aibibula et al., 2018 J thromb haemost 16). Activated platelets present CD40L ligand which stimulates the production of Tissue factor (TF) expression and thrombin generation (Lindmark et al., 2000 Artherioscler Thromb Vasc Biol; Sanguini et al., 2005 J Am Col Cardiol 45), both linked to causing disseminated intravascular coagulation (DIC) which is associated with a number of pathologies including Sepsis, Trauma, Serious tissue injury, Head injury, Fat embolism, Cancer, Myeloproliferative diseases, Solid tumors (e.g., pancreatic carcinoma, prostatic, carcinoma), Obstetrical complications, Amniotic-fluid embolism, Abruptio placentae, Vascular disorders, Giant hemangioma (Kasabach-Merritt syndrome), Aortic aneurysm, Reactions to toxins (e.g., snake venom, drugs, amphetamines), Immunologic disorders, Severe allergic reaction, Hemolytic transfusion reaction, Acute respiratory distress syndrome (ARDS) (Gando et al., 2016 Nat Rev Dis Prim 2). TF inhibition has been proposed as a therapeutic strategy for different indication and multiple preclinical studies showed promising results, including several studies using PPARa activators/agonists, as PPARa was shown to reduce TF activity both in patients as well as in vitro in human monocytes/macrophages (Levi et al., 1994 J Clin Invest 93; Taylor et al., 1991 Circ Shock 33; Pixley et al., 1993 J Clin Invest; Levi et al., 1999 NEJM 341; Marx et al., 2001 Circulation 103; Bernadette et al., 2001 Circulation 103).

Platelet-derived growth factor (PDGF) is one among numerous growth factors that regulate cell growth and division. In particular, PDGF plays a significant role in blood vessel formation, the growth of blood vessels from already-existing blood vessel tissue, mitogenesis, i.e. proliferation, of mesenchymal cells such as fibroblasts, osteoblasts, tenocytes, vascular smooth muscle cells and mesenchymal stem cells as well as chemotaxis, the directed migration, of mesenchymal cells. The receptor for PDGF, PDGFR is a receptor tyrosine kinase (RTK) cell surface receptor. Upon activation by PDGF, these receptors activate signal transduction, for example, through the PI3K pathway or through reactive oxygen species (ROS)-mediated activation of the STAT3 pathway. PDGF overstimulation has been linked to smooth muscle cell (SMC) proliferation, atherosclerosis and cardiovascular disease, restenosis, pulmonary hypertension, and retinal diseases, as well as in fibrotic diseases, including pulmonary fibrosis, liver cirrhosis, scleroderma, glomerulosclerosis, and cardiac fibrosis (Raines, 2004 Cytokine Growth Factor Rev 15, Andrae et al., 2008 Genes & Dev 22), mesangioproliferative glomerulonephritis and interstitial fibrosis and has also been suggested in other renal diseases such as acute kidney injury, vascular injury and hypertendive as well as diabetic nephropathy (Boor, et al., 2014 Nephrology Dial Transpl 29).

Bone morphogenetic protein-7 is a protein of the TGF-β super family and increasingly regarded as a counteracting molecule against TGF-β. A large variety of evidence shows an anti-fibrotic role of BMP-7 in chronic kidney disease, and this effect is largely mediated via counterbalancing the profibrotic effect of TGF-β. Besides, BMP-7 reduced ECM formation by inactivating matrix-producing cells and promoting mesenchymal-to-epithelial transition (MET) and increased ECM degradation (Li et al., 2015 Front Physiol 6).

Other elements of immune response include Eotaxin-3, a chemokine that mediates recruitment of eosinophils, basophils into sites of tissue inflammation (Ogilvie et al., 2003 Blood 102), VCAM-1, a cell adhesion molecule that mediates adhesion of monocyte and T cells to endothelial cells (Deem and Cook-Mills, 2004 Blood 104), P-selectin, a cell adhesion molecule that helps platelet-endothelial cell and PBMC and is expressed on the surface of both stimulated endothelial cells and activated platelets, helping cancer cells invade into the bloodstream for metastasis and providing local multiple growth factors, respectively (Chen and Geng, 2006 Arch Immunol Ther Exp 54). Furthermore, vascular endothelial growth factor (VEGF), a signal protein produced by cells that stimulates the formation of blood vessels, has been implicated in inflammation through VCAM-1 and P-selectin recruitment of inflammatory T-cells (Stannard et al., 2006 Arter Thromb Vasc Biol 27) and its decrease has been implicated in atopic dermatitis and allergic inflammation (Samochocki et al., 2016 Int J Dermatol 55). VEGF is also induced by HIF1-a (Semenza et al., 2000 Genes & Dev 14).

B cells, also known as B lymphocytes, are part of the adaptive immune system with their main function secreting antibodies, presenting antigens (they are also classified as professional antigen-presenting cells (APCs)) and secreting various cytokines. Autoimmune disease can result from abnormal B cell recognition of self-antigens followed by the production of autoantibodies. Such autoimmune diseases include scleroderma, multiple sclerosis, systemic lupus erythematosus, type 1 diabetes, and rheumatoid arthritis and in multiple studies B-cell targeted therapy showed promising results (Koichi et al., 2008 Immunol Rev 223; Edwards et al., 2004 N Engl J Med 350; Donahue and Fruman, 2003 J Immunol 170; Morawski and Bolland 2017, Trends Immunol 38). Malignant transformation of B cells and their precursors can cause a host of cancers, including chronic lymphocytic leukemia (CLL), acute lymphoblastic leukemia (ALL), hairy cell leukemia, follicular lymphoma, non-Hodgkin's lymphoma, Hodgkin's lymphoma, and plasma cell malignancies such as multiple myeloma, Waldenstrom's macroglobulinemia, and certain forms of amyloidosis (Shaffer et al., 2012 Ann Revc Immunol 30; Castillo, 2016 Primary care 43).

B-cell activating factor (BAFF) is a cytokine that belongs to the tumor necrosis factor (TNF) ligand family and is expressed in B cell lineage cells acting as a potent B cell activator. It has been also shown to play an important role in the proliferation and differentiation of B cells. Inadequate levels of BAFF leads to immunodeficiency, however excessive levels of BAFF causes abnormally high antibody production and results in systemic lupus erythematosus, rheumatoid arthritis, and many other autoimmune diseases (Steri et al., 2017 NEJM 376) and it has been therapeutic target in several clinical trials for treatment of Systemic lupus erythematosus and other autoimmune diseases (Navarra et al., 2011 Lancet 377). BAFF may also be a new mediator of food-related inflammation. In patients with celiac disease, serum BAFF levels are reduced after a gluten-free diet (Fabris et al., 2007 Sc J Gastroenterol 42). BAFF is also a specific inducer of insulin resistance and can be a strong link between inflammation and diabetes or obesity (Kim et al., 2009 BMJ 345; Hamada et al., 2011 Obesity 19).

Furthermore, the stromal cell-derived factor 1 (SDF1) is a chemokine protein that is ubiquitously expressed in many tissues and cell types. SDF1 signaling has been associated with multiple diseases including several cancers, multiple sclerosis, Alzheimer's disease and coronary artery disease and has been considered as a therapeutic target including in preclinical as well as clinical testing for many of those (Guo et al., 2016 Oncotarget 7; Sorrentino et al., 2016 Oncotarget 7; Mega et al., 2015 Lancet 385; Pozzobon et al., 2016 Immunology Lett 177).

Furthermore, CXCL1 (also known as GRO or GROα) is expressed by macrophages, neutrophils and epithelial cells, and has neutrophil chemoattractant activity. CXCL1 plays a role in spinal cord development by inhibiting the migration of oligodendrocyte precursors and is involved in the processes of angiogenesis, arteriogenesis, inflammation, wound healing, and tumorigenesis. A study in mice showed evidence that CXCL1 decreased the severity of multiple sclerosis and may offer a neuro-protective function (Omani et al., 2009 Am J Pathol 174). Overexpression of CXCL1 is implicated in melanoma pathogenesis (Richmond et al., 1988 J Cell Biochem 36).

Furthermore, CXCL10 (also known as Interferon gamma-induced protein 10 or IP-10) is secreted by several cell types including monocytes, endothelial cells and fibroblasts in response to IFN-γ. CXCL10 has been attributed to several roles, such as chemoattraction for monocytes/macrophages, T cells, NK cells, and dendritic cells, promotion of T cell adhesion to endothelial cells, antitumor activity, and inhibition of bone marrow colony formation and angiogenesis (Dufour et al., 2002 J Immunol 268). CXCL9, CXCL10 and CXCL11 have proven to be valid biomarkers for the development of heart failure and left ventricular dysfunction, suggesting an underlining pathophysiological relation between levels of these chemokines and the development of adverse cardiac remodeling and cardiovascular disease including atherosclerosis, aneurysm formation and myocardial infarction (van de Borne et al., 2014 BioMed Res Int 2014; Altara et al., 2015 PLoS One 19).

Furthermore, Interleukin-1 (IL-1), a potent inflammatory cytokine that plays a central role in the innate immune response mediating the acute phase of inflammation by inducing local and systemic responses, such as pain sensitivity, fever, vasodilation, and hypotension and promoting the expression of adhesion molecules on endothelial cells, which allows the infiltration of inflammatory and immunocompetent cells into the tissues, has been implicated in many inflammatory diseases, including atopic dermatitis (Abramovits et al., 2013 Dermatol Clin 31), many hereditary autoinflammatory diseases, nonhereditary inflammatory diseases, Schnizler syndrome, Sjögrens syndrome and rheumatoid arthritis (Gabay et al., 2010 Net Rev Rheym 6; Norheim et al., 2012 PLoS One 7) and IL-1 inhibitors have been used with promising results in many monogenic and multi-factorial autoinflammatory and metabolic diseases, including in Mevalonate kinase deficiency (MKD) (Federici et al., 2013 Front Immunol 4; Frenkel et al., 2002 Arhtritis Rheum 4).

Furthermore, Interleukin-8 (IL-8), a cytokine produced by mononuclear cells involved in polymorphonuclear neutrophil leukocyte (PMN) recruitment and activation, had been implicated in IBD and kidney inflammatory disease (Subramanian et al., 2008 Inflamm Bowel Dis 14), hypercholesterolemia and atherothrombotic disease (Porreca et al., 1999 Atheroclerosis 146).

Furthermore, Prostaglandin E2 (PGE2) is a principal lipid mediator of inflammation and has been a therapeutic target in various inflammatory diseases including rheumatoid arthritis and osteoarthritis (Park et al., 2006 Clin Immunol 119) as well as inflammaton-associated pain (Kawabata, 2011 Biol Pharm Bull 34).

Tumor necrosis factor (TNF, also known as TNFα, cachexin, or cachectin) an inflammatory cytokine produced mainly by macrophages/monocytes, but also by many other cell types such as CD4+ lymphocytes, NK cells, neutrophils, mast cells, eosinophils, and neurons, during acute inflammation and is responsible for a diverse range of signalling events within cells, leading to necrosis or apoptosis, cachexia, inflammation and to inhibit tumorigenesis and viral replication and respond to sepsis via IL1- & IL6-producing cells. Dysregulation of TNF production has been implicated in a variety of human diseases including many autoimmune and inflammation diseases, Alzheimer's disease, cancer, major depression, psoriasis and inflammatory bowel disease (IBD) (Wong et al., 2008 Clin Immunol 126; Swardfager et al., 2010 Biol Psychiatry 68; Locksley et al., 2001 Cell 104; Dowlati et at, 2010 Biol Psychiatry 67; Victor and Gottlieb, 2002 J Drugs Dermatol 1; Brynskov et al., 2001 Gut 51). Additionally, Interleukin-17 (IL-17), a pro-inflammatory cytokine produced by T helper 17 cells (Th17), often acts in concert with TNF and IL-1 and activation of IL-17 signalling is often observed in the pathogenesis of various autoimmune disorders. Overactivation of Th17 cells, particularly auto-specific Th17 cells, is also associated with autoimmune diseases such as multiple sclerosis, rheumatoid arthritis, and psoriasis (Zambrano-Zaragoza et al., 2014 Int J Inflam) and may contribute to the development of late phase asthmatic response due to its increases in gene expression relative to Treg cells (Won et al., 2011 PLoS One 6). Inhibition of TNF and IL-17 has been shown to have promising effects in diseases such as psoriasis, postular psoriasis, rheumatoid arthritis, IBD and systemic lupus erythematosus (Bartlett and Million, 2015 Nat Rev Drug Disc 14; Baeten and Kuchroo, 2013 Nat Med 19; Fabre et al., 2016 Int J Mol Sci 17; Cecher and Pantelyushin 2012 Nat Med 18).

Furthermore, Interleukin-2 (IL-2), a cytokine responsible for the immune system response to microbial infection, is produced by activated CD4+ T cells and CD8+ T cells, and mediates its effects by binding to IL-2 receptors, which are expressed by lymphocytes. IL-2 has been used in clinical trials for the treatment of cancer (Jiang et al., 2016 Oncoimmunol 5), chronic viral infections (Molloy et al., 2009 J Immunol 182; Giedlin and Zimmerman, 1993 Cuff Opin Biotech 4) and a moderate increase in IL-2 has shown early success in modulating the immune system in disease like type 1 diabetes, vasculitis and ischaemic heart disease (Hartemann et al., 2013 The Lancet Diab Endocrinol 1; Zhao et al., 2018 BMJ Open 8; Naran et al., 2018 Front Microbiol 9).

Interleukin 6 (IL-6) is an interleukin that acts as both a pro-inflammatory cytokine and an anti-inflammatory myokine. IL-6's role as an anti-inflammatory myokine is mediated through its inhibitory effects on TNF-alpha and IL-1, and activation of IL-1ra and IL-10. L-6 stimulates the inflammatory and auto-immune processes in many diseases such as diabetes, atherosclerosis, depression, Alzheimer's Disease, systemic lupus erythematosus, multiple myeloma, prostate cancer, Behcet's disease, and rheumatoid arthritis (Fisher et al., 2014 Semin Immumol 26; Kristiansen and Madrup-Poulsen, 2015 Diabetes 54; Dowlati et al., Biol Psych 27; Swardfager et al., 2010 Biol Psych 68; Tackey et al., 2004 Lupus 13; Gado et al., 2000 Cell Biol Int 24; Smith et at, 2001 Cytok Growth Fact Rev 12; Hirohata et al., 2012 Inter Med 51; Nishimoto, 2006 Curr Op Rheum 18). Hence, there is an interest in developing anti-IL-6 agents as therapy against many of these diseases (Barton, 2005 Exp Opin Therap Tar 9; Smolen and Maini, 2006 Arthritis Res Ther 8). Obesity is a known risk factor in the development of severe asthma. Recent data suggests that the inflammation associated with obesity, potentially mediated by the cytokine IL6, plays a role in causing poor lung function and increased risk for developing asthma exacerbations (Peters et al., 2016 The Lancet Resp Med 4).

Biologically Multiplexed Activity Profiling (BioMAP) provides rapid characterization of drug function, including mechanism of action, secondary or off-target activities, and insights into clinical phenomena, using standardized and validated multiplex human primary cell-based assays and a broad panel of translational biomarkers relevant to vascular inflammation and immune activation (Kunkel et al., 2004 FASEB J 18; Raghavendra and Pullaiah in Advances in Cell and Molecular Diagnostics, 2018 298p ch1). In chronically inflamed tissues, endothelial cells are exposed to multiple proinflammatory cytokines, including IL-10, TNF-α, and IFN-γ and protein readouts are selected for their potential or known relevance to vascular inflammation, including VCAM-1, ICAM-1, and E-selectin (vascular adhesion molecules for leukocytes); MHC class II (antigen presentation); MIG/CXCL9, MCP-1/CCL2, and IL-8/CXCL8 (chemokines that mediate selective leukocyte recruitment from the blood); and CD31 (leukocyte transmigration). Multicellular systems are used comprising peripheral blood mononuclear cells (PBMC; a mixture of CD4+ and CD8+ T cells, monocytes, NK cells, and other mononuclear leukocytes) and EC, either stimulating the T cell receptor complex with superantigen (the "SAg system") or stimulating toll receptor signaling with lipopolysaccharide (the "LPS system") and readout parameters include CD3 (a T cell marker); CD14 (a monocyte marker); CD38, and CD69 (early activation markers); CD40 (a TNFR family member important for lymphocyte costimulation); E-selectin and VCAM-1 (endothelial adhesion molecules); tissue factor (TF; also known as CD142, an initiator of coagulation); IL-1α, IL-17A, IL-17F, IL-2, IL-6, M-CSF, IL-8, MCP-1, and MIG (major cytokines and chemokines) (Kunkel et al., 2004 FASEB J 18). Multiple drug discovery and development programs have used the BioMAP platform to demonstrate efficacy and activity of a diverse functional drug classes, including glucocorticoids; immunosuppressants; TNF-α antagonists; and inhibitors of HMG-CoA reductase, calcineurin, IMPDH, PDE4, PI-3 kinase, hsp90, and p38 MAPK, among others (Berg et al., 2006 J Pharm Tox Meth 53, O'Mahony et al., 2018 J Transl Med 16; Haselmayer et al., 2019 J Immunol 202; Shah et al., 2017 Cell Chem Biol 24; dos Santos et al., 2018 Clinics 73; Singer et al., 2019 PLoS One).

Decreasing MCP-1, for example, was shown great promise for treatment of interstitial lung disease and airway inflammation and allergic asthma (Iyonaga et al., 1994 Hum Pathol 25; Inoshima et al., 2004 Am J Physiol Lung Cell Mol Physiol 286; Lee et al., 2015 Am J Respir Cell Mol Biol 52). As chemoattractant, MCP-1 recruits T-cell and monocytes at site of inflammation and its decrease was shown beneficial in skin fibrosis (scleroderma) and psoriasis, assisted also by decrease in VCAM-1 (which mediates adhesion of monocytes and T-cell, inducible by TGB), collagen-1 and collagen-3 (which contribute to fibrosis), M-CSF (which helps macrophage differentiation and in response to Th2 milieu induced by TGF-beta responds to M2 polarization to enhance fibrosis), TIMP-1, TIMP-2, IL-8 and IL-1α(Ferreira et al., 2006 J Invest Dermatol 126; Needleman, 1992 Curr Opin Rheumatol 4; Castro and Jimenez 2010 Biomark Med 4; Pendregrass et al., 2010 PLoS One 5, Glazewska et al., 2016 Ther Clin Risk Manag 12; Lembo et al., 2014 J Dermatolog Treat 25). In animal studies, a murine monocyte chemoattractant protein 5 (MCP-5) was described as structural and functional homologue of human MCP-1 (Sarafi et al., 1997 J Exp Med 185).

Furthermore, decreasing IL-1α was shown to be beneficial in airway epithelium and lung fibroblast in Chronic obstructive pulmonary disease (COPD) (Osei et al., 2016 Eur Resp J 48); decreasing MMP-1 was shown to be beneficial in Idiopathic pulmonary fibrosis (IPF), decreased invasiveness of human chondrosarcoma (Rosas et al., 2008 PLoS Med 5; Craig et al., 2015 Am J Respir Cell Mol Biol 53; Jiang et al., 2003 J Orthop Res 21) and decreasing inflammatory markers CD40, CD69 and IL-8 suggests beneficial effect in infection, cardiac, Lupus, lupus nephritis & overall chronic inflammation (Su and Konecny, 2018 J Heart Res 1; Lee et al., 2019 Artherioscl Thromb Vasc Biol 39; Wang et al., 2017 Sci Rep 7).

Autophagy is a highly conserved lysosomal degradation process that degrades certain intracellular contents in both physiological and pathological conditions. This process is controlled by highly conserved autophagy-related proteins (ATGs), p62 (sequestosome) and LC3.

Autophagy-related proteins (ATG) are key players in this pathway, among which ATG5 is indispensable in both canonical and non-canonical autophagy. Recent studies demonstrate that ATG5 modulates the immune system and crosstalks with apoptosis and has been referred to in the literature as a "guardian of immune integrity" (Ye et al., 2018 Front Immunol 9). ATG5 also regulates autophagic activity to alter the polarization of macrophages, subsequently modifying the extent of inflammation. ATG5 knockout hepatic macrophages, for example, hyperpolarized to the M1 phenotype, and therefore secreted more cytokines (IL-6 and TNF) to increase the inflammatory response, demonstrating that ATG5-dependent autophagy is responsible for regulating macrophage polarization (Liu et al., 2015 Autophagy 11).

ATG5 knockout mice presented with a heavier $M.$ $tuberculosis$ burden, more severe inflammation, and higher levels of IL-1 (Castillo et al., 2012 PNAS 109). Mouse embryonic fibroblasts infected with Group A $Streptococcus$ (GAS) presented GAS-containing autophagosome-like vacuoles, while ATG5-deleted cells failed to produce such structures. Recently, ATG5-mediated restriction of microbial infection via LAP was confirmed, and silencing or inactivation of ATG5 inhibited LAP activity and increased the survival of pathogens, including adherent and invasive $Escherichia$ $coli,$ $Shigella$ $flexneri,$ $M.$ $tuberculosis,$ $Aspergillus$ $fumigatus,$ and HIV (Chamilos et al., 2016 Autophagy 12; Koster et al., 2017 PNAS 114; Baxt et al., 2014 PLoS One 9).

ATG5 is also responsible for the activation and the differentiation of various immune cells in innate and adaptive immunity. ATG5 recruited IFN-γ-inducible p47 GTPase IIGP1 (Irga6), which triggered IFN-γ-mediated clearance of $Toxoplasma$ $gondii$ (Zhao et al., 2008 Cell Host Microbe 4). ATG5 assists antigen presentation through autophagy, and thus is responsible for indirect lymphocyte activation by promoting the interaction between T or B cells and antigen presenting cells (APCs) (Dongre et al., 2001 J Immunol 31). ATG5 is also directly responsible for regulating lymphocytes. ATG5-deleted CD8+T lymphocytes were prone to cell death, and ATG5-deleted CD4+ and CD8+ T cells failed to undergo efficient proliferation after T-cell receptor (TCR) stimulation (Pua et al., 2007 Autophagy 3). The decreased survival of ATG5-deleted T cells was caused by the accumulation of abnormal autophagic structures and dysregulation of mitochondrial and ER homeostasis (Pua et al., 2007 J exp Med 204). Finally, ATG5 has been shown to be involved with multiple other diseases whose pathogenesis interferes with autophagy or apoptosis; for example, the large spectrum of autoinflammatory and autoimmune diseases as well as some neurological disorders, including Crohn's disease, Type 2 diabetes mellitus, Systemic lupus erythematosus, Multiple sclerosis, Experimental autoimmune encephalomyelitis (EAE), Neuromyelitis optica (NMO) and others (Ye et al., 2018 Front Immunol 9).

Microtubule-associated protein light chain 3 (LC3) is a central protein in the autophagy pathway where it functions in autophagy substrate selection and autophagosome biogenesis. LC3 is the most widely used marker of autophagosomes. The lipid modified form of cytoplasmic LC3, referred to as LC3-II, is believed to be involved in autophagosome membrane expansion and fusion events and is often used as a marker of impaired or abberant autphagic flux (Hsieh et al., 2018 Oncotarget 9; Satyavarapu et al., 2018 Cell Death & Disease 9; Satoh et al., 2014 Ophanet J Rare Dis 9).

Multifunctional protein p62 is a receptor of autophagy located throughout the cell and involved in many signal transduction pathways, including the Keap1-Nrf2 pathway. It is involved in the proteasomal degradation of ubiquitinated proteins. Altered p62 levels have been associated with several diseases including metabolic diseases, neurodegenerative diseases and cancer. In addition, p62 and the proteasome can modulate the activity of HDAC6 deacetylase, thus influencing the autophagic degradation (Liu et al., 2016 Cell Mol Biol Lett 21; Islam et al., 2018 Int J Mol Sci 19; Ma et al., 2019 ACS Chem Neurosci 10; Long et al., 2017 Trends endocrine metab 28).

Dickkopf WNT signaling pathway inhibitor 1 (DKK1) is a protein-coding gene that acts from the anterior visceral endoderm and is an antagonist of the Wnt/β-catenin signalling pathway that acts by isolating the LRP6 co-receptor so that it cannot aid in activating the WNT signaling pathway. DKK1 was also demonstrated to antagonize the Wnt/β-catenin pathway via a reduction in β-catenin and an increase in OCT4 expression. Elevated levels of DKK1 in bone marrow, plasma and peripheral blood is associated with the presence of osteolytic bone lesions in patients with multiple myeloma. Due to the role of DKK1 in inflammation induced bone loss DKK1 has been under investigation as therapeutic target including in breast cancer, Androgenetic alopecia and Alopecia areata, multiple myeloma and others (Sun et al., J Buon 2019 24; Mahmoud et al., 2019 Am J Dermatopathol 41; Feng et al., 2019 Cancer Biomark 24).

Alpha-smooth muscle actin or (α-SMA) is one of 6 different actin isoforms and is involved in the contractile apparatus of smooth muscle. Disruptions in α-SMA cause a variety of vascular diseases, such as thoracic aortic disease, coronary artery disease, stroke, pulmonary fibrosis, Moyamoya disease, and multisystemic smooth muscle dysfunction syndrome and α-SMA is often used as a marker of myofibroblast formation (Nagamoto et al., 2000 Invest Ophthalmol Vis Sci 41; Yuan et al., 2018 Anatol J Cadiol 19; Yu et al., 1993 J Korean Med Sci 8; Liu et al., 2017 PNAS 114, Xie et al., 2018 Cell Reports 22).

CTGF, also known as CCN2 or connective tissue growth factor, is a matricellular protein with important role in many biological processes, including cell adhesion, migration, proliferation, angiogenesis, skeletal development, and tissue wound repair. Aberrant CTGF expression is critically involved in fibrotic diseases and is also associated with many types of malignancies, diabetic nephropathy and retinopathy, arthritis, and cardiovascular diseases. Several clinical trials are now ongoing that investigate the therapeutic value of targeting CTGF in fibrosis, diabetic nephropathy, and pancreatic cancer. (Jun et al., 201 Nat Rev Drug Discov 10; Hall-Glenn and Lyons 2011 Cell Mol Life Sci 68; Kubota et al., 2011 J Cell Commun Signal 5; Ungvari et al., 2017 GeroScience 39).

Other factors involved in immune response and inflammation include Adipsin, an adipokine also known as complement factor D (FD), which is strongly correlated with β cell function in type 2 diabetes, obesity, metabolic syndrome and lipodystrophy (Wu et al., 2018 J Immunol 200; Lo et al., 2014 J Am Coll Cardiol 63; Lo et al., 2015 Cell 158) and has also been associated with neurodegenerative diseases such as multiple sclerosis (Natarajan et al., 2015 Multiple sclerosis Int 2015), inflammatory arthritis (Li et al., 2019 Cell Reports 27).

Furthermore, CD93 is a highly glycosylated transmembrane protein expressed on monocytes, neutrophils, endothelial cells, and stem cells. Antibodies directed at CD93 modulate phagocytosis, and CD93-deficient mice are defective in the clearance of apoptotic cells from the inflamed peritoneum (Bohlson et al., 2005 J Immunol 175) and the role of CD93 has been directly implicated in a number of diseases including allergic asthma, cerebral ischemia reperfusion, neutrophil dependent inflammation, peritonitis, systemic lupus erythematosus (SLE), rheumatoid arthritis, coronary heart disease and cancer (Greenlee-Wacker et al., 2012 Current Drug Targets 13; Park et al., 2019 J Allergy Clin Immunol 143).

Furthermore, Chemokine (C—C motif) ligand 5 (also CCL5 or RANTES) is a chemokine for T cells, eosinophils, and basophils, and plays an active role in recruiting leukocytes into inflammatory sites. With the help of particular cytokines (i.e., IL-2 and IFN-γ) that are released by T cells, CCL5 also induces the proliferation and activation of certain natural-killer (NK) cells to form CHAK (CC-Chemokine-activated killer) cells (Maghazachi et al., 1996 Eur J Immunol 26). CCL5 is of broad clinical importance in an array of human diseases including renal diseases, HIV and other chronic viral infection, cancer, atherosclerosis, asthma, transplantation, Parkinson's disease and autoimmune diseases such as arthritis, diabetes and glomerulonephritis (Krensky and Ahn, 2007 Nat Clin Pract Nephrol 3; Tang et al., 2014 Oxid Med Cell Longevity 2014; Crawford et al., 2011 PLoS Pathogens).

Troponin, or the troponin complex, is a complex of three regulatory proteins that is integral to muscle contraction in skeletal muscle and cardiac muscle, but not smooth muscle. Blood troponin levels are increased in cardiac disease and cardiac injury (ischemia or other causes) including acute myocardial infarction (AMI) and acute coronary sundrome (ACS) but also of chronic renal failure, chronic kidney disease, advanced heart failure, cerebrovascular accidents, acute pulmonary embolism, chronic obstructive pulmonary disease (COPD), acute pericarditis, actute inflammatory myocarditis, tachycardia (Tanidi and Cemri 2011 Vas Health Risk Manag 7; Apple et al., 2017 Clin Chem 63; Michos et al., 2014 Compar Effectiveness Rev 135). Troponin complex is considered as a potential therapeutic target against heart failure and other diseases (Sorsa et al., 2004 MolCell Biochem 266; Gore and de Lemos, 2016 Circulation cardiovasc intervent 9).

Cystatin C is a 13.3-kDa protein is involved in extracellular matrix remodeling and glomerular filtration rate (GFR) and is associated with both renal function, chronic kidney disease (CKD) and atherosclerotic cardiovascular disease (ASCVD) and has also been correlated with disease activity in rheumatoid arhrtitis patients (Srpegard et al., 2016 J Am Heart Assoc 5; Grubb, 2017 EJIFCC 28; Targonska-Stepniak and Majdan, 2011 Scand J Rheumatol 40).

Epidermal gorwth factor (EGF) is a mitogen for adult and fetal hepatocytes and stimulates proliferation and differentiation of epidermal and epithelial tissues. It also plays an important physiological role in the maintenance of oroesophageal and gastric tissue integrity and its expression is up-regulated during liver regeneration. Decreased EGF was observed in patients with severe chronic obstructive pulmonary disease (COPD) (Soemarwoto et al., 2019 Pneumologia 68), however its overexpression has been associated with fibrosis and has been considered a therapeutic target for chronic kidney disease, obesity and coronary artery disease and other fibrotic diseases (Kok et al., 2014 Nat Rev Nephol 10; Matsumoto et al., 2002 BBRC 292).

Mounting evidence supports a role for EGF in malignant transformation and tumor progression. EGF induces transformation to anchorage-independent growth and enhances in vitro growth of human epithelial- and mesenchymal-derived tumors. Overexpression of a secreted human EGF fusion protein in fibroblasts enhances their transformation to fibrosarcomas. Transgenic mice with liver-targeted overexpression of the secreted EGF fusion protein develop hepatocellular carcinoma (Tanabe et al., 2008 JAMA 299).

Creatinine is the breakdown product of creatine, a key participant in the generation and recycling of ATP and is frequently used as an estimate of renal function and glomerular filtration rate. Serum creatinine is an established marker for renal health and disease as well as for several types of cancer including prostate cancer and primary epithelial ovarian cancer (Weinstein et al., 2009 Cancer epidemiol biomarkers prev 10; Lafleur et al., 2018 Anticancer res 38).

Due to its importance in energy metabolism and ATP recycling, disturbance in the creatine/creatinine metabolism is indicative of metabolic dysregulation and is strongly correlated with diseases of impaired energy metabolism as well as diseases of high energy demanding organs, such as muscle and brain. Diseases often associated with abberant creatine/creatinine levels include muscle diseases such as Duchenne muscular dystrophy and Becker muscular dystrophy, facioscapulohumeral dystrophy, limb-girdle muscular dystrophy, myotonic dystrophy, spinal muscle atrophy, amyotrophic lateral sclerosis, myasthenia gravis, poliomyelitis anterior, myositis, or diabetic myopathy, and the like; gyrate atrophy; myopathies; mitochondria) diseases such as CPEO, MELAS, Kearns-Sayre syndrome; neurological diseases such as Huntington's and Parkinson's disease; cardiac disease; ischemia and many others (Wyss and Kaddurah-Daouk, 2000 Pysiological Reviews 80; Adhihetty and Beal, 2008 Neuromolecular Med 10).

Recently, anti-inflammatory role of creatinine has been demonstrated with creatinine altering anti-inflammatory responses by interfering with the activation of the NF-κB pathway. Exposing human and mouse macrophage cells to creatinine hydrochloride significantly reduced TNF-α mRNA and protein levels compared to control-treated cultures in all cell lines tested. Lipopolysaccharide (LPS), a potent inducer of inflammation, was employed with in mouse macrophage cell lines and cells treated with LPS and creatinine hydrochloride had significantly reduced TNF-α levels compared to cells treated with LPS alone. Additionally, cells exposed to creatinine had significantly lower levels of NF-κB in the nucleus compared to control-treated cells (Reisberg et al., 2018 Cytokine 110).

Immunotherapy can be used to treat infectious diseases. Infectious diseases can be, but are not limited to, (a) a bacterial infection whereby a bacteria can be, for example, *Acinetobacter* spp., *Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter* sp, *Enterobacter cloacae, Enterococcus faecalis, Enterococcus faecium, Enterococcus gallinarum, Escherichia coli, Francisella tularensis, Haemophilus influenza, Helicobacter pylori, Klepsiella* spp., *Klebsiella aerogenes, Klebsiella pneumoniae, Listeria monocytogenes, Moraxella catarrhalis, Morganella morganii, Mycobacterium tuberculosis, Mycobacterium ulcer-* ans, *Mycobacterium avium, Neisseria meningitides, Proteus mirabilis, Providencia stuartii, Pseudomonas* spp., *Pseudomonas aeruginosa, Salmonella* sp, *Serratia marcescens, Shigella* sp, *Staphylococcus aureus, Staphylococcus epidermis, Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pneumoniae, Streptococcus pyogenes, Streptococcus oralis, Streptococcus sanguis*, Group C *Streptococcus, Yersinia enterocolitica, Yersinia pestis*, and drug-resistant strains thereof; b) a viral infection whereby a virus can be, for example, Japanese encephalitis, virus, yellow fever virus, dengue virus, tickborne encephalitis virus and West Nile virus (WNV), viral hepatitis, influenza virus and HIV infection, respiratory syncytial viruses (RSV), hepatitis B, hepatitis C, infectious mononucleosis, Epstein-Barr virus (EBV), human choriomeningitis virus (HCMV), murine lymphocytic choriomeningitis virus (LCMV), human cytomegalovirus virus (HCMV), herpes simplex virus (HSV), and measles virus; c) a fungal infection whereby a fungus can be, for example, *Aspergillus fumigatus, A. flavus, A. terreus, A. niger, Candida* sp., *C. albicans, C. dubliniensis, C. Tropicalis* and *C. krusei*; d) a parasitic infection whereby a parasite can be, for example, *Leishmania* and *Plasmodium falciparum* and *schistosomes*.

The present disclosure provides a method of treating an inflammatory disease in a subject comprising administering to the subject a therapeutically effective amount of at least one compound of the present disclosure. The present disclosure provides at least one compound of the present disclosure for use in treating an inflammatory disease in a subject, wherein the compound is for administration to the subject in at least one therapeutically effective amount. The present disclosure provides a use of at least one compound of the present disclosure for the manufacture of a medicament for treating an inflammatory disease in a subject, wherein the compound is for administration to the subject in at least one therapeutically effective amount.

The present disclosure provides a method of preventing an inflammatory disease in a subject comprising administering to the subject a therapeutically effective amount of at least one compound of the present disclosure. The present disclosure provides at least one compound of the present disclosure for use in preventing an inflammatory disease in a subject, wherein the compound is for administration to the subject in at least one therapeutically effective amount. The present disclosure provides a use of at least one compound of the present disclosure for the manufacture of a medicament for preventing an inflammatory disease in a subject, wherein the compound is for administration to the subject in at least one therapeutically effective amount.

Inflammatory diseases can include, but are not limited to, arthritis, inflammatory bowel disease, hypertension, septic shock, colitis and graft-versus-host-disease (GVHD), inflammatory skin diseases, including psoriasis and dermatitis (e.g. atopic dermatitis); dermatomyositis; lichen planus; mast cell activation syndrome (MCAS); mast cell activation disorder (MCAD); mastocytosis; mastocytomas; mast cell sarcoma; mast cell leukemia; mast cell activation syndrome (MCAS); systemic scleroderma and sclerosis; responses associated with inflammatory bowel disease (such as Crohn's disease and ulcerative colitis); respiratory distress syndrome (including adult or acute respiratory distress syndrome—ARDS); dermatitis; meningitis; encephalitis; uveitis; colitis; glomerulonephritis; allergic conditions, such as eczema and asthma, and other conditions involving infiltration of T-cells and chronic inflammatory responses; atherosclerosis; leukocyte adhesion deficiency; rheumatoid arthritis; systemic lupus erythematosus (SLE); diabetes mellitus (including Type II diabetes mellitus, Type I diabetes mellitus, or insulin dependent diabetes mellitus); Type A syndrome hypoglycemia with insulin resistance; obesity; polycystic ovary syndrome (PCOS); leprechaunism; Rabson-Mendenhall syndrome; multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis; sarcoidosis; polymyositis; granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; antiglomerular basement membrane disease; antiphospholipid syndrome; Antiphospholipid antibody syndrome; allergic neuritis; Graves' disease; Lambert-Eaton myasthenic syndrome; Inclusion body myositis (IBM); pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; Hashimoto's disease; Wegener's granulomatosis; cold agglutinin disease associated with indolent lymphoma; acquired factor VIII inhibitors disease; as well as other autoimmune diseases, such as Ankylosing spondylitisis; Autoimmune Oophoritis; Coeliac disease; Gestational pemphigoid; Goodpasture's syndrome; Guillan-Barre syndrome; Opsoclonus myoclonus syndrome; Optic neuritis; Ord's thyroiditis; Polyarthritis; Primary biliary cirrhosis; Takayasu's arteritis; Warm autoimmune hemolytic anemia; Ischemia-reperfusion injury; acute kidney injury. The term "chronic inflammatory diseases" may include but are not limited to Tuberculosis; Chronic cholecystitis; Bronchiectasis; ulcerative colitis; chronic kidney disease; end-stage renal disease and kidney fibrosis; autsomal dominant polycystic kidney disease (ADPKD); Alport syndrome; silicosis and other pneumoconiosis; sepsis, trauma, serious tissue injury, head injury, fat embolism, myeloproliferative diseases, solid tumors (e.g., pancreatic carcinoma, prostatic, carcinoma), obstetrical complications, amniotic-fluid embolism, abruptio placentae, vascular disorders, giant hemangioma (kasabach-Merritt syndrome), aortic aneurysm, reactions to toxins (e.g., snake venom, drugs, amphetamines), immunologic disorders, severe allergic reaction, hemolytic transfusion reaction; Addison's disease; adult and juvenile Still's disease; age-related macular degeneration; ANCA-associated vasculitis; ankylosing spondylitis; anti-synthetase syndrome; arthritis uratica; asthma; atopic dermatitis; atopic eczema; autoimmune atrophic gastritis; autoimmune gastritis; autoimmune haemolytic anaemia; autoimmune retinopathy; autoimmune uveitis; benign lymphocytic angiitis; Blau's Syndrome; bullous skin disorders; childhood autoimmune hemolytic anemia; chondrocalcinosis; chronic action hepatitis; chronic immune polyneuropathy; chronic liver disease; chronic polyarthritis; chronic prostatitis and TNF receptor-associated periodic syndrome (TRAPS); chronic urticaria; cirrhosis; Cold Agglutinin Disease; collagen diseases; connective tissue disease; Crohn's disease; cryoglobulinemic vasculitis; cryropyrinopathy;

cutaneous and articular syndrome; degenerative rheumatism; Devic's disease; eczema; Evans syndrome; extra-articular rheumatism; familial cold-induced auto-inflammatory syndrome; familial Mediterranean fever; fibromyositis; gastritis; gingivitis; gout; gouty arthritis; Graves' ophthalmopathy; Henoch-Schonlein purpura; hepatitis; Hyper IgD syndrome; idiopathic autoimmune hemolytic anemia; idiopathic thrombocytopenia; immunoglobulin A nephropathy; inflammatory rheumatism; insulin dependent diabetes mellitus; juvenile rheumatoid arthritis; liver fibrosis; macrophage activation syndrome; membranous glomerulonephropathy; microscopic polyangiitis; Muckle-Wells syndrome; muscular rheumatism; myocarditis; myogelosis; myositis; neonatal onset multisystemic inflammatory disease; neuromyelitis optica; normocomplementemic urticarial vasculitis; panarteritis nodosa; pancreatitis; PAPA Syndrome; pemphigus vulgarus; periarthritis humeroscapularis; pericarditis; periodontitis; Prevention of development of Autoimmune Anti-Factor VIII Antibodies in Acquired Hemophilia A; primary myxedema; primary progressive multiple sclerosis; progressive systemic scleroderma; psoriasis; psoriasis arthropathica; psoriatic arthritis; pure red cell aplasia; Refractory or chronic Autoimmune Cytopenias; rheumatic disease; rosacea; Schnitzler's syndrome; scleritis; scleroderma; sympathetic ophthalmia; thrombocytopenic purpura; urticaria; vasculitis; experimental autoimmune encephalomyelitis (EAE) as well as above listed autoimmune diseases.

The present disclosure provides a method of reducing inflammation in a subject comprising administering to the subject a therapeutically effective amount of at least one compound of the present disclosure.

A reduction in inflammation can be about a 1%, or about a 2%, or about a 3%, or about a 4%, or about a 5%, or about a 6%, or about a 7%, or about an 8%, or about a 9%, or about a 10%, or about a 15%, or about a 20%, or about a 25%, or about a 30%, or about a 35%, or about a 40%, or about a 45%, or about a 50%, or about a 55%, or about a 60%, or about a 65%, or about a 70%, or about a 75%, or about an 80%, or about a 85%, or about a 90%, or about a 95%, or about a 99%, or about a 99.5% or about a 100% reduction in inflammation.

The present disclosure provides a method of reducing fibrosis in a subject comprising administering to the subject a therapeutically effective amount of at least one compound of the present disclosure.

A reduction in fibrosis can be about a 1%, or about a 2%, or about a 3%, or about a 4%, or about a 5%, or about a 6%, or about a 7%, or about an 8%, or about a 9%, or about a 10%, or about a 15%, or about a 20%, or about a 25%, or about a 30%, or about a 35%, or about a 40%, or about a 45%, or about a 50%, or about a 55%, or about a 60%, or about a 65%, or about a 70%, or about a 75%, or about an 80%, or about a 85%, or about a 90%, or about a 95%, or about a 99%, or about a 99.5% or about a 100% reduction in fibrosis.

The present disclosure provides a method of stimulating the activity of Regulatory T cells in a subject comprising administering to the subject a therapeutically effective amount of at least one compound of the present disclosure.

Stimulating activity of regulatory T cells can comprise an increase in the activity of regulatory T cells. An increase in activity of regulatory T cells can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in the activity of regulatory T cells.

The present disclosure provides a method of increasing or decreasing at least one biomarker associated with an inflammatory disease in a subject comprising administering to the subject at least one therapeutically effective amount of a compound of the present disclosure. The biomarkers associated with an inflammatory disease are presented herein.

Inflammatory bowel diseases (IBD) are chronic inflammatory disorders of the intestinal tract and comprise Crohn's disease (CD), ulcerative colitis (UC) and colitis of uncertain type/aetiology. The etiology of IBD remains unknown and disease pathogenesis not fully understood but it appears that genetic, environmental, microbiological and immunological factors drive uncontrolled intestinal inflammatory activation leading to cycles of tissue damage and repair. Although the etiology of IBD is largely unknown, epigenetics is considered an important factor in IBD onset and pathogenesis. Epigenetic alterations such as differential patterns of histone acetylation are found in both biopsies from IBD patients and mouse models of colitis and HDAC inhibitors have demonstrated successful prevention of chronic inflammation and suppressing pro-inflammatory cytokines and chemokines in colitis model (Noor Ali et al., 2018 Acta Histochem Cytochem 51). Metabolic reprogramming and macrophage activation also plays a major role in IBD and inflammation and literature is strongly suggestive of therapeutic potential in restoring metabolic homeostasis and shift to alternative (M2) macrophage activation (Na et al., 2019 Nat Rev Gastroent Hepat 16).

Crohn's disease is an inflammatory bowel disease that can involve different areas of the digestive tract and often spreads deep into the layers of affected bowel tissue. Crohn's disease can be both painful and debilitating, and sometimes may lead to life-threatening complications. Active disease usually presents with diarrhea, often bloody, fever, and pain. The inflammation may also present in the skin, eyes, joints or liver. A long-term complication of the chronic inflammation in Crohn's is the development of colorectal cancer and the risk increases significantly with duration as well as with extension of disease. There is no cure for Crohn's disease and there is no one treatment that works for everyone but the goal of medical treatment is to reduce the inflammation. A number of anti-inflammatory and immune suppressor drugs are utilized and up to 50% of patients will require at least one surgery to remove damaged bowel.

In murine models of colitis or chronic intestinal inflammation, HDACis were found to reduce inflammation and tissue damage by increasing the expression of human B-defensin-2 (peptide that protects intestinal mucosa against bacterial invasion as part of the innate defense system toward a proinflammatory response), acetylation of transcription factors, increased mononuclear apoptosis, reduction of proinflammatory cytokine release, and increase in the number and activity of Regulatory T cells. Moreover, HDACis have been found to decrease tumor number and size in models of inflammation-driven tumorigenesis suggesting that in addition to having antiproliferative effects, their antiinflammatory effects and, as a consequence, mucosal healing may contribute to preventing colorectal cancer. Tregs act as the nucleus in enforcing immune tolerance and also function to preserve intestinal homeostasis and participate in tissue repair. One such promising approach to treating colitis focuses on stimulating Tregs and reported alleviation of bowel inflammation in murine models (Spalinger et al., 2018 J Crohns Colitis 13). HDAC inhibition was found to attenuate inflammatory changes in a dextran sulfate sodium-induced colitis mouse model by suppressing local secretion of pro-inflammatory cytokines and chemokines and also by suppressing mobilization and accumulation of inflammatory cells.

Ulcerative colitis (UC) is an inflammatory bowel disease that causes long-lasting inflammation and ulcers in the innermost lining of the colon and rectum. UC can be debilitating and the main symptom is usually bloody diarrhea, sometimes with pus, and other problems include crampy abdominal pain, fever, urgency to defecate, and sometime perforation of the colon. The inflammation may also present in the eyes and joints as pain or as canker sores or result in bone loss. UC does increase the risk of colon cancer. Diet and a number of anti-inflammatory and immune suppressor drugs are utilized for treatment but if these treatments don't work or if the disease is severe, a colectomy may be needed.

The present disclosure provides a method of treating Crohn's disease in a subject comprising administering to the subject a therapeutically effective amount of at least one compound of the present disclosure. The present disclosure provides a method of preventing Crohn's disease in a subject comprising administering to the subject a therapeutically effective amount of at least one compound of the present disclosure.

The present disclosure provides at least one compound of the present disclosure for use in treating Crohn's disease in a subject, wherein the at least one compound of the present disclosure is for administration to the subject in at least one therapeutically effective amount. The present disclosure provides at least one compound of the present disclosure for use in preventing Crohn's disease in a subject, wherein the at least one compound of the present disclosure is for administration to the subject in at least one therapeutically effective amount.

The present disclosure provides a use of at least one compound of the present disclosure for the manufacture of a medicament for treating Crohn's disease in a subject, wherein the at least one compound of the present disclosure is for administration to the subject in at least one therapeutically effective amount. The present disclosure provides a use of at least one compound of the present disclosure for the manufacture of a medicament for preventing Crohn's disease in a subject, wherein the at least one compound of the present disclosure is for administration to the subject in at least one therapeutically effective amount.

The present disclosure provides a method of treating colitis in a subject comprising administering to the subject a therapeutically effective amount of at least one compound of the present disclosure. The present disclosure provides a method of preventing colitis in a subject comprising administering to the subject a therapeutically effective amount of at least one compound of the present disclosure.

The present disclosure provides at least one compound of the present disclosure for use in treating colitis in a subject, wherein the at least one compound of the present disclosure is for administration to the subject in at least one therapeutically effective amount. The present disclosure provides at least one compound of the present disclosure for use in preventing colitis in a subject, wherein the at least one compound of the present disclosure is for administration to the subject in at least one therapeutically effective amount.

The present disclosure provides a use of at least one compound of the present disclosure for the manufacture of a medicament for treating colitis in a subject, wherein the at least one compound of the present disclosure is for administration to the subject in at least one therapeutically effective amount. The present disclosure provides a use of at least one compound of the present disclosure for the manufacture of a medicament for preventing colitis in a subject, wherein the at least one compound of the present disclosure is for administration to the subject in at least one therapeutically effective amount.

The present disclosure provides a method of treating chronic intestinal inflammation in a subject comprising administering to the subject a therapeutically effective amount of at least one compound of the present disclosure. The present disclosure provides a method of preventing chronic intestinal inflammation in a subject comprising administering to the subject a therapeutically effective amount of at least one compound of the present disclosure.

The present disclosure provides at least one compound of the present disclosure for use in treating chronic intestinal inflammation in a subject, wherein the at least one compound of the present disclosure is for administration to the subject in at least one therapeutically effective amount. The present disclosure provides at least one compound of the present disclosure for use in preventing chronic intestinal inflammation in a subject, wherein the at least one compound of the present disclosure is for administration to the subject in at least one therapeutically effective amount.

The present disclosure provides a use of at least one compound of the present disclosure for the manufacture of a medicament for treating chronic intestinal inflammation in a subject, wherein the at least one compound of the present disclosure is for administration to the subject in at least one therapeutically effective amount. The present disclosure provides a use of at least one compound of the present disclosure for the manufacture of a medicament for preventing chronic intestinal inflammation, wherein the at least one compound of the present disclosure is for administration to the subject in at least one therapeutically effective amount.

Autosomal dominant polycystic kidney disease (ADPKD) is a prevalent genetic disorder caused by loss-of-function mutations in PKD1 or PKD2 and characterized by renal cysts that lead to kidney failure. Cysts may also develop other organs, such as the liver, seminal vesicles, pancreas, and arachnoid membrane, as well as other abnormalities, such as intracranial aneurysms and dolichoectasias, aortic root dilatation and aneurysms, mitral valve prolapse, and abdominal wall hernias. Over 50% of patients with ADPKD eventually develop end stage kidney disease and require dialysis or kidney transplantation. Recent studies have shown that ADPKD cells undergo a wide-ranging metabolic reprogramming including increased glycolysis and glutaminolysis and a reduction in fatty acid odixation (Podrini et al., 2018 Comm Biol 194). A 3D cyst culture model with both PKD patient cells as well as murine PKD epithelial cells was recently demonstrated with good recapitulation of the disease pathology and promising results have been shown with several potential ADPKD drugs using this model (Booij et al., 2017 SLAS Discov 22; Booij et al., 2019 JMCB).

The present disclosure provides a method of treating autosomal dominant polycystic kidney disease in a subject comprising administering to the subject a therapeutically effective amount of at least one compound of the present disclosure. The present disclosure provides a method of preventing autosomal dominant polycystic kidney disease in a subject comprising administering to the subject a therapeutically effective amount of at least one compound of the present disclosure.

The present disclosure provides at least one compound of the present disclosure for use in treating autosomal dominant polycystic kidney disease in a subject, wherein the at least one compound of the present disclosure is for administration to the subject in at least one therapeutically effective amount. The present disclosure provides at least one compound of the present disclosure for use in preventing autosomal dominant polycystic kidney disease in a subject, wherein the at least one compound of the present disclosure is for administration to the subject in at least one therapeutically effective amount.

The present disclosure provides a use of at least one compound of the present disclosure for the manufacture of a medicament for treating autosomal dominant polycystic kidney disease in a subject, wherein the at least one compound of the present disclosure is for administration to the subject in at least one therapeutically effective amount. The present disclosure provides a use of at least one compound of the present disclosure for the manufacture of a medicament for preventing autosomal dominant polycystic kidney disease, wherein the at least one compound of the present disclosure is for administration to the subject in at least one therapeutically effective amount.

The present disclosure provides a method of stimulating NK cells in a subject comprising administering to the subject a therapeutically effective at least one compound of the present disclosure. The present disclosure provides at least one compound of the present disclosure for use in stimulating NK cells in a subject, wherein the at least one compound of the present disclosure is for administration to the subject in at least one therapeutically effective amount. The present disclosure provides a use of at least one compound of the present disclosure for the manufacture of a medicament for stimulating NK cells in a subject, wherein the at least one compound of the present disclosure is for administration to the subject in at least one therapeutically effective amount.

The present disclosure provides a method of inhibiting NK cells in a subject comprising administering to the subject a therapeutically effective at least one compound of the present disclosure. The present disclosure provides at least one compound of the present disclosure for use in inhibiting NK cells in a subject, wherein the at least one compound of the present disclosure is for administration to the subject in at least one therapeutically effective amount. The present disclosure provides a use of at least one compound of the present disclosure for the manufacture of a medicament for inhibiting NK cells in a subject, wherein the at least one compound of the present disclosure is for administration to the subject in at least one therapeutically effective amount.

The present disclosure provides a method of stimulating dendritic cells in a subject comprising administering to the subject a therapeutically effective at least one compound of the present disclosure. The present disclosure provides at least one compound of the present disclosure for use in stimulating dendritic cells in a subject, wherein the at least one compound of the present disclosure is for administration to the subject in at least one therapeutically effective amount. The present disclosure provides a use of at least one compound of the present disclosure for the manufacture of a medicament for stimulating dendritic cells in a subject, wherein the at least one compound of the present disclosure is for administration to the subject in at least one therapeutically effective amount.

The present disclosure provides a method of inhibiting dendritic cells in a subject comprising administering to the subject a therapeutically effective at least one compound of the present disclosure. The present disclosure provides at least one compound of the present disclosure for use in inhibiting dendritic cells in a subject, wherein the at least one compound of the present disclosure is for administration to the subject in at least one therapeutically effective amount. The present disclosure provides a use of at least one compound of the present disclosure for the manufacture of a medicament for inhibiting dendritic cells in a subject, wherein the at least one compound of the present disclosure is for administration to the subject in at least one therapeutically effective amount.

The present disclosure provides a method of stimulating IFN-γ in a subject comprising administering to the subject a therapeutically effective at least one compound of the present disclosure. The present disclosure provides at least one compound of the present disclosure for use in stimulating IFN-γ in a subject, wherein the at least one compound of the present disclosure is for administration to the subject in at least one therapeutically effective amount. The present disclosure provides a use of at least one compound of the present disclosure for the manufacture of a medicament for stimulating IFN-γ in a subject, wherein the at least one compound of the present disclosure is for administration to the subject in at least one therapeutically effective amount.

The present disclosure provides a method of treating a disease characterized by and/or associated with an impaired adaptive immune system in a subject comprising administering to the subject a therapeutically effective at least one compound of the present disclosure. The present disclosure provides at least one compound of the present disclosure for use in treating a disease characterized by and/or associated with an impaired adaptive immune system in a subject, wherein the at least one compound of the present disclosure is for administration to the subject in at least one therapeutically effective amount. The present disclosure provides a use of at least one compound of the present disclosure for the manufacture of a medicament for treating a disease characterized by and/or associated with an impaired adaptive immune system in a subject, wherein the at least one compound of the present disclosure is for administration to the subject in at least one therapeutically effective amount.

The present disclosure provides a method of treating an autoimmune disease in a subject comprising administering to the subject a therapeutically effective at least one compound of the present disclosure. The present disclosure provides at least one compound of the present disclosure for use in treating an autoimmune disease in a subject, wherein the at least one compound of the present disclosure is for administration to the subject in at least one therapeutically effective amount. The present disclosure provides a use of at least one compound of the present disclosure for the manufacture of a medicament for treating an autoimmune disease in a subject, wherein the at least one compound of the present disclosure is for administration to the subject in at least one therapeutically effective amount.

The present disclosure provides a method of inducing tolerance for graft versus host disease in a subject comprising administering to the subject a therapeutically effective at least one compound of the present disclosure. The present disclosure provides at least one compound of the present disclosure for use in inducing tolerance for graft versus host disease in a subject, wherein the at least one compound of the present disclosure is for administration to the subject in at least one therapeutically effective amount. The present disclosure provides a use of at least one compound of the present disclosure for the manufacture of a medicament for inducing tolerance for graft versus host disease in a subject, wherein the at least one compound of the present disclosure is for administration to the subject in at least one therapeutically effective amount.

The present disclosure provides a method of treating atherosclerosis in a subject comprising administering to the subject a therapeutically effective at least one compound of the present disclosure. The present disclosure provides at least one compound of the present disclosure for use in treating atherosclerosis in a subject, wherein the at least one compound of the present disclosure is for administration to the subject in at least one therapeutically effective amount. The present disclosure provides a use of at least one compound of the present disclosure for the manufacture of a medicament for treating atherosclerosis in a subject, wherein the at least one compound of the present disclosure is for administration to the subject in at least one therapeutically effective amount.

The present disclosure provides a method of treating cardiovascular disease in a subject comprising administering to the subject a therapeutically effective at least one compound of the present disclosure. The present disclosure provides at least one compound of the present disclosure for use in treating cardiovascular disease in a subject, wherein the at least one compound of the present disclosure is for administration to the subject in at least one therapeutically effective amount. The present disclosure provides a use of at least one compound of the present disclosure for the manufacture of a medicament for treating cardiovascular disease in a subject, wherein the at least one compound of the present disclosure is for administration to the subject in at least one therapeutically effective amount.

The present disclosure provides a method of treating type I diabetes in a subject comprising administering to the subject a therapeutically effective at least one compound of the present disclosure. The present disclosure provides at least one compound of the present disclosure for use in treating type I diabetes in a subject, wherein the at least one compound of the present disclosure is for administration to the subject in at least one therapeutically effective amount. The present disclosure provides a use of at least one compound of the present disclosure for the manufacture of a medicament for treating type I diabetes in a subject, wherein the at least one compound of the present disclosure is for administration to the subject in at least one therapeutically effective amount.

The present disclosure provides a method of treating type II diabetes in a subject comprising administering to the subject a therapeutically effective at least one compound of the present disclosure. The present disclosure provides at least one compound of the present disclosure for use in treating type II diabetes in a subject, wherein the at least one compound of the present disclosure is for administration to the subject in at least one therapeutically effective amount. The present disclosure provides a use of at least one compound of the present disclosure for the manufacture of a medicament for treating type II diabetes in a subject, wherein the at least one compound of the present disclosure is for administration to the subject in at least one therapeutically effective amount.

The present disclosure provides a method of treating hypertension in a subject comprising administering to the subject a therapeutically effective at least one compound of the present disclosure. The present disclosure provides at least one compound of the present disclosure for use in treating hypertension in a subject, wherein the at least one compound of the present disclosure is for administration to the subject in at least one therapeutically effective amount. The present disclosure provides a use of at least one compound of the present disclosure for the manufacture of a medicament for treating hypertension in a subject, wherein the at least one compound of the present disclosure is for administration to the subject in at least one therapeutically effective amount.

The present disclosure provides a method of treating a chronic inflammation disease in a subject comprising administering to the subject a therapeutically effective at least one compound of the present disclosure. The present disclosure provides at least one compound of the present disclosure for use in treating a chronic inflammation disease in a subject, wherein the at least one compound of the present disclosure is for administration to the subject in at least one therapeutically effective amount. The present disclosure provides a use of at least one compound of the present disclosure for the manufacture of a medicament for treating a chronic inflammation disease in a subject, wherein the at least one compound of the present disclosure is for administration to the subject in at least one therapeutically effective amount.

The present disclosure provides a method of treating a mast cell activation disease in a subject comprising administering to the subject a therapeutically effective at least one compound of the present disclosure. The present disclosure provides at least one compound of the present disclosure for use in treating a mast cell activation disease in a subject, wherein the at least one compound of the present disclosure is for administration to the subject in at least one therapeutically effective amount. The present disclosure provides a use of at least one compound of the present disclosure for the manufacture of a medicament for treating a mast cell activation disease in a subject, wherein the at least one compound of the present disclosure is for administration to the subject in at least one therapeutically effective amount.

The present disclosure provides a method of treating a disease characterized by and/or associated with M1 macrophage polarization in a subject comprising administering to the subject a therapeutically effective at least one compound of the present disclosure. The present disclosure provides at least one compound of the present disclosure for use in treating a disease characterized by and/or associated with M1 macrophage polarization in a subject, wherein the at least one compound of the present disclosure is for administration to the subject in at least one therapeutically effective amount. The present disclosure provides a use of at least one compound of the present disclosure for the manufacture of a medicament for treating a disease characterized by and/or associated with M1 macrophage polarization in a subject, wherein the at least one compound of the present disclosure is for administration to the subject in at least one therapeutically effective amount.

The present disclosure provides a method of treating an infectious disease in a subject comprising administering to the subject a therapeutically effective at least one compound of the present disclosure. The present disclosure provides at least one compound of the present disclosure for use in treating an infectious disease in a subject, wherein the at least one compound of the present disclosure is for administration to the subject in at least one therapeutically effective amount. The present disclosure provides a use of at least one compound of the present disclosure for the manufacture of a medicament for treating an infectious disease in a subject, wherein the at least one compound of the present disclosure is for administration to the subject in at least one therapeutically effective amount.

The present disclosure provides a method of treating a viral infection in a subject comprising administering to the subject a therapeutically effective at least one compound of the present disclosure. The present disclosure provides at least one compound of the present disclosure for use in treating a viral infection in a subject, wherein the at least one compound of the present disclosure is for administration to the subject in at least one therapeutically effective amount. The present disclosure provides a use of at least one compound of the present disclosure for the manufacture of a medicament for treating a viral infection in a subject, wherein the at least one compound of the present disclosure is for administration to the subject in at least one therapeutically effective amount.

The present disclosure provides a method of treating a bacterial infection in a subject comprising administering to the subject a therapeutically effective at least one compound of the present disclosure. The present disclosure provides at least one compound of the present disclosure for use in treating a bacterial infection in a subject, wherein the at least one compound of the present disclosure is for administration to the subject in at least one therapeutically effective amount. The present disclosure provides a use of at least one compound of the present disclosure for the manufacture of a medicament for treating a bacterial infection in a subject, wherein the at least one compound of the present disclosure is for administration to the subject in at least one therapeutically effective amount.

The present disclosure provides a method of treating a fungal infection in a subject comprising administering to the subject a therapeutically effective at least one compound of the present disclosure. The present disclosure provides at least one compound of the present disclosure for use in treating a fungal infection in a subject, wherein the at least one compound of the present disclosure is for administration to the subject in at least one therapeutically effective amount. The present disclosure provides a use of at least one compound of the present disclosure for the manufacture of a medicament for treating a fungal infection in a subject, wherein the at least one compound of the present disclosure is for administration to the subject in at least one therapeutically effective amount.

The present disclosure provides a method of increasing activation of and/or enhancing antigen presentation in a subject comprising administering to the subject a therapeutically effective at least one compound of the present disclosure. The present disclosure provides at least one compound of the present disclosure for use in increasing activation of and/or enhancing antigen presentation in a subject, wherein the at least one compound of the present disclosure is for administration to the subject in at least one therapeutically effective amount. The present disclosure provides a use of at least one compound of the present disclosure for the manufacture of a medicament for increasing activation of and/or enhancing antigen presentation in a subject, wherein the at least one compound of the present disclosure is for administration to the subject in at least one therapeutically effective amount.

Systemic autoimmune rheumatic diseases such as rheumatic arthritis (RA), juvenile idiopathic arthritis, and systemic lupus erythematosus (SLE) are characterized by chronic inflammation and pain, which consequently leads to tissue destruction and reduction of patients' mobility. Immune cells play a key role in inflammation due to involvement in initiation and maintenance of the chronic inflammatory stages and epigenetic mechanisms can mediate the development of chronic inflammation. Rheumatoid arthritis (RA) and juvenile idiopathic arthritis (JIA) are autoimmune diseases characterized by chronic joint inflammation with pain and swelling, joint destruction and disability. Activation of nonspecific innate immunity, results in persistent chronic inflammation orchestrated by uncontrolled production of many proinflammatory mediators, such as cytokines, chemokines and other soluble factors, becoming a loop of self-reverberating inflammation that becomes independent of the original trigger. Cytokines such as tumor necrosis factor (TNF) and interleukin (IL)-1β produced by macrophages and lymphocytes infiltrating the synovial tissue lead to the abnormal activation of fibroblast-like synoviocytes (FLS), which in turn causes bone and cartilage deterioration. Inhibition of HDAC activity can contribute to the immunopathology of RA and JIA via epigenetic mechanisms. When comparing healthy individuals and RA disease controls, synovial tissue displays a marked reduction in total HDAC activity and HDAC1 and HDAC2 protein expression, particularly in synovial macrophages. The use of pan-HDACis reduce cytokine production in in fibroblast-like synoviocytes and in immune cells from patients with RA, display antiarthritic properties in vivo and demonstrated primary clinical efficacy in the treatment of rheumatic diseases. This demonstrates that protein acetylation plays a role in treating rheumatic diseases.

The present disclosure provides a method of treating rheumatic disease including rheumatoid arthritis and juvenile idiopathic arthritis in a subject comprising administering to the subject a therapeutically effective amount of at least one compound of the present disclosure. The present disclosure provides at least one compound of the present disclosure for use in treating rheumatic disease including rheumatoid arthritis and juvenile idiopathic arthritis in a subject, wherein the at least one compound of the present disclosure is for administration to the subject in at least one therapeutically effective amount. The present disclosure provides a use of at least one compound of the present disclosure for the manufacture of a medicament for treating rheumatic disease including rheumatoid arthritis and juvenile idiopathic arthritis in a subject, wherein the at least one compound of the present disclosure is for administration to the subject in at least one therapeutically effective amount.

The present disclosure provides a method of increasing crotonylation of histones in a subject comprising administering to the subject a therapeutically effective amount of an acetyl-CoA precursor. The present disclosure provides at least one compound of the present disclosure for use in increasing crotonylation of histones in a subject, wherein the at least one compound of the present disclosure is for administration to the subject in at least one therapeutically effective amount. The present disclosure provides a use of at least one compound of the present disclosure for the manufacture of a medicament for increasing crotonylation of histones in a subject, wherein the at least one compound of the present disclosure is for administration to the subject in at least one therapeutically effective amount.

Systemic lupus erythematosus (SLE) is a systemic autoimmune disease characterized by the activation of autoreactive T and B cells. SLE can affect many parts of the body, including the joints, skin, kidneys, heart, lungs, blood vessels and brain but some of the most common symptoms include extreme fatigue, painful or swollen joints, fever, photosensitivity, hair loss, skin rashes (specifically the characteristic red butterfly or malar rash across the nose and cheeks), and renal impairment. SLE treatment consists primarily of immunosuppressive drugs. HDAC expression and activity is found to be upregulated in murine models of disease and HDAC inhibitors can reduce disease in lupus-prone mice (Regina et al., 2015 Int Immunopharmacol 29; Regina et al., 2016 Clin Immunol 162; Reilly et al., Mol Med 17).

The present disclosure provides a method of treating SLE in a subject comprising administering to the subject a therapeutically effective amount of at least one compound of the present disclosure. The present disclosure provides at least one compound of the present disclosure for use in treating SLE in a subject, wherein the at least one compound of the present disclosure is for administration to the subject in at least one therapeutically effective amount. The present disclosure provides a use of at least one compound of the present disclosure for the manufacture of a medicament for treating SLE in a subject, wherein the at least one compound of the present disclosure is for administration to the subject in at least one therapeutically effective amount.

Combinations of anti-HIV drugs can effectively suppress virus replication but infected individuals possess a reservoir of latent HIV-1. Upon cessation of drugs, viruses in this reservoir reactivate and re-kindle infection. HIV-1 persistence in long-lived cellular reservoirs remains a major barrier to a cure. Patients have to remain on anti-HIV drugs the rest of their lives and there is a strong incentive to be able to either reduce or stop these drugs given the long-term side-effects and burden of taking these drugs. A strategy is being explored to reactivate latent HIV without inducing global T cell activation whereupon a patient's immune system can potentially eradicate the virus. HDACis have been found to reactivate these latently infected cells in nonclinical models and in initial human studies. However, HDACis do not have the ability to completely rid the body of latently infected cells and this approach may need to be combined with an immune modulator, such as IFN-alpha2a, to significantly affect the latent HIV reservoir (Hakre et al., 2011 Curr Opin HIV AIDS 6; Rasmussen et al., 2014 Lancet HIV 1).

Without being bound by theory, an increase in the acetylation of histones and nonhistone proteins through HATs and non-enzymatic acetylation could stimulate HIV-1 latency reduction or eradication by reactivating latent HIV without inducing global T cell activation. This reactivation would make the HIV infected cells visible to the immune system; the immune response (native plus addition of an immune modulator such as IFN-alpha2a) and antiretroviral cocktail would then be able to attack and eliminate the infected cells.

The present disclosure provides a method of treating HIV in a subject comprising administering to the subject a therapeutically effective amount of at least one compound of the present disclosure. The present disclosure provides at least one compound of the present disclosure for use in treating HIV in a subject, wherein the at least one compound of the present disclosure is for administration to the subject in at least one therapeutically effective amount. The present disclosure provides a use of at least one compound of the present disclosure for the manufacture of a medicament for treating HIV in a subject, wherein the at least one compound of the present disclosure is for administration to the subject in at least one therapeutically effective amount.

The present disclosure provides a method of treating HIV in a subject comprising administering to the subject a combination of a therapeutically effective amount of at least one compound of the present disclosure and a therapeutically effective amount of an immune modulator compound.

An immune modulator compound can include, but is not limited to, IFN-alpha 2A or an antiretroviral cocktail.

The present disclosure provides a method of treating HIV in a subject comprising administering to the subject a combination of a therapeutically effective amount of at least one compound of the present disclosure and a therapeutically effective amount of an anti-HIV agent.

Anti-HIV agents include, but are not limited to, abacavir, emtricitabine, lamivudine, tenofovir disoproxil fumarate, zidovudine, doravirine, efavirenz, etravirine, nevirapine, rilpivirine, atazanavir, darunavir, fosamprenavir, ritonavir, saquinavir, tipranavir, enfuvirtide, maraviroc, dolutegravir, raltegravir, ibalizumab, cobicistat, abacavir/lamivudine combination, abacavir/dolutegravir/lamivudine combination, abacavir/lamivudine/zidovudine combination, atazanavir/cobicistat combination, bictegravir/emtricitabine/tenofovir alafenamide combination, darunavir/cobicistat combination, darunavir/cobicistat/emtricitabine/tenofovir alafenamide combination, dolutegravir/rilpivirine combination, doravirine/lamivudine/tenofovir disoproxil fumarate combination, efavirenz emtricitabine/tenofovir disoproxil fumarate combination, efavirenz lamivudine/tenofovir disoproxil fumarate combination, elvitegravir/cobicistat/emtricitabine/tenofovir alafenamide fumarate combination, elvitegravir/cobicistat/emtricitabine/tenofovir disoproxil fumarate combination, emtricitabine/rilpivirine/tenofovir alafenamide combination, emtricitabine/rilpivirine/tenofovir disoproxil fumarate combination, emtricitabine/tenofovir alafenamide combination, emtricitabine/tenofovir disoproxil fumarate combination, lamivudine/tenofovir disoproxil fumarate combination, lamivudine/zidovudine combination, lopinavir/ritonavir combination or any combination thereof.

The present disclosure provides a method of reactivating latent HIV in a subject comprising administering to the subject a therapeutically effective amount of at least one compound of the present disclosure. The present disclosure provides at least one compound of the present disclosure for use in reactivating latent HIV in a subject, wherein the at least one compound of the present disclosure is for administration to the subject in at least one therapeutically effective amount. The present disclosure provides a use of at least one compound of the present disclosure for the manufacture of a medicament for treating reactivating latent HIV in a subject, wherein the at least one compound of the present disclosure is for administration to the subject in at least one therapeutically effective amount.

The present disclosure provides a method of reactivating latent HIV without inducing global T cell activation in a subject comprising administering to the subject a therapeutically effective amount of at least one compound of the present disclosure. The present disclosure provides at least one compound of the present disclosure for use in reactivating latent HIV without inducing global T cell activation in a subject, wherein the at least one compound of the present disclosure is for administration to the subject in at least one therapeutically effective amount. The present disclosure provides a use of at least one compound of the present disclosure for the manufacture of a medicament for treating reactivating latent HIV without inducing global T cell activation in a subject, wherein the at least one compound of the present disclosure is for administration to the subject in at least one therapeutically effective amount.

Acute Coronary Syndrome (ACS) is a group of conditions including unstable angina and myocardial infarctions (MI) with or without an observed ST elevation with atherosclerosis being the primary cause. Acute therapy involves interventional and/or medical therapy (anti-thrombotic, anticoagulant, anti-ischemic, anti-lipid). Secondary prevention treatment post ACS includes lifestyle changes, medical treatment to control risk factors and continued anti-thrombotic therapy. Despite SOC, there remains a significant risk of reinfarction, ischemic stroke, and death (up to 18% in the first year post ACS).

Studies have shown that acetylation level through HDACs is associated with cardiovascular disease, such as hypertension, diabetic cardiomyopathy, coronary artery disease, arrhythmia, and heart failure. Moreover, HDACs appear to be closely linked with in the progression of atherosclerosis and HDAC inhibitors successfully prevent the progression of atherosclerosis. Positive effects of pan-selective HDAC inhibitors, which increase the acetylation of histones and nonhistone proteins, in rodent models of heart failure have been reviewed extensively. Importantly, HDAC inhibition is capable of regressing established cardiac hypertrophy and systolic dysfunction in mice subjected to aortic constriction. In a rabbit ischemic-reperfusion injury, the use of an HDACi protected cardiac tissue and function by inhibition of pathological remodeling through autophagy which serves to protect cardiomyocytes during ischemia by resupplying energy and by reducing inflammation, oxidative stress and fibrosis (Granger et al., 2008 FASEB J 22; Lyu et al., 2019 Ther Adv Chronic Dis 10; McLendon et al., 2014 PNAS; Wang et al., 2014 Oxid Med Cel Long 2014).

The present disclosure provides a method of treating Acute Coronary Syndrome in a subject comprising administering to the subject a therapeutically effective amount of at least one compound of the present disclosure. The present disclosure provides at least one compound of the present disclosure for use in treating Acute Coronary Syndrome in a subject, wherein the at least one compound of the present disclosure is for administration to the subject in at least one therapeutically effective amount. The present disclosure provides a use of at least one compound of the present disclosure for the manufacture of a medicament for treating Acute Coronary Syndrome in a subject, wherein the at least one compound of the present disclosure is for administration to the subject in at least one therapeutically effective amount.

The present disclosure provides a method of reducing damage to cardiac cells in a subject having acute coronary syndrome comprising administering to the subject a therapeutically effective amount of at least one compound of the present disclosure. The present disclosure provides at least one compound of the present disclosure for use in reducing damage to cardiac cells in a subject having acute coronary syndrome, wherein the at least one compound of the present disclosure is for administration to the subject in at least one therapeutically effective amount. The present disclosure provides a use of at least one compound of the present disclosure for the manufacture of a medicament reducing damage to cardiac cells in a subject having acute coronary syndrome, wherein the at least one compound of the present disclosure is for administration to the subject in at least one therapeutically effective amount.

The present disclosure provides a method of reducing damage imparted by ischemia, inflammation, fibrotic remodeling or any combination thereof in a subject comprising administering to the subject a therapeutically effective amount of at least one compound of the present disclosure. The present disclosure provides at least one compound of the present disclosure for use in reducing damage imparted by ischemia, inflammation, fibrotic remodeling or any combination thereof in a subject, wherein the at least one compound of the present disclosure is for administration to the subject in at least one therapeutically effective amount. The present disclosure provides a use of at least one compound of the present disclosure for the manufacture of a medicament for treating Acute reducing damage imparted by ischemia, inflammation, fibrotic remodeling or any combination thereof in a subject, wherein the at least one compound of the present disclosure is for administration to the subject in at least one therapeutically effective amount.

Acute Coronary Syndrome can include, but is not limited to, a heart attack, an unstable angina, ST elevation myocardial infarction, non ST elevation myocardial infarction or any combination thereof.

The present disclosure provides a method of preventing reinfarction in a subject comprising administering to the subject a therapeutically effective amount of at least one compound of the present disclosure. The present disclosure provides at least one compound of the present disclosure for use in preventing reinfarction in a subject, wherein the at least one compound of the present disclosure is for administration to the subject in at least one therapeutically effective amount. The present disclosure provides a use of at least one compound of the present disclosure for the manufacture of a medicament for preventing reinfarction in a subject, wherein the at least one compound of the present disclosure is for administration to the subject in at least one therapeutically effective amount.

The present disclosure provides a method of preventing ischemic stroke in a subject comprising administering to the subject a therapeutically effective amount of at least one compound of the present disclosure. The present disclosure provides at least one compound of the present disclosure for use in preventing ischemic stroke in a subject, wherein the at least one compound of the present disclosure is for administration to the subject in at least one therapeutically effective amount. The present disclosure provides a use of at least one compound of the present disclosure for the manufacture of a medicament for preventing ischemic stroke in a subject, wherein the at least one compound of the present disclosure is for administration to the subject in at least one therapeutically effective amount.

The present disclosure provides a method of increasing the survival of cardiac cells in a subject comprising administering to the subject a therapeutically effective amount of at least one compound of the present disclosure. The present disclosure provides at least one compound of the present disclosure for use in increasing the survival of cardiac cells in a subject, wherein the at least one compound of the present disclosure is for administration to the subject in at least one therapeutically effective amount. The present disclosure provides a use of at least one compound of the present disclosure for the manufacture of a medicament for increasing the survival of cardiac cells in a subject, wherein the at least one compound of the present disclosure is for administration to the subject in at least one therapeutically effective amount An increase in survival of cardiac cells can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in the survival of cardiac cells.

Pulmonary arterial hypertension (PAH) is a rare but devastating disease, in which the normally low pulmonary artery pressure becomes elevated due to vasoconstriction and to the remodelling of pulmonary vessels. This in turn increases workload on the right side of the heart, causing right heart hypertrophy, fibrosis and ultimately heart failure.

Interventions used in the management of PAH are traditionally targeted on the vasculature, with the aim of enhancing vasodilation and anti-proliferation pathways. These include the prostacyclin analogues and nitric oxide (NO) (Chester et al., 2017 Glob Cardiol Sci Pract 2).

Metabolic reprogramming in PAH is now recognized as a major contributor to the pathogenesis of pulmonary vascular disease (Assad et al., 2015 Curr Hypertens Rep 17; Fessel et al., 2012 Pulm Circ 2). The pulmonary vasculature in PAH displays a normoxic activation of hypoxia-inducible factor 1-alpha (HIF-1α), which creates a "pseudo-hypoxic" environment despite normal oxygen availability (Ryan et al., 2015 Circulation 131). One of the consequences of HIF-1α activation is a metabolic shift toward aerobic glycolysis (the "Warburg effect"), which has been described in the development of the PAH (Rehman et al., 2010 Adv Exp Md Biol). Previous studies have shown that HIF-1α activates over 100 genes involved in the development of hypoxic pulmonary hypertension (Tuder et al., 2012 Am J Respir Crit Care Med 185; Shimoda et al., 2001 Am J Physiol Lung Cell Mol Physiol 281) and, specifically, upregulation of glucose transporters (GLUT1 and GLUT3) and of pyruvate dehydrogenase kinase 1 and 4 (PDK1 and PDK4), which promote the inhibition of pyruvate dehydrogenase (PDH) activity and block the entrance of pyruvate into the Krebs cycle (Kim et al., 2006 Cell Metab 3). These significant alterations induce an increase in glucose uptake and a reduction of glucose flux into the mitochondria. As a consequence, TCA cycle activity is decreased, and the activity of anaplerotic pathways that replenish the intermediates of the TCA cycle is increased (Fessel et al., 2012 Pulm Circ 2). Lipid metabolism has also been highlighted as one of the hallmarks of PAH progression. It was demonstrated that the inhibition of fatty acid oxidation due to the absence of malonyl-coenzyme A decarboxylase (MCD) promotes glucose oxidation and prevents the metabolic shift toward glycolysis and metabolic modulators that are used clinically and that mimic the lack of MCD can reverse PAH induced by hypoxia or monocrotaline (Sutendra et al., 2010 Sci Transl Med 2; Guarnieri et al., 1988 Biochem Pharmacol 37). PPARγ agonist has also been shown in recent studies on PAH animal models to reverse pylmonary hypertension and prevent right heart failure via fatty acid oxidation (Legchenko et at, 2018 Sci Transl Med 19) and PPARβ/S agonists were shown to protect the right heart in hypoxia-driven pulmonary hypertension and reduce right heart hypertrophy and failure without affecting vascular remodeling (Kojonazarov et al., 2013 Pulm Circ 3).

The present disclosure provides a method of reducing pulmonary arterial hypertension, vasoconstriction and/or right heart hypertrophy in a subject comprising administering to the subject a therapeutically effective amount of at least one compound of the present disclosure. The present disclosure provides at least one compound of the present disclosure for use in reducing pulmonary arterial hypertension, vasoconstriction and or right heart hypertrophy in a subject, wherein the at least one compound of the present disclosure is for administration to the subject in at least one therapeutically effective amount. The present disclosure provides a use of at least one compound of the present disclosure for the manufacture of a medicament for reducing pulmonary arterial hypertension, vasoconstriction and/or right heart hypertrophy in a subject, wherein the at least one compound of the present disclosure is for administration to the subject in at least one therapeutically effective amount.

Nonalcoholic Steatohepatitis (NASH) is the advanced form of nonalcoholic fatty liver disease (NAFLD) and is defined histologically by the presence of hepatic fat (steatosis) with inflammation and hepatocellular ballooning. Accumulation of fat within the hepatocytes when import or synthesis of fat exceeds its export or degradation. NASH is a progressive disease that can lead to further liver injury, advanced fibrosis, cirrhosis, and hepatocellular carcinoma. A cascade of events occurs in these lipotoxic hepatocytes, including activation of immune mediators and inflammation, hepatic cell damage/death with matrix remodeling via fibrogenesis and fibrinolysis, angiogenesis, and mobilization of liver progenitor cells. Moreover, mitochondrial dysfunction appears to be a key component of the progressing disease, including inappropriate fatty acid oxidation, oxidative stress, and impaired energy production and reprogramming of metabolic pathways including hepatic glycogen and lipid metabolism (Koyama and Brenner, 2017 J Clin Invest 127; Machado and Diehl, 2016 Gastroenterol 150; Farrell et al., 2018 Adv Exp Med Biol 1061; Marra and Svegliati-Baroni, 2018 J Hepatol 68; d'Avignon 2018 JCI Insight 3). There are no approved therapies for NASH but there has been an increasing focus on modulating the mediators of these pathways as the therapeutic target.

A central feature of NASH is the aberrant regulation of lipids within hepatocytes. Increased lipogenesis, impaired fatty acid oxidation, and the generation of biologically active fatty acid signaling molecules are factors in NASH pathogenesis leading to lipotoxicity including metabolic and oxidative stress in the liver cells and lead to increased synthesis and deposition of triglycerides. Increased malonyl-CoA, which inhibits carnitine-palmitoyl transferase, inhibited fatty acid oxidation. The critical role of beta oxidation and ketogenesis in prevention of steatohepatitis is further demonstrated by a murine model of mitochondrial 3-hydroxymethylglutaryl CoA synthase (HMGCS2)-deficiency. When fed a high-fat diet, these mice suffer from defective Krebs cycle and gluconeogenesis caused by CoA sequestration and develop severe hepatocyte injury and inflammation. Gluconeogenesis and Krebs cycle are normalized upon supplementation of CoA precursors pantothenic acid and cysteine (Cotter et al., 2014 FASEB J 28). This demonstrates the role of CoA homeostasis in NAFLD.

The present disclosure provides a method of treating nonalcoholic steatohepatitis in a subject comprising administering to the subject a therapeutically effective amount of at least one compound of the present disclosure. The present disclosure provides a method of preventing nonalcoholic steatohepatitis in a subject comprising administering to the subject a therapeutically effective amount of at least one compound of the present disclosure.

The present disclosure provides at least one compound of the present disclosure for use in treating nonalcoholic steatohepatitis in a subject, wherein the at least one compound of the present disclosure is for administration to the subject in at least one therapeutically effective amount. The present disclosure provides at least one compound of the present disclosure for use in preventing nonalcoholic steatohepatitis in a subject, wherein the at least one compound of the present disclosure is for administration to the subject in at least one therapeutically effective amount.

The present disclosure provides a use of at least one compound of the present disclosure for the manufacture of a medicament for treating nonalcoholic steatohepatitis in a subject, wherein the at least one compound of the present disclosure is for administration to the subject in at least one therapeutically effective amount. The present disclosure provides a use of at least one compound of the present disclosure for the manufacture of a medicament for preventing nonalcoholic steatohepatitis in a subject, wherein the at least one compound of the present disclosure is for administration to the subject in at least one therapeutically effective amount.

The present disclosure provides a method of treating nonalcoholic fatty liver disease in a subject comprising administering to the subject a therapeutically effective amount of at least one compound of the present disclosure. The present disclosure provides a method of preventing nonalcoholic fatty liver disease in a subject comprising administering to the subject a therapeutically effective amount of at least one compound of the present disclosure.

The present disclosure provides at least one compound of the present disclosure for use in treating nonalcoholic fatty liver disease in a subject, wherein the at least one compound of the present disclosure is for administration to the subject in at least one therapeutically effective amount. The present disclosure provides at least one compound of the present disclosure for use in preventing nonalcoholic fatty liver disease in a subject, wherein the at least one compound of the present disclosure is for administration to the subject in at least one therapeutically effective amount.

The present disclosure provides a use of at least one compound of the present disclosure for the manufacture of a medicament for treating nonalcoholic fatty liver disease in a subject, wherein the at least one compound of the present disclosure is for administration to the subject in at least one therapeutically effective amount. The present disclosure provides a use of at least one compound of the present disclosure for the manufacture of a medicament for preventing nonalcoholic fatty liver disease in a subject, wherein the at least one compound of the present disclosure is for administration to the subject in at least one therapeutically effective amount.

Acute kidney injury (AKI) is a potentially lethal condition for which no therapy is available beyond replacement of renal function. The primary causes of AKI include ischemia, hypoxia or nephrotoxicity leading to inflammation, elevated reactive oxygen species, metabolic disredulation and followed by a rapid decline in GFR usually associated with decreases in renal blood flow. The underlying basis of renal injury appears to be impaired energetics of the highly metabolically active nephron segments, which can trigger conversion from transient hypoxia to intrinsic renal failure (Basile et al., 2014 Compr Physiol 2, Makris and Spanou, 2016 Clin Biochem Rev 37; Ralto and Parikh, 2016 Semin Nephrol 36; Pan and Sheikh-Hamad, 2019 Med Res Arch 7). Restoration of mitochondrial health and biogenesis has been a promising therapeutic target for AKI drug development (Ishimoto and Inagi, 2016 Nephr Dial Transpl 31).

Post-translational histone modifications has also been implicated in modulation of gene expression and kidney injury. Histone crotonylation is a post-translational modification and is physiologically significant and functionally distinct from or redundant to histone acetylation. Histone crotonylation exhibits a crucial role in a wide range of biological processes and may be critically implicated in the pathogenesis of diseases. Enrichment of histone crotonylation is observed at the genes encoding the mitochondrial biogenesis regulator PGC-1α and the sirtuin-3 decrotonylase in AKI kidney tissue. Addition of crotonate increases the expression of PGC-1α and sirtuin-3, and decreases CCL2 expression in cultured tubular cells and healthy kidneys. Systemic crotonate administration protected from experimental AKI, preventing the decrease in renal function and in kidney PGC-1α and sirtuin-3 levels as well as the increase in CCL2 expression. Increasing histone crotonylation has a beneficial effect on AKI and indicates the strong in vivo potential of the therapeutic manipulation of histone crotonylation in a disease state (Guo et al., 2019 Nat Rev Nephrol 15; Ruiz-Andres et al., 106 Dis Model Mech 2016 9; Morgado-Pascual et al., 2018 Mediat Inflammat 2018).

Methods of Use Post Translational Modifications

Protein acetylation, in which the acetyl group from acetyl-CoA is transferred to a specific site on a polypeptide chain, is an important post-translational modification that enables the cell to react specifically and rapidly to internal and external perturbations. Acetyl-CoA mediated acetylation of proteins can alter the functional profile of a specific protein by influencing its catalytic activity, its capacity to interact with other molecules (including other proteins), its subcellular localization, and/or its stability. Acetylation and deacetylation occurs on histones and nonhistone proteins within the nucleus, cytoplasm, and mitochondria by a complex interaction between histone deacetylases (HDACs), histone acetyltransferases (HATs), lysine acetyltransferases (KATs), and non-enzymatic acetylation. The 18 identified mammalian HDACs are divided into four classes with Class I, II and IV primarily distributed in the nucleus and cytoplasm whereas Class III (sirtuins) are additionally located in mitochondria. Histone acetylation and deacetylation can regulate chromosome assembly, gene transcription, and posttranslational modification. Acetylation is almost invariably associated with activation of transcription. Many non-histone proteins have been identified that are substrates for one or another of the HDACs and these substrates include proteins that have regulatory roles in cell proliferation, cell migration, and cell death.

Dysregulation of histone or protein acetylation and/or acylation or disruption or aberrant acetyltransferase and/or acyltransferase activity has been correlated with many human diseases including mitochondrial diseases, metabolic syndrome and other metabolic diseases, inflammatory diseases, neurodegenerative diseases, neuropsychiatric diseases, cancer and others (McCullough and Marmorstein, 2016 ACS Chem Biol 11; Carrico et al., 2018 Cell Metab 27; Wei et al., 2017 J Proteome Res 26; Choundray et al., 2014 Nat rev mol cell biol 15; Ronowska et al., 2018 Front Cel Neurosc 12; Serrano, 2018 Handbook Clin Neurol 155; Domankovic et al., 2007 Mol Cancer Res 5; Drazic et al., 2016 BBA 1864; Wang et al., 2014 Oxid Med Cell Long; de Conti et al., 2017 Mol Cancer Res 15).

O-linked β-N-acetylglucosamine (O-GlcNAc) addition is another important post-translational regulatory mechanism underlying normal liver physiology and has been implicated in metabolic diseases and inflammation, particularly in liver fibrosis, chronic liver disease. This post-translational modification is controlled by O-GlcNAc transferase (OGT) and O-GlcNAcase (OGA). It was demonstrated that liver-specific OGT knockout mice develop hepatomegaly, ballooning degeneration, and fibrosis in the liver and expression of OGC suppresses necroptosis and liver fibrosis (Zhang et al., 2019 JCI Insight 4).

The present disclosure provides a method of increasing the post-translational modification of proteins in a subject comprising administering to the subject a therapeutically effective amount of at least one compound of the present disclosure.

An increase in post-translational modification of proteins can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in post-translational modification of proteins.

Post-translational modification of proteins includes but is not limited to acetylation, N-terminal acetylation, lysine acetylation, acylation, O-acylation, N-acylation, S-acylation, Myristoylation, palmitoylation, isoprenylation, prenylation, farnesylation geranilgeranilatyon, glycosylphosphatidylinositol (GPI) anchor formation, lipoylation, flavin moiety (FMN or FAD) attachment, heme C attachment, phosphopantetheinylation, retinylidene Schiff base formation, diphthamide formation, ethanolamine phosphoglycerol attachment, hypusine formation, beta-Lysine addition, formylation, alkylation, methylation, amidation at C-terminus. amide bond formation, amino acid addition, arginylation, polyglutamylation, polyglycylation, butyrylation, gamma-carboxylation, glycosylation, polysialylation, malonylation, hydroxylation, iodination, nucleotide addition, phosphate ester formation, phosphoramidate formation, phosphorylation, adenylylation, uridylylation, propionylation, pyroglutamate formation, S-glutathionylation, S-nitrosylation, S-sulfenylation (S-sulphenylation), S-sulfinylation, S-sulfonylation, succinylation, sulfation, O-GlcNAc addition or any combination thereof. In some preferred aspects, post-translational modification of proteins includes but is not limited to acetylation of histones, acetylation of tubulin, or any combination thereof. Post-translational modification of proteins also includes, but is not limited to the modification of lysine by an acyl group, including, but not limited to, a formyl group, a acetyl group, a propionyl group, a butyryl group, a crotonyl group, a malonyl group, a succinyl group, a glutaryl group, a myristoyl group or any combination thereof.

The present disclosure provides a method of increasing acetylation of proteins in a subject comprising administering to the subject a therapeutically effective amount of at least one compound of the present disclosure. The present disclosure provides a method of increasing acetylation of histones in a subject comprising administering to the subject a therapeutically effective amount of at least one compound of the present disclosure. The present disclosure provides a method of increasing acetylation of tubulin in a subject comprising administering to the subject a therapeutically effective amount of at least one compound of the present disclosure.

An increase in acetylation can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%/o, or about a 500%, or about a 600%, or about a 700%, or about an 800%, or about a 900%, or about a 1000°% increase in acetylation.

An increase in acetylation can be an increase in acetylation by at least one HAT. An increase in acetylation can be an increase in acetylation by a non-enzymatic acetylation mechanism.

Acetylation of histones can include, but is not limited to, acetylation at Lysine 5 of H2A, at Lysine 9 of H2A, at lysine 2 of H2B, at Lysine 5 of H2B, Lysine 12 of H2B, Lysine 15 of H2B, Lysine 20 of H2B, Lysine 9 of H3, Lysine 14 of H3, Lysine 18 of H3, Lysine 23 of H3, Lysine 27 of H3, Lysine 36 of H3, Lysine 56 of H3, Lysine 5 of H4, Lysine 8 of H4, Lysine 12 of H4, Lysine 16 of H4 or any combination thereof. Acetylation of tubulin can include, but is not limited to, acetylation at Lysine 40 of α-tubulin.

In some aspects, a disease can be a disease characterized by and/or associated with decreased post-translational modification (for example, but not limited to, hypo-acetylation). The present disclosure provides a method of restoring reduced post-translational modification by about 5%, or about 10%0, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100% back towards normality comprising administering to the subject a therapeutically effective amount of at least one compound of the present disclosure.

In some aspects, the present disclosure provides a method of restoring acetylation of proteins from a hypo-acetylated state comprising administering to the subject a therapeutically effective amount of at least one compound of the present disclosure.

The present disclosure provides a method of increasing crotonylation of proteins in a subject comprising administering to the subject a therapeutically effective amount of at least one compound of the present disclosure. The present disclosure provides a method of increasing crotonylation of histones in a subject comprising administering to the subject a therapeutically effective amount of at least one compound of the present disclosure.

An increase in crotonylation can be about a 10%, or about a 20%, or about a 30%, or about a 40%, or about a 50%, or about a 60%, or about a 70%, or about an 80%, or about a 90%, or about a 100%, or about a 110%, or about a 120%, or about a 130%, or about a 140%, or about a 150%, or about a 160%, or about a 170%, or about a 180%, or about a 190%, or about a 200%, or about a 250%, or about a 300%, or about a 350%, or about a 400%, or about a 450%, or about a 500%, or about a 600%, or about a 700%, or about an 800%, or about a 900%, or about a 1000% increase in crotonylation.

In multiple cardiac models of heart failure and ischemio-reperfusion injury, the use of an HDACis, which increase the acetylation of histones and nonhistone proteins, protected cardiac tissue and function by inhibition of pathological remodeling through autophagy which serves to protect cardiomyocytes during ischemia by resupplying energy and by reducing inflammation, oxidative stress and fibrosis. In murine models of colitis or chronic intestinal inflammation, HDACis were found to reduce inflammation and tissue damage by acetylation of transcription factors, increased mononuclear apoptosis, reduction of proinflammatory cytokine release, and increase in the number and activity of Regulatory T cells (Tregs). Tregs act as the nucleus in enforcing immune tolerance and also function to preserve intestinal homeostasis and participate in tissue repair. Immuron's oral IMM-124E approach to treating NASH focuses on stimulating Tregs. HDAC inhibition was found to attenuate inflammatory changes in a dextran sulfate sodium-induced colitis mouse model by suppressing local secretion of pro-inflammatory cytokines and chemokines and also by suppressing mobilization and accumulation of inflammatory cells.

Methods of Use—Neurological Diseases and Disorders

Increasing evidence suggests that metabolic alterations strongly influence the initiation and progression of neurodegenerative disorders. Accordingly, brain aging is accompanied by metabolic, morphological and neurophysiological changes leading to the development of neurodegenerative diseases like Alzheimer's disease (AD), Parkinson's disease (PD), Huntington's disease (HD), multiple sclerosis (Procaccini et al., 2016. Metabolism 65), Amyotrophic Lateral Sclerosis (ALS), Spinocerebellar Ataxia (SCA), diabetic retinopathy (Abcouwer et al., 2014 Ann NY Acad Sci 1311) and many others. Since each of these disorders involve impaired energy metabolism and/or adverse changes in the cerebral vasculature, a reduction in energy availability to neurons may contribute to increased vulnerability of the brain to develop neurodegenerative processes (Camandola and Mattson, 2017. EMBO J 36). Impaired mitochondrial health and function, impaired energy production and reduced mitochondrial membrane potential as well as diminished mitochondrial biogenesis (Wang et al., 2019 CNS Neurosc Therap 25; John and Beal, 2012 J Pharmacol Exp Ther 342; Hroudova et al., 2014 BioMed Res Int, Franco-Iborra et al., 2018 Front Neurosci, Li et al., 2017 J Neurosci Res 95), alterations in the reduction-oxidation (redox) homeostasis including elevated ROS production, impaired glutathione sythesis and reduced GSH/GSSG ratio (Cenini et al., 2019 Oxidative Medicine and Cellular Longevity; Aoyama and Nakaki, 2013 Int J Mol Sci 14; Rani et al., 2017 Front Neurol 8), elevated brain lactate (Ross et al., 2010 PNAS 107) and epigenetic changes in gene and protein regulation (Poulose and Raju, 2015 Biochim Biophys Acta 1852, Ronowska et al., 2018 Front Cell Neurosci 12; Serrano, 2018 Handbook of Clin Neurol 155) have been recognised as major drivers of the metabolic change and disease pathology.

Recently, a growing number of studies have demonstrated an anti-inflammatory activity for the Peroxisome Proliferator-Activated Receptor (PPARs) agonists, which in several pathological instances have been able to decrease the production of proinflammatory genes, including cytokines and chemokines (Klotz et al., 2007 J Immunol 178; Pascual et al., 2005 Nature 2005; Straus et al., 2007 Trends Immunol 28). Based on these observations, the therapeutic impact of PPARs agonists has been more recently studied also in chronic neurodegenerative disorders characterized by neuroinflammatory processes, like Multiple Sclerosis, Alzheimer's disease, Parkinson's disease and Amyotrophic Lateral Sclerosis (ALS) including to improve mitochondrial function (Qi et al., 2015 Int J Clin Exp Med 8; Corona and Duchen 2016 Free Radic Biol Med 100). In animal models of different neurodegenerative diseases, PPARs agonists proved to be efficacious in attenuating the manifestations of the pathology, and this effect was ascribed to their ability in reducing the production of proinflammatory mediators (Drew et al., 2006 Neurochem Int 49; Deplanque, 2004 Therapy 59) including Multiple Sclerosis (Bright et al., 2008 Expert Opin Ther Targets 12), Parkinson's Disease (Hirsch et al., 2003 Ann NY Acad Sci, Dehmer et al., 2004 J Neurochem 88), Alzheimer's disease (Sastre et al., 2006 PNAS 103; Heneka et al., 2007 Nat Clin Pract Neurol 3; Combs et al., 2000 J Neurosci 20; Yan et al., 2003 J Neurosci), ALS (Kieai et al., 2005 Exp Neurol 191; Schutz et al., 2005 J Neurosci 25) and stroke (Shimazu et al., 2005 Stroke 36; Sundararajan et al., 2005 Neuroscience 130; Zhao et al., 2005 Eur J Neurosci 22).

Oligodendrocyte progenitor cells (OPCs), also known as oligodendrocyte precursor cells, NG2-glia or polydendrocytes), are a subtype of glial cells in the CNS and are precursors to oligodendrocytes and may differentiate into neurons and astrocytes. The loss or lack of OPCs, and consequent lack of differentiated oligodendrocytes, is associated with a loss of myelination and subsequent impairment of neurological functions and has been observed in many neurological and neurodegenerative diseases (Ohtomo et al., 2018 Int J Mol Sci 19; Ettle et al., 2016 Mol Neurobiol 53; Alexandra et al., 2018 Dialogues in Clin Neurosci 20; Gregath and Lu, 2018 FEBS left 592; Ahmed et al., 2013 Brain Pathol 23) and multiple approaches have been taken towards remyelination through OPCs stimulation and/or transplantation with promising results to treat various neurological and neurodegenerative diseases (Zhang et al., 2019 Front Cell Neurosci 13; Dulamea, 2017 Neural Regen Res 12; Baaklini et al., 2019 Front Mol Neurosci 12; De La Fuente et al., 2017 Cell Rep 20; Li and Li, 2017 Neuronal Regen Res 12).

Emerging evidence has revealed that HIF-1α activity and expression of its downstream genes, such as VEGF and erythropoietin, are altered in a range of neurodegenerative diseases. At the same time, experimental and clinical evidence has demonstrated that regulating HIF-1α might ameliorate the cellular and tissue damage in the neurodegenerative diseases and HIF-1α as a potential medicinal target for the neurodegenerative diseases has been explored with promising results in ischemic stroke, in Alzheimer's (AD), Parkinson's (PD), Huntington's diseases (HD), and amyotrophic lateral sclerosis (ALS) (Zhang et al., 2011 Curr Med Chem 18).

The present disclosure provides a method of treating a neurodegenerative disease in a subject comprising administering to the subject a therapeutically effective amount of at least one compound of the present disclosure. The present disclosure provides at least one compound of the present disclosure for use in treating a neurodegenerative disease in a subject, wherein the at least one compound of the present disclosure is for administration to the subject in at least one therapeutically effective amount. The present disclosure provides a use of at least one compound of the present disclosure precursor for the manufacture of a medicament for treating a neurodegenerative disease in a subject, wherein the at least one compound of the present disclosure is for administration to the subject in at least one therapeutically effective amount.

The present disclosure provides a method of preventing a neurodegenerative disease in a subject comprising administering to the subject a therapeutically effective amount of at least one compound of the present disclosure. The present disclosure provides at least one compound of the present disclosure for use in preventing a neurodegenerative disease in a subject, wherein the at least one compound of the present disclosure is for administration to the subject in at least one therapeutically effective amount. The present disclosure provides a use of at least one compound of the present disclosure precursor for the manufacture of a medicament for preventing a neurodegenerative disease in a subject, wherein the at least one compound of the present disclosure is for administration to the subject in at least one therapeutically effective amount.

Neurodegenerative diseases include, but are not limited to, Alzheimer's disease, dementia, Parkinson's disease, Parkinson's disease-related disorders, Prion diseases, motor neuron diseases, Huntington's disease, Spinocerebellar ataxia (multiple types with varying characteristics), Spinal muscular atrophy, Amyotrophic lateral sclerosis (ALS), Batten disease, Argyrophilic grain disease, tauopathy, Pick's disease, FTD with parkinsonism linked to chromosome 17 (FTDP-17), Dementia lacking distinctive histology, progressive supranuclear palsy (PSP), corticobasal degeneration, multiple system atrophy, ataxias, familial British dementia, Dementia with Lewy Bodies (DLB), fronto-temporal degeneration (FTD), fronto-temporal dementia, primary progressive aphasia, and semeantic dementia, Adrenoleukodystrophy, Agenesis of the Corpus Callosum, Aicardi Syndrome, Alexander's disease, Alper's disease, Ataxia telangiectasia, Barth Syndrome, Bell's Palsy, Bovine spongiform encephalopathy (BSE), CADASIL, Canavan disease, Cerebellar Degeneration, Cervical spondylosis, Charcot-Marie-Tooth disease, Cockayne syndrome, Creutzfeldt-Jakob disease, Demyelinating diseases, Diabetic neuropathy, Epilepsy, Fabry's Disease, Fatal familial insomnia (FFI), Frontotemporal lobar degeneration, Gerstmann-Straussler-Scheinker syndrome (GSS), Glossopharyngeal neuralgia, Guillain-Barre syndrome, Inherited muscular atrophy, Invertebrate disk syndromes, Kennedy's disease, Krabbe's disease, Leigh's Disease, Lesch-Nyhan Syndrome, Machado-Joseph disease (Spinocerebellar ataxia type 3), Menkes Disease, Mitochondrial Myopathies and NINDS Colpocephaly, Multiple sclerosis, Muscular dystrophy, Myasthenia gravis, Neuroborreliosis, Niemann Pick disease, Parkinson's-plus diseases, Pelizaeus-Merzbacher Disease, Peripheral neuropathies, Photoreceptor degenerative diseases, Plexus disorders, Primary lateral sclerosis (PLS), Progressive bulbar palsy, Progressive muscular atrophy, Prophyria, Pseudobulbar palsy, Refsum's disease, Sandhoffs disease, Schilder's disease, Spielmeyer-Vogt-Sjogren-Batten disease (also known as Batten disease), Steele-Richardson-Olszewski disease, Subacute combined degeneration of spinal cord secondary to pernicious anemia, Tabes dorsalis, Thoracic outlet destruction syndromes, Trigeminal neuralgia, Wet or dry macular degeneration.

Alzheimer's disease (AD) is an irreversible, progressive brain disorder that slowly destroys memory and thinking skills leading to dementia. Damage to the brain starts a decade or more before memory and other cognitive problems appear. Toxic changes, including abnormal deposits of proteins forming extracellular amyloid-β (Aβ) plaques and intra-neuronal neurofibrillary tau protein type degenerative tangles, initially occur in the hippocampus, the part of the brain essential in forming memories. By the final stage of AD, damage becomes widespread, and the entire brain will have shrunken significantly. The "amyloid hypothesis" which maintains that the accumulation of Aβ is the primary driver of AD-related pathogenesis, including neurofibrillary tangle formation, synapse loss, and neuronal cell death remains as the predominant thinking for the root cause of the disease. Implicit in the amyloid hypothesis is that the Aβ peptide harbors neurotoxic properties and one hypothesis proposes that proinflammatory molecules, such as cytokines, in the AD brain produced principally by activated microglia clustered around senile plaques are responsible (Bamberger 2001). Growing evidence indicates that mitochondrial dysfunction is an early event during the progression of AD and one of the key intracellular mechanisms associated with the pathogenesis of this disease. Aβ accumulates in synapses and synaptic mitochondria, leading to abnormal mitochondrial dynamics and synaptic degeneration in AD neurons. However, the precise mechanism by which Aβ exerts these putative toxic effects on neurons remains unclear.

FDA approved cholinesterase inhibitors drugs directly increase synaptic acetylcholine while FDA approved Namenda is a NMDA antagonist. These drugs are used separately and in combination and may help reduce symptoms but they don't change the underlying disease process, are only effective for a subset of patients, and usually help for only a limited amount of time.

While defective cholinergic pathways may not be the root cause of AD, they do play a major role in the symptomology of the disease and changes have been observed early in course of the disease. Brain neurons, to support their neurotransmitter functions, require a much higher supply of glucose than quiescent cells. Glucose-derived pyruvate is a principal source of acetyl-CoA in all brain cells, through the pyruvate dehydrogenase complex (PDHC) reaction. Decreased PDHC activity and other enzymes of TCA cycle (e.g. α-ketoglutarate dehydrogenase complex (KGDHC)) have been reported in postmortem studies of AD brains yielding depression of acetyl-CoA synthesis. This attenuates metabolic flux through the TCA cycle, yielding energy deficits, reduced ATP production, disrupted NAD+/NADH homeostasis and inhibition of diverse synthetic acetylation reactions throughout the neuron which may directly affect acetylcholine synthesis, histone and nonhistone acetylations, and gene expression.

Epigenetic mechanisms including histone acetylation may also be involved in the pathology of AD. Evidence in rodents indicates that histone acetylation plays a role in rescuing learning and memory impairment. Studies have shown that histone acetylation is reduced in various neurodegenerative disorders, such as AD. In AD animal models, HDACis have shown some promise by showing improvement in learning and memory deficits by promoting neural stem cell generation and synaptic development and by increasing hippocampal nerve growth factor in transgenic AD mice, correlating with cognitive improvement. In addition, HDACis have been shown to lower levels of Aβ, and to improve learning and memory and ameliorate clinical symptoms in AD mice. Another HDAC inhibitor has demonstrated suppression of Aβ neurotoxicity by inhibiting microglial-mediated neuroinflammation.

Mitochondria are the energy-generating system of the cell all of which is necessary to fuel the numerous normal cell functions but also needed to protect the cell against the harmful inflammatory and oxidative stresses of the external environment and needed to remove toxic by products that form in deteriorating cells. Mitochondria are also regulating the pro-inflammatory response of the cell through activation of the inflammasome, a multi-protein complex on which proIL-1β and proIL-18 processing occurs. The inflammasome, detects the inflammatory aggregates of Aβ and inactive IL-1β, and responds by secreting caspase-1 (Casp-1) to activate IL-10 (Saco et al., 2014). Inflammasome activation is crucial in the pathogenesis of AD (Walsh et al., 2014) and has been proposed to be associated with mitochondria) dysfunction including: mitochondrial ROS (Zhou et al., 2011), mitochondrion-derived damage associated molecular patterns (mtDAMPs), such as oxidized mitochondrial DNA (Shimada et al., 2012; Wilkins et al., 2015), and translocation of cardiolipin from the inner to the outer mitochondrial membrane (Iyer et al., 2013). Additionally, extracellular ATP at various concentrations can activate microglia and induce neuroprotective or neurotoxic effects by expressing pro- or anti-inflammatory cytokines (Inoue, 2002; Davalos et al., 2005). Several studies in cell lines, genetic rodent models, and humans indicate that redox control might serve as a bidirectional link between energy metabolism, redox control and neuroinflammatory responses in the brain that might serve as an integrated mechanism for AD etiology (Yin et al., 2016). It has been reported that small molecule inhibitors of the NLRP3 inflammasome ameliorate AD pathology in animal models of AD (Dempsey et al., 2017; Yin et al., 2017). Further, CAD-31, an orally active and brain-penetrant neurotrophic drug that targets inflammation has been shown to reduce synaptic loss, normalize cognitive skills and enhance brain bioenergetics in genetic mouse models of AD (Daugherty et al., 2017).

Furthermore, Aβ plaques were found to deplete $Ca^{2+}$ ions storage in the endoplasmic reticulum (ER), resulting in cytosolic $Ca^{2+}$ overload, which causes a reduction in endogenous glutathione (GSH) levels and reactive oxygen species (ROS) accumulation (Ferreiro et al. 2009 Neurobiology of Disease 30). ROS-induced oxidative stress is one of the important contributing factors in the pathogenesis of AD as ROS overproduction is thought to play a critical role in the accumulation and deposition of Aβ peptides in AD (Bonda et al. 2010 Neuropharmacology 483). The important role of mitochondria) ROS has been also confirmed by the results obtained with the antioxidants, which prevented cognitive decline, Aβ peptide accumulation, microglia inflammation, and synaptic loss in a transgenic mouse model of AD (McManus et al. 2011 J Neurosci 31) and extended lifespan and improve health in a transgenic *Caenorhabditis elegans* model of AD (Ng et al. 2014 Free Radical Biology and Medicine 71). A reduction in complex IV activity has been demonstrated in mitochondria from the hippocampus and platelets of AD patients and in AD cybrid cells (Sheehan et al. 1997 J of Neuroscience 17; Du et al. 2010 PNAS 107). Aggregation of Aβ peptides leads to oxidative stress, mitochondrial dysfunction, and energy failure prior to the development of plaque pathology (Caspersen et al. 2005 FASEB Journal 19) and can reduce mitochondrial respiration in neurons and astrocytes via the inhibition of complexes I and IV, thus causing ROS production (Casley et al. 2002 J of Neurochemistry 80). A number of promising approaches have been demonstrated in targeting ROS and mitochondrial health for potential treatment of AD (Hroudova et al., 2014 BioMed Res Int).

It has recently been shown that both insufficiency in substrates entering into the oxidative phosphorylation system and functional disturbances in the electron transport system complex are responsible for the decrease in respiration observed in intact platelets of AD patients (Fisar et al. 2016 Current Alzheimer Resarch 13) and NAD+ supplementation with NAD+ precursor nicotinamide riboside (NR) to increase and restore cellular NAD+ levels and NAD+/NADH homeostasis was shown to have positive effects in the 3×TgAD/Polβ$^{+/-}$ mouse model of AD, that has a reduced cerebral NAD+/NADH ratio with impaired cerebral energy metabolism, and which is normalized by NR treatment. NR treated mice also exhibited lessened pTau pathology, reduced DNA damage, neuroinflammation, and apoptosis of hippocampal neurons and increased activity of SIRT3 in the brain (Hou et al. 2017 PNAS 115).

Lactic acid, a natural by-product of glycolysis, is produced at excess levels in response to impaired mitochondrial function, high-energy demand, and low oxygen availability. The enzyme involved in the production of β-amyloid peptide (Aβ) of Alzheimer's disease, BACE1, functions optimally at lower pH. Findings suggest that sustained elevations in lactic acid levels could be a risk factor in amyloidogenesis related to Alzheimer's disease through enhanced APP interaction with ER chaperone proteins and aberrant APP processing leading to increased generation of amyloid peptides and APP aggregates (Xiang et al. 2010 PILoS One 5).

Elevated serum methylmalonic acid, homocysteine and deficiency in cobalamin (vitamin B12) also strongly correlated with Alzheimer's disease and addressing this was suggested as a treatment strategy (Kristensen et al., 1993 Act Neurol Scand 87; Serot et al., J Neurol Neurosurg Psych 76).

PPARγ agonists improve both lipid and glucose metabolism, mainly by increasing peripheral insulin sensitivity, which ameliorates the metabolic dysfunction brought on by the diabetic pathophysiology. There is increasing evidence demonstrating the efficacy of PPARγ agonists for the treatment of AD. PPARγ activation suppresses the expression of inflammatory genes, which, clinically, has been shown to ameliorate neurodegeneration (Daynes et al. 2002 Nat Rev Immunol 2). Experimentally, treatment with PPARγ agonists has been associated with both reduced Aβ plaque load and improved behavioral outcomes in an animal model of AD (Landreth et al. 2008 Neurotherapeutics 5). Clinical studies have corroborated this finding; i.e. treatment with a PPARγ agonist reduces disease-related pathology, improves learning and memory, and enhances attention in AD patients (Landreth et al. 2008 Neurotherapeutics 5). The cyclooxygenase inhibitor Ibuprofen (iso-butyl-propanoic-phenolic acid), which can activate PPARγ, has been demonstrated to significantly reduce amyloid pathology and reduce microglial-mediated inflammation in a mouse model of AD, potentially via PPARγ signaling (Lihm et al., 2000 J Neurosci 20; Lehmann et al., 1997 J Biol Chem 272). In addition, PPARγ agonists have been shown to reduce Aβ plaque burden and Aβ42 (a specifically toxic form of Aβ) levels in the brain by approximately 20-25%, restore insulin responsiveness and lower glucocorticoid levels in mouse models of AD (Haneka et al., 2005 Brain; Pedersen et al., 2006 Exp Neurol 199). These results suggest that induction of PPARγ may be useful for the treatment of AD, a hypothesis greatly strengthened by both experimental and clinical studies demonstrating that rosiglitazone can attenuate learning and memory deficits in AD (Pedersen et al., 2006 Exp Neurol 199; Risner et al., 2006 Pharmacogenomics J 6; Cai et al., 2012 Cuff Alzheimer Res 9).

The insulin-like growth factor (IGF) 2 mRNA-binding protein 2 (IGF2BP2, also known as IMP-2) associates with IGF2 and other transcripts to mediate their processing and has been reported to participate in a wide range of physiological processes, such as embryonic development, neuronal differentiation, and metabolism. Its dysregulation is associated with insulin resistance, diabetes, and carcinogenesis and may potentially be a powerful biomarker and candidate target for relevant diseases (Cao et al., 2018 Stem Cells Int 2018).

Without being bound by theory, the present disclosure is based on, inter cilia, the discovery that by improving mitochondrial function, it the high energy requiring neurons, especially cholinergic ones, function better overall and are better able to provide sufficient amounts of acetylcholine, have a reduced level of inflammation and ROS production, improved energy and ATP production and restored NAD+/NADH homeostasis. Preserving a proper supply of acetyl-CoA in the diseased brain restores functional post-translational protein and (epigenetic) gene regulation, reduces lactic acidosis and attenuates the high susceptibility of cholinergic neurons to AD. For example, the FDA approved cholinesterase inhibitors improve symptoms in AD for some period of time so preserving acetylcholine levels is beneficial. Eventually these drugs lose their effectiveness as the neurons die.

In some aspects, the present disclosure provides a method of treating having Alzheimer's disease in a subject comprising administering to the subject a therapeutically effective amount of at least one compound of the present disclosure. The present disclosure provides a method of preventing Alzheimer's disease in a subject comprising administering to the subject a therapeutically effective amount of at least one compound of the present disclosure.

The present disclosure provides at least one compound of the present disclosure for use in treating Alzheimer's disease in a subject, wherein the at least one compound of the present disclosure is for administration to the subject in at least one therapeutically effective amount. The present disclosure provides a use of at least one compound of the present disclosure for the manufacture of a medicament for treating Alzheimer's disease in a subject, wherein the at least one compound of the present disclosure is for administration to the subject in at least one therapeutically effective amount.

The present disclosure provides at least one compound of the present disclosure for use in preventing Alzheimer's disease in a subject, wherein the at least one compound of the present disclosure is for administration to the subject in at least one therapeutically effective amount. The present disclosure provides a use of at least one compound of the present disclosure for the manufacture of a medicament for preventing Alzheimer's disease in a subject, wherein the at least one compound of the present disclosure is for administration to the subject in at least one therapeutically effective amount.

The present disclosure provides a method of improving mitochondrial health in a subject comprising administering to the subject a therapeutically effective amount of at least one compound of the present disclosure.

The present disclosure provides a method of reducing neuroinflammation in a subject comprising administering to the subject a therapeutically effective amount of at least one compound of the present disclosure.

The present disclosure provides a method of improving neuronal function comprising administering to the subject a therapeutically effective amount of at least one compound of the present disclosure.

The present disclosure provides a method of improving neuronal survival comprising administering to the subject a therapeutically effective amount of at least one compound of the present disclosure.

The present disclosure provides a method of inhibiting microglial-mediated neuroinflammation comprising administering to the subject a therapeutically effective amount of at least one compound of the present disclosure.

Parkinson's disease (PD) is progressive, irreversible neurodegenerative disease, typically manifesting with a characteristic movement disorder, consisting of bradykinesia, rigidity, rest tremor and postural instability, as well as depression, anxiety, sleep abnormalities, constipation and cognitive decline with dementia. Pathologically, PD is characterized by the presence of abnormal infra-neuronal aggregates of α-synuclein, termed Lewy bodies and Lewy neurites (Spillantini et al., 1997 Nature 388), selective loss of dopaminergic neurons of the substantia nigra pars compacta and widespread neurodegeneration, affecting the cortex and a number of brainstem regions (Selikhova et al., 2009 Brain 132; Kalia and Lang, 2015 Curr. Opin. Neurol. 26). Since the introduction of levodopa in the 1960s, there have been relatively few developments in the treatment of PD. There are no disease-modifying treatments, and the chronic use of levodopa results in significant adverse effects, which themselves constitute an important part of advanced PD (Kalia and Lang, 2015 Curr. Opin. Neurol. 26; Stoker et al. 2018 Front Neurosci).

Disrupted mitochondrial function and energy homeostasis is being increasingly recognised as a key contributing factor in the neurodegenerative process of PD. Multiple genes that are relevant for mitochondrial homeostasis have been unequivocally linked to the disease including presynaptic protein alpha-synuclein, the E3 ubiquitin ligase Parkin, PTEN-induced putative kinase 1 (PINK1), the protein deglycase DJ-1, Leucine-rich repeat kinase 2 (LRRK2), ATPase 13A2 (ATP13A2) and vacuolar protein sorting-associated protein 35 (VPS35) (Larsen et al., 2018 Cell Tissue Res 373).

Respiratory chain impairment is a key feature in PD patients and there is growing evidence that links proteins encoded by PD-associated genes to disturbances in mitochondrial function. (Grunewald et al. 2019 Progress in Neurobiology 177). Oxygen consumption profiles were determined with an extracellular flux analyser showed reduced rotenone-sensitive respiration in PD patient fibroblast cells (Ambrosi et al., 2014 Biochim Biphys Acta 1842). Mitochondrial ROS equilibrium was shown to be disturbed in PD (Bosco et al., 2006 Nat Chem Biol 2) with papers suggesting mitochondrial oxidative stress is mediated by aberrant dopamine metabolism (Blesa et al., 2015 Front Neuroanat 9). A study using induced pluripotent stem cell (iPSC)-derived neurons from human and mice with mutant or depleted DJ-1 demonstrated a species-specific relationship between dopamine oxidation mitochondrial dysfunction and lysosomal dysfunction in PD including disturbed mitochondrial respiration, increased ROS, decreased membrane potential, altered mitochondrial morphology and impaired autophagy (Burbulla et al., 2017 Science 357; Hirota et al., 2015 Autophagy 11).

Recently it has been demonstrated both in vitro as well as in vivo that PINK1 and Parkin regulate adaptive immunity and suppress antigen presentation from the mitochondria in immune cells via mitochondria-derived vesicles and not by mitophagy, suggesting autoimmune mechanism involvement in Parkinson's disease (Matheoud et al., 2016 Cell 166; Garetti et al., 2019 Front Immunol 10). New treatments targeting the immune system are being tested on PD patients and a recombinant drug recently demonstrated improvement in PD patients with increased Treg numbers and function compared to placebo group (Gendelman et al., 2017 NPJ Parkinson's Dis 3).

Tyrosine hydroxylase (TH), tetrahydrobiopterin (BH4)-dependent and iron-containing monooxygenase, catalyzes the conversion of L-tyrosine to L-3,4-dihydroxyphenylalanine (L-DOPA), which is the initial and rate-limiting step in the biosynthesis of catecholamines (DA, noradrenaline, and adrenaline). Reduction of TH expression results in diminished dopamine synthesis and leads to PD and was shown to be essential in the pathogenesy of PD. It has also been shown that dysregulation of TH activity will contribute to PD. For example, α-synuclein represses TH not only by inhibiting phosphorylation at Ser40 of TH, but also by stimulating protein phosphatase 2A activity, which decreases dopamine synthesis and leads to parkinsonism. A therapeutic strategy aimed to improve striatal TH expression in PD has received wide interest and early studies aiming to increase nigrostriatal TH expression demonstrated this as a promising therapy for PD (Zhu et al., 2012 CNS Neurol Disord Drug Targets 11; Nagatsu et al., 2019 J Neural Transam 126).

Because of its effects on the respiratory chain, which results in a loss of bioenergetic function, oxidative stress and impaired calcium homeostasis (Desai et al., 1996; Langston, 2017), MPTP/MPP+ has long been considered the "gold standard" for modelling PD in animals (Francardo, 2018 Behav Brain Res 352) and paraquat and rotenone are sometimes used as alternatives to induce parkinsonian phenotypes in animals to generate ROS and inhibit respiratory chain complex I. Contrary to MPTP, both pesticides cause alpha-synuclein aggregation and Lewy body-like inclusions but less reliably reproduce the PD-associated loss of dopamine in the nigrostriatal pathway (Jackson-Lewis et al., 2012 Parkinsonism relat disord. 18).

6-Hydroxydopamine (6-OHDA) is another neurotoxin used as a model for PD; it is a highly oxidizable dopamine analog, which can be captured through the dopamine transporter (DAT) and induces the production of hydrogen peroxide, superoxide and hydroxyl radicals, formation of hydrogen peroxide by the effect of monoamine oxidase, inhibition of the mitochondrial respiratory chain I complex and generation of reactive oxygen species (ROS). 6-OHDA has been used extensively as a PD model both in vitro as well as in vivo to support drug development for Parkinson's disease (Hernandez-Baltazar 2017 Exp Animal models of human diseases; Boix et al., 2018 Front Behav Neurosci 12; Simola et al., 2007 Neurotox Res 11; Chu and Han, 2018 Med Sci Monit 24).

Similarly as in Alzheimer's disease, elevated serum methylmalonic acid and homocysteine, particularly in patients with Peripheral neuropathy, correlated with Parkinson's disease (Toth et al., 2010 Ann Neurol 68; Park et al., 2017 Neurol Sci 38).

Several recent drug discovery efforts have shown great promosse in rescuing PD phenotype in vitro and in vivo (Liu et al. 2018 Am J Transl Res 10; Braungart et al., 2004 Neurodegener Dis 1; Guo et al. 2019 Front Neurol). Several antioxidants demonstrated effective reversal of the complex I deficit in PD (Winkler-Stuck et al., 2004 J Neurol Sci 220; Milanese et al., 2018 Antioxid Redox Signal 28) and other antioxidants were used with promising results in various other mechanistic in vitro, in vivo and in some cases even in early clinical trials, inclusing some via induction of PGC-1α and/or Nrf2 pathway (Biju et al., 2018 Neuroscience 380; Langley et al., 2017 Antioxid. Redox Signal 27; Shin et al., 2016 Mol Neurobiol 53; Xi et al., 2018 BBA 1864; Kaidery and Thomas 2018 Neurochem Int 117; Monti et al., 2016 PLoS One 11; Abuja et al., 2016 J. Neurosci 36). Drugs targeting cellular energy homeostasis (Mo et al., 2017 BMC Neurol), enhancement of mitophagy (Moors et al., 2017 Mol Neurodegener 12), modification of Ca2+ homeostasis (Guzman et al., 2018 J Clin Invest 128) and PPARg agonists (Wilkins and Morris, 2017 Cuff Pharm Des 23; Barbiero et al., 2014 Behav Brain Res 274) were also used in various preclinical studies and PD models with promising results.

The present disclosure provides a method of treating Parkinson's Disease in a subject comprising administering to the subject a therapeutically effective amount of at least one compound of the present disclosure. The present disclosure provides at least one compound of the present disclosure for use in treating Parkinson's Disease in a subject, wherein the at least one compound of the present disclosure is for administration to the subject in at least one therapeutically effective amount. The present disclosure provides a use of at least one compound of the present disclosure precursor for the manufacture of a medicament for treating Parkinson's Disease in a subject, wherein the at least one compound of the present disclosure is for administration to the subject in at least one therapeutically effective amount.

The present disclosure provides a method of preventing Parkinson's Disease in a subject comprising administering to the subject a therapeutically effective amount of at least one compound of the present disclosure. The present disclosure provides at least one compound of the present disclosure for use in preventing Parkinson's Disease in a subject, wherein the at least one compound of the present disclosure is for administration to the subject in at least one therapeutically effective amount. The present disclosure provides a use of at least one compound of the present disclosure precursor for the manufacture of a medicament for preventing Parkinson's Disease in a subject, wherein the at least one compound of the present disclosure is for administration to the subject in at least one therapeutically effective amount.

Huntington's disease (HD) is a progressive neurological disorder for which there are no disease-modifying treatments. HD is caused by a mutation encoding an abnormal expansion of trinucleotide (CAG)-encoded polyglutamine repeats in a protein called huntingtin (htt) and is manifested by progressive behavioral and motor impairment accompanied by cognitive decline.

Metabolic disregulation, energy impairment and altered mitochondrial morphology is a hallmark of HD and different abnormalities can be seen in different cell types. In peripheral tissues (lymphoblast, myoblast and fibroblasts) mitochondria present an enlarged morphology, while neurons are characterized by increased mitochondrial fragmentation. Altered mitochondrial structure correlates with mitochondrial dysfunction in all HD cells which is manifested by decreased electron transport chain activity, oxygen consumption, Ca2+ buffering and decreased ATP and NAD+ production as well as impaired apoptosis. Limited glucose uptake and reduced Glut1 and Glut3 transporters has also been observed in HD and PGC-1α, a master regulator of mitochondrial biogenesis, is decreased in HD (Jimenez-Sanchez et al., 2017 Cold Spring Harb Persp Med 7; Gamberino et al., 1996 J Neurochem 63, Dubinsky, 2017 J Huntingt Dis 6; Oliveira, 2010 J Neurochem 114). It has been proposed that mutant HTT (mHTT)-mediated mitochondrial abnormalities significantly affect striatal medium spiny neurons (MSNs) due to the high-energy demand of this neuronal subtype (Pickrell et al., 2011 J Neurosci 31). Dysregulation of two main transcription factors p53 and PGC-1α has been extensively studied in HD for their roles in mediating mitochondrial dysfunction, apoptosis, and neurodegeneration. In recent years there has been much effort in developing therapeutic strategies towards improving mitochondrial function such as those aimed to stabilize mitochondria by boosting the production of ATP and/or activation of AMPK pathway, activation of PGC-1α and PPARγ, decreasing membrane permeability and/or preventing oxidative damage (Reddy and Reddy, 2011 Cuff Alzheimer Res 8; Vazquez-Manrique et al., 2016 Hum Mol Genet 25; Tsunemi et al., 2012 Sci Transl Med 4; Cui et al., 2006 Cell 127; Corona and Duchen, 2016 Free Radic Biol Med 100, Intihar et al., Front Cell Neurosci 13, Zheng et al., 2018 Front Mol Neurosci 11).

The transcriptional activation and repression regulated by chromatin acetylation has been found to be impaired in HD pathology and a clear link correlating mhtt interaction with various HDACs has been established. For example it has been observed that inhibiting HDAC1 increases acetylated forms of mhtt and improved mint clearance from the cell. HDAC3 has been reported to be selectively toxic to neurons. It has been demonstrated that normal htt interacts with HDAC3 and protects neurons through its sequestration. In HD it has been shown that the mhtt interacts poorly with HDAC3, and hence de-repressing its neurotoxic activity and mhtt neurotoxicity was inhibited by the knock-down of HDAC3 and markedly reduced in HDAC3-deficient neurons. HDAC4 is traditionally associated with roles in transcription repression and recent findings have increasingly described a widespread peripheral organ pathology in HD, such as skeletal muscles atrophy and heart failure often associated with an increased HDAC4 expression. Interestingly, in addition to these, elevated HDAC4 levels have been shown in post mortem HD brains. It has been well demonstrated that HDAC4 genetic knockdown ameliorates the HD phenotype in mouse models. (Sharma and Taliyan 2015 Phar Res 100) and reduction of HDAC4 levels delayed cytoplasmic aggregate formation indifferent brain regions and rescued cortico-striatal neuronal synaptic function in HD mouse models accompanied by an improvement in motor co-ordination, neurological phenotypes and increased lifespan. HDAC6, Sirtuin1 and Sirtuin2 inhibition have also been linked to diminished mhtt toxicity. Further studies carried out in cell culture, yeast, *Drosophila* and rodent model(s) have indicated that HDAC inhibitors (HDACis) might provide useful class of therapeutic agents for HD. Clinical trials have also reported the beneficial effects of HDACis in patients suffering from HD. (Naia et al., 2017 J Neurosc 8; Sadri-Vakili and Cho, 2006 Cuff Alzheimer Res 3; Gray, 2011 Clin Epigenetics 2; Siebzehnriibl et al., 2018 PNAS 115; Suelves et al., 2017 Sci Reports 7; Xiang et al., 2018 Front Mol Neurosci)

The present disclosure provides a method of treating Huntington's disease in a subject comprising administering to the subject a therapeutically effective amount of at least one compound of the present disclosure. The present disclosure provides at least one compound of the present disclosure for use in treating Huntington's disease in a subject, wherein the at least one compound of the present disclosure is for administration to the subject in at least one therapeutically effective amount. The present disclosure provides a use of at least one compound of the present disclosure precursor for the manufacture of a medicament for treating Huntington's disease in a subject, wherein the at least one compound of the present disclosure is for administration to the subject in at least one therapeutically effective amount.

The present disclosure provides a method of preventing Huntington's disease in a subject comprising administering to the subject a therapeutically effective amount of at least one compound of the present disclosure. The present disclosure provides at least one compound of the present disclosure for use in preventing Huntington's disease in a subject, wherein the at least one compound of the present disclosure is for administration to the subject in at least one therapeutically effective amount. The present disclosure provides a use of at least one compound of the present disclosure precursor for the manufacture of a medicament for preventing Huntington's disease in a subject, wherein the at least one compound of the present disclosure is for administration to the subject in at least one therapeutically effective amount.

Ataxias are a heterogeneous group of disorders characterized by loss of coordination due to the degeneration of the neuronal networks closely linked to cerebellar function.

Friedreich's Ataxia is the most prevalent form of hereditary ataxia and is caused by downregulation of the FXN gene, which encodes frataxin, a mitochondria) protein involved in many cellular functions, including Fe—S cluster assembly, heme biosynthesis, iron homeosatsis and regulation of cellular antioxidant defenses. Friedreich ataxia displays a number of features of mitochondrial disfunction, including loss of mitochondrial DNA, decreased Complex I, II, and III, aconitase, and CoQ10 levels, with mitochondrial Fe overload, chronic oxidative stress, impaired glutathione homeostasis and glutathione deficiency (Cooper et al., 2009 Eur J Neurol 15; Sparaco et al., 2009 J Neurol Sci 287; Santos et al., 2010 Antiox Redox Sig 13) In addition to homozygous mutation consisting of a GAA repeat impeding the progress of RNA polymerase, FXN silencing has also been shown to be caused by histone hypoacetylation, which inhibits access of transcription factors to the FXN gene. Several studies have shown that HDAC inhibitors were able to reverse the FXN silencing and restore frataxin levels in both patient neurons and mouse models (Sorgani et al., 2014 Ann Neurol 76). Furthermore, studies have shown benefit by targeting ROS and oxidative stress (Meier et al., 2009 J Neurol 256). Decreased protein succinylation of TCA cycle enzymes is another post-translational modification that has been reported in Friedreich's Ataxia. The same study also showed a wide-ranging metabolic disregulation affecting glycolysis and lipid metabolism (Worth et al., 2015 Bioanalysis 7).

The spinocerebellar ataxia type 3 (SCA-3), also named Machado-Joseph disease is caused by mutation of ATXN3 gene, which encodes ataxin-3. The mutated protein can interact with and impair neuroprotective transcription factors and histone acetyltransferase activity, resulting in histone hypoacetylation and transcriptional defects. Literature suggests that HDAC inhibitor could prevent ataxin-3-Q79-induced hypoacetylation of H3 and H4 histones associated with proximal promoters of downregulated genes in the cerebella of SCA3 transgenic mice. Several *Drosophila* and mouse model studies have demonstrated effectiveness with HDAC inhibitors in ameliorating ataxic symptoms, reducing neuronal cell death and attenuating cytotoxicity (Yi et al., 2013 PLoS One 8; Chou et al., 2011 Neurobiol Dis 41; Lin et al., 2014 Int J Dev Neurosci 38; Wang et al. 2018 CNS Neurosci Ther 24)

Spinocerebellar ataxia type 1 (SCA-1) is a dominantly inherited neurodegenerative disorder caused by mutations in ATXN1. ATXN1 normally binds HDAC3, a class I HDAC, but in its mutated form it no longer inhibits the HDAC3, thereby resulting in repressed gene transcription through a decrease in histone acetylation at the promoters of genes.

Spinocerebellar ataxia type 7 (SCA-7) presents with autosomal-dominant cerebellar ataxia, representing the only SCA that affects the retina. The SCA7 gene product, ataxin-7, is an integral component of the mammalian SAGA-like complexes, a transcriptional coactivator complex that has histone acetyltransferase activity. In the murine model of SCA7 the ataxin-7 mutation leads to reduced levels of acetylated H3 on promoter/enhancer regions of photoreceptor genes, and thereby contributing to the transcriptional alterations observed in SCA7 retinal degeneration. This phenomenon occurs concomitantly with onset of retinal degeneration. Concerning cerebellar degeneration, a cultured SCA7 human astrocyte model has been used to study the effects of treatment with trichostatin A, but not other HDAC inhibitors, which partially restored RELN transcription.

The present disclosure provides a method of treating an ataxia disease in a subject comprising administering to the subject a therapeutically effective amount of at least one compound of the present disclosure. The present disclosure provides a method of preventing an ataxia in a subject comprising administering to the subject a therapeutically effective amount of at least one compound of the present disclosure. In some aspects, the ataxia can be, but is not limited to, Friedreich's Ataxia, spinocerebellar ataxia type 3 (SCA-3), Spinocerebellar ataxia type 1 (SCA-1) or Spinocerebellar ataxia type 7 (SCA-7).

Multiple sclerosis is a debilitating neurological pathology in which an abnormal response of the body's immune system is directed against the central nervous system, causing inflammation that damages myelin as well as the nerve fibers themselves, and the specialized cells that make myelin. Tecfidera (dimethyl fumarate), an FDA approved drug for treatment of psoriasis and multiple sclerosis has been known to have anti-oxidant properties through its activation a protein called Nrf2, however its anti-inflammatory mode of action has not been well understood until recently, when the direct molecular target of DMF has been identified confirming the mechanism how DMF is able to inhibit several pathways linked to a set of proteins called toll-like receptors (TLRs), which play a key role in innate immune system responses and cytokine production. It been well established that acylation, and in particular acetylation, determines the Toll-like receptor (TLR)-dependent regulation of pro-inflammatory Cytokines, including directly as well as indirectly through related regulatory and signaling pathways such as acetylation of mitogen-activated protein kinase phosphatase-1, which inhibits the Toll-like receptor signaling, reducing inflammation.

The present disclosure provides a method of treating multiple sclerosis in a subject comprising administering to the subject a therapeutically effective amount of at least one compound of the present disclosure. The present disclosure provides at least one compound of the present disclosure for use in treating multiple sclerosis in a subject, wherein the at least one compound of the present disclosure is for administration to the subject in at least one therapeutically effective amount. The present disclosure provides a use of at least one compound of the present disclosure for the manufacture of a medicament for treating multiple sclerosis in a subject, wherein the at least one compound of the present disclosure is for administration to the subject in at least one therapeutically effective amount.

The present disclosure provides a method of preventing multiple sclerosis in a subject comprising administering to the subject a therapeutically effective amount of at least one compound of the present disclosure. The present disclosure provides at least one compound of the present disclosure for use in preventing multiple sclerosis in a subject, wherein the at least one compound of the present disclosure is for administration to the subject in at least one therapeutically effective amount. The present disclosure provides a use of at least one compound of the present disclosure for the manufacture of a medicament for preventing multiple sclerosis in a subject, wherein the at least one compound of the present disclosure is for administration to the subject in at least one therapeutically effective amount.

Amyotrophic lateral sclerosis (ALS), also known as "Lou Gehrig's Disease" or "motor neuron disease" is a progressive and fatal neurodegenerative disorder that primarily affects motor neurons. A growing body of evidence shows disturbances in energy metabolism in ALS with remarkable vulnerability of motor neurons to ATP depletion (Vandoorne et al., 2018 Acta Neuropathol 135). ALS shares clinical and pathological features with several other adult-onset degenerative disorders, including, frontotemporal dementia (FTD). Neuroinflammation, elevated ROS production, elevated synaptic glutamate leading to excitotoxicity.

Mitochondrial dysfunction in the spinal cord is a hallmark of amyotrophic lateral sclerosis (ALS) with brain and systemic hypermetabolism having been observed in ALS patients, suggesting that energy-wasting mechanisms contribute to either ALS pathogenesis or adaptation to the disease. Numerous studies have investigated oxidative phosphorylation (OXPHOS) in different ALS models and revealed a global inhibition of the mitochondrial respiratory chain (Ghiasi et al., 2012 Neurol Res 34; Israelson et al., 2010 Neuron 67; Piexoto et al., 2013 Mol Cell Neurosci 57; Palamiuc et al., 2015 EMBO Mol Med 7; Szelechowski et al., 2018 Sci Reports 8); the same was shown in patients with inhibition of respiratory chain enzymes complex activity in patients' muscle (Wiedemann et al., J Neurol Sci 156) and spinal cord (Borthwick et al., 1999 Ann Neurol) samples. Animal model studies have shown defective OXPHOS system, reduced respiration and lower coupling, ATP depletion as well as increased fragmentation of the mitochondrial network in ALS mice motor neurons and reduced mitochondrial transmembrane potential (Szelechowski et al., 2018 Sci Reports 8). HADHA (a trifunctional enzyme complex involved in fatty acid oxidation) is significantly elevated in both ALS mice motor neurons as well as patient skin fibroblasts, with HADHA being positively regulated by PPARa, which was also shown to be elevated in the spinal cord of the SODG93A ALS mouse model (Qi et al., 2015 Int J Clin Exp Med 8).

Oxidative stress is another major contributory factor to ALS pathology and affects the presynaptic transmitter releasing machinery and motoneuron death (Rojas et al., 2015 Front Cell Neurosci). In ALS mouse models nerve terminals are sensitive to reactive oxygen species (ROS) suggesting that oxidative stress, along with compromised mitochondria and increased intracellular $Ca^{2+}$ amplifies the presynaptic decline in neuromuscular junctions. This initial dysfunction is followed by a neurodegeneration induced by inflammatory agents and loss of trophic support. Several molecules with antioxidant capabilities have shown good promisse as therapeutic approaches against ALS in animal models (Pollari et al., 2014 Front Cell Neurosci 8; Ari et al., 2014 PloS One).

Neuroinflammation is one of the major hallmarks of ALS. Nuclear factor-kappa B (NF-κB), a master regulator of inflammation, is upregulated in spinal cords of ALS patients and SOD1-G93A mice and inhibition of NF-κB signaling in microglia rescued MNs from microglial-mediated death in vitro and extended survival in ALS mice by impairing proinflammatory microglial activation (Frakes et al., 2014 Neuron 81).

Furthermore in ALS mice model microglia are activated and proliferating whereas the T cells and dendritic cells infiltrate into the spinal cord (Henkel et al., 2006 Mol Cel Neurosci 31). Moreover, there is marked increase in pro-inflammatory cytokines and enzymes, such as interleukin-6 (IL-6), monocyte chemoattractant protein-1 (MCP-1), IL-8, and cyclooxygenase-2 (Cox-2) (Sekizawa et al., 1998 J Neurol Sci 154; Almer et al., 2001 Ann Neurol 49; Elliott, 2001 Brain Res 95; Kuhle et al., 2009 Eur J Neurol 16). Astrocytes expressing mSOD1 are also prone to exhibit an activated pro-inflammatory state (Hensley et al., 2006 J Neuroinflammation 3; Di Giorgio et al., 2008 Cell Stem Cell 3; Marchetto et al., 2008 Cell Stem Cell 3). Activated pro-inflammatory M1 microglia cause ROS and glutamate excitotoxicity induced motoneuron injury and death (Zhao et al., 2004 J Neuropathol Exp Neurol 63). MSOD1 induced oligodendrocyte dysfunction drives demyelination in the spinal cord and accelerates motoneuron degeneration (Kang et al., 2013 Nat Neurosci 16). Immune responses are also activated in peripheral tissues of ALS patients (Mantovani et al., 2009 J Neuroimmunol 210). Regulatory T (Treg) cells lower neuroinflammation through microglia by inducing secretion of anti-inflammatory cytokines IL-10 and transforming growth factor TGF-β (Kipnis et al., 2004 PNAS 101; Mantovani et al., 2009 J Neuroimmunol 210). In ALS patients, elevated levels of Treg cells and CD4 T cells in blood correlate with slow disease progression (Beers et al., 2011 Brain 134).

Several studies have demonstrated an anti-inflammatory activity for the Peroxisome Proliferator-Activated Receptor (PPARs) agonists, which have been able to decrease the production of proinflammatory mediators in ALS transgenic mouse model. In these studies, administration of Pioglitazone, before the onset of the symptoms, improved the motor performance and reduced the weight loss, attenuated motor neuron death and increased the survival delaying the onset. These effects were associated to reduced microglial activation and gliosis in the spinal cord as well as decreased production of proinflammatory mediators like iNOS, NF-kβ and COX2 (Kieai et al., 2005 Exp Neurol 191; Schutz et al., 2005 J Neurosci 25).

The present disclosure provides a method of treating ALS in a subject comprising administering to the subject a therapeutically effective amount of at least one compound of the present disclosure. The present disclosure provides at least one compound of the present disclosure for use in treating ALS in a subject, wherein the at least one compound of the present disclosure is for administration to the subject in at least one therapeutically effective amount. The present disclosure provides a use of at least one compound of the present disclosure for the manufacture of a medicament for treating ALS in a subject, wherein the at least one compound of the present disclosure is for administration to the subject in at least one therapeutically effective amount.

The present disclosure provides a method of preventing ALS in a subject comprising administering to the subject a therapeutically effective amount of at least one compound of the present disclosure. The present disclosure provides at least one compound of the present disclosure for use in preventing ALS in a subject, wherein the at least one compound of the present disclosure is for administration to the subject in at least one therapeutically effective amount. The present disclosure provides a use of at least one compound of the present disclosure for the manufacture of a medicament for preventing ALS in a subject, wherein the at least one compound of the present disclosure is for administration to the subject in at least one therapeutically effective amount.

Epilepsy is a neurological disorder in which brain activity becomes abnormal, causing seizures or periods of unusual behavior, sensations, and sometimes loss of awareness. HDAC inhibitor valproic acid has been used as an anticonvulsant and mood-stabilizer drugs in the treatment of epilepsy and bipolar disorder as well as major depression and Schizophrenia without much knowledge of mode of action. Additionally, stringent ketogenic diet has been shown to be very positive for patients with epilepsy and although the exact mechanisms of the diet are unknown, ketone bodies have been hypothesized to contribute to the anticonvulsant and antiepileptic effects and provide an efficient source of Acetyl-CoA for the neural cells. A role for cytosolic Acyl-CoA thioester hydrolase (ACOT) in neurological function was recently suggested by the discovery of low to absent levels of an isoform of ACOT7 in the hippocampus of patients with mesial temporal lobe epilepsy. A very characteristic phenotype of epilepsy with mild intellectual disability, and abnormal behavior was demonstrated also in ACOT7 $N^{-/-}$ mouse model. Cytosolic Acyl-CoA thioester hydrolases are necessary to release CoA from cytosolic Acyl-CoA and allow carboxylic acids to be transported to mitochondria for further metabolism. In epilepsy patients with aberrant ACOT7 levels the cytosolic Acyl-CoAs cannot be processed efficiently enough and thus are sequestering the free CoA.

Epilepsy also features NFκB-induced upregulation of NOS II gene expression with decrease of Complex I activity and increased Complex-III-dependent production of epileptic brain mitochondria; seizure-related ROS formation and a protective effect of acetyl-1-carnitine indicate concomitant oxidative stress in epilepsy. Decrease of lipoic acid synthetase suggests inhibition of TCA cycle along with defective mitochondrial energy metabolism (Chuang et al., 2010 Neur Taiw 19; Malinska et al., 2010 BBA Bioenergetics 1797; Mayr et al., 2011 Am J Hum Gen 89; Garcia-Gimenez et al., 2013 Free Rad Biol Med 65).

The present disclosure provides a method of treating epilepsy in a subject comprising administering to the subject a therapeutically effective amount of at least one compound of the present disclosure. The present disclosure provides at least one compound of the present disclosure for use in treating epilepsy in a subject, wherein the at least one compound of the present disclosure is for administration to the subject in at least one therapeutically effective amount. The present disclosure provides a use of at least one compound of the present disclosure for the manufacture of a medicament for treating epilepsy in a subject, wherein the at least one compound of the present disclosure is for administration to the subject in at least one therapeutically effective amount.

The present disclosure provides a method of preventing epilepsy in a subject comprising administering to the subject a therapeutically effective amount of at least one compound of the present disclosure. The present disclosure provides at least one compound of the present disclosure for use in preventing epilepsy in a subject, wherein the at least one compound of the present disclosure is for administration to the subject in at least one therapeutically effective amount. The present disclosure provides a use of at least one compound of the present disclosure for the manufacture of a medicament for preventing epilepsy in a subject, wherein the at least one compound of the present disclosure is for administration to the subject in at least one therapeutically effective amount.

Schizophrenia is a complex disorder that is influenced by both genes and environment and can result in presenting an aberrant epigenetic mechanism. The hallmark of these epigenetic mechanisms is monitored through the altered state of histone modifications and other post-translational modifications and miRNAs. The dynamic nature and reversibility of the epigenetic marks raise the possibility that the epigenetic defects can be corrected by therapeutic interventions addressing these epigenetic aberrations. Several lines of evidence suggest that histone modifications in the candidate genes of schizophrenia specific loci may contribute to the pathogenesis of prefrontal dysfunction. Histone H3K9K14 levels were shown to be hypoacetylated at the promoter regions of GAD67, HTR2C, TOMM70A and PPM1E genes in young subjects with schizophrenia. Microarray analysis of a postmortem brain collection of 19 subjects with schizophrenia compared with 25 controls revealed significantly increased expression of the class I histone deacetylase, in prefrontal cortex (on average 30-50%). Recent findings in preclinical model systems corroborate that epigenetic modulation might emerge as a promising target for the treatment of cognitive disorders.

An extensive body of evidence points to the occurrence of oxidative stress, nitrosative stress, and proinflammatory condition in schizophrenia. In particular excess lipid peroxidation, damage to proteins and DNA, decreased plasma total antioxidant status, and antioxidant levels were observed in schizophrenia patients, along with autoimmune responses, as excess IL-6 and PCC levels. An involvement of mitochondria) disfunction in schizophrenia pathogenesis is shown by a recent report on a significant decrease in Complex I activity and suggested by the abovementioned decrease in CoQ10 levels (Anderson et al., 2013 Prog Neur Psy Biol Psy 42; Pedrini et al., 2012 J Pry Res 46; kulak et al., 2012 Antiox Redox Sig 18; Zhang et al., 2012 Schiz Res 139 1-3; Gubert et al., 2013 J Psych Res 47).

The present disclosure provides a method of treating schizophrenia in a subject comprising administering to the subject a therapeutically effective amount of at least one compound of the present disclosure. The present disclosure provides at least one compound of the present disclosure for use in treating schizophrenia in a subject, wherein the at least one compound of the present disclosure is for administration to the subject in at least one therapeutically effective amount. The present disclosure provides a use of at least one compound of the present disclosure for the manufacture of a medicament for treating schizophrenia in a subject, wherein the at least one compound of the present disclosure is for administration to the subject in at least one therapeutically effective amount.

The present disclosure provides a method of preventing schizophrenia in a subject comprising administering to the subject a therapeutically effective amount of at least one compound of the present disclosure. The present disclosure provides at least one compound of the present disclosure for use in preventing schizophrenia in a subject, wherein the at least one compound of the present disclosure is for administration to the subject in at least one therapeutically effective amount. The present disclosure provides a use of at least one compound of the present disclosure for the manufacture of a medicament for preventing schizophrenia in a subject, wherein the at least one compound of the present disclosure is for administration to the subject in at least one therapeutically effective amount.

Major depressive disorder is a chronic, remitting syndrome involving widely distributed circuits in the brain. Stable alterations in gene expression that contribute to structural and functional changes in multiple brain regions are implicated in the heterogeneity and pathogenesis of the illness. Epigenetic events that alter chromatin structure to regulate programs of gene expression have been associated with depression-related behavior, antidepressant action, and resistance to depression or 'resilience' in animal models, with increasing evidence for similar mechanisms occurring in postmortem brains of depressed humans.

The role of epigenetics and more specifically histone acetylation in depression comes primarily from chronic stress derived animal models. Certain behavioral alterations induced by chronic stress are long-lasting and can be effectively reversed by a chronic treatment antidepressant regimen that could be considered comparable with that used in depressed patients. Chronic stress paradigms involve prolonged exposure to either physical stressors or bouts of social subordination that produce anhedonia-like symptoms, characterized by a decrease in reward-related behaviors such as preferences for sucrose or high fat diets and social interaction. The potential importance of histone acetylation in depression was initially suggested by observations that HDAC inhibition alone, or in combination with, antidepressant treatment ameliorated depression-like behaviors in rodents. Changes in brain-derived neurotrophic factor (BDNF) and nerve growth factor (VGF) in the prefrontal cortex, hippocampus, and nucleus accumbens have been implicated in depressed humans and/or following chronic stress in rodent models and can be reversed by chronic treatment with antidepressants (Sun et al, 2013 Neuropsychopharmacology 38). Histone acetylation has been found to be persistently increased in the nucleus accumbens (NAc; and HDAC2 reduced) in a chronic social defeat stress animal model. These changes were also observed in the NAc of depression patients in postmortem examination. Similarly, a large body of literature has suggested that histone acetylation in the hippocampus has an overall adaptive role in stress and antidepressant responses.

The present disclosure provides a method of treating major depressive disorder in a subject comprising administering to the subject a therapeutically effective amount of at least one compound of the present disclosure. The present disclosure provides at least one compound of the present disclosure for use in treating major depressive disorder in a subject, wherein the at least one compound of the present disclosure is for administration to the subject in at least one therapeutically effective amount. The present disclosure provides a use of at least one compound of the present disclosure for the manufacture of a medicament for treating major depressive disorder in a subject, wherein the at least one compound of the present disclosure is for administration to the subject in at least one therapeutically effective amount.

The present disclosure provides a method of preventing major depressive disorder in a subject comprising administering to the subject a therapeutically effective amount of at least one compound of the present disclosure. The present disclosure provides at least one compound of the present disclosure for use in preventing major depressive disorder in a subject, wherein the at least one compound of the present disclosure is for administration to the subject in at least one therapeutically effective amount. The present disclosure provides a use of at least one compound of the present disclosure for the manufacture of a medicament for preventing major depressive disorder in a subject, wherein the at least one compound of the present disclosure is for administration to the subject in at least one therapeutically effective amount.

The present disclosure provides a method of reversing acetylation patterns induced by major depressive disorder in a subject comprising administering to the subject a therapeutically effective amount of at least one compound of the present disclosure. The present disclosure provides at least one compound of the present disclosure for use in reversing acetylation patterns induced by major depressive disorder in a subject, wherein the at least one compound of the present disclosure is for administration to the subject in at least one therapeutically effective amount. The present disclosure provides a use of at least one compound of the present disclosure for the manufacture of a medicament for reversing acetylation patterns induced by major depressive disorder in a subject, wherein the at least one compound of the present disclosure is for administration to the subject in at least one therapeutically effective amount.

The present disclosure provides a method of augmenting the therapeutic effect of an anti depressant compound in a subject comprising administering to the subject a combination of a therapeutically effective amount of the anti-depressant compound and a therapeutically effective amount of at least one compound of the present disclosure. The present disclosure provides at least one compound of the present disclosure for use in augmenting the therapeutic effect of an anti-depressant compound in a subject, wherein the at least one compound of the present disclosure is for administration to the subject in at least one therapeutically effective amount. The present disclosure provides a use of at least one compound of the present disclosure for the manufacture of a medicament for augmenting the therapeutic effect of an anti-depressant compound in a subject, wherein the at least one compound of the present disclosure is for administration to the subject in at least one therapeutically effective amount.

Anti-depressant compounds can include, part are not limited to, selective serotonin reuptake inhibitors, serotonin-norepinephrine reuptake inhibitors, serotonin modulators and stimulators, serotonin antagonists and reuptake inhibitors, norepinephrine reuptake inhibitors, norepinephrine-dopamine reuptake inhibitors, tricyclic antidepressants, tetracyclic antidepressants, monoamine oxidase inhibitors and atypical antipsychotics. Anti-depressant compounds can include, part are not limited to, Citalopram, Escitalopram, Paroxetine, Fluoxetine, Fluvoxamine, Sertraline, lndalpine, zimelidine, Desvenlafaxine, Duloxetine, Levomilnacipran, Milnacipran, Venlafaxine, Vilazodone, Vortioxetine, Nefazodone, Trazodone, Etoperidone, Reboxetine, Teniloxazine, Viloxazine, reboxetine, Atomoxetine, Bupropion, Amineptine, Methylphenidate, Lisdexamfetamine, Amitriptyline, Amitriptylinoxide, Clomipramine, Desipramine, Dibenzepin, Dimetacrine, Dosulepin, Doxepin, Imipramine, Lofepramine, Melitracen, Nitroxazepine, Nortriptyline, Opipramol, Pipofezine, Protriptyline, Trimipramine, Butriptyline, demexiptiline, fluacizine, imipraminoxide, iprindole, metapramine, propizepine, quinupramine, Tiazesim, tofenacin, Amineptine, tianeptine, Amoxapine, Maprotiline, Mianserin, Mirtazapine, Setiptiline, Isocarboxazid, Phenelzine, Tranylcypromine, benmoxin, iproclozide, iproniazid, mebanazine, nialamide, octamoxin, phenizprazine, phenoxypropazine, pivhydrazine, safrazine, Selegiline, Caroxazone, Metralindole, Moclobemide, Pirlindole, Toloxatone, Eprobemide, minaprine, Bifemelane, Amisulpride, Lurasidone, Quetiapine, Agomelatine, Ketamine, Tandospirone, Tianeptine, α-Methyltryptamine, Etryptamine, Indeloxazine, Medifoxamine, Oxaflozane, Pivagabine, Ademetionine, *Hypericum* perforatum, Oxitriptan, Rubidium chloride, Tryptophan, Aripiprazole, Brexpiprazole, Lurasidone, Olanzapine, Quetiapine, Risperidone, Buspirone, Lithium, Thyroxine, Triiodothyronine, Pindolol, Amitriptyline/perphenazine, Flupentixol/melitracen, Olanzapine/fluoxetine, Tranylcypromine/trifluoperazine or any combination thereof.

Methods of Use—Cancer

The hallmarks of cancer comprise six biological capabilities acquired during the multistep development of human tumors: sustaining proliferative signaling, evading growth suppressors, resisting cell death, enabling replicative immortality, inducing angiogenesis, and activating invasion and metastasis (Hanahan 2011 Cell 144(5)). Mitochondria, are at the crossroads of energy metabolism and metabolic and signaling pathways, and regulaiton of cell life and death (cell growth and proliferation vs autopghagy and apoptosis). Malignant cell transformation and tumor progression are associated with alterations in glycolysis, fatty acid synthesis, amino acid delivery and production of reactive oxygen species. Numerous promising agents targeting altered metabolic pathways are being assessed in preclinical development as well as in Phase I-III clinical trials (Sborov et al. 2014 Epert Opin Investig Drugs 24).

Proliferating tumor cells show increased glycolysis and convert the majority of glucose to lactate, even in normoxic conditions. This reprogramming of energy metabolism is known as the Warburg effect and is an emerging hallmark of cancer development (Warburg 1956 Science 123; Pavlova 2016 Cell Metab 23; Vander Heiden 2017 Cell 168). The metabolic shift to glycolysis allows the cancer cells to utilize glycolytic intermediates for the pentose phosphate pathway, serine biosynthesis, and lipid biosynthesis, as opposed to complete oxidation by mitochondrial respiration. Multiple approaches have been taken recently to target inhibition of glycolysis as an emerging approach to combat cancer (Akins et al. 2018 Curr Top Med Chem 18; Xu et al. 2005 65; Pelicano et al. 2006 Oncogene 25; Gill et al. 2016 BBA Reviews on Cancer 1866).

Hypoxia-inducible factor 1 alpha (HIF-1α) orchestrates cellular adaptation to low oxygen and nutrient-deprived environment and drives progression to malignancy in human solid cancers. Its canonical regulation involves prolyl hydroxylases (PHDs), which in normoxia induce degradation, whereas in hypoxia allow stabilization of HIF-1α (Dengler et al. 2014 Crit Rev Biochem Biol 49; Semenza 2004 Physiology 19). However, in certain circumstances, HIF-1a regulation goes beyond the actual external oxygen levels and involves PHD-independent mechanisms including stabilization of HIF-1α in normoxia by succinate, allosteric inhibitor of PHD (Selak 2005 Cancer Cell 7), pyruvate and lactate are suggested to promote pseudohypoxia (Sonveaux et at 2012 PloS One 7; Lu et al. 2002 J Biol Chem 277; Jung et al. 2011 Int J Ohcol 38), whereas the PHD substrate alpha-ketoglutarate (αKG), as well as PHD co-factors ascorbate and $Fe^{2+}$, were all shown to confer a dose-dependent HIF-1α destabilization in hypoxia (Pan et al. 2007 Mol Cell Biol 27). As a solid cancer progresses, transformed cells usually activate HIF-1-mediated adaptations to hypoxic stress, which include downregulation of mitochondrial respiration to decrease the cells' requirement for oxygen (Puissegur et al. 2011 Cell Ceadh Differ 18; Zhang et al. 2008 J Biol Chem 283; Papandreou et al. 2006 Cell Metab 3). Inhibition of HIF-1α was shown as sufficient to block tumor growth both in vitro as well as in transgenic mouse models (Ryan et at 2000 Cancer Res 60; Liao et al. 2007 Cancer Res 67).

Additionally, PGC-1α is downregulated in HIF-1α-activated renal cell carcinomas, reinforcing a switch to glycolytic metabolism in low oxygen conditions (LaGory et al., 2015; Zhang et al., 2007). PGC-1α-dependent mitochondrial biogenesis may contribute to tumor metastatic potential. Proteomic analysis identified upregulation of mitochondrial proteins involved in metabolism and biogenesis upon low-attachment culture conditions (Lamb et al., 2014). and increased mitochondrial mass co-enriched with tumor-initiating activity in patient-derived breast cancer lines, which could be blocked by PGC-1α inhibition (De Luca et al., 2015). These findings remain relevant in vivo, as circulating tumor cells (CTCs) developed from primary orthotopic breast tumors show increased mitochondrial biogenesis and respiration, with PGC-1a silencing decreasing CTCs and metastasis (LeBleu et al., 2014).

Glutamine can be a substrate for TCA cycle oxidation and a starting material for macromolecule synthesis (DeBerardinis et al., 2007). The amide nitrogen on glutamine is used in nucleotide and amino acid synthesis, and glutamine-derived carbons are used in glutathione, amino acid, and lipid synthesis. Catabolism of glutamine, termed glutaminolysis, is elevated in many glutamine-addicted tumors and is often driven by c-Myc upregulation of glutaminase (GLS), which converts glutamine to glutamate and ammonia (Stine et al., 2015). Glutamate is oxidized to a-ketoglutarate (a-KG) by GDH, providing an entry point into the TCA cycle. This process is inhibited by the mitochondrial-localized sirtuin, SIRT4, a tumor suppressor in multiple cancer models. SIRT4 expression in B cell lymphoma cells downregulates glutamine uptake and inhibits growth, whereas SIRT4 loss in an Em-myc B cell lymphoma model increases glutamine consumption and accelerates tumorigenesis (Jeong et al., 2014). In addition, transaminases utilize glutamate nitrogen to couple a-KG production to synthesis of non-essential amino acids, and tumor cells can utilize this pathway to support biosynthesis and redox homeostasis. For example, oncogenic K-Ras reprograms glutamine metabolism by transcriptional downregulation of GDH1 and upregulation of GOT1, the aspartate transaminase, to produce cytosolic oxaloacetate, which can ultimately lead to an increase in NADPH/NADP+ ratio through conversion to pyruvate (Son et al., 2013). Because glutaminolysis plays a critical role in cancer cell metabolism, cell signaling, and cell growth, it has been considered as a therapeutic target in many cancers and several molecules have shown positive results in various preclinical models and/or are currently under clinical development. Benzylserine and L-γ-glutamyl-p-nitroanilide (GPNA) inhibit the activity of a facile glutamine transporter, ASCT2, and suppress tumor cell proliferation in vitro and in vivo. The emergence of smallmolecule inhibitors has led to new avenues of metabolism-targeted drugs that block GLS activity and glutaminolysis. Preclinical trials of these drugs have shown some promise for metabolic therapies in breast cancer and lymphoma (Yang et al. 2017, Annu Rev Biomed Eng 19; Huang et al., J Biol Chem 2018 293).

Inflammation has been recognized as a hallmark of cancer and is known to play an essential role in the development and progression of most cancers, even those without obvious signs of inflammation and infection. Nuclear factor-κB (NF-κB), a transcription factor that is essential for inflammatory responses, is one of the most important molecules linking chronic inflammation to cancer, and its activity is tightly regulated by several mechanisms (Taniguchi 2018 Nat Rev Immunol 18). Activation of NF-κB is primarily initiated by bacterial endotoxins such as lipopolysaccharide and pro-inflammatory cytokines such as tumour necrosis factor and IL-1. NF-κB activation occurs in cancer cells and in the tumour microenvironments of most solid cancers and haematopoietic malignancies. NF-κB activation induces various target genes, such as pro-proliferative and anti-apoptotic genes, and NF-κB signalling crosstalk affects many signalling pathways, including those involving STAT3, API, interferon regulatory factors, NRF2, Notch, WNT-β-catenin and p53 (Taniguchi 2018 Nat Rev Immunol 18). In addition to enhancing cancer cell proliferation and survival, NF-κB and inflammation promote genetic and epigenetic alterations, cellular metabolic changes, the acquisition of cancer stem cell properties, epithelial-to-mesenchymal transition, invasion, angiogenesis, metastasis, therapy resistance and the suppression of antitumour immunity. The prevalence of NF-κB activation in cancer-related inflammation makes it an attractive therapeutic target and its inhibition has shown promisse in multiple in vitro and in vivo studies (Taniguchi 2018 Nat Rev Immunol 18; Xia et al. 2014 Cancer Immunol Res 2; Park 2017 Pharmacogenomics 18).

As part of the immune system, macrophages have a central role in immune response and inflammation and research studies have shown that infiltration of macrophages can account for >50% of the tumor mass in some cancers, aid in metastasis by inducing angiogenesis, and signify a poor prognosis. Macrophages that migrate to the tumor site, remain there, and aid in angiogenesis and metastasis are termed tumor associated macrophages (TAMs) and are thought to express an M2 phenotype (Weagel et al. 2015 J Clin Cell Immunol 6). In the context of cancer, classically activated M1 macrophages are thought to play an important role in the recognition and destruction of cancer cells, and their presence usually indicates good prognosis. After recognition, malignant cells can be destroyed through several mechanisms, which include contact-dependent phagocytosis and cytotoxicity (i.e. cytokine release such as TNF-α) (Sinha et al. 2005 J Immunol 174). Environmental signals such as the tumor microenvironment or tissue-resident cells, however, can polarize M1 macrophages to alternatively activated M2 macrophages. In vivo studies of murine macrophages have shown that macrophages are plastic in their cytokine and surface marker expression and that repolarizing macrophages to an M1 phenotype in the presence of cancer can help the immune system reject tumors (Guiducci et al. 2005 Cancer Res 65). Cells exposed to a tumor microenvironment behave differently. For example, tumor associated macrophages found in the periphery of solid tumors are thought to help promote tumor growth and metastasis, and have a M2-like phenotype (Mantovani et al. 2008 Nature 454). Because the tumor mass contains a great number of M2-like macrophages, TAMs can be used as a target for cancer treatment. Reducing the number of TAMs or polarizing them towards an M1 phenotype can help destroy cancer cells or impair tumor growth (Gazzaniga et al. 2007 J Invest Dermatol 127; Lo et al. 2006 J Clin Invest 116; Zeisberger et al. 2006 J Clin Invest 116; Weagel et al. 2015 J Clin Cell Immunol 6; Geeraerts et al. 2017 Front Immunol 8; Brown et al. 2017 Clin Cancer Res 23).

Although most malignant tumors can be recognized by the host immune-surveillance defensive system, namely natural killer (NK) and T-cells, cancer cells evolve to acquire genetic instabilities and other associated "hallmarks" that can enable immune evasion and persistent growth (Hanahan 2011 Cell 144). Natural killer (NK) cells are innate immune cells endowed with potent cytolytic activity against tumors, and meanwhile act as regulatory cells for the immune system. NK cells can eliminate a variety of abnormal or stressed cells without prior sensitization, and even preferentially kill stem-like cells or cancer stem cells. Upon forming immune synapses with target cells, NK cells release preformed cytolytic granules, including perforin, and granzymes, of which function is to induce cell lysis. Several studies have successfully exploited adoptive transfer of NK cells against various tumors, especially hematological malignancies and many NK-targeted programs are currently undergoing preclinical development and/or clinical trials (O'Sullivan et al. 2015 Immunity 43; Vivier et al. 2011 Science 331; Grossenbacher et al. 2016 J ImmunoTher Cancer 4, Hu et al. 2019 Front Immunol 10, Chen et al. 2019 Cancers 11, Lorenzo-Herrero 2019 Cancers 11; Barrow 2019 Cancers 11, Paul and Lal, 2017 Front Immunol 8). The efficacy of NK cell-mediated immunotherapy can be enhanced by immune stimulants such as cytokines and antibodies, and adoptive transfer of activated NK cells expanded ex vivo. In addition, NK cells can arm themselves with chimeric antigen receptors (CARs), which may greatly enhance their antitumor activity (Hu et al. 2019 Front Immunol 10).

Furthermore, immune checkpoint receptor pathways represent a major class of "immune synapse," a cell-cell contact that suppresses T-lymphocyte effector functioning and tumors can exploit these mechanisms to evade immune detection. Hence, such mechanisms provide opportunities for immunotherapy intervention. A plethora of such therapies are currently in preclinical development and clinical application. These include T-cell immune receptor modulating monoclonal antibodies (mAb's), vaccines, adoptive cellular therapy (ACT), engineered oncolytic viruses (OVs), small-molecule targeting drugs, and cytokine-based adjuvant therapies. Checkpoint inhibitors, both as monotherapies and in combination, have generated significant therapeutic efficacies at least in subpopulations of cancer patients. Notably, proof-of-principle has been provided for checkpoint inhibitor mAb's, e.g., anti-CTLA-4 and anti-PD-1 (Marshall et al., 2018 Front Oncol 8).

Dendritic cell (DC) based cancer immunotherapy aims at the activation of the immune system, and in particular tumor-specific cytotoxic T lymphocytes (CTLs) to eradicate the tumor. DCs represent a heterogeneous cell population, including conventional DCs (cDCs), consisting of cDC1s, cDC2s, plasmacytoid DCs (pDCs), and monocyte-derived DCs (moDCs). These DC subsets differ both in ontogeny and functional properties, such as the capacity to induce CD4+ and CD8+ T-cell activation. DCs are able to present exogenous antigens on MHC-II peptides, as well as cross-present exogenously captured antigens on MHC I-associated peptides, thereby effectively presenting tumor associated antigens to CD8+ T-cells (Huber et al. 2018 Front Immunol 9). Positive results have been achieved recently in combating cancer by targeting DC activation and enhanced antigen presentation both with small molecules (Kalijn et al. 2016 Clin Cancer Res 22; Li et al. 2019 Theranostics 9; Huck et al. 2018 Angew Chem Int Ed 57) as well as dendritic cell vaccines (Constantino et al. 2017 Immunol Res 65; Bol et al., 2016 Clin Cancer Res 22; Garg et al. 2017 Trends Immunol 38).

The fundamental patterns of epigenetic components, such as histone modifications, are frequently altered in tumor cells. Epigenetic re-programming has evolved as a means to provide cancer cells a survival advantage by altering the expression of genes associated with key cell regulating effects and suppressing immune response to the altered cell. HDACs are involved in modulating most key cellular processes, including transcriptional regulation, apoptosis, DNA damage repair, cell cycle control, autophagy, metabolism, senescence and chaperone function. Because HDACs have been found to function incorrectly or have aberrant expression in cancer, resulting in abnormal acetylation patterns, various histone deacetylase inhibitors (HDACis) have been investigated to act as cancer chemotherapeutics.

HDACis are a class of epigenetic-modifying drugs that dose-dependently inhibit HDACs and induce acetylation of histone and non-histone proteins, resulting in a variety of effects on cell proliferation, differentiation, anti-inflammation, and anti-apoptosis. Changes in cell differentiation are often the cause for tumor progression and acquired resistance to anti-cancer treatment. Four HDACis have FDA approval to treat hematologic cancers and several more are in various stages of development to treat a wide range of hematologic and solid cancers. Multiple HDAC inhibitors have shown benefits in cancer therapy by induction of tumor cell apoptosis, cell cycle arrest, differentiation and senescence, by enhancing the body's own immune response against the cancer, by inhibition of angiogenesis, and through augmentation of the apoptotic effects of other anti-cancer agents. The sensitivity of tumor cells and relative resistance of normal cells to HDACi may reflect the multiple defects that make cancer cells less likely than normal cells to compensate for inhibition of one or more prosurvival factors or activation of a pro-death pathway (Yoon and Eom, 2016 Chonnam Med J 52; Suraweera et al., 2018 Front Oncol 8).

Proper mitotic progression and maintenance of genomic stability has a central role in cell health its dysregulation is associated with many types of cancer. A recently discovered protein called Mediator of DNA damage checkpoint 1 (MDC1) was shown to be a central player in checkpoint activation and ataxia telangiectasia-mutated (ATM) mediated response to DNA double-strand breaks (DSBs), and thus involves the pathogenesis of several DNA damage-related diseases such as cancer and moderately reduced expression of the MDC1 protein was found for lung cancer, breast carcinoma, gastric carcinoma, and glioma. Mice with reduced levels of MDC1 showed an elevated level of spontaneous tumors in aged animals (Wang et al., 2014 PLoS One 10; Li et al., 2017 Mol Cell Biol 37).

Angiopoietin 2 (ANG2) is a proangiogenic cytokine which binds to the Tie2 receptor on endothelial cells in blood vessels. Neutralizing molecules to ANG2 can block tumor growth in vitro, which subsequently led to the use of anti-ANG2 monoclonal antibodies in clinical trials for the treatment of solid tumors (Monk et al., 2014 Lancet Oncol 15; Papadopolous et al., 2015 Clin Cancer Res). Upregulated ANG2 has recently been implicated also in neovascular age related macular degeneration (nAMD) and its levels correlated with severity of disease at presentation (Ng et al., 2017 Sci Reports 7).

In some aspects, the present disclosure provides a method of treating a subjecting having a cancer comprising administering to the subject a therapeutically effective amount of at least one compound of the present disclosure. The present disclosure provides at least one compound of the present disclosure for use in treating a cancer in a subject, wherein the at least one compound of the present disclosure is for administration to the subject in at least one therapeutically effective amount. The present disclosure provides a use of at least one compound of the present disclosure for the manufacture of a medicament for treating a cancer in a subject, wherein the at least one compound of the present disclosure is for administration to the subject in at least one therapeutically effective amount.

The present disclosure provides a method of preventing a cancer in a subject comprising administering to the subject a therapeutically effective amount of at least one compound of the present disclosure. The present disclosure provides at least one compound of the present disclosure for use in preventing a cancer in a subject, wherein the at least one compound of the present disclosure is for administration to the subject in at least one therapeutically effective amount. The present disclosure provides a use of at least one compound of the present disclosure for the manufacture of a medicament for preventing a cancer in a subject, wherein the at least one compound of the present disclosure is for administration to the subject in at least one therapeutically effective amount.

In some aspects, the present disclosure provides a method of reducing the size of a tumor comprising administering to the subject a therapeutically effective amount of at least one compound of the present disclosure.

The present disclosure provides a method of inducing tumor cell apoptosis in a subject comprising administering to the subject a therapeutically effective amount of at least one compound of the present disclosure.

The present disclosure provides a method of inducing cell cycle arrest in a tumor cell in a subject comprising administering to the subject a therapeutically effective amount of at least one compound of the present disclosure.

The present disclosure provides a method of inducing differentiation of a cell in a subject comprising administering to the subject a therapeutically effective amount of at least one compound of the present disclosure. The present disclosure provides a method of inducing senescence in a cell in a subject comprising administering to the subject a therapeutically effective amount of at least one compound of the present disclosure. A cell can be a cancerous cell.

The present disclosure provides a method of enhancing an immune response against cancer in a subject comprising administering to the subject a therapeutically effective amount of at least one compound of the present disclosure.

The present disclosure provides a method of inhibiting angiogenesis in a subject comprising administering to the subject a therapeutically effective amount of at least one compound of the present disclosure.

The present disclosure provides a method of enhancing the apoptotic effect of an anti cancer agent comprising administering to a subject a combination of a therapeutically effective amount of the anti-cancer agent and a therapeutically effective amount of at least one compound of the present disclosure.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, leukemia and germ cell tumors. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer, cervical cancer, Acute lymphoblastic leukemia (ALL), Acute myeloid leukemia (AML), Adrenal gland tumors, Anal cancer, Bile duct cancer, Bladder cancer, Bone cancer, Bowel cancer, Brain tumors, Breast cancer, Cancer of unknown primary (CUP), Cancer spread to bone, Cancer spread to brain, Cancer spread to liver, Cancer spread to lung, Carcinoid, Cervical cancer, Children's cancers, Chronic lymphocytic leukemia (CLL), Chronic myeloid leukemia (CML), Colorectal cancer, Ear cancer, Endometrial cancer, Eye cancer, Follicular dendritic cell sarcoma, Gallbladder cancer, Gastric cancer, Gastro esophageal junction cancers, Germ cell tumors, Gestational trophoblastic disease (GTD), Hairy cell leukemia, Head and neck cancer, Hodgkin lymphoma, Kaposi's sarcoma, Kidney cancer, Laryngeal cancer, Leukemia, Linitis plastica of the stomach, Liver cancer, Lung cancer, Lymphoma, Malignant schwannoma, Mediastinal germ cell tumors, Melanoma skin cancer, Men's cancer, Merkel cell skin cancer, Mesothelioma, Molar pregnancy, Mouth and oropharyngeal cancer, Myeloma, Nasal and paranasal sinus cancer, Nasopharyngeal cancer, Neuroblastoma, Neuroendocrine tumors, Non-Hodgkin lymphoma (NHL), Esophageal cancer, Ovarian cancer, Pancreatic cancer, Penile cancer, Persistent trophoblastic disease and choriocarcinoma, Phaeochromocytoma, Prostate cancer, Pseudomyxoma peritonei, Rectal cancer, Retinoblastoma, Salivary gland cancer, Secondary cancer, Signet cell cancer, Skin cancer, Small bowel cancer, Soft tissue sarcoma, Stomach cancer, T cell childhood non Hodgkin lymphoma (NHL), Testicular cancer, Thymus gland cancer, Thyroid cancer, Tongue cancer, Tonsil cancer, Tumors of the adrenal gland, Uterine cancer, Vaginal cancer, Vulval cancer, Wilms' tumor, Womb cancer and gynaecological cancer. Examples of cancer also include, but are not limited to, Hematologic malignancies, Lymphoma, Cutaneous T-cell lymphoma, Peripheral T-cell lymphoma, Hodgkin's lymphoma, Non-Hodgkin's lymphoma, Multiple myeloma, Chronic lymphocytic leukemia, chronic myeloid leukaemia, acute myeloid leukaemia, Myelodysplastic syndromes, Myelofibrosis, Biliary tract cancer, Hepatocellular cancer, Colorectal cancer, Breast cancer, Lung cancer, Non-small cell lung cancer, Ovarian cancer, Thyroid Carcinoma, Renal Cell Carcinoma, Pancreatic cancer, Bladder cancer, skin cancer, malignant melanoma, merkel cell carcinoma, Uveal Melanoma or Glioblastoma multiforme.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

An anti-cancer agent can comprise, but is not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-1G, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cori, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin- 11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, *Erwinia* L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte—Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, lmlygic, lnlvta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Orapred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perjeta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

Definitions

Unless otherwise stated, the following terms used in the specification and claims have the following meanings set out below.

As use herein, the phrase "compound of the present disclosure" refers to those compounds which are disclosed herein generically, sub-generically, and specifically (i.e., at species level).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, adamantly, hexahydroindacenyl. It is understood that for polycyclic (e.g., fused, bridged, or spiro rings) system, only one of the rings therein needs to be non-aromatic. For example, the cycloalkyl may be hexahydroindacenyl.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, TH-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic non-aromatic rings, only one of the rings needs to be non-aromatic (e.g., 1,2,3,4-tetrahydronaphthalenyl or 2,3-dihydroindole).

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. In some embodiments, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and $S(O)_P$, where p=1 or 2). It is to be noted that total number of S and O atoms in the aromatic heterocycle is not more than 1. Examples of heteroaryl groups include, but are not limited to, pyrrole, furan, thiophene, thiazole, isothiazole, imidazole, triazole, tetrazole, pyrazole, oxazole, isoxazole, pyridine, pyrazine, pyridazine, pyrimidine, benzoxazole, benzodioxazole, benzothiazole, benzoimidazole, benzothiophene, quinoline, isoquinoline, naphthrydine, indole, benzofuran, purine, benzofuran, deazapurine, and indolizine.

As used herein, the term "optionally substituted", unless specified otherwise, refers to being unsubstituted or having designated substituents replacing one or more hydrogen atoms on one or more designated atoms of the referred moiety. Suitable substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

As used herein, the term "halo" or "halogen" refers to fluoro, chloro, bromo and iodo.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The terms "effective amount" and "therapeutically effective amount" of an agent or compound are used in the broadest sense to refer to a nontoxic but sufficient amount of an active agent or compound to provide the desired effect or benefit.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

Organelles can include, but are not limited to, lysosomes, the endoplasmic reticulum, endosomes, the nucleus, mitochondria, the golgi apparatus, the vacuole and peroxisomes. The phrase "particular organelle" is also used to refer to specific substructures within an organelle, such as, but not limited to, intermembrane space of mitochondria, the cristae of mitochondria, the matrix of mitochondria, the perinuclear space of the nucleus, the rough endoplasmic reticulum, the smooth endoplasmic reticulum, the cis golgi and the trans golgi.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is an imprinting disorder. It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having an imprinting disorder. A subject in need thereof can also be one who has (e.g., is suffering from) an imprinting disorder. Alternatively, a subject in need thereof can be one who has an increased risk of developing such disorder relative to the population at large (i.e., a subject who is predisposed to developing such disorder relative to the population at large). A subject in need thereof can have a refractory or resistant imprinting disorder (i.e., an imprinting disorder that doesn't respond or hasn't yet responded to treatment). The subject may be resistant at start of treatment or may become resistant during treatment. In some embodiments, the subject in need thereof received and failed all known effective therapies for an imprinting disorder. In some embodiments, the subject in need thereof received at least one prior therapy. In a preferred embodiment, the subject has an imprinting disorder.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "preventing," "prevent," or "protecting against" describes reducing or eliminating the onset of the symptoms or complications of such disease, condition or disorder.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is understood that, when a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

It is understood that, when any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

It is to be understood that, throughout the description, where compositions are described as having, including, or comprising specific components, it is contemplated that compositions also consist essentially of, or consist of the recited components. Similarly, where methods or processes are described as having, including, or comprising specific process steps, the processes also consist essentially of, or consist of the recited processing steps. Further, it should be understood that the order of steps or order for performing certain actions is immaterial so long as the invention remains operable. Moreover, two or more steps or actions can be conducted simultaneously.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, 18t edition (1990). These texts can, of course, also be referred to in making or using an aspect of the disclosure.

It is to be understood that, for the compounds of the present disclosure being capable of further forming salts, all of these forms are also contemplated within the scope of the claimed disclosure.

It is to be understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

It is to be understood that the compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

It is to be understood that dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

It is to be understood that a pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., imprinting disorders, and the like) and the health of the patient should preferably be closely monitored during and for a reasonable period after treatment.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

It is to be understood that the pharmaceutical compositions can be included in a container, pack, or dispenser together with instructions for administration.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Preparative Example 1: Synthesis of Compound 872

Step 1: Synthesis of (4R,4'R)—N,N'-(((disulfanediylbis(ethane-2,1-diyl))bis(azanediyl))bis(3-oxopropane-3,1-d yl))bis(2-(4-methoxyphenyl)-5,5-dimethyl-1,3-dioxane-4-carboxamide)

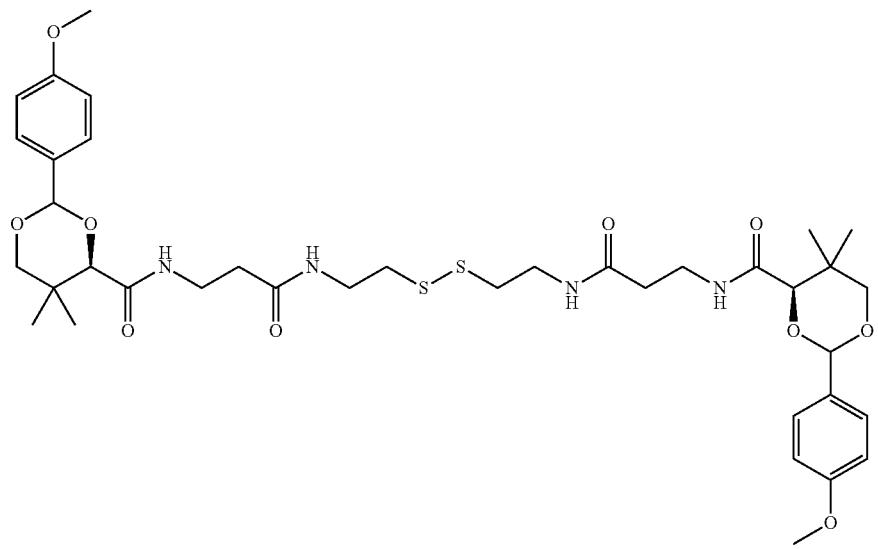

To a stirred solution of D-pantethine (20 g, 1 equiv., 36.055 mmol) in anhydrous DMF (200 mL) at room temperature was added 4-anisaldehyde dimethyl acetal (12.2 mL, 2.0 equiv., 72.111 mmol) followed by 4M HCl in dioxane (2 mL). The reaction mixture was stirred at the same temperature for 16 h. The solvent was evaporated and the residue was purified by combi-flash on silica gel eluting with 2-3% Methanol in DCM to afford (4R,4'R)—N,N'-(((disulfanediylbis(ethane-2, 1-diyl))bis(azanediyl))bis(3-oxopropane-3,1-diyl))bis(2-(4-methoxyphenyl)-5,5-dimethyl-1,3-dioxane-4-carboxamide (13.0 g, 16.435 mmol, 45%) as an off-white solid. LCMS (M+1)=791.3 amu.

Step 2: Synthesis of Compound 872: Synthesis of (4R)—N-(3-((2-mercaptoethyl)amino)-3-oxopropyl)-2-(4-methoxyphenyl)-5,5-dimethyl-1, 3-dioxane-4-carboxamide

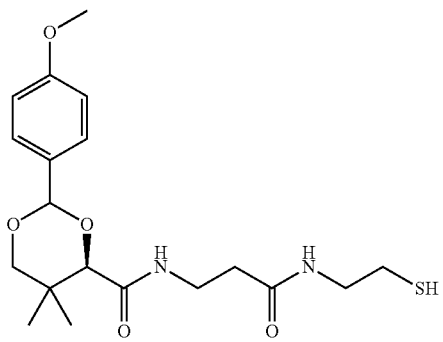

To a stirred solution of (4R,4'R)—N,N'-(((disulfanediyl-bis(ethane-2,1-diyl))bis(azanediyl))bis(3-oxopropane-3,1-diyl))bis(2-(4-methoxyphenyl)-5,5-dimethyl-1,3-dioxane-4-carboxamide (13 g, 1 equiv., 16.435 mmol) and in acetonitrile (50 mL) and H$_2$O (5 mL) was added Tributyl phosphine (50% in ethyl acetate) (16.62 ml, 2.5 equiv., 41.087 mmol) at 0° C. Then the reaction mixture was stirred at room temperature for 1 h. The reaction mixture was quenched with water and extracted with ethyl acetate. The organic layer was washed with brine solution, dried over Na$_2$SO$_4$, filtered and concentrated. The residue was purified by combi-flash on silica gel, eluting with 80-85% EtOAc in hexane to afford (4R)—N-(3-((2-mercaptoethyl)amino)-3-oxopropyl)-2-(4-methoxyphenyl)-5,5-dimethyl-1, 3-dioxane-4-carboxamide (10 g, 25.220 mmol, 77%) as a yellow solid. LCMS (M+1)=397.2 amu.

Alternate Step 2: Alternate Procedure for the Synthesis of Compound 872: Synthesis of (4R)—N-(3-((2-mercaptoethyl)amino)-3-oxopropyl)-2-(4-methoaybenzyl)-5,5-dimethyl-1,3-diozane-4-carboxamide

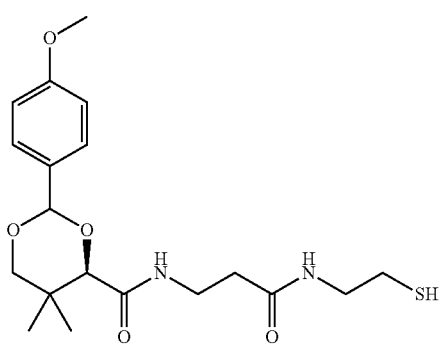

To a stirred solution of (4R,4'R)—N,N'-(((disulfanediyl-bis(ethane-2,1-diyl))bis(azanediyl))bis(3-oxopropane-3,1-diyl))bis(2-(4-methoxybenzyl)-5,5-dimethyl-1,3-dioxane-4-carboxamide (12 g, 15.189 mmoL) in methanol (60 mL) and water (60 mL) was added DTT (3.5 g, 22.784 mmoL) at 0° C. Resulting reaction mixture was stirred at RT for 16 h. Progress of the reaction was monitored by TLC. After completion of the reaction, the reaction mixture was partitioned between DCM (2×120 mL) and water (120 mL). The organic layer was then washed with saturated NaHCO$_3$ solution, dried over Na$_2$SO$_4$, and concentrated under reduced pressure. The obtained crude mixture was purified by column chromatography using silica (100-200 mesh) and eluted with 2% MeOH in DCM to afford the title compound (4R)—N-(3-((2-mercaptoethyl)amino)-3-oxopropyl)-2-(4-methoxybenzyl)-5, 5-dimethyl-1,3-dioxane-4-carboxamide as white solid (9.5 g, 77%).

$^1$H NMR (400 MHz, DMSO-D6) δ 8.05 (m, 1H), 7.43-7.41 (m, 3H), 6.92 (d, J=8.4 Hz, 2H). 5.51 (s. 1H), 4.07 (s, 1H), 3.75 (s, 3H), 3.65-3.58 (m, 2H), 3.32 (m, 1H), 3.23 (m, 1H), 3.16-3.15 (m, 2H), 2.27 (t, J=6.4 Hz, 2H), 0.99 (s, 3H), 0.94 (s, 3H).

Preparative Example 2: Alternate Procedure for the Synthesis of Compound 872 Synthesis of (4R)—N-(3-((2-mercaptoethyl)amino)-3-oxopropyl)-2-(4-methoxybenzyl)-5,5-dimethyl-1,3-dioxane-4-carboxamide Step 1: Synthesis of 3-{[(4R)-2-(p-Methoxyphenyl)-5,5-dimethyl-1,3-dioxan-4-yl]carbonylamino}propionic Acid

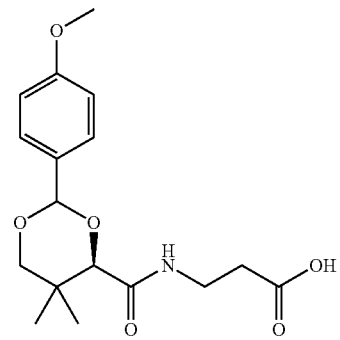

To a mixture of D-pantothenic acid hemicalcium salt (4.76 g, 10 mmol) in anhydrous DMF (60 mL) was added concentrated H$_2$SO$_4$ (980 mg, 10 mmol) slowly. And the mixture was stirred at 20° C. for 30 min. 4-Anisaldehyde dimethyl acetal (2.18 g, 12 mmol) and CSA (230 mg, 1 mmol) were added and the reaction was stirred for 16 hours. Solvents were removed in vacuo and the resulting syrup was partitioned between EtOAc (300 mL) and H$_2$O (100 mL). The organic layer was washed with H$_2$O (2×50 mL). The organic layer was then dried (Na$_2$SO$_4$) and evaporated to give the crude product, which was purified by column chromatography (SiO$_2$, 30-100% Ethyl acetate in Petroleum ether, Rf=0.3) to afford the title compound (2.44 g, 7.24 mmol, 65.9% yield) as an off-white solid.

$^1$H NMR (400 MHz, CDCl$_3$) 7.39-7.29 (m, 2H), 6.98 (t, J=6.0 Hz, 1H), 6.88-6.78 (m, 2H), 5.39 (s, 1H), 4.03 (s, 1H), 3.74 (s, 3H), 3.61 (q, J=9.2 Hz, 2H), 3.45 (dd, J=10.8, 7.0 Hz, 2H), 2.53 (t, J=6.4 Hz, 2H), 1.03 (d, J=4.4 Hz, 6H).

Step 2: Synthesis of 3-{[(4R)-2-(p-Methoxyphenyl)-5,5-dimethyl-1,3-dioxan-4-yl]carbonylamino}-1-(2-mercaptoethylamino)-1-propanone

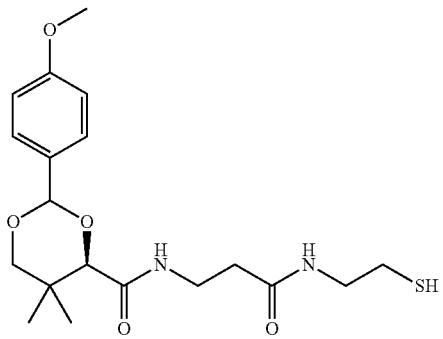

To a suspension of the product from Preparative Example 2 Step 1 (2.44 g, 7.24 mmol) in THF (36 mL) was added CDI (1.24 g, 10.9 mmol) at 20° C. under N2. After stirring for 30 min, cysteamine (1.78 g, 10.9 mmol) and DIEA (1.42 g, 10.9 mmol) were added to the above mixture. The mixture was stirred for 16 hours under $N_2$ at 20° C. TLC (EtOAc, Rf 0.4) showed the reaction was finished. The reaction was quenched by a.q $NH_4Cl$ (20 mL). The mixture was partitioned between EtOAc (80 mL) and $H_2O$ (50 mL) and the organic layer was washed with brine (2×30 mL). The organic layer was then dried ($Na_2SO_4$) and evaporated to give the crude product, which was purified by column chromatography ($SiO_2$, 30-80% Ethyl acetate in Petroleum ether, Rf=0.4) to obtain the title compound (2.24 g, 5.65 mmol, 78.0% yield) as an off-white solid. $^1$H NMR (400 MHz, MeOD) 7.44 (d, 0.1=8.4 Hz, 2H), 6.98-6.91 (m, 2H), 5.53 (s, 1H), 4.14 (s, 1H), 3.80 (s, 3H), 3.70 (d, 0.1=9.2 Hz, 2H), 3.48 (dd, 0.1=6.4, 4.4 Hz, 2H), 3.27 (s, 2H), 2.53 (t, 0.1=6.8 Hz, 2H), 2.41 (t, 0.1=6.4 Hz, 2H), 1.10 (s, 3H), 1.04 (s, 3H).

Preparative Example 3: Synthesis of Compound 873 Synthesis of (R)—N-(3-((2-mercaptoethyl)amino)-3-oxopropyl)-2,2,5,5-tetramethyl-1,3-dioxane-4-carboxamide

Step 1: Synthesis of 3-{[(R)-2,2,5,5-tetramethyl-1,3-dioxan-4-yl]carbonylamino}propionic Acid

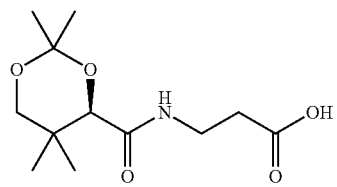 [SMILES: CC1(C)OCC(C)(C)[C@H](C(=O)NCCC(=O)O)O1]

A mixture of calcium (R)-pantothenate (5 g, 10.49 mmol), p-toluenesulfonic acid monohydrate (4.79 g, 25.18 mmol), 3A molecular sieves (5 g) and 250 mL HPLC grade acetone were stirred overnight at room temperature. The suspension was filtered through celite, washed three times with 100 mL acetone and the solvent was evaporated. The residue was dissolved in 200 mL EtOAc, washed two times with 100 mL brine and dried over $Na_2SO_4$. Most of the solvent was removed and hexane was added slowly to precipitate the product (2.0 g, Yield 36.8%) as a white solid. LCMS (ESI): m/z 258.1 (M–H)$^-$, RT=1.383 min.

Step 2: Synthesis of Compound 873: Synthesis of 3-{[(R)-2,2,5,5-tetramethyl-1,3-dioxan-4-yl]carbonylamino}-1-(2-mercaptoethylamino)-1-propanone

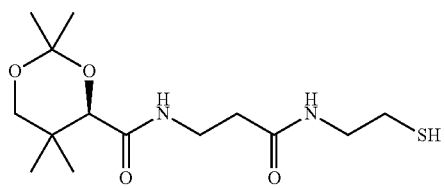 [SMILES: CC1(C)OCC(C)(C)[C@H](C(=O)NCCC(=O)NCCS)O1]

The freshly prepared compound from Preparative Example 3 Step 1 (2.2 g, 8.48 mmol) was dissolved in 40 mL dry THF, treated with 1,1'-carbonyldiimidazole (CDI) (2.06 g, 12.73 mmol) and stirred for one hour at room temperature. Cysteamine hydrochloride (1.44 g, 12.73 mmol) was added to this solution and the mixture was stirred at room temperature overnight. THF was removed in vacuo and the residue was dissolved in DCM (50 mL). The organic phase was washed with 50 mL saturated $NH_4Cl$ solution and then 50 mL brine, dried over $Na_2SO_4$, filtered and concentrated. The crude product was purified by flash chromatography on silica (EtOAc/pentane 70:30 to 100% EtOAc) to give the title compound (1.9 g, yield 78.0%) as a white solid. LCMS (ESI): m/z 319.2 (M+H)+, RT=1.488 min.

Preparative Example 4: Alternate Procedure for the Synthesis of Compound 873

Step 1: Synthesis of (R)-3-(2,4-dihydroxy-3,3-dimethylbutanamido) propanoic Acid (Pantothenic Acid)

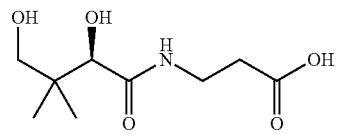

To a mixture of calcium 3-[(2R)-2,4-dihydroxy-3,3-dimethylbutanamido]propanoate (40.0 g, 83.9 mmol) in $H_2O$ (150 mL) was added the solution of oxalic acid (7.55 g, 83.9 mmol) in $H_2O$ (100 mL), then the mixture was stirred at 20° C. for 2 hours. The mixture was filtered through Celite, and eluted with $H_2O$ (30 mL), then the mixture was extracted by EtOAc (200 mL×10), dried over $Na_2SO_4$, filtered and concentrated to give the title compound (R)-3-(2,4-dihydroxy-3,3-dimethylbutanamido)propanoic acid (35 g, 95.11%) as a colorless oil, which was used in the next step directly without further purification.

$^1$H NMR (400 MHz, DMSO-d$_6$): δ 0.78 (s, 3H), 0.80 (s, 3H), 2.40 (t, J=7.2 Hz, 2H), 3.10-3.35 (m, 4H), 3.70 (d, J=5.2 Hz, 1H), 4.46 (t, J=5.2 Hz, 1H), 5.38 (d, J=5.2 Hz, 1H), 7.71 (t, J=6.0 Hz, 1H), 12.23 (s, 1H).

Step 2: Synthesis of (R)-3-(2,2,5,5-tetramethyl-1,3-dioxane-4-carbozamido) propanoic acid

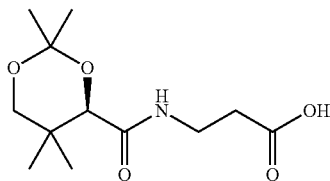 [SMILES: CC1(C)OCC(C)(C)[C@H](C(=O)NCCC(=O)O)O1]

To a mixture of 3-[(2R)-2,4-dihydroxy-3,3-dimethylbutanamido]propanoic acid (1.0 g, 4.6 mmol) in acetone (20 mL) was added subsequently 2-methoxyprop-1-ene (995 mg, 13.8 mmol) and TsOH·H$_2$O (44 mg. 0.2 mmol) at 0° C., then the mixture was stirred at 0° C. for 10 minutes and 20° C. for 0.5 hour. LCMS showed the raw material was consumed and a new peak was formed. The mixture was quenched by NaHCO$_3$ (20 mL) and concentrated to provide a residue. Then the reaction mixture was diluted with EtOAc (50 mL), the organic phase was dried over Na$_2$SO$_4$, filtered and concentrated to give the product of (R)-3-(2,2,5,5-tetramethyl-1,3-dioxane-4-carboxamido)propanoic acid (1.2 g, 95%) as an off-white solid. MS:(ES, m/s): 282.1 [M+Na]$^+$.

$^1$H NMR (400 MHz, DMSO-d$_6$): δ 0.87 (s, 3H), 0.91 (s, 3H), 1.36 (s, 3H), 1.37 (s, 3H), 2.38 (t, J=6.8 Hz, 2H), 3.18 (d, J=11.6 Hz, 1H), 3.19-3.26 (m, 1H), 3.28-3.38 (m, 1H), 3.63 (d, J=11.6 Hz, 1H), 4.02 (s, 1H), 7.43 (t, J=6.0 Hz, 1H).

Step 3: Synthesis of Compound 873: Synthesis of (R)—N-(3-((2-mercaptoethyl) amino)-3-oxopropyl)-2,2,5,5-tetramethyl-1,3-dioaane-4-carboxamide

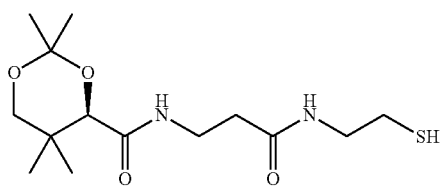 [SMILES: CC1(C)OCC(C)(C)[C@H](C(=O)NCCC(=O)NCCS)O1]

To a mixture of 3-{[(4R)-2,2,5,5-tetramethyl-1,3-dioxan-4-yl]formamido}propanoic acid (1.2 g, 4.63 mmol) in DCM (20 mL) was added 2-aminoethanethiol hydrochloride (1.05 g, 9.26 mmol), PyBOP (3.61 g, 6.945 mmol) and DIPEA (2.69 g, 20.835 mmol). Then the mixture was stirred at 20° C. for 16 hours. LCMS showed the raw material was consumed and the desired mass peak was formed. The reaction was diluted with DCM (30 mL), then was washed with water (20 mL) and brine (20 mL), dried over Na$_2$SO$_4$, filtered and concentrated to give the crude product. The crude product was purified by flash chromatography (12 g silica gel, 100°% PET/EtOAc with EtOAc from =0 to 100%) to yield the title compound (R)—N-(3-((2-mercaptoethyl)amino)-3-oxopropyl)-2,2,5,5-tetramethyl-1,3-dioxane-4-carboxamide (1200 mg, 73.25%) as colorless oil. MS:(ES, m/s): 319.2 [M+H]$^+$.

$^1$H NMR (400 MHz, CDCl$_3$): δ 0.96 (s, 3H), 1.02 (s, 3H), 1.41-1.45 (m, 6H), 2.48 (t, J=6.0 Hz, 2H), 2.60-2.70 (m, 2H), 3.27 (d, J=11.6 Hz, 1H), 3.35-3.50 (m, 2H), 3.53-3.60 (m, 2H), 3.67 (d, J=11.6 Hz, 1H), 4.07 (s, 1H), 6.38-6.45 (m, 1H), 7.05-7.13 (m, 1H).

Preparative Example 5: Synthesis of (R)-2,4-dihydroxy-N-(3-((2-mercaptoethyl)amino)-3-oxopropyl)-3,3-dimethylbutanamide (Pantetheine)

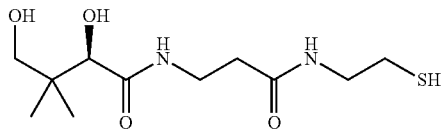 [SMILES: CC(C)(CO)[C@@H](O)C(=O)NCCC(=O)NCCS]

To a stirring solution of bis-(N-pantothenylamidoethyl) disulfide (5 g, 9.02 mmol) in methanol and water (75 mL, 1:1) was added dithiothreitol (2.22 g, 14.43 mmol) at room temperature and stirred for 16 h. After consumption of the starting material (by TLC), volatiles were evaporated under reduced pressure and the crude product was extracted with EtOAc (2×100 mL), organic layer was dried over anhydrous Na$_2$SO$_4$ and concentrated under reduced pressure. The crude material was purified by silica gel column chromatography eluting with 5% MeOH/CH$_2$Cl$_2$ to afford Pantetheine (4.5 g, 90%) as a colorless oily liquid.

$^1$H NMR (400 MHz, D$_2$O): δ 4.01 (s, 1H), 3.65-3.58 (m, 3H), 3.72-3.65 (m, 4H), 2.71 (t, J=6.6 Hz, 2H), 2.56 (t, J=6.5 Hz, 2H), 0.94 (d, J=13.6 Hz, 6H); LCMS (ESI): m/z 279.0 [M+H]$^+$

Preparative Example 6: Synthesis of Compound 871

Synthesis of (4R,4'R)—N,N'-(((disulfanediylbis(ethane-2,1-diyl))bis(azanediyl))bis(3-oxopropane-3,1-diyl))bis(2-(4-methoxyphenyl)-5,5-dimethyl-1,3-dioxane-4-carboxamide)

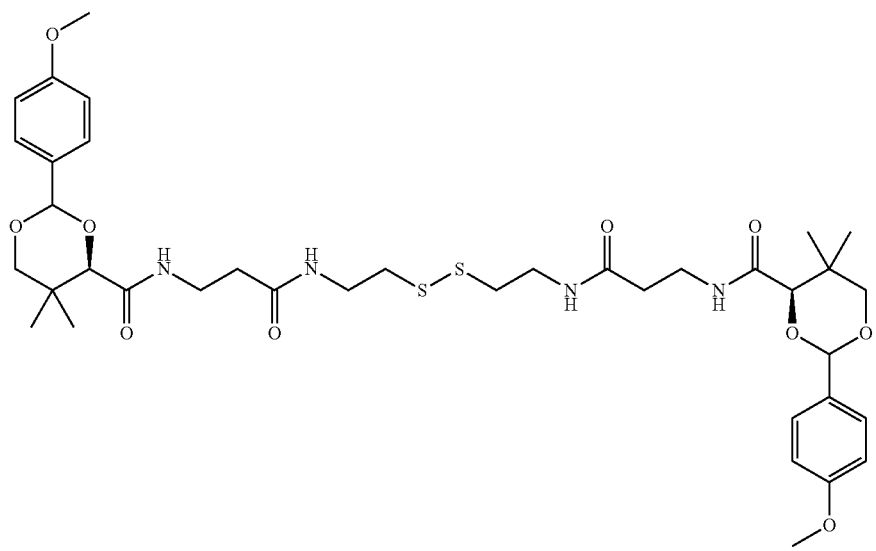

To a stirred solution of (2R,2'R)—N,N-(((disulfanediylbis(ethane-2,1-diyl))bis(azanediyl))bis(3-oxopropane-3,1-diyl))bis(2,4-dihydroxy-3,3-dimethylbutanamide) (12g, 21.660 mmoL) in THF (120 mL) was added camphor sulfonic acid (1.2 g, 5.415 mmoL) followed by the addition of PMPCH(OMe)$_2$, (11.8 g, 64.981 mmoL). Reaction was then stirred at RT for 16 h. Progress of the reaction was monitored by TLC. After completion of the reaction, the reaction mixture was partitioned between ethyl acetate (2×150 mL) and water (150 mL). Organic layer was separated and then dried over Na$_2$SO$_4$, concentrated under reduced pressure to get the crude compound. The crude mixture was purified by column chromatography using silica (100-200 mesh) eluted with 2% methanol in DCM to afford (4R,4'R)—N,N-(((disulfanediylbis(ethane-2,1-diyl))bis(azanediyl))bis(3-oxopropane-3,1-diyl))bis(2-(4-methoxybenzyl)-5,5-dimethyl-1,3-dioxane-4-carboxamide) as a white solid (12.5 g, 73% yield).

Note: This is a symmetrical molecule, 1HNMR is half integrated. $^1$H NMR (400 MHz, DMSO-d6) δ 8.09 (m, 1H), 7.45-7.41 (m, 3H), 6.91 (d, J=8.4 Hz, 2H), 5.50 (s, 1H) 4.06 (s, 1H), 3.74 (s, 3H), 3.61-3.60 (m, 2H), 3.32-3.24 (m, 3H), 2.72-2.70 (t, J=6.8 Hz, 3H), 2.26 (t, J=6.8 Hz, 2H), 0.98 (s, 3H), 0.93 (s, 3H).

Example 1: In Vitro Biology Experimental Procedures a for Testing Compounds of the Present Disclosure Efficacy of compounds of the present disclosure can be assessed via similar procedures as those described in examples 1-9 by one skilled in the art. Compounds of the present disclosure can be dosed in cells (included but not limited to cell lines, patient derived cells, iPSC of any kind, EC and tissue organoids) with metabolic impartments (including but not limited to impaired amino acid metabolism, impaired fatty acid metabolism, impaired TCA cycle, impaired glucose metabolism, impaired metabolic respiration, impaired carbohydrate metabolism, impartments of organic acid metabolism and the like) by incubating several concentrations of compounds of the present disclosure, either alone or in combination (with other small molecule drugs, biologic drugs, adjuvant therapies) in a suitable vehicle formulation (such as but not limited to saline, HPMC, PEG400, HPBCD and the like) over a period of minutes, hours up to several days. Following incubations, cells (including supernatants) can be assayed in multiple ways (as indicated in Biology Experimental 1-8) including but not limited to bioanalytical, biochemical, biomarker, functional. One can analyze tissues for CoA and Acyl-CoA species (such as but not limited to Acetyl-CoA, Succinyl-CoA, Malonyl-CoA, TCA cycle intermediates and the like), Acyl-Carnitines, Carnitine and AcylCarnitine Transport and transporters, ketone bodies, Organic Acids, and other metabolites consistent with the biochemical and metabolic pathways, utilizing analytical methods including but not limited to HPLC, MS, LCMS, MRI, western blot, ELISA, PCR, Reactive Oxygen Species, tubulin acetylation and other Post Translation Modifications, Next Generation Sequence, enzyme processing, enzyme inhibition, complex formation and the like. One can measure functional aspects and changes in functional readouts such as Mitochondrial Bioenergetics (including but not limited to OCR, ECAR, Complex formation, ATP production), mitochondrial membrane potential, mitochondrial morphology and/or architectural changes (including but not limited to fusion, fission, membrane structure and morphology), Patch-clamp electrophysiology. One can measure metabolomic changes and improvements in metabolic flux and TCA function.

Example 2: Isolation and Purification of Acyl-Coenzyme a Esters (Including Acetyl-CoA)

Sample Preparation for Acyl-CoA Profiling (In Vivo)

Animals could be killed by exposure to CO2 followed by cervical dislocation. The liver was rapidly excised, frozen in liquid nitrogen and then powdered under liquid nitrogen. For each analysis, precisely-measured amounts (between 0.1 to 0.2 g) of powdered tissue were spiked to a final concentration of 20 ppm in a final volume of 100 mL with the [D3]acetyl-CoA standard, then homogenized in 2 mL ice-cold 10% trichloroacetic acid with 2 mM DTT using a Polytron (Kinematica Inc, Bohemia, NY). The tubes were vortexed for 5 sec and centrifuged at 4 uC for 5 min at 13,000 g. The supernatants were then applied to a 3 cc Oasis HLB solid-phase extraction column (Waters, Milford, MA, USA) preconditioned with 2 mL of methanol and 2 mL of water. The column was then washed with 2 mL of 2 mM DTT in water and eluted with 2 mL of 2 mM DTT in methanol. The eluate was evaporated under a stream of nitrogen, reconstituted in 100 mL of 2 mM DTT in water. 20 mL served for high performance liquid chromatography coupled to tandem mass spectrometry (HPLC/MS/MS) analysis.

HPLC/MS/MS Assay of Short Chain Acyl-CoAs

The HPLC/MS/MS system consists of a 2795 Waters HPLC coupled to a Micromass Quattro Premier XE (Milford, MA, USA). The column was a 15063 mm Gemini-NX C18 (5 microns) from Phenomenex (Torrance, CA). Eluent A was 2 mM ammonium acetate in water and eluent B was 2 mM ammonium acetate in acetonitrile. The gradient was 100% A for 5 min, going to 50% B after 30 min, then to 100% B after 31 min, maintained at this composition until 36 min, returning to the initial composition at 37 min and stabilized until 42 min. Flow rate was 0.4 mL/min. The MS was operated in negative ionization electrospray with the following settings: desolvation gas 100 L/Hr; cone gas 10 L/Hr; capillary voltage 2.5 kV; source temperature 120 uC; and cone voltage 20 V. The mass spectrometric data were obtained in multiple reaction monitoring acquisition mode for nine short chain acyl-CoA species using the following transitions (m/z) and collision energies: free CoA (382.5.685.9, 17 V), succinyl-CoA (432.5.685.7, 15 V), isovaleryl-CoA (424.5.769.9, 18 V), HMG-CoA (454.5.382.5, 15 V), acetoacetyl-CoA (424.6.382.4, 11 V), butyryl-CoA (417.7.755.7, 17 V), methylcrotonyl-CoA (423.7.685.7, 20 V), acetyl-CoA (403.6.728, 15 V) and the internal standard [D3]acetyl-CoA (404.6.730.9, 15 V). The parent and daughter ions and the collision energy used for each acyl-CoA multiple reaction monitoring were determined using pure samples. Standard curves were constructed for each acyl-CoA using pure molecules. Standard curves were spiked with the internal standard [D3]acetyl-CoA to compare the relative response factor between each molecule and the standard for the quantification of those short chain acyl-CoAs in the mouse liver sample.

MS Determination of Unidentified Acyl-CoAs

To identify unknown acyl-CoA species, analyses were performed on a 6224 TOF MS coupled to a 1260 Infinity HPLC system, both from Agilent Technologies Inc. Ionization was performed in negative mode on a dual spray ESI source and mass spectra were acquired from m/z 100 to 3200. Samples were diluted to 50 mL, then 2 mL aliquots were injected into the LC-MS system. The chromatographic column was an XBridge C18, 3.5 mm, 4.6650 mm from Waters. Elution was performed under a two step gradient using acetonitrile and 10 mM ammonium acetate as mobile phases. Deprotonated species were taken into account for accurate mass calculation.

In a 12×75-mm glass tube was placed powdered rat liver (20-26 mg) and radiolabeled acyl-coenzyme A standards ranging 44,440-55,000 dpm and 0.35-0.46 nmol. These amounts of added radiolabeled acyl-coenzyme A esters are in the concentration ranges reported in the literature.

Next, 1.5 ml of acetonitrile/isopropanol (3+1, v+v) was added and a 30-s homogenization was performed using an OMNI 2000 tissue homogenizer followed by addition of 0.5 ml of 0.1 M KH2PO4 (pH 6.7) and a second 30-s homogenization. The resulting homogenate was vortex-mixed (5 s), and two 200-11 aliquots were transferred to scintillation vials for radioactivity determination (100% recovery). The remainder was transferred to a microcentrifuge tube and centrifuged for 5 min at 16,000 g. Two 200-11 aliquots were removed from the supernatant for determination of recovery by radioactivity counting, and 1 ml of the remaining supernatant was transferred to a 12×75-mm glass tube and acidified by adding 0.25 ml of glacial acetic acid and vortex-mixing. The SPE column was conditioned with 1 ml of acetonitrile/isopropanol/water/acetic acid (9+3+4+4, v+v+v+v). This solution ensures protonation of the pyridyl functional group, so that it will function as an anion-exchanger. Following application and flowthrough of the supernatant (collected in 625-11 aliquots), the SPE column was washed with 1 ml of acetonitrile/isopropanol/water/acetic acid (9+3+4+4, v+v+v+v) to remove unretained species (collected in 500-II aliquots). Acyl-coenzyme A esters were then eluted with 2 ml of methanol/250 mM ammonium formate (4+1,v+v; collected in 500-ll aliquots). This eluent has a pH of 7, which neutralizes the pyridyl functional group. All aliquots had their radioactivity content determined by liquid scintillation counting. This was performed, following the addition of 4 ml/vial of Ultima Gold scintillation cocktail (Perkin Elmer, Waltham, MA), using an LS 6500 scintillation counter (Beckman Coulter, Fullerton, CA). Recoveries were calculated from the determined radioactivity using correction factors for the percentage of the volume that was counted.

Example 3: Determination of Reactive Oxygen Species (ROS)

Human neurons were incubated with Alexa Fluor 647 mouse anti-human CD56 (anti-NCAM, BD Biosciences, diluted 1:40) for 1 h, with 20 µM of 2',7'-dichlorodihydrofluorescein diacetate ($H_2DCFDA$; Molecular Probes) for 15 min, and with 2 µg/ml of Hoechst 33342 for 2 min. All incubations were performed at 37° C. The cells were washed and randomly analyzed using an IN Cell Analyzer 1000 system (GE Healthcare). The fluorescence of DCF from NCAM-positive cells was collected to compare the relative ROS contents. The quantification of the signal was performed using the NIH image software, ImageJ. A minimum of 100 neurons for each patient and control was analyzed in at least three independent experiments for each sample.

Example 4: Determination of Mitochondria) Membrane Potential

Human neurons were incubated with Alexa Fluor 488 mouse anti-human CD 56 (anti-NCAM; BD Biosciences) for 1 h, with 20 nM of TMRM (Molecular Probes) for 15 min, and with 2 µg/ml of Hoechst 33342 for 2 min. All of these incubations were performed at 37° C. The cells were washed and randomly analyzed by IN Cell Analyzer 1000 system (GE Healthcare). The fluorescence of TMRM from NCAM-positive cells was collected to compare the relative mitochondrial membrane potential. A minimum of 100 neurons for each patient and control was analyzed in at least three independent experiments for each sample.

Example 5: Patch-Clamp Electrophysiology (iPSC Neuronal)

Co-culture experiments of $6 \times 10^4$ cells (half GFP controls and half tdTomato patients) were seeded on Matrigel-coated covers. After 5 days, $2 \times 10^4$ cortical mice neurons were added to improve differentiation and electrophysiological activity. Individual slides containing co-cultured PKAN and control neurons were transferred in a recording chamber mounted on the stage of an upright BX51 WI microscope (Olympus, Japan) equipped with differential interference contrast optics (DIC) and an optical filter set for the detection of GFP and tdTomato fluorescence (Semrock, Rochester, NY, USA). Cells were perfused with artificial cerebrospinal fluid (ACSF) containing (in mM): 125 NaCl, 3.5 KCl, 1.25 $NaH_2PO_4$, 2 $CaCl_2$, 25 $NaHCO_3$, 1 $MgCl_2$, and 11 D-glucose, saturated with 95% 02 and 5% CO2 (pH 7.3). The ACSF was continuously flowing at a rate of 2-3 ml/min at room temperature. Whole-cell patch-clamp recordings were performed using glass pipettes filled with a solution containing the following (in mM): 10 NaCl, 124 $KH_2PO_4$, 10 HEPES, 0.5 EGTA, 2 $MgCl_2$, 2 $Na_2$-ATP, 0.02 Na-GTP, (pH 7.2, adjusted with KOH; tip resistance: 4-6 MΩ). All recordings were performed using a MultiClamp 700B amplifier interfaced with a PC through a Digidata 1440A (Molecular Devices). Data were acquired using pClamp10 software (Molecular Devices) and analyzed with GraphPad Prism 5 and SigmaStat 3.5 (Systat Software Inc.). Voltage- and current-clamp traces were sampled at a frequency of 10 kHz and low-pass filtered at 2 kHz. The input resistance ($R_{in}$) was calculated by dividing the steady-state voltage response to a negative current step (−10 to −50 pA, 1 s) by the amplitude of the injected current. Labeled GFP or tdTomato neurons were randomly chosen for measurement, and no blind experiments were done for electrophysiology studies.

Example 6: Determination of Respiratory Activity (Basal, ATP Production-Linked, Maximal, and Proton Leak-Linked Oxygen Consumption Rate)

Oxygen consumption rate (OCR) was measured in PKAN and control neurons with a XF96 Extracellular Flux Analyzer (Seahorse Bioscience, Billerica, MA, USA). Each control and PKAN NPC was seeded on a XF 96-well cell culture microplate (Seahorse Bioscience) at a density of $15-20 \times 10^3$ cells/well and differentiated as previously described. After replacing the growth medium with 180 µl of bicarbonate-free DMEM pre-warmed at 37° C., cells were incubated at 37° C. without $CO_2$ for 1 h before starting the assay procedure. Then, baseline measurements of OCR, after addition of 1 µM oligomycin and of 2.1 µM carbonyl cyanide 4-(trifluoromethoxy) phenylhydrazone (FCCP), were measured using an already established protocol (Invernizzi et al, 2012). Data were expressed as pmol of $O_2$ per minute and normalized by cell number measured by the CyQUANT Cell proliferation kit (Invitrogen), which is based on a fluorochrome binding to nucleic acids. Fluorescence was measured in a microplate luminometer with excitation wavelength at 485±10 nm and emission detection wavelength at 530±12.5 nm.

Example 7: Western Blot Analysis of Tubulin Acetylation in Livers from Mice

Livers were homogenized on ice with a glass-glass potter and lysed using RIPA buffer (50 mM Tris pH 8, 150 mM NaCl, 1% NP40, 0.5% Na-deoxycholate, 0.1% SDS, 5 mM EDTA pH 8) with addition of protease inhibitor cocktail (Roche). Proteins were quantified by BioRad protein assay according to manufacturer instructions. Equal amounts of proteins (20 µg) were resolved on a 12% SDS-polyacrilamide gel and electroblotted onto nitrocellulose membrane. Filters were incubated with mouse monoclonal anti-acetylated tubulin antibody (clone 6-11B-1, Sigma). Equal loading was verified using a mouse monoclonal anti-GAPDH antibody (clone 6C5, Millipore). Peroxidase-conjugated secondary antibodies (Amersham) were visualized using the ECL method with autoradiography film.

Example 8: Mitochondrial Protein Acetylation: Lysine Acetylation on Proteins

Acetyl Lysine Analysis in Human Fibroblasts

Human dermal fibroblasts were routinely cultured in DMEM supplemented with 10% (v/v) fetal calf serum, 2 mm glutamine and 1% (v/v/v) pen/strep/fungizone. For acetyl lysine analysis we incubated cells either in serum-free Eagle's minimal essential medium (MEM) supplemented with 400 µml-carnitine and 120 µm palmitate for 96 h [a metabolic condition characterized by high fatty acid turnover] or in DMEM. After exposure, the cell pellet was resuspended in 50 mm $NH_4CO_3$ buffer containing deacetylase inhibitors (1 µm Trichostatin A and 10 mm nicotinamide) followed by sonication at 40 Ms. To digest the protein into amino acids, samples were incubated with pronase at a protein to pronase ratio of 10:1, in 50 mm $NH_4CO_3$ for 4 h at 37° C. The reaction was stopped with 5 volumes of acetonitrile, 10 µl 2.5 mm D4-labeled 1-lysine internal standard (DLM-2640, Cambridge Isotopes Laboratories) and 10 µl 10 µm D8-labelled acetyl lysine internal standard (D-6690, CDN Isotopes). The samples were briefly vortexed and centrifuged at 14 000 rpm, 4° C. 10 for 10 min followed by solvent evaporation at 40° C. under a gentle stream of nitrogen. Samples were then taken up in 0.01% heptafluorobutyric acid and analyzed with LC-MS/MS.

Acetyl-Lysine Measurement Using LC MMS/MS

Ten microliters of the sample extract was injected onto a BEH C18 column (2.1×100 mm, 1.7 µm, Waters Corp. Milford MA) using a UPLC system consisting of an Acquity solvent manager with degasser and an Acquity Sample Manager with column oven (Waters Corp.). The system was controlled by MassLynx 4.1 software. The flow rate was set to 500 µl/min. Elution solvent A consisted of 0.1% heptafluorobutyric acid and solvent B was 80% acetonitrile. The chromatographic conditions were as follows: 0-2 min 100% A, 2-5 min to 50% B, 5-6 min to 100% B, at 6.1 min back to 100% A and equilibration time with 100% A was 3 min. Separation was performed at 50° C. The Quattro Premier XE triple-quadrupole mass spectrometer (Waters Corp.) was used in the positive electrospray ionization (ESI) mode. Nitrogen was used as nebulizing gas and argon was used as collision gas at a pressure of 2.5e-3 mbar. The capillary voltage was 3.0 kV, the source temperature was 120° C. and desolvation temperature was 300° C. Cone gas flow was 501/h and desolvation gas flow was 900 l/h. All components were measured by using multiple reaction monitoring (MRM) in the positive ionization mode, using the transitions: m/z 147.0>84.1 for lysine, 151.0>88.1 for lysine-$^2H_4$ (internal standard), 189.2>84.1 for N-acetyl lysine and 197.2>91.1 for N-acetyl lysine-$^2$H$_8$ (internal standard) with optimal collision energy of 20 eV for lysine and 30 eV for N-acetyl lysine.

Example 9: General In Vivo Biology Experimental Procedures for Testing Compounds Administration of compounds of the present disclosure to animals generated in Biology Experimentals 10-B10 or other models of metabolic diseases (including but not limited to impaired amino acid metabolism models, impaired fatty acid metabolism models, impaired TCA cycle models, impaired glucose metabolism models, impaired metabolic respiration models, organ transplant models, impaired carbohydrate metabolism models, models of disorders of organic acid metabolism and the like) or other models of post-translational modification (including but not limited to impaired histone prenylation (such as Acetylation) models, impaired tubulin prenylation (such as Acetylation) models and the like), by dosing (either orally, ip, sc, iv or other route of administration) and either alone or in combination with another compound or another agent (such as but not limited to other small molecule drugs, biologic drugs, adjuvant therapies, gene therapies and the like) in a suitable vehicle formulation (such as but not limited to saline, HPMC, PEG400, HPBCD and the like) over a period of minutes to days (up to several months), would demonstrate benefit. Following dosing, animals can be sacrificed and tissues and organs collected (such as but not limited to blood, plasma, serum, CSF, liver, brain, heart, kidney, lungs, skin, muscle). These animals and tissue samples can be analyzed in multiple ways, including but not limited to clinical signs, bioanalytical, biochemical, biomarker, functional, behavioral, movement, cognitive and metabolic measures of efficacy. One can analyze tissues for CoA and Acyl-CoA species (such as but not limited to Acetyl-CoA, Succinyl-CoA, Malonyl-CoA, TCA cycle intermediates and the like), Acyl-Carnitines, Carnitine and AcylCarnitine Transport and transporters, ketone bodies, Organic Acids, and other metabolites consistent with the biochemical and metabolic pathways, utilizing analytical methods including but not limited to HPLC, MS, LCMS, MRI, CAT scan, PET scan, western blot, ELISA, PCR, enzyme processing, enzyme inhibition, complex formation and the like. One can measure functional aspects and changes in functional readouts such as Mitochondrial Bioenergetics (including but not limited to OCR, ECAR, Complex formation, ATP production), mitochondrial morphology and/or architectural changes (including but not limited to fusion, fission, membrane structure and morphology). One can measure prolongation of life in these animal models, temperature changes, mobility (including but not limited to walking, running, open field test, maze, treadmill), motor coordination (such as but not limited to Rotarod test), strength, and other functional measures of movement and cognition following treatment of Compounds. One can measure metabolomic changes and improvements in metabolic and TCA function.

Example 10: Generation of a Hypomorphic Model of Propionic Acidemia (hPCCA Hypomorph Mice)

Segments of human PCCA cDNA with mutations leading to A75P or A138T defects were synthesized by GenScript USA (Piscataway, NJ). These were used to replace wild-type Pcca in plasmid pShuttleCMV-FL-hPCCA-IRES-hrGFP. These mutant PCCA cDNAs were transferred to pCALL2-Δ-LoxP to generate plasmids pCALL2-Δ-LoxP-hPC.Y4-A75P and pCALL2-Δ-LoxP-hPCCA-A138T in which hPCCA is followed by an IRES-EGFP element to allow screening for transgenics. The pCALL2-Δ-LoxP plasmids were digested with BamHI and BsaWI and this transgene fragment was microinjected into the fertilized eggs of FVB mice. Founder mice were screened for GFP expression and by PCR using primers specific for the transgene cassette (F: CGGATTACGCGTAGCATGGTGAGCAA R: GCCTAAACGCGTTTACTTGTACAGCT). Positive mice were then crossed to Pcca+/− mice. All resulting progeny were screened using primers specific for the endogenous mPCCA gene, neomycin resistance gene (neo) and the transgene cassette described previously.

Example 11: Production of Liver-Specific 1M-Deficient Mice

Construction of the gene targeting vector and targeting in embryonal stem cells are described in Supplemental Information. Targeted embryonal stem cell clones were microinjected into C57BL/6J blastocysts and transferred to pseudopregnant recipients. We obtained 4 chimeras from one clone and 6 from the other. Chimeras were bred to C57BL/6J mice. Agouti offspring were genotyped to identify heterozygotes (HL+/L). In order to obtain the excision in liver of HL exon 2, which is catalytically essential [16], HL heterozygotes (HL+/L) were bred to Alb-Cre mice (B6.Cg-Tg (Alb-cre) 21 Mgn/J, 003574. Alb-Cre mice express Cre recombinase from the hepatocyte-specific albumin promoter. HL+/LCre+ mice were crossed to obtain Cre transgenic HLL/L homozygotes (HLL/LCre+; henceforth designated HL liver knockout (HLLKO) mice).

Example 12: Generation of Mutki/Ki and Mutko/Ki Mouse Models, which Survive Long Term The generation of mice carrying the Mut-p.Met698Lys mutation was performed by Polygene (Rumlang, Switzerland) using embryonic stem cell targeting. To generate Mut$^{ko/ki}$ mice, female Mut$^{ko/wt}$ (Peters H, 2003) were crossed to Mut$^{ki/ki}$ males. Mouse genotyping was performed on genomic DNA from ear punch biopsies using the primers 5'-GTGGGTGTCAGCACACTTG-3' (forward) and 5'-CGTATGACTGGGATGCCT-3' (reverse) for the ki allele and 5'-ACAACTCCTTGTGTAGGTC-3' (forward) and 5'-CCTTTAGGATGTCATTCTG-3' (reverse) for the ko allele.

Example 13: Generation of PDC-Deficient Mice

Generation of a mouse colony harboring a silent mutation in the Pdha1 gene (two loxP sites into intron sequences flanking exon 8; referred to as the Pdha1flox8 allele). These mice were maintained on a standard rodent laboratory diet and water ad libitum. To initiate deletion of exon 8 in vivo in all tissues of the progeny, homozygous floxed females (genotypes: Pdha1flox8/Pdha1-flox8) were bred with homozygous males from an EIIa-Cre transgenic mouse line (genotype: Pdha1wt/Y; CreaII+; referred to as Cre transgenic males) to generate experimental heterozygous female progeny (referred to as PDC-deficient females with the genotype: Pdha1wt/PDHa1Dex8, CreaII+). The transgenic CreaII+ mouse strain was homozygous for an autosomally integrated Cre transgene under the control of the adenovirus EIIa promoter that targets expression of Cre recombinase beginning on embryonic day 1. To generate control female progeny (referred to as controls) wild-type males (without carrying a Cre transgene), were bred with homozygous Pdha1flox8 females.

Example 14: Generation of Long-Chain Acyl-CoA Dehydrogenase-Deficient Mice (LCADD-Mice)

The targeting vector pAcadl$^{tm1Uab}$ was constructed by using a 7.5-kb Acadl (Nod/HindIII) fragment of 129/SvJ DNA and a neo$^r$ cassette derived from PGKneobpA, under the control of the phosphoglycerate kinase gene promoter and a bovine poly(A) signal and subcloned into pGEM-11zf (+) (Promega). An 821-bp deletion of the Acadl sequence, spanning exon 3 with flanking intron sequence, was created in the vector before electroporation and served as the site of linearization. Repair of this deletion on homologous recombination via the double-stranded-break repair model (Scostak J W, 1983) served as the basis for screening ES cell colonies for correct targeting by Southern blot analysis. Duplication of exon 3 can occur only on homologous recombination. Linearized vector was electroporated into TC-1 ES cells derived from 129/SvEvTacfBR (129) mice, and G418-resistant clones were analyzed by using Southern blot analysis. Correctly targeted clones were microinjected into C57BL/6J (B6) blastocysts to generate chimeras that were backcrossed to C57BL/6NTacfBR mice (Taconic). All mice analyzed in these studies were generation 2-3 with B6,129 Acadl$^{tm1Uab/tm1Uab}$ (LCAD−/−) or B6,129-Acadl$^{+/+}$ (normal control) genotypes from intercrosses of B6,129-Acadl$^{tm1Uab/+}$ (LCAD−/+) mice. Genotypes were determined by using Southern blot analysis. Mice were negative for murine pathogens based on a panel of 10 virus serologies, aerobic bacterial cultures of nasopharynx and cecum, endo- and ectoparasite exams, and histopathology of all major organs.

Example 15: Generation of Glutaryl-CoA Dehydrogenase-Deficient Mice

A line of Gcdh$^{-/-}$ mice [Gcdh$^{tm1Dmk(-/-)}$] was generated via homologous insertion of a gene targeting vector which resulted in a deletion of the first 7 exons of the Gcdh gene, and the insertion of a β-galactosidase reporter gene (nlacF) controlled by Gcdh chromosomal regulatory elements. Homologous insertion of the targeting vector was identified by PCR analysis of both the 5' and 3' ends of the locus. Enzymatic assay of glutaryl-CoA dehydrogenase activity from samples of liver confirmed a complete loss of activity in Gcdh$^{-/-}$ animals (not shown). Genotype analysis of the progeny of heterozygote-by-heterozygote matings (Gcdh$^{+/-}$×Gcdh$^{+/-}$) showed the expected Mendelian segregation ratio, indicating that Gcdh$^{-/-}$ animals have normal fetal and post-natal viability. There was no effect of genotype on birth weight, neonatal growth or final adult weight.

Example 16: Generation of Carnitine Palmitoyltransferase 1a (Liver Isoform) Deficiency Model Construction of Targeting Vector and Gene Targeting in ES Cells The Cpt-1a targeting vector was constructed from genomic DNA fragments derived from a mouse 129X1/SvJ genomic P1 clone, PV1. The P1 clone was identified by screening a mouse 129X1/SvJ strain genomic library by PCR Exons 11-18 were deleted by a replacement gene targeting strategy by gene transfer into ES cells. The targeted ES cells were used to generate mice with a null allele (Cpt-1a$^{tm1Uab}$). ES cells (TC-1) were originally derived from 129S6/SvEv mice. Screening for recombinant ES cell clones was done by G418 selection (350 µg/ml) for 7 days. Surviving colonies were picked and expanded for Southern blot analysis.

Mice

Chimeric mice were produced by microinjection of gene targeted ES cells into C57BL/6NTac (B6) embryos. The chimeric founders were bred to 129S6/SvEvTac (129) or B6 for perpetuation of mice used in these studies. All three genotypes (wild-type, heterozygous mutants and homozygous mutants) on both B6; 129 and 129 backgrounds were produced for these studies.

Example 17: Generation of Carnitine Palmitoyltransferase 1b (Muscle Isoform) Deficiency Model The mutant mouse line had been generated previously using a targeted mutagenesis strategy by replacing a segment of 1468 bp (exons 1-3) in mouse Cpt-1b with a 3 kb neo-tk cassette in the C57BL/6J×129X1/SvJ ES cells. Mice in the current study were the second generation from 3 male founders, which were offspring from a male chimera and C57BL/6J (B6J) females. Mice were fasted for ~18 h and euthanized with $CO_2$ before collecting blood for biochemical markers. The mice were also fasted for ~18 h prior to cold tolerance testing. Alternatively, the mice used to measure mRNA expression and for collecting tissue for activity assays were not fasted before being euthanized with CO2 inhalation. Also, two different mating pair arrangements were setup to obtain fetal tissue for genotyping and to isolate the corresponding placenta for RNA preparation. One strategy included male CPT-1b+/+ mice mated with female CPT-1b+/− mice; the other included male CPT-1b+/− mice mated with female CPT-1b+/+ mice. At embryonic day 12-14, pregnant females were sacrificed.

Example 18: Generation of Medium-Chain Acyl-CoA Dehydrogenase Deficiency Model MCAD insertion vector (MCAD 1V2) was designed to undergo gap repair of the 1.3-kb deleted region upon homologous recombination in 129P2 (129P2/OlaHsd) ES cells E14-1. Correct targeting of the MCAD locus resulted in a duplication of exons 8, 9, and 10 and integration of flanking plasmid and Neo sequences. The insertion vector was designed to duplicate exon 8, 9, and 10 at the MCAD locus. Translation of the duplicated exon 8 region results in the formation of premature stop codons resulting in truncation of the MCAD monomer. Specifically, the first premature stop codon arises after translation of only seven amino acids from the duplicated exon 8. The resulting MCAD monomer is missing the C-terminal domain α-helixes that are responsible for making intersubunit contacts to generate the functional MCAD homotetramer.

ES cell clones were screened by PCR and confirmed by Southern blot analysis. Southern blot analysis used an exon 10 probe (probe A), not present in the targeting vector, hybridized to a 13.2-kb band in addition to the 3.1-kb endogenous band indicating targeted insertion of the vector at the Acadm locus. Correctly targeted ES cell clones were microinjected into B6 (C57BL/6NTac) blastocysts to generate chimeric mice. Chimeric mice were backcrossed to both 129P2 and B6 inbred mice to produce MCAD$^{+/-}$ and eventually MCAD$^{-/-}$ mice on a B6/129 mixed background.

The studies described here were conducted exclusively on the B6/129 mixed background compared with littermate controls or B6/129 control groups maintained by intercrosses as were the mutants. Perpetuating this mutation as a congenic mutant line on the 129P2 background proved impractical. The 129P2 mice were poor breeders as wild-types, and when introduced, the Acadm mutation was nearly lost on this background because of the high rate of neonatal death. Because of the molecular structure of the targeted allele, it proved virtually impossible to distinguish all three potential genotypes. One could clearly detect the presence or absence of the targeted allele, however, whether a particular mouse was MCAD$^{-/-}$ or MCAD$^{+/-}$ could not be determined by Southern blot or PCR of genomic DNA. Ultimately MCAD$^{-/-}$ mice were ascertained by immunoblot analysis of offspring with subsequent perpetuation of MCAD$^{-/-}$ and MCAD$^{+/+}$ mice as separate groups.

Example 23: Synthesis of Compound 874

Synthesis of methyl 2-((2-(3-((4R)-2-(4-methoxyphenyl)-5,5-dimethyl-1,3-dioxane-4-carboxamido)propanamido)ethyl)thio)-2-oxoacetate

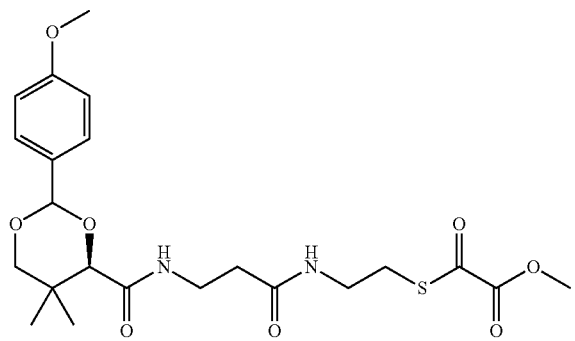

To a stirred solution of (4R)—N-(3-((2-mercaptoethyl)amino)-3-oxopropyl)-2-(4-methoxyphenyl)-5,5-dimethyl-1,3-dioxane-4-carboxamide (4.0 g, 1 eq., 10.096 mmol) in DCM (50 mL) at −78° C. was added methyl chlorooxoacetate (1.01 ml. 1.1 eq., 11.106 mmol). Then the reaction mixture was stirred at same temperature for 4 h. The reaction mixture was quenched with Et$_3$N (2.84 ml, 2 eq., 20.176 mmol). The reaction mixture was warmed to room temperature and portioned between water (100 mL) and DCM (3×100 mL). The organic layer was dried over Na$_2$SO$_4$, filtered and concentrated. The residue was purified by combi flash on silica gel eluting 65-75% EtOAc in hexane to afford methyl 2-((2-(3-((4R)-2-(4-methoxyphenyl)-5,5-dimethyl-1,3-dioxane-4-carboxamido)propanamido)ethyl)thio)-2-oxoacetate (3.0 g, 6.216 mmol, 62%) as a light yellow oil. LCMS (M+1)=483.05.

Example 24: Synthesis of Compound 875

Synthesis of methyl 4-((2-(3-((4R)-2-(4-methoxyphenyl)-5,5-dimethyl-1,3-dioxane-4-carboxamido)propanamido)ethyl)thio)-4-oxobutanoate

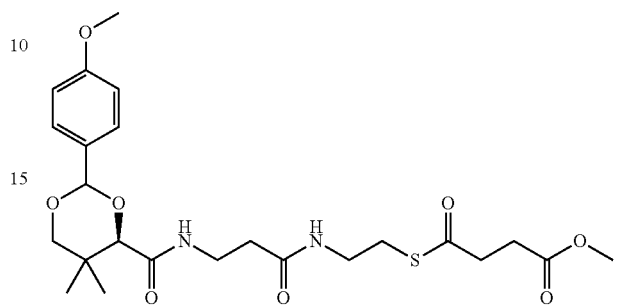

To a stirred solution of the organic acid 4-methoxy-4-oxobutanoic acid (2.665 g, 2 eq., 20.176 mmol), EDC HCl (3.868 g, 2 eq., 20.176 mmol) followed by DMAP (2.46 g, 0.2 eq., 20.176 mmol) in DMF at 0° C. was added DIPEA (7.823 g, 6 eq., 60.528 mmol). After 10 minutes stirring at same temperature (4R)—N-(3-((2-mercaptoethyl)amino)-3-oxopropyl)-2-(4-methoxyphenyl)-5,5-dimethyl-1, 3-dioxane-4-carboxamide carboxamide (4 g, 1 eq., 10.088 mmol; from Preparatory Example 1 Step 2) was added. Then the reaction mixture was stirred at room temperature for 16 h. The reaction mixture was quenched with water and extracted with EtOAc (3 times). The combined organic layer was washed with sat. NaHCO$_3$ solution followed by brine solution, dried over dried over Na$_2$SO$_4$, filtered and concentrated. The residue was purified by combi-flash on silica gel eluting 1-3% MeOH in DCM to afford corresponding methyl 4-((2-(3-((4R)-2-(4-methoxyphenyl)-5, 5-dimethyl-1, 3-dioxane-4-carboxamido)propanamido)ethyl)thio)-4-oxobutanoate (3.5 g, 6.854 mmol, 68%) as a yellow oil. LCMS (M+1)=511.2.

Example 25: Synthesis of Compound 876

Synthesis of S-(2-(3-((4R)-2-(4-methoxyphenyl)-5,5-dimethyl-1,3-dioxane-4-carboxamido) propanamido)ethyl) (E)-but-2-enethioate

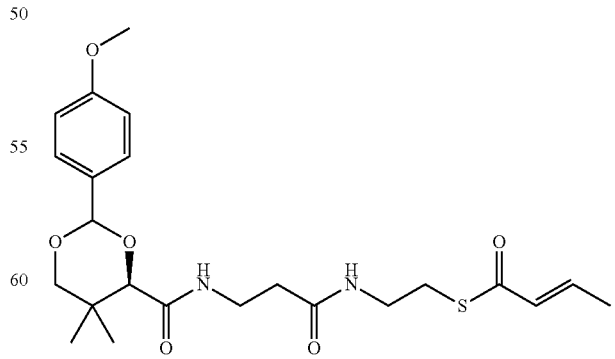

The title compound, S-(2-(3-((4R)-2-(4-methoxyphenyl)-5,5-dimethyl-1,3-dioxane-4-carboxamido) propanamido) ethyl) (E)-but-2-enethioate (0.3 g, 0.645 mmol, 25%) was synthesized as a yellow oil from (4R)—N-(3-((2-mercaptoethyl)amino)-3-oxopropyl)-2-(4-methoxyphenyl)-5,5-dimethyl-1, 3-dioxane-4-carboxamide from Preparatory Example 1 Step 2 (1.0 g, 1 eq., 2.522 mmol) by using the general procedure from Example 23 and crotonic acid as the organic acid. LCMS (M+1)=465.2.

Example 26: Synthesis of Compound 877

Synthesis of Methyl (E)-4-((2-(3-((4R)-2-(4-methoxyphenyl)-5,5-dimethyl-1,3-dioxane-4-carboxamido)propanamido)ethyl)thio)-4-oxobut-2-enoate

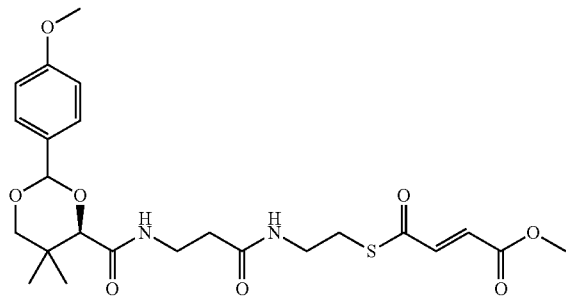

To a stirred solution of monomethyl fumarate (3.28 g, 2.5 eq., 25.246 mmol) in THF (60 mL) was added EDC.HCl (5.8 g, 3.0 eq., 30.2952 mmol) followed by DMAP (0.031 g, 0.05 eq., 0.504 mmol) and the reaction mixture was stirred at room temperature for 15 min. (4R)—N-(3-((2-mercaptoethyl)amino)-3-oxopropyl)-2-(4-methoxyphenyl)-5,5-dimethyl-1,3-dioxane-4-carboxamide from Preparatory Example 1 Step 2 (4.0 g, 1 eq; 10.098 mmol) was then added and the reaction mixture was stirred at room temperature for 16 h. The progress of the reaction was monitored by TLC. The reaction mixture was concentrated and the residue was purified by combi-flash on silica gel eluting with 2-3% MeOH in DCM to afford the title compound methyl (E)-4-((2-(3-((4R)-2-(4-methoxyphenyl)-5, 5-dimethyl-1,3-dioxane-4-carboxamido)propanamido)ethyl)thio)-4-oxobut-2-enoate (4.0 g, 7.871 mmol; 77%) as a yellow oil. LCMS (M−1)=507.15

Example 35: Synthesis of Compound 878

Synthesis of dimethyl 2-((2-(3-((4R)-2-(4-methoxyphenyl)-5,5-dimethyl-1,3-dioxane-4-carboxamido)propanamido)ethyl)thio) succinate

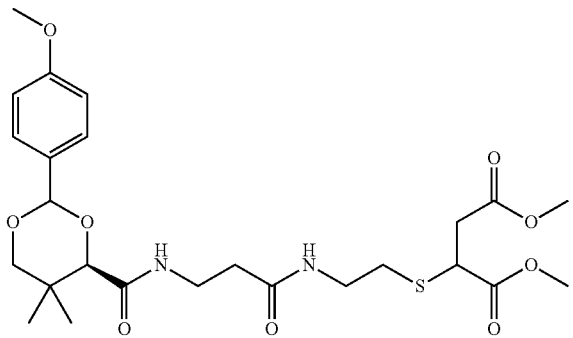 [SMILES: COC(=O)CC(SCCNC(=O)CCNC(=O)[C@@H]1OC(c2ccc(OC)cc2)OCC1(C)C)C(=O)OC]

To a stirred solution of (4R)—N-(3-((2-mercaptoethyl)amino)-3-oxopropyl)-2-(4-methoxyphenyl)-5,5-dimethyl-1, 3-dioxane-4-carboxamide from Preparatory Example 1 Step 2 (3.0 g, 1 eq., 7.573 mmol) and dimethyl maleate (1.2 g, 1.1 eq., 8.331 mmol) in methanol (70 mL) was added triethyl amine (1.3 ml, 1.2 eq., 9.088 mmol) and the reaction mixture was stirred at 60° C. for 16 h. The progress of the reaction was monitored by TLC. The reaction mixture was concentrated. The residue was purified by combi-flash on silica gel eluting with 3-4% MeOH in DCM to afford the title compound dimethyl 2-((2-(3-((4R)-2-(4-methoxyphenyl)-5,5-dimethyl-1,3-dioxane-4-carboxamido)propanamido)ethyl)thio)succinate (2.7 g; 4.998 mmol; 66%) as yellow oil. LCMS (M+1)=541.10.

Example 40: Synthesis of Compound 924

Synthesis of methyl (S)-4-[2-(3-{[(R)-2,2,5,5-tetramethyl-1,3-dioxan-4-yl]carbonylamino}propionylamino)ethylthio)carbonyl]-4-(tert-butoxycarbonylamino) butyrate

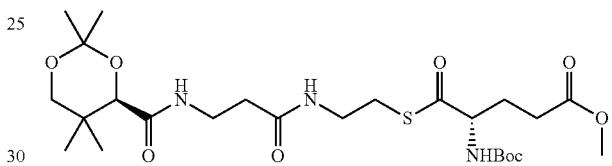

A flask was charged with the product from Preparative Example 3 Step 2 (200 mg, 0.6 mmol), (S)-2-((tert-butoxycarbonyl)amino)-5-methoxy-5-oxopentanoic acid (197 mg, 0.75 mmol) and EDC (180 mg, 0.94 mmol). CH$_2$Cl$_2$ (20 mL) followed by diisopropylethylamine (0.21 mL, 1.25 mmol) were added. The reaction mixture was allowed to stir for 18 h. The reaction mixture was washed with water and brine solution. The organic layer was dried over sodium sulfate and dried under vacuum. The crude material was purified by flash column chromatography (hexane/EtOAc 2:8) to yield 180 mg of the product.

Example 41: Synthesis of Compound 925

Synthesis of methyl 2-[2-(3-{[(R)-2,2,5,5-tetramethyl-1,3-dioxan-4-yl]carbonylamino}propionylamino)ethylthio)carbonyl] propionate

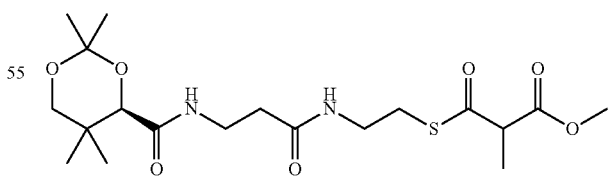

A flask was charged with the product of Preparatory Example 3 Step 2 (1 g, 3.1 mmol), 2-methoxycarbonylpropionic acid (450 mg, 3.4 mmol) and EDC (900 mg, 4.7 mmol). CH$_2$Cl$_2$ (100 mL) followed by diisopropylethylamine (1.07 mL, 6.2 mmol) were added. The reaction mixture was allowed to stir for 18 h. The reaction mixture was washed with water and brine solution. The organic layer was

621 dried over sodium sulfate and dried under vacuum. The crude material was purified by flash column chromatography (hexane/EtOAc 2:8) to yield 800 mg of the title Compound 925.

Example 42: Synthesis of Compound 879

Synthesis of methyl (S)-3-[2-(3-{[(R)-2,2,5,5-tetramethyl-1,3-dioxan-4-yl]carbonylamino}propionylamino)ethylthio)carbonyl]-2-(tert-butoxycarbonylamino) propionate

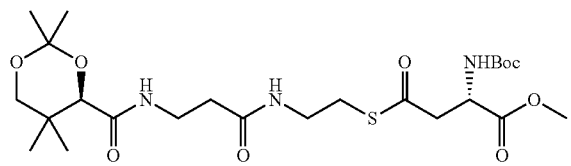

A flask was charged with the product of Preparatory Example 3 Step 2 (250 mg, 0.78 mmol), (S)-3-methoxycarbonyl-3-(tert-butoxycarbonylamino)propionic acid (291 mg, 1.1 mmol) and EDC (225 mg, 1.1 mmol), followed by CH₂Cl₂ (15 mL) and diisopropylethylamine (0.26 mL, 1.5 mmol). The reaction was allowed to stir for 18 h. The reaction mixture was washed with water and brine solution. The organic layer was dried over sodium sulfate and dried under vacuum. The crude material was purified by flash column chromatography (hexane/EtOAc 2:8) to yield 200 mg compound of the title Compound 879.

Example 44: Synthesis of Compound 880

Synthesis of methyl (S)-3-[2-(3-{[(R)-2,2,5,5-tetramethyl-1,3-dioxan-4-yl]carbonylamino}propionylamino)ethylthio)carbonyl]-3-(tert-butoxycarbonylamino) propionate

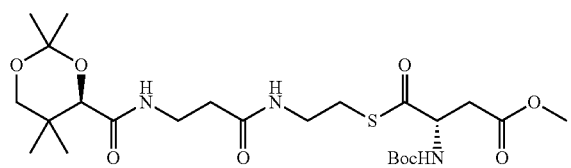 [SMILES: COC(=O)C[C@H](NC(=O)OC(C)(C)C)C(=O)SCCNC(=O)CCNC(=O)[C@@H]1OC(C)(C)OCC1(C)C]

A flask was charged with the product of Preparatory Example 3 Step 2 (100 mg, 0.3 mmol), (S)-3-methoxycarbonyl-2-(tert-butoxycarbonylamino)propionic acid (116 mg, 0.47 mmol) and EDC (90 mg, 0.47 mmol), followed by CH₂Cl₂ (10 mL) and diisopropylethylamine (0.104 mL, 0.62 mmol). The reaction mixture was allowed to stir for 18 h. The reaction mixture was washed with water and brine solution. The organic layer was dried over sodium sulfate and dried under vacuum. The crude material was purified by flash column chromatography (hexane/EtOAc 2:8) to yield 80 mg of the title Compound 880.

622

Example 45: Synthesis of Compound 881

Synthesis of S-2-(3-{[(R)-2,2,5,5-tetramethyl-1,3-dioxan-4-yl]carbonylamino}propionylamino)ethyl 5-oxo-2-pyrrolidinecarbothioate

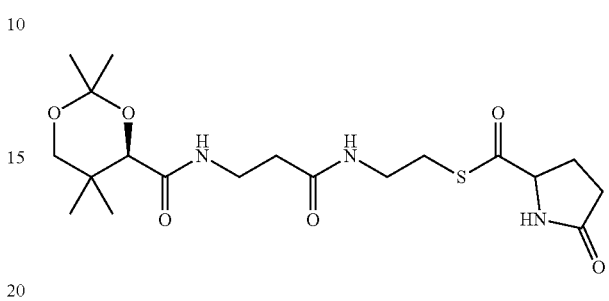

A flask was charged with the product of Preparatory Example 3 Step 2 (200 mg, 0.62 mmol), 5-oxo-2-pyrrolidinecarboxylic acid (121 mg, 0.94 mmol), EDC (179 mg, 0.94 mmol), followed by CH₂Cl₂ (10 mL) and diisopropylethylamine (0.215 mL, 1.25 mmol). The reaction was stirred for 18 h. After this time, the reaction mixture was washed with water and brine solution. The organic layer was dried over sodium sulfate and dried under vacuum. The crude material was purified by flash column chromatography (hexane/EtOAc 2:8) to yield 150 mg of the title Compound 881.

Example 47: Synthesis of Compound 882

Synthesis of S-2-(3-{[(R)-2,2,5,5-Tetramethyl-1,3-dioxan-4-yl]carbonylamino}propionylamino)ethyl 5-oxo-3,4-dihydro-2H-furan-2-carbothioate

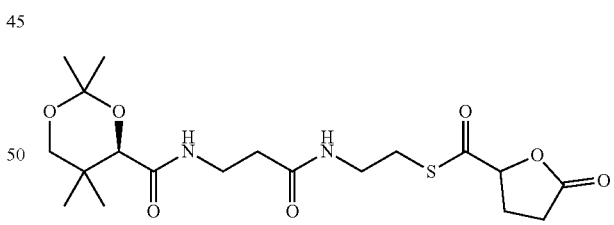

A flask was charged with the product of Preparatory Example 3 Step 2 (200 mg, 0.62 mmol), CH₂Cl₂ (10 mL), diisopropylethylamine (0.215 mL, 1.25 mmol) and 5-oxo-3,4-dihydro-2H-furan-2-carboxylic acid (122 mg, 0.94 mmol) followed by EDC (179 mg, 0.94 mmol). The reaction mixture was stirred for 18 h. After this time, reaction mixture was washed with water and brine solution. The organic layer was dried over sodium sulfate and dried under vacuum. The crude material was purified by flash column chromatography (hexane/EtOAc 2:8) to yield 150 mg of the title Compound 882.

Example 50: Synthesis of Compound 883

Synthesis of tert-Butyl (S)-4-[2-(3-{[(2R)-4-hydroxy-3,3-dimethyltetrahydro-2H-pyran-2-yl]carbonylamino}propionylamino)ethylthio)carbonyl]-4-(tert-butoxycarbonylamino)butyrate

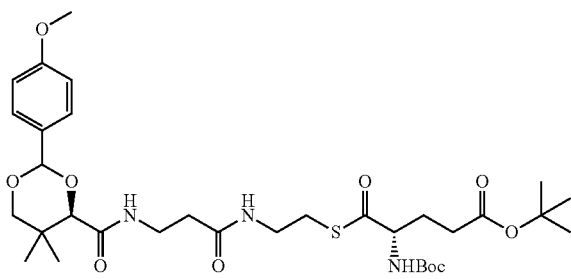

To a solution of the product of Preparatory Example 1 Step 2 (900 mg, 2.27 mmol) in DCM (20 mL) was added (S)-5-(tert-butoxy)-2-((tert-butoxycarbonyl)amino)-5-oxo-pentanoic acid (827 mg, 2.73 mmol), EDCI (654 mg, 3.41 mmol) and DIEA (732 mg, 5.68 mmol) at 20° C. under $N_2$. The mixture was stirred at 20° C. for 12 hours. TLC (60% EtOAc in Petroleum ether, Rf=0.4) showed the reaction was finished. The reaction was quenched by a.q $NH_4Cl$ (10 mL). The mixture was partitioned between DCM (80 mL) and $H_2O$ (20 mL). The organic layer was washed with brine (2×30 mL). The organic layer is then dried ($Na_2SO_4$) and evaporated to give crude product, which was purified by column chromatography (S102, 15-60% Ethyl acetate in Petroleum ether, Rf=0.4) to give the title compound (1.27 g, 1.86 mmol, 82.1% yield) as an off white solid.

$^1$H NMR (400 MHz, $CDCl_3$) 7.44 (d, J=8.4 Hz, 2H), 6.95-6.90 (m, 1H), 6.85 (d, J=8.0 Hz, 2H), 6.30-6.25 (m, 1H), 5.39 (s, 1H), 5.30-5.25 (m, 1H), 4.30-4.24 (m, 1H), 4.03 (s, 1H), 3.74 (s, 3H), 3.65-3.60 (m, 2H), 3.49-3.40 (m, 2H), 3.30-3.25 (m, 2H), 2.85 (t, J=6.4 Hz, 2H), 2.35-2.25 (m, 4H), 2.15-2.05 (m, 1H), 1.85-1.75 (m, 1H), 1.46 (s, 18H), 1.03 (d, J=4.8 Hz, 6H).

Example 52: Synthesis of Compound 884

Synthesis of tert-butyl (S)-3-[2-(3-{[(4R)-2-(p-methoxyphenyl)-5,5-dimethyl-1,3-dioxan-4-yl]carbonylamino}propionylamino)ethylthio)carbonyl]-3-(tert-butoxycarbonylamino) propionate

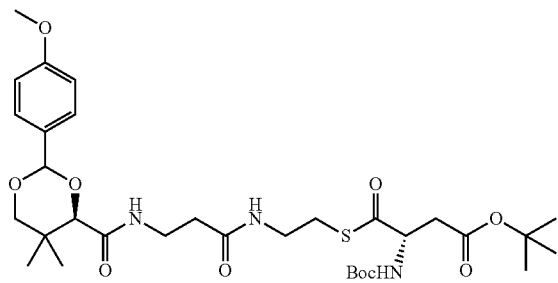

To a solution of the product of Preparatory Example 1 Step 2 (600 mg, 1.51 mmol) in DCM (20 mL) was added (S)-3-tert-butoxycarbonyl-2-(tert-butoxycarbonylamino) propionic acid (524 mg, 1.81 mmol), EDCI (435 mg, 2.27 mmol) and DIEA (487 mg, 3.77 mmol) at 20° C. under N2. The mixture was stirred at 20° C. for 12 hours. TLC (60% EtOAc in Petroleum ether, Rf=0.4) showed the reaction was finished. The reaction was quenched by a.q $NH_4Cl$ (10 mL). The mixture was portioned between DCM (50 mL) and $H_2O$ (20 mL). The organic layer was washed with brine (2×30 mL). The organic layer is then dried ($Na_2SO_4$) and evaporated to give crude product, which was purified by column chromatography ($SiO_2$, 15-60% Ethyl acetate in Petroleum ether, Rf=0.4) to give the title Compound 884 (770 mg, 1.15 mmol, 76.4% yield) as an off white solid.

$^1$H NMR (400 MHz, $CDCl_3$) 7.36 (d, J=8.8 Hz, 2H), 6.95 (d, J=18.8 Hz, 1H), 6.90-6.79 (m, 2H), 6.05 (s, 1H), 5.60 (d, J=9.6 Hz, 1H), 5.39 (s, 1H), 4.48 (dd, J=9.6, 4.8 Hz, 1H), 4.01 (s, 1H), 3.75 (s, 3H), 3.61 (q, J=11.6 Hz, 2H), 3.52-3.42 (m, 2H), 3.35 (s, 2H), 2.98-2.84 (m, 3H), 2.63 (d, J=4.4 Hz, 1H), 2.31 (dd, J=16.4, 10.4 Hz, 2H), 1.37 (dd, J=15.2, 10.4 Hz, 18H), 1.03 (d, J=3.2 Hz, 6H).

Example 54: Synthesis of Compound 885

Synthesis of S-2-(3-{[(R)-2,2,5,5-tetramethyl-1,3-dioxan-4-yl]carbonylamino}propionylamino)ethyl 2,2-dimethyl-1,3-dioxolane-4-carbothioate

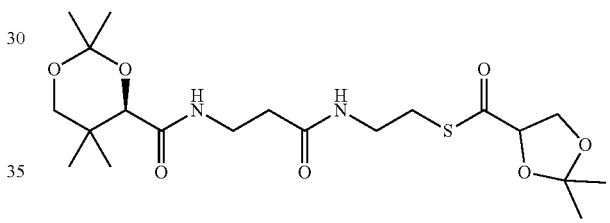

A mixture of the product from Preparatory Example 3 Step 2 (400 mg, 1.26 mmol), 2,2-dimethyl-1,3-dioxolane-4-carboxylic acid (200 mg, 1.37 mmol), EDCI (265 mg, 138 mmol) and DMAP (31 mg, 0.25 mmol) in DCM (5 mL) was stirred at room temperature for 16 h. The solvent was removed and the residue purified by Prep-HPLC to give the title Compound 885 (170 mg, yield 30.3%) as a colorless oil. LCMS (ESI): m/z 447.2 (M+H)$^+$, RT=1.720 min.

Example 55: Synthesis of Compound 886

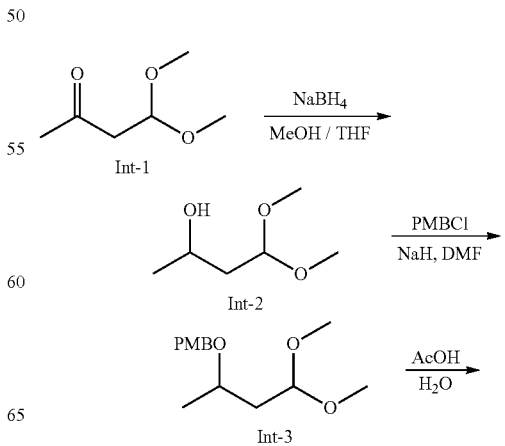

-continued

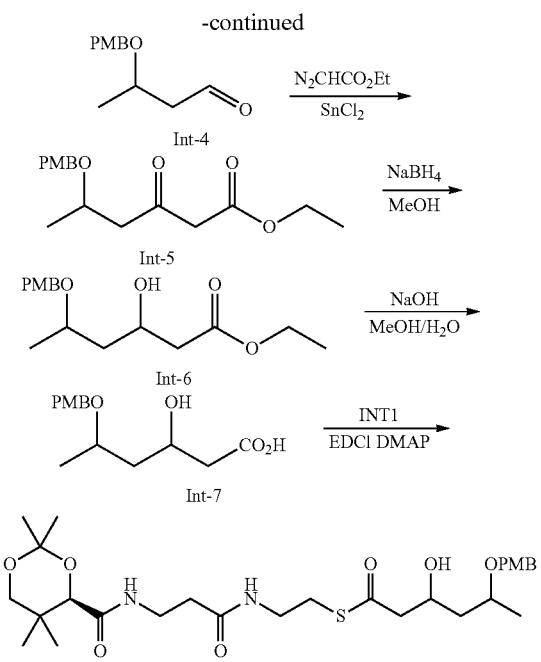

Step 1: Synthesis of 4,4-dimethoxy-2-butanol

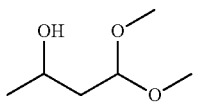

The starting material Int-1 (25 g, 189 mmol) was dissolved in methanol (100 mL) and THF (100 mL), then NaBH₄ (7.2 g, 189 mmol) was added at 0° C. The mixture was stirred at room temperature for 2 hours. After the reaction completed, the solvent was removed in vacuum and NH₄Cl was added to adjust the pH to 5-6. The crude product was extracted with 100 mL ethyl acetate and purified by column chromatography on silica gel (5:1 v:v, petroleum ether:ethyl acetate) to give the product Int-2 (20 g, Yield 79%) as colorless oil which was used directly.

Step 2: Synthesis of 1,1-dimethoxy-3-[(p-methoxyphenyl)methoxy]butane

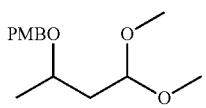

The product from Example 55 Step 1 (Int-2) (20 g, 149 mmol) was dissolved in DMF (50 mL), and NaH (7.2 g, 298 mmol) was added at 0° C. After stirring for 30 min, PMBCl (28 g, 179 mmol) was added. The reaction mixture was stirred at room temperature for 5 h. After the reaction was complete, the reaction mixture was quenched with ice-cold water (20 mL) and extracted with ethyl acetate (50 mL×3). The organic phase was dried over Na₂SO₄ and concentrated in vacuum to give the product Int-3 (22 g, Yield 58%) as a colorless oil which was used directly.

Step 3: Synthesis of 3-[(p-methoxyphenyl)methoxy]butyraldehyde

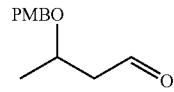

The product from Example 55 Step 2 (Int-3) (22 g, 86.5 mmol) was dissolved in acetic acid (25 mL) and water (25 mL). The mixture was stirred at 65° C. overnight. After the reaction was complete, NaHCO₃ was added to the reaction mixture to adjust pH to 7, then extracted with ethyl acetate (25 mL×3). The organic phase was dried over Na₂SO₄ and concentrated in vacuum to give the product Int-4 (18 g, Yield 99%) as a colorless oil which was used directly.

Step 4: Synthesis of ethyl 5-[(p-methoxyphenyl)methoxy]-3-oxohexanoate

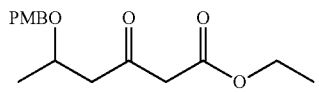

To a mixture of SnCl₂ (0.912 g, 4.8 mmol) in DCM (10 mL) was added dropwise ethyl diazoacetate (3.3 g, 28.8 mmol). Then a solution of the product from Example 55 Step 3 (Int-4) (2 g, 9.6 mmol) in DCM (10 mL) was added when nitrogen observed. The reaction mixture was stirred at room temperature for 30 min. The solvent was removed in vacuum. The residue was purified by column chromatography on silica gel (PE/EA=5/1) to give the product Int-5 (1.3 g, Yield 46%) as a yellow oil which was used directly. LCMS (ESI): m/z 295.1 (M+H)⁺, RT=2.065 min.

Step 5: Synthesis of ethyl 3-hydroxy-5-[(p-methoxyphenyl)methoxy]hexanoate

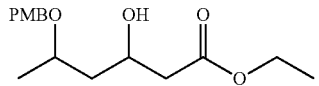

The product from Example 55 Step 4 (Int-5) (1.3 g, 4.42 mmol) was dissolved in methanol (10 mL), and NaBH₄ (84 mg, 2.21 mmol) was added at 0° C. The mixture was stirred at room temperature for 2 hours. After the reaction completed, the solvent was removed in vacuum and then NH₄Cl was added to adjust the pH to 5-6. The mixture was extracted with 50 mL ethyl acetate and purified with column chromatography on silica gel (PE/EA=5/1) to give the product Int-6 (686 mg, Yield 52%) as colorless oil which was used directly. LCMS (ESI): m/z 319.0 (M+23)⁺, RT=1.644 min.

Step 6: Synthesis of 3-hydroxy-5-[(p-methoxyphenyl)methoxy]hexanoic Acid

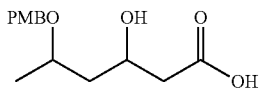

The product from Example 55 Step 5 (Int-6) (686 mg, 2.32 mmol) was dissolved in methanol (6 mL). To the solution was added dropwise a solution of NaOH (185 mg, 4.63 mmol) in water (2 mL). The mixture was stirred at 40° C. for 2 hours. The excess methanol was removed in vacuum and the mixture was diluted with water. Then 1N HCl was added to adjust the pH to 5-6 and extracted with 50 mL ethyl acetate. The organic phase was washed with brine and the solvent was removed in vacuum to give the product Int-7 (600 mg, Yield 96%) as a colorless oil which was used directly. LCMS (ESI): m/z 291.0 (M+23)$^+$, RT=1.263 min.

Step 7: Synthesis of Compound 886

Synthesis of S-2-(3-{[(R)-2,2,5,5-tetramethyl-1,3-dioxan-4-yl]carbonylamino}propionylamino) ethyl 3-hydroxy-5-[(p-methoxyphenyl)methoxy]hexanethioate

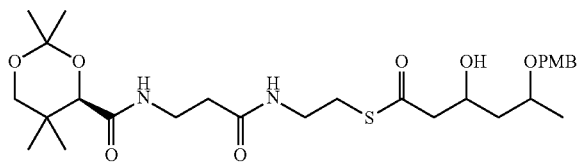

The product from Example 55 Step 6 (Int-7) (600 mg, 2.24 mmol) was dissolved in DCM (20 mL). To the solution was added EDCI (470 mg, 2.46 mmol), DMAP (27 mg, 0.22 mmol) and the product from Preparative Example 3 Step 2 ((R)—N-(3-((2-mercaptoethyl)amino)-3-oxopropyl)-2,2,5,5-tetramethyl-1,3-dioxane-4-carboxamide) (783.15 mg, 2.46 mmol). The mixture was stirred at room temperature for 2 hours. After the reaction completed, the excess solvent was removed in vacuum, and the crude was purified by reversed phase column chromatography (HCOOH as additive) to give the title Compound 886 (546 mg Yield 42%) as a colorless oil which was used directly. LCMS (ESI): m/z 569.2 (M+H)$^+$, RT=1.586 min.

Example 57: Synthesis of Compound 887

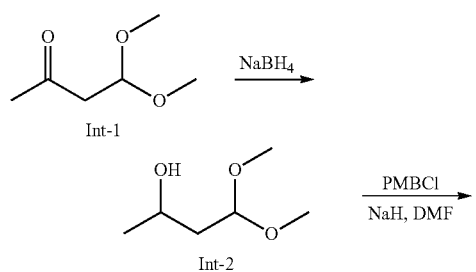

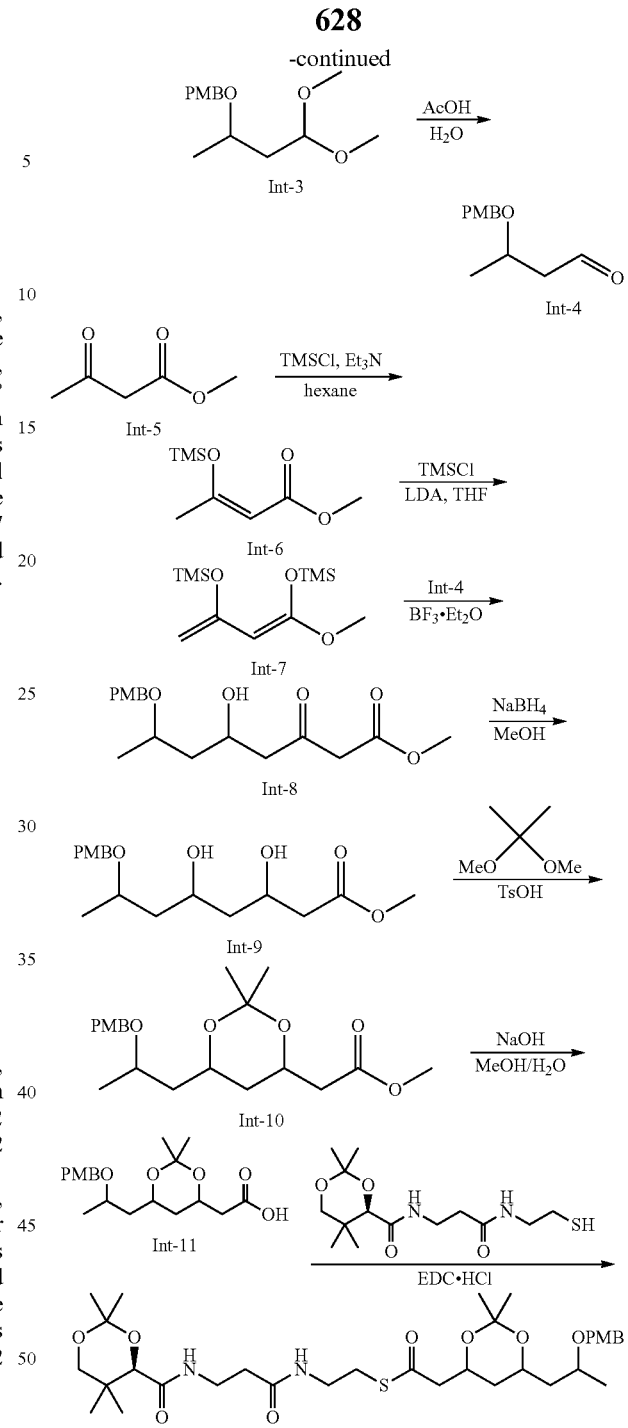

Step 1: Synthesis of methyl (Z)-3-trimethylsilane-2-butenoate

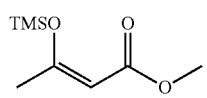

To a solution of methyl acetoacetate (Int-5) (20 g, 172 mmol) in hexane (500 mL) was added TMSCl (26 g, 240 mmol) and triethylamine (52 g, 510 mmol). The reaction mixture was stirred at 0° C. overnight. The solution was filtered and washed with excess hexane. The filtrate was concentrated in vacuum to give the product Int-6 (18.6 g, Yield 57%) as a yellow oil which was used directly.

Step 2: Synthesis of (1Z)-1-methoxy-1,3-trimethylsilane-1,3-butadiene

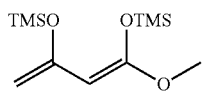

To a solution of LDA (59 mL, 118 mmol) in THF (20 mL) was added the product from Example 57 Step 1 (Int-6) (18.6 g, 98.89 mmol) in THF (40 mL) dropwise at −78° C. The mixture was stirred for 1 hour. Then, TMSCl (12.9 g, 118 mmol) was added to the mixture dropwise. The mixture was stirred for 30 minutes and was allowed to warm up to 0° C., and stirred for an additional 30 minutes. When the reaction was complete, excess solvent was removed under reduced pressure. The residue was diluted by hexane, filtered and washed with excess hexane.

The filtrate was removed in vacuum to give the product Int-7 (12 g, Yield 46%) as yellow oil which was used directly.

Step 3: Synthesis of methyl 5-hydroxy-7-[(p-methoxyphenyl)methoxy]-3-oxooctanoate

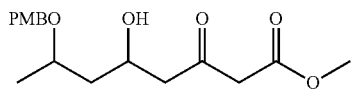

The product from Example 55 Step 3 (Int-4) (3 g, 14.42 mmol) was dissolved in DCM (80 mL). To the solution was added the product from Example 57 Step 2 (Int-7) (7.5 g, 28.82 mmol) and BF$_3$·Et$_2$O (1.95 mL) dropwise at 0° C. and stirred for 0.5 hour. After that, the excess solvent was removed under reduced pressure. The residue was dissolved in excess ethyl acetate, and then washed with sodium bicarbonate twice. Then, the solvent was removed under reduced pressure. The crude product was purified by prep-HPLC (FA as additive) to give the product Int-8 (2.6 g, Yield 55%) as colorless oil which was used directly. LCMS (ESI): m/z 347.1 (M+23)$^+$, RT=1.429 min.

Step 4: Synthesis of methyl 3,5-dihydroxy-7-[(p-methoxyphenyl)methoxy]octanoate

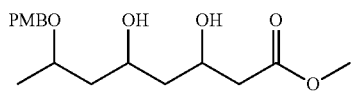

The product from Example 57 Step 3 (Int-8) (2.6 g, 8.02 mmol) was dissolved in methanol (40 mL), and NaBH$_4$ (152 mg, 4.01 mmol) was added at 0° C. After the reaction was complete, NH$_4$Cl was added to adjust the PH to 5-6. Then the solvent was removed in vacuum. The residue was extracted with 50 mL ethyl acetate and purified by column chromatography on silica gel (PE/EA=5/1) to give the product Int-9 (1.87 g, Yield 71%) as colorless oil which was used directly.

Step 5: Synthesis of methyl (6-{2-[(p-methoxyphenyl)methozy]propyl}-2,2-dimethyl-1,3-dioxan-4-yl)acetate

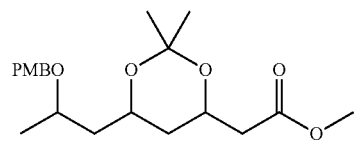

The product from Example 57 Step 4 (Int-9) (1.87 g, 5.72 mmol) was dissolved in DCM (20 mL). To the solution was added 2,2-dimethoxypropane (1.19 g, 11.47 mmol) and 4-methylbenzenesulfonic acid (49.31 mg, 0.29 mmol). The reaction mixture was stirred at room temperature overnight. After the reaction was complete, the NaHCO$_3$ was added to adjust the pH to 7-8. The solvent DCM was removed in vacuum. The residue was extracted with 50 mL ethyl acetate, washed with brine and dried over Na$_2$SO$_4$ to give the product Int-10 (1.16 g, Yield 55%) as colorless oil which was used directly.

Step 6: Synthesis of (6-{2-[(p-methoxyphenyl)methozy]propyl}-2,2-dimethyl-1,3-dioxan-4-yl)acetic Acid

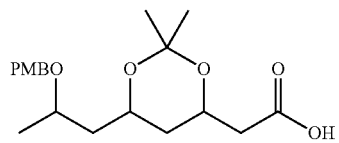

The product from Example 57 Step 5 (Int-10) (1.16 g, 3.18 mmol) was dissolved in methanol (10 mL). To the solution was added a solution of NaOH (254.6 mg, 6.36 mmol) in H$_2$O (3 mL) dropwise. The mixture was stirred at 40° C. for 1 hour. After the reaction completed, the excess methanol was removed in vacuum and the mixture was added 1N HCl to adjust the pH to 4 or 5 and extracted with 50 mL ethyl acetate. The organic phase was washed with brine, dried over Na$_2$SO$_4$ to give the product Int-11 (941 mg, Yield 83%) as a colorless oil which was used directly. LCMS (ESI): m/z 375.1 (M+23)$^+$, RT=0.740 min.

Step 7: Synthesis of Compound 887

Synthesis of S-(6-{2-[(p-methoxyphenyl)methoxy]propyl}-2,2-dimethyl-1,3-dioxan-4-yl)methyl 3-(3-{[(R)-2,2,5,5-tetramethyl-1,3-dioxan-4-yl]carbonylamino}propionylamino) propanethioate

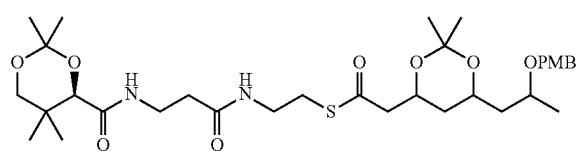

The product from Example 57 Step 6 (Int-11) (941 mg, 2.67 mmol) was dissolved in DCM (20 mL). To the solution was added EDCI (562 mg, 2.94 mmol) DMAP (33 mg, 0.27 mmol) and the product from Preparative Example 3 Step 2 ((R)—N-(3-((2-mercaptoethyl)amino)-3-oxopropyl)-2,2,5,5-tetramethyl-1,3-dioxane-4-carboxamide) (935 mg, 2.94 mmol). The reaction mixture was stirred at room temperature for 2 hours. After the reaction completed, the excess solvent was removed in vacuum, and the crude was purified by prep-HPLC to obtain the title Compound 887 (1.03 g, Yield 58%) as a colorless oil. LCMS (ESI): m/z 653.4 (M+H)+, RT=2.033 min.

Example 59: Synthesis of Compound 852

Synthesis of methyl 3-[2-(3-{[(R)-2,2,5,5-tetramethyl-1,3-dioxan-4-yl]carbonylamino}propionylamino) ethylthio)carbonyl] propionate

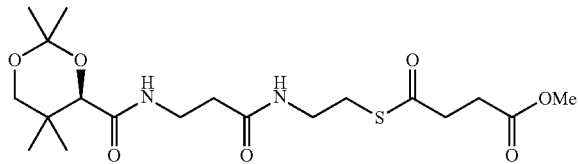 [SMILES: COC(=O)CCC(=O)SCCNC(=O)CCNC(=O)[C@@H]1OC(C)(C)OCC1(C)C]

The product from Preparative Example 3 Step 2 ((R)—N-(3-((2-mercaptoethyl)amino)-3-oxopropyl)-2,2,5,5-tetramethyl-1,3-dioxane-4-carboxamide) (200 mg, 628 umol, 1.00 eq) was dissolved in DCM (3.00 mL) in a 25 mL vial at 25° C. TEA (76.27 mg, 754 umol, 105 uL, 1.20 eq) was added to the vial. Methyl 4-chloro-4-oxo-butanoate (113 mg, 754 umol, 93.0 uL, 1.20 eq) was dissolved in DCM, and the solution was added dropwise to the mixture above at 0° C. The mixture was stirred at 0° C. for 2 hrs under Ar atmosphere. LCMS and TLC (EtOAc:MeOH=8:1, Rf=0.53) showed the compound from Preparative Example 3 Step 2 was consumed and one peak with desired MS was detected. The reaction mixture was concentrated and the residue was purified by column chromatography/prep-TLC (Ethy acetate:Methanol=8:1) to provide the title Compound 852 (90 mg, crude) as a colorless oil. LCMS (ESI): m/z: 433.2 [M+H]+

Example 60: Synthesis of Compound 849

Synthesis of S-2-(3-{[(R)-2,2,5,5-tetramethyl-1,3-dioxan-4-yl]carbonylamino}propionylamino) ethyl (E)-2-butenethioate

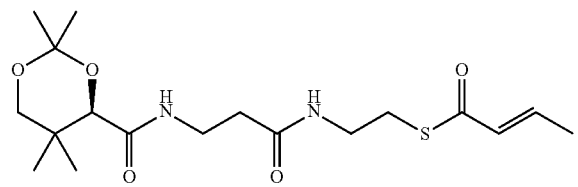 [SMILES: C/C=C/C(=O)SCCNC(=O)CCNC(=O)[C@@H]1OC(C)(C)OCC1(C)C]

EDCI (216 mg, 1.13 mmol, 1.20 eq) was added to a mixture of the product from Preparative Example 3 Step 2 ((R)—N-(3-((2-mercaptoethyl)amino)-3-oxopropyl)-2,2,5, 5-tetramethyl-1,3-dioxane-4-carboxamide) (300 mg, 942 umol, 1.00 eq), crotonic acid (97.3 mg, 1.13 mmol, 1.20 eq), DIEA (365 mg, 2.83 mmol, 492 uL, 3.00 eq) and DMAP (11.5 mg, 94.2 umol, 0.100 eq) in DCM (5.00 mL) at 10-15° C. The mixture was stirred at 10-15° C. for 2 hrs. TLC (Dichloromethane:Methanol=10:1) showed that the reaction was complete. The mixture was washed by HCl solution (1.00 N, 5.00 mL) and separated. The aqueous phase was extracted with DCM (5.00 mL*2). The combined organic layer was washed by NaHCO₃ (0.500 N, 20.0 mL) and dried over Na₂SO₄. The product was purified by silica gel chromatography (100-200 mesh silica gel, Petroleum ether/Ethyl acetate=50/1-0/1) to afford the product (106 mg, 274 umol, 29.1% yield) as a yellow gum.

Example 61: Synthesis of Compound 850

Synthesis of S-2-(3-{[(R)-2,2,5,5-Tetramethyl-1,3-dioxan-4-yl]carbonylamino}propionylamino)ethyl 3-methyl-2-butenethioate

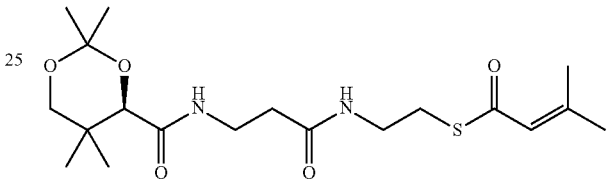

To a solution of the product from Preparative Example 3 Step 2 ((R)—N-(3-((2-mercaptoethyl)amino)-3-oxopropyl)-2,2,5,5-tetramethyl-1,3-dioxane-4-carboxamide) (0.30 g, 942 umol, 1.00 eq) in DCM (15.0 mL) was added 3,3-dimethylacrylic acid (113 mg, 1.13 mmol, 1.20 eq), EDCI (217 mg, 1.13 mmol, 1.20 eq) and DIEA (365 mg, 2.83 mmol, 492 uL, 3.00 eq). Then DMAP (11.5 mg. 94.2 umol, 0.10 eq) was added to the mixture, and the mixture was stirred at 20° C. for 1 hr. TLC (Ethyl acetate:Methanol=20: 1) indicated the product from Preparative Example 3 Step 2 was consumed, and one major new spot with lower polarity was detected. The mixture was poured into H₂O (20.0 mL), extracted with CH₂Cl₂ 30.0 mL (10.0 mL*3), dried over Na₂SO₄, filtered and concentrated under reduced pressure to give a residue. The residue was purified by column chromatography (SiO₂, DCM:MeOH=20:1) to provide the title Compound 850 (280 mg, 699 umol, 74.2% yield) as a light yellow oil which was used directly. LCMS (ESI): m/z 401.2 [M+H]+

Example 62: Synthesis of Compound 888

Synthesis of S-2-(3-[(2,2,5,5-tetramethyl-1,3-dioxan-4-yl)carbonylamino]propionylamino)ethyl (R)-3-hydroxybutanethioate

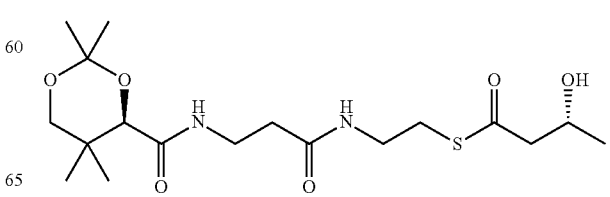

To a solution of the product from Preparative Example 3 Step 2 ((R)—N-(3-((2-mercaptoethyl)amino)-3-oxopropyl)-2,2,5,5-tetramethyl-1,3-dioxane-4-carboxamide) (500 mg, 1.57 mmol, 1.00 eq) and (R)-3-hydroxybutyric acid (180 mg, 1.73 mmol, 1.10 eq) in DCM (5.00 mL) was added DIEA (406 mg. 3.14 mmol, 547 uL, 2.00 eq), EDCI (452 mg. 2.36 mmol, 1.50 eq), and DMAP (0.02 g, 163 umol, 1.04e−1 eq) at 25° C. The mixture was stirred at 25° C. for 12 hrs. TLC showed the product from Preparative Example 3 Step 2 was consumed completely. The residue was purified by prep-TLC (SiO$_2$, DCM:MeOH=10:1) to provide the title Compound 888 (170 mg, 412 umol, 26.2% yield, 98.0% purity) as a white solid. HPLC: 98.4% purity at 215 nm, RT 1.604

Example 63: Synthesis of Compound 851

Step 1: Synthesis of (2,2-dimethyl-5-oxo-1,3-dioxolan-4-yl)acetic Acid

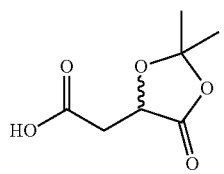

The commercially available alpha-hydroxysuccinic acid (5.00 g, 37.3 mmol, 1.00 eq) was suspended in DCM (25.0 mL) and 2,2-dimethoxypropane (11.7 g, 112 mmol, 13.7 mL, 3.00 eq) and TosOH (64.2 mg, 373 umol, 0.01 eq) were added. The mixture was stirred at 25° C. for 4 hours. TLC (Petroleum ether: Ethyl acetate=1:1) indicated the starting material was consumed, and one major new spot with lower polarity was detected. The mixture was concentrated under reduced pressure to obtain yellow oil. The residue was purified by column chromatography (SiO$_2$, Petroleum ether/Ethyl acetate=1/1) to yield the product (2,2-dimethyl-5-oxo-1,3-dioxolan-4-yl)acetic acid (3.40 g, 19.5 mmol, 52.4% yield) as a white solid which was used directly. $^1$H NMR: 400 MHz DMSO-d$_6$ δ 1.51 (d, J=6.0 Hz, 6H), 2.79-2.67 (m, 2H), 4.77 (t, J=4.7 Hz, 1H), 12.58 (s, 1H)

Step 2: Synthesis of Compound 851

Synthesis of S-(2,2-dimethyl-5-oxo-1,3-dioxolan-4-yl)methyl 3-(3-{[(R)-2,2,5,5-tetramethyl-1,3-dioxan-4-yl]carbonylamino}propionylamino)propanethioate

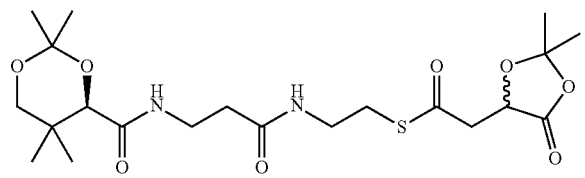 [SMILES: CC1(C)OC(=O)C(CC(=O)SCCNC(=O)CCNC(=O)[C@@H]2OC(C)(C)OCC2(C)C)O1]

To a solution of the product from Preparative Example 3 Step 2 ((R)—N-(3-((2-mercaptoethyl)amino)-3-oxopropyl)-2,2,5,5-tetramethyl-1,3-dioxane-4-carboxamide) (400 mg, 1.26 mmol, 1.00 eq) in DCM (10.0 mL) was added the product from Example 63 Step 1 (284 mg, 1.63 mmol, 1.30 eq), EDCI (289 mg, 1.51 mmol, 1.20 eq) and DIEA (487 mg, 3.77 mmol, 656 uL, 3.00 eq), Then DMAP (15.4 mg, 126 umol, 0.10 eq) was added to the mixture above. The mixture was stirred at 20° C. for 1 hr. TLC (Ethyl acetate:Methanol=20:1) indicated that the product from Preparative Example 3 Step 2 was consumed, and one major new spot with lower polarity was detected. LC-MS indicated the desired peak was detected. The mixture was poured into H$_2$O (20.0 mL), extracted with CH$_2$Cl$_2$ 30.0 mL (10.0 mL*3), dried over Na$_2$SO$_4$, filtered and concentrated under reduced pressure to give a residue. The residue was purified by column chromatography (SiO$_2$, DCM:MeOH=20:1) to give a light yellow oil which was further purified by pre-MPLC (SiO$_2$, DCM:MeOH=20:1). The title Compound 851 (170 mg, 358 umol, 28.5% yield) was obtained as a colorless oil. LCMS (ES): m/z 475.1 [M+H]+

Example 67: Synthesis of Compound 889

Synthesis of tert-butyl (2S)-2-((tert-butoxycarbonyl)amino)-5-((2-(3-((4R)-2-(4-methoxybenzyl)-5,5-dimethyl-1,3-dioxane-4-carboxamido)propanamido)ethyl)thio)-5-oxopentanoate

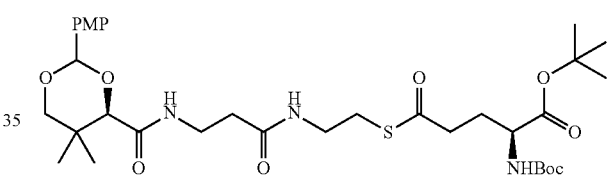

To a solution of the product from Preparative Example 1 Step 2 (4R)—N-(3-((2-mercaptoethyl)amino)-3-oxopropyl)-2-(4-methoxyphenyl)-5,5-dimethyl-1,3-dioxane-4-carboxamide (1 g, 2.523 mmoL) in DCM (10 mL) was added EDC·HCl (967 mg, 5.0497 mmoL), (S)-5-(tert-butoxy)-4-((tert-butoxycarbonyl)amino)-5-oxopentanoic acid (918 mg, 3.0287 mmoL) and DIPEA (1.32 mL, 7.571 mmoL). The reaction mixture was stirred at RT for 16 h. Progress of the reaction was monitored by TLC. After completion of the reaction, the reaction mixture was diluted with water (20 mL) and extracted with DCM (2×20 mL). The total organic layer was then washed with saturated NaHCO$_3$, dried over Na$_2$SO$_4$ and concentrated over a rotary evaporator. The obtained crude product was purified over column using silica (100-200 mesh) and eluted with 1-3% MeOH in DCM to afford the title Compound 889 as white solid (850 mg, 50% yield).

$^1$H NMR (400 MHz, DMSO-D6) δ 8.09 (m, 1H), 7.45-7.40 (m, 3H), 7.17 (d, J=8 Hz, 1H), 6.91 (d, J=8.4 Hz, 2H), 4.06 (s, 1H), 3.85-3.75 (m, 5H), 3.62-3.58 (m, 2H), 3.29-3.22 (m, 1H), 3.16-3.11 (m, 2H), 2.87-2.84 (m, 2H), 2.66-2.62 (m, 2H), 2.24 (t, J=6.8 Hz, 2H), 1.94-1.92 (m, 1H), 1.78-1.76 (m, 1H), 1.36-1.33 (m, 18H), 0.98 (s, 3H), 0.88 (s, 3H).

Example 69: Synthesis of Compound 890

Synthesis of tert-butyl (3S)-3-((tert-butoxycarbonyl) amino)-4((2-(3-((4R)-2-(4 methoxybenzyl)-5,5-dimethyl-1,3-dioxane-4-carboxamido)propanamido) ethyl)thio)-4-oxobutanoate

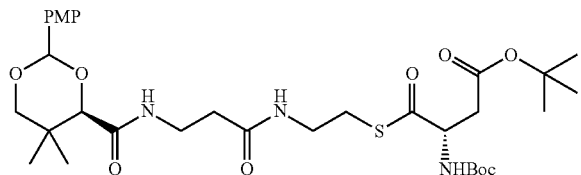

To a stirred solution of the product from Preparative Example 1 Step 2 (4R)—N-(3-((2-mercaptoethyl)amino)-3-oxopropyl)-2-(4-methoxyphenyl)-5,5-dimethyl-1,3-dioxane-4-carboxamide (1 g, 2.52 mmoL) in DCM (10 mL) was added EDC·HCl (966 mg, 5.04 mmoL), (S)-4-(tert-butoxy)-2-((tert-butoxycarbonyl)amino)-4-oxobutanoic acid (875 mg, 3.02 mmoL) and DIPEA (1.3 mL, 7.56 mmoL) at 0° C. The resulting reaction mixture was stirred at RT for 16 h. Progress of the reaction was monitored by TLC. After completion of the reaction, the reaction mixture was diluted with water (20 mL) and extracted with DCM (2×20 mL). The total organic layer was then washed with saturated NaHCO₃, dried over Na₂SO₄ and concentrated over a rotary evaporator. The obtained crude product was purified on column using silica (100-200 mesh) and eluted with 1-3% MeOH in DCM to afford the title Compound 890 as a white solid (950 mg, 59% yield).

¹H NMR (400 MHz, DMSO-D6) δ 8.09 (bs, 1H), 7.63 (d, J=8 Hz, 1H), 7.42-7.40 (m, 3H), 6.92 (m, 2H), 5.50 (s, 1H), 4.85 (m, 1H), 4.06, (s, 1H), 3.75 (s, 3H), 3.61 (m, 2H), 3.32 (m, 2H), 3.11 (m, 2H), 2.81 (m, 2H), 2.49 (m, 2H), 1.38-1.37 (m, 18H), 0.98 (s, 3H), 0.93 (s, 3H).

Example 70: Synthesis of Compound 895

Step 1: Synthesis of (3S)-3-hydroxybutanoic Acid

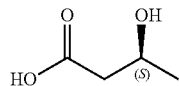

To the solution of KOH (842 mg, 15.0 mmol) in H₂O (15 mL) was added methyl (3S)-3-hydroxybutanoate (1.18 g, 10.0 mmol) at 0° C., then the mixture was stirred at 20° C. for 32 hours. LCMS showed the desired mass peak was formed. The mixture was extracted with EtOAc (30 mL×2, discarded), then the aqueous phase was acidified by 2N HCl to pH ~2, then the mixture was extracted by EtOAc (50 mL×8). The organic phase was dried over Na₂SO₄, filtered and concentrated to give the product of (S)-3-hydroxybutanoic acid (0.55 g, 50%) as a colorless oil.

¹H NMR (400 MHz, DMSO-d6): δ 1.08 (d, J=6.0 Hz, 3H), 2.18-2.33 (m, 2H), 3.90-4.00 (m, 1H), 4.65 (br s, 1H), 11.97 (br s, 1H).

Step 2: Synthesis of N-(2-{[(3R)-3-hydroxybutanoyl]sulfanyl}ethyl)-3-{[(4R)-2,2,5,5-tetramethyl-1,3-dioxan-4-yl]formamido}propanamide

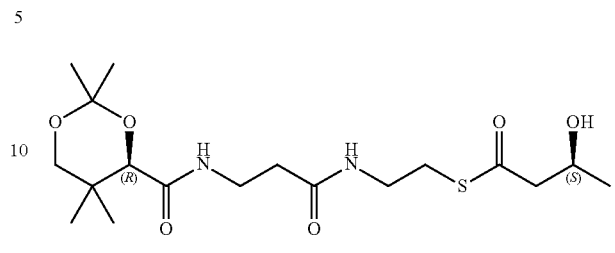

To a mixture of the product from Preparatory Example 3 Step 2 3-[{(R)-2,2,5,5-tetramethyl-1,3-dioxan-4-yl]carbonylamino}-1-(2-mercaptoethylamino)-1-propanone (1400 mg, 4.4 mmol), (3S)-3-hydroxybutanoic acid from Example 70 Step 1 (504 mg, 4.84 mmol) and EDCI (1.27 g, 6.6 mmol) in DCM (35 mL) was added DIPEA (1.14 ml, 8.8 mmol). Then the mixture was stirred at 20° C. for 16 hours. LCMS showed the starting material was consumed and the desired mass peak was formed. The reaction mixture was diluted with DCM (50 mL), then was washed with water (20 mL) and brine (20 mL), dried over Na₂SO₄, filtered and concentrated to give the crude product. The crude product was purified by flash chromatography (20 g silica gel, 100% petroleum ether/ethyl acetate with ethyl acetate from =0 to 100%) to yield the desired product of N-(2-{[(3S)-3-hydroxybutanoyl]sulfanyl}ethyl)-3-{[(4R)-2,2,5,5-tetramethyl-1,3-dioxan-4-yl]formamido}propanamide (Compound 895)(760 mg, 40.56%) as colorless oil. MS:(ES, m/s): 405.2 [M+H]⁺.

1H NMR (400 MHz, CDCl₃): δ 0.96 (s, 3H), 1.03 (s, 3H), 1.25 (d, J=6.0 Hz, 3H), 1.41-1.48 (m, 6H), 2.43 (t, J=6.4 Hz, 2H), 2.95-3.12 (m, 2H), 3.13-3.23 (m, 1H), 3.28 (d, J=12.0 Hz, 1H), 3.43-3.60 (m, 4H), 3.68 (d, J=12.0 Hz, 1H), 3.66-3.76 (m, 1H), 4.08 (s, 1H), 4.25-4.33 (m, 1H), 6.03 (brs, 1H), 6.38 (s, 1H), 7.02 (s, 1H).

Example 76: Synthesis of Compound 891

Synthesis of (R)—S-(2-(3-(2,2,5,5-tetramethyl-1,3-dioxane-4carboxamido)propanamido)ethyl) ethanethioate

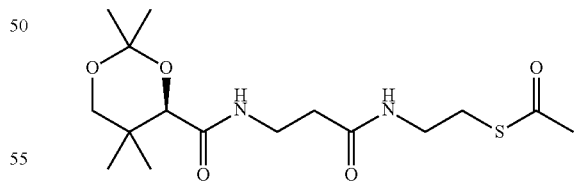

The product from Preparative Example 3 Step 2 ((R)—N-(3-((2-mercaptoethyl)amino)-3-oxopropyl)-2,2,5,5-tetramethyl-1,3-dioxane-4-carboxamide) (1.3 g, 4.08 mmol, 1.0 eq), AcOH (163 mg, 4.08 mmol, 1.0 eq), EDCI (934 mg, 4.89 mmol, 1.2 eq) and DIEA (4.48 g, 34.74 mmol, 3.0 eq) were combined with DCM (20 mL) and the mixture was stirred at 25 degrees for 2 h. Reaction progress was monitored by LCMS. After completion, the crude product was purified by silica gel column chromatography (eluted with PE/EtOAc (1:1)) to afford the title compound (R)—S-(2-(3-

(2,2,5,5-tetramethyl-1,3-dioxane-4carboxamido)propanamido)ethyl) ethanethioate (Compound 891)(1.4 g, 95%) as a yellow solid. LCMS (ES, m/z): 361 [M+H]+.

Example 78: Synthesis of Compound 888

Step 1: Synthesis of (3R)-3-hydroxybutanoic acid

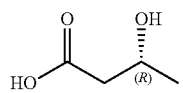

To the solution of KOH (842 mg, 15.0 mmol) in H2O (15 mL) was added methyl (3R)-3-hydroxybutanoate (1.18 g, 10.0 mmol) at 0° C., then the mixture was stirred at 20° C. for 32 hours. LCMS showed the desired mass peak was formed. The mixture was extracted with EtOAc (30 mL×2, discarded), then the aqueous phase was acidified by 2N HCl to pH ~2, then the mixture was extracted with EtOAc (50 mL×5). The organic phase was dried over Na2SO4, filtered and concentrated to give the product of (3R)-3-hydroxybutanoic acid (0.48 g, 44%) as a colorless oil.

1H NMR (400 MHz, DMSO-d6): δ 1.08 (d, J=6.4 Hz, 3H), 2.18-2.33 (m, 2H), 3.90-4.00 (m, 1H), 4.68 (brs, 1H), 11.99 (brs, 1H).

Step 2: Synthesis of Compound 888

N-(2-{[(3R)-3-hydroxybutanoyl]sulfanyl}ethyl)-3-{[(4R)-2,2,5,5-tetramethyl-1,3-dioxan-4-yl]formamido}propanamide

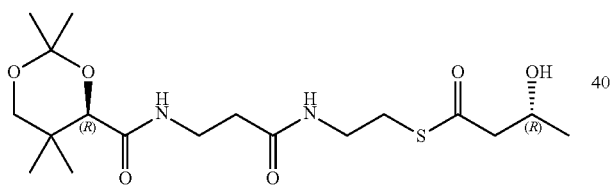

To a mixture of the product from Preparative Example 3 Step 2 (N-(2-sulfanylethyl)-3-[{(4R)-2,2,5,5-tetramethyl-1,3-dioxan-4-yl]formamido}propenamide) (600 mg, 1.88 mmol), the product from Example 78 Step 1 ((3R)-3-hydroxybutanoic acid) (235 mg, 2.256 mmol) and EDCI (541 mg, 2.82 mmol) in DCM (25 mL) was added DIPEA (729 mg, 5.64 mmol). Then the mixture was stirred at 20° C. for 16 hours. LCMS showed the starting material was consumed and the desired mass peak was formed. The reaction mixture was diluted with DCM (30 mL), then was washed with water (20 mL) and brine (20 mL), dried over Na2SO4, filtered and concentrated to give the crude product. The crude product was purified by flash chromatography (12 g silica gel, 100% petroleum ether/ethyl acetate with ethyl acetate from =0 to 100%) to yield the desired product of N-(2-{[(3R)-3-hydroxybutanoyl]sulfanyl}ethyl)-3-{[(4R)-2,2,5,5-tetramethyl-1,3-dioxan-4-yl]formamido}propenamide (Compound 888) (320 mg, 39.97%) as a colorless oil. MS:(ES, m/s): 405.1 [M+H]+.

1H NMR (400 MHz, CDCl3): δ 0.96 (s, 3H), 1.03 (s, 3H), 1.25 (d, J=6.0 Hz, 3H), 1.41-1.48 (m, 6H), 2.42 (t, J=6.4 Hz, 2H), 2.95-3.12 (m, 2H), 3.13-3.23 (m, 1H), 3.28 (d, J=12.0 Hz, 1H), 3.33-3.43 (m, 2H), 3.48-3.60 (m, 2H), 3.68 (d, J=12.0 Hz, 1H), 3.66-3.76 (m, 1H), 4.08 (s, 1H), 4.25-4.33 (m, 1H), 6.01 (brs, 1H), 6.37 (s, 1H), 7.01 (s, 1H).

Example 79: Synthesis of Compound 892

Synthesis of 3-[(R)-2-[2-(3-{[(2R)-4-Hydroxy-3,3-dimethyltetrahydro-2H-pyran-2-yl]carbonylamino}propionylamino)ethylthio)carbonyl]-1-methylethoxycarbonyl]propionic Acid

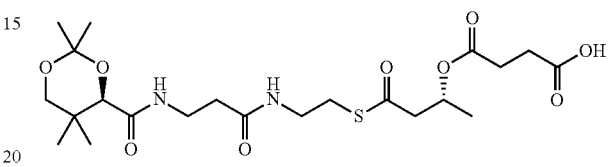

To a mixture of the product from Example 78 Step 2 (N-(2-{[(3R)-3-hydroxybutanoyl]sulfanyl}ethyl)-3-([(4R)-2,2,5,5-tetramethyl-1,3-dioxan-4-yl]formamido)propenamide) (800 mg, 1.98 mmol) and oxolane-2,5-dione (594 mg, 5.94 mmol) in DCM (30 mL) was added DMAP (121 mg, 0.99 mmol) and pyridine (313 mg. 3.96 mmol) at 20° C., then the mixture was stirred at 20° C. for 32 hours. LCMS showed the starting material was consumed and na ew peak was formed. The mixture was concentrated to give the title Compound 892 (800 mg, 48.01%) as a colorless oil. MS: (ES, m/s): 503.2 [M−H]−.

Example 80: Synthesis of Compound 893

Step 1: Synthesis of Methyl (3R)-3-hydroxy-2-methylbutanoate

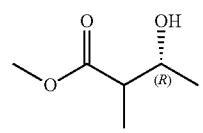

To a solution of lithium bis(trimethylsilyl)amide (40 ml, 2M in THF) in THF (70 mL) at −78° C. under N2, a solution of methyl (3R)-3-hydroxybutanoate (5 g, 42.23 mmol) in THF (30 ml) was added. After 1 hour, the mixture of MeI (9 g, 63.4 mmol) and HMPA (13.7 g, 76.6 mmol) was added dropwise, via cannula, and the mixture was stirred for 3 hours at −78° C. The reaction was warmed to −40° C. and stirred for an additional 1 hour. The reaction mixture was quenched with saturated NH4Cl solution (100 mL). The mixture was extracted with EtOAc (200 mL×2) and the combined organic extracts were washed with cold 1M HCl (20 mL) and then dried over MgSO4, filtered and concentrated under reduced pressure. The residue was purified by flash column chromatography, eluting with EtOAc/PET (0%-50%) to afford the product of methyl (3R)-3-hydroxy-2-methylbutanoate (2.6 g, 44.2%) as a yellow oil.

1H NMR (400 MHz, CDCl3): δ 0.80-0.90 (m, 6H), 2.33-2.52 (m, 1H), 2.70 (m, 1H), 3.70 (s, 3H), 3.80-3.90 (m, 1H).

Step 2: (4R)-4-hydroxy-2,3-dimethylpentanoic Acid

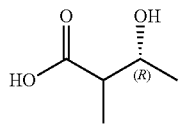

To a mixture of the product from Example 80 Step 1 (methyl (4R)-4-hydroxy-2,3-dimethylpentanoate) (2600 mg, 1.14 mmol) in H₂O (20 mL) was added KOH (1817 mg, 32.457 mmol), then the mixture was stirred at 15° C. for 12 hours. The reaction was quenched with water (10 mL). The mixture was extracted with DCM (30 mL 0.2, discarded). The aqueous phase was acidified with 4M HCl pH~4-5, and the mixture was extracted with EtOAc (20 mL×5), then was washed with brine (20 mL), dried over Na₂SO₄, filtered and concentrated to give the desired product of (4R)-4-hydroxy-2,3-dimethylpentanoic acid (1900 mg, 76.08%) as a yellow oil.

¹H NMR (400 MHz, DMSO-d6): δ 0.93 (d, J=6.4 Hz, 3H), 0.99 (d, J=6.4 Hz, 3H), 2.18-2.38 (m, 1H), 3.70-3.85 (m, 1H), 4.63 (br s, 1H), 11.94 (br s, 1H).

Step 3: N-(2-{[(3R)-3-hydroxy-2-methylbutanoyl]sulfanyl}ethyl)-3-{[(4R)-2,2,5,5-tetramethyl-1,3-dioxan-4-yl]formamido}propenamide

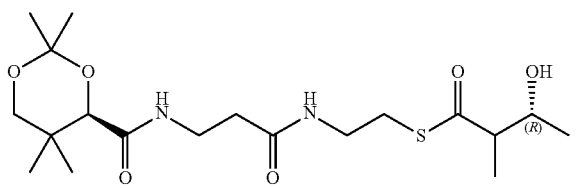

To a mixture of the product from Preparative Example 3 Step 2 (N-(2-sulfanylethyl)-3-{[(4R)-2,2,5,5-tetramethyl-1,3-dioxan-4-yl]formamido}propenamide) (1200 mg, 3.77 mmol), (3R)-3-hydroxy-2-methylbutanoic acid from Example 80 Step 2 (445 mg, 3.77 mmol) and EDCI (1084 mg, 5.655 mmol) in DCM (25 mL) was added DIPEA (974 mg, 7.54 mmol). Then the mixture was stirred at 20° C. for 16 hours. LCMS showed the starting material was consumed and the desired mass peak was formed. The reaction was diluted with DCM (30 mL), then was washed with water (20 mL) and brine (20 mL), dried over Na₂SO₄, filtered and concentrated to give the crude product. The crude product was purified by flash chromatography (12 g silica gel, 100% petroleum ether/ethyl acetate with ethyl acetate from =0 to 100%) to yield the title Compound 893 (320 mg, 19.27%) as a colorless oil. MS:(ES, m/s): 419.2 [M+H]⁺.

Example 81: Synthesis of Compound 894

N-(2-{[(3R)-3-hydroxypentanoyl]sulfanyl}ethyl)-3-{[(4R)-2,2,5,5-tetramethyl-1,3-dioxan-4-yl]formamido}propenamide

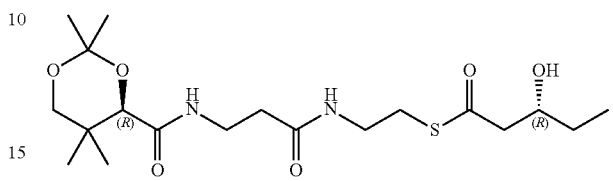

To a mixture of the product of Preparative Example 3 Step 2 (N-(2-sulfanylethyl)-3-{[(4R)-2,2,5,5-tetramethyl-1,3-dioxan-4-yl]formamido}propenamide) (700 mg, 2.2 mmol), (3R)-3-hydroxypentanoic acid (247 mg, 2.09 mmol) and EDCI (0.633 g, 3.3 mmol) in DCM (20 mL) was added DIPEA (569 mg, 4.4 mmol). Then the mixture was stirred at 20° C. for 16 hours. LCMS showed the starting material was consumed and the desired mass peak was formed. The reaction mixture was diluted with DCM (50 mL), then was washed with water (20 mL) and brine (20 mL), dried over Na₂SO₄, filtered and concentrated to give the crude product. The crude product was purified by flash chromatography (12 g silica gel, 100% petroleum ether/ethyl acetate with ethyl acetate from =0 to 100%) to yield the desired product of N-(2-{[(3R)-3-hydroxypentanoyl]sulfanyl}ethyl)-3-{[(4R)-2,2,5,5-tetramethyl-1,3-dioxan-4-yl]formamido}propanamide (Compound 894) (230 mg, 22.48%) as a colorless oil. MS:(ES, m/s): 419.2 [M+H]⁺.

Example 82: Synthesis of Compound 896

Synthesis of 4-oxo-4-{[(2S)-4-oxo-4-{[2-(3-{[(4R)-2,2,5,5-tetramethyl-1,3-dioxan-4-yl]formamido}propanamido)ethyl]sulfanyl}butan-2-yl]oxy}butanoic Acid

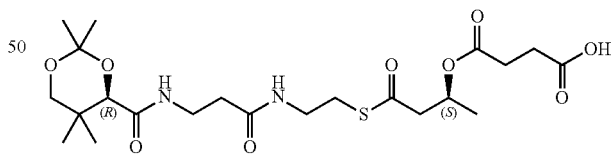

To a mixture of the product of Example 70 Step 2 N-(2-{[(3S)-3-hydroxybutanoyl]sulfanyl}ethyl)-3-{[(4R)-2,2,5,5-tetramethyl-1,3-dioxan-4-yl]formamido}propanamide (750 mg, 1.85 mmol) and oxolane-2,5-dione (557 mg, 5.56 mmol) in DCM (30 mL) added DMAP (113 mg, 0.925 mmol) and pyridine (293 mg, 3.708 mmol) at 20° C., then the mixture was stirred at 20° C. for 32 hours. LCMS showed the raw material was consumed and a new peak was formed. The mixture was concentrated to give the title Compound 896 (750 mg, 48.21%) as a colorless oil. MS:(ES, m/s): 503.2 [M−H]⁻.

Example 83: Synthesis of Compound 897

Step 1: Synthesis of Methyl (3S)-3-hydroxy-2-methylbutanoate

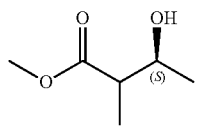

To a solution of lithium bis(trimethylsilyl)amide (40 ml, 2M in THF) in THE (70 mL) at −78° C. under N2, was added a solution of methyl (3S)-3-hydroxybutanoate (5 g, 42.23 mmol) in THF (30 ml). After 1 hour, the mixture of MeI (9 g, 63.4 mmol) and HMPA (13.7 g, 76.6 mmol) was added dropwise, via cannula, and the mixture was stirred for 3 hours at −78° C. The reaction mixture was warmed to −40° C. and stirred for an additional 1 hour. The reaction mixture was quenched with saturated $NH_4C_1$ solution (100 mL). The product was extracted with EtOAc (200 mL×2) and the combined organic extracts were washed with cold 1M HCl (20 mL) and then dried over $MgSO_4$, filtered and concentrated under reduced pressure. The residue was purified by flash column chromatography eluting with EtOAc/Petroleum ether (0%-50%) to afford the product of methyl (3S)-3-hydroxy-2-methylbutanoate (2.2 g, 37.35%) as a yellow oil.

$^1$H NMR (400 MHz, $CDCl_3$): δ 1.10-1.20 (m, 6H), 2.30-2.45 (m, 1H), 2.68 (d, J=7.2 Hz, 1H), 3.70 (s, 3H), 3.80-3.90 (m, 1H).

Step 2: (4S)-4-hydroxy-2,3-dimethylpentanoic acid

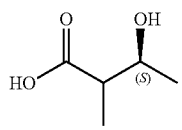

To a mixture of KOH (1.1 g, 19.6 mmol) in $H_2O$ (20 mL) was added the product of Example 83 Step 1 methyl (4S)-4-hydroxy-2,3-dimethylpentanoate (2100 mg, 1.31 mmol), and then the mixture was stirred at 20° C. for 32 hours. LCMS showed the desired mass peak was formed. The mixture was extracted with EtOAc (30 mL×2, discarded), then the aqueous phase was acidified by 2N HCl to pH ~2, and then the mixture was extracted with EtOAc (50 mL×8). The organic phase was dried over $Na_2SO_4$, filtered and concentrated to give the product of (4S)-4-hydroxy-2,3-dimethylpentanoic acid 3 (1.3 g, 61.07%) as a yellow oil.

$^1$H NMR (400 MHz, DMSO-d6): δ 0.97 (d, 0.1=6.8 Hz, 3H), 1.02 (d, J=6.4 Hz, 3H), 2.26-2.36 (m, 1H), 3.74-3.85 (m, 1H), 4.63 (br s, 1H), 11.91 (br s, 1H)

Step 3: N-(2-{[(3S)-3-hydroxy-2-methylbutanoyl]sulfanyl}ethyl)-3-{[(4R)-2,2,5,5-tetramethyl-1,3-dioxan-4-yl]formamido}propenamide

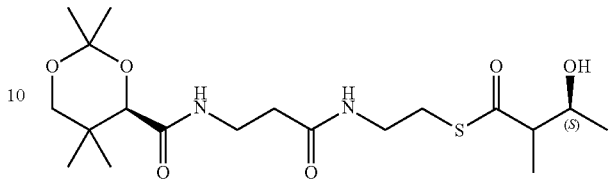

To a mixture of N-(2-sulfanylethyl)-3-{[(4R)-2,2,5,5-tetramethyl-1,3-dioxan-4-yl]formamido}propenamide from Preparative Example 3 Step 2 (1200 mg, 3.85 mmol), (3S)-3-hydroxybutanoic acid from Example 83 Step 2 (500 mg, 4.9697 mmol) and EDCI (1107 mg, 5.775 mmol) in DCM (30 mL) was added DIPEA (993 mg, 7.7 mmol). Then the mixture was stirred at 20° C. for 12 hours. LCMS showed the raw material was consumed and the desired mass peak was formed. The reaction mixture was diluted with DCM (30 mL), then was washed with water (20 mL) and brine (20 mL), dried over $Na_2SO_4$, filtered and concentrated to give the crude product. The crude product was purified by flash chromatography (12 g silica gel, 100% petroleum ether/ethyl acetate with ethyl acetate from =0 to 100%) to yield the desired product of N-(2-{[(3S)-3-hydroxy-2-methylbutanoyl]sulfanyl}ethyl)-3-{[(4R)-2,2,5,5-tetramethyl-1,3-dioxan-4-yl]formamido}propenamide (Compound 897) (500 mg, 24.82%) as a yellow oil. MS:(ES, m/s): 419.3 $[M+H]^+$

Example 84: Synthesis of Compound 898

Synthesis of N-(2-{[(3S)-3-hydroxypentanoyl]sulfanyl}ethyl)-3-{[(4R)-2,2,5,5-tetramethyl-1,3-dioxan-4-yl]formamido}propenamide

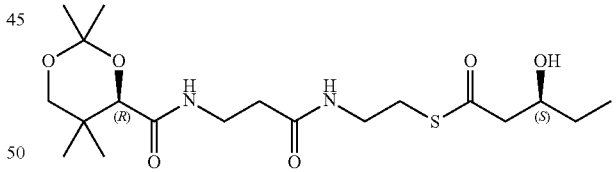

To a mixture of N-(2-sulfanylethyl)-3-{[(4R)-2,2,5,5-tetramethyl-1,3-dioxan-4-yl]formamido}propenamide from Preparative Example 3 Step 2 (700 mg, 2.2 mmol), (3S)-3-hydroxypentanoic acid (247 mg, 2.09 mmol) and EDCI (0.633 g, 3.3 mmol) in DCM (20 mL) was added DIPEA (569 mg, 4.4 mmol). Then the mixture was stirred at 20° C. for 16 hours. LCMS showed the raw material was consumed and the desired mass peak was formed. The reaction mixture was diluted with DCM (50 mL), then washed with water (20 mL) and brine (20 mL), dried over $Na_2SO_4$, filtered and concentrated to give the crude product. The crude product was purified by flash chromatography (20 g silica gel, 100% petroleum ether/ethyl acetate with ethyl acetate from =0 to 100%) to yield the desired product of N-(2-{[(3S)-3-hydroxypentanoyl]sulfanyl}ethyl)-3-{[(4R)-2,2,5,5-tetramethyl-1,3-dioxan-4-yl]formamido}propanamide (Compound 898) (250 mg, 25.79%) as colorless oil. MS:(ES, m/s): 419.2 [M+H]⁺.

Example 90: Synthesis of Compound 899

Step 1: tert-butyl 2-(5-oxotetrahydrofuran-2-yl)acetate

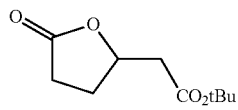

To a solution of tert-butyl (E)-2-(5-oxodihydrofuran-2(3H)-ylidene)acetate (3.0 g, 15.1 mmol, 1.0 eq) in ethyl acetate (30 mL) was added Pd/C (300 mg), and the reaction mixture was stirred at rt for 16 h. The resulting mixture was filtered and the filter cake was washed with ethyl acetate (50 mL). The filtrate was concentrated under reduced pressure to give tert-butyl 2-(5-oxotetrahydrofuran-2-yl)acetate (3.0 g, 99% yield) as a colorless oil. LCMS (ESI, m/z):223.1 [M+Na]+

Step 2: 2-(5-Oxotetrahydrofuran-2-yl)acetic Acid

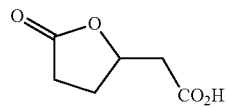

To a solution of tert-butyl 2-(5-oxotetrahydrofuran-2-yl)acetate from Example 90 Step 1 (3.0 g, 15.0 mmol, 1.0 eq) in DCM (30 mL) was added TFA (10 mL), and the reaction mixture was stirred at rt for 1 h. The resulting mixture was concentrated under reduced pressure to give 2-(5-oxotetrahydrofuran-2-yl)acetic acid (2.0 g, 92% yield) as a red oil. LCMS (ESI, m/z):145.1 [M+H]+

Step 3: S-(2-(3-((R)-2,2,5,5-tetramethyl-1,3-dioxane-4-carboxamido)propanamido)ethyl) 2-(5-oxotetrahydrofuran-2-yl)ethanethioate

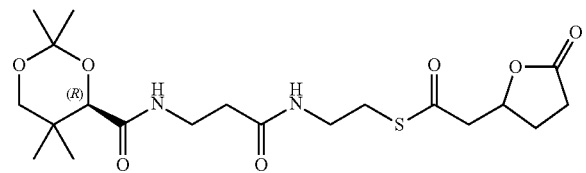

To a solution of (R)—N-(3-((2-mercaptoethyl)amino)-3-oxopropyl)-2,2,5,5-tetramethyl-1,3-dioxane-4-carboxamide from Preparative Example 3 Step 2 (3.0 g, 9.42 mmol, 1.0 eq) in DCM (30 mL) were added 2-(5-oxotetrahydrofuran-2-yl)acetic acid from Example 90 Step 2 (2.0 g, 14.1 mmol, 1.5 eq), DMAP (115 mg, 0.942 mmol, 0.1 eq) and EDCI (2.7 g, 14.1 mmol, 1.5 eq) at 0° C., then the reaction mixture was stirred at rt for 16 h. The mixture was diluted with water (50 mL), extracted with DCM (3×100 mL), and the combined organic layer was washed with brine, dried over Na₂SO₄, filtered and concentrated. The residue was purified by silica gel chromatography (pet ether: ethyl acetate=1:3) to afford S-(2-(3-((R)-2,2,5,5-tetramethyl-1,3-dioxane-4-carboxamido)propanamido)ethyl) 2-(5-oxotetrahydrofuran-2-yl)ethanethioate (Compound 899) (1.8 g, 43% yield) as a colorless oil. LCMS (ESI, m/z):445.2 [M+H]

Example 92: Synthesis of Compound 900

Step 1: tert-butyl (E)-2-(5-oxodihydrofuran-2(3H)-ylidene)acetate

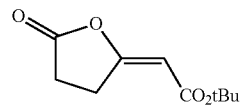

To a solution of tert-Butyl(triphenylphosphoranylidene)acetate (10.0 g, 26.6 mmol, 1.0 eq) in toluene (50 mL) was added dihydrofuran-2,5-dione (2.7 g, 26.6 mmol, 1.0 eq), heated to 50° C. and stirred for 10 h. The resulting mixture was concentrated under reduced pressure and purified by FCC (PE/ethyl acetate=10/1) to afford tert-butyl (E)-2-(5-oxodihydrofuran-2(3H)-ylidene)acetate (3.2 g, 61%) as a white solid. MS: (ES, m/s): 143.1 [M−56+H]

Step 2: (E)-2-(5-oxodihydrofuran-2(3H)-ylidene) acetic Acid

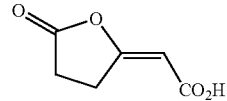

To a solution of tert-butyl (E)-2-(5-oxodihydrofuran-2(3H)-ylidene)acetate from Example 92 Step 1 (3.2 g, 16.2 mmol, 1.0 eq) in DCM (20 mL) was added TFA (4 mL) and the mixture was stirred for 1 h at rt. The resulting mixture was concentrated under reduced pressure to afford (E)-2-(5-oxodihydrofuran-2(3H)-ylidene)acetic acid (2.0 g, 87%) as a white solid. MS: (ES, m/s): 143.2[M+H]⁺

Step 3: (R)—S-(2-(3-(2,2,5,5-tetramethyl-1,3-dioxane-4-carboxamido)propanamido)ethyl) (E)-2-(5-oxodihydrofuran-2(3H)-ylidene)ethanethioate

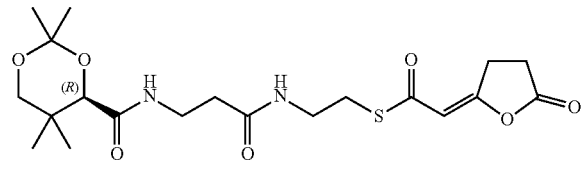

To a solution of (E)-2-(5-oxodihydrofuran-2(3H)-ylidene) acetic acid from Example 92 Step 2 (1.0 g, 7.0 mmol, 1.0 eq) in DCM (20 mL) was added (R)—N-(3-((2-mercaptoethyl)amino)-3-oxopropyl)-2,2,5,5-tetramethyl-1,3-dioxane-4-carboxamide from Preparatory Example 3 Step 2 (2.2 g, 7.0 mmol, 1.0 eq) and DMAP (85 mg, 0.7 mmol, 0.1 eq) and the mixture was stirred for 10 min at 0° C.; then EDCI (2.0 g, 10.5 mmol, 1.5 eq) was added slowly, and stirred for an additional 12 h at rt. The resulting mixture was concentrated under reduced pressure and purified by FCC (DCM/MeOH=100/2) to afford the product (R)—S-(2-(3-(2,2,5,5-tetramethyl-1,3-dioxane-4-carboxamido)propanamido)ethyl) (E)-2-(5-oxodihydrofuran-2(3H)-ylidene)ethanethioate (Compound 900) (600 mg, 19%) as colorless gel. MS: (ES, m/s): 443.2[M+H]⁺

Example 93: Synthesis of Compound 901

Synthesis of tert-butyl (R)-6-hydroxy-8-oxo-8-((2-(3-((R)-2,2,5,5-tetramethyl-1,3-dioxane-4-carboxamido) propanamido) ethyl) thio) octanoate Step 1: tert-butyl methyl adipate

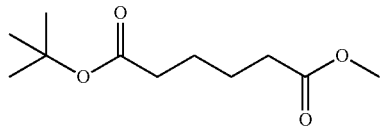

To a solution of 6-methoxy-6-oxohexanoic acid (16.0 g, 0.1 mol) in CH₂Cl₂ (30 mL) at 0° C. was added oxalyl chloride (26.0 mL, 0.3 mol) dropwise. After addition, four drops of DMF were added into the reaction mixture and the reaction mixture was stirred at 0° C. for 1 h. The reaction mixture was concentrated in vacuum and the residue was dissolved in CH₂Cl₂ (140 mL) and pyridine (12.0 mL, 0.15 mol). To the reaction mixture was added ᵗBuOH (10.0 mL, 0.13 mol) at 0° C. and the reaction mixture was stirred at rt for 1 h. The reaction mixture was poured into water (100 mL) and extracted with EtOAc (3×50 mL). The combined organic layer was washed with brine (20 mL) and dried over anhydrous Na₂SO₄, filtered and the filtrate was concentrated in vacuum. The residue was purified by silica gel chromatography (PE:EtOAc=30:1) to afford the product tert-butyl methyl adipate (12.8 g, 67% yield) as a light-yellow oil Step 2: 6-(tert-butoxy)-6-oxohexanoic Acid

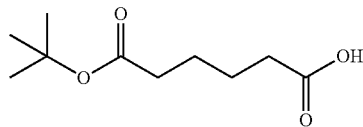

To a solution of tert-butyl methyl adipate from Example 93 Step 1 (12.8 g, 59.18 mmol) in THF (100 mL) and H₂O (100 mL) was added KOH (4.98 g, 88.78 mmol) at rt. The reaction mixture was stirred at rt for 16 h. The reaction mixture was adjusted to pH 6.0 using 1 M HCl and extracted with EtOAc (3×50 mL). The combined organic layer was washed with brine (20 mL) and dried over anhydrous Na₂SO₄, then filtered, and the filtrate was concentrated in vacuum to afford the product 6-(tert-butoxy)-6-oxohexanoic acid (8.0 g, 67% yield) as a light-yellow oil.

Step 3: tert-butyl 6-(2,2-dimethyl-4,6-dioxo-1,3-dioxan-5-ylidene)-6-hydroxyhexanoate

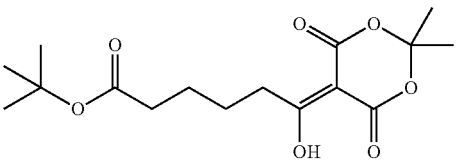 [SMILES: CC(C)(C)OC(=O)CCCCC(O)=C1C(=O)OC(C)(C)OC1=O]

A mixture of 6-(tert-butoxy)-6-oxohexanoic acid from Example 93 Step 2 (6.5 g, 32.14 mmol), DCC (8.6 g, 41.78 mmol), 2,2-dimethyl-1,3-dioxane-4,6-dione (6.94 g, 48.21 mmol) and DMAP (0.04 g, 0.3 mmol) in CH₂Cl₂ (260 mL) was stirred at rt for 16 h. The reaction mixture was poured into water (100 mL) and filtered, and the filtrate was extracted with EtOAc (3×50 mL). The combined organic layer was washed with brine (20 mL) and dried over anhydrous Na₂SO₄, then filtered and the filtrate was concentrated in vacuum. The residue was purified by silica gel chromatography (PE:EtOAc=2:1) to afford the product tert-butyl 6-(2,2-dimethyl-4,6-dioxo-1,3-dioxan-5-ylidene)-6-hydroxyhexanoate (6.3 g, 60% yield) as a light-yellow oil.

Step 4: 8-(tert-butyl) 1-methyl 3-oxooctanedioate

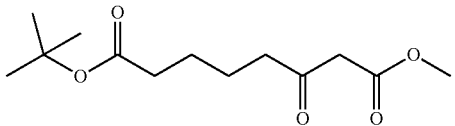 [SMILES: COC(=O)CC(=O)CCCCC(=O)OC(C)(C)C]

A solution of tert-butyl 6-(2,2-dimethyl-4,6-dioxo-1,3-dioxan-5-ylidene)-6-hydroxyhexanoate from Example 93 Step 3 (6.3 g, 19.19 mmol) in MeOH (80 mL) was stirred at reflux for 18 h. The reaction mixture was concentrated in vacuum. The residue was purified by silica gel chromatography (PE:EtOAc=15:1) to afford the product 8-(tert-butyl)-1-methyl 3-oxooctanedioate (1.85 g, 85% yield) as a light-yellow oil.

Step 5: 8-(tert-butyl) 1-methyl (R)-3-hydroxyoctanedioate

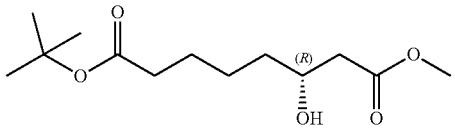

A mixture of 8-(tert-butyl)-1-methyl-3-oxooctanedioate from Example 93 Step 4 (5.0 g, 19.36 mmol) and (R)-BINAP-Ru (500 mg, 0.5 mmol) in MeOH (10 mL) under H₂ (g) 100 atm was stirred at 55° C. for 6 h. The reaction mixture was concentrated in vacuum. The residue was purified by silica gel chromatography (PE:EtOAc=6:1) to afford the product 8-(tert-butyl)-1-methyl-(R)-3-hydroxyoctanedioate (4.2 g, 83% yield) as a light-yellow oil.

Step 6: (R)-8-(tert-butoxy)-3-hydroxy-8-oxooctanoic Acid

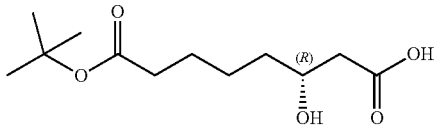

A solution of 8-(tert-butyl) 1-methyl (R)-3-hydroxyoctanedioate from Example 93 Step 5 (2.6 g, 10.01 mmol) and LiOH—H$_2$O (0.84 g, 20.02 mmol) in MeOH (5 mL), THF (5 mL) and H$_2$O (5 mL) was stirred at rt for 1 h. The reaction mixture was concentrated in vacuum to remove most of the organic solvent. To the residue was added ice-water (50 g) and added HCl (1 M) to adjust to pH 6. The mixture was extracted with EtOAc (3×20 mL). The combined organic layer was washed with brine (20 mL) and dried over anhydrous Na$_2$SO$_4$, then filtered and the filtrate was concentrated in vacuum. The residue was purified by silica gel chromatography (PE:EtOAc=2: 1) to afford the product (R)-8-(tert-butoxy)-3-hydroxy-8-oxooctanoic acid (1.4 g, 57% yield) as a light-yellow oil.

Step 7: tert-butyl (R)-6-hydroxy-8-oxo-8-((2-(3-((R)-2,2,5,5-tetramethyl-1,3-dioxane-4-carboxamido) propanamido) ethyl) thio) octanoate

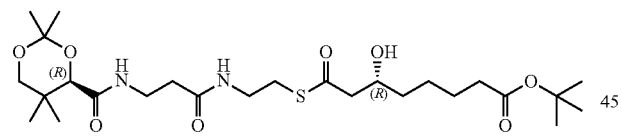

To a solution of (R)-8-(tert-butoxy)-3-hydroxy-8-oxooctanoic acid from Example 93 Step 6 (1.36 g, 5.52 mmol) and (R)—N-(3-((2-mercaptoethyl)amino)-3-oxopropyl)-2,2,5,5-tetramethyl-1,3-dioxane-4-carboxamide from Preparative Example 3 Step 2 (1.76 g, 5.52 mmol) in CH$_2$Cl$_2$ (30 mL) at rt was added EDCI (1.29 g, 8.28 mmol) and DMAP (66 mg, 0.54 mmol). The reaction mixture was stirred at rt for 16 h. The reaction mixture was poured into H$_2$O (200 mL) and extracted with CH$_2$Cl$_2$ (3×20 mL). The combined organic layer was washed with brine (20 mL) and dried over anhydrous Na$_2$SO$_4$., then filtered and the filtrate was concentrated in vacuum. The residue was purified by silica gel chromatography (PE:EtOAc=2:1) to afford the product tert-butyl (R)-6-hydroxy-8-oxo-8-((2-(3-((R)-2,2,5,5-tetramethyl-1,3-dioxane-4-carboxamido) propanamido) ethyl) thio) octanoate (Compound 901) (2.5 g, 83% yield) as a light-yellow oil.

Example 134: Alternate Synthesis of Compound 852

Synthesis of methyl 4-oxo-4-[[2-(3-[[(4R)-2,2,5,5-tetramethyl-1,3-dioxan-4-yl]formamido]propanamido)ethyl]sulfanyl]butanoate

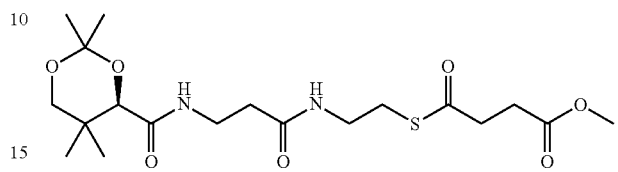

Into a 40 mL vial were added butanedioic acid monomethyl ester (497.9 mg, 3.768 mmol, 1.20 equiv) and DCM (8.00 mL), EDCI (782.6 mg, 4.083 mmol, 1.30 equiv), the mixture was stirred for 10 min. Then N-(2-sulfanylethyl)-3-[[(4R)-2,2,5,5-tetramethyl-1,3-dioxan-4-yl]formamido] propanamide from Preparative Example 3 Step 2 (1.00 g, 3.140 mmol, 1.00 equiv) and DIEA (1.22 g, 9.421 mmol, 3.00 equiv) was added. The resulting mixture was stirred for 1.0 h at 25 degrees C. The reaction was quenched with H$_2$O (30 mL). The resulting mixture was extracted with DCM (3×30 mL). The combined organic layers were dried over anhydrous Na$_2$SO$_4$. After filtration, the filtrate was concentrated under reduced pressure. The residue was purified by silica gel column chromatography, eluted with (MeOH:DCM=1:30) to afford the desired product methyl 4-oxo-4-[[2-(3-[[(4R)-2,2,5,5-tetramethyl-1, 3-dioxan-4-yl]formamido]propanamido)ethyl]sulfanyl]butanoate (940 mg, 69.20%) as a yellow oil. LCMS (ES, m/z): 433.0 [M+H]$^+$.

Example 138: Synthesis of Compound 903

Step 1: Synthesis of 5-[(2E)-but-2-enoyl]-2,2-dimethyl-1,3-diozane-4,6-dione

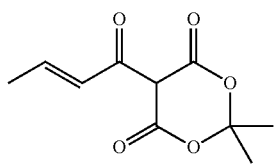

To a stirred mixture of meldrum's acid (20.0 g, 138.9 mmol, 1.00 equiv) in DCM (100.0 mL) was added Pyridine (22.0 g, 277.9 mml, 2.0 equiv) at room temperature under nitrogen atmosphere. The reaction mixture was stirred at room temperature for 30 min. To this mixture was added 2-butenoyl chloride (26.0 g, 166.7 mmol, 1.2 equiv) in DCM (10 mL) dropwise at 0° C. The reaction mixture was stirred at 0° C. for 2 hours. The resulting mixture was concentrated under reduced pressure. The residue was taken up in ethyl acetate and the mixture was washed with water (200 mL×3), dried over Na$_2$SO$_4$ The solvent was removed under vacuum and the residue was purified with reserve phase Chromatography on C18 silica (330 g), eluting with 61% MeCN/10 mM ammonium bicarbonate solution. This resulted in the isolation of the desired compound as 5-[(2E)-but-2-enoyl]-2,2-dimethyl-1,3-dioxane-4,6-dione (4.0 g) as an off-white solid. LCMS (ES, m/z): 213 [M+H]$^+$

Step 2: Synthesis of (R)—S-(2-(3-(2,2,5,5-tetramethyl-1,3-dioxane-4-carbozamido)propanamido)ethyl) (E)-3-oxohex-4-enethioate

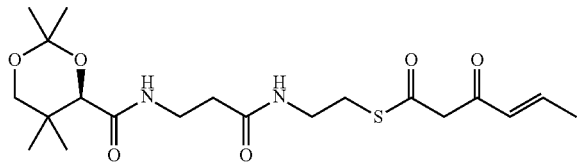 [SMILES: C/C=C/C(=O)CC(=O)SCCNC(=O)CCNC(=O)[C@@H]1OC(C)(C)OCC1(C)C]

A mixture of (E)-5-(but-2-enoyl)-2,2-dimethyl-1,3-dioxane-4,6-dione from Example 138 Step 1 (1.0 g, 6.7 mmol, 1.0 equiv) and (R)—N-(3-((2-mercaptoethyl)amino)-3-oxopropyl)-2,2,5,5-tetramethyl-1,3-dioxane-4-carboxamide from Preparative Example 3 Step 2 (1.0 g, 6.7 mmol, 1.0 equiv) in toluene (10.0 mL) was stirred at 110° C. for 1 hour under microwave condition. The resulting mixture was concentrated under reduced pressure and the residue was taken up in water. The mixture was extracted with ethyl acetate (3×5 mL) and the combined organic layers were dried over anhydrous Na$_2$SO$_4$. After filtration, the filtrate was concentrated under reduced pressure and the residue was purified with prep-TLC (PE:EtOAc=1:1) to give the desired product as (R)—S-(2-(3-(2,2,5,5-tetramethyl-1,3-dioxane-4-carboxamido)propanamido)ethyl) (E)-3-oxohex-4-enethioate (Compound 903) (700 mg) as a light yellow oil. LCMS (ES, m/z): 429 [M+H]$^+$.

Example 139: Synthesis of Compound 857

Synthesis of (2E)-4-oxo-4-[[2-(3-[[(4R)-2,2,5,5-tetramethyl-1,3-dioxan-4-yl]formamido]propanamido)ethyl]sulfanyl]but-2-enoic acid Synthesis of (2E)-4-oxo-4-[[2-(3-[[(4R)-2,2,5,5-tetramethyl-1,3-dioxan-4-yl]formamido]propanamido)ethyl]sulfanyl]but-2-enoic acid

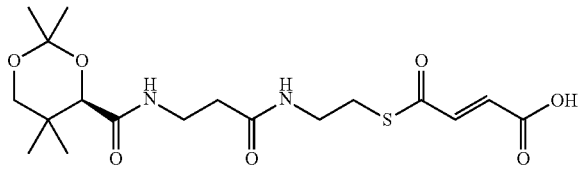 [SMILES: CC1(C)OCC(C)(C)[C@H](C(=O)NCCC(=O)NCCSC(=O)/C=C/C(=O)O)O1]

A stirred solution of fumaryl chloride (1.44 g, 9.4 mmol, 1.5 equiv) in THF (20.0 mL) was cooled to −50 degrees C. under nitrogen atmosphere. To the above mixture was added a solution of N-(2-sulfanylethyl)-3-[[(4R)-2,2,5,5-tetramethyl-1,3-dioxan-4-yl]formamido]propanamide from Preparative Example 3 Step 2 (2.0 g, 6.28 mmol, 1.0 equiv) and triethylamine (953.3 mg, 9.4 mmol, 1.5 equiv) in THF (10.0 mL) dropwise at −50 degrees C. The resulting mixture was stirred for additional 1 h under nitrogen atmosphere. The reaction was quenched by the addition of ice Water (5 mL) at −20 degrees C. The resulting mixture was extracted with dichloromethane. The combined organic layers were dried over anhydrous Na$_2$SO$_4$. After filtration, the filtrate was concentrated under reduced pressure. The residue was purified by silica gel column chromatography, eluted with DCM/MeOH (10:1) to afford the title Compound 857 (200 mg, 7.6%) as a yellow oil. LCMS (ES, m/z): 417 [M+H]$^+$.

Example 140: Synthesis of Compound 858

Synthesis of methyl (2E)-4-oxo-4-[[2-(3-[[(4R)-2,2,5,5-tetramethyl-1,3-dioxan-4-yl]formamido]propanamido)ethyl]sulfanyl]but-2-enoate

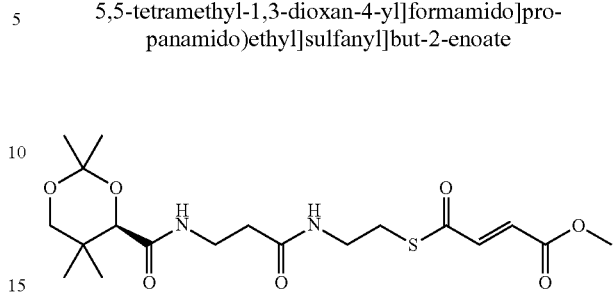

To a stirred mixture of methyl (2E)-4-chloro-4-oxobut-2-enoate (466.5 mg, 3.14 mmol, 2 equiv) and triethylamine (317.8 mg, 3.14 mmol, 2 equiv) in DCM (10 mL) was added N-(2-sulfanylethyl)-3-[[(4R)-2,2,5,5-tetramethyl-1,3-dioxan-4-yl]formamido]propanamide from Preparative Example 3 Step 2 (500.0 mg, 1.57 mmol, 1.0 equiv) in portions at room temperature under nitrogen atmosphere. The resulting mixture was stirred for overnight at room temperature under nitrogen atmosphere. The resulting mixture was concentrated under vacuum. The residue was purified by silica gel column chromatography, eluted with CH$_2$Cl$_2$/MeOH (15:1) to afford the title Compound 858 (130 mg, 18%) as a yellow solid. LCMS (ES, m/z): 431 [M+H]$^+$

Example 141: Synthesis of Compound 859

Synthesis of methyl 4-oxo-3,4-bis([[2-(3-[[(4R)-2,2,5,5-tetramethyl-1,3-dioxan-4-yl]formamido]propanamido)ethyl]sulfanyl])butanoate

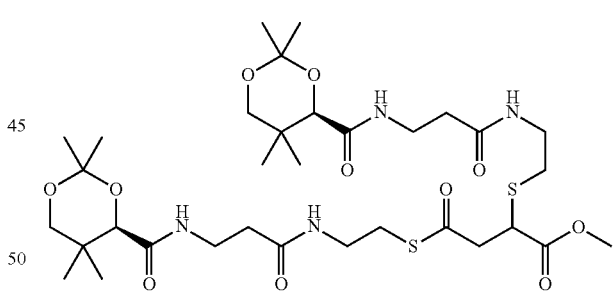

To a stirred mixture of N-(2-sulfanylethyl)-3-[[(4R)-2,2,5,5-tetramethyl-1,3-dioxan-4-yl]formamido]propanamide from Preparative Example 3 Step 2 (499.9 mg, 1.57 mmol. 1.5 equiv), DCC (228.9 mg, 1.11 mmol, 1.06 equiv) and DMAP (12.8 mg, 0.105 mmol, 0.1 equiv) in DCM (20.0 mL) was added (2E)-4-methoxy-4-oxobut-2-enoic acid (136.2 mg, 1.05 mmol, 1.0 equiv) at room temperature under nitrogen atmosphere. The resulting mixture was stirred for overnight at room temperature under nitrogen atmosphere. The resulting mixture was concentrated under vacuum. The residue was purified by silica gel column chromatography, eluted with PE/EtOAc (1:1) to afford the title Compound 859 (500 mg, 64%) as a colorless oil. LCMS (ES, m/z): 749 [M+H]+

Example 142: Synthesis of Compound 904

Step 1: Synthesis of 1,4-dimethyl 2-[[2-(3-[[(4R)-2,2,5,5-tetramethyl-1,3-dioxan-4-yl]formamido]propanamido)ethyl]sulfanyl]butanedioate

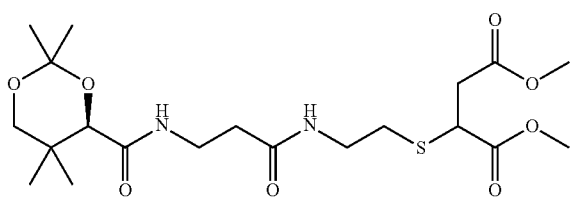 [SMILES: COC(=O)CC(SCCNC(=O)CCNC(=O)[C@@H]1OC(C)(C)OCC1(C)C)C(=O)OC]

To a solution of N-(2-sulfanylethyl)-3-[[(4R)-2,2,5,5-tetramethyl-1,3-dioxan-4-yl]formamido]propanamide from Preparative Example 3 Step 2 (2.0 g, 6.24 mmol, 1.0 equiv) and dimethyl fumarate (0.9 g, 6.24 mmol, 1.0 equiv) in MeOH (10.0 mL) stirred at room temperature was added triethylamine (0.64 g, 6.32 mmol, 1.01 equiv). The reaction mixture was stirred at room temperature for 16 hours. The resulting mixture was concentrated under vacuum. The residue was purified by silica gel column chromatography, eluted with DCM: MeOH (99:1) to afford the title Compound 904 (2.5 g, 86%) as a light yellow solid. LCMS (ES, m/z): 463 [M+H]$^+$

Example 143: Synthesis of Compound 926

Synthesis of 2-[2-(3-{[(R)-2,2,5,5-Tetramethyl-1,3-dioxan-4-yl]carbonylamino}propionylamino)ethylthio]succinic acid

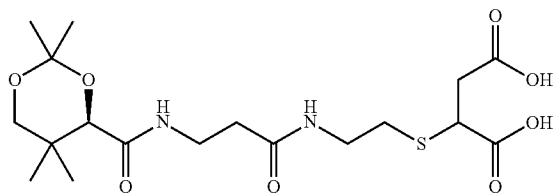 [SMILES: CC1(C)OCC(C)(C)[C@H](C(=O)NCCC(=O)NCCSC(CC(=O)O)C(=O)O)O1]

To a solution of 1,4-dimethyl 2-[[2-(3-[[(4R)-2,2,5,5-tetramethyl-1,3-dioxan-4-yl]formamido]propanamido)ethyl]sulfanyl]butanedioate from Example 142 (1.0 g, 2.16 mmol, 1.0 equiv) in H$_2$O (25.0 mL) and THF (10.0 mL) stirred at room temperature was added NaOH (216.2 mg, 5.41 mmol, 2.5 equiv). The reaction was stirred at room temperature for 2 hours. The mixture was concentrated in vacuo to give a crude product which was used in the next step directly without further purification.

Example 144: Synthesis of Compound 905

Step 1: Synthesis of (2-[[(2Z)-3-carboxyprop-2-enoyl]oxy]ethyl)trimethylazanium

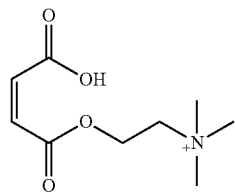

To a solution of maleic anhydride (5.0 g, 51.0 mmol, 1.0 equiv) in toluene (50.0 mL) was added choline chloride (7.12 g, 51.0 mmol, 1.0 equiv). The reaction was stirred at 80° C. for 16 hours. The resulting mixture was concentrated under vacuum to give a crude product. The crude product was washed with DCM and filtrated. The filter cake was dried under high vacuum to give the desired product as (2-[[(2Z)-3-carboxyprop-2-enoyl]oxy]ethyl)trimethylazanium (7 g, 68%) as white solid. LCMS (ES, m/z): 202 [M]$^+$

Step 2: Synthesis of [2-[(3-carboxy-3-[[2-(3-[[(4R)-2,2,5,5-tetramethyl-1,3-dioxan-4-yl]formamido]propanamido)ethyl]sulfanyl]propanoyl)oxy]ethyl]trimethylazanium

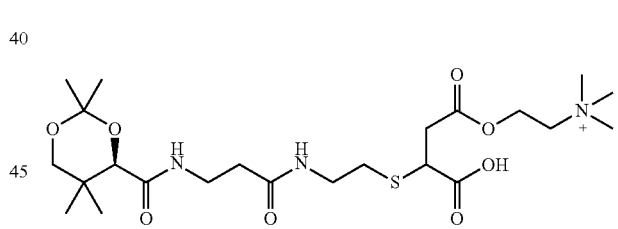

To a stirred mixture of (R)—N-(3-((2-mercaptoethyl)amino)-3-oxopropyl)-2,2,5,5-tetramethyl-1,3-dioxane-4-carboxamide from Preparative Example 3 Step 2 (1.0 g, 1.5 equiv) and (2-[[(2Z)-3-carboxyprop-2-enoyl]oxy]ethyl)trimethylazanium (0.95 g, 1.0 equiv) in acetonitrile (10.0 mL) was added triethylamine (0.32 g, 1.1 equiv) room temperature under N2 atmosphere. The resulting mixture was stirred overnight at room temperature under nitrogen atmosphere. The resulting mixture was concentrated under vacuum and the crude product was purified by Prep-HPLC with the following conditions (2#SHIMADZU (HPLC-01)): Column, XBridge Shield RP18 OBD Column, 19*250 mm, 10 um; mobile phase, water (10 mmol/L NH4HCO3) and ACN (0% PhaseB up to 15% in 10 min). This gave the title Compound 905 (200.0 mg, 13%). LCMS (ES, m/z): 520 [M]$^+$

Example 145: Synthesis of Compound 906

Synthesis of N-[2-[(2,5-dioxooxolan-3-yl)sulfanyl]ethyl]-3-[[(4R)-2,2,5,5-tetramethyl-1,3-dioxan-4-yl]formamido]propanamide

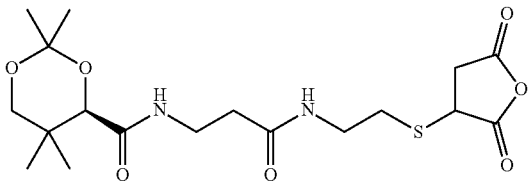 [SMILES: CC1(C)OCC(C)(C)[C@H](C(=O)NCCC(=O)NCCSC2CC(=O)OC2=O)O1]

To a stirred mixture of maleic anhydride (250 mg, 2.55 mmol, 1.0 equiv) and N-(2-sulfanylethyl)-3-[[(4R)-2,2,5,5-tetramethyl-1,3-dioxan-4-yl]formamido]propenamide from Preparative Example 3 Step 2 (832 mg, 2.55 mmol, 1.0 equiv) in acetonitrile (10.0 mL) was added triethylamine (2.5 g, 25.5 mmol, 10.0 equiv) dropwise at room temperature under $N_2$ atmosphere. The resulting mixture was stirred for 3 days at room temperature. The resulting mixture was concentrated under reduced pressure to afford the title Compound 906. LCMS (ES, m/z): 417 $[M+H]^+$

Example 146: Synthesis of Compound 907

Synthesis of benzyl N-(4-oxo-4-[[2-(3-[[(4R)-2,2,5,5-tetramethyl-1,3-dioxan-4-yl]formamido]propanamido)ethyl]sulfanyl]butyl)carbamate

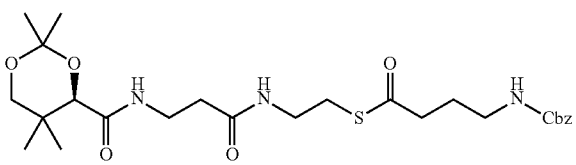 [SMILES: CC1(C)OCC(C)(C)[C@H](C(=O)NCCC(=O)NCCSC(=O)CCCNC(=O)OCc2ccccc2)O1]

To a stirred mixture of 4-[[(benzyloxy)carbonyl]amino]butanoic acid (372.0 mg, 1.0 equiv) and N-(2-sulfanylethyl)-3-[[(4R)-2,2,5,5-tetramethyl-1,3-dioxan-4-yl]formamido]propanamide from Preparatory Example 3 Step 2 (500.0 mg, 1.0 equiv) in DCM (10.0 mL) was added EDCI (450.0 mg, 1.50 equiv), DIPEA (405.0 mg, 2.0 equiv) at 25° C. under N2 atmosphere. The resulting mixture was stirred overnight at room temperature. To the reaction was added brine (20 mL) and the mixture was extracted with DCM (10 mL*3). The organic phase was dried and concentrated under vacuum. The residue was purified by silica gel column chromatography, eluted with PE:EA to afford the title Compound 907 (500 mg) as a colorless oil. LCMS (ES, m/z): 538 $[M+H]^+$

Example 147: Synthesis of Compound 927

Step 1: Synthesis of N-[2-[(4-acetamidobutanoyl)sulfanyl]ethyl]-3-[[(4R)-2,2,5,5-tetramethyl-1,3-dioxan-4-yl]formamido]propanamide

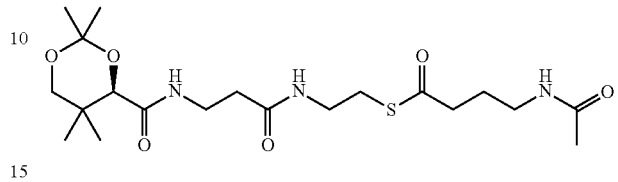

To a stirred mixture of 4-acetamidobutyrate (228.0 mg, 1.57 mmol, 1.0 equiv) and N-(2-sulfanylethyl)-3-[[(4R)-2,2,5,5-tetramethyl-1,3-dioxan-4-yl]formamido]propanamide from Preparatory Example 3 Step 2 (499.5 mg, 1.57 mmol, 1.0 equiv) in DCM (10.0 mL) were added EDCI (451.7 mg, 2.35 mmol, 1.5 equiv) and DIPEA (609 mg, 4.7 mmol, 3.0 equiv) at 25 degrees C. under nitrogen atmosphere. The resulting mixture was stirred for 16 h at 25 degrees C. under nitrogen atmosphere. To the mixture was added ice-water (10 mL) and the mixture was extracted with DCM (20 ml*3). The organic phase was dried and concentrated under reduced pressure. The residue was purified by silica gel column chromatography, eluted with PE/EtOAc (from 0%-30% ethyl acetate-petroleum solvent gradient over 20 mins to pure EtOAc over 40 mins) to afford the title Compound 927 (500 mg, 71%) as a colorless oil. LCMS (ES, in/z): 446 [M+H]+

Example 148: Synthesis of Compound 854

Synthesis of tert-butyl N-[(2S)-3-(3,4-dihydroxyphenyl)-1-oxo-1-[[2-(3-[[(4R)-2,2,5,5-tetramethyl-1,3-dioxan-4-yl]formamido]propanamido)ethyl]sulfanyl]propan-2-yl]carbamate

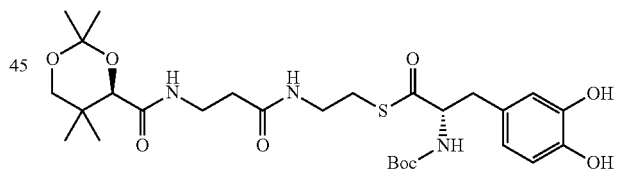

To a stirred mixture of (2S)-2-[(tert-butoxycarbonyl)amino]-3-(3,4-dihydroxyphenyl)propanoic acid (3.3 g, 6.7 mmol, 1.0 equiv) in DCM (10.0 mL) was added EDCI (1.8 g, 10.1 mmol, 1.5 equiv), DIEA (1.6 g, 13.5 mmol, 2.0 equiv) and N-(2-sulfanylethyl)-3-[[(4R)-2,2,5,5-tetramethyl-1,3-dioxan-4-yl]formamido]propanamide from Preparative Example 3 Step 2 (2.0 g, 6.7 mmol, 1.0 equiv) at room temperature. The reaction was stirred at room temperature for overnight. The resulting mixture was concentrated under reduced pressure and the residue was taken up in water. The mixture was extracted with ethyl acetate (3×100 mL) and the combined organic layers were dried over anhydrous $Na_2SO_4$. After filtration, the filtrate was concentrated under reduced pressure and the crude product was purified with prep-TLC (PE:EtOAc=1:1) to afford the title Compound 854 (1.6 g, 43%) as a light yellow oil. LCMS (ES, m/z): 598 $[M+H]^+$

Example 149: Synthesis of Compound 855

Synthesis of N-[2-(heptanoylsulfanyl)ethyl]-3-[[(4R)-2,2,5,5-tetramethyl-1,3-dioxan-4-yl]formamido]propanamide

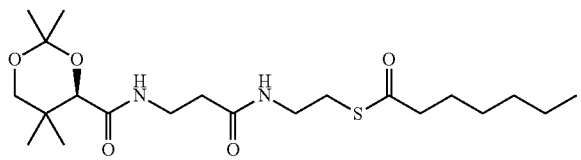 [SMILES: CCCCCCC(=O)SCCNC(=O)CCNC(=O)[C@@H]1OC(C)(C)OCC1(C)C]

To a stirred solution of N-(2-sulfanylethyl)-3-[[(4R)-2,2,5,5-tetramethyl-1,3-dioxan-4-yl]formamido]propanamide from Preparative Example 3 Step 2 (200.0 mg, 0.63 mmol, 1.0 equiv), EDCI (180.6 mg, 0.94 mmol, 1.5 equiv) and DIEA (162.3 mg, 1.25 mmol, 2.0 equiv) in DCM (20.0 mL) was added heptanoic acid (98.1 mg, 0.75 mmol, 1.2 equiv) at room temperature under nitrogen atmosphere. The resulting mixture was stirred for overnight at room temperature under nitrogen atmosphere. To the mixture was added water (10 mL) and the mixture was extracted with DCM (15 ml*3). The organic phase was dried and concentrated under reduced pressure. The residue was purified by silica gel column chromatography (PE/EtOAc=4:1 to afford the title Compound 855 (100 mg, 33%) as an off-white solid. LCMS (ES, m/z): 431 [M+H]$^+$

Example 150: Synthesis of Compound 928

Synthesis of [2-[(3-carboxy-2-[[2-(3-[[(4R)-2,2,5,5-tetramethyl-1,3-dioxan-4-yl]formamido]propanamido)ethyl]sulfanyl]propanoyl)oxy]ethyl]trimethylazanium

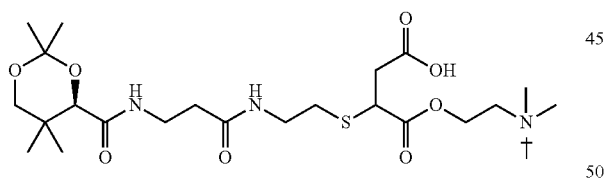

To a stirred mixture of N-[2-[(2,5-dioxooxolan-3-yl)sulfanyl]ethyl]-3-[[(4R)-2,2,5,5-tetramethyl-1,3-dioxan-4-yl]formamido]propanamide from Example 145 Step 1 (980.0 mg, 2.35 mmol, 1.0 equiv) in Toluene (10.0 mL) was added choline chloride (1642 mg, 11.76 mmol, 5.0 equiv) under nitrogen atmosphere. The resulting mixture was stirred for 16 h at 80 degrees C. under nitrogen atmosphere. The resulting mixture was concentrated under vacuum and the crude product was purified by Prep-HPLC with the following conditions (2#SHIMADZU (HPLC-01)): Column, XBridge Prep C18 OBD Column, 150 mm 5um; mobile phase, Water (10 MMOL/L NH4HCO3) and ACN (5% PhaseB up to 25% in 7 min). This resulted in the isolation of the desired product Compound 928 (300 mg, 24%). LCMS (ES, m/z): 520 [M]$^+$

Example 153: Synthesis of Compound 908

Synthesis of N-(2-[[(5S)-5-[(tert-butyldimethylsilyl)oxy]-3-oxohexanoyl]sulfanyl]ethyl)-3-[[(4R)-2,2,5,5-tetramethyl-1,3-dioxan-4-yl]formamido]propanamide Step 1

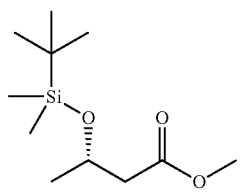

To a stirred mixture of methyl-(S)-3-hydroxybutyrate (25.0 g, 211.6 mmol, 1.0 equiv) in DMF (250.0 mL) were added t-butyldimethylchlorosilane (38.3 g, 253.9 mmol, 1.2 equiv) and 1H-imidazole (21.6 g, 317.4 mmol, 1.5 equiv) at 0 degrees C. The resulting mixture was stirred for overnight at room temperature. The resulting mixture was diluted with water (500 mL). The resulting mixture was extracted with EtOAc (3×500 mL). The combined organic layers were washed with brine (2×500 mL), dried over anhydrous MgSO4. After filtration, the filtrate was concentrated under reduced pressure. The residue was purified by silica gel column chromatography, eluted with PE/EtOAc (1:1) to afford the desired compound methyl (3S)-3-[(tert-butyldimethylsilyl)oxy]butanoate (33 g, 62%) as colorless oil. LCMS (ES, m/z): 233 [M+H]$^+$ Step 2

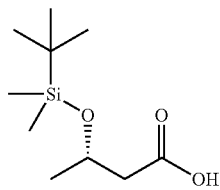

A mixture of methyl (3S)-3-[(tert-butyldimethylsilyl)oxy]butanoate from Example 153 Step 1 (33.0 g, 1.0 equiv), NaOH (2.58 g, 5.0 equiv) and H$_2$O (500.0 mL) in MeOH (200.0 mL) at room temperature was stirred for 3 hours. To the reaction was added 1M HCl dropwise to adjust the PH 3-4. The mixture was extracted with EA. The combined organic phase was dried over NaSO4 and the solvent removed under reduced pressure to give 24 g of the product as an off-white solid. LCMS (ES, m/z): 219 [M+H]$^+$ Step 3

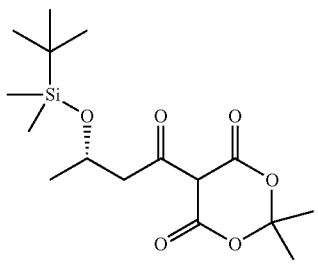

To a stirred mixture of (3S)-3-[(tert-butyldimethylsilyl)oxy]butanoic acid from Example 153 Step 2 (5.0 g, 22.9 mmol, 1.0 equiv) and DMAP (4.2 g, 34.34 mmol, 1.5 equiv) in DCM (150.00 mL) was added dicyclohexylcarbodiimide (5.67 g, 27.48 mmol, 1.2 equiv) in DCM (100.0 mL) at room temperature under nitrogen atmosphere. The resulting mixture was stirred for 1 h at room temperature under nitrogen atmosphere. To the above mixture was added meldrums acid (3.3 g, 22.90 mmol, 1.0 equiv) at room temperature. The resulting mixture was stirred for additional overnight at room temperature. The resulting mixture was filtered, the filter cake was washed with DCM (3×100 mL). The filtrate was washed with 5% KHSO4 and brine, dried over anhydrous MgSO4. After filtration, the filtrate was concentrated under reduced pressure. This resulted in 5-[(3S)-3-[(tert-butyldimethylsilyl)oxy]butanoyl]-2,2-dimethyl-1,3-dioxane-4,6-dione (7.9 g, 96%) as an off-white solid. LCMS (ES, m/z): 345 [M+H]+

Step 4

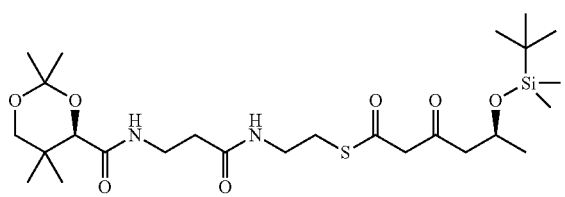 [SMILES: C[C@@H](CC(=O)CC(=O)SCCNC(=O)CCNC(=O)[C@@H]1OC(C)(C)OCC1(C)C)O[Si](C)(C)C(C)(C)C]

To a stirred mixture of 5-[(3S)-3-[(tert-butyldimethylsilyl)oxy]butanoyl]-2,2-dimethyl-1,3-dioxane-4,6-dione from Example 153 Step 3 (2.0 g, 5.80 mmol, 1.0 equiv) in Toluene (160.0 mL) was added N-(2-sulfanylethyl)-3-[[(4R)-2,2,5,5-tetramethyl-1,3-dioxan-4-yl]formamido]propanamide (1.85 g, 5.81 mmol, 1.0 equiv) at room temperature under nitrogen atmosphere. The resulting mixture was stirred for 4 h at 75 degrees C. under nitrogen atmosphere. The resulting mixture was concentrated under vacuum. The residue was purified by silica gel column chromatography, eluted with CH2Cl2/MeOH (12:1) to afford N-(2-[[(5S)-5-[(tert-butyldimethylsilyl)oxy]-3-oxohexanoyl]sulfanyl]ethyl)-3-[[(4R)-2,2,5,5-tetramethyl-1,3-dioxan-4-yl]formamido]propenamide (Compound 908) (900 mg, 26%) as a yellow oil. LCMS (ES, m/z): 561 [M+H]+

Example 154: Synthesis of Compound 909

Synthesis of N-(2-[[(5R)-5-[(tert-butyldimethylsilyl)oxy]-3-oxohexanoyl]sulfanyl]ethyl)-3-[[(4R)-2,2,5,5-tetramethyl-1,3-dioxan-4-yl]formamido]propenamide Step 1: Synthesis of methyl (3R)-3-[(tert-butyldimethylsilyl)oxy]butanoate

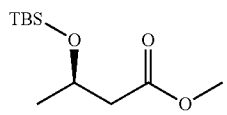

Into a 500 mL flask was placed methyl-(R)-3-hydroxybutyrate (15.00 g, 126.977 mmol, 1.00 equiv), DMF (150.00 mL), the t-butyldimethylchlorosilane (22.97 g, 152.372 mmol, 1.20 equiv) and 1H-imidazole (12.97 g, 190.519 mmol, 1.50 equiv) was added at 0 degrees C. The mixture was stirred for 15.0 h at 25 degrees C. The mixture was poured into 500 mL of H2O. The resulting mixture was extracted with EA (500 mL×1). The organic layers were washed with brine (500 mL×4), dried over anhydrous Na2SO4. After filtration, the filtrate was concentrated under reduced pressure. The residue was purified by silica gel column chromatography, eluted with EA:PE=1:10 to afford methyl (3R)-3-[(tert-butyldimethylsilyl)oxy]butanoate (20.0 g, 67.78%) as a colorless oil.

LCMS: (ES, m/z): 233.0 [M+H]+.

Step 2: Synthesis of (3R)-3-[(tert-butyldimethylsilyl)oxy]butanoic Acid

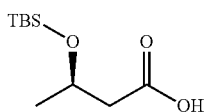

Into a 2.0 L 3-necked flask was placed methyl (3R)-3-[(tert-butyldimethylsilyl)oxy]butanoate from Example 154 Step 1 (20.00 g, 86.060 mmol, 1.00 equiv), MeOH (800.00 mL), NaOH (1.0 mol/L, 430.30 mL, 430.300 mmol, 5.00 equiv). The mixture was stirred for 4.0 h at 25 degrees C. The MeOH was concentrated under reduced pressure. The aqueous layer was extracted with EA (400 mL x1) then acidified to pH 2 with HCl (2.0 mol/L). The resulting mixture was extracted with EA (500 mL×3). The combined organic layers were dried over anhydrous Na2SO4. After filtration, the filtrate was concentrated under reduced pressure. This resulted in (3R)-3-[(tert-butyldimethylsilyl)oxy]butanoic acid (13.2 g, 70.24%) as light yellow oil. LCMS: (ES, m/z): 219.0 [M+H]−.

Step 3: Synthesis of 5-[(3R)-3-[(tert-butyldimethyl-silyl)oxy]butanoyl]-2,2-dimethyl-1,3-dioxane-4,6-dione

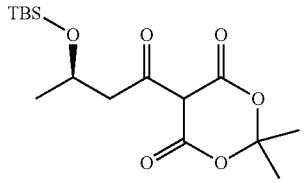

Into a 500 mL 3-necked flask was placed (3R)-3-[(tert-butyldimethylsilyl)oxy]butanoic acid from Example 154 Step 2 (10.00 g, 45.794 mmol, 1.00 equiv), DCM (120.00 mL), meldrum's acid (7.26 g, 50.374 mmol, 1.10 equiv), DMAP (8.38 g, 68.691 mmol, 1.50 equiv). The DCC (10.38 g, 50.374 mmol, 1.10 equiv) in 180 mL DCM was added at −5 degrees C. The mixture was stirred for 16.0 h at 25 degrees C. The resulting mixture was filtered. The filtrate was washed with KHSO4 (5%, 300 mL×3), brine (300 mL×1). The organic layer were dried over anhydrous Na$_2$SO$_4$. After filtration, the filtrate was concentrated under reduced pressure. The residue was purified by silica gel column chromatography, eluted with MeOH:DCM=1:100 to afford 5-[(3R)-3-[(tert-butyldimethylsilyl)oxy]butanoyl]-2,2-dimethyl-1,3-dioxane-4,6-dione (11.0 g, 69.73%) as yellow oil.

LCMS: (ES, m/z): 345.0 [M+H]$^+$.

Step 4: Synthesis of N-(2-[[(5R)-5-[(tert-butyldimethylsilyl)oxy]-3-oxohexanoyl]sulfanyl]ethyl)-3-[[(4R)-2,2,5,5-tetramethyl-1,3-dioxan-4-yl]formamido]propenamide

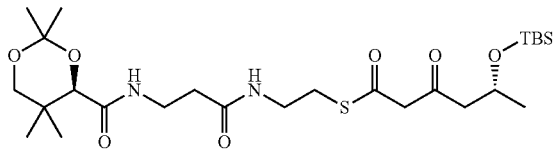

Into a 250 mL flask was placed 5-[(3R)-3-[(tert-butyldimethylsilyl)oxy]butanoyl]-2,2-dimethyl-1,3-dioxane-4,6-dione from Example 154 Step 3 (4.00 g, 11.612 mmol, 1.00 equiv), Toluene (80.00 mL), N-(2-sulfanylethyl)-3-[[(4R)-2,2,5,5-tetramethyl-1,3-dioxan-4-yl]formamido]propanamide from Preparative Example 3 Step 2 (3.70 g, 11.620 mmol, 1.00 equiv). The mixture was stirred for 3.0 h at 75 degrees C. The mixture was allowed to cool down to 25 degrees C. The resulting mixture was concentrated under reduced pressure. The residue was purified by silica gel column chromatography, eluted with MeOH:DCM=1:30 to afford N-(2-[[(5R)-5-[(tert-butyldimethylsilyl)oxy]-3-oxohexanoyl]sulfanyl]ethyl)-3-[[(4R)-2,2,5,5-tetramethyl-1,3-dioxan-4-yl]formamido]propanamide (Compound 909) (3.86 g, 59.27%) as red oil. LCMS (ES, m/z): 561.0 [M+H]$^+$.

Example 155: Synthesis of Compound 910

Step 1: Synthesis of (2E)-4-(2,2-dimethyl-4,6-dioxo-1,3-dioxan-5-yl)-4-oxobut-2-enoic Acid

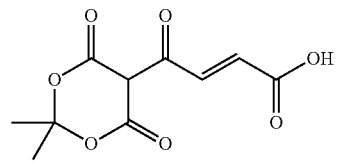 [SMILES: CC1(C)OC(=O)C(C(=O)/C=C/C(=O)O)C(=O)O1]

To a mixture of methyl (2E)-4-(2,2-dimethyl-4,6-dioxo-1,3-dioxan-5-yl)-4-oxobut-2-enoate (290 mg, 1.13 mmol, 1.00 equiv) in THF (8 mL) was added LiOH (136 mg, 5.66 mmol, 5 equiv) in H$_2$O (8 mL) at 0 degrees C. The resulting mixture was stirred for 1 h at the same temperature. The resulting mixture was concentrated under reduced pressure. The mixture was acidified to pH 3 with HCl (1 M, aq.). The precipitated solids were collected by filtration and washed with water (3×5 mL). The resulting solid was dried under infrared light. This resulted in (2E)-4-(2,2-dimethyl-4,6-dioxo-1,3-dioxan-5-yl)-4-oxobut-2-enoic acid (190 mg, 66%) as a white solid. MS: (ES, m/z): 243 [M+H]$^+$

Step 2: Synthesis of (2E)-4,6-d oxo-6-[[2-(3-[[(4R)-2,2,5,5-tetramethyl-1,3-dioxan-4-yl]formamido]propanamido)ethyl]sulfanyl]hex-2-enoic Acid

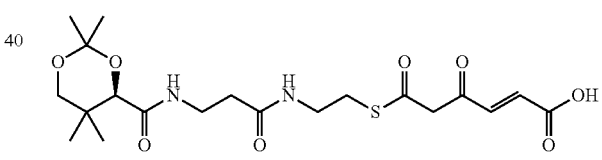

To a stirred mixture of N-(2-sulfanylethyl)-3-[[(4R)-2,2,5,5-tetramethyl-1,3-dioxan-4-yl]formamido]propanamide from Preparative Example 3 Step 2 (250 mg, 0.79 mmol, 1.00 equiv) in toluene (10 mL) was added (2E)-4-(2,2-dimethyl-4,6-dioxo-1,3-dioxan-5-yl)-4-oxobut-2-enoic acid from Example 155 Step 1 (190 mg, 0.79 mmol, 1 equiv). The resulting mixture was stirred at 80 degrees C. for 2 h. The mixture was allowed to cool down to room temperature. The resulting mixture was concentrated under reduced pressure. The residue was purified by reverse flash chromatography with the following conditions: column, C18 silica gel; mobile phase, water (0.05% TFA) and (10$^4$)/0 to 37% gradient in 15 min); detector, UV 220 nm. The collected fraction was extracted with CH$_2$Cl$_2$ (2×200 mL), washed with brine (200 mL), dried over anhydrous Na$_2$SO$_4$. After filtration, the filtrate was concentrated under reduced pressure to afford the title Compound 910 (150 mg, 39.6%) as yellow solid. MS: (ES, m/z): 459 [M+H]$^+$

Example 156: Synthesis of Compound 911

Step 1: Synthesis of methyl (2E)-4-(2,2-dimethyl-4,6-dioxo-1,3-dioxan-5-yl)-4-oxobut-2-enoate

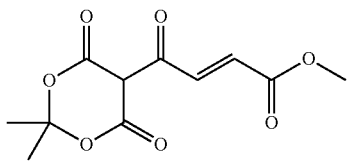

To a stirred mixture of meldrums acid (22.2 g, 153.7 mmol, 1.00 equiv), DCC (34.9 g, 169.1 mmol, 1.1 equiv) and DMAP (20.7 g, 169.1 mmol, 1.10 equiv) in DCM (300 mL) was added (2E)-4-methoxy-4-oxobut-2-enoic acid (20.0 g, 153.7 mmol, 1.00 equiv) in portions at 0 degrees C. The resulting mixture was stirred for 15 h at 25 degrees C. The resulting mixture was filtered. The filtrate was concentrated under reduced pressure. The residue was acidified to pH 2 with 2% KHSO4 (aq.), extracted with Et$_2$O (3×300 mL), washed with 2% KHSO4 (aq.) (300 mL) and water (300 mL), dried over anhydrous Na$_2$SO$_4$. After filtration, the filtrate was concentrated under reduced pressure. The residue was purified by silica gel column chromatography, eluted with PE/EtOAc (1:1) to afford crude product. The residue was purified by reverse flash chromatography with the following conditions: column, C18 silica gel; mobile phase, water (0.05% TFA) and ACN (0 to 50% gradient in 25 min); detector, UV 254/220 nm. This resulted in methyl (2I)-4-(2,2-dimethyl-4,6-dioxo-1,3-dioxan-5-yl)-4-oxobut-2-enoate (570 mg, 1.4%) as a white solid. MS: (ES, m/z): 257 [M+H]$^+$

Step 2: Synthesis of (2E)-4,6-dioxo-6-[[2-(3-[[(4R)-2,2,5,5-tetramethyl-1,3-dioxan-4-yl]formamido]propanamido)ethyl]sulfanyl]hex-2-enoate

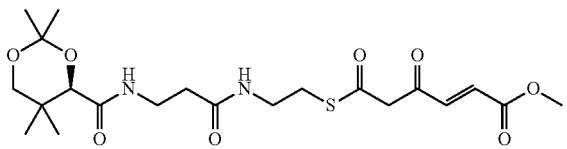 [SMILES: COC(=O)/C=C/C(=O)CC(=O)SCCNC(=O)CCNC(=O)[C@@H]1OC(C)(C)OCC1(C)C]

A mixture of N-(2-sulfanylethyl)-3-[[(4I)-2,2,5,5-tetramethyl-1,3-dioxan-4-yl]formamido]propanamide from Preparative Example 3 Step 2 (298 mg, 0.94 mmol, 1.00 equiv) and methyl (2E)-4-(2,2-dimethyl-4,6-dioxo-1,3-dioxan-5-yl)-4-oxobut-2-enoate from Example 156 Step 1 (240 mg, 0.94 mmol, 1.00 equiv) in toluene (10 mL) was stirred for 2 h at 80 degrees C. under nitrogen atmosphere. The mixture was allowed to cool down to room temperature and concentrated under reduced pressure. The residue was purified by reverse flash chromatography with the following conditions: column, C$_{1-8}$ silica gel; mobile phase, water (0.05% TFA) and ACN (0 to 37% gradient in 15 min); detector, UV 254/220 nm. This resulted in methyl (2E)-4,6-dioxo-6-[[2-(3-[[(4R)-2,2,5,5-tetramethyl-1,3-dioxan-4-yl]formamido]propanamido)ethyl]sulfanyl]hex-2-enoate (Compound 911) (170 mg, 50% purity, 19%) as a yellow solid. MS: (ES, m/z): 473 [M+H]$^+$

Example 157: Synthesis of Compound 856

Synthesis of (R)-4-[(3-{2-[(methoxycarbonylthio)carbonyl]ethylamino}-3-oxopropylamino)carbonyl]-2,2,5,5-tetramethyl-1,3-dioxane

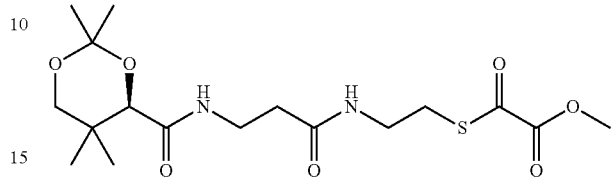

To a stirred solution of N-(2-sulfanylethyl)-3-[[(4R)-2,2,5,5-tetramethyl-1,3-dioxan-4-yl]formamido]propenamide from Preparative Example 3 Step 2 (500 mg, 1.57 mmol, 1.0 equiv) in DCM (5.0 mL) was added TEA (317 mg, 3.14 mmol, 2.0 equiv) and ethyl oxalochloridate (192 mg, 1.57 mmol, 1.0 equiv) at 0° C. The reaction was stirred for 4 hours at room temperature. The reaction mixture was directly purified with prep-TLC (PE:EtOAc=1:1) to give 350 mg (55%) of the desired product as a colorless oil. LCMS (ES, m/z): 405 [M+H]$^+$

Example 163: Synthesis of Compound 912

Synthesis of N-[2-[(2-methyl-3-oxobutanoyl)sulfanyl]ethyl]-3-[[(4R)-2,2,5,5-tetramethyl-1,3-dioxan-4-yl]formamido]propanamide

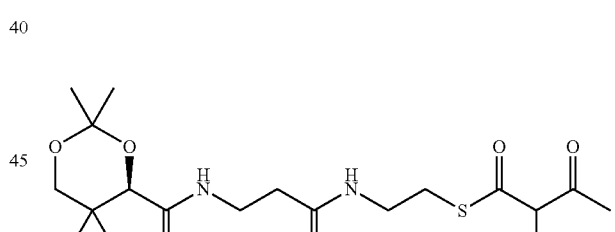

To a stirred mixture of N-(2-sulfanylethyl)-3-[[(4R)-2,2,5,5-tetramethyl-1,3-dioxan-4-yl]formamido]propanamide from Preparative Example 3 Step 2 (850 mg, 2.40 mmol, 1.00 equiv, 90%) in Toluene (30 mL) was added tetramethyl-1,3-dioxin-4-one (563 mg, 3.60 mmol, 1.50 equiv, 99%) at room temperature under nitrogen atmosphere. The resulting mixture was stirred for 12 h at 120 degrees C. under nitrogen atmosphere. The mixture was allowed to cool down to room temperature. The resulting mixture was concentrated under reduced pressure. The residue was purified by silica gel column chromatography, eluted with CH$_2$Cl$_2$/MeOH (10:1) to afford the title Compound 912 (650 mg, 62%) as a colorless oil. MS: (ES, m/s): 417 [M+H]$^+$

Example 164: Synthesis of Compound 860

Step 1: Synthesis of 5-acetyl-2,2-dimethyl-1,3-dioxane-4,6-done

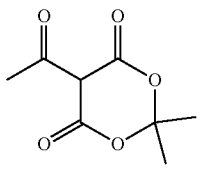

To a stirred solution of meldrums acid (5.0 g, 34.6 mmol, 1.00 equiv), pyridine (5.5 g, 70 mmol, 1.00 equiv) and DMAP (424 mg, 3.47 mmol, 0.10 equiv) in CH$_2$Cl2 (50 mL) was added acetyl chloride (3.8 g, 48.4 mmol, 1.4 equiv) dropwise at 0 degrees C. under nitrogen atmosphere. The resulting mixture was stirred for 1 h at 25 degrees C. under nitrogen atmosphere. The resulting mixture was washed with 2 M HCl (3×50 mL). The organic layers were dried over anhydrous Na$_2$SO$_4$. After filtration, the filtrate was concentrated under reduced pressure. The residue was purified by silica gel column chromatography, eluted with CH$_2$Cl$_2$/MeOH (10:1) to afford 5-acetyl-2,2-dimethyl-1,3-dioxane-4,6-dione (5.5 g, 80.90%) as a white solid. MS: (ES, m/i): 187 [M+H]$^+$.

Step 2: Synthesis of N-[2-[(3-oxobutanoyl)sulfanyl]ethyl]-3-[[(4R)-2,2,5,5-tetramethyl-1,3-dioxan-4-yl]formamido]propenamide

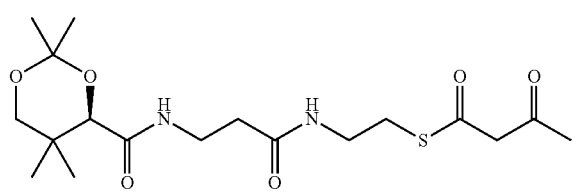

To a stirred solution of N-(2-sulfanylethyl)-3-[[(4R)-2,2,5,5-tetramethyl-1,3-dioxan-4-yl]formamido]propanamide from Preparative Example 3 Step 2 (58 mg, 0.17 mmol, 1.0 equiv) in toluene (3 mL) was added 5-acetyl-2,2-dimethyl-1,3-dioxan-4-one from Example 164 Step 1 (95 mg, 0.55 mmol, 3.19 equiv). The resulting mixture was stirred for 2 h at 80 degrees C. under nitrogen atmosphere. The mixture was allowed to cool down to room temperature. The resulting mixture was concentrated under vacuum. The residue was purified by silica gel column chromatography, eluted with CH$_2$Cl$_2$/MeOH (10:1) to afford N-[2-[(3-oxobutanoyl)sulfanyl]ethyl]-3-[[(4R)-2,2,5,5-tetramethyl-1,3-dioxan-4-yl]formamido]propanamide (60 mg, 81.84%) as a white solid. MS: (ES, m/z): 403 [M+H]$^+$.

Example 165: Synthesis of Compound 913

Synthesis of N-[2-[(2-acetyl-3-oxobutanoyl)sulfanyl]ethyl]-3-[[(4R)-2,2,5,5-tetramethyl-1,3-dioxan-4-yl]formamido]propanamide

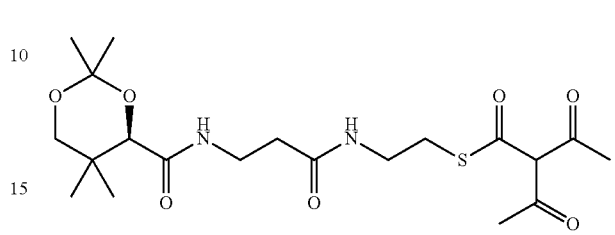

To a stirred solution of N-[2-[(3-oxobutanoyl)sulfanyl]ethyl]-3-[[(4R)-2,2,5,5-tetramethyl-1,3-dioxan-4-yl]formamido]propanamide from Example 164 Step 2 (300 mg, 0.74 mmol, 1.00 equiv) and MgCl$_2$ (72 mg, 0.76 mmol, 1.0 equiv) in dichloromethane was added Pyridine (120 mg, 1.52 mmol, 2.0 equiv) dropwise at 0 degrees C. under nitrogen atmosphere. Then acetyl chloride (70 mg, 0.9 mmol, 1.2 equiv) was added dropwise at 0 degrees C. under nitrogen atmosphere. The resulting mixture was stirred for 1 h at room temperature under nitrogen atmosphere. The mixture was neutralized to pH 7 with 1 M HCl (0.5 mL). The organic layers were washed with brine (10 mL), dried over anhydrous Na$_2$SO$_4$. After filtration, the filtrate was concentrated under reduced pressure. This resulted in the isolation of the desired product N-[2-[(2-acetyl-3-oxobutanoyl)sulfanyl]ethyl]-3-[[(4R)-2,2,5,5-tetramethyl-1,3-dioxan-4-yl]formamido]propanamide (300 mg, 86.02%) as a colorless oil. MS: (ES, m/z): 445 [M+H]$^+$.

Example 166: Synthesis of Compound 915

Step 1: Synthesis of 3-(tert-butoxy)-2-methyl-3-oxopropanoic Acid

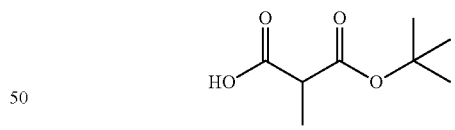

To a stirred solution of methylmalonic acid (1 g, 8.46 mmol, 1.00 equiv) in THF (10 ml) was added tert-butanol (1.13 g, 15.3 mmol, 1.8 equiv) and pyridine (1.5 mL) was added at 0 degrees C. MsCl (1.00 g, 0.009 mmol) was added dropwise 0 degrees C. The reaction was stirred at 25 degrees C. for 3 h. The solid was filtered out. The filtrate was concentrated and 30 ml of H$_2$O was added. The solution was adjusted to PH=12 by using 4 N NaOH (aq.) and washed with DCM (3×50 ml). The aqueous layer was acidified to PH=4 with 4 N HCl (aq.), extracted with DCM (4×50 ml), dried over anhydrous Na$_2$SO$_4$. The organic layer was combined and concentrated to provide the product 3-(tert-butoxy)-2-methyl-3-oxopropanoic acid (540 mg, 36%) as colorless oil. MS: (ES, m/z): 175 [M+H]$^+$.

Step 2: Synthesis of tert-butyl 2-methyl-3-oxo-3-[(2-[3-[(2,2,5,5-tetramethyl-1,3-dioxan-4-yl)formamido]propanamido]ethyl)sulfanyl]propanoate

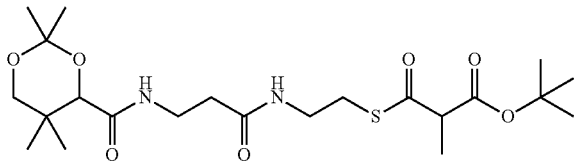 [SMILES: CC(C(=O)OC(C)(C)C)C(=O)SCCNC(=O)CCNC(=O)C1OC(C)(C)OCC1(C)C]

To a stirred solution of 3-(tert-butoxy)-2-methyl-3-oxopropanoic acid from Example 166 Step 1 (18 mg, 0.10 mmol, 1.20 equiv) and N-(2-sulfanylethyl)-3-[(2,2,5,5-tetramethyl-1,3-dioxan-4-yl)formamido]propanamide from Preparative Example 3 Step 2 (28 mg, 0.08 mmol, 1.00 equiv) in DCM (20 ml) were added EDCI (16 mg, 0.13 mmol, 0.10 equiv) and DIEA (272 mg, 1.32 mmol, 1.00 equiv) at 0 degrees C. The resulted mixture was stirred at 25 degrees C. for 1 h. The reaction was quenched with H$_2$O (10 ml). The resulting mixture was extracted with CH$_2$Cl$_2$ (3×20 mL). The combined organic layers were washed with brine (30 ml), dried over anhydrous Na$_2$SO$_4$. After filtration, the filtrate was concentrated under reduced pressure. The residue was purified by silica gel column chromatography, eluted with PE/EtOAc (1:1) to afford the title Compound 915 (350 mg. 56%) as a yellow oil. MS: (ES, m/z): 475 [M+H]$^+$.

Example 167: Synthesis of Compound 916

Step 1: Synthesis of 2,2-dimethyl-5-propionyl-1,3-dioxane-4,6-dione

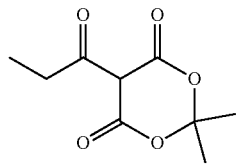

To a stirred solution of meldrum's acid (5.00 g, 34.7 mmol, 1.0 equiv) and DMAP (424 mg, 3.5 mmol, 0.1 equiv) in dichloromethane (50 mL) were added pyridine (5.49 g, 69.4 mmol, 2.0 equiv) and propionyl chloride (2.50 g, 34.7 mmol, 1.0 equiv) dropwise at 0 degrees C. under nitrogen atmosphere. The resulting mixture was stirred for 1 h at room temperature under nitrogen atmosphere. The resulting mixture was diluted with dichloromethane (250 mL). The resulting mixture was washed with hydrochloric acid (1 N) (3×200 mL). The resulting solution was dried over anhydrous sodium sulfate. The resulting mixture was concentrated under vacuum. This resulted in 2,2-dimethyl-5-propanoyl-1,3-dioxane-4,6-dione (4.8 g, 62%) as a white solid. LCMS- (ES, m/s): 201 [M+H]+.

Step 2: Synthesis of (R)—S-(2-(3-(2,2,5,5-tetramethyl-1,3-dioxane-4-carboxamido)propanamido)ethyl) 3-oxopentanethioate

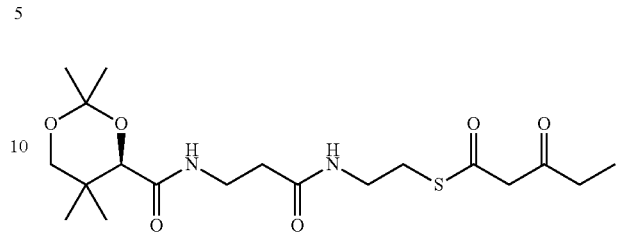

A mixture of N-(2-sulfanylethyl)-3-[[(4R)-2,2,5,5-tetramethyl-1,3-dioxan-4-yl]formamido]propanamide from Preparative Example 3 Step 2 (480 mg, 1.5 mmol, 1.0 equiv) and 2,2-dimethyl-5-propanoyl-1,3-dioxane-4,6-dione from Example 167 Step 1 (302 mg, 1.5 mmol, 1.0 equiv) in toluene (4 mL) was stirred for 3 h at 80 degrees C. under nitrogen atmosphere. The mixture was cooled to 20 degrees C. The resulting mixture was concentrated under vacuum. The residue was purified by reverse flash chromatography with the following conditions: column, C18 silica gel; mobile phase, ACN in water (NH$_4$HCO$_3$, 10 mmol/L), 0% to 50% gradient in 30 min; detector, UV 254 nm. This resulted in the isolation of the title Compound 916 (200 mg, 25%) as a yellow oil. LCMS: (ES, m/s): 417 [M+H]+.

Example 168: Synthesis of Compound 861

Synthesis of N-[2-(propanoylsulfanyl)ethyl]-3-[[(4R)-2,2,5,5-tetramethyl-1,3-dioxan-4-yl]formamido]propanamide

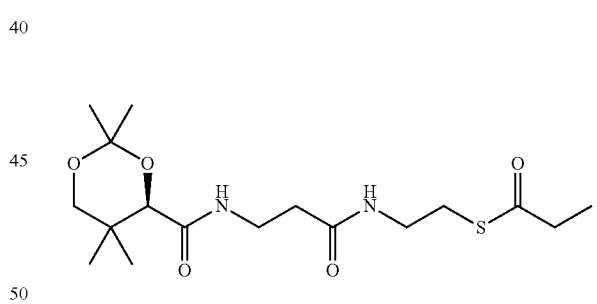

The mixture of propanoic acid (75 mg, 1.01 mmol, 1.20 equiv) and EDCI (243 mg, 1.27 mmol, 1.50 equiv) in DCM (10 mL) was stirred for 10 min at 25 degrees C. To the above mixture was added N-(2-sulfanylethyl)-3-[[(4R)-2,2,5,5-tetramethyl-1,3-dioxan-4-yl]formamido]propanamide from Preparative Example 3 Step 2 (300 mg, 0.84 mmol, 1.00 equiv, 90%) and DIPEA (328 mg, 2.54 mmol, 3.00 equiv) at 0 degrees C. The resulting mixture was stirred for 12 h at 25 degrees C. The resulting mixture was concentrated under reduced pressure. The residue was purified by Prep-TLC (CH$_2$Cl$_2$/MeOH 10:1) to afford the title Compound 861 (90 mg, 27%) as a colorless oil. MS: (ES, m/s): 375 [M+H

Example 169: Synthesis of Compound 902

Synthesis of methyl 3-[5,5-dimethyl-2-(2-oxo-2-[[2-(3-[[(4R)-2,2,5,5-tetramethyl-1,3-dioxan-4-yl]formamido]propanamido)ethyl]sulfanyl]ethyl)-1,3-dioxan-2-yl]propanoate

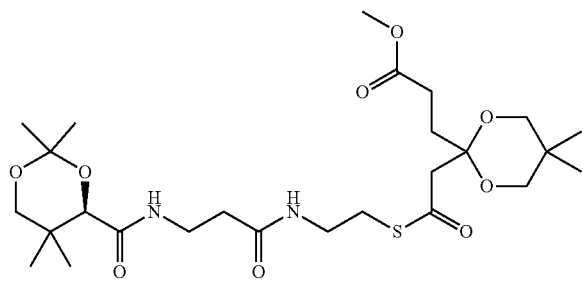 [SMILES: COC(=O)CCC1(CC(=O)SCCNC(=O)CCNC(=O)[C@@H]2OC(C)(C)OCC2(C)C)OCC(C)(C)CO1]

To a stirred solution of N-(2-sulfanylethyl)-3-[[(4R)-2,2,5,5-tetramethyl-1,3-dioxan-4-yl]formamido]propanamide from Preparative Example 3 Step 2 (1.35 g, 5.1 mmol, 1.1 equiv) and in DCM (60 ml). EDCI (0.96 g, 4.97 mmol, 1.30 equiv) was added in portions at 0 degrees C. under nitrogen atmosphere. The mixture was stirred at 25 degrees C. for 10 min. [2-(3-methoxy-3-oxopropyl)-5,5-dimethyl-1,3-dioxan-2-yl]acetic acid (1 g, 3.84 mmol, 1.00 equiv) and DIEA (1.49 g, 11.5 mmol, 3 equiv) were added. The mixture was stirred at 25 degrees C. for 1 h. The mixture was purified by silica gel column chromatography, eluted with $CH_2Cl_2$/MeOH (10:1) to afford methyl 3-[5,5-dimethyl-2-(2-oxo-2-[[2-(3-[[(4R)-2,2,5,5-tetramethyl-1,3-dioxan-4-yl]formamido]propanamido)ethyl]sulfanyl]ethyl)-1,3-dioxan-2-yl]propanoate (1.5 g, 56%) as yellow oil. (ES, m/z): 561 $[M+H]^+$.

Example 170: Synthesis of Compound 932

Synthesis of 3-[5,5-dimethyl-2-(2-oxo-2-[[2-(3-[[(4R)-2,2,5,5-tetramethyl-1,3-dioxan-4-yl]formamido]propanamido)ethyl]sulfanyl]ethyl)-1,3-dioxan-2-yl]propanoic acid

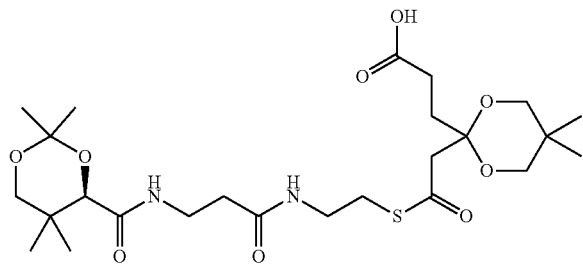 [SMILES: CC1(C)COC(CCC(=O)O)(CC(=O)SCCNC(=O)CCNC(=O)[C@@H]2OC(C)(C)OCC2(C)C)OC1]

To a stirred solution of $Na_2HPO_4$ (3.31 g, 23 mmol, 8.72 equiv) and $NaH_2PO_4$ (0.90 g, 8 mmol, 2.81 equiv) in water (60 mL) was added Triton X-100 (1.50 g), methyl 3-[5,5-dimethyl-2-(2-oxo-2-[[2-(3-[[(4R)-2,2,5,5-tetramethyl-1,3-dioxan-4-yl]formamido]propanamido)ethyl]sulfanyl]ethyl)-1,3-dioxan-2-yl]propanoate from Example 169 (1.50 g, 2.67 mmol, 1.00 equiv) in DMSO (2 mL) and enzyme-HLE 14 (800 mg). The resulting mixture was stirred for 2 days at 35 degrees C. The resulting mixture was concentrated under vacuum. The residue was purified by reverse flash chromatography with the following conditions: column, C18 silica gel; mobile phase, ACN in water, 10% to 50% gradient in 10 min; detector, UV 220 nm. The collected fraction was lyophilized to give 3-[5,5-dimethyl-2-(2-oxo-2-[[2-(3-[[(4R)-2,2,5,5-tetramethyl-1,3-dioxan-4-yl]formamido]propanamido)ethyl]sulfanyl]ethyl)-1,3-dioxan-2-yl]propanoic acid (Compound 932) (500 mg, 34%) as a white solid. (ES, m/z): 547 $[M+H]^+$.

Example 171: Synthesis of Compound 914

Synthesis of N-(2-[[3-hydroxy-2-(1-hydroxyethyl)butanoyl]sulfanyl]ethyl)-3-[[(4R)-2,2,5,5-tetramethyl-1,3-dioxan-4-yl]formamido]propanamide

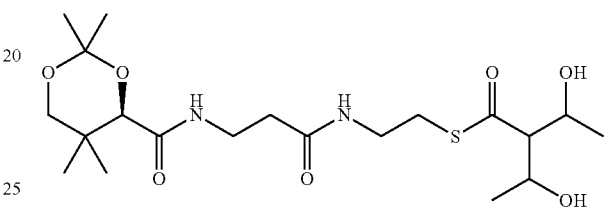

To a stirred solution of N-[2-[(2-acetyl-3-oxobutanoyl)sulfanyl]ethyl]-3-[[(4R)-2,2,5,5-tetramethyl-1,3-dioxan-4-yl]formamido]propanamide from Example 165 (400 mg, 0.90 mmol, 1.00 equiv) in THF (5 mL) were added potassium borohydride (200 mg, 3.71 mmol, 4.12 equiv) slowly at 0 degrees C. The resulting mixture was stirred for 2 h at 25 degrees C. The residue was purified by reverse flash chromatography with the following conditions: column, C18 silica gel; mobile phase, water (0.05% FA) and ACN (10% Phase B up to 50% in 20 min); detector, UV 254 nm. This resulted in the formation of the title Compound 914 (300 mg, 70.61%) as a colorless oil. MS: (ES, m/z): 449 $[M+H]^+$.

Example 172: Synthesis of Compound 917

Synthesis of tert-butyl 4-oxo-4-[[2-(3-[[(4R)-2,2,5,5-tetramethyl-1,3-dioxan-4-yl]formamido]propanamido)ethyl]sulfanyl]butanoate

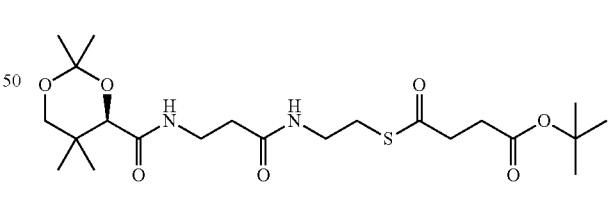

To a stirred solution of 4-(tert-butoxy)-4-oxobutanoic acid (3.94 g, 22.6 mmol, 1.20 equiv) in DCM (100 mL) was added EDC·HCl (4.70 g, 24.5 mmol, 1.3 equiv) at 0 degrees C. After stirring for 10 min at 25 degrees C., N-(2-sulfanylethyl)-3-[[(4R)-2,2,5,5-tetramethyl-1,3-dioxan-4-yl]formamido]propanamide from Example 170 Step 2 or from Preparative Example 3 Step 2 (6.00 g, 18.8 mmol, 1.00 equiv) and DIEA (7.31 g, 56.5 mmol, 3 equiv) were added at 0 degrees C. The resulting solution was stirred for 1 h at 25 degrees C. The resulting mixture was concentrated under reduced pressure. The residue was purified by silica gel column chromatography, eluted with $CH_2Cl_2$/MeOH (93:7)

to afford the title Compound 917 (7.5 g, 80%) as a colorless oil. MS: (ES, m/s): 475 [M+H]+

Example 177: Alternate Synthesis of Compound 852

Synthesis of methyl 4-oxo-4-[[2-(3-[[(4R)-2,2,5,5-tetramethyl-1,3-dioxan-4-yl]formamido]propanamido)ethyl]sulfanyl]butanoate

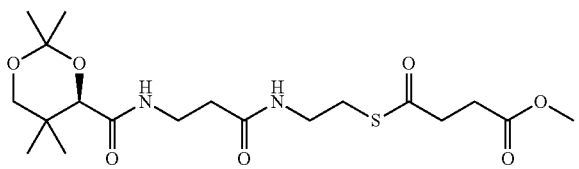 [SMILES: COC(=O)CCC(=O)SCCNC(=O)CCNC(=O)[C@@H]1OC(C)(C)OCC1(C)C]

To a stirred mixture of N-(2-sulfanylethyl)-3-[[(4R)-2,2,5,5-tetramethyl-1,3-dioxan-4-yl]formamido]propenamide from Preparative Example 3 Step 2 (1.00 g, 3.140 mmol, 1.00 equiv) and butanedioic acid monomethyl ester (0.50 g, 3.768 mmol, 1.20 equiv) in DCM were added EDCI (0.78 g, 4.083 mmol, 1.30 equiv) and DIEA (1.22 g, 9.421 mmol, 3.00 equiv) in portions at room temperature under nitrogen atmosphere. The reaction mixture was stirred for 1 h at room temperature. The resulting mixture was concentrated under vacuum. The residue was purified by silica gel column chromatography, eluted with PE/EtOAc (1:1) to afford the title Compound 852 (1.15 g, 72.81%) as a colorless oil. LCMS: (ES, m/z): 433.0 [M+H]+.

Example 195: Synthesis of Compound 924

Synthesis of methyl (4S)-4-[(tert-butoxycarbonyl)amino]-5-oxo-5-[[2-(3-[[(4R)-2,2,5,5-tetramethyl-1,3-dioxan-4-yl]formamido]propanamido)ethyl]sulfanyl]pentanoate

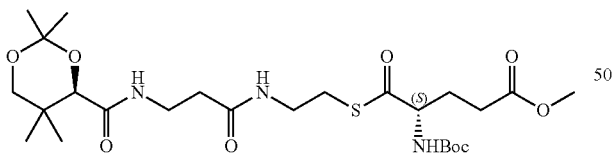

A solution of (2S)-2-[(tert-butoxycarbonyl)amino]-5-methoxy-5-oxopentanoic acid (410 mg, 1.57 mmol) and EDCI (361 mg, 1.88 mmol) in DCM (10.0 mL) was stirred for 10 min at 25 degrees C. N-(2-sulfanylethyl)-3-[[(4R)-2,2,5,5-tetramethyl-1,3-dioxan-4-yl]formamido]propenamide from Preparative Example 3 Step 2 (500 mg, 1.57 mmol) and DIEA (0.820 mL, 4.71 mmol) were added. The resulting mixture was stirred for 2 h at 25 degrees C. The resulting solution was concentrated under vacuum. The residue was purified by silica gel column chromatography (eluting with 1:10 MeOH/DCM) to afford the title Compound 924 as a colorless oil (680 mg, 73%). LCMS (ES, m/z): 562 [M+H]+.

Example 196: Synthesis of Compound 918

Step 1: Synthesis of methyl (4S)-4-[(tert-butozycarbonyl)amino]-5-oxo-5-[[2-(3-[[(4R)-2,2,5,5-tetramethyl-1,3-dioxan-4-yl]formamido]propanamido)ethyl]sulfanyl]pentanoate

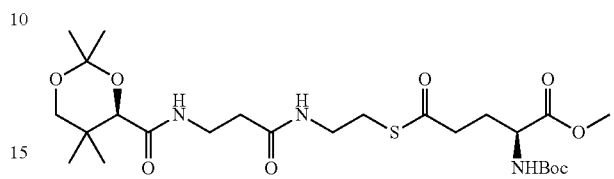

A solution of (4S)-4-[(tert-butoxycarbonyl)amino]-5-methoxy-5-oxopentanoic acid (820 mg, 3.14 mmol) and EDCI (722 mg, 3.76 mmol) in DCM (20.0 mL) was stirred for 10 min at 25 degrees C. N-(2-sulfanylethyl)-3-[[(4R)-2,2,5,5-tetramethyl-1,3-dioxan-4-yl]formamido]propenamide from Preparative Example 3 Step 2 (1.00 g, 3.14 mmol) and DIEA (1.64 mL, 9.41 mmol) was added. The resulting mixture was stirred for 2 h at 25 degrees C. The residue was purified by silica gel column chromatography (eluting with 1:10 MeOH/DCM) to afford methyl (4S)-4-[(tert-butoxycarbonyl)amino]-5-oxo-5-[[2-(3-[[(4R)-2,2,5,5-tetramethyl-1,3-dioxan-4-yl]formamido]propanamido)ethyl]sulfanyl]pentanoate as a colorless oil (Compound 918)(1.2 g, 64%). LCMS (ES, m/z): 562 [M+H]+.

Example 197: Synthesis of Compound 919

Synthesis of tert-butyl (2S)-2-[(tert-butoxycarbonyl)amino]-5-oxo-5-[[2-(3-[[(4R)-2,2,5,5-tetramethyl-1,3-dioxan-4-yl]formamido]propanamido)ethyl]sulfanyl]pentanoate

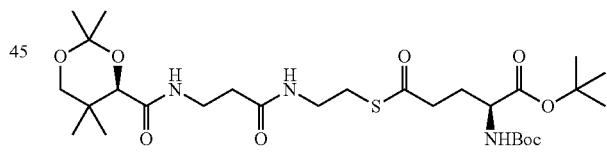

To a stirred solution of (4S)-5-(tert-butoxy)-4-[(tert-butoxycarbonyl)amino]-5-oxopentanoic acid (1.14 g, 3.76 mmol, 1.20 equiv) in DCM (20 mL) was added EDC·HCl (0.78 g, 4.07 mmol, 1.3 equiv) at 0 degrees C. After stirring for 10 min at 25 degrees C., N-(2-sulfanylethyl)-3-[[(4R)-2,2,5,5-tetramethyl-1,3-dioxan-4-yl]formamido]propanamide from Preparative Example 3 Step 2 (1.00 g, 3.14 mmol, 1.00 equiv) and DIEA (1.22 g, 9.45 mmol, 3 equiv) were added at 0 degrees C. The resulting solution was stirred for 1 h at 25 degrees C. The resulting mixture was concentrated under reduced pressure. The residue was purified by silica gel column chromatography, eluted with CH2Cl2/MeOH (96:4) to afford tert-butyl (2S)-2-[(tert-butoxycarbonyl)amino]-5-oxo-5-[[2-(3-[[(4R)-2,2,5,5-tetramethyl-1, 3-dioxan-4-yl]formamido]propanamido)ethyl]sulfanyl]pentanoate (1.42 g, 71%) as a white solid. MS: (ES, m/s): 604 [M+H]+

Example 200: Synthesis of Compound 929

Step 1: Synthesis of 4-[(tert-butyldimethylsilyl)oxy]butanoic Acid

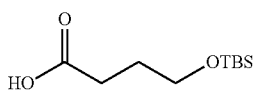

A mixture of sodium 4-hydroxybutanoate (700 mg, 5.55 mmol) and TBSCl (837 mg, 5.55 mmol) in DMA (5.00 mL) was stirred for 3 h at 25° C. The reaction was quenched with NaHCO$_3$ (sat. aq., 10 mL), and the resulting mixture extracted with EtOAc (1×15 mL). The aqueous phase was acidified to pH 4-5 with phosphoric acid and extracted with EtOAc (3×15 mL). The combined organic layers were dried over anhydrous Na$_2$SO$_4$. After filtration, the filtrate was concentrated under vacuum to afford 4-[(tert-butyldimethylsilyl) oxy]butanoic acid as a colorless oil (600 mg, crude). LCMS (ES, m/z): 217 [M−H]$^+$.

Step 2. Synthesis of N-[2-([4-[(tert-butyldimethylsilyl)oxy]butanoyl]sulfanyl)ethyl]-3-[[(4R)-2,2,5,5-tetramethyl-1,3-dioxan-4-yl]formamido]propenamide

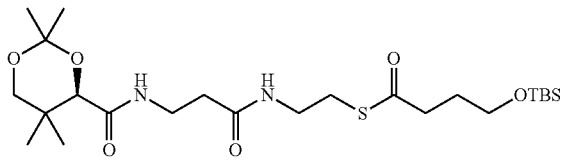 [SMILES: CC1(C)OCC(C)(C)[C@H](C(=O)NCCC(=O)NCCSC(=O)CCCO[Si](C)(C)C(C)(C)C)O1]

A solution of the crude product from Example 200 Step 1 (343 mg, 1.57 mmol) and EDC·HCl (331 mg, 1.73 mmol, 1.10 equiv) in DCM (5.00 mL) was stirred for 10 min at 25° C. Then the product from Preparative Example 3 Step 2 (500 mg, 1.57 mmol) and TEA (0.44 mL, 3.17 mmol) were added. The resulting mixture was stirred for 1 h at 25° C. The reaction was concentrated, and the residue purified by silica gel column chromatography (eluting with 95:5 CH$_2$Cl$_2$: MeOH v/v) to afford the title Compound 929 as a colorless oil (350 mg, 40%). LCMS (ES, m/z): 519[M+H]$^+$.

Example 201: Synthesis of Compound 930

Step 1: Synthesis of benzyl 4-bromobutanoate

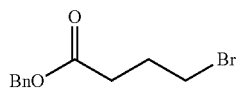 [SMILES: O=C(CCCBr)OCc1ccccc1]

A solution of 4-bromobutanoic acid (5.00 g, 29.9 mmol), PTSA (515 mg. 2.99 mmol) and benzyl alcohol (4.21 g, 38.9 mmol) in cyclohexane (50.0 mL) was stirred for 16 h at 85° C. under nitrogen atmosphere. The resulting solution was diluted with water (100 mL), and then extracted with EA (3×50 mL). The organic layers were combined, washed with brine (3×50 mL), dried over anhydrous sodium sulfate, filtered and concentrated under vacuum to give benzyl 4-bromobutanoate as colorless oil (6.80 g, 83%). GCMS: 256, 258

Step 2. Synthesis of benzyl 4-(acetyloxy)butanoate

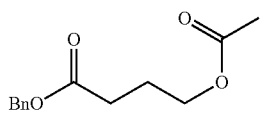 [SMILES: CC(=O)OCCCC(=O)OCc1ccccc1]

A solution of the crude product from Example 201 Step 1 (6.80 g, 26.4 mmol) and potassium acetate (5.19 g, 52.8 mmol) in ACN (100 mL) was refluxed for 18 h at 90° C. under a nitrogen atmosphere. The resulting solution was diluted with water (100 mL), then extracted with EA (3×50 mL). The organic layers were combined, washed with brine (3×50 mL), dried over anhydrous sodium sulfate, filtered and concentrated under vacuum. The residue was purified by silica gel column chromatography (eluting with 1:3 ethyl acetate/petroleum ether) to afford benzyl 4-(acetyloxy)butanoate as colorless oil (4.00 g, 60%). LCMS (ES, in/z): 237 [M+H]$^+$ Step 3. Synthesis of Aceburic Acid

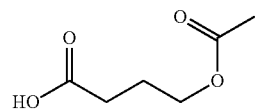

A mixture of the product from Example 201 Step 2 (2.00 g, 8.46 mmol) and Pd/C (200 mg, 10%) in MeOH (30.0 mL) was stirred for 2 h at 25° C. under an atmosphere of hydrogen (balloon). The solids were filtered out. The filtrate was concentrated under vacuum to give aceburic acid as a colorless oil (1.20 g, 92%). LCMS (ES, m/z): 147 [M+H]$^+$ Step 4. Synthesis of 4-oxo-4-[[2-(3-[[(4R)-2,2,5,5-tetramethyl-1,3-dioxan-4-yl]formamido]propanamido)ethyl]sulfanyl]butyl acetate

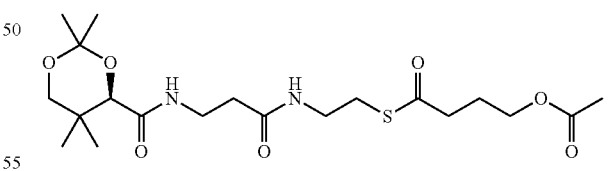

A solution of the product from Example 201 Step 3 (137 mg, 0.942 mmol) and EDCI (216 mg, 1.13 mmol) in DCM (5.00 mL) was stirred for 10 min at 25° C. The product from Preparative Example 3 Step 2 (300 mg, 0.942 mmol) and DIPEA (0.490 mL, 3.81 mmol) were added, and the resulting mixture stirred for 1 h at 25° C. The residue was purified by silica gel column chromatography (eluting with 1:10 MeOH/DCM) to afford 4-oxo-4-[[2-(3-[[(4R)-2,2,5,5-tetramethyl-1,3-dioxan-4-yl]formamido]propanamido)ethyl]sulfanyl]butyl acetate (Compound 930) as colorless oil (300 mg, 67%). LCMS (ES, m/z): 447 [M+H]$^+$

Example 211: Synthesis of Compound 931

Step 1: Synthesis of 3-(tert-butoxycarbonyl)pentanoic Acid

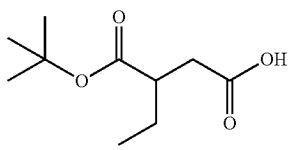

To a stirred solution of lithium diisopropylamide (63.14 mL, 2.2 equiv., 126.29 mmol) in THF (75 mL) at −78° C. was added solution of 4-(tert-butoxy)-4-oxobutanoic acid (10 g, 1.0 equiv., 57.40 mmol) in THF (75 mL). The reaction mixture was stirred at 0° C. for 2 h. Reaction mixture was recooled to −78° C. and Ethyl iodide (6.45 mL, 1.4 equiv., 80.36 mmol) was added dropwise. Reaction mixture was warmed to rt and stirred for 24 h. Reaction was quenched with 1 M HCl and extracted with Ethyl acetate organic layer dried over Na$_2$SO$_4$. Volatiles were removed under vacuum. Residue was purified by combi-flash on silica gel eluting with 0-10% ethyl acetate in hexane to afford 3-(tert-butoxycarbonyl)pentanoic acid (4.3 g, 21.26 mmol, 37.03%) as colourless liquid.

Step 2: Synthesis of 1-(tert-butyl) 4-methyl 2-ethylsuccinate

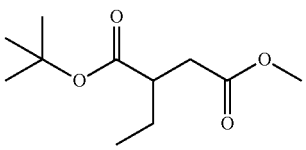

To a stirred solution of the product from Example 211 Step 1 (4.3 g, 1.0 equiv., 21.26 mmol) in DMF (43 mL) at rt was added KHSO4 (3.8 g, 1.8 equiv., 38.26 mmol). The reaction mixture was cooled to 0° C. and methyl iodide (3.6 g, 1.2 equiv., 25.51 mmol) was added dropwise. Reaction mixture was warmed to rt and stirred for 16 h. Volatiles were removed under vacuum, and residue was diluted with water and extracted with ethyl acetate. The organic layer was dried over Na$_2$SO$_4$, and the residue purified by combi-flash on silica gel eluting with 0-10% ethyl acetate in hexane to afford 1-(tert-butyl) 4-methyl 2-ethylsuccinate (4.0 g, 18.49 mmol, 86.9%) as colourless liquid.

Step 3: Synthesis of 2-ethyl-4-methoxy-4-oxobutanoic Acid

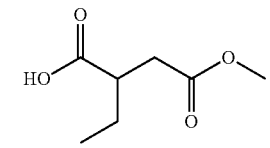

To a stirred solution of the product from Example 211 Step 2 (1.0 g, 1.0 equiv., 4.623 mmol) in DCM (5 mL) at rt, was added TFA (2.64 g, 5.0 equiv., 23.11 mmol) and the reaction stirred for 3 h. Volatiles were removed under vacuum, to afford 2-ethyl-4-methoxy-4-oxobutanoic acid (0.73 g, 4.56 mmol, 98.26%) as colourless liquid, which was taken forward as crude product without further purification.

Step 4: Synthesis of methyl 3-(((2-(3-((4R)-2-(4-methoxyphenyl)-5,5-dimethyl-1,3-dioxane-4-carboxamido)propanamido)ethyl)thio)carbonyl)pentanoate To a stirred solution of the product from Example 211 Step 3 (940 mg, 1.0 equiv., 5.868 mmol) and the product from Preparatory Example 1 Step 2 (1.86 g, 0.8 equiv., 4.695 mmol) in DCM (30 mL) was added DCC (1.21 g, 1.0 equiv., 5.868 mmol) and DMAP (0.143 g, 0.2 equiv., 1.173 mmol). The reaction mixture was stirred for 16 h, diluted with ethyl acetate, and the organic layer washed with water, followed by brine, and dried over Na$_2$SO$_4$. Volatiles were removed under vacuum, and the residue was purified by combi-flash on silica gel eluting with 0-10% EA in Hexane to afford 3 methyl 3-(((2-(3-((4R)-2-(4-methoxyphenyl)-5,5-dimethyl-1,3-dioxane-4-carboxamido)propanamido)ethyl)thio)carbonyl)pentanoate (Compound 931) (2.1 g, 3.898 mmol, 66.43%) as white semisolid.

Example 212: Synthesis of Compound 883

Synthesis of tert-Butyl (S)-4-[2-(3-{[(4R)-2-(p-methoxyphenyl)-5,5-dimethyl-1,3-dioxan-4-yl]carbonylamino}propionylamino) ethylthio)carbonyl]-4-(tert-butoxycarbonylamino)butyrate

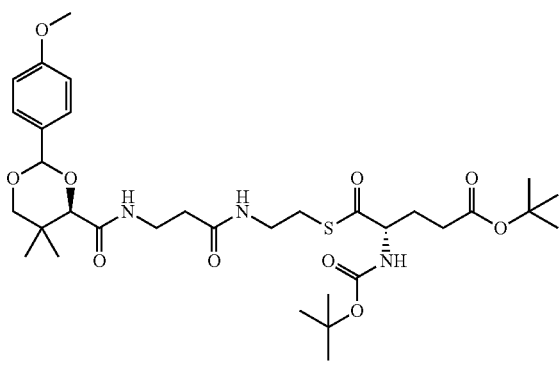

To a stirred solution of the product from Preparatory Example 1 Step 2 (1 g, 2.522 mmoL) in DCM (10 mL) was added EDC·HCl (966 mg, 5.044 mmoL), (S)-5-(tert-butoxy)-2-((tert-butoxycarbonyl)amino)-5-oxopentanoic acid (948 mg, 5.044 mmoL), and DIPEA (1.3 mL, 7.566 mmoL) at 0° C. The resulting reaction mixture was stirred at RT for 16 h. After completion of the reaction, as observed by TLC, the reaction mixture was diluted with water (10 mL) and extracted with DCM (2×10 mL). The total organic layer was then washed with saturated NaHCO$_3$, dried over Na$_2$SO$_4$, and concentrated under vacuum, before being purified over column using silica (100-200 mesh) eluting with 1-3% MeOH in DCM to afford the title Compound 883 as a white solid (700 mg, 41% yield, 94% purity).

$^1$H NMR (400 MHz, DMSO-D6) δ 8.08 (m, 1H), 7.57 (d, J=7.6 Hz, 1H), 7.45-7.40 (m, 3H), 6.91 (d, J=8.4 Hz, 2H), 5.51 (s, 1H), 4.07 (s, 2H), 3.75 (s, 3H), 3.65-3.58 (m, 2H), 3.26-3.22 (m, 1H), 3.12-3.10 (m, 2H), 2.83-2.82 (m, 2H), 2.24 (t, J=6.68 Hz, 2H), 1.95-1.91 (m, 1H), 1.69-1.63 (m, 1H), 1.39 (s, 18H), 0.99 (s, 3H), 0.94 (s, 3H).

Example 213: Synthesis of Compound 920

Synthesis of S-(2-(3-((4R)-2-(4-methoxybenzyl)-5,5-dimethyl-1,3-dioxane-4-carboxamido)propanamido)ethyl) (2S)-5-amino-2-((tert-butoxycarbonyl)amino)-5-oxopentanethioate

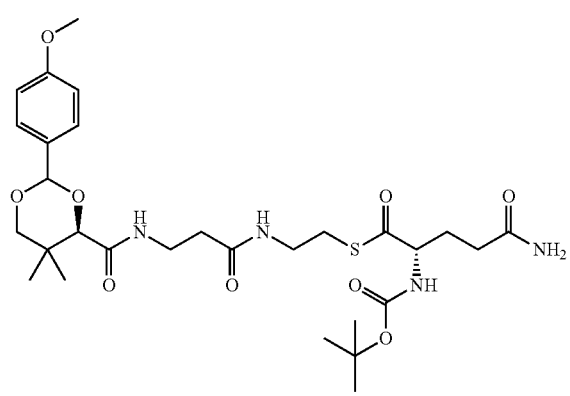

To a stirred solution of the product from Preparatory Example 1 Step 2 (11 g, 2.522 mmoL) in DCM (10 mL) was added EDC·HCl (967 mg, 5.047 mmoL), (tert-butoxycarbonyl)-L-glutamine (745 mg, 3.028 mmol), DIPEA (1.34 mL, 7.571 mmoL) at 0° C. The resulting reaction mixture was stirred at RT for 16 h. After completion of the reaction, as observed by TLC, the reaction mixture was diluted with water (20 mL) and extracted with DCM (2×20 mL). The total organic layer was then washed with saturated NaHCO$_3$, dried over Na$_2$SO$_4$ and concentrated under vacuum, before being purified over column using silica (100-200 mesh) eluting with 1-3% MeOH in DCM to afford the title Compound 920 as white solid (900 mg, 60% yield).

$^1$H NMR (400 MHz, DMSO-D6) δ 8.09 (m, 1H), 7.59 (d, J=7.2 Hz, 1H), 7.45-7.41 (m, 3H), 7.26 (s, 1H), 6.91 (d, J=8 Hz, 2H), 6.76 (s, 1H), 5.5 (s, 1H), 4.06 (s, 1H), 4.00 (m, 1H), 3.75 (s, 3H), 3.61 (dd, J=17.4 Hz, 11.6 Hz), 3.25-3.20 (m, 1H), 3.11-3.10 (m, 2H), 2.81 (m, 2H), 2.26-2.23 (m, 2H), 2.11 (t, J=7.2 Hz, 2H), 1.93-1.91 (m, 1H), 1.68-1.63 (m, 1H), 1.38 (s, 9H), 0.98 (s, 3H), 0.94 (s, 3H).

Example 214: Synthesis of Compound 921

Synthesis of S-(2-(3-((4R)-2-(4-methoxybenzyl)-5,5-dimethyl-1,3-dioxane-4-carboxamido)propanamido)ethyl) (2S)-2,5-bis((tert-butoxycarbonyl)amino)pentanethioate

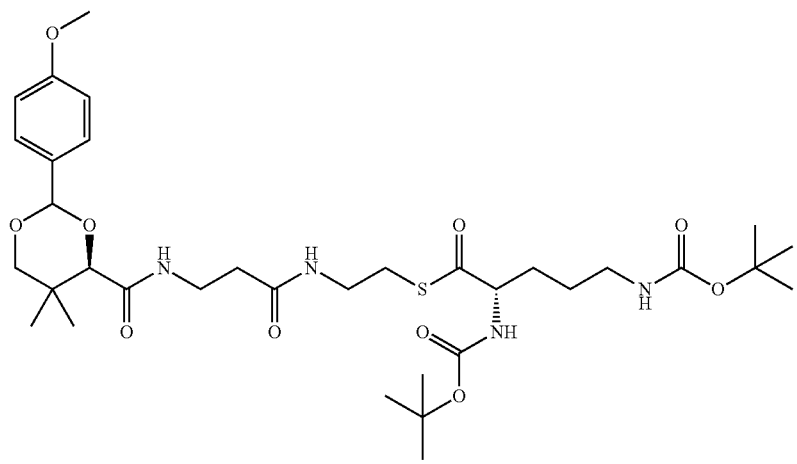

To a stirred solution of the product from Preparatory Example 1 Step 2 (900 mg, 2.26 mmoL) in DCM (10 mL) was added EDC·HCl (870 mg, 4.53 mmoL), (S)-2,5-bis((tert-butoxycarbonyl)amino)pentanoic acid (905 mg, 2.72 mmoL), DIPEA (1.2 ml, 6.80 mmoL) at 0° C. after which RM was stirred at RT for 16 h. After completion of the reaction, as observed by TLC, the reaction mixture was diluted with water (20 mL) and extracted with DCM (2×20 mL). Total organic layer was then washed with saturated NaHCO₃, dried over Na₂SO₄, and concentrated over rotary evaporator. Obtained crude was purified over column using silica (100-200 mesh) and eluted with 1-3% MeOH in DCM to afford S-(2-(3-((4R)-2-(4-methoxybenzyl)-5,5-dimethyl-1,3-dioxane-4-carboxamido)propanamido)ethyl) (2S)-2,5-bis((tert-butoxycarbonyl)amino)pentanethioate as white solid (700 mg, 43% yield).

Note: 1HNMR shows little grease and other aliphatic impurities and LCMS purity was ~87%.

$^1$H NMR (400 MHz, DMSO-D6) δ 8.09 (m, 1H), 7.55 (m, 1H), 7.42-7.40 (m, 3H), 6.91 (d, J=8.4 Hz, 2H), 6.76 (m, 1H), 5.74 (s, 3H), 5.51 (s, 1H), 3.75 (s, 3H), 3.60 (m, 2H), 3.09 (s, 3H), 2.87-2.80 (m, 6H), 2.31 (m, 2H), 1.38-1.35 (m, 18H), 0.98 (s, 3H), 0.93 (s, 3H).

Example 215: Synthesis of Compound 922

Synthesis of S-(2-(3-((4R)-2-(4-methoxybenzyl)-5,5-dimethyl-1,3-dioxane-4-carboxamido)propanamido)ethyl) (4S)-5-amino-4-((tert-butoxycarbonyl)amino)-5-oxopentanethioate

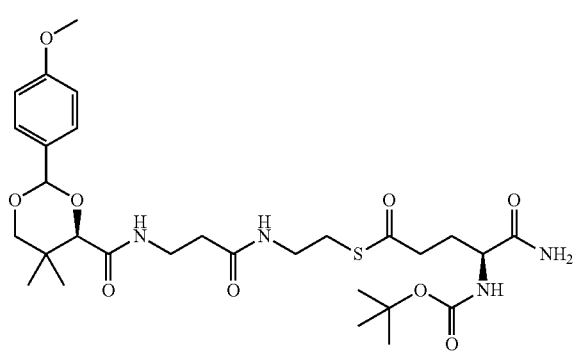

To a stirred solution of the product from Preparatory Example 1 Step 2 (500 mg, 1.26 mmoL) in DCM (10 mL) was added EDC·HCl (483 mg, 2.52 mmoL), (S)-5-amino-4-((tert-butoxycarbonyl)amino)-5-oxopentanoic acid (372 mg, 1.51 mmoL), DIPEA (0.6 mL, 3.78 mmoL) at 0° C. after which RM is stirred at RT for 16 h. After completion of the reaction, as observed by TLC, the reaction mixture was diluted with water (20 mL) and extracted with DCM (2×20 mL). Total organic layer was then washed with saturated NaHCO$_3$, dried over Na$_2$SO$_4$ and concentrated over rotary evaporator. Obtained crude was purified over column using silica (100-200 mesh) and eluted with 1-3% MeOH in DCM to afford S-(2-(3-((4R)-2-(4-methoxybenzyl)-5,5-dimethyl-1,3-dioxane-4-carboxamido)propanamido)ethyl) (4S)-5-amino-4-((tert-butoxycarbonyl)amino)-5-oxopentanethioate as white solid (210 mg, 26% yield).

$^1$H NMR (400 MHz, DMSO-D6) δ 8.10 (m, 1H), 7.44-7.40 (m, 3H), 7.25 (s, 1H), 7.01 (s, 1H), 6.91 (d, J=8 Hz, 2H), 6.83 (d, J=8 Hz, 1H), 5.50 (s, 1H), 4.06 (s, 1H), 3.76 (s, 3H), 3.85-3.84 (m, 1H), 3.75 (s, 1H), 3.61 (dd, J=16.4 Hz, 11.2 Hz, 2H), 3.21-3.22 (m, 1H), 3.15-3.13 (m, 2H), 2.85 (t, J=6.4 Hz, 2H), 2.58 (m, 2H), 2.252 (t, J=6.4 Hz, 2H), 1.89 (m, 1H), 1.77-1.74 (1H), 1.36 (s, 9H), 0.98 (s, 3H), 0.94 (s, 3H).

Example 216: Synthesis of Compound 923

Synthesis of tert-butyl (2S)-2-((tert-butoxycarbonyl)amino)-4-((2-(3-((4R)-2-(4-methoxybenzyl)-5,5-dimethyl-1,3-dioxane-4-carboxamido)propanamido)ethyl)thio)-4-oxobutanoate

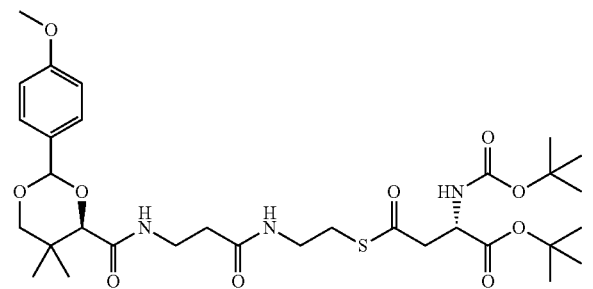

To a stirred solution of the product from Preparatory Example 1 Step 2 (1 g, 2.52 mmoL) in DCM (10 mL) was added EDC·HCl (966 mg, 5.04 mmoL), ((S)-4-(tert-butoxy)-3-((tert-butoxycarbonyl)amino)-4-oxobutanoic acid (875 mg, 3.02 mmoL), DIPEA (1.3 mL, 7.56 mmoL) at 0° C. Resulting RM was stirred at RT for 24 h. Progress of the reaction was monitored by TLC. After completion of the reaction RM was diluted with water (20 mL) and extracted with DCM (2×20 mL). Total organic layer was then washed with saturated NaHCO$_3$, dried over Na$_2$SO$_4$ and concentrated over rotary evaporator. Obtained crude was purified over column using silica (100-200 mesh) and eluted with 1-3% MeOH in DCM to afford tert-butyl (3S)-3-((tert-butoxycarbonyl)amino)-4-((2-(3-((4R)-2-(4-methoxybenzyl)-5,5-dimethyl-1,3-dioxane-4-carboxamido)propanamido)ethyl)thio)-4-oxobutanoate as white solid (800 mg, 50% yield).

$^1$H NMR (400 MHz, DMSO-D6) δ 8.09 (m, 1H), 7.42-7.40 (m, 3H), 7.20 (d, J=8.4 Hz, 1H), 7.26 (s, 1H), 6.91 (d, J=8 Hz, 2H), 4.26-4.21 (m, 1H), 4.06 (s, 1H), 3.75 (s, 3H), 3.61 (dd, J=17.6 Hz, 11.2 Hz, 2H), 3.25-3.22 (m, 1H), 3.15-3.13 (m, 2H), 3.96-2.81 (5H), 2.25 (t, J=6.8 Hz, 2H), 1.35 (s, 18H), 0.98 (s, 3H), 0.93 (s, 3H).

Example 217: Synthesis of Compound 871

Synthesis of (4R,4'R)—N,N'-(((disulfanediylbis(ethane-2,1-diyl))bis(azanediyl))bis(3-oxopropane-3,1-diyl))bis(2-(4-methoxyphenyl)-5, 5-dimethyl-1,3-dioxane-4-carboxamide)

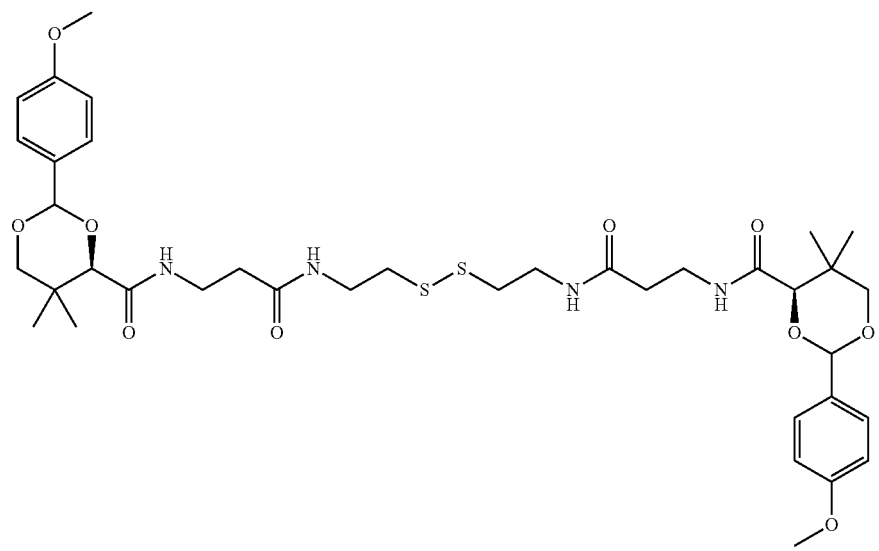

The title Compound 871 was synthesized according to the procedure in Preparative Example 6 as a white solid (12.5 g, 73% yield).

Note: This is a symmetrical molecule, 1 HNMR is half integrated. $^1$H NMR (400 MHz, DMSO-d6) δ 8.09 (m, 1H), 7.45-7.41 (m, 3H), 6.91 (d, J=8.4 Hz, 211), 5.50 (s, 1H) 4.06 (s, 1H), 3.74 (s, 3H), 3.61-3.60 (m, 2H), 3.32-3.24 (m, 3H), 2.72-2.70 (t, J=6.8 Hz, 3H), 2.26 (t, J=6.8 Hz, 2H), 0.98 (s, 3H), 0.93 (s, 3H).

Example 218: Synthesis of Compound 872

Synthesis of (4R)—N-(3-((2-mercaptoethyl)amino)-3-oxopropyl)-2-(4-methoxyphenyl)-5,5-dimethyl-1,3-dioxane-4-carboxamide

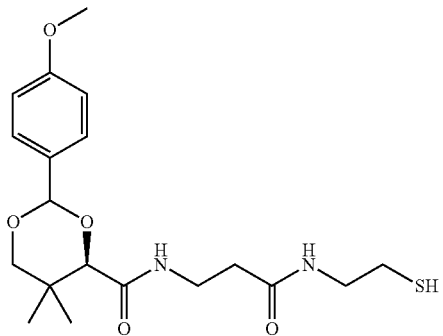

The title Compound 872 was synthesized according to the procedure in Preparative Example 1 as a white solid (9.5 g, 77%). LCMS (M+1)=397.2 amu. $^1$H NMR (400 MHz, DMSO-D6) δ 8.05 (m, 1H), 7.43-7.41 (m, 3H), 6.92 (d, J=8.4 Hz, 2H), 5.51 (s, 1H), 4.07 (s, 1H), 3.75 (s, 3H), 3.65-3.58 (m. 2H), 3.32 (m, 1H), 3.23 (m, 1H), 3.16-3.15 (m. 2H), 2.27 (t, J=6.4 Hz. 2H), 0.99 (s, 3H). 0.94 (s, 3H).

Example 219: Synthesis of Compound 873

Synthesis of (R)—N-(3-((2-mercaptoethyl) amino)-3-oxopropyl)-2,2,5,5-tetramethyl-1,3-dioxane-4-carboxamide

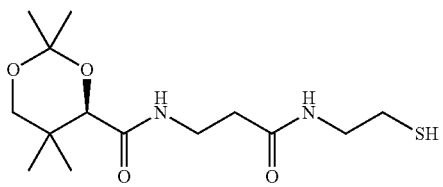 [SMILES: CC1(C)OCC(C)(C)[C@H](C(=O)NCCC(=O)NCCS)O1]

The title Compound 873 was synthesized according to the procedure in Preparative Example 3 as colorless oil. (1200 mg, 73.25%) MS:(ES, m/s): 319.2 [M+H]$^+$. $^1$H NMR (400 MHz, CDCl$_3$): δ 0.96 (s. 3H), 1.02 (s, 3H), 1.41-1.45 (m, 6H), 2.48 (t, J=6.0 Hz, 2H), 2.60-2.70 (m, 2H), 3.27 (d, J=11.6 Hz, 1H), 3.35-3.50 (m, 2H). 3.53-3.60 (m, 2H). 3.67 (d, J=11.6 Hz, 1H), 4.07 (s, 1H), 6.38-6.45 (m, 1H), 7.05-7.13 (m, 1H).

Example 800: Effect of Compounds on Mitochondrial Respiration

The effect of the compounds of the present disclosure on mitochondrial respiration was measured with a XFe96 Extracellular Flux Analyzer (Seahorse Bioscience, Agilent Technologies) and Oxygen consumption Rate (OCR) and Extracellular acidification rate (ECAR) determined.

Cell culture and treatments. Primary adherent fibroblasts were cultured in minimum essential medium (MEM) (Gibco, 25030081) supplemented with 2 mM L-Glutamine (Gibco, 25030081), 15% fetal bovine serum (FBS) (Gibco, 26400044) and 1°/o penicillin/streptomycin (Gibco, 5140122) at 37° C. and 5% CO2. Cells were collected for either passaging or experiment at ~70-80% confluence. Cells were obtained by trypsinization and seeded at 20000 cells/well in cell culture microplates (Seahorse Bioscience, 101085-004) and allowed to adhere for 16 hours in culture media.

By profiling different primary cells and/or optimizing their culture media or environmental components one can select cell lines and/or conditions that are appropriate for the biological or disease model. In the present example, 24 hours prior to OCR and ECAR profiling, media was changed to Dulbecco's Modified Eagle Medium (DMEM, Agilent Seahorse 103575-100) with the appropriate supplements for the different primary cells (10 mM glucose, 2 mM L-glutamine, 1 mM pyruvate, 10% FBS; 1 mM glucose, 2 mM L-glutamine, 1 mM pyruvate, 10% FBS; 10 mM glucose, 10% FBS; 5 mM glucose 10% FBS; 1 mM glucose 10% FBS). Cells used in this example were: Propionic Acidemia (PA) (GM00371, GM03590 Coriell Institute for Medical Research, Tsi 6337, Tsi 4626, Tsi 3618 Trans-Hit Bio), Methylmalonic Acidemia (MMA) (GM01673, Coriell Institute for Medical Research, Tsi 5224 Trans-Hit Bio), Branched chain ketoacid dehydrogenase kinase (BCKDK) (GM00612, GM00649 Coriell Institute for Medical Research), Subnormal activation of pyruvate dehydrogenase complex (PDH) (GM01503 Coriell Institute for Medical Research), Very long-chain acyl-CoA dehydrogenase (VL-CAD) (GM17475), Leigh Syndrome (LS) (GM03672, GM13411 Coriell Institute for Medical Research), Pyruvate Carboxylase Deficiency (PC) (GM00444 Coriell Institute for Medical Research), Glutaric Acidemia-I (GA) (GM10653), Friedreich's Ataxia (FXN) (GM04078 Coriell Institute for Medical Research, Huntington's disease (HD) (GM21756 Coriell Institute for Medical Research), Ornithine Transcarbamylase Deficiency (OTC) (GM12756 Coriell Institute for Medical Research), Kearns-Sayre Syndrome (KSS) (GM06225 Coriell Institute for Medical Research).

One hour before the assay, the cells were washed with freshly prepared unbuffered serum free-Seahorse XF Assay medium (Seahorse Bioscience, North America, USA, 103575-100) with the same supplements as for the previous 24 hour incubation.

After baseline measurements of OCR, cells were challenged with compounds of the present disclosure at different concentrations (10 to 50 μM) or vehicle (DMSO, 0.1%) and a post-compound baseline was recorded. OCR was measured after sequentially adding to each well 1 μg/ml oligomycin (inhibitor of ATP synthase Sigma-Aldrich, 753531), then maximal OCR was determined with carbonyl cyanide 4-(trifluoromethoxy) phenylhydrazone (FCCP, Sigma-Aldrich, C2920), (uncoupler of oxidative phosphorylation) and 0.5 μM of rotenone (Sigma-Aldrich, R8875) plus antimycin A (Sigma-Aldrich, A8674) (inhibitors of mitochondrial complex I and III) for determination of rotenone-antimycin insensitive respiration together with Hoechst for nuclear staining in situ when normalized to cell counts. After the analysis and nuclear staining, the XFp microplate was transferred to the Cytation 5, and the nuclear images were captured, the individual nuclei were identified and counted by BioTek Gen5 software. Data were expressed as pmol of 02 per minute and normalized by nuclear staining and baselined to pre-compound addition.

Assay conditions were as stated below.

| Condition | Cycles | Time |
| --- | --- | --- |
| Baseline | 4 cycles | 24 min |
| Compound Injection | 3 cycles | 18 min |
| Oligomycin Injection | 3 cycles | 18 min |
| FCCP injection | 20/40 cycles | 120 min |
| Antimycin A/Rotenone/Hoechst | 3 cycles | 18 min |

Assay specifics on assay conditions are indicated below when readouts were normalized to cell counts.

| Conditions used | Supplements in DMEM | Disease Cell | Cell Line | FCCP (μM) | Post-FCCP cycles |
| --- | --- | --- | --- | --- | --- |
| A | 10 mM glucose, 2 mM L-glutamine, 1 mM pyruvate, 10% FBS | PA | GM00371 | 2 | 40 |
|  |  |  | Tsi 6337 | 8 | 20 |
|  |  | MMA | GM01673 | 2 | 40 |
|  |  |  | Tsi 5224 | 4 | 20 |
| B | 1 mM glucose, 2 mM L-glutamine, 1 mM pyruvate, 10% FBS | PA | GM00371 | 2 | 40 |
|  |  |  | Tsi 6337 | 8 | 20 |
|  |  | MMA | GM01673 | 2 | 40 |
|  |  |  | Tsi 5224 | 8 | 20 |
| C | 10 mM glucose, 10% FBS | PA | GM00371 | 2 | 40 |
| D | 1 mM glucose, 10% FBS | PA | GM00371 | 2 | 40 |
|  |  |  | Tsi 6337 | 4 | 20 |
|  |  | MMA | GM01673 | 2 | 40 |
|  |  |  | Tsi 5224 | 4 | 20 |

Assay specifics on assay conditions are indicated below when readouts were not normalized to cell counts.

| Conditions used | Supplements in DMEM | Disease Cell | Cell Line | FCCP (μM) | Post-FCCP cycles |
| --- | --- | --- | --- | --- | --- |
| E | 1 mM glucose, 2 mM L-glutamine, 1 mM pyruvate | PA | GM00371 | 0.75 | 20 |
|  |  |  | GM03590 | 0.75 | 20 |
|  |  |  | Tsi 6337 (E1) | 0.75 | 20 |
|  |  |  | Tsi 6337 (E2) | 8.0 | 20 |
|  |  | VLCAD | GM17475 | 0.75 | 20 |
|  |  | LS | GM13411 | 0.75 | 20 |
| F | 5 mM glucose | PA | Tsi 4626 | 2 | 10 |
| F | 5 mM glucose | BCKAD | GM00612 | 2 | 10 |
|  |  | VLCAD | GM00649 | 3 | 10 |
|  |  | GA-1 | GM10653 | 2 | 10 |
|  |  | FXN | GM04078 | 2 | 10 |
|  |  | Huntington disease | GM21756 | 2 | 10 |
|  |  | KSS | GM06225 | 2 | 10 |
|  |  | Niemann-Pick disease | GM22870 | 2 | 10 |
|  |  | OTC | GM12604 | 2 | 10 |
| G | 1 mM glucose | PA | GM03590 | 1.0 | 10 |
| G | 1 mM glucose | PDH | GM01503 | 3.0 | 10 |
| G | 1 mM glucose | Leigh | GM003672 | 1.0 | 10 |
| G | 1 mM glucose | Leigh | GM13411 | 2.0 | 10 |
| G | 1 mM glucose | GA-1 | GM10653 | 2.0 | 10 |
| G | 1 mM glucose | GA-1 | GM10653 | 2.0 | 10 |

Determining the optimized cell density and stress test such as FCCP were achieved through methods well known to those of skill in the art.

Extracellular acidification rate (ECAR) was also measured on the Seahorse XFe96 analyser simultaneously with the OCR measurements in the same wells.

OCR and ECAR values were expressed relative to vehicle.

Several parameters were evaluated as follows:

Mitochondrial Basal OCR (corresponds to baseline OCR minus rotenone/antimycin-insensitive OCR).

ATP-linked OCR (corresponds to basal OCR minus oligomycin-insensitive OCR).

Proton leak-linked OCR (corresponds to oligomycin-insensitive OCR minus rotenone/antimycin-insensitive OCR).

Maximal OCR (corresponds to FCCP-induced OCR minus rotenone/antimycin-insensitive OCR).

Spare respiratory capacity measured as the difference between Maximal and Basal OCR Non-mitochondrial OCR (corresponds to rotenone/antimycin-insensitive OCR).

Maximal OCR Area Under the Curve (AUC) (corresponds to AUC from the first measurement after FCCP injection to the last FCCP measurement minus non-mitochondrial respiration).

Spare Capacity AUC (corresponds to AUC of the first measurement after FCCP injection to the last FCCP).

AUC ECAR (between post-oligomycin injection and pre-FCCP injection).

Example 801: Effect of Compounds on Cell Proliferation

The effect of the compounds of the present disclosure on cancer cell proliferation was determined with CyQUANT direct assay according to manufacturer's instructions (Invitrogen, C7026). Briefly, 100 μL of cell suspension was seeded into black clear bottom tissue culture treated plates (Corning, 165305) in complete medium and incubated overnight in a $CO_2$ incubator as listed in the following table:

| Cell Line | Description | Complete medium | Seeding Density (cells/well) |
|---|---|---|---|
| PANC-1 (ATCC, CRL-1469) | pancreas, ductal carcinoma | DMEM (Gibco, 11960-051), 10% FBS (Thermo fisher Scientific, 16000044) | 2500 |
| MCF-7 (ATCC, CRL-3435) | breast, adenocarcinoma (pleural effusion) | Eagle's Minimum Essential Medium (Gibco, 11095080), 0.01 mg/ml bovine insulin (Sigma, 11882), 10% FBS | 3000 |
| HuH-7 (Sigma, 01042712) | hepatoma, differentiated | DMEM (Low glucose, 5 mM, Gibco, 10567014), 2 mM L-glutamine, 10% FBS | 5000 |
| LoVo (ATCC, CCL-229) | colon, adenocarcinoma | F-12K (Gibco, 21127022), 10% FBS | 2000 |
| A549 (ATCC, CCL-185) | lung, carcinoma | F-12K, 10% FBS | 2500 |
| NCI-H460 (ATCC, HTB-177) | lung, large cell lung cancer | RPMI1640 (Gibco, 11875093), 10% FBS | 1250 |
| Caco-2 (ATCC, HTB-37) | colon, adenocarcinoma | Eagle's Minimum Essential Medium, 20% FBS | 1000 |
| MCF 10A (ATCC, CRL-10317) | breast, human fibrocystic disease | Mammary Epithelial Cell Growth Basal Medium (MEBM, ATCC, PCS-600-030) | 5000 |
| HT-29 (ATCC, HTB-38) | colon, adenocarcinoma | McCoy's 5A (Gibco, 16600082), 10% FBS | 2500 |
| A-673 (ATCC, CRL-1598) | muscle, rhabdomyosarcoma | DMEM, 10% FBS | 3000 |
| Hep3B (ATCC, HB-8064) | liver, hepatocellular carcinoma | DMEM, 10% FBS | 2500 |
| ES-2 (ATCC, CRL-1978) | ovary, clear cell carcinoma | McCoy's 5a, 10% FBS | 5000 |
| BxPC-3 (ATCC, CRL-1687) | pancreas, adenocarcinoma | RPMI1640, 10% FBS | 3000 |
| Calu-3 (ATCC, HTB-55) | lung, adenocarcinoma | EMEM, 10% FBS | 5000 |
| LNCaP clone FGC (ATCC, CRL-1740) | prostate, carcinoma | RPMI1640, 10% FBS | 4000 |
| HCC70 (ATCC, CRL-2315) | breast, primary ductal carcinoma | RPMI1640, 10% FBS | 1000 |
| Capan-1 (ATCC, HTB_79) | pancreas, adenocarcinoma | IMDM (Gibco, 12440061), 20% FBS | 2000 |
| SW480 (ATCC, CCL-228) | colon, adenocarcinoma | Leibovitz's L-15 (Gibco, 11415064), 10% FBS | 2000 |
| HCT 116 (ATCC, CCL-247) | colon, carcinoma | McCoy' 5A, 10% FBS | 600 |

Compounds of the present disclosure (50-5 µM), Staurosporine (2 µM) as positive control and vehicle DMSO control (0.2%) were added to the wells containing cells in complete medium. Compounds and media were refreshed every 24 hours for a total of 120 hours. Fluorescent signal (480 nm) was detected with a laser-based Acumen eX3 instrument Example 802: Effect of Compounds on Oligodendrocytes Proliferation The effect of compounds of the present disclosure was determined on oligodendrocyte precursor cells proliferation (OPC).

Cell culture. Brains of wild type mice (whole brain from 1 or 2 mouse pups) less than postnatal day (P) 2 were isolated and cultured. Briefly, following removal of the meninges, cells were dissociated with 0.25% EDTA/CMF-DMEM and 1% Trypsin (1:1), plated at a density of 75,000 cells/on 0.1 mg/ml poly-L-lysine coated borosilicate glass coverslips in 24-well plates, grown in OPC differentiation media (Oligo media) consisting of DMEM/F12 (Invitrogen 21331-020) supplemented with 1% FBS, 1% N2 Neural Supplement (Invitrogen 17502-048) and PDGF receptor alpha growth factor (Invitrogen 17502-048). Cells were fed every other day and allowed to grow for 7 days in vitro (DIV).

OPCs treatment with compounds of the present disclosure. Cells were treated with compounds of the present disclosure (50-10 µM) or vehicle (0.1% DMSO) starting at 7 DIV. Media was replaced daily with freshly made working solutions of compounds or vehicle for either 48 h (9 DIV total) or 96 h (11 DIV). The 48 h group consisted of 1 coverslip per condition. The 96 h group was treated in duplicate.

Fresh aliquots of compounds of the present disclosure were made up on the day of treatment, briefly, a 50 mM stock was thawed and used to make up fresh 50 µM working solution in Oligo Media. The fresh 50 µM working solution was diluted further in Oligo Media to make 10 µM working solution. Vehicle controls was made up in fresh Oligo Media using the appropriate amount of vehicle (DMSO). Coverslips were stored in clean 24-well plates at 4° C. until fixed-staining. Cells were imaged using Leica DM5500 fluorescent microscope with LAS-X software. Exposure settings were maintained at the same rate across compounds of the same time-point. Cells were imaged at 20× and 40× magnifications. At least 5 images were taken per condition. Most conditions had at least 5 images that were counted. 20× images were utilized for counting DAPI (cell nuclei) and O4+ cells.

Total DAPI per image for all images was counted using ImageJ as here indicated:
- Image was converted to 8 bit
- Blue Channel (DAPI) was automatically thresholded by default ImageJ settings
- Image noise was reduced by ImageJ>Process>Noise>Despeckle
- ImageJ>Process>Binary>Watershed was used to automatically separate merged cell nuclei
- ImageJ>Analyze>Analyze Particles was used to obtain final count of DAPI per image Total number of DAPI-positive cells Total number of O4+ cells per 20× image was manually counted using Adobe Photoshop:
- All cell bodies of OPCs with underlying DAPI stain were counted as an O4+ cell
- Total number of O4+ cells were recorded in Excel Spreadsheet O4+ cells in mixed brain cultures of wild type mice <P2 treated with compounds of the present disclosure or vehicle were quantified per condition (time point and concentration).

The following formula was used to normalize the total cell counts within a compound as well as across compounds treated for the same duration (48 h vs. 96 h):

(number of O4+ cell counts in Compound X/Average DAPI count for Compound X)*Total Average DAPI count across compounds of same Time Point Values were plotted as Scatter Interval plots in Origin. Each data point represents a single image from which O4+ cell values were obtained. Data are presented as mean±S.E.

Images are at 20× magnification and represent 1-2 coverslips per group. Scale bar, 50 μm.

Example 803: Effect of Compounds on Neuroprotective Effect on Damage Induced by 6-OHDA on Culture of Mesencephalic Neurons The protective effect of compounds of the present disclosure was determined on 6-OHDA-mediated injury on mesencephalon neuronal cultures.

A female Wistar rat (Janvier; France) of 15 days gestation was terminated by cervical dislocation, the fetuses were removed from the uterus and their brains were harvested and placed in ice-cold medium (Leibovitz's L15 medium, Gibco). Only ventral mesencephalic flexure was used for the cell preparations. The midbrain was dissociated by trypsinization. The reaction was stopped, and the suspension was triturated and centrifuged. The pellet of dissociated cells was resuspended in chemically defined medium consisted of Neurobasal (Gibco, 21103049), containing B27 supplement (Gibco, A3582801) and L-glutamine (Gibco, 25030081), 10 ng/ml (BDNF; Pepro Tech, France, 450-02) and 1 ng/ml (GDNF; Pepro Tech, 450-51).

Viable primary rat embryo mesencephalic cells were counted and seeded on 96-multi-wells plate precoated with poly-L-lysine. Cells were maintained in a humidified incubator at 37° C. in 5% CO2-95% air atmosphere and medium changed on day 2. On day 6, the culture medium was removed and replaced by new media without neurotrophic factors containing the compounds of the present disclosure (50-10 μM) or vehicle (0.1% DMSO). After 1 exposure, injury of mesencephalon neuronal cultures was induced by 6-OHDA (15 μM) for further 48 h. A mixture of the growth factors GDNF (1 ng/ml) and BDNF (10 ng/ml) were used as reference compound.

On day 8, the tyrosine hydroxylase positive neurons were evaluated. Cultures were fixed 30 min at 4° C. with paraformaldehyde in PBS (4%, Sigma). After, cells were permeabilized with 0.1% Triton X100 for 30 min, saturated with PBS containing 3% of BSA (bovine serum albumin) and incubated 2 h with anti-tyrosine hydroxylase antibody (Sigma, 1:10000; clone TH-2) at 1/10000 in PBS containing 0.5% of BSA. Cells were washed three times with PBS containing 0.5% of BSA and incubated 1 h with goat anti mouse antibody coupled with AF488 (lnvitrogen A11001) diluted at 1/1000 in PBS containing 0.5% of BSA. Finally, nuclei were stained with DAN (Thermo fisher, D1306) at 1/1000 in PBS containing 0.5% of BSA. After rinsing with PBS, the plate was visualized and examined with Cell Insight HCS (Thermo Scientific) to determine the number of tyrosine hydroxylase positive cells per well.

The results for each well were expressed as a percentage by setting the density of tyrosine hydroxylase positive cells under control conditions to 100%. Then the result for each condition was reported as mean±SEM from 4 independent cultures.

A global analysis of the data was performed using a one-way analysis of variance (ANOVA), followed by Fisher's Protected Least Significant Difference when applicable. The level of significance was set to $p<0.05$.

Example 804: Measurement of Neuroprotective Effect of Compounds on Damage Induced by MPP+ on Culture of Mesencephalic Neurons A female Wistar rat (Janvier; France) of 15 days gestation was terminated by cervical dislocation, the fetuses were removed from the uterus and their brains were harvested and placed in ice-cold medium (Leibovitz's L15 medium, Gibco). Only ventral mesencephalic flexure was used for the cell preparations. The midbrain was dissociated by trypsinization. The reaction was stopped, and the suspension was triturated and centrifuged. The pellet of dissociated cells was resuspended in chemically defined medium consisted of Neurobasal (Gibco), containing B27 supplement (Gibco) and L-glutamine (Gibco), 10 ng/ml (BDNF; Pepro Tech, France) and 1 ng/ml (GDNF; Pepro Tech).

Viable primary rat embryo mesencephalic cells were counted and seeded on 96-multi-wells plate precoated with poly-L-lysine. Cells were maintained in a humidified incubator at 37° C. in 5% $CO_2$-95% air atmosphere and medium changed on day 2. On day 6, the culture medium was removed and replaced by new media without neurotrophic factors containing the compounds of the present disclosure (50-10 μM) or vehicle (0.1% DMSO). After 1 exposure, injury of mesencephalon neuronal cultures was induced by MPP+(50 μM) for further 48 h. A mixture of the growth factors GDNF (1 ng/ml) and BDNF (10 ng/ml) were used as reference compound.

On day 8, the tyrosine hydroxylase positive neurons were evaluated. Cultures were fixed 30 min at 4° C. with paraformaldehyde in PBS (4%, Thermo Scientific, 28908). After, cells were permeabilized with 0.1% Triton X100 for 30 min, saturated with PBS containing 3% of BSA (bovine serum albumin) and incubated 2 h with anti-tyrosine hydroxylase antibody (Sigma, 1:10000; clone TH-2) at 1/10000 in PBS containing 0.5% of BSA. Cells were washed three times with PBS containing 0.5% of BSA and incubated 1 h with goat anti mouse antibody coupled with AF488 (Invitrogen A11001) diluted at 1/1000 in PBS containing 0.5% of BSA. Finally, nuclei were stained with DAPI at 1/1000 in PBS containing 0.5% of BSA. After rinsing with PBS, the plate was visualized and examined with Cell Insight HCS (Thermo Scientific) to determine the number of tyrosine hydroxylase positive cells per well.

The results for each well were expressed as a percentage by setting the density of tyrosine hydroxylase positive cells under control conditions to 100%. Then the result for each condition was reported as mean±SEM from 4 independent cultures.

A global analysis of the data was performed using a one-way analysis of variance (ANOVA), followed by Fisher's Protected Least Significant Difference when applicable. The level of significance was set to $p<0.05$.

Example 805: NK Cell Activation and K562 (Erythroleukemia) Killing Assay

Primary NK cells were isolated from PBMC by negative isolation with EasySep human NK cell isolation kit (Stem Cell, 17955). NK cells were 99% viable with 96% purity as evaluated by FACS (BD Fortessa) to be CD3-CD56+(Biolegend 300317, 318344). Isolated NK cells were placed at 80,000 cells/well with 20 ng/ml IL-2 (R&D, 202-IL-050) in the presence of CD107a antibody (clone H4A3, 565113) in RPMI (Invitrogen, 22400089) complete media with 10% FBS (Hyclone SV30087.03), 1% P/S in the presence of compounds at the dose of 10 and 50 µM for 24 h. K562 cells were collected and stained with cell trace proliferation kit (Invitrogen, C34557) and co-cultured with K562 cells (20,000 cells/well) along with addition of compounds at 10 and 50 µM and monitored cell lysis at 2, 4 and 6 h post incubation. Cells were collected and stained cells in the presence of Fc Block (Biolegend, 422302) with CD69, a NK cell activation marker, (Biolegend, 318344), PI, a viability marker (Biolegend, 310910) and analyzed by flow cytometry (BD Fortessa). Cells were first gated side versus forward scatter (SSC-A Vs FSC-A). K562 cells were further gated as SSC-A vs cell trace violet and further analyzed for dead cells by their uptake of PI (PI Vs cell trace violet dye). Cell trace negative cells were gated as NK cells which were further gated for CD56+Vs CD69+ to determine activated NK cells.

Example 806: Tolerogenic DC Differentiation Assay

Monocytes will be isolated by positive isolation with CD14+ microbeads (Miltenyi, 130-050-201). Monocytes would be 99% viable and would be 96% purity as analyzed by FACS and CD14+(BD, 563561). 200,000 monocytes would be placed along with compounds at the dose of 10 and 50 µM and allowed to differentiate to dendritic cells with 50 ng/ml GMCSF (R&D, 15-GM-050/CF) in combination with 25 ng/ml IL-4 (R&D 204-IL-050/CF) in RPMI complete media with 15% FBS (Hyclone SV30087.03) and 1% Penicillin-Streptomycin (Gibco, 15140-122). On day 3 half the media will be refreshed with fresh GM-CSF and IL-4 and compounds at 10 and 50 µM dose. On day 5 the dendritic cells would be further differentiated to tolerogenic dendritic cells with vitamin D3, 100 nM (Selleck S4063) and dexamethasone 10 nM (Selleck S1322). On day 6 LPS would be added (Sigma, L6143) at final concentration of 10 ng/ml and cells collected for flow analysis and supernatant for IL-10 (DKW, 1110003) measurement by ELISA. Cells would be stained with live/dead APC (Invitrogen, L10120), Percp-Cy5.5 mouse anti-human HLA-DR (BD 560652), PE mouse anti-human CD83 (BD 556855), Alexa Fluor® 488 anti-human CD86 Antibody (Biolegend 305414), BV510 mouse anti-human CD141(BD, 563298), PE/Cy7 anti-human CD85k (ILT3) (Biolegend, 33012), or with corresponding isotype controls (Percp-Cy5.5 Mouse IgG2a,κ, BD, 552577), PE Mouse IgG1,κ (BD, 555749), Alexa Fluor® 488 Mouse IgG2b, κ Isotype Ctrl (Biolegend, 400329), BV510 Mouse BALB/c IgG1,κ (BD, 562946) Pe/Cy7 Mouse IgG1, κ Isotype Ctrl Antibody (Biolegend, 400126). Tolerogenic cells would be defined as live, CD83-CD86-HLA-DR+CDI 41+CD85k+ and increased production of IL-10.

Example 807: M1 Differentiation Assay

Monocytes were isolated by positive isolation with CD14+ microbeads (Miltenyi, 130-050-201). Monocytes were 99% viable and were 96% purity as analyzed by FACS and CD14+(BD, 563561). 100,000 monocytes along with compounds at the dose of 10 and 50 µM were allowed to differentiate to macrophages with 10 ng/ml GMCSF (R&D, 15-GM-050/CF) in RPMI complete media (Invitrogen, 22400089) with 15% FBS (Hyclone SV30087.03) and 1% Penicillin-Streptomycin (Gibco, 15140-122). On day 2 and 4 half the media was refreshed with fresh GM-CSF and compounds at 10 and 50 µM dose. On day 6 the macrophages were matured with GMCSF, IFNγ (R&D 285-IF-100/CF) and LPS (Sigma, L6143) in the presence of 10 µM and 50 µM of compounds. After 24 h, supernatant was collected for the measurement of TNFα (DKW, 1117202) IL6 (DKW, 1110602), IL10 (DKW, 1110003) by ELISA. Macrophages were detached gently on ice with EDTA (Invitrogen, 15575-038) and analyzed by FACS (BD LSR Fortessa, 853492). Cells were stained for live/dead dye, surface and intracellular markers with fixation/permeabilization solution (BD, 554714) and ALIVE/DEAD™ Fixable Near-IR Dead Cell Stain Kit (BD, L34976), mouse anti human CD86 APC (BD, 555660), mouse anti-human CD163 PE (BD, 556018), mouse anti-human CD68 FITC (BD, 562117) or isotype controls anti-mouse IgG1 κ PE (BD, 559320) and anti-mouse IgG1 κ APC (BD, Anti mouse IgG1 κ APC (BD, 55571). Mature M1 macrophages were defined as CD86+CD68+CD163− and increase in TNFα, IL6, and decrease in IL-10.

Example 808: Myeloid Derived Suppressor Cells (MDSC) Suppression Assay

Monocytes would be isolated by positive isolation with CD14+ microbeads (Miltenyi, 130-050-201). Monocytes would be 99% viable with 96% purity as analyzed by FACS and CD14+(BD, 563561). 100,000 monocytes will be incubated with compounds at the dose of 10 and 50 µM±PD-1 (Nivolumab) and differentiated to MDSC with 10 ng/ml GMCSF (R&D, 215-GM-050/CF) and IL-6 (R&D 206-IL-050/CF) in RPMI complete media (Invitrogen, 22400089) with 15% FBS (Hyclone SV30087.03) and 1% Penicillin-Streptomycin (Gibco, 15140-122). On day 2, 4 and 6 half the media will be refreshed with fresh GM-CSF and compounds at dose of 10 and 50 µM. Autologous T-cell will be isolated by negative selection with EasySep Human T cell isolation kit (Stem cell, 17951) and stained with Cell Trace™ Violet Cell Proliferation Kit for flow cytometry (Invitrogen, C34557). MDSC were cocultured with T cells activated with dyna bead (human CD3/CD2, Invitrogen, 11131D) at the ratio of MDSC:T cells:dynabead 0.5:1:1 along with the compounds for 4 days. The supernatant would be collected for the measurement of IFNγ (Dakewe, 1110002). Next, MDSC and T cells would be stained and will be analyzed by FACS (BD LSR Fortessa, 853492), live dead fixable far red (Invitrogen, L34974), anti-Human CD33 (BD 555626), mouse Anti-Human CD15 (BD 560827), mouse anti-Human CD14 (BD 563561), mouse anti-Human HLA-DR (BD, 560652), mouse anti-Human CD4 (BD 563550), anti-human CD8 Antibody (Biolegend, 344714), anti-human CD11b (Biolegend, 301332), mouse IgG2a isotype controls (BD 550927). MDSC are defined as CD11 b+, CD33+, CD15+, CD14-, HLA-DR-. CD4 and CD8 are T-cell markers to understand the proliferative capacity of both CD4+ and CD8+ T cells in the presence of MDSC in presence and absence of the compounds.

Example 809: Th17 Differentiation Assay

Naïve CD4+ T cells (Stemcell, Cat #17555) were isolated from PBMC and seeded (20,000 cells/well) in a 96-well flat bottom plate (Eppendorf, 30730119) pre-coated with 10 µg/ml anti-CD3 antibody (EBioscience, 16-0037-85) for 3 hours at 37° C. in an X-VIVO15 medium (Lonza, 04-418Q) supplemented with 15% FBS (Hyclone, SV30087.03) and 1% Penicillin-Streptomycin (Hyclone, SV30010). Th17 differentiation cocktail was added (Biolegend, 423303), including 2 µg/ml anti-CD28 (BD 555725), 10 ng/ml IL-1β (R&D, 201-LB-005) 10 ng/ml IL-6 (R&D, 206-IL-010), 10 µg/ml anti-IL-4 (BD, 554481), 10 ng/ml IL-23 (R&D, 1290-IL-010/CF), 10 µg/ml anti-human IFNγ (BD, 16-7318-85), 10 ng/ml TGF-β1 (R&D, 240-B-010) in the presence of the compounds at 10 and 50 µM dose. On day 3 and day 8 half of the medium, was refreshed with Th17 differentiation cocktail as above and compounds (10 and 50 µM). Th17 cells were stained and analyzed by FACS (BD LSR Fortessa, 853492). On day 10, cells were collected and were stained for live/dead dye (Life technology, L34975), surface and intracellular IL-17a with fixation/permeabilization solution (BD, 554722), and mouse anti human CD4 (BD, Cat #564651), anti-human IL-17a (BD, 560490) and/or mouse anti-human IgG1κ (BD, 557714).

Example 810: Treg Differentiation Assay

Naïve CD4+ T cells (Stemcell, 17555) were isolated from PBMC and placed (20,000 cells/well) in 10 µg/ml anti-CD3 antibody (eBioscience, 16-0037-85) pre-coated 96-well flat bottom plate (Eppendorf, Cat #30730119) for 3 hours at 37° C. in an X-VIVO15 medium (Lonza, 04-418Q) supplemented with 15% FBS (Hyclone SV30087.03) and 1% Penicillin-Streptomycin (Hyclone, SV30010). Treg induction cocktail was added including 2 µg/ml anti-CD28 (eBioscience 16-0289-85), 20 ng/ml IL-2 (R&D, 202-1L-050) 0.2 ng/ml TGF-β 1 (Peprotech, 100-21-50) in the presence of the compounds at 10 and 50 µM dose. On day 3 half of the medium, was refreshed with Treg differentiation cocktail as above and compounds (10 and 50 µM). On day 5 cells were collected and the following staining were performed: live/dead (Invitrogen, L34963), and Foxp3/Transcription Factor Staining Buffer Set (EBioscience, 00-5523-00), mouse anti-human FoxP3 (BD, 560046) or mouse IgG1,κIsotype control (BD, 555749) and analyzed by FACS (BD LSR Fortessa, 853492).

Example 811: Mast Cell Activation Assay

MC/9 cell line (ATCC, CRL-8306) would be thawed and will be grown in DMEM High Glucose (Gibco 11995-065) supplemented with 10% FBS (Hyclone, SV30087.03), 1% Penicillin-Streptomycin (Hyclone, SV30010), along with T-Cell Supplement (Corning, 354115). 500,000 cells/well would be placed in Tyrode's buffer (100 µl) together with anti-CD107a antibody. The assay will be done in 2 sets; in the first set MC/9 cell line would be treated directly with the compounds at 10 and 50 µM and in the second set, cells would be treated with the compounds at 10 and 50 µM dose in the presence of C48/80 compound (Sigma, C2313) to induce mast cell degranulation. Induction would be done for 30 min-1 h. After incubation, 30 µl supernatant would be collected and incubated with 10 µl substrate solution (p-nitrophenyl-N-acetyl-β-D-glucosaminide) for 30 mins at 37° C. Then 100 µl of carbonate buffer would be added (according to manufacturing instruction, N-Acetylglucosaminidase (beta-NAG) Activity Assay Kit, Abcam Ab204705) and absorbance was read at 405 nm.

Example 812: Measurement of ROS

Primary adherent fibroblasts were cultured in minimum essential medium (MEM) (Gibco, 25030081) supplemented with 2 mM L-Glutamine (Gibco, 25030081), 15% fetal bovine serum (FBS) (Gibco, 26400044) and 1% penicillin/streptomycin (Gibco, 5140122) at 37° C. and 5% $CO_2$. Cells were collected for either passaging or experiment at ~70-80% confluence. Cells were obtained by trypsinization and seeded in cell culture microplates either white plate (Thermo Fisher Scientific, 152028) for luminescent measurement or black plate (Thermo Fisher Scientific, 165305) for fluorescent based read out for different assays listed below. Cells were obtained by trypsinization and 5000 K cells were seeded and allowed to adhere for 16-18 hours to have confluency around 70-80% in the cell well with culture media. After 24 hours prior to measurements (37° C., 5% CO2) media was changed to Dulbecco's Modified Eagle Medium (DMEM, Agilent Seahorse cat #103575-100) with the appropriate supplements as stated below.

| Conditions used | Supplements in DMEM |
| --- | --- |
| A | 1 mM glucose, 2 mM L-glutamine, 1 mM pyruvate, 10% FBS |
| B | 1 mM glucose, 2 mM L-glutamine, 1 mM pyruvate |
| C | 1 mM glucose, 10% FBS |

Primary fibroblasts assayed were Healthy controls (GM00041, GM05659, GM23974 Coriell Institute for Medical Research), Propionic Acidemia (PA) (GM00371, GM03590 Coriell Institute for Medical Research, Tsi 6337 Trans-Hit Bio), Methylmalonic Acidemia (MMA) (GM01673. Coriell Institute for Medical Research, Tsi 5224, Tsi 4290 Trans-Hit Bio), Branched chain ketoacid dehydrogenase kinase (BCKDK) (GM00612, GM00649 Coriell Institute for Medical Research), Subnormal activation of pyruvate dehydrogenase complex (PDH) (GM01503 Coriell Institute for Medical Research), Very long-chain acyl-CoA dehydrogenase (VLCAD) (GM17475), Leigh Syndrome (LS) (GM03672, GM13411 Coriell Institute for Medical Research), Pyruvate Carboxylase Deficiency (PC) (GM00444 Coriell Institute for Medical Research), Glutaric Acidemia-I (GA), Impaired VLCFA oxidation (VLCFA) (GM13262), Kearns-Sayre Syndrome (KSS) (GM06225 Coriell Institute for Medical Research), Friedreich's Ataxia (FXN), Huntington's disease (HD) (GM21756 Coriell Institute for Medical Research). Next, cells were treated with compounds (10 µM) and ROS H2DCFDA (22 µM) dye for 2 hours in PA, MMA lines and for 24 h for the other fibroblast lines. Kinetic read was started immediately with a i3x plate reader (492/527 nm) for 60 minutes.

A total dead cell count was performed as described in Example 817 and only alive cells were used for analysis.

Example 813: Measurement of Total NAD⁺+NADH and NAD⁺

Primary adherent fibroblasts were cultured in minimum essential medium (MEM) (Gibco, 25030081) supplemented with 2 mM L-Glutamine (Gibco, 25030081), 15% fetal bovine serum (FBS) (Gibco, 26400044) and 1% penicillin/streptomycin (Gibco, 5140122) at 37° C. and 5% $CO_2$. Cells were collected for either passaging or experiment at ~70-80% confluence. Cells were obtained by trypsinization and seeded in cell culture microplates either white plate (Thermo Fisher Scientific, 152028) for luminescent measurement or black plate (Thermo Fisher Scientific, 165305) for fluorescent based read out for different assays listed below. Cells were obtained by trypsinization and 5000 K cells were seeded and allowed to adhere for 16-18 hours to have confluency around 70-80% in the cell well with culture media. After 24 hours prior to measurements (37° C., 5% CO2) media was changed to Dulbecco's Modified Eagle Medium (DMEM, Agilent Seahorse cat #103575-100) with the appropriate supplements as stated below.

| Conditions used | Supplements in DMEM |
|---|---|
| A | 1 mM glucose, 2 mM L-glutamine, 1 mM pyruvate, 10% FBS |
| B | 1 mM glucose, 2 mM L-glutamine, 1 mM pyruvate |
| C | 1 mM glucose, 10% FBS |

Primary fibroblasts assayed were Propionic Acidemia (PA) (GM03590 Coriell Institute for Medical Research, Tsi 6337 Trans-Hit Bio), Methylmalonic Acidemia (MMA) (Tsi 5224 Trans-Hit Bio), Subnormal activation of pyruvate dehydrogenase complex (PDH) (GM01503 Coriell Institute for Medical Research), Very long-chain acyl-CoA dehydrogenase (VLCAD) (GM17475), Leigh Syndrome (LS) (GM03672, GM13411 Coriell Institute for Medical Research), Pyruvate Carboxylase Deficiency (PC) (GM00444 Coriell Institute for Medical Research). 10 µM of Compounds were added for 2 hours in PA, MMA lines and for 24 h for the other fibroblast lines.

Assay was performed according to manufacturer instructions (NAD/NADH-Glo Assay Promega, G9072). The NAD/NADH-Glo Assay is a bioluminescent assay for detecting total oxidized and reduced nicotinamide adenine dinucleotides (NAD+ and NADH, respectively) from which ratio of NAD/NADH can be calculated. Briefly, for every assay a 12-point standard curve was prepared ranging from 400 nM to 0.625 nM. Media was removed and replaced with 50 µl of PBS for both assays.

For individual NAD+ and NADH measurement, 50 µl of 1% DTAB (Sigma Cat #D5047) (cell lysis reagent) in 0.2N NaOH was added to the plate and a total 100 µl of lysate was split into two plates with 50 µl each. 25 µl of 0.4N HCl were added to the NAD+ plate and both NAD+ and NADH plate were heated at 60° C. for 15 minutes. The acid and heat treatment destroyed NADH allowing individual NAD+ measurement while heating in basic conditions destroys NAD+ allowed individual NADH measurements. The plates were allowed to come to room temperature for 10 minutes and Trizma base (Sigma, T1699) was added to the NAD+ plate to neutralize the acid and HCl Trizma hydrochloride (Sigma, T2694) was added to the NADH plate. The NAD-NADH glo reagent was prepared by adding: 625 µl of NAD cycling substrate, 125 µl of reductase, 125 µl of reductase substrate, 125 µl NAD cycling enzyme to total of the 25 ml of NAD GLO reagent. 1:1 ratio of total volume of reagent was added to the individual NAD+, NADH measurement (total 100 µl) and 50 µl for total NAD/NAH measurement. Luminescence was read between 30-60 minutes within the linear range.

A total dead cell count was performed as described in Example 817 and only alive cells were used for analysis.

Example 814: Measurement of NADP+/NADPH

Primary adherent fibroblasts were cultured in minimum essential medium (MEM) (Gibco, 25030081) supplemented with 2 mM L-Glutamine (Gibco, 25030081), 15% fetal bovine serum (FBS) (Gibco, 26400044) and 1% penicillin/streptomycin (Gibco, 5140122) at 37° C. and 5% CO2. Cells were collected for either passaging or experiment at ~70-80% confluence. Cells were obtained by trypsinization and seeded in cell culture microplates either white plate (Thermo Fisher Scientific, 152028) for luminescent measurement or black plate (Thermo Fisher Scientific, 165305) for fluorescent based read out for different assays listed below. Cells were obtained by trypsinization and 5000 K cells were seeded and allowed to adhere for 16-18 hours to have confluency around 70-80% in the cell well with culture media. After 24 hours prior to measurements (37° C., 5% CO2) media was changed to Dulbecco's Modified Eagle Medium (DMEM, Agilent Seahorse cat #103575-100) with the appropriate supplements as stated below.

| Conditions used | Supplements in DMEM |
|---|---|
| A | 10 mM glucose, 2 mM L-glutamine, 1 mM pyruvate, 10% FBS |
| B | 1 mM glucose, 2 mM L-glutamine, 1 mM pyruvate, 10% FBS |

Primary fibroblasts assayed were Propionic Acidemia (PA) (GM03590 Coriell Institute for Medical Research, Tsi 6337 Trans-Hit Bio), Methylmalonic Acidemia (MMA) (Tsi 5224 Trans-Hit Bio), Subnormal activation of pyruvate dehydrogenase complex (PDH) (GM01503 Coriell Institute for Medical Research), Very long-chain acyl-CoA dehydrogenase (VLCAD) (GM17475), Leigh Syndrome (LS) (GM03672, GM13411 Coriell Institute for Medical Research), Pyruvate Carboxylase Deficiency (PC) (GM00444 Coriell Institute for Medical Research). 10 µM of Compounds were added for 2 hours in PA, MMA lines and for 24 h for the other fibroblast lines.

Assay was performed according to manufacturer instructions (NADP+/NADPH-Glo Assay Promega, G9082). Assay required a plate for total measurement of NADP+/NADPH and a plate for individual measurement of NADP+ or NADPH. For every assay a 12-point standard curve is prepared ranging from 400 nM to 0.625 nM. Media is removed and replaced with 50 µl of PBS for both assays.

For individual NADP+/NADPH measurements, 50 µl of 1% DTAB (Sigma, D5047) (cell lysis reagent) in 0.2N NaOH was added to the plates and 100 µl of lysate was split into two plates with 50 µl each from which ratio of NADP/NADPH can be calculated. 25 µl of 0.4N HCl were added to the NADP+ plates and both NADP+ and NADPH plates were heated at 60° C. for 15 minutes. The acid and heat treatment destroyed NADPH allowing individual NADP+ measurements while heating in basic conditions destroys NADP+ allowing individual NADPH measurement. After 15 minutes plates were allowed to come to room temperature and Trizma base (Sigma, T1699) was added to the NADP+ plates to neutralize the acid and HCl Trizma hydrochloride (Sigma, T2694) was added to the NADPH plates. The NADNADPH glo reagent was prepared by adding 125 µl of NAD cycling substrate, 125 µl of reductase, 125 µl of reductase substrate, 125 µl NAD cycling enzyme to a total of the 25 ml of NAD GLO reagent. 1:1 ratio of total volume of reagent was added to the individual NADP+, NADPH measurements (total 100 µl) and 50 µl were added for the total NAD/NADPH measurements. Luminescence was measured for 30-60 minutes within the linear range.

A total dead cell count was performed as described in Example 817 and only alive cells were used for analysis.

Example 815: Measurement of ATP

Primary adherent fibroblasts were cultured in minimum essential medium (MEM) (Gibco, 25030081) supplemented with 2 mM L-Glutamine (Gibco, 25030081), 15% fetal bovine serum (FBS) (Gibco, 26400044) and 1% penicillin/streptomycin (Gibco, 5140122) at 37° C. and 5% CO2. Cells were collected for either passaging or experiment at ~70-80% confluence. Cells were obtained by trypsinization and seeded in cell culture microplates either white plate (Thermo Fisher Scientific, 152028) for luminescent measurement or black plate (Thermo Fisher Scientific, 165305) for fluorescent based read out for different assays listed below. Cells were obtained by trypsinization and 5000k cells were seeded and allowed to adhere for 16-18 hours to have confluency around 70-80% in the cell well with culture media. After 24 hours prior to measurements (37° C., 5% CO2) media was changed to Dulbecco's Modified Eagle Medium (DMEM, Agilent Seahorse cat #103575-100) with the appropriate supplements as stated below.

| Conditions used | Supplements in DMEM |
|---|---|
| A | 1 mM glucose, 2 mM L-glutamine, 1 mM pyruvate, 10% FBS |
| B | 1 mM glucose, 2 mM L-glutamine, 1 mM pyruvate |
| C | 1 mM glucose, 10% FBS |

Primary fibroblasts assayed were Propionic Acidemia (PA) (GM03590 Coriell Institute for Medical Research, Tsi 6337 Trans-Hit Bio), Methylmalonic Acidemia (MMA) (Tsi 5224 Trans-Hit Bio), Subnormal activation of pyruvate dehydrogenase complex (PDH) (GM01503 Coriell Institute for Medical Research), Very long-chain acyl-CoA dehydrogenase (VLCAD) (GM17475), Leigh Syndrome (LS) (GM03672, GM13411 Coriell Institute for Medical Research), Pyruvate Carboxylase Deficiency (PC) (GM00444 Coriell Institute for Medical Research), α-Ketoglutarate dehydrogenase deficiency Trans-Hit Bio 962, Citrullinemia Type 11 Trans-Hit Bio 2930, Friedreich's Ataxia (FXN) (GM04078 Coriell Institute for Medical Research. 10 µM of Compounds were added for 2 hours in PA, MMA lines and for 24 h for the other fibroblast lines.

Assay was performed according to manufacturer instructions (ATPlite Assay Perkin Elmer, 6016941). 50 µl of cell lysis buffer was added to each well with cells in 100 µl of media and incubated for 5 mins at RT in an orbital shaker at 700 rpm to lyse the cells and stabilize the ATP. After, 50 µL luciferase-based reagent was added to the wells. The amount of signal was directly proportional to the ATP content.

A total dead cell count was performed as described in Example 817 and only alive cells were used for analysis.

Example 816: Measurement of Total GSH and GSSG Dimer

Primary adherent fibroblasts were cultured in minimum essential medium (MEM) (Gibco, 25030081) supplemented with 2 mM L-Glutamine (Gibco, 25030081), 15% fetal bovine serum (FBS) (Gibco, 26400044) and 1% penicillin/streptomycin (Gibco, 5140122) at 37° C. and 5% CO2. Cells were collected for either passaging or experiment at ~70-80% confluence. Cells were obtained by trypsinization and seeded in cell culture microplates either white plate (Thermo Fisher Scientific, 152028) for luminescent measurement or black plate (Thermo Fisher Scientific, 165305) for fluorescent based read out for different assays listed below. Cells were obtained by trypsinization and 5000 K cells were seeded and allowed to adhere for 16-18 hours to have confluency around 70-80% in the cell well with culture media. After 24 hours prior to measurements (37° C., 5% CO2) media was changed to Dulbecco's Modified Eagle Medium (DMEM, Agilent Seahorse cat #103575-100) with the appropriate supplements as stated below.

| Conditions used | Supplements in DMEM |
|---|---|
| A | 1 mM glucose, 2 mM L-glutamine, 1 mM pyruvate, 10% FBS |
| B | 1 mM glucose, 2 mM L-glutamine, 1 mM pyruvate |
| C | 1 mM glucose, 10% FBS |

Primary fibroblasts assayed were Healthy controls (GM00041, GM05659, GM23974 Coriell Institute for Medical Research), Propionic Acidemia (PA) (GM00371, GM03590 Coriell Institute for Medical Research, Tsi 6337, Tsi 3618 Trans-Hit Bio), Methylmalonic Acidemia (MMA) (GM01673, Coriell Institute for Medical Research, Tsi 5224, Tsi 4290 Trans-Hit Bio), Branched chain ketoacid dehydrogenase kinase (BCKDK) (GM00612, GM00649 Coriell Institute for Medical Research), Subnormal activation of pyruvate dehydrogenase complex (PDH) (GM01503 Coriell Institute for Medical Research), Very long-chain acyl-CoA dehydrogenase (VLCAD) (GM17475), Leigh Syndrome (LS) (GM03672, GM13411 Coriell Institute for Medical Research), Pyruvate Carboxylase Deficiency (PC) (GM00444 Coriell Institute for Medical Research), Glutaric Acidemia-I (GA), Impaired VLCFA oxidation (VLCFA) (GM13262), α-Ketoglutarate dehydrogenase deficiency Trans-Hit Bio 962, Citrullinemia Type II Trans-Hit Bio 2930, MELAS Syndrome Trans-Hit Bio V877. Assay was performed according to manufacturer instructions (Promega, V6612). At the end of appropriate time point, assay requires, one plate for total measurement of GSH and one plate for GSSG. For every assay a 11-point standard curve is prepared ranging from 8 µM to 0.013 µM. Media is removed completely. For total GSH measurements, 50 µl/well of total glutathione lysis reagent were added for GSH identification and 50 µl/well of oxidized glutathione lysis reagent were added to all wells for GSSG identification (5 minute, shaking condition). Next, 50 µl/well of Luciferin Generation Reagent were added to all wells and allowed to incubate at RT for 30 minutes under shaking conditions.

Finally, 100 µl/well of Luciferin Detection reagent were added and incubated for 15 minutes before the chemiluminescence was detected.

Free GSH/GSSG ratio was calculated as (Total GSH-GSSH)/(GSSG/2).

A total dead cell count was performed as described in Example 817 and only alive cells were used for analysis.

Example 817: Measurement of Total and Dead Cell Count

For Example 812, Example 813, Example 814, Example 815 and Example 816, a total dead cell count was performed and only alive cells were used for analysis. Assay was performed according to manufacturer instructions (EarlyTox Cell Integrity Kit, Molecular Devices, R8214). Media was gently removed and 100 µl per well of total live red dye and dead green dye (1:2000) were added and further incubated for 15-30 minutes at 37° C. and 5% CO2. The reactive Live Red Dye is cell permeant and stained both live and dead cells resulting in the total cell count measurements (Excitation: 622 nm/Emission: 645 nm). In contrast, the reactive Dead Green Dye is cell impermeant and stained only cells with damaged outer membranes i.e. dead cells (Excitation: 503 nm/Emission: 526 nm/Em: 713 nm). Alive cells were calculated as (Total cells minus dead cells).

Example 818: mPKD Cyst Swelling Assay

Cell model and control compounds. mIMCD3 WT cells were obtained via ATCC and modified to create the mIMRFNPKD 5E4 cell line, which has a CRISPR-Cas mediated knockout for Pkd1 as described SLAS Discov. 2017 September; 22(8):974-984. doi: 10.1177/2472555217716056. Cells were cultured in DMEM/F12 (Sigma)+10% FBS (Sigma)+0.5% Pen/Strep (Gibco)+1% GluMax (Gibco). Control compounds used were forskolin (Calbiochem, 344282), Rapamycin (Selleckchem, S1039) and Staurosporin (Selleckchem, S1421).

The 3D mouse cyst swelling assay was performed with Pkd1$^{-/-}$ mouse inner medullary collecting duct cells (mIMRFNPKD 5E4). The cyst swelling protocol that was used was described previously (SLAS Discov. 2017 September; 22(8):974-984. doi: 10.1177/2472555217716056), with further optimization.

3D culture and compound exposure. mIMRFNPKD 5E4 cells were mixed with Cyst-Gel (OcellO BV). 15 µL of cell-gel mix was pipetted to 384-well plates (Greiner µClear, Greiner Bio-One B.V.) using a CyBio Felix 96/60 robotic liquid dispenser (Analyik Jena AG). Gel-cell mix was plated at a final cell density of 2250 cells per well. After gel polymerization at 37° C. for 30 minutes, 33 µL culture medium was added to each well. Cells were grown in the gel for 96 hours, after which the cells were co-exposed with forskolin (Calbiochem, 344282) and one the following molecules: reference compound Rapamycin (SelleckChem, S1039), toxic control compound Staurosporin (SelleckChem, S1421) or test compounds.

Sample processing. After 72 hours, cultures were fixed with 4% Formaldehyde (Sigma Aldrich) and simultaneously permeabilized with 0.2% Triton-X100 (Sigma Aldrich) and stained with 0.25 µM rhodamine-phalloidin (Sigma Aldrich) and 0.1% Hoechst 33258 (Sigma Aldrich) in 1xPBS (Sigma Aldrich) for 2 days at 4° C., protected from light. After fixation and staining, plates were washed with 1xPBS, sealed with a Greiner SilverSeal (Greiner Bio-One B.V.) and stored at 4° C. prior to imaging.

Imaging and image analysis. Imaging was done using Molecular Devices ImageXpress Micro XLS (Molecular Devices) with a 4xNIKON objective. For each well around 35 images in the Z-direction were made for both channels, capturing the whole z-plane in each image. Image analysis was performed using Ominer™ software (OcellO BV). Cysts were segmented using detection of Hoechst-stained nuclei and Rhodamine-phalloidin-stained cellular f-actin. Cyst area was determined by calculating for the area in px of each object in every in-focus plain. This was averaged per well. (N represented is number of wells) Fraction of apoptotic nuclei as an indicator of toxicity was calculated as the amount of nuclei without actin signal relative to the total amount of nuclei, both as count-measurements. Statistics was done using KNIME Analytics Platform (Konstanz, Germany, http://www.knime.org/), graphs were prepared in GraphPad Prism 6 (GraphPad Software, La Jolla, CA).

Example 819: Measurement of Mitochondria) Membrane Potential Changes Using the JC-1 Assay Primary fibroblasts used were: Mitochondrial Encephalopathy, Lactic Acidosis, and Stroke-like episodes (MELAS) Syndrome (K605, Trans-Hit Bio); Amyothrophic Lateral Sclerosis (ALS) (K773, Trans-Hit Bio); Succinil-CoA:3-Ketoacid CoA transferase deficiency (SCOT) (10474, Trans-Hit Bio); Citrullinemia Type II (9673, Trans-Hit Bio); Glutaric Acidemia (GA) (GM05002, Coriell Institute for Medical Research); Isovaleric acidemia (IVA) (GM00947, Coriell Institute for Medical Research) and Very long-chain acyl-CoA dehydrogenase (VLCAD) (GM11408, Coriell Institute for Medical Research).

Cells were cultured in minimum essential medium (MEM) (Thermo Fisher Scientific) supplemented with 2 mM L-Glutamine (Thermo Fisher Scientific), 15% fetal bovine serum (FBS) (Gibco) and 1% penicillin/streptomycin at 37° C. and 5% $CO_2$, and plated at a density of 75,000 cells/well in 24 well plates (2 plates per cell line) in MEM growth media. Once attached (about 2-3 h later), media was aspirated and replaced with 450 µl/A Media: 10 mM glucose, 2 mM glutamine, 1 mM pyruvate, 10% FBS or B Media: 1 mM glucose, 10% FBS) (1 plate of each). A working compound plate was prepared with all compounds at 10 mM. Immediately before adding to cells, compounds were diluted to 100 µM (10x) in starved media, and 50 µl/well was added to the cells in 24 well plates. Final concentration was 10 µM. After 24 hours, the media was aspirated, and cells were washed once with 500 µl D-PBS (no additions). After aspirating the wash buffer, 200 µl/well trypsin was added, and the plates were incubated at room temperature (RT) until cells detached. Trypsin was inactivated with 100 µl FBS, and cells were transferred to a 96 well v bottom plate and for centrifugation at 250 g for 5 minutes at RT. Supernatant was removed and cells were washed with PBS. Cells were then resuspended in 50 µl staining buffer and FCCP was added to 10 µM in control wells. The plate was incubated at RT for 5 min, then 2xJC-1/DAPI was added at 50 µl per well. Cells were taken to the flow cytometer (Miltenyi MACSQuant Analyzer), and acquisition was initiated immediately. Channels used were V1 (DAPI), B1 (JC-1 monomers) and B2 (JC-1 aggregates). Data were analyzed with FlowJo by TreeStar, and compensation was performed digitally in the analysis program using the FCCP-treated samples as the maximally green fluorescence control (corresponding to JC-1 monomers). Each cell line was analyzed individually to ensure proper gating. Geometric mean fluorescence intensity for JCI aggregates (corresponding to red fluorescence) and monomers (corresponding to green fluorescence) was determined within the DAPI negative population (live cells). The ratio of red:green was calculated and expressed related to vehicle (vehicle=1).

Example 820: Effects of Test Compounds on Mitobiogenesis In-Cell ELISA Assay

We determined the effect of compounds of the present disclosure on the levels of two mitochondrial proteins using MitoBiogenesis™ In-Cell ELISA Kit (Abram ab110216) according to manufacturer's instructions. The two proteins are each subunits of a different oxidative phosphorylation enzyme complex, one protein being subunit I of Complex IV (COX-I), which is mitochondrial (mt)DNA-encoded, and the other being the 70 kDa subunit of Complex II (SDH-A), which is nuclear (n)DNA-encoded. Complex IV includes several proteins which are encoded in the mitochondrion, while the proteins of Complex II are entirely encoded in the nucleus. HepG2 cells (ATCC, HB-8065) were cultured (5% CO2 at 37° C.) and plated in Poly-D-Lysine 384-Well plate (Corning, 356663) at a density of 40,000 cells/mL in 50 μL. Culture and assay media consisted of DMEM (Gibco, 11995-065) supplemented with 1% Penicillin-Streptomycin and 10% FBS (Hyclone, SV30087.03). Cells were allowed to settle for 30 min at room temperature and further incubated overnight (37° C. and 5% CO2) for adherence. Next day, 50-5 μM of the negative control Chloramphenicol (Selleck, S1677), test compounds (50-10 μM) and vehicle DMSO (0.2%) were added at the recommended volumes to the 384-well plate for 7 days without media change using a Tecan compound dispenser. All the solutions and wash buffers were prepared and dispensed according to manufacturer's volumes for a 384-well plate format. Effects of compounds on mtDNA-encoded protein expression (COX-I) and nuclear DNA-encoded mitochondrial protein expression (SDH-A) were expressed as relative signal (nm) to vehicle of a n=2 per conditions.

Example 821: Effects of Test Compounds on Glucose Uptake

The effect of compounds from the present disclosure on glucose uptake was determined in HepG2 cells (ATCC, HB-8065) using the glucose uptake Glo Assay Kit (Promega, 11343 according to manufacturer instructions. HepG2 cells were cultured in complete DMEM-glucose media (Gibco) supplemented with 10% FBS (37° C. incubator with 5% $CO_2$) and seeded in 96-well plates at 30,000 cells/well. After removing the complete media, 100 μL/well of serum-free, high-glucose DMEM media were added to the wells and incubated overnight (37° C. incubator with 5% CO2). Media was then replaced with 100 μl/well DPBS containing 0.6% BSA and starved for 1 hour. Next, DPBS was removed and 45 μl/well of insulin (100 nM) or compounds (10 μM-50 μM) were added to the wells and incubated for 10 minutes (37° C. incubator with 5% CO2). Insulin and compounds were prepared in DPBS with 0.6% BSA with a final DMSO concentration of 0.1%. Next, 5 μl of 2DG (10 mM) in DPBS were added per well and allowed to incubate for 20 minutes followed by addition of 25 μl stop buffer. 37.5 μl of the mixture were then transferred to a new plate and 12.5 μl of Neutralization buffer added to the wells. After, 50 μl of 2DG6P detection Reagent were added and incubated for 0.5-1 hour at room temperature. Luminescence was measured with 0.3-1 second integration on a luminometer.

Example 822: Effects of Compounds on Ammonia Levels

The effect of compounds from the present disclosure on ammonia levels were determined in patient derived fibroblasts (Coriell Institute for Medical Research GM00371 Propionic Acidemia and Coriell Institute for Medical Research GM01673 Methylmalonic Acidemia) and Healthy control (Coriell Institute GM00041).

The cell culture medium was Eagles Minimal Essential Medium containing non-essential amino acids, supplemented with 10% non-inactivated FBS for GM01673 and 15% FBS for GM00371 and GM0041 with 0.3% penicillin/streptomycin. Supplier conditions for thawing, growing, feeding and harvesting of each cell line were strictly followed.

Cells were cultured in four T-25 cm2 cell culture flasks for each compound challenge (three replicate flasks for sample preparation, one flask for representative cell count). Cells were challenged for 4 hours and this was performed in each culture media consisting of A Media: 10 mM glucose, 2 mM glutamine, 1 mM pyruvate or B Media: 1 mM glucose) with compounds at one test concentration of 50 μM in 0.5% vehicle. For GM00041 cells, one representative flask was challenged with each test condition required.

Ammonia determination. Ammonia values were measured on freshly prepared media samples (T0) and after completion of treatment (T4) via Modified Berthelot, Ammonia Assay Kit (Colorimetric, Abeam, ab102509). T4 values were taken from each triplicate flask from each cell line directly at treatment end point.

Cell counts were taken using standard cell counting with bright field microscope from 1 parallel flask for each culture condition.

Example 823: Effects of Compounds on Gene Expression

Cells growth and treatment was performed as in Example 822.

Gene expression. qPCR gene expression analysis of the following markers (Table x) was performed on RNA prepared from the parallel cell count flask from each test condition.

Description of Markers Analysed Via qPCR

| Gene | Description of protein encoded |
| --- | --- |
| ACOT8 | A peroxisomal Acyl-CoA thioesterase involved in the oxidation of fatty acids |
| ACOT4 | A peroxisomal succinyl-coenzyme A thioesterase which can also hydrolyse glutaryl-CoA and long chain saturated acyl-CoAs. |
| FGF21 | A member of the fibroblast growth factor (FGF) family, possessing broad mitogenic, cell survival and metabolic regulation activities. |
| PPARα | A member of the nuclear receptor family of ligand-activated transcription factors that heterodimerise with the retinoic X receptor (RXR) to regulate gene expression. Regulates the peroxisomal beta-oxidation pathway of fatty acids. |

-continued

| Gene | Description of protein encoded |
|---|---|
| PPARγ | A member of the nuclear receptor family of ligand-activated transcription factors that heterodimerise with RXR to regulate gene expression. Implicated in the pathology of numerous diseases including obesity, diabetes, atherosclerosis and cancer. |
| GLUT1 | Glucose transporter enabling movement of hydrophilic glucose across the cell membrane. |
| HIF1α | Alpha subunit of transcription factor hypoxia-inducible factor-1, Functions as a master regulator of cellular and systemic homeostatic response to hypoxia by activating transcription of genes, involved in energy metabolism, angiogenesis and apoptosis. |
| GLUT4 | An insulin-regulated facilitative glucose transporter. Upon insulin stimulation, the sequestered protein moves to the cell surface and begins to transport glucose across the cell membrane. |
| SIRT3 | Member of the sirtuin family of class III histone deacetylases. Found exclusively in mitochondria, where it can eliminate reactive oxygen species and inhibit apoptosis. Involved in nuclear gene expression and metabolic control. |
| SIRT5 | NAD-dependent lysine demalonylase, desuccinylase and deglutarylase. Contributes to the regulation of ammonia levels during fasting. |
| GAPDH | An enzyme which catalyses glycolysis and breaks down glucose. Used as a control(housekeeping) marker. |

Primers used in the assay are stated below.

| Gene | Species | Sequence (5'-3') |
|---|---|---|
| HIF1α | human | AAAATCTCATCCAAGAAGCC AATGTTCCAATTCCTACTGC |
| ACOT8 | human | CATCTATCCCCATTCCTGAG TTTTTCCAGTGGTATCAGTC |
| ACOT4 | human | CTTTGAAGATCTCCCCAATAAC GATCCATTGATGGAAACTGTG |
| FGF21 | human | TACCTCTACACAGATGATGC CCCAAGATTTGAATAACTCCC |
| PPARα | human | CCTAAAAAGCCTAAGGAAACC GATCTCCACAGCAAATGATAG |
| PPARγ | human | AAAGAAGCCAACACTAAACC TGGTCATTTCGTTAAAGGC |
| GLUT 1 | human | ACCTCAAATTTCATTGTGGG GAAGATGAAGAACAGAACCAG |
| GLUT 4 | human | CCATTGTTATCGGCATTCTG ATTCTGGATGATGTAGAGGTAG |
| SIRT3 | human | GAAACTGGGAAGCTTGATG CTTGTCAGAATTGGGATGTG |
| SIRT5 | human | ATTCAGGTTTCATTTCCAGG GATTGTTCAGTACTCAGCTC |
| GAPDH | human | ACCCACTCCTCCACCTTTGA CTGTTGCTGTAGCCAAATTCGT |

For reverse transcription (RT) of total RNA to single-stranded cDNA (2 μl) we used the High Capacity cDNA Reverse Transcription Kit (AB Applied Biosystems, 042557). For real time (RT) PCR we used the Power SYBR® Green PCR Master Mix and Power SYBR® Green RT-PCR Reagents Kit (Thermo Fisher Scientific, 042179). Master Mix reaction consisted of 10 μl SybrGreen (2×), 1.2 μl primer Reverse (of 5 μM dilution), 1.2 μl primer Forward (of 5 μM dilution) and 5.6 μl RNA fre/DNA free water.

Example 824: BioMAP Assays to Evaluate Efficacy of Compounds in In-Vitro Primary Cell-Based Models The BioMAP platform (BioMAP® Diversity PLUS Panel from Eurofins) is an in vitro phenotypic profiling technology that screened the compounds of the present disclosure (hereafter indicated as test agents) in human primary cell-based systems modelling complex tissue and disease states. The BioMAP assays were performed using the Eurofin's BioMAP Technology Platform as (see references 1 to 13 in the example 824 section) to model different diseases on primary cell-based model systems. These systems consisted of either single primary cell types or co-culture cells. Adherent cell types were cultured or co-cultured in 96 or 384-well plates until confluence followed by the addition of compounds prepared in DMSO at a final concentration of ≤0.1%. In each cell-based system, primary cells from heathy donors (2-6 donors) were pooled and treated with compounds at 1 and 10 μM dose 1 h prior to stimulation and remain in culture as indicated in Example 825, Example 826, Example 827, Example 828, Example 829, Example 830, Example 831, Example 832, Example 833, Example 834, Example 835, Example 836 and Example 837. For on the BioMAP® Diversity PLUS® Panel, please see the following references, which are incorporate herein.

Kunkel E J, Dea M, Ebens A, Hytopoulos E, Melrose J, Nguyen D, Ota K S, Plavec I, Wang Y, Watson S R, Butcher E C, Berg E L. An integrative biology approach for analysis of drug action in models of human vascular inflammation. The FASEB Journal. 18, 1279-81 (2004); Kunkel E J, Plavec I, Nguyen D, Melrose J, Rosier E S, Kao L T, Wang Y, Hytopoulos E, Bishop A C, Bateman R, Shokat K M, Butcher E C, Berg E L. Rapid structure-activity and selectivity analysis of kinase inhibitors by BioMAP analysis in complex human primary cell-based models. Assay Drug Dev Technol. 2, 431-41 (2004); Berg E L, Kunkel E J, Hytopoulos E and Plavec 1. Characterization of compound mechanisms and secondary activities by BioMAP analysis. Journal of Pharmacological and Toxicological Methods. 53, 67-74 (2006); Houck K A, Dix D J, Judson R S, Kavlock R J, Yang J and Berg E L. Profiling Bioactivity of the ToxCast Chemical Library Using BioMAP Primary Human Cell Systems. Society for Biomolecular Sciences. 14, 1054-1066

(2009); Xu D, Kim Y, Postelnek J, Vu M D, Hu D Q, Liao C, Bradshaw M, Hsu J, Zhang J, Pashine A, Srinivasan D, Woods J, Levin A, O'Mahony A, Owens T D, Lou Y, Hill R J, Narula S, DeMartino J and Fine J S. RN486 [6-Cyclopropyl-8-fluoro-2-(2-hydroxymethyl-3-{1-methyl-5-[5-(4-methylpiperazin-1-yl)-pyridin-2-ylamino]-6-oxo-1,6-dihydro-pyridin-3-yl}-phenyl)-2Hisoquinolin-1-one], a selective Bruton's tyrosine kinase (Btk) inhibitor, abrogates immune hypersensitivity responses and arthritis in rodents. Journal of Pharmacology and Experimental Therapeutics. 3341, 90-103 (2012); Bergamini G, Bell K, Shimamura S, Werner T, Cansfield A, Müller K, Perrin J, Rau C, Ellard K, Hopf C, Doce C, Leggate D, Mangano R, Mathieson T, O'Mahony A, Plavec I, Rharbaoui F, Reinhard F, Savitski M M, Ramsden N, Hirsch E, Drewes G, Rausch O, Bantscheff M and Neubauer G. A selective inhibitor reveals PI3Kγ dependence of T(H)17 cell differentiation. Nature Chemical Biology. 8, 576-82 (2012); Melton A C, Melrose J, Alajoki L, Privat S, Cho H, Brown N, Plavec A M, Nguyen D, Johnston E D, Yang J, Polokoff M A, Plavec I, Berg E L and O'Mahony A. Regulation of IL-17A production is distinct from IL-17F in a primary human cell co-culture model of T cell-mediated B cell activation. PLoS One. 2013; 8:e58966. Berg E L, Polokoff M A, O'Mahony A, Nguyen D and Li X. Elucidating mechanisms of toxicity using phenotypic data from primary human cell systems—a chemical biology approach for thrombosis-related side effects. Int J Mol Sci. 16, 1008-29 (2015); Berg E L and O'Mahony A. Complex Primary Human Cell Systems for Drug Discovery. Human-based Systems for Translational Research, Chapter 5. Ed. R Coleman RSC Drug Discovery. ISBN: 978-1-84973-825-5 (2014); Berg E L, Polokoff M A, O'Mahony A, Nguyen D and Li X. Elucidating mechanisms of toxicity using phenotypic data from primary human cell systems—a chemical biology approach for thrombosis-related side effects. Int J Mol Sci. 16, 1008-29 (2015); Berg E L, Hsu Y C and Lee J A. Consideration of the cellular microenvironment: physiologically relevant co-culture systems in drug discovery. Adv Drug Deliv Rev. 69-70, 190-204 (2014); Berg E L, Yang J, Melrose J, Nguyen D, Privat S, Rosler E, Kunkel E J and Ekins S. Chemical target and pathway toxicity mechanisms defined in primary human cell systems. Journal of Pharmacological and Toxicological Methods. 61, 3-15 (2010); Kleinstreuer N C, Yang J, Berg E L, Knudsen T B, Richard A M, Martin M T, Reif D M, Judson R S, Polokoff M, Dix D J, Kavlock R J and Houck K A. Phenotypic screening of the ToxCast chemical library to classify toxic and therapeutic mechanisms. Nat Biotechnol. 32, 583-91 (2014).

Example 825: BioMAP Assay

Following the general procedure as described in Example 824, Venular Endothelial cells (HUVEC) (3C system) were treated with IL-1β, TNFα, IFNγ for 24 h to model Th1 driven cardiovascular and chronic inflammation diseases in the presence or absence of the compounds. Biomarker read out were; Tissue Factor, ICAM-1, E-selectin, uPAR (CD87), IL-8, MEG, HLA-DR, proliferation and SRB (Sulfo-rhodamine i.e. staining for protein content).

Example 826: BioMAP Assay

Following the general procedure as described in Example 824, Venular Endothelial cells (HUVEC) (4H system) were treated with IL-4 and histamine for 24 h to model Th2 driven allergy and autoimmunity in the presence or absence of compounds. Biomarkers read out were; MCP-1, Eotaxin-3. VCAM-1, P-selectin, uPAR (CD87), SRB and VEGFRII.

Example 827: BioMAP Assay

Following the general procedure as described in Example 824, Peripheral blood mononuclear cells co-cultured with venular endothelial cells (HUVEC) (LPS system) were stimulated with LPS for 24 h in the presence or absence of compounds, to model cardiovascular disease and chronic inflammation. Biomarkers read out were; MCP-1, VCAM-1, Thrombomodulin, Tissue Factor, CD40, E-selectin, CD69, IL-8, IL-1α, M-CSF, sPGE2, SRB and TNFα.

Example 828: BioMAP Assay

Following the general procedure as described in Example 824, Peripheral blood mononuclear cells were co-cultured with venular endothelial cells and treated with soluble antigen (T-cell ligands) (Sag system) in the presence or absence of compounds to model autoimmune and chronic inflammation. Biomarkers read out were; MCP-1, CD38, CD40, E-selectin, CD69, IL-8, MIG, PBMC cytotoxicity, Proliferation and SRB.

Example 829: BioMAP Assay

Following the general procedure as described in Example 824, Peripheral blood mononuclear cells were co-cultured with B-cells (BT system) were treated with either α-IgM and TCR ligands for 72 h in the presence or absence of the compounds to model asthma, allergy, oncology and autoimmunity. Biomarkers read out were; B-cell proliferation, PBMC cytotoxicity, secreted IgG, sIL-17A, sIL-17F, sIL-2, sIL-6 and s-TNFα.

Example 830

Following the general procedure as described in Example 824, Bronchial epithelial cells were co-cultured with dermal fibroblast (BF4T system) and were treated with TNFα and IL-4 for 24 h in the presence or absence of the compounds to model asthma, allergy, fibrosis, lung inflammation. Biomarkers read out were; MCP-1, Eotaxin-3, VCAM-1, ICAM-1, CD90, IL-8, IL-1α, keratin 8/18, MMP-1, MMP-3, MMP-9, PAI-1, SRB, tPA, uPA.

Example 831

Following the general procedure as described in Example 824, Bronchial epithelial cells (BE3C system) were treated with IL-1β, TNFα and IFNγ for 24 h in the presence or absence of the compounds to model lung inflammation and chronic obstructive pulmonary disease (COPD). Biomarkers read out were; ICAM-1, uPAR, IP-10, I-TAC, IL-8, MIG, EGFR, HLA-DR, IL-1α, Keratin 8/18, MMP-1, MMP-9, PAI-1, SRB, tPA, uPA.

Example 832

Following the general procedure as described in Example 824, Coronary artery smooth muscle cells (CASM3C system) were treated with IL-1β, TNFα and IFNγ for 24 h in the presence or absence of the compounds to model cardiovascular inflammation and restenosis. Biomarker reads out were; MCP-1, VCAM-1, Throbomodulin, Tissue factor, uPAR, IL-8, MIG, HLA-DR, IL-6, LDLR, M-CSF, PAI-1, Proliferation, SAA and SRB Example 833

Following the general procedure as described in Example 824, Dermal fibroblasts (HDF3CGF system) were treated with IL-1β, TNFα and IFNγ, EGF, bFGF and PDGF-BB for 24 h in the presence or absence of the compounds to model fibrosis and chronic inflammation. Biomarkers read out were; MCP-1, VCAM-1, ICAM-1, Collagen-I, Collagen-III, IP-10, I-TAC, IL-8, MIG, EGFR, M-CSF, MMP-1, PAI-1, SRB, TIMP-1, TIMP-2 and proliferation was measured for 72 h.

Example 834

Following the general procedure as described in Example 824, Keratinocytes were co-cultured with dermal fibroblast (KF3CT system) and treated with IL-113, TNFα, IFNγ and TGFβ for 24 h in the presence or absence of the compounds to model psoriasis, dermatitis and skin biology. Biomarkers read out were; MCP-1, ICAM-1, IP-10, IL-8, MIG, IL-1α, MMP-9, PAI-1, SRB, TIMP-2, uPA.

Example 835

Following the general procedure as described in Example 824, Lung fibroblast (MyoF system) were treated with TNFα and TGFβ for 48 h in the presence or absence of the compounds to model fibrosis, chronic inflammation, wound healing, matrix remodelling. Biomarker read out were; α-SM Actin, bFGF, VCAM-1, Collagen-I, Collagen-III, Collagen-IC, IL-8, decorin, MMP-1, PAI-1, TIMP-1, SRB Example 836

Following the general procedure as described in Example 824, Venular endothelial cells co-cultured with macrophages (Mphg system) and treated with TLR2 ligand for 24 h in the presence or absence of the compounds to mimic cardiovascular inflammation, restenosis and chronic inflammation. Biomarkers read out were; MCP-1, MIP-1α, VCAM-1, CD40, E-selectin, CD69, IL-8, IL-1α, M-CSF, sIL-10 and SRB.

Example 837

Effect of compounds on mitochondrial fusion and networking Methylmalonic Acidemia (MMA) cells (Tsi 4290) were seeded o/n in 96-well plates (density 5000 cells/well) in culture minimum MEM (GIBCO, 10370-021) supplemented with 2 mM L-Glutamine (Thermo Fisher Scientific), 10% FBS (Thermo Fisher Scientific 26400044) and 0.03% penicillin/streptomycin. Cells were incubated for 24 h with the following conditional medium: Agilent XF DMEM (Agilent 103575-100), pH 7.4 supplemented with 1 mM glucose, 2 mM L-glutamine and 1 mM pyruvate.

After 24 hours incubation, cells were treated with 10 µM compounds from the present disclosure, 1% DMSO vehicle and 20 µM FCCP as control for 2 hours. After treatment, cells were stained with 100 µl of 1× mixture dye solution of 2 µM Hoechst (Thermo Fisher Scientific, 62249), 100 ng/ml MitoSox red (Thermo Fisher Scientific, M36008) and 50 ng/ml MitoTracker deep red (Thermo Fisher Scientific) at 37° C. for 30 minutes. Next, staining was removed, and cells fixed with 100 µl of 4% PFA for 10 minutes at RT. After the cells were washed one time with PBS, cells were permeabilized with 100 µl of 0.3% Triton X-100 for 10 minutes at RT. Analysis was carried out using a Thermo Scientific CellInsight CX7 High-Content Screening Platform.

Example 838: Measurement of MMP, ROS and ATP Multiplex

Cell culture and treatments. Primary adherent fibroblasts were cultured in minimum essential medium (MEM) (Gibco, 25030081) supplemented with 2 mM L-Glutamine (Gibco, 25030081), 15% fetal bovine serum (FBS) (Gibco, 26400044) and 1% penicillin/streptomycin (Gibco, 5140122) at 37° C. and 5% CO2. Cells were collected for either passaging or experiment at ~70-80% confluence. Cells were obtained by trypsinization and seeded at 10000 cells/well in cell culture microplates (Seahorse Bioscience, 101085-004) and allowed to adhere for 16 hours in culture media. After media was refreshed with DMEM (Agilent Seahorse 103575-100) supplemented with 1 mM glucose and 10% FBS (Gibco, 26400044). At the end of the incubation period, the cells were loaded with the relevant dye/ antibody for each cell health marker. The assay provided simultaneous measurement of cell health parameters including cell count, ROS formation (DHE), mitochondrial membrane potential (MitoTracker®) and cellular ATP content (CellTiter-Glo®, Promega). The plates were then scanned using an automated fluorescent cellular imager, ArrayScan® (Thermo Scientific Cellomics). Assay conditions were optimized by one skilled in the art.

Primary cells used in this example were obtained from Coriell Institute for Medical Research and consisted of GM00649, MSUD (Maple Syrup Urine Disease) Tyle IA; GM06225, Kearns-Sayre Syndrome; GM00612, MSUD (Maple Syrup Urine Disease) Tyle II GM00444, Pyruvate Carboxylase Deficiency and GM03672, Leigh Syndrome.

Example 839: Vitamin B12 Deficiency Mouse Model

A vitamin B12 deficiency mouse model was used following the methods described at Ghosh et al 2016.

Animal maintenance and feeding. Female weanling C57BL/6 mice (n=65) were obtained at 3 weeks of age from Shanghai Sippe-Bk Lab Animal Co., Ltd. The mice were housed in a SPF environment and maintained at 20° C.±6, under standard lighting conditions (12-h light/dark cycle). Animals were divided into 5 animals per cage during modelling, and 3 animals per cage during compound test. The 3-week old mice were fed ad libitum with either AIN-76A control diet (D100010 designated as control diet group or the same diet deficient in vitamin B12 (D07012902) with pectin as the source of fiber (designated as Cbl cobalamin deficient) referred to as B12R+ by Ghosh et al. (Research Diets Inc., New Brunswick, NJ, USA). Cobalamin-restricted diet with pectin (B12R+) contained 50 g pectin/kg diet, because it has been shown earlier that pectin binds the intrinsic factor in the intestine and makes vitamin B12 less bioavailable. The control diet contained 50 g cellulose/kg diet as the fiber source instead of pectin. The mice also had ad libitum access to deionized water. Food intake and body weights were recorded every week.

Compound treatment. After 6 weeks of feeding on either control or Cbl−/− diet, 9-week-old mice on Cbl−/− diet were randomly assigned into 5 groups with 3 mice per group per treatment. Mice in each group were IP treated with vehicle (1% HPBCD, Sigma, H107) or were dosed at 50 mpk with compounds of the present invention BID. One group of mice were sacrificed at 24 h after the first dose. $2^{nd}$ group of mice were sacrificed at 72 h after the first dose. $3^{rd}$ group of mice were sacrificed after 168 h (i.e 7 days) after the first dose. $4^{th}$ group of mice were fasted for 12 h before sacrificing after 72 h of the first dose. $5^{th}$ group of mice were first fasted for 12 h before any vehicle or compound treatment and sacrificed after 72 h after the first dose.

Tissue and sample collection. At above specified timepoints, mice were weighed and anesthetized with $CO_2$ before sample collection. For blood collection, the chest was opened to expose the heart. Up to 300 μl blood was drawn from the left ventricle with 1 ml syringe rinsed with EDTA-Na and dispensed into a K3EDTA mini collect tube (Greiner Bio-One) for haematology analysis. Then a new syringe was used to draw remaining blood from heart as much as possible. Serum was isolated by centrifugation at 5000 rpm for 10 min, aliquoted and kept at −80° C. until further use. For tissue collection after blood was drawn, mice were perfused with ice cold saline from the left ventricle. Heart, liver, kidney, spleen, brain was weighed after isolation. Then left leg was kept in ice cold PBS and bone marrow was isolated for further immunophenotype analysis. The liver was cut into one piece of 100 mg for homogenization, other pieces of 40 mg or 100 mg were snap frozen and were stored at −80° C. before use. Heart, liver and kidney were also cut into a piece of 40 mg, snap frozen in liquid nitrogen and other part was stored at −80° C. For brain isolation, skull was cut open to expose the brain and was carefully taken out with forceps. Pieces of 40 mg were cut and snap frozen and stored at −80° C.

Example 840: Vitamin B12 Deficiency Mouse Model. Hematology Analysis

Blood hematology was performed with XN-1000-Hematology-Analyzer (Sysmex America, Inc.). Sample processing was performed as described in Example 839.

Example 841: Vitamin B12 Deficiency Mouse Model. Biochemistry Parameters

Creatinine, Urea in urine and blood would be measured using biochemical analyzer Mindray BS-380 (Mindray, Shenzhen, P.R. China). Sample processing was performed as described in Example 839.

Example 842: Vitamin B12 Deficiency Mouse Model. Immunophenotyping Analysis

Sample processing was performed as described in Example 839. All bone marrow cells were collected, and cell suspension were filtered through 70 μM cell strainer and washed with PBS. Red blood cells were removed by using 1×RBC Lysis Buffer (Sigma, R7757). Cells were stained for live/dead dye (FVS780, BD 565388), surface and intracellular markers with fixation/permeabilization solution (eBioscience, 88-8824-00) with anti-mouse CD45 (eBioscience, 69-0451-82), anti-mouse CD11b (eBioscience, 12-0112085), anti-mouse F4/80 (Biolegend, 123116), anti-mouse MHC-II (BD, 553623), anti-mouse CD206 (Biolegend, 141717), anti-Ly6G (BD, 560602), and anti-Ly6C (Biolegend, 128017). Cells were gated on singlets followed by live cells, CD45, CD11b, & F4/80 and CD11b+F4/80 dim were defined as macrophages. Further M1 macrophages were gated as MHC-II positive and CD206+ were gated as M2 macrophages.

Example 843: Vitamin B12 Deficiency Mouse Model. Mouse Liver Protein Determination Sample processing was performed as described in Example 839. ELISAS in the liver homogenates were performed according to manufacture instructions for TNFα and protein carbonyls. One could perform the other ELISAs as described and instructed by manufacturing protocols. Below is the list of ELISA assay kits and catalog number for each assays

| Reagents | Cat Number |
|---|---|
| Mice Glu ELISA Kit | JL18293 |
| Mice GSH ELISA Kit | JL20360 |
| Mice GSSG ELISA Kit | JL20647 |
| Mice SMA ELISA Kit | JL46310 |
| Mice MDA ELISA Kit | JL13329 |
| Mice PCO ELISA Kit | JL46483 |
| Mice CAT ELISA Kit | JL18163 |
| Mice SOD ELISA Kit | JL12237 |
| Mice TG ELISA Kit | JL46662 |
| Mice LDL-C ELISA Kit | JL20313 |
| Mice HDL-C ELISA Kit | JL20356 |
| Mice MPO ELISA Kit | JL10367 |
| Mice AH3 ELISA Kit | JL48757 |
| Mice AH4 ELISA Kit | JL48753 |
| Mice Acetylated α-tubulin ELISA Kit | JL48751 |
| Mice FGF-21 ELISA Kit | JL20295 |
| Mice ADEN ELISA Kit | JL20696 |
| Mice PPAR-α ELISA Kit | JL12627 |
| Mice PPAR-γ ELISA Kit | JL20369 |
| Mice Acetylated Lysine ELISA Kit | JL48758 |
| Mice ALT ELISA Kit | JL13983 |
| Mice ALP ELISA Kit | JL26471 |
| Mice AST ELISA Kit | JL13939 |
| Mice OGT ELISA Kit | JL45999 |
| Mice NRF1 ELISA Kit | JL48755 |
| Mice NRF2 ELISA Kit | JL48768 |
| Mice YY1 ELISA Kit | JL48770 |
| Mice ERα ELISA Kit | JL48767 |
| Mice SIRT1 ELISA Kit | JL20291 |
| Mice SIRT2 ELISA Kit | JL47860 |
| Mice SIRT3 ELISA Kit | JL48783 |
| Mice SIRT4 ELISA Kit | JL48762 |
| Mice SIRT5 ELISA Kit | JL48778 |
| Mice SIRT6 ELISA Kit | JL48771 |
| Mice TNF-α ELISA Kit | JL29365 |
| Mice IL-6 ELISA Kit | JL12523 |
| Mice IL-1β ELISA Kit | JL46166 |
| Mice IL-10 ELISA Kit | JL10138 |
| Mice IL-4 ELISA Kit | JL11806 |
| BCA Kit | JL48943 |
| Lysis buffer | Bioshar-BL504A |
| PMSF | P0100 |
| Deacetylase inhibitor cocktail | Tianenzhe 130521-1 |

Example 844: Vitamin B12 Deficiency Mouse Model

Analyte determination in serum. Mouse serum samples from Example 839 would be used to measure analytes in multiplex panels 1, 2 and 3 using Luminex_LX 200 following the manufacturer recommendations. AYOXXA LUNARIS based method would be used to measure analytes in Panel 4 and 5 following the manufacturer recommendations.

Panel descriptions would be as described below.

Panel 1 would consist of mouse serum diluted 1:2 with the buffer provided in the kits (R&D customized panel) with the following analytes measured: Angiopoietin-2, BaFF/BLyS/ TNPSP1311, ClqR1/CD93, MCP-1, CCL3/MTP-1 alpha, CCT A/MIP-1beta, CCLS/RANTES, CCI-1, 1/Eotaxin, CCI,1 2/MCP-5, CCL20/MIP-3 alpha, CCL221MDC, KC, MIP-2, IP-10, CXCL1 2/SDF-I alpha, Dkk-1, EGP, PGP2, FGF-21, G-CSf, GM-CSR, IFN-gamma, IL-Iα/IL-F1, IL-1 beta/IL-1F2, IL-2, IL-3, IL-4, IL-6, IL-10, IL12, p70, IL-13, IL-17/IL-17 A, IL-17E/IL-25, IL-27, IL-33, Leptin/OB, LIX, M-CSF, TNF-alpha, and VEGF.

Panel 2 (R&D systems) would consist of 1 plex where Adiponectin was measured in 1:4000 diluted serum.

Panel 3 (R&D systems) would consist of 5 plex where Cystatin C, IVIMP2 IM P-2, IYIM P-3, MCP-2, and Adipsit were measured in 1:200 diluted serum.

Panel 4 (Millipore) would consist of 2 plex where Glucagon and Insulin were measured in 1:5 diluted serum.

Panel 5 (Millipore, Cardiovascular Disease) would consist of 3 plex where Troponin-T, Troponin-1, and sCD40L were measured in 1:20 diluted serum.

For the Luminex Assay Protocol, samples would be thawed at 4° C. prior to the start of assay and kept on ice throughout the assay procedures. Manufacturers' protocols would be followed for all panels with a general protocol as follows. All kit components would be brought to room temperature. Reagents were prepared according to the kit's instructions (wash buffers, beads, standards, etc.). Assay plates (96-well) were loaded with assay buffer, standards, samples, and beads and then covered and incubated on the plate shaker (500 rpm) overnight at 4° C. After the primary incubation, plates would be washed twice and then the detection antibody cocktail was added to all the wells; the plates were covered and left to incubate at room temperature for 1 hour on the plate shaker. After the one hour incubation, streptavidin-phycoerythrin fluorescent reporter will be added to all the wells, and the plate will be covered and incubated for 30 minutes at room temperature on the plate shaker. Plates were then washed twice and the beads were resuspended in sheath fluid, placed on the shaker for 5 minutes, and then read on Bio-Plex®200 following manufacturers' specifications and using Bio-Plex Manager software v6.0. Samples were analysed following techniques known to those having skill in the art.

For the AYOXXA Assay Protocol, samples were thawed at 4° C. prior to the start of assay and kept on ice throughout the assay procedures. Sample dilutions would be prepared first in a 96 or 384 well plate for ease of transfer to the Lunaris™ BioChip. Manufacturers' protocols would be followed for all panels with a general protocol as follows: all kit components were brought to room temperature, with the exception of the SA-PE and antibodies. Reagents were prepared as per kit's instructions (wash buffers, standards, etc.). Assay plates were loaded with blanks, standards, and samples and then covered, centrifuged for 1 min at 700×g, and incubated at room temperature for 3 hours. Detection antibody was prepared 10 minutes prior to use. After the sample incubation, plates were washed three times and then the detection antibody cocktail were added to all the wells; the plates were covered, centrifuged, and left to incubate at room temperature for 1 hour. SA-PE was prepared 10 min prior to use. After the one hour incubation, the plates were washed three times and streptavidin-phycoerythrin fluorescent reporter was added to all the wells. The plate was covered, centrifuged, and incubated for 30 minutes at room temperature, and protected from light. Plates were then washed a total of 6 times and then dried for 1.5 hours in a sterile fume hood, avoiding direct light. Plates were then imaged on a specialized LUNARIS™ Reader™ using LUNARIS™ Control Software and LUNARIS™ Analysis Suite for readout settings known to those having skill in the art.

The presence of assay biomarkers in the samples, controls, and standards generates a fluorescent signal that is detected with a fluorescent microscope or Lunaris™ Reader. Quantification of the readout is performed entirely by the Lunaris™ Analysis Suite. Data generated included fluorescence intensity, observed concentration, LOD, LLOQ, and ULOQ exported as a Microsoft Excel file.

Example 845: Vitamin B12 Deficiency Mouse Model. Effect of Compounds on Plasma Organic Acid Levels The effect of the compounds of the present disclosure on circulating concentrations of methylmalonic acid in plasma can be determined by liquid chromatography-tandem mass spectrometry (LC-MS/MS) after O-benzylhydroxylamine (O-BHA) derivatization under aqueous conditions. One can analyse sample processing by the procedure described in Example 839. Sample preparation: Working Solutions of 5000 ng/mL D3-methylmalonic acid (d3-MMA, Sigma, 490318) and 5000 ng/mL D4-succinic acid (d4-SA, Sigma, 293075) would be prepared in methanol. 20 µL of working solutions will be diluted with methanol to a final volume of 200 µL, and the resulting Calibration Standard Solution containing 500 ng/ml d3-MMA and 500 ng/ml d4-SA was added into 50 µL of murine plasma. The samples would be thoroughly mixed, centrifuged (5800 rpm, 4° C., 10 min), and a 180 µL aliquot of supernatant was dried under a stream of nitrogen, before being reconstituted in 100 µL water and vortexed for 10 min. 50 µL of 1M O-benzylhydroxylamine (O-BHA) and 50 µL of 1M 1-ethyl-3-(3-dimethylamino) propyl carbodiimide hydrochloride (EDC) in pyridine buffer (50 mM Pyridine/acetic acid, pH 5.5) was added to the sample, which was mixed and incubated at room temperature. After 1 hr 500 µL ethyl acetate was added, and the plates would be shaken for 10 min using a vortexer, followed by centrifugation (5800 rpm, 4° C., 10 min). An aliquot of 400 µL supernatant would be dried under a stream of nitrogen, reconstituted in 150 µL methanol:water (50:50 v % v), vortexed and centrifuged (5800 rpm, 4° C., 10 min). 5 µL of supernatant was injected for LC-MS/MS analysis.

Sample analysis: A Triple Quad 6500 ACQUITY UPLC System (AB Sciex Instruments, API6500, triple quadruple) LC-MS/MS instrument would be used, controlled by Analyst 1.6.2 Software (AB Sciex Instruments). The chromatographic separation of the analytes will be performed on a Waters BEH C18 Column (2.1×50 mm, 1.7 µm) with a column temperature held at 60° C. Eluent A consisted of ultrapure water plus 0.1% formic acid (ULC-MS grade). Eluent B consisted of methanol plus 0.1% formic acid (ULC-MS grade). Gradient elution at a flow of 0.60 mL/min was performed by changing % B as follows: 0.0-1.0 min: 2% to 30%; 1.0-5.5 min: 30% to 40%; 5.5-5.6 min: 40% to 98%; 5.6-6.2 min: 98%; 6.2-6.3 min: 98% to 2%; 6.3-7.0 min: 2%.

All analytes and ISs were measured in positive electrospray ion mode; the dwell times were 20 ms each. Optimized MS/MS settings are summarized in the following Table

| Analyte | Parent mass (Da) | Daughter mass (Da) | Declustering potential (DP) | Collision energy (CE) | Retention time (min) |
| --- | --- | --- | --- | --- | --- |
| Methylmalonic acid | 329.1 | 91.1 | 60 | 38 | 3.5 |
| D3-Methylmalonic acid | 332.1 | 91.0 | 70 | 38 | 3.48 |
| Succinic acid | 329.1 | 206.0 | 60 | 14 | 3.35 |
| D4-Succinic acid | 333.3 | 210.1 | 60 | 14 | 3.33 |

The final Turbo Spray IonDrive source settings were the following: curtain gas flow 35 psig; collision gas 8 psig; nebulizer gas 60 psig; turbo gas 60 psig; source temperature (at setpoint) 500.0 C; entrance potential 10 V; collision cell exit potential 6 V.

Similar or non-derivatized liquid chromatography-tandem mass spectrometry (LC-MS/MS) methods can be used for the analysis of endogenous biomarkers, Acyl-CoA species (such as but not limited to Acetyl-CoA, Succinyl-CoA, Malonyl-CoA, TCA cycle intermediates and the like), Acyl-Carnitines, Carnitine and AcylCarnitine Transport and transporters, ketone bodies, Organic Acids, and other metabolites consistent with the biochemical and metabolic pathways, in biological samples including tissues (such as but not limited to liver, kidney, heart, muscle, bone, or skin tissue, and fluids, such as but not limited to blood, serum, plasma, urine, or cerebrospinal fluid). A variety of techniques known to those having skill in the art can be used, to extend these methods to alternative sample types, including but not limited to grinding, precipitation, centrifugation, and filtration.

Example 846: Vitamin B12 Deficiency Mouse Model. Measuring Muscle Strength by Grip Test Analysis of Cbl−/− Mice Vs Mice on Control Diet Mice at 18 weeks of age were either fed on control diet (n=12 mice) or cbl−/− diet (n=30 mice) for 15 weeks. Grip strength test was measured by using a Grip Strength test meter for mice and rats (Jiangsu, SANS Biological Technology, CO. LTD, SA417) and recorded as day zero grip strength analysis. Briefly, machine was turned on (push peak) and calibrated to zero. Front leg strength was measured by pulling the mice away from the bar by holding the tail of the mice. Totals values were measured for each mouse. After the measurement the cbl−/− mice were divided into three groups of N=10 mice per group. Each group received either vehicle (0.1% saline) or compounds of the present invention, IP at the dose of 50 mpk QD. Grip strength was again measured in the above treated groups i.e. control diet, cbl−/− diet vehicle treated, or treated with compounds of the present invention after 5, 12 and 19 days.

Example 847: Effect of Compounds on Mitochondria) Membrane Potential

HepG2 cells (ATCC, HB-8065) were cultured (5% CO2 at 37° C.) and plated in Poly-D-Lysine 384-Well plate (Corning, 356663) at a density of 160000 cells/mL in 50 µL/well. Culture and assay media consisted of DMEM (Gibco, 11995-065) supplemented with 1% Penicillin-Streptomycin and 10°/o FBS (Hyclone, SV30087.03).

MITO-ID® MP detection Kit (ENZ-51018) was used and manufacturer instructions followed. Cells were allowed to settle for 30 min at room temperature and further incubated overnight (37° C. and 5% CO2) for adherence. Next day, test compounds (50-10 µM) and vehicle DMSO (0.2%) were added at the recommended volumes to the 384-well plate for 7 days without media change using a Tecan compound dispenser. All the solutions and wash buffers were prepared and dispensed according to manufacturer's volumes for a 384-well plate format.

Example 848: Neuroprotective Effect of Test Compounds on Damage Induced by LPS on Culture of Mesencephalic Neurons Drug preparation. Six mg of 15 compounds (Entry No, Comet Therapeutics No and molecular weight as seen in the Table below) will be sent by the sponsor and will be tested under two concentrations: 10 µM and 50 µM. The stock solutions will be prepared 1000× the concentration in 100% DMSO. The final concentration of the vehicle (DMSO) is set at 0.1%.

Test animals. Pregnant Wistar rats (Janvier; France) are used for the study. They are group-housed and maintained in a room with controlled temperature (21-22° C.) and a reversed light-dark cycle (12 h/12 h; lights on: 17:30-05:30; lights off: 05:30-17:30) with food and water available ad libitum.

The protocol is performed in 3 independent cultures. For each culture, each condition is performed in sextuplicate.

| Day | Tasks |
| --- | --- |
| 0 | Plating of a primary culture of rat embryo mesencephalic cells. This culture contains microglia, astrocytes and neurons |
| 2 | Renewal of medium |
| 5 | Renewal of medium |
| 7 | Compound application (1 h before LPS injury) + LPS exposure |
| 8 (24 h post-LPS) | Measure of nitric oxide (NO), TNF-α and IL1-β release |
| 12 (day 5 post-LPS) | Measure of death of dopaminergic neurons (Tyrosine hydroxylase positive neurons) and release of NO in the supernatant |

Female rat of 15 days gestation is killed by cervical dislocation. Fetuses are removed from the uterus and their brains are harvested and placed in ice-cold medium (Leibovitz's L15 medium, Gibco). Only ventral mesencephalic flexure is used for the cell preparations. The midbrain is dissociated by trypsinization. The reaction is stopped, and the suspension is triturated and centrifuged. The pellet of dissociated cells is resuspended in culture medium consisted of DMEM-F12 (Gibco), containing 10% FBS (ATCC), 10% Horse serum (Gibco) and 2 mM L-glutamine (Gibco). Viable cells are counted and seeded on 96-well plates, precoated with poly-L-lysine. Cells are maintained in a humidified incubator at 37° C. in 5% CO2-95% air atmosphere. Half of the medium is changed on day 2 and day 5.

Treatment. On day 7, culture media are removed and replaced by new medium consisting of DMEM-F12 (Gibco) supplemented with 2% FBS (ATCC), 2% Horse serum (Gibco) and 2 mM L-glutamine (Gibco) and containing vehicle or test substances. After 1-hour exposure, LPS at 10 ng/ml is added and exposure further continued for 24 hours or 5 days period.

Inflammatory response measurement and neuronal death evaluation. NO production is measured in the media 24 h and 5 days after LPS exposure using the Griess reagent kit (Molecular Probes). The Griess reagent Assay is a colorimetric reaction assay which measures the conversion of a sulfanilic salt into an azo dye product by nitrite. Visible wavelength absorbance data is collected using a 96-well plate reader at 570 nm (Multiskan EX, Thermo Fisher, France).

IL-10 and TNF-α release are measured in the media 24 h after LPS exposure using the ELISA development kit (PeproTech). The ELISA plate, previously coated with anti-IL-10 or anti-TNF-α antibody at 1 µg/ml, is incubated 1 h with PBS containing 1% of BSA (bovine serum albumin). After washing four times with PBS containing 0.05% of Tween-20, the plate is successively incubated 2 h with supernatant, 2 h with biotinylated antibody at 0.5 µg/ml in PBS containing 0.1% of BSA and 0.05% of Tween-20, 45 min with Avidin-HRP conjugated at 1/2000 and 30 min with color ABTS substrate (Sigma). Visible wavelength absorbance data is collected using a 96-well plate reader at 405 nm with wavelength correction set at 650 nm (Multiskan EX, Thermo Fisher, France).

Immunodetection of tyrosine hydroxylase positive neurons. On day 12 (5 days after LPS exposure), cultures are fixed 30 min at 4° C. with paraformaldehyde in PBS (4%, Sigma). Then, cells are successively permeabilized with 0.1% Triton X100 for 30 min, saturated with PBS containing 3% of BSA (bovine serum albumin) and are incubated 2 h with anti-tyrosine hydroxylase antibody (Sigma, 1:10000; clone TH-2) at 1/10 000 in PBS containing 0.5% of BSA. Cells are washed three times with PBS containing 0.5% of BSA, and they are incubated 1 h with goat anti mouse antibody coupled with AF488 (Invitrogen A11001) diluted at 1/1000 in PBS containing 0.5% of BSA. Finally, nuclei are stained with DAPI at 1/1000 in PBS containing 0.5% of BSA. After rinsing with PBS, the plate is visualized and examined with Cell Insight HCS (Thermo Scientific) to determine the number of tyrosine hydroxylase positive cells per well.

Statistical Analysis. The drug-induced effect on NO and cytokines is calculated by setting the response of the LPS-stimulated control as 100%. The drug-induced effect on TH-positive neurons by setting the non-intoxicated culture condition as 100%. A global analysis of the data is performed using a one-way analysis of variance (ANOVA), followed by Fisher's Protected Least Significant Difference when applicable. The level of significance is set to $p<0.05$. Study results in a form of Excel spreadsheet that contains individual data and graphs.

Example 850

Using the procedure described in Example 800 the following cell lines listed in the Table below were screened and demonstrated an increase in glycolysis by at least 10% upon treatment with the indicated Compounds of the present invention using the Assay condition as stated below.

| Disease | Cell Line | Example No of Procedure used | Assay Condition used in Example No | The following Compounds Increased glycolysis by at least 10% |
|---|---|---|---|---|
| NIEMANN-PICK DISEASE | GM22870 | E059 | 5 mM Glucose | 42, 448 |
| OTC | GM12604 | E057 | 5 mM Glucose | 42, 448 |
| Huntington Disease | GM21756 | E054 | 5 mM Glucose | 42, 448 |
| PC | GM00444 | E048 | 5 mM Glucose | 42, 448 |
| GA-1 | GM10653 | E045 | 5 mM Glucose | 485 |
| Leigh (ATP6) | GM13411 | E036 | 1 mM Glucose | 42, 448 |
| Leigh | GM03672 | E035 | 1 mM Glucose | 5, 447, 485 |
| PA | TSI4626 | E039 | 1 mM Glucose | 1, 39, 61 |

Example 851

Using the procedure described in Example 800, the following cell lines listed in the Table below were screened and demonstrated an increase in glycolysis by at least 30% upon treatment with the indicated Compounds of the present invention using the Assay condition as stated below.

| Disease | Cell Line | Example No of Procedure used | Assay Condition used in Example No | The following Compounds Increased Glycolysis by at least 30% |
|---|---|---|---|---|
| NIEMANN-PICK DISEASE | GM22870 | E059 | 5 mM Glucose | 42, 448 |
| Huntington Disease | GM21756 | E054 | 5 mM Glucose | 448 |
| GA-1 | GM10653 | E045 | 5 mM Glucose | 485 |
| Leigh (ATP6) | GM13411 | E036 | 1 mM Glucose | 485 |
| Leigh | GM03672 | E035 | 1 mM Glucose | 5, 447, 485 |
| PA | TSI4626 | E039 | 1 mM Glucose | 1, 39 |

Example 852

Using the procedure described in Example 800, the following cell lines listed in the Table below were screened and demonstrated an increase in glycolysis by at least 50% upon treatment with the indicated Compounds of the present invention using the Assay condition as stated below.

| Disease | Cell Line | Example No of Procedure used | Assay Condition used in Example No | The following Compounds Increased Glycolysis by at least 50% |
|---|---|---|---|---|
| NIEMANN-PICK DISEASE | GM22870 | E059 | 5 mM Glucose | 42 |

-continued

| Disease | Cell Line | Example No of Procedure used | Assay Condition used in Example No | The following Compounds Increased Glycolysis by at least 50% |
|---|---|---|---|---|
| Leigh | GM03672 | E035 | 1 mM Glucose | 5, 447, 485 |
| PA | TSI4626 | E039 | 1 mM Glucose | 39 |

Example 852

Using the procedure described in Example 800, the following cell lines listed in the Table below were screened and demonstrated an increase in Maximal Respiration AUC by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased Maximal Respiratory Capacity by at least 10% |
|---|---|---|---|---|
| MMA | Tsi 5224 | 800 | A 10 μM | 39, 36, 6, 20, 39, 42 |
| MMA | GM01673 | 800 | A 10 μM | 448 |
| MMA | GM01673 | 800 | A 50 μM | 1, 21, 61, 451, 485, 633 |
| MMA | GM01673 | 800 | D 50 μM | 1 |
| MMA | GM01673 | 800 | B 50 μM | 633 |
| PA | Tsi 6337 | 800 | B 10 μM | 39, 36 |
| PA | GM00371 | 800 | D 10 μM | 21 |
| PA | GM00371 | 800 | A 50 μM | 21 |
| PA | GM00371 | 800 | D 50 μM | 1, 61 |

Example 853

Using the procedure described in Example 800, the following cell lines listed in the Table below were screened and demonstrated an increase in Maximal Respiration AUC by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased Maximal Respiratory Capacity by at least 30% |
|---|---|---|---|---|
| PA | Tsi 6337 | 800 | B 10 μM | 39, 36 |
| PA | GM00371 | 800 | D 50 μM | 61 |

Example 854

Using the procedure described in Example 800, the following cell lines listed in the Table below were screened and demonstrated an increase in Maximal Respiration AUC by at least 50% upon treatment with the indicated Compounds of the present invention using the Assay condition as stated below.

| Disease or Healthy Control Cell | Cell Line | Example No of Procedure used | Assay Condition used in Example No | The following Compounds Increased Maximal Respiratory Capacity by at least 50% |
|---|---|---|---|---|
| PA | GM00371 | 800 | D 10 μM | 21 |
| PA | GM00371 | 800 | D 50 μM | 61 |

Example 855

Using the procedure described in Example 800, the following cell lines listed in the Table below were screened and demonstrated an increase in Spare Capacity AUC by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased Spare Capacity by at least 10% |
|---|---|---|---|---|
| MMA | GM01673 | 800 | A 50 μM | 1 |
| MMA | GM01673 | 800 | B 50 μM | 633 |
| PA | GM00371 | 800 | A 10 μM | 21 |

Example 866

Using the procedure described in Example 800, the following cell lines listed in the Table below were screened and demonstrated an increase in Spare Capacity AUC by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased Spare Capacity by at least 30% |
|---|---|---|---|---|
| MMA | GM01673 | 800 | A 50 μM | 1 |

Example 857

Using the procedure described in Example 800, the following cell lines listed in the Table below were screened and demonstrated an increase in Spare Capacity AUC by at least 50% upon treatment with the indicated Compounds of the present invention using the Assay condition as stated below.

| Disease or Healthy Control Cell | Cell Line | Example No of Procedure used | Assay Condition used in Example No | The following Compounds Increased Spare Capacity by at least 50% |
|---|---|---|---|---|
| MMA | GM01673 | 800 | A 50 μM | 1 |

Example 858

Using the procedure described in Example 816, the following cell lines listed in the Table below were screened and demonstrated a decrease in Glutathione Dimer (GS-SG) by at least 10% upon treatment with the indicated Compounds of the present invention using the Assay condition as stated below.

| Disease or Healthy Control Cell | Cell Line | Example No of Procedure used | Assay Condition used in Example No | The following Compounds Decreased GS-SG Dimer by at least 10% |
|---|---|---|---|---|
| PA | Tsi 6337 | 816 | B | 61 |
| PDH | GM01503 | 816 | B | 39, 42, 448 |
| α-Ketoglutarate dehydrogenase deficiency | 962 | 816 | B | 61 |

Example 859

Using the procedure described in Example 816, the following cell lines listed in the Table below were screened and demonstrated a decrease in Glutathione Dimer (GS-SG) by at least 30% upon treatment with the indicated Compounds of the present invention using the Assay condition as stated below.

| Disease or Healthy Control Cell | Cell Line | Example No of Procedure used | Assay Condition used in Example No | The following Compounds Decreased GS-SG Dimer by at least 30% |
|---|---|---|---|---|
| PA | Tsi 6337 | | B | 61 |

Example 860

Using the procedure described in Example 816, the following cell lines listed in the Table below were screened and demonstrated an increase in Total Glutathione (Total GSH) by at least 10% upon treatment with the indicated Compounds of the present invention using the Assay condition as stated below.

| Disease or Healthy Control Cell | Cell Line | No of Procedure used | Assay Condition used in Example No | The following Compounds Increased Total GSH by at least 10% |
|---|---|---|---|---|
| Healthy | GM00041 | 816 | B | 61 |
| Healthy | GM05659-20191031 | 816 | B | 61 |
| Healthy | GM23974 | 816 | B | 61 |
| PA | Tsi 3618 | 816 | B | 61 |
| MMA | Tsi 5224-20191107 | 816 | B | 61 |
| MMA | Tsi 4290 | 816 | B | 61 |
| VLCAD | GM17475 | 816 | B | 448 |
| α-Ketoglutarate dehydrogenase deficiency | 926 | 816 | B | 42, 61 |
| MELAS Syndrome | V877 | 816 | B | 42, 61 |

Example 861

Using the procedure described in Example 816, the following cell lines listed in the Table below were screened and demonstrated an increase in Total Glutathione (Total GSH) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased Total GSH by at least 30% |
|---|---|---|---|---|
| Healthy | GM05659-20191031 | 816 | B | 61 |
| MELAS Syndrome | V877 | 816 | B | 42 |

Example 862

Using the procedure described in Example 816, the following cell lines listed in the Table below were screened and demonstrated an increase in Free Glutathione-to-Glutathione Dimer (Ratio GSH:GS-SG) by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased Ratio of Free GSH-to-GS-SG Dimer by at least 10% |
|---|---|---|---|---|
| Healthy | GM05659-20191031 | 816 | B | 42 |
| PA | Tsi 3618 | 816 | B | 61 |
| PA | Tsi 6337 | 816 | B | 61 |
| PDH | GM1503A | 816 | B | 39, 42, 448 |
| α-Ketoglutarate dehydrogenase deficiency | 962 | 816 | B | 42, 61 |

Example 863

Using the procedure described in Example 816, the following cell lines listed in the Table below were screened and demonstrated an increase in Free Glutathione-to-Glutathione Dimer (Ratio GSH:GS-SG) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased Ratio of Free GSH-to-GS-SG Dimer by at least 30% |
|---|---|---|---|---|
| PA | Tsi 6337 | 816 | B | 61 |
| α-Ketoglutarate dehydrogenase deficiency | 962 | 816 | B | 61 |

Example 864

Using the procedure described in Example 816, the following cell lines listed in the Table below were screened and demonstrated an increase in Free Glutathione-to-Glutathione Dimer (Ratio GSH:GS-SG) by at least 50% upon treatment with the indicated Compounds of the present invention using the Assay condition as stated below.

| Disease or Healthy Control Cell | Cell Line | Example No of Procedure used | Assay Condition used in Example No | The following Compounds Increased Ratio of Free GSH-to-GS-SG Dimer by at least 50% |
|---|---|---|---|---|
| PA | Tsi 6337 | 816 | B | 61 |

Example 865

Using the procedure described in Example 800, the following cell lines listed in the Table below were screened and demonstrated an increase in ECAR by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased ECAR by at least 10% |
|---|---|---|---|---|
| PA | Tsi 6337 | | A | 6, 20, 36, 39, 42 |
| MMA | Tsi 5224 | | A | 6, 20, 36, 39, 42 |

Example 866

Using the procedure described in Example 800, the following cell lines listed in the Table below were screened and demonstrated an increase in ECAR by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased ECAR by at least 30% |
|---|---|---|---|---|
| PA | Tsi 6337 | | A | 6, 20, 36, 39, 42 |

Example 867

Using the procedure described in Example 800, the following cell lines listed in the Table below were screened and demonstrated an increase in ECAR by at least 50% upon treatment with the indicated Compounds of the present invention using the Assay condition as stated below.

| Disease or Healthy Control Cell | Cell Line | Example No of Procedure used | Assay Condition used in Example No | The following Compounds Increased ECAR by at least 50% |
|---|---|---|---|---|
| PA | Tsi 6337 | | A | 6, 20, 36, 39, 42 |
| MMA | Tsi 5224 | | A | 6, 20, 36, 39, 42 |

Example 868

Using the procedure described in Example 829 the Compounds of the present invention listed below increased sIL-2 by at least the percentage indicated when tested at the indicated concentration (1 or 10 microMolar).

| Compound No. | Concentration Tested (uM) | % increase in sIL-2 |
|---|---|---|
| 633 | 10 | ≥20% |

Example 869

Using the procedure described in Example 829 the Compounds of the present invention listed below increased sIL-6 by at least the percentage indicated when tested at the indicated concentration (1 or 10 microMolar).

| Compound No. | Concentration Tested (uM) | % increase in sIL-6 |
|---|---|---|
| 36 | 10 | ≥10% |
| 61 | 10 | ≥10% |
| 633 | 10 | ≥20% |
| 61 | 10 | ≥10% |
| 206 | 10 | ≥20% |

Example 870

Using the procedure described in Example 829 the Compounds of the present invention listed below decreased sTNFα by at least the percentage indicated when tested at the indicated concentration (1 or 10 microMolar).

| Compound No. | Concentration Tested (uM) | % decrease in sTNFα |
|---|---|---|
| 6 | 10 | ≥10% |
| 36 | 1 | ≥10% |
| 42 | 10 | ≥20% |
| 451 | 1 | ≥20% |
| 633 | 10 | ≥10% |

Example 871

Using the procedure described in Example 830 the Compounds of the present invention listed below increased Eotaxin-3 by at least the percentage indicated when tested at the indicated concentration (1 or 10 microMolar).

| Compound No. | Concentration Tested (uM) | % increase in Eotaxin-3 |
|---|---|---|
| 42 | 10 | ≥10% |
| 61 | 10 | ≥10% |
| 451 | 10 | ≥10% |
| 633 | 10 | ≥10% |

Example 872

Using the procedure described in Example 830 the Compounds of the present invention listed below increased VCAM-1 by at least the percentage indicated when tested at the indicated concentration (1 or 10 microMolar).

| Compound No. | Concentration Tested (uM) | % increase in VCAM-1 |
|---|---|---|
| 6 | 10 | ≥10% |
| 42 | 10 | ≥10% |
| 451 | 10 | ≥10% |

Example 873

Using the procedure described in Example 830, the Compounds of the present invention listed below decreased MMP-9 by at least the percentage indicated when tested at the indicated concentration (1 or 10 microMolar).

| Compound No. | Concentration Tested (uM) | % decrease in MMP-9 |
|---|---|---|
| 633 | 1 | ≥10% |

Example 874

Using the procedure described in Example 831, the Compounds of the present invention listed below increased IL-8 by at least the percentage indicated when tested at the indicated concentration (1 or 10 microMolar).

| Compound No. | Concentration Tested (uM) | % increase in IL-8 |
|---|---|---|
| 633 | 1 | ≥10% |

Example 875

Using the procedure described in Example 831, the Compounds of the present invention listed below decreased MMP-9 by at least the percentage indicated when tested at the indicated concentration (1 or 10 microMolar).

| Compound No. | Concentration Tested (uM) | % decrease in MMP-9 |
|---|---|---|
| 42 | 1 | ≥10% |
| 61 | 1 | ≥10% |
| 451 | 1 | ≥10% |
| 633 | 10 | ≥10% |

Example 876

Using the procedure described in Example 831, the Compounds of the present invention listed below decreased tPA by at least the percentage indicated when tested at the indicated concentration (1 or 10 microMolar).

| Compound No. | Concentration Tested (uM) | % decrease in tPA |
|---|---|---|
| 451 | 10 | ≥10% |

Measurement VCAM-1

Example 877

Using the procedure described in Example 832, the Compounds of the present invention listed below decreased VCAM-1 by at least the percentage indicated when tested at the indicated concentration (1 or 10 microMolar).

| Compound No. | Concentration Tested (uM) | % decrease in VCAM-1 |
|---|---|---|
| 6 | 1 | ≥10% |
| 36 | 1 | ≥10% |
| 61 | 1 | ≥10% |
| 451 | 1 | ≥10% |
| 633 | 1 | ≥10% |

Example 878

Using the procedure described in Example 832, the Compounds of the present invention listed below decreased Thrombomodulin by at least the percentage indicated when tested at the indicated concentration (1 or 10 microMolar).

| Compound No. | Concentration Tested (uM) | % decrease in Thrombomodulin |
|---|---|---|
| 6 | 10 | ≥20% |
| 36 | 10 | ≥20% |
| 42 | 10 | ≥10% |
| 61 | 10 | ≥20% |
| 451 | 1 | ≥10% |
| 633 | 1 | ≥10% |
| 61 | 10 | ≥20% |

Example 879

Using the procedure described in Example 832 the Compounds of the present invention listed below decreased Tissue Factor by at least the percentage indicated when tested at the indicated concentration (1 or 10 microMolar).

| Compound No. | Concentration Tested (uM) | % decrease in Tissue Factor |
|---|---|---|
| 36 | 10 | ≥10% |
| 61 | 1 | ≥10% |
| 633 | 1 | ≥10% |

Example 880

Using the procedure described in Example 832 the Compounds of the present invention listed below decreased uPAR by at least the percentage indicated when tested at the indicated concentration (1 or 10 microMolar).

| Compound No. | Concentration Tested (uM) | % decrease in uPAR |
|---|---|---|
| 36 | 1 | ≥10% |
| 633 | 1 | ≥10% |

Example 881

Using the procedure described in Example 832 the Compounds of the present invention listed below decreased IL-8 by at least the percentage indicated when tested at the indicated concentration (1 or 10 microMolar).

| Compound No. | Concentration Tested (uM) | % decrease in IL-8 |
|---|---|---|
| 42 | 10 | ≥10% |
| 633 | 10 | ≥10% |

Example 882

Using the procedure described in Example 807 the Compounds of the present invention listed below decreased levels of IL6 protein by at least the percentage indicated when tested at the indicated concentration (10 or 50 microMolar).

| Compound | Concentration Tested (uM) | % decrease in Macrophage IL-6 Secretion |
|---|---|---|
| 850 | 10 | ≥30% |
| 851 | 10 | ≥30% |

Example 883

Using the procedure described in Example 807 the Compounds of the present invention listed below increased IL-10 secretion by at least the percentage indicated when tested at the indicated concentration (10 or 50 microMolar).

| Compound | Concentration Tested (uM) | % Increase in IL-10 Secretion |
|---|---|---|
| 851 | 10 | ≥30% |

Example 884

Using the procedure described in Example 207 the Compounds of the present invention listed below decreased levels of TNF protein by at least the percentage indicated when tested at the indicated concentration (10 or 50 microMolar).

| Compound | Concentration Tested (uM) | % decrease in Macrophage TNFα Secretion |
|---|---|---|
| 850 | 50 | ≥30% |
| 851 | 10 | ≥30% |

Example 885

Using the procedure described in Example 814, the following cell lines listed in the Table below were screened and demonstrated an increase in NADP+(Nicotinamide Adenine Dinucleotide Phosphate) by at least 10% upon treatment with the indicated Compounds of the present invention using the Assay condition as stated below.

| Disease or Healthy Control Cell | Cell Line & Passage | Example No of Procedure used | Assay Condition used in Example No | The following Compounds Increased NADP+ by at least 10% |
|---|---|---|---|---|
| PA | Tsi 6337 P10 | 814 | A | 42 |
| PA | Tsi 6337 P10 |  | B | 39, 42 |
| Leigh | GM03672 P9 | 814 | A | 1, 485 |
| Leigh | GM03672 P9 | 814 | B | 1, 485, 49 |
| VLCAD | GM17475 P10 | 814 | A | 448 |
| VLCAD | GM17475 P10 | 814 | B | 448 |

Example 886

Using the procedure described in Example 814, the following cell lines listed in the Table below were screened and demonstrated an increase in NADP+(Nicotinamide Adenine Dinucleotide Phosphate) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased NADP+ by at least 30% |
|---|---|---|---|---|
| PA | Tsi 6337 P10 | 814 | B | 42 |
| Leigh | GM03672 P9 | 814 | A | 382 |
| Leigh | GM03672 P9 | 814 | B | 1, 39, 485 |
| PDH | GM1503A P10 | 814 | B | 1285 |
| VLCAD | GM17475 P10 | 814 | A | 448 |

Example 887

Using the procedure described in Example 814, the following cell lines listed in the Table below were screened and demonstrated an increase in NADP+(Nicotinamide Adenine Dinucleotide Phosphate) by at least 50% upon treatment with the indicated Compounds of the present invention using the Assay condition as stated below.

| Disease or Healthy Control Cell | Cell Line | Example No of Procedure used | Assay Condition used in Example No | The following Compounds Increased NADP+ by at least 50% |
|---|---|---|---|---|
| Leigh | GM03672 P9 | 814 | B | 1, 39, 485 |
| VLCAD | GM17475 P10 | 814 | A | 448 |

Example 888

Using the procedure described in Example 814, the following cell lines listed in the Table below were screened and demonstrated an increase in NADPH (Nicotinamide Adenine Dinucleotide Phosphate Reduced Form) by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased NADPH by at least 10% |
|---|---|---|---|---|
| PA | GM03590 P11 | 814 | A | 61 |
| MMA | Tsi 5224 P12 | 814 | A | 61 |
| Leigh | GM03672 P9 | 814 | A | 1, 39, 447 |
| Leigh | GM03672 P9 | 814 | B | 1, 39, 485 |
| PDH | GM1503A P10 | 814 | A | 39, 448 |
| PDH | GM1503A P10 | 814 | B | 42, 448 |
|  |  | 814 |  |  |
| VLCAD | GM17475 P10 | 814 | A | 39, 42, 448 |

Example 889

Using the procedure described in Example 814, the following cell lines listed in the Table below were screened and demonstrated an increase in NADPH (Nicotinamide Adenine Dinucleotide Phosphate Reduced Form) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased NADPH by at least 30% |
|---|---|---|---|---|
| Leigh | GM03672 P9 | 814 | A | 39 |
| Leigh | GM03672 P9 | 814 | B | 39, 447 |
| VLCAD | GM17475 P10 | 814 | A | 39, 42, 448 |

Example 890

Using the procedure described in Example 814, the following cell lines listed in the Table below were screened and demonstrated an increase in NADPH (Nicotinamide Adenine Dinucleotide Phosphate Reduced Form) by at least 50% upon treatment with the indicated Compounds of the present invention using the Assay condition as stated below.

| Disease or Healthy Control Cell | Cell Line | Example No of Procedure used | Assay Condition used in Example No | The following Compounds Increased NADPH by at least 50% |
|---|---|---|---|---|
| Leigh | GM03672 P9 | 814 | B | 447 |
| VLCAD | GM17475 P10 | 814 | A | 42, 448 |

Example 891

Using the procedure described in Example 800, the following cell lines listed in the Table below were screened and demonstrated an increase in Maximal Respiration AUC by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased Maximal Respiration AUC by at least 10% |
|---|---|---|---|---|
| PA | GM0371 | 800 | E | 61 |
| PA | GM03590 | 800 | E | 21, 35, 39, 42, 61, 485 |
| PA | GM03590 | 800 | G | 1, 39, 61 |
| PA | Tsi 6337 | 800 | E | 1, 39 |
|  |  | 800 | E | 1 |
| PA | Tsi 4626 | 800 | F | 1, 39, 61 |
|  |  | 800 | F | 5 |
|  |  | 800 | F | 1 |
|  |  | 800 | G | 5, 447, 485 |
| Leigh | GM13411 | 800 | E | 1, 39 |
|  |  | 800 | G | 5, 447, 485 |
| GAI | GM10653 | 800 | G | 4, 447, 485, |
|  |  | 800 | F | 5 |
| Huntington's Disease | GM21756 | 800 | F | 42, 448 |
| OTC | GM12756 | 800 |  | 42, 448 |

Example 892

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 868 | 10 | ≥30% |
| 858 | 10 | ≥30% |
| 866 | 10 | ≥30% |
| 853 | 10 | ≥30% |
| 856 | 10 | ≥30% |

Example 893

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 855 | 50 | ≥30% |
| 861 | 50 | ≥20% |
| 863 | 50 | ≥10% |

Example 894

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 852 | 50 | ≥20% |
| 862 | 10 | ≥20% |
| 860 | 50 | ≥10% |
| 864 | 50 | ≥20% |
| 865 | 10 | ≥20% |
| 867 | 10 | ≥20% |
| 609 | 10 | ≥10% |

Example 895

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 869 | 10 | ≥10% |

Example 896

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 36 | 50 | ≥30% |
| 20 | 50 | ≥30% |

Example 897

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 42 | 10 | ≥30% |
| 870 | 10 | ≥30% |

Example 898

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 3 | 10 | ≥10% |
| 485 | 50 | ≥10% |
| 451 | 50 | ≥20% |

Example 899

Using the procedure described in Example 821, the Compounds of the present invention listed below increased Glucose Uptake of HepG2 cells by at least the percentage indicated when tested at the indicated concentration (10 or 50 microMolar).

| Compound Number | Concentration Tested (uM) | % increase in Glucose Uptake |
|---|---|---|
| 61 | 50 | ≥10% |
| 39 | 50 | ≥10% |
| 862 | 50 | ≥10% |

Example 900

Using the procedure described in Example 800, the following cell lines listed in the Table below were screened and demonstrated an increase in Maximal Respiration AUC by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased Maximal Respiration AUC by at least 30% |
|---|---|---|---|---|
| PA | GM03590 | 800 | E | 21, 36, 39, 42, 61, 485 |
| PA | GM03590 | 800 | G | 1 |
| | | 800 | G | 5, 447, 485 |

OCR Spare Capacity AUC

Results Table

Example 901

Using the procedure described in Example 800, the following cell lines listed in the Table below were screened and demonstrated an increase in Spare Capacity AUC by at least 10% upon treatment with the indicated Compounds of the present invention using the Assay condition as stated below.

| Disease | Cell Line | Example No of Procedure used | Assay Condition used in Example No | The following Compounds Increased Spare Capacity AUC by at least 10% |
|---|---|---|---|---|
| PA | GM03590 | 800 | E | 21, 36, 39, 42, 61, 485 |
| PA | Tsi 6337 | 800 | E | 1 |
| PA | Tsi4626 | 800 | F | 1, 39, 62 |
| VLCAD | GM17475 | 800 | E | 39 |
| Leigh | GM13411 | 800 | E | 1 |
| | | 800 | G | 5, 447, 485 |
| PDH | GM01503 | 800 | G | 1, 39, 62 |
| GA-1 | GM10653 | 800 | G | 5, 447, 485 |
| | | 800 | F | 5 |
| | | 800 | F | 1, 42, 448 |
| Huntington Disease | GM21756 | 800 | F | 42, 448 |

Example 902

Using the procedure described in Example 800, the following cell lines listed in the Table below were screened and demonstrated an increase in Spare Capacity AUC by at least 30% upon treatment with the indicated Compounds of the present invention using the Assay condition as stated below.

| Disease | Cell Line | Example No of Procedure used | Assay Condition used in Example No | The following Compounds Increased Spare Capacity AUC by at least 30% |
|---|---|---|---|---|
| PA | GM03590 | 800 | E | 21, 36, 39, 42, 61, 485 |
| PA | Tsi 6337 | 800 | E | 1 |
| PA | Tsi4626 | 800 | F | 1, 39, 61 |
| | | 800 | G | 5, 447, 485, |
| PDH | GM01503 | 800 | G | 1, 39, 62 |
| GA-1 | GM10653 | 800 | G | 5, 447 485 |
| | | 800 | F | 5 |
| | | 800 | F | 42 |
| Huntington Disease | GM21756 | 800 | F | 42, 448 |

Example 903

Using the procedure described in Example 800, the following cell lines listed in the Table below were screened and demonstrated an increase in Spare Capacity AUC by at least 50% upon treatment with the indicated Compounds of the present invention using the Assay condition as stated below.

| Disease or Healthy Control Cell | Ceil Line | Example No of Procedure used | Assay Condition used in Example No | The following Compounds Increased Spare Capacity AUC by at least 50% |
|---|---|---|---|---|
| PA | GM03590 | 800 | E | 21, 36, 39, 42, 61, 485 |
| PA | Tsi 6337 | 800 | E | 1, 485 |
| PA | Tsi4626 | 800 | F | 1, 39, 61 |
| | | 800 | G | 485 |
| PDH | GM01503 | 800 | G | 39, 62 |
| GA-1 | GM10653 | 800 | G | 5, 447, 485 |
| Huntington Disease | GM21756 | 800 | F | 43, 448 |

-continued

| Disease or Healthy Control Cell | Ceil Line | Example No of Procedure used | Assay Condition used in Example No | The following Compounds Increased Spare Capacity AUC by at least 50% |
|---|---|---|---|---|

Example 904

Using the procedure described in Example 800, the following cell lines listed in the Table below were screened and demonstrated an increase in Spare Capacity AUC by at least 100% upon treatment with the indicated Compounds of the present invention using the Assay condition as stated below.

Spare Capacity Results Table

| Disease or Healthy Control Cell | Cell Line | Example No of Procedure used | Assay Condition used in Example No | The following Compounds Increased Spare Capacity AUC by at least 100% |
|---|---|---|---|---|
| PA | GM03590 | E009 | E | 21, 36, 39, 42, 61, 485 |
| PA | Tsi4626 | E041 | F | 1, 39, 61 |
| PDH | GM01503 | E033 | G | 39, 61 |
| GA-1 | GM10653 | E038 | G | 447, 485 |
| Huntington Disease | GM21756 | E054 | F | 42, 448 |

Example 905

Using the procedure described in Example 800, the following cell lines listed in the Table below were screened and demonstrated an increase Spare Capacity by at least 10% upon treatment with the indicated Compounds of the present invention using the Assay condition as stated below. Disease or

| Disease or Healthy Control Cell | Cell Line | Example No of Procedure used | Assay Condition used in Example No | The following Compounds Increased Spare Capacity by at least 10% |
|---|---|---|---|---|
| MMA | Tsi 5224 | 800 | D | 36 |

Example 906

Using the procedure described in Example 800, the following cell lines listed in the Table below were screened and demonstrated an increase Spare Capacity AUC by at least 30% upon treatment with the indicated Compounds of the present invention using the Assay condition as stated below.

Prevention of forskolin-induced cyst swelling Results Table

| Disease or Healthy Control Cell | Cell Line | Example No of Procedure used | Assay Condition used in Example No | The following Compounds Increased Spare Capacity by at least 30% |
|---|---|---|---|---|
| MMA | Tsi 5224 | 800 | D | 36 |

Example 907

Using the procedure described in Example 818 the Compounds of the present invention listed below prevented forskolin-induced cyst swelling by at least 15% when tested at the indicated concentration (10 or 50 microMolar) after 72 hours of forskolin exposure.

ROS Results Table

| Compound No. | Concentration Tested (uM) | % prevention of forskolin-induced cyst swelling |
|---|---|---|
| 21 | 50 | ≥10% |

Example 908

Using the procedure described in Example 812 or Example 838, the following cell lines listed in the Table below were screened and demonstrated a reduction in ROS (Reactive Oxygenated Species) by at least 10% upon treatment with the indicated Compounds of the present invention using the Assay condition as stated below.

| Disease or Healthy Control Cell | Cell Line | Example No of Procedure used | Assay Condition used in Example No | The following Compounds Decreased ROS by at least 10% |
|---|---|---|---|---|
| Healthy | GM00041 | 812 | A | 61 |
| BCKD | GM00649 | 812 | C | 39 |
| PDH | GM01503 | 812 | C | 448 |
| Leigh | GM13411 | 812 | C | 61 |
| PC | GM00444 | 812 | C | 42 |
| GA | GM10653 | 812 | C | 36, 42 |
| FXN | GM04078 | 812 | C | 42, 61, 448 |
| NPC1 | GM22879 | 812 | C | 61 |
| HD | GM21756 | 812 | C | 42 |

Example 909

Using the procedure described in Example 812 or Example 838, the following cell lines listed in the Table below were screened and demonstrated a reduction in ROS (Reactive Oxygenated Species) by at least 30% upon treatment with the indicated Compounds of the present invention using the Assay condition as stated below.

Total NAD$^+$ + NADH Results Table

| Disease or Healthy Control Cell | Cell Line | Example No of Procedure used | Assay Condition used in Example No | The following Compounds Decreased ROS by at least 30% |
|---|---|---|---|---|
| Healthy | GM00041 | 812 | A | 61 |
| PDH | GM01503 | 812 | C | 42 |
| VLCAD | GM17475 | 812 | C | 42 |
| Leigh | GM03672 | 812 | C | 61 |
| Leigh | GM13411 | 812 | C | 61 |
| PC | GM00444 | 812 | C | 42 |
| GA | GM10653 | 812 | C | 36, 42 |
| FXN | GM04078 | 812 | C | 42, 61 |
| NPC1 | GM22879 | 812 | C | 61 |
| HD | GM21756 | 812 | C | 42 |

Example 910

Using the procedure described in Example 813, the following cell lines listed in the Table below were screened and demonstrated an increase in Total NAD$^+$+NADH (Total Nicotinamide Adenine Dinucleotide Oxidized Form+Nicotinamide Adenine Dinucleotide Reduced Form) by at least 10% upon treatment with the indicated Compounds of the present invention using the Assay condition as stated below.

Total NADP$^+$ + NADPH Results Table

| Disease or Healthy Control Cell | Cell Line | Example No of Procedure used | Assay Condition used in Example No | The following Compounds Increased Total NAD$^+$ + NADH by at least 10% |
|---|---|---|---|---|
| PA | GM03590 P11 | 814 | A | 61 |
| PA | GM03590 P11 | 814 | B | 61 |
| PDH | GM1503A P10 | 814 | A | 448 |
| PDH | GM1503A P10 | 814 | B | 39 |
| VLCAD | GM17475 P10 | 814 | A | 39, 448 |
| VLCAD | GM17475 P10 | 814 | B | 39, 448 |
| PC | GM00444 P7 | 814 | A | 42 |
| PC | GM00444 P7 | 814 | B | 42 |

Example 911

Using the procedure described in Example 814, the following cell lines listed in the Table below were screened and demonstrated an increase in Total NADP$^+$+NADPH (Total Nicotinamide Adenine Dinucleotide Phosphate+Nicotinamide Adenine Dinucleotide Phosphate Reduced Form) by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased Total NADP$^+$ + NADPH by at least 10% |
|---|---|---|---|---|
| PA | Tsi 6337 P10 | 814 | A | 39 |
| PA | Tsi 6337 P10 | 814 | B | 39 |
| PA | GM03590 P11 | 814 | A | 61 |
| MMA | Tsi 5224 P12 | 814 | A | 61 |
| Leigh | GM03672 P8 | 814 | A | 61 |
| Leigh | GM03672 P8 | 814 | B | 61 |

| Disease or Healthy Control Cell | Cell Line | Example No of Procedure used | Assay Condition used in Example No | The following Compounds Increased Total NADP⁺ + NADPH by at least 10% |
|---|---|---|---|---|
| Leigh | GM03672 P9 | 814 | A | 1, 447 |
| PDH | GM01503 P10 | 814 | A | 39, 42 |
| PDH | GM01503 P10 | 814 | B | 39, 42 |
| VLCAD | GM17475 P10 | 814 | A | 39, 42 |
| VLCAD | GM17475 P10 | 814 | B | 39, 42 |
| PC | GM00444 P7 | 814 | A | 42 |
| PC | GM00444 P7 | 814 | B | 42 |

Example 912

Using the procedure described in Example 814, the following cell lines listed in the Table below were screened and demonstrated an increase in Total NADP⁺+NADPH (Total Nicotinamide Adenine Dinucleotide Phosphate+Nicotinamide Adenine Dinucleotide Phosphate Reduced Form) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased Total NADP⁺ + NADPH by at least 30% |
|---|---|---|---|---|
| PA | Tsi 6337 P10 | 814 | A | 39 |
| PA | Tsi 6337 P10 | 814 | B | 39 |
| PC | GM00444 P7 | 814 | A | 42 |

Example 913

Using the procedure described in Example 814, the following cell lines listed in the Table below were screened and demonstrated an increase in Total NADP⁺+NADPH (Total Nicotinamide Adenine Dinucleotide Phosphate+Nicotinamide Adenine Dinucleotide Phosphate Reduced Form) by at least 50% upon treatment with the indicated Compounds of the present invention using the Assay condition as stated below.

| Disease or Healthy Control Cell | Cell Line | Example No of Procedure used | Assay Condition used in Example No | The following Compounds Increased Total NADP⁺ + NADPH by at least 50% |
|---|---|---|---|---|
| PA | Tsi 6337 P10 | 814 | B | 39 |

Example 914

Using the procedure described in Example 800, the following cell lines listed in the Table below were screened and demonstrated an increase in glycolysis capacity by at least 10% upon treatment with the indicated Compounds of the present invention using the Assay condition as stated below.

| Disease | Cell Line | Example No of Procedure used | Assay Condition used in Example No | The following Compounds Increased Glycolysis Capacity by at least 10% |
|---|---|---|---|---|
| NIEMANN-PICK DISEASE | GM22870 | | F | 42, 448 |
| Huntington Disease | GM21756 | | F | 42, 448 |
| PC | GM00444 | | F | 447, 485 |
| VLCAD | GM17475 | | F | 1, 39 |
| PA | Tsi 4626 | | F | 39 |
| Leigh (ATP6) | GM13411 | | G | 5, 447, 485 |
| Leigh | GM03672 | | G | 5, 447, 485 |
| PA | TSI4626 | | G | 1, 61 |

Example 915

Using the procedure described in Example 800, the following cell lines listed in the Table below were screened and demonstrated an increase in glycolysis capacity by at least 30% upon treatment with the indicated Compounds of the present invention using the Assay condition as stated below.

| Disease | Cell Line | Example No of Procedure used | Assay Condition used in Example No | The following Compounds Increased Glycolysis Capacity by at least 30% |
|---|---|---|---|---|
| NIEMANN-PICK DISEASE | GM22870 | | F | 42, 448 |
| Huntington Disease | GM21756 | | F | 42, 448 |
| PC | GM00444 | | F | 447, 485 |
| Leigh (ATP6) | GM13411 | | G | 5, 447, 485 |
| Leigh | GM03672 | | G | 5, 447, 485 |
| PA | TSI4626 | | G | 1, 61 |

Example 916

Using the procedure described in Example 832 the Compounds of the present invention listed below decreased HLA-DR by at least the percentage indicated when tested at the indicated concentration (1 or 10 microMolar).

| Compound No. | Concentration Tested (uM) | % decrease in HLA-DR |
|---|---|---|
| 6 | 1 | ≥10% |
| 36 | 10 | ≥10% |
| 451 | 10 | ≥10% |
| 633 | 1 | ≥10% |

Example 917

Using the procedure described in Example 832, the Compounds of the present invention listed below increased IL-6 by at least the percentage indicated when tested at the indicated concentration (1 or 10 microMolar).

| Compound No. | Concentration Tested (uM) | % increase in IL-6 |
|---|---|---|
| 451 | 10 | ≥10% |

Example 918

Using the procedure described in Example 832 the Compounds of the present invention listed below decreased LDLR by at least the percentage indicated when tested at the indicated concentration (1 or 10 microMolar).

| Compound No. | Concentration Tested (uM) | % decrease in LDLR |
|---|---|---|
| 36 | 1 | ≥10% |
| 42 | 10 | ≥10% |
| 61 | 10 | ≥10% |
| 633 | 1 | ≥10% |

Example 919

Using the procedure described in Example 832 the Compounds of the present invention listed below decreased M-CSF by at least the percentage indicated when tested at the indicated concentration (1 or 10 microMolar).

| Compound No. | Concentration Tested (uM) | % decrease in M-CSF |
|---|---|---|
| 6 | 1 | ≥10% |
| 36 | 10 | ≥10% |
| 633 | 1 | ≥10% |

Example 920

Using the procedure described in Example 833, the Compounds of the present invention listed below decreased Collagen III by at least the percentage indicated when tested at the indicated concentration (1 or 10 microMolar).

| Compound No. | Concentration Tested (uM) | % decrease in Collagen III |
|---|---|---|
| 451 | 1 | ≥10% |

Example 921

Using the procedure described in Example 833, the Compounds of the present invention listed below decreased EGFR by at least the percentage indicated when tested at the indicated concentration (1 or 10 microMolar).

| Compound No. | Concentration Tested (uM) | % decrease in EGFR |
|---|---|---|
| 36 | 1 | ≥10% |
| 633 | 1 | ≥10% |

Example 922

Using the procedure described in Example 833, the Compounds of the present invention listed below decreased MMP-1 by at least the percentage indicated when tested at the indicated concentration (1 or 10 microMolar).

| Compound No. | Concentration Tested (uM) | % decrease in MMP-1 |
|---|---|---|
| 36 | 10 | ≥10% |

Example 923

Using the procedure described in Example 833, the Compounds of the present invention listed below increased PAI-I by at least the percentage indicated when tested at the indicated concentration (1 or 10 microMolar).

| Compound No. | Concentration Tested (uM) | % increase in PAI-I |
|---|---|---|
| 633 | 10 | ≥10% |

Example 924

Using the procedure described in Example 833, the Compounds of the present invention listed below increased cell proliferation by at least the percentage indicated when tested at the indicated concentration (1 or 10 microMolar).

| Compound No. | Concentration Tested (uM) | % increase in 72 Hour Proliferation |
|---|---|---|
| 6 | 1 | ≥10% |
| 36 | 10 | ≥10% |
| 633 | 10 | ≥10% |

Example 925

Using the procedure described in Example 833, the Compounds of the present invention listed below decreased TIMP-1 by at least the percentage indicated when tested at the indicated concentration (1 or 10 microMolar).

| Compound No. | Concentration Tested (uM) | % decrease in TIMP-1 |
|---|---|---|
| 6 | 1 | ≥10% |
| 36 | 1 | ≥10% |
| 61 | 10 | ≥10% |
| 451 | 1 | ≥10% |
| 633 | 1 | ≥20% |

Example 926

Using the procedure described in Example 833, the Compounds of the present invention listed below decreased TIMP-2 by at least the percentage indicated when tested at the indicated concentration (1 or 10 microMolar).

| Compound No. | Concentration Tested (uM) | % decrease in TIMP-2 |
|---|---|---|
| 36 | 1 | ≥20% |
| 42 | 10 | ≥10% |
| 633 | 1 | ≥10% |

Example 927

Using the procedure described in 834 the Compounds of the present invention listed below decreased MCP-1 by at least the percentage indicated when tested at the indicated concentration (1 or 10 microMolar).

| Compound No. | Concentration Tested (uM) | % decrease in MCP-1 |
|---|---|---|
| 6 | 10 | ≥10% |
| 42 | 1 | ≥10% |
| 61 | 1 | ≥20% |
| 451 | 1 | ≥10% |
| 633 | 1 | ≥10% |

Example 928

Using the procedure described in 834 the Compounds of the present invention listed below decreased MCP-1 by at least the percentage indicated when tested at the indicated concentration (1 or 10 microMolar).

| Compound No. | Concentration Tested (uM) | % decrease in MCP-1 |
|---|---|---|
| 6 | 10 | ≥10% |
| 42 | 1 | ≥10% |
| 61 | 1 | ≥20% |
| 451 | 1 | ≥10% |
| 633 | 1 | ≥10% |

Example 929

Using the procedure described in Example 826, the Compounds of the present invention listed below decreased Eotaxin-3 by at least the percentage indicated when tested at the indicated concentration (1 or 10 microMolar).

| Compound No. | Concentration Tested (uM) | % decrease in Eotaxin-3 |
|---|---|---|
| 36 | 1 | ≥10% |
| 42 | 1 | ≥10% |
| 451 | 1 | ≥10% |
| 633 | 1 | ≥10% |

Example 930

Using the procedure described in Example 826, the Compounds of the present invention listed below decreased VEGFRII by at least the percentage indicated when tested at the indicated concentration (1 or 10 microMolar).

| Compound No. | Concentration Tested (uM) | % decrease in VEGFRII |
|---|---|---|
| 6 | 1 | ≥10% |
| 36 | 1 | ≥20% |
| 42 | 1 | ≥10% |
| 451 | 1 | ≥10% |
| 633 | 1 | ≥10% |

Example 931

Using the procedure described in Example 826, the Compounds of the present invention listed below decreased E-Selectin by at least the percentage indicated when tested at the indicated concentration (1 or 10 microMolar).

| Compound No. | Concentration Tested (uM) | % decrease in E-Selectin |
|---|---|---|
| 36 | 1 | ≥20% |
| 42 | 1 | ≥10% |
| 61 | 10 | ≥10% |
| 451 | 1 | ≥10% |
| 633 | 1 | ≥20% |

Example 932

Using the procedure described in Example 825, the Compounds of the present invention listed below increased proliferation of HUVEC by at least the percentage indicated when tested at the indicated concentration (1 or 10 microMolar).

| Compound No. | Concentration Tested (uM) | % increase in Proliferation (HUVEC) |
|---|---|---|
| 6 | 10 | ≥20% |
| 36 | 10 | ≥20% |
| 451 | 10 | ≥20% |
| 633 | 1 | ≥20% |

Example 933

Using the procedure described in Example 825, the Compounds of the present invention listed below decreased 111-8 by at least the percentage indicated when tested at the indicated concentration (1 or 10 microMolar).

| Compound No. | Concentration Tested (uM) | % decrease in IL-8 |
|---|---|---|
| 6 | 1 | ≥10% |
| 36 | 10 | ≥10% |
| 61 | 1 | ≥10% |
| 451 | 1 | ≥10% |
| 633 | 10 | ≥20% |

Example 934

Using the procedure described in Example 827, the Compounds of the present invention listed below decreased IL-8 by at least the percentage indicated when tested at the indicated concentration (1 or 10 microMolar).

| Compound No. | Concentration Tested (uM) | % decrease in IL-8 |
|---|---|---|
| 6 | 1 | ≥10% |
| 36 | 1 | ≥20% |
| 42 | 1 | ≥20% |
| 61 | 10 | ≥20% |
| 451 | 10 | ≥20% |
| 633 | 1 | ≥20% |

Example 935

Using the procedure described in Example 827, the Compounds of the present invention listed below decreased IL-1α by at least the percentage indicated when tested at the indicated concentration (1 or 10 microMolar).

| Compound No. | Concentration Tested (uM) | % decrease in IL-1α |
|---|---|---|
| 36 | 1 | ≥10% |
| 42 | 1 | ≥10% |
| 61 | 1 | ≥10% |
| 451 | 1 | ≥10% |

Example 936

Using the procedure described in Example 827, the Compounds of the present invention listed below decreased M-CSF by at least the percentage indicated when tested at the indicated concentration (1 or 10 microMolar).

| Compound No. | Concentration Tested (uM) | % decrease in M-CSF |
|---|---|---|
| 6 | 1 | ≥10% |
| 36 | 1 | ≥20% |
| 42 | 1 | ≥20% |
| 61 | 1 | ≥10% |
| 451 | 1 | ≥20% |
| 633 | 1 | ≥10% |

Example 937

Using the procedure described in Example 827, the Compounds of the present invention listed below decreased sPGE2 by at least the percentage indicated when tested at the indicated concentration (1 or 10 microMolar).

| Compound No. | Concentration Tested (uM) | % decrease in sPGE2 |
|---|---|---|
| 36 | 10 | ≥10% |
| 633 | 1 | ≥10% |

Example 938

Using the procedure described in Example 827, the Compounds of the present invention listed below decreased Thrombomodulin by at least the percentage indicated when tested at the indicated concentration (1 or 10 microMolar).

| Compound No. | Concentration Tested (uM) | % decrease in Thrombomodulin |
|---|---|---|
| 36 | 1 | ≥10% |
| 42 | 1 | ≥10% |
| 451 | 1 | ≥10% |
| 633 | 1 | ≥20% |

Example 939

Using the procedure described in Example 827, the Compounds of the present invention listed below decreased Tissue Factor by at least the percentage indicated when tested at the indicated concentration (1 or 10 microMolar).

| Compound No. | Concentration Tested (uM) | % decrease in Tissue Factor |
|---|---|---|
| 6 | 1 | ≥10% |
| 36 | 10 | ≥10% |
| 42 | 10 | ≥10% |
| 61 | 10 | ≥10% |
| 451 | 10 | ≥10% |
| 633 | 1 | ≥10% |

Example 940

Using the procedure described in Example 827, the Compounds of the present invention listed below decreased sTNFα by at least the percentage indicated when tested at the indicated concentration (1 or 10 microMolar).

| Compound No. | Concentration Tested (uM) | % decrease in sTNFα |
|---|---|---|
| 6 | 1 | ≥20% |
| 36 | 10 | ≥10% |
| 61 | 1 | ≥10% |
| 633 | 1 | ≥10% |

Example 941

Using the procedure described in Example 827, the Compounds of the present invention listed below increased sTNFα by at least the percentage indicated when tested at the indicated concentration (1 or 10 microMolar).

| Compound No. | Concentration Tested (uM) | % increase in sTNFα |
|---|---|---|
| 42 | 10 | ≥20% |
| 61 | 10 | ≥10% |
| 633 | 10 | ≥10% |

Example 942

Using the procedure described in Example 826, the Compounds of the present invention listed below decreased MCP-1 by at least the percentage indicated when tested at the indicated concentration (1 or 10 microMolar).

| Compound No. | Concentration Tested (uM) | % decrease in MCP-1 |
|---|---|---|
| 6 | 1 | ≥10% |
| 36 | 1 | ≥10% |
| 61 | 10 | ≥10% |
| 451 | 10 | ≥10% |
| 633 | 10 | ≥10% |

Example 942

Using the procedure described in Example 828, the Compounds of the present invention listed below increased CD69 by at least the percentage indicated when tested at the indicated concentration (1 or 10 microMolar).

| Compound No. | Concentration Tested (uM) | % increase in CD69 |
|---|---|---|
| 42 | 10 | ≥10% |

Example 943

Using the procedure described in Example 828 the Compounds of the present invention listed below decreased CXCL8/IL-8 by at least the percentage indicated when tested at the indicated concentration (1 or 10 microMolar).

| Compound No. | Concentration Tested (uM) | % decrease in CXCL8/IL-8 |
|---|---|---|
| 36 | 10 | ≥10% |
| 451 | 10 | ≥10% |

Example 944

Using the procedure described in Example 828, the Compounds of the present invention listed below increased MCP-1 by at least the percentage indicated when tested at the indicated concentration (1 or 10 microMolar).

| Compound No. | Concentration Tested (uM) | % increase in MCP-1 |
|---|---|---|
| 6 | 1 | ≥10% |
| 42 | 10 | ≥10% |

Example 945

Using the procedure described in Example 828, the Compounds of the present invention listed below increased PBMC Cytotoxicity by at least the percentage indicated when tested at the indicated concentration (1 or 10 microMolar).

| Compound No. | Concentration Tested (uM) | % increase in PBMC Cytotoxicity |
|---|---|---|
| 61 | 10 | ≥10% |

Example 946

Using the procedure described in Example 829 the Compounds of the present invention listed below decreased B-cell proliferation by at least the percentage indicated when tested at the indicated concentration (1 or 10 microMolar).

| Compound No. | Concentration Tested (uM) | % decrease in B-cell proliferation |
|---|---|---|
| 42 | 10 | ≥10% |

Example 947

Using the procedure described in Example 829 the Compounds of the present invention listed below increased B-cell proliferation by at least the percentage indicated when tested at the indicated concentration (1 or 10 microMolar).

| Compound No. | Concentration Tested (uM) | % increase in B-cell Proliferation |
|---|---|---|
| 36 | 10 | ≥20% |
| 61 | 10 | ≥10% |
| 451 | 1 | ≥10% |
| 633 | 10 | ≥20% |

Example 948

Using the procedure described in Example 829 the Compounds of the present invention listed below decreased sIL-17 by at least the percentage indicated when tested at the indicated concentration (1 or 10 microMolar).

| Compound No. | Concentration Tested (uM) | % decrease in sIL-17 |
|---|---|---|
| 42 | 10 | ≥20% |

Example 949

Using the procedure described in Example 848, the Compounds of the present invention listed below prevented LPS-induced neuronal degradation by at least 15% when tested at the indicated concentration (10 or 50 microMolar) after 5 days of LPS exposure.

| Compound No. | Concentration Tested (uM) | % reversion of TH positive neurons |
|---|---|---|
| 42 | 10 | ≥15% |

Example 950

Using the procedure described in Example 848, the Compounds of the present invention listed below prevented LPS-induced neuronal degradation by at least 50% when tested at the indicated concentration (10 or 50 microMolar) after 5 days of LPS exposure.

| Compound No. | Concentration Tested (uM) | % reversion of TH positive neurons |
|---|---|---|
| 42 | 10 | ≥50% |

Example 951

Using the procedure described in Example 848, the Compounds of the present invention listed below prevented LPS-induced NO (Nitric Oxide) release from neurons by at least the percentage indicated (compared to LPS induction alone) when tested at the indicated concentration (10 or 50 microMolar) after 5 days of LPS exposure.

| Compound No. | Concentration Tested (uM) | % reversion of NO release from neurons |
|---|---|---|
| 42 | 10 | ≥10% |

Example 952

Using the procedure described in Example 819, the following cell lines listed in the Table below were screened and demonstrated an increase in MMP (Mitochondrial Membrane Potential) by at least 10% upon treatment with the indicated Compounds of the present invention using the Assay condition as stated below.

| Disease or Healthy Control Cell | Cell Line | Assay Condition used in Example No | Compound |
|---|---|---|---|
| MELAS Syndrome | K605 | A | 633 |
| IVA | GM00947 | A | 1, 633 |
| IVA | GM00947 | B | 1 |
| VLCAD | GM11408 | A | |
| VLCAD | GM11408 | B | 633 |

Using the procedure described in Example 819, the following cell lines listed in the Table below were screened and demonstrated an increase in MMP (Mitochondrial Membrane Potential) by at least 30% upon treatment with the indicated Compounds of the present invention using the Assay condition as stated below.

| Disease or Healthy Control Cell | Cell Line | Assay Condition used in Example No | Compound |
|---|---|---|---|
| MELAS Syndrome | K605 | A | 633 |
| IVA | GM00947 | A | 1, 633 |
| IVA | GM00947 | B | 1 |
| VLCAD | GM11408 | B | 633 |

Using the procedure described in Example 819, the following cell lines listed in the Table below were screened and demonstrated an increase in MMP (Mitochondrial Membrane Potential) by at least 50% upon treatment with the indicated Compounds of the present invention using the Assay condition as stated below.

| Disease or Healthy Control Cell | Cell Line | Assay Condition used in Example No | Compound |
|---|---|---|---|
| IVA | GM00947 | A | 633 |

Example 95

Using the procedure described in Example 819, the following cell lines listed in the Table below were screened and demonstrated a decrease in MMP (Mitochondrial Membrane Potential) by at least 10% upon treatment with the indicated Compounds of the present invention using the Assay condition as stated below.

| Disease or Healthy Control Cell | Cell Line | Assay Condition used in Example No | The following Compounds Decreased MMP by at least 10% Compound |
|---|---|---|---|
| MELAS Syndrome | K605 | B | 1 |
| Amyothrophic Lateral Sclerosis (ALS) | K773 | A | 1, 633 |
| Amyothrophic Lateral Sclerosis (ALS) | K773 | B | 1, 633 |
| VLCAD | GM11408 | A | 1 |

Using the procedure described in Example 819, the following cell lines listed in the Table below were screened and demonstrated a decrease in MMP (Mitochondrial Membrane Potential) by at least 30% upon treatment with the indicated Compounds of the present invention using the Assay condition as stated below.

| Disease or Healthy Control Cell | Cell Line | Assay Condition used in Example No | Compound |
|---|---|---|---|
| Succinil-CoA: 3-Ketoacid CoA transferase deficiency (SCOT) | 10474 | B | 42, 633 |
| MELAS Syndrome | K605 | B | 1 |
| Amyothrophic Lateral Sclerosis (ALS) | K773 | B | 1, 633 |

Using the procedure described in Example 819, the following cell lines listed in the Table below were screened and demonstrated a decrease in MMP (Mitochondrial Membrane Potential) by at least 50% upon treatment with the indicated Compounds of the present invention using the Assay condition as stated below.

| Disease or Healthy Control Cell | Cell Line | Assay Condition used in Example No | Compound |
|---|---|---|---|
| Succinil-CoA: 3-Ketoacid CoA transferase deficiency (SCOT) | 10474 | B | 633 |
| Amyothrophic Lateral Sclerosis (ALS) | K773 | B | 1, 633 |

Example 953

Using the procedure described in Example 813, the following cell lines listed in the Table below were screened and demonstrated an increase in NAD$^+$ by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased NAD+ by at least 10% |
|---|---|---|---|---|
| PA | GM03590 Passage 11 | 813 | A | 61 |
| MMA | Tsi 5224 Passage 12 | 813 | A | 61 |
| Leigh | GM13411 Passage 14 | 813 | C | 61 |
| Leigh | GM03672 Passage 8 | 813 | A | 142 |
| Leigh | GM03672 Passage 8 | 813 | C | 61 |
| PDH | GM1503A Passage 10 | 813 | A | 39, 42, 448 |
| VLCAD | GM17475 Passage 10 | 813 | A | 448 |
| PC | GM00444 Passage7 | 813 | C | 42 |

Example 954

Using the procedure described in Example 813, the following cell lines listed in the Table below were screened and demonstrated an increase in NAD$^+$ by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased NAD+ by at least 10% |
|---|---|---|---|---|
| MMA | Tsi 5224 Passage 12 | 813 | A | 61 |
| Leigh | GM03672 Passage 8 | 813 | A | 61 |
| Leigh | GM03672 Passage 8 | 813 | C | 61 |
| PDH | GM1503A Passage 10 | 813 | A | 39, 42 |

Example 955

Using the procedure described in Example 813, the following cell lines listed in the Table below were screened and demonstrated an increase in NAD$^+$ by at least 50% upon treatment with the indicated compounds of the present invention using the Assay condition as stated below.

| Disease or Healthy Control Cell | Cell Line | Example No of Procedure used | Assay Condition used in Example No | The following Compounds Increased NAD+ by at least 50% |
|---|---|---|---|---|
| Leigh | GM03672 Passage 8 | 813 | A | 61 |
| PDH | GM1503A Passage 10 | 813 | A | 39 |

Example 956

Using the procedure described in Example 813, the following cell lines listed in the Table below were screened and demonstrated an increase in NADH (Nicotinamide Adenine Dinucleotide Reduced Form) by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased NADH by at least 10% |
|---|---|---|---|---|
| PA | GM03590 Passage 11 | | A | 61 |
| PA | GM03590 Passage11 | | C | 61 |
| MMA | Tsi 5224 Passage 12 | | C | 61 |
| PDH | GM1503A Passage10 | | A | 448 |
| PDH | GM1503A Passage 10 | | C | 448 |
| PC | GM00444 Passage7 | | C | 42 |

Example 957

Using the procedure described in Example 813, the following cell lines listed in the Table below were screened and demonstrated an increase in NADH (Nicotinamide Adenine Dinucleotide Reduced Form) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased NADH by at least 30% |
|---|---|---|---|---|
| PDH | GM1503A P10 | | A | 448 |
| PC | GM00444 P7 | | C | 42 |

Example 958

Using the procedure described in Example 815, the following cell lines listed in the Table below were screened and demonstrated an increase in ATP (Luminescence) by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased ATP by at least 10% |
|---|---|---|---|---|
| Healthy | GM00041 | 815 | | 61 |
| PA | GM00371 | 815 | | 61 |
| PA | GM03590 | 815 | | 61 |
| PDH | GM01503 | 815 | C | 448 |
| VLCAD | GM17475 | 815 | C | 448 |
| PC | GM00444 | 815 | C | 42 |
| α-Ketoglutarate dehydrogenase deficiency | 962 | 815 | C | 42, 61 |
| Citrullinemia Type II | 2930 | 815 | C | 42, 61 |

Example 959

Using the procedure described in Example 815, the following cell lines listed in the Table below were screened and demonstrated an increase in Total Glutathione (Total GSH) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased ATP by at least 30% |
|---|---|---|---|---|
| PA | GM00371 | 815 | | 61 |
| VLCAD | GM17475 | 815 | | 448 |
| α-Ketoglutarate dehydrogenase deficiency | 962 | 815 | | 42, 61 |
| Citrullinemia Type II | 2930 | 815 | | 42, 61 |

Example 960

Using the procedure described in Example 836, the Compounds of the present invention listed below increased MIP-1α by at least the percentage indicated when tested at the indicated concentration (1 or 10 microMolar).

| Compound No. | Concentration Tested (uM) | % increase in MIP-1α |
|---|---|---|
| 36 | 10 | ≥10% |

Example 961

Using the procedure described in Example 836, the Compounds of the present invention listed below decreased α-SMA by at least the percentage indicated when tested at the indicated concentration (1 or 10 microMolar).

| Compound No. | Concentration Tested (uM) | % decrease in α-SMA |
|---|---|---|
| 6 | 1 | ≥10% |
| 42 | 1 | ≥10% |
| 61 | 10 | ≥10% |
| 451 | 1 | ≥10% |
| 633 | 10 | ≥10% |

Example 962

Using the procedure described in Example 836, the Compounds of the present invention listed below increased MMP-1 by at least the percentage indicated when tested at the indicated concentration (1 or 10 microMolar).

| Compound No. | Concentration Tested (uM) | % increase in MMP-1 |
|---|---|---|
| 6 | 10 | ≥10% |
| 42 | 1 | ≥10% |
| 61 | 10 | ≥10% |
| 451 | 10 | ≥10% |

Example 963

Using the procedure described in Example 836, the Compounds of the present invention listed below decreased VCAM-1 by at least the percentage indicated when tested at the indicated concentration (1 or 10 microMolar).

| Compound No. | Concentration Tested (uM) | % decrease in VCAM-1 |
|---|---|---|
| 451 | 10 | ≥10% |
| 633 | 1 | ≥10% |

Example 964

Using the procedure described in Example 835, the Compounds of the present invention listed below decreased uPA by at least the percentage indicated when tested at the indicated concentration (1 or 10 microMolar).

| Compound No. | Concentration Tested (uM) | % decrease in uPA |
|---|---|---|
| 36 | 10 | ≥10% |
| 633 | 10 | ≥10% |

Example 966

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 1264 | 50 | ≥20% |
| 47 | 50 | ≥10% |
| 1263 | 50 | ≥30% |
| 1268 | 50 | ≥30% |

Example 967

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 1307 | 50 | ≥30% |
| 1275 | 10 | ≥20% |
| 63 | 50 | ≥30% |
| 1277 | 10 | ≥10% |

Example 968

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 1304 | 10 | ≥20% |
| 1 | 10 | ≥30% |
| 1305 | 10 | ≥10% |

Example 969

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 141 | 50 | ≥30% |
| 410 | 50 | ≥30% |
| 370 | 50 | ≥30% |
| 371 | 10 | ≥30% |
| 397 | 10 | ≥20% |
| 211 | 50 | ≥30% |
| 144 | 50 | ≥30% |
| 460 | 50 | ≥30% |

Example 970

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 2 | 10 | ≥10% |
| 185 | 50 | ≥30% |
| 382 | 50 | ≥30% |
| 213 | 50 | ≥30% |
| 1306 | 10 | ≥30% |
| 117 | 10 | ≥30% |
| 183 | 10 | ≥30% |
| 393 | 10 | ≥30% |
| 145 | 10 | ≥30% |

Example 971

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 157 | 50 | ≥20% |
| 498 | 50 | ≥10% |
| 57 | 50 | ≥20% |

Example 972

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 214 | 10 | ≥20% |
| 503 | 50 | ≥20% |
| 1271 | 10 | ≥10% |
| 1298 | 50 | ≥20% |
| 1296 | 10 | ≥10% |

Example 973

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 868 | 10 | ≥30% |
| 858 | 10 | ≥30% |

-continued

| Compound Table No. | Concentration Tested (uM) | % increase in Glucose Uptake |
|---|---|---|
| 866 | 10 | ≥30% |
| 853 | 10 | ≥30% |
| 856 | 10 | ≥30% |

Example 974

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 855 | 50 | ≥30% |
| 861 | 50 | ≥20% |
| 863 | 50 | ≥10% |

Example 975

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 852 | 50 | ≥20% |
| 862 | 10 | ≥20% |
| 860 | 50 | ≥10% |
| 864 | 50 | ≥20% |
| 865 | 10 | ≥20% |
| 867 | 10 | ≥20% |
| 609 | 10 | ≥10% |

Example 976

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 869 | 10 | ≥10% |

Example 977

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 36 | 50 | ≥30% |
| 20 | 50 | ≥30% |

Example 978

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 42 | 10 | ≥30% |
| 870 | 10 | ≥30% |

Example 979

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 3 | 10 | ≥10% |
| 485 | 50 | ≥10% |
| 451 | 50 | ≥20% |

Example 980

Using the procedure described in Example 821, the Compounds of the present invention listed below increased Glucose Uptake of HepG2 cells by at least the percentage indicated when tested at the indicated concentration (10 or 50 microMolar).

| Compound Table No. | Concentration Tested (uM) | % increase in Glucose Uptake |
|---|---|---|
| 61 | 50 | ≥10% |
| 39 | 50 | ≥10% |
| 862 | 50 | ≥10% |

Example 981

Using the procedure described in Example 826, the Compounds of the present invention listed below decreased Eotaxin-3 by at least the percentage indicated when tested at the indicated concentration (1 or 10 microMolar).

| Compound No. | Compound No. | Concentration Tested (uM) | % decrease in Eotaxin-3 |
|---|---|---|---|
| 36 | 36 | 1 | ≥10% |
| 42 | 42 | 1 | ≥10% |
| 451 | 451 | 1 | ≥10% |
| 633 | 633 | 1 | ≥10% |

Example 982

Using the procedure described in Example 826, the Compounds of the present invention listed below decreased VEGFRII by at least the percentage indicated when tested at the indicated concentration (1 or 10 microMolar).

| Compound No. | Compound No. | Concentration Tested (uM) | % decrease in VEGFRII |
|---|---|---|---|
| 6 | 6 | 1 | ≥10% |
| 36 | 36 | 1 | ≥20% |
| 42 | 42 | 1 | ≥10% |
| 451 | 451 | 1 | ≥10% |
| 633 | 633 | 1 | ≥10% |

Example 983

Using the procedure described in Example 826, the Compounds of the present invention listed below decreased E-Selectin by at least the percentage indicated when tested at the indicated concentration (1 or 10 microMolar).

| Compound No. | Concentration Tested (uM) | % decrease in E-Selectin |
|---|---|---|
| 36 | 1 | ≥20% |
| 42 | 1 | ≥10% |
| 61 | 10 | ≥10% |
| 451 | 1 | ≥10% |
| 633 | 1 | ≥20% |

Example 984

Using the procedure described in Example 825, the Compounds of the present invention listed below increased proliferation of HUVEC by at least the percentage indicated when tested at the indicated concentration (1 or 10 microMolar).

| Compound No. | Concentration Tested (uM) | % increase in Proliferation (HUVEC) |
|---|---|---|
| 6 | 10 | ≥20% |
| 36 | 10 | ≥20% |
| 451 | 10 | ≥20% |
| 633 | 1 | ≥20% |

Example 985

Using the procedure described in Example 825, the Compounds of the present invention listed below decreased IL-8 by at least the percentage indicated when tested at the indicated concentration (1 or 10 microMolar).

| Compound No. | Concentration Tested (uM) | % decrease in IL-8 |
|---|---|---|
| 6 | 1 | ≥10% |
| 36 | 10 | ≥10% |
| 61 | 1 | ≥10% |
| 451 | 1 | ≥10% |
| 633 | 10 | ≥20% |

Example 986

Using the procedure described in Example 827, the Compounds of the present invention listed below decreased IL-8 by at least the percentage indicated when tested at the indicated concentration (1 or 10 microMolar).

| Compound No. | Concentration Tested (uM) | % decrease in IL-8 |
|---|---|---|
| 6 | 1 | ≥10% |
| 36 | 1 | ≥20% |
| 42 | 1 | ≥20% |
| 61 | 10 | ≥20% |
| 451 | 10 | ≥20% |
| 633 | 1 | ≥20% |

Example 987

Using the procedure described in Example 827, the Compounds of the present invention listed below decreased IL-1α by at least the percentage indicated when tested at the indicated concentration (1 or 10 microMolar).

| Compound No. | Concentration Tested (uM) | % decrease in IL-1α |
|---|---|---|
| 36 | 1 | ≥10% |
| 42 | 1 | ≥10% |
| 61 | 1 | ≥10% |
| 451 | 1 | ≥10% |

Example 988

Using the procedure described in Example 827, the Compounds of the present invention listed below decreased M-CSF by at least the percentage indicated when tested at the indicated concentration (1 or 10 microMolar).

| Compound No. | Concentration Tested (uM) | % decrease in M-CSF |
|---|---|---|
| 6 | 1 | ≥10% |
| 36 | 1 | ≥20% |
| 42 | 1 | ≥20% |
| 61 | 1 | ≥10% |
| 451 | 1 | ≥20% |
| 633 | 1 | ≥10% |

Example 989

Using the procedure described in Example 827, the Compounds of the present invention listed below decreased sPGE2 by at least the percentage indicated when tested at the indicated concentration (1 or 10 microMolar).

| Compound No. | Concentration Tested (uM) | % decrease in M-CSF |
|---|---|---|
| 36 | 10 | ≥10% |
| 633 | 1 | ≥10% |

Example 990

Using the procedure described in Example 827, the Compounds of the present invention listed below decreased Thrombomodulin by at least the percentage indicated when tested at the indicated concentration (1 or 10 microMolar).

| Compound No. | Concentration Tested (uM) | % decrease in Thrombomodulin |
|---|---|---|
| 36 | 1 | ≥10% |
| 42 | 1 | ≥10% |
| 451 | 1 | ≥10% |
| 633 | 1 | ≥20% |

Example 991

Using the procedure described in Example 827, the Compounds of the present invention listed below decreased Tissue Factor by at least the percentage indicated when tested at the indicated concentration (1 or 10 microMolar).

| Compound No. | Concentration Tested (uM) | % decrease in TissueFactor |
|---|---|---|
| 6 | 1 | ≥10% |
| 36 | 10 | ≥10% |
| 42 | 10 | ≥10% |
| 61 | 10 | ≥10% |
| 451 | 10 | ≥10% |
| 633 | 1 | ≥10% |

Example 992

Using the procedure described in Example 827, the Compounds of the present invention listed below decreased sTNFα by at least the percentage indicated when tested at the indicated concentration (1 or 10 microMolar).

| Compound No. | Concentration Tested (uM) | % decrease in sTNFα |
|---|---|---|
| 6 | 1 | ≥20% |
| 36 | 10 | ≥10% |
| 61 | 1 | ≥10% |
| 633 | 1 | ≥10% |

Example 993

Using the procedure described in Example 827, the Compounds of the present invention listed below increased sTNFα by at least the percentage indicated when tested at the indicated concentration (1 or 10 microMolar).

| Compound No. | Concentration Tested (uM) | % increase in sTNFα |
|---|---|---|
| 42 | 10 | ≥20% |
| 61 | 10 | ≥10% |
| 633 | 10 | ≥10% |

Example 994

Using the procedure described in Example 826, the Compounds of the present invention listed below decreased MCP-1 by at least the percentage indicated when tested at the indicated concentration (1 or 10 microMolar).

| Compound No. | Concentration Tested (uM) | % decrease in MCP-1 |
|---|---|---|
| 6 | 1 | ≥10% |
| 36 | 1 | ≥10% |
| 61 | 10 | ≥10% |
| 451 | 10 | ≥10% |
| 633 | 10 | ≥10% |

Example 995

Using the procedure described in Example 828, the Compounds of the present invention listed below increased CD69 by at least the percentage indicated when tested at the indicated concentration (1 or 10 microMolar).

| Compound No. | Concentration Tested (uM) | % increase in CD69 |
|---|---|---|
| 42 | 10 | ≥10% |

Example 996

Using the procedure described in Example 828 the Compounds of the present invention listed below decreased CXCL8/IL-8 by at least the percentage indicated when tested at the indicated concentration (1 or 10 microMolar).

| Compound No. | Concentration Tested (uM) | % decrease in CXCL8/IL-8 |
|---|---|---|
| 36 | 10 | ≥10% |
| 451 | 10 | ≥10% |

Example 997

Using the procedure described in Example 828, the Compounds of the present invention listed below increased MCP-1 by at least the percentage indicated when tested at the indicated concentration (1 or 10 microMolar).

| Compound No. | Compound No. | Concentration Tested (uM) | % increase in M-CSF |
|---|---|---|---|
| 6 | 6 | 1 | ≥10% |
| 42 | 42 | 10 | ≥10% |

Example 998

Using the procedure described in Example 828, the Compounds of the present invention listed below increased PBMC Cytotoxicity by at least the percentage indicated when tested at the indicated concentration (1 or 10 microMolar).

| Compound No. | Concentration Tested (uM) | % increase in PBMC Cytotoxicity |
|---|---|---|
| 61 | 10 | ≥10% |

Example 999

Using the procedure described in Example 829 the Compounds of the present invention listed below decreased B-cell proliferation by at least the percentage indicated when tested at the indicated concentration (1 or 10 microMolar).

| Compound No. | Concentration Tested (uM) | % decrease in B-cell proliferation |
|---|---|---|
| 42 | 10 | ≥10% |

Example 1000

Using the procedure described in Example 829 the Compounds of the present invention listed below increased B-cell proliferation by at least the percentage indicated when tested at the indicated concentration (1 or 10 microMolar).

| Compound No. | Concentration Tested (uM) | % increase in B-cell Proliferation |
|---|---|---|
| 36 | 10 | ≥20% |
| 61 | 10 | ≥10% |
| 451 | 1 | ≥10% |
| 633 | 10 | ≥20% |

Example 1001

Using the procedure described in Example 829 the Compounds of the present invention listed below decreased sIL-17 by at least the percentage indicated when tested at the indicated concentration (1 or 10 microMolar).

| Compound No. | Concentration Tested (uM) | % decrease in sIL-17 |
|---|---|---|
| 42 | 10 | ≥20% |

Example 1002

Using the procedure described in Example 848, the Compounds of the present invention listed below prevented LPS-induced neuronal degradation by at least 15% when tested at the indicated concentration (10 or 50 microMolar) after 5 days of LPS exposure.

| Compound No. | Concentration Tested (uM) | % reversion of TH positive neurons |
|---|---|---|
| 42 | 10 | ≥15% |

Example 1003

Using the procedure described in Example 848, the Compounds of the present invention listed below prevented LPS-induced neuronal degradation by at least 50% when tested at the indicated concentration (10 or 50 microMolar) after 5 days of LPS exposure.

| Compound No. | Concentration Tested (uM) | % reversion of TH positive neurons |
|---|---|---|
| 42 | 10 | ≥50% |

Example 1004

Using the procedure described in Example 848, the Compounds of the present invention listed below prevented LPS-induced NO (Nitric Oxide) release from neurons by at least the percentage indicated when tested at the indicated concentration (10 or 50 microMolar) after 5 days of LPS exposure.

| Compound No. | Concentration Tested (uM) | % reversion of NO release from neurons |
|---|---|---|
| 42 | 10 | ≥10% |

Example 1005

Using the procedure described in Example 819, the following cell lines listed in the Table below were screened and demonstrated an increase in MMP (Mitochondrial Membrane Potential) by at least 10% upon treatment with the indicated Compounds of the present invention using the Assay condition as stated below.

| Disease or Healthy Control Cell | Cell Line | Assay Condition used in Example No | Compound |
|---|---|---|---|
| MELAS Syndrome | K605 | A | 633 |
| IVA | GM00947 | A | 1, 633 |
|  |  | B | 1 |
| VLCAD | GM11408 | A |  |
|  |  | B | 633 |

Using the procedure described in Example 819, the following cell lines listed in the Table below were screened and demonstrated an increase in MMP (Mitochondrial Membrane Potential) by at least 30% upon treatment with the indicated Compounds of the present invention using the Assay condition as stated below.

| Disease or Healthy Control Cell | Cell Line | Assay Condition used in Example No | Compound |
|---|---|---|---|
| MELAS Syndrome | K605 | A | 633 |
| IVA | GM00947 | A | 1, 633 |
|  |  | B | 1 |
| VLCAD | GM11408 | A |  |
|  |  | B | 633 |

Using the procedure described in Example 819, the following cell lines listed in the Table below were screened and demonstrated an increase in MMP (Mitochondrial Membrane Potential) by at least 50% upon treatment with the indicated Compounds of the present invention using the Assay condition as stated below.

| Disease or Healthy Control Cell | Cell Line | Assay Condition used in Example No | Compound |
|---|---|---|---|
| IVA | GM00947 | A | 633 |

Example 1006

Using the procedure described in Example 819, the following cell lines listed in the Table below were screened and demonstrated a decrease in MMP (Mitochondrial Membrane Potential) by at least 10% upon treatment with the indicated Compounds of the present invention using the Assay condition as stated below.

| Disease or Healthy Control Cell | Cell Line | Assay Condition used in Example No | The following Compounds Decreased MMP by at least 10% | Compound |
|---|---|---|---|---|
| Succinil-CoA: 3-Ketoacid CoA transferase deficiency (SCOT) |  | B |  | 42, 633 |
| MELAS Syndrome | K605 | A |  |  |
|  |  | B |  | 1 |
| Amyothrophic Lateral Sclerosis (ALS) | K773 | A |  | 1, 633 |
|  |  | B |  | 1, 633 |
| VLCAD | GM11408 | A |  | 1 |

Using the procedure described in Example 819, the following cell lines listed in the Table below were screened and demonstrated a decrease in MMP (Mitochondrial Membrane Potential) by at least 30% upon treatment with the indicated Compounds of the present invention using the Assay condition as stated below.

| Disease or Healthy Control Cell | Cell Line | Assay Condition used in Example No | Compound |
|---|---|---|---|
| Succinil-CoA: 3-Ketoacid CoA transferase deficiency (SCOT) | 10474 | A |  |
|  |  | B | 42, 633 |
| MELAS Syndrome | K605 | A |  |
|  |  | B | 1 |
| Amyothrophic Lateral Sclerosis (ALS) | K773 | A |  |
|  |  | B | 1, 633 |

Using the procedure described in Example 819, the following cell lines listed in the Table below were screened and demonstrated a decrease in MMP (Mitochondrial Membrane Potential) by at least 50% upon treatment with the indicated Compounds of the present invention using the Assay condition as stated below.

| Disease or Healthy Control Cell | Cell Line | Assay Condition used in Example No | Compound |
|---|---|---|---|
| Succinil-CoA: 3-Ketoacid CoA transferase deficiency (SCOT) | 10474 | A |  |
|  |  | B | 633 |
| Amyothrophic Lateral Sclerosis (ALS) | K773 | A |  |
|  |  | B | 1,633 |

Example 1007

Using the procedure described in Example 813, the following cell lines listed in the Table below were screened and demonstrated an increase in NAD$^+$ by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased NAD$^+$ by at least 10% |
|---|---|---|---|---|
| PA | GM03590 Passage 11 | 813 | A | 61 |
| MMA | Tsi 5224 Passage 12 | 813 | A | 61 |
| Leigh | GM13411 Passage 14 | 813 | C | 61 |
| Leigh | GM03672 Passage 8 | 813 | A | 142 |
| Leigh | GM03672 Passage 8 | 813 | C | 61 |
| PDH | GM1503A Passage 10 | 813 | A | 39, 42, 448 |
| VLCAD | GM17475 Passage 10 | 813 | A | 448 |
| PC | GM00444 Passage7 | 813 | C | 42 |

Example 1008

Using the procedure described in Example 813, the following cell lines listed in the Table below were screened and demonstrated an increase in NAD$^+$ by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased NAD$^+$ by at least 30% |
|---|---|---|---|---|
| MMA | Tsi 5224 Passage 12 | 813 | A | 61 |
| Leigh | GM03672 Passage 8 | 813 | A | 61 |
| Leigh | GM03672 Passage 8 | 813 | C | 61 |
| PDH | GM1503A Passage 10 | 813 | A | 39, 42 |

Example 1009

Using the procedure described in Example 813, the following cell lines listed in the Table below were screened and demonstrated an increase in NAD$^+$ by at least 50% upon treatment with the indicated compounds of the present invention using the Assay condition as stated below.

| Disease or Healthy Control Cell | Cell Line | Example No of Procedure used | Assay Condition used in Example No | The following Compounds Increased NAD$^+$ by at least 50% |
|---|---|---|---|---|
| Leigh | GM03672 Passage 8 | 813 | A | 61 |
| PDH | GM1503A Passage 10 | 813 | A | 39 |

Example 1010

Using the procedure described in Example 813, the following cell lines listed in the Table below were screened and demonstrated an increase in NADH (Nicotinamide Adenine Dinucleotide Reduced Form) by at least 10% upon treatment with the indicated Compounds of the present invention using the Assay condition as stated below.

| Disease or Healthy Control Cell | Cell Line | Example No of Procedure used | Assay Condition used in Example No | The following Compounds Increased NADH by at least 10% |
|---|---|---|---|---|
| PA | GM03590 Passage 11 | | A | 61 |
| PA | GM03590 Passage 11 | | C | 61 |
| MMA | Tsi 5224 Passage 12 | | C | 61 |
| PDH | GM1503A Passage 10 | | A | 448 |
| PDH | GM1503A Passage 10 | | C | 448 |
| PC | GM00444 Passage 7 | | C | 42 |

Example 1011

Using the procedure described in Example 813, the following cell lines listed in the Table below were screened and demonstrated an increase in NADH (Nicotinamide Adenine Dinucleotide Reduced Form) by at least 30% upon treatment with the indicated Compounds of the present invention using the Assay condition as stated below.

| Disease or Healthy Control Cell | Cell Line | Example No of Procedure used | Assay Condition used in Example No | The following Compounds Increased NADH by at least 30% |
|---|---|---|---|---|
| PDH | GM1503A P10 | | A | 448 |
| PC | GM00444 P7 | | C | 42 |

EQUIVALENTS

The foregoing description has been presented only for the purposes of illustration and is not intended to limit the disclosure to the precise form disclosed. The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

What is claimed is:

1. A compound of Formula (I'):

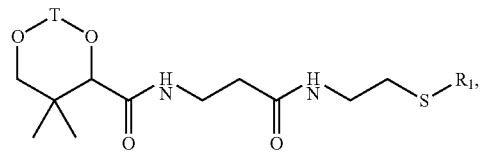

(I')

or a pharmaceutically acceptable salt or solvate thereof, wherein:

T is

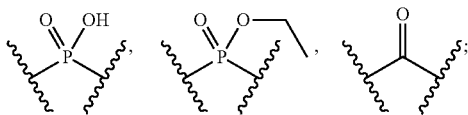

$R_1$ is —C(=O)$R_{1b}$, —C(=O)$R_{1z}$,

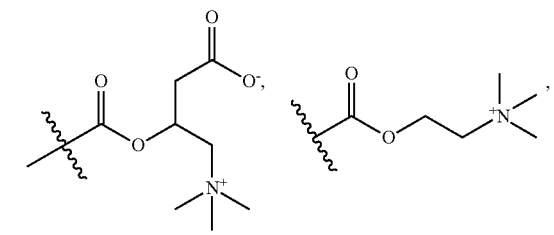

—C(=O)—(CH=CH)$_n$—$R_{1a}$,

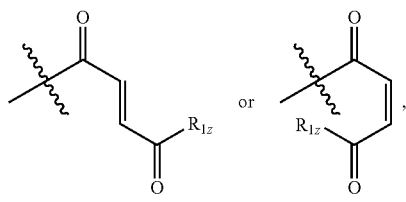 or

—C(=O)CH$_2$—[C(=O)CH$_2$]$_p$—[CH$_2$]$_q$—$R_{1a}$,

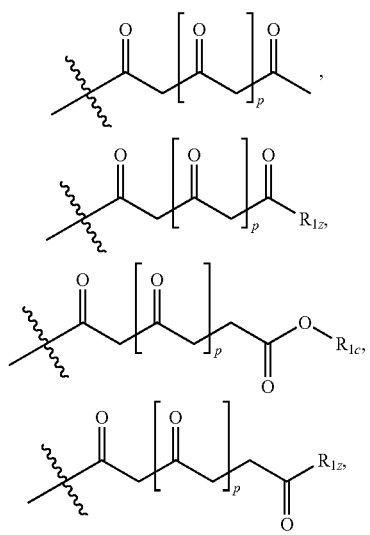

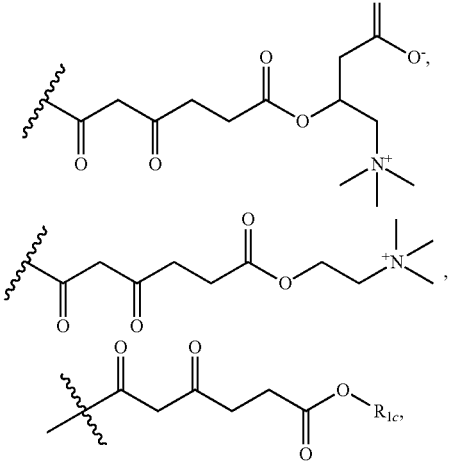

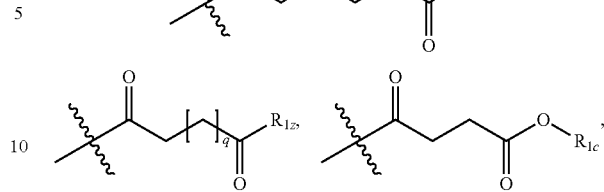

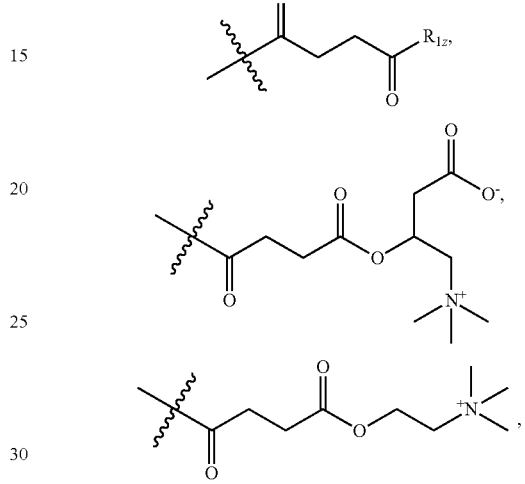

—C(=O)CH($R_{1a}$)—[C(=O)CH($R_{1a}$)]$_p$—[CH$_2$]$_q$—$R_{1a}$,

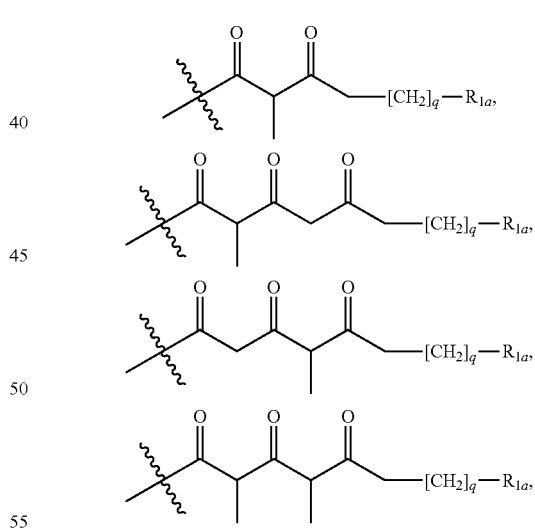

—C(=O)CH$_2$—[CH(O$R_{1c}$)—CH$_2$]$_p$—[CH$_2$]$_q$—$R_{1a}$,
—C(=O)CH$_2$—[C(=O)CH$_2$]$_p$—[CH(O$R_{1c}$)—CH$_2$]$_r$—[CH$_2$]$_q$—$R_{1a}$, —C(=O)CH$_2$—[CH(O$R_{1c}$)—CH$_2$]$_r$—[C(=O)CH$_2$]$_p$—[CH$_2$]$_q$—$R_{1a}$, —C(=O)O$R_{1c}$, C(=O)N($R_{1c}$)$_2$, —C(=O)—CH=CH—C(=O)O$R_{1c}$, —C(=O)—[CH$_2$]$_q$—C(=O)O$R_{1c}$, —C(=O)—CH$_2$CH$_2$—C(=O)O$R_{1c}$, —C(=O)CH$_2$—[C(=O)CH$_2$]$_p$—[CH$_2$]$_q$—C(=O)O$R_{1c}$, —C(=O)—[CH$_2$]$_q$—C(=O)$R_{1z}$, —C(=O)—CH$_2$CH$_2$—C(=O)$R_{1z}$, —C(=O)CH$_2$—[C(=O)CH$_2$]$_p$—[CH$_2$]$_q$—C(=O)$R_{1z}$,

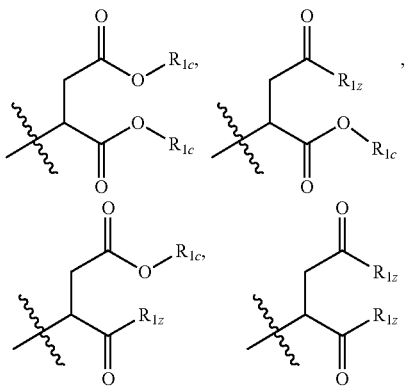

each $R_{1a}$ is independently H, oxo, halogen, $C_1$-$C_{20}$ alkyl, $C_2$-$C_{20}$ alkenyl, —$OR_{1c}$, —$C(=O)OR_{1c}$, —$C(=O)N(R_{1c})_2$, —$N(R_{1c})_2$, —$N(R_{1c})C(=O)R^{1b}$, —$N(R_{1c})C(=O)R_{1z}$, —$N(R_{1c})C(=O)OR_{1c}$, —$OC(=O)R^{1b}$, —$OC(=O)R_{1z}$, —$OC(=O)OR_{1c}$, —$OSi(R_{1g})_3$, —$SC(=O)R^{1b}$, —$SC(=O)R_{1z}$, —$SC(=O)OR_{1c}$, —$SC(=O)N(R_{1c})_2$, —$C(=O)R^{1b}$, —$C(=O)R_{1z}$, —$SR_{1a}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1e}$;

each $R_{1b}$ is independently H, $C_1$-$C_{20}$ alkyl, $C_2$-$C_{20}$ alkenyl, $C_2$-$C_{20}$ alkynyl, —$(CH_2)_q$—$C(=O)OR_{1c}$, —$CH_2$—$C(=O)$—$(CH_2)_q$-$C(=O)OR_{1c}$, —$CH_2$—$[C(=O)CH_2]_p$—$[CH_2]_q$—$C(=O)OR_{1c}$, —$CH=CH$—$C(=O)OR_{1c}$, —$C(=O)OR_{1c}$, —$C(=O)N(R_{1c})_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1e}$;

each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$; or two $R_{1c}$ together with the one or more intervening atoms to which they are connected, form $C_3$-$C_{12}$ cycloalkyl or $C_3$-$C_{12}$ heterocycloalkyl, wherein the $C_3$-$C_{12}$ cycloalkyl or $C_3$-$C_{12}$ heterocycloalkyl is optionally substituted with one or more $R_{1e}$;

each $R_{1d}$ is independently H, $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1e}$;

each $R_{1e}$ is independently H, halogen, $C_1$-$C_{20}$ alkyl, $C_2$-$C_{20}$ alkenyl, $C_2$-$C_{20}$ alkynyl, —$OR_{1g}$, —$C(=O)OR_{1g}$, —$C(=O)N(R_{1g})_2$, —$N(R_{1g})_2$, —$N(R_{1g})C(=O)$ $R_{1f}$, —$N(R_{1g})C(=O)R_{1z}$, —$N(R_{1g})C(=O)OR_{1g}$, —$OC(=O)R_{1f}$, —$OC(=O)R_{1z}$, —$OC(=O)OR_{1g}$, —$OSi(R_{1g})_3$, —$SR_{1g}$, —$N^+(R_{1g})_3$, —$SC(=O)R_{1f}$, —$SC(=O)R_{1z}$, —$SC(=O)OR_{1g}$, —$SC(=O)N(R_{1g})_2$, —$C(=O)R_{1f}$, —$C(=O)R_{1z}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1f}$ is independently H, $C_1$-$C_{20}$ alkyl, $C_2$-$C_{20}$ alkenyl, $C_2$-$C_{20}$ alkynyl, —$OSi(R_{1g})_3$, —$CH_2C(=O)OR_{1g}$, —$CH=CH$—$C(=O)OR_{1g}$, —$C(=O)OR_{1g}$, —$C(=O)N(R_{1g})_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1g}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —($C_1$-$C_{20}$ alkyl)-($C_3$-$C_{12}$ cycloalkyl), —($C_1$-$C_{20}$ alkyl)-($C_3$-$C_{12}$ heterocycloalkyl), —($C_1$-$C_{20}$ alkyl)-($C_3$-$C_{12}$ aryl), or —($C_1$-$C_{20}$ alkyl)-($C_3$-$C_{12}$ heteroaryl) is optionally substituted with one or more $R_{1z}$;

each $R_{1z}$ is independently

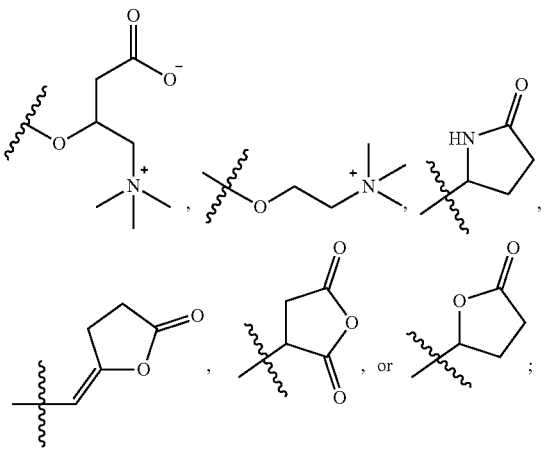

each n is independently an integer ranging from 0 to 20;

each p is independently an integer ranging from 0 to 20;

each q is independently an integer ranging from 0 to 20; and each r is independently an integer ranging from 0 to 20.

2. The compound of claim 1, wherein the compound is of Formula (I'):

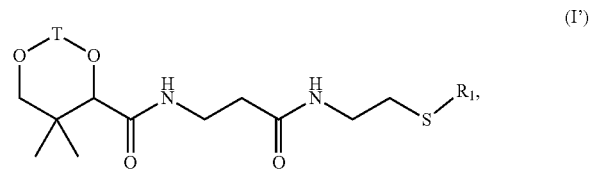

(I')

or a pharmaceutically acceptable salt or solvate thereof, wherein:

each T is independently

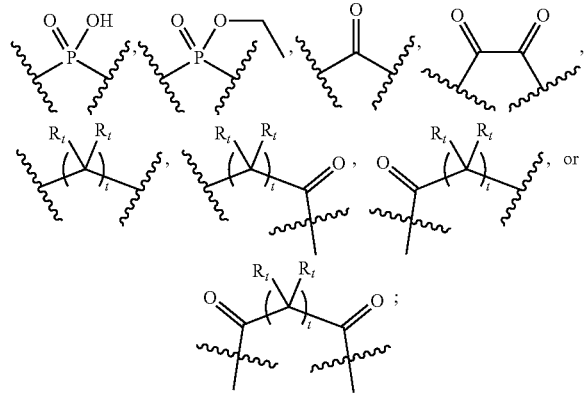

each $R_t$ is independently $R_1$, $R_{1a}$, or $R_{1b}$; or two $R_t$, together with the one or more intervening atoms they are attached to, form a $C_3$-$C_{12}$ cycloalkyl or $C_3$-$C_{12}$ heterocycloalkyl, wherein $C_3$-$C_{12}$ cycloalkyl or $C_3$-$C_{12}$ heterocycloalkyl is optionally substituted with one or more Ria;

t is an integer ranging from 0 to 5;

each $R_{1a}$ is independently H, oxo, halogen, $C_1$-$C_{20}$ alkyl, $C_2$-$C_{20}$ alkenyl, —$OR_{1c}$, —$C(=O)OR_{1c}$, —$C(=O)N(R_{1c})_2$, —$N(R_{1c})_2$, —$N(R_{1c})C(=O)R_{1b}$, —$N(R_{1c})C(=O)R_{1z}$, —$N(R_{1c})C(=O)OR_{1c}$, —$OC(=O)R_{1b}$, —$OC(=O)R_{1z}$, —$OC(=O)OR_{1c}$, —$SC(=O)R_{1b}$, —$SC(=O)R_{1z}$, —$SC(=O)OR_{1c}$, —$SC(=O)N(R_{1c})_2$, —$C(=O)R_{1b}$, —$C(=O)R_{1z}$, —$SR_{1a}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1e}$;

each $R_{1b}$ is independently H, $C_1$-$C_{20}$ alkyl, $C_2$-$C_{20}$ alkenyl, $C_2$-$C_{20}$ alkynyl, —$(CH_2)_q$—$C(=O)OR_{1c}$, —$CH_2$—$C(=O)$—$(CH_2)_q$—$C(=O)OR_{1c}$, —$CH_2$—$[C(=O)CH_2]_p$—$[CH_2]_q$—$C(=O)OR_{1c}$, —$CH=CH$—$C(=O)OR_{1c}$, —$C(=O)OR_{1c}$, —$C(=O)N(R_{1c})_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1e}$;

each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) is optionally substituted with one or more $R_{1e}$;

each $R_{1d}$ is independently H, $C_1$-$C_{20}$ alkyl, $C_2$-$C_{20}$ alkenyl, $C_2$-$C_{20}$ alkynyl, $C_3$-$C_{10}$ cycloalkyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) is optionally substituted with one or more $R_{1e}$;

each $R_{1e}$ is independently H, halogen, $C_1$-$C_{20}$ alkyl, $C_2$-$C_{20}$ alkenyl, $C_2$-$C_{20}$ alkynyl, —$OR_{1g}$, —$C(=O)OR_{1g}$, —$C(=O)N(R_{1g})_2$, —$N(R_{1g})_2$, —$N(R_{1g})C(=O)R_{1f}$, —$N(R_{1g})C(=O)R_{1z}$, —$N(R_{1g})C(=O)OR_{1g}$, —$OC(=O)R_{1f}$, —$OC(=O)R_{1z}$, —$OC(=O)OR_{1g}$, —$SR_{1g}$, —$N^+(R_{1g})_3$, —$SC(=O)R_{1f}$, —$SC(=O)R_{1z}$, —$SC(=O)OR_{1g}$, —$SC(=O)N(R_{1g})_2$, —$C(=O)R_{1f}$, —$C(=O)R_{1z}$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1f}$ is independently H, $C_1$-$C_{20}$ alkyl, $C_2$-$C_{20}$ alkenyl, $C_2$-$C_{20}$ alkynyl, —$CH_2C(=O)OR_{1g}$, —$CH=CH$—$C(=O)OR_{1g}$, —$C(=O)OR_{1g}$, —$C(=O)N(R_{1g})_2$, or $R_{1z}$, wherein the $C_1$-$C_{20}$ alkyl, $C_2$-$C_{20}$ alkenyl, or $C_2$-$C_{20}$ alkynyl is optionally substituted with one or more $R_{1z}$;

each $R_{1g}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) is optionally substituted with one or more $R_{1z}$;

each $R_{1z}$ is independently

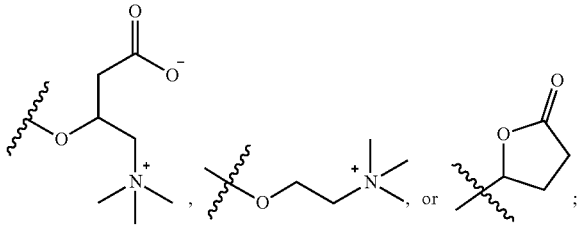

each n is independently an integer ranging from 0 to 20;
each p is independently an integer ranging from 0 to 20;
each q is independently an integer ranging from 0 to 20; and
each r is independently an integer ranging from 0 to 20.

3. The compound of claim 1, or a pharmaceutically acceptable salt thereof, wherein each $R_{1c}$ is independently H, $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl), wherein the $C_1$-$C_{20}$ alkyl, $C_2$-$C_{20}$ alkenyl, $C_2$-$C_{20}$ alkynyl, $C_3$-$C_{12}$ cycloalkyl, $C_3$-$C_{12}$ heterocycloalkyl, $C_3$-$C_{12}$ aryl, $C_3$-$C_{12}$ heteroaryl, —$(C_1$-$C_{20}$ alkyl)-$(C_3$-$C_{12}$ cycloalkyl), —$(C_1$-$C_{20}$ alkyl)-$(C_3$-$C_{12}$ heterocycloalkyl), —$(C_1$-$C_{20}$ alkyl)-$(C_3$-$C_{12}$ aryl), or —$(C_1$-$C_{20}$ alkyl)-$(C_3$-$C_{12}$ heteroaryl) is optionally substituted with one or more $R_{1e}$;

each R$_{12}$ is independently

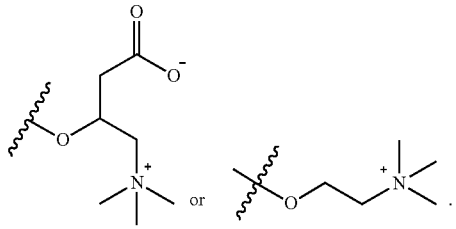

4. The compound of claim 1, or a pharmaceutically acceptable salt thereof, wherein each R$_{1a}$ is independently H, C$_1$-C$_{20}$ alkyl, C$_2$-C$_{20}$ alkenyl, —OR$_{1c}$, —C(=O)OR$_{1c}$, —C(=O)R$^{1b}$, —C(=O)R$_{1z}$, or R$_{1z}$.

5. The compound of claim 1, or a pharmaceutically acceptable salt thereof, wherein each R$_{1b}$ is independently C$_1$-C$_{20}$ alkyl, C$_2$-C$_{20}$ alkenyl, —(CH$_2$)$_q$—C(=O)OR$_{1c}$, —CH$_2$—C(=O)—(CH$_2$)$_q$—C(=O)OR$_{1c}$, —CH$_2$—[C(=O)CH$_2$]$_p$—[CH$_2$]$_q$—C(=O)OR$_{1c}$, —CH=CH—C(=O)OR$_{1c}$, or R$_{1z}$.

6. The compound of claim 1, or a pharmaceutically acceptable salt thereof, wherein each R$_{1c}$ is independently H, C$_{1-20}$ alkyl, C$_{2-20}$ alkenyl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl).

7. The compound of claim 1, or a pharmaceutically acceptable salt thereof, each R$_{1d}$ is independently H, C$_1$-C$_{20}$ alkyl, C$_2$-C$_{20}$ alkenyl, C$_3$-C$_{12}$ cycloalkyl, C$_3$-C$_{12}$ heterocycloalkyl, C$_3$-C$_{12}$ aryl, C$_3$-C$_{12}$ heteroaryl, —(C$_1$-C$_{20}$ alkyl)-(C$_3$-C$_{12}$ cycloalkyl), —(C$_1$-C$_{20}$ alkyl)-(C$_3$-C$_{12}$ heterocycloalkyl), —(C$_1$-C$_{20}$ alkyl)-(C$_3$-C$_{12}$ aryl), or —(C$_1$-C$_{20}$ alkyl)-(C$_3$-C$_{12}$ heteroaryl).

8. The compound of claim 1, or a pharmaceutically acceptable salt thereof, wherein each R$_{1e}$ is independently H, C$_1$-C$_{20}$ alkyl, C$_2$-C$_{20}$ alkenyl, —OR$_{1g}$, —C(=O)OR$_{1g}$, —C(=O)OR$_{1f}$, —C(=O)R$_{1z}$, —N(R$_{1g}$)C(=O)R$_{1z}$, —OC(=O)R$_{1z}$, —N$^+$(R$_{1g}$)$_3$, or R$_{1z}$.

9. The compound of claim 1, or a pharmaceutically acceptable salt thereof, wherein each R$_{1f}$ is independently H, C$_1$-C$_{20}$ alkyl, C$_2$-C$_{20}$ alkenyl, —CH$_2$C(=O)OR$_{1g}$, —CH=CH—C(=O)OR$_{1g}$, or —C(=O)OR$_{1g}$, R$_{1z}$.

10. The compound of claim 1, or a pharmaceutically acceptable salt thereof, wherein each R$_{1z}$ is independently

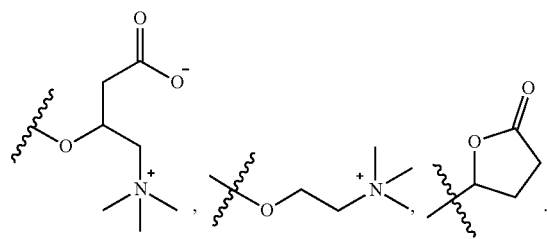

11. The compound of claim 1, being of Formula (I'-1) or (I'-2):

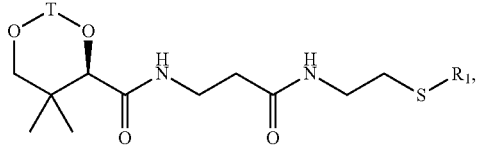

(I'-1)

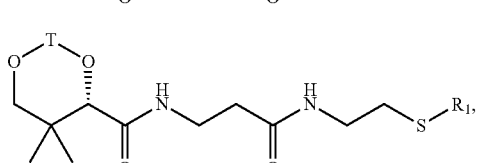

(I'-2)

or a pharmaceutically acceptable salt or solvate thereof.

12. The compound of claim 1, wherein T is

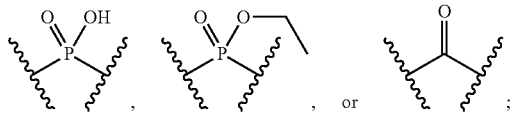

and R$_1$ is —C(=O)—R$_{1a}$, —C(=O)—CH$_2$—R$_{1a}$, —C(=O)—CH$_2$CH$_2$—R$_{1a}$ or —C(=O)—CH=CH—R$_{1a}$, wherein R$_{1a}$ is C$_1$-C$_{20}$ alkyl, —C(=O)R$^{1b}$, or —C(=O)OR$_{1c}$, wherein the C$_1$-C$_{20}$ alkyl is optionally substituted with one or more R$_{1e}$.

13. The compound of claim 1, or a pharmaceutically acceptable salt thereof, wherein T is

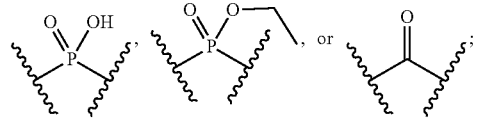

and R$_1$ is —C(=O)—CH$_3$, —C(=O)—CH$_2$—CH(OH)—CH$_3$, —C(=O)—CH$_2$—C(=O)—CH$_3$, —C(=O)—CH$_2$CH$_2$—C(=O)OH, —C(=O)—CH$_2$CH$_2$—C(=O)OCH$_3$, —C(=O)—CH=CH—CH$_3$, —C(=O)—CH=CH—C(=O)OH, or —C(=O)—CH=CH—C(=O)OCH$_3$.

14. The compound of claim 1, wherein the compound is of Formula (II-1), (II-2), (IIaa), (IIab), (IIac), (IIad), (IIaa-1), (IIaa-2), (IIab-1), (IIab-2), (IIac-1), (IIac-2), (IIad-1), (IIad-2), (IIae), (IIaf), (IIag), (IIah), (IIae-1), (IIae-2), (IIaf-1), (IIaf-2), (IIag-1), (IIag-2), (IIah-1), (IIah-2), (IIai), (IIaj), (IIak), (IIal), (IIam), (IIan), (IIai-1), (IIai-2), (IIaj-1), (IIaj-2), (IIak-1), (IIak-2), (IIal-1), (IIal-2), (IIam-1), (IIam-2), (IIan-1), or (IIan-2):

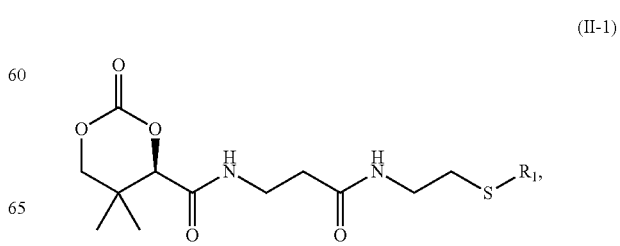

(II-1)

(II-2)
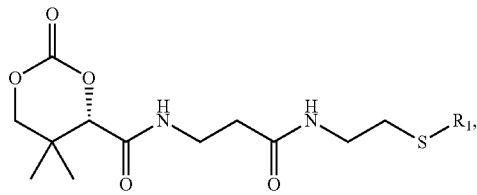
(IIab-1)
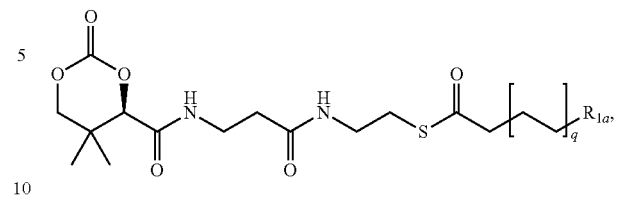
(IIaa)
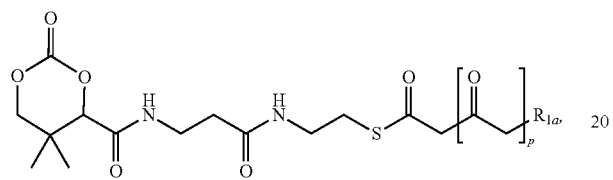
(IIab-2)
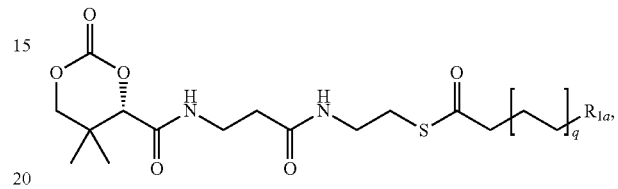
(IIab)
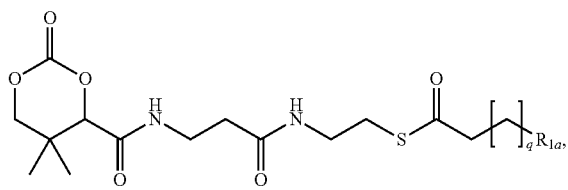
(IIac-1)
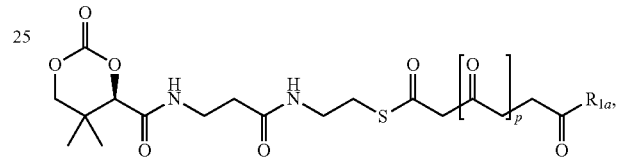
(IIac)
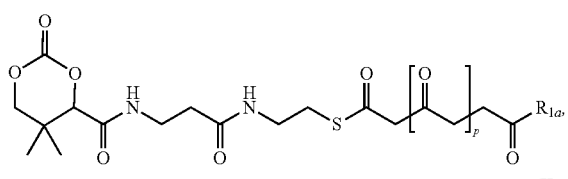
(IIac-2)
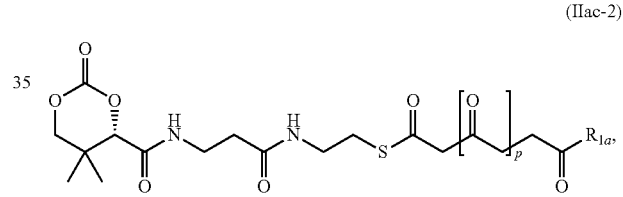
(IIad)
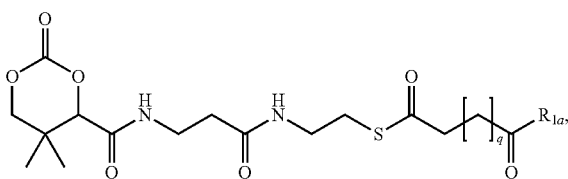
(IIad-1)
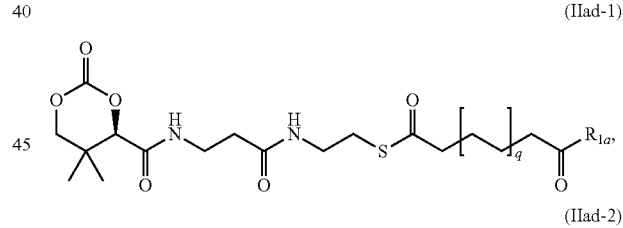
(IIaa-1)
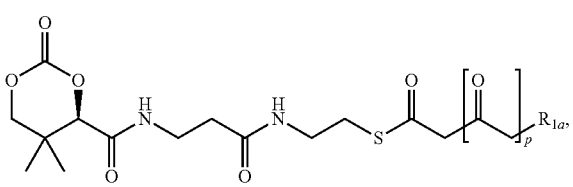
(IIad-2)
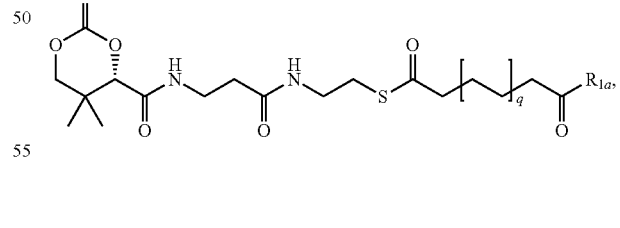
(IIaa-2)
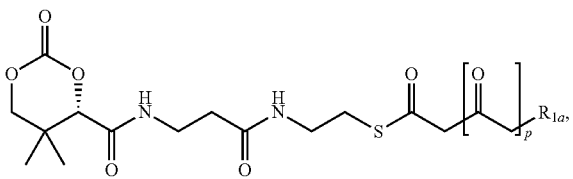
(IIae)
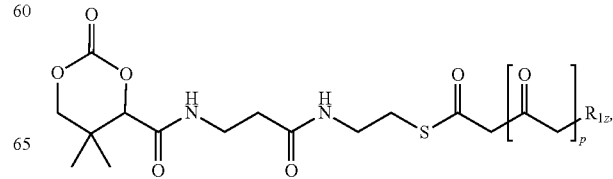

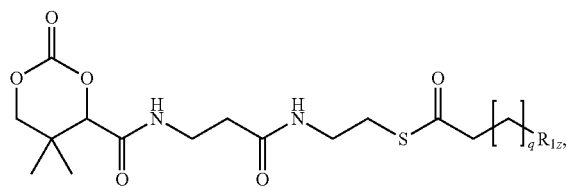
(IIaf)
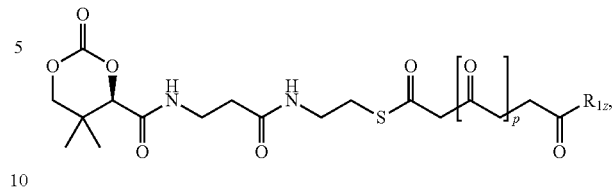
(IIag-1)
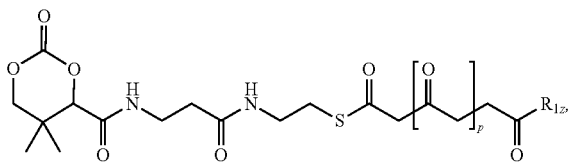
(IIag)
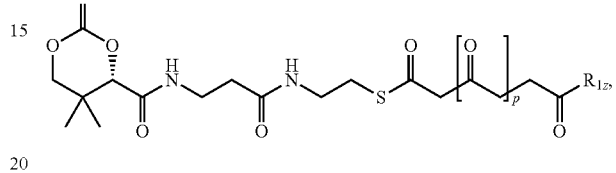
(IIag-2)
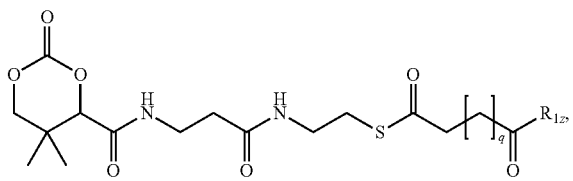
(IIah)
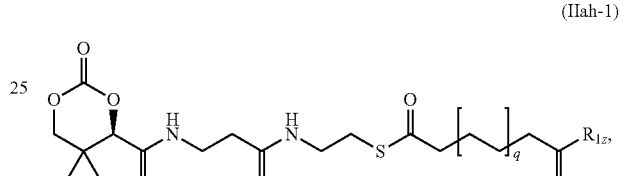
(IIah-1)
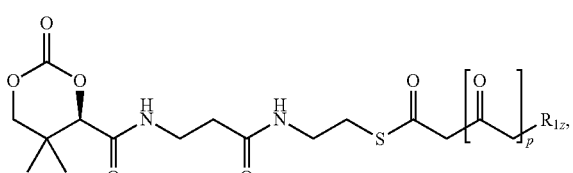
(IIae-1)
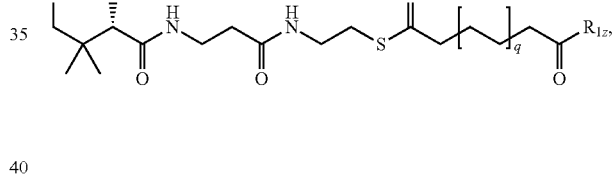
(IIah-2)
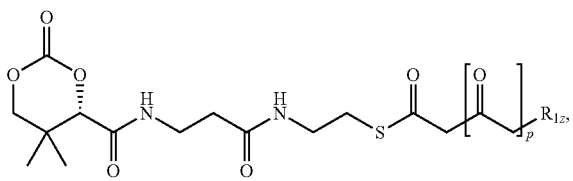
(IIae-2)
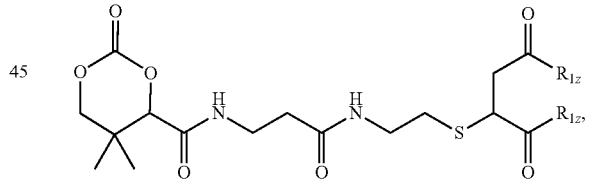
(IIai)
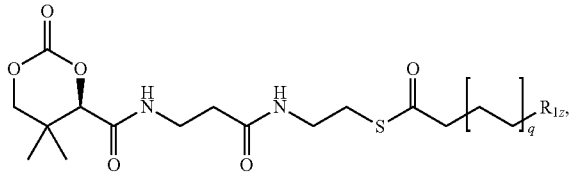
(IIaf-1)
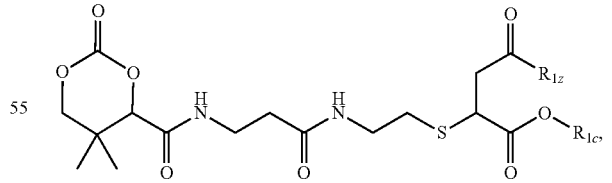
(IIaj)
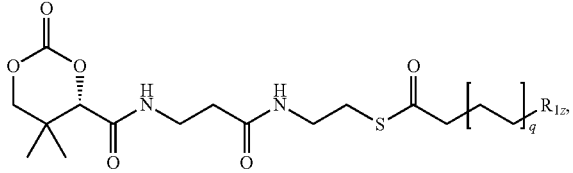
(IIaf-2)
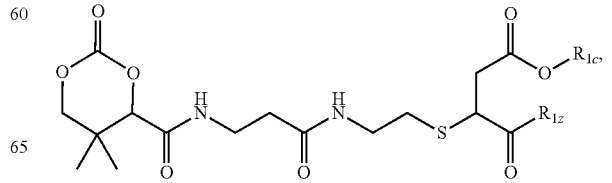
(IIak)

(IIal)
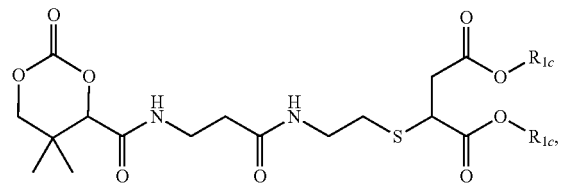
(IIam)
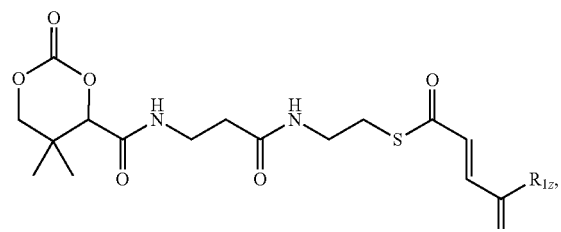
(IIan)
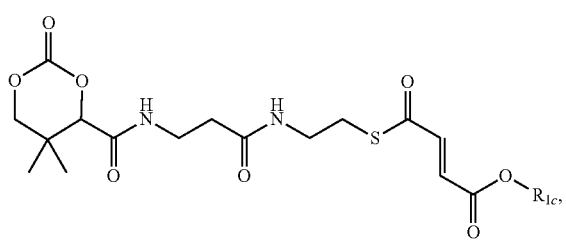
(IIai-1)
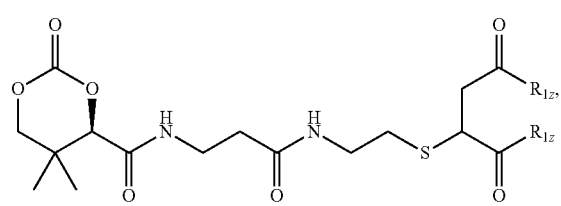
(IIai-2)
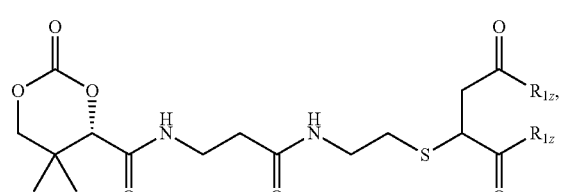
(IIaj-1)
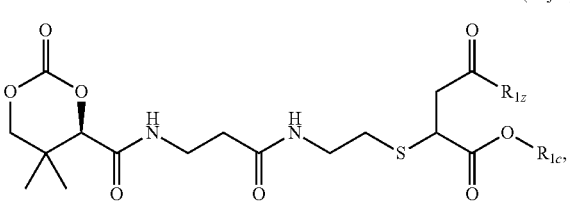
(IIaj-2)
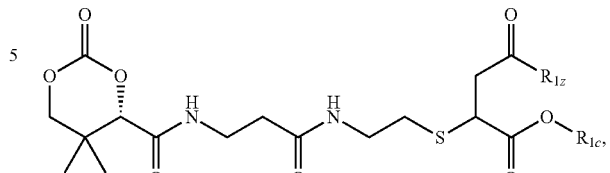
(IIak-1)
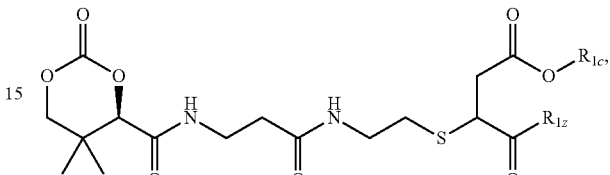
(IIak-2)
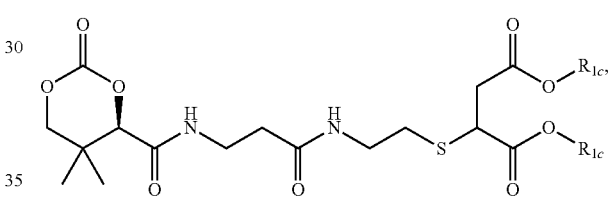
(IIal-1)
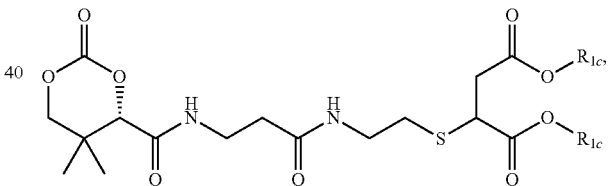
(IIal-2)
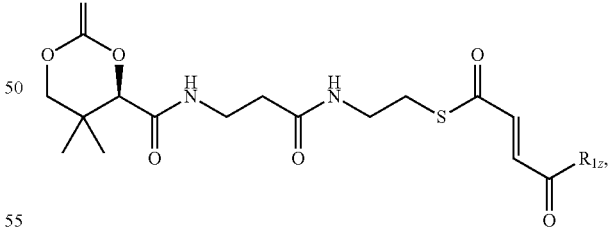
(IIam-2)
(IIam-2)
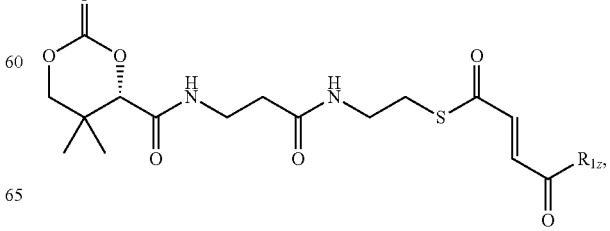

-continued (IIan-1)
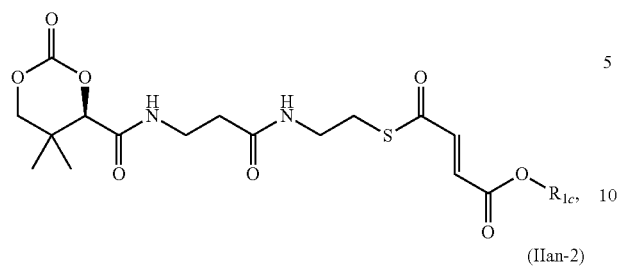

(IIan-2)
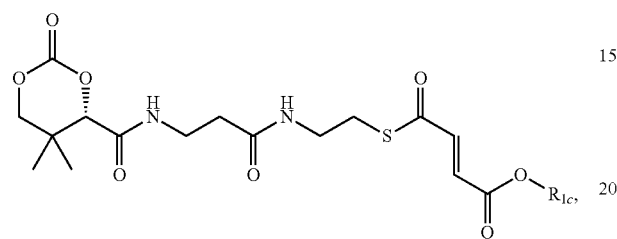

or a pharmaceutically acceptable salt or solvate thereof.

15. The compound of claim 1, wherein the compound is of Formula (IIaa), (IIab), (IIac), or (IIad):

(IIaa)
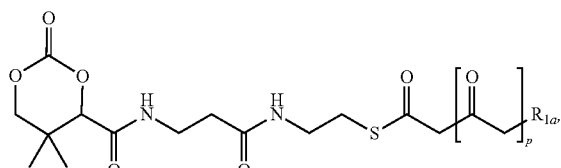

-continued (IIab)
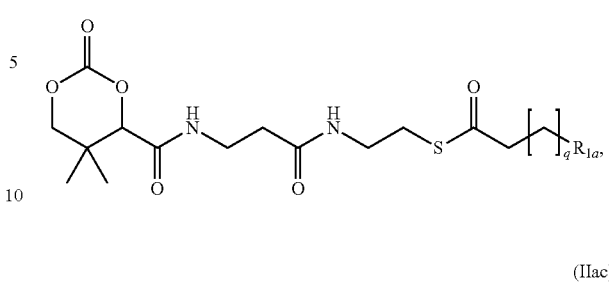

(IIac)
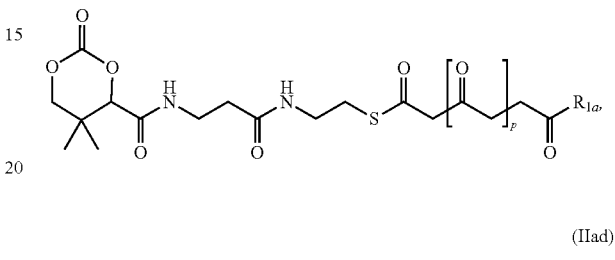

(IIad)
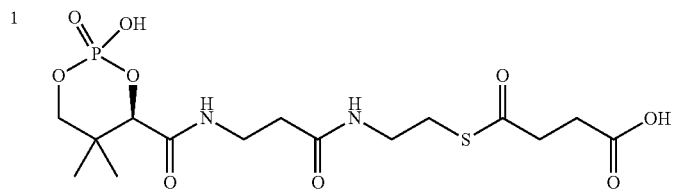

or a pharmaceutically acceptable salt or solvate thereof.

16. The compound of claim 1, wherein the compound is selected from Compound Nos. 1, 3, 5, 21, 36, 39, 42, 61, 447, 448, 451 and 485, and pharmaceutically acceptable salts thereof:

1
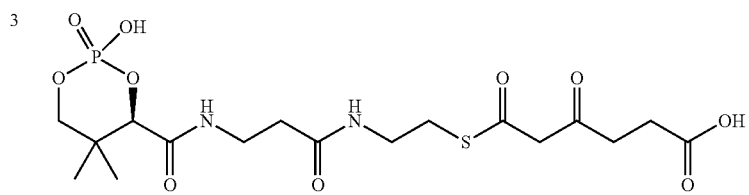

3
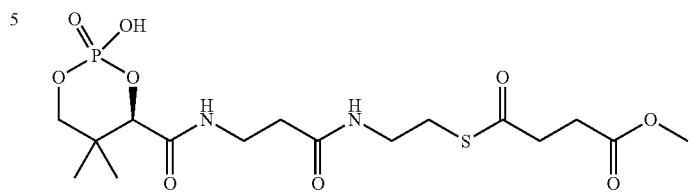

5

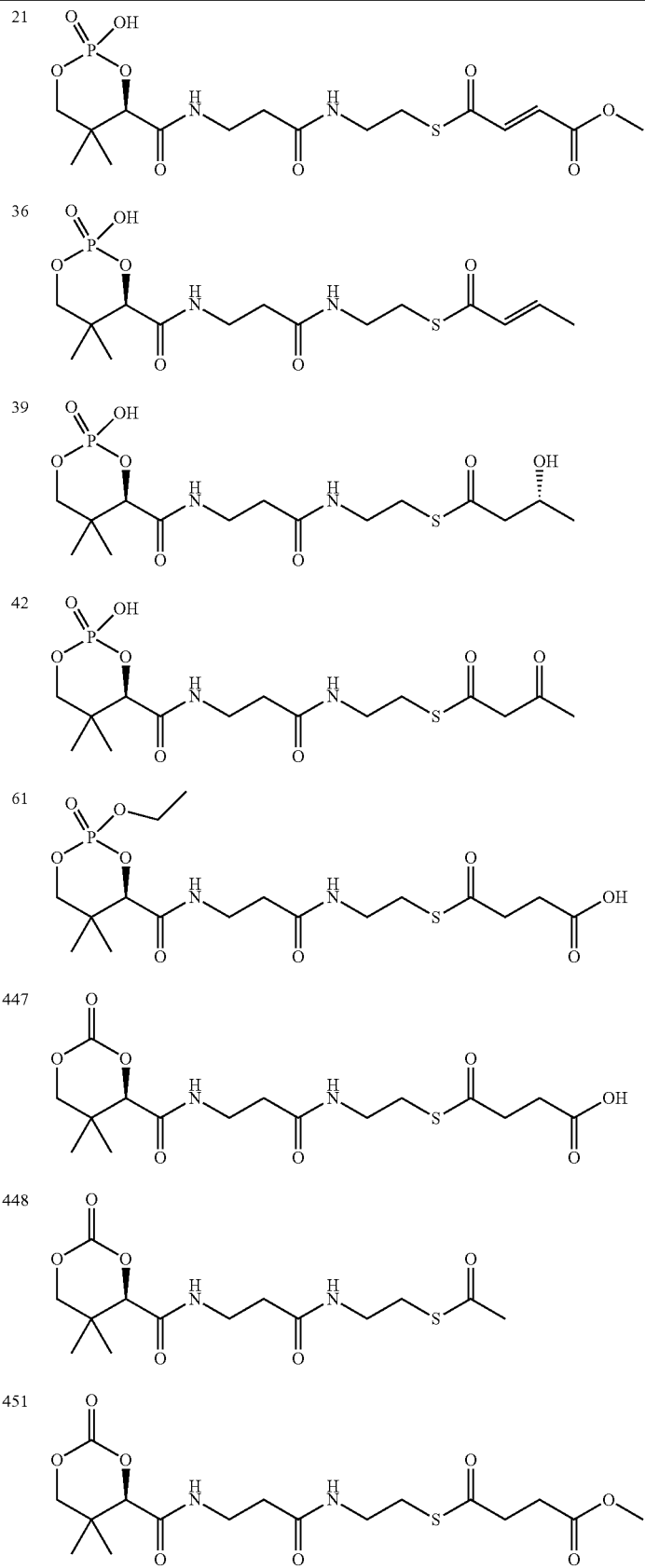

485 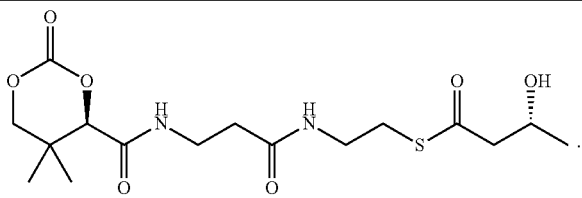

17. A pharmaceutical composition comprising the compound of claim 1 or a pharmaceutically acceptable salt thereof.

18. A method of treating or preventing a disease characterized by and/or associated with decreased concentrations of one or more of free CoA, acetyl-CoA, acyl-CoA, a precursor of free CoA, an active metabolite of free CoA, an active metabolite of a free CoA precursor, a precursor of acetyl-CoA, an active metabolite of acetyl-CoA, an active metabolite of an acetyl-CoA precursor, a precursor of acyl-CoA, an active metabolite of acyl-CoA, and/or an active metabolite of an acyl-CoA precursor in a subject, the method comprising administering to the subject a therapeutically effective amount of a compound of claim 1, or a pharmaceutically acceptable salt thereof.

* * * * *

SEQUENCE LISTING

<160> NUMBER OF SEQ ID NOS: 28

<210> SEQ ID NO 1
<211> LENGTH: 25
<212> TYPE: DNA

```
<213> ORGANISM: Artificial Sequence
<220> FEATURE:
<223> OTHER INFORMATION: transgene cassette specific primer

<400> SEQUENCE: 1
ggattacgcg tagcatggtg agcaa                                        25

<210> SEQ ID NO 2
<211> LENGTH: 26
<212> TYPE: DNA
<213> ORGANISM: Artificial Sequence
<220> FEATURE:
<223> OTHER INFORMATION: transgene cassette specific primer

<400> SEQUENCE: 2
gcctaaacgc gtttacttgt acagct                                       26

<210> SEQ ID NO 3
<211> LENGTH: 19
<212> TYPE: DNA
<213> ORGANISM: Artificial Sequence
<220> FEATURE:
<223> OTHER INFORMATION: ki allele genotyping primer

<400> SEQUENCE: 3
gtgggtgtca gcacacttg                                               19

<210> SEQ ID NO 4
<211> LENGTH: 18
<212> TYPE: DNA
<213> ORGANISM: Artificial Sequence
<220> FEATURE:
<223> OTHER INFORMATION: ki allele genotyping primer

<400> SEQUENCE: 4
cgtatgactg ggatgcct                                                18

<210> SEQ ID NO 5
<211> LENGTH: 19
<212> TYPE: DNA
<213> ORGANISM: Artificial Sequence
<220> FEATURE:
<223> OTHER INFORMATION: ko allele genotyping primer

<400> SEQUENCE: 5
acaactcctt gtgtaggtc                                               19

<210> SEQ ID NO 6
<211> LENGTH: 19
<212> TYPE: DNA
<213> ORGANISM: Artificial Sequence
<220> FEATURE:
<223> OTHER INFORMATION: ko allele genotyping primer

<400> SEQUENCE: 6
cctttaggat gtcattctg                                               19

<210> SEQ ID NO 7
<211> LENGTH: 20
<212> TYPE: DNA
<213> ORGANISM: Homo sapiens

<400> SEQUENCE: 7
aaaatctcat ccaagaagcc                                              20
```

<210> SEQ ID NO 8
<211> LENGTH: 20
<212> TYPE: DNA
<213> ORGANISM: Homo sapiens

<400> SEQUENCE: 8
aatgttccaa ttcctactgc                                          20

<210> SEQ ID NO 9
<211> LENGTH: 20
<212> TYPE: DNA
<213> ORGANISM: Homo sapiens

<400> SEQUENCE: 9
catctatccc cattcctgag                                          20

<210> SEQ ID NO 10
<211> LENGTH: 20
<212> TYPE: DNA
<213> ORGANISM: Homo sapiens

<400> SEQUENCE: 10
tttttccagt ggtatcagtc                                          20

<210> SEQ ID NO 11
<211> LENGTH: 22
<212> TYPE: DNA
<213> ORGANISM: Homo sapiens

<400> SEQUENCE: 11
ctttgaagat ctccccaata ac                                       22

<210> SEQ ID NO 12
<211> LENGTH: 21
<212> TYPE: DNA
<213> ORGANISM: Homo sapiens

<400> SEQUENCE: 12
gatccattga tggaaactgt g                                        21

<210> SEQ ID NO 13
<211> LENGTH: 20
<212> TYPE: DNA
<213> ORGANISM: Homo sapiens

<400> SEQUENCE: 13
tacctctaca cagatgatgc                                          20

<210> SEQ ID NO 14
<211> LENGTH: 21
<212> TYPE: DNA
<213> ORGANISM: Homo sapiens

<400> SEQUENCE: 14
cccaagattt gaataactcc c                                        21

```
<210> SEQ ID NO 15
<211> LENGTH: 21
<212> TYPE: DNA
<213> ORGANISM: Homo sapiens

<400> SEQUENCE: 15
cctaaaaagc ctaaggaaac c                                              21

<210> SEQ ID NO 16
<211> LENGTH: 21
<212> TYPE: DNA
<213> ORGANISM: Homo sapiens

<400> SEQUENCE: 16
gatctccaca gcaaatgata g                                              21

<210> SEQ ID NO 17
<211> LENGTH: 20
<212> TYPE: DNA
<213> ORGANISM: Homo sapiens

<400> SEQUENCE: 17
aaagaagcca acactaaacc                                                20

<210> SEQ ID NO 18
<211> LENGTH: 19
<212> TYPE: DNA
<213> ORGANISM: Homo sapiens

<400> SEQUENCE: 18
tggtcatttc gttaaaggc                                                 19

<210> SEQ ID NO 19
<211> LENGTH: 20
<212> TYPE: DNA
<213> ORGANISM: Homo sapiens

<400> SEQUENCE: 19
acctcaaatt tcattgtggg                                                20

<210> SEQ ID NO 20
<211> LENGTH: 21
<212> TYPE: DNA
<213> ORGANISM: Homo sapiens

<400> SEQUENCE: 20
gaagatgaag aacagaacca g                                              21

<210> SEQ ID NO 21
<211> LENGTH: 20
<212> TYPE: DNA
<213> ORGANISM: Homo sapiens

<400> SEQUENCE: 21
ccattgttat cggcattctg                                                20

<210> SEQ ID NO 22
<211> LENGTH: 22
<212> TYPE: DNA
<213> ORGANISM: Homo sapiens
```

```
<400> SEQUENCE: 22
attctggatg atgtagaggt ag                                    22

<210> SEQ ID NO 23
<211> LENGTH: 19
<212> TYPE: DNA
<213> ORGANISM: Homo sapiens

<400> SEQUENCE: 23
gaaactggga agcttgatg                                        19

<210> SEQ ID NO 24
<211> LENGTH: 20
<212> TYPE: DNA
<213> ORGANISM: Homo sapiens

<400> SEQUENCE: 24
cttgtcagaa ttgggatgtg                                       20

<210> SEQ ID NO 25
<211> LENGTH: 20
<212> TYPE: DNA
<213> ORGANISM: Homo sapiens

<400> SEQUENCE: 25
attcaggttt catttccagg                                       20

<210> SEQ ID NO 26
<211> LENGTH: 20
<212> TYPE: DNA
<213> ORGANISM: Homo sapiens

<400> SEQUENCE: 26
gattgttcag tactcagctc                                       20

<210> SEQ ID NO 27
<211> LENGTH: 20
<212> TYPE: DNA
<213> ORGANISM: Homo sapiens

<400> SEQUENCE: 27
acccactcct ccacctttga                                       20

<210> SEQ ID NO 28
<211> LENGTH: 22
<212> TYPE: DNA
<213> ORGANISM: Homo sapiens

<400> SEQUENCE: 28
ctgttgctgt agccaaattc gt                                    22
```